(12) United States Patent
Zhang et al.

(10) Patent No.: US 9,309,231 B2
(45) Date of Patent: Apr. 12, 2016

(54) BRIDGED RING COMPOUNDS AS HEPATITIS C VIRUS (HCV) INHIBITORS AND PHARMACEUTICAL APPLICATIONS THEREOF

(71) Applicant: SUNSHINE LAKE PHARMA CO., LTD, Dongguan, Guangdong (CN)

(72) Inventors: Yingjun Zhang, Dongguan (CN); Jiancun Zhang, Dongguan (CN); Hongming Xie, Dongguan (CN); Qingyun Ren, Dongguan (CN); Yumei Tan, Dongguan (CN); Huichao Luo, Dongguan (CN)

(73) Assignee: Sunshine Lake Pharma Co., Ltd., Dongguan, Guangdong (CN)

( * ) Notice: Subject to any disclaimer, the term of this patent is extended or adjusted under 35 U.S.C. 154(b) by 0 days.

(21) Appl. No.: 14/397,200

(22) PCT Filed: Aug. 5, 2013

(86) PCT No.: PCT/CN2013/000915
§ 371 (c)(1),
(2) Date: Oct. 27, 2014

(87) PCT Pub. No.: WO2014/019344
PCT Pub. Date: Feb. 6, 2014

(65) Prior Publication Data
US 2015/0079028 A1 Mar. 19, 2015

(30) Foreign Application Priority Data

Aug. 3, 2012 (CN) .......................... 2012 1 0273491
Apr. 3, 2013 (CN) .......................... 2013 1 0116933

(51) Int. Cl.
| | | |
|---|---|---|
| A61K 31/4178 | (2006.01) |
| C07D 403/14 | (2006.01) |
| C07D 401/14 | (2006.01) |
| C07D 413/14 | (2006.01) |
| C07D 409/14 | (2006.01) |
| C07D 417/14 | (2006.01) |
| C07D 453/06 | (2006.01) |
| C07D 471/08 | (2006.01) |
| C07D 491/056 | (2006.01) |
| C07D 493/08 | (2006.01) |
| C07D 519/00 | (2006.01) |
| A61K 31/4184 | (2006.01) |
| A61K 31/427 | (2006.01) |
| A61K 31/439 | (2006.01) |
| A61K 31/4545 | (2006.01) |
| A61K 31/5377 | (2006.01) |
| A61K 45/06 | (2006.01) |
| C07D 491/113 | (2006.01) |
| C07D 405/14 | (2006.01) |

(52) U.S. Cl.
CPC .......... *C07D 403/14* (2013.01); *A61K 31/4178* (2013.01); *A61K 31/4184* (2013.01); *A61K 31/427* (2013.01); *A61K 31/439* (2013.01); *A61K 31/4545* (2013.01); *A61K 31/5377* (2013.01); *A61K 45/06* (2013.01); *C07D 401/14* (2013.01); *C07D 405/14* (2013.01); *C07D 409/14* (2013.01); *C07D 413/14* (2013.01); *C07D 417/14* (2013.01); *C07D 453/06* (2013.01); *C07D 471/08* (2013.01); *C07D 491/056* (2013.01); *C07D 491/113* (2013.01); *C07D 493/08* (2013.01); *C07D 519/00* (2013.01)

(58) Field of Classification Search
CPC ....................................................... C07D 403/14
See application file for complete search history.

(56) References Cited

U.S. PATENT DOCUMENTS

| | | | |
|---|---|---|---|
| 7,659,270 B2 | 2/2010 | Bachand et al. |
| 7,704,992 B2 | 4/2010 | Bachand et al. |
| 8,143,414 B2 | 3/2012 | Lavoie et al. |

(Continued)

FOREIGN PATENT DOCUMENTS

| | | |
|---|---|---|
| WO | WO2010138790 | 12/2010 |
| WO | WO2011087740 | 7/2011 |

(Continued)

OTHER PUBLICATIONS

Montalbetti et al. Tetrahedron, 2005, 61, p. 10827-10852. Amide bond formation and peptide coupling.*

*Primary Examiner* — Brian McDowell
(74) *Attorney, Agent, or Firm* — Kam W. Law; Squire Patton Boggs (US) LLP

(57) ABSTRACT

Provided herein is a compound having Formula (I), or a stereoisomer, a geometric isomer, a tautomer, an N-oxide, a hydrate, a solvate, a metabolite, a pharmaceutically acceptable salt or a prodrug thereof, which can be used for treating HCV infection or a HCV disorder. Also provided herein are pharmaceutical compositions comprising the compounds disclosed herein, which can be used for treating HCV infection or a HCV disorder.

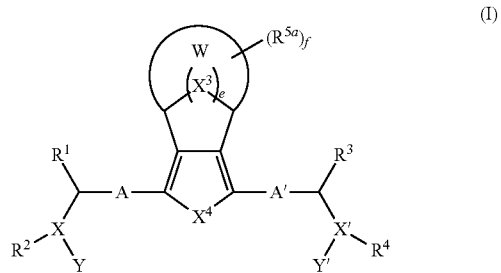

(I)

15 Claims, No Drawings

(56) References Cited

U.S. PATENT DOCUMENTS

| | | |
|---|---|---|
| 8,221,737 B2 | 7/2012 | Or et al. |
| 8,273,341 B2 | 9/2012 | Guo et al. |
| 8,303,944 B2 | 11/2012 | Bachand et al. |
| 8,314,135 B2 | 11/2012 | Qiu et al. |
| 8,354,419 B2 | 1/2013 | Henderson et al. |
| 8,362,068 B2 | 1/2013 | Dousson et al. |
| 2010/0226883 A1 | 9/2010 | Qiu et al. |
| 2011/0112100 A1 | 5/2011 | Milbank et al. |
| 2011/0274648 A1 | 11/2011 | Lavoie et al. |
| 2011/0312996 A1 | 12/2011 | Buckman et al. |
| 2012/0028978 A1 | 2/2012 | Zhong et al. |
| 2012/0039847 A1 | 2/2012 | Zhao |
| 2012/0040962 A1 | 2/2012 | Li et al. |
| 2012/0083483 A1 | 4/2012 | Coburn et al. |
| 2012/0115841 A1 | 5/2012 | Bur et al. |
| 2012/0115855 A1 | 5/2012 | Li et al. |
| 2012/0115918 A1 | 5/2012 | DeGoey et al. |
| 2012/0122864 A1 | 5/2012 | Zhong et al. |
| 2012/0195857 A1 | 8/2012 | Belema et al. |
| 2012/0251491 A1 | 10/2012 | Rosenblum et al. |
| 2012/0258909 A1 | 10/2012 | Liepold et al. |
| 2012/0264780 A1 | 10/2012 | Kullmann et al. |
| 2012/0276047 A1 | 11/2012 | Rosenblum et al. |
| 2013/0072523 A1 | 3/2013 | Liu et al. |

FOREIGN PATENT DOCUMENTS

| | | |
|---|---|---|
| WO | WO2011119853 | 9/2011 |
| WO | WO2011119870 | 9/2011 |
| WO | WO2011149856 | 12/2011 |
| WO | WO2011156543 | 12/2011 |
| WO | WO2012003642 | 1/2012 |
| WO | WO2012013643 | 2/2012 |
| WO | WO2012018534 | 2/2012 |
| WO | WO2012040923 | 4/2012 |
| WO | WO2012040924 | 4/2012 |
| WO | WO2012041014 | 4/2012 |
| WO | WO2012041227 | 4/2012 |
| WO | WO2012050848 | 4/2012 |
| WO | WO2012050918 | 4/2012 |
| WO | WO2012083048 | 6/2012 |
| WO | WO2012083053 | 6/2012 |
| WO | WO2012122716 | 9/2012 |
| WO | WO2012125926 | 9/2012 |
| WO | WO2013021337 | 2/2013 |
| WO | WO2013022810 | 2/2013 |

* cited by examiner

BRIDGED RING COMPOUNDS AS HEPATITIS C VIRUS (HCV) INHIBITORS AND PHARMACEUTICAL APPLICATIONS THEREOF

CROSS-REFERENCE TO RELATED APPLICATIONS

This is a U.S. national stage application of the International Patent Application No. PCT/CN2013/000915, filed Aug. 5, 2013, which claims priorities to Chinese Patent Application No. 201210273491.8, filed Aug. 3, 2012, and No. 201310116933.2, filed Apr. 3, 2013, all of which are incorporated herein by reference in their entirety.

FIELD OF THE INVENTION

The present invention relates to the field of medicine. The invention relates to compounds for treating Hepatitis C virus (HCV) infection, compositions comprising such compounds, the use and the methods thereof. In particular, the invention relates to bridged ring compounds as NS5A protein inhibitors. More specifically, the invention relates to compounds which can inhibit the function of the NS5A protein encoded by Hepatitis C virus (HCV), pharmaceutical compositions comprising such compounds, and methods for inhibiting the function of the NS5A protein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. Chronic HCV infection is thus a major worldwide cause of liver-related premature mortality.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. The treatment has side effects in many patients, so they do not durably respond to treatment. Thus, new and effective methods of treating HCV infection are urgently needed.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame (ORF).

Considerable heterogeneity is found within nucleotide and encoded amino acid sequence throughout the HCV genome. At least seven major genotypes have been characterized, and more than 50 subtypes have been described. In HCV infected cells, viral RNA is translated into a polyprotein that is cleaved into ten individual proteins. At the amino terminus are structural proteins, follows E1 and E2. Additionally, there are six non-structural proteins, NS2, NS3, NS4A, NS4B, NS5A and NS5B, which play a function role in the HCV lifecycle (see, for example, Lindenbach et al., Nature, 2005, 436, 933-938).

The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A and NS5B) is effected by two viral proteases. The first one is believed to be a metalloprotease and cleaves at the NS2-NS3 junction; the second one is a serine protease within the N-terminal region of NS3 (also referred herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan et al., *Virology*, 2001, 284, 1-12; and in Park et al., *J. Biol. Chem.*, 2003, 278, 30711-30718.

SUMMARY OF THE INVENTION

The present disclosure describes novel bridged ring compounds and methods of their use to treat HCV infection. Specifically, it has been found that compounds disclosed herein, and compositions thereof, are effective as inhibitors of HCV infection, especially the non-structural 5A (NS5A) protein of HCV.

In one aspect, provided herein are compounds having Formula (I) as shown below:

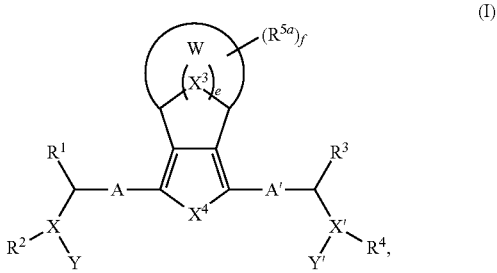

(I)

or a stereoisomer, a geometric isomer, a tautomer, an N-oxide, a hydrate, a solvate, a metabolite, a pharmaceutically acceptable salt or a prodrug thereof, wherein each of A and A' is independently a bond, alkyl, alkenyl, cycloalkyl, heterocycloalkyl, —$(CR^8R^{8a})_n$—O—

—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, or —(CR$^8$R$^{8a}$)$_n$—N(R$^5$)—C(=O)—O—(CR$^8$R$^{8a}$)$_p$—, or each of A and A' is independently

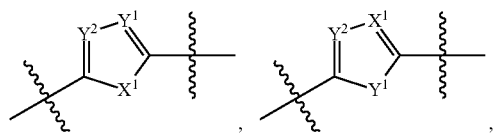
,

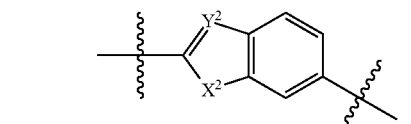
,

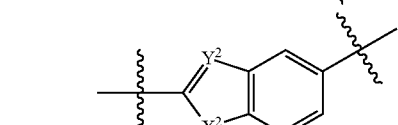
,

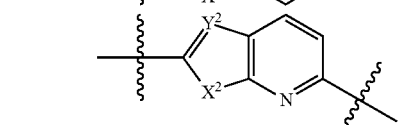
,

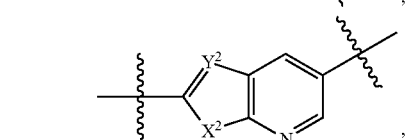
,

,

,

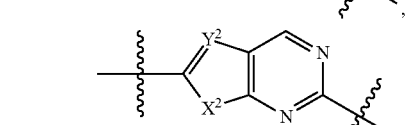
,

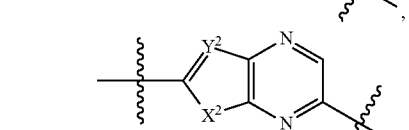
,

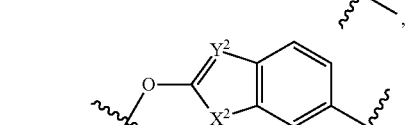
,

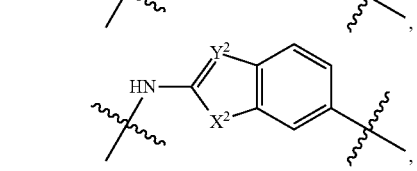
,

-continued

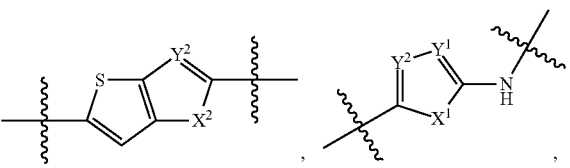
,

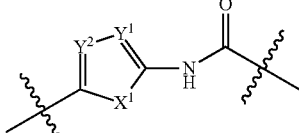
,

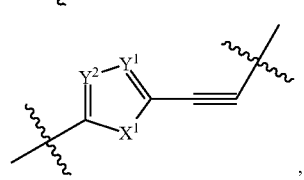
,

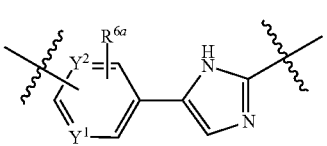
,

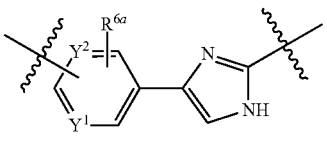
,

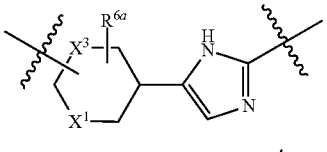
,

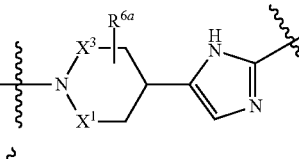
,

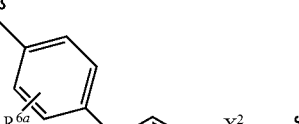
,

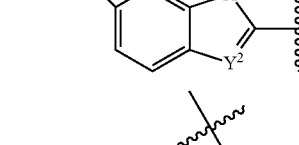
,

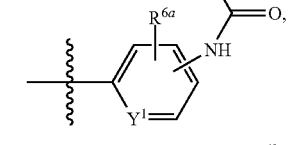
,

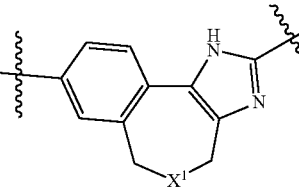
,

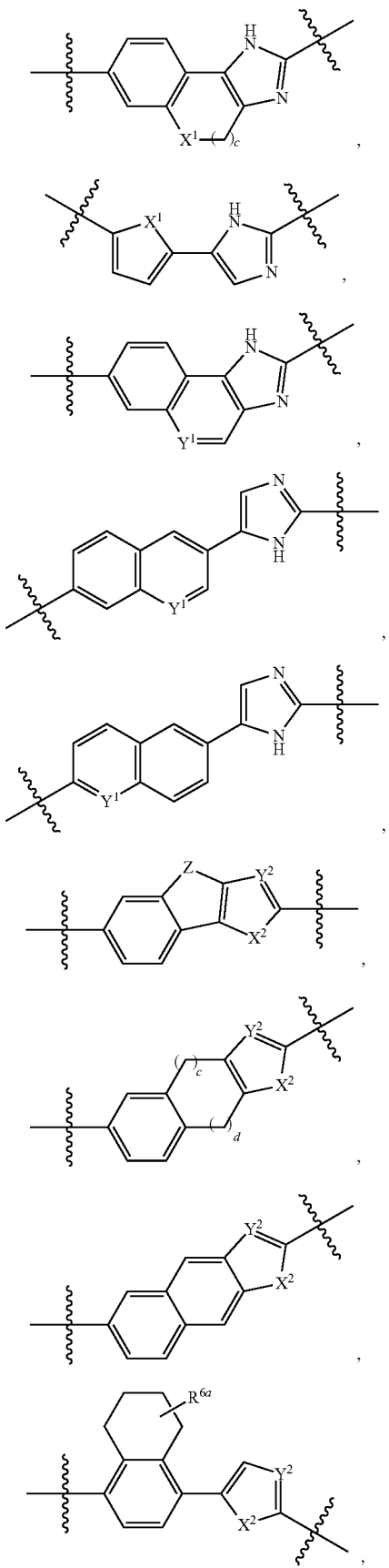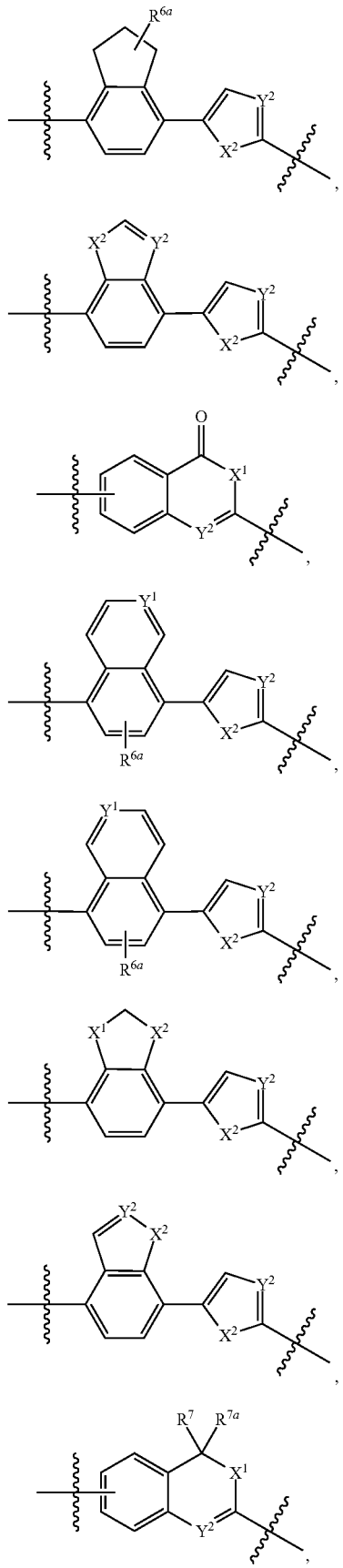

-continued

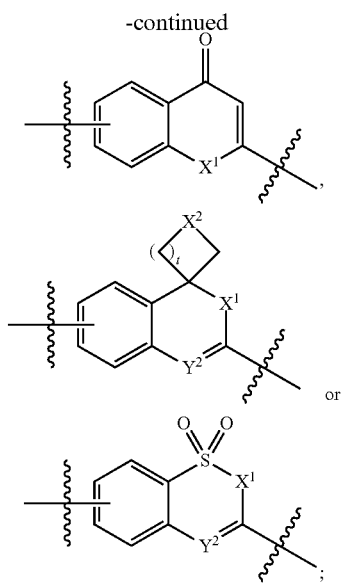

wherein each $X^1$ is independently O, S, $NR^6$, or $CR^7R^{7a}$;
each $X^2$ is independently $NR^6$, O or S;
each $X^3$ is independently O, S, $NR^6$, C(=O) or $CR^7R^{7a}$;
$X^4$ is $(CR^7R^{7a})_n$

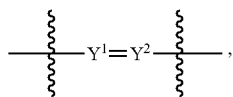

O, S or $NR^6$;

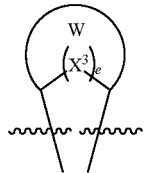

is carbocyclyl or heterocyclyl;
each $Y^1$ and $Y^2$ is independently N or $CR^7$;
Z is —$(CH_2)_a$—, —CH=CH—, —N=CH—, —$(CH_2)_a$—N($R^5$)—$(CH_2)_b$—, or —$(CH_2)_a$—O—$(CH_2)_b$—, wherein each a and b is independently 0, 1, 2 or 3;
each c is independently 1 or 2;
each d is independently 1 or 2;
each n is independently 0, 1, 2 or 3;
each p is independently 0, 1, 2 or 3;
each r is independently 0, 1 or 2;
e is 0, 1, 2, 3 or 4 with the proviso that where $X^3$ is O, S or $NR^6$, e is 1;
f is 0, 1, 2, 3 or 4;
each of X and X' is independently N or $CR^7$;
each of Y and Y' is independently H, deuterium, alkyl, heteroalkyl, cycloalkyl, heterocyclyl, aryl, heteroaryl, aralkyl, a group derived from α-amino acid or an optical isomer thereof, or each of Y and Y' is independently —[U—$(CR^9R^{9a})_t$—N($R^{10}$—$(CR^9R^{9a})_t]_k$—U—$(CR^9R^{9a})_t$—N($R^{11}$)—$(CR^9R^{9a})_t$—$R^{12}$, —U—$(CR^9R^{9a})_t$—$R^{12}$ or —[U—$(CR^9R^{9a})_t$—N($R^{10}$)—$(CR^9R^{9a})_t]_k$—U—$(CR^9R^{9a})_t$—O—$(CR^9R^{9a})_t$—$R^{12}$;

each U is independently —C(=O)—, —C(=S)—, —S(=O)— or —S(=O)$_2$—;
each t is independently 0, 1, 2, 3 or 4;
each k is independently 0, 1 or 2;
each of $R^1$, $R^2$, $R^3$ and $R^4$ is independently H, deuterium, alkyl, heteroalkyl, aralkyl, cycloalkyl, heterocyclyl, heteroaryl or aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle;
each $R^5$ is independently H, deuterium, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;
each $R^{5a}$ is independently H, deuterium, oxo (=O), hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$-alkyl, $R^7S$(=O)-alkyl, $R^7R^{7a}N$—C(=O)-alkyl, $R^{7a}R^7N$-alkoxy, $R^7S$(=O)-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, aralkoxy, heteroarylalkoxy, heterocyclyloxy, heterocyclylalkoxy, heterocyclylamino, heterocyclylalkylamino or aryloxy;
each $R^6$ is independently H, deuterium, $R^7R^{7a}NC$(=O)—, $R^7OC$(=O)—, $R^7C$(=O)—, $R^7R^{7a}NS$(=O)—, $R^7OS$(=O)—, $R^7S$(=O)—, $R^7R^{7a}NS$(=O)$_2$—, $R^7OS$(=O)$_2$—, $R^7S$(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;
each $R^{6a}$ is independently H, deuterium, hydroxy, amino, F, Cl, Br, I, cyano, oxo (=O), $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$-alkyl, $R^7S$(=O)-alkyl, $R^7R^{7a}N$—C(=O)-alkyl, $R^{7a}R^7N$-alkoxy, $R^7S$(=O)-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, aralkoxy, heteroarylalkoxy, heterocyclyloxy, heterocyclylalkoxy, heterocyclylamino, heterocyclylalkylamino, or aryloxy;
each $R^7$ and $R^{7a}$ is independently H, deuterium, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylamino aliphatic, heterocyclylaminoaliphatic, cycloalkylaminoaliphatic, aryl, heteroaryl, heterocyclyl or carbocyclyl, with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring;

each $R^8$ and $R^{8a}$ is independently H, deuterium, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_c$—, alkyl-S(=O)$_c$O—, alkyl-S(=O)$_c$—, or aminosulfonyl;

each $R^9$, $R^{9a}$, $R^{10}$ and $R^{11}$ is independently H, deuterium, alkyl, heteroalkyl, cycloalkyl, heterocyclyl, aryl, heteroaryl, aralkyl, haloalkyl, hydroxyalkyl, heteroarylalkyl, heterocyclylalkyl, or cycloalkylalkyl;

each $R^{12}$ is independently $R^{13a}R^{13}N$—, —C(=O)$R^{13}$, —C(=S)$R^{13}$, —C(=O)—O—$R^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, $R^{13}R^{13a}N$—S(=O)$_2$—, $R^{13}S(=O)_2$—, $R^{13}S(=O)_2N(R^{13a})$—, $R^{13}OS(=O)_2$—, alkyl, heteroalkyl, cycloalkyl, heterocyclyl, aryl, heteroaryl or aralkyl; or $R^{11}$ and $R^{12}$ are optionally joined to form a 4-7 membered ring; and each $R^{13}$ and $R^{13a}$ is independently H, deuterium, alkyl, heteroalkyl, cycloalkyl, heterocyclyl, aryl, heteroaryl, or aralkyl;

wherein each of —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, —(CR$^8$R$^{8a}$)$_n$—N(R$^5$)—C(=O)—O—(CR$^8$R$^{8a}$)$_p$—, —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(CR$^9$R$^{9a}$)$_t$—R$^{12}$, —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$, NR$^6$, CR$^7$R$^{7a}$, CR$^7$, —(CH$_2$)$_a$—, —CH=CH—, —N=CH—, —(CH$_2$)$_a$—N(R$^5$)—(CH$_2$)$_b$—, —(CH$_2$)$_a$—O—(CH$_2$)$_b$—, $R^{13a}R^{13}N$—, —C(=O)$R^{13}$, —C(=S)$R^{13}$, —C(=O)—O—$R^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, $R^{13}R^{13a}N$—S(=O)$_2$—, $R^{13}S(=O)_2$—, $R^{13}S(=O)_2N(R^{13a})$—, $R^{13}OS(=O)_2$—, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, $R^7S(=O)_2$—, $R^7S(=O)_2N(R^{7a})$—, alkyl-OC(=O)—, alkyl-C(=O)—, alkyl-OS(=O)$_c$—, alkyl-S(=O)$_c$O—, alkyl-S(=O)$_c$—, —R$^7$R$^{7a}$NC(=O)—, $R^7$OC(=O)—, $R^7$C(=O)—, $R^7R^{7a}$NS(=O)—, $R^7$OS(=O)—, $R^7$S(=O)—, $R^7R^{7a}$NS(=O)$_2$—, $R^7$OS(=O)$_2$—, $R^{7a}R^7N$-alkyl, $R^7S(=O)$-alkyl, $R^7R^{7a}N$—C(=O)-alkyl, $R^{7a}R^7N$-alkoxy, $R^7S(=O)$-alkoxy, $R^7R^{7a}N$—C(=O)-alkylamino, alkyl, heteroalkyl, carbocyclyl, cycloalkyl, heterocyclyl, heterocycloalkyl, aryl, heteroaryl, aralkyl, a group derived from α-amino acid, $C_{5-12}$ fused bicycle, $C_{5-12}$ fused heterobicycle, $C_{5-12}$ spiro bicycle, $C_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted with one or more substituents, wherein the substituent is deuterium, hydroxy, amino, halo, cyano, aryl, heteroaryl, alkoxy, alkylamino, alkylthio, alkyl, alkenyl, alkynyl, hetero-cyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, or carboxy-substituted alkoxy.

In some embodiments,

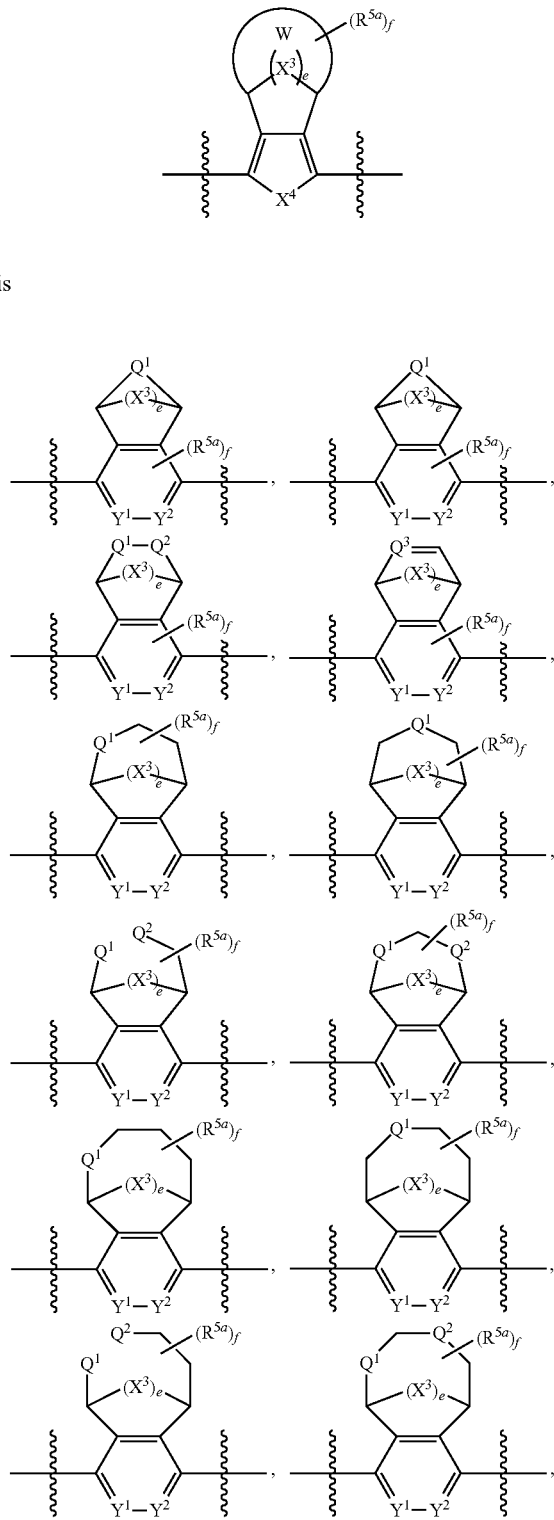

is

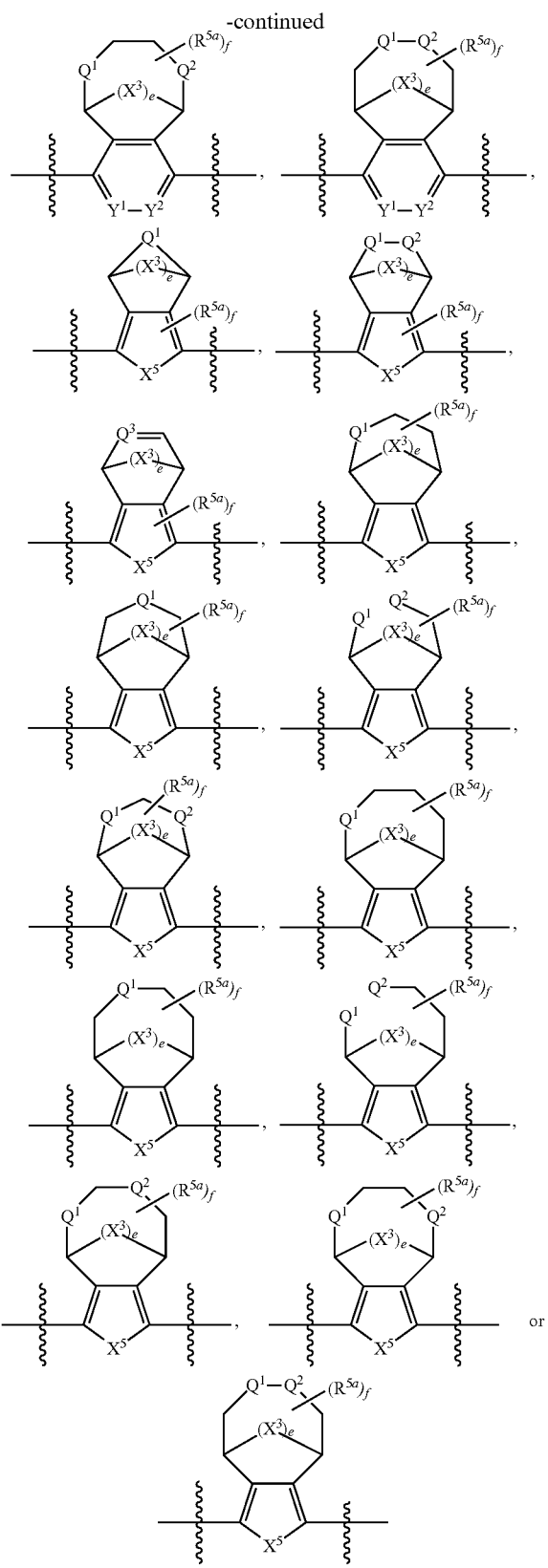

each $Y^1$ and $Y^2$ is independently N or $CR^7$;
each $X^3$ is independently O, S, $NR^6$, C(=O) or $CR^7R^{7a}$;
each $X^5$ is independently $CR^7R^{7a}$, O, S or $NR^6$;
each $Q^1$ and $Q^2$ is independently $NR^6$, O, S, C(=O), or $CR^7R^{7a}$;
each $Q^3$ is independently N or $CR^7$;
each e is independently 0, 1, 2, 3 or 4 with the proviso that where $X^3$ is O, S or $NR^6$, e is 1;
each f is independently 0, 1, 2 or 3;
each $R^{5a}$ is independently H, deuterium, oxo (=O), hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aralkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino or $C_{6-10}$ aryloxy;
each $R^6$ is independently H, deuterium, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl, $C_{6-10}$ aryl, $C_{3-9}$ heterocyclyl or $C_{3-8}$ carbocyclyl; and
each $R^7$ and $R^{7a}$ is independently H, deuterium, F, Cl, $C_{1-6}$ alkyl, $C_{1-6}$ heteroalkyl, $C_{1-6}$ haloalkyl, hydroxy, amino, $C_{1-6}$ alkoxy, $C_{6-10}$ aryl, $C_{2-9}$ heterocyclyl, $C_{3-9}$ cycloalkyl, $C_{6-10}$ aryloxy, $C_{2-9}$ heterocyclyloxy, $C_{6-10}$ arylamino, $C_{2-9}$ heterocyclylamino, $C_{3-9}$ cycloalkylamino, $C_{1-9}$ heteroaryl or $C_{3-9}$ carbocyclyl, with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring.

In other embodiments,

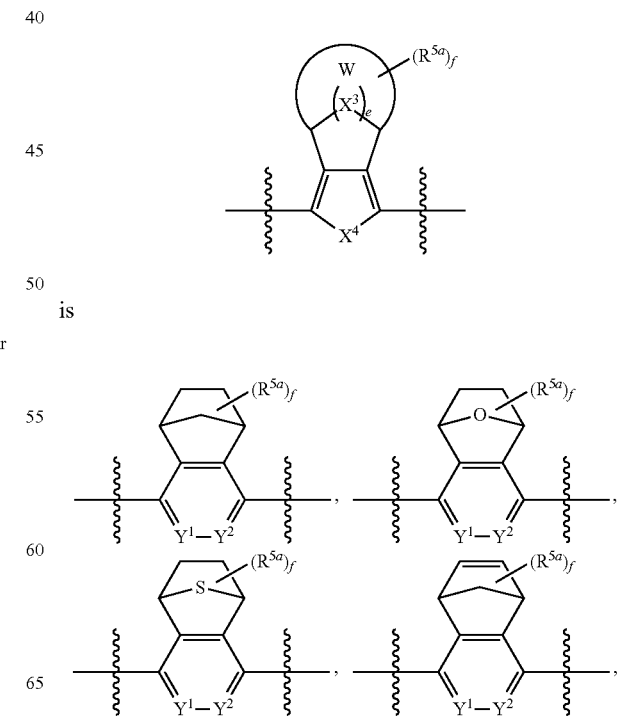

is

-continued

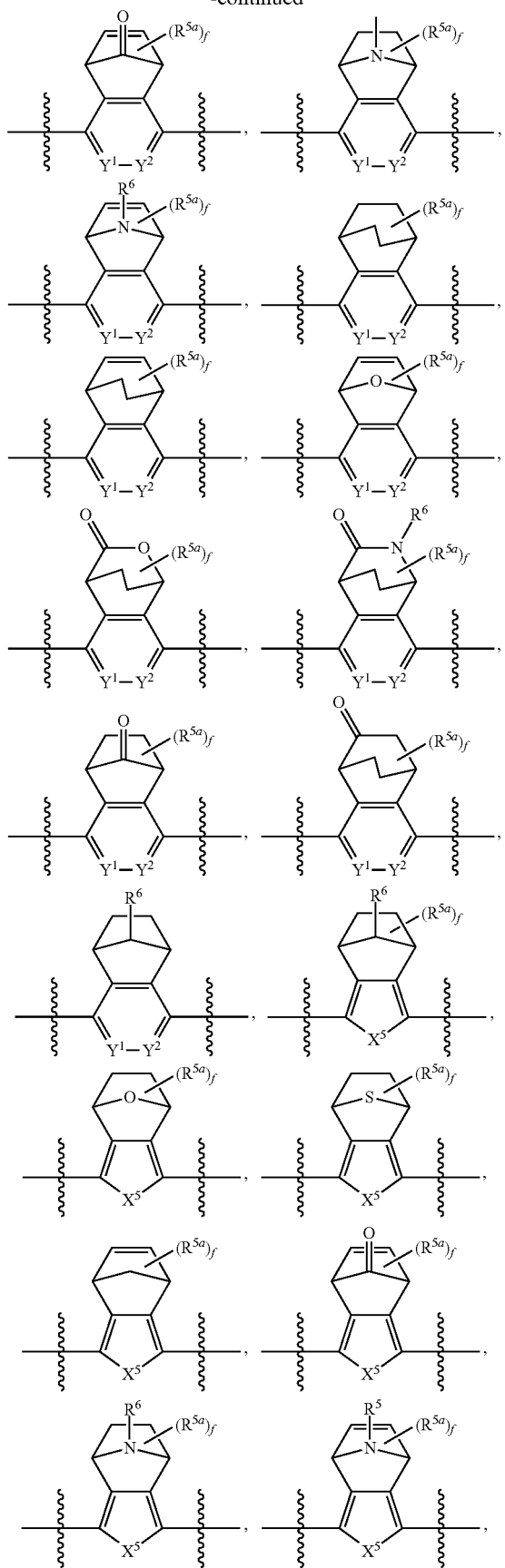

-continued

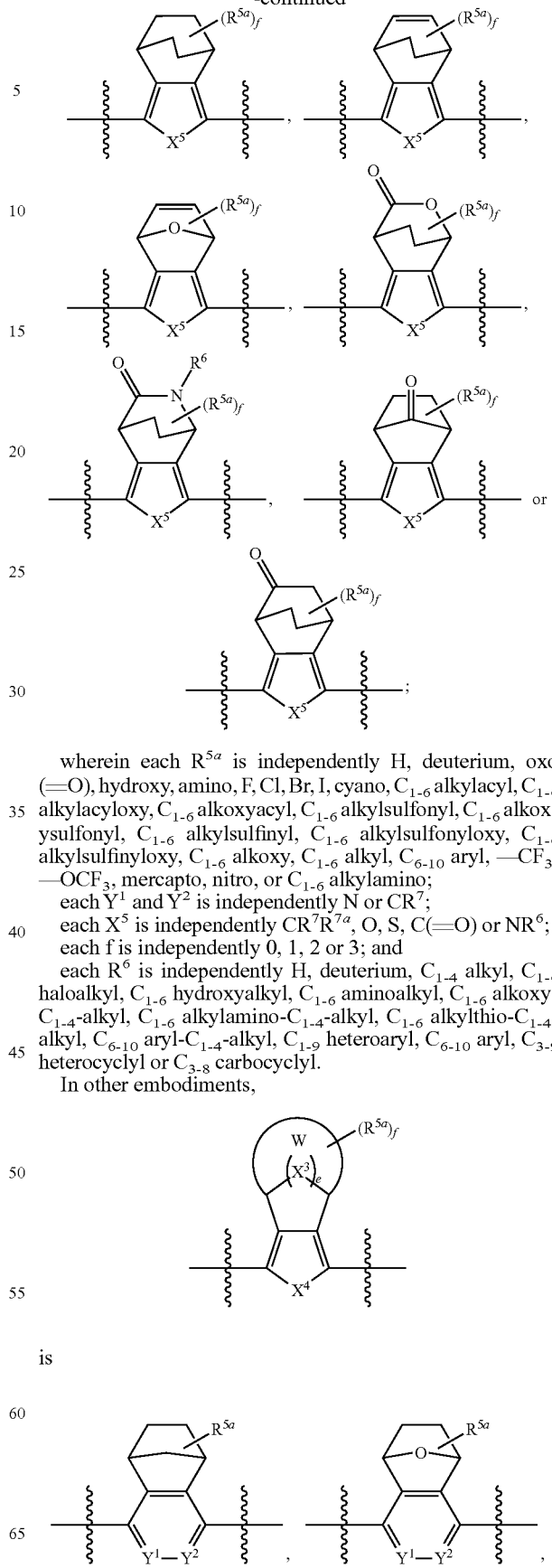

wherein each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, or $C_{1-6}$ alkylamino;

each $Y^1$ and $Y^2$ is independently N or $CR^7$;

each $X^5$ is independently $CR^7R^{7a}$, O, S, C(=O) or $NR^6$;

each f is independently 0, 1, 2 or 3; and each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl.

In other embodiments,

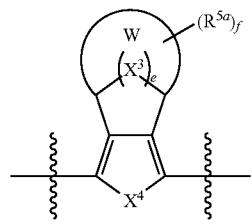

is

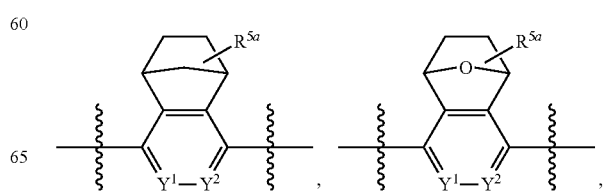

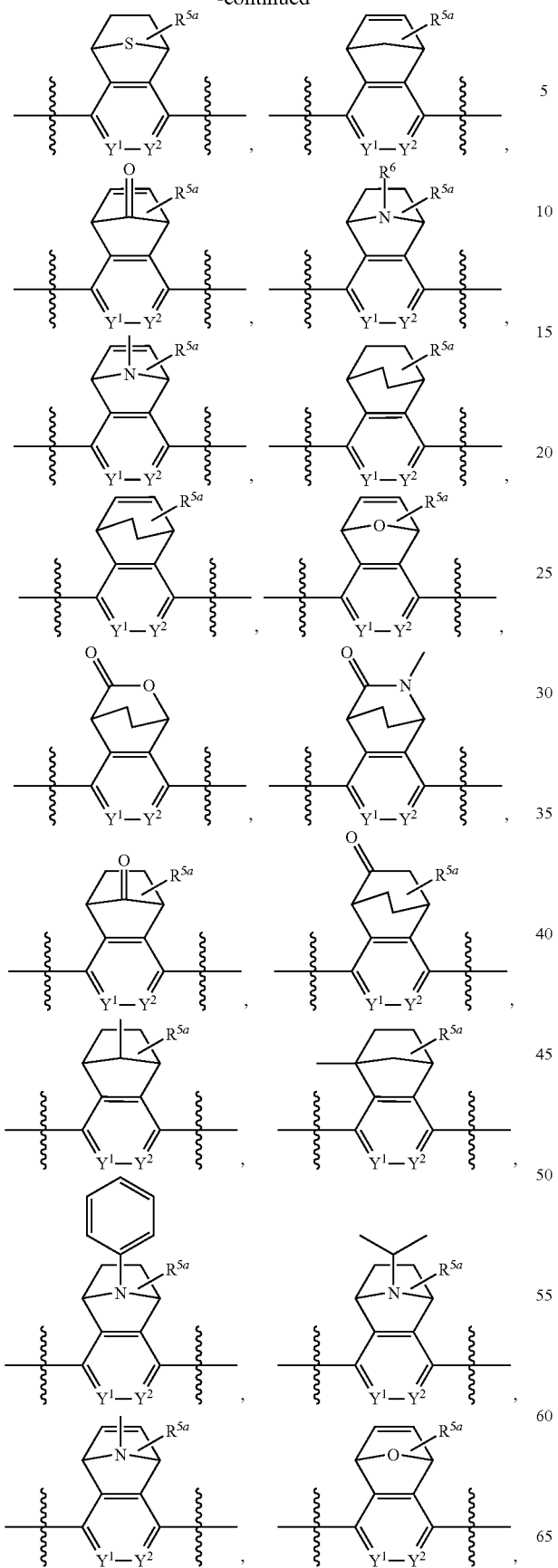
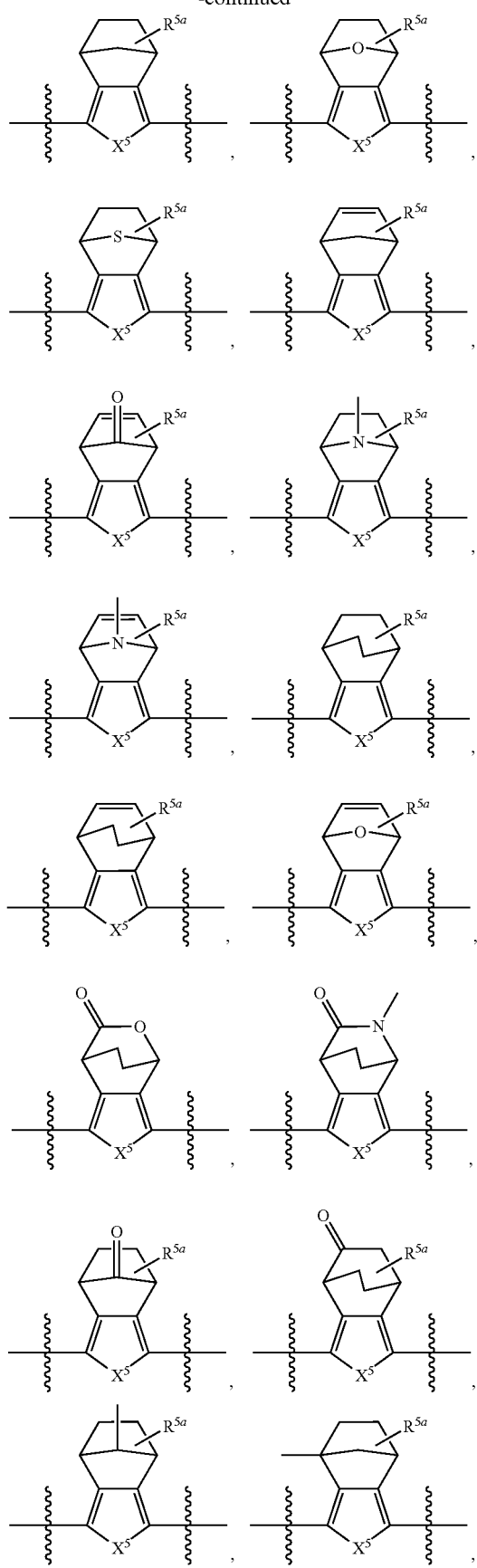

17
-continued

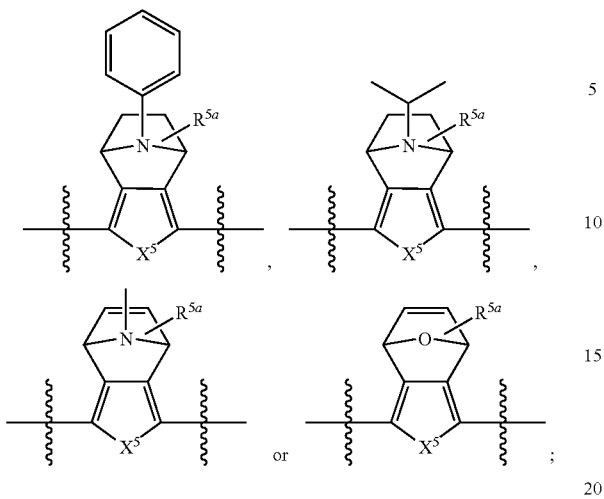

wherein each $R^{5a}$ is independently H, deuterium, oxo (=O), hydroxy, amino, F, Cl, Br, I, cyano, $C_{1-4}$ alkyl, —$CF_3$, —$OCF_3$, mercapto, nitro, or $C_{1-4}$ alkylamino;

each $Y^1$ and $Y^2$ is independently N or CH;

each $X^5$ is independently $CH_2$, O, S or $NR^6$; and each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$ alkyl, $C_{1-9}$ heteroaryl, $C_{6-10}$ aryl, $C_{3-9}$ heterocyclyl or $C_{3-8}$ carbocyclyl.

In some embodiments, each of A and A' is independently a bond, $C_{1-6}$ alkyl, $C_{2-6}$ alkenyl, $C_{3-8}$ cycloalkyl, $C_{2-10}$ heterocycloalkyl, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—N($R^5$)—C(=O)—O—$(CR^8R^{8a})_p$—, or each of A and A' is independently

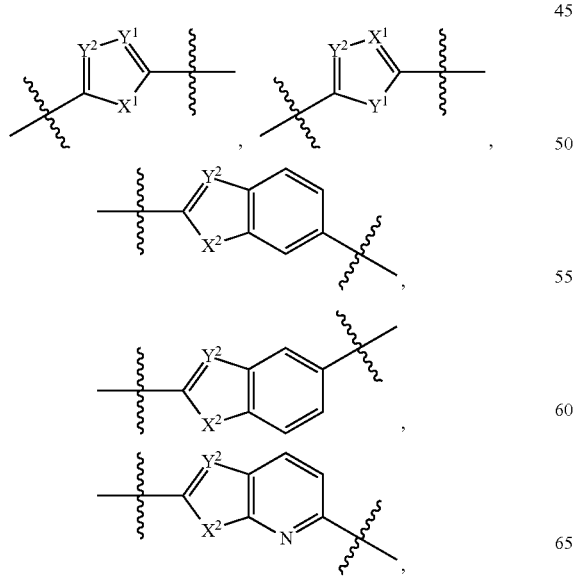

18
-continued

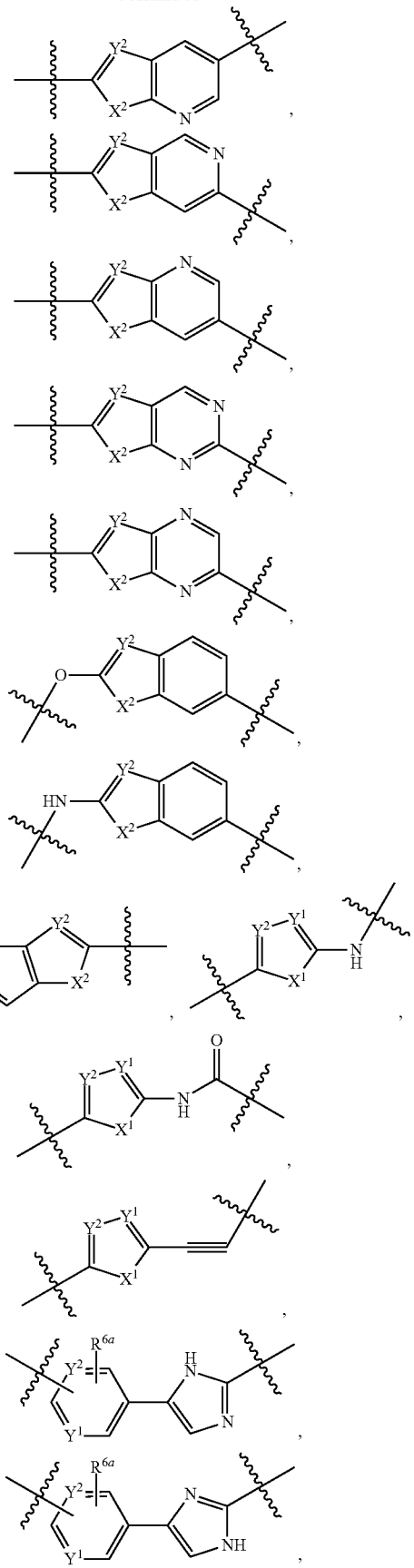

-continued
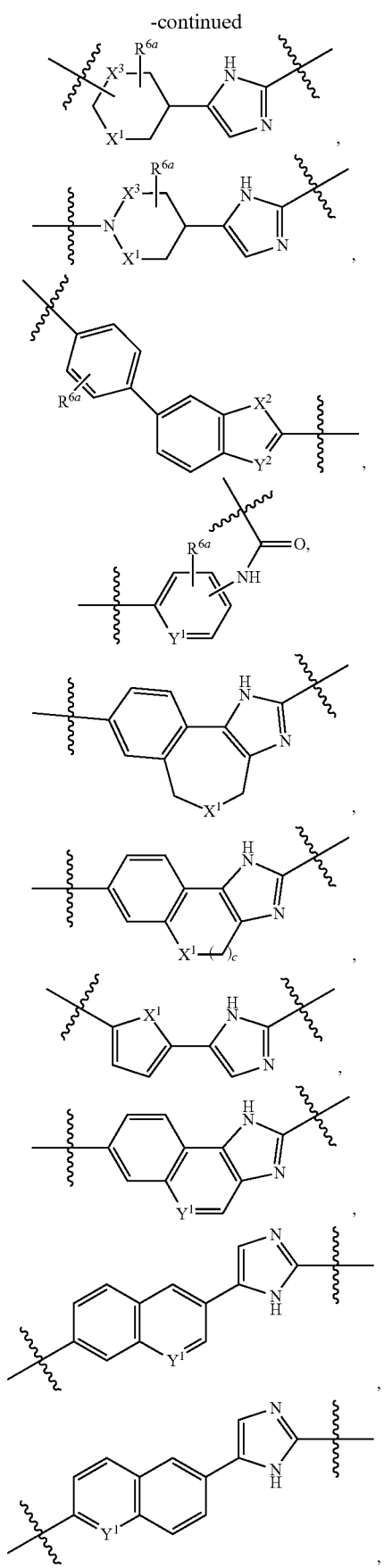
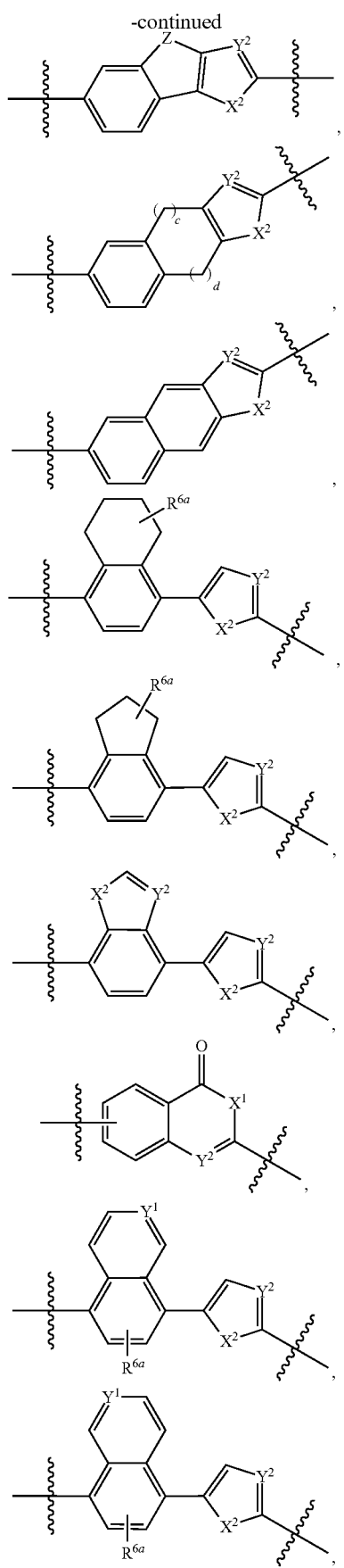

-continued

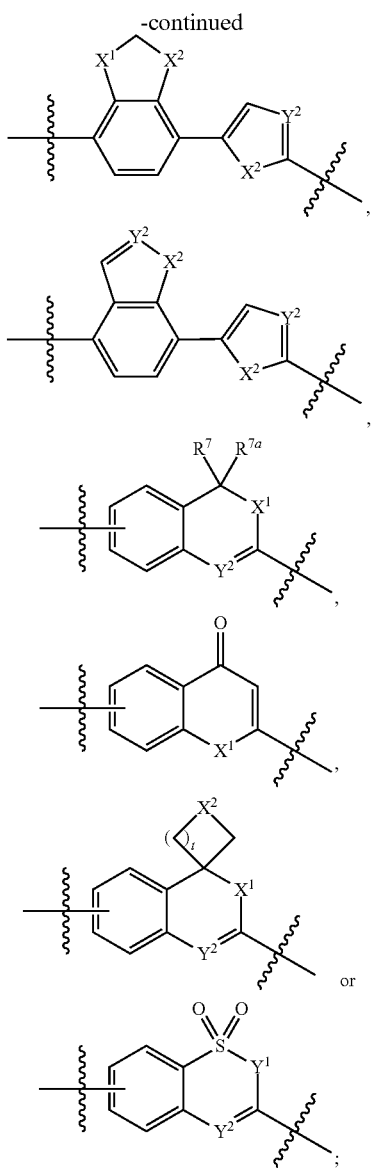

wherein each $R^5$ is independently H, deuterium, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each $R^{6a}$ is independently H, deuterium, oxo (=O), hydroxy, amino, F, Cl, Br, I, cyano, $R^{7a}R^7N$—, —C(=O)NR$^7R^{7a}$, —OC(=O)NR$^7R^{7a}$, —OC(=O)OR$^7$, —N(R$^7$)C(=O)NR$^7R^{7a}$, —N(R$^7$)C(=O)OR$^{7a}$, —N(R$^7$)C(=O)—R$^{7a}$, $R^7R^{7a}N$—S(=O)$_2$—, $R^7S$(=O)$_2$—, $R^7S$(=O)$_2$N(R$^{7a}$)—, $R^7R^{7a}N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino, or $C_{6-10}$ aryloxy;

each $R^7$ and $R^{7a}$ is independently H, deuterium, F, Cl, $C_{1-6}$ alkyl, $C_{1-6}$ heteroalkyl, $C_{1-6}$ haloaliphatic, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heterocyclyl-$C_{1-6}$-alkyl, $C_{3-8}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-8}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-8}$ cycloalkylamino-$C_{1-6}$-alkyl, $C_{6-10}$ aryl, $C_{1-9}$ heteroaryl, $C_{2-10}$ heterocyclyl, or $C_{3-8}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted $C_{5-12}$ spiro or fused bicyclic ring; and each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl.

In some embodiments, each of A and A' is independently a bond, —CH$_2$—, —(CH$_2$)$_2$—, —CH=CH—, —CH=CH—CH$_2$—, —N(R$^6$)—, —C(=O)—, —C(=S)—, —C(=O)—O—, —C(=O)N(R$^6$)—, —OC(=O)N(R$^6$)—, —OC(=O)O—, —N(R$^6$)C(=O)N(R$^6$)—, —(R$^6$)N—S(=O)$_2$—, —S(=O)$_2$—, —OS(=O)$_2$—, —(R$^6$)N—S(=O)—, —S(=O)—, —OS(=O)—, or each of A and A' is independently

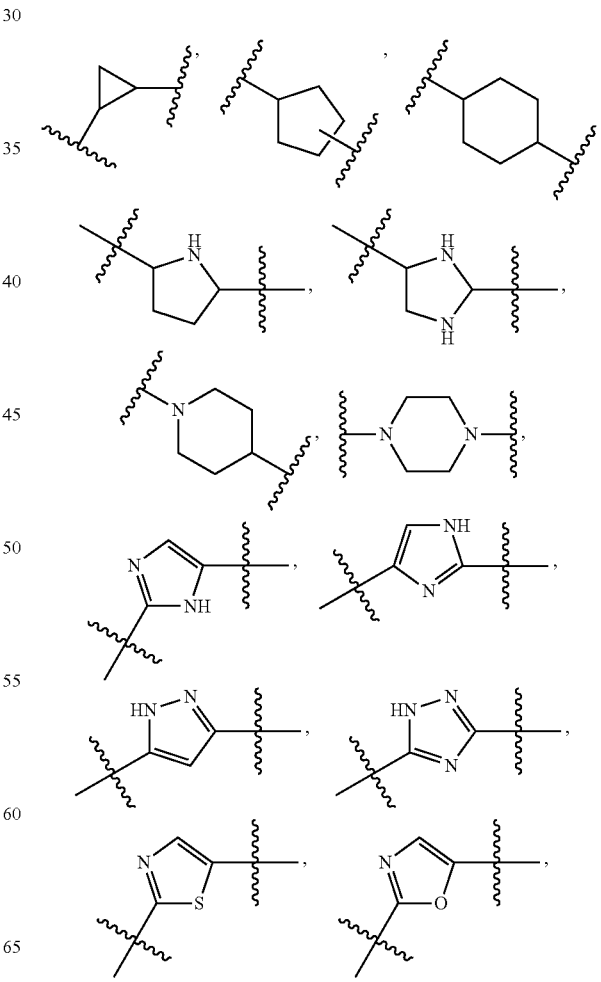

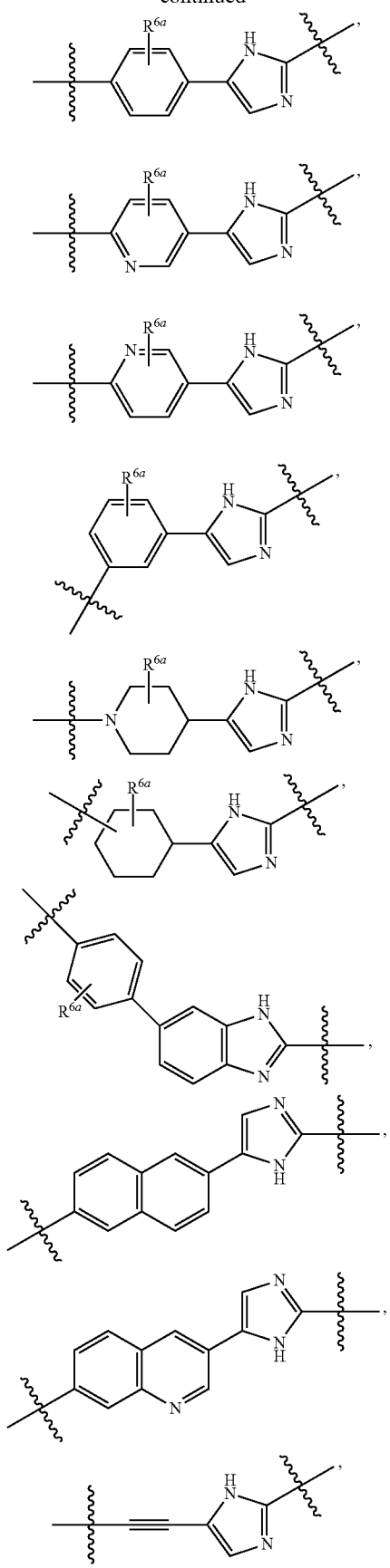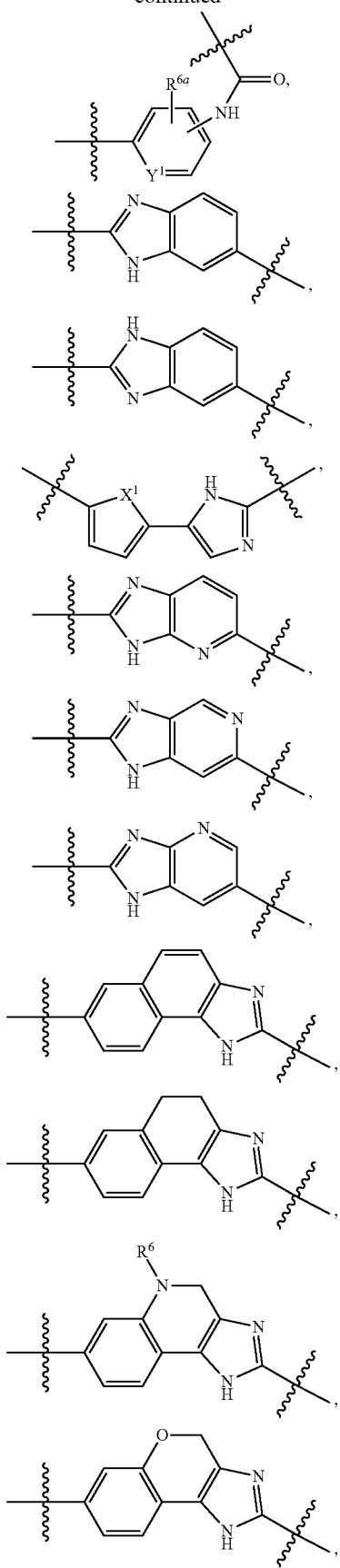

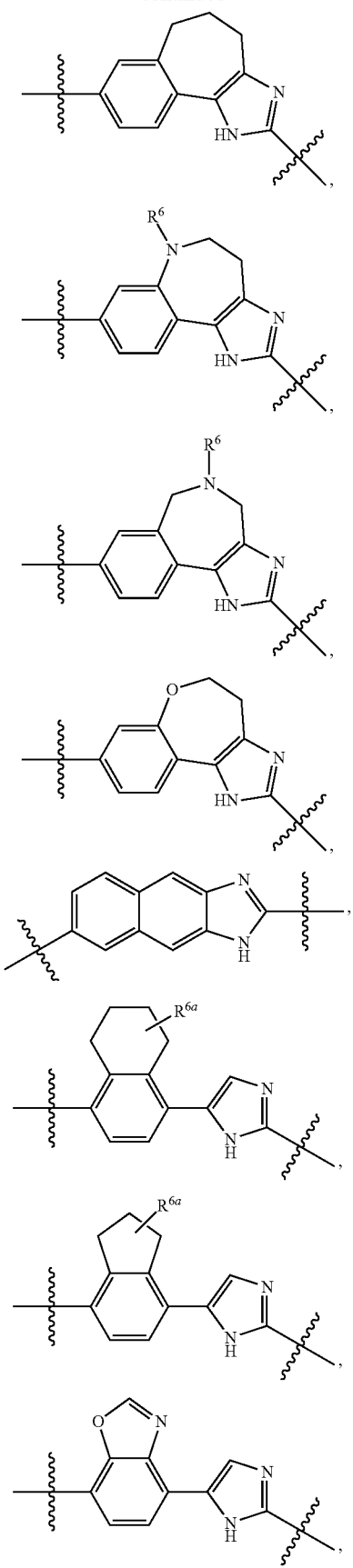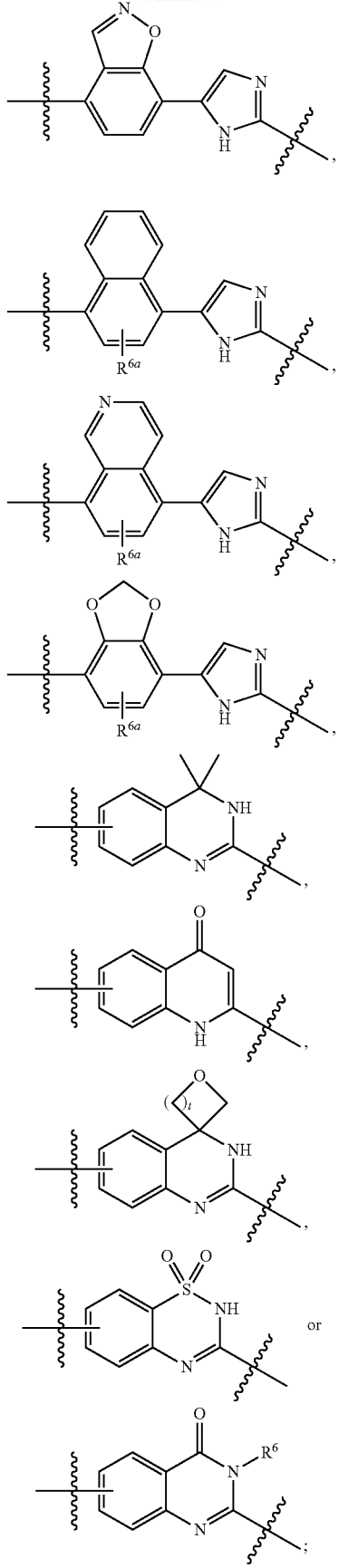

wherein $X^1$ is O or S;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl;

each $R^{6a}$ is independently H, deuterium, oxo (=O), hydroxy, amino, F, Cl, Br, I, cyano, $R^{7a}R^7N—$, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro; and each $R^7$ and $R^{7a}$ is independently H, deuterium, F, Cl, $C_{1-6}$ alkyl, $C_{1-6}$ heteroalkyl, $C_{1-6}$ haloalkyl, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, or $C_{1-6}$ alkylthio-$C_{1-6}$-alkyl.

In some embodiments, each of $R^1$, $R^2$, $R^3$ and $R^4$ is independently H, deuterium, $C_{1-8}$ alkyl, $C_{1-8}$ heteroalkyl, $C_{6-10}$ aryl-$C_{1-6}$-alkyl, $C_{3-10}$ cycloalkyl, $C_{2-10}$ heterocyclyl, $C_{1-9}$ heteroaryl or $C_{6-10}$ aryl; or $R^1$ and $R^2$, together with X—CH which they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH which they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$ and $R^2$, together with X—CH which they are attached to, or $R^3$ and $R^4$, together with X'—CH which they are attached to, optionally form a 3-8 membered heterocycle, $C_{5-12}$ fused bicycle, $C_{5-12}$ fused heterobicycle, $C_{5-12}$ spiro bicycle or $C_{5-12}$ spiro heterobicycle.

In other embodiments, the $R^1$, $R^2$ and X—CH together form one of the following monovalent groups:

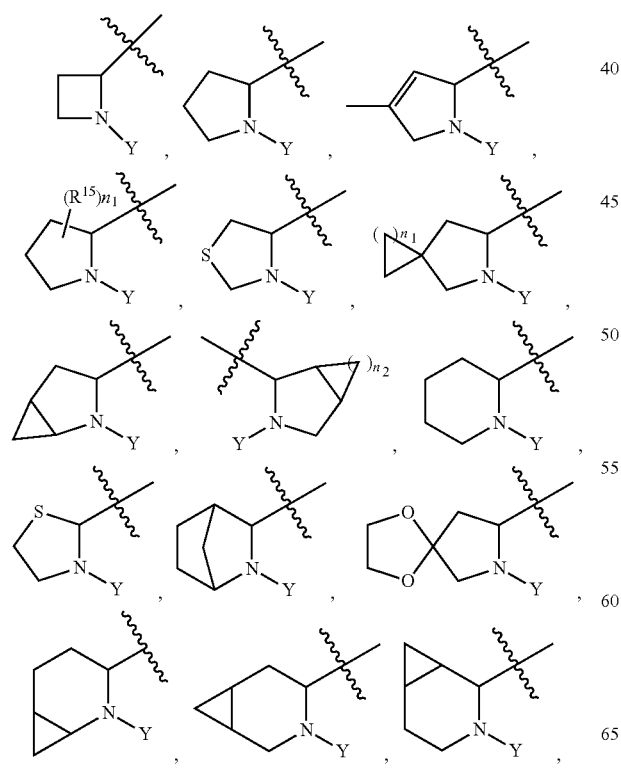

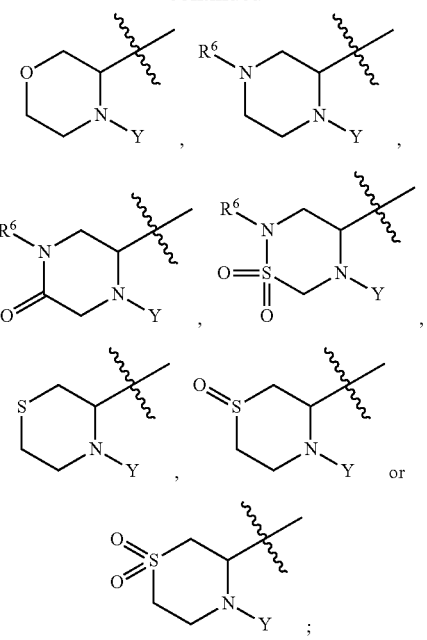

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl;

and each $n_1$ and $n_2$ is independently 1, 2, 3 or 4.

In other embodiments, the $R^3$, $R^4$ and X'—CH together form one of the following monovalent groups:

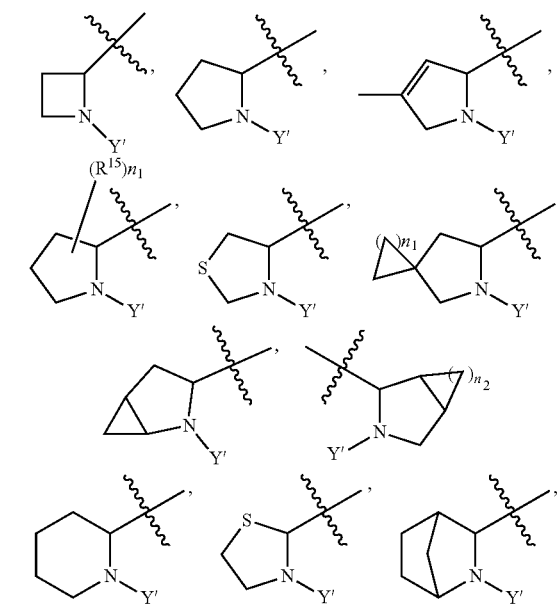

-continued

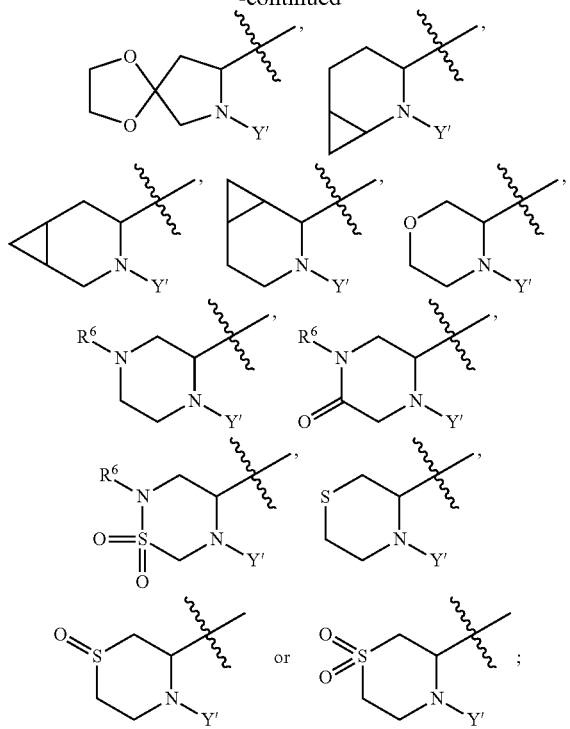

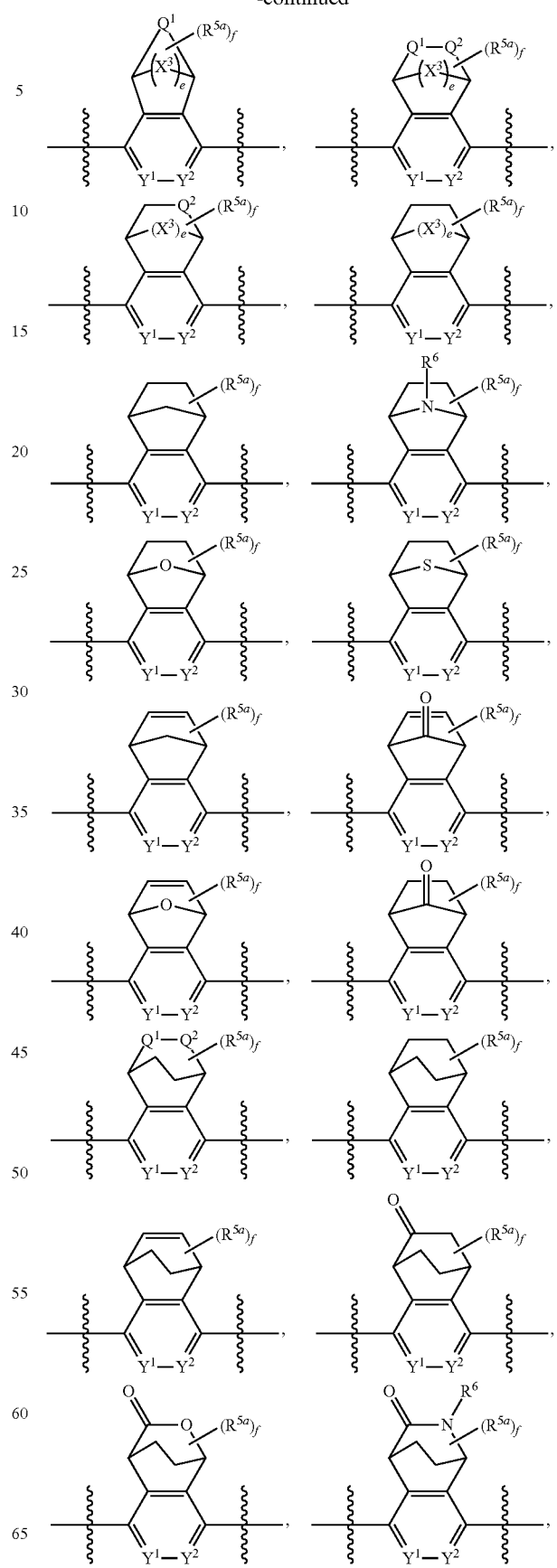

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In some embodiments, Formula (II) is (II)

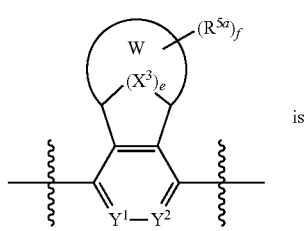

wherein is

-continued

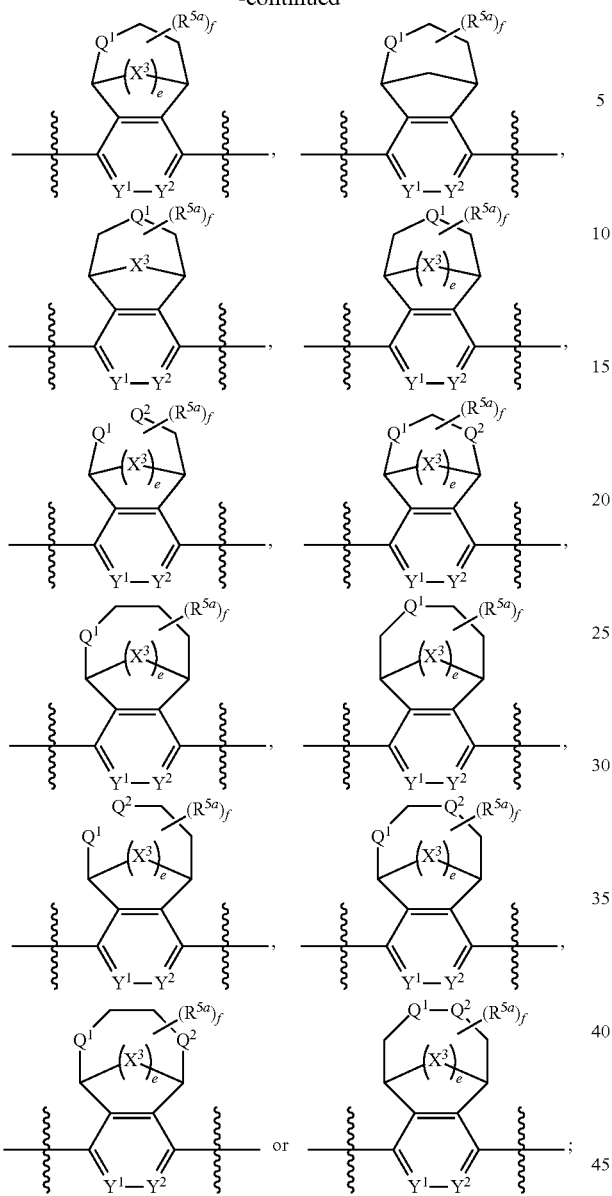

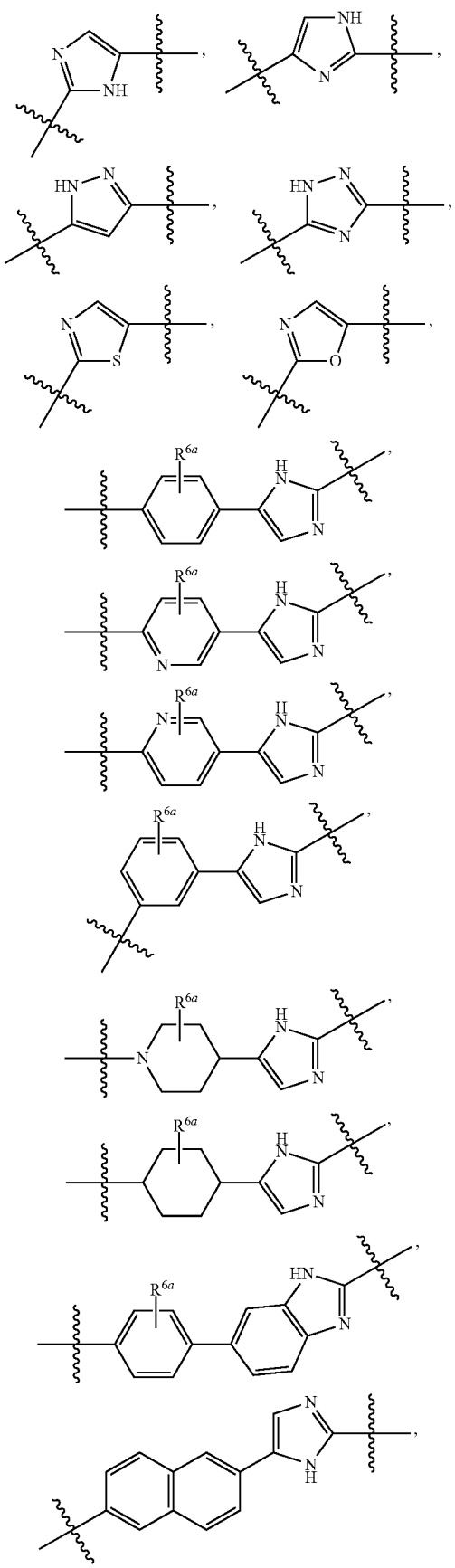

wherein each $Q^1$ and $Q^2$ is independently $NR^6$, O, S, C(=O) or $CH_2$;

each $X^3$ is independently O, S, $NR^6$, C(=O) or $CR^7R^{7a}$;

each e is independently 0, 1, 2, 3 or 4 with the proviso that where $X^3$ is O, S or $NR^6$, e is 1;

each $Y^1$ and $Y^2$ is independently N or $CR^7$;

each f is independently 0, 1, 2, 3 or 4;

each of A and A' is independently a bond, $C_{1-6}$ alkyl, $C_{2-6}$ alkenyl, $C_{3-8}$ cycloalkyl, $C_{2-10}$ heterocycloalkyl, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently -continued
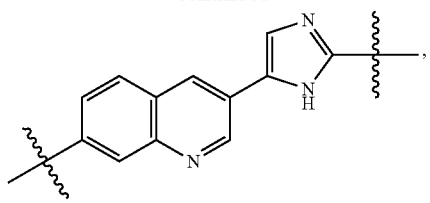
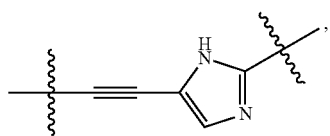
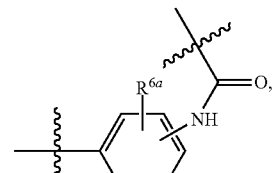
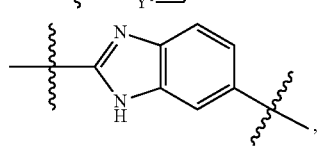
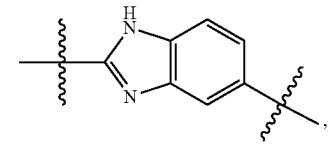
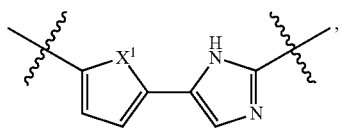
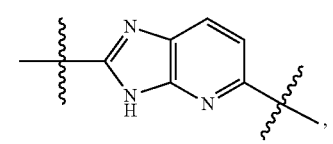
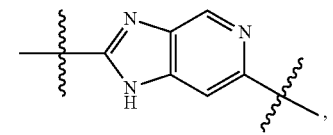
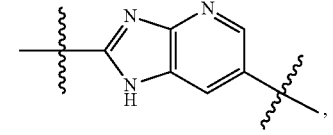
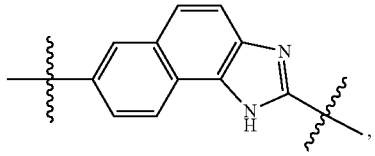
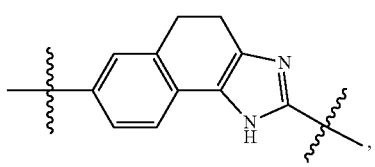
-continued
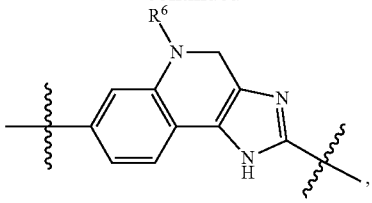
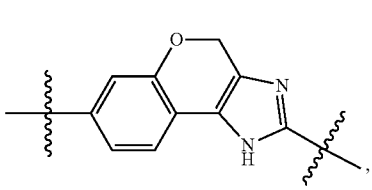
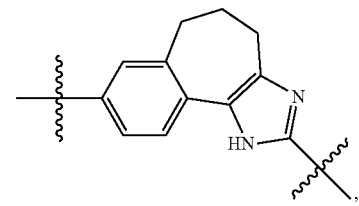
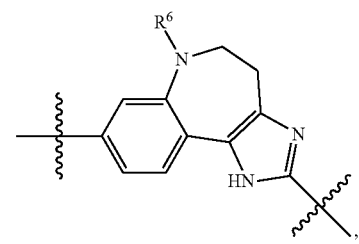
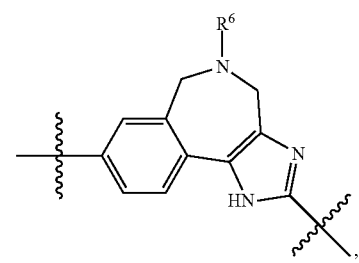
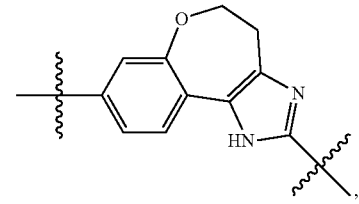
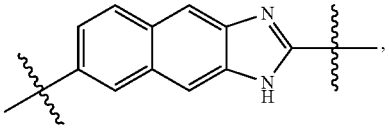
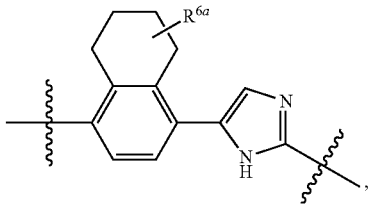

-continued

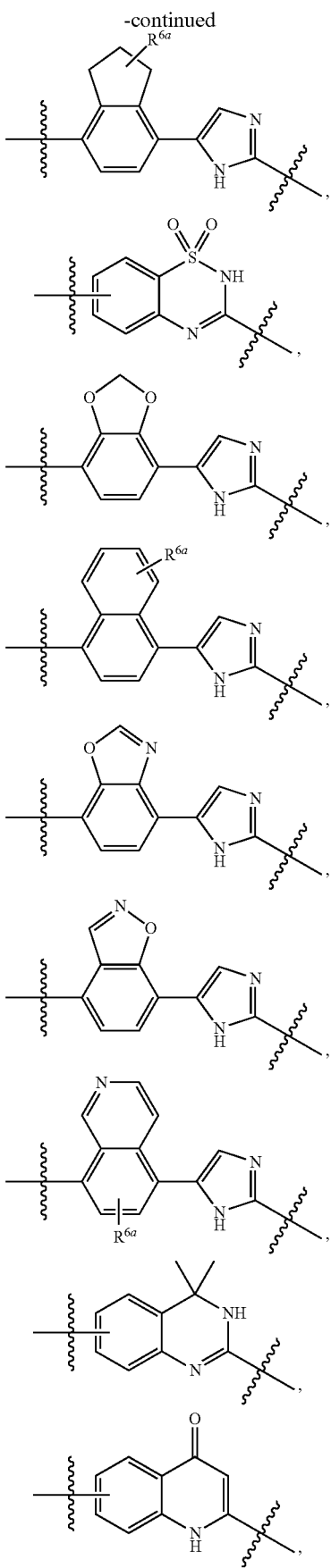

-continued

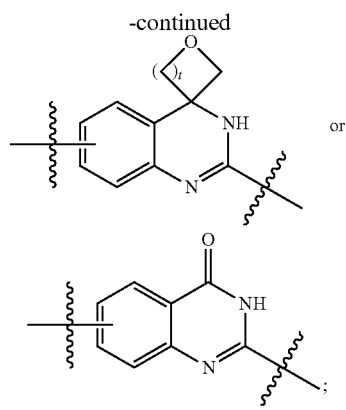

each $R^5$ is independently H, deuterium, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^6$ is independently H, deuterium, $R^7R^{7a}$NC(=O)—, $R^7$OC(=O)—, $R^7$C(=O)—, $R^7R^{7a}$NS(=O)—, $R^7$OS(=O)—, $R^7$S(=O)—, $R^7R^{7a}$NS(=O)$_2$—, $R^7$OS(=O)$_2$—, $R^7$S(=O)$_2$—, $C_{1-6}$ aliphatic, $C_{1-6}$ alkoxy-$C_{1-6}$-aliphatic, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^{6a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^7$ and $R^{7a}$ is independently H, deuterium, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$-cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring;

each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, —CF$_2$—, —CHR$^{5a}$— or —CH$_2$N(R$^6$)—;

each n is independently 0, 1, 2 or 3;

each p is independently 0, 1, 2 or 3; and
each r is independently 0, 1 or 2.
In some embodiments, Formula (II') is
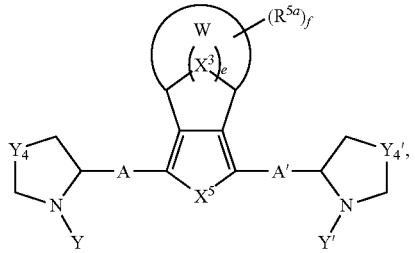
(II')
wherein
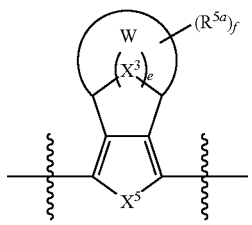
is
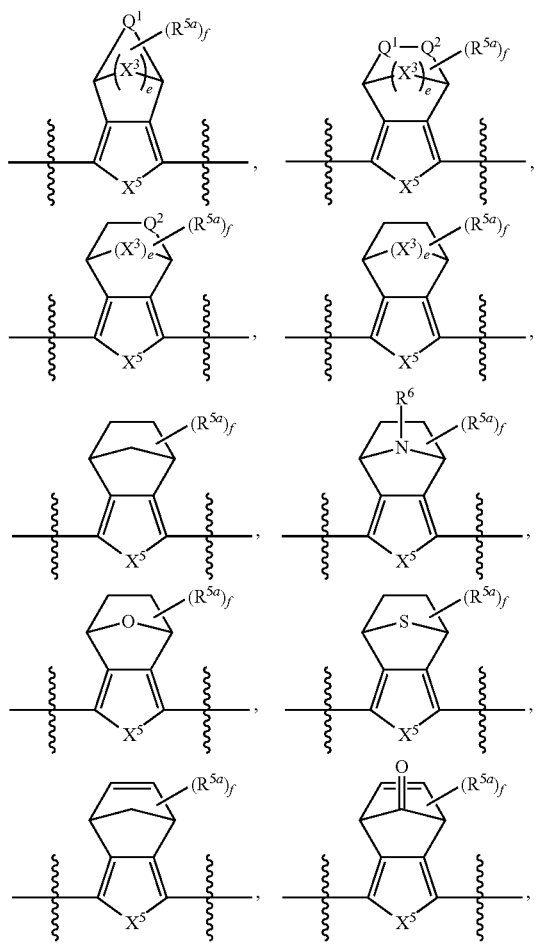
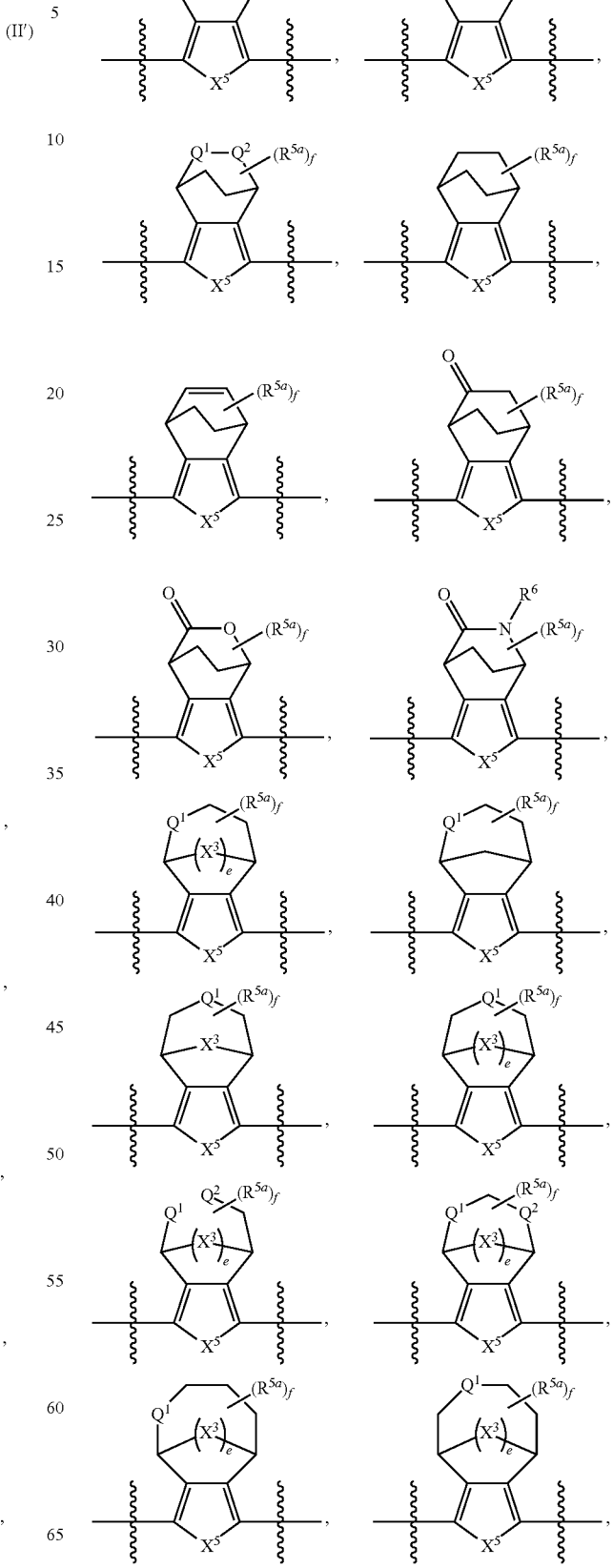

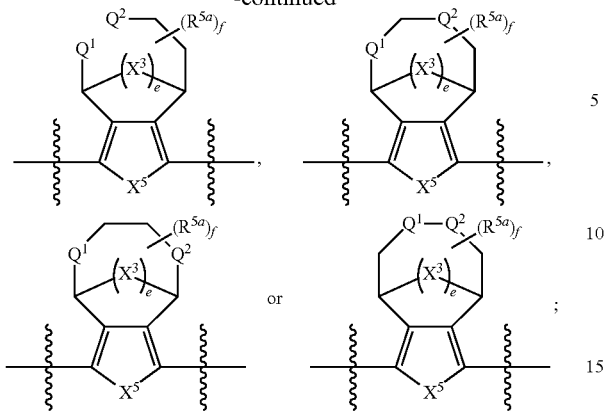

wherein each $Q^1$ and $Q^2$ is independently $NR^6$, O, S, C(=O) or $CH_2$;

each $X^3$ is independently O, S, $NR^6$, C(=O) or $CR^7R^{7a}$; e is 0, 1, 2, 3 or 4 with the proviso that where $X^3$ is O, S or $NR^6$, e is 1;

each $X^5$ is independently $CR^7R^{7a}$, O, S or $NR^6$;

each f is independently 0, 1, 2, 3 or 4;

each of A and A' is independently a bond, $C_{1-6}$ alkyl, $C_{2-6}$ alkenyl, $C_{3-8}$ cycloalkyl, $C_{2-10}$ heterocycloalkyl, —$(CR^8R^{8a})_n$—O—$(CR^8R^{8a})_p$—, —$(CR^8R^{8a})_n$—$N(R^5)$—$(CR^8R^{8a})_p$—, —$(CR^8R^{8a})_n$—S(=O)$_r$—$N(R^5)$—$(CR^8R^{8a})_p$—, —$(CR^8R^{8a})_n$—C(=O)—$N(R^5)$—$(CR^8R^{8a})_p$—, —$(CR^8R^{8a})_n$—$N(R^5)$—C(=O)—$N(R^5)$—$(CR^8R^{8a})_p$—, —$(CR^8R^{8a})_n$—C(=O)—O—$(CR^8R^{8a})_p$—, —$(CR^8R^{8a})_n$—$N(R^5)$—S(=O)$_r$—$N(R^5)$—$(CR^8R^{8a})_p$—, —$(CR^8R^{8a})_n$—$N(R^5)$—C(=O)—O—$(CR^8R^{8a})_p$—, or each of A and A' is independently

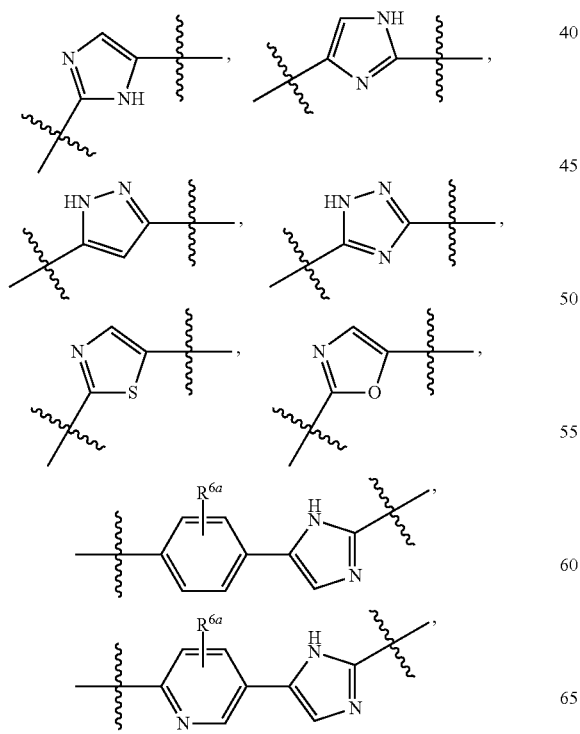

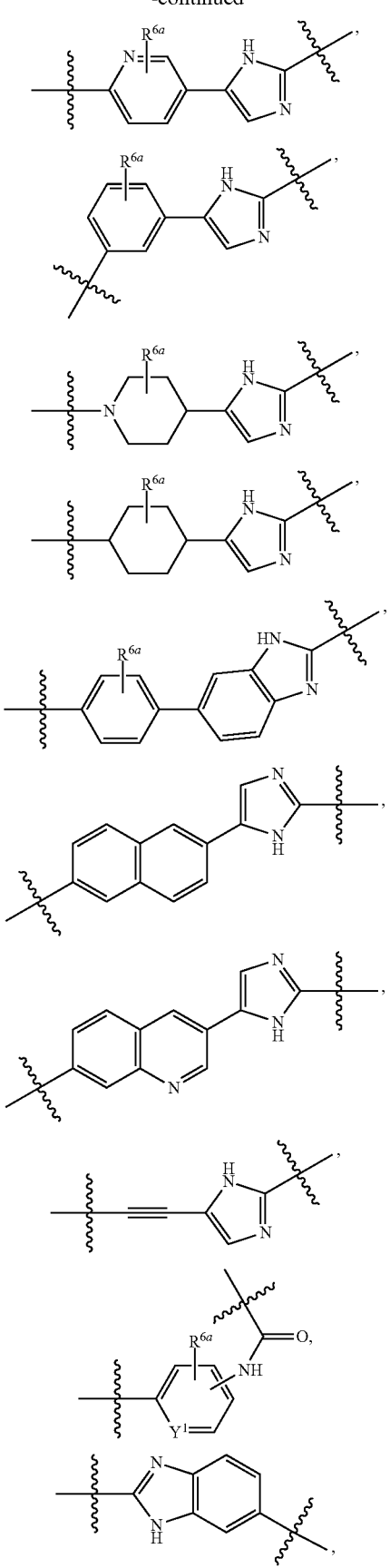

-continued
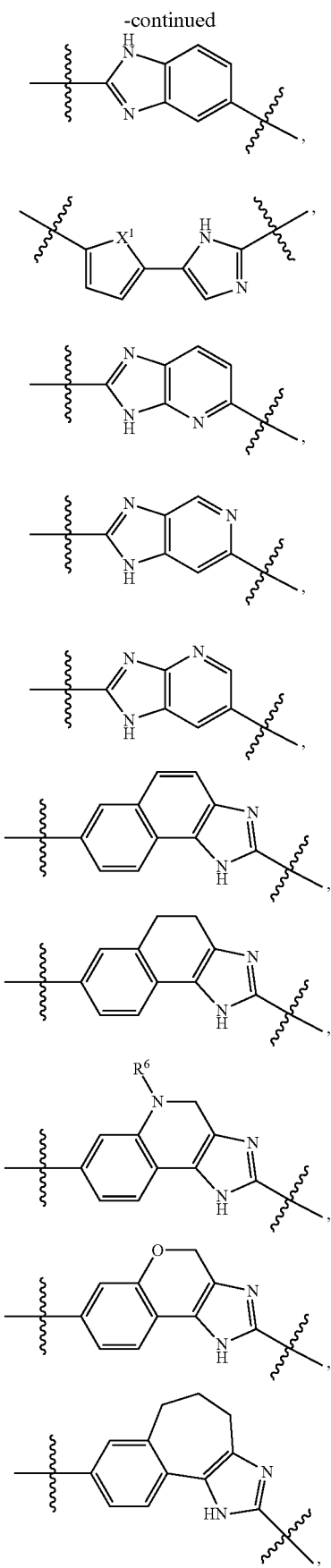
-continued
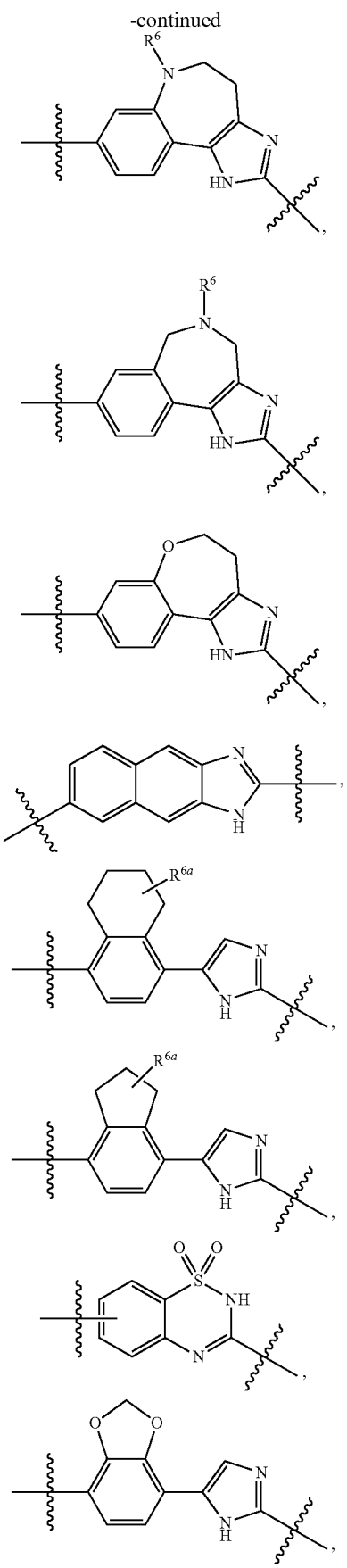

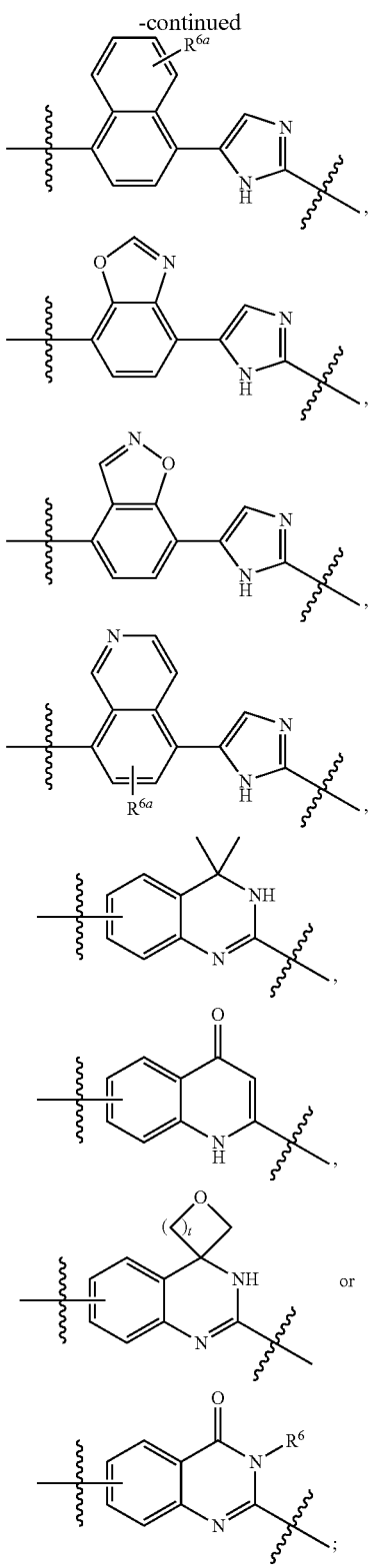

each $R^5$ is independently H, deuterium, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^{6a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^7$ and $R^{7a}$ is independently H, deuterium, $C_{1-6}$ alkyl, $C_{1-6}$ heteroalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring;

each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, —CF$_2$—, —CHR$^{5a}$— or —CH$_2$N(R$^6$)—;

each n is independently 0, 1, 2 or 3;
each p is independently 0, 1, 2 or 3; and
each r is independently 0, 1 or 2.

In other embodiments, Formula (III) is

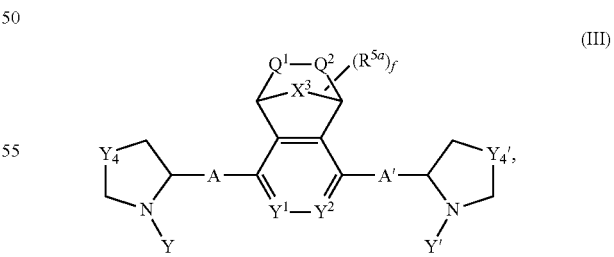

(III)

wherein each $Q^1$ and $Q^2$ is independently O, S, C(=O), NR$^6$ or CH$_2$;

$X^3$ is O, S, NR$^6$, C(=O) or CR$^7R^{7a}$;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^7$ and $R^{7a}$ is independently H, deuterium, $C_{1-6}$ alkyl, $C_{1-6}$ heteroalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$ alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring; and f is 0, 1, 2, 3 or 4.

In other embodiments, Formula (IV) is

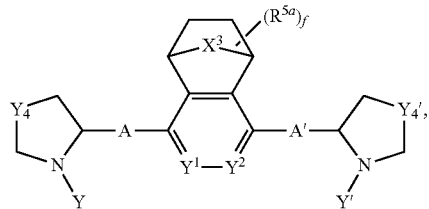

(IV)

wherein $X^3$ is O, S, $NR^6$, C(=O) or $CR^7R^{7a}$;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

f is 0, 1, 2, or 3; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (V) is

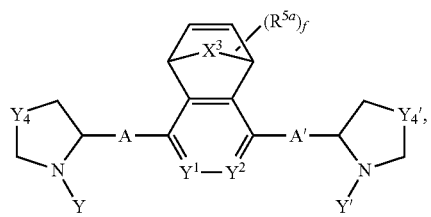

(V)

wherein $X^3$ is O, S, $NR^6$, C(=O) or $CR^7R^{7a}$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

f is 0, 1, 2, or 3; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (VI) is

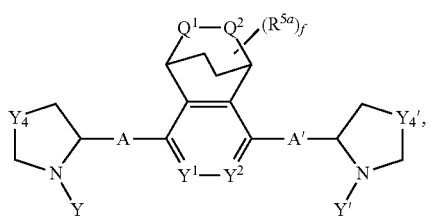

(VI)

wherein each $Q^1$ and $Q^2$ is independently O, S, C(=O), $NR^6$ or $CH_2$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and f is 0, 1, 2, 3 or 4.

In other embodiments, Formula (III') is

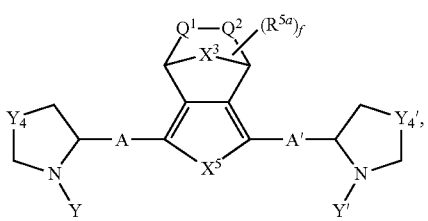

(III')

wherein each $Q^1$ and $Q^2$ is independently O, S, C(=O), $NR^6$ or $CH_2$;

$X^3$ is O, S, $NR^6$, C(=O) or $CR^7R^{7a}$;

f is 0, 1, 2 or 3;

$X^5$ is $CH_2$, O, S or $NR^6$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)-$, $R^7OC(=O)-$, $R^7C(=O)-$, $R^7R^{7a}NS(=O)-$, $R^7OS(=O)-$, $R^7S(=O)-$, $R^7R^{7a}NS(=O)_2-$, $R^7OS(=O)_2-$, $R^7S(=O)_2-$, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (IV') is

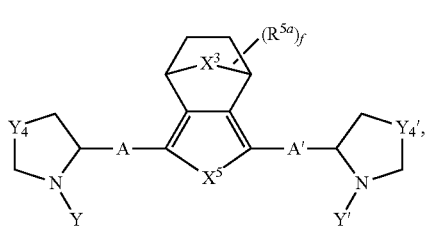

(IV')

wherein $X^5$ is $CH_2$, O, S or $NR^6$;
$X^3$ is O, S, $NR^6$, $C(=O)$ or $CR^7R^{7a}$;
f is 0, 1, 2 or 3;
each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, $-CF_3$, $-OCF_3$, mercapto, nitro, $C_{1-6}$ alkylamino, $C_{3-8}$ cycloalkyl or $C_{6-10}$ aryloxy; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (V') is

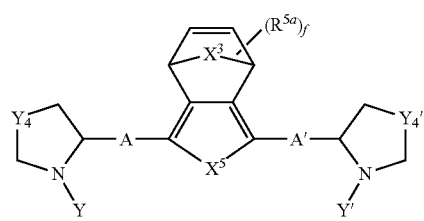

(V')

wherein $X^3$ is O, S, $NR^6$, $C(=O)$ or $CR^7R^{7a}$;
$X^5$ is $CH_2$, O, S or $NR^6$;
each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, $-CF_3$, $-OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)-$, $R^7OC(=O)-$, $R^7C(=O)-$, $R^7R^{7a}NS(=O)-$, $R^7OS(=O)-$, $R^7S(=O)-$, $R^7R^{7a}NS(=O)_2-$, $R^7OS(=O)_2-$, $R^7S(=O)_2-$, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (VI') is

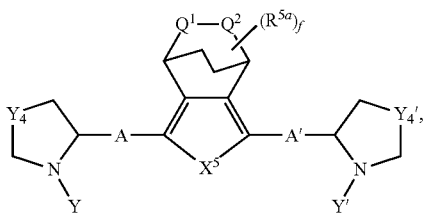

(VI')

wherein each $Q^1$ and $Q^2$ is independently O, S, C=(O), $NR^6$ or $CH_2$;
f is 0, 1, 2 or 3;
$X^5$ is $CH_2$, O, S or $NR^6$;
each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, $-CF_3$, $-OCF_3$, mercapto, nitro, $C_{1-6}$ alkylamino, $C_{3-8}$ cycloalkyl or $C_{6-10}$ aryloxy; and each $R^6$ is independently H, deuterium, $R^7R^{7a}NC(=O)-$, $R^7OC(=O)-$, $R^7C(=O)-$, $R^7R^{7a}NS(=O)-$, $R^7OS(=O)-$, $R^7S(=O)-$, $R^7R^{7a}NS(=O)_2-$, $R^7OS(=O)_2-$, $R^7S(=O)_2-$, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl.

In some embodiments, each of Y and Y' is independently a group derived from α-amino acid and the group derived from α-amino acid is optionally substituted with one or more substituents, wherein the substituent is deuterium, F, Cl, Br, I, hydroxy or cyano.

In other embodiments, the group derived from α-amino acid is formed by isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, the α-amino acid is in the L configuration.

In other embodiments, each of Y and Y' is independently $-[U-(CR^9R^{9a})_t-N(R^{10})-(CR^9R^{9a})_t]_k-U-(CR^9$ $R^{9a})_t$—N($R^{11}$)—(C$R^9R^{9a}$)$_t$—$R^{12}$, —U—(C$R^9R^{9a}$)$_t$—$R^{12}$ or —[U—(C$R^9R^{9a}$)$_t$—N($R^{10}$)—(C$R^9R^{9a}$)$_t$]$_k$—U—(C$R^9R^{9a}$)$_t$—O—(C$R^9R^{9a}$)$_t$—$R^{12}$.

In other embodiments, each of Y and Y' is independently —[U—(C$R^9R^{9a}$)$_t$—N($R^{10}$)—(C$R^9R^{9a}$)$_t$]$_k$—U—(C$R^9R^{9a}$)$_t$—N($R^{11}$)—(C$R^9R^{9a}$)$_t$—$R^{12}$.

In other embodiments, each of Y and Y' is independently —U—(C$R^9R^{9a}$)$_t$—N($R^{10}$)—(C$R^9R^{9a}$)$_t$—U—(C$R^9R^{9a}$)$_t$—N($R^{11}$)—(C$R^9R^{9a}$)$_t$—$R^{12}$.

In other embodiments, each of Y and Y' is independently —U—(C$R^9R^{9a}$)$_t$—N($R^{11}$)—(C$R^9R^{9a}$)$_t$—$R^{12}$.

In other embodiments, each of Y and Y' is independently —[C(=O)—(C$R^9R^{9a}$)$_t$—N($R^{10}$)—(C$R^9R^{9a}$)$_t$]$_k$—U—(C$R^9R^{9a}$)$_t$—N($R^{11}$)—(C$R^9R^{9a}$)$_t$—$R^{12}$.

In other embodiments, each of Y and Y' is independently —C(=O)—(C$R^9R^{9a}$)$_t$—N($R^{10}$)—(C$R^9R^{9a}$)$_t$—U—(C$R^9R^{9a}$)$_t$—N($R^{11}$)—(C$R^9R^{9a}$)$_t$—$R^{12}$.

In other embodiments, each of Y and Y' is independently —[C(=O)—(C$R^9R^{9a}$)$_t$—N($R^{10}$)—(C$R^9R^{9a}$)$_t$]$_k$—C(=O)—(C$R^9R^{9a}$)$_t$—N($R^{11}$)—(C$R^9R^{9a}$)$_t$—$R^{12}$.

In other embodiments, each of Y and Y' is independently —C(=O)—(C$R^9R^{9a}$)$_t$—N($R^{10}$)—(C$R^9R^{9a}$)$_t$—C(=O)—(C$R^9R^{9a}$)$_t$—N($R^{11}$)—(C$R^9R^{9a}$)$_t$—$R^{12}$.

In other embodiments, each of Y and Y' is independently —C(=O)—(C$R^9R^{9a}$)$_t$—N($R^{11}$)—(C$R^9R^{9a}$)$_t$—$R^{12}$.

In other embodiments, each of Y and Y' is independently —C(=O)—(C$R^9R^{9a}$)$_n$—N($R^{11}$)—(C$R^9R^{9a}$)$_n$—C(=O)—$R^{13}$.

In other embodiments, each of Y and Y' is independently —C(=O)—(C$R^9R^{9a}$)$_n$—N($R^{11}$)—C(=O)—$R^{13}$.

In other embodiments, each of Y and Y' is independently —C(=O)—(C$R^9R^{9a}$)$_n$—N($R^{11}$)—(C$R^9R^{9a}$)$_n$—C(=O)—O—$R^{13}$.

In other embodiments, each of Y and Y' is independently —C(=O)—(C$R^9R^{9a}$)$_n$—N($R^{11}$)—C(=O)—O—$R^{13}$.

In other embodiments, each of Y and Y' is independently —U—(C$R^9R^{9a}$)$_t$—$R^{12}$.

In other embodiments, each of Y and Y' is independently —C(=O)—(C$R^9R^{9a}$)$_t$—$R^{12}$.

In other embodiments, each of Y and Y' is independently —[U—(C$R^9R^{9a}$)$_t$—N($R^{10}$)—(C$R^9R^{9a}$)$_t$]$_k$—U—(C$R^9R^{9a}$)$_t$—O—(C$R^9R^{9a}$)$_t$—$R^{12}$.

In other embodiments, each of Y and Y' is independently —U—(C$R^9R^{9a}$)$_t$—N($R^{10}$)—(C$R^9R^{9a}$)$_t$—U—(C$R^9R^{9a}$)$_t$—O—(C$R^9R^{9a}$)$_t$—$R^{12}$.

In other embodiments, each of Y and Y' is independently —C(=O)—(C$R^9R^{9a}$)$_t$—N($R^{10}$)—(C$R^9R^{9a}$)$_t$—C(=O)—(C$R^9R^{9a}$)$_t$—O—(C$R^9R^{9a}$)$_t$—$R^{12}$.

In other embodiments, each of Y and Y' is independently —U—(C$R^9R^{9a}$)$_t$—O—(C$R^9R^{9a}$)$_t$—$R^{12}$.

In other embodiments, each of Y and Y' is independently —C(=O)—(C$R^9R^{9a}$)$_t$—O—(C$R^9R^{9a}$)$_t$—$R^{12}$.

In other embodiments, each of Y and Y' is independently —C(=O)—(C$R^9R^{9a}$)$_n$—N($R^{11}$)—$R^{12}$, wherein $R^{11}$ and $R^{12}$, together with the nitrogen atom they are attached to, form a 4-7 membered ring.

In other embodiments, each $R^9$, $R^{9a}$, $R^{19}$ and $R^{11}$ is independently H, deuterium, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ haloalkyl, $C_{1-6}$ hydroxyalkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

each $R^{12}$ is independently $R^{13a}R^{13}N$—, —C(=O)$R^{13}$, —C(=S)$R^{13}$, —C(=O)—O—$R^{13}$, —C(=O)N$R^{13}R^{13a}$, —OC(=O)N$R^{13}R^{13a}$, —OC(=O)O$R^{13}$, —N($R^{13}$)C(=O)N$R^{13}R^{13a}$, —N($R^{13}$)C(=O)O$R^{13a}$, —N($R^{13}$)C(=O)—$R^{13a}$, $R^{13}R^{13a}N$—S(=O)$_2$—, $R^{13}S)_2$—, $R^{13}S(=O)_2N(R^{13})$—, $R^{13}OS(=O)_2$—, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; or $R^{11}$ and $R^{12}$, together with the nitrogen atom they are attached to, form a 4-7 membered ring; and each $R^{13}$ and $R^{13a}$ is independently H, deuterium, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl.

In other embodiments, each $R^9$, $R^{9a}$, $R^{19}$ and $R^{11}$ is independently H, deuterium, methyl, ethyl, isopropyl, cyclohexyl, isobutyl or phenyl;

each $R^{12}$ is independently —C(=O)$R^{13}$, —C(=O)—O—$R^{13}$, —C(=O)N$R^{13}R^{13a}$, methyl, ethyl, propyl, phenyl, cyclohexyl, morpholinyl or piperidinyl, or $R^{11}$ and $R^{12}$, together with the nitrogen atom they are attached to, form a 4-7 membered ring; and each $R^{13}$ and $R^{13a}$ is independently H, deuterium, methyl, ethyl, propyl, phenyl, cyclohexyl, morpholinyl or piperidinyl.

In other embodiments, Formula (VII) is

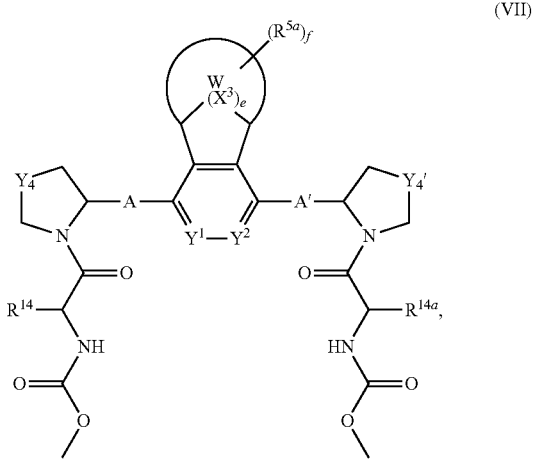

(VII)

wherein each of $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

wherein each of $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano.

In other embodiments, Formula (VIII) is

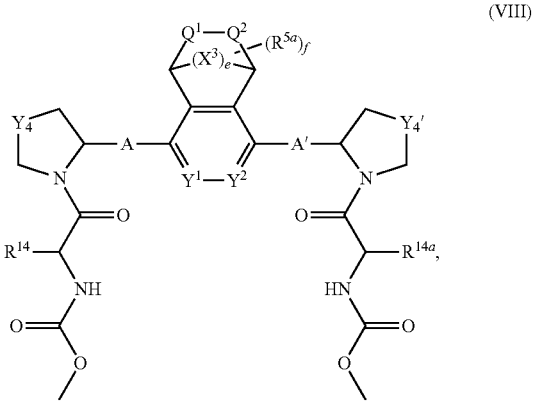

(VIII)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, —NR$^7$R$^{7a}$, benzyl, piperazinyl, cyclopentyl, cyclopropyl, cyclohexyl, or C$_{1-9}$ heteroaryl; wherein each of methyl, ethyl, isopropyl, isobutyl, tert-butyl, allyl, propargyl, trifluoroethyl, phenyl, pyranyl, morpholinyl, —NR$^7$R$^{7a}$, benzyl, piperazinyl, cyclopentyl, cyclopropyl and cyclohexyl is optionally substituted with one or more substituents, wherein the substituent is deuterium, F, Cl, Br, hydroxy or cyano;

each Q$^1$ and Q$^2$ is independently NR$^6$, O, S, C(=O) or CH$_2$;

each Y$^1$ and Y$^2$ is independently N or CR$^7$;

each X$^3$ is independently O, S, NR$^6$, C(=O) or CR$^7$R$^{7a}$; e is 0, 1, 2, or 3 with the proviso that where X$^3$ is O, S, C(=O) or NR$^6$, e is 1;

f is 0, 1, 2, 3 or 4;

each of A and A' is independently a bond, C$_{1-6}$ alkyl, C$_{2-6}$ alkenyl, C$_{3-8}$ cycloalkyl, C$_{2-10}$ heterocycloalkyl, —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, —(CR$^8$R$^{8a}$)$_n$—N(R$^5$)—C(=O)—O—(CR$^8$R$^{8a}$)$_p$—, or each of A and A' is independently

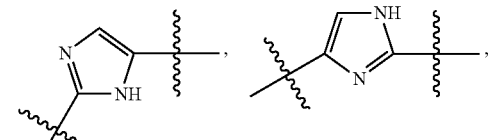

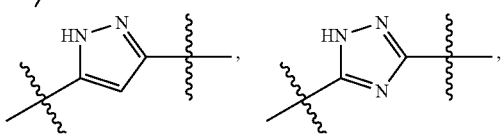

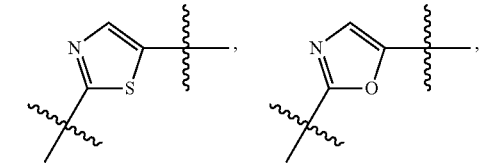

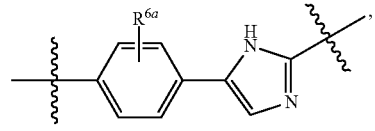

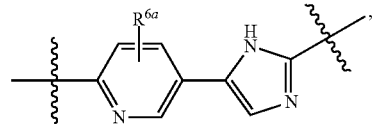

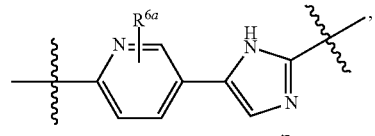

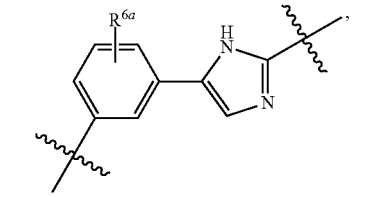

-continued

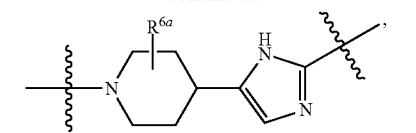

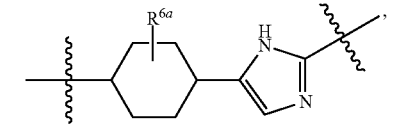

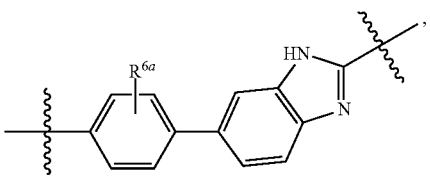

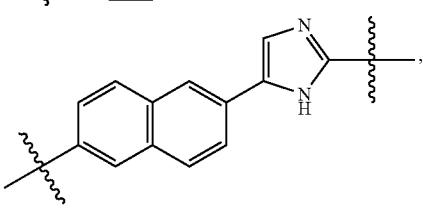

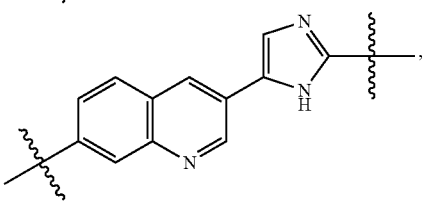

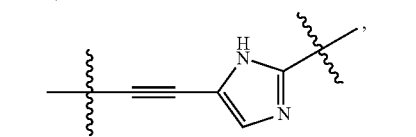

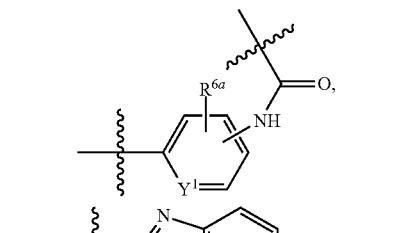

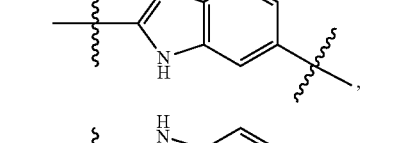

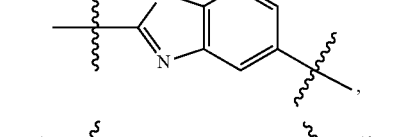

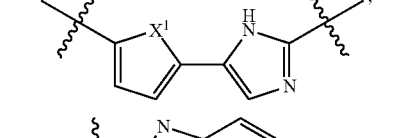

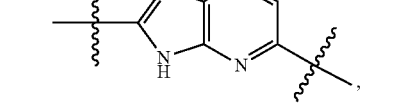

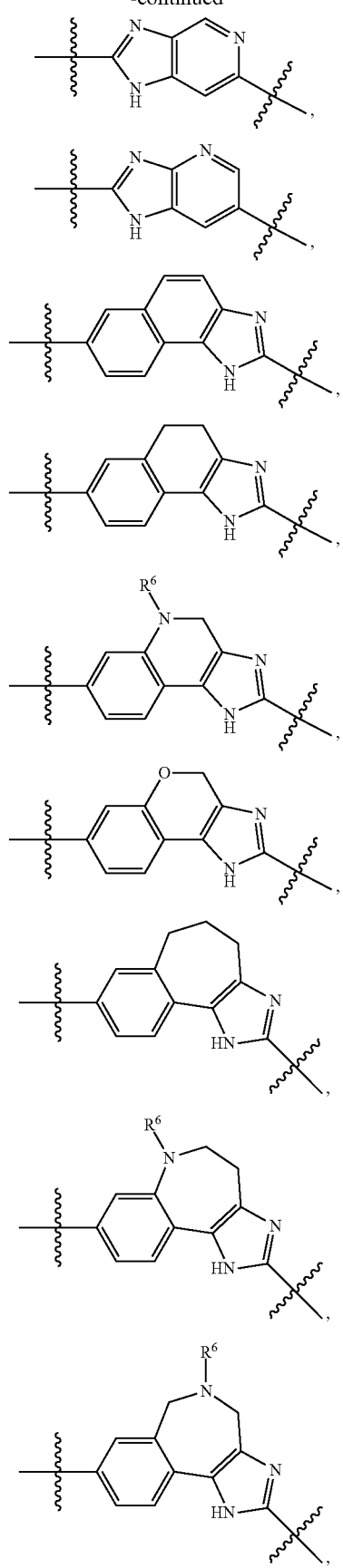
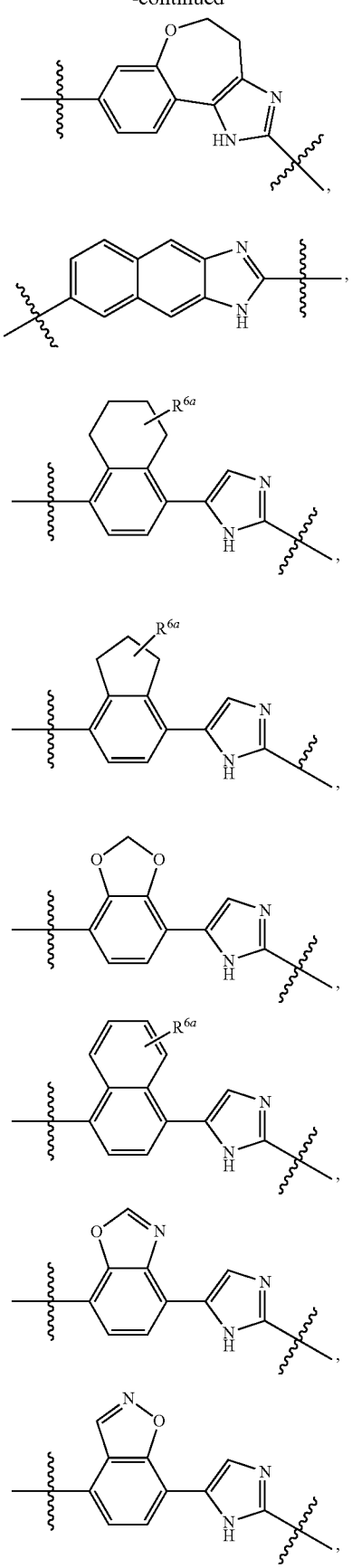

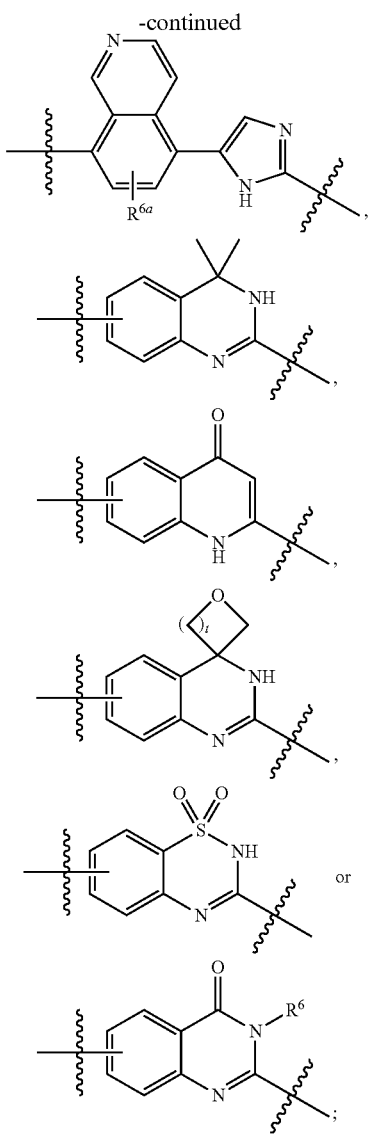

and each of $Y_4$ and $Y_4'$ is independently a bond, O, S, $-(CH_2)_n-$, $-CH=CH-$, $-S(=O)_r-$, $-CH_2O-$, $-CH_2S-$, $-CH_2S(=O)_r-$, $-CF_2-$, $-CHR^{5a}-$ or $-CH_2N(R^6)-$.

In some embodiments, Formula (IX) is

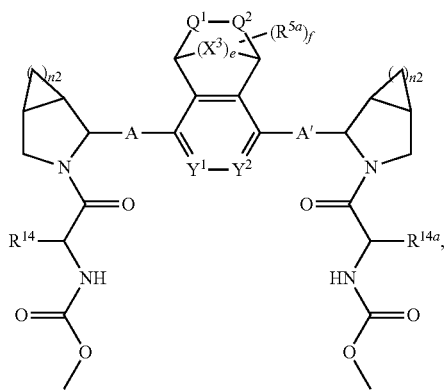

(IX)

wherein of each $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4;

wherein each of $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano.

In some embodiments, Formula (X) is

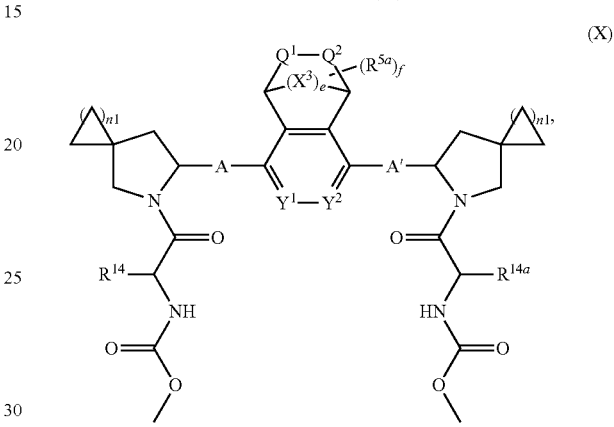

(X)

wherein each $Q^1$ and $Q^2$ is independently $CH_2$, $CF_2$, O, $C(=O)$ or $NR^6$;

each of $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

In some embodiments, Formula (XI) is

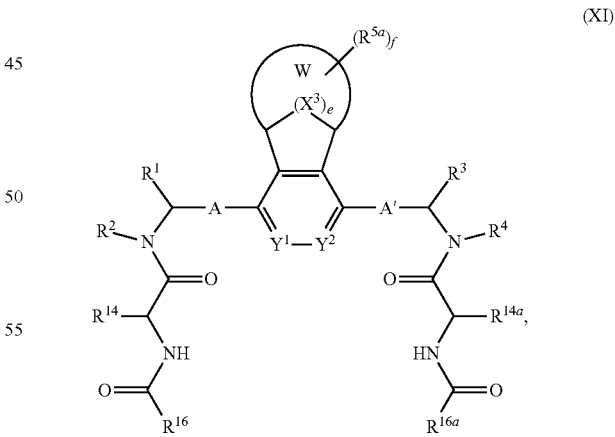

(XI)

wherein each $R^{5a}$ is independently H, deuterium, methyl, ethyl, F, Cl, Br or I;

each of $R^{14}$ and $R^{14a}$ is independently H, deuterium, methyl, ethyl, phenyl, cyclohexyl, 1-methyl propyl, isopropyl or tert-butyl;

each of $R^{16}$ and $R^{16a}$ is independently hydroxy, methoxy, ethoxy, phenoxy,

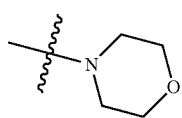 [SMILES: *N1CCOCC1]
or tert-butoxy;
wherein each of methyl, ethyl, phenyl, cyclohexyl, 1-methyl propyl, isopropyl, methoxy, ethoxy, tert-butoxy and tert-butyl is optionally substituted with one or more substituents, wherein the substituent is deuterium, F, Cl, Br, hydroxy or cyano;
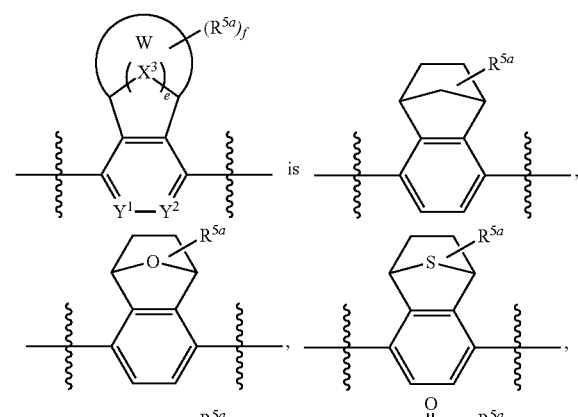
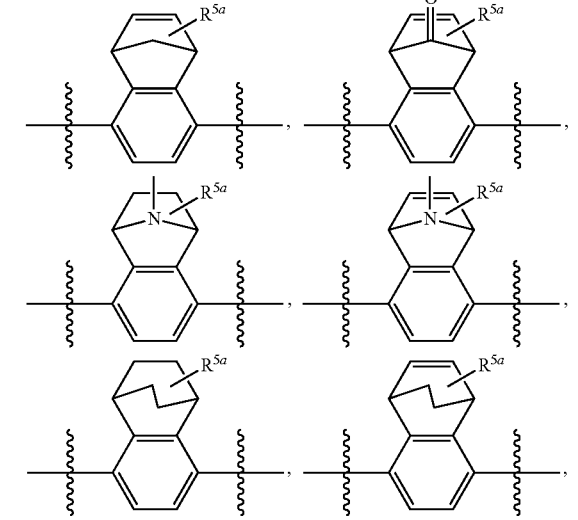
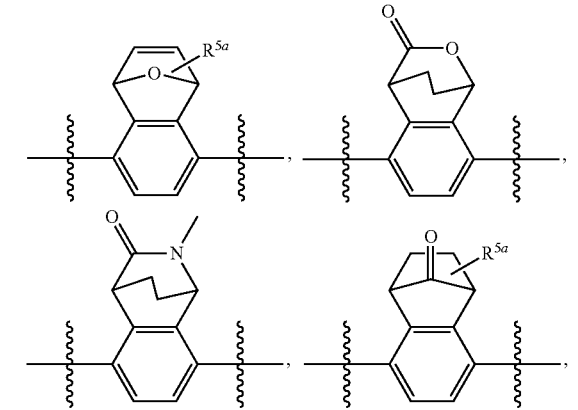
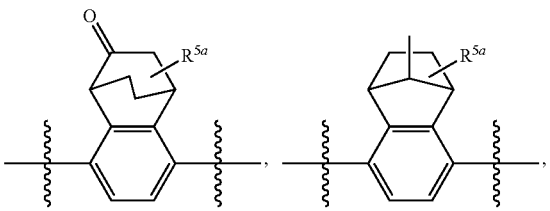
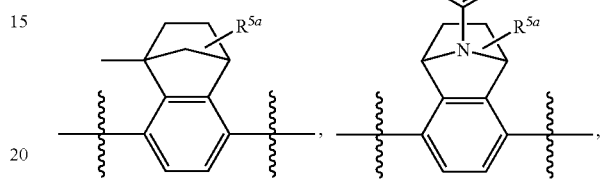
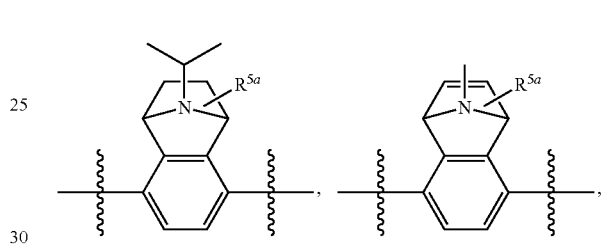
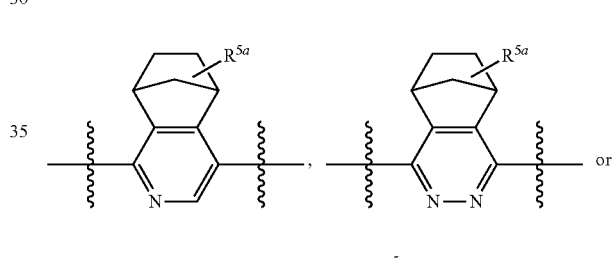
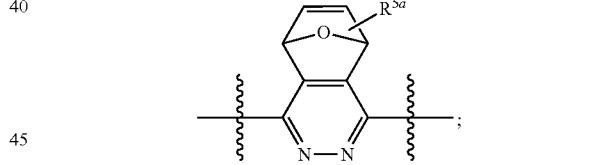 or
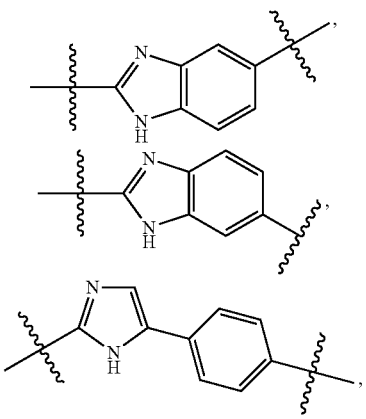
each of A and A' is independently -continued
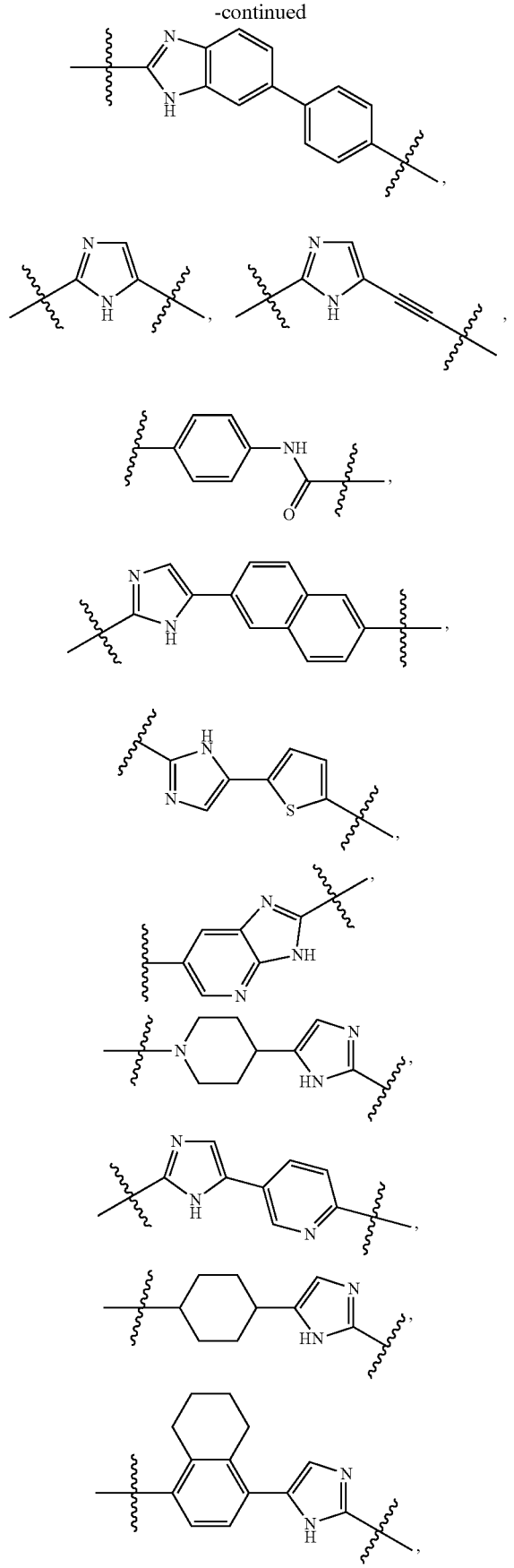
-continued
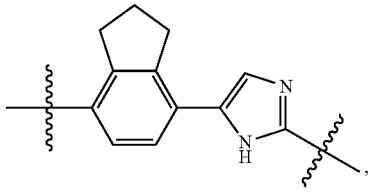
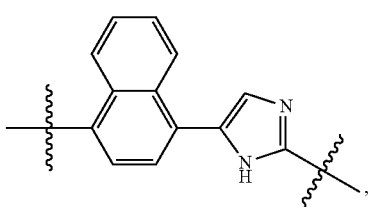
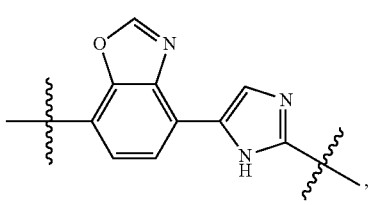
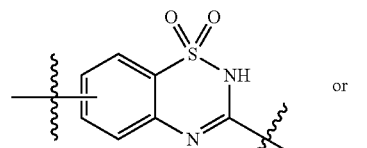
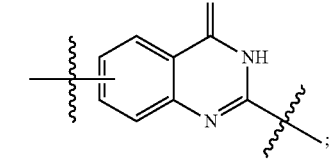
$R^1$, $R^2$ and N—CH together form one of the following divalent groups:
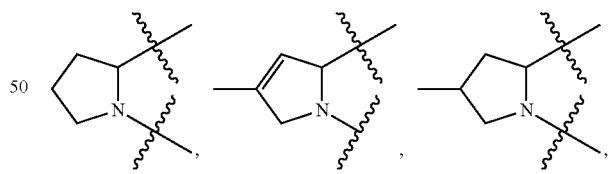
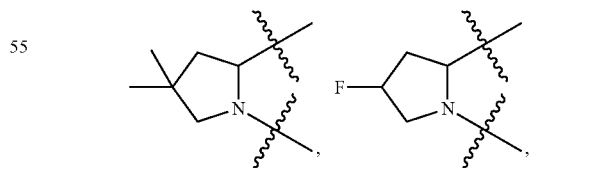
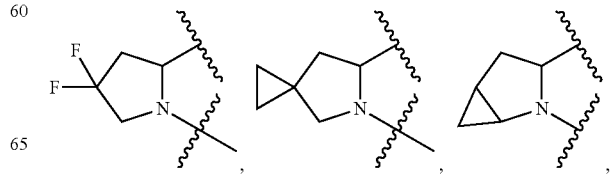

-continued

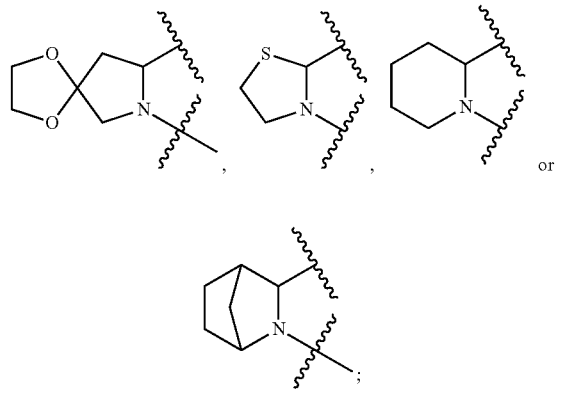

and

R³, R⁴ and N—CH together form one of the following divalent groups:

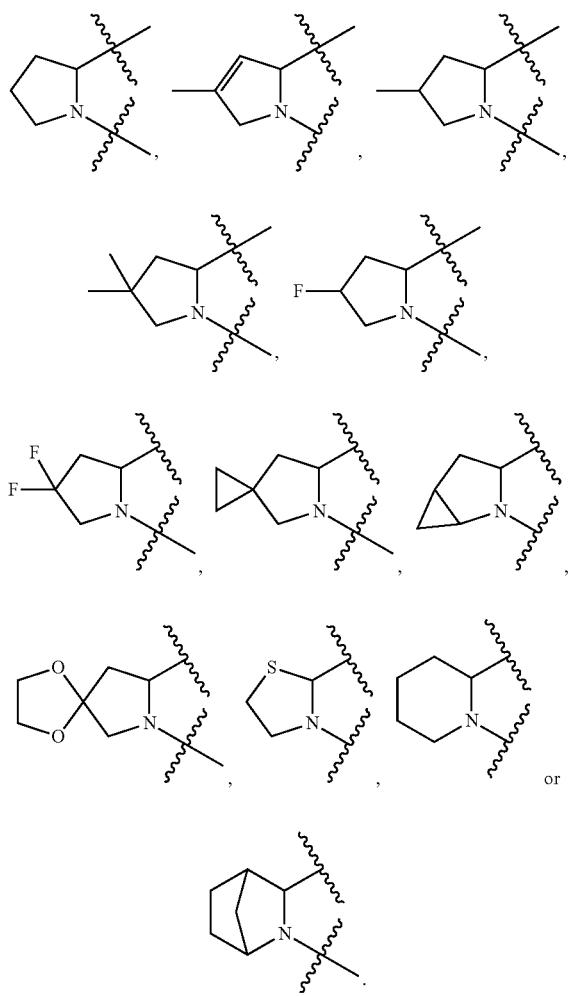

In other embodiments, Formula (XII) is

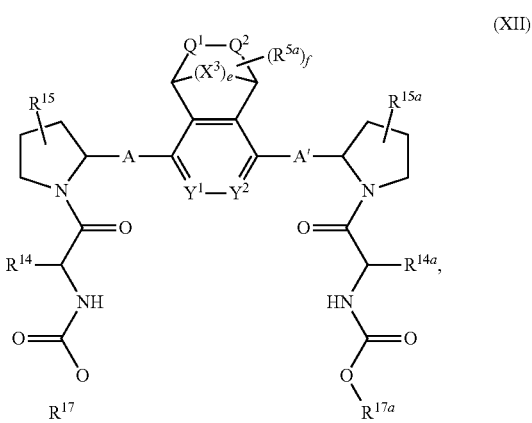

wherein R$^{5a}$ is H or methyl;
each of Q$^1$ and Q$^2$ is independently CH$_2$, CF$_2$, O, C(=O) or NR$^6$;
each of Y$^1$ and Y$^2$ is independently N or CR$^7$;
R$^7$ is H, deuterium, methyl, ethyl, isopropyl, phenyl, F, Cl, Br, I, OH or cyano;
each of R$^{14}$ and R$^{14a}$ is independently H, deuterium, methyl, ethyl, isobutyl, cyclohexyl, phenyl or isopropyl;
each of R$^{15}$ and R$^{15a}$ is independently H, deuterium, F, Cl, Br, methyl, ethyl, isopropyl or tert-butyl;
each of R$^{17}$ and R$^{17a}$ is independently methyl, phenyl or ethyl;
each X$^3$ is independently O, S, NR$^6$, C(=O) or CH$_2$;
each R$^6$ is independently H, methyl, ethyl, cyclohexyl, phenyl or isopropyl;
e is 0, 1, 2 or 3 with the proviso that where X$^3$ is O, S, or NR$^6$, e is 1;
wherein each of methyl, ethyl, phenyl, cyclohexyl, isopropyl and tert-butyl is optionally substituted with one or more substituents, wherein the substituent is deuterium, F, Cl, Br, hydroxy or cyano; and
each of A and A' is independently

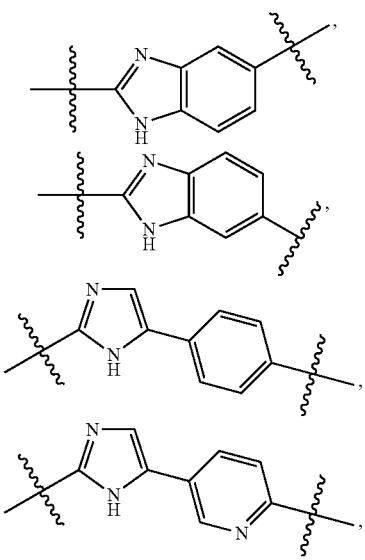

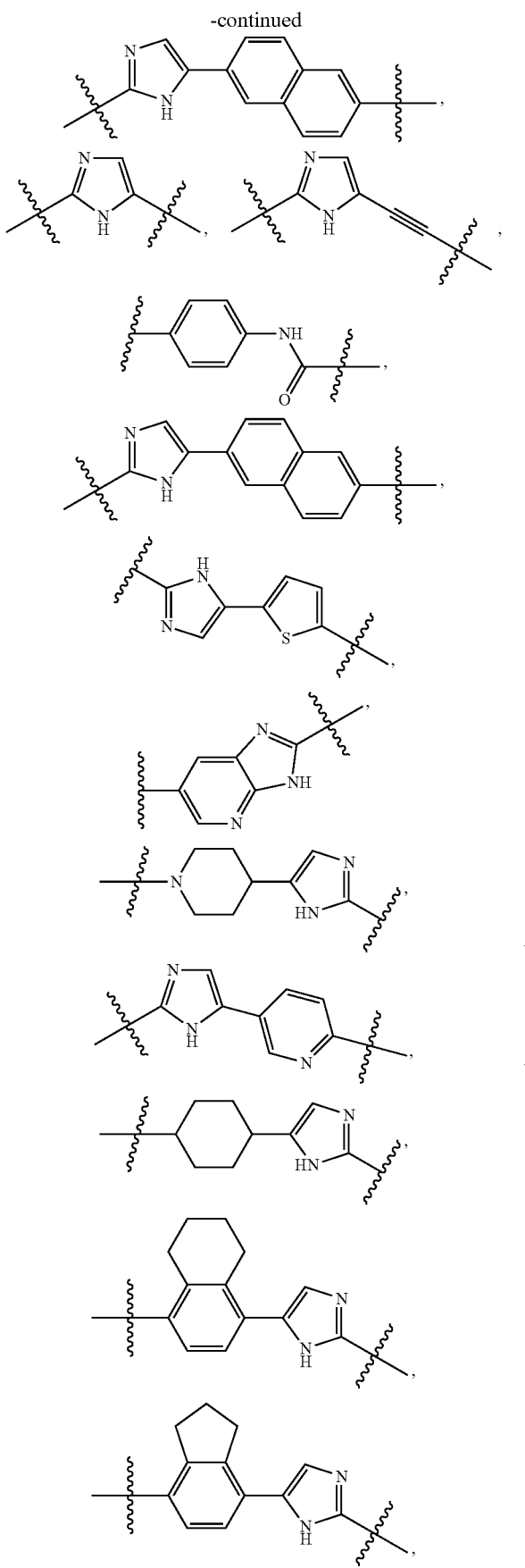
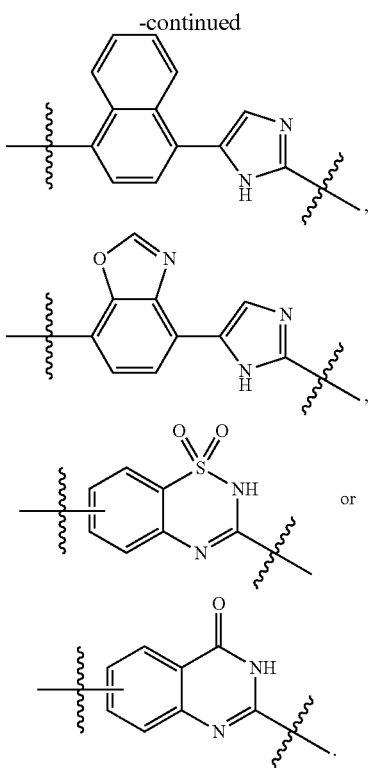
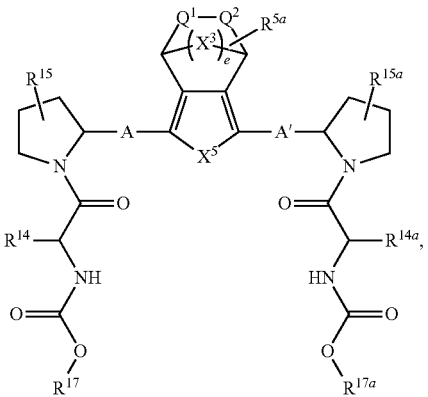

In some embodiments, Formula (XII') is (XII')

wherein $R^{5a}$ is H or methyl;
each of $Q^1$ and $Q^2$ is independently $CH_2$, $CF_2$, O, C(=O) or $NR^6$;
$X^5$ is $CH_2$, O, S or $NR^6$;
each of $R^{14}$ and $R^{14a}$ is independently H, deuterium, methyl, ethyl, isobutyl, cyclohexyl, phenyl or isopropyl;
each of $R^{15}$ and $R^{15a}$ is independently H, deuterium, F, Cl, Br, methyl, ethyl, isopropyl or tert-butyl;
each of $R^{17}$ and $R^{17a}$ is independently methyl, phenyl or ethyl;
each $X^3$ is independently O, S, $NR^6$, C(=O) or $CH_2$;
each $R^6$ is independently H, deuterium, methyl, ethyl, cyclohexyl, phenyl or isopropyl;
e is 0, 1, 2 or 3 with the proviso that where $X^3$ is O, S, or $NR^6$, e is 1;

wherein each of methyl, ethyl, phenyl, cyclohexyl, isopropyl and tert-butyl is optionally substituted with one or more substituents, wherein the substituent is deuterium, F, Cl, Br, hydroxy or cyano; and
each of A and A' is independently
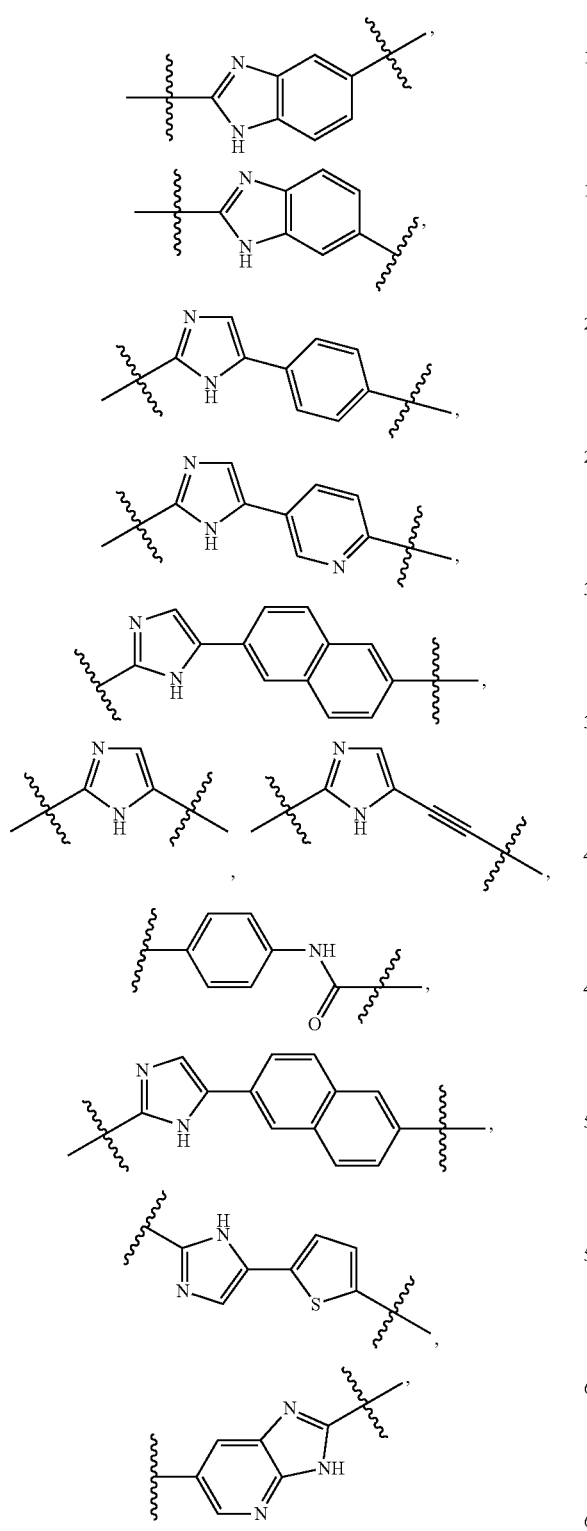
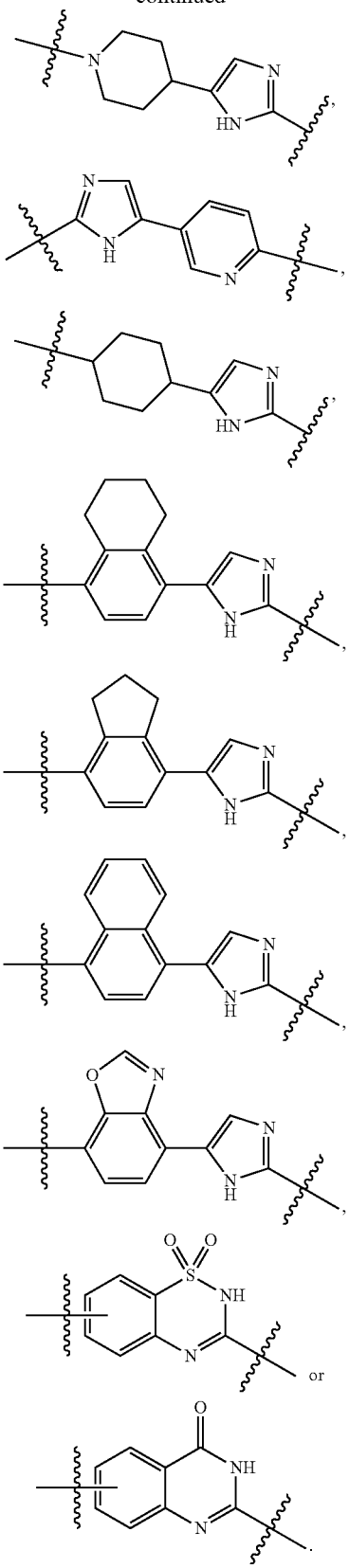
In one aspect, provided herein are pharmaceutical compositions comprising a compound disclosed herein; and a pharmaceutically acceptable carrier, excipient, diluent, adjuvant, vehicle or a combination thereof.

In some embodiments, the pharmaceutical compositions further comprising an anti-HCV agent.

In other embodiments, the anti-HCV agent is an interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, ribavirin, bavituximab, hunman hepatitis C immune globulin (CIVACIR™), boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZd-2795, TMC647055 or a combination thereof.

In other embodiments, the interferon is interferon α-2b, pegylated interferon α, interferon α-2a, pegylated interferon α-2a, consensus interferon-α, or interferon γ.

In other embodiments, the pharmaceutical composition further comprising at least one HCV inhibitor, and wherein the HCV inhibitor inhibits HCV viral protein, HCV replication or HCV viral protein and HCV replication, wherein the HCV viral protein is helicase, proteinase, polymerase, metalloproteinase, serine proteinase, non-structural protein NS4A, non-structural protein NS5A, or non-structural protein NS4B, and wherein the HCV replication is HCV entry, HCV assembly, HCV egress, internal ribosome entrysite (IRES) or inosine-5'-monophosphate dehydrogenase (IMPDH).

In other embodiments, provided herein is a compound or a pharmaceutical composition for use in inhibiting HCV viral protein, HCV replication or HCV viral protein and HCV replication, wherein the HCV viral protein is helicase, proteinase, polymerase, metalloproteinase, serine proteinase, non-structural protein NS4A, non-structural protein NS5A, or non-structural protein NS4B, and wherein the HCV replication is HCV entry, HCV assembly, HCV egress, internal ribosome entrysite (IRES) or inosine-5'-monophosphate dehydrogenase (IMPDH).

In another aspect, provided herein is a compound or a pharmaceutical composition for use in preventing, managing, treating or lessening the severity of HCV infection or a HCV disorder in a patient.

In another aspect, provided herein is use of the compound or the pharmaceutical composition disclosed herein in the manufacture of a medicament for preventing, managing, treating or lessening the severity of HCV infection or a HCV disorder in a patient.

In another aspect, provided herein is use of the compound or pharmaceutical composition disclosed herein for preventing, managing, treating or lessening the severity of HCV infection or a HCV disorder in a patient, which comprises administering a pharmaceutically effective amount of the (a) compound or pharmaceutical composition disclosed herein to the patient.

In another aspect, provided herein include methods of preparing, methods of separating, and methods of purifying compounds of Formula (I), (II), (III), (IV), (V), (VI), (VII), (VIII), (IX), (X), (XI), (XII), (II'), (III'), (IV'), (V'), (VI') or (XII').

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the *Handbook of Chemistry and Physics*, $75^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents described herein include, but are not limited to, deuterium, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. In other embodiments, aliphatic groups contain 1-3 carbon atoms. Some non-limiting examples of aliphatic groups include linear or branched, substituted or unsubstituted alkyl, alkenyl, or alkynyl groups, as methyl, ethyl, propyl, isopropyl, butyl, tert-butyl, hexyl, isobutyl, sec-butyl, vinyl, and the like.

The term "haloaliphatic" refers to an aliphatic group substituted with one or more of the same or different halogen atoms (i.e., F, Cl, Br or I,), wherein the aliphatic group is as defined herein. Some non-limiting examples include trifluoromethyl, trifluoroethyl, chloromethyl, 2-chlorovinyl, and the like.

The term "hydroxyaliphatic" refers to an aliphatic group substituted with one or more hydroxy groups, wherein the aliphatic group is as defined herein. Some non-limiting examples include hydroxyethyl, 2-hydroxypropyl, hydroxymethyl, and the like.

The term "aminoaliphatic" refers to an aliphatic group substituted with one or more amino groups, wherein the aliphatic group is as defined herein. Some non-limiting examples include aminomethyl, 2-aminoethyl, 2-amino isopropyl, and the like.

The term "alkyl" refers to a saturated linear or branched chain monovalent hydrocarbon radical of one to twenty carbon atoms, or one to ten carbon atoms, or one to eight carbon atoms, or one to six carbon atoms, or one to four carbon atoms, or one to three carbon atoms, wherein the alkyl radical may be optionally substituted independently with one or more substituents described below. The examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like. The terms "alkyl" and the prefix "alk-" are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to linear or branched-chain monovalent hydrocarbon radical of two to twelve carbon atoms, or two to eight carbon atoms, or two to six carbon atoms, or two to four carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Some non-limiting examples include ethenyl or vinyl (—CH═$CH_2$), allyl (—$CH_2$CH═$CH_2$), and the like.

The term "alkynyl" refers to a linear or branched-chain monovalent hydrocarbon radical of two to twelve carbon atoms, or two to eight carbon atoms, or two to six carbon atoms, or two to four carbon atoms, with at least one site of unsaturation, i.e., a carbon-carbon, sp triple bond, wherein the alkynyl radical may be optionally substituted independently with one or more substituents described herein. Some non-limiting examples include ethynyl (—C≡CH), propynyl (propargyl, —$CH_2$C≡CH), and the like.

The terms "hydroxy-substituted alkyl" refers to an alkyl group substituted with one or more hydroxy groups, wherein the alkyl group is as defined herein. Some non-limiting examples include hydroxymethyl, hydroxyethyl, 1,2-dihydroxyethyl, and the like.

The term "haloalkyl" refers to an alkyl group substituted with one or more of the same or different halogen atoms (i.e., F, Cl, Br or I,), wherein the alkyl group is as defined herein. Some non-limiting examples include trifluoromethyl, trifluoroethyl, chloromethyl, fluoromethyl, and the like.

The term "hydroxyalkyl" refers to an alkyl group substituted with one or more hydroxy groups, wherein the alkyl group is as defined herein. Some non-limiting examples include hydroxyethyl, 2-hydroxypropyl, hydroxymethyl, and the like.

The term "aminoalkyl" refers to an alkyl group substituted with one or more amino groups, wherein the alkyl group is as defined herein. Some non-limiting examples include aminomethyl, 2-aminoethyl, 2-amino isopropyl, and the like.

The term "alkylene" refers to a saturated divalent hydrocarbon group derived from a straight or branched-chain saturated hydrocarbon by the removal of two hydrogen atoms. The alkylene group is optionally substituted with one or more substituents. The substituents include, but are not limited to, deuterium, hydroxy, amino, halo, cyano, aryl, heteroaryl, alkoxy, alkyl, alkenyl, alkynyl, heterocyclyl, mercapto, nitro, or aryloxy. Some non-limiting examples include methylene, ethylene (—$CH_2$—$CH_2$—), isopropylidene (—$CH_2$—CH($CH_3$)—), ethylidene, 2-methoxy-1,1-propylidene, 2-hydroxy-1,1-propylidene, 2-methyl-2-hydroxy-1,1-propylidene, and the like.

The term "alkenylene" refers to an unsaturated divalent hydrocarbon group derived from a straight or branched-chain unsaturated hydrocarbon alkene by the removal of two hydrogen atoms. The alkenylene group is optionally substituted with one or more substituents. The substituents include, but are not limited to, deuterium, hydroxy, amino, halo, cyano, aryl, heteroaryl, alkoxy, alkyl, alkenyl, alkynyl, heterocyclyl, mercapto, nitro, or aryloxy. Some non-limiting examples include ethenylene, isopropenylene, 3-methoxy-1,1-propenylidene, 2-methyl-1,1-butenylidene, and the like.

The term "carbocyclylene" or "cycloalkylene" refers to a saturated divalent hydrocarbon ring derived from a monocyclic ring having 3 to 12 carbon atoms or a bicyclic ring having 7 to 12 carbon atoms by the removal of two hydrogen atoms, wherein the carbocyclyl group or the cycloalkyl group is as defined herein. Some non-limiting examples include cyclopropylene, cyclobutylene, cyclopentylene, cyclohexylene, 1-cyclopent-1-enylene, 1-cyclopent-2-enylene, and the like.

The term "heterocyclylene" refers to a monocyclic, bicyclic, or tricyclic ring system in which one or more ring members are an independently selected heteroatom and that is completely saturated or that contains one or more units of unsaturation, but which is not aromatic, that has two points of attachment to the rest of the molecule, wherein the heterocyclyl group is as defined herein. Some non-limiting examples include piperidin-1,4-ylene, piperazin-1,4-ylene, tetrahydrofuran-2,4-ylene, tetrahydrofuran-3,4-ylene, azetidin-1,3-ylene, pyrrolidin-1,3-ylene, and the like.

The term "heterocyclylalkylene" refers to a divalent group derived from a heterocyclylalkyl by the removal of two hydrogen atoms, wherein the heterocyclylalkyl group is as defined herein. Some non-limiting examples include morpholin-4-methylmethylene, piperidin-N-methylmethylene, piperazin-4-ethyl-1-yl, piperidin-4-ethyl-1-yl, pyrrolidon-2-methyl-1-yl, and the like.

The term "haloalkylene" refers to haloalkyl system having two points connected to the rest of the molecule, wherein the haloalkyl group is as defined herein. Some non-limiting examples include difluoromethylene.

The term "arylene" refers to aryl system having two connection points connected to the rest of the molecule, wherein the aryl radical is as defined herein. Some non-limiting examples include phenylene, p-fluorophenylene, and the like.

The term "aralkylene" refers to aralkyl system having two connection points connected to the rest of the molecule, wherein the aralkyl radical is as defined herein. Some non-limiting examples include benzylene, phenylethylene, and the like.

The term "heteroarylene" refers to heteroaryl system having two connection points connected to the rest of the molecule, wherein the heteroaryl radical is as defined herein. Some non-limiting examples include pyridylene, pyrrylene, thiazolylene, imidazolylene, and the like.

The term "heteroarylalkylene" refers to heteroarylalkyl system having two connection points connected to the rest of the molecule, wherein the heteroarylalkyl group is as defined herein. Some non-limiting examples include pyridine-2-ethylene, thiazole-2-methylene, imidazole-2-ethylene, pyrimidine-2-methylene, and the like.

The term "fused bicyclylene" refers to fused bicyclyl system having two connection points connected to the rest of the molecule, wherein the fused bicyclyl group is as defined herein. Some non-limiting examples include bicyclo[3.1.0]hexane-3,6-ylene.

The term "fused heterobicyclylene" refers to fused heterobicyclyl system having two connection points connected to the rest of the molecule, wherein the fused heterobicyclyl group is as defined herein. Some non-limiting examples include 3-azabicyclo[3.1.0]hexane-3,6-ylene.

The term "fused bicyclylalkylene" refers to fused bicyclylalkyl system having two connection points connected to the rest of the molecule, wherein the fused bicyclylalkyl group is as defined herein.

The term "fused heterobicyclylalkylene" refers to fused heterobicyclylalkyl system having two connection points connected to the rest of the molecule, wherein the fused heterobicyclylalkyl group is as defined herein.

The term "spiro bicyclylene" refers to spiro bicyclyl system having two connection points connected to the rest of the molecule, wherein the fused spiro bicyclyl group is as defined herein. Some non-limiting examples include 5-spiro[2,4]heptane-5,7-ylene, spiro[4,4]nonane-2,7-ylene, and the like.

The term "spiro heterobicyclylene" refers to spiro heterobicyclyl system having two connection points connected to the rest of the molecule, wherein the fused spiro heterobicyclyl group is as defined herein. Some non-limiting examples include 5-azaspiro[2,4]heptane-5,7-ylene, 2-azaspiro[4,4]nonane-2,7-ylene, and the like.

The term "spiro bicyclylalkylene" refers to spiro bicyclylalkyl system having two connection points connected to the rest of the molecule, wherein the fused spiro bicyclylalkyl group is as defined herein.

The term "spiro heterobicyclylalkylene" refers to spiro heterobicyclylalkyl system having two connection points connected to the rest of the molecule, wherein the fused spiro heterobicyclylalkyl group is as defined herein.

The term "heteroalkyl" refers to hydrocarbon chain, inserted with one or more heteroatoms. Unless otherwise specified, heteroalkyl groups contain 1-10 carbon atoms. In other embodiments, heteroalkyl groups contain 1-8 carbon atoms. In still other embodiments, heteroalkyl groups contain 1-6 carbon atoms, and in yet other embodiments, heteroalkyl groups contain 1-4 carbon atoms. In other embodiments, heteroalkyl groups contain 1-3 carbon atoms. Some non-limiting examples include $CH_3OCH_2$—, $CH_3CH_2OCH_2$—, $CH_3SCH_2$—, $(CH_3)_2NCH_2$—, $(CH_3)_2CH_2OCH_2$—, $CH_3OCH_2CH_2$—, $CH_3CH_2OCH_2CH_2$—, and the like.

The term "cycloaliphatic", "carbocycle", "carbocyclyl", or "cycloalkyl" refers to a monovalent or multivalent non-aromatic, saturated or partially unsaturated ring exclusive of heteroatoms, having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopentyl-1-enyl, 1-cyclopentyl-2-enyl, 1-cyclopentyl-3-enyl, cyclohexyl, 1-cyclohexyl-1-enyl, 1-cyclohexyl-2-enyl, 1-cyclohexyl-3-enyl, cyclohexadienyl, cycloheptyl, cyclooctyl, cyclononyl, cyclodecyl, cycloundecyl, cyclododecyl, and the like. The term "cycloaliphatic", "carbocycle", "carbocyclyl", or "cycloalkyl" may be substituted or unsubstituted, wherein the substitutent may be, but is not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_{2-5}$ carboxy alkoxy, and the like.

The term "cycloalkyloxy" or "carbocyclyloxy" refers to an optionally substituted cycloalkyl or carbocyclyl radical, as defined herein, attached to an oxygen atom, wherein the oxygen atom serves as the attaching point to the rest of the molecule. Some non-limiting examples include cyclopropyloxy, cyclopentyloxy, cyclohexyloxy, hydroxy-substituted cyclopropyloxy, and the like.

The term "cycloalkylamino" refers to an amino group substituted with one or two cycloalkyl radicals, wherein the cycloalkyl group is as defined herein. Some non-limiting examples include cyclopropylamino, cyclopentylamino, cyclohexylamino, hydroxy-substituted cyclopropylamino, dicyclohexylamino, dicyclopropylamino, and the like.

The term "carbocyclyloxyalkoxy" refers to an alkoxy group substituted with one or more carbocyclyloxy groups, wherein the alkoxy group and carbocyclyloxy group are as defined herein. Some non-limiting examples include cyclopropyloxymethoxy, cyclopropyloxyethoxy, cyclopentyloxyethoxy, cyclohexyloxyethoxy, cyclohexenyl-3-oxyethoxy, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples include cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more cycloalkylamino groups, wherein the aliphatic group and cycloalkylamino group are as defined herein. Some non-limiting examples include cyclopropylaminomethyl, cyclopropylaminoethyl, cyclopentylaminomethyl, cyclopentylaminoethyl, cyclohexylaminoethyl, halocyclopropylaminoethyl, and the like.

The term "cycloalkylaliphatic" refers to an aliphatic group substituted with one or more cycloalkyl groups, wherein the cycloalkyl group and aliphatic group are as defined herein. Some non-limiting examples include cyclopropylmethyl, cyclopropylethyl, cyclopropylpropyl, cyclopentylmethyl, cyclohexylethyl, and the like.

The term "cycloalkylalkoxy" or "carbocyclylalkoxy" refers to an alkoxy group substituted with one or more cycloalkyl groups or carbocyclyl groups, wherein the carbocyclyl group, cycloalkyl group and alkoxy group are as defined herein. Some non-limiting examples include cyclopropylmethoxy, cyclopropylethoxy, cyclopentylethoxy, cyclohexylethoxy, cyclohexylmethoxy, cyclopropylpropoxy, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidyl, morpholinyl, thiomorpholinyl, thioxanyl, thiazolidinyl, oxazolidinyl, piperazinyl, homopiperazinyl, azetidinyl, oxetanyl, thietanyl, homopiperidinyl, epoxypropyl (oxiranyl), azepanyl, oxepanyl, thiepanyl, 4-methoxy-piperidin-1-yl, 1,2,3,6-tetrahydro-pyridine-1-yl, oxazepinyl, diazepinyl, thiazepinyl, pyrrolidin-1-yl, 2-pyrrolinyl, 3-pyrrolinyl, 2H-indolinyl, 2H-pyranyl, 4H-pyranyl, dioxolan-2-yl, 1,3-dioxopenyl, pyrazolinyl, dithianyl, ditholanyl, dihydrothienyl, pyrazolidinylimidazolinyl, imidazolidinyl, 1,2,3,4-tetrahydroisoquinolinyl, 1,2,6-dithiazinyl, 1,1-dioxo-2-yl, 4-hydroxy-1,4-azaphosphine-4-oxide-1-yl, 2-hydroxy-1-(piperazin-1-yl)ethanone-4-yl, 2-hydroxy-1-(5,6-dihydro-1,2,4-triazin-1(4H)-yl)ethanone-4-yl, 5,6-dihydro-4H-1,2,4-oxadiazine-4-yl, 2-hydroxy-1-(5,6-diludine-1(2H)-yl)ethanone-4-yl, 3-azabicyclo[3,1,0]hexyl, 3-azabicyclo[4,1,0]heptyl, azabicyclo[2,2,2]hexyl, 2-methyl-5,6,7,8-tetrahydro-[1,2,4]triazole[1,5-c]pyrimidine-6-yl, 4,5,6,7-teterhydro-isoxazolo[4,3-c]pyrimidine-5-yl, 3H-indoxyl-2-oxo-5-azabicyclo[2,2,1]heptane-5-yl, 2-oxo-5-azabicyclo[2,2,2]octane-5-yl, quinolizinyl and N-pyridyl urea. Some non-limiting examples of a heterocyclic ring include 1,1-dioxo-thiomorpholinyl and heterocyclic group wherein 2 carbon atoms on the ring are substituted with oxo (=O) moieties are pyrimidindionyl. The heterocyclic groups herein may be substituted or unsubstituted, wherein the substituent may be, but is not limited to, oxo (=O), hydroxy, amino, halo, cyano, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. Wherein the heterocyclyl, alkyl, alkoxy and alkylamino group are as defined herein. Some non-limiting examples include pyrrol-2-ylmethyl, morpholin-4-ylethyl, morpholin-4-ylethoxy, piperazin-4-ylethoxy, piperidin-4-ylethylamino, and the like.

The term "heterocyclylaliphatic" refers to heterocyclic-substituted aliphatic group, wherein the heterocyclic radical and aliphatic group are as defined herein. Some non-limiting examples include pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples include pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein the heterocyclyl group is as defined herein. Some non-limiting examples include pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyalkoxy" refers to an alkoxy radical substituted with one or more heterocyclyloxy groups, wherein the alkoxy radical and heterocyclyloxy group are as defined herein. Some non-limiting examples include pyrrol-2-yloxymethoxy, pyrrol-3-yloxyethoxy, piperidin-2-yloxyethoxy, piperidin-3-yloxyethoxy, piperazin-2-yloxymethoxy, piperidin-4-yloxyethoxy, and the like.

The term "heterocyclyloxyaliphatic" refers to an aliphatic group substituted with one or more heterocyclyloxy groups, wherein the aliphatic group and heterocyclyloxy group are as defined herein. Some non-limiting examples include pyrrol-2-yloxymethyl, piperazin-3-yloxyethyl, piperazin-2-yloxyethyl, morpholin-2-yloxymethyl, piperidin-2-yloxyethyl, and the like.

The term "heterocyclylaminoaliphatic" refers to an aliphatic group substituted with one or more heterocyclylamino groups, wherein the aliphatic group and heterocyclylamino group are as defined herein. Some non-limiting examples include pyrrol-2-ylaminomethyl, piperazin-3-lyaminoethyl, piperazin-2-lyaminoethyl, piperidin-2-lyaminoethyl, morpholin-2-lyaminomethyl, and the like.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to a moiety having one or more units of unsaturation.

The term "alkoxy" refers to an alkyl group, as previously defined, attached to the principal carbon chain through an oxygen ("alkoxy") atom. Some non-limiting examples include methoxy, ethoxy, propoxy, butoxy, and the like. And the alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxyalkoxy" refers to an alkoxy group substituted with one or more hydroxy groups, wherein the alkoxy group is as defined above. Some non-limiting examples include hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples include aminomethoxy, 2-aminoethoxy, 2-aminopropoxy, 2-aminoisopropoxy, and the like.

The term "azidoalkoxy" refers to an alkoxy group substituted with one or more azido groups, wherein the alkoxy group is as defined above. Some non-limiting examples include 2-azidoethoxy, 3-azidopropoxy, 2-azidopropoxy, and the like.

The term "alkoxyalkoxy" refers to an alkoxy group substituted with one or more alkoxy groups, wherein the alkoxy group is as defined above. Some non-limiting examples include methoxymethoxy, methoxyethoxy, ethoxymethoxy, ethoxyethoxy, ethoxypropoxy, and the like.

The term "alkoxyaliphatic" refers to an aliphatic group substituted with one or more alkoxy groups, wherein the aliphatic group and alkoxy group are as defined herein. Some non-limiting examples include methoxymethyl, ethoxymethyl, ethoxyethyl, ethoxypropenyl, and the like.

The term "alkylaminoaliphatic" refers to an aliphatic group substituted with one or more alkylamino groups, wherein the aliphatic group and alkylamino group are as defined herein. Some non-limiting examples include dimethylaminoethyl, methylaminoethyl, diethylaminomethyl, diethylaminoethyl, and the like.

The term "alkylthioaliphatic" refers to an aliphatic group substituted with one or more alkylthio groups, wherein the aliphatic group and alkylthio group are as defined herein. Some non-limiting examples include methylthioethyl, methylthiopropyl, ethylthioethyl, methylthiopropenyl, and the like.

The term "haloalkyl", "haloalkenyl" or "haloalkoxy" refers to an alkyl group, alkenyl group or alkoxy group substituted with one or more halogen atoms. Some non-limiting examples include trifluoromethyl, 2-chloro-ethenyl, trifluoromethoxy, and the like.

The term "aryl" used alone or as part of a larger moiety as in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthryl. The aryl may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "arylaliphatic" refers to an aliphatic group substituted with one or more aryl groups, wherein the aliphatic group and the aryl group are as defined herein. Some non-limiting examples include phenylethyl, benzyl, (p-tolyl)ethyl, styryl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non-limiting examples include phenyloxy, methylphenyloxy, ethylphenyloxy, and the like.

The term "arylamino" refers to an amino group substituted with one or two aryl groups, wherein the aryl group is as defined herein. Some non-limiting examples include phenylamino, (p-fluorophenyl)amino, diphenylamino, ditolylamino, (di-p-tolyl)amino, and the like.

The term "aryloxyalkoxy" refers to an alkoxy group substituted with one or more aryloxy groups, wherein the alkoxy group and the aryloxy group are as defined herein. Some non-limiting examples include phenyloxymethoxy, phenyloxyethoxy, phenyloxypropoxy, and the like.

The term "aryloxyaliphatic" refers to an aliphatic group substituted with one or more aryloxy groups, wherein the aryloxy group and the aliphatic group are as defined herein. Some non-limiting examples include phenyloxymethyl, phenyloxyethyl, phenyloxypropyl, and the like.

The term "arylaminoaliphatic" refers to an aliphatic group substituted with one or more arylamino groups, wherein the arylamino group and the aliphatic group are as defined herein. Some non-limiting examples include phenylaminomethyl, phenylaminoethyl, tolylaminoethyl, phenylaminopropyl, phenylaminoallyl, and the like.

The term "arylalkoxy" refers to an alkoxy group substituted with one or more aryl groups, wherein the aryl group and the alkoxy group are as defined herein. Some non-limiting examples include phenylmethoxy, phenylethoxy, (p-tolyl)methoxy, phenylpropoxy, and the like.

The term "arylalkylamino" refers to an alkylamino group substituted with one or more aryl groups, wherein the aryl group and the alkylamino group are as defined herein. Some non-limiting examples include phenylmethylamino, phenylethylamino, phenylpropylamino, (p-tolyl)methylamino, and the like.

The term "heteroaryl" used alone or as part of a larger moiety as in "heteroarylalkyl" or "heteroarylalkoxy" refers to monocyclic, bicyclic, and tricyclic ring systems having a total of five to fourteen ring members, wherein at least one ring in the system is aromatic, and at least one ring in the system is inclusive of one or more hetero atoms, wherein each ring in the system contains 3 to 7 ring members and that has a single point of attachment to the rest of the molecule. The term "heteroaryl" may be used interchangeably with the term "heteroaryl ring" or "heteroaromatic compound". The heteroaryl defined herein may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazolyl-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidine-5-yl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, pyrazine-2-yl, 1,3,5-triazinyl, benzo[d]thiazol-2-yl, imidazo[1,5-a]pyridin-6-yl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to an optionally substituted aryl radical, as defined herein, attached to an oxygen atom, wherein the oxygen atom serves as the attaching point to the rest of the molecule. Some non-limiting examples include pyrid-2-yloxy, thiazol-2-yloxy, imidazol-2-yloxy, pyrimidin-2-yloxy, and the like.

The term "heteroaryloxyaliphatic" refers to an aliphatic group substituted with one or more heteroaryloxy groups, wherein the aliphatic group and the heteroaryloxy group are as defined herein. Some non-limiting examples include pyrid-2-yloxyethyl, thiazol-2-yloxymethyl, imidazol-2-yloxyethyl, pyrimidin-2-yloxypropyl, and the like.

The term "sulfonyl", whether used alone or linked to other terms such as "alkylsulfonyl", refers to respectively divalent radicals —SO$_2$—. The term "alkylsulfonyl", refers to a sulfonyl radical substituted with an alkyl radical, forming an alkylsulfonyl (—SO$_2$CH$_3$).

The term "sulfamyl", "aminosulfonyl" or "sulfonamidyl" refer to a sulfonyl radical substituted with an amine radical, forming a sulfonamide (—SO$_2$NH$_2$).

The term "carboxy" or "carboxyl", whether used alone or with other terms, such as "carboxyalkyl", refers to —CO$_2$H.

The term "carbonyl", whether used alone or with other terms, such as "aminocarbonyl" or "carbonyloxy", refers to —(C=O)—.

The term "carboxyalkoxy" refers to an alkoxy group substituted with one or more carboxy groups, wherein the alkoxy group and the carboxy group are as defined herein. Some non-limiting examples include carboxymethoxy, carboxyethoxy, and the like.

The term "aralkyl" or "arylalkyl" refers to aryl-substituted alkyl radicals. In some embodiments, aralkyl radicals are "lower aralkyl" radicals having aryl radicals attached to alkyl radicals having one to six carbon atoms. In other embodiments, aralkyl radicals are "phenylalkylenyl" attached to alkyl portions having one to three carbon atoms. Some non-limiting examples of such radicals include benzyl, diphenylmethyl and phenylethyl. The aryl in said aralkyl can be additionally substituted with halo, alkyl, alkoxy, haloalkyl or haloalkoxy.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" include methylthio (CH$_3$S—).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino" wherein amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "alkylaminohaloalkoxy" refers to a haloalkoxy group substituted with one or more alkylamino groups, wherein the haloalkoxy group and the alkylamino group are as defined herein. Some non-limiting examples include methylaminodifluoromethoxy, ethylaminotrifluoromethoxy, and the like.

The term "heteroarylamino" refers to amino groups substituted with one or two heteroaryl radicals, wherein the heteroaryl radical is as defined herein. Some non-limiting examples of heteroarylamino include N-thienylamino. In other embodiments, the "heteroarylamino" radicals include substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of heteroarylaliphatic include thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein. Some non-limiting examples of heteroarylalkyl include imidazol-2-methyl, furan-2-ethyl, indol-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of heteroarylalkylamino include pyridin-2-methylamino, thiazol-2-ethylamino, imidazol-2-ethylamino, pyrimidin-2-propylamino, pyrimidin-2-methylamino, and the like.

The term "aminoalkyl" refers to a linear or branched-alkyl radical having one to ten carbon atoms, substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl and aminohexyl.

The term "alkylaminoalkyl" refers to alkyl radicals substituted with alkylamino radicals. In some embodiments, alkylaminoalkyl radicals are "lower alkylaminoalkyl" radicals having alkyl radicals of one to six carbon atoms. In other embodiments, alkylaminoalkyl radicals are lower alkylaminoalkyl radicals having alkyl radicals of one to three carbon atoms. Some non-limiting examples of suitable alkylaminoalkyl radicals include mono and dialkyl substituted, such as N-methylaminomethyl, N,N-dimethyl-aminoethyl, N,N-diethylaminomethyl, and the like.

The term "carboxyalkyl" refers to a linear or branched alkyl radical having one to ten carbon atoms substituted with one or more carboxy radicals. Some non-limiting examples of such radicals include carboxymethyl, carboxypropyl, and the like.

The term "aryloxy" refers to optionally substituted aryl radicals, as defined above, attached to an oxygen atom, wherein the oxygen atom serves as the attaching point to the rest of the molecule. Some non-limiting examples of such radicals include phenoxy.

The term "heteroarylalkoxy" refers to oxy-containing heteroarylalkyl radicals attached through an oxygen atom to other radicals, wherein the heteroarylalkyl radical is as defined herein. Some non-limiting examples of such radicals include pyridin-2-ylmethoxy, thiazol-2-ylethoxy, imidazol-2-ylethoxy, pyrimidin-2-ylpropoxy, pyrimidin-2-ylmethoxy, and the like.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The term "fused bicyclic", "fused cyclic", "fused bicyclyl" or "fused cyclyl" refer to unsaturated or saturated fused cyclic system and bridged ring system that is not aromatic. For example, as depicted below (Formula (a1)), ring A1 and ring A2 share a bond that is a alkyl or heteroalkyl chain, wherein j is 0, 1, 2, 3 or 4. Such a system may contain isolated or conjugated unsaturation, but not aromatic or heteroaromatic rings in its core structure (but may have aromatic substitution thereon). Each cyclic ring in a fused bicyclyl can be either a carbocyclic or a heteroalicyclic. Some non-limiting examples of fused bicyclic ring system or bridged ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, bicyclo[2.2.1]heptane, 2-azabicyclo[2.2.1]heptane, and 1,2,3,4,4a,5,8,8a-octahydro-naphthalene. The fused bicyclyl defined herein may be substituted or unsubstituted, wherein the substituents include, but are not limited to, deuterium, oxo (═O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxy alkoxy, and the like.

(a1)

The term "fused heterobicyclyl" refers to unsaturated or saturated fused cyclic system and bridged ring system that is not aromatic. Such a system may contain isolated or conjugated unsaturation, but not aromatic or heteroaromatic rings in its core structure (but may have aromatic substitution thereon). And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or SO$_2$, PO or PO$_2$. Some non-limiting examples of fused heterobicyclic ring system include hexahydro-furo[3,2-b]furan, 6-azabicyclo[3.2.0]heptane, 2-azabicyclo[3.1.0]heptane, 3-azabicyclo[3.1.0]heptane, 2-azabicyclo[2.2.1]heptane, and the like. The fused heterobicyclyl defined herein may be substituted or unsubstituted, wherein the substituents include, but are not limited to, deuterium, oxo (═O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxy alkoxy, and the like.

The term "spirocyclyl", "spirocyclic", "spiro bicyclyl" or "spiro bicyclic" refers to a ring originating from a particular annular carbon of another ring. For example, as depicted below, ring A and ring B share a carbon atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples of such radicals include 2,7-diazaspiro[4.4]non-2-yl, 7-oxo-2-azaspiro[4.5]dec-2-yl, 4-azaspiro[2.4]hept-5-yl, 4-oxaspiro[2.4]hept-5-yl, 5-azaspiro[2.4]hept-5-yl, spiro[2.4]heptyl, spiro[4.4]nonyl, 7-hydroxy-5-azaspiro[2.4]hept-5-yl, and the like. The spirocyclyl or spiro bicyclyl may be substituted or unsubstituted, wherein the substituents include, but are not limited to, oxo (═O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxy alkoxy, and the like.

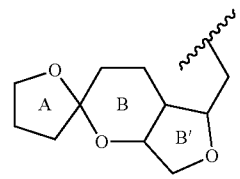

The term "spiro bicyclylene" refers to spiro bicyclyl system having two connection points connected to the rest of the molecule, wherein spiro bicyclyl radical is as defined herein.

The terms "spiro heterobicyclyl" refers to a ring originating from a particular annular carbon of another ring. For example, as depicted above, ring A and ring B share a carbon atom between the two saturated ring system, which terms as a "spirocyclyl". And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or SO$_2$, PO or PO$_2$. Some non-limiting examples of such radicals include 4-azaspiro[2,4]hept-5-yl, 4-oxaspiro[2,4]hept-5-yl, 5-azaspiro[2,4]hept-5-yl, 7-hydroxy-5-azaspiro[2,4]hept-5-yl, 5-azaspiro[2,4]hept-6-yl, 1,4-dioxo-7-azaspiro[4,4]non-8-yl, and the like. The spiro heterobicyclyl defined herein may be substituted or unsubstituted, wherein the substituents include, but are not limited to, oxo (═O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxy alkoxy, and the like.

As described herein, the group derived from α-amino acid refers to an α-amino acid radical derived from an α-amino acid by the removal of one hydroxy in carboxy, which attached to X or X', and the group derived from α-amino acid is optionally substituted with one or more substituents, wherein the substituent is deuterium, F, Cl, Br, I, hydroxy or cyano. For example,

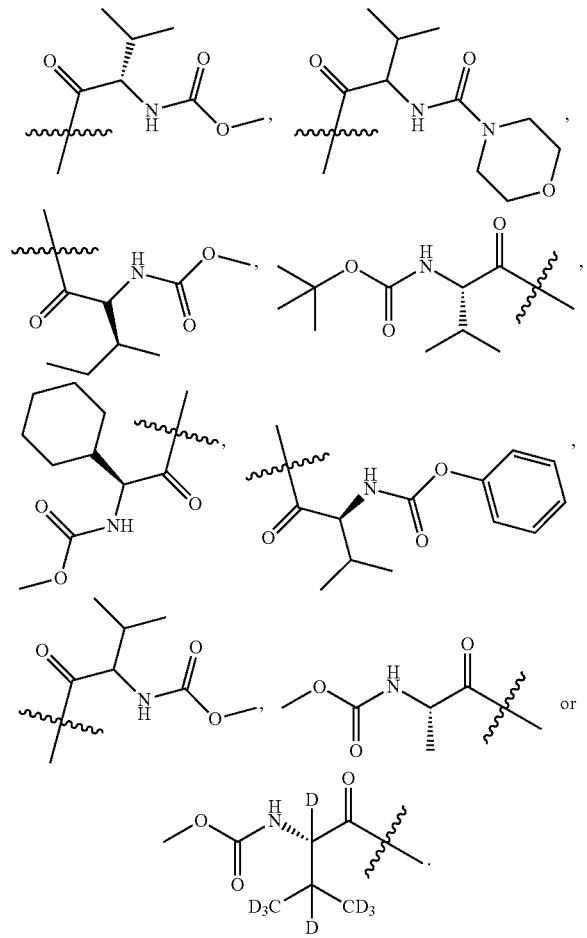

As described herein, a bond drawn from a substituent to the center of one ring within a ring system (as shown in Figure a) represents substitution of the substituent $(R^{5a})_f$ at any substitutable position on the rings (W1, W2, and W). For example, Figure a represents possible substitution in any of the positions on the W1, W2, and W ring.

Figure (a)

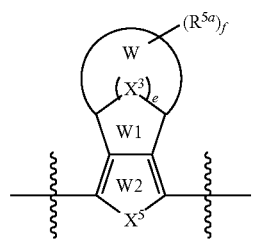

As described herein, two attaching points either E or E', within a ring system (as shown in Figure b), attach to the rest of the molecule, e.g., E and E' may be used interchangeably with each other.

Figure (b)

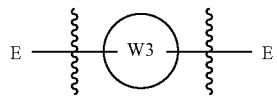

As described herein, a dot line drawn together with a bond within a ring system (as shown in Figure c) represents either a double bond or a single bond. For example, structure in Figure c represents any structures selected from Figure d.

Figure (c)

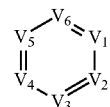

Figure (d)

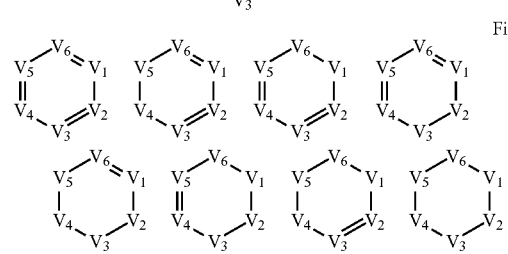

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66: 1-19, which is incorporated herein by reference. Some non-limiting examples of pharmaceutically salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, sodium malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see Greene et al., Protective Groups in Organic Synthesis, John Wiley & Sons, New York, 1991 and Kocienski et al., Protecting Groups, Thieme, Stuttgart, 2005.

DESCRIPTION OF COMPOUNDS OF THE INVENTION

Disclosed herein are bridge ring compounds, and pharmaceutical formulations thereof, that are useful in inhibiting HCV infection, especially inhibiting the activity of the nonstructural 5A ("NS5A") protein.

In one aspect, provided herein are compounds having Formula (I) as shown below:

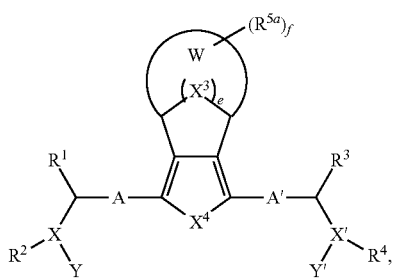
(I)

or a stereoisomer, a geometric isomer, a tautomer, an N-oxide, a hydrate, a solvate, a metabolite, a pharmaceutically acceptable salt or a prodrug thereof, wherein each of A and A' is independently a bond, alkyl, alkenyl, cycloalkyl, heterocycloalkyl, —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, or —(CR$^8$R$^{8a}$)$_n$—N(R$^5$)—C(=O)—O—(CR$^8$R$^{8a}$)$_p$—, or each of A and A' is independently

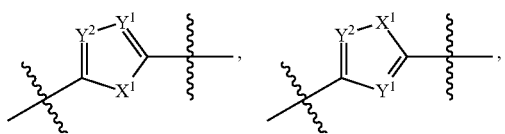

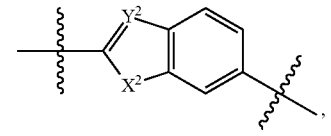

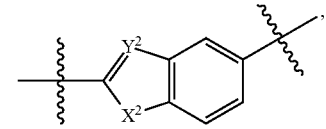

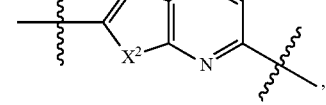

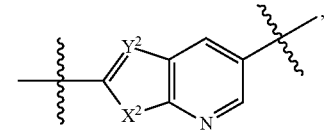

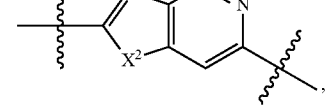

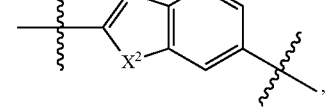

-continued

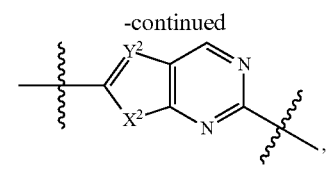

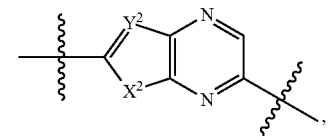

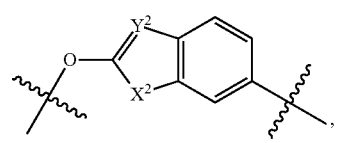

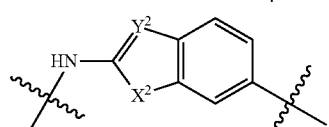

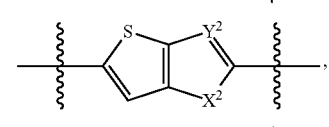

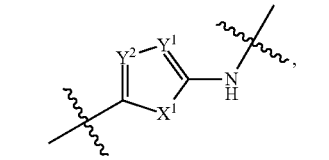

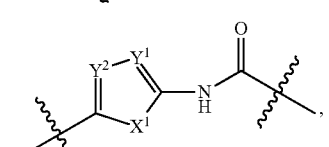

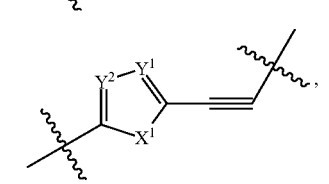

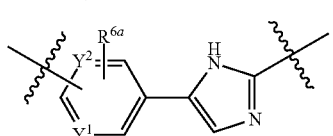

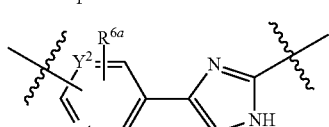

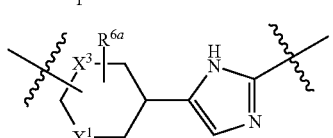

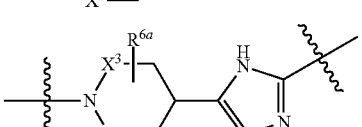

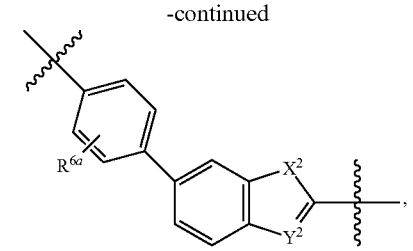,
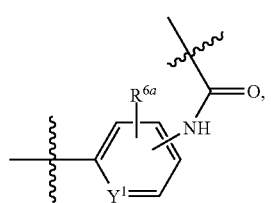,
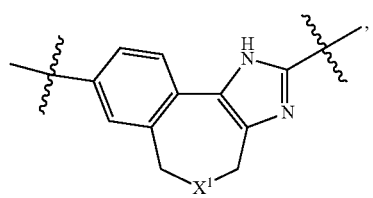,
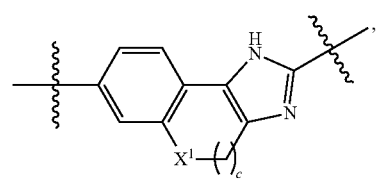,
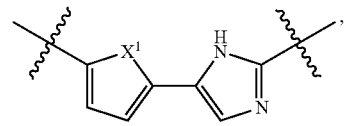,
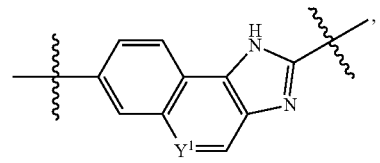,
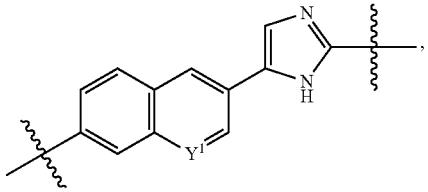,
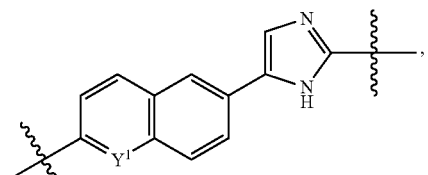,
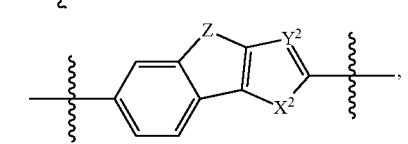,
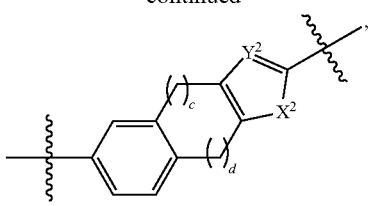,
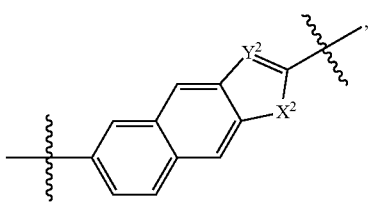,
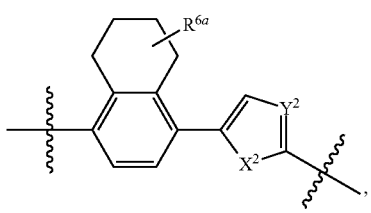,
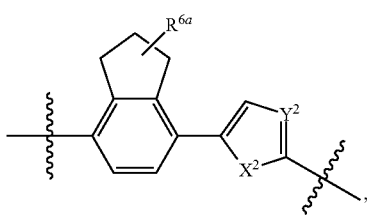,
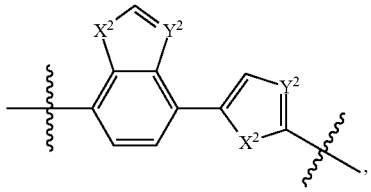,
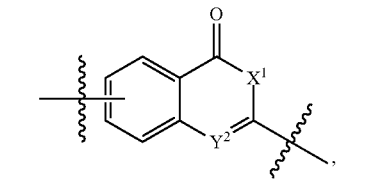,
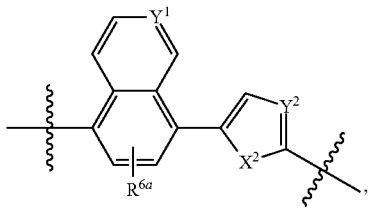,
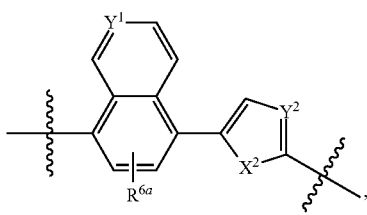,

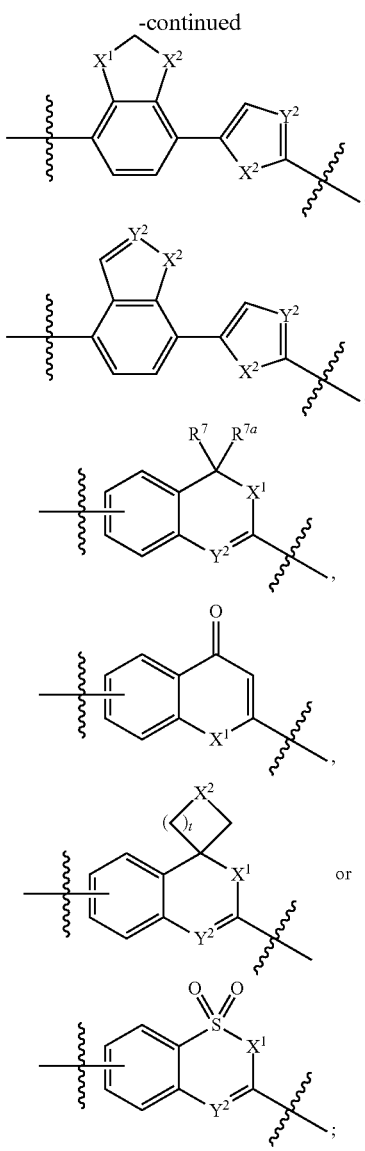

wherein each $X^1$ is independently O, S, $NR^6$, or $CR^7R^{7a}$;
each $X^2$ is independently $NR^6$, O or S;
each $X^3$ is independently O, S, $NR^6$, C(=O) or $CR^7R^{7a}$;
$X^4$ is $(CR^7R^{7a})_n$,

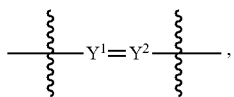

O, S or $NR^6$;

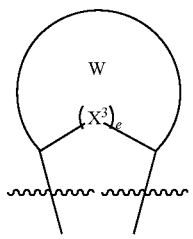

is carbocyclyl or heterocyclyl;
each $Y^1$ and $Y^2$ is independently N or $CR^7$;

Z is —$(CH_2)_a$—, —CH=CH—, —N=CH—, —$(CH_2)_a$—$N(R^5)$—$(CH_2)_b$—, or —$(CH_2)_a$—O—$(CH_2)_b$—, wherein each a and b is independently 0, 1, 2 or 3;
each c is independently 1 or 2;
each d is independently 1 or 2;
each n is independently 0, 1, 2 or 3;
each p is independently 0, 1, 2 or 3;
each r is independently 0, 1 or 2;
e is 0, 1, 2, 3 or 4 with the proviso that where $X^3$ is O, S or $NR^6$, e is 1;
f is 0, 1, 2, 3 or 4;
each of X and X' is independently N or $CR^7$;
each of Y and Y' is independently H, deuterium, alkyl, heteroalkyl, cycloalkyl, heterocyclyl, aryl, heteroaryl, aralkyl, a group derived from α-amino acid or an optical isomer thereof, or each of Y and Y' is independently —[U—$(CR^9R^{9a})_t$—$N(R^{10})$—$(CR^9R^{9a})_t]_k$—U—$(CR^9R^{9a})_t$—N$(R^{11})$—$(CR^9R^{9a})_t$—$R^{12}$, —U—$(CR^9R^{9a})_t$—$R^{12}$ or —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$;
each U is independently —C(=O)—, —C(=S)—, —S(=O)— or —S(=O)$_2$—;
each t is independently 0, 1, 2, 3 or 4;
each k is independently 0, 1 or 2;
each of $R^1$, $R^2$, $R^3$ and $R^4$ is independently H, deuterium, alkyl, heteroalkyl, aralkyl, cycloalkyl, heterocyclyl, heteroaryl or aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle;
each $R^5$ is independently H, deuterium, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;
each $R^{5a}$ is independently H, deuterium, oxo (=O), hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N$($R^{7a}$)—, $R^{7a}R^7N$-alkyl, $R^7S$(=O)-alkyl, $R^7R^{7a}N$—C(=O)-alkyl, $R^{7a}R^7N$-alkoxy, $R^7S$(=O)-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;
each $R^6$ is independently H, deuterium, $R^7R^{7a}NC$(=O)—, $R^7OC$(=O)—, $R^7C$(=O)—, $R^7R^{7a}NS$(=O)—, $R^7OS$(=O)—, $R^7S$(=O)—, $R^7R^{7a}NS$(=O)$_2$—, $R^7OS$(=O)$_2$—, $R^7S$(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;
each $R^{6a}$ is independently H, deuterium, hydroxy, amino, F, Cl, Br, I, cyano, oxo (=O), $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, R⁷R⁷ᵃN—S(=O)₂—, R⁷S(=O)₂—, R⁷S(=O)₂N(R⁷ᵃ)—, R⁷ᵃR⁷N-alkyl, R⁷S(=O)-alkyl, R⁷R⁷ᵃN—C(=O)-alkyl, R⁷ᵃR⁷N-alkoxy, R⁷S(=O)-alkoxy, R⁷R⁷ᵃN—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino, or aryloxy;

each R⁷ and R⁷ᵃ is independently H, deuterium, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylamino aliphatic, heterocyclylaminoaliphatic, cycloalkylaminoaliphatic, aryl, heteroaryl, heterocyclyl or carbocyclyl, with the proviso that where R⁷ and R⁷ᵃ are bonded to the same nitrogen atom, R⁷ and R⁷ᵃ, together with the nitrogen atom they are attached to, optionally form a substituted or unsubstituted 3-8 membered ring, or a substituted or unsubstituted spiro or fused bicyclic ring;

each R⁸ and R⁸ᵃ is independently H, deuterium, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)ₑ—, alkyl-S(=O)ₑ—, alkyl-S(=O)ₑ—, or aminosulfonyl;

each R⁹, R⁹ᵃ, R¹⁰ and R¹¹ is independently H, deuterium, alkyl, heteroalkyl, cycloalkyl, heterocyclyl, aryl, heteroaryl, aralkyl, haloalkyl, hydroxyalkyl, heteroarylalkyl, heterocyclylalkyl, or cycloalkylalkyl;

each R¹² is independently R¹³ᵃR¹³N—, —C(=O)R¹³, —C(=S)R¹³, —C(=O)—O—R¹³, —C(=O)NR¹³R¹³ᵃ, —OC(=O)NR¹³R¹³ᵃ, —OC(=O)OR¹³, —N(R¹³)C(=O)NR¹³R¹³ᵃ, —N(R¹³)C(=O)OR¹³ᵃ, —N(R¹³)C(=O)—R¹³ᵃ, R¹³R¹³ᵃN—S(=O)₂—, R¹³S(=O)₂—, R¹³S(=O)₂N(R¹³ᵃ)—, R¹³OS(=O)₂—, alkyl, heteroalkyl, cycloalkyl, heterocyclyl, aryl, heteroaryl or aralkyl; or R¹¹ and R¹² are optionally joined to form a 4-7 membered ring; and each R¹³ and R¹³ᵃ is independently H, deuterium, alkyl, heteroalkyl, cycloalkyl, heterocyclyl, aryl, heteroaryl, or aralkyl;

wherein each of —(CR⁸R⁸ᵃ)ₙ—O—(CR⁸R⁸ᵃ)ₚ—, —(CR⁸R⁸ᵃ)ₙ—N(R⁵)—(CR⁸R⁸ᵃ)ₚ—, —(CR⁸R⁸ᵃ)ₙ—S(=O)ᵣ—N(R⁵)—(CR⁸R⁸ᵃ)ₚ—, —(CR⁸R⁸ᵃ)ₚ—C(=O)—N(R⁵)—(CR⁸R⁸ᵃ)ₚ—, —(CR⁸R⁸ᵃ)ₙ—N(R⁵)—C(=O)—N(R⁵)—(CR⁸R⁸ᵃ)ₚ—, —(CR⁸R⁸ᵃ)ₙ—C(=O)—O—(CR⁸R⁸ᵃ)ₚ—, —(CR⁸R⁸ᵃ)ₙ—N(R⁵)—S(=O)ᵣ—N(R⁵)—(CR⁸R⁸ᵃ)ₚ—, —(CR⁸R⁸ᵃ)ₙ—N(R⁵)—C(=O)—O—(CR⁸R⁸ᵃ)ₚ—, —[U—(CR⁹R⁹ᵃ)ₜ—N(R¹⁰)—(CR⁹R⁹ᵃ)ₜ]ₖ—U—(CR⁹R⁹ᵃ)ₜ—N(R¹¹)—(CR⁹R⁹ᵃ)ₜ—R¹², —U—(CR⁹R⁹ᵃ)ₜ—R¹², [—U—(CR⁹R⁹ᵃ)ₜ—N(R¹⁰)—(CR⁹R⁹ᵃ)ₜ]ₖ—U—(CR⁹R⁹ᵃ)ₜ—O—(CR⁹R⁹ᵃ)ₜ—R¹², NR⁶, CR⁷R⁷ᵃ, CR⁷, —(CH₂)ₐ—, —CH=CH—, —N=CH—, —(CH₂)ₐ—N(R⁵)—(CH₂)ᵦ—, —(CH₂)ₐ—O—(CH₂)ᵦ—, R¹³ᵃR¹³N—, —C(=O)R¹³, —C(=S)R¹³, —C(=O)—O—R¹³, —C(=O)NR¹³R¹³ᵃ, —OC(=O)NR¹³R¹³ᵃ, —OC(=O)OR¹³, —N(R¹³)C(=O)NR¹³R¹³ᵃ, —N(R¹³)C(=O)OR¹³ᵃ, —N(R¹³)C(=O)—R¹³ᵃ, R¹³R¹³ᵃN—S(=O)₂—, R¹³S(=O)₂—, R¹³S(=O)₂N(R¹³ᵃ)—, R¹³OS(=O)₂—, R⁷ᵃR⁷N—, —C(=O)NR⁷R⁷ᵃ, —OC(=O)NR⁷R⁷ᵃ, —OC(=O)OR⁷, —N(R⁷)C(=O)NR⁷R⁷ᵃ, —N(R⁷)C(=O)OR⁷ᵃ, —N(R⁷)C(=O)—R⁷ᵃ, R⁷R⁷ᵃN—S(=O)₂—, R⁷S(=O)₂—, R⁷S(=O)₂N(R⁷ᵃ)—, alkyl-OC(=O)—, alkyl-C(=O)—, alkyl-OS(=O)—, alkyl-S(=O)ₑO—, alkyl-S(=O)ₑ—, R⁷R⁷ᵃNC(=O)—, R⁷OC(=O)—, R⁷C(=O)—, R⁷R⁷ᵃNS(=O)—, R⁷OS(=O)—, R⁷S(=O)—, R⁷R⁷ᵃNS(=O)₂—, R⁷OS(=O)₂—, R⁷ᵃR⁷N-alkyl, R⁷S(=O)-alkyl, R⁷R⁷ᵃN—C(=O)-alkyl, R⁷ᵃR⁷N-alkoxy, R⁷S(=O)-alkoxy, R⁷R⁷ᵃN—C(=O)-alkylamino, alkyl, heteroalkyl, carbocyclyl, cycloalkyl, heterocyclyl, heterocycloalkyl, aryl, heteroaryl, aralkyl, a group derived from α-amino acid, C₅₋₁₂ fused bicycle, C₅₋₁₂ fused heterobicycle, C₅₋₁₂ spiro bicycle, C₅₋₁₂ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted with one or more substituents, wherein the substituent is deuterium, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)₂—, hydroxy-substituted alkyl-S(=O)—, hydroxy-substituted alkyl-S(=O)₂—, or carboxy-substituted alkoxy.

In some embodiments,

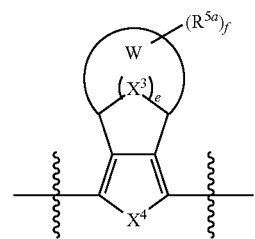

is

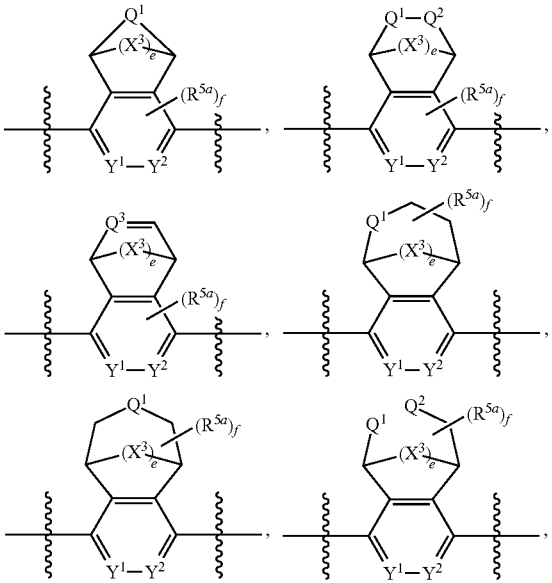

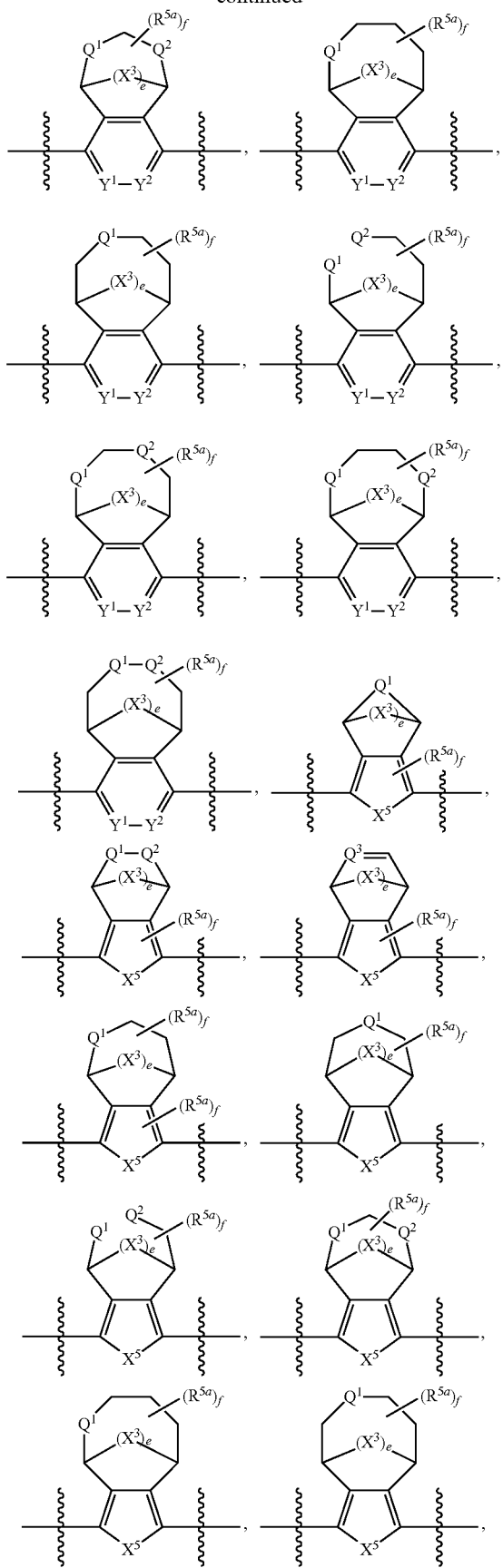

each $Y^1$ and $Y^2$ is independently N or $CR^7$;

each $X^3$ is independently O, S, $NR^6$, C(=O) or $CR^7R^{7a}$;

each $X^5$ is independently $CR^7R^{7a}$, O, S or $NR^6$;

each $Q^1$ and $Q^2$ is independently $NR^6$, O, S, C(=O), or $CR^7R^{7a}$;

each $Q^3$ is independently N or $CR^7$;

each e is independently 0, 1, 2, 3 or 4 with the proviso that where $X^3$ is O, S or $NR^6$, e is 1;

each f is independently 0, 1, 2 or 3;

each $R^{5a}$ is independently H, deuterium, oxo (=O), hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —$N(R^7)$C(=O)$NR^7R^{7a}$, —$N(R^7)$C(=O)$OR^{7a}$, —$N(R^7)$C(=O)—$R^{7a}$, $R^7R^{7a}N$—S(=O)$_2$—, $R^7S(=O)_2$—, $R^7S(=O)_2N(R^{7a})$—, $R^{7a}R^7N$—$C_{1-6}$ alkyl, $R^7S(=O)$—$C_{1-6}$ alkyl, $R^7R^{7a}N$—C(=O)—$C_{1-6}$ alkyl, $R^{7a}R^7N$—$C_{1-6}$ alkoxy, $R^7S(=O)$—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aralkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino or $C_{6-10}$ aryloxy;

each $R^6$ is independently H, deuterium, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl, $C_{6-10}$ aryl, $C_{3-9}$ heterocyclyl or $C_{3-8}$ carbocyclyl; and each $R^7$ and $R^{7a}$ is independently H, deuterium, F, Cl, $C_{1-6}$ alkyl, $C_{1-6}$ heteroalkyl, $C_{1-6}$ haloalkyl, hydroxy, amino, $C_{1-6}$ alkoxy, $C_{6-10}$ aryl, $C_{2-9}$ heterocyclyl, $C_{3-9}$ cycloalkyl, $C_{6-10}$ aryloxy, $C_{2-9}$ heterocyclyloxy, $C_{6-10}$ arylamino, $C_{2-9}$ heterocyclylamino, $C_{3-9}$ cycloalkylamino, $C_{1-9}$ heteroaryl or $C_{3-9}$ carbocyclyl, with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring.

In other embodiments,
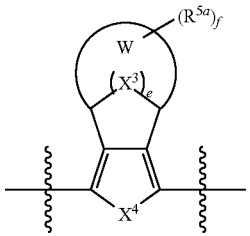
is
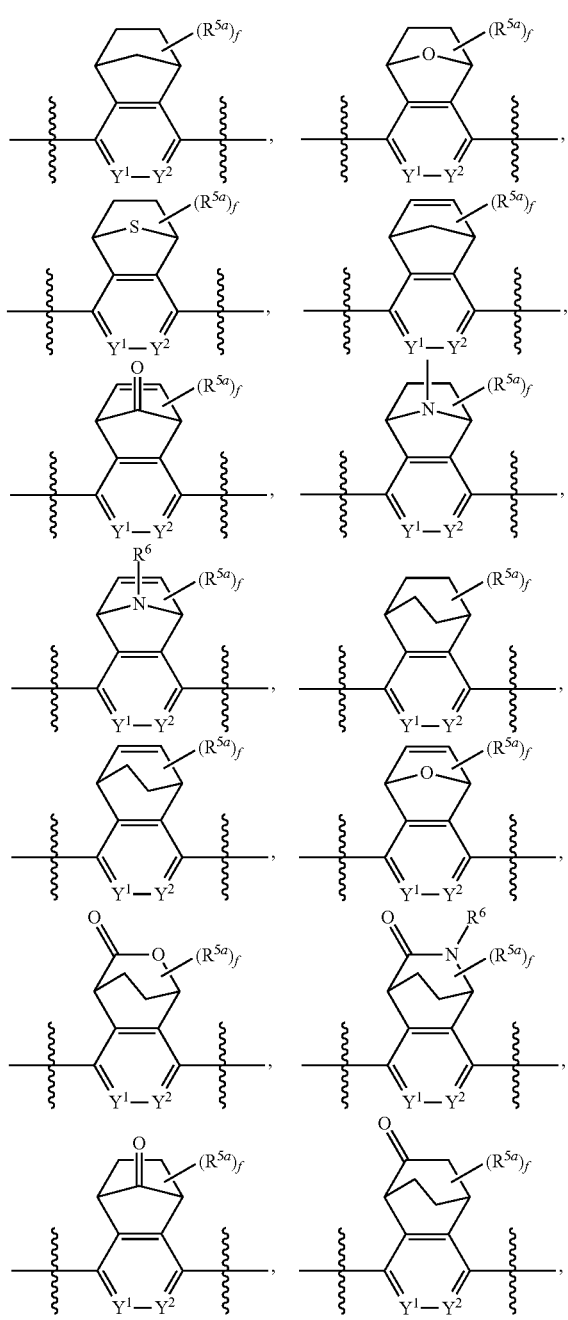
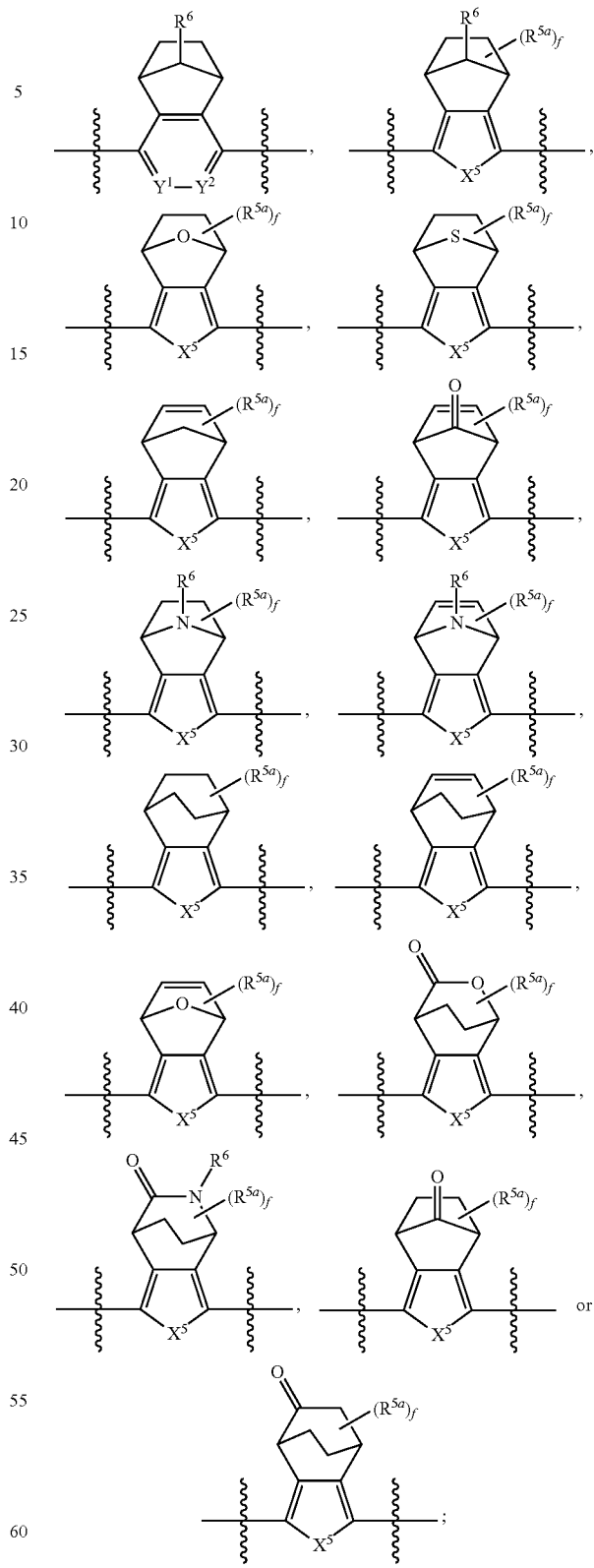
wherein each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, or $C_{1-6}$ alkylamino;

each $Y^1$ and $Y^2$ is independently N or $CR^7$;

each $X^5$ is independently $CR^7R^{7a}$, O, S, C(=O) or $NR^6$;

each f is independently 0, 1, 2 or 3; and each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl.

In other embodiments,

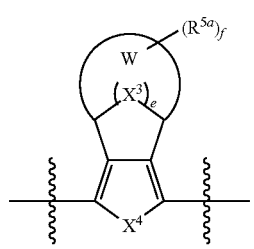

is

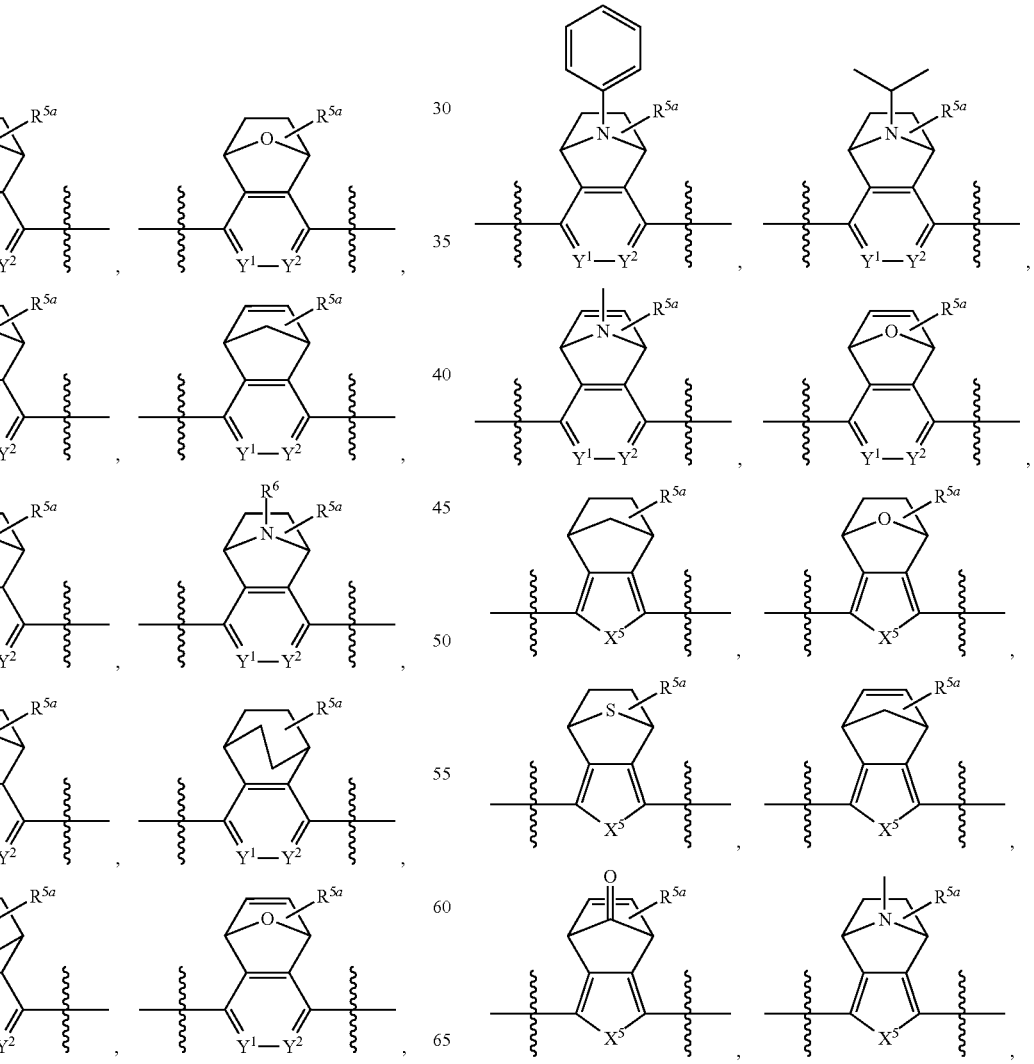

-continued

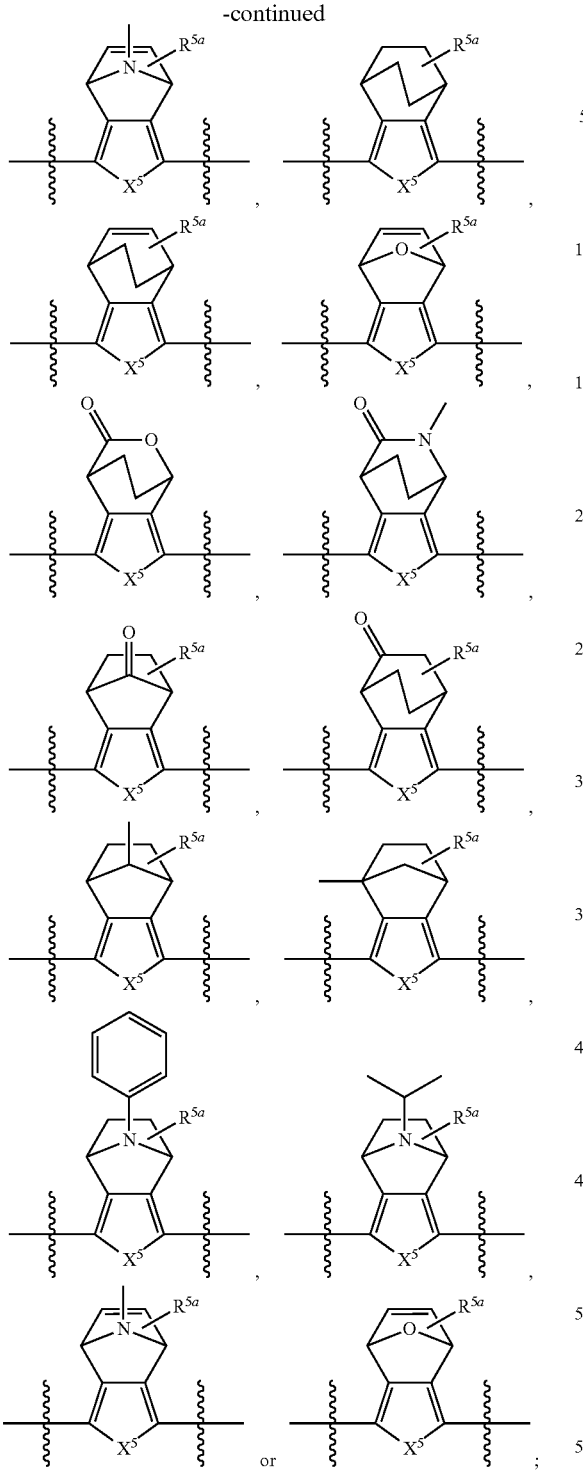

wherein each $R^{5a}$ is independently H, deuterium, oxo (=O), hydroxy, amino, F, Cl, Br, I, cyano, $C_{1-4}$ alkyl, —$CF_3$, —$OCF_3$, mercapto, nitro, or $C_{1-4}$ alkylamino;

each $Y^1$ and $Y^2$ is independently N or CH;

each $X^5$ is independently $CH_2$, O, S or $NR^6$; and each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$ alkyl, $C_{1-9}$ heteroaryl, $C_{6-10}$ aryl, $C_{3-9}$ heterocyclyl or $C_{3-8}$ carbocyclyl.

In some embodiments, each of A and A' is independently a bond, $C_{1-6}$ alkyl, $C_{2-6}$ alkenyl, $C_{3-8}$ cycloalkyl, $C_{2-10}$ heterocycloalkyl, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—N($R^5$)—C(=O)—O—$(CR^8R^{8a})_p$—, or each of A and A' is independently

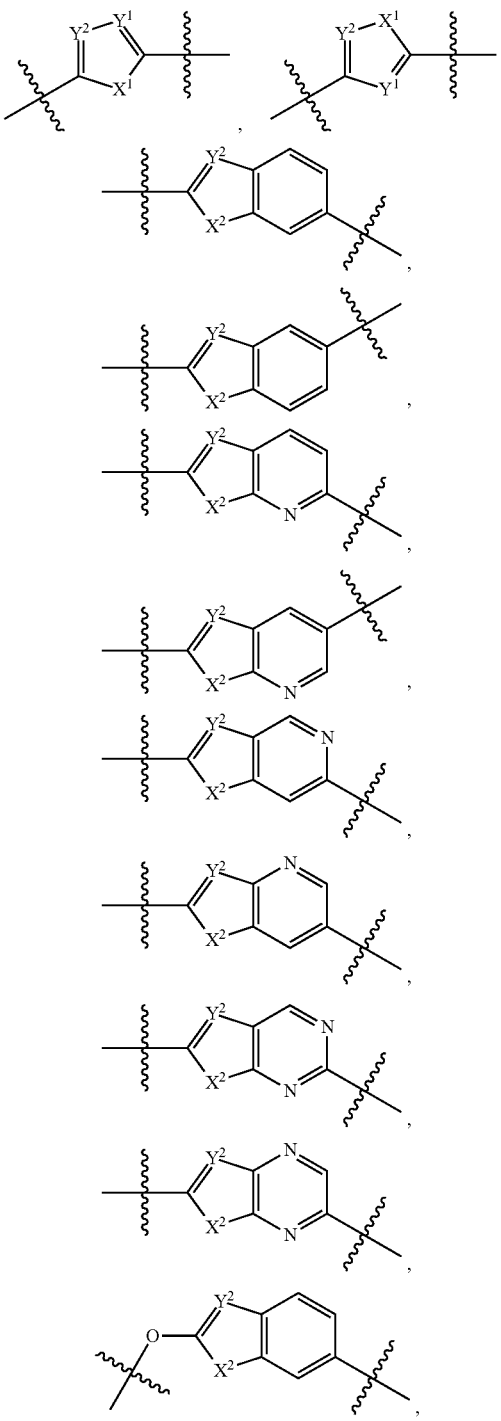

-continued
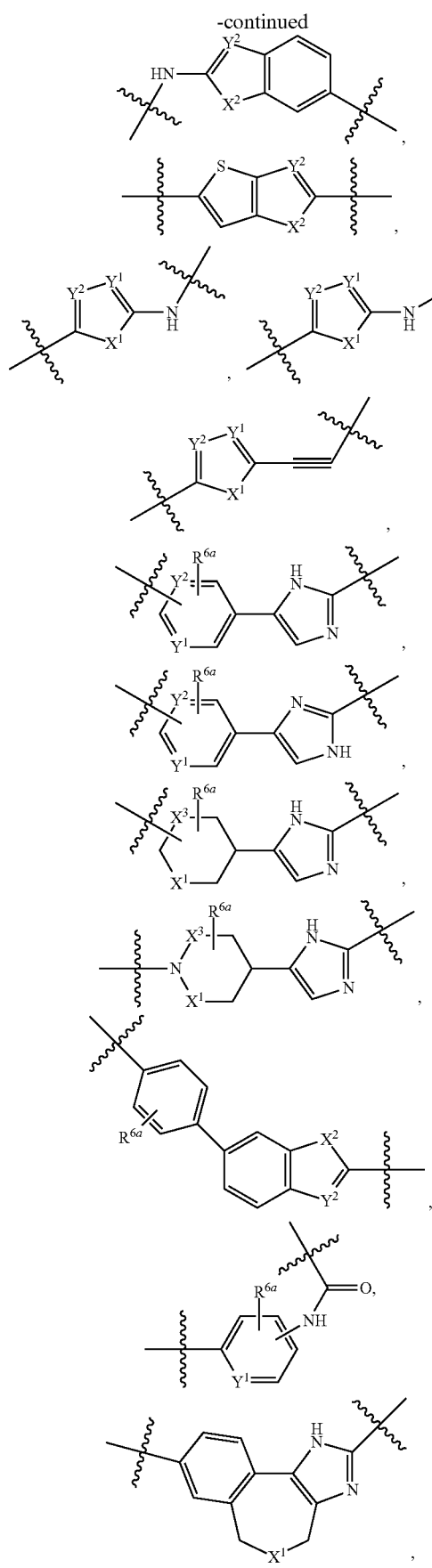
,
-continued
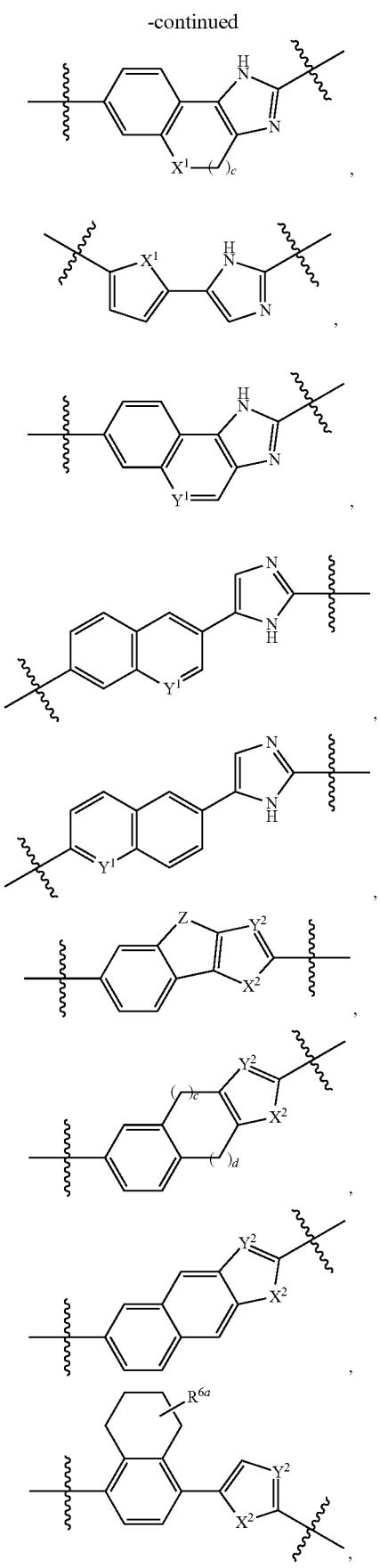
,

-continued

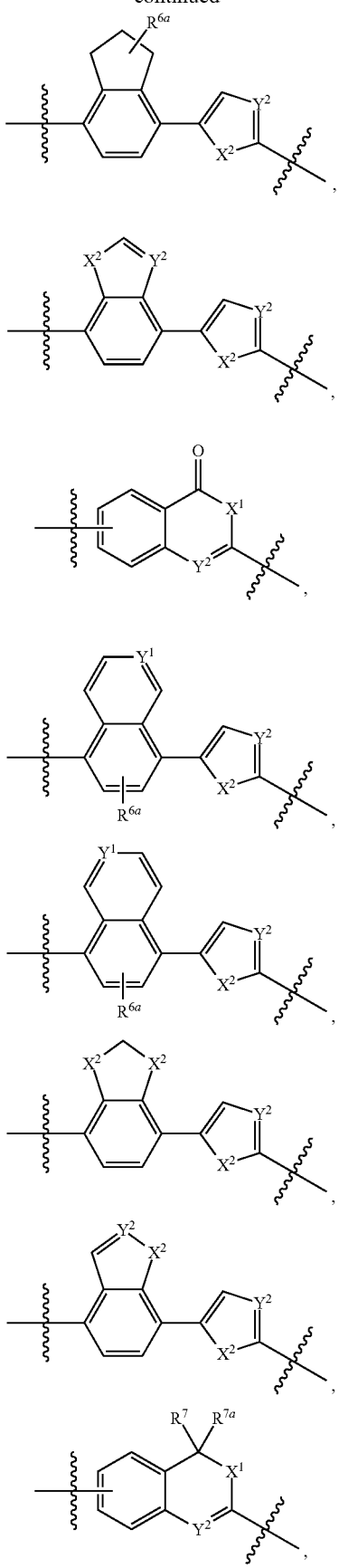

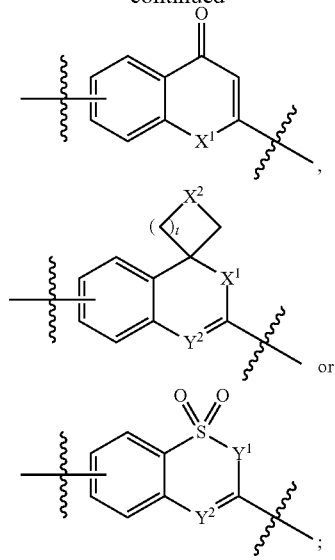

wherein each $R^5$ is independently H, deuterium, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each $R^{6a}$ is independently H, deuterium, oxo (=O), hydroxy, amino, F, Cl, Br, I, cyano, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N—$C_{1-6}$ alkyl, R$^7$S(=O)—$C_{1-6}$ alkyl, R$^7$R$^{7a}$N—C(=O)—$C_{1-6}$ alkyl, R$^{7a}$R$^7$N—$C_{1-6}$ alkoxy, R$^7$S(=O)—$C_{1-6}$ alkoxy, R$^7$R$^{7a}$N—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino, or $C_{6-10}$ aryloxy;

each $R^7$ and $R^{7a}$ is independently H, deuterium, F, Cl, $C_{1-6}$ alkyl, $C_{1-6}$ heteroalkyl, $C_{1-6}$ haloaliphatic, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heterocyclyl-$C_{1-6}$-alkyl, $C_{3-8}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-8}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-8}$ cycloalkylamino-$C_{1-6}$-alkyl, $C_{6-10}$ aryl, $C_{1-9}$ heteroaryl, $C_{2-10}$ heterocyclyl, or $C_{3-8}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted $C_{5-12}$ spiro or fused bicyclic ring; and each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl.

In some embodiments, each of A and A' is independently a bond, —CH$_2$—, —(CH$_2$)$_2$—, —CH=CH—, —CH=CH—CH$_2$—, —N(R$^6$)—, —C(=O)—, —C(=S)—, —C(=O)—

O—, —C(=O)N(R⁶)—, —OC(=O)N(R⁶)—, —OC(=O)O—, —N(R⁶)C(=O)N(R⁶)—, —(R⁶)N—S(=O)₂—, —S(=O)₂—, —OS(=O)₂—, —(R⁶)N—S(=O)—, —S(=O)—, —OS(=O)—, or each of A and A' is independently
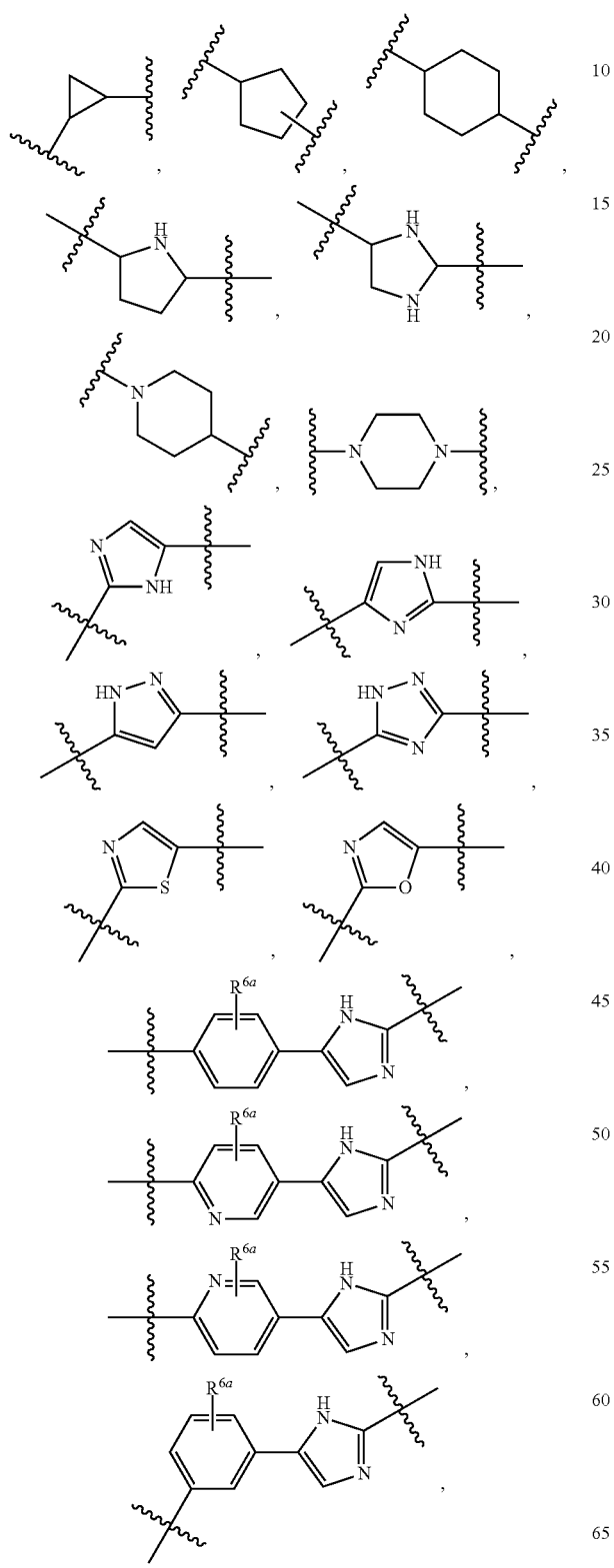
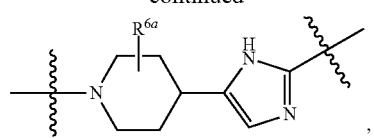
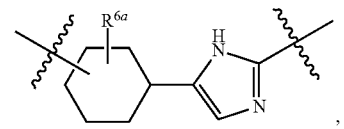
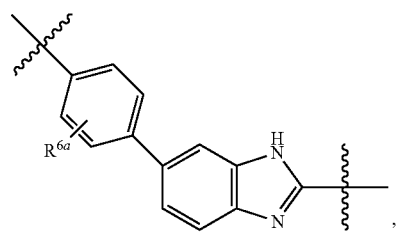
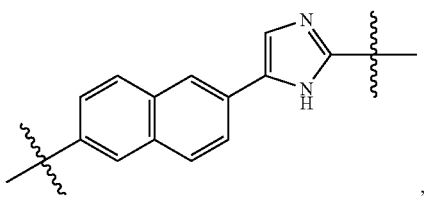
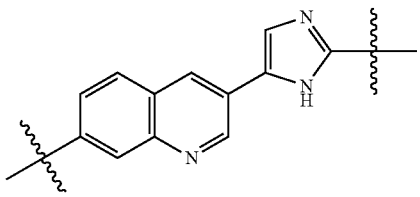
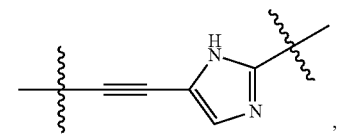
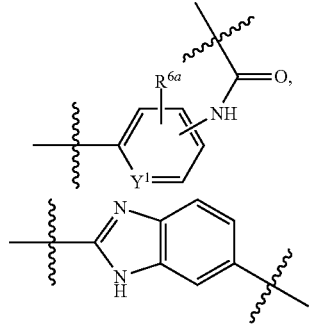
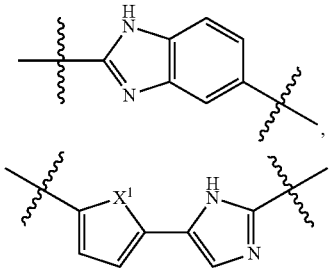

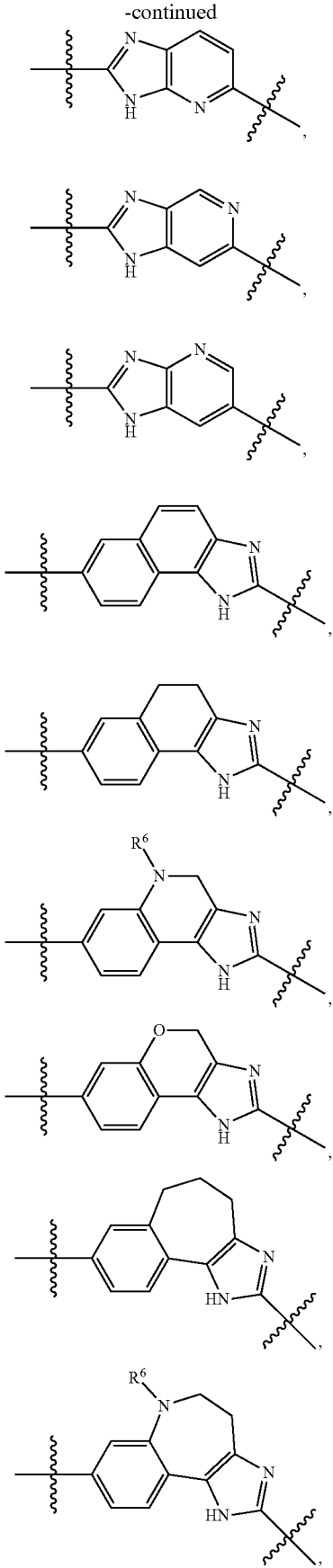
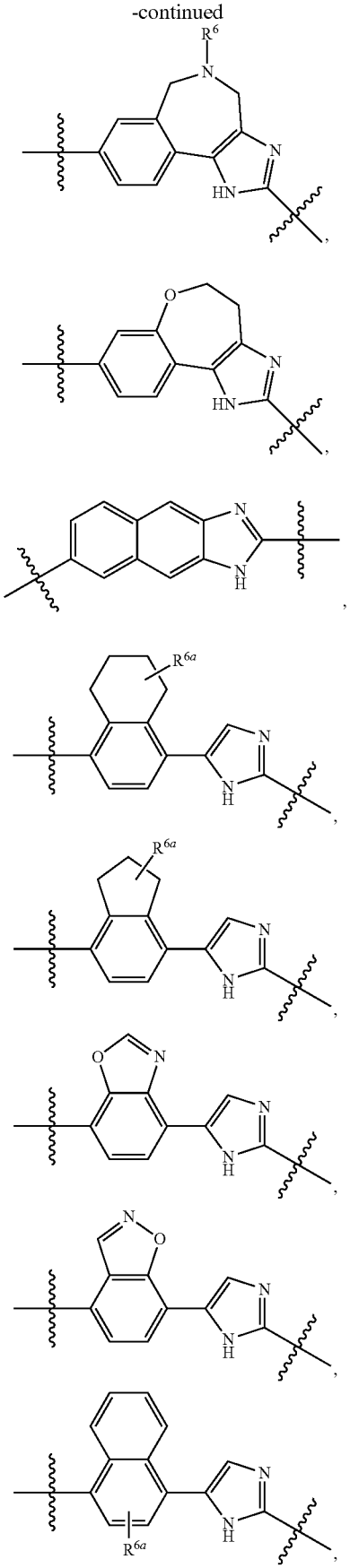

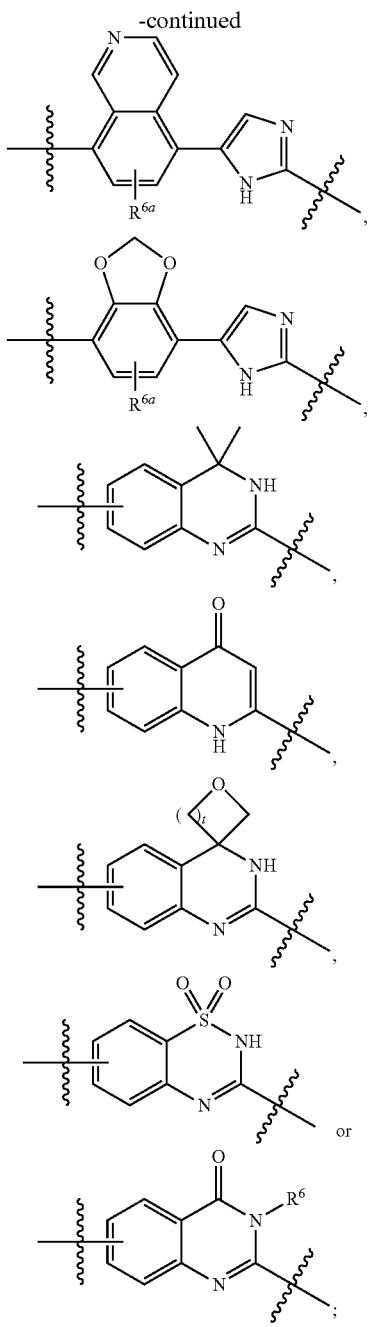

aryl-$C_{1-6}$-alkyl, $C_{3-10}$ cycloalkyl, $C_{2-10}$ heterocyclyl, $C_{1-9}$ heteroaryl or $C_{6-10}$ aryl; or $R^1$ and $R^2$, together with X—CH which they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH which they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$ and $R^2$, together with X—CH which they are attached to, or $R^3$ and $R^4$, together with X'—CH which they are attached to, optionally form a 3-8 membered heterocycle, $C_{5-12}$ fused bicycle, $C_{5-12}$ fused heterobicycle, $C_{5-12}$ spiro bicycle or $C_{5-12}$ spiro heterobicycle.

In other embodiments, the $R^1$, $R^2$ and X—CH together form one of the following monovalent groups:

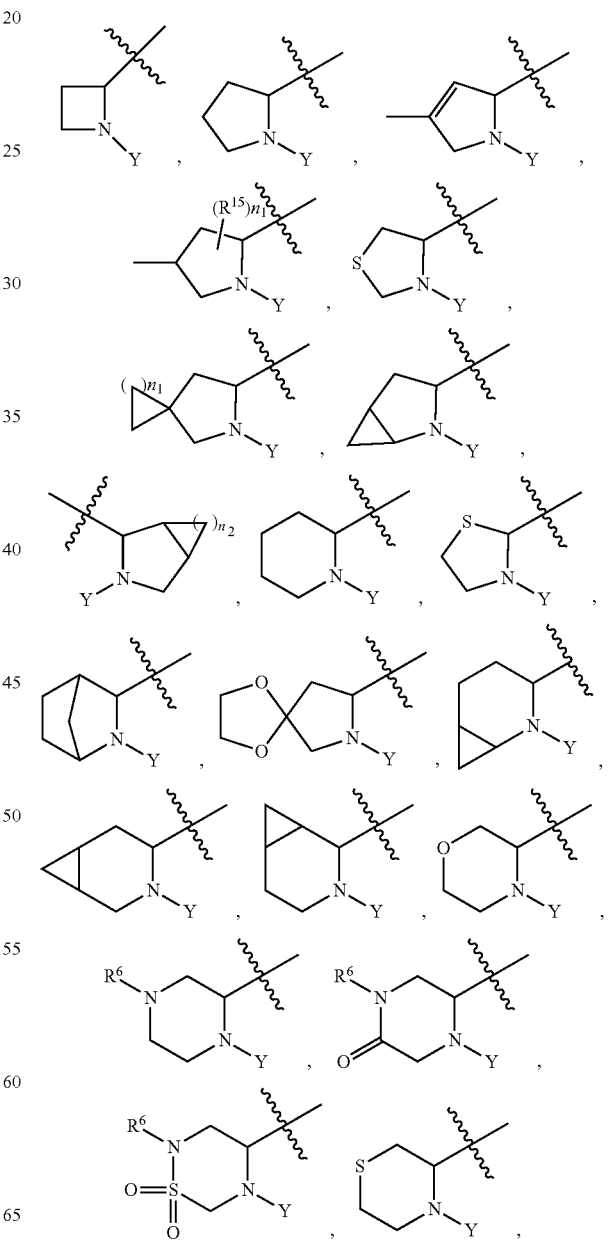

wherein $X^1$ is O or S;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl;

each $R^{6a}$ is independently H, deuterium, oxo (=O), hydroxy, amino, F, Cl, Br, I, cyano, $R^{7a}R^7N$—, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro; and each $R^7$ and $R^{7a}$ is independently H, deuterium, F, Cl, $C_{1-6}$ alkyl, $C_{1-6}$ heteroalkyl, $C_{1-6}$ haloalkyl, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, or $C_{1-6}$ alkylthio-$C_{1-6}$-alkyl.

In some embodiments, each of $R^1$, $R^2$, $R^3$ and $R^4$ is independently H, deuterium, $C_{1-8}$ alkyl, $C_{1-8}$ heteroalkyl, $C_{6-10}$

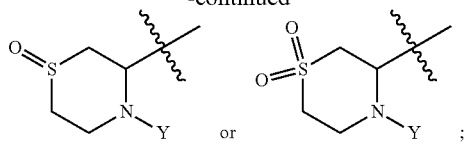 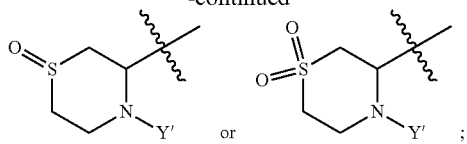

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl;

and each $n_1$ and $n_2$ is independently 1, 2, 3 or 4.

In other embodiments, the $R^3$, $R^4$ and X'—CH together form one of the following monovalent groups:

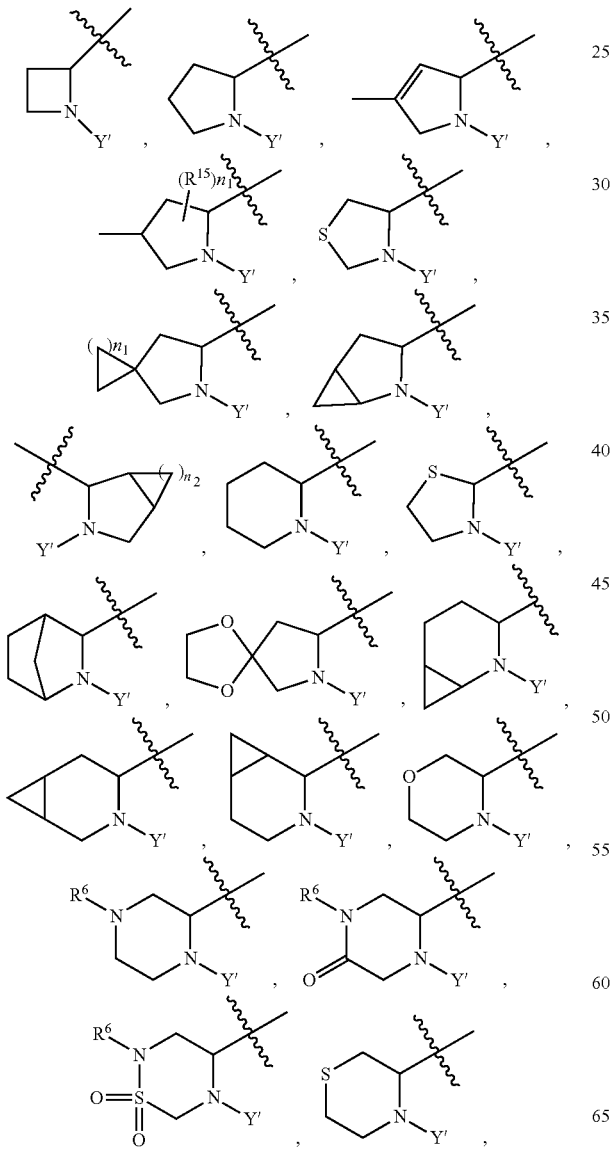

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In some embodiments, Formula (II) is

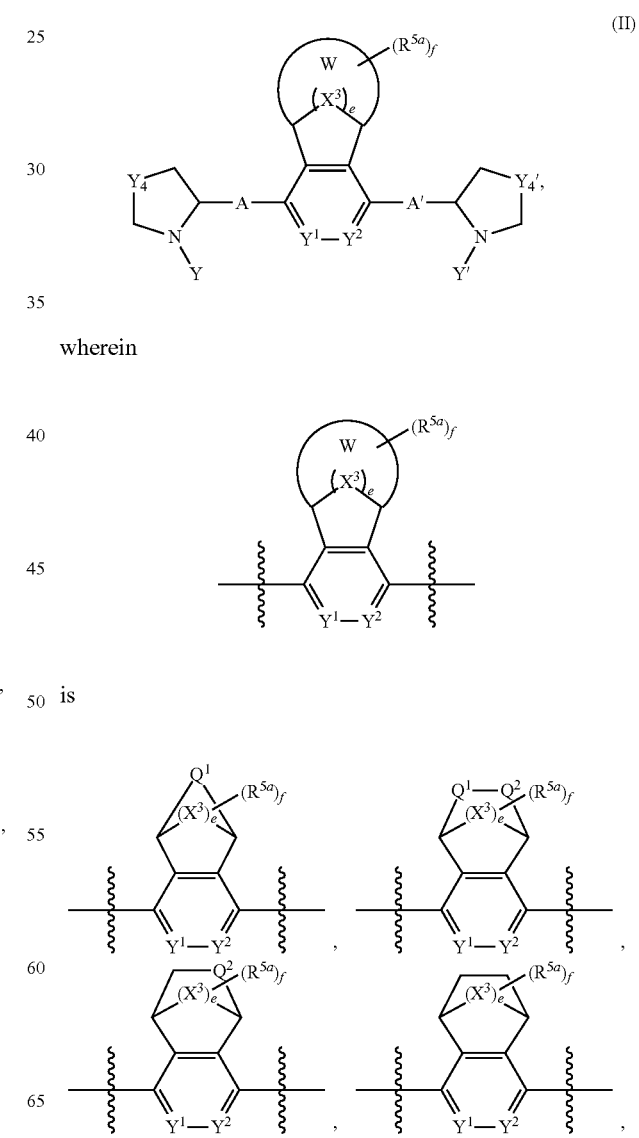

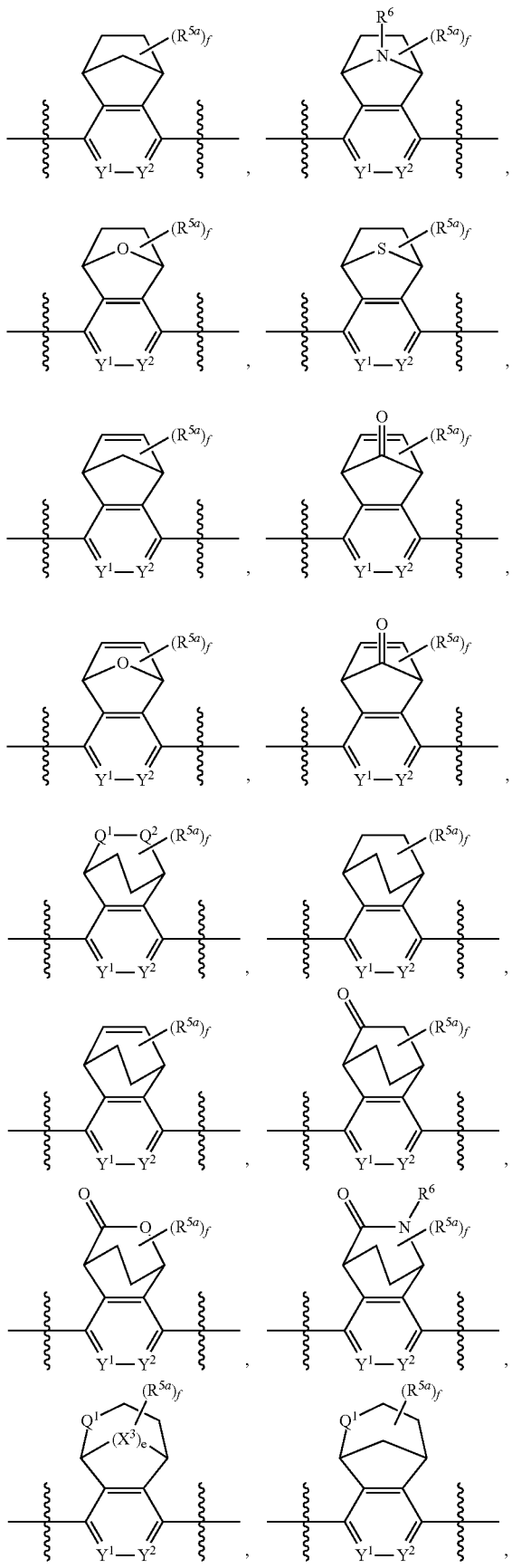

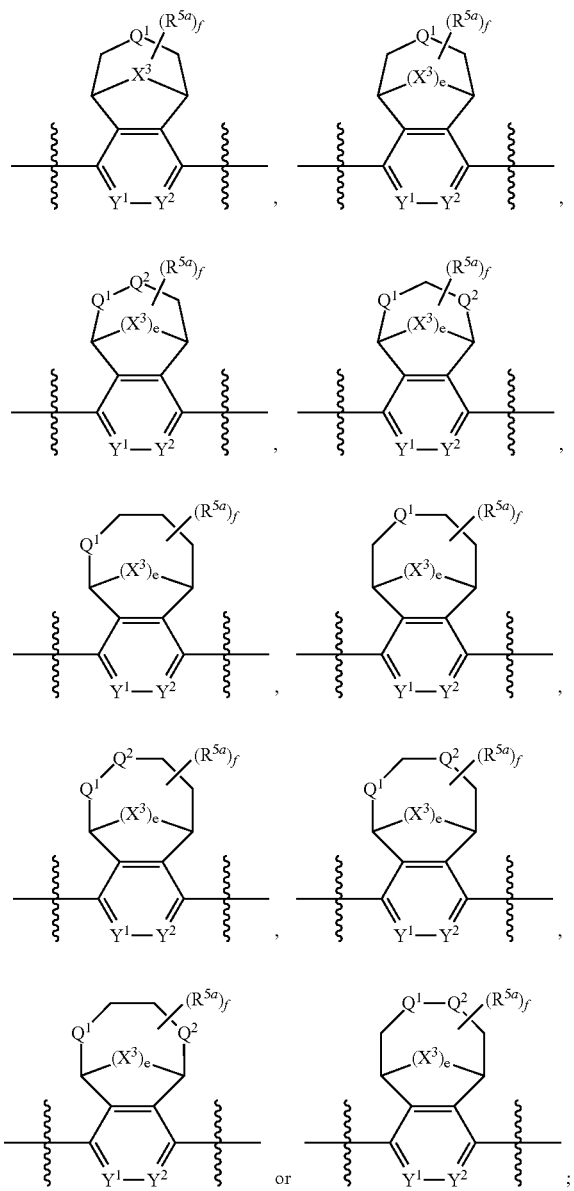

wherein each $Q^1$ and $Q^2$ is independently $NR^6$, O, S, C(=O) or $CH_2$;

each $X^3$ is independently O, S, $NR^6$, C(=O) or $CR^7R^{7a}$;

each e is independently 0, 1, 2, 3 or 4 with the proviso that where $X^3$ is O, S or $NR^6$, e is 1;

each $Y^1$ and $Y^2$ is independently N or $CR^7$;

each f is independently 0, 1, 2, 3 or 4;

each of A and A' is independently a bond, $C_{1-6}$ alkyl, $C_{2-6}$ alkenyl, $C_{3-8}$ cycloalkyl, $C_{2-10}$ heterocycloalkyl, $—(CR^8R^{8a})_n—O—(CR^8R^{8a})_p—$, $—(CR^8R^{8a})_n—N(R^5)—(CR^8R^{8a})_p—$, $—(CR^8R^{8a})_n—S(=O)_r—N(R^5)—(CR^8R^{8a})_p—$, $—(CR^8R^{8a})_n—C(=O)—N(R^5)—(CR^8R^{8a})_p—$, $—(CR^8R^{8a})_n—N(R^5)—C(=O)—N(R^5)—(CR^8R^{8a})_p—$, $—(CR^8R^{8a})_n—C(=O)—O—(CR^8R^{8a})_p—$, $—(CR^8R^{8a})_n—N(R^5)—S(=O)_r—N(R^5)—(CR^8R^{8a})_p—$, $—(CR^8R^{8a})_n—N(R^5)—C(=O)—O—(CR^8R^{8a})_p—$, or each of A and A' is independently

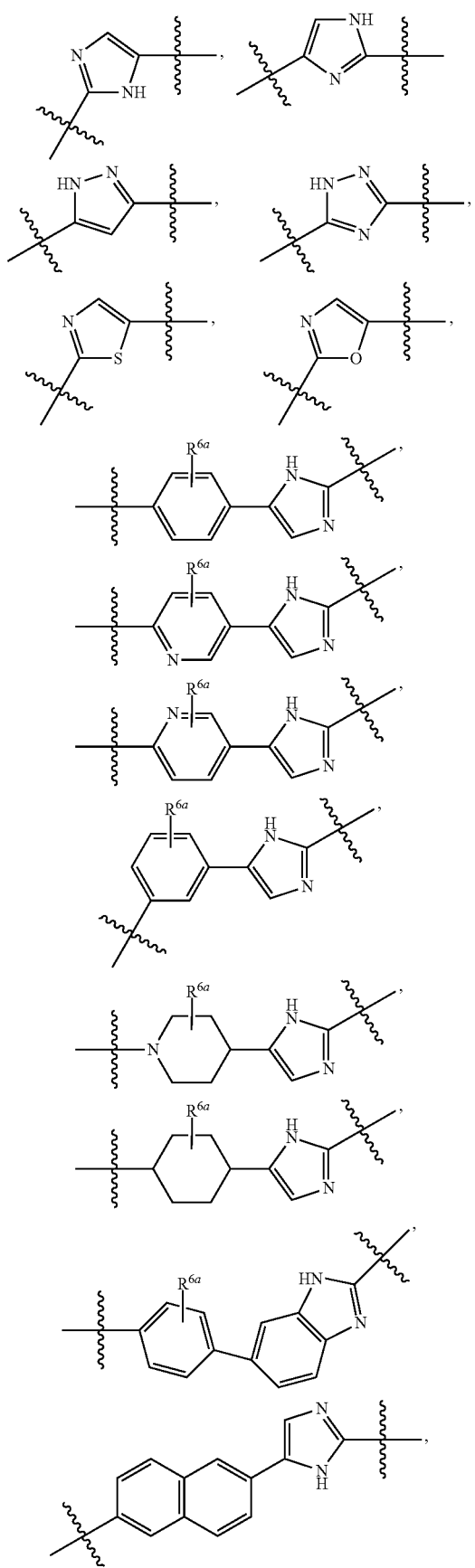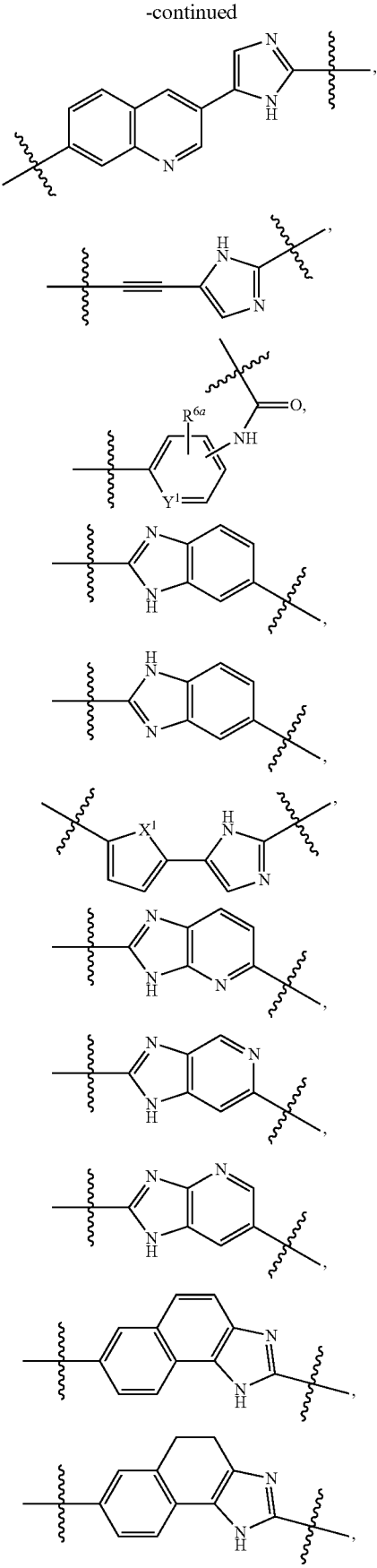

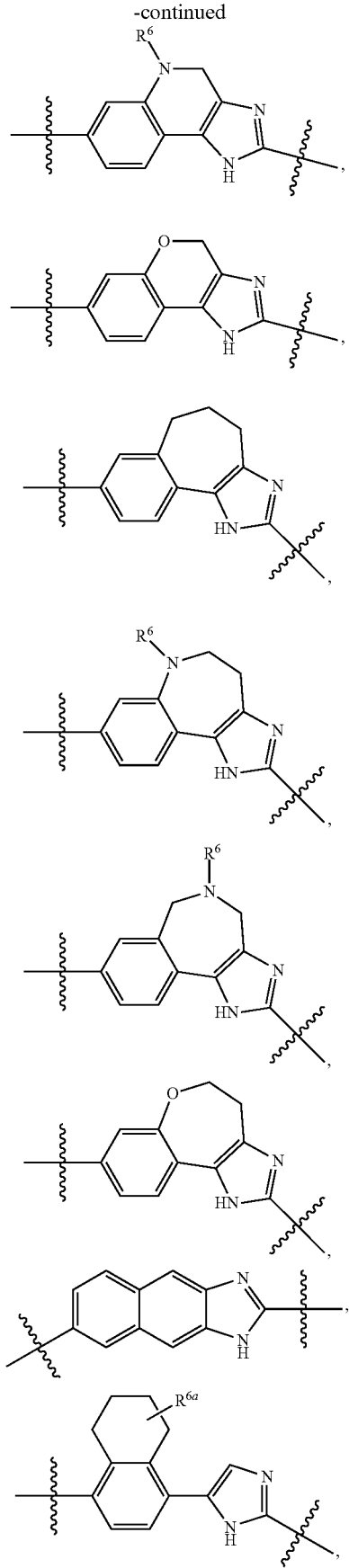
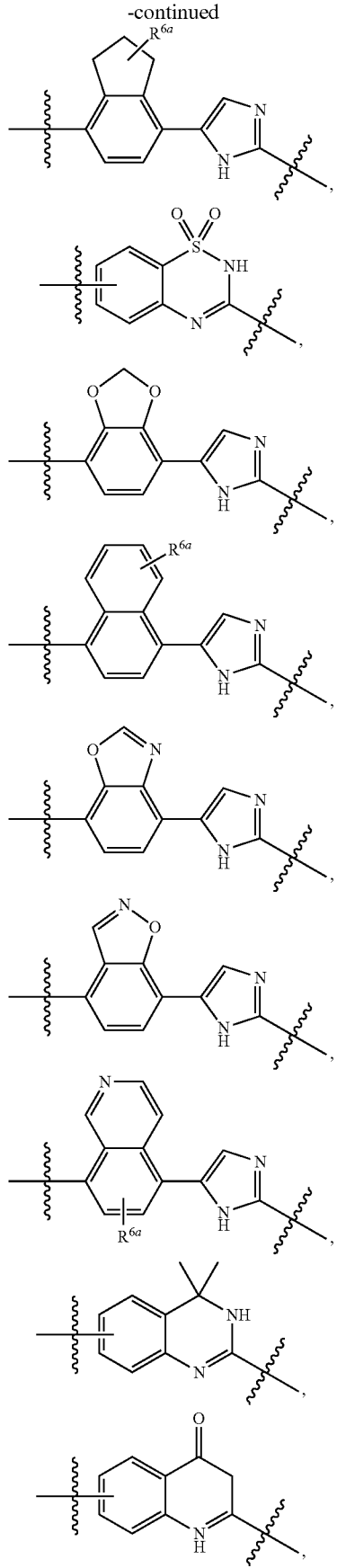

-continued

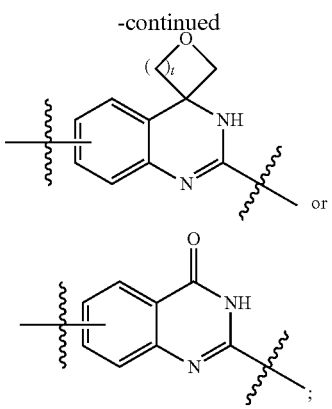

or

;

each $R^5$ is independently H, deuterium, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^{6a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^7$ and $R^{7a}$ is independently H, deuterium, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$-cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring;

each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, —CF$_2$—, —CHR$^{5a}$— or —CH$_2$N(R$^6$)—;

each n is independently 0, 1, 2 or 3;

each p is independently 0, 1, 2 or 3; and each r is independently 0, 1 or 2.

In some embodiments, Formula (II') is

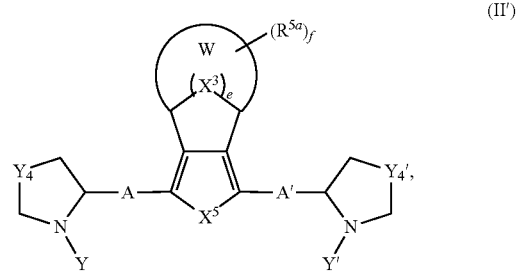

(II')

wherein

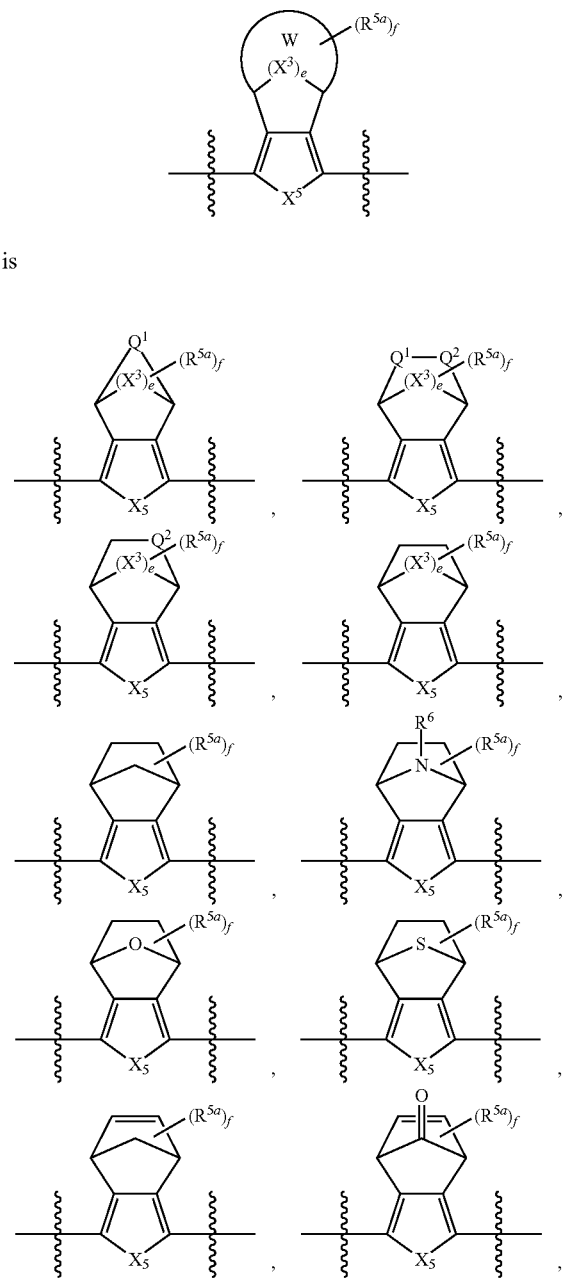

is

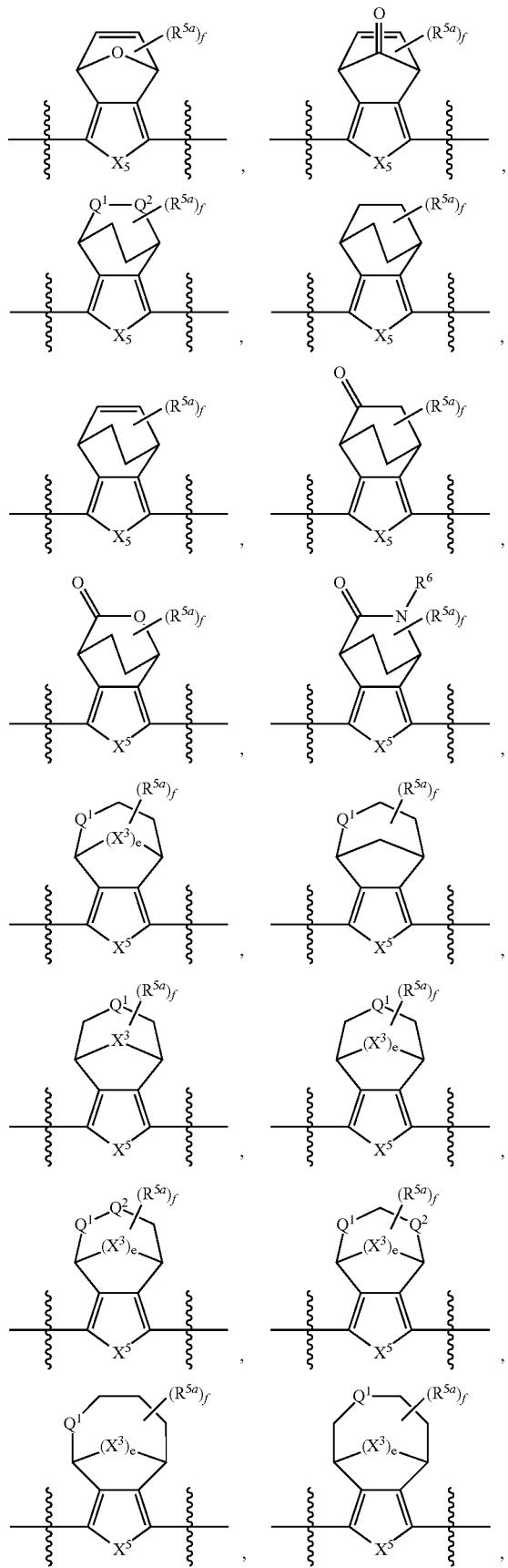
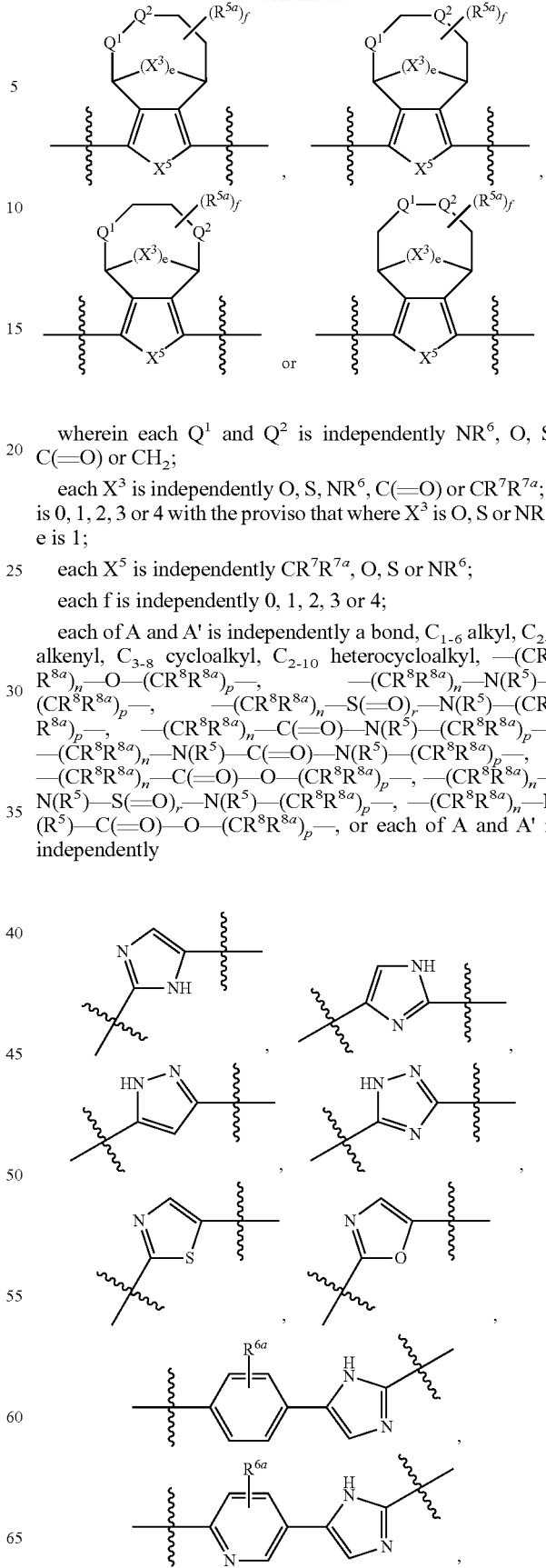

wherein each $Q^1$ and $Q^2$ is independently $NR^6$, O, S, C(=O) or $CH_2$;

each $X^3$ is independently O, S, $NR^6$, C(=O) or $CR^7R^{7a}$; e is 0, 1, 2, 3 or 4 with the proviso that where $X^3$ is O, S or $NR^6$, e is 1;

each $X^5$ is independently $CR^7R^{7a}$, O, S or $NR^6$;

each f is independently 0, 1, 2, 3 or 4;

each of A and A' is independently a bond, $C_{1-6}$ alkyl, $C_{2-6}$ alkenyl, $C_{3-8}$ cycloalkyl, $C_{2-10}$ heterocycloalkyl, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently

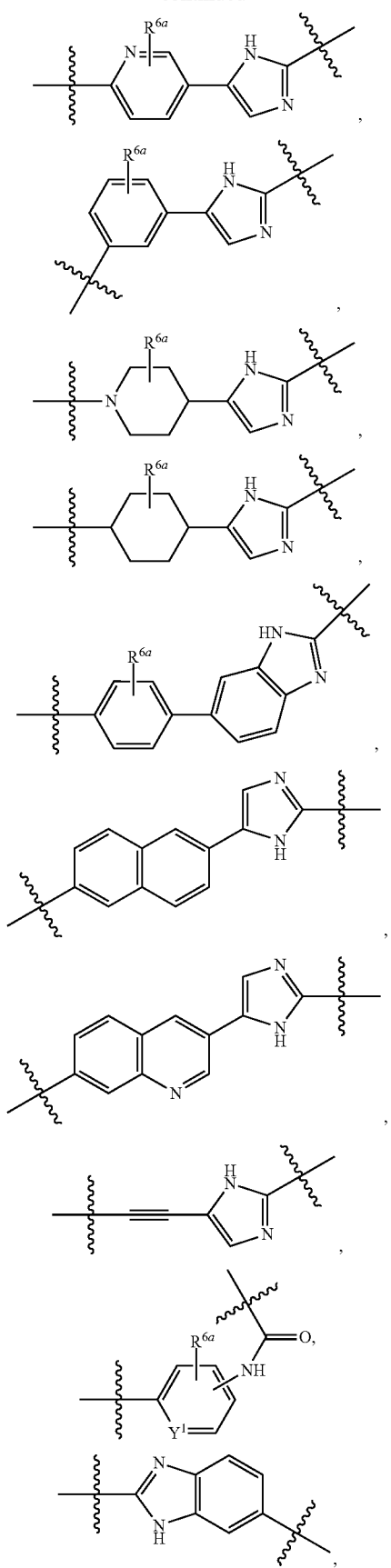
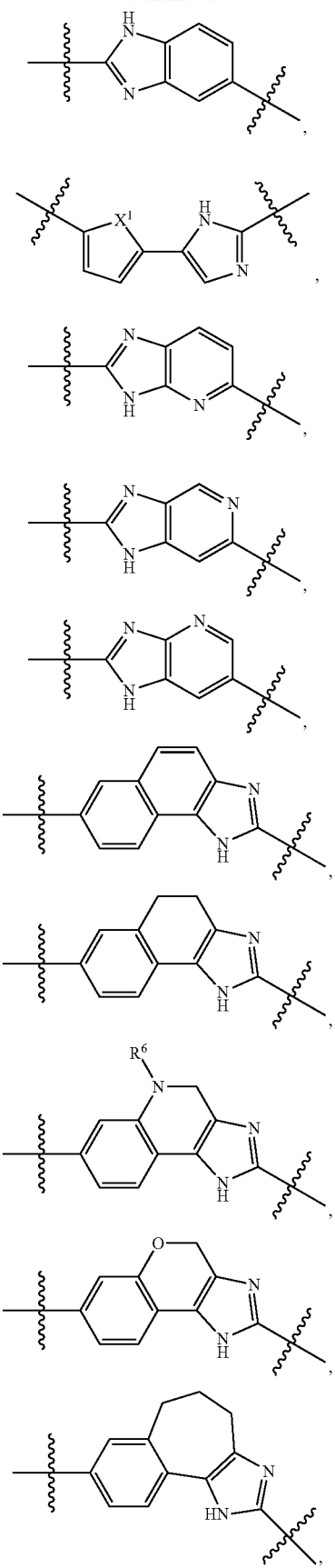

-continued
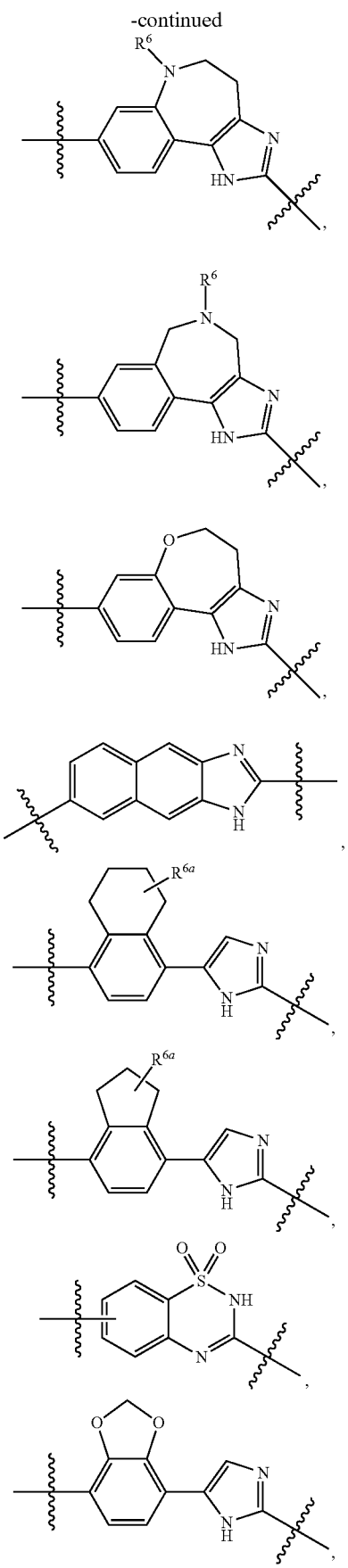
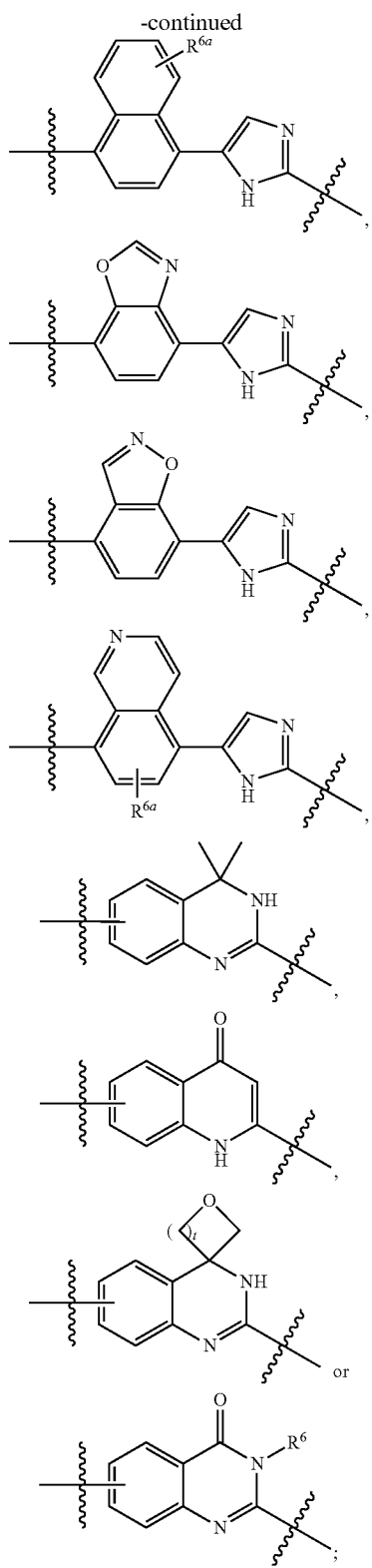
each $R^5$ is independently H, deuterium, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^{6a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^7$ and $R^{7a}$ is independently H, deuterium, $C_{1-6}$ alkyl, $C_{1-6}$ heteroalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring;

each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, —CF$_2$—, —CHR$^{5a}$— or —CH$_2$N(R$^6$)—;

each n is independently 0, 1, 2 or 3;
each p is independently 0, 1, 2 or 3; and
each r is independently 0, 1 or 2.

In other embodiments, Formula (III) is

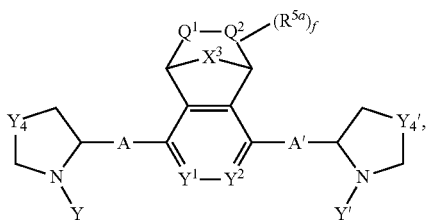

(III)

wherein each $Q^1$ and $Q^2$ is independently O, S, C(=O), NR$^6$ or CH$_2$;
$X^3$ is O, S, NR$^6$, C(=O) or CR$^7R^{7a}$;
each R$^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl;

each $R^7$ and $R^{7a}$ is independently H, deuterium, $C_{1-6}$ alkyl, $C_{1-6}$ heteroalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$ alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring; and f is 0, 1, 2, 3 or 4.

In other embodiments, Formula (IV) is

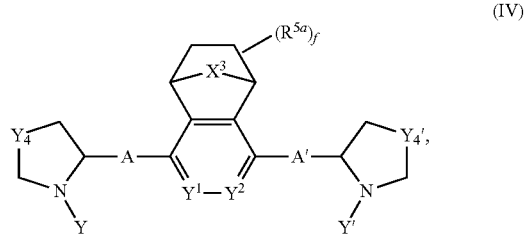

(IV)

wherein $X^3$ is O, S, NR$^6$, C(=O) or CR$^7R^{7a}$;
each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

f is 0, 1, 2, or 3; and
each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (V) is

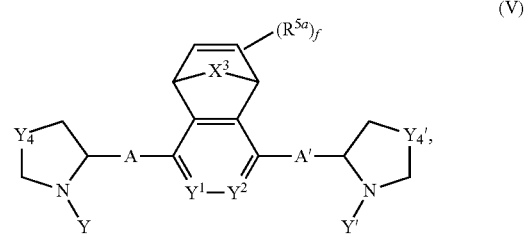

(V)

wherein $X^3$ is O, S, NR$^6$, C(=O) or CR$^7R^{7a}$;
each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

f is 0, 1, 2, or 3; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (VI) is

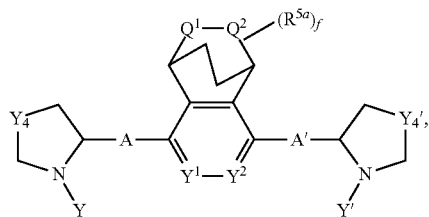

(VI)

wherein each $Q^1$ and $Q^2$ is independently O, S, C(=O), $NR^6$ or $CH_2$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and f is 0, 1, 2, 3 or 4.

In other embodiments, Formula (III') is

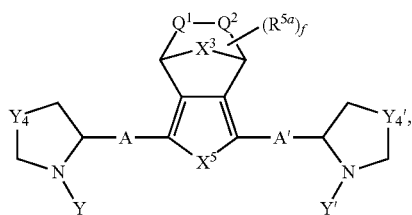

(III')

wherein each $Q^1$ and $Q^2$ is independently O, S, C(=O), $NR^6$ or $CH_2$;

$X^3$ is O, S, $NR^6$, C(=O) or $CR^7R^{7a}$;

f is 0, 1, 2 or 3;

$X^5$ is $CH_2$, O, S or $NR^6$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (IV') is

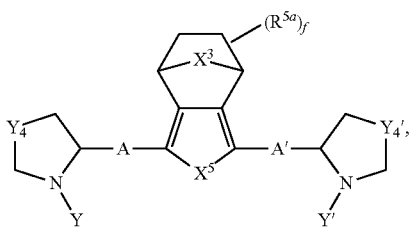

(IV')

wherein $X^5$ is $CH_2$, O, S or $NR^6$;

$X^3$ is O, S, $NR^6$, C(=O) or $CR^7R^{7a}$;

f is 0, 1, 2 or 3;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (V') is

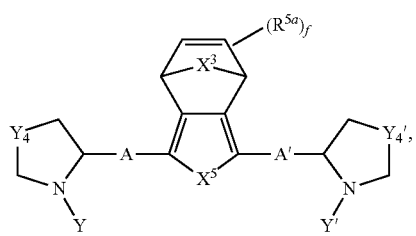

(V')

wherein $X^3$ is O, S, $NR^6$, C(=O) or $CR^7R^{7a}$;

$X^5$ is $CH_2$, O, S or $NR^6$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy;

each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-9}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

In other embodiments, Formula (VI') is

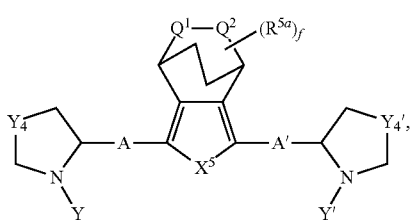

(VI')

wherein each $Q^1$ and $Q^2$ is independently O, S, C=(O), $NR^6$ or $CH_2$;

f is 0, 1, 2 or 3;

$X^5$ is $CH_2$, O, S or $NR^6$;

each $R^{5a}$ is independently H, deuterium, oxo (=O), hydroxy, amino, F, Cl, Br, I, cyano, $C_{1-4}$ alkylacyl, $C_{1-4}$ alkylacyloxy, $C_{1-4}$ alkoxyacyl, $C_{1-4}$ alkylsulfonyl, $C_{1-4}$ alkoxysulfonyl, $C_{1-4}$ alkylsulfinyl, $C_{1-4}$ alkylsulfonyloxy, $C_{1-4}$ alkylsulfinyloxy, $C_{1-4}$ alkoxy, $C_{1-4}$ alkyl, $C_{6-10}$ aryl, —$CF_3$, —$OCF_3$, mercapto, nitro, $C_{1-6}$ alkylamino, $C_{3-8}$ cycloalkyl or $C_{6-10}$ aryloxy; and each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-10}$ carbocyclyl.

In some embodiments, each of Y and Y' is independently a group derived from α-amino acid group and the group derived from α-amino acid is optionally substituted with one or more substituents, wherein the substituent is deuterium, F, Cl, Br, I, hydroxy or cyano.

In other embodiments, the group derived from α-amino acid is formed by isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, the α-amino acid is in the L configuration.

In other embodiments, each of Y and Y' is independently —[U—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$, —U—$(CR^9R^{9a})_t$—$R^{12}$ or —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$.

In other embodiments, each of Y and Y' is independently —[U—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$.

In other embodiments, each of Y and Y' is independently —U—$(CR^9R^{9a})_t$—$N(R^{10})$—$(CR^9R^{9a})_t$—U—$(CR^9R^{9a})_t$—$N(R^{11})$—$(CR^9R^{9a})_t$—$R^{12}$.

In other embodiments, each of Y and Y' is independently —U—$(CR^9R^{9a})_t$—$N(R^{11})$—$(CR^9R^{9a})_t$—$R^{12}$.

In other embodiments, each of Y and Y' is independently —[C(=O)—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—U—$(CR^9R^{9a})_t$—$N(R^{11})$—$(CR^9R^{9a})_t$—$R^{12}$.

In other embodiments, each of Y and Y' is independently —[C(=O)—$(CR^9R^{9a})_t$—$N(R^{10})$—$(CR^9R^{9a})_t]_k$—C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_n$—$N(R^{11})$—$(CR^9R^{9a})_n$—C(=O)—$R^{13}$.

In other embodiments, each of Y and Y' is independently —C(=O)—$(CR^9R^{9a})_n$—$N(R^{11})$—C(=O)—$R^{13}$.

In other embodiments, each of Y and Y' is independently —C(=O)—$(CR^9R^{9a})_n$—$N(R^{11})$—$(CR^9R^{9a})_n$—C(=O)—O—$R^{13}$.

In other embodiments, each of Y and Y' is independently —C(=O)—$(CR^9R^{9a})_n$—$N(R^{11})$—C(=O)—O—$R^{13}$.

In other embodiments, each of Y and Y' is independently —U—$(CR^9R^{9a})_t$—$R^{12}$.

In other embodiments, each of Y and Y' is independently —C(=O)—$(CR^9R^{9a})_t$—$R^{12}$.

In other embodiments, each of Y and Y' is independently —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$.

In other embodiments, each of Y and Y' is independently —U—$(CR^9R^{9a})_t$—$N(R^{10})$—$(CR^9R^{9a})_t$—U—$(CR^9R^{9a})_t$—O—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—C(=O)—$(CR^9R^{9a})_t$—O—$(CR^9R^{9a})_t$—$R^{12}$.

In other embodiments, each of Y and Y' is independently —U—$(CR^9R^{9a})_t$—O—$(CR^9R^{9a})_t$—$R^{12}$.

In other embodiments, each of Y and Y' is independently —C(=O)—$(CR^9R^{9a})_t$—O—$(CR^9R^{9a})_t$—$R^{12}$.

In other embodiments, each of Y and Y' is independently —C(=O)—$(CR^9R^{9a})_n$—$N(R^{11})$—$R^{12}$, wherein $R^{11}$ and $R^{12}$, together with the nitrogen atom they are attached to, form a 4-7 membered ring.

In other embodiments, each $R^9$, $R^{9a}$, $R^{10}$ and $R^{11}$ is independently H, deuterium, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ haloalkyl, $C_{1-6}$ hydroxyalkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

each $R^{12}$ is independently $R^{13a}R^{13}N-$, $-C(=O)R^{13}$, $-C(=S)R^{13}$, $-C(=O)-O-R^{13}$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $R^{13}OS(=O)_2-$, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; or $R^{11}$ and $R^{12}$, together with the nitrogen atom they are attached to, form a 4-7 membered ring; and each $R^{13}$ and $R^{13a}$ is independently H, deuterium, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl.

In other embodiments, each $R^9$, $R^{9a}$, $R^{10}$ and $R^{11}$ is independently H, deuterium, methyl, ethyl, isopropyl, cyclohexyl, isobutyl or phenyl;

each $R^{12}$ is independently $-C(=O)R^{13}$, $-C(=O)-O-R^{13}$, $-C(=O)NR^{13}R^{13a}$, methyl, ethyl, propyl, phenyl, cyclohexyl, morpholinyl or piperidinyl, or $R^{11}$ and $R^{12}$, together with the nitrogen atom they are attached to, form a 4-7 membered ring; and each $R^{13}$ and $R^{13a}$ is independently H, deuterium, methyl, ethyl, propyl, phenyl, cyclohexyl, morpholinyl or piperidinyl.

In other embodiments, Formula (VII) is

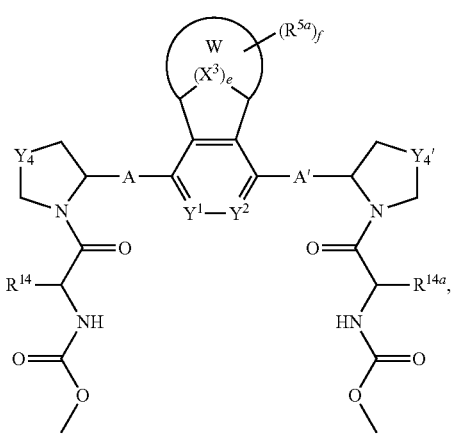

(VII)

wherein each of $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

wherein each of $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano.

In other embodiments, Formula (VIII) is

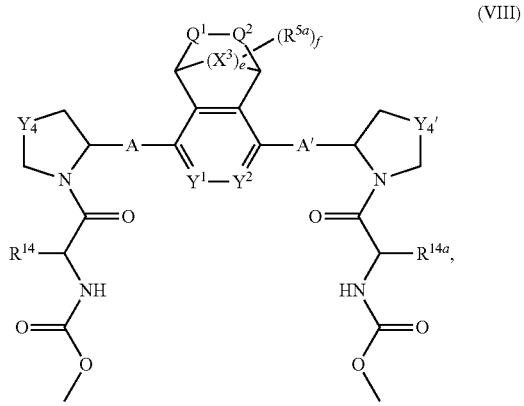

(VIII)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, $-NR^7R^{7a}$, benzyl, piperazinyl, cyclopentyl, cyclopropyl, cyclohexyl, or $C_{1-9}$ heteroaryl; wherein each of methyl, ethyl, isopropyl, isobutyl, tert-butyl, allyl, propargyl, trifluoroethyl, phenyl, pyranyl, morpholinyl, $-NR^7R^{7a}$, benzyl, piperazinyl, cyclopentyl, cyclopropyl and cyclohexyl is optionally substituted with one or more substituents, wherein the substituent is deuterium, F, Cl, Br, hydroxy or cyano;

each $Q^1$ and $Q^2$ is independently $NR^6$, O, S, $C(=O)$ or $CH_2$;

each $Y^1$ and $Y^2$ is independently N or $CR^7$;

each $X^3$ is independently O, S, $NR^6$, $C(=O)$ or $CR^7R^{7a}$; e is 0, 1, 2, or 3 with the proviso that where $X^3$ is O, S, $C(=O)$ or $NR^6$, e is 1;

f is 0, 1, 2, 3 or 4;

each of A and A' is independently a bond, $C_{1-6}$ alkyl, $C_{2-6}$ alkenyl, $C_{3-8}$ cycloalkyl, $C_{2-10}$ heterocycloalkyl, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently

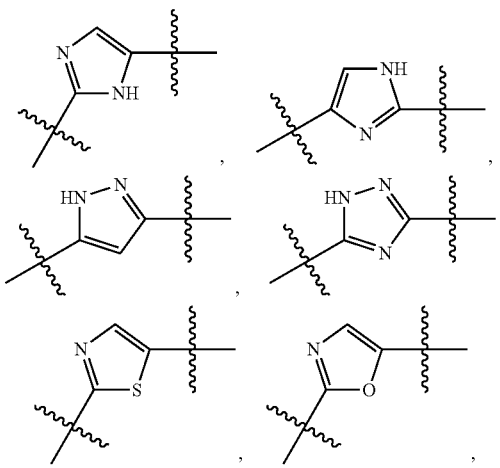

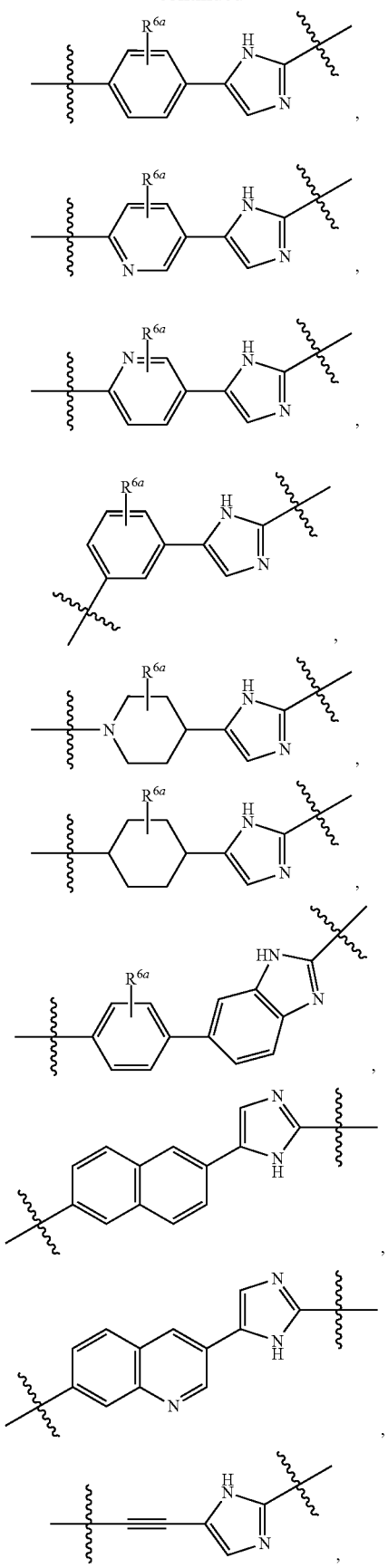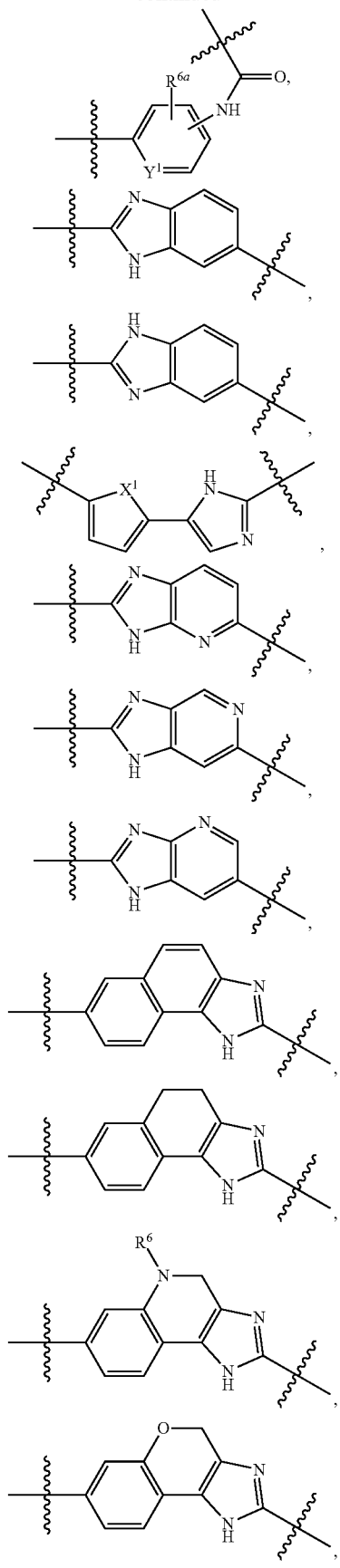

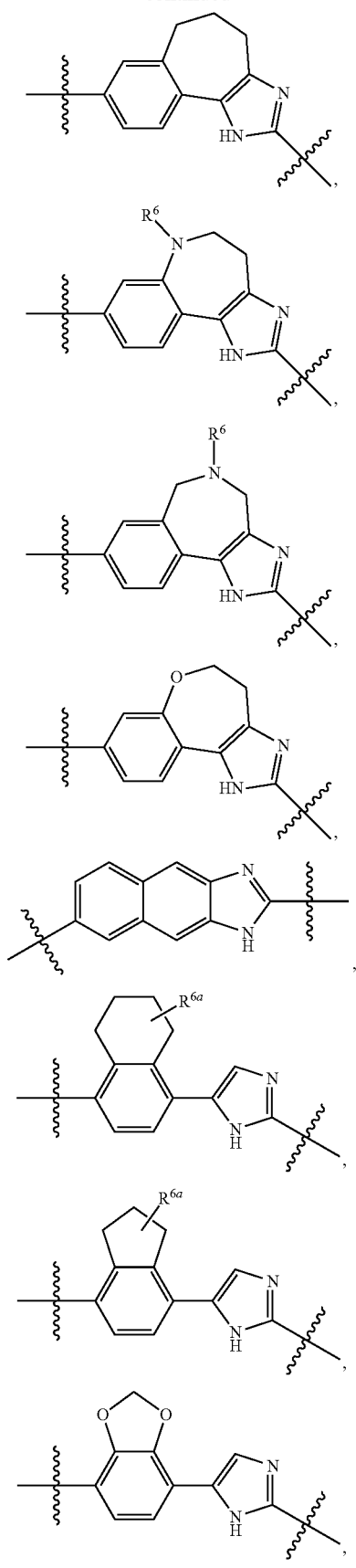
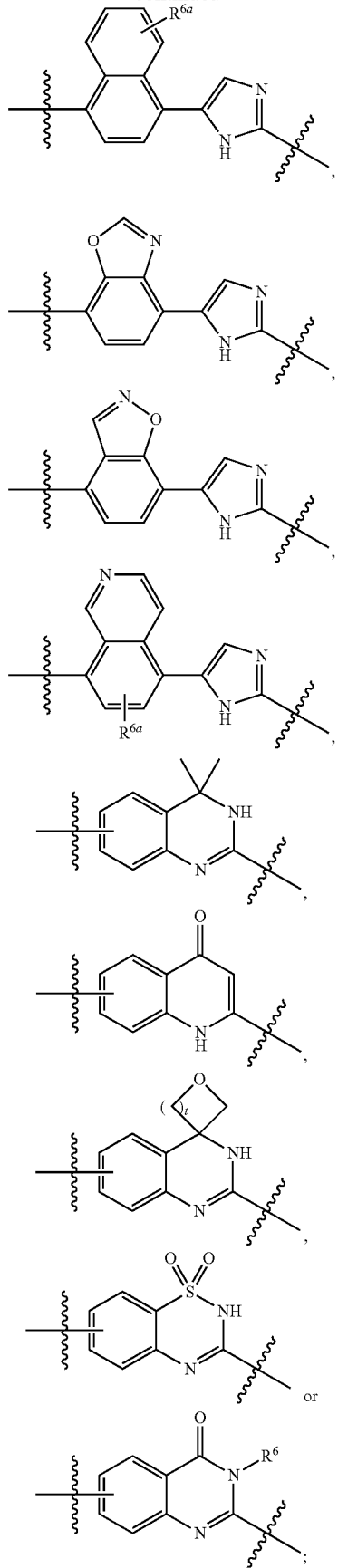

and
each of $Y_4$ and $Y_4'$ is independently a bond, O, S, —$(CH_2)_n$—, —CH=CH—, —S(=O)$_r$—, —$CH_2O$—, —$CH_2S$—, —$CH_2S(=O)_r$—, —$CF_2$—, —$CHR^{5a}$— or —$CH_2N(R^6)$—.

In some embodiments, Formula (IX) is

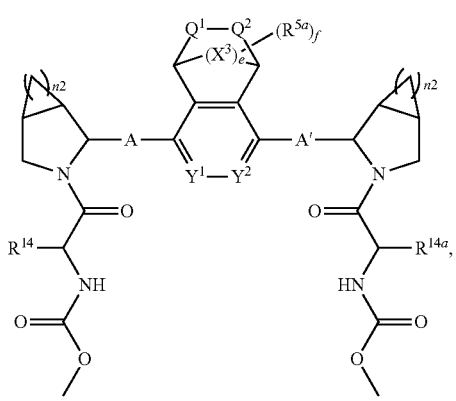

(IX)

wherein each of $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4;

wherein each of $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano.

In some embodiments, Formula (X) is

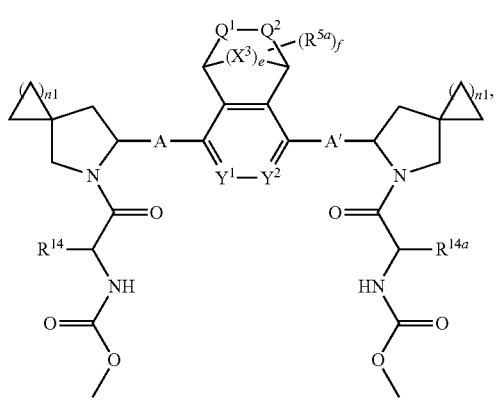

(X)

wherein each $Q^1$ and $Q^2$ is independently $CH_2$, $CF_2$, O, C(=O) or $NR^6$;

each of $R^{14}$ and $R^{14a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

In some embodiments, Formula (XI) is

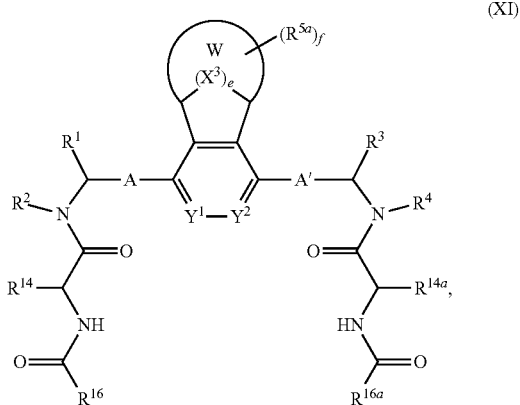

(XI)

wherein each $R^{5a}$ is independently H, deuterium, methyl, ethyl, F, Cl, Br or I;

each of $R^{14}$ and $R^{14a}$ is independently H, deuterium, methyl, ethyl, phenyl, cyclohexyl, 1-methyl propyl, isopropyl or tert-butyl;

each of $R^{16}$ and $R^{16a}$ is independently hydroxy, methoxy, ethoxy, phenoxy,

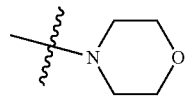

or tert-butoxy;

wherein each of methyl, ethyl, phenyl, cyclohexyl, 1-methyl propyl, isopropyl, methoxy, ethoxy, tert-butoxy and tert-butyl is optionally substituted with one or more substituents, wherein the substituent is deuterium, F, Cl, Br, hydroxy or cyano;

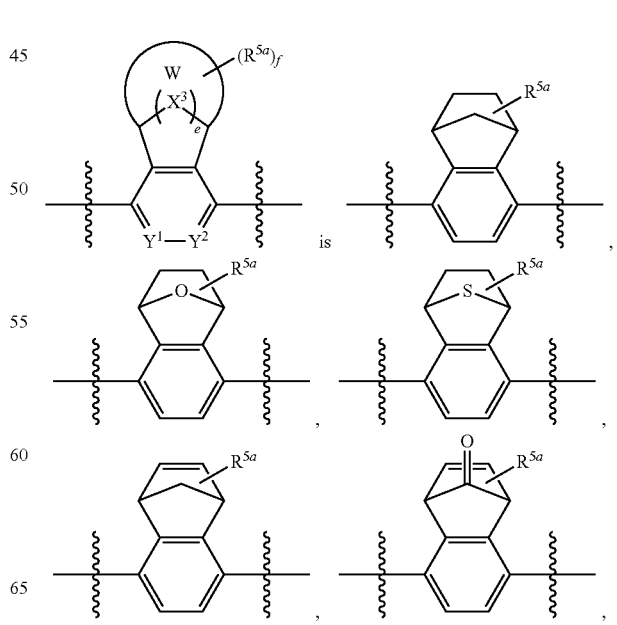

141
-continued
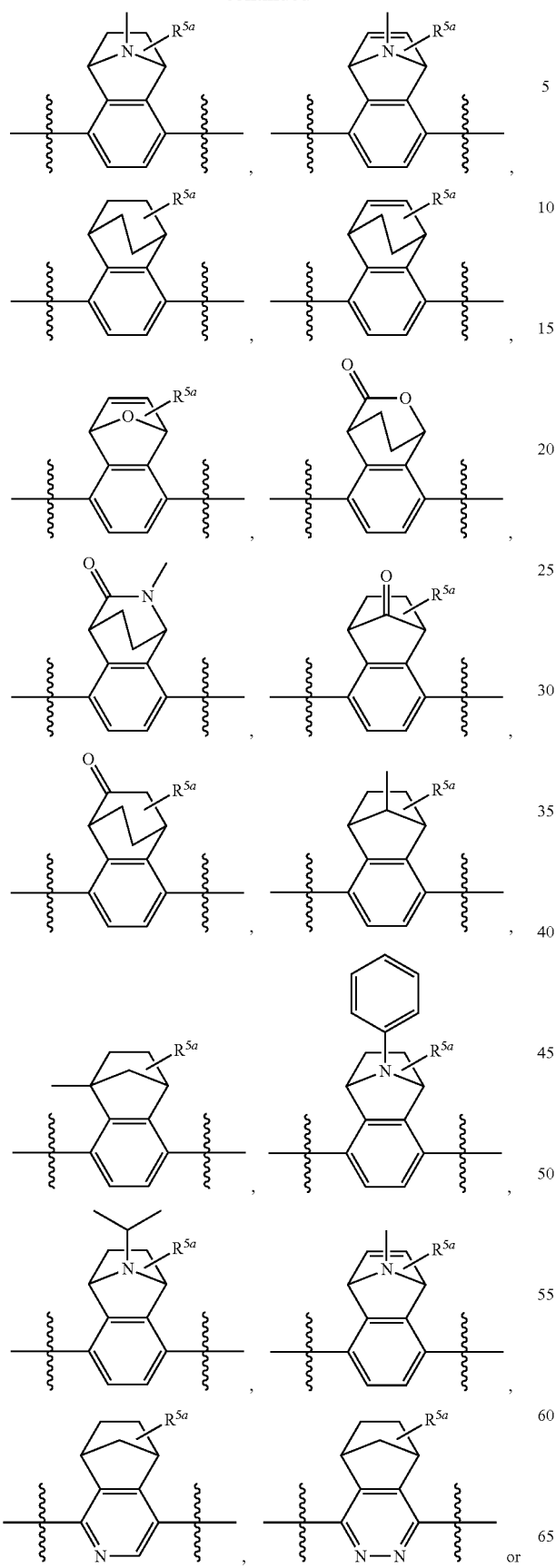
142
-continued
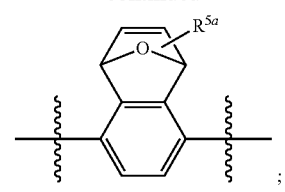
each of A and A' is independently
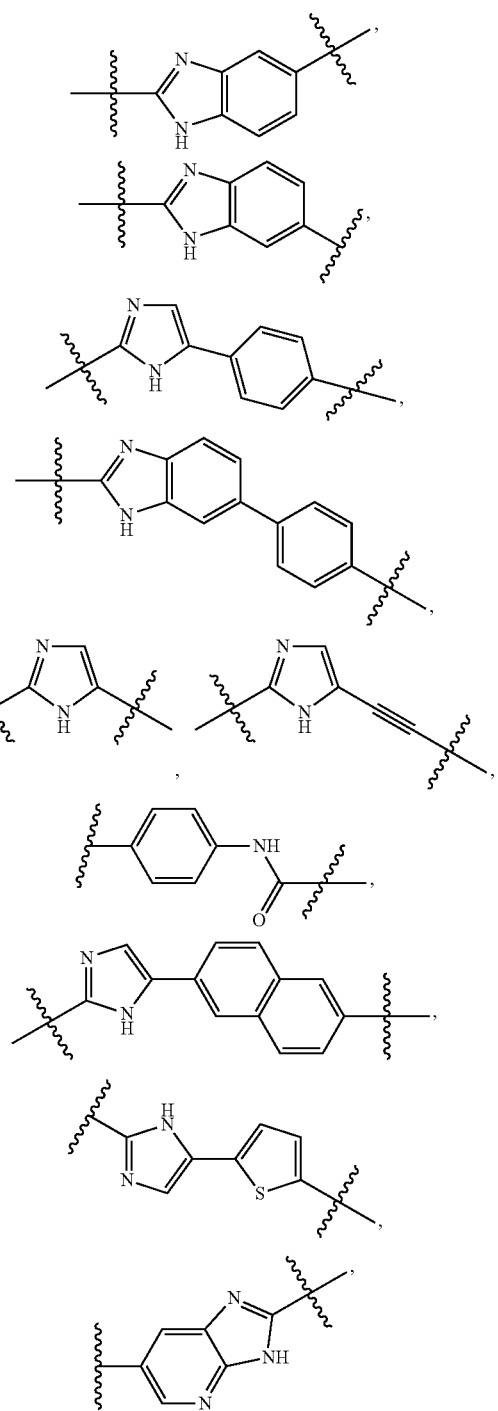

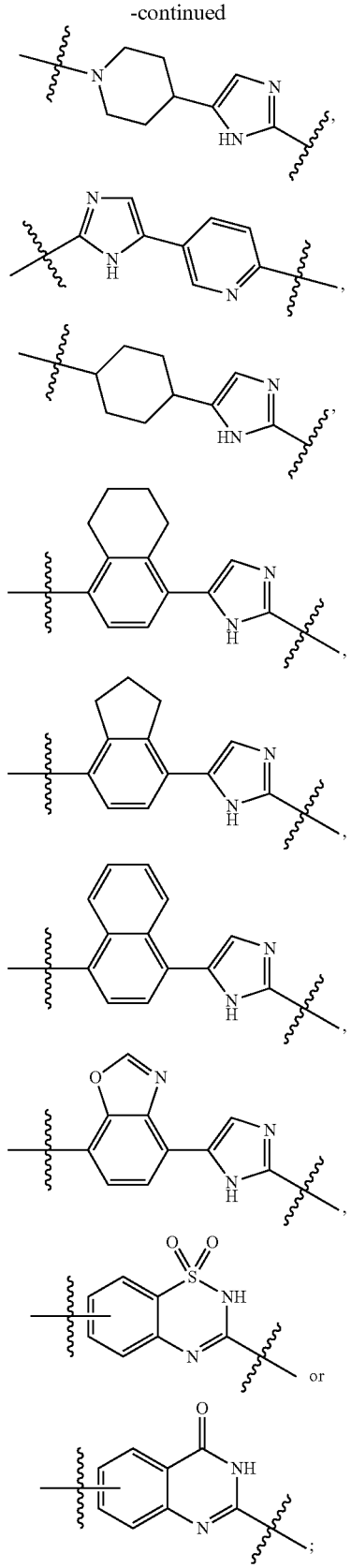
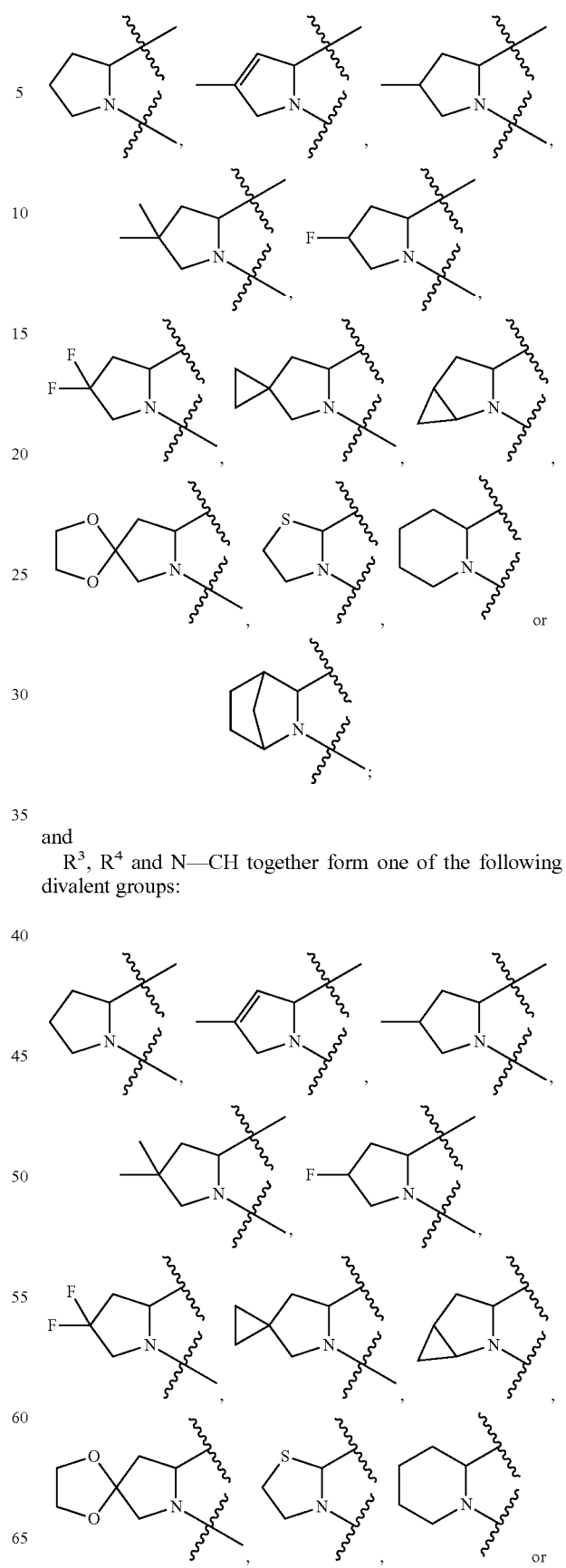
$R^1$, $R^2$ and N—CH together form one of the following divalent groups:
and
$R^3$, $R^4$ and N—CH together form one of the following divalent groups:

-continued

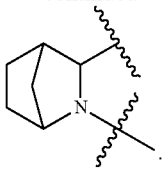

In other embodiments, Formula (XII) is

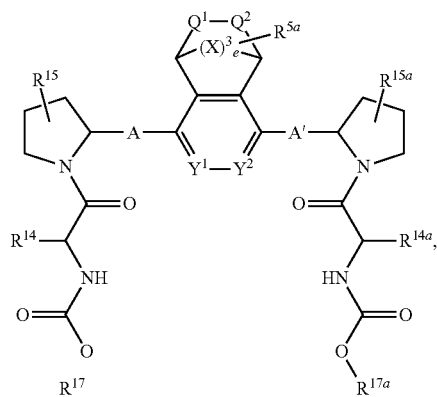

wherein $R^{5a}$ is H or methyl;

each of $Q^1$ and $Q^2$ is independently $CH_2$, $CF_2$, O, C(=O) or $NR^6$;

each of $Y^1$ and $Y^2$ is independently N or $CR^7$;

$R^7$ is H, deuterium, methyl, ethyl, isopropyl, phenyl, F, Cl, Br, I, OH or cyano;

each of $R^{14}$ and $R^{14a}$ is independently H, deuterium, methyl, ethyl, isobutyl, cyclohexyl, phenyl or isopropyl;

each of $R^{15}$ and $R^{15a}$ is independently H, deuterium, F, Cl, Br, methyl, ethyl, isopropyl or tert-butyl;

each of $R^{17}$ and $R^{17a}$ is independently methyl, phenyl or ethyl;

each $X^3$ is independently O, S, $NR^6$, C(=O) or $CH_2$;

each $R^6$ is independently H, methyl, ethyl, cyclohexyl, phenyl or isopropyl;

e is 0, 1, 2 or 3 with the proviso that where $X^3$ is O, S, or $NR^6$, e is 1;

wherein each of methyl, ethyl, phenyl, cyclohexyl, isopropyl and tert-butyl is optionally substituted with one or more substituents, wherein the substituent is deuterium, F, Cl, Br, hydroxy or cyano; and each of A and A' is independently

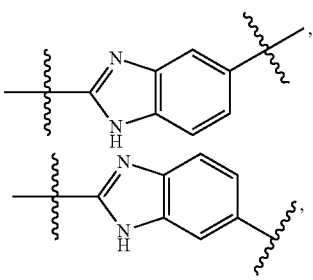

-continued

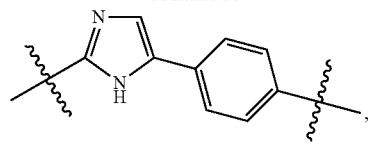

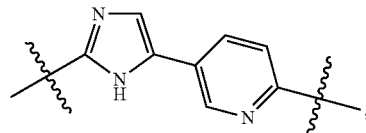

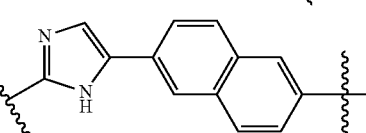

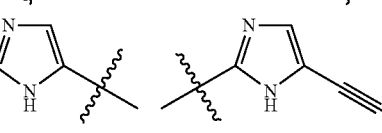

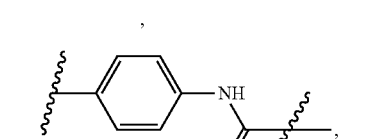

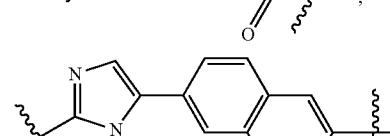

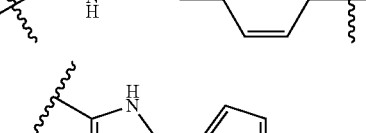

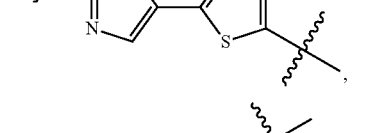

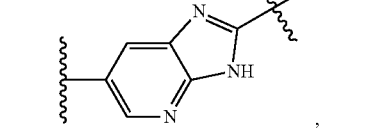

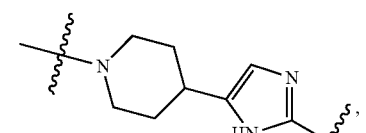

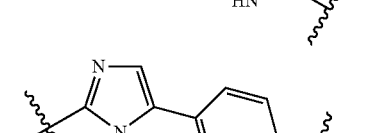

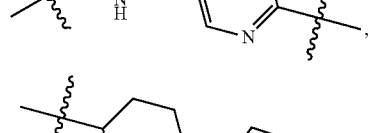

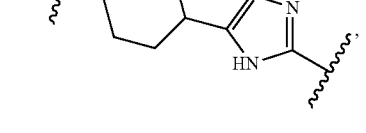

wherein $R^{5a}$ is H or methyl;

each of $Q^1$ and $Q^2$ is independently $CH_2$, $CF_2$, O, C(=O) or $NR^6$;

$X^5$ is $CH_2$, O, S or $NR^6$;

each of $R^{14}$ and $R^{14a}$ is independently H, deuterium, methyl, ethyl, isobutyl, cyclohexyl, phenyl or isopropyl;

each of $R^{15}$ and $R^{15a}$ is independently H, deuterium, F, Cl, Br, methyl, ethyl, isopropyl or tert-butyl;

each of $R^{17}$ and $R^{17a}$ is independently methyl, phenyl or ethyl;

each $X^3$ is independently O, S, $NR^6$, C(=O) or $CH_2$;

each $R^6$ is independently H, deuterium, methyl, ethyl, cyclohexyl, phenyl or isopropyl;

e is 0, 1, 2 or 3 with the proviso that where $X^3$ is O, S, or $NR^6$, e is 1;

wherein each of methyl, ethyl, phenyl, cyclohexyl, isopropyl and tert-butyl is optionally substituted with one or more substituents, wherein the substituent is deuterium, F, Cl, Br, hydroxy or cyano; and each of A and A' is independently

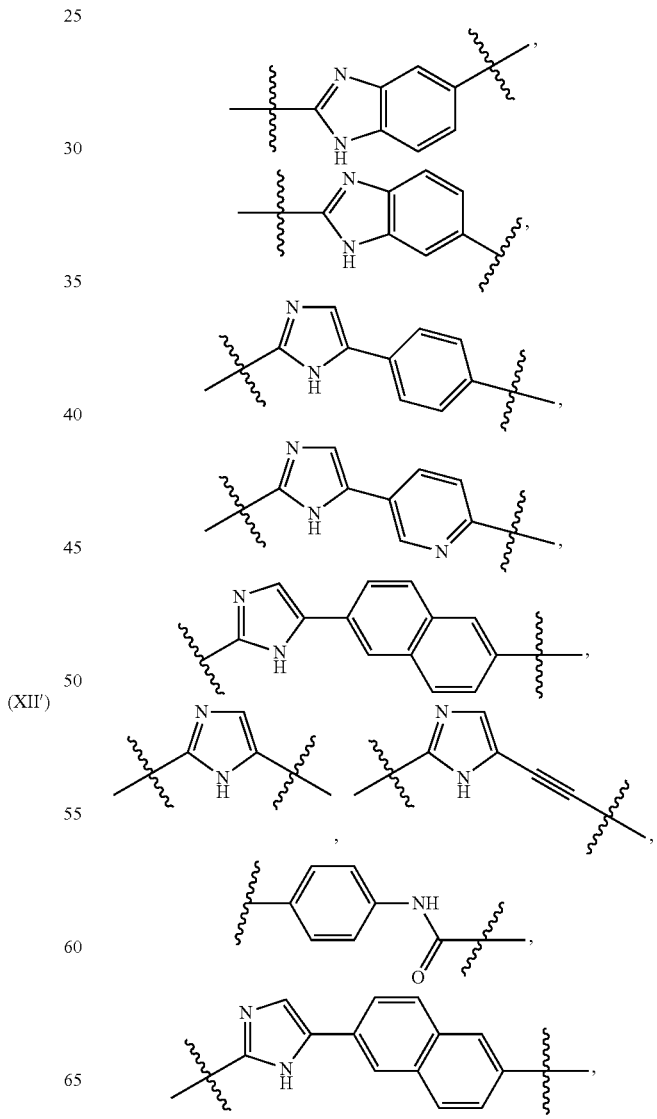

In some embodiments, Formula (XII') is

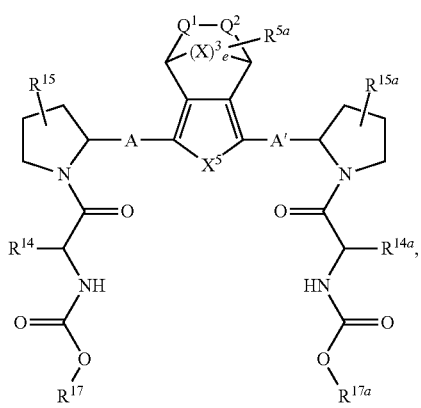

(XII')

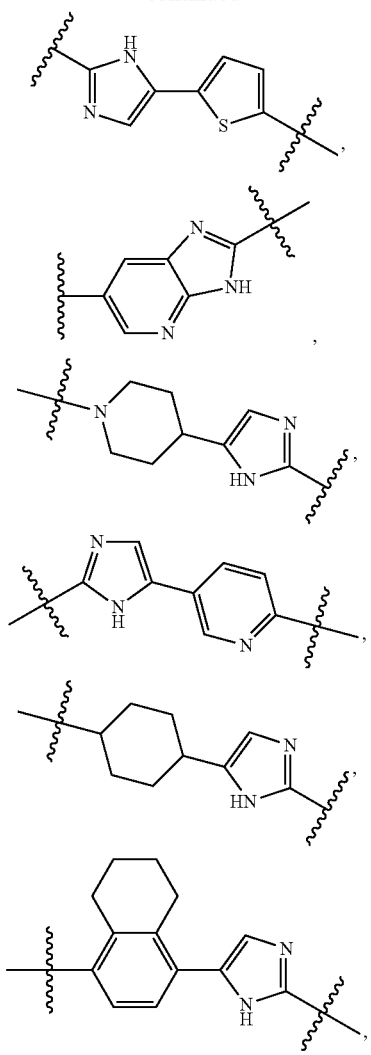
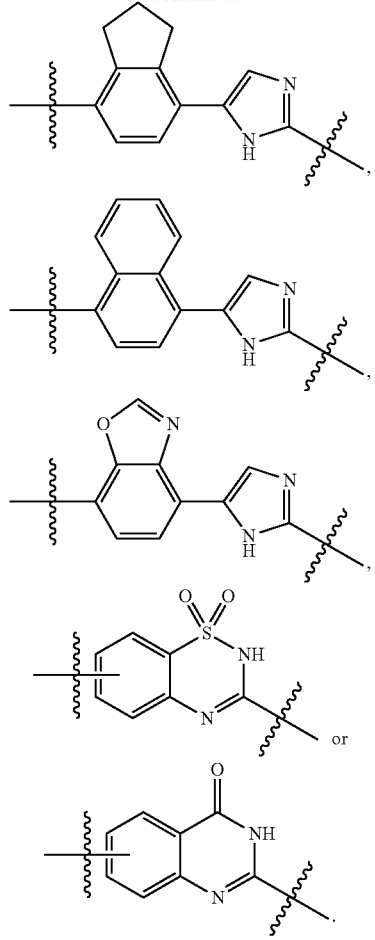
In another aspect, provided herein are one of the compounds as follows, or a stereoisomer, geometric isomer, tautomer, nitrogen oxide, hydrate, solvate, or pharmaceutically acceptable salt thereof, and not limited to:
(1)
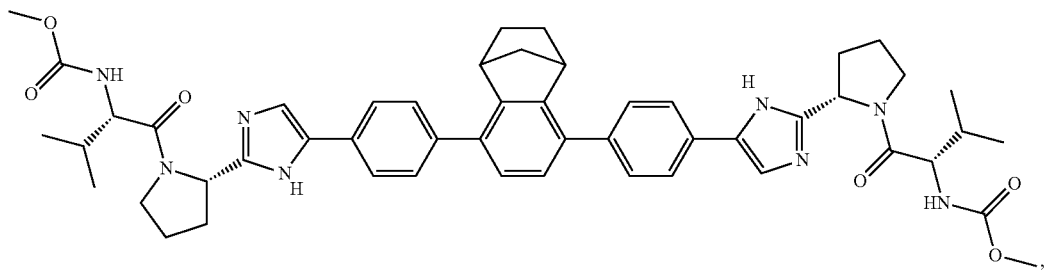
(2)
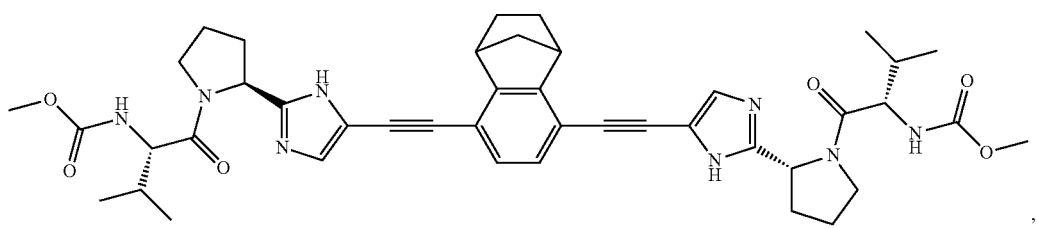

(3)
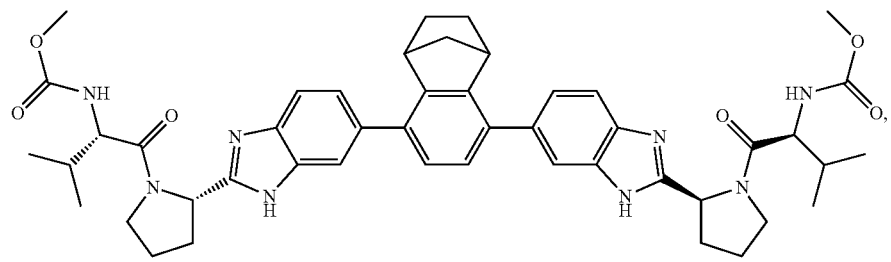
(4)
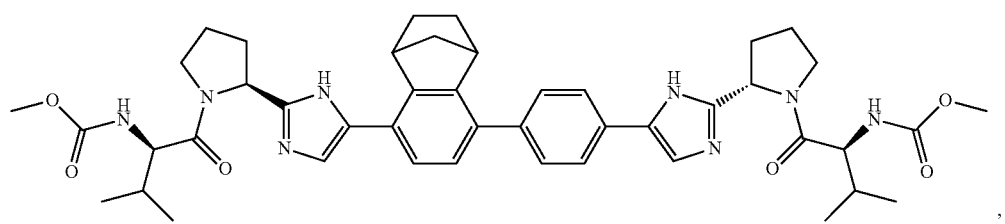
(5)
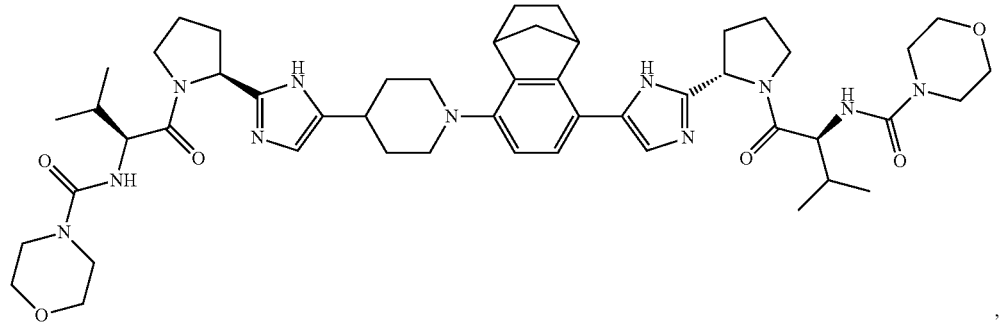
(6)
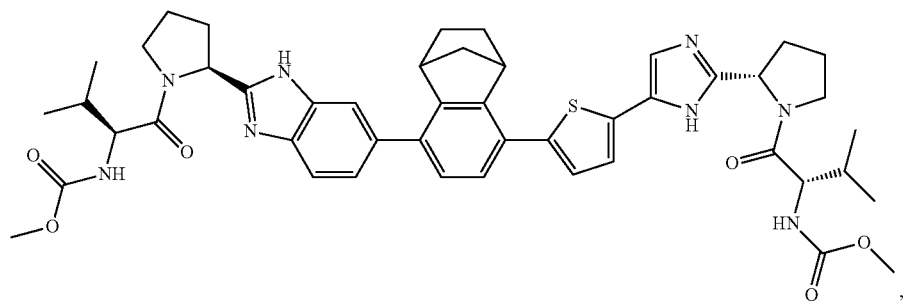
(7)
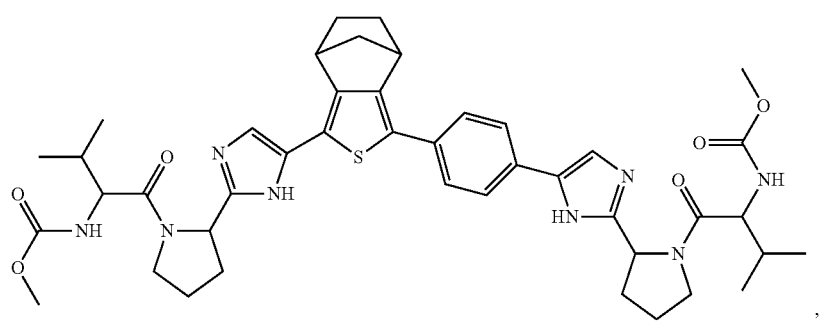

(8)
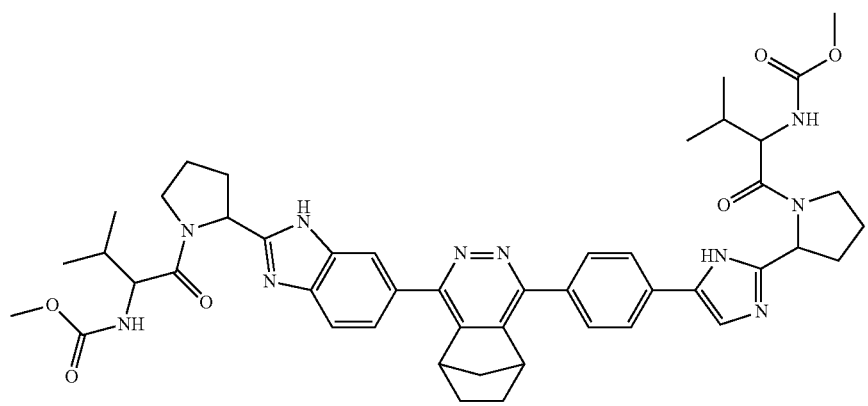
(9)
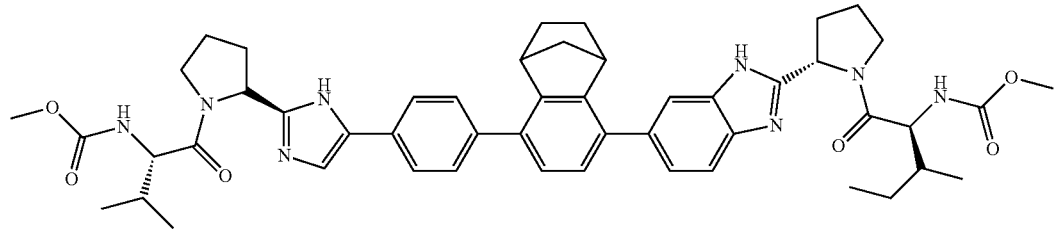
(10)
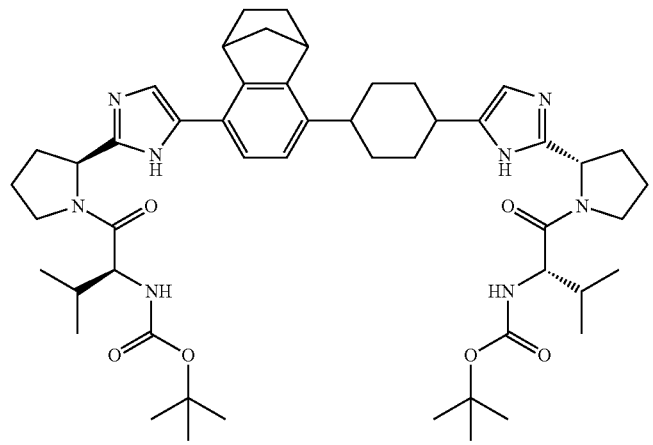
(11)
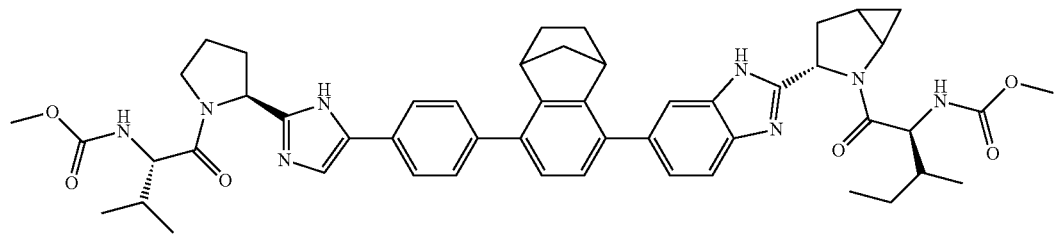
(12)
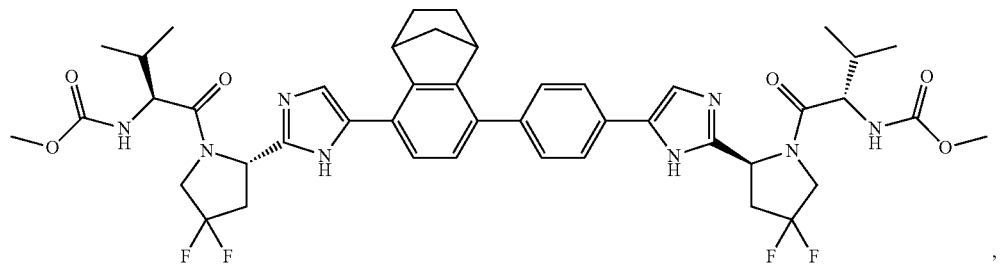

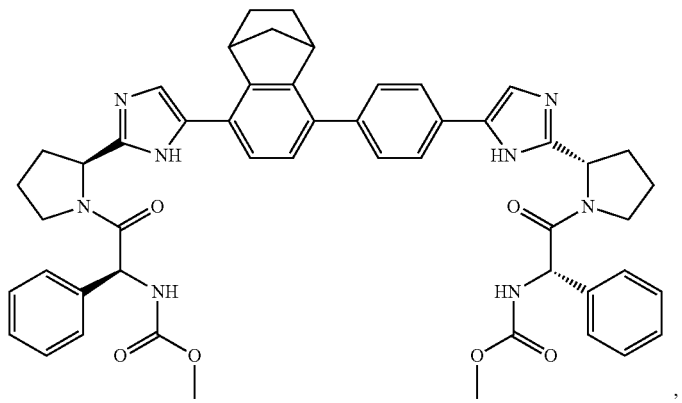
(13)
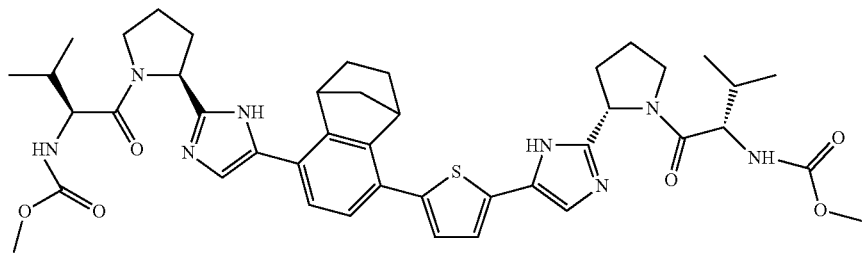
(14)
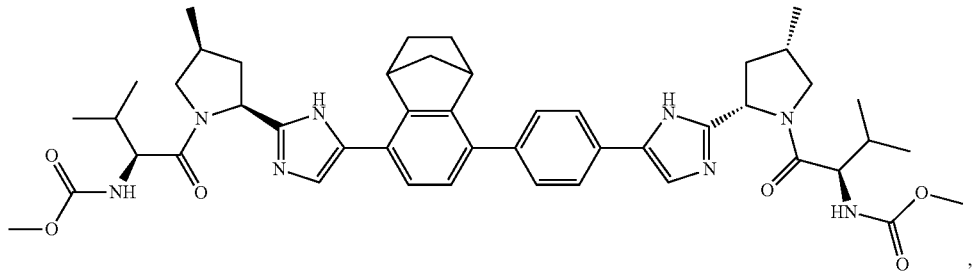
(15)
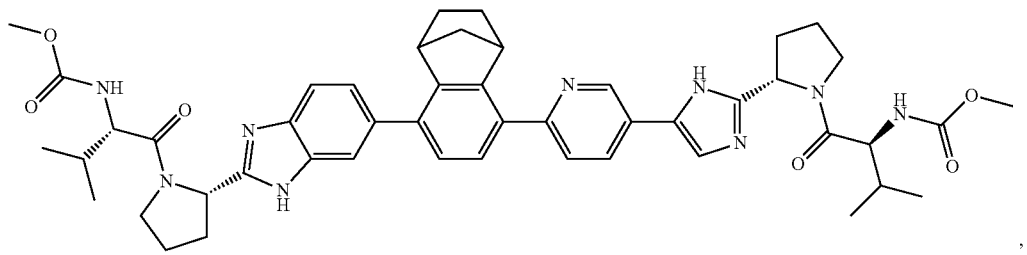
(16)
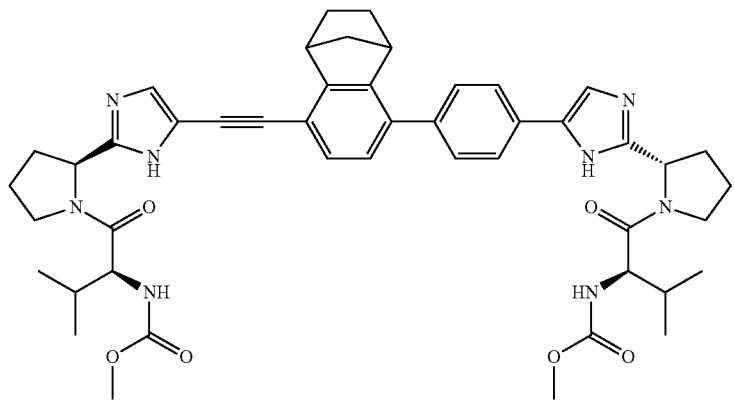
(17)

(18)
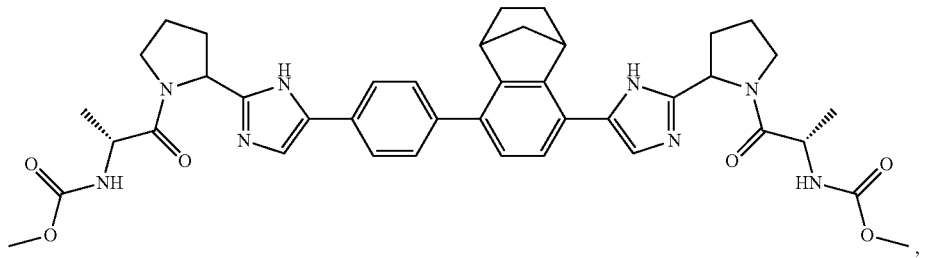
(19)
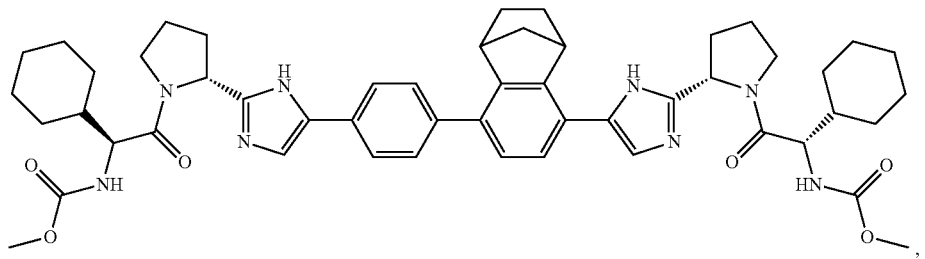
(20)
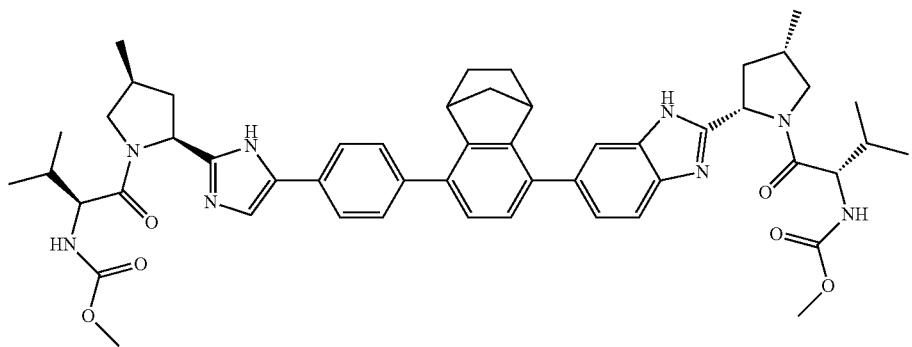
(21)
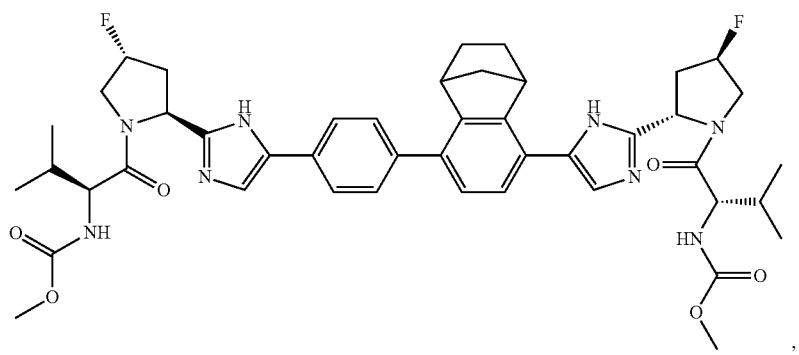
(22)
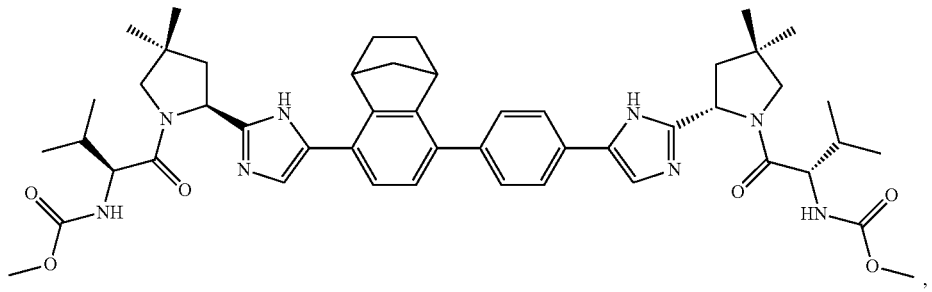

(23)
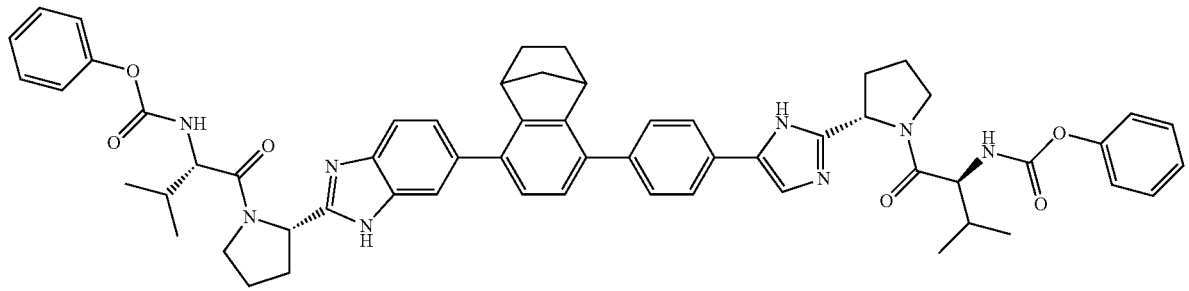
(24)
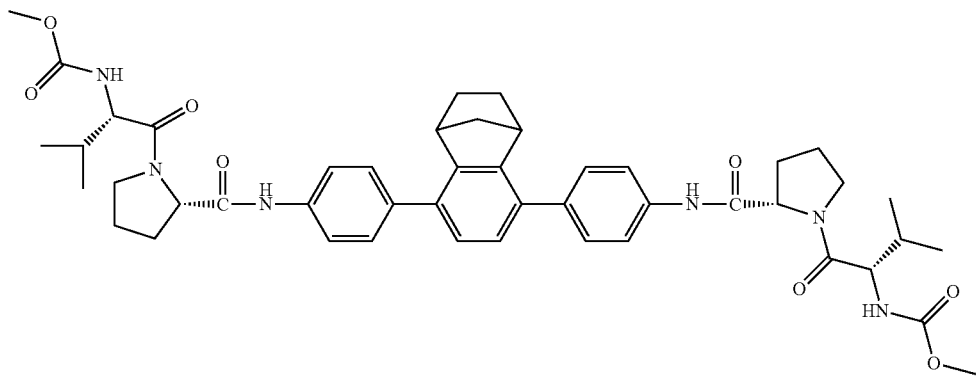
(25)
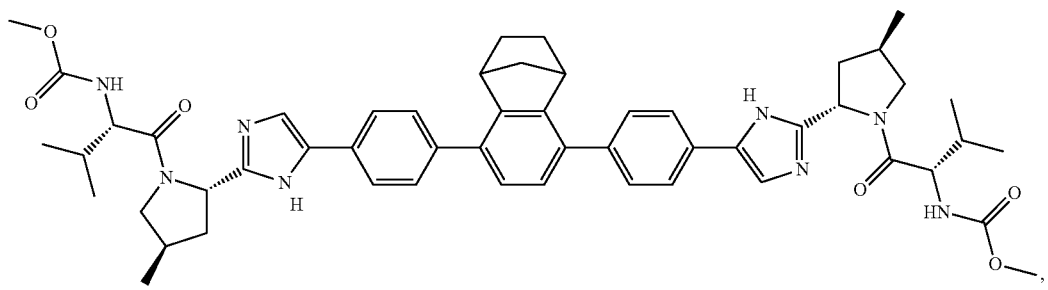
(26)
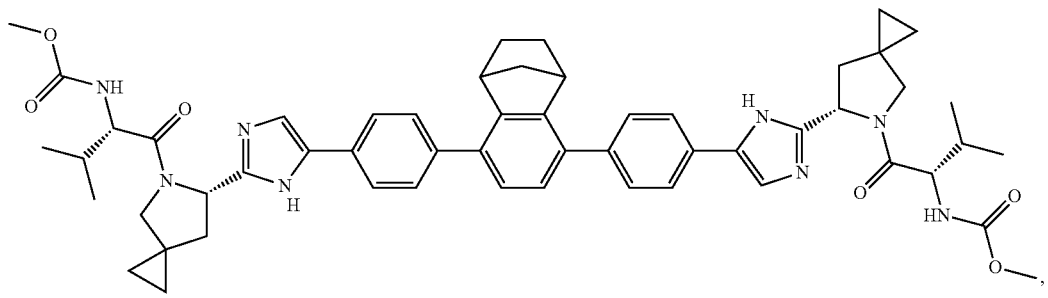
(27)
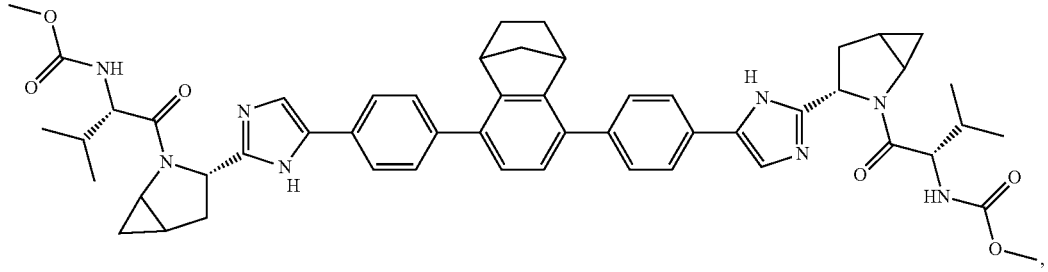

-continued
(28)
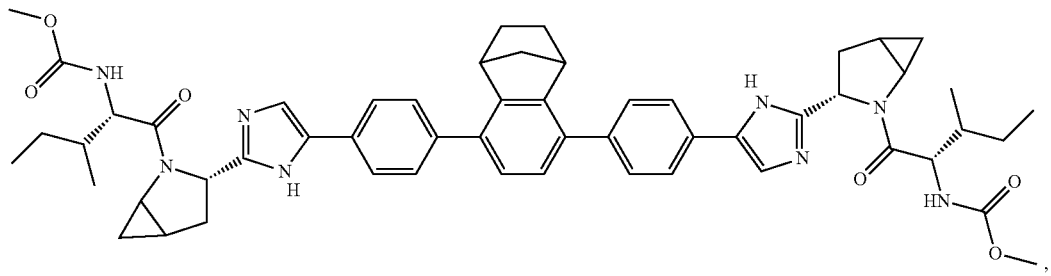
(29)
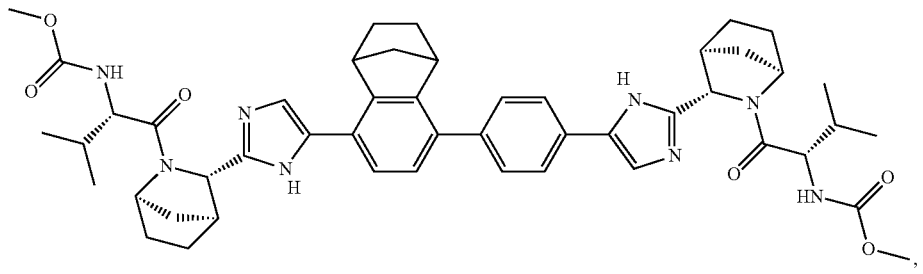
(30)
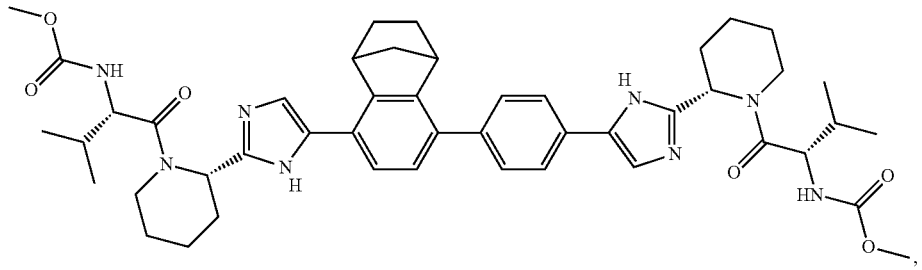
(31)
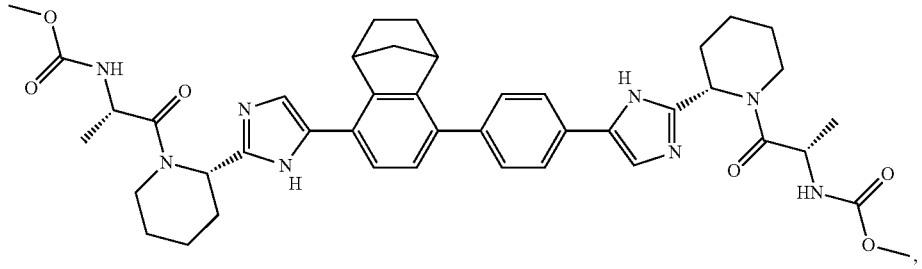
(32)
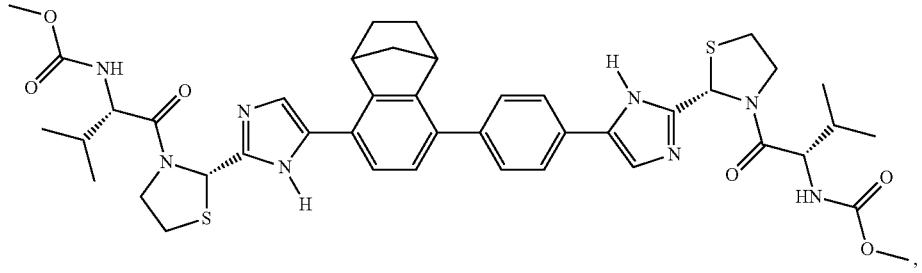
(33)
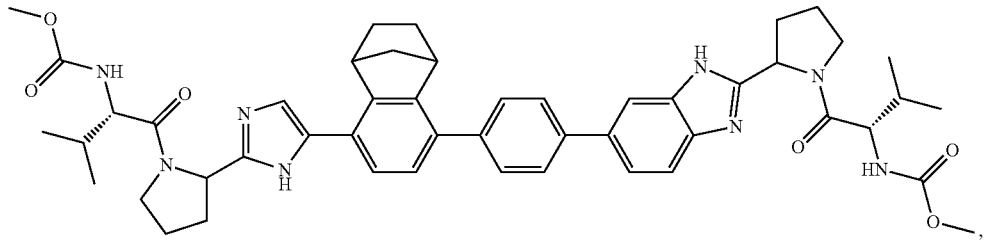

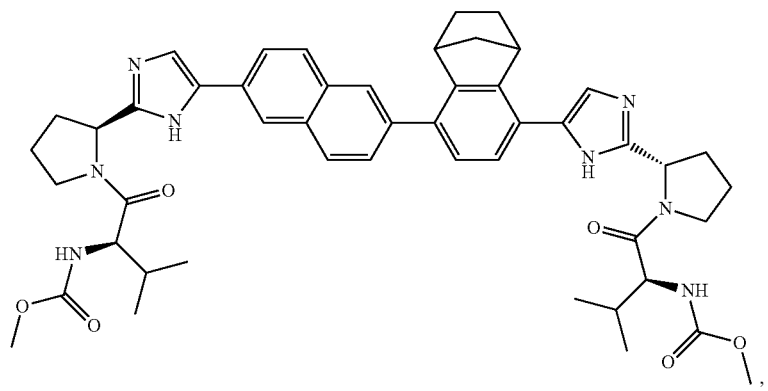
(34)
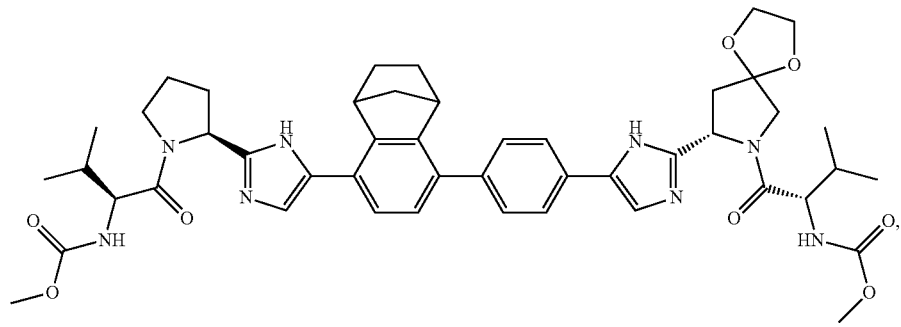
(35)
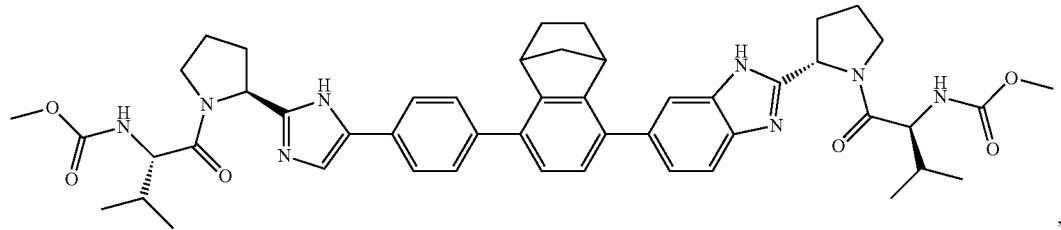
(36)
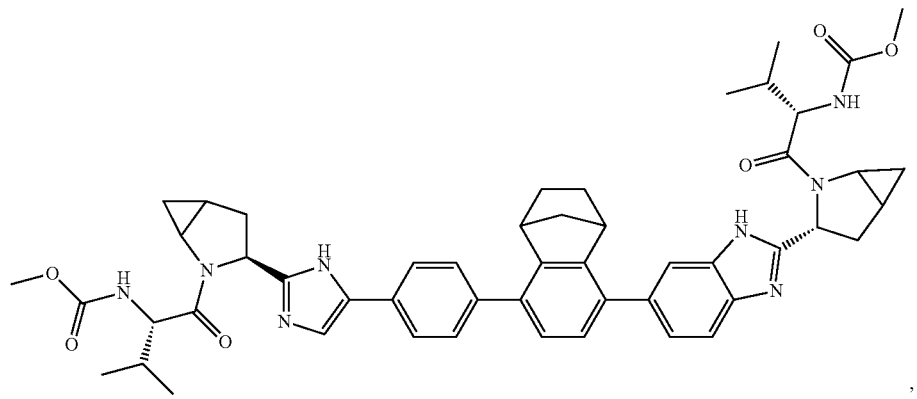
(37)

(38)
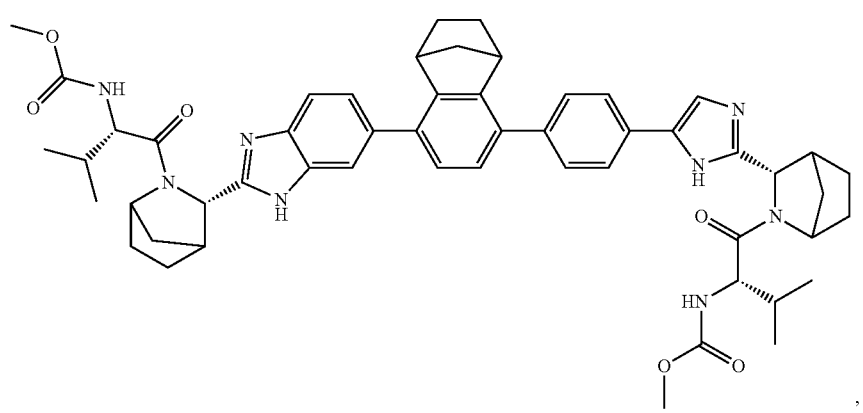
(39)
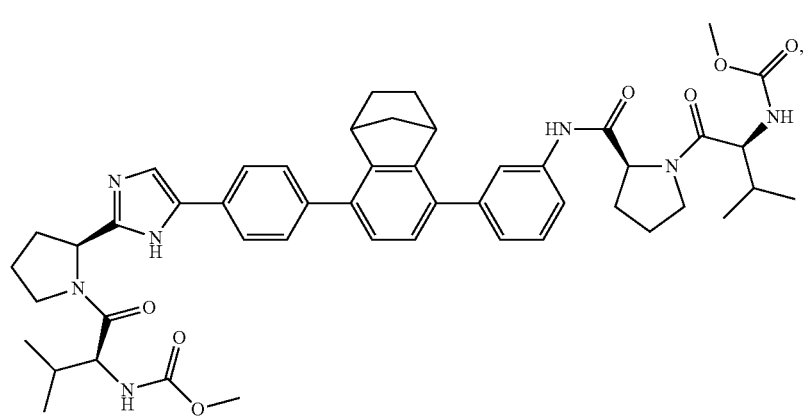
(40)
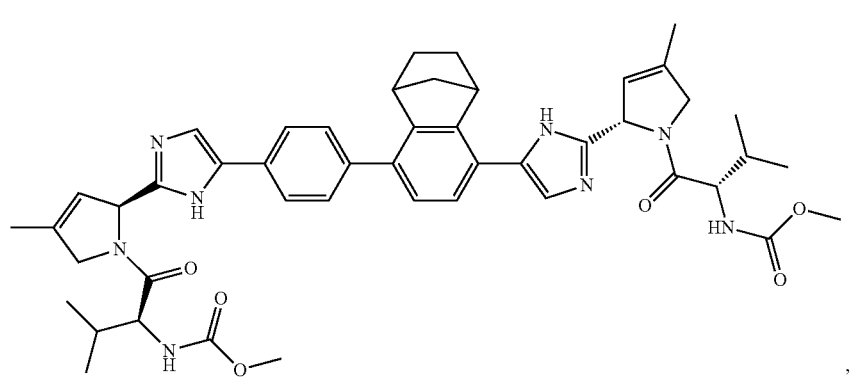
(41)
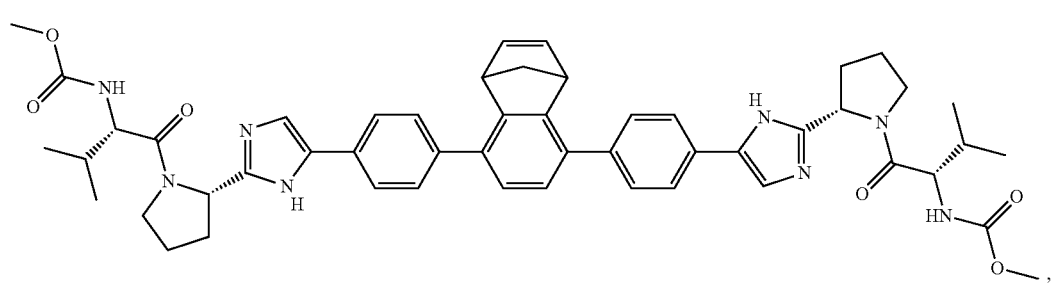

-continued
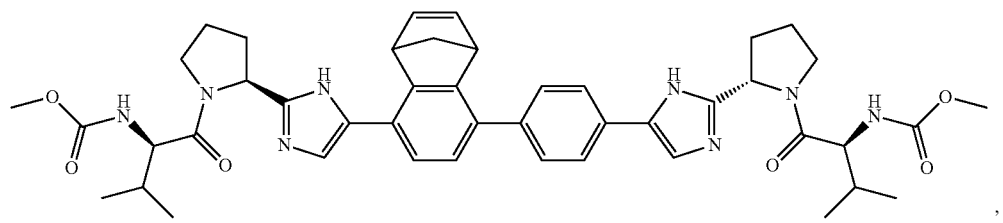
(42)
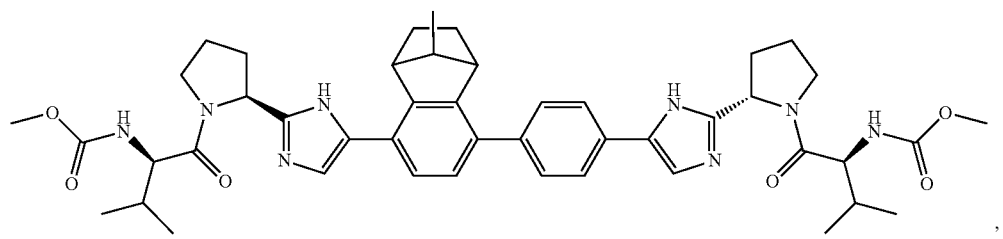
(43)
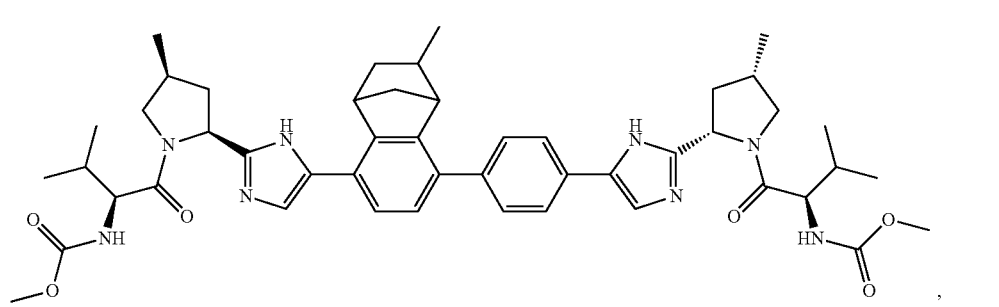
(44)
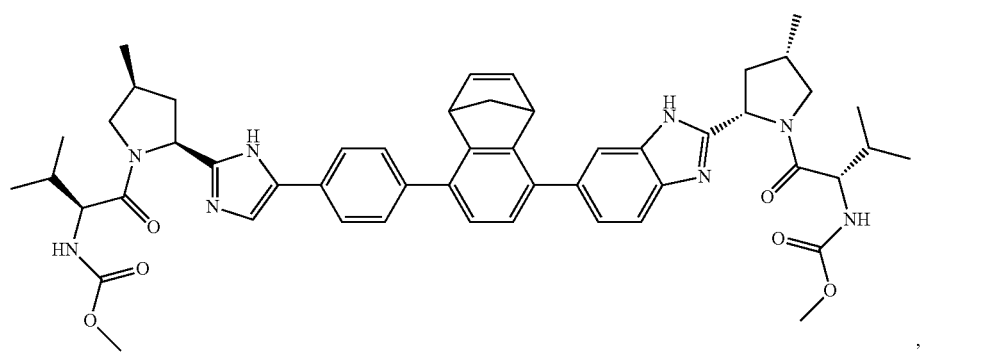
(45)
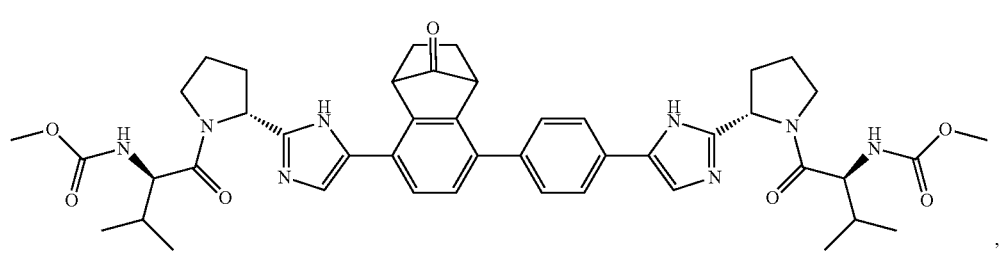
(46)
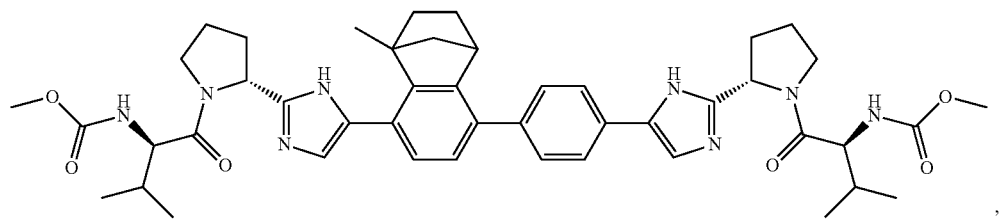
(47)

-continued
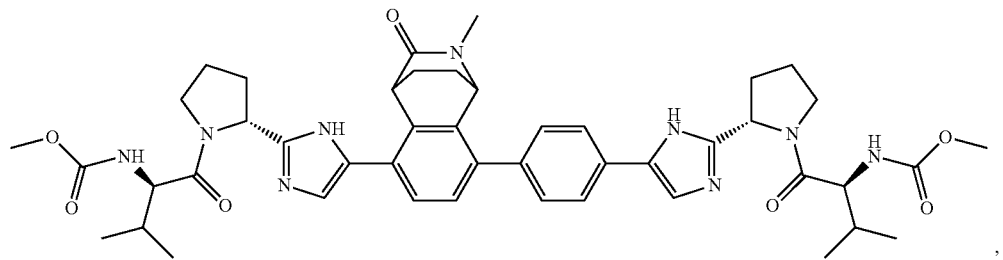
(48)
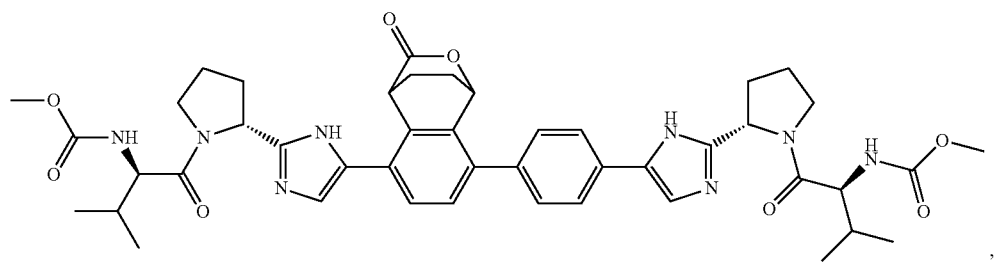
(49)
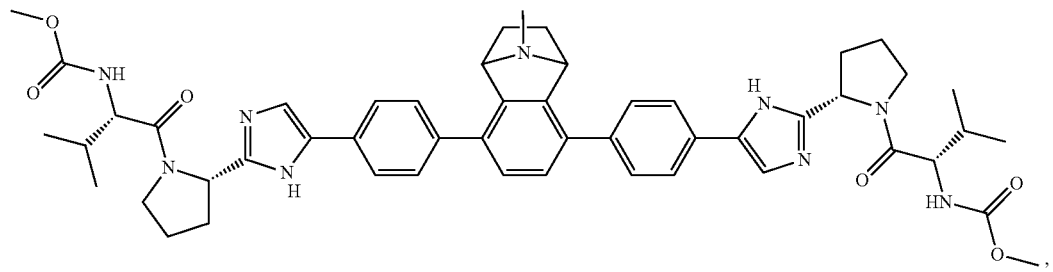
(50)
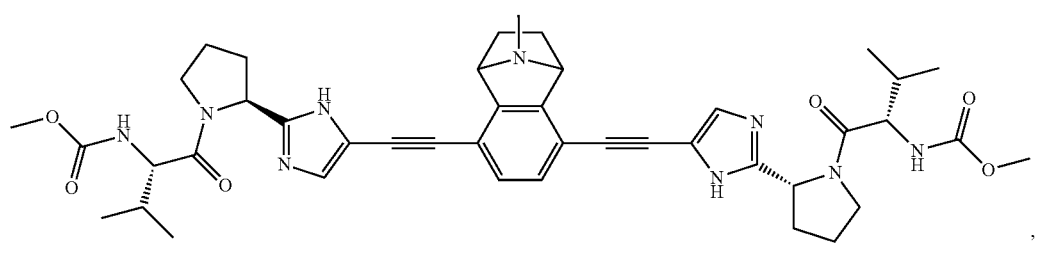
(51)
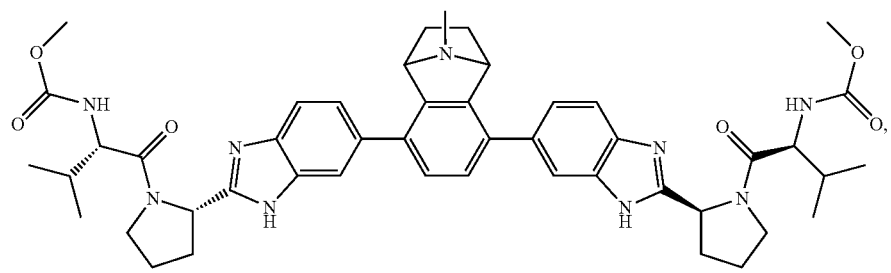
(52)
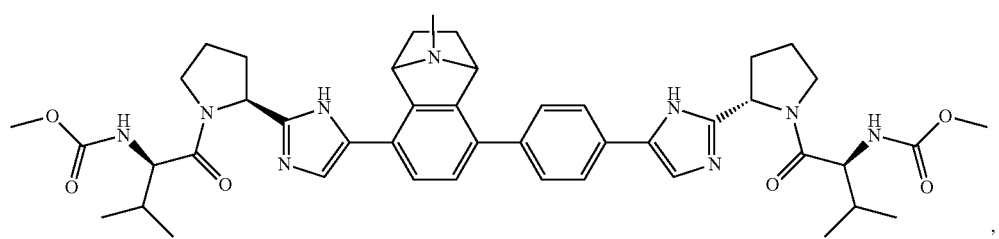
(53)

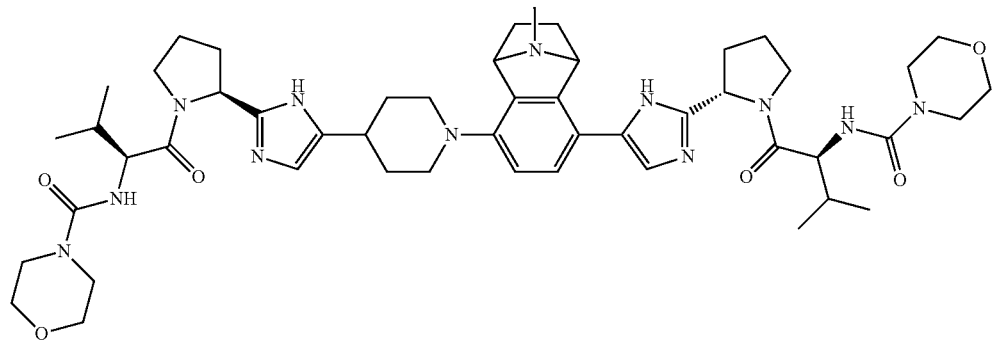
(54)
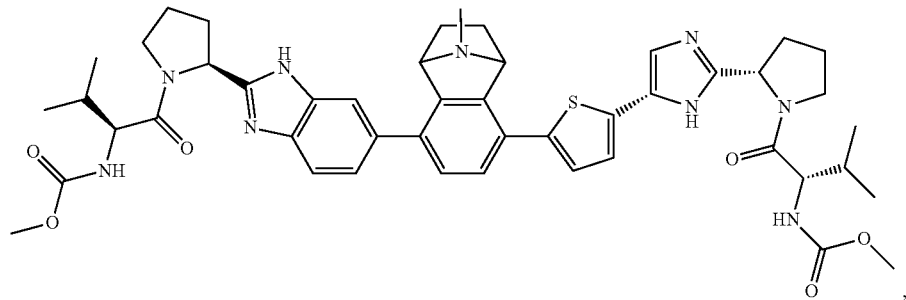
(55)
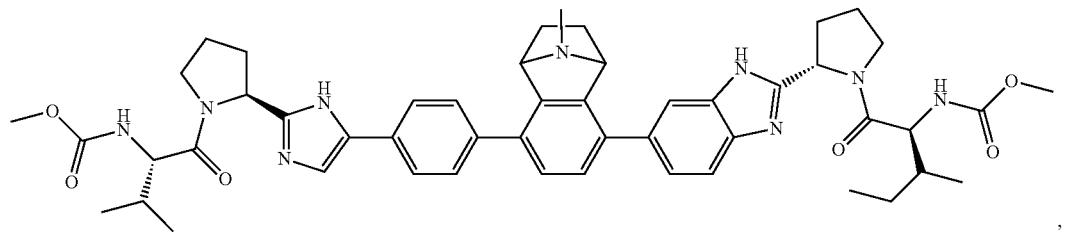
(56)
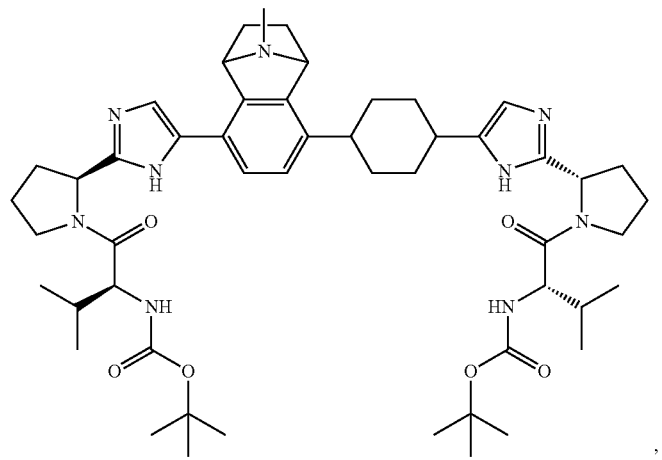
(57)
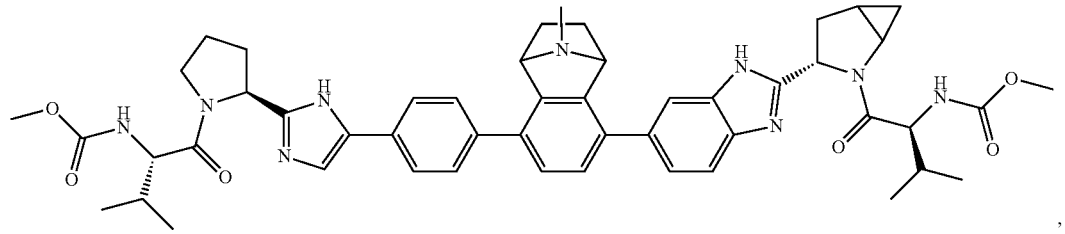
(58)

-continued
(59)
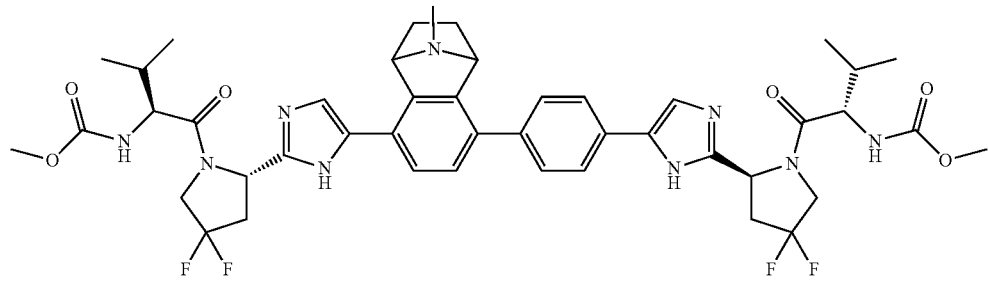
(60)
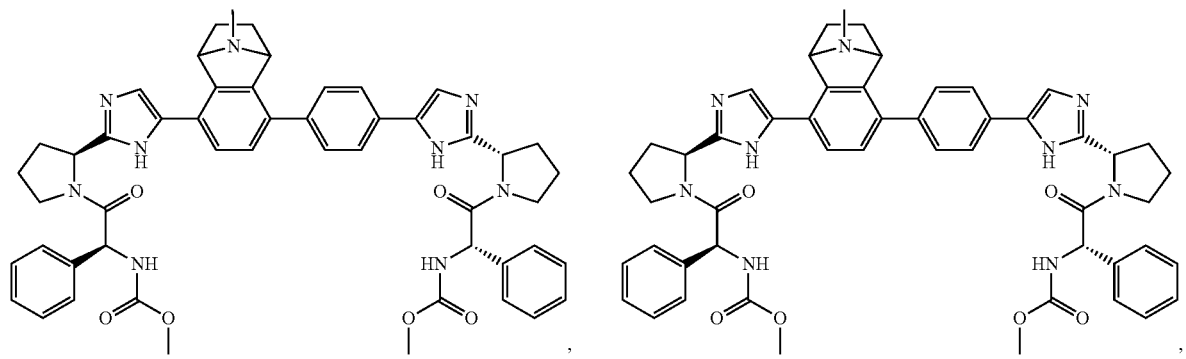
(61)
(62)
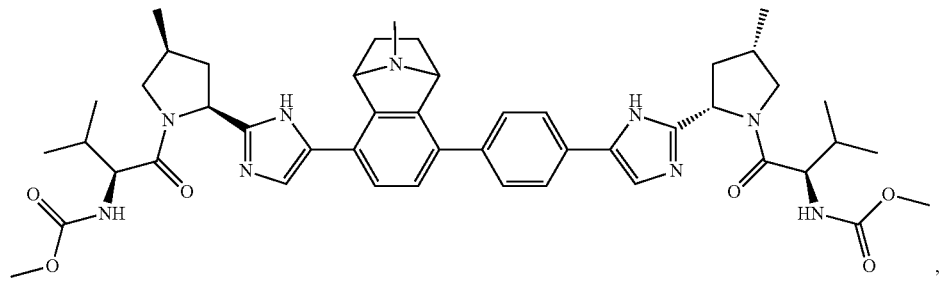
(63)
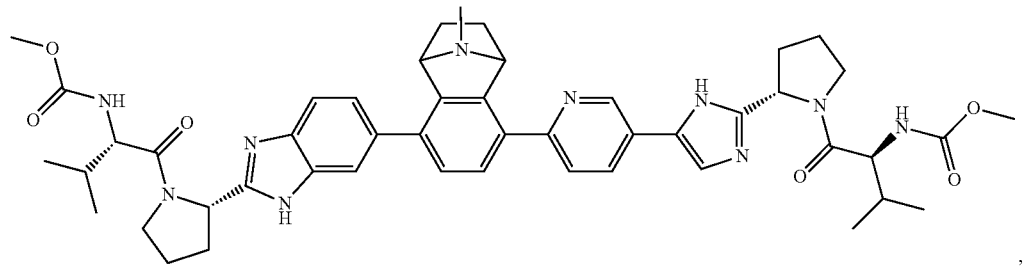
(64)
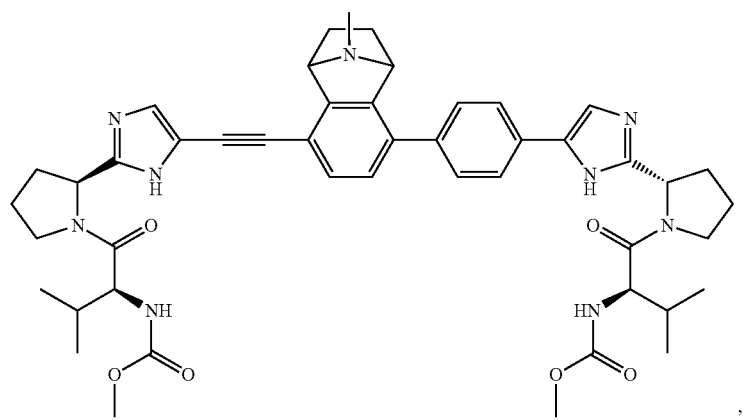

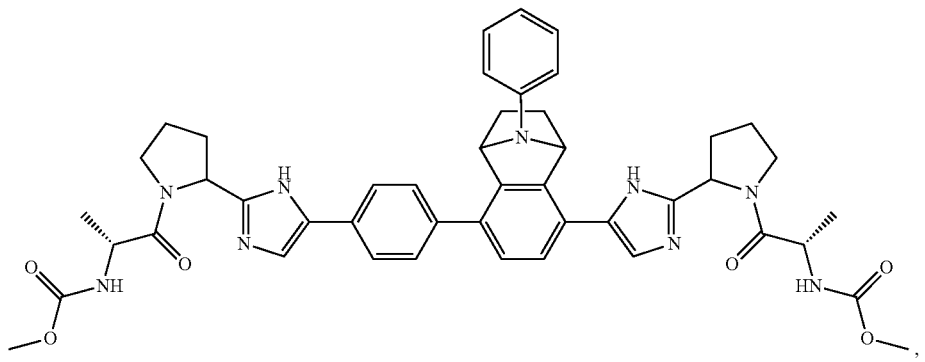
(65)
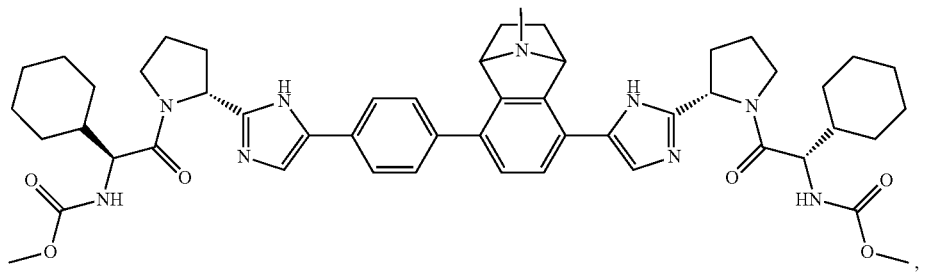
(66)
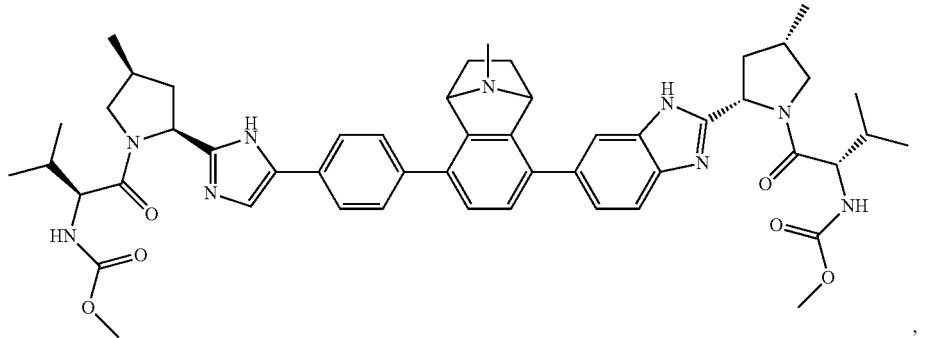
(67)
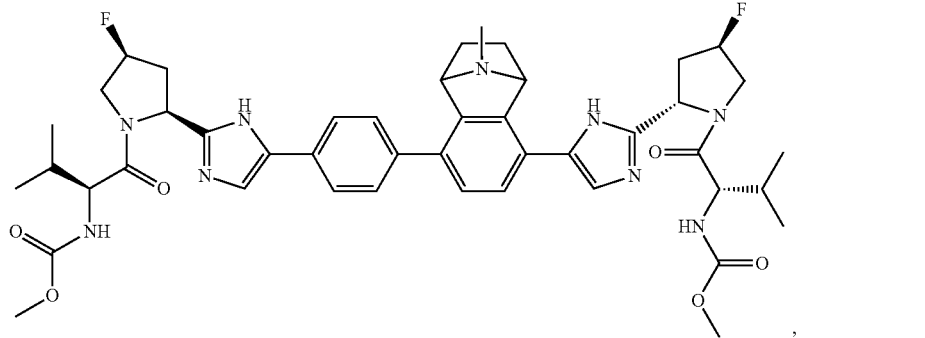
(68)
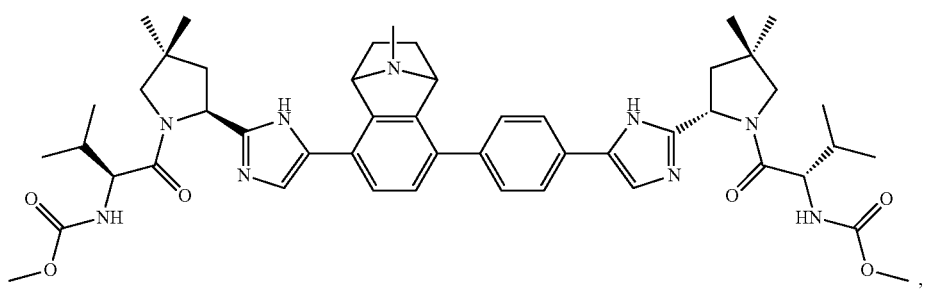
(69)

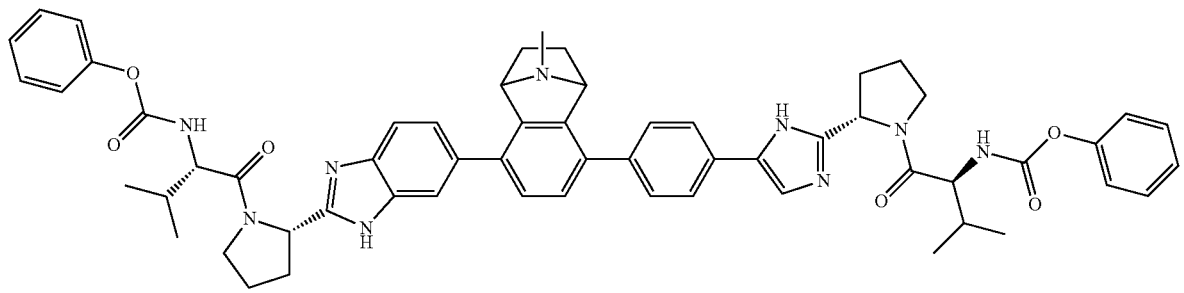
(70)
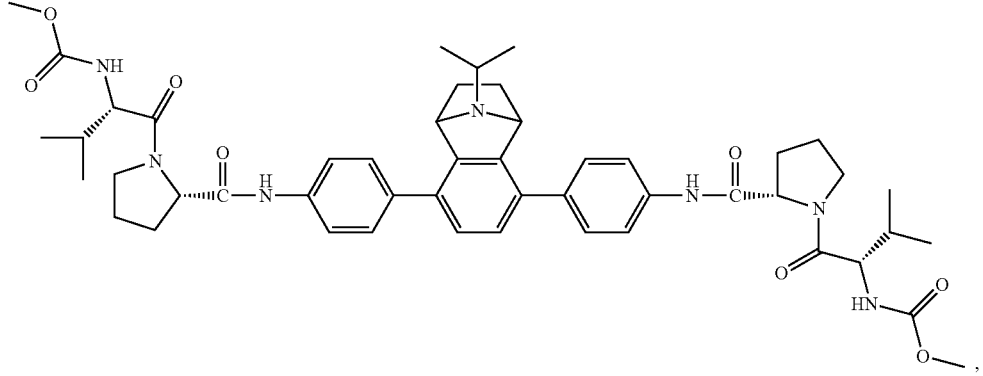
(71)
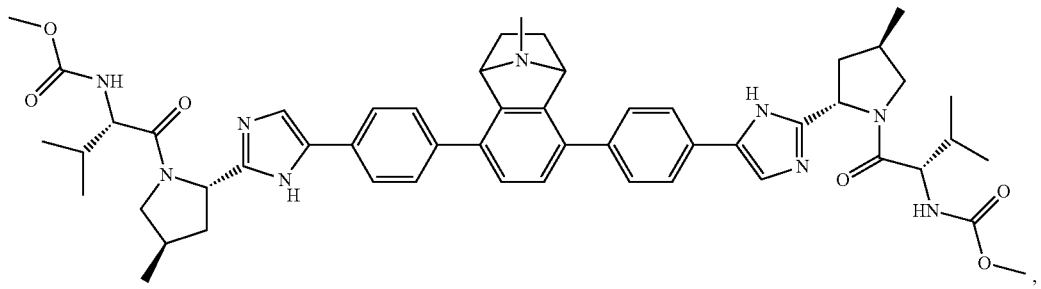
(72)
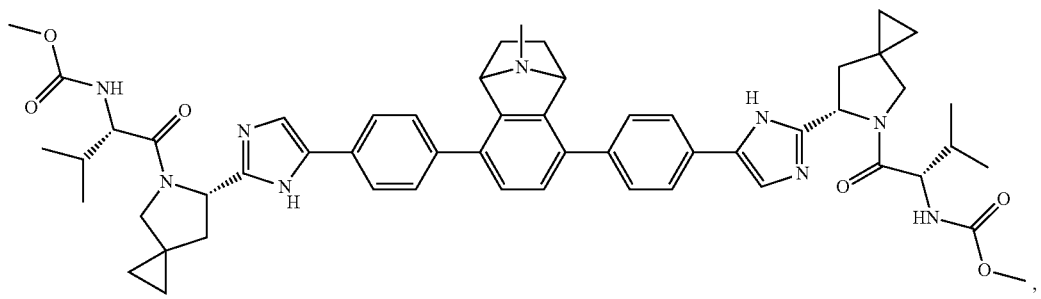
(73)
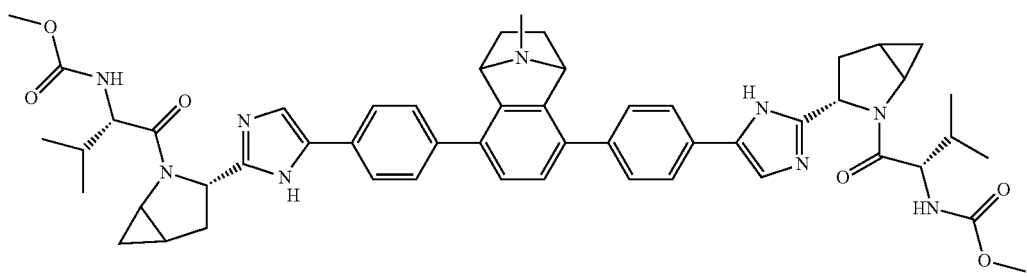
(74)

-continued
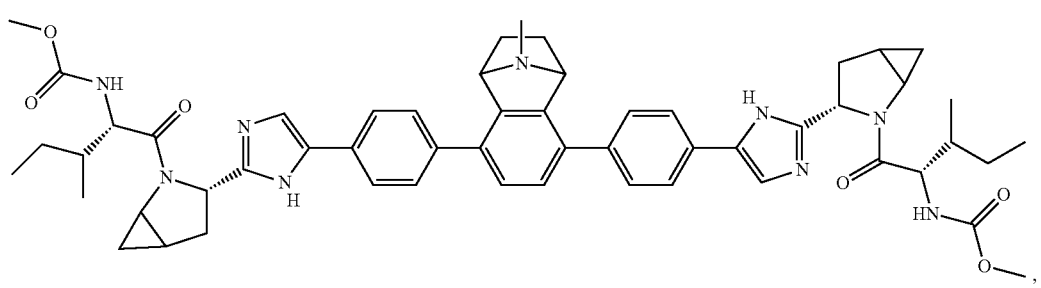
(75)
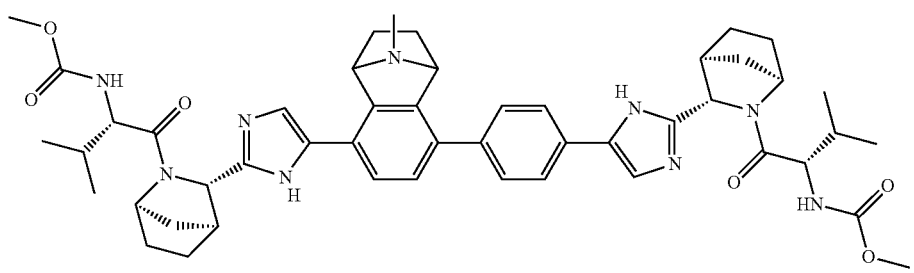
(76)
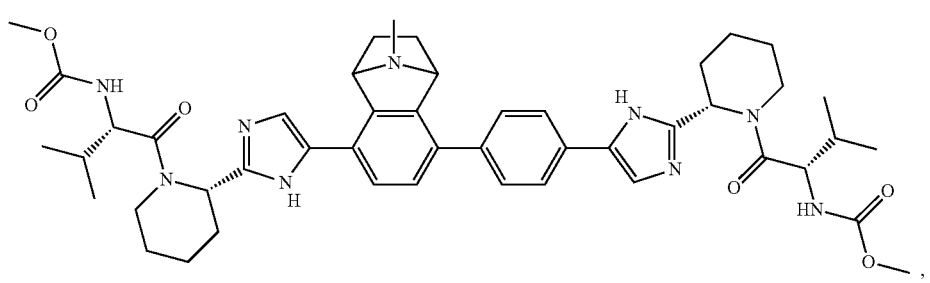
(77)
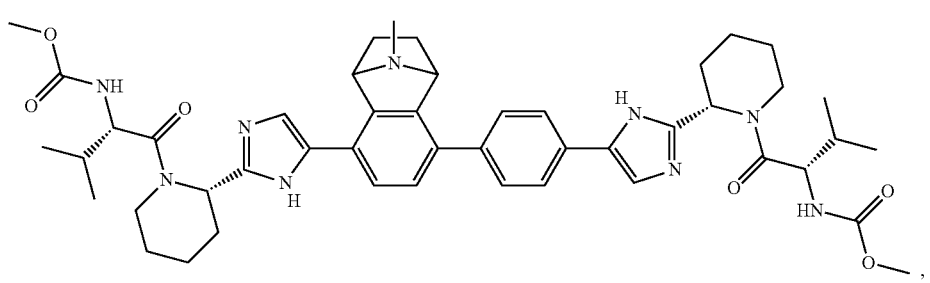
(78)
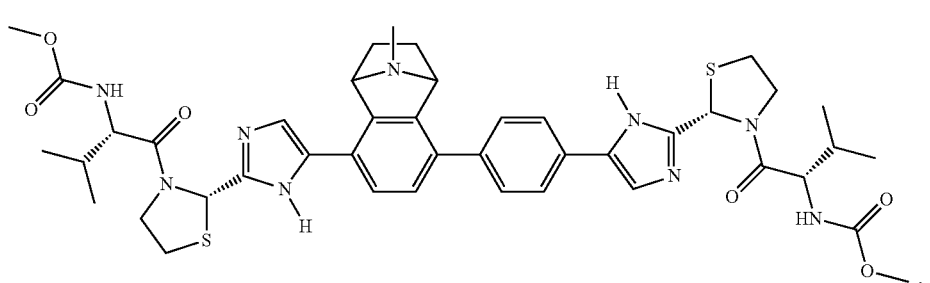
(79)
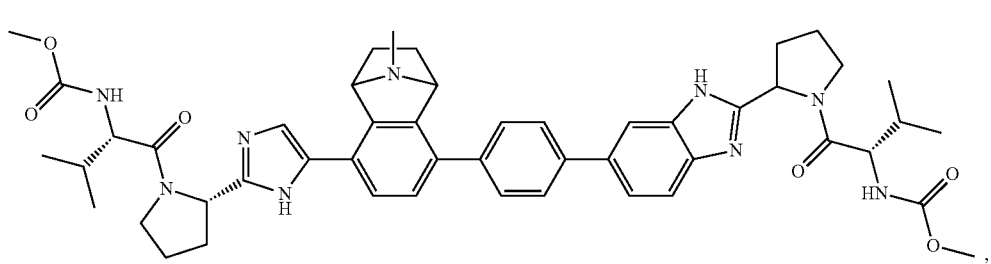
(80)

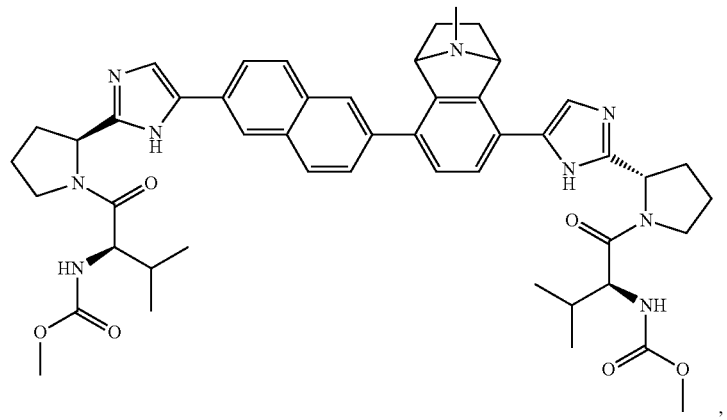
(81)
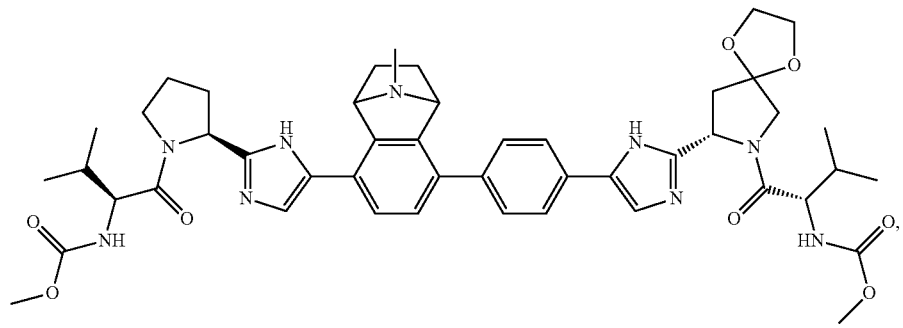
(82)
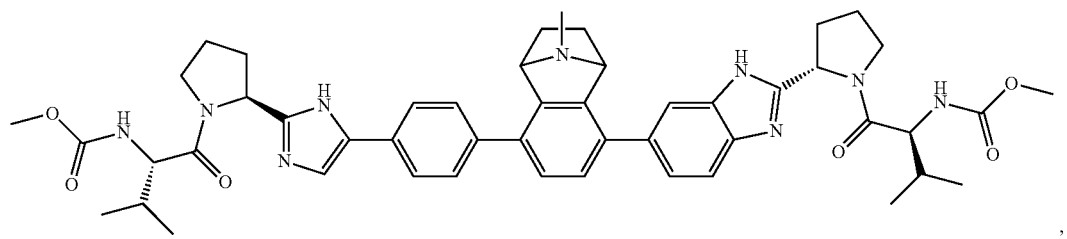
(83)
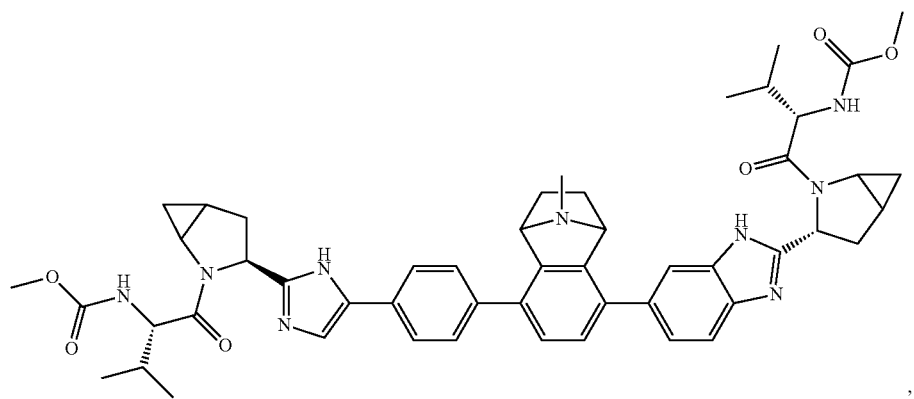
(84)

(85)
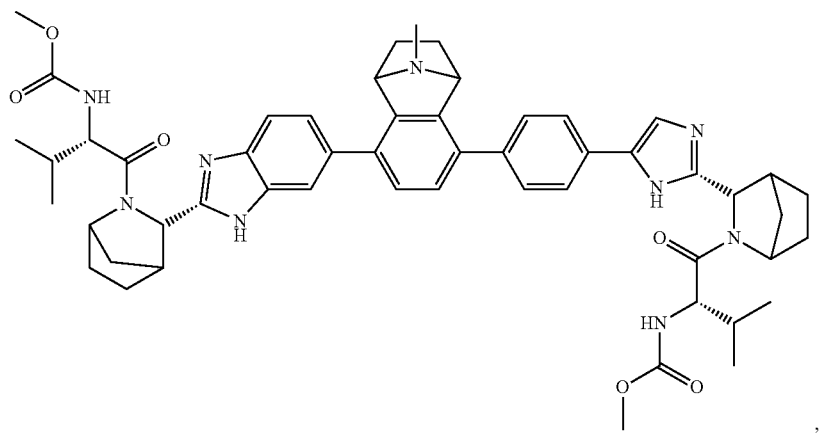
(86)
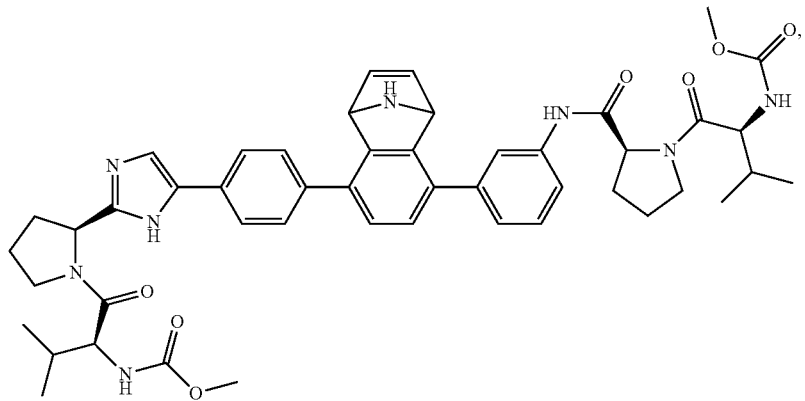
(87)
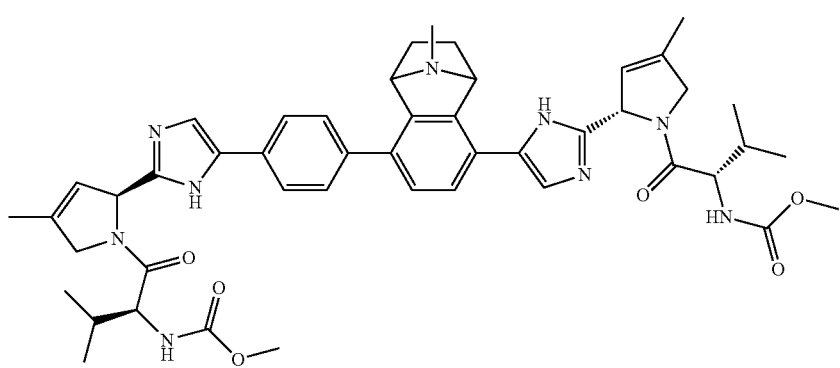
(88)
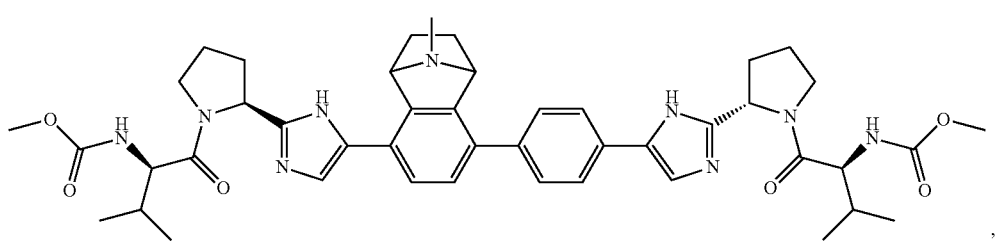

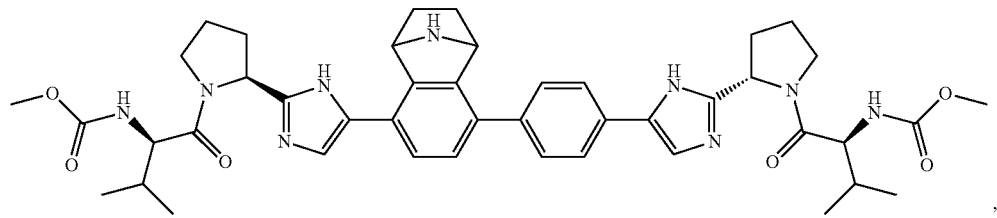
(89)
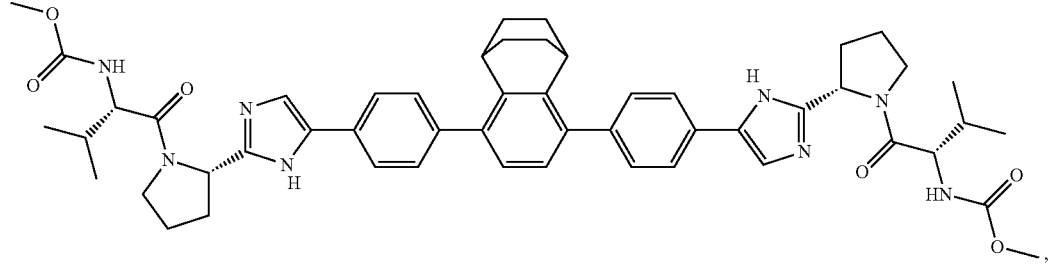
(90)
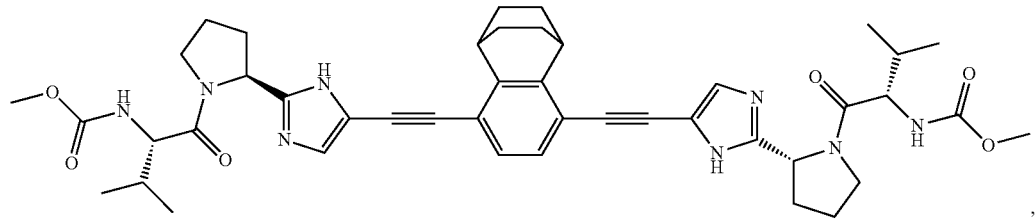
(91)
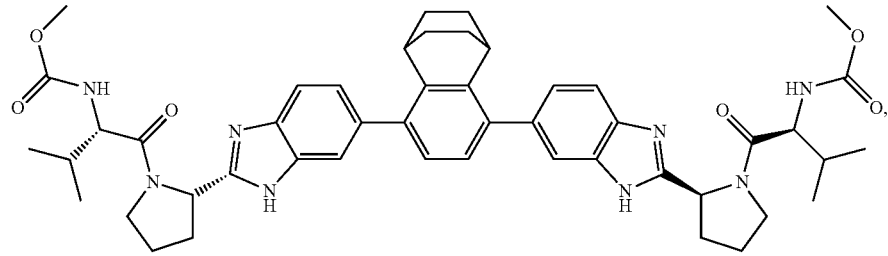
(92)
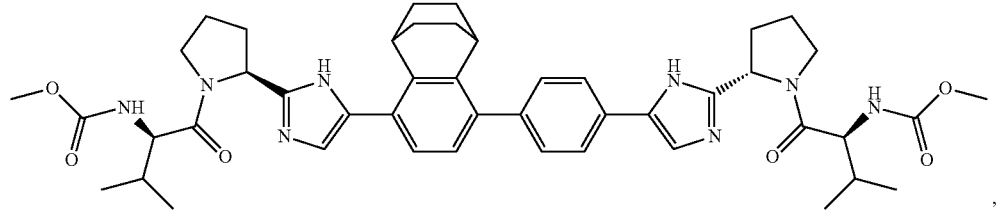
(93)
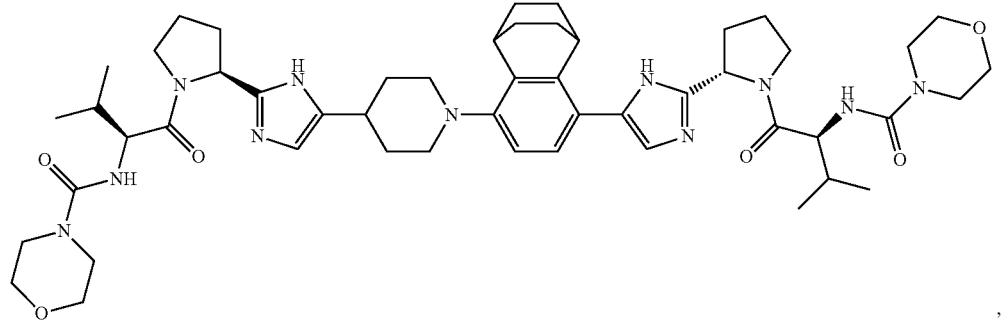
(94)

(95)
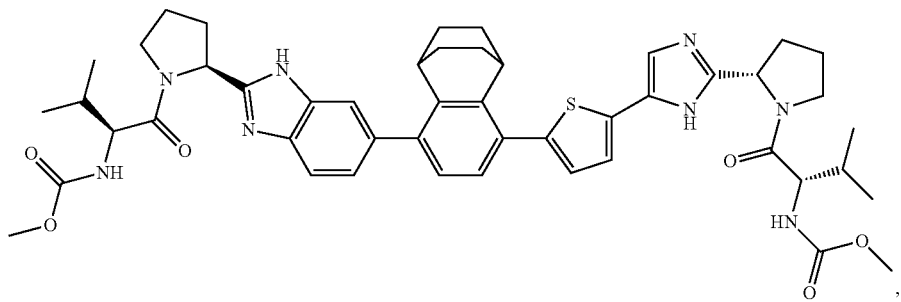
(96)
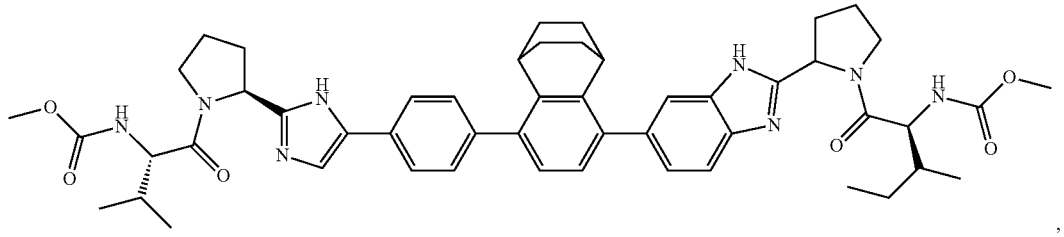
(97)
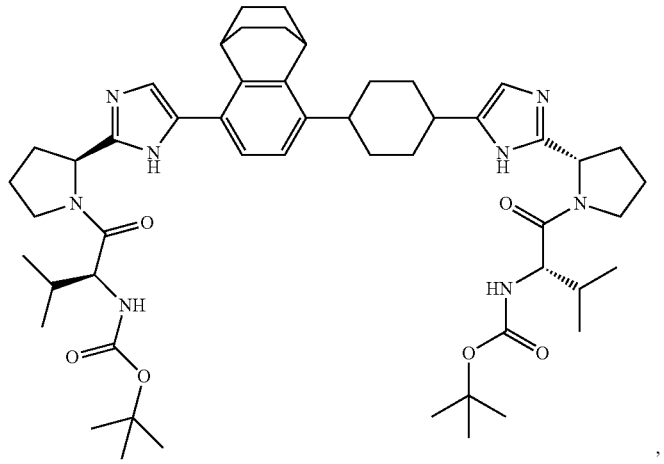
(98)
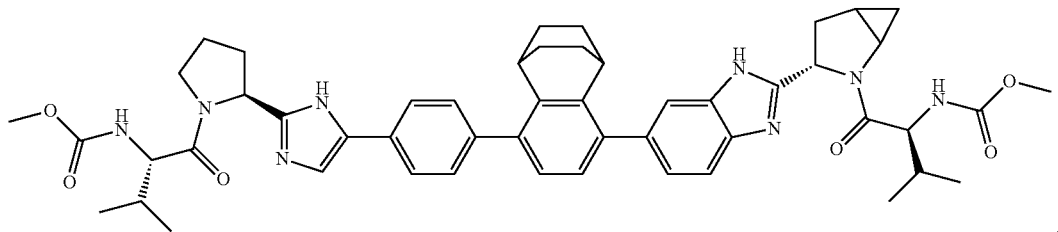
(99)
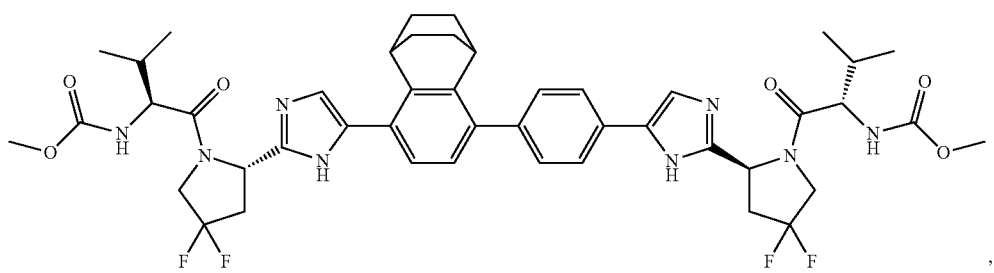

-continued
(100)
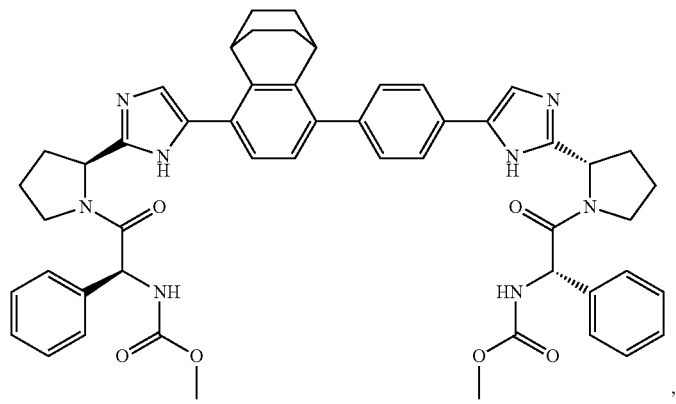
(101)
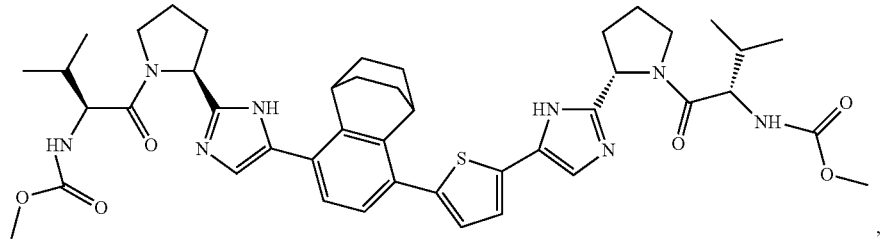
(102)
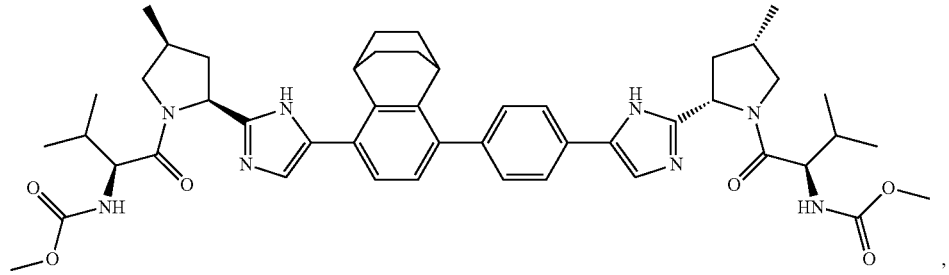
(103)
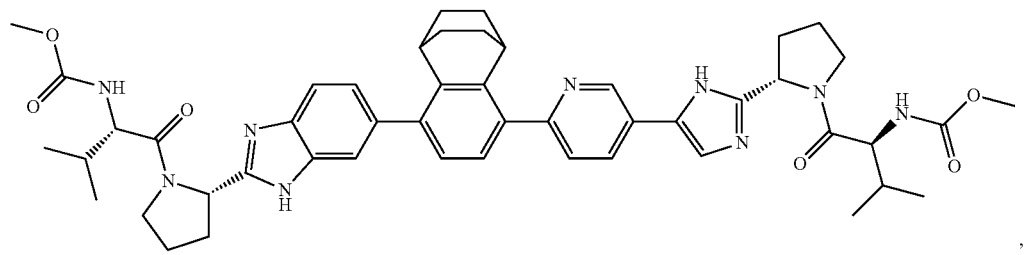
(104)
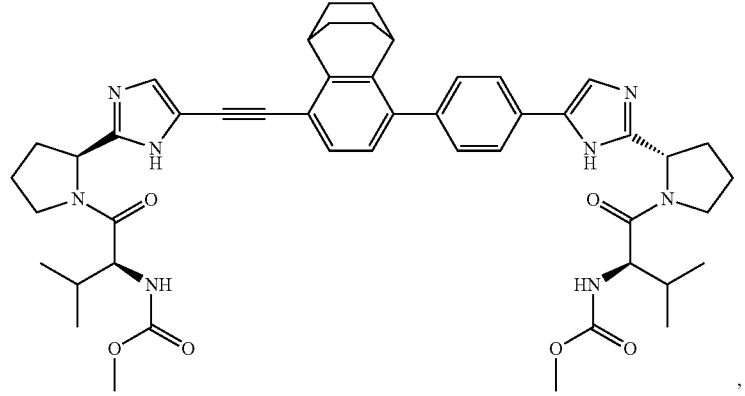

(105)
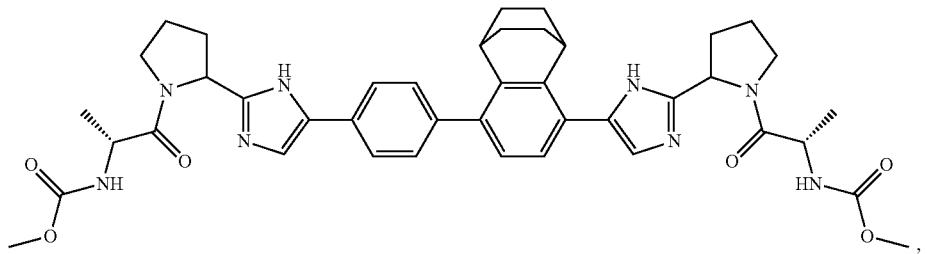
(106)
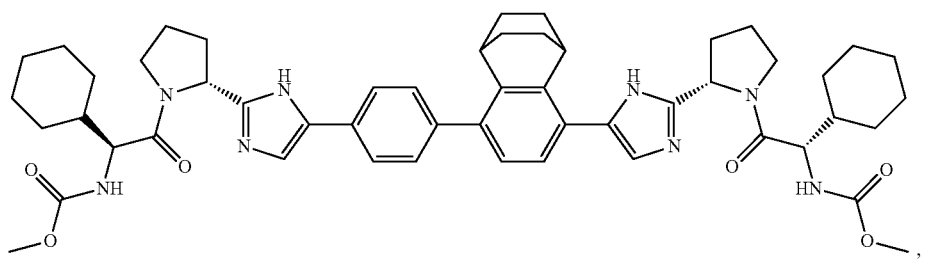
(107)
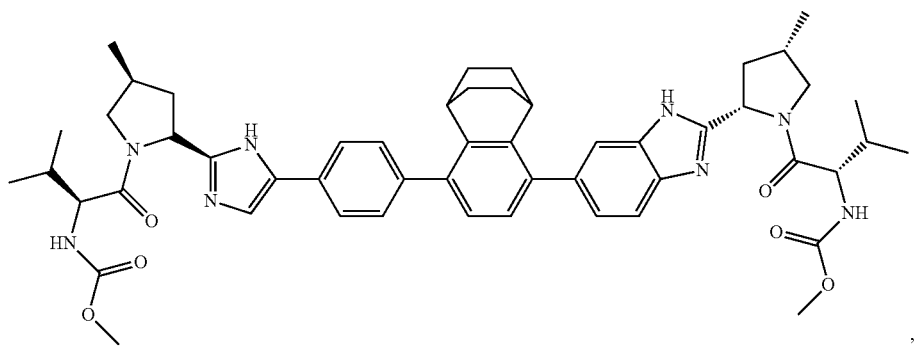
(108)
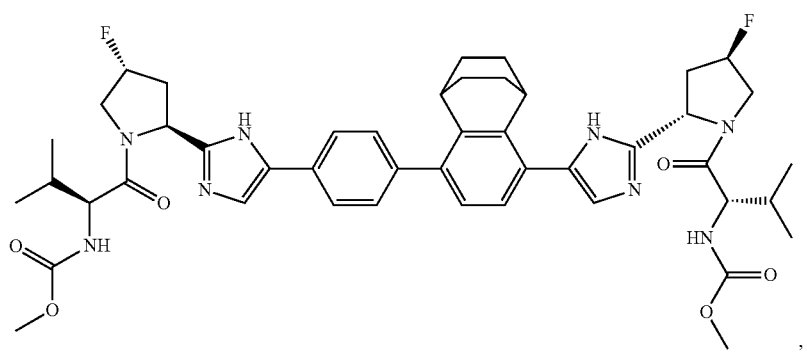
(109)
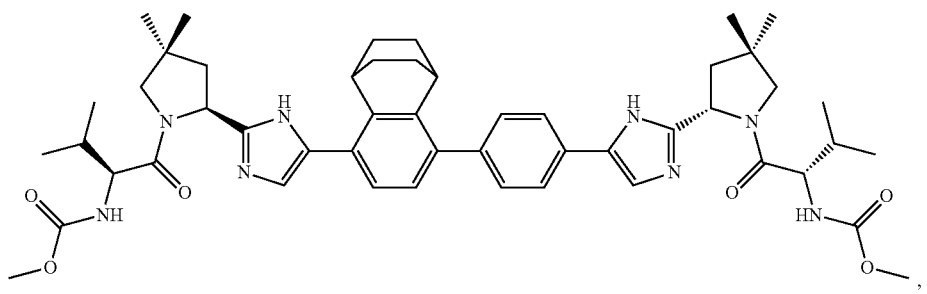

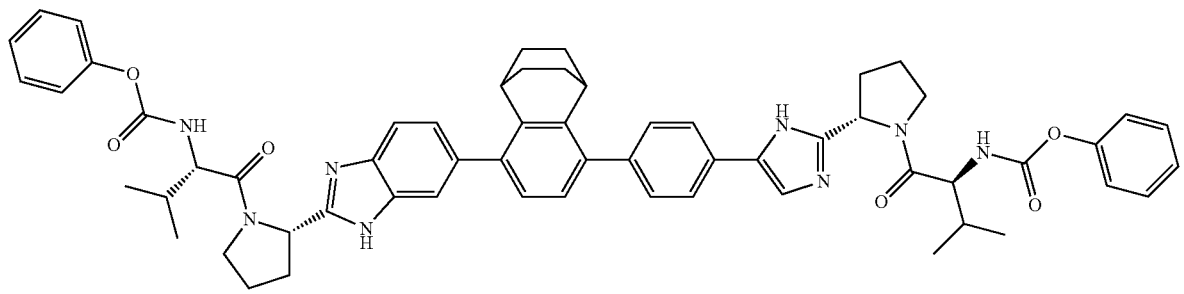
(110)
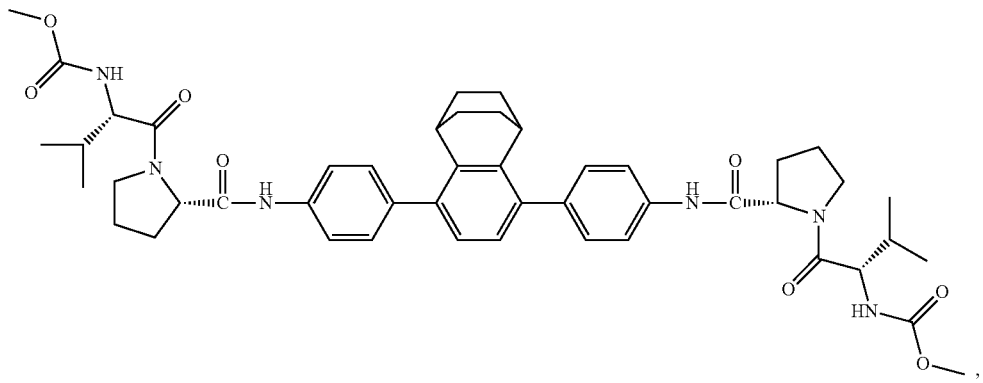
(111)
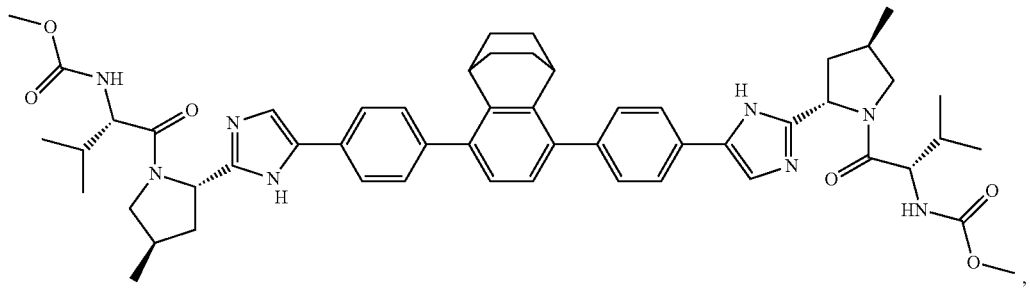
(112)
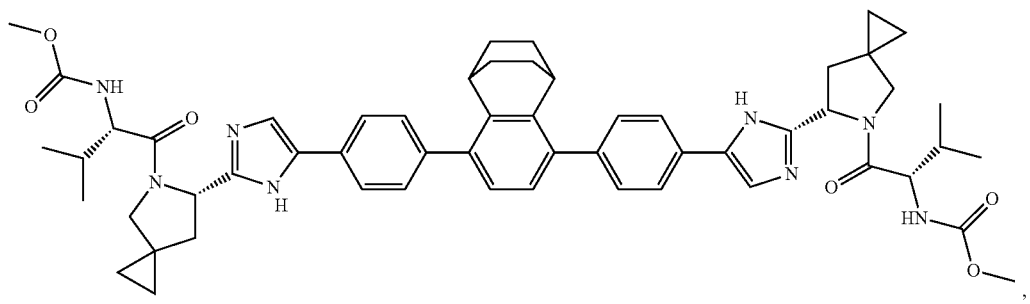
(113)
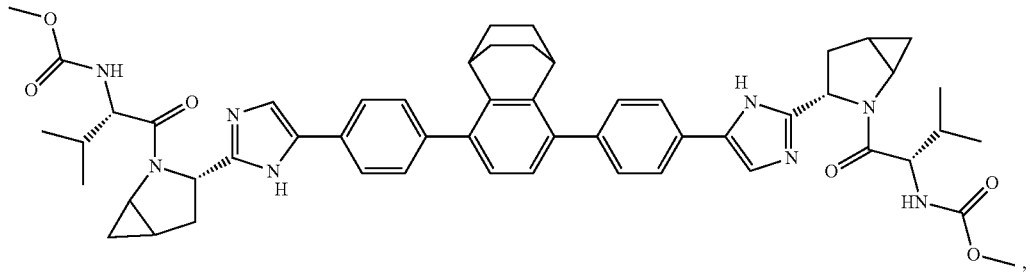
(114)

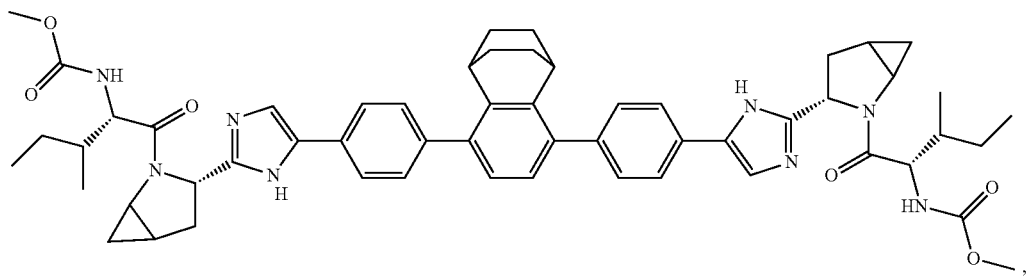
(115)
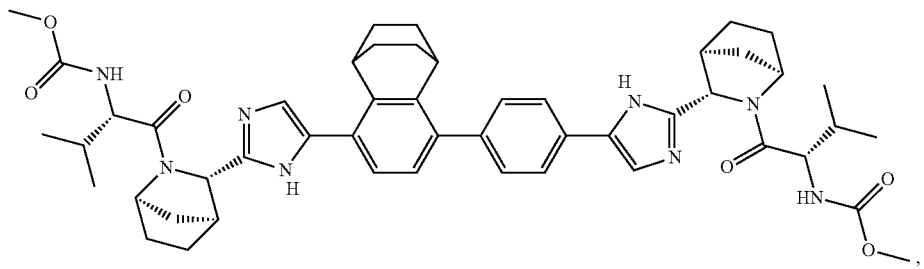
(116)
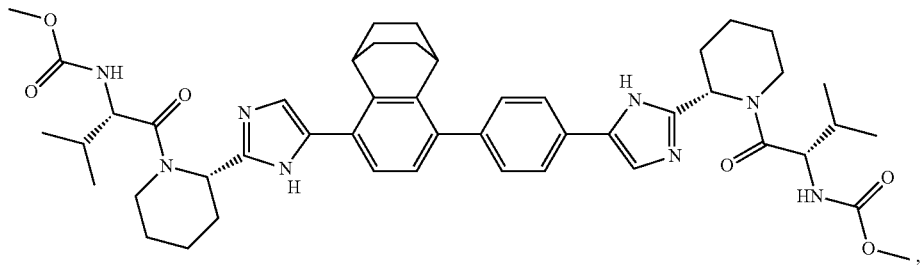
(117)
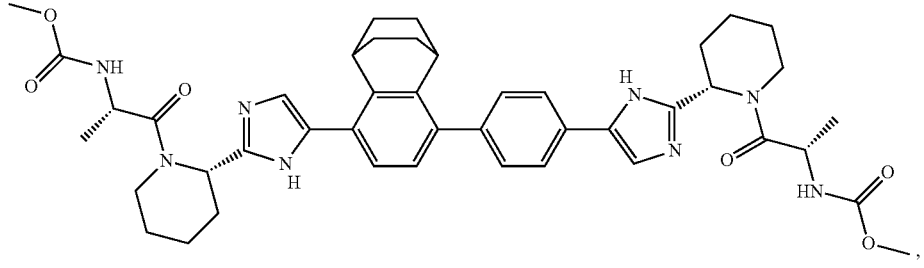
(118)
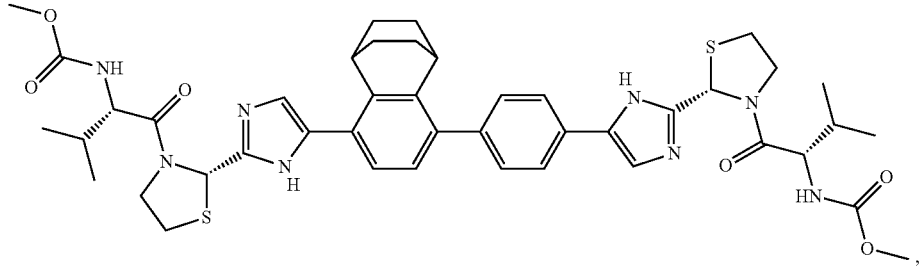
(119)
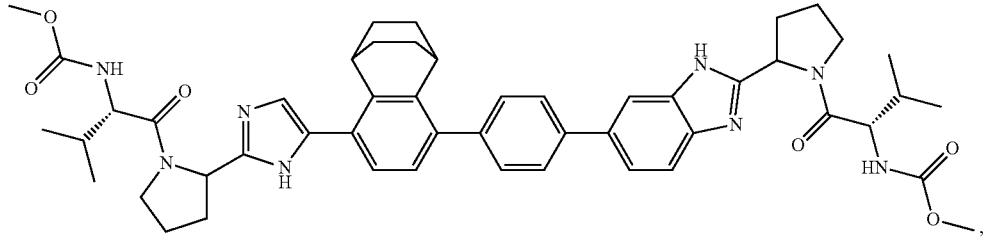
(120)

(121)
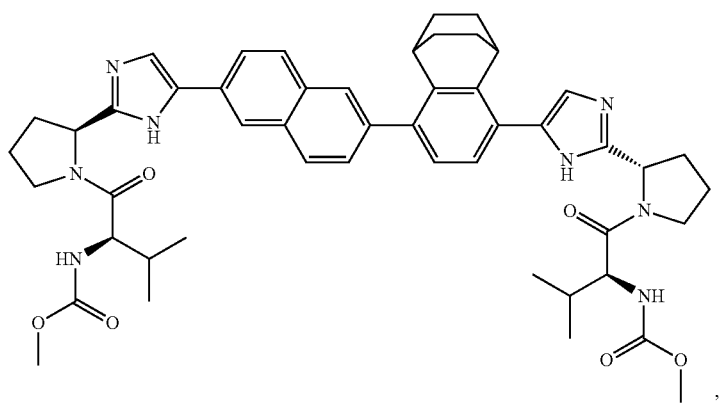
(122)
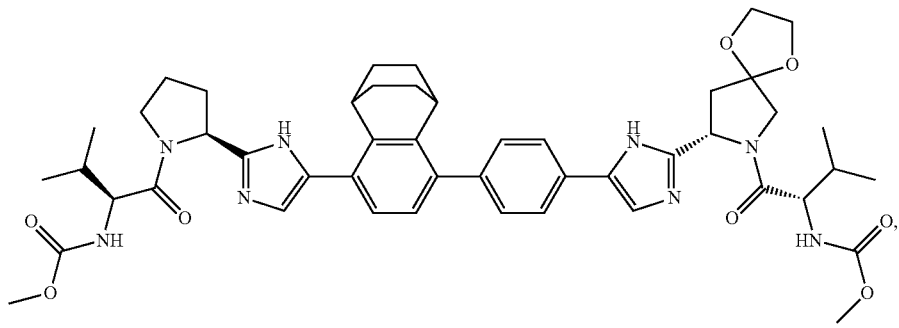
(123)
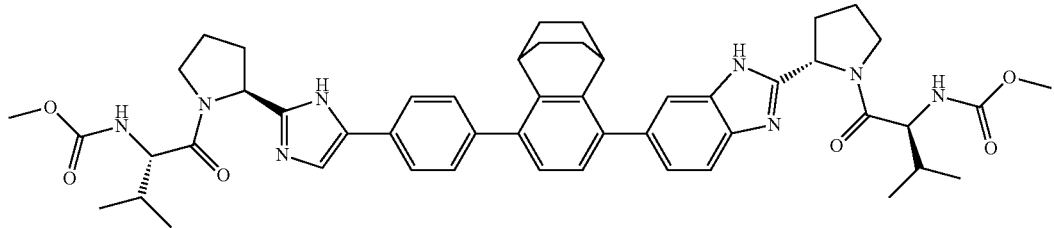
(124)
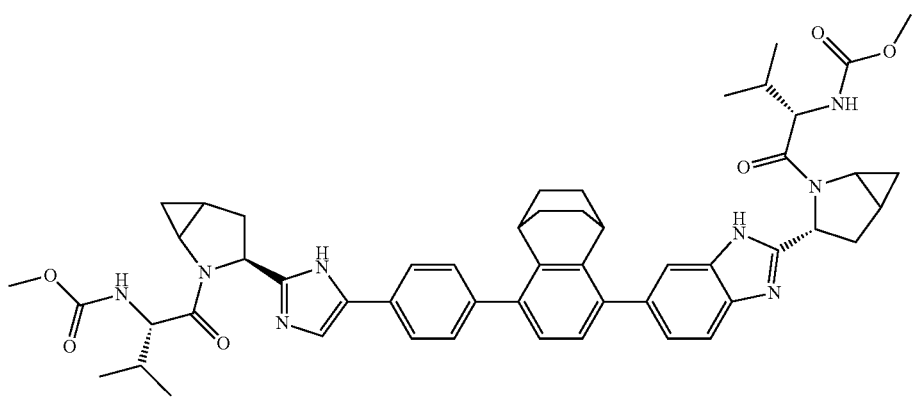

(125)
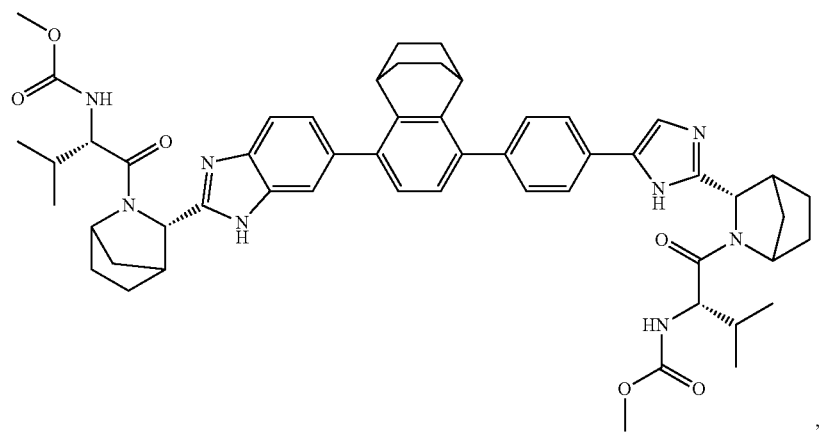
(126)
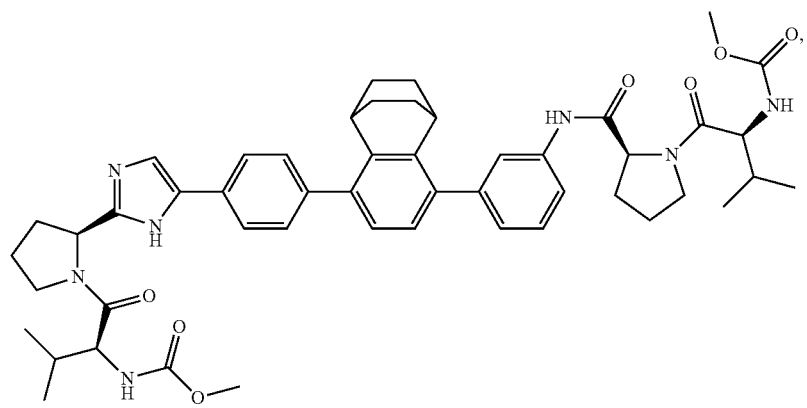
(127)
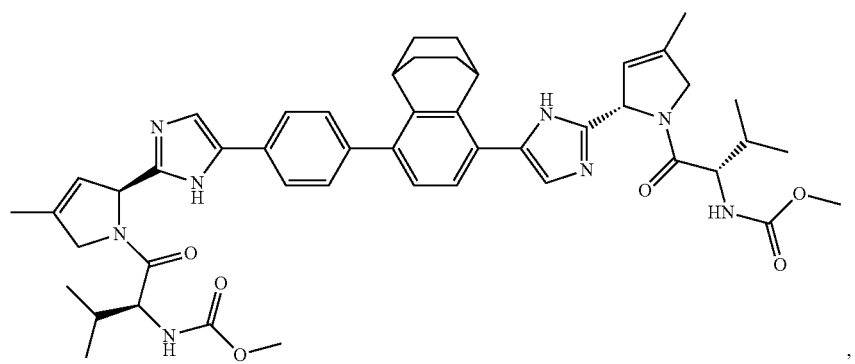
(128)
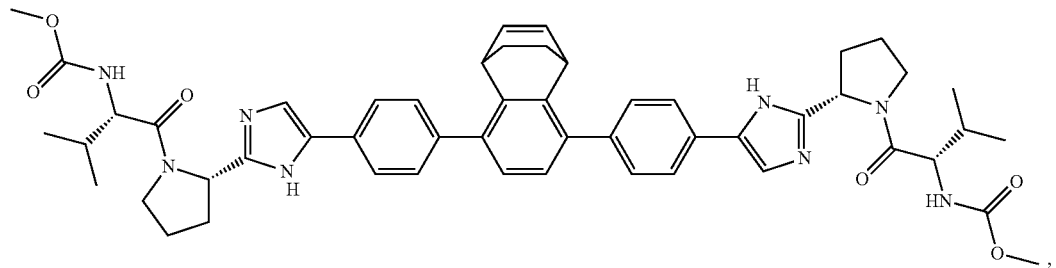

-continued
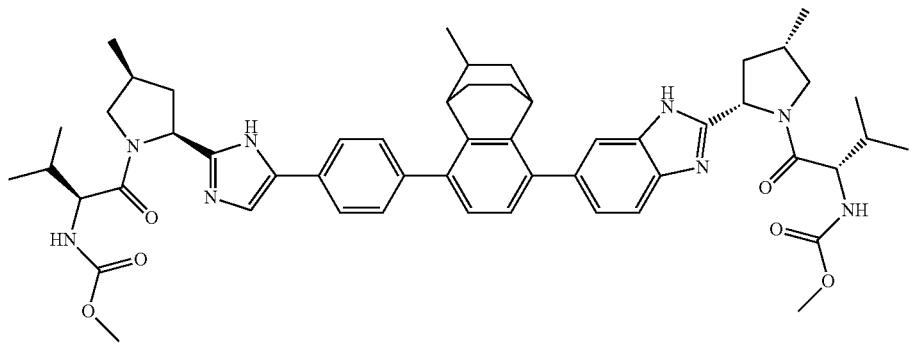
(129)
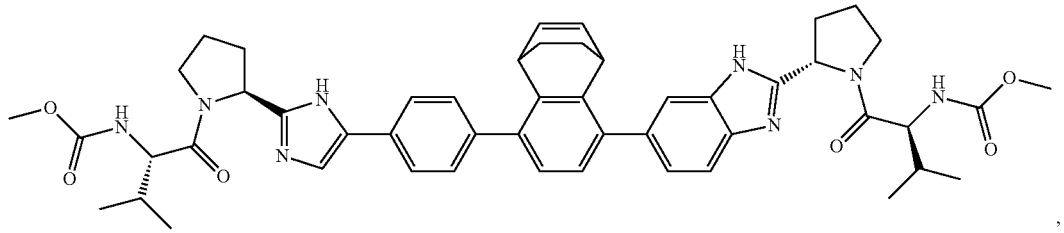
(130)
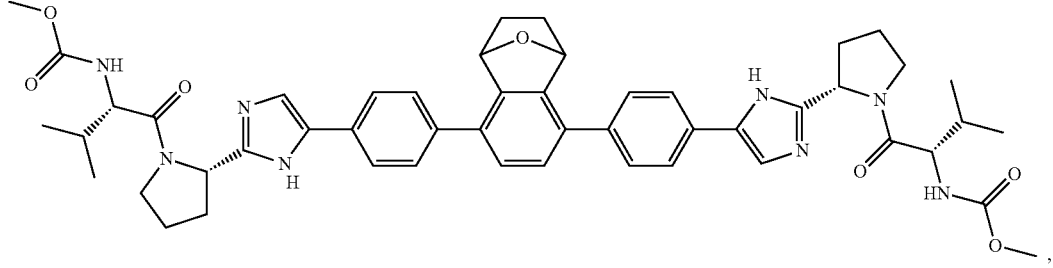
(131)
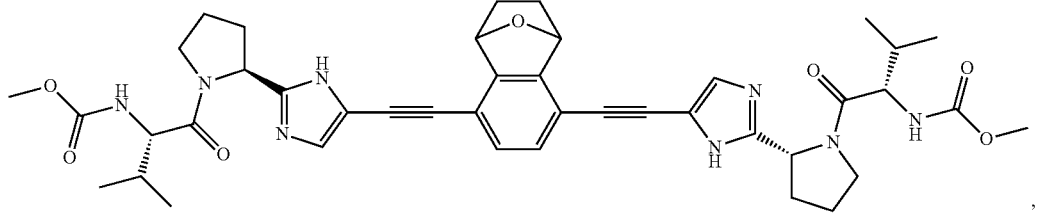
(132)
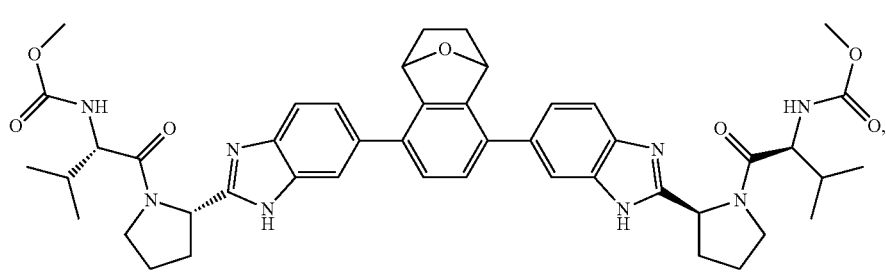
(133)
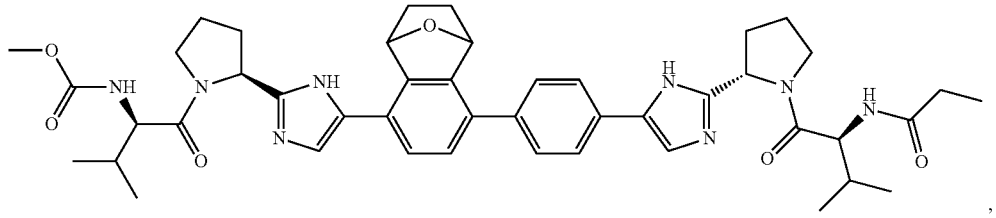
(134)

-continued
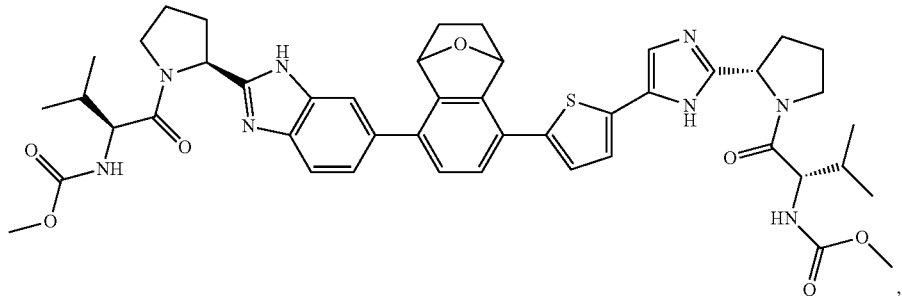
(135)
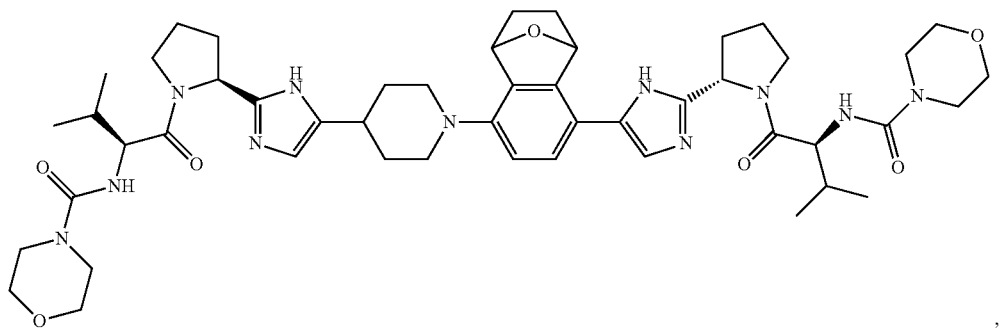
(136)
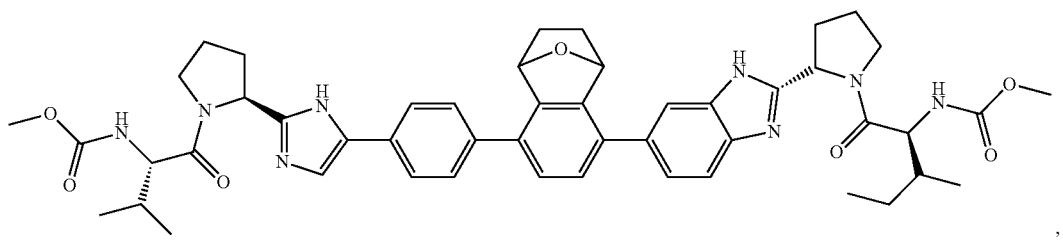
(137)
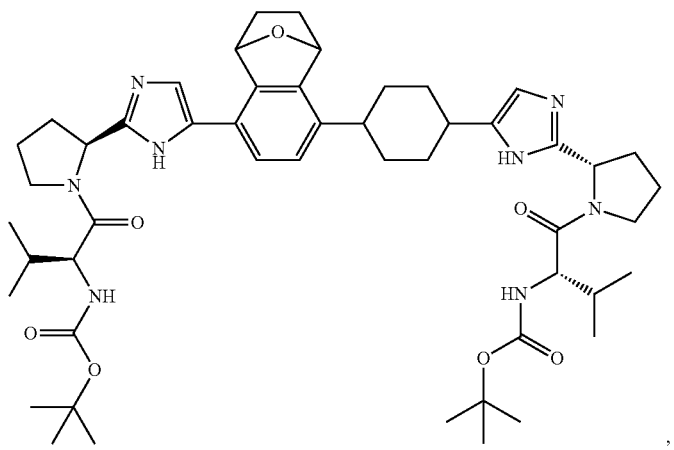
(138)
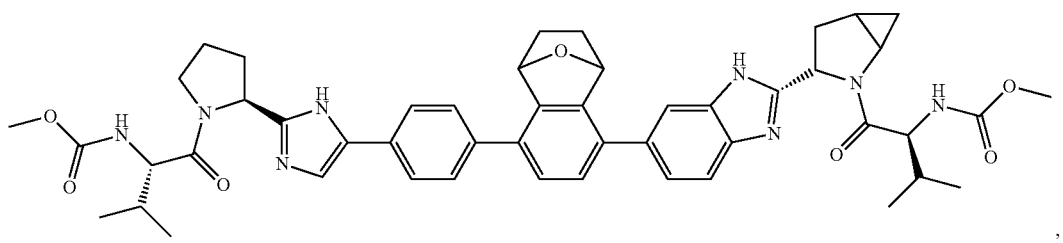
(139)

(140)
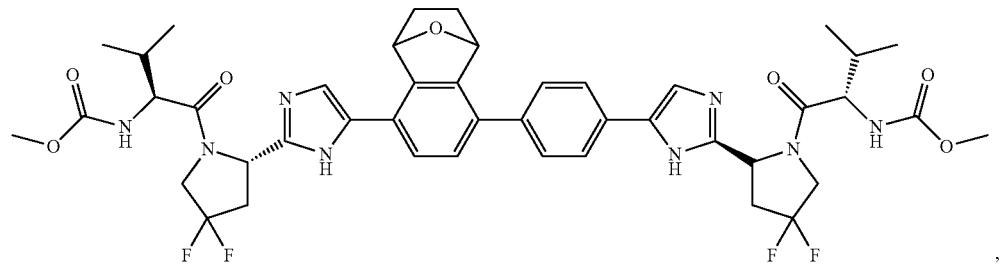
(141)
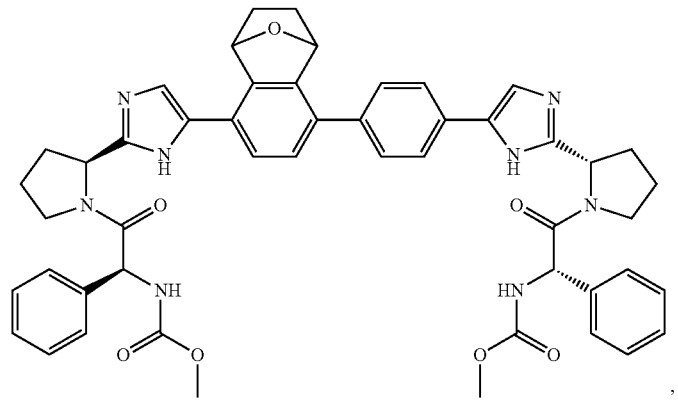
(142)
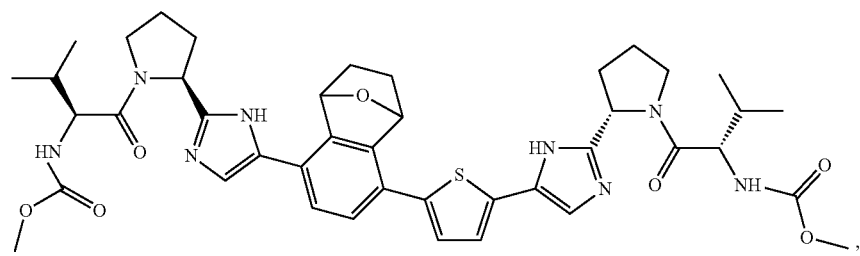
(143)
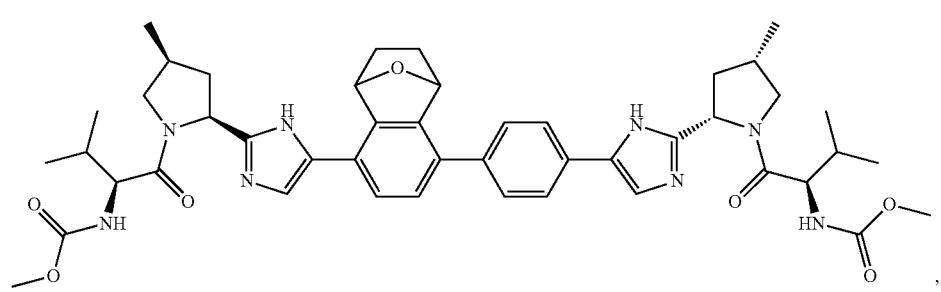
(144)
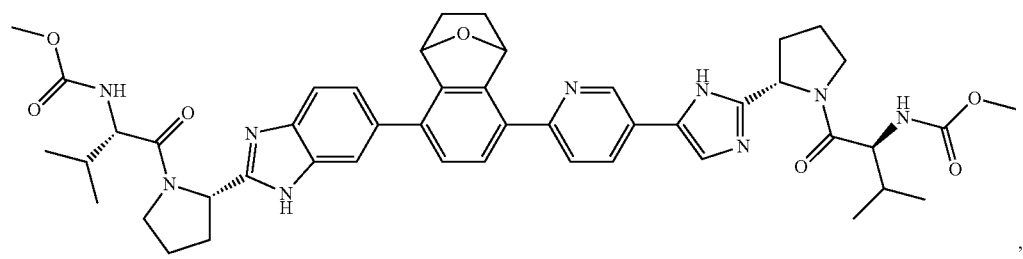

(145)
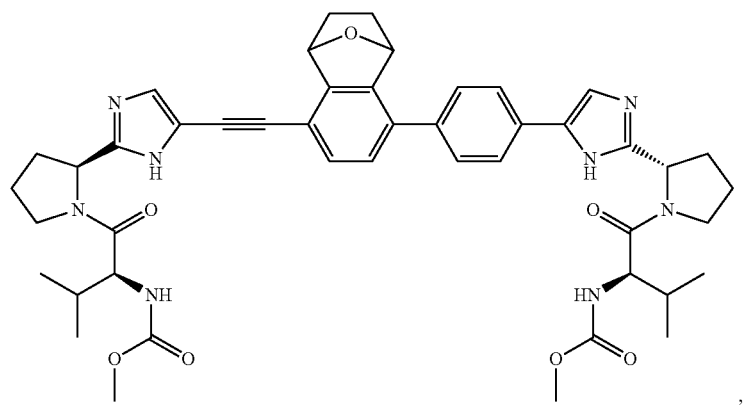
(146)
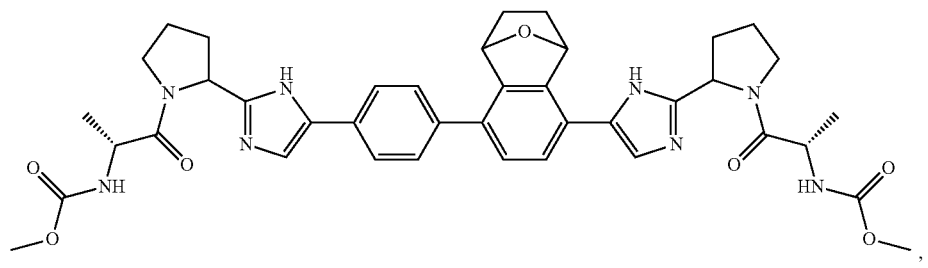
(147)
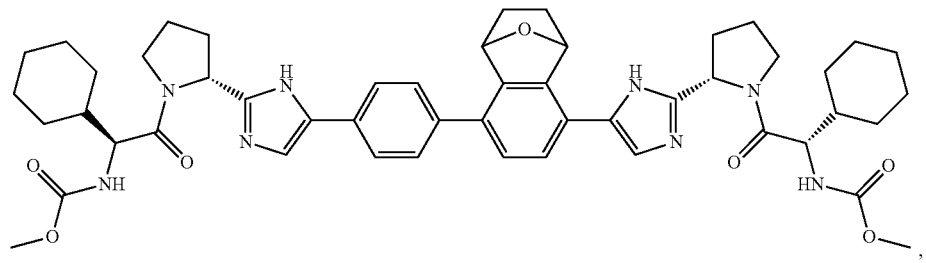
(148)
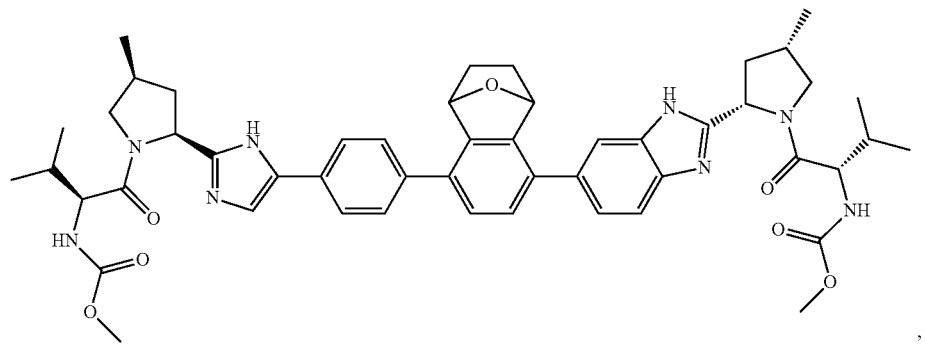
(149)
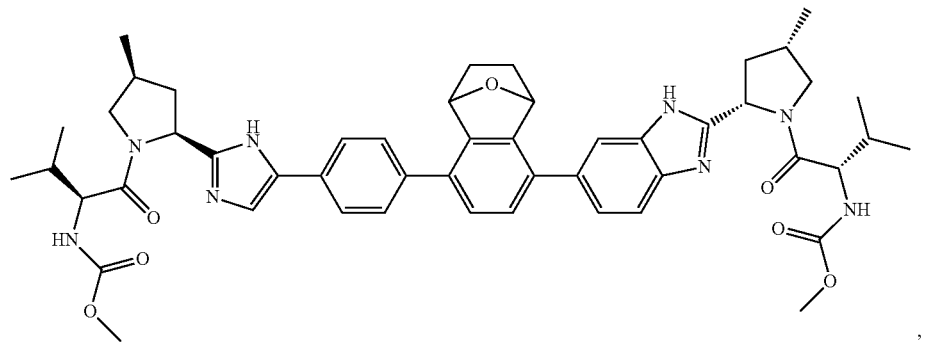

(150)
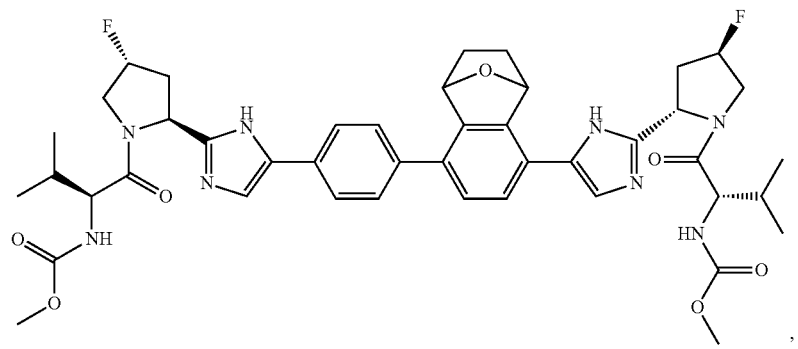
(151)
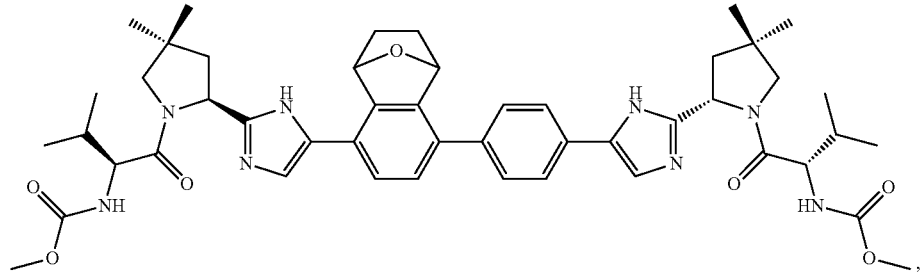
(152)
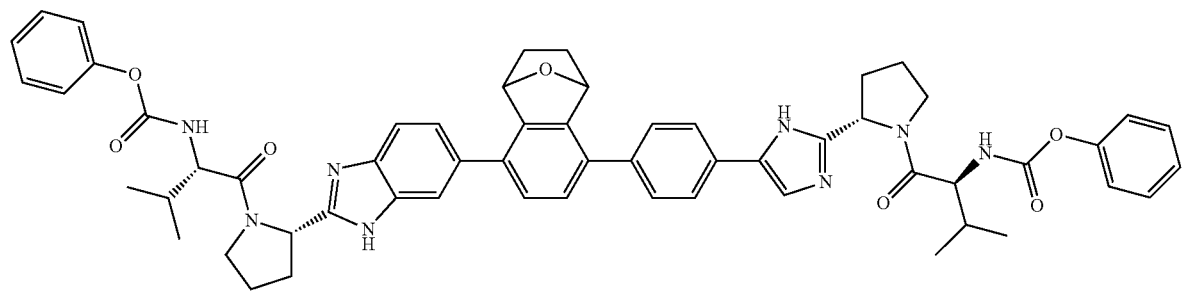
(153)
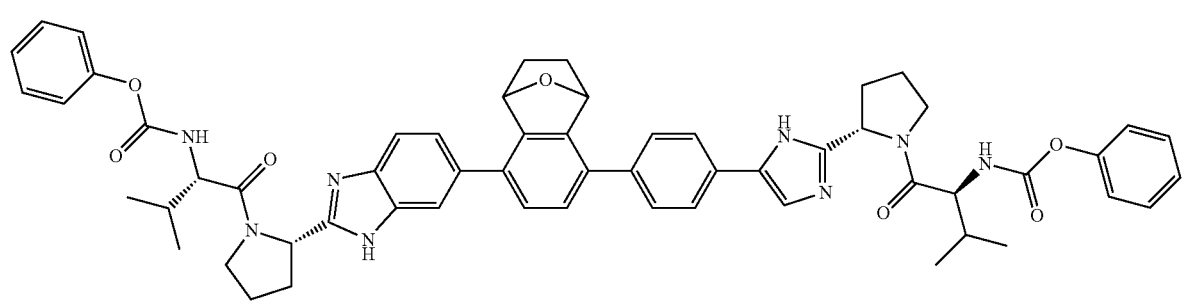
(154)
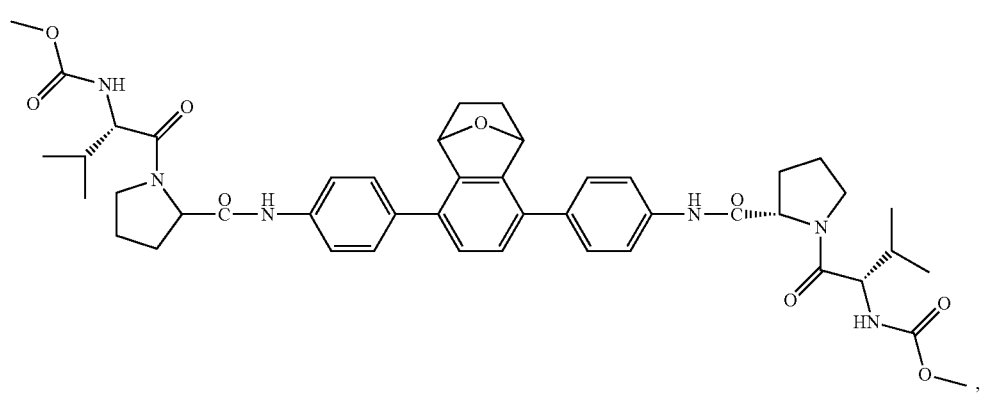

(155)
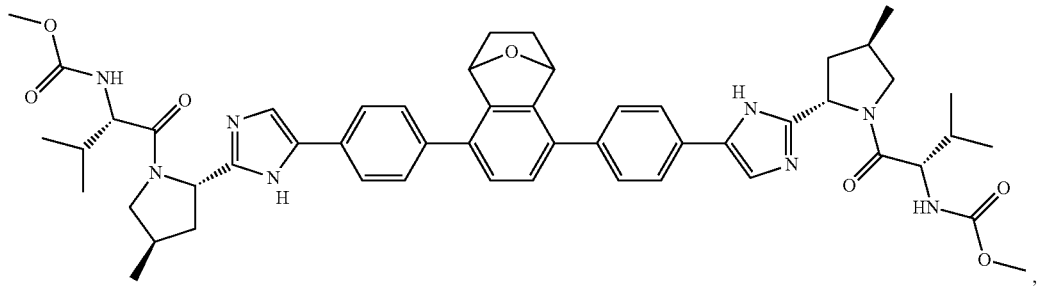
(156)
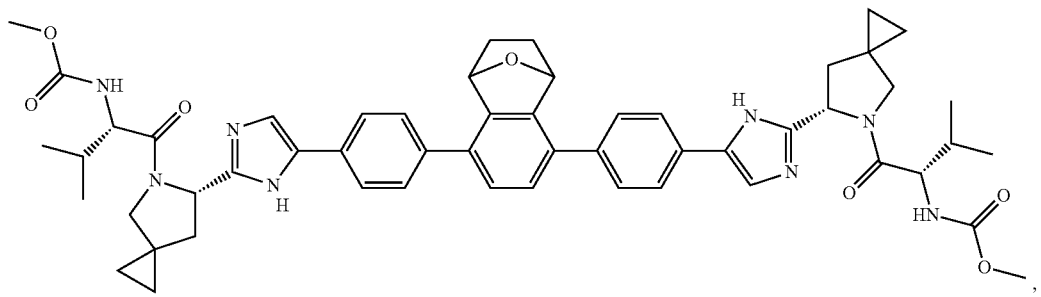
(157)
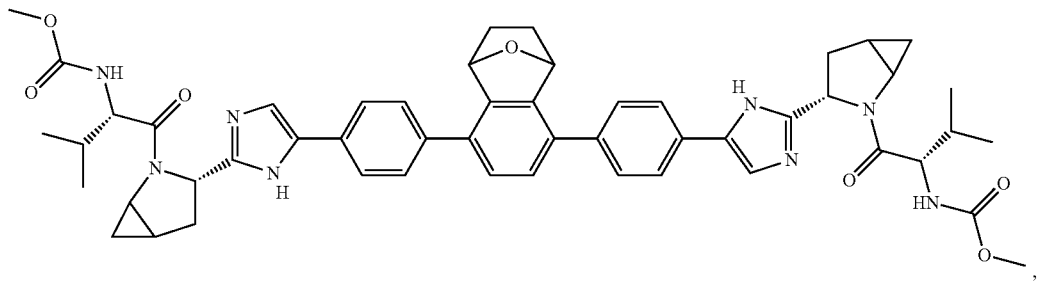
(158)
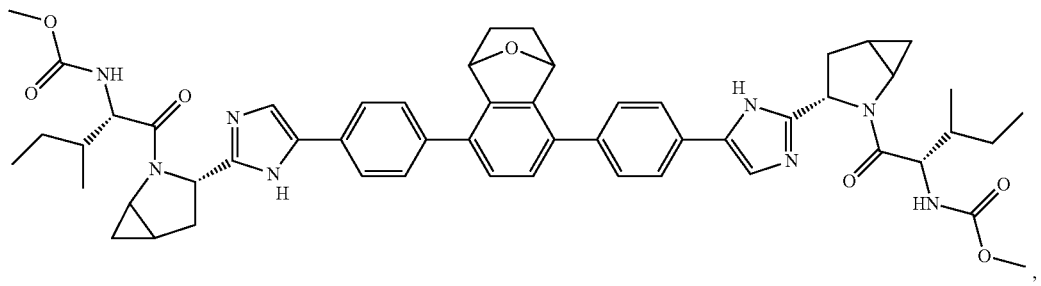
(159)
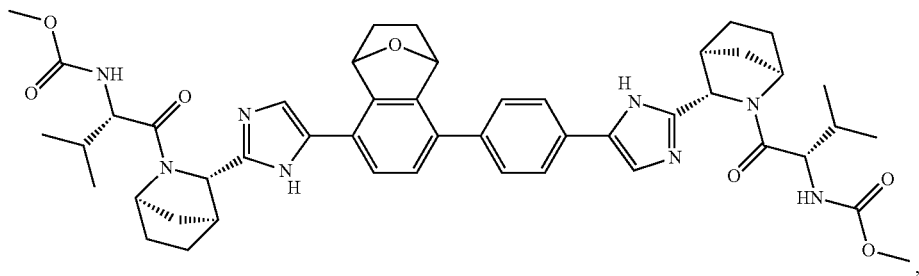

(160)
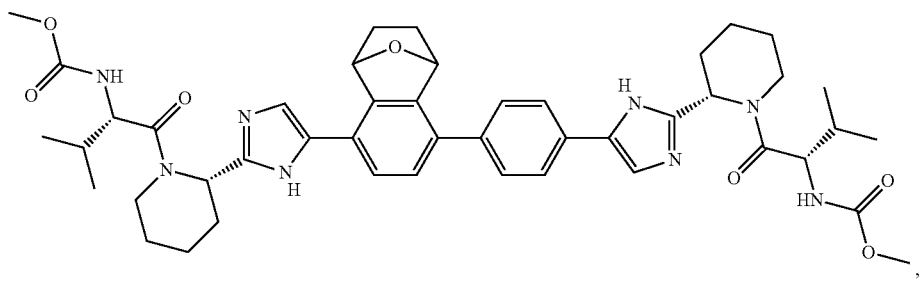
(161)
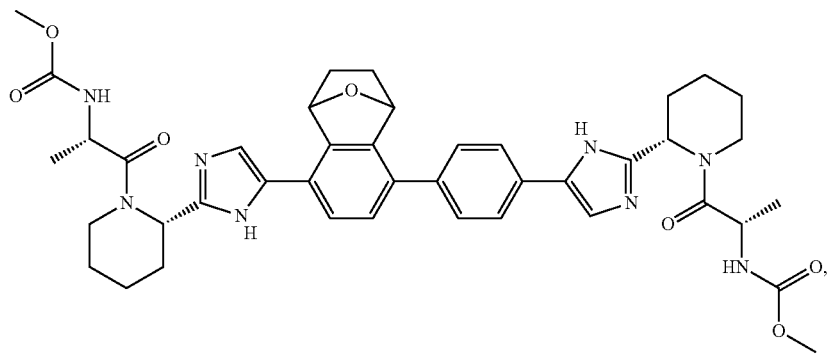
(162)
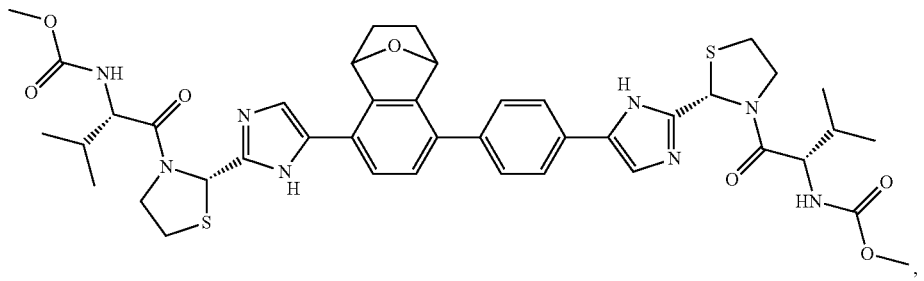
(163)
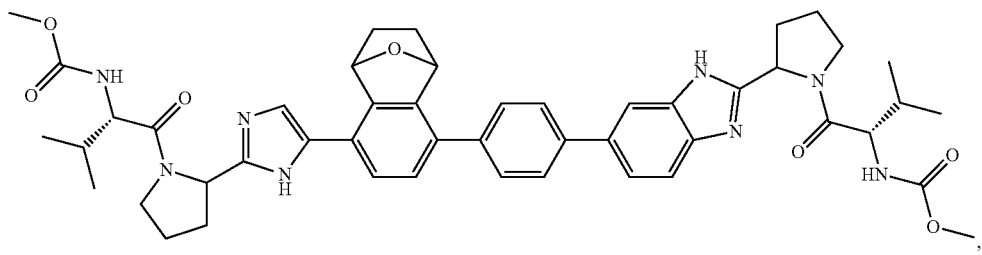
(164)
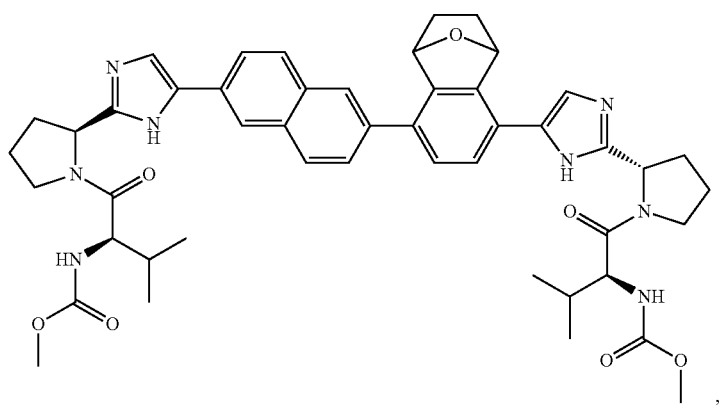

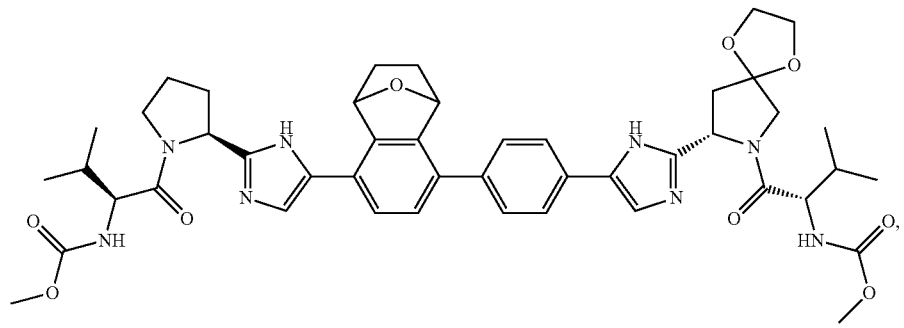
(165)
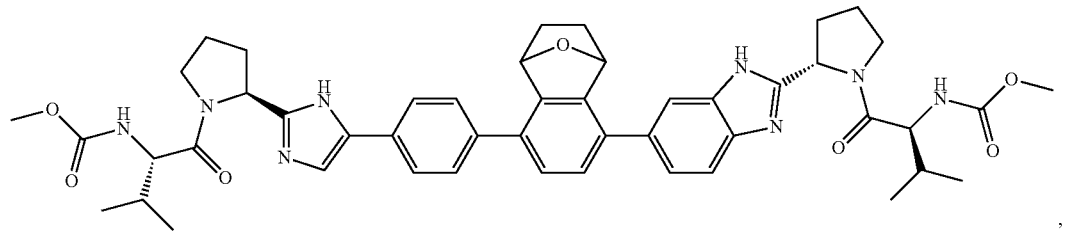
(166)
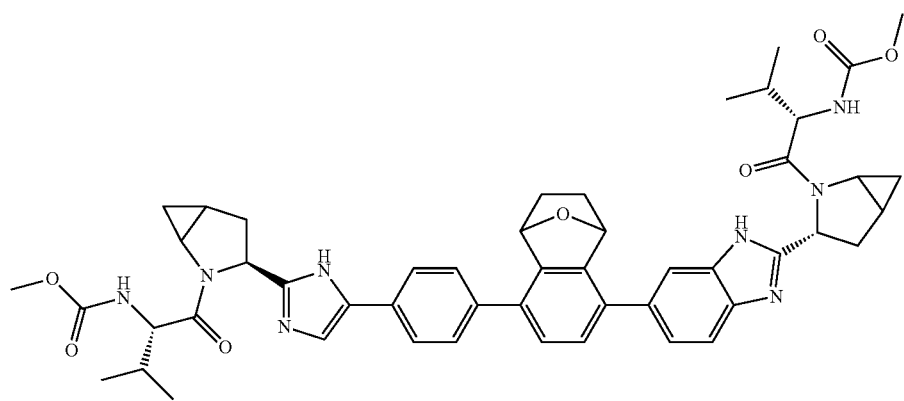
(167)
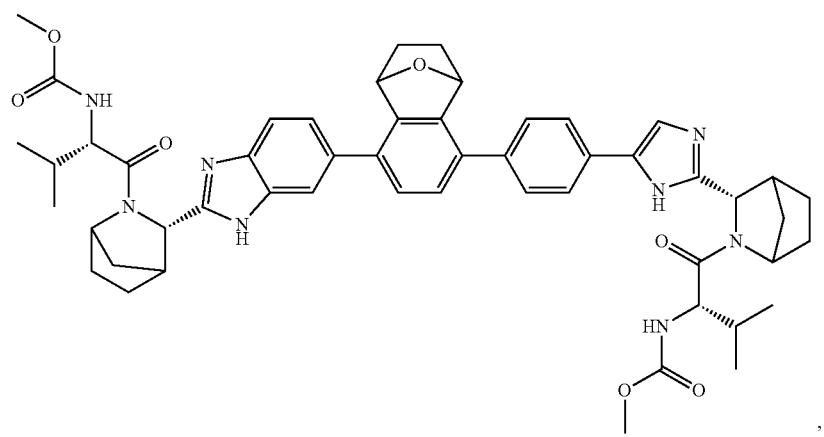
(168)

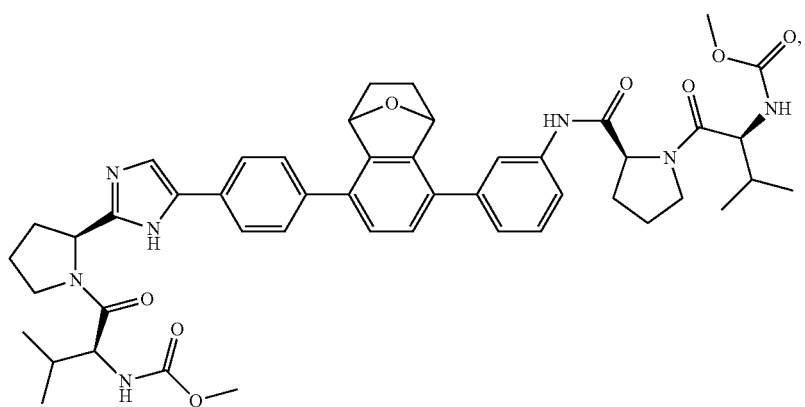
(169)
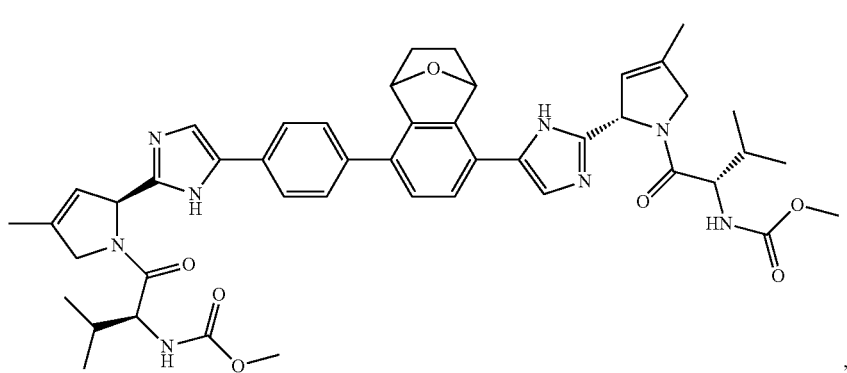
(170)
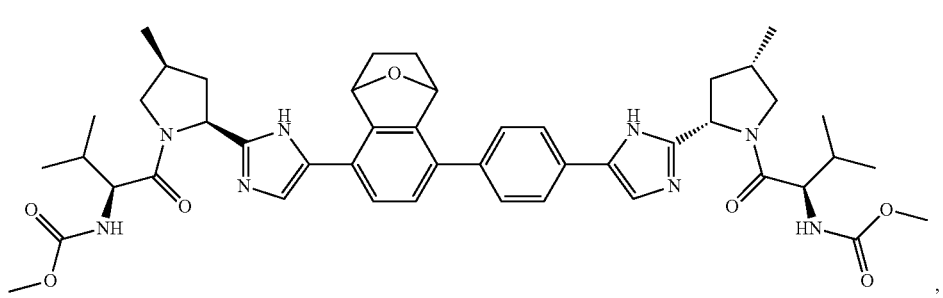
(171)
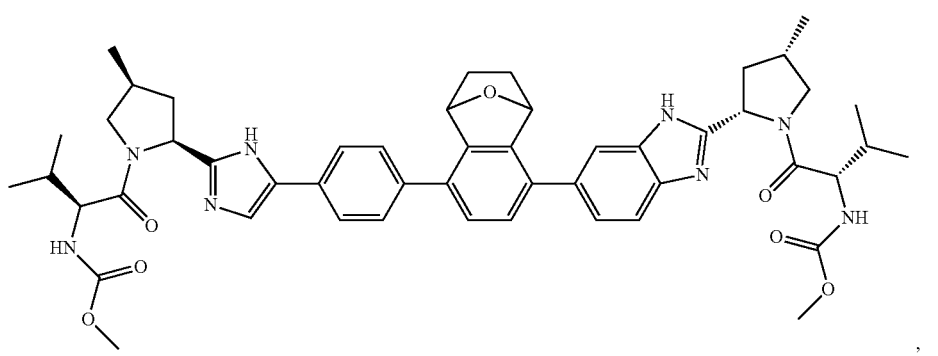
(172)

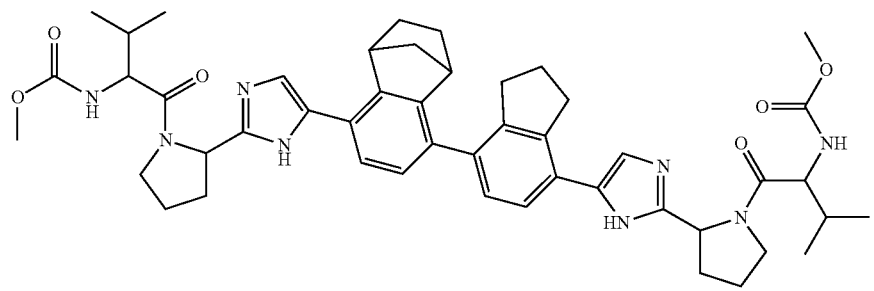
(173)
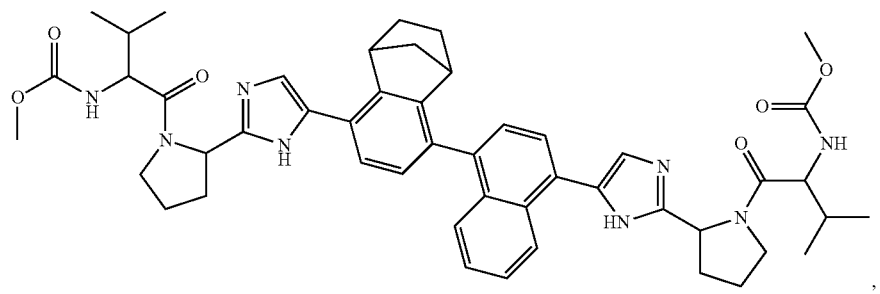
(174)
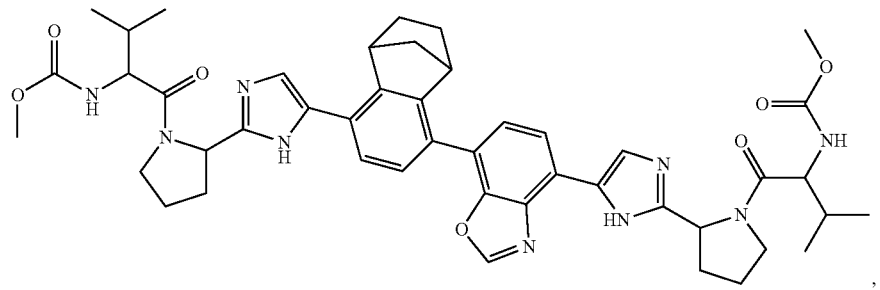
(175)
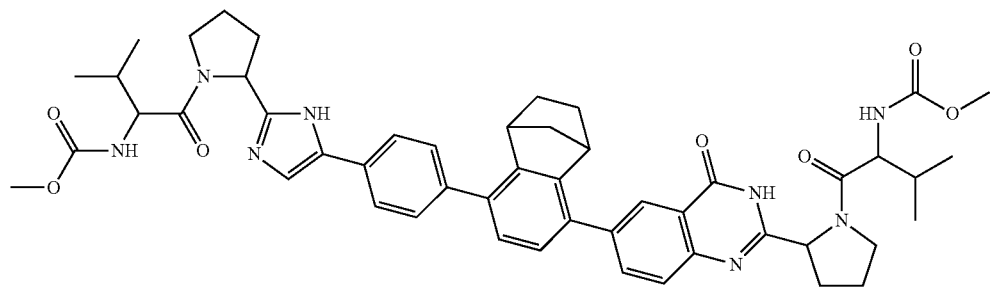
(176)
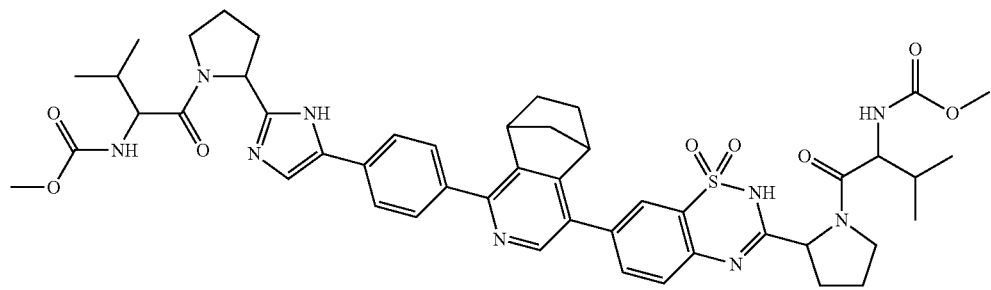
(177)

-continued (178)

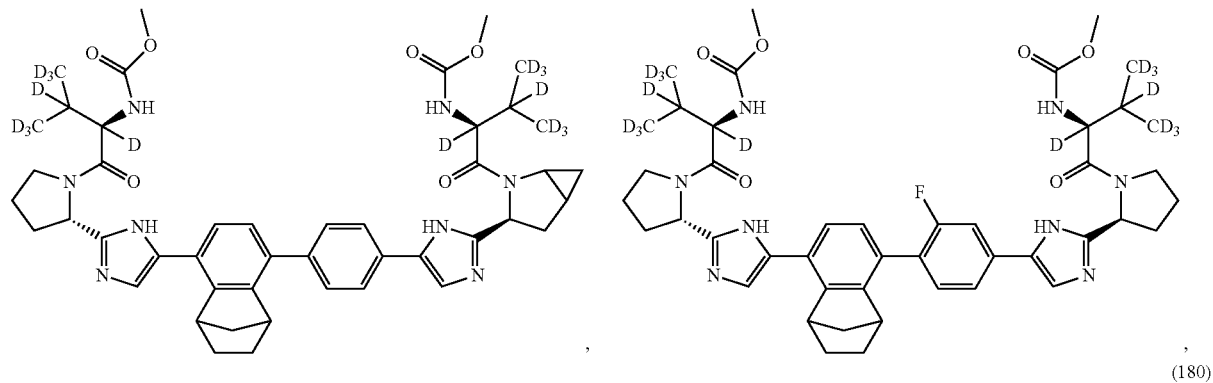

(179)

(180)

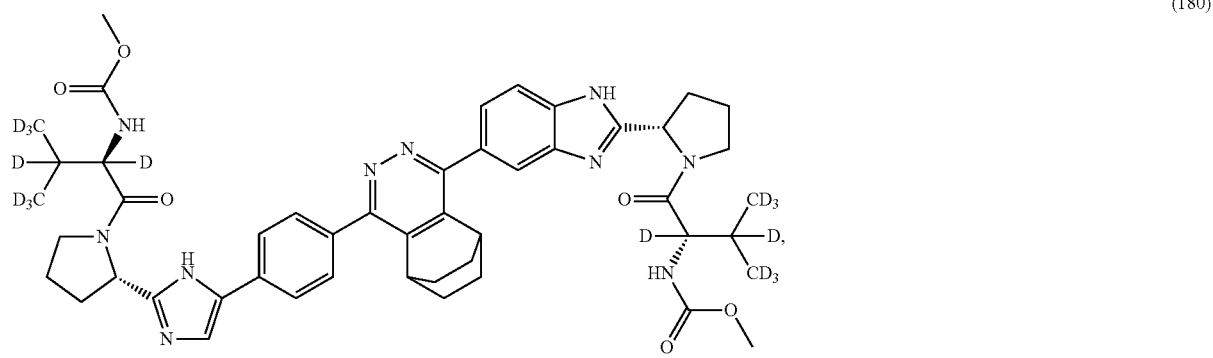

(181)

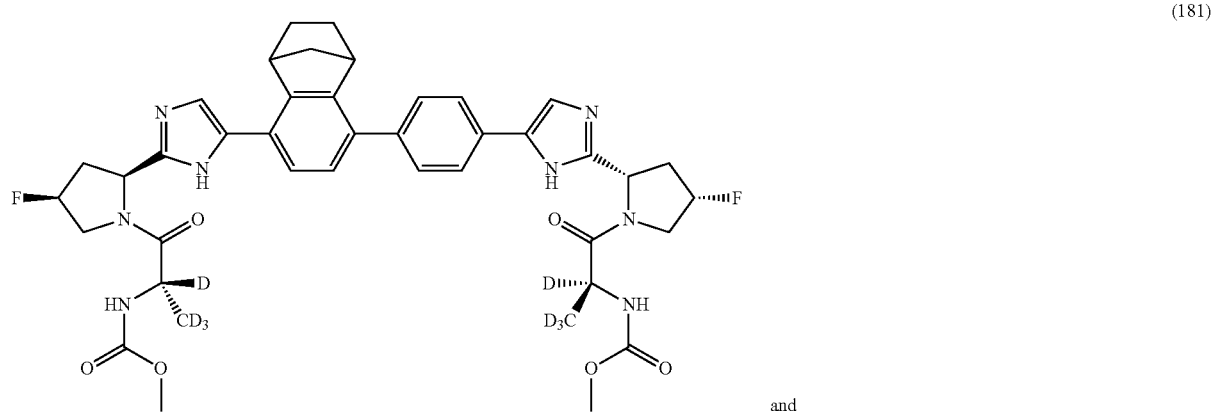

and (182)

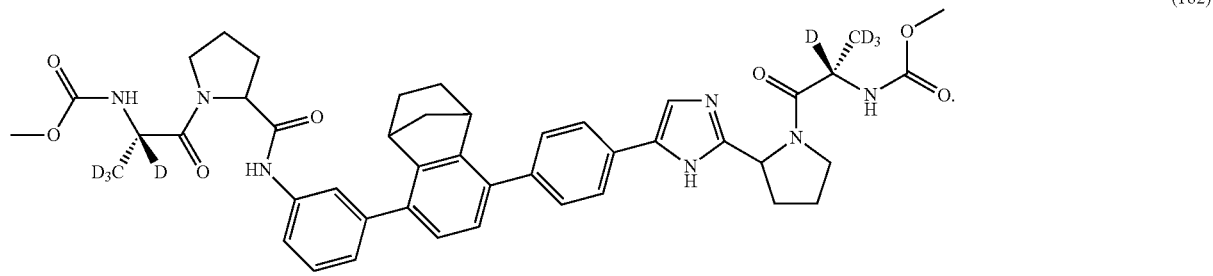

Provided herein includes the use of a compound disclosed herein, or a pharmaceutically acceptable salt thereof, in the manufacture of a medicament for the treatment either acutely or chronically of HCV infection in a patient, including those described herein. Provided herein is use of the compound in the manufacture of an anti-HCV medicament. Provided herein is the use of the compound disclosed herein, in the manufacture of a medicament to attenuate, prevent, manage or treat disorders through inhibition of HCV, especially HCV's NS5A protein. Also provided herein is a pharmaceutical composition comprising a therapeutically effective amount of a compound of Formula (I) in association with at least one pharmaceutically acceptable carrier, adjuvant or diluent.

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith.

The compounds disclosed herein also include salts of such compounds which are not necessarily pharmaceutically acceptable salts, and which may be useful as intermediates for preparing and/or purifying compounds of Formula (I) and/or for separating enantiomers of compounds of Formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

When it is possible that, for use in therapy, therapeutically effective amounts of a compound of Formula (I), as well as pharmaceutically acceptable salts thereof, may be administered as the raw chemical, it is possible to present the active ingredient as a pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount" refers to the total amount of each active component that is sufficient to show a meaningful patient benefit (e.g., a reduction in viral load). When applied to individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluents(s), or excipient(s) must be acceptable in the sense of being compatible with the other ingredients of the formulation and not deleterious to recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable" refers to those compounds, materials, composition, and/or dosage forms which are, within the scope of sound medical judgment, suitable for use in contact with the tissues of patients without excessive toxicity, irritation, allergic response, or other problem complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 15%, and more preferably between about 10 to 80% of the dosage normally administered in a monotherapy regimen. Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules, cachets or tablets; powders or granules; solution or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose, β-lactose, corn sweetener, natural gum and synthetic resin, such as Arabic gum, tragacanth or sodium alginate, carboxymethylcellulose, polyethylene glycol, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluents or base as described above, and optionally, with a binder such as carboxymethylcellulose, an alginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solution of cellulosic or polymeric materials and forcing through a screen. As an alternative to granulation, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating of embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, poly(ε-caprolactone), polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to ingredients particularly mentioned above, the formulations may include other agents conventional in the art having regard to the type of formulation in question, for example those suitable for oral administration may include flavoring agents.

Uses of the Compounds and Compositions of the Invention

According to another aspect, the invention features pharmaceutical compositions that include a compound of Formula (I), a compound listed herein, and a pharmaceutically acceptable carrier, adjuvant, or vehicle.

The amount of the compound in the compositions disclosed herein is such that is effective to detectably treat HCV infection, such as HCV metalloproteinase, HCV serine proteinase, HCV polymerase, HCV helicase, non-structural protein NS4B, HCV entry, HCV assembly, HCV egress, non-structural protein NS5A or inosine5'-monophosphate dehydrogenase (IMPDH).

Also provided herein is a method, which comprises the compound or the pharmaceutical composition disclosed herein, further comprising administering to the patient additional anti-HCV agents (combination therapy), wherein the anti-HCV agent is an interferon, ribavirin, IL-2, IL-6, IL-12, a compound that enhances the development of a type helper T cell response, interfering RNA, anti-sense RNA, imiquimod, an inosine-5'-monophosphate dehydrogenase inhibitor, amantadine, rimantadine, ribavirin, bavituximab, human hepatitis C immune globulin (CIVACIR™), boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZd-2795, TMC647055 or a combination thereof. Wherein the interferon is interferon α-2b, pegylated interferon α, interferon α-2a, pegylated interferon α-2a, consensus interferon-α, or interferon γ.

The treatment method that includes administering a compound or composition disclosed herein can further include administering to the patient an additional anti-HCV agent, wherein the additional anti-HCV drug is administered together with a compound or composition disclosed herein as a single dosage form or separately from the compound or composition as part of a multiple dosage form. The additional anti-HCV agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

General Synthetic Procedures

Generally, the compounds disclosed herein may be prepared by methods described herein, wherein the substituents are as defined for Formula (I), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

| Time (min) | A($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were also assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, $CH_3CN$ acetonitrile
$NH_3$ ammonia
$NH_4Cl$ ammonium chloride
$BBr_3$ boron tribromide
BSA bovine serum albumin
$Br_2$ bromine
BOC, Boc tert-butyloxycarbonyl
$Cs_2CO_3$ cesium carbonate
$CHCl_3$ chloroform
$CDCl_3$ chloroform deuterated
Cu copper
CuI copper (I) iodide
$Et_2O$ diethyl ether
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
Dppa diphenylphosphoryl azide
EtOAc ethyl acetate
EA ethyl acetate
HBr hydrobromic acid
HCl hydrochloric acid
HOAt, HOAT 1-hydroxy-7-azabenzotriazole
HOBT 1-hydroxybenzotriazole hydrate
$H_2$ hydrogen
$H_2O_2$ hydrogen peroxide
Fe iron
LDA lithium diisopropylamide
MCPBA meta-chloroperbenzoic acid
$MgSO_4$ magnesium sulfate
MeOH, $CH_3OH$ methanol
MeI methyl iodide
$CH_2Cl_2$, DCM methylene chloride
NMP N-methylpyrrolidinone
mL, m milliliter
$N_2$ nitrogen
Pd/C palladium on carbon
PE petroleum ether (60-90° C.)
PBS phosphate buffered saline
$POCl_3$ phosphorous oxychloride
$Pd(PPh_3)_4$ palladium tetrakis triphenylphosphine
$Pd(dppf)Cl_2$ 1,1-bis(diphenylphosphino)ferrocene palladium chloride
$K_2CO_3$ potassium carbonate
KOH potassium hydroxide
RT, rt room temperature
Rt retention time
$NaHCO_3$ sodium bicarbonate
$NaBH_4$ sodium borohydride
$NaBH_3CN$ sodium cyanoborohydride
NaOtBu sodium tert-butoxide
NaOH sodium hydroxide
$NaClO_2$ sodium chlorite
NaCl sodium chloride
$NaH_2PO_4$ sodium dihydric phosphate
NaH sodium hydride
NaI sodium iodide
$Na_2SO_4$ sodium sulfate
TBTU O-benzotriazol-1-yl-N,N,N',N'-tetramethyluronium tetrafluoroborate
THF tetrahydrofuran
$Et_3N$, TEA triethylamine
TFA trifluoroacetic acid
$P(t-bu)_3$ tri(tert-butyl)phosphine
NBS N-bromosuccinimide
TBAI tetrabutylammonium iodide
$H_2O$ water
TEAF formic acid triethylamine complex 5:2
PPA polyphosphoric acid
$Tf_2O$ Trifluoromethanesulfonic anhydride
HCl.EA a solution of HCl in ethyl acetate
DIPEA N,N-diisopropylethylamine
DME 1,2-dimethoxyethane
HATU 2-(7-aza-1H-benzotriazole-1-yl)-1,1,3,3-tetramethyluronium hexafluorophosphate
NIS N-iodosuccinimide
TFAA trifluoroaceticanhydride
SEMCl 2-(Trimethylsilyl)ethoxymethyl chloride
Dess-Martin(Dess-Martin periodinane) (1,1,1-Triacetoxy)-1,1-dihydro-1,2-benziodoxol-3(1H)-one
TsOH p-toluenesulfonic acid
TMSA Trimethyl silyl acetylene
Meldrum's acid 2,2-Dimethyl-1,3-dioxane-4,6-dione
BAST Bis(2-methoxyethyl)aminosulphurtrifluoride Deoxofluor
$SbCl_3$ antimony trichloride
$SmCl_3$ samarium chloride
LiHMDS lithium hexamethyldisilazide
TMSCl trimethyl chlorosilane
PhNTf$_2$ N,N-Bis(trifluoromethylsulfonyl)aniline
TBDMSOTf tert-butyldimethylsilyl triflate
$Et_2NSF_3$ diethylaminosulfur trifluoride
MTBE methyl tert-butyl ether
$LiN(SiMe_3)_2$ Lithium bis(trimethylsilyl)amide
$PPh_3MeBr$ Methyltriphenylphosphonium bromide
Lawesson's Reagent 2,4-bis(4-methoxyphenyl)-1,3-dithia-2,4-diphosphetane 2,4-disulfide
$I_2$ iodine

Scheme 1

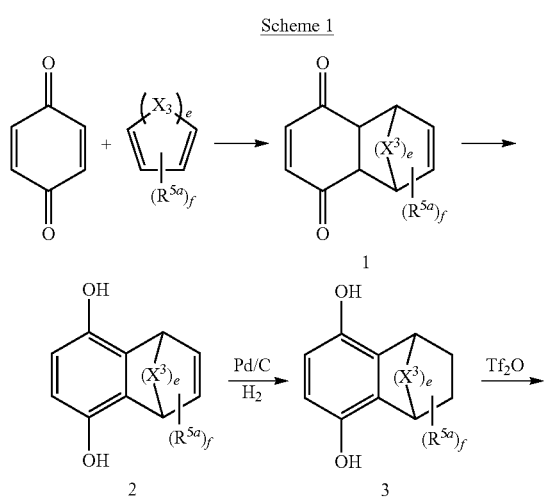

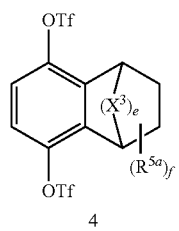

Compound 4, wherein each of $R^{5a}$, $X^3$, e and f is as defined above, can be prepared by the process illustrated in Scheme 1. Compound 1 is obtained by Diels-Alder reaction of benzoquinone and conjugated dienes. Compound 1 is then converted to compound 2 by rearrangement in the presence of base. Compound 2 is reduced under hydrogenation condition in the presence of Pd/C to give compound 3. Compound 3 can be reacted with trifluoromethanesulfonic anhydride to afford compound 4 by base catalysis.

Scheme 2

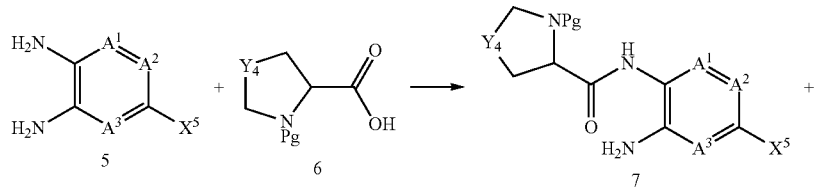

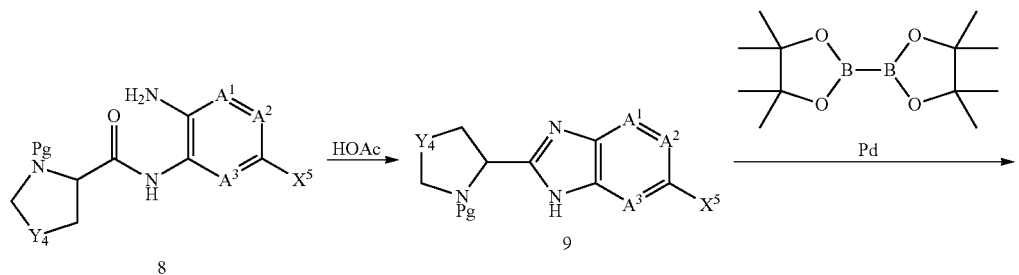

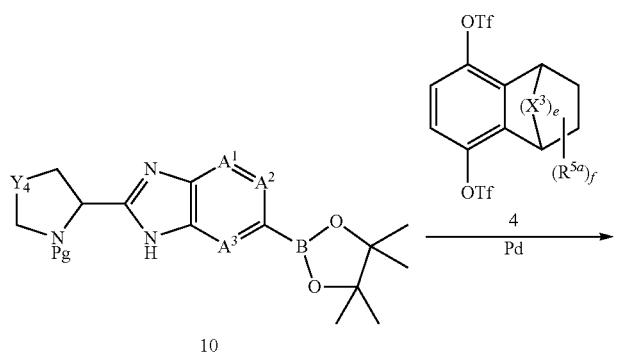

-continued

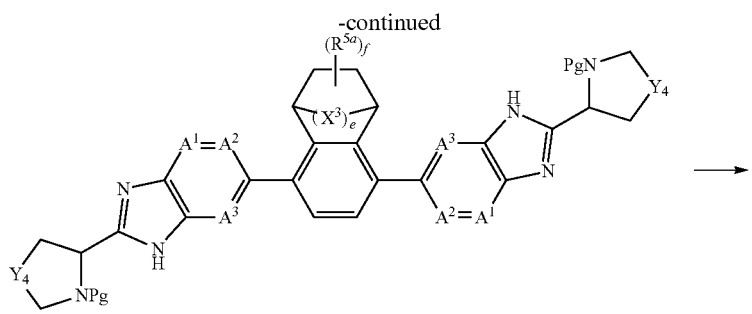

11

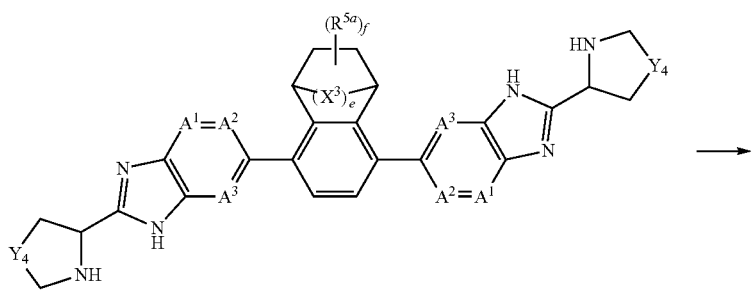

12

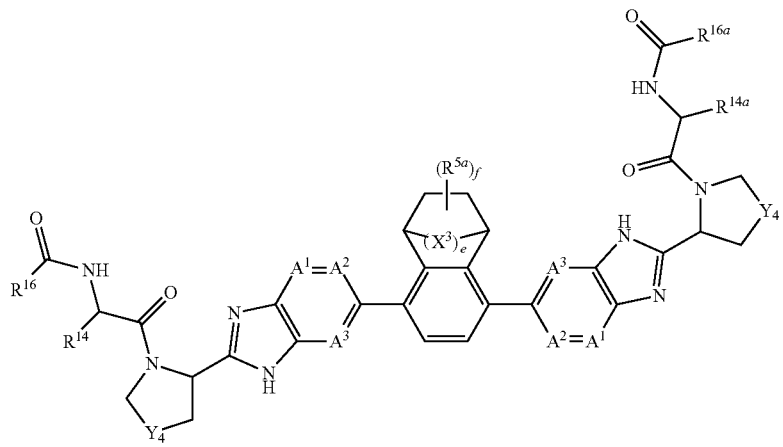

13

Compound 13 can be prepared by the process illustrated in Scheme 2. Wherein each $A^1$, $A^2$ and $A^3$ is independently N or $CR^7$, each $X^5$ is F, Cl, Br or I and each of $Y_4$, $R^{5a}$, $X^3$, e, f, $R^{14}$, $R^{14a}$, $R^{16}$ and $R^{16a}$ is as defined above. Pg is amino-protecting group such as Boc, Fmoc or Cbz. Condensation of compound 5 with compound 6 can give the mixture of compound 7 and compound 8. Then compound 7 and compound 8 can give compound 9 at elevated temperature in acetic acid system by cyclization. Compound 9 is further reacted with bis(pinacolato)diboron in the presence of Pd catalyst to afford compound 10. Coupling reaction of compound 10 with compound 4 in the presence of Pd catalyst can give compound 11. The protecting group Pg is removed to provide compound 12. Compound 12 is condensed with amino acid to afford compound 13.

Scheme 3

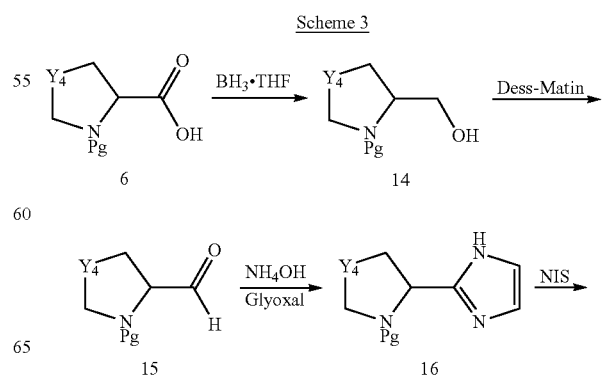

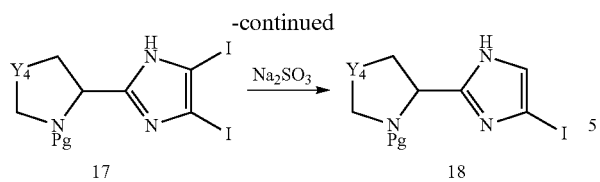

Compound 18 can be prepared by the process illustrated in Scheme 3. Wherein each $Y_4$ is as defined above, and Pg is amino-protecting group such as Boc, Fmoc or Cbz. Reduction of compound 6 reacted with reductant such as diborane can give compound 14. Compound 14 can be oxidized to give compound 15 with oxidants such as Dess-Martin agent. Compound 15 can be cyclized in the presence of ammonium hydroxide and glyoxal to form compound 16. Compound 16 can be transformed to compound 17 by reacting with NIS agent. One atom of iodine is then removed in the presence of sodium sulfite to provide compound 18.

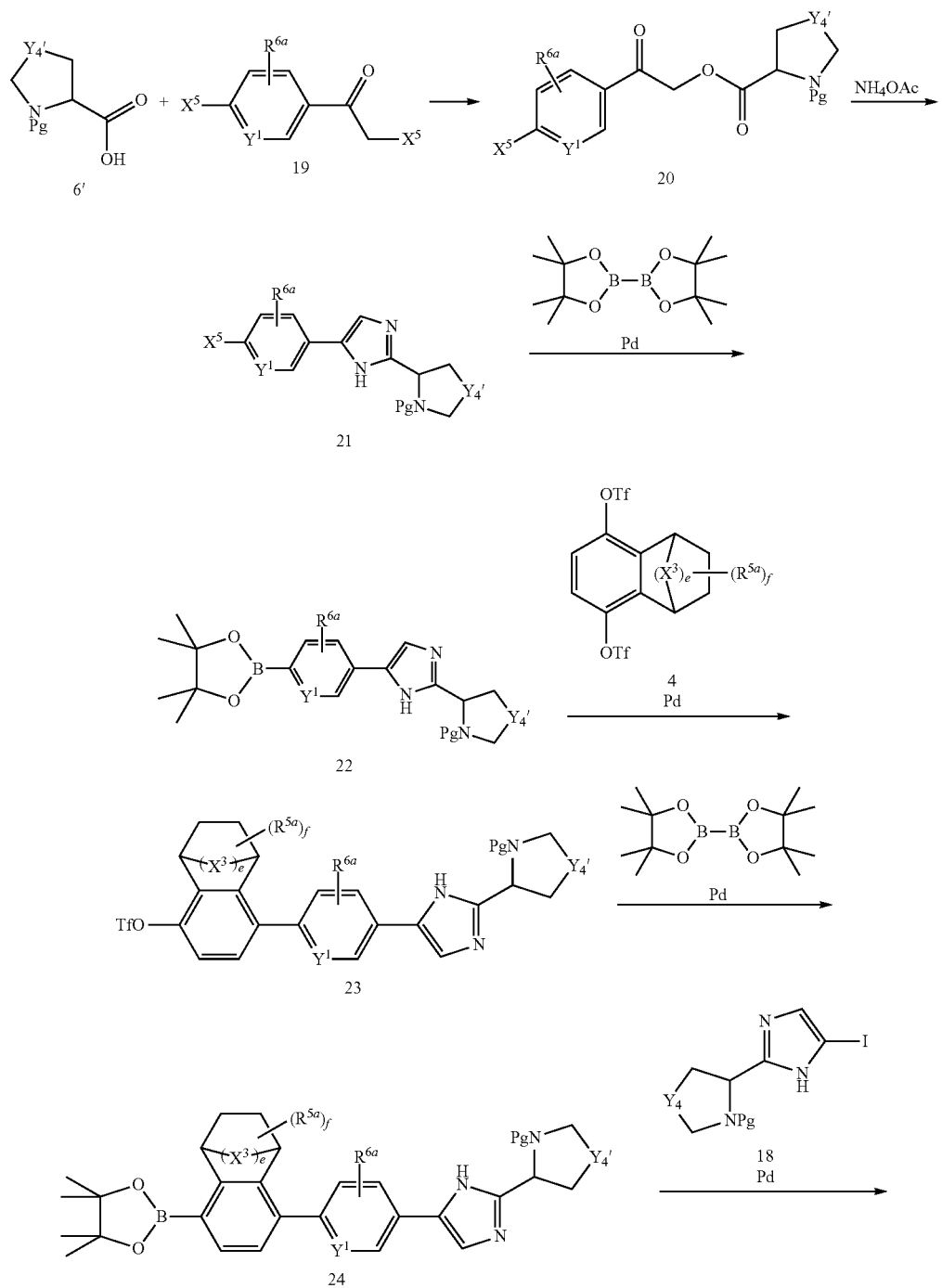

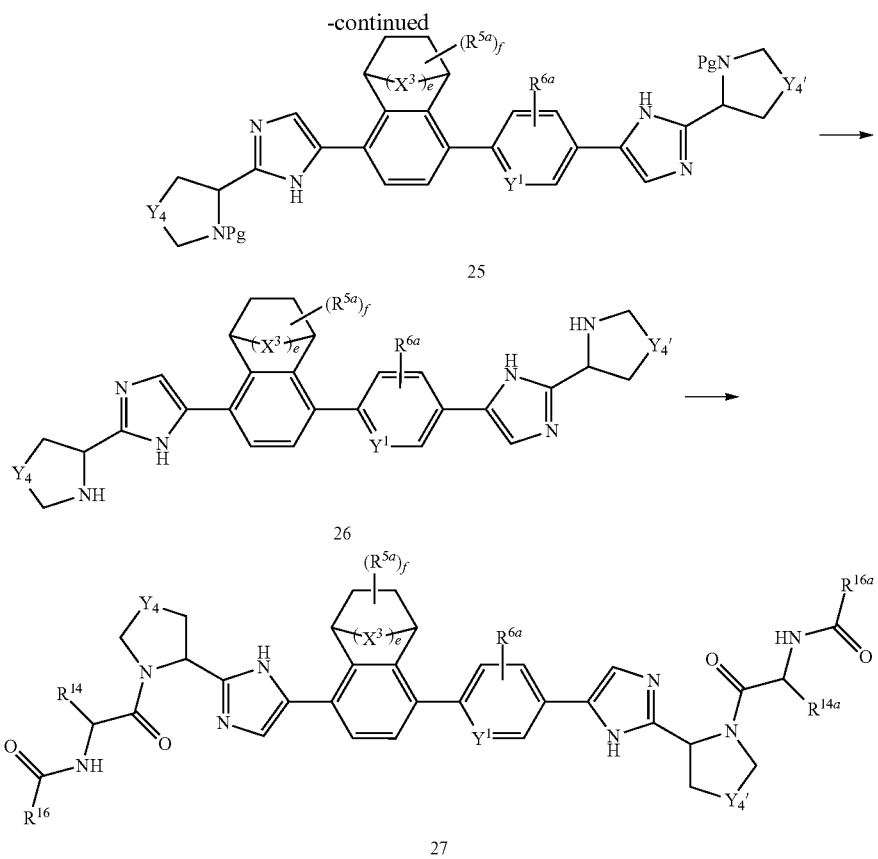

Compound 27 can be synthesized through the procedure depicted in Scheme 4. Wherein each of $Y_4'$, $Y_4$, $R^{5a}$, $R^{6a}$, $X^3$, e, $Y^1$, f, $R^{14}$, $R^{14a}$, $R^{16}$ and $R^{16a}$ is as defined above, and each $X^5$ is independently F, Cl, Br or I. Pg is amino-protecting group such as Boc, Fmoc or Cbz. Condensation of compound 19 with compound 6' can give the compound 20. Compound 20 can be cyclized in the presence of ammonium acetate to form compound 21. Reaction of compound 21 with bis(pinacolato)diboron can afford compound 22 by Pd catalysis. Coupling reaction of compound 22 with compound 4 in the presence of Pd catalyst can give compound 23. Compound 23 is further reacted with bis(pinacolato)diboron in the presence of Pd catalyst to afford compound 24. Compound 24 can be converted to compound 25 by reacting with compound 18 in the presence of Pd catalyst. The protecting group Pg is removed to afford compound 26. Compound 26 is condensed with amino acid to provide compound 27.

Scheme 5

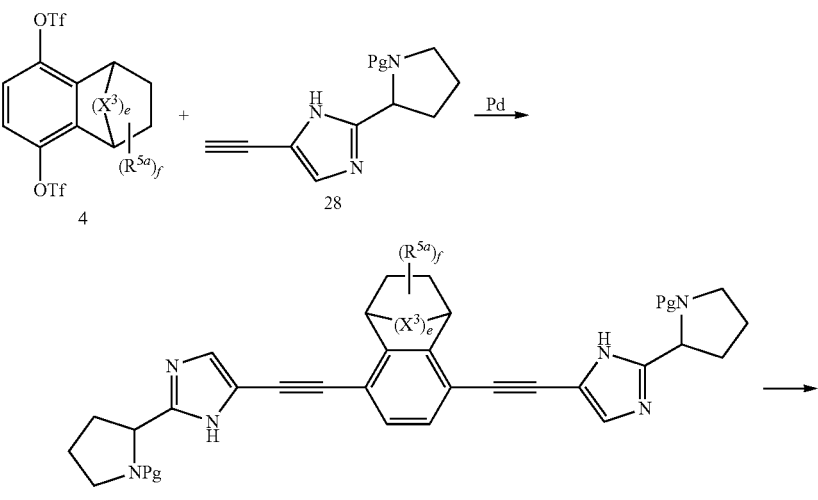

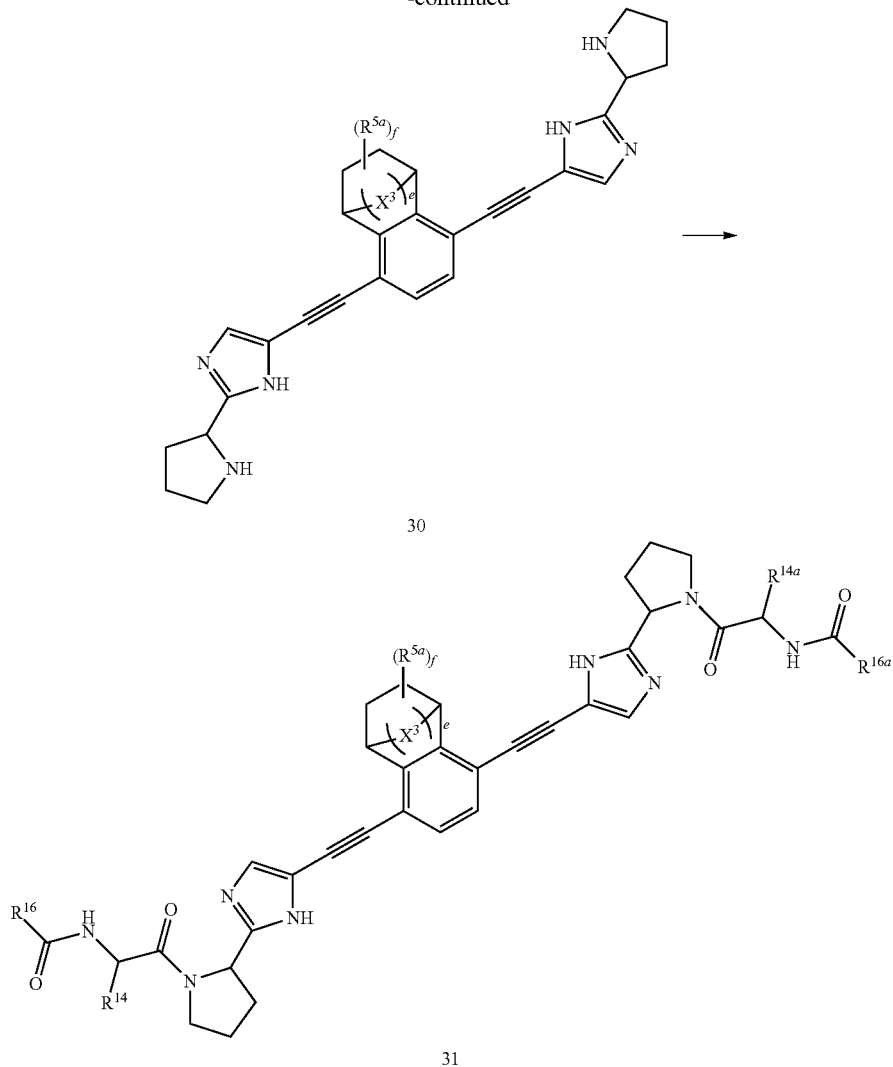

Compound 31 can be synthesized through the procedure depicted in Scheme 5. Wherein each of $R^{5a}$, $X^3$, e, f, $R^{14}$, $R^{14a}$, $R^{16}$ and $R^{16a}$ is as defined above, and Pg is amino-protecting group such as Boc, Fmoc or Cbz. Coupling reaction of compound 28 with compound 4 in the presence of Pd catalyst can give compound 29, then the protecting group Pg is removed to afford compound 30. Compound 30 is condensed with amino acid to provide compound 31.

Scheme 6

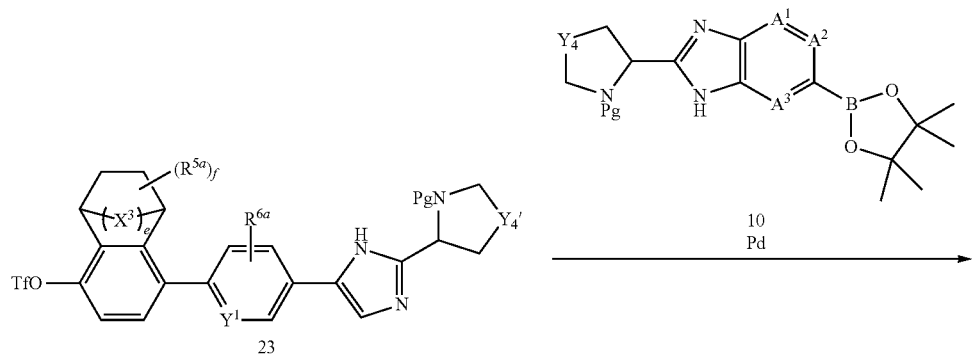

-continued

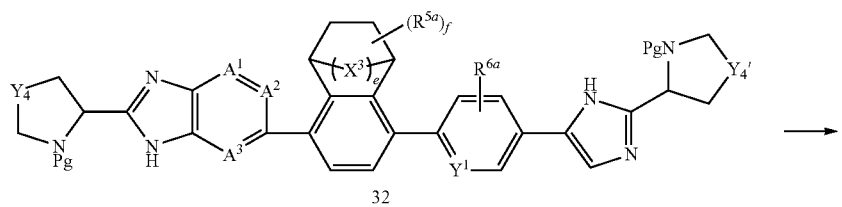

32

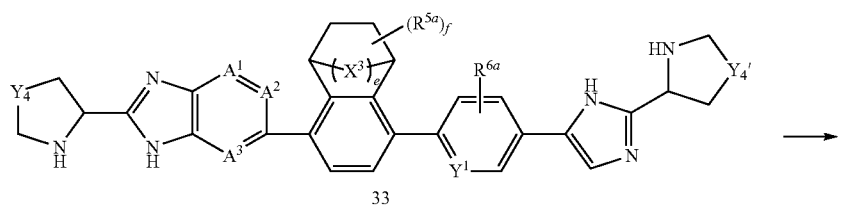

33

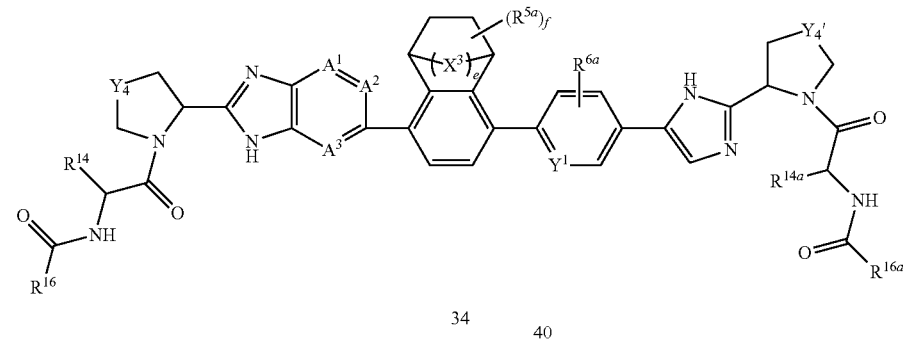

34

Compound 34 can be prepared by the process illustrated in Scheme 6. Wherein each of $R^{5a}$, $R^{6a}$, $Y^1$, $Y_4$, $Y_4'$, $X^3$, e, f, $R^{14}$, $R^{14a}$, $R^{16}$ and $R^{16a}$ is as defined above and each of $A^1$, $A^2$ and $A^3$ is independently N or $CR^7$. Pg is amino-protecting group such as Boc, Fmoc or Cbz. Coupling reaction of compound 23 with compound 10 in the presence of Pd catalyst can give compound 32. Then the protecting group Pg in compound 32 can be removed to yield compound 33. Compound 33 is condensed with amino acid to provide compound 34.

Scheme 7

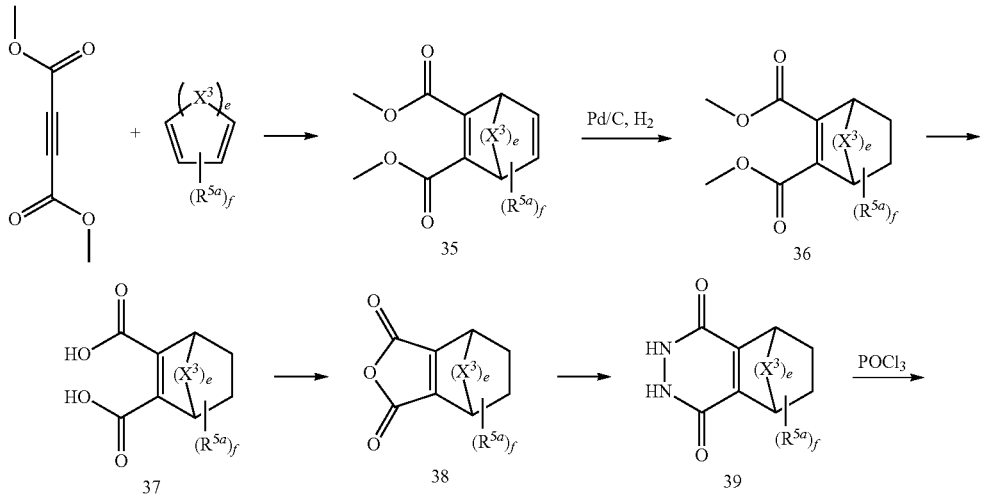

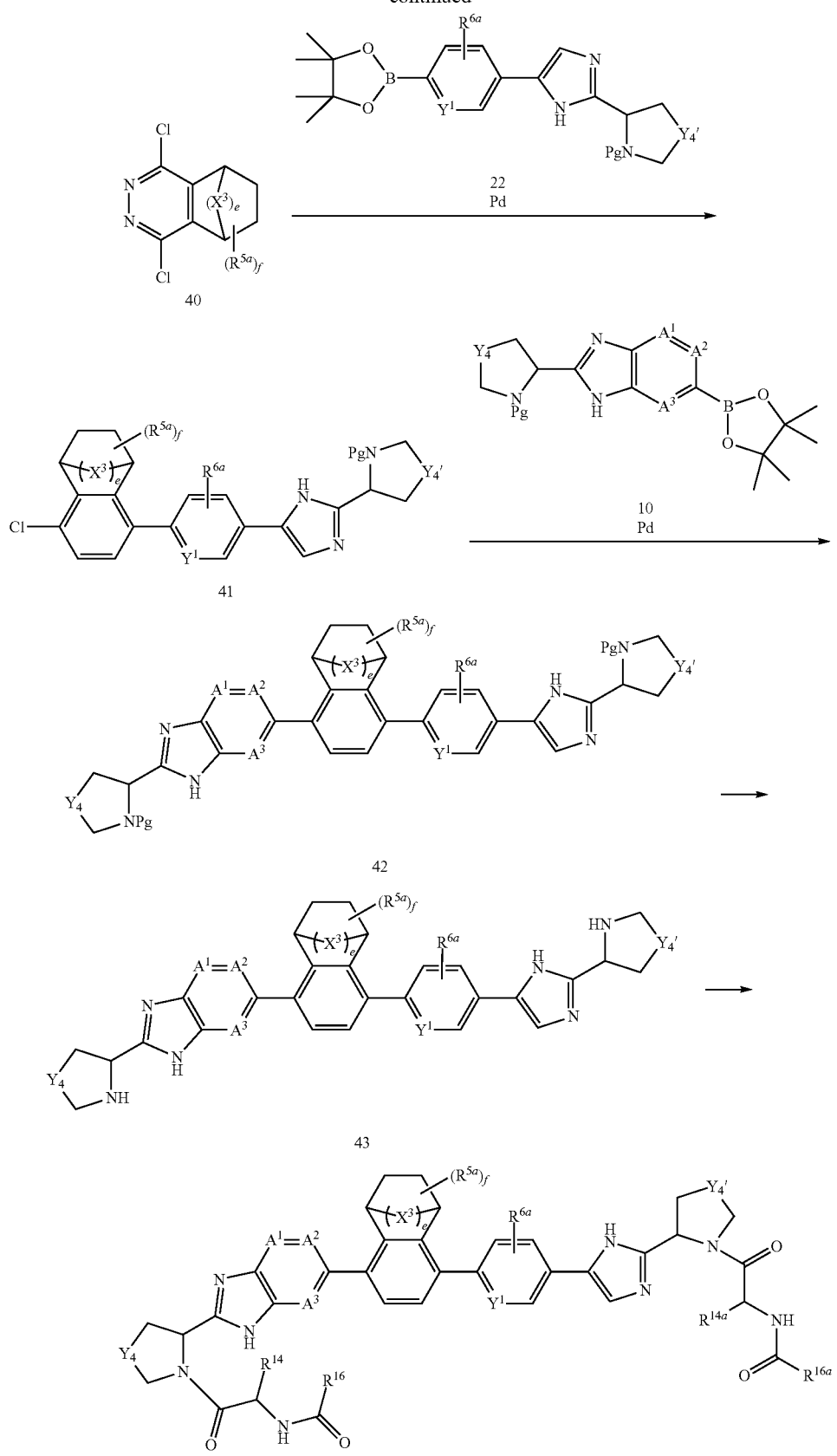

Compound 44 can be synthesized through the procedure depicted in Scheme 7. Wherein each of $R^{5a}$, $X^3$, e, f, $R^{6a}$, $Y_4$, $Y_4'$, $Y^1$, $R^{14}$, $R^{14a}$, $R^{16}$ and $R^{16a}$ is as defined above and each of $A^1$, $A^2$ and $A^3$ is independently N or $CR^7$. Pg is amino-protecting group such as Boc, Fmoc or Cbz. Compound 35 is obtained by Diels-Alder reaction of dimethyl but-2-ynedioate and conjugated dienes. Reduction of Compound 35 with a reducing agent, such as Pd/C through the process of catalytic hydrogenation can afford compound 36. Compound 36 can give compound 37 by base catalysis. Cyclic condensation of compound 37 can yield compound 38 under condensation agents. Compound 38 can be transformed to compound 39 by reacting with hydrazine hydrate and acetic acid under heating condition. Compound 39 can be converted to compound 40 in the presence of phosphorus oxychloride. Coupling reaction of compound 40 with compound 22 in the presence of Pd catalyst can give compound 41. Compound 41 is further reacted with compound 10 in the presence of Pd catalyst to afford compound 42. Then the protecting group Pg in compound 42 can be removed to yield compound 43. Compound 43 is condensed with amino acid to provide compound 44.

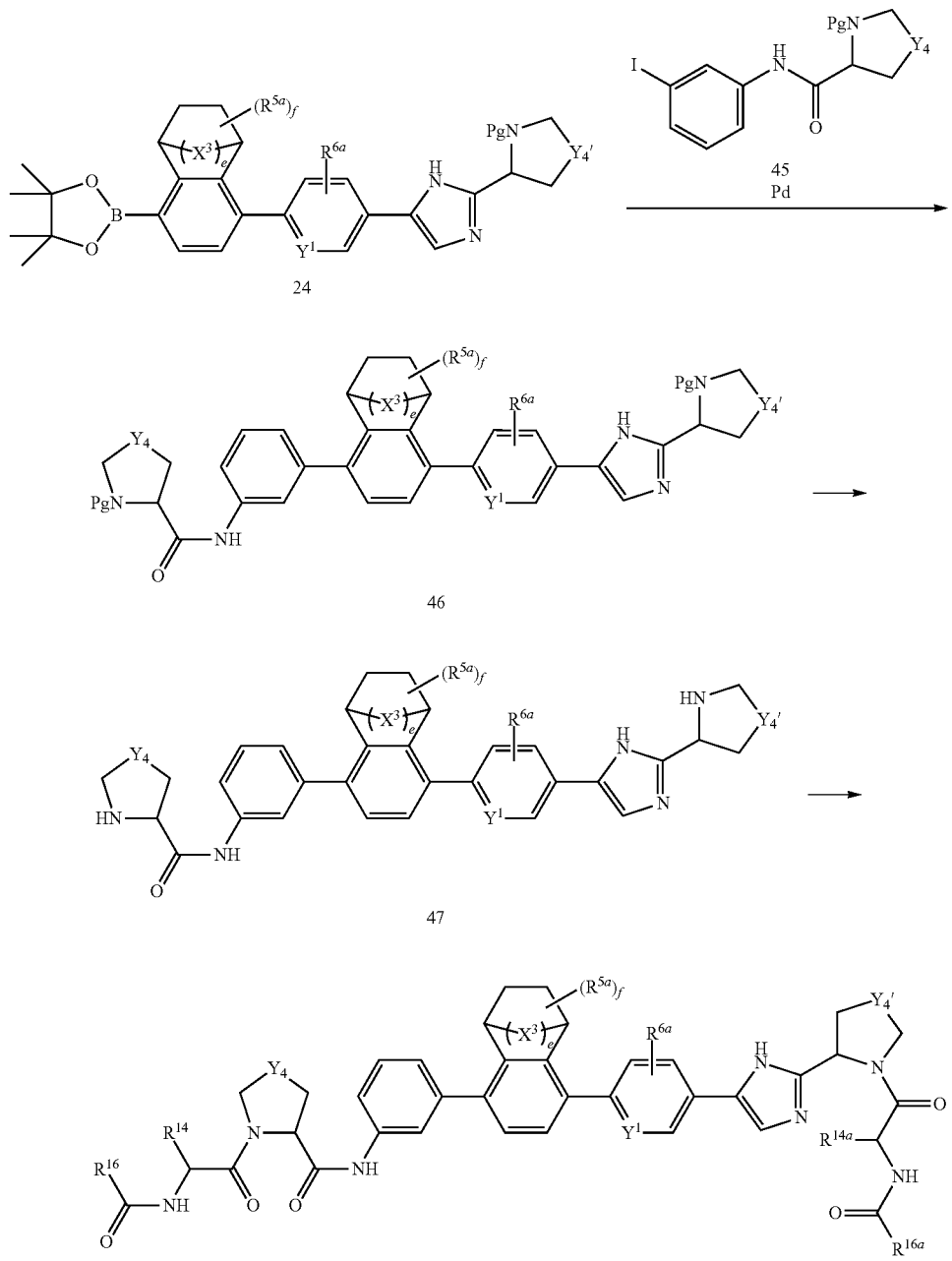

Scheme 8

Compound 48, wherein each of $R^{5a}$, $X^3$, e, f, $R^{6a}$, $Y_4$, $Y_4'$, $Y^1$, $R^{14}$, $R^{14a}$, $R^{16}$ and $R^{16a}$ is as defined above, can be prepared by the process illustrated in Scheme 8. Pg is amino-protecting group such as Boc, Fmoc or Cbz. Coupling reaction of compound 24 with compound 45 in the presence of Pd catalyst can give compound 46. The protecting group Pg in compound 46 can be removed to afford compound 47, which is condensed with amino acid to provide compound 48.

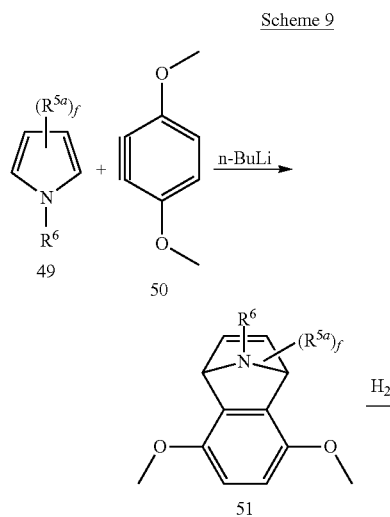

Scheme 9

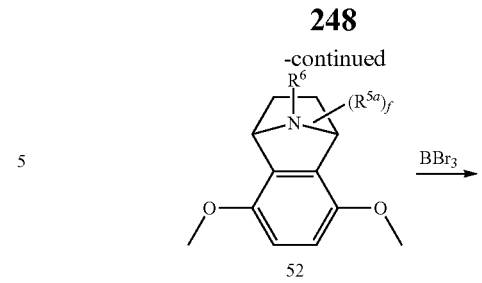

Compound 54, wherein each of $R^{5a}$, f and $R^6$ is as defined above, can be prepared by the process illustrated in Scheme 9. Compound 51 is obtained by Diels-Alder reaction of compound 49 and compound 50 in the presence of n-BuLi. Reduction of compound 51 with a reducing agent, such as Pd/C through the process of catalytic hydrogenation can afford compound 52. The methyl group in compound 51 is then removed in the presence of boron tribromide to provide compound 53. Compound 53 can be reacted with trifluoromethanesulfonic anhydride to afford compound 54 by base catalysis.

Scheme 10

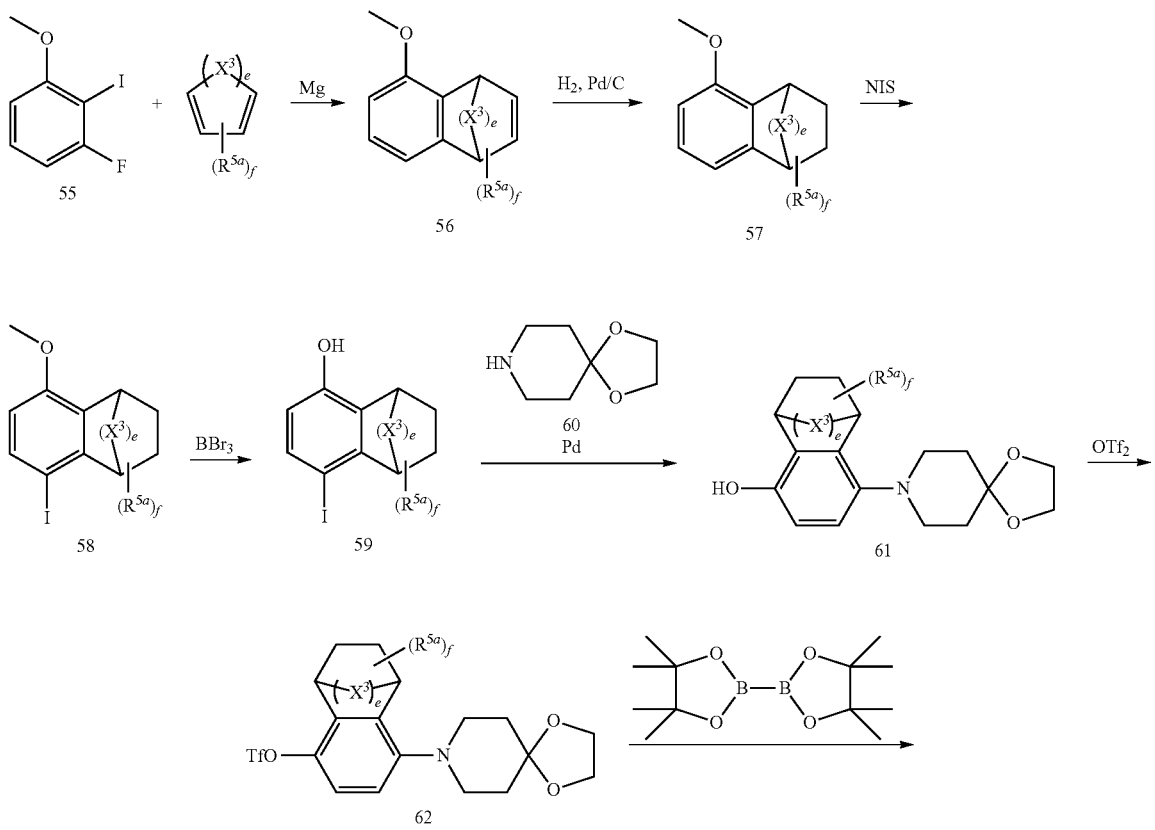

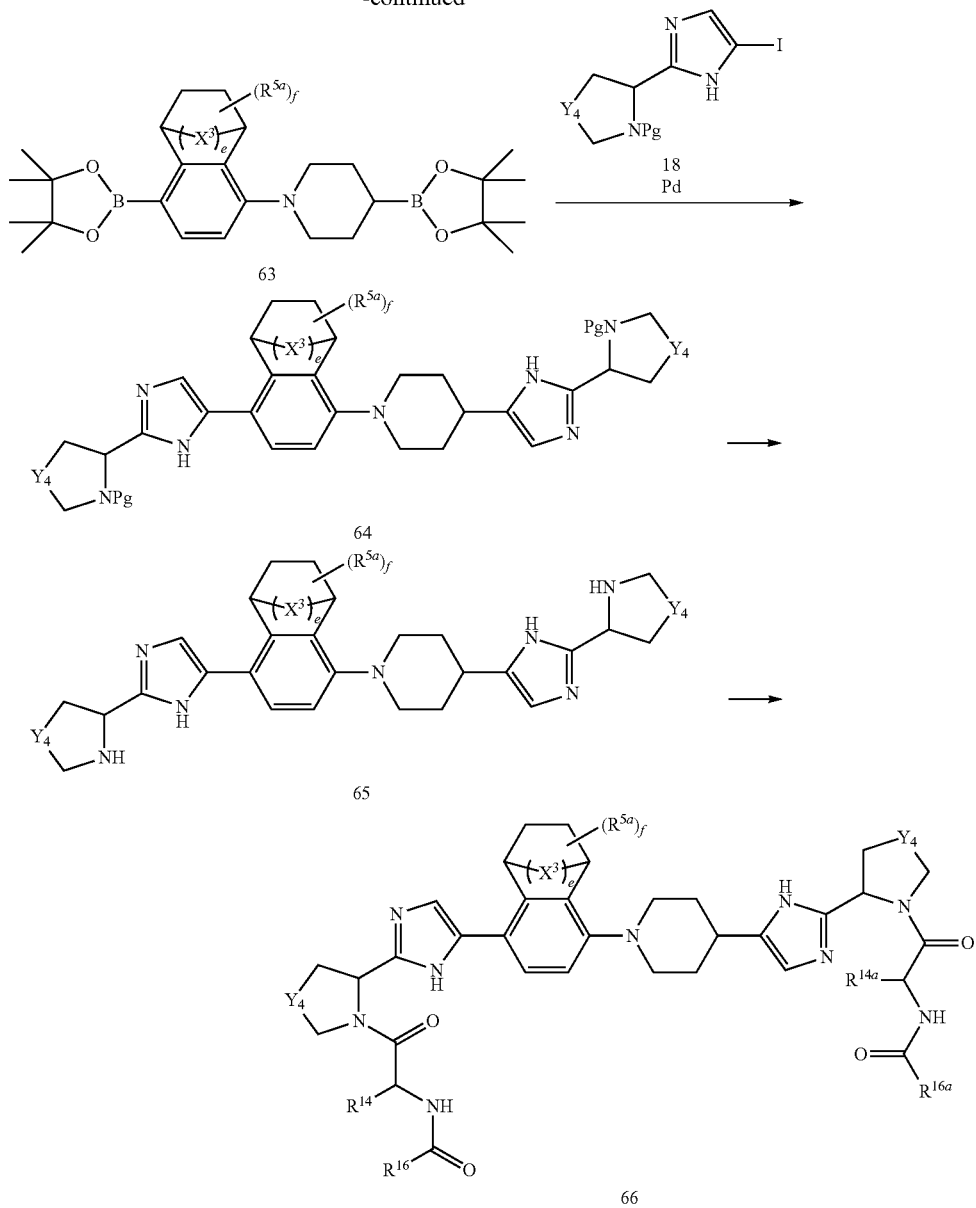

Compound 66 can be synthesized through the procedure depicted in Scheme 10. Wherein each of $R^{5a}$, $X^3$, e, f, $Y_4$, $R^{14}$, $R^{14a}$, $R^{16}$ and $R^{16a}$ is as defined above and Pg is amino-protecting group such as Boc, Fmoc or Cbz. Reaction of compound 55 with conjugated dienes under magnesium in polar solvent such as THF can give compound 56. Reduction of compound 56 with a reducing agent, such as Pd/C through the process of catalytic hydrogenation can afford compound 57. Compound 57 can be transformed to compound 58 by reacting with NIS agent. The methyl group in compound 58 is then removed in the presence of boron tribromide to provide compound 59. Coupling reaction of compound 59 with compound 60 in the presence of Pd catalyst can give compound 61. Compound 61 can be reacted with trifluoromethane-sulfonic anhydride to afford compound 62 by base catalysis. Compound 62 is reacted with $SmCl_3$/TMSCl and LiHMDS/ $PhNTf_2$ to afford an Intermediate in polar solvent such as THF, then the Intermediate is further reacted with bis(pina- colato)diboron in the presence of Pd catalyst to afford compound 63. Compound 63 can be converted to compound 64 by reacting with compound 18 in the presence of Pd catalyst. The protecting group Pg is removed to afford compound 65, which is condensed with amino acid to provide compound 66.

Scheme 11

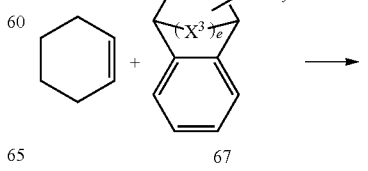

67

-continued

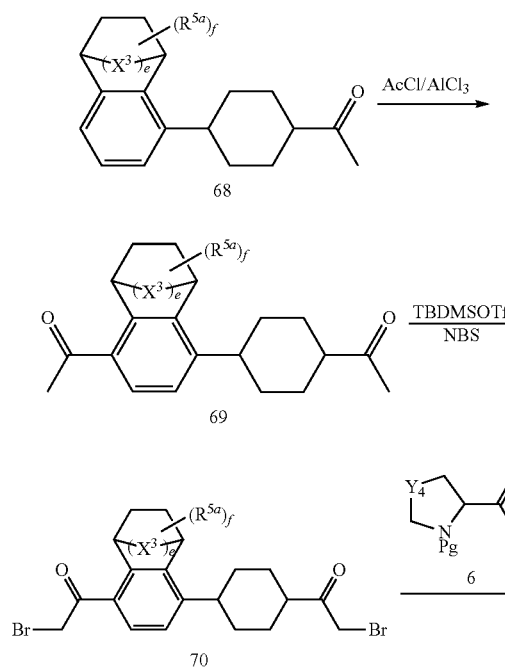

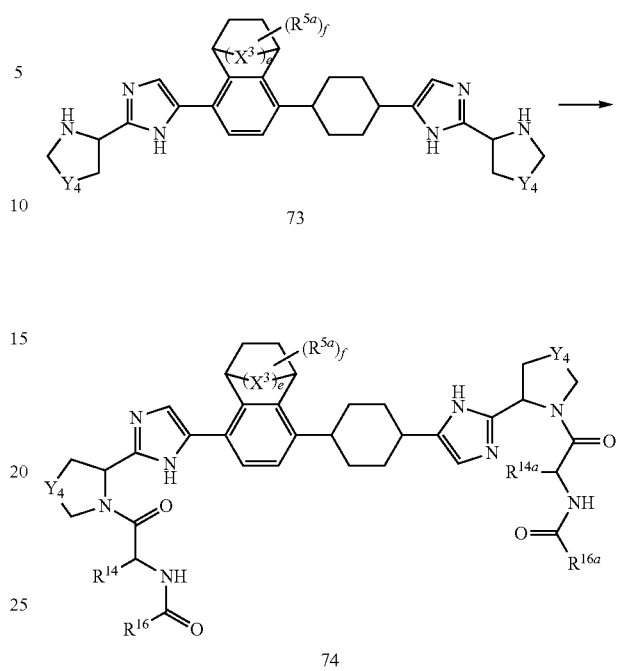

Compound 74, wherein each of $R^{5a}$, $X^3$, e, f, $Y_4$, $R^{14}$, $R^{14a}$, $R^{16}$ and $R^{16a}$ is as defined above, can be prepared by the process illustrated in Scheme 11. Pg is amino-protecting group such as Boc, Fmoc or Cbz. Compound 67 can be converted to compound 68 by reacting with cyclohexene in the presence of acyl chloride and aluminium chloride in polar solvent such as $CS_2$. Compound 68 can be reacted with acetyl chloride to afford compound 69 in the presence of aluminium chloride. Compound 69 can be converted to compound 70 in the presence of brominating agents such as TBDMSOTf and NBS. Condensation of compound 70 with compound 6 can give the compound 71. Compound 71 can be cyclized in the presence of ammonium acetate to form compound 72. The protecting group Pg in compound 72 is removed to afford compound 73, which is condensed with amino acid to provide compound 74.

Scheme 12

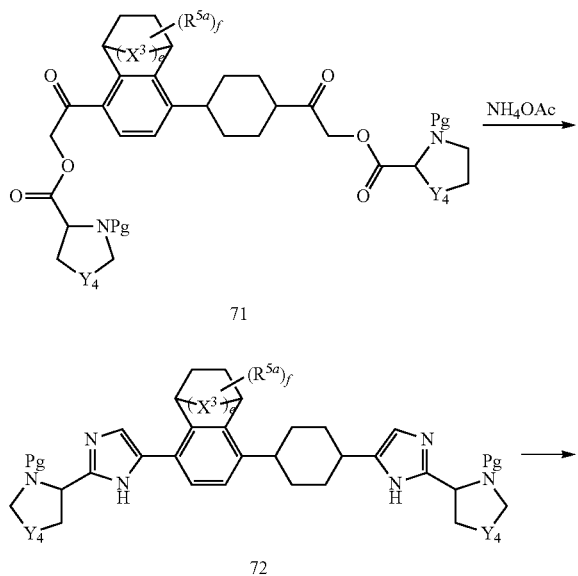

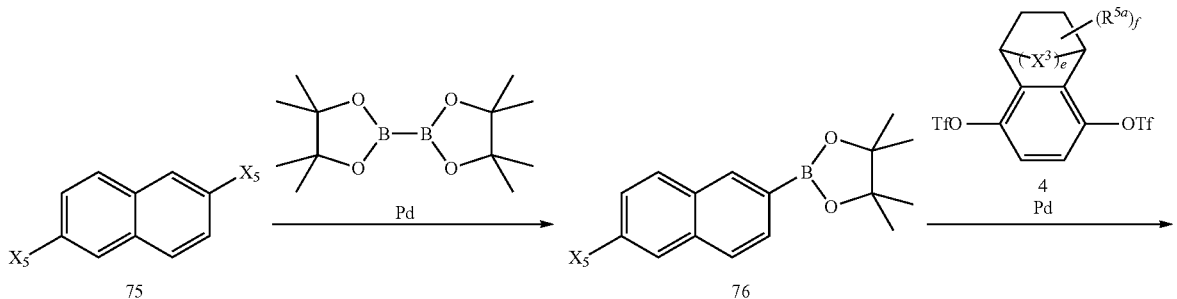

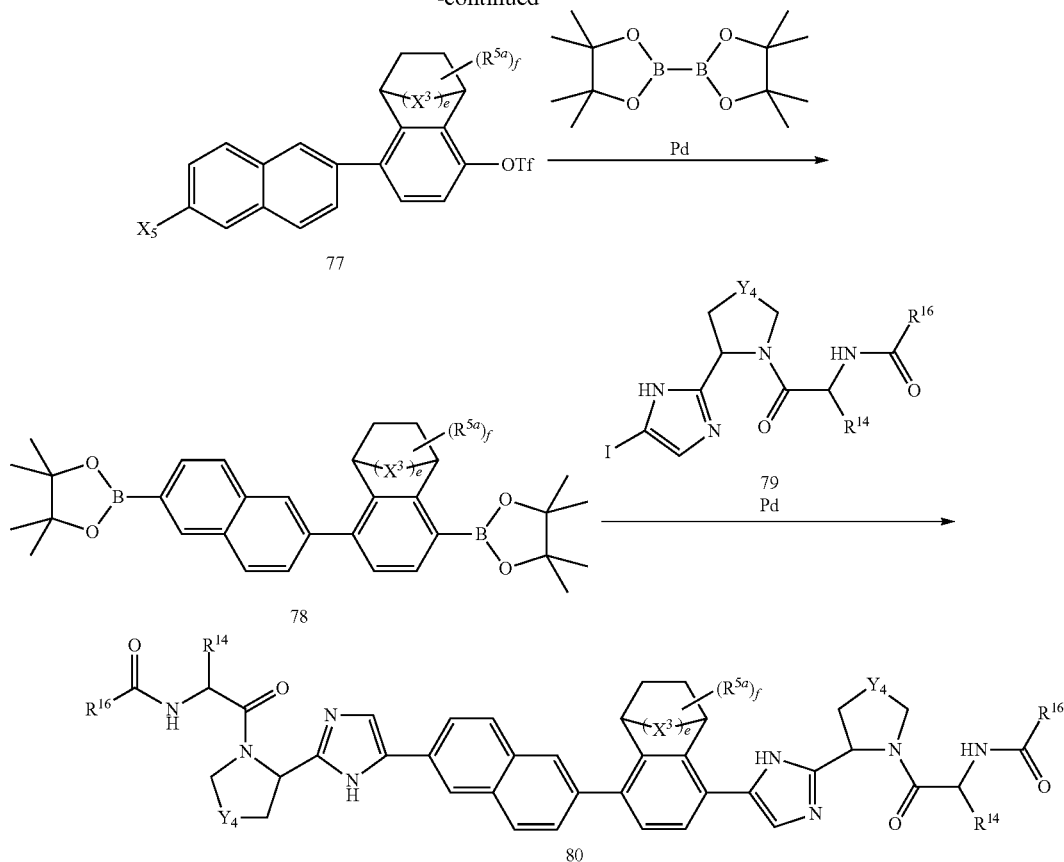

Compound 80 can be prepared by the process illustrated in Scheme 12. Wherein each $X^5$ is F, Cl, Br or I and each of $Y_4$, $R^{5a}$, $X^3$, e, f, $R^{14}$, $R^{16}$ is as defined above. Reaction of compound 75 with bis(pinacolato)diboron can afford compound 76 by Pd catalysis. Coupling reaction of compound 76 with compound 4 in the presence of Pd catalyst can give compound 77. Compound 77 is further reacted with bis(pinacolato)diboron in the presence of Pd catalyst to afford compound 78. Compound 78 can be converted to compound 80 by reacting with compound 79 in the presence of Pd catalyst.

Scheme 13

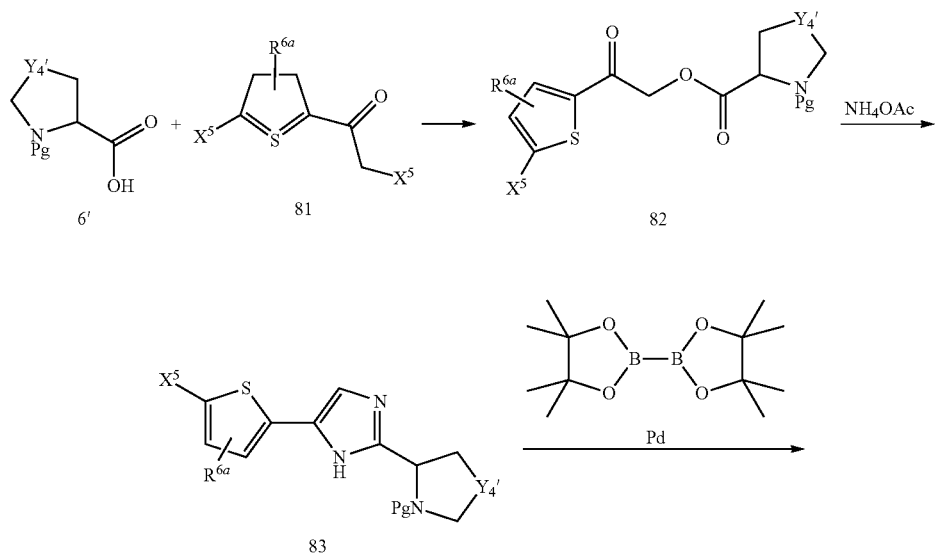

-continued
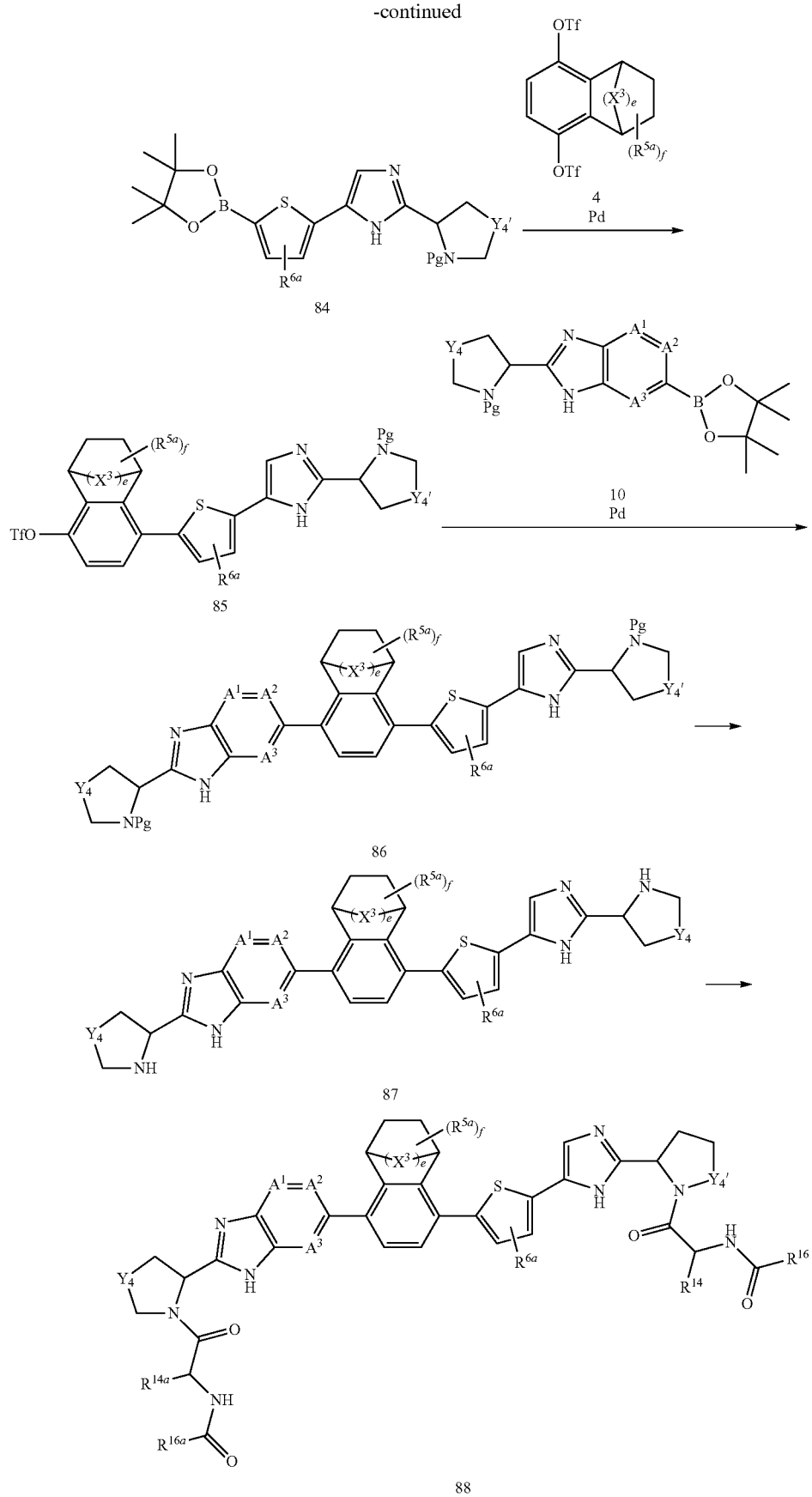

Compound 88 can be synthesized through the procedure depicted in Scheme 13. Wherein each of $Y^{4t}$, $Y_4$, $R^{5a}$, $R^{6a}$, $X^3$, e, f, $R^{14}$, $R^{14a}$, $R^{16}$ and $R^{16a}$ is as defined above, each $X^5$ is independently F, Cl, Br or I, and each of $A^1$, $A^2$ and $A^3$ is independently N or $CR^7$. Pg is amino-protecting group such as Boc, Fmoc or Cbz. Condensation of compound 81 with compound 6' can give the compound 82 by base catalysis. Compound 82 can be cyclized in the presence of ammonium acetate to form compound 83. Reaction of compound 83 with bis(pinacolato)diboron can afford compound 84 by Pd catalysis. Coupling reaction of compound 84 with compound 4 in the presence of Pd catalyst can give compound 85. Compound 85 is further reacted with compound 10 in the presence of Pd catalyst to afford compound 86. The protecting group Pg in compound 86 is removed to afford compound 87, which is condensed with amino acid to provide compound 88.

Scheme 14

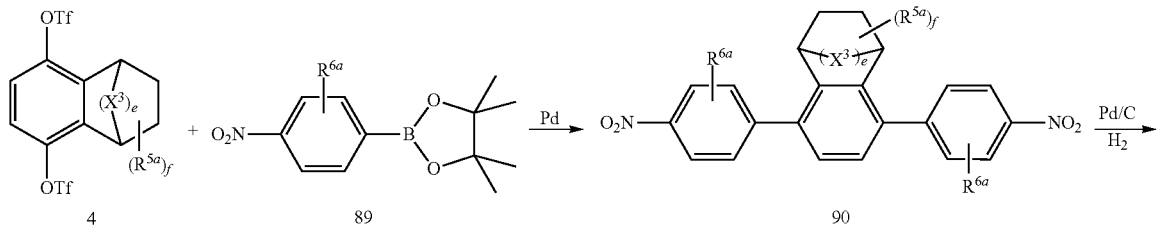

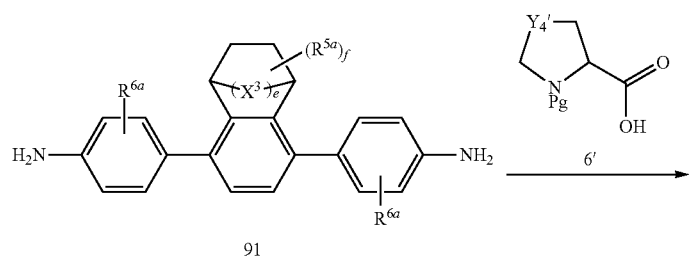

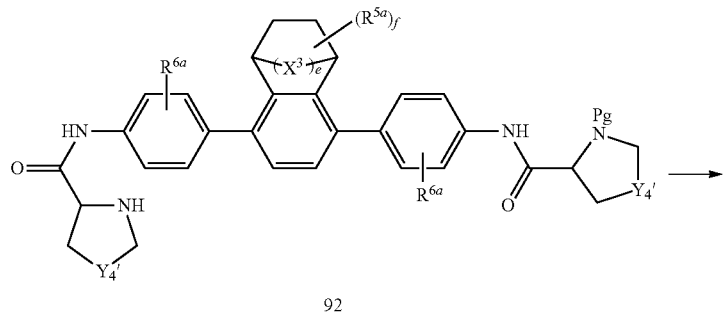

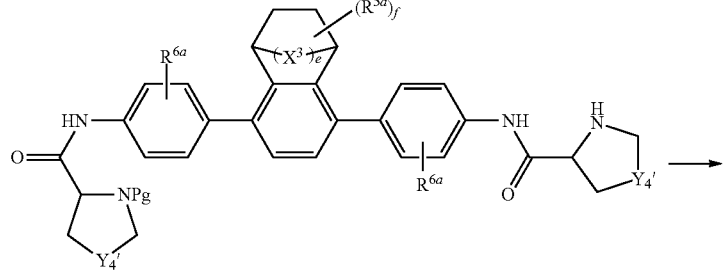

-continued

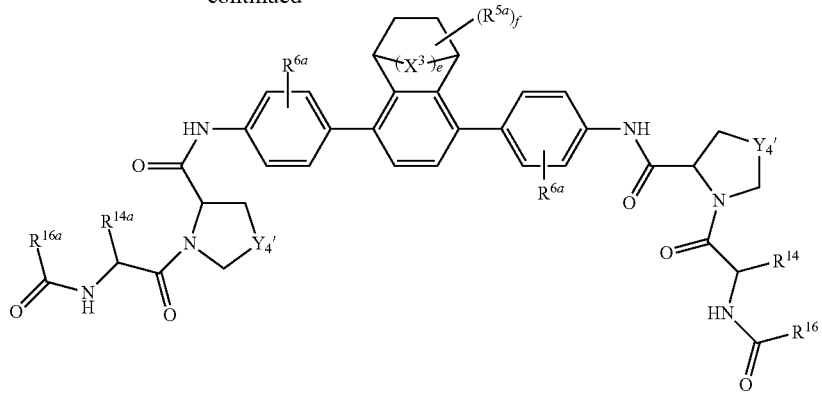

94

Compound 94, wherein each of $R^{5a}$, $X^3$, e, f, $R^{6a}$, $Y_4'$, $R^{14}$, $R^{14a}$, $R^{16}$ and $R^{16a}$ is as defined above, can be prepared by the process illustrated in Scheme 14. Pg is amino-protecting group such as Boc, Fmoc or Cbz. Coupling reaction of compound 89 with compound 4 in the presence of Pd catalyst can give compound 90. Reduction of compound 90 with a reducing agent, such as Pd/C through the process of catalytic hydrogenation can afford compound 91. Condensation of compound 91 with compound 6' can give the compound 92 by base catalysis. The protecting group Pg in compound 92 is removed to afford compound 93, which is condensed with amino acid to provide compound 94.

Scheme 15

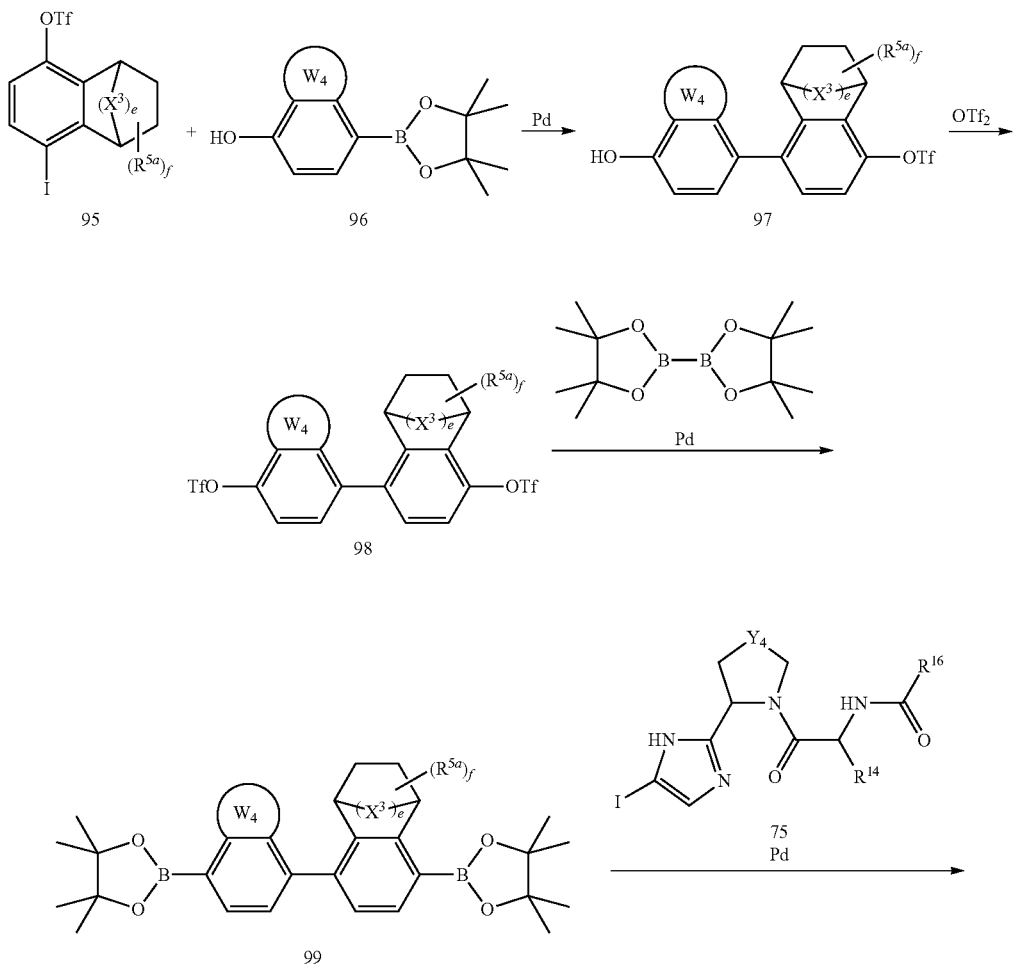

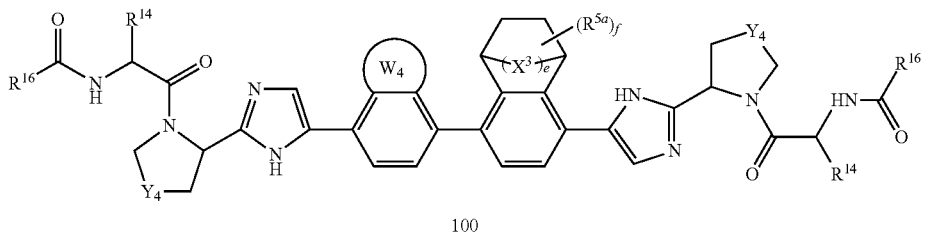

100

Compound 100 can be prepared by the process illustrated in Scheme 15. Wherein each $W_4$ is carbocycle or aromatic ring and each of $Y_4$, $R^{5a}$, $X^3$, e, f, $R^{14}$, and $R^{16}$ is as defined above. Coupling reaction of compound 95 with compound 96 in the presence of Pd catalyst can give compound 97. Compound 97 can be reacted with trifluoromethanesulfonic anhydride to afford compound 98 by base catalysis. Reaction of compound 98 with bis(pinacolato)diboron can afford compound 99 by Pd catalysis. Coupling reaction of compound 99 with compound 75 in the presence of Pd catalyst can give compound 100.

Scheme 16

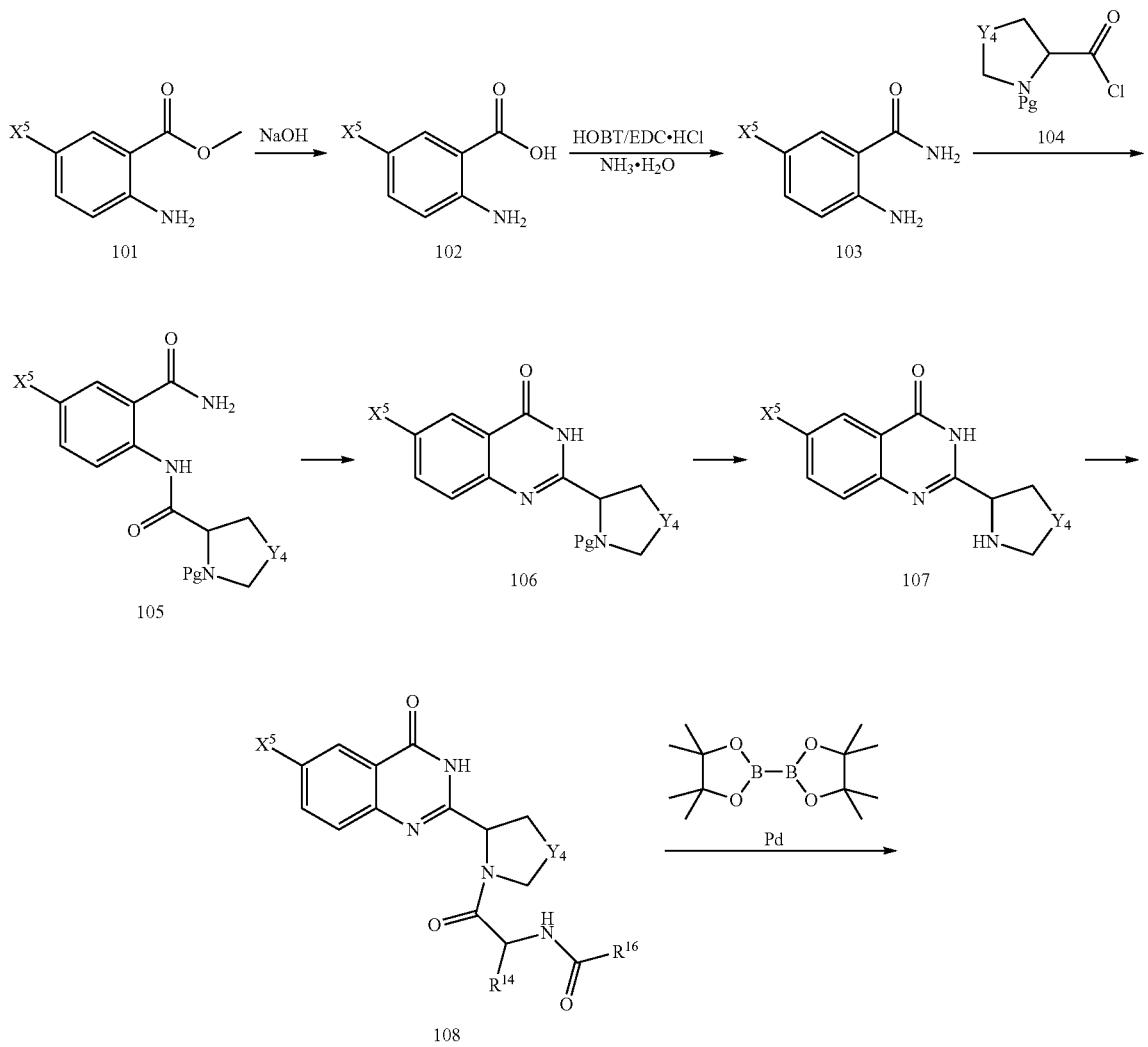

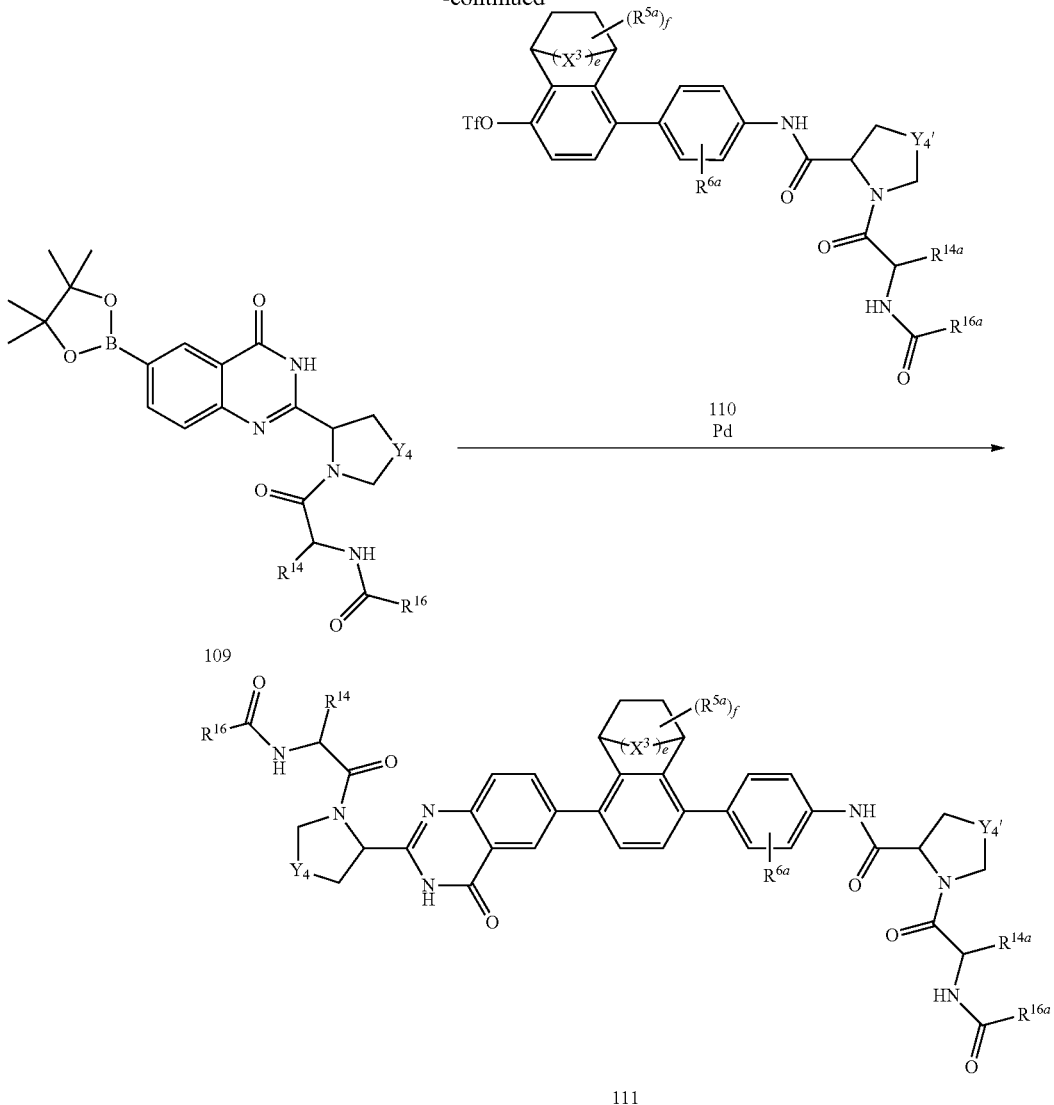

Compound III can be synthesized through the procedure depicted in Scheme 16. Wherein each of $Y^{4'}$, $Y_4$, $R^{5a}$, $R^{6a}$, $X^3$, e, f, $R^{14}$, $R^{14a}$, $R^{16}$ and $R^{16a}$ is as defined above, each $X^5$ is independently F, Cl, Br or I, and Pg is amino-protecting group such as Boc, Fmoc or Cbz. Compound 101 can be converted to compound 102 by base catalysis. Compound 102 can be converted to compound 103 in the presence of HOBT/EDCI and ammonium hydroxide. Condensation of compound 103 with compound 104 can give the compound 105 by base catalysis. Compound 105 can be cyclized in the presence of base to form compound 106. The protecting group Pg in compound 106 is removed to afford compound 107, which is condensed with amino acid to provide compound 108. Reaction of compound 108 with bis(pinacolato)diboron can afford compound 109 by Pd catalysis. Coupling reaction of compound 109 with compound 110 in the presence of Pd catalyst can give compound 111.

Scheme 17

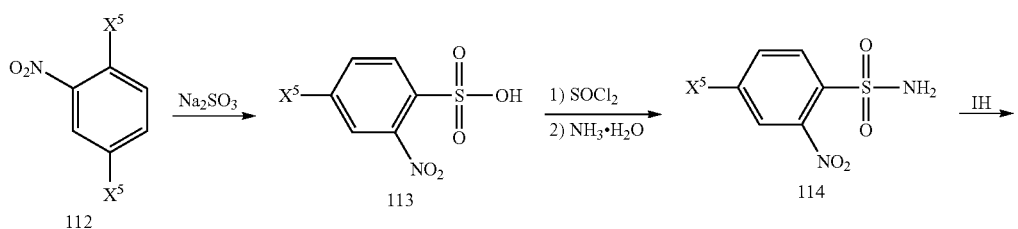

-continued
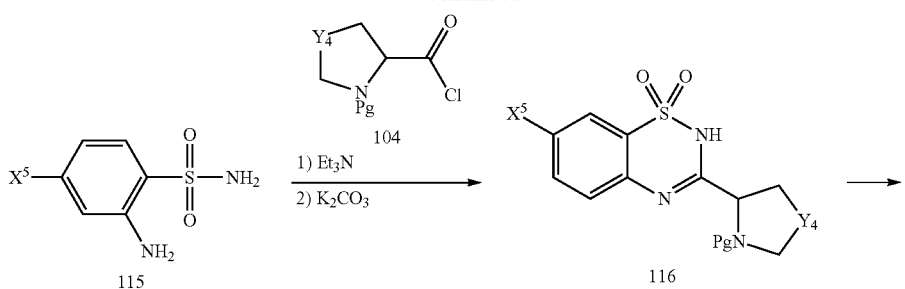
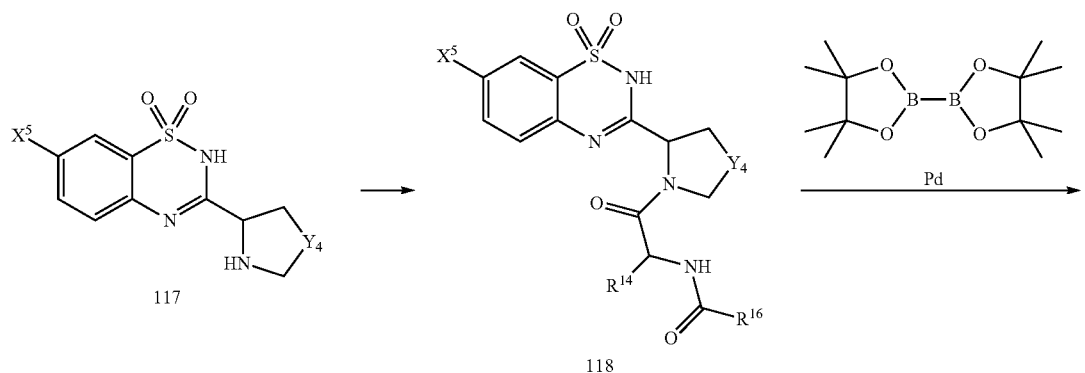
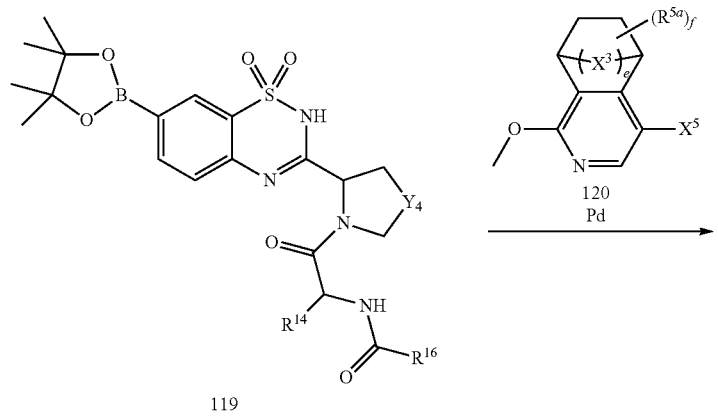
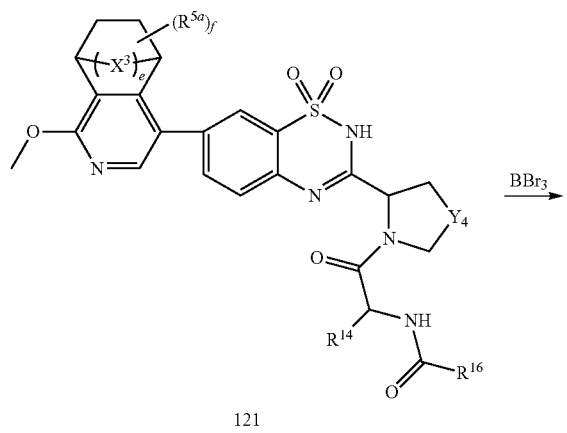

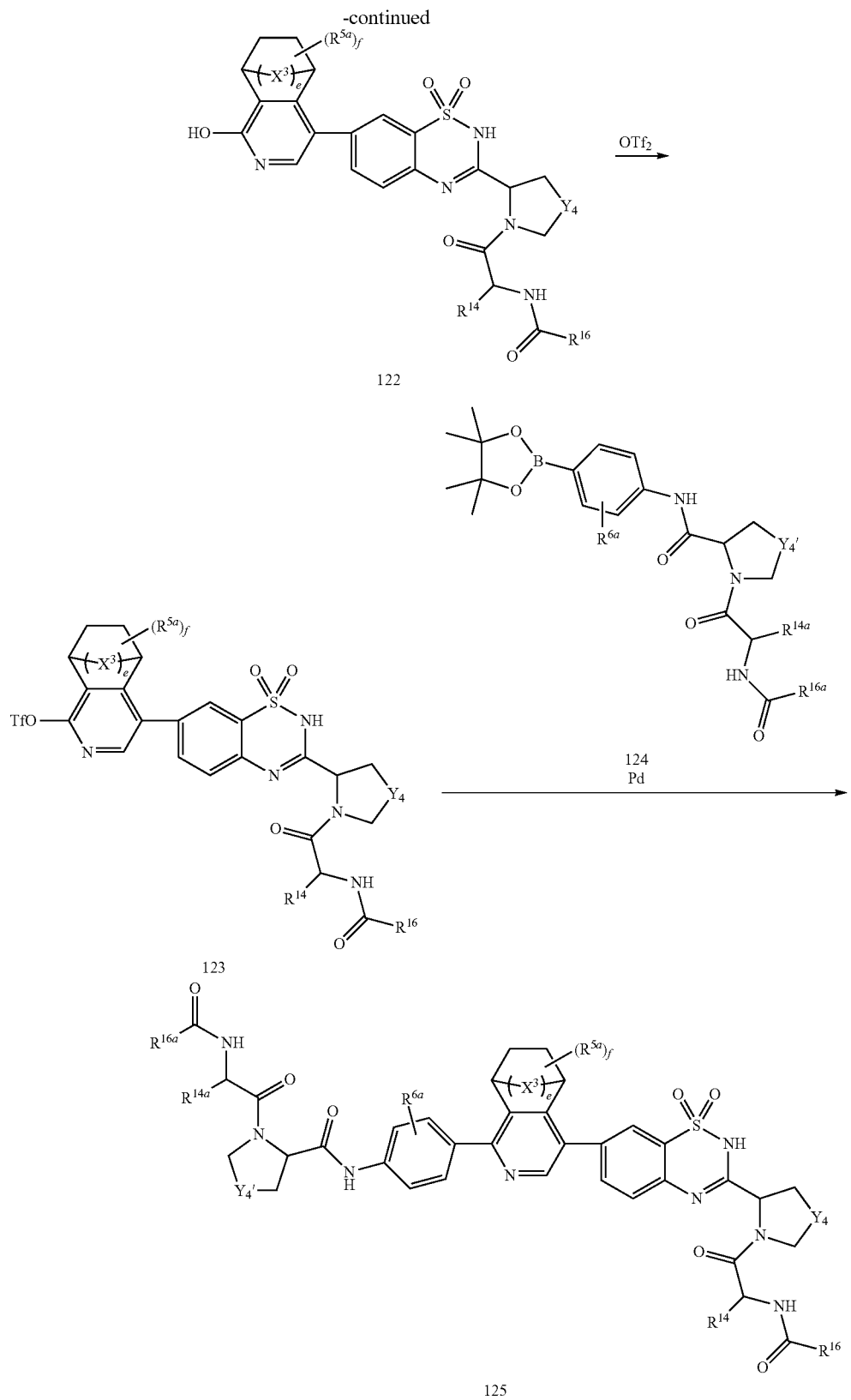
Compound 125 can be synthesized through the procedure depicted in Scheme 17. Wherein each of $Y_4'$, $Y_4$, $R^{5a}$, $R^{6a}$, $X^3$, e, f, $R^{14}$, $R^{14a}$, $R^{16}$ and $R^{16a}$ is as defined above, each $X^5$ is independently F, Cl, Br or I, and Pg is amino-protecting group such as Boc, Fmoc or Cbz. Compound 112 can be transformed to compound 113 by reacting with sodium sulfite.

Compound 113 can be converted to compound 114 in the presence of Thionyl chloride and ammonium hydroxide. Reduction of compound 114 with a reducing agent, such as HI can afford compound 115. Cyclization of compound 115 with compound 104 can form compound 116 in the presence of base. The protecting group Pg in compound 116 is removed to afford compound 117, which is condensed with amino acid to provide compound 118. Reaction of compound 118 with bis(pinacolato)diboron can afford compound 119 by Pd catalysis. Coupling reaction of compound 119 with compound 120 in the presence of Pd catalyst can give compound 121. The methyl group in compound 121 is then removed in the presence of boron tribromide to provide compound 122. Compound 122 can be reacted with trifluoromethanesulfonic anhydride to afford compound 123 by base catalysis. Coupling reaction of compound 123 with compound 124 in the presence of Pd catalyst can give compound 125.

Scheme 18

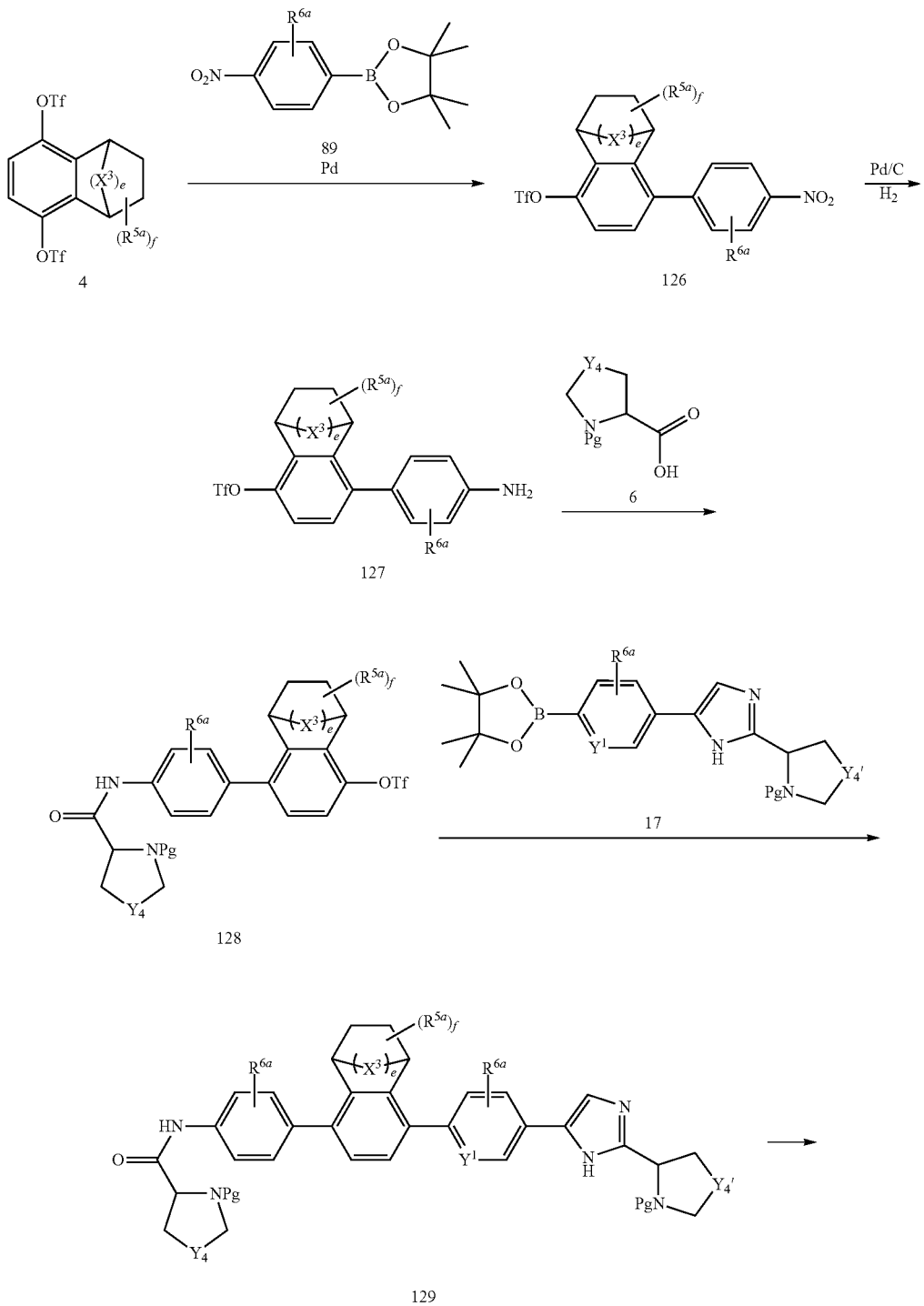

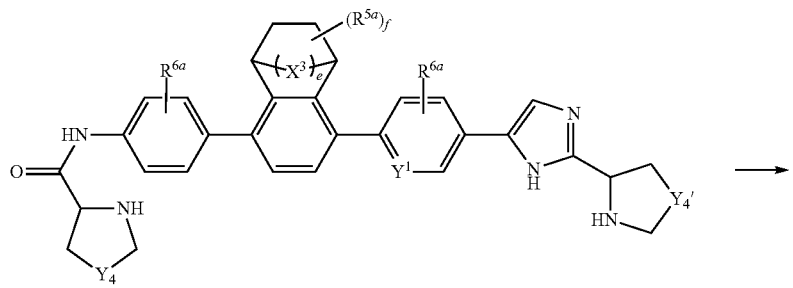

130

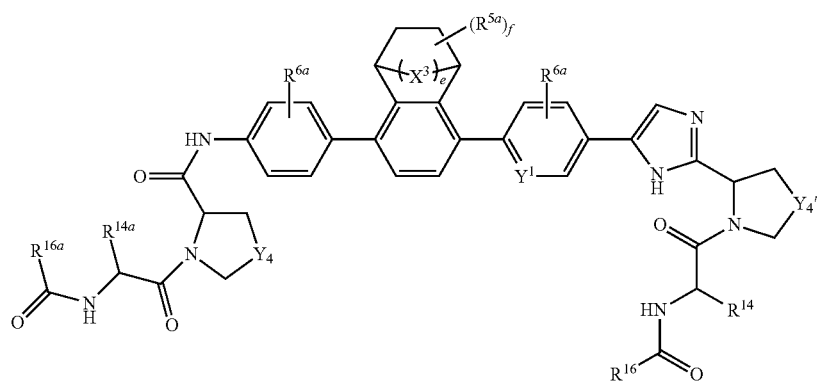

131

Compound 131, wherein each of $Y_4'$, $Y_4$, $R^{5a}$, $R^{6a}$, $X^3$, e, f, $R^{14}$, $R^{14a}$, $R^{16}$ and $R^{16a}$ is as defined above, can be prepared by the process illustrated in Scheme 18. Pg is amino-protecting group such as Boc, Fmoc or Cbz. Coupling reaction of compound 4 with compound 89 in the presence of Pd catalyst can give compound 126. Reduction of compound 126 with a reducing agent, such as Pd/C through the process of catalytic hydrogenation can afford compound 127. Condensation of compound 127 with compound 6 can give the compound 128 by base catalysis. Coupling reaction of compound 128 with compound 17 in the presence of Pd catalyst can give compound 129. The protecting group Pg in compound 129 is removed to afford compound 130, which is condensed with amino acid to provide compound 131.

Scheme 19

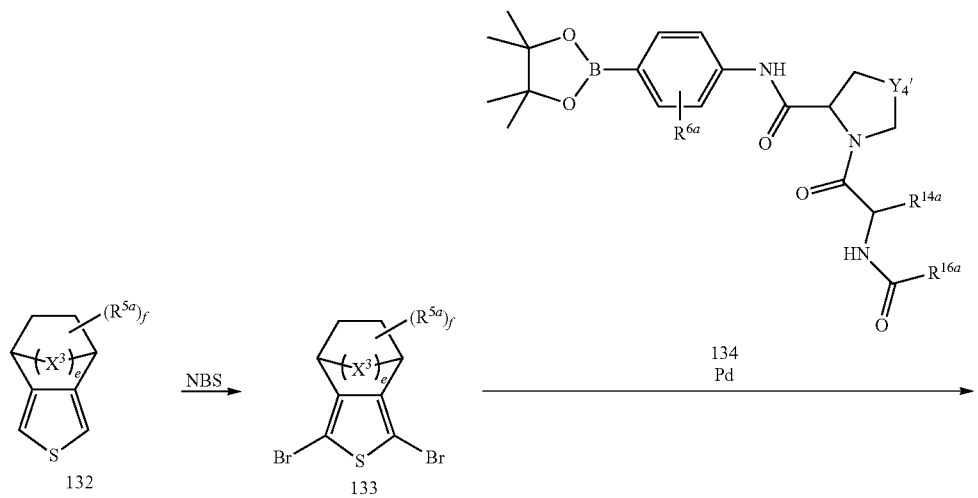

-continued

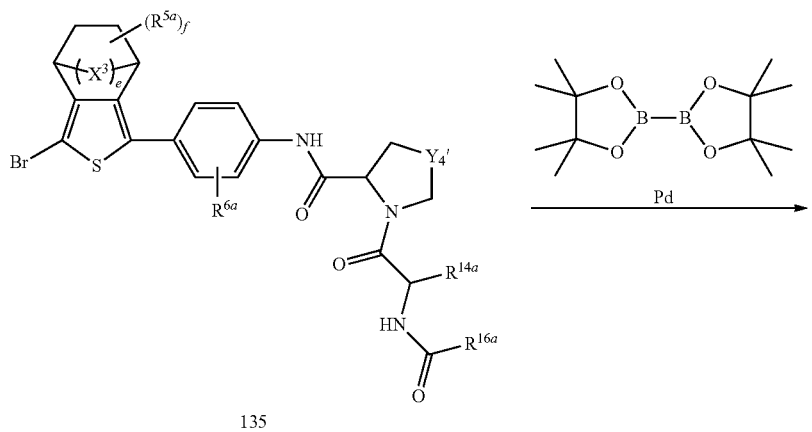

135

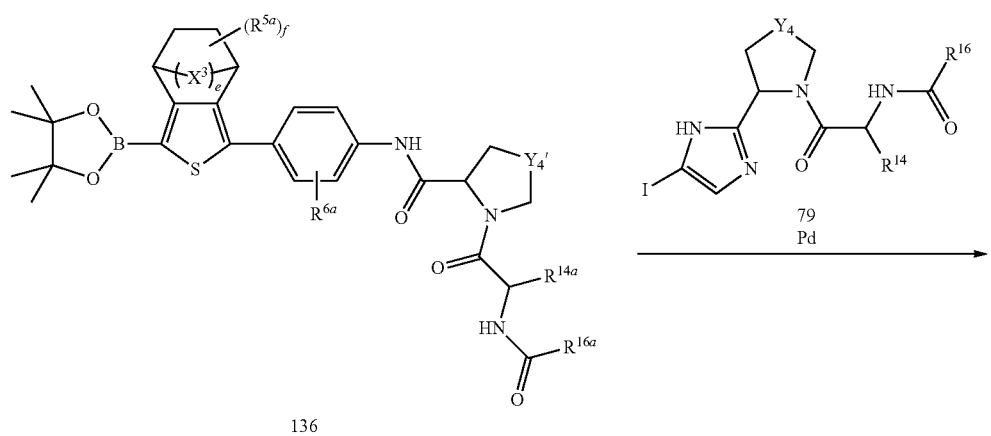

136

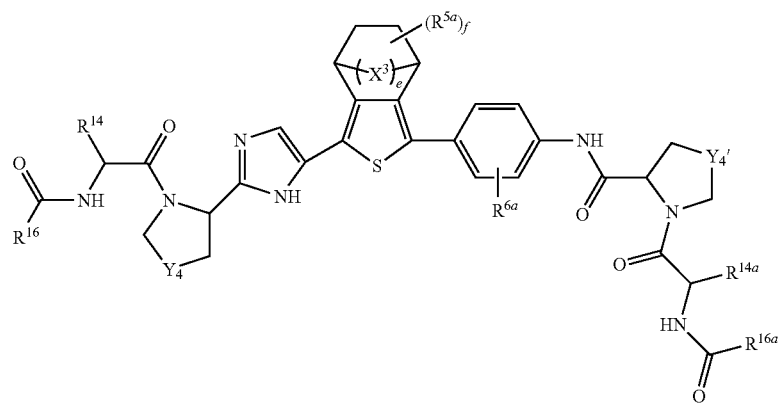

137

Compound 137, wherein each of $Y^{4'}$, $Y_4$, $R^{5a}$, $R^{6a}$, $X^3$, e, f, $R^{14}$, $R^{14a}$, $R^{16}$ and $R^{16a}$ is as defined above, can be prepared by the process illustrated in Scheme 19. Compound 132 can be converted to compound 133 in the presence of brominating agents such as NBS. Coupling reaction of compound 133 with compound 134 in the presence of Pd catalyst can give compound 135. Reaction of compound 135 with bis(pinacolato)diboron can afford compound 136 by Pd catalysis. Coupling reaction of compound 136 with compound 79 in the presence of Pd catalyst can give compound 137.

EXAMPLES
Example 1
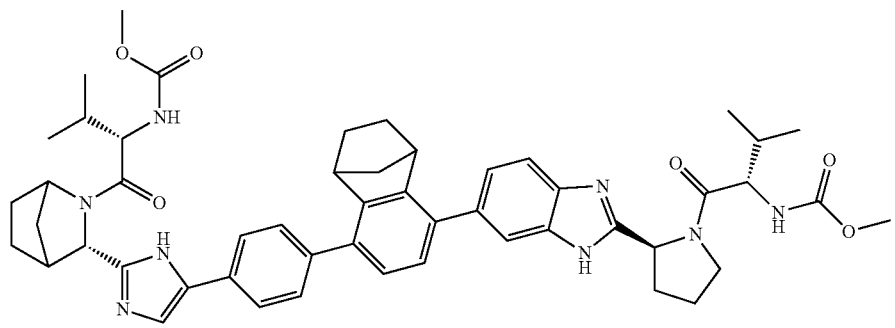 [SMILES: COC(=O)N[C@H](C(=O)N1CCC[C@H]1c1nc2ccc(-c3ccc(-c4ccc(-c5cnc([C@@H]6C7CCC(C7)N6C(=O)[C@@H](NC(=O)OC)C(C)C)[nH]5)cc4)c4c3C3CCC4C3)cc2[nH]1)C(C)C]
Synthetic Route:
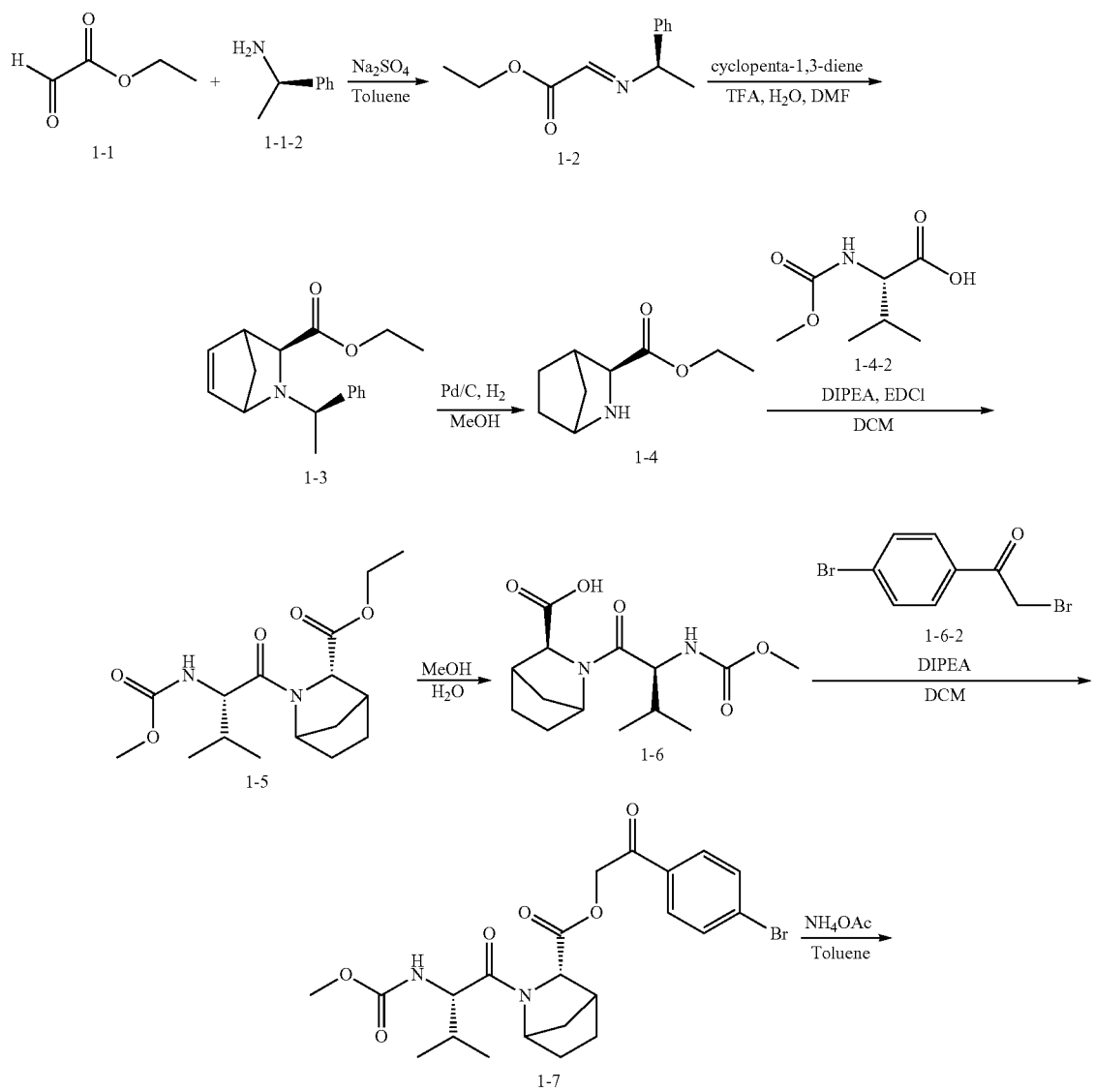

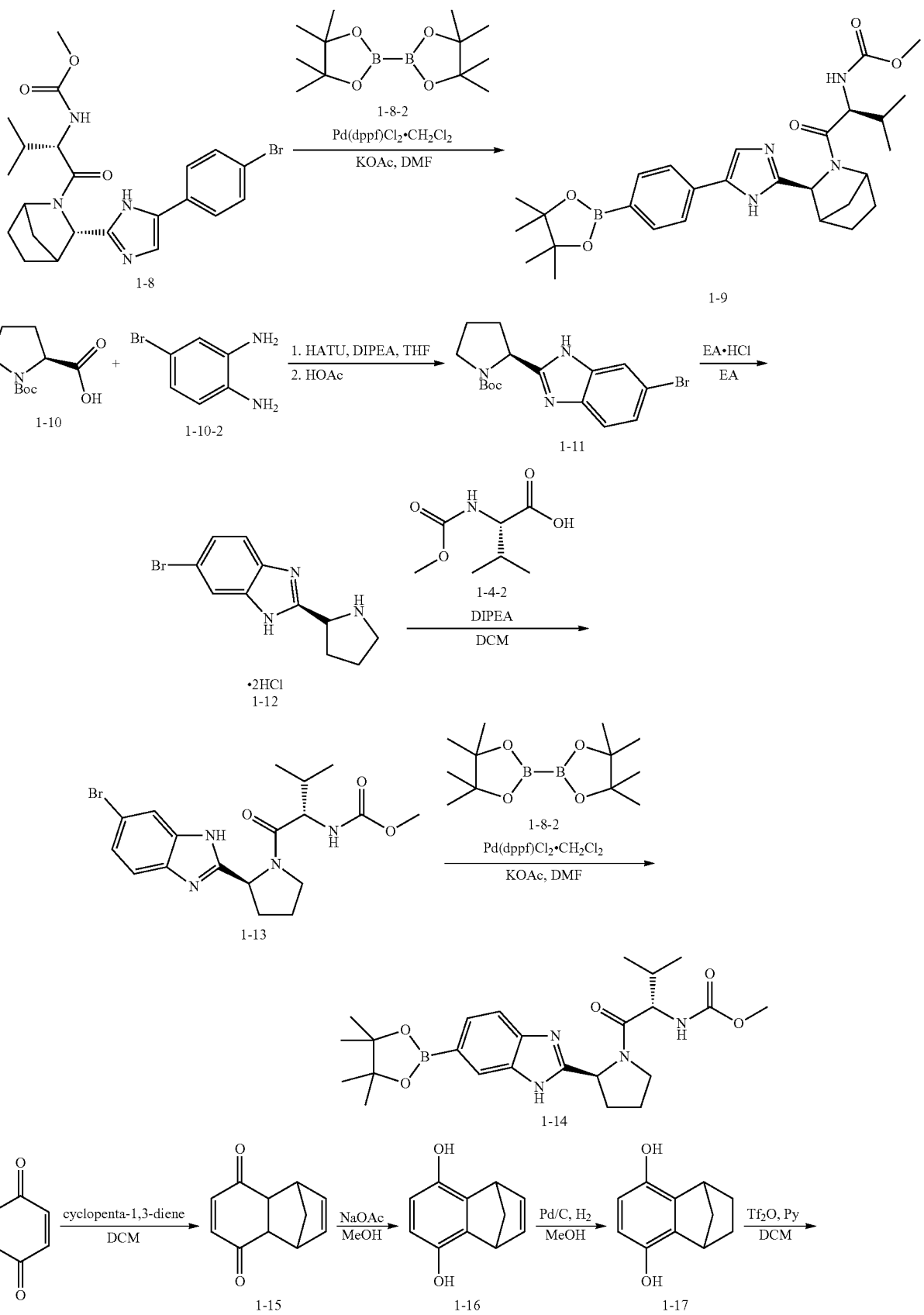

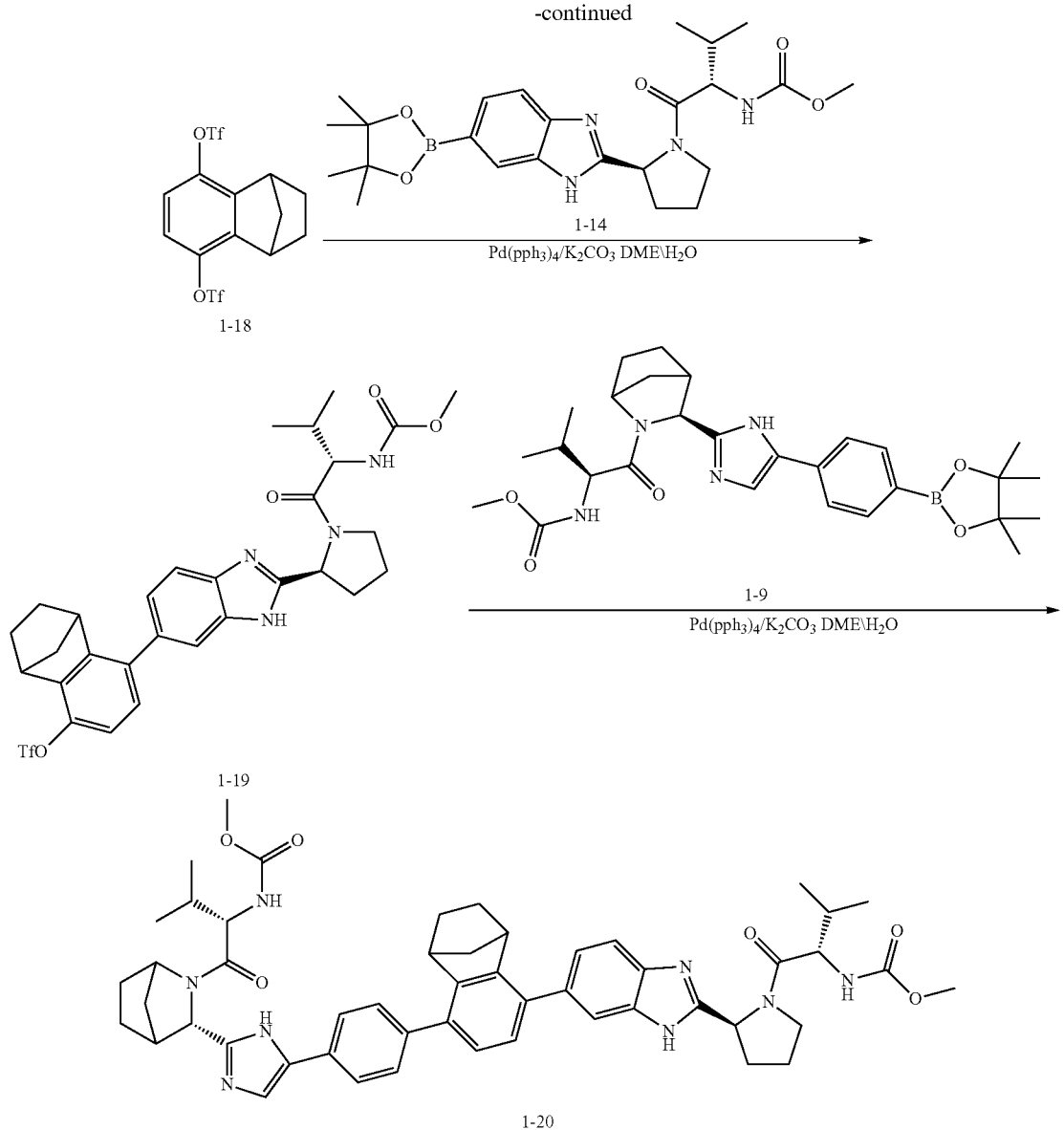

Step 1) the Preparation of Compound 1-2

To a solution of (R)-1-phenylethylamine (1.3 mL, 10.1 mmol) in toluene (15 mL) was added anhydrous $Na_2SO_4$ (3.48 g, 24.5 mmol) at rt, followed by ethyl glyoxalate (1 mL, 10.1 mmol) dropwise. The mixture was stirred at rt for 1 hr and filtered. The filtrate was concentrated in vacuo to give the title compound 1-2 as yellow liquid (1.9 g, 91.8%), which was used for the next step without further purification.

Step 2) the Preparation of Compound 1-3

To a solution of compound 1-2 (2.0 g, 9.7 mmol) in DMF (15 mL) was added TFA (0.75 mL, 10.1 mmol). After 2 mins, to the mixture were added fresh 1,3-cyclopentadiene (1.29 g, 19.5 mmol) and two drops of water in turn. The reaction mixture was stirred for another 12 hrs, then the solvent DMF was removed and a $NaHCO_3$ aqueous solution (20 mL, 10%) was added. The mixture was adjusted to pH 8 with $Na_2CO_3$ and extracted with PE (25 mL×3). The combined organic layers were dried over anhydrous $Na_2SO_4$ and concentrated in vacuo. The residue was purified by a silica gel column chromatography (PE/EtOAc (v/v)=10/1) to give the title compound 1-3 as pale yellow liquid (2.38 g, 90.0%). The compound was characterized by the following spectroscopic data:

$^1$H NMR (400 MHz, $CDCl_3$) δ (ppm): 7.17-7.35 (m, 5H), 6.42 (br, 1H), 6.26-6.28 (br, 1H), 4.30-4.34 (m, 2H), 3.78-3.82 (m, 2H), 3.02-3.04 (m, 1H), 2.90 (br, 1H), 2.20 (br, 1H), 2.13 (m, 1H), 1.41 (d, 3H, J=6.6 Hz), 0.95 (t, 3H, J=7.2 Hz).

Step 3) the Preparation of Compound 1-4

To a solution of compound 1-3 (2 g, 7.37 mmol) in ethanol (60 mL) was added Pd/C (0.7 g). The mixture was stirred at rt under 20 atm of $H_2$ gas for 24 hrs. The reaction mixture was filtered. The filtrate was concentrated in vacuo to give the title compound 1-4 as yellow liquid (1.2 g, 96.2%). The compound was characterized by the following spectroscopic data:

MS (ESI, pos.ion) m/z: 170.2 $[M+H]^+$;

$^1$H NMR (400 MHz, $CDCl_3$) δ (ppm): 4.15-4.21 (m, 2H), 3.55 (br, 1H), 3.33 (br, 1H), 2.63 (br, 1H), 2.32 (br, 1H), 1.60-1.64 (m, 2H), 1.47-1.53 (m, 2H), 1.36-1.42 (m, 2H), 1.28 (t, 3H, J=7.1 Hz).

Step 4) the Preparation of Compound 1-5

To a solution of compound 1-4 (0.68 g, 4.02 mmol), compound 1-4-2 (1.057 g, 6.03 mmol) and EDCI (1.543 g, 8.05 mmol) in DCM (25 mL) was added DIPEA (2.1 mL, 12.7 mmol) dropwise at 0° C., and the mixture was stirred at rt overnight. After the reaction was completed, 30 mL of water was added to the mixture, and the resulting mixture was extracted with $CH_2Cl_2$ (35 mL×3). The combined organic layers were dried over anhydrous $Na_2SO_4$ and concentrated in vacuo. The residue was purified by a silica gel column chromatography (PE/EtOAc (v/v)=2/1) to give the title compound 1-5 as a white solid (0.74 g, 56.4%). The compound was characterized by the following spectroscopic data:

MS (ESI, pos.ion) m/z: 170.2 $[M+H]^+$;
$^1$H NMR (400 MHz, $CDCl_3$) δ (ppm): 5.44 (br, 1H), 4.40 (br, 1H), 4.30-4.33 (m, 1H), 4.14-4.19 (m, 2H), 4.02 (br, 1H), 3.66 (s, 3H), 2.74 (br, 1H), 2.04 (br, 1H), 1.88-1.91 (m, 2H), 1.74-1.80 (m, 2H), 1.54-1.56 (m, 1H), 1.38-1.43 (m, 1H), 1.26 (t, 3H, J=7.1 Hz), 1.07 (d, 3H, J=6.8 Hz), 0.97 (d, 3H, J=6.8 Hz).

Step 5) the Preparation of Compound 1-6

To a solution of compound 1-5 (0.74 g, 2.27 mmol) in THF (25 mL) was added lithium hydroxide monohydrate aqueous solution (0.4767 g, 11.35 mmol, 10 mL) at 0° C., and the mixture was stirred at 40° C. for 12 hrs. The solvent THF was removed and 20 mL of water was added to the mixture, the resulting mixture was washed with EtOAc (15 mL×3), and the aqueous phase was adjusted to pH 1 with hydrochloric acid (10%) and extracted with EtOAc (25 mL×3). The combined organic layers were washed by brine, dried over anhydrous $Na_2SO_4$ and concentrated in vacuo to give the title compound 1-6 as a white solid (0.55 g, 81.3%). The compound was characterized by the following spectroscopic data:

MS (ESI, pos.ion) m/z: 299.2 $[M+H]^+$;
$^1$H NMR (400 MHz, $CD_3OD$) δ (ppm): 4.52 (br, 1H), 4.20 (d, 1H, J=7.8 Hz), 3.93 (br, 1H), 3.63 (s, 3H), 2.73 (br, 1H), 1.98-2.01 (m, 4H), 1.75-1.85 (m, 2H), 1.46-1.54 (m, 2H), 1.05 (d, 3H, J=6.8 Hz), 0.98 (d, 3H, J=6.8 Hz).

Step 6) the Preparation of Compound 1-7

To a mixture of compound 1-6-2 (308 mg, 1.1074 mmol) and compound 1-6 (300 mg, 1.0067 mmol) in $CH_3CN$ (30.0 mL) was added DIPEA (0.20 mL, 1.2081 mmol) dropwise under $N_2$ at 0° C., and the reaction mixture was stirred at rt for 3 hrs. After the reaction was completed, to the mixture was added water (20 mL). Most of $CH_3CN$ was removed in vacuo and 20 mL of water was added to the residue. The resulting mixture was extracted with EtOAc (50 mL×3), and the combined organic layers were washed with brine, dried over anhydrous $Na_2SO_4$ and concentrated in vacuo. The residue was purified by a silica gel column chromatography (PE/EtOAc (v/v)=1/2) to give the title compound 1-7 as a pale yellow solid (332.6 mg, 66.7%). The compound was characterized by the following spectroscopic data:

MS (ESI, pos.ion) m/z: 495.3 $[M+H]^+$;
$^1$H NMR (400 MHz, $CDCl_3$) δ (ppm): 7.75 (d, 2H, J=8.52 Hz), 7.68 (d, 2H, J=8.56 Hz), 5.45 (d, 1H, J=9.4 Hz), 5.24 (d, 1H, J=16.56 Hz), 4.55-4.59 (m, 1H), 3.67 (s, 3H), 3.57 (m, 1H), 2.65-2.73 (m, 2H), 2.19-2.27 (m, 1H), 2.04 (s, 1H), 1.77-1.84 (m, 2H), 1.46-1.49 (m, 1H), 1.24-1.27 (m, 1H), 1.07-1.08 (br, 1H), 1.03-1.05 (m, 1H), 0.89-0.91 (m, 6H).

Step 7) the Preparation of Compound 1-8

To a solution of compound 1-7 (332.6 mg, 0.6714 mmol) in toluene (8 mL) was added $NH_4OAc$ (1.035 g, 13.43 mmol), and the mixture was stirred at 120° C. After the reaction was completed, the mixture was cooled to rt, 20 mL of water was added, and the resulting mixture was extracted with EtOAc (20 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound as a yellow solid (188 mg, 58.94%). The compound was characterized by the following spectroscopic data:

MS (ESI, pos.ion) m/z: 476.3 $[M+H]^+$;
$^1$H NMR (400 MHz, $CDCl_3$) δ (ppm): 10.35 (s, 1H), 7.62-7.64 (d, 2H, J=8.52 Hz), 7.45-7.55 (d, 2H, J=1.84 Hz), 7.16 (s, 1H), 5.46-5.54 (br, 2H), 4.53-4.57 (m, 1H), 3.70 (s, 3H), 3.58 (m, 1H), 2.69 (m, 1H), 2.48-2.54 (m, 1H), 1.76-1.87 (m, 4H), 1.45-1.47 (m, 2H), 0.81-0.85 (m, 6H).

Step 8) the Preparation of Compound 1-9

To a mixture of compound 1-8 (188.1 mg, 0.3957 mmol), compound 1-8-2 (150.75 mg, 0.5935 mmol), Pd(dppf)$Cl_2.CH_2Cl_2$ (33 mg, 0.03956 mmol) and KOAc (116.45 mg, 1.187 mmol) was added DMF (10 mL) via syringe under $N_2$, and the mixture was stirred at 90° C. for 3 hrs. After the reaction was completed, the mixture was cooled to rt, 50 mL of water was added, and the resulting mixture was extracted with EtOAc (40 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound 1-9 as a beige solid (200 mg, 80%). The compound was characterized by the following spectroscopic data:

MS (ESI, pos.ion) m/z: 523.3 $[M+H]^+$;
$^1$H NMR (400 MHz, $CDCl_3$) δ (ppm): 10.48 (s, 1H), 7.75-7.81 (m, 4H), 7.41-7.43 (d, J=8.0 Hz, 1H), 5.39-5.49 (m, 2H), 4.53-4.58 (m, 2H), 3.67 (s, 3H), 3.57 (m, 1H), 2.65 (m, 1H), 2.47-2.54 (m, 1H), 2.04-2.10 (m, 2H), 1.79-1.83 (m, 1H), 1.46-1.49 (m, 2H), 1.38 (s, 12H), 0.81-0.85 (m, 6H).

Step 9) the Preparation of Compound 1-11

To a solution of compound 1-10 (20 g, 107 mmol) and compound HATU (48.82 g, 128.4 mmol) in THF (250 mL) was added DIPEA (19.5 mL, 118 mmol) at 0° C. After stirring at 0° C. for 0.5 hr, to the solution was added the compound 1-10-2 (25.6 g, 119 mmol) in a portionwise manner, then the reaction mixture was stirred at rt for 4 hrs. After the reaction was completed, the reaction was quenched with water (100 mL), the solvent THF was removed, and the resulting mixture was extracted with EtOAc (200 mL×3). The combined organic layers were dried over anhydrous $Na_2SO_4$ and concentrated in vacuo. The residue was dissolved in glacial acetic acid (100 mL). The solution was stirred at 40° C. overnight, and HOAc was removed. The resulting mixture was dissolved in EtOAc (400 mL), washed with $Na_2CO_3$ aq (150 mL×3) and dried over anhydrous $Na_2SO_4$ and concentrated in vacuo. The residue was purified by a silica gel column chromatography (PE/EtOAc (v/v)=1/2) to give the title compound (35 g, 81%). The compound was characterized by the following spectroscopic data:

MS (ESI, pos.ion) m/z: 367.3 $[M+H]^+$;
$^1$H NMR (400 MHz, $CDCl_3$) δ (ppm): 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H).

Step 10) the Preparation of Compound 1-12

To a solution of compound 1-11 (10.0 g, 27.39 mmol) in EtOAc (50.0 mL) was added a solution of HCl in EtOAc (60.0 mL, 4 M) dropwise at 0° C., and the mixture was stirred at rt. After the reaction was completed, the mixture was filtered, and the filter cake was washed with EtOAc to give the title compound as a pale yellow solid (8.0 g, 86.49%). The compound was characterized by the following spectroscopic data:

MS (ESI, pos.ion) m/z: 313.2 $[M+H]^+$;

¹H NMR (400 MHz, CDCl₃) δ (ppm): 8.01 (s, 1H), 7.70-7.76 (m, 2H), 5.25-5.27 (m, 1H), 3.30-3.31 (m, 2H), 2.74-2.77 (m, 1H), 2.54-2.52 (m, 1H), 2.40-2.37 (m, 1H), 2.30-2.10 (m, 1H).

Step 11) the Preparation of Compound 1-13

To a solution of compound 1-12 (6.0 g, 18.8 mmol), compound 1-4-2 (4.9 g, 28.2 mmol) and EDCI (5.4 g, 28.2 mmol) in DCM (100.0 mL) was added DIPEA (18.64 mL, 112.8 mmol) dropwise at 0° C., and the mixture was stirred at rt. After the reaction was completed, 100 mL of water was added to the mixture, and the resulting mixture was extracted with CH₂Cl₂ (150 mL×3). The combined organic layers were dried over anhydrous Na₂SO₄ and concentrated in vacuo, and the residue was purified by a silica gel column chromatography (PE/EtOAc (v/v)=1/2) to give the title compound as a solid (5.77 g, 85%). The compound was characterized by the following spectroscopic data:

MS (ESI, pos.ion) m/z: 423.3 [M+H]⁺;
¹H NMR (400 MHz, CDCl₃) δ (ppm): 7.59-7.51 (m, 1H), 7.34-7.21 (m, 2H), 5.42-5.38 (m, 2H), 4.34-4.30 (m, 1H), 3.87-3.76 (m, 1H), 3.70 (s, 3H), 3.66-3.62 (m, 1H), 3.04-2.98 (m, 1H), 2.25-2.20 (m, 1H), 2.20-2.13 (m, 2H), 1.96-1.94 (m, 1H), 0.88-0.84 (m, 6H).

Step 12) the Preparation of Compound 1-14

To a mixture of compound 1-13 (3.0 g, 7.1 mmol), compound 1-8-2 (2.72 g, 10.7 mmol), Pd(dppf)Cl₂·CH₂Cl₂ (653 mg, 0.8 mmol) and KOAc (2.09 g, 21.3 mmol) was added DMF (30 mL) via syringe under N₂, and the mixture was stirred at 90° C. After the reaction was completed, the mixture was cooled to rt, 60 mL of water was added, and the resulting mixture was extracted with EtOAc (50 mL×3). The combined organic layers were washed with brine, dried over anhydrous Na₂SO₄ and concentrated in vacuo. The residue was purified by a silica gel column chromatography (PE/EtOAc (v/v)=1/2) to give the title compound as a beige solid (2.1 g, 62.8%). The compound was characterized by the following spectroscopic data:

MS (ESI, pos.ion) m/z: 471.3 [M+H]⁺;
¹H NMR (400 MHz, CDCl₃) δ (ppm): 7.87-7.80 (m, 1H), 7.71-7.66 (m, 2H), 5.47-5.42 (m, 2H), 4.34-4.30 (m, 1H), 3.86-3.84 (m, 1H), 3.70 (s, 3H), 3.64-3.62 (m, 1H), 3.04-2.98 (m, 1H), 2.25-2.20 (m, 1H), 2.20-2.13 (m, 2H), 1.96-1.94 (m, 1H), 1.35 (s, 12H), 0.88-0.84 (m, 6H).

Step 13) the Preparation of Compound 1-15

To a solution of 1,4-benzoquinone (10.0 g, 92.5 mmol) in DCM (100 mL) was added fresh 1,3-cyclopentadiene (9.20 g, 138.8 mmol) dropwsie at −10° C., and the mixture was stirred at −10° C. for 1 hr and then at rt for another 0.5 hr. After the reaction was completed, the mixture was concentrated in vacuo, 500 mL of hexane was added and the resulting mixture was stirred and filtered. The filtrate was concentrated in vacuo to give the title compound as a pale yellow solid (10.5 g, 65.2%), which was used for the next step without further purification. The compound was characterized by the following spectroscopic data:

MS (ESI, pos.ion) m/z: 175.1 [M+H]⁺;
¹H NMR (400 MHz, CDCl₃) δ (ppm): 6.57 (s, 2H), 6.68 (s, 2H), 3.55 (s, 2H), 3.22-3.21 (m, 2H), 1.56-1.42 (m, 2H).

Step 14) the Preparation of Compound 1-16

A solution of compound 1-15 (5.50 g, 31.6 mmol) and sodium acetate (7.77 g, 94.7 mmol) in methanol (100 mL) was stirred at 50° C. under N₂ for 3 hrs. After the reaction was completed, the reaction mixture was concentrated in vacuo. The residue was purified by a silica gel column chromatography (DCM) to give the title compound as a white solid (5.10 g, 92.7%). The compound was characterized by the following spectroscopic data:

MS (ESI, pos.ion) m/z: 175.1 [M+H]⁺;
¹H NMR (400 MHz, CDCl₃) δ (ppm): 6.80-6.79 (m, 2H), 6.35 (s, 2H), 3.55 (s, 2H), 4.10-4.09 (m, 2H), 2.25-2.18 (m, 2H).

Step 15) the Preparation of Compound 1-17

A suspension of compound 1-16 (4.70 g, 27.0 mmol) and a catalytic amount of Pd/C (470 mg) in methanol (50 mL) was stirred at rt under 1 atm of H₂ gas for 1.5 hrs. After the reaction was completed, the mixture was filtered, and the filtrate was concentrated in vacuo. The residue was purified by recrystallization to give the title compound as a white solid (3.55 g, 74.6%). The compound was characterized by the following spectroscopic data:

¹H NMR (400 MHz, d₆-DMSO) δ (ppm): 8.27 (s, 2H), 6.29 (s, 2H), 3.47 (s, 2H), 1.79-1.77 (m, 2H), 1.48-1.46 (m, 1H), 1.36-1.34 (m, 1H), 1.01-0.99 (m, 2H).

Step 16) the Preparation of Compound 1-18

To a solution of compound 1-17 (3.35 g, 19 mmol) in DCM (50 mL) was added pyridine (9.00 g, 114 mmol) dropwise at 0° C. After the mixture was stirred for 10 mins, trifluoromethanesulfonic anhydride (21 g, 76 mmol) was added, and then the reaction mixture was stirred at rt for 1 hr. After the reaction was completed, the mixture was diluted with DCM (50 mL), washed with brine, dried over anhydrous Na₂SO₄ and concentrated in vacuo. The residue was purified by a silica gel column chromatography (PE/DCM (v/v)=10/1) to give the title compound as colorless oil (8.2 g, 98.0%). The compound was characterized by the following spectroscopic data:

¹H NMR (400 MHz, CDCl₃) δ (ppm): 7.05 (s, 2H), 3.71-3.70 (m, 2H), 2.05-2.02 (m, 2H), 1.90-1.87 (m, 1H), 1.69-1.68 (m, 1H), 1.38-1.34 (m, 2H).

Step 17) the Preparation of Compound 1-19

To a mixture of compound 1-18 (447 mg, 1.016 mmol), compound 1-14 (478 mg, 1.016 mmol), Pd(PPh₃)₄ (117 mg, 0.1016 mmol) and K₂CO₃ (420.7 mg, 3.048 mmol) were added DME (10.0 mL) and pure water (2.5 mL) via syringe, and the mixture was stirred at 90° C. under N₂ for 3 hrs. After the reaction was completed, the mixture was cooled to rt and diluted with EtOAc (20 mL), then 10 mL of water was added, and the resulting mixture was extracted with EtOAc (20 mL×3). The combined organic layers were washed with brine, dried over anhydrous Na₂SO₄ and concentrated in vacuo. The residue was purified by a silica gel column chromatography (DCM/EtOH (v/v)=100/1) to give the title compound as a pale yellow solid (340 mg, 53%). The compound was characterized by the following spectroscopic data:

MS (ESI, pos.ion) m/z: 635.3 [M+H]⁺;
¹H NMR (400 MHz, CDCl₃) δ (ppm): 7.85-7.79 (m, 2H), 7.42-7.41 (m, 2H), 7.27 (s, 1H), 4.95-5.12 (m, 1H), 4.68-4.83 (m, 1H), 3.72 (s, 3H), 3.59-3.63 (m, 2H), 3.32-3.35 (m, 2H), 3.02-3.12 (m, 2H), 2.94-2.89 (m, 1H), 1.98-2.02 (m, 2H), 1.75-1.87 (m, 6H), 0.91-1.02 (m, 6H).

Step 18) the Preparation of Compound 1-20

To a mixture of compound 1-19 (332 mg, 0.522 mmol), compound 1-9 (300 mg, 0.574 mmol), Pd(PPh₃)₄ (60.29 mg, 0.0522 mmol) and K₂CO₃ (216 mg, 1.566 mmol) were added DME (6.0 mL) and pure water (1.5 mL) via syringe, and the mixture was stirred at 90° C. under N₂ for 3 hrs. After the reaction was completed, the mixture was cooled to rt and diluted with EtOAc (20 mL), then 10 mL of water was added, and the resulting mixture was extracted with EtOAc (20 mL×3). The combined organic layers were washed with brine, dried over anhydrous Na₂SO₄ and concentrated in vacuo. The residue was purified by a silica gel column chromatography (DCM/EtOH (v/v)=100/1) to give the title compound as a pale yellow solid (230.4 mg, 50%). The compound was characterized by the following spectroscopic data:
MS (ESI, pos.ion) m/z: 441.3 [M+H]$^+$;
$^1$H NMR (400 MHz, CDCl$_3$) δ (ppm): 7.89-7.91 (m, 2H), 7.71-7.74 (m, 2H), 7.52-7.59 (m, 4H), 7.31-7.33 (m, 2H), 5.40-5.44 (m, 2H), 4.69-4.71 (m, 1H), 4.21-4.30 (br, 1H), 3.73 (s, 6H), 3.49-3.54 (m, 2H), 3.0-3.02 (d, 4H, J=8.0 Hz), 2.51-2.60 (br, 1H), 2.32-2.41 (br, 1H), 2.17-2.20 (br, 2H), 2.10 (s, 1H), 2.04 (s, 1H), 1.91-1.96 (br, 2H), 1.58-1.66 (m, 2H), 1.24-1.27 (m, 2H), 1.14 (s, 6H), 0.81-0.85 (m, 12H).
Example 2
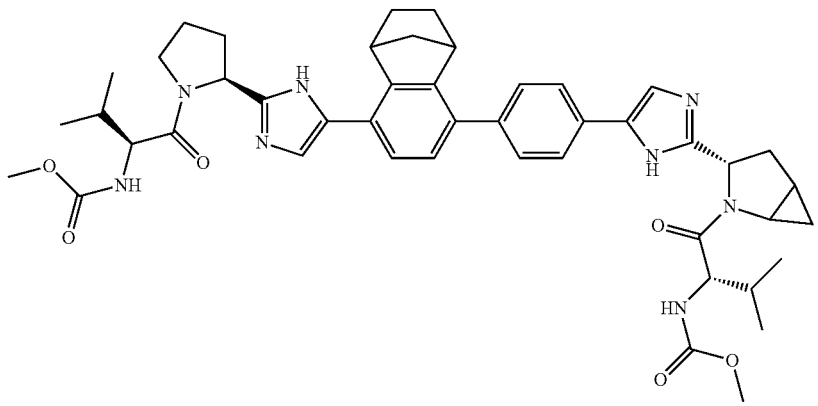 [SMILES: COC(=O)N[C@H](C(=O)N1CCC[C@H]1c1ncc(-c2ccc(-c3ccc(-c4cnc([C@@H]5CC6CC6N5C(=O)[C@@H](NC(=O)OC)C(C)C)[nH]4)cc3)c3c2C2CCC3C2)[nH]1)C(C)C]
Synthetic Route:
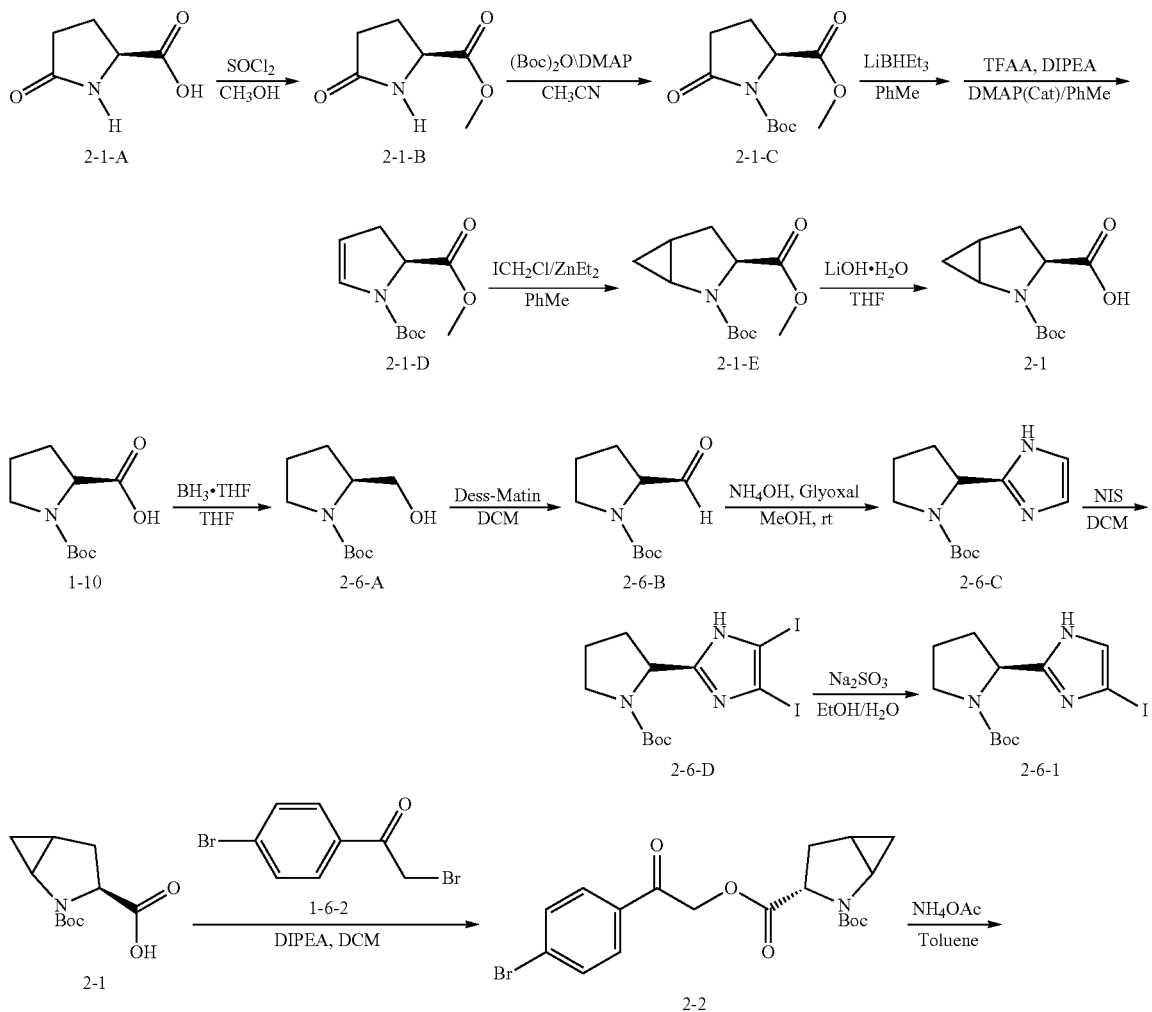

-continued
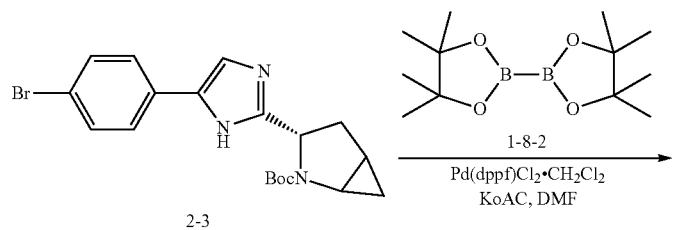
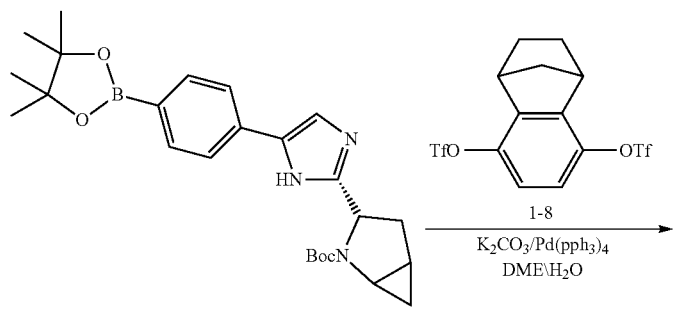
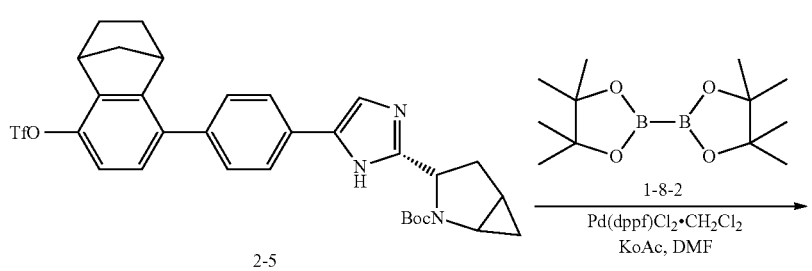
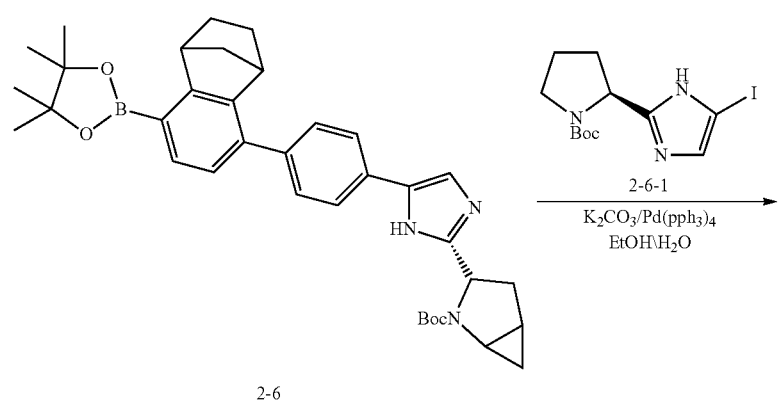
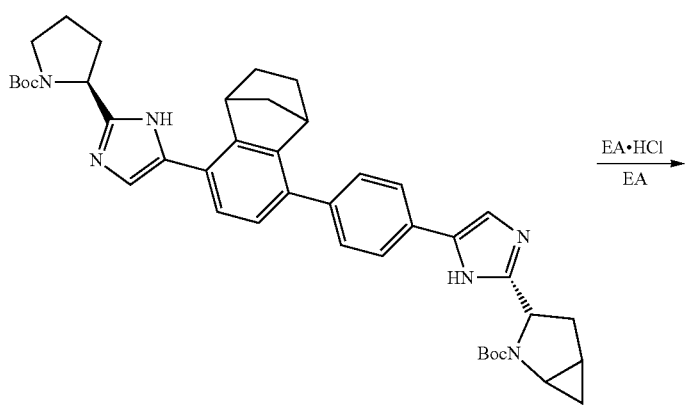

-continued

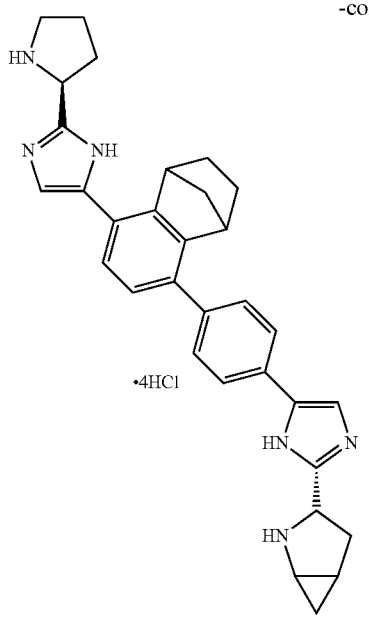
2-8

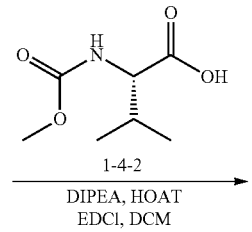
1-4-2
DIPEA, HOAT
EDCl, DCM

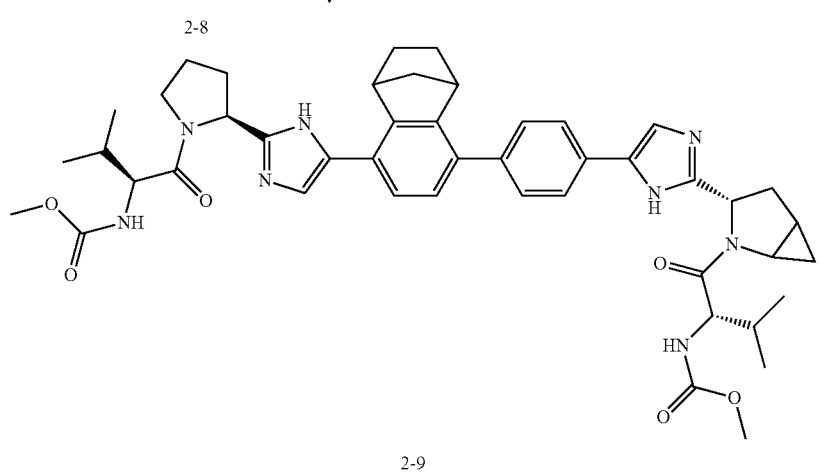
2-9

Step 1) the Preparation of Compound 2-1-B

To a solution of compound 2-1-A (10 g, 77.5 mmol) in MeOH (50 mL) was added thionyl chloride (5.5 mL, 75.8 mmol) dropwise at 0° C., and the mixture was stirred at 0° C. for 1.0 hr and then at rt for another 2.0 hrs. After the reaction was completed, a NaHCO₃ aqueous solution was added to the mixture, and the solvent MeOH was removed. To the residue was added 30 mL of water, and the resulting mixture was extracted with CH₂Cl₂ (35 mL×3). The combined organic layers were dried over anhydrous Na₂SO₄ and concentrated in vacuo. The residue was purified by a silica gel column chromatography (EtOAc) to give the title compound 2-1-B as colorless liquid (7.5 g, 67.6%). The compound was characterized by the following spectroscopic data:

MS (ESI, pos.ion) m/z: 144.2 [M+H]$^+$;

$^1$H NMR (400 MHz, CDCl₃) δ (ppm): 7.38 (br, 1H), 4.16-4.20 (m, 1H), 3.67 (s, 3H), 2.23-2.39 (m, 3H), 2.07-2.14 (m, 1H).

Step 2) the Preparation of Compound 2-1-C

To a solution of compound 2-1-B (6.45 g, 45.06 mmol) in MeCN (30 mL) was added DMAP (0.5503 g, 4.5 mmol) at 0° C., followed by di-tert-butyl dicarbonate (10.816 g, 49.56 mmol) dropwise, and the mixture was stirred at 0° C. for 30 mins and then at rt for another 2 hrs. After the reaction was completed, the mixture was concentrated in vacuo, the residue was purified by a silica gel column chromatography (PE/EtOAc (v/v)=1/1) to give the title compound 2-1-C as colorless liquid (5.0 g, 45.6%). The compound was characterized by the following spectroscopic data:

MS (ESI, pos.ion) m/z: 144.2 [M-Boc]$^+$;

$^1$H NMR (400 MHz, CDCl₃) δ (ppm): 4.57-4.60 (m, 1H), 3.75 (s, 3H), 2.55-2.65 (m, 1H), 2.42-2.50 (m, 1H), 2.24-2.36 (m, 1H), 1.96-2.04 (m, 1H), 1.45 (s, 9H).

Step 3) the Preparation of Compound 2-1-D

To a solution of compound 2-1-C (3.74 g, 15.4 mmol) in toluene (50 mL) was added lithium triethylborohydride dropwise (1.793 g, 16.9 mmol) at −78° C. After the mixture was stirred at −78° C. for 70 mins, DIPEA (3.2 mL, 19.4 mmol), DMAP (0.1877 g, 1.54 mmol) and TFAA (3 mL, 40.4 mmol) were added in turn, and then the mixture was stirred at rt for 2 hrs. After the reaction was completed, the mixture was concentrated in vacuo. The residue was purified by a silica gel column chromatography (PE/EtOAc (v/v)=10/1) to give the title compound 2-1-D as yellow liquid (2.26 g, 64.8%). The compound was characterized by the following spectroscopic data:

MS (ESI, pos.ion) m/z: 128.2 [M-Boc]$^+$;

$^1$H NMR (400 MHz, CDCl$_3$) δ (ppm): 6.52-6.65 (br, 1H), 4.91-4.96 (br, 1H), 4.57-4.68 (m, 1H), 3.76 (s, 3H), 3.00-3.12 (m, 1H), 2.61-2.71 (m, 1H), 1.44-1.49 (br, 9H).

Step 4) the Preparation of Compound 2-1-E

To a solution of diethylzinc (0.4871 g, 3.94 mmol) in toluene (6 mL) was added chloroiodomethane (1.394 g, 7.9 mmol) at 0° C. After the mixture was stirred at 0° C. for 45 mins, a solution of compound 2-1-D (300 mg, 1.32 mmol) in toluene (4 mL) was added, and then the mixture was stirred for 18 hrs. After the reaction was completed, the reaction was quenched with saturated NH$_4$Cl aqueous solution (15 mL), and the mixture was extracted with EtOAc (25 mL×3). The combined organic layers were dried over anhydrous Na$_2$SO$_4$ and concentrated in vacuo. The residue was purified by a silica gel column chromatography (PE/EtOAc (v/v)=10/1) to give the title compound 2-1-E as yellow liquid (0.19 g, 59.7%). The compound was characterized by the following spectroscopic data:

MS (ESI, pos.ion) m/z: 142.2 [M-Boc]$^+$;

$^1$H NMR (400 MHz, CDCl$_3$) δ (ppm): 4.51-4.64 (m, 1H), 3.70 (s, 3H), 3.45-3.56 (m, 1H), 2.54-2.64 (m, 1H), 2.01-2.05 (m, 1H), 1.50, 1.41 (s, s, 9H), 0.65-0.75 (m, 3H).

Step 5) the Preparation of Compound 2-1

To a solution of compound 2-1-E (1.02 g, 4.23 mmol) in THF (20 mL) was added lithium hydroxide monohydrate aqueous solution (0.8888 g, 21.2 mmol, 10 mL) at 0° C., and the mixture was stirred at 40° C. for 12 hrs. After the reaction was completed, THF was removed and 10 mL of water was added to the mixture. The resulting mixture was washed with EtOAc (25 mL×3), and the aqueous phase was adjusted to pH 1 with hydrochloric acid (10%) and extracted with EtOAc (25 mL×3). The combined organic layers were dried over anhydrous Na$_2$SO$_4$ and concentrated in vacuo to give the title compound 2-1 as a white solid (0.8371 g, 87%). The compound was characterized by the following spectroscopic data:

MS (ESI, neg.ion) m/z: 226.2 [M–H]$^-$;

$^1$H NMR (400 MHz, CD$_3$OD) δ (ppm): 4.46-4.53 (m, 1H), 3.42-3.48 (m, 1H), 2.57-2.70 (m, 1H), 2.01-2.05 (m, 1H), 1.54-1.60 (m, 1H), 1.48, 1.41 (s, s, 9H), 0.80-0.89 (m, 1H), 0.66-0.73 (m, 1H).

Step 6) the Preparation of Compound 2-6-A

To a solution of compound 1-10 (10.0 g, 46.6 mmol) in THF (100 mL) was added diborane (100 mL, 1M/L in THF) dropwise at 0° C. At the end of addition, the mixture was stirred at 0° C. for 3 hrs. After the reaction was completed, the reaction was quenched with MeOH (80 mL), and the mixture was concentrated in vacuo. The residue was purified by a silica gel column chromatography (PE/EtOAc (v/v)=3/2) to give the title compound 2-6-A as colorless oil (7.0 g, 75.2%). The compound was characterized by the following spectroscopic data:

$^1$H NMR (400 MHz, CDCl$_3$) δ (ppm): 3.87-3.99 (br, 1H), 3.51-3.68 (m, 2H), 3.39-3.48 (m, 1H), 3.25-3.34 (m, 1H), 1.92-2.05 (m, 2H), 1.71-1.88 (m, 2H), 1.45 (s, 9H).

Step 7) the Preparation of Compound 2-6-B

To a solution of compound 2-6-A (7.0 g, 34.8 mmol) in DCM (250 mL) was added Dess-Martin periodinane (20.7 g, 48.8 mmol) in a portionwise manner at 0° C. At the end of addition, the mixture was stirred at rt for 2 hrs. After the reaction was completed, 250 mL of water was added to the mixture, and the resulting mixture was filtered. After the layers were partitioned, the organic layer was washed with brine, dried over anhydrous Na$_2$SO$_4$ and concentrated in vacuo. The residue was purified by a silica gel column chromatography (PE/EtOAc (v/v)=3/2) to give the title compound 2-6-B as colorless oil (3.5 g, 50.7%). The compound was characterized by the following spectroscopic data:

$^1$H NMR (400 MHz, CDCl$_3$) δ (ppm): 9.46 (d, 1H, J=2.8 Hz), 4.03-4.08 (m, 1H), 3.42-3.51 (m, 2H), 1.84-1.91 (m, 2H), 1.93-2.01 (m, 2H), 1.43 (s, 9H).

Step 8) the Preparation of Compound 2-6-C

To a solution of compound 2-6-B (3.5 g, 17.6 mmol) and ammonia (13 mL) in MeOH (30 mL) was added glyoxal (8 mL, 40% in H$_2$O) dropwsie at 0° C. At the end of addition, the mixture was stirred at rt overnight. After the reaction was completed, the mixture was concentrated in vacuo. The residue was purified by a silica gel column chromatography (PE/EtOAc (v/v)=3/2) to give the title compound 2-6-C as a white solid (2.0 g, 47.6%). The compound was characterized by the following spectroscopic data:

MS (ESI, pos.ion) m/z: 238.2 [M+H]$^+$;

$^1$H NMR (400 MHz, CDCl$_3$) δ (ppm): 6.96 (s, 1H), 4.94 (dd, 1H, J=7.68, 2.40 Hz), 3.38 (t, 2H, J=6.24 Hz), 2.03-2.17 (m, 2H), 1.91-1.99 (m, 2H), 1.48 (s, 9H).

Step 9) the Preparation of Compound 2-6-D

To a solution of compound 2-6-C (2.0 g, 8.4 mmol) in DCM (60 mL) was added N-iodosuccinimide (3.8 g, 16.8 mmol) at 0° C. in portionwise manner, and the mixture was continued to stir for 1.5 hrs. After the reaction was completed, the mixture was washed with brine, dried over anhydrous Na$_2$SO$_4$ and concentrated in vacuo. The residue was purified by a silica gel column chromatography (PE/EtOAc (v/v)=3/2) to give the title compound 2-6-D as a white solid (2.6 g, 63.1%). The compound was characterized by the following spectroscopic data:

MS (ESI, pos.ion) m/z: 490.0 [M+H]$^+$;

$^1$H NMR (400 MHz, CDCl$_3$) δ (ppm): 4.89 (dd, 1H, J=7.64, 2.52 Hz), 3.36 (t, 2H), 2.02-2.14 (m, 2H), 1.85-1.97 (m, 2H), 1.49 (s, 9H).

Step 10) the Preparation of Compound 2-6-1

To a suspension of compound 2-6-D (1.6 g, 3.27 mmol) in mixed solvents of ethanol and water (50 mL, v/v=3/7) was added Na$_2$SO$_3$ (3.7 g, 29 mmol), and the mixture was refluxed for 17 hrs. After the reaction was completed, most of ethanol was removed in vacuo, and 20 mL of water was added to the mixture. The resulting mixture was extracted with EtOAc (30 mL×3). The combined organic layers were dried over anhydrous Na$_2$SO$_4$ and concentrated in vacuo. The residue was purified by a silica gel column chromatography (PE/EtOAc (v/v)=3/2) to give the title compound 2-6-1 as a white solid (1.0 g, 84%). The compound was characterized by the following spectroscopic data:

MS (ESI, pos.ion) m/z: 364.1 [M+H]$^+$;
MS (ESI, neg.ion) m/z: 362.1 [M–H]$^-$;

$^1$H NMR (400 MHz, CDCl$_3$) δ (ppm): 7.04 (d, 1H, J=1.84 Hz), 4.89 (dd, 1H, J=7.72 Hz, 2.56 Hz), 3.36 (t, 2H), 2.03-2.18 (m, 2H), 1.82-1.97 (m, 2H), 1.47 (s, 9H).

Step 11) the Preparation of Compound 2-2

To a solution of compound 2-1 (4.79 g, 17.228 mmol) and compound 1-6-2 (4.5 g, 19.81 mmol) in DCM (60 mL) was added DIPEA (3.4 mL, 20.67 mmol) dropwise at 0° C. At the end of addition, the mixture was stirred at rt for 3 hrs. After the reaction was completed, the reaction was quenched with water (80 mL), and the resulting mixture was extracted with DCM (100 mL×3). The combined organic layers were dried over Na$_2$SO$_4$ and concentrated in vacuo. The residue was purified by a silica gel column chromatography (PE/EtOAc (v/v)=5/1) to give the title compound 2-2 as a white solid (4.5 g, 61.73%). The compound was characterized by the following spectroscopic data:

MS (ESI, pos.ion) m/z: 424.3 [M+H]$^+$;

¹H NMR (400 MHz, CDCl₃) δ (ppm): 7.73-7.77 (m, 2H), 7.62-7.64 (m, 2H), 5.09-5.53 (m, 2H), 4.67-4.78 (m, 1H), 3.46-3.59 (m, 1H), 2.62-2.69 (m, 1H), 2.40-2.43 (m, 1H), 1.42 (s, 9H), 0.96-1.00 (m, 1H), 0.69-0.76 (m, 2H).

Step 12) the Preparation of Compound 2-3

A mixture of compound 2-2 (4.5 g, 10.64 mmol) and acetamide (16.4 g, 212.73 mmol) in toluene (50 mL) was stirred at 120° C. for 5 hrs. After the reaction was completed, the mixture was cooled to rt, and 50 mL of water was added. The resulting mixture was extracted with EtOAc (100 mL×3), and the combined organic layers were dried over anhydrous Na₂SO₄ and concentrated in vacuo. The residue was purified by a silica gel column chromatography (PE/EtOAc (v/v)=8/1) to give the title compound (1.38 g, 50%). The compound was characterized by the following spectroscopic data:

MS (ESI, pos.ion) m/z: 404.3 [M+H]⁺;
¹H NMR (400 MHz, CDCl₃) δ (ppm): 7.52-7.62 (br, 2H), 7.46-7.49 (d, 2H, J=12 Hz), 7.21 (s, 1H), 5.24-5.27 (d, 1H, J=10.0 Hz), 3.27-3.31 (m, 1H), 1.67-1.71 (m, 2H), 1.52 (s, 9H), 0.86-0.89 (m, 1H), 0.64-0.69 (m, 2H).

Step 13) the Preparation of Compound 2-4

A mixture of compound 2-3 (2.1 g, 5.2 mmol), compound 1-8-2 (1.59 g, 6.25 mmol), Pd(dppf)Cl₂·CH₂Cl₂ (425 mg, 0.52 mmol) and KOAc (1.54 g, 15.63 mmol) in DMF (30 mL) was stirred at 90° C. under N₂ for 3 hrs. After the reaction was completed, the mixture was cooled to rt, diluted with EtOAc (50 mL) and filtered through a celite pad. To the filtrate was added 150 mL of water, and the mixture was extracted with EtOAc (50 mL×3). The combined organic layers were washed with brine, dried over anhydrous Na₂SO₄ and concentrated in vacuo. The residue was purified by a silica gel column chromatography (PE/EtOAc (v/v)=2/1) to give the title compound (2.27 g, 97%). The compound was characterized by the following spectroscopic data:

MS (ESI, pos.ion) m/z: 452.3 [M+H]⁺;
¹H NMR (400 MHz, CDCl₃) δ (ppm): 7.79-7.81 (d, 2H, J=8.04 Hz), 7.60 (br, 2H), 7.26 (s, 1H), 5.26-5.28 (d, 1H, J=8.0 Hz), 3.53 (br, 1H), 3.27-3.30 (br, 1H), 1.66-1.67 (m, 2H), 1.52 (s, 9H), 1.34 (s, 12H), 0.86-0.89 (m, 1H), 0.64-0.69 (m, 2H).

Step 14) the Preparation of Compound 2-5

To a mixture of compound 1-18 (500 mg, 1.14 mmol), compound 2-4 (512.4 mg, 1.14 mmol), Pd(PPh₃)₄ (131 mg, 0.114 mmol) and K₂CO₃ (391 mg, 2.84 mmol) were added DME (10 mL) and pure water (2.4 mL) via syringe, and the mixture was stirred at 90° C. under N₂ for 3 hrs. After the reaction was completed, the mixture was cooled to rt and diluted with EtOAc (20 mL), then 20 mL of water was added, and the resulting mixture was extracted with EtOAc (50 mL×3). The combined organic layers were washed with brine, dried over anhydrous Na₂SO₄ and concentrated in vacuo. The residue was purified by a silica gel column chromatography (DCM/EtOH (v/v)=100/1) to give the title compound as an offwhite solid (392 mg, 56.16%). The compound was characterized by the following spectroscopic data:

MS (ESI, pos.ion) m/z: 616.3 [M+H]⁺;
¹H NMR (400 MHz, CDCl₃) δ (ppm): 7.73 (br, 1H), 7.42-7.45 (d, 2H, J=8.12 Hz), 7.29 (s, 2H), 7.18-7.20 (d, 1H, J=8.8 Hz), 7.02-7.04 (d, 1H, J=8.56 Hz), 5.29-5.32 (m, 1H), 3.59 (br, 1H), 3.33-3.36 (m, 1H), 2.02-2.03 (m, 2H), 1.56-1.58 (m, 8H), 1.54 (s, 9H), 0.86-0.89 (br, 1H), 0.64-0.70 (m, 2H).

Step 15) the Preparation of Compound 2-6

A mixture of compound 2-5 (250 mg, 0.406 mmol), compound 1-8-2 (123.8 mg, 0.487 mmol), Pd(dppf)Cl₂·CH₂Cl₂ (33.18 mg, 0.0406 mmol) and KOAc (120 mg, 1.22 mmol) in DMF (4.0 mL) was stirred at 90° C. under N₂ for 3 hrs. After the reaction was completed, the mixture was cooled to rt, diluted with EtOAc (30 mL) and filtered through a celite pad. To the filtrate was added 30 mL of water, and the mixture was extracted with EtOAc (30 mL×3). The combined organic layers were washed with brine, dried over anhydrous Na₂SO₄ and concentrated in vacuo. The residue was purified by a silica gel column chromatography (DCM/MeOH (v/v)=150/1) to give the title compound as a pale yellow solid (0.15 g, 62.24%). The compound was characterized by the following spectroscopic data:

MS (ESI, pos.ion) m/z: 594.3 [M+H]⁺;
¹H NMR (400 MHz, CDCl₃) δ (ppm): 7.64-7.73 (m, 2H), 7.57-7.59 (d, 1H, J=8.0 Hz), 7.49-7.51 (m, 2H), 7.31 (m, 1H), 7.14-7.16 (d, 1H, J=8.0 Hz), 5.33-5.34 (br, 1H), 3.98 (br, 1H), 2.11-2.26 (m, 2H), 1.94 (br, 1H), 1.80-1.82 (d, 2H, J=8.0 Hz), 1.56-1.59 (m, 3H), 1.39-1.42 (m, 11H), 1.24 (s, 12H), 0.86-0.89 (br, 1H), 0.64-0.70 (m, 2H).

Step 16) the Preparation of Compound 2-7

To a mixture of compound 2-6 (150.3 mg, 0.2533 mmol), compound 2-6-1 (91.95 mg, 0.2533 mmol), Pd(PPh₃)₄ (29.26 mg, 0.02533 mmol) and K₂CO₃ (123.23 mg, 0.8866 mmol) were added EtOH (4.0 mL) and pure water (1.0 mL) via syringe, and the mixture was stirred at 90° C. under N₂. After the reaction was completed, the mixture was cooled to rt and diluted with EtOAc (20 mL), then 10 mL of water was added, and the resulting mixture was extracted with EtOAc (20 mL×3). The combined organic layers were washed with brine, dried over anhydrous Na₂SO₄ and concentrated in vacuo. The residue was purified by a silica gel column chromatography (DCM/MeOH (v/v)=80/1) to give the title compound as a pale yellow solid (103 mg, 57.9%). The compound was characterized by the following spectroscopic data:

MS (ESI, pos.ion) m/z: 703.3 [M+H]⁺;
¹H NMR (400 MHz, CDCl₃) δ (ppm): 7.64-7.69 (m, 2H), 7.52-7.55 (m, 1H), 7.46-7.48 (m, 2H), 7.35 (br, 1H), 7.24 (s, 1H), 7.18-7.21 (br, 1H), 5.27-5.29 (br, 1H), 4.96-4.97 (br, 1H), 3.77-3.97 (br, 2H), 3.66 (br, 1H), 3.54-3.60 (m, 2H), 2.02-2.04 (m, 4H), 1.49-1.54 (m, 8H), 1.45 (s, 18H), 0.86-0.89 (br, 1H), 0.64-0.70 (m, 2H).

Step 17) the Preparation of Compound 2-8

To a solution of compound 2-7 (153 mg, 0.2178 mmol) in EtOAc (4 mL) was added a solution of HCl in EtOAc (3 mL, 4 M) dropwise, and the mixture was stirred at rt for 8 hrs. After the reaction was completed, the mixture was concentrated in vacuo, and EtOAc (10 mL) was added. The resulting mixture was filtered, and the filter cake was washed with EtOAc to give the title compound as a pale yellow solid (103 mg, 73%), which was used for the next step without further purification. The compound was characterized by the following spectroscopic data:

MS (ESI, pos.ion) m/z: 503.3 [M+H]⁺.

Step 18) the Preparation of Compound 2-9

To a suspension of compound 2-8 (103 mg, 0.159 mmol), compound 1-4-2 (58.42 mg, 0.333 mmol), EDCI (63.84 mg, 0.333 mmol) and HOAT (32.42 mg, 0.238 mmol) in DCM (5.0 mL) was added DIPEA (0.21 mL, 1.27 mmol) dropwise at 0° C., and the mixture was stirred at rt for 3 hrs. The resulting mixture was diluted with DCM (20 mL), washed with NH₄Cl aqueous solution and brine, dried over Na₂SO₄ and concentrated in vacuo. The residue was purified by a silica gel column chromatography (DCM/MeOH (v/v)=60/1) to give the title compound as a yellow solid (33.9 mg, 26.27%). The compound was characterized by the following spectroscopic data:

MS (ESI, pos.ion) m/z: 409.3 [M+2H]²⁺;
¹H NMR (400 MHz, CDCl₃) δ (ppm): 7.85-7.87 (d, 2H, J=8.0 Hz), 7.47 (m, 3H), 7.38 (s, 1H), 7.18 (br, 2H), 5.16-5.22 (br, 2H), 4.64 (br, 2H), 4.19-4.24 (m, 2H), 3.69 (s, 6H), 3.59-3.57 (m, 2H), 3.24 (br, 2H), 2.33-2.40 (m, 4H), 2.24-2.26 (m, 3H), 1.73-1.75 (m, 4H), 1.51 (m, 2H), 0.97-1.05 (m, 12H), 0.86-0.89 (br, 1H), 0.64-0.70 (m, 2H).

Example 3
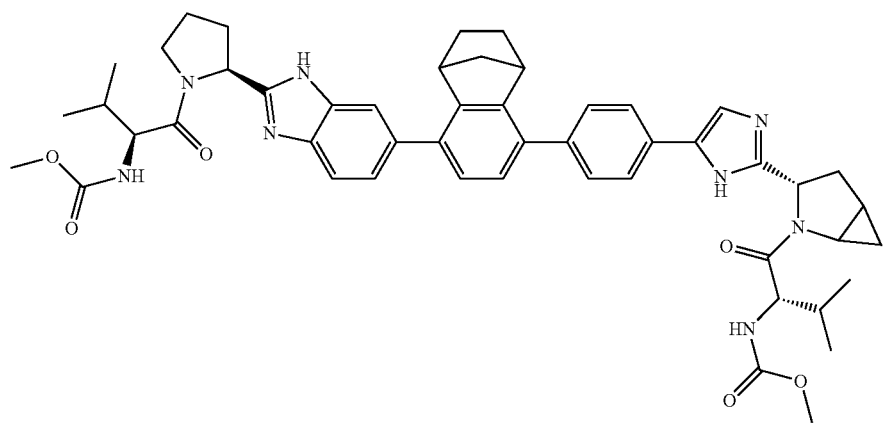 [SMILES: COC(=O)N[C@H](C(=O)N1CCC[C@H]1c1nc2ccc(-c3ccc(-c4ccc(-c5cnc([C@@H]6CC7CC7N6C(=O)[C@@H](NC(=O)OC)C(C)C)[nH]5)cc4)c4c3C3CCC4C3)cc2[nH]1)C(C)C]
20
Synthetic Route:
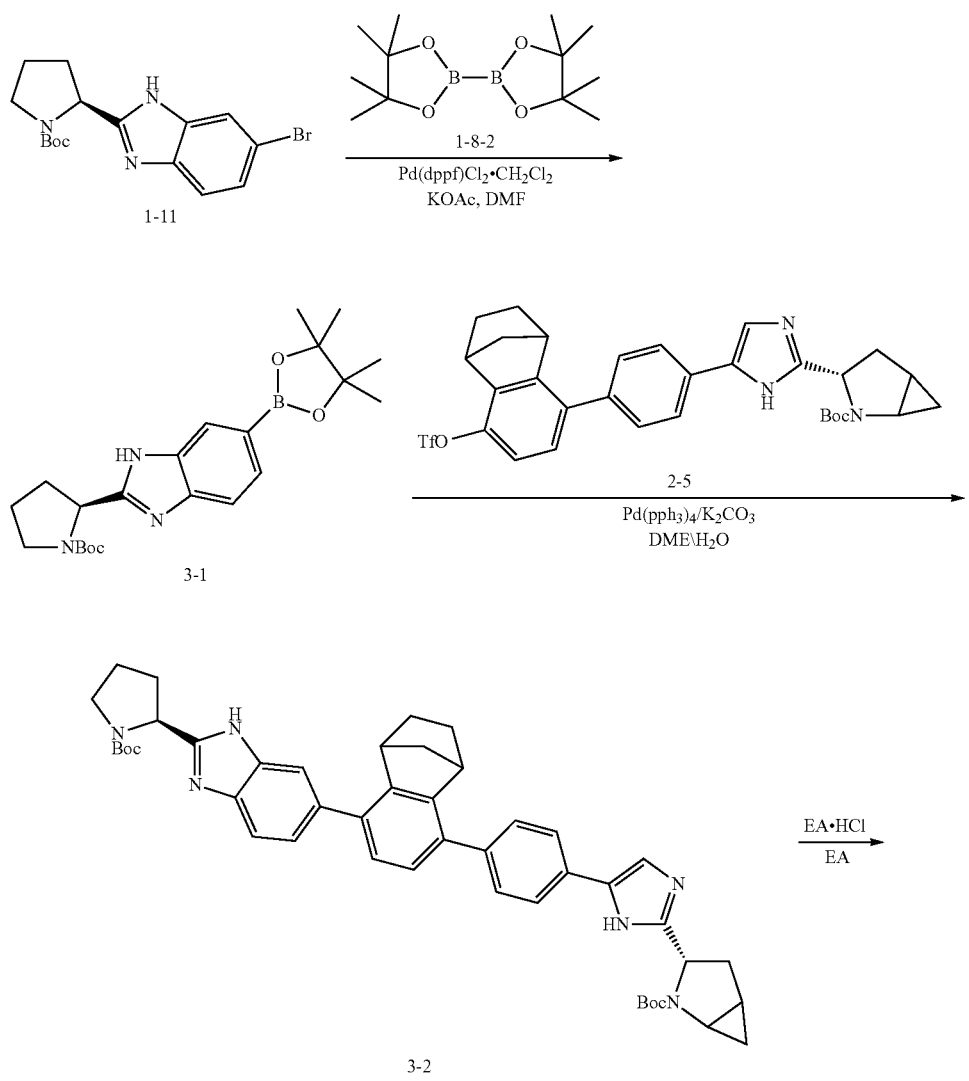

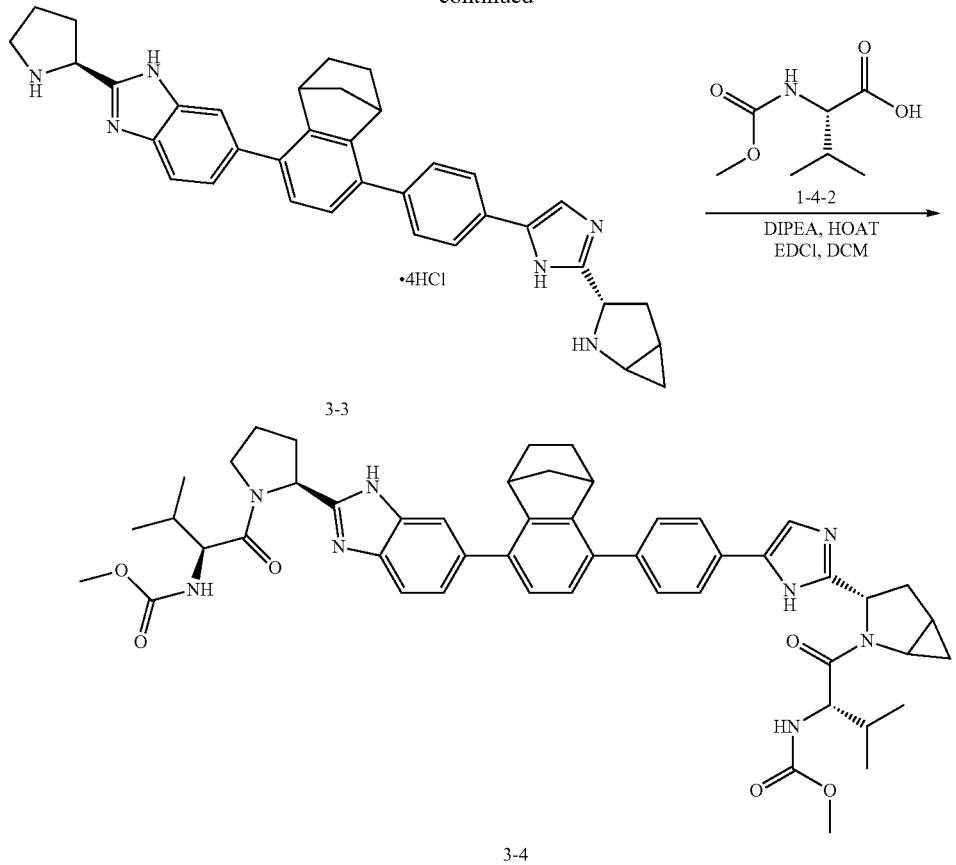

Step 1) the Preparation of Compound 3-1

A mixture of compound 1-11 (3.0 g, 11.27 mmol), compound 1-8-2 (4.29 g, 16.9 mmol), Pd(dppf)Cl$_2$·CH$_2$Cl$_2$ (653 mg, 0.8 mmol) and KOAc (2.09 g, 21.3 mmol) in DMF (30 mL) was stirred at 90° C. under N$_2$ for 3 hrs. After the reaction was completed, the mixture was cooled to rt, 60 mL of water was added, and the mixture was extracted with EtOAc (30 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound as a beige solid (2.2 g, 65%). The compound was characterized by the following spectroscopic data:

MS (ESI, pos.ion) m/z: 414.3 [M+H]$^+$;

$^1$H NMR (400 MHz, CDCl$_3$) δ (ppm): 7.69 (s, 1H), 7.45-7.43 (m, 1H), 7.32-7.30 (m, 1H), 5.12-5.10 (m, 1H), 3.45-3.43 (m, 2H), 2.95-2.94 (m, 1H), 2.25-2.22 (m, 2H), 2.01-1.91 (m, 1H), 1.49 (s, 9H), 1.35 (s, 12H).

Step 2) the Preparation of Compound 3-2

To a mixture of compound 2-5 (127.7 mg, 0.207 mmol), compound 3-1 (89.53 mg, 0.207 mmol), Pd(PPh$_3$)$_4$ (23.97 mg, 0.0207 mmol) and K$_2$CO$_3$ (85.93 mg, 0.6227 mmol) were added DME (4.0 mL) and pure water (1.0 mL) via syringe, and the mixture was stirred at 90° C. under N$_2$. After the reaction was completed, the mixture was cooled to rt and diluted with EtOAc (20 mL), then 20 mL of water was added, and the resulting mixture was extracted with EtOAc (50 mL×3). The combined organic layers were washed with brine, dried over anhydrous Na$_2$SO$_4$ and concentrated in vacuo. The residue was purified by a silica gel column chromatography (DCM/EtOH (v/v)=100/1) to give the title compound as a pale yellow solid (149.6 mg, 95.72%). The compound was characterized by the following spectroscopic data:

MS (ESI, pos.ion) m/z: 378.3 [M+2H]$^{2+}$;

$^1$H NMR (400 MHz, CDCl$_3$) δ (ppm): 7.51-7.64 (m, 3H), 7.42-7.50 (m, 5H), 7.33-7.35 (m, 1H), 7.21 (s, 1H), 5.25-5.27 (d, 1H, J=8.0 Hz), 5.14-5.16 (br, 1H), 3.60 (br, 2H), 3.44-3.53 (m, 3H), 2.01-2.21 (m, 12H), 1.51 (s, 18H), 0.80-0.85 (m, 1H), 0.61-0.63 (m, 2H).

Step 3) the Preparation of Compound 3-3

To a solution of compound 3-2 (149.6 mg, 0.198 mmol) in EtOAc (4 mL) was added a solution of HCl in EtOAc (3 mL, 4 M) dropwise, and the mixture was stirred at rt for 8 hrs. After the reaction was completed, the mixture was concentrated in vacuo, and EtOAc (10 mL) was added. The resulting mixture was filtered, and the filter cake was washed with EtOAc to give the title compound as a pale yellow solid (114 mg, 82.4%), which was used for the next step without further purification. The compound was characterized by the following spectroscopic data:

MS (ESI, pos.ion) m/z: 553.3 [M+H]$^+$.

Step 4) the Preparation of Compound 3-4

To a suspension of compound 3-3 (114.3 mg, 0.163 mmol), compound 1-4-2 (60.22 mg, 0.343 mmol), EDCI (65.89 mg, 0.343 mmol) and HOAT (33.41 mg, 0.245 mmol) in DCM (5.0 mL) was added DIPEA (0.216 mL, 1.309 mmol) dropwise at 0° C. The mixture was stirred at rt for 3 hrs and diluted with DCM (20 mL). The resulting mixture was washed with NH$_4$Cl aqueous solution and brine, dried over anhydrous Na$_2$SO$_4$ and concentrated in vacuo. The residue was purified by a silica gel column chromatography (DCM/EtOH (v/v)=

60/1) to give the title compound as a yellow solid (85 mg, 60%). The compound was characterized by the following spectroscopic data:
MS (ESI, pos.ion) m/z: 434.3[M+2H]$^{2+}$;
$^1$H NMR (400 MHz, CDCl$_3$) δ (ppm): 7.56-7.65 (m, 3H), 7.48-7.53 (m, 5H), 7.35-7.38 (m, 1H), 7.26 (s, 1H), 5.26-5.28 (d, 1H, J=8.0 Hz), 5.14-5.16 (br, 1H), 4.83-4.85 (m, 2H), 3.72 (s, 6H), 3.61 (br, 2H), 3.44-3.53 (m, 4H), 1.95-2.18 (m, 13H), 1.05-1.08 (m, 12H), 0.80-0.85 (m, 1H), 0.61-0.63 (m, 2H).
Example 4
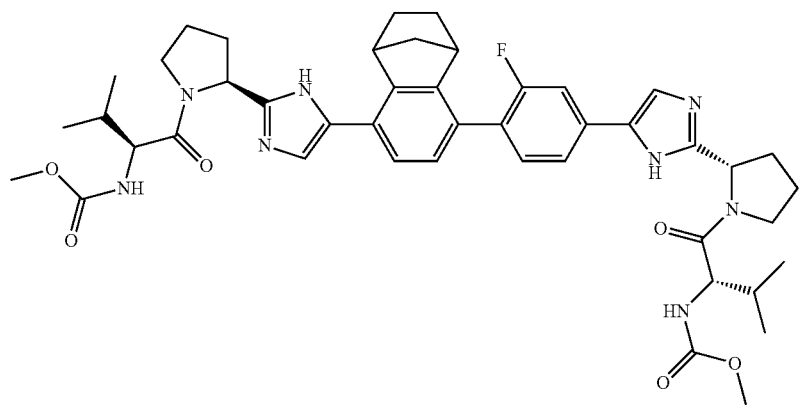 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3C3CCC4C3)c(F)c2)[nH]1)C(C)C]
Synthetic Route:
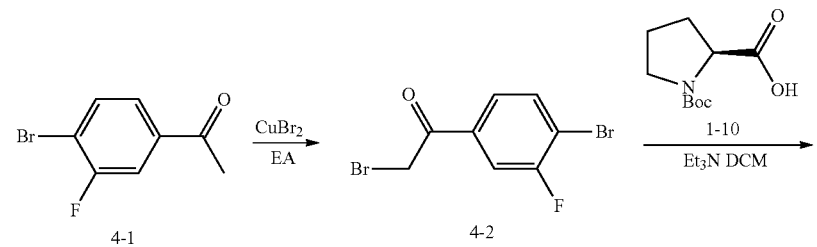
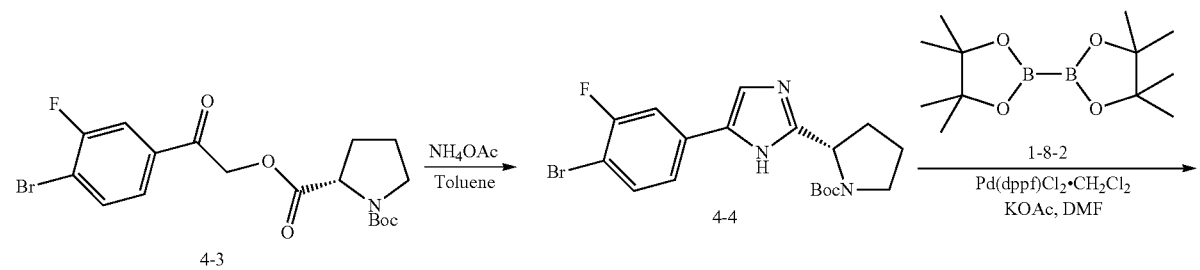
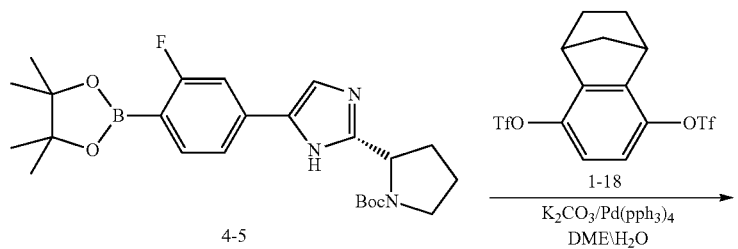

-continued

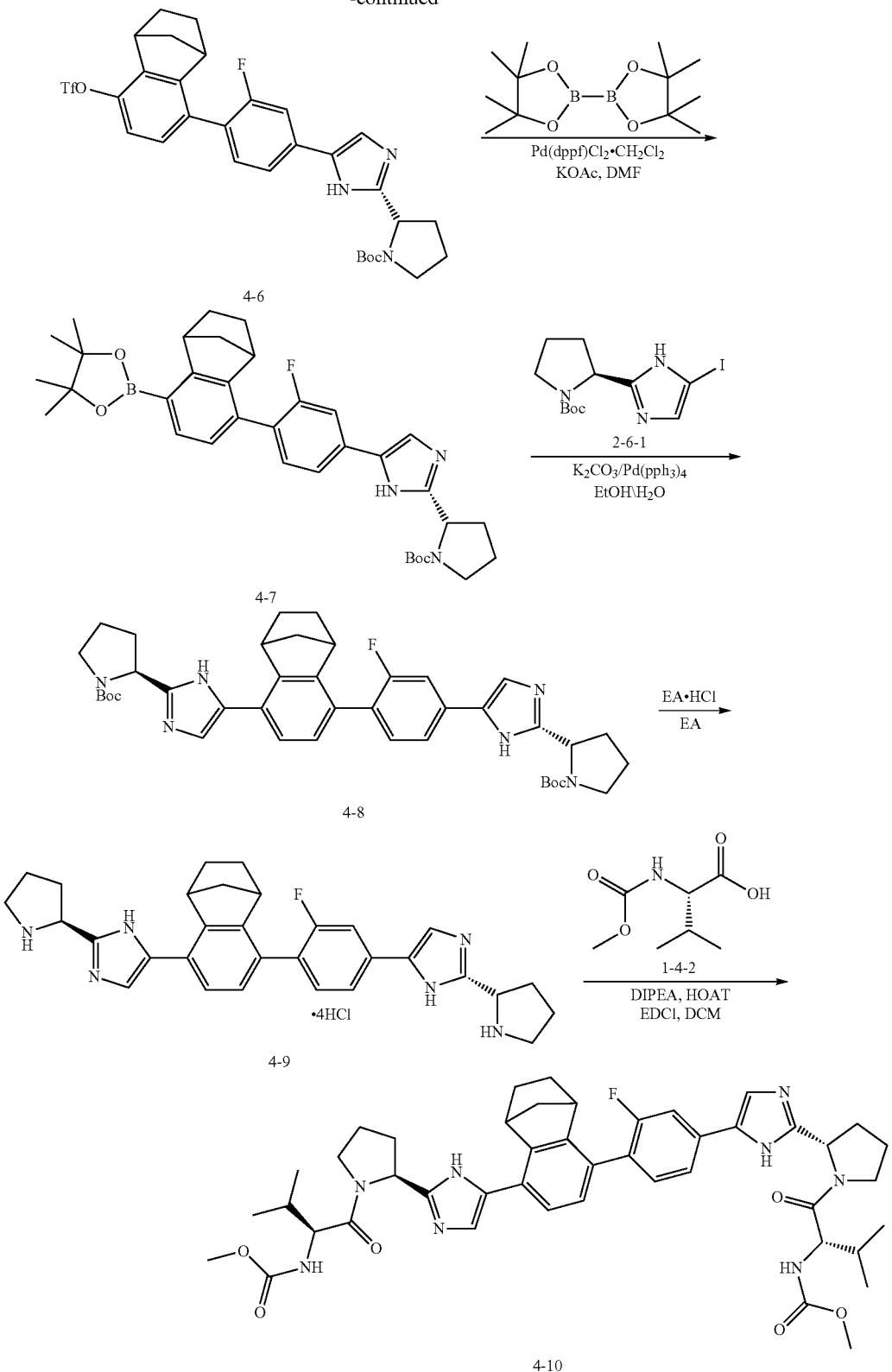

Step 1) the Preparation of Compound 4-2

A solution of compound 4-1 (0.5 g, 2.3 mmol) and CuBr$_2$ (1.13 g, 4.84 mmol) in EtOAc (5.0 mL) was stirred at 60° C. for 4 hrs. After the reaction was completed, the mixture was cooled to rt and filtered. 20 mL of water was added to the filtrate and the resulting mixture was extracted with EtOAc (50 mL×3). The combined organic layers were dried over anhydrous Na$_2$SO$_4$ and concentrated in vacuo to give the title compound as a yellow solid (0.78 g), which was used for the next step without further purification.

Step 2) the Preparation of Compound 4-3

To a solution of compound 4-2 (0.78 g, 2.64 mmol) in DCM (15 mL) was added Et$_3$N (0.55 mL, 3.96 mmol) at −10° C., followed by compound 1-10 (0.68 g, 3.16 mmol), and the mixture was stirred at rt for 2 hrs. After the reaction was completed, 20 mL of water was added to the mixture, and the resulting mixture was extracted with EtOAc (50 mL×3). The combined organic layers were dried over anhydrous Na$_2$SO$_4$ and concentrated in vacuo. The residue was purified by a silica gel column chromatography (PE/EtOAc (v/v)=6/1) to give the title compound 4-3 as a white solid (0.48 g, 42.5%). The compound was characterized by the following spectroscopic data:

MS (ESI, pos.ion) m/z: 319.1 [M+H]$^+$;

$^1$H NMR (400 MHz, CDCl$_3$) δ (ppm): 7.84-7.82 (m, 1H), 7.45-7.38 (m, 2H), 5.38-5.05 (m, 2H), 4.47-4.38 (m, 1H), 2.32-2.30 (m, 2H), 2.59 (m, 1H), 1.93-1.91 (m, 1H), 1.46-1.44 (m, 9H).

Step 3) the Preparation of Compound 4-4

A suspension of compound 4-3 (5.12 g, 11.93 mmol) and ammonium acetate (9.19 g, 119.3 mmol) in toluene (60 mL) was stirred at 110° C. for 3 hrs. After the reaction was completed, the reaction was quenched with water (50 mL), and the resulting mixture was extracted with EtOAc (50 mL×3). The combined organic layers were dried over anhydrous Na$_2$SO$_4$ and concentrated in vacuo to give title compound as yellow oil (3.6 g, 73.62%). The compound was characterized by the following spectroscopic data:

MS (ESI, pos.ion) m/z: 411.28 [M+H]$^+$;

$^1$H NMR (400 MHz, CDCl$_3$) δ (ppm): 7.93 (s, 1H), 7.40-7.39 (d, 1H, J=3.36 Hz), 7.33-7.31 (m, 1H), 7.29-7.27 (m, 1H), 5.00-4.98 (m, 1H), 2.04 (m, 2H), 2.17-1.99 (m, 2H), 1.99-1.97 (m, 2H), 1.58-1.38 (m, 9H).

Step 4) the Preparation of Compound 4-5

A mixture of compound 4-4 (3.6 g, 8.77 mmol), compound 1-8-2 (2.27 g, 8.95 mmol), PdCl$_2$(PPh$_3$)$_2$ (0.31 g, 0.44 mmol) and KOAc (2.15 g, 21.9 mmol) in DME (50 mL) was stirred at 90° C. under N$_2$ for 2 hrs. After the reaction was completed, the mixture was filtered. 50 mL of water was added to the filtrate, and the mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=10/1) to give the title compound as a pale yellow solid (2.63 g, 65.6%). The compound was characterized by the following spectroscopic data:

MS (ESI, pos.ion) m/z: 458.3 [M+H]$^+$;

$^1$H NMR (400 MHz, CDCl$_3$) δ (ppm): 7.95 (s, 1H), 7.42-7.40 (d, 1H, J=3.36 Hz), 7.35-7.33 (m, 1H), 7.29-7.27 (m, 1H), 5.02-5.00 (m, 1H), 2.06-2.04 (m, 2H), 2.17-1.99 (m, 2H), 1.99-1.97 (m, 2H), 1.58-1.38 (m, 9H), 1.24 (s, 12H).

Step 5) the Preparation of Compound 4-6

A mixture of compound 4-5 (1.0 g, 2.665 mmol), compound 5-2 (1.17 g, 2.665 mmol), Pd(PPh$_3$)$_4$ (0.154 g, 0.133 mmol) and KF (0.31 g, 5.329 mmol) in mixed solvents of DME (6 mL) and H$_2$O (1.5 mL) was stirred at 90° C. under N$_2$ for 3 hrs. After the reaction was completed, the mixture was filtered. 50 mL of water was added to the filtrate, and the mixture was extracted with EtOAc (50 mL×3). The combined organic layers were dried over anhydrous Na$_2$SO$_4$ and concentrated in vacuo. The residue was purified by a silica gel column chromatography (PE/EtOAc (v/v)=8/1) to give the title compound as a pale yellow solid (0.96 g, 70.59%). The compound was characterized by the following spectroscopic data:

MS (ESI, pos.ion) m/z: 622.15 [M+H]$^+$;

$^1$H NMR (400 MHz, CDCl$_3$) δ (ppm): 7.52-7.50 (m, 2H), 7.28-7.27 (m, 2H), 7.20-7.19 (m, 1H), 7.05-7.03 (m, 1H), 5.20-5.18 (m, 2H), 3.73-3.69 (m, 1H), 3.63-3.60 (m, 1H), 2.68-2.46 (m, 2H), 2.10-1.05 (m, 1H), 2.03-2.01 (m, 2H), 1.62-21.59 (m, 2H), 1.58-1.46 (m, 4H), 1.32 (s, 9H).

Step 6) the Preparation of Compound 4-7

A mixture of compound 4-6 (0.94 g, 1.02 mmol), compound 1-8-2 (0.46 g, 1.81 mmol), PdCl$_2$(dppf).CH$_2$Cl$_2$ (0.123 g, 0.15 mmol) and KOAc (0.37 g, 3.78 mmol) in DME (15 mL) was stirred at 120° C. under N$_2$. After the reaction was completed, the reaction was quenched with water, and the mixture was extracted with EtOAc (50 mL×3). The combined organic layers were dried over anhydrous Na$_2$SO$_4$ and concentrated in vacuo. The residue was purified by a silica gel column chromatography (PE/EtOAc (v/v)=8/1) to give the title compound as a white solid (0.61 g, 67%). The compound was characterized by the following spectroscopic data:

MS (ESI, pos.ion) m/z: 622.15 [M+H]$^+$;

$^1$H NMR (400 MHz, CDCl$_3$) δ (ppm): 7.04 (s, 1H), 5.35-5.09 (m, 2H), 3.98-3.63 (m, 1H), 3.58-3.29 (m, 1H), 2.55-2.34 (m, 2H), 1.48 (s, 9H).

Step 7) the Preparation of Compound 4-8

To a mixture of compound 4-7 (0.61 g, 1.02 mmol), compound 2-6-1 (0.406 g, 1.12 mmol), Pd(PPh$_3$)$_4$ (58.8 mg, 0.051 mmol) and K$_2$CO$_3$ (0.421 g, 3.05 mmol) were added EtOH (6.0 mL) and H$_2$O (1.5 mL) via syringe, and the mixture was stirred at 90° C. under N$_2$ for 3 hrs. After the reaction was completed, the mixture was filtered. Water (20 ml) was added to the filtrate, and the mixture was extracted with EtOAc (50 mL×3). The combined organic layers were dried over anhydrous Na$_2$SO$_4$ and concentrated in vacuo. The residue was purified by a silica gel column chromatography (DCM/MeOH (v/v)=50/1) to give the title compound as a pale yellow solid (700 mg, 97.2%). The compound was characterized by the following spectroscopic data:

MS (ESI, pos.ion) m/z: 709.25 [M+H]$^+$;

$^1$H NMR (400 MHz, CDCl$_3$) δ (ppm): 7.56-7.58 (d, 2H, J=8.0 Hz), 7.45 (br, 1H), 7.31 (br, 1H), 7.20 (br, 1H), 7.13-7.15 (d, 1H, J=8.0 Hz), 5.03 (br, 1H), 3.54 (br, 1H), 3.42 (br, 2H), 2.11-2.26 (m, 2H), 2.02-2.04 (m, 2H), 1.94 (br, 1H), 1.80-1.82 (d, 2H, J=8.0 Hz), 1.56-1.59 (m, 12H), 1.39-1.42 (m, 1H), 1.35 (s, 12H).

Step 8) the Preparation of Compound 4-9

To a solution of compound 4-8 (0.7 g, 0.998 mmol) in EtOAc (10 mL) was added a solution of HCl in EtOAc (5 mL, 4 M) dropwise, and the mixture was stirred at rt overnight. After the reaction was completed, the mixture was concentrated in vacuo, and the residue was washed with EtOAc to give the title compound as a brown solid (450 mg, 69.23%). The compound was characterized by the following spectroscopic data:

MS (ESI, pos.ion) m/z: 557.20 [M+H]$^+$.

Step 9) the Preparation of Compound 4-10

To a mixture of compound 4-9 (0.45 g, 0.687 mmol), compound 1-4-2 (0.265 g, 1.51 mmol), EDCI (0.28 g, 1.51 mmol) and HOAT (0.187 g, 0.137 mmol) in DCM (5.0 mL) at −10° C. was added DIPEA (0.144 mL, 0.87 mmol) dropwise. At the end of addition, the mixture was stirred at rt. After the reaction was completed, the reaction was quenched with saturated NH$_4$Cl aqueous solution. The resulting mixture was extracted with DCM (50 mL×3), and the combined organic layers were dried over anhydrous Na$_2$SO$_4$ and concentrated in vacuo. The residue was purified by a silica gel column chromatography (DCM/EtOH (v/v)=40/1) to give the title compound as a white solid (380 mg, 67.18%). The compound was characterized by the following spectroscopic data:

MS (ESI, pos.ion) m/z: 412.25 [M+2H]$^{2+}$;
$^1$H NMR (400 MHz, CDCl$_3$) δ (ppm): 7.85-7.87 (d, 2H, J=8.0 Hz), 7.47 (m, 2H), 7.38 (s, 1H), 7.18 (br, 2H), 5.16-5.22 (br, 2H), 4.64 (br, 2H), 4.19-4.24 (m, 2H), 3.69 (s, 6H), 3.59-3.57 (m, 4H), 3.24 (br, 2H), 2.33-2.40 (m, 4H), 2.24-2.26 (m, 4H), 1.73-1.75 (m, 4H), 1.51 (m, 2H), 0.97-1.05 (m, 12H).
Example 5
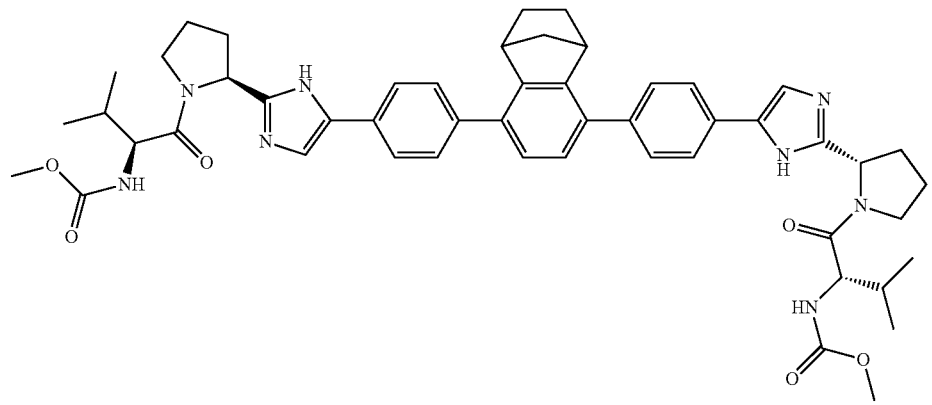 [SMILES: COC(=O)N[C@H](C(=O)N1CCC[C@H]1c1ncc(-c2ccc(-c3ccc(-c4ccc(-c5cnc([C@@H]6CCCN6C(=O)[C@@H](NC(=O)OC)C(C)C)[nH]5)cc4)c4c3C3CCC4C3)cc2)[nH]1)C(C)C]
Synthetic Route:
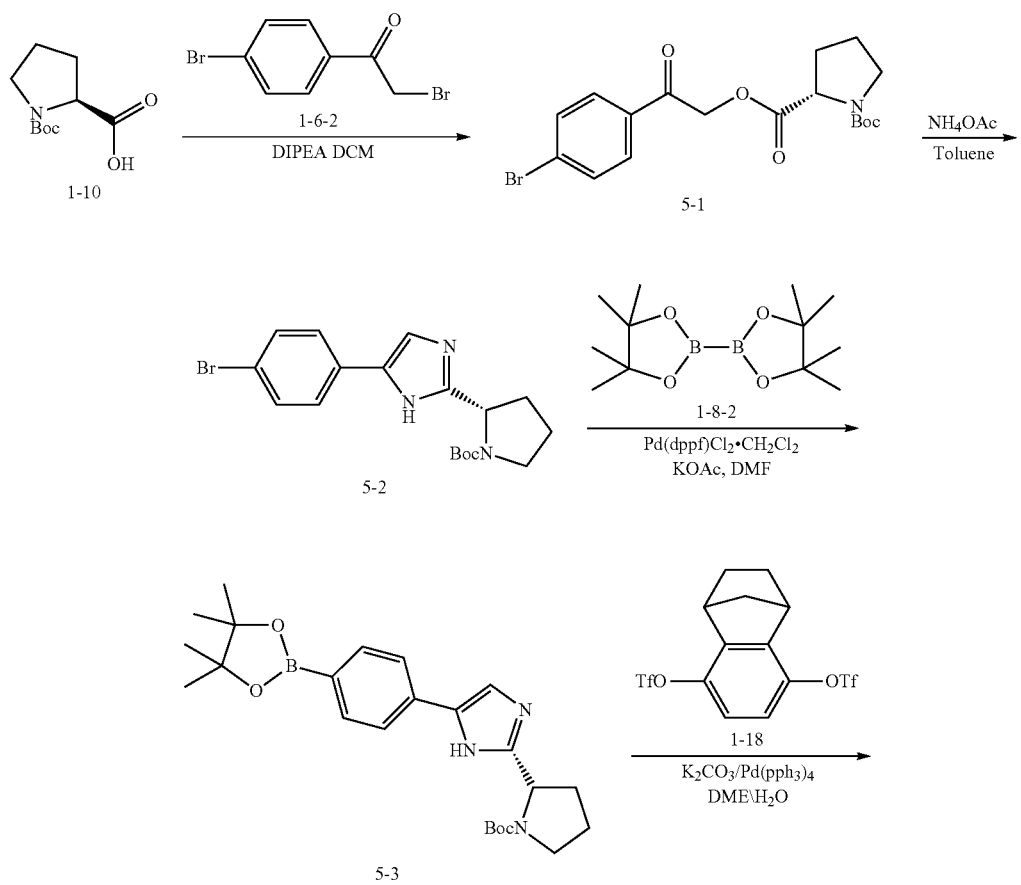

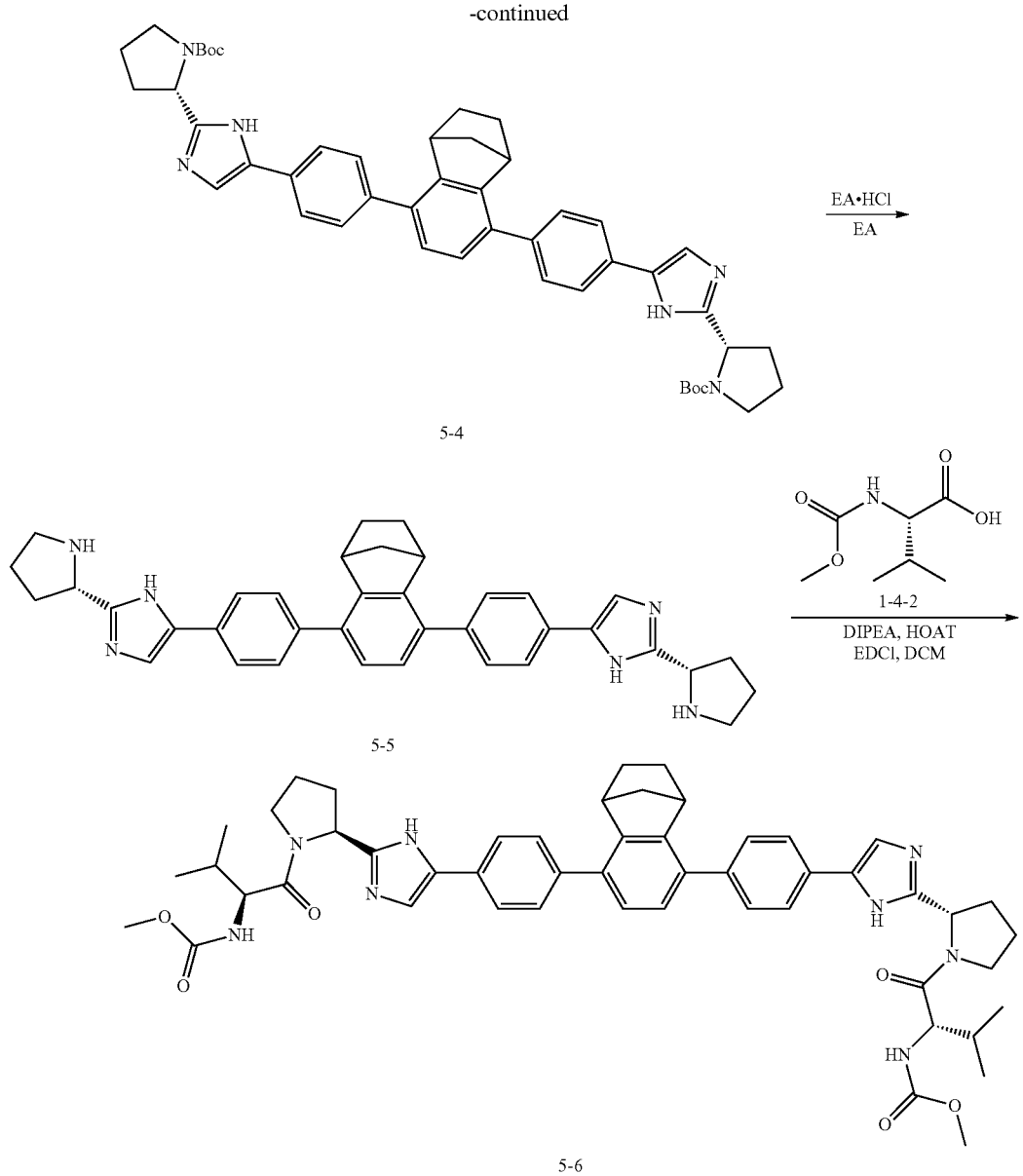

Step 1) the Preparation of Compound 5-1

To a solution of compound 1-6-2 (30 g, 107.9 mmol) and compound 1-10 (25.6 g, 118.7 mmol) in MeCN (250 mL) was added DIPEA (21.4 mL, 129.5 mmol) dropwise at 0° C. At the end of addition, the mixture was stirred at rt for 3 hrs. After the reaction was completed, the reaction was quenched with ice water (100 mL), and the resulting mixture was extracted with EtOAc (100 mL×3). The combined organic layers were dried over anhydrous $Na_2SO_4$ and concentrated in vacuo. The residue was purified by a silica gel column chromatography (PE/EtOAc (v/v)=10/1) to give the title compound as a white solid (40 g, 91%). The compound was characterized by the following spectroscopic data:

MS (ESI, pos.ion) m/z: 412.7 [M+H]$^+$;

$^1$H NMR (400 MHz, CDCl$_3$) δ (ppm): 7.78-7.75 (m, 2H), 7.65-7.63 (m, 2H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Step 2) the Preparation of Compound 5-2

A suspension of compound 5-1 (15 g, 36.4 mmol) and ammonium acetate (42 g, 54.6 mmol) in toluene (150 mL) was stirred at 120° C. After the reaction was completed, the mixture was cooled to rt and the reaction was quenched with 100 mL of water. The resulting mixture was extracted with EtOAc (100 mL×3), and the combined organic layers were dried over anhydrous $Na_2SO_4$ and concentrated in vacuo. The residue was purified by a silica gel column chromatography (PE/EtOAc (v/v)=5/1) to give the title compound 5-2 (12.12 g, 85%). The compound was characterized by the following spectroscopic data:

MS (ESI, pos.ion) m/z: 392.2 [M+H]$^+$;

$^1$H NMR (400 MHz, CDCl$_3$) δ (ppm): 7.78-7.75 (m, 2H), 7.65-7.63 (m, 2H), 7.21-7.20 (m, 1H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Step 3) the Preparation of Compound 5-3

A mixture of compound 5-2 (4.0 g, 10.23 mmol), compound 1-8-2 (2.86 g, 11.25 mmol), PdCl$_2$(dppf).CH$_2$Cl$_2$ (418 mg, 0.51 mmol) and KOAc (2.51 g, 25.57 mmol) in DMF (40 mL) was stirred at 90° C. under N$_2$ for 3 hrs. After the reaction was completed, the mixture was cooled to rt, diluted with EtOAc (80 mL) and filtered through a celite pad. 150 mL of water was added to the filtrate, and the resulting mixture was extracted with EtOAc (50 mL×3). The combined organic layers were dried over anhydrous Na$_2$SO$_4$ and concentrated in vacuo. The residue was purified by a silica gel column chromatography (PE/EtOAc (v/v)=2/1) to give the title compound (3.6 g, 80%). The compound was characterized by the following spectroscopic data:

$^1$H NMR (400 MHz, CDCl$_3$) δ (ppm): 7.35 (m, 4H), 7.10 (s, 1H), 4.93 (t, 1H, J=8.2 Hz), 3.88-3.66 (m, 2H), 2.90 (t, 1H, J=8.0 Hz), 2.50-2.47 (m, 2H), 2.27-2.25 (m, 1H), 1.48 (s, 9H), 1.26 (s, 12H).

Step 4) the Preparation of Compound 5-4

To a mixture of compound 1-18 (1.5 g, 3.4 mmol), compound 5-3 (3.24 g, 7.38 mmol), Pd(PPh$_3$)$_4$ (196.7 mg, 0.17 mmol) and K$_2$CO$_3$ (1.412 g, 10.22 mmol) were added DME (12.0 mL) and H$_2$O (3.0 mL) via syringe, and the mixture was stirred at 90° C. under N$_2$. After the reaction was completed, the mixture was cooled to rt, diluted with EtOAc (20 mL), and 20 mL of water was added. The resulting mixture was extracted with EtOAc (60 mL×3). The combined organic layers were dried over anhydrous Na$_2$SO$_4$ and concentrated in vacuo. The residue was purified by a silica gel column chromatography (DCM/MeOH (v/v)=60/1) to give the title compound as a pale yellow solid (1.56 g, 60%). The compound was characterized by the following spectroscopic data:

MS (ESI, pos.ion) m/z: 767.3 [M+H]$^+$;

$^1$H NMR (400 MHz, CDCl$_3$) δ (ppm): 7.72 (m, 4H), 7.50-7.52 (d, 6H, J=8.0 Hz), 7.24 (s, 2H), 5.00-5.01 (d, 2H, J=4.0 Hz), 3.59-3.63 (br, 2H), 3.37-3.47 (br, 2H), 2.94-3.06 (br, 2H), 2.11-2.24 (m, 4H), 1.98-2.06 (m, 8H), 1.73-1.75 (m, 2H), 1.51 (s, 18H).

Step 5) the Preparation of Compound 5-5

To a solution of compound 5-4 (750 mg, 0.978 mmol) in EtOAc (5 mL) was added a solution of HCl in EtOAc (5 mL, 4 M) dropwise, and the mixture was stirred at rt for 8 hrs. After the reaction was completed, the mixture was concentrated in vacuo, and the residue was washed with EtOAc (20 mL) to give the title compound as a pale yellow solid (697 mg, 100%), which was used for the next step without further purification. The compound was characterized by the following spectroscopic data:

MS (ESI, pos.ion) m/z: 567.3 [M+H]$^+$.

Step 6) the Preparation of Compound 5-6

To a mixture of compound 5-5 (480 mg, 0.674 mmol), compound 1-4-2 (235.8 mg, 1.35 mmol), EDCI (271.3 mg, 1.415 mmol) and HOAT (137.58 mg, 1.01 mmol) in DCM (20 mL) at 0° C. was added DIPEA (0.89 mL, 5.39 mmol) dropwise. At the end of addition, the mixture was stirred at rt for 3 hrs. The mixture was diluted with DCM (40 mL), washed with saturated NH$_4$Cl aqueous solution and brine, dried over anhydrous Na$_2$SO$_4$ and concentrated in vacuo. The residue was purified by a silica gel column chromatography (DCM/EtOH (v/v)=60/1) to give the title compound as a white solid (356 mg, 60%). The compound was characterized by the following spectroscopic data:

MS (ESI, pos.ion) m/z: 441.3 [M+2H]$^{2+}$;

$^1$H NMR (400 MHz, CDCl$_3$) δ (ppm): 7.79-7.87 (m, 2H), 7.62-7.69 (m, 2H), 7.45-7.52 (m, 6H), 7.24 (m, 2H), 5.26-5.34 (m, 2H), 4.30-4.41 (m, 2H), 3.75-3.78 (m, 2H), 3.72 (s, 6H), 3.64-3.68 (br, 2H), 3.60-3.63 (br, 2H), 2.20-2.32 (m, 6H), 2.05-2.07 (m, 2H), 1.81-1.93 (m, 6H), 0.94-0.97 (m, 12H).

Example 6

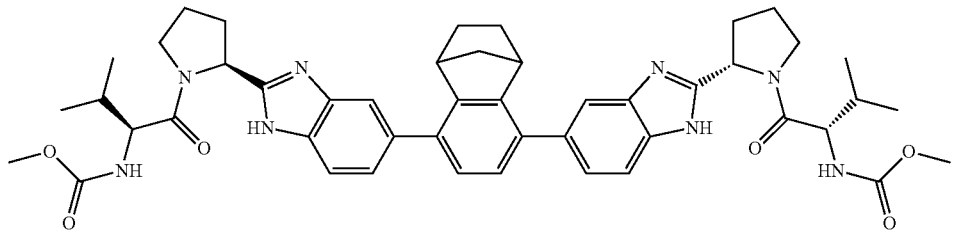

Synthetic Route:

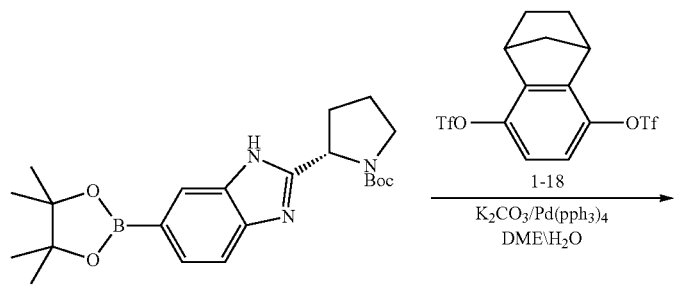

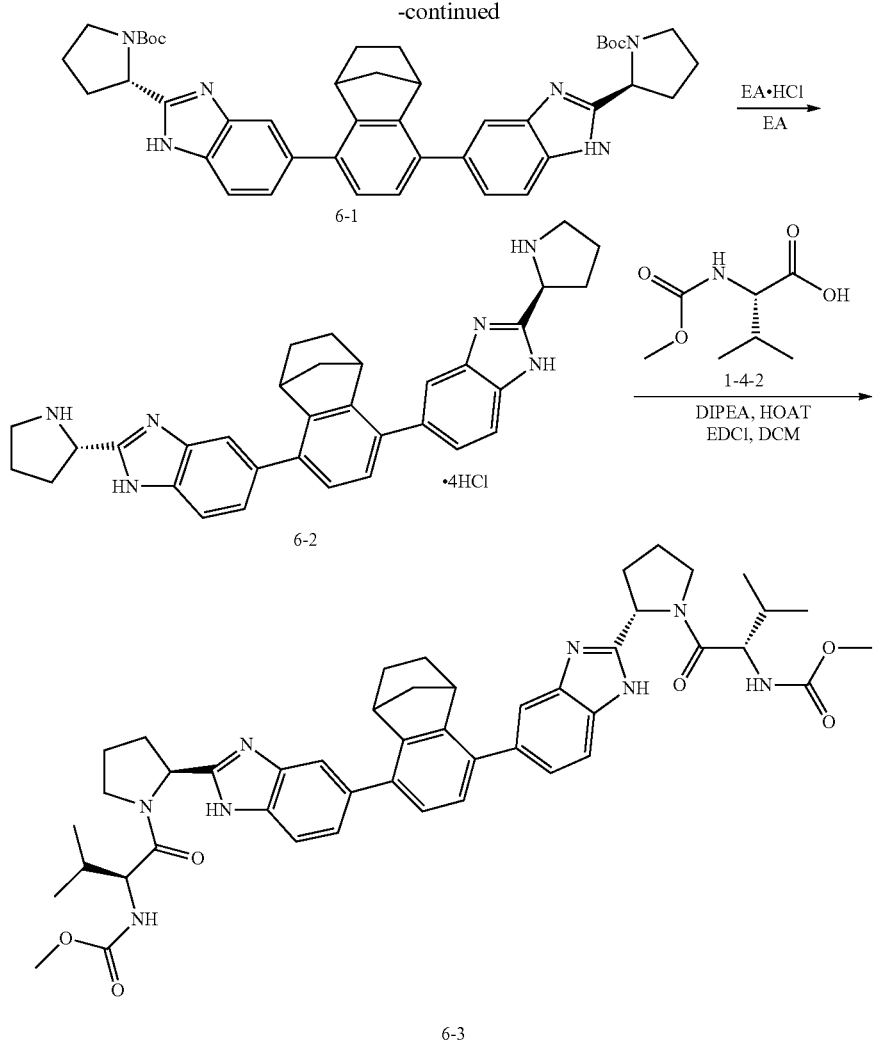

Step 1) the Preparation of Compound 6-1

To a mixture of compound 1-18 (1.5 g, 3.4 mmol), compound 3-1 (2.886 g, 6.98 mmol), Pd(PPh$_3$)$_4$ (196.7 mg, 0.17 mmol) and K$_2$CO$_3$ (1.412 g, 10.22 mmol) were added DME (12.0 mL) and H$_2$O (3.0 mL) via syringe, and the mixture was stirred at 90° C. under N$_2$ for 3 hrs. After the reaction was completed, the mixture was cooled to rt, diluted with EtOAc (40 mL), and 50 mL of water was added. The resulting mixture was extracted with EtOAc (60 mL×3). The combined organic layers were dried over anhydrous Na$_2$SO$_4$ and concentrated in vacuo. The residue was purified by a silica gel column chromatography (DCM/MeOH (v/v)=60/1) to give the title compound as a pale yellow solid (1.0 g, 42%). The compound was characterized by the following spectroscopic data:

MS (ESI, pos.ion) m/z: 358.3 [M+H]$^+$;

$^1$H NMR (400 MHz, CDCl$_3$) δ (ppm): 7.85 (s, 1H), 7.72-7.74 (m, 1H), 7.61 (d, 1H, J=7.6 Hz), 7.52-7.53 (m, 2H), 7.35-7.40 (m, 3H), 5.15-5.16 (m, 2H), 3.45 (br, 2H), 3.05 (m, 2H), 2.20-2.24 (br, 4H), 1.67-1.69 (br, 6H), 1.40-1.43 (br, 6H), 1.26 (s, 18H).

Step 2) the Preparation of Compound 6-2

To a solution of compound 6-2 (750 mg, 1.049 mmol) in EtOAc (5 mL) was added a solution of HCl in EtOAc (5 mL, 4 M) dropwise, and the mixture was stirred at rt for 8 hrs. After the reaction was completed, the mixture was concentrated in vacuo, and the residue was washed with EtOAc (20 mL) to give the title compound as a pale yellow solid (692.7 mg, 100%), which was used for the next step without further purification. The compound was characterized by the following spectroscopic data:

MS (ESI, pos.ion) m/z: 515.3 [M+H]$^+$.

Step 3) the Preparation of Compound 6-3

To a mixture of compound 6-2 (617 mg, 0.9344 mmol), compound 1-4-2 (344 mg, 1.96 mmol), EDCI (376 mg, 1.96 mmol) and HOAT (190.78 mg, 1.40 mmol) in DCM (20 mL) at 0° C. was added DIPEA (1.23 mL, 7.47 mmol) dropwise. At the end of addition, the mixture was stirred at rt for 3 hrs. The mixture was diluted with DCM, washed with saturated NH$_4$Cl aqueous solution and brine, dried over anhydrous Na$_2$SO$_4$ and concentrated in vacuo. The residue was purified by a silica gel column chromatography (DCM/MeOH (v/v)=60/1) to give the title compound as a white solid (387 mg, 50%). The compound was characterized by the following spectroscopic data:

MS (ESI, pos.ion) m/z: 415.3 [M+2H]$^{2+}$;

$^1$H NMR (400 MHz, CDCl$_3$) δ (ppm): 7.88 (d, 1H, J=4.6 Hz), 7.80 (d, 1H, J=8.3 Hz), 7.47 (s, 1H), 7.45-7.23 (m, 5H), 5.72-5.36 (m, 2H), 4.44-4.34 (m, 2H), 3.72 (s, 6H), 3.20-3.07 (m, 2H), 3.02-2.87 (m, 2H), 2.50-2.37 (m, 2H), 2.35-2.14 (m, 2H), 2.10-1.95 (m, 2H), 1.55-1.32 (m, 12H), 0.98-0.80 (m, 12H).

Example 7
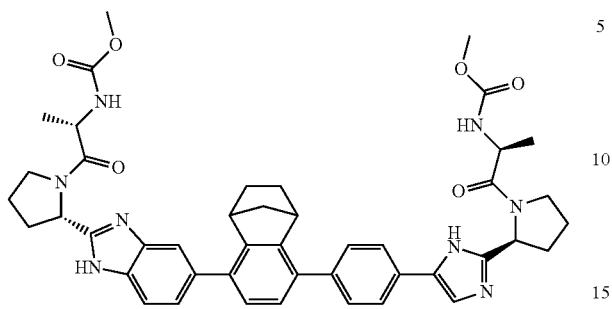
Synthetic Route:
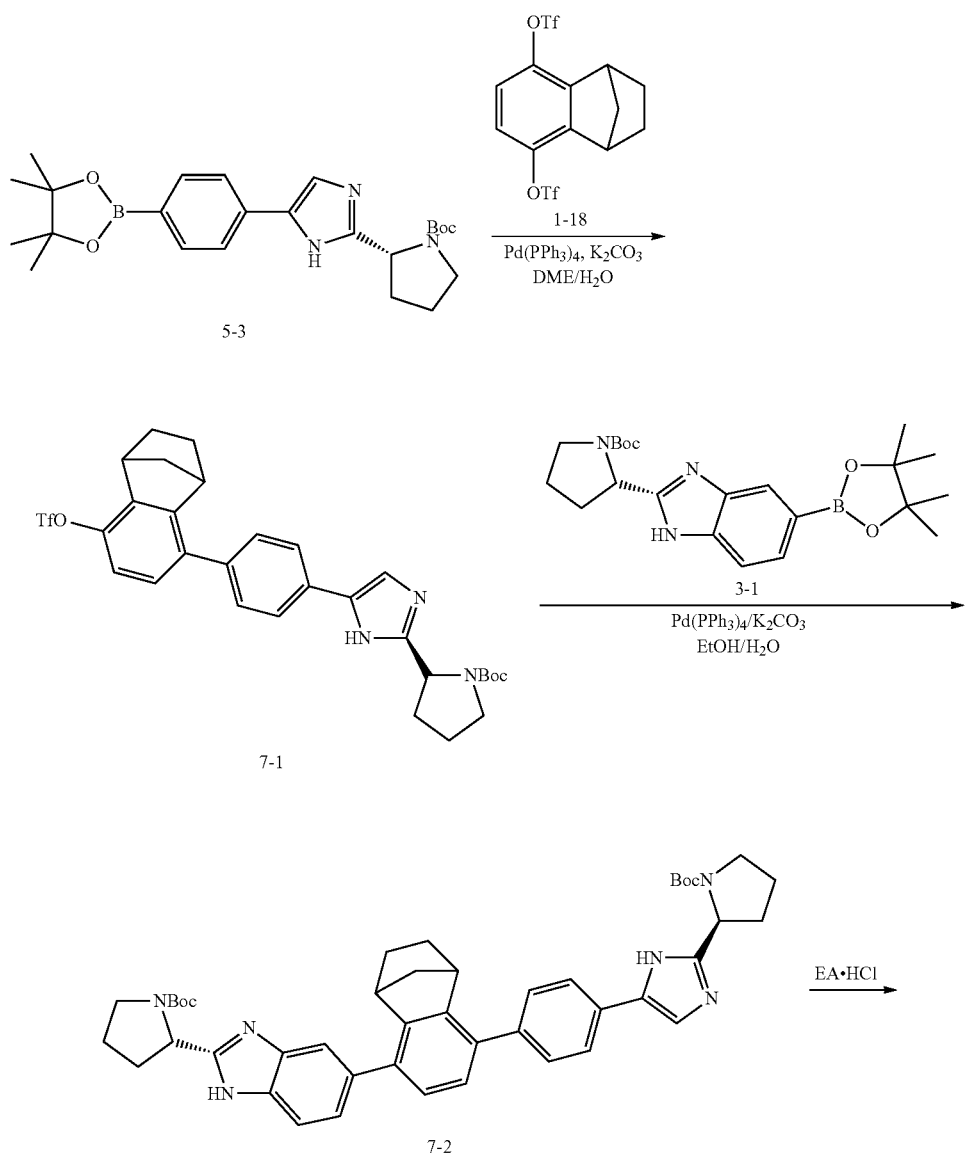

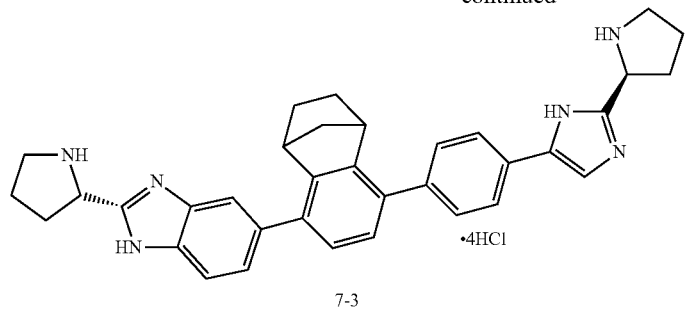
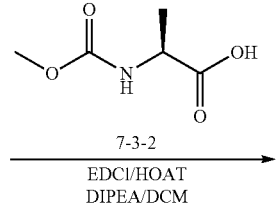

7-3

7-3-2
EDCl/HOAT
DIPEA/DCM

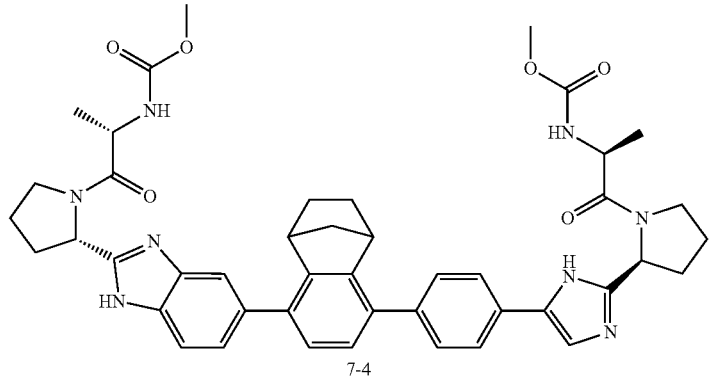

7-4

Step 1) the Preparation of Compound 7-1

A suspension of compound 1-18 (8.30 g, 18.8 mmol), compound 5-3 (8.45 g, 19.2 mmol), Pd(PPh$_3$)$_4$ (1.10 g, 0.94 mmol) and K$_2$CO$_3$ (10.4 g, 75.4 mmol) in mixed solvents of DME and H$_2$O (80 mL, v/v=3/1) was stirred at 90° C. under N$_2$ for 3 hrs. After the reaction was completed, 50 mL of EtOAc was added to the mixture and the resulting mixture was washed with brine, dried over anhydrous Na$_2$SO$_4$ and concentrated in vacuo. The residue was purified by recrystallization to give the title compound as a white solid (5.50 g, 48.7%). The compound was characterized by the following spectroscopic data:

MS (ESI, pos.ion) m/z: 604.3 [M+H]$^+$;

$^1$H NMR (400 MHz, CDCl$_3$) δ (ppm): 10.53 (brs, 1H), 7.83 (brs, 1H), 7.42 (d, 2H, J=8.1 Hz), 7.26 (m, 2H), 7.20 (d, 1H, J=8.6 Hz), 7.02 (d, 1H, J=8.6 Hz), 4.98 (d, 1H, J=5.2 Hz), 3.70 (s, 1H), 3.60 (s, 1H), 3.48-3.35 (m, 2H), 2.25-2.10 (m, 2H), 2.04-1.96 (m, 3H), 1.82-1.80 (m, 1H), 1.59-1.56 (m, 1H), 1.51 (s, 9H), 1.43-1.39 (m, 3H).

Step 2) the Preparation of Compound 7-2

A suspension of compound 3-1 (0.34 g, 0.83 mmol), compound 7-1 (0.5 g, 0.83 mmol), Pd(PPh$_3$)$_4$ (48 mg, 0.04 mmol) and K$_2$CO$_3$ (0.28 g, 2.07 mmol) in mixed solvents of EtOH and H$_2$O (8 mL, v/v=4/1) was stirred at 90° C. under N$_2$ for 3 hrs. After the reaction was completed, the mixture was poured into 30 mL of water and the resulting mixture was filtered. The filter cake was dissolved in EtOAc (30 mL), the solution was washed with brine and dried over anhydrous Na$_2$SO$_4$ and concentrated in vacuo. The residue was purified by a silica gel column chromatography (DCM/MeOH (v/v)=50/1) to give the title compound as a white solid (0.54 g, 88%). The compound was characterized by the following spectroscopic data:

MS (ESI, pos.ion) m/z: 741.3 [M+H]$^+$;

$^1$H NMR (400 MHz, CDCl$_3$) δ (ppm): 10.80 (brs, 1H), 10.54 (brs, 1H), 7.80-7.72 (m, 3H), 7.52-7.50 (m, 4H), 7.40-7.38 (m, 2H), 5.16 (d, 1H, J=6.0 Hz), 5.00 (d, 1H, J=4.0 Hz), 3.64 (s, 2H), 3.43 (s, 4H), 3.08-3.03 (m, 2H), 2.22-2.17 (m, 4H), 2.04-1.97 (m, 6H), 1.80-1.88 (m, 2H), 1.76-1.74 (m, 8H), 1.51 (s, 18H).

Step 3) the Preparation of Compound 7-3

To a solution of compound 7-2 (0.54 g, 0.73 mmol) in EtOAc (8.0 mL) was added a solution of HCl in EtOAc (4 mL, 4 M) dropwise, and the mixture was stirred at rt for 8 hrs. The reaction process was monitored by LC-MS. After the reaction was completed, the mixture was filtered. The filter cake was washed with EtOAc (20 mL) to give the title compound as a white solid (0.36 g, 72%), which was used for the next step without further purification. The compound was characterized by the following spectroscopic data:

MS (ESI, pos.ion) m/z: 540.3 [M+H]$^+$.

Step 4) the Preparation of Compound 7-4

A suspension of compound 7-3 (0.36 g, 0.52 mmol), compound 7-3-2 (193 mg, 1.31 mmol), EDCI (221 mg, 1.15 mmol) and HOAT (142 mg, 1.05 mmol) in DCM (5.0 mL) was stirred at 0° C. for 5 mins, then DIPEA (0.87 mL, 5.24 mmol) was added dropwise. At the end of addition, the mixture was stirred at rt for 10 hrs. After the reaction was completed, the mixture was diluted with DCM (20 mL), washed with saturated NH$_4$Cl aqueous solution, dried over anhydrous Na$_2$SO$_4$ and concentrated in vacuo. The residue was purified by a silica gel column chromatography (DCM/MeOH (v/v)= 50/1) to give the title compound as a white solid (400 mg, 95%). The compound was characterized by the following spectroscopic data:

MS (ESI, pos.ion) m/z: 799.9 [M+H]$^+$;

$^1$H NMR (400 MHz, CDCl$_3$) δ (ppm): 10.64 (brs, 2H), 7.85-7.70 (m, 2H), 7.52-7.48 (m, 4H), 7.39-7.36 (m, 2H), 7.23-7.22 (m, 2H), 5.69-5.67 (m, 2H), 5.46-5.45 (m, 2H), 4.60-4.54 (m, 2H), 3.92-3.78 (m, 2H), 3.70 (s, 6H), 2.90-2.15 (m, 2H), 2.48-2.29 (m, 2H), 2.25-1.85 (m, 8H), 1.60-1.35 (m, 4H), 1.15-1.00 (m, 6H).

Example 8
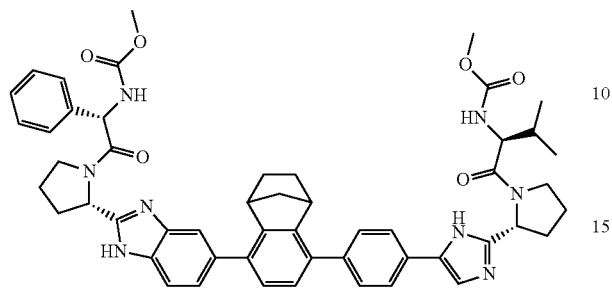
Synthetic Routes
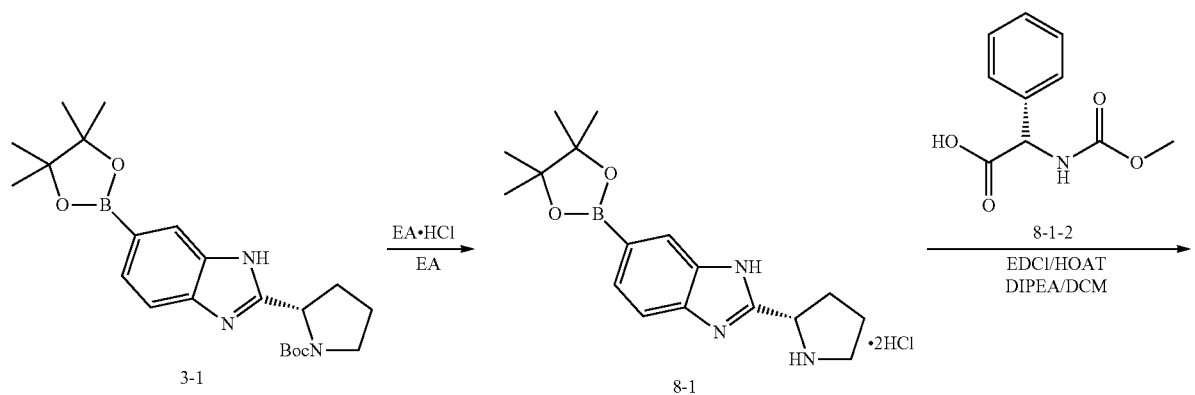
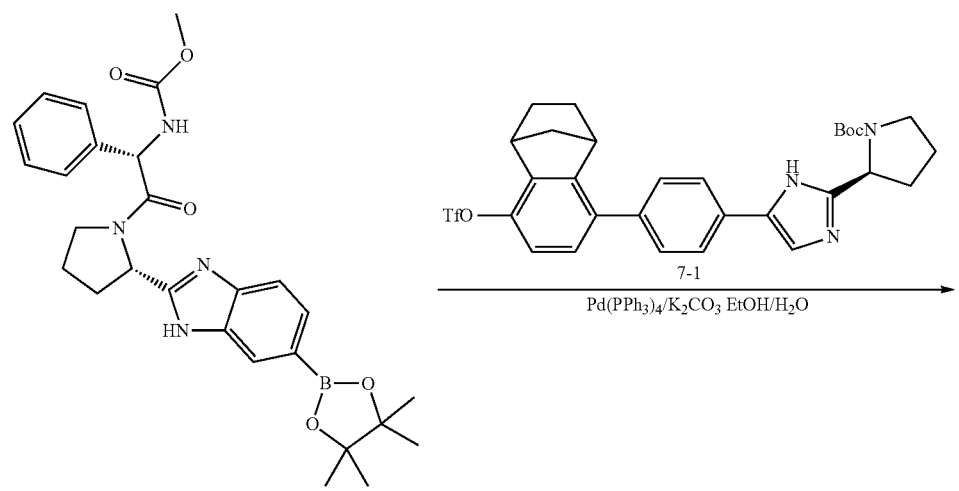

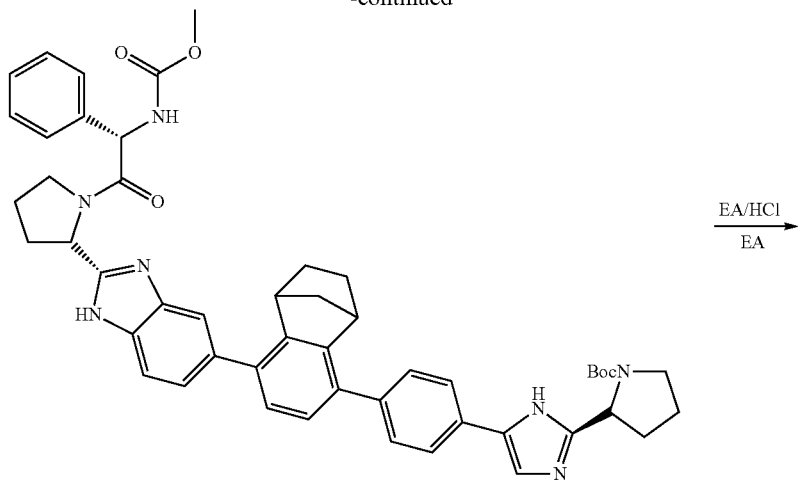
8-3
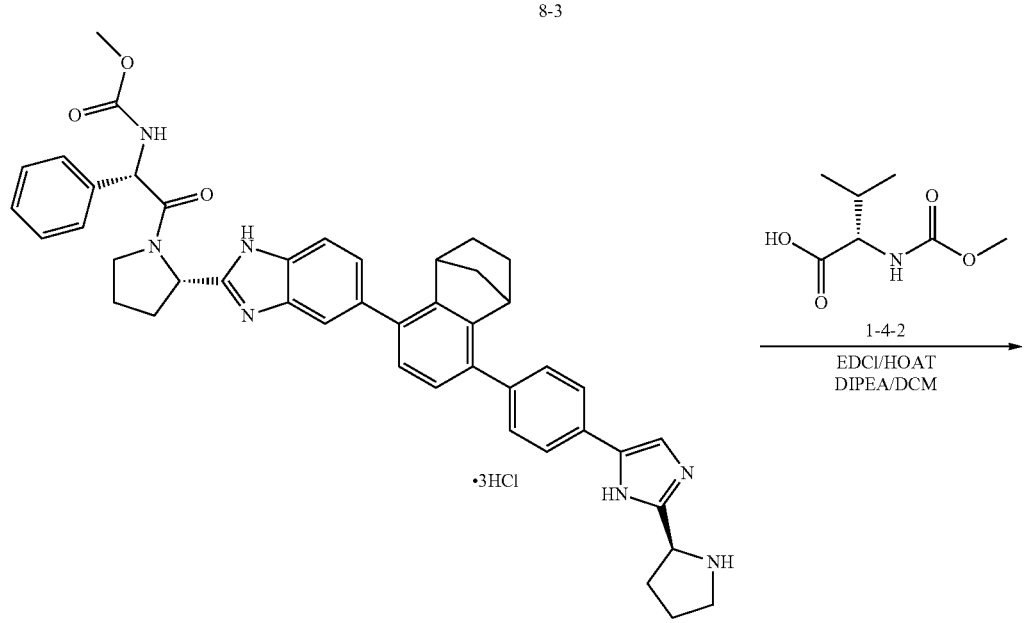
8-4
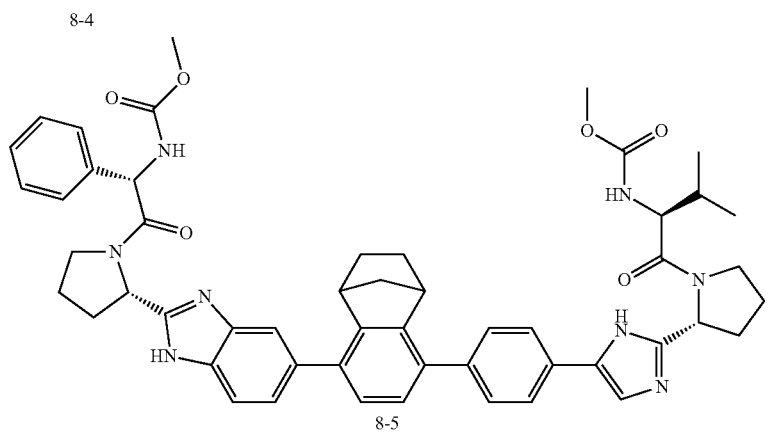
8-5
Step 1) the Preparation of Compound 8-1
To a solution of compound 3-1 (5.0 g, 12.1 mmol) in EtOAc (40 mL) was added a solution of HCl in EtOAc (15 mL, 4 M) dropwise, and the mixture was stirred at rt for 8 hrs. The reaction process was monitored by LC-MS. After the reaction was completed, the mixture was concentrated in vacuo, then washed with EtOAc (50 mL) and filtered to give the title compound as a white solid (3.5 g, 75%). The compound was characterized by the following spectroscopic data:

MS (ESI, pos.ion) m/z: 386.1 [M+H]⁺.

Step 2) the Preparation of Compound 8-2

A suspension of compound 8-1 (1.0 g, 2.6 mmol), compound 8-1-2 (0.6 g, 2.86 mmol), EDCI (0.55 g, 2.86 mmol) and HOAT (0.36 g, 2.6 mmol) in DCM (15 mL) was stirred at 0° C., then DIPEA (1.72 mL, 10.4 mmol) was added dropwise. At the end of addition, the mixture was stirred at rt for 3 hrs. After the reaction was completed, the mixture was diluted with DCM (40 mL), washed with NH₄Cl aqueous solution and brine, dried over anhydrous Na₂SO₄ and concentrated in vacuo. The residue was purified by a silica gel column chromatography (PE/EtOAc (v/v)=1/2) to give the title compound as a white solid (0.75 g, 58%). The compound was characterized by the following spectroscopic data:

¹H NMR (400 MHz, CDCl₃) δ (ppm): 10.6 (brs, 1H), 8.81 (m, 1H), 7.90 (m, 1H), 7.73-7.67 (m, 2H), 7.44-7.37 (m, 4H), 7.24-7.26 (m, 1H), 6.00-6.02 (m, 1H), 5.47-5.42 (m, 2H), 3.79-3.73 (m, 1H), 3.69 (s, 3H), 3.25-3.23 (m, 1H), 2.94-2.96 (m, 1H), 2.07-2.09 (m, 1H), 2.04-2.01 (m, 2H), 1.95-1.99 (m, 1H), 1.37 (s, 12H).

Step 3) the Preparation of Compound 8-3

A suspension of compound 8-2 (0.41 g, 0.81 mmol), compound 7-1 (0.49 g, 0.81 mmol), Pd(PPh₃)₄ (47 mg, 0.04 mmol) and K₂CO₃ (0.29 g, 2.04 mmol) in mixed solvents of EtOH and H₂O (7.5 mL, v/v=4/1) was stirred at 90° C. under N₂ for 4 hrs. After the reaction was completed, the mixture was poured into 40 mL of water and the resulting mixture was filtered. The filter cake was dissolved in EtOAc (30 mL). The solution was washed with brine, dried over anhydrous Na₂SO₄ and concentrated in vacuo. The residue was purified by a silica gel column chromatography (DCM/MeOH (v/v)=50/1) to give the title compound as a white solid (0.35 g, 52%). The compound was characterized by the following spectroscopic data:

M (ESI, pos.ion) m/z: 890.05 [M+H]⁺;

¹H NMR (400 MHz, CDCl₃) δ (ppm): 10.98 (brs, 1H), 10.50 (brs, 1H), 7.86-7.78 (m, 3H), 7.53-7.47 (m, 6H), 7.42-7.40 (m, 4H), 7.26-7.24 (m, 2H), 6.03-5.98 (m, 1H), 5.49-5.45 (m, 2H), 4.99 (s, 1H), 3.82-3.78 (m, 1H), 3.70 (s, 3H), 3.65 (m, 2H), 3.43 (m, 2H), 3.31-3.25 (m, 1H), 3.07 (m, 1H), 2.95 (m, 1H), 2.20-2.17 (m, 4H), 2.08-1.98 (m, 5H), 1.51 (s, 12H).

Step 4) the Preparation of Compound 8-4

To a solution of compound 8-3 (0.35 g, 0.4 mmol) in EtOAc (4.0 mL) was added a solution of HCl in EtOAc (3 mL, 4 M) dropwise, and the mixture was stirred at rt for 8 hrs. The reaction process was monitored by LC-MS. After the reaction was completed, the mixture was filtered. The filter cake was washed with EtOAc to give the title compound as a white solid (0.28 g, 82%). The compound was characterized by the following spectroscopic data:

MS (ESI, pos.ion) m/z: 732.9 [M+H]⁺.

Step 5) the Preparation of Compound 8-5

A suspension of compound 8-4 (288 mg, 0.34 mmol), compound 1-4-2 (75 mg, 0.41 mmol), EDCI (73 mg, 0.38 mmol) and HOAT (47 mg, 0.34 mmol) in DCM (8.0 mL) was stirred at 0° C. for 5 mins, then DIPEA (0.28 mL, 1.72 mmol) was added dropwise. At the end of addition, the mixture was stirred at rt for 12 hrs. After the reaction was completed, the mixture was diluted with DCM (20 mL), washed with saturated NH₄Cl aqueous solution, dried over anhydrous Na₂SO₄ and concentrated in vacuo. The residue was purified by a silica gel column chromatography (DCM/MeOH (v/v)=50/1) to give the title compound as a white solid (220 mg, 75%). The compound was characterized by the following spectroscopic data:

MS (ESI, pos.ion) m/z: 890.05 [M+H]⁺;

¹H NMR (400 MHz, CDCl₃) δ (ppm): 10.65 (brs, 1H), 7.84-7.61 (m, 4H), 7.52-7.47 (m, 3H), 7.42-7.30 (m, 5H), 7.26-7.24 (m, 3H), 5.70-5.50 (m, 2H), 5.47-5.44 (m, 1H), 5.30-5.27 (m, 1H), 4.38-4.33 (m, 2H), 3.88-3.84 (m, 2H), 3.73 (s, 3H), 3.71 (s, 3H), 2.48-2.33 (m, 2H), 2.32-2.18 (m, 2H), 2.15-1.94 (m, 8H), 1.58-1.36 (m, 4H), 1.13-1.02 (m, 1H), 0.97-0.71 (m, 6H).

Example 9

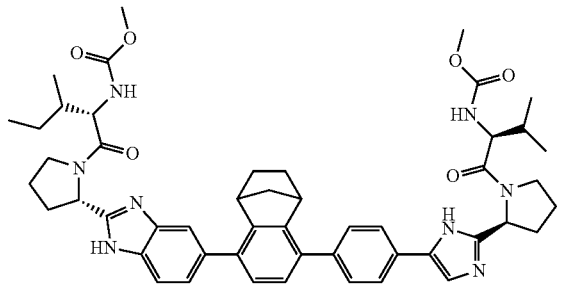 [SMILES: CCC(C)[C@H](NC(=O)OC)C(=O)N1CCC[C@H]1c1nc2cc(-c3ccc(-c4ccc(-c5cnc([C@@H]6CCCN6C(=O)[C@@H](NC(=O)OC)C(C)C)[nH]5)cc4)c4c3C3CCC4C3)ccc2[nH]1]

Synthetic Route:

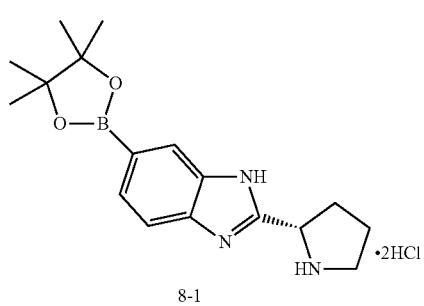

8-1

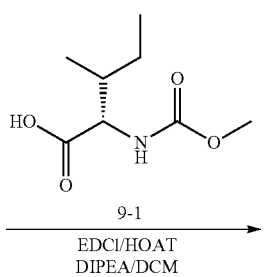

9-1

EDCI/HOAT
DIPEA/DCM

-continued
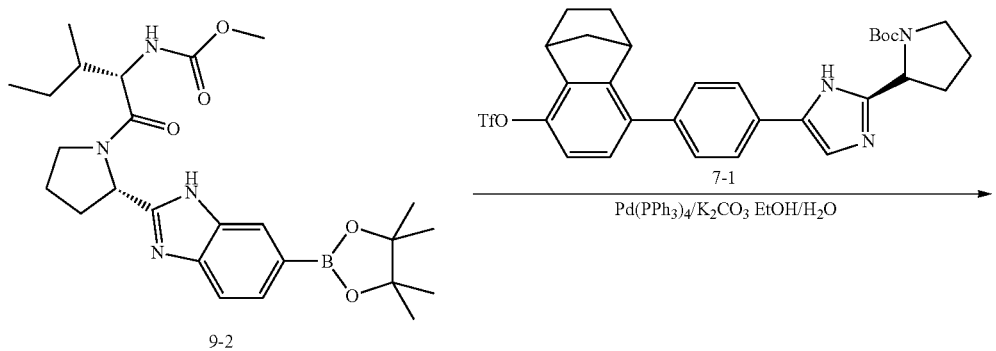
9-2
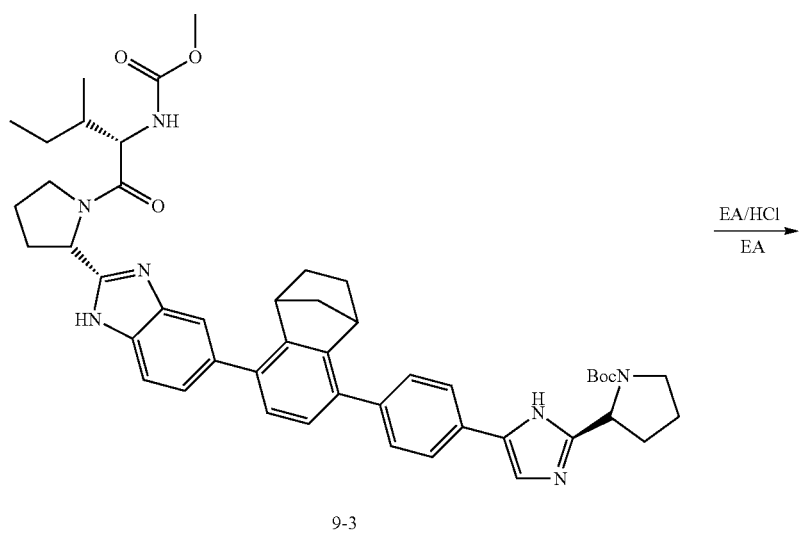
9-3
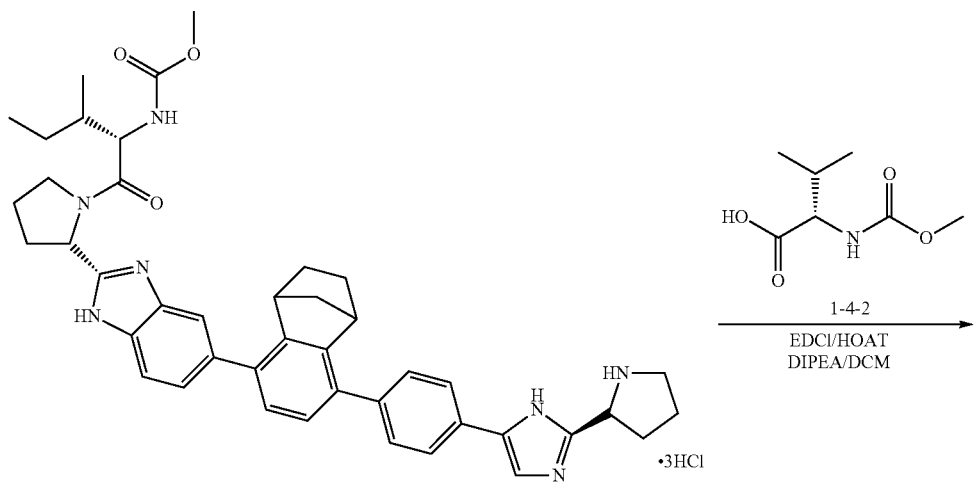
9-4

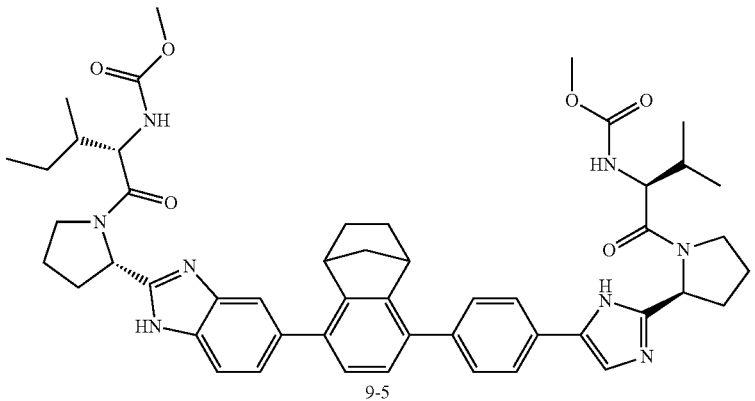 [SMILES: CCC(C)[C@H](NC(=O)OC)C(=O)N1CCC[C@H]1c1nc2cc(-c3ccc(-c4ccc(-c5cnc([C@@H]6CCCN6C(=O)[C@@H](NC(=O)OC)C(C)C)[nH]5)cc4)c4c3C3CCC4C3)ccc2[nH]1]

9-5

Step 1) the Preparation of Compound 9-2

A suspension of compound 8-1 (1.0 g, 2.6 mmol), compound 9-1 (0.59 g, 3.1 mmol), EDCI (0.55 g, 2.86 mmol) and HOAT (0.35 g, 2.6 mmol) in DCM (15 mL) was stirred at 0° C., then DIPEA (1.72 mL, 10.4 mmol) was added dropwise. At the end of addition, the mixture was stirred at rt for 3 hrs. After the reaction was completed, the mixture was diluted with DCM (40 mL), washed with $NH_4Cl$ aqueous solution and brine, dried over anhydrous $Na_2SO_4$ and concentrated in vacuo. The residue was purified by a silica gel column chromatography (PE/EtOAc (v/v)=1/2) to give the title compound as a white solid (1.17 g, 93%). The compound was characterized by the following spectroscopic data:

MS (ESI, pos.ion) m/z: 485.4 $[M+H]^+$;

$^1H$ NMR (400 MHz, $CDCl_3$) δ (ppm): 10.62 (brs, 1H), 8.22 (m, 1H), 7.73-7.65 (m, 2H), 5.72 (d, 1H, J=8.0 Hz), 5.43 (d, 1H, J=8.0 Hz), 4.35-4.31 (m, 1H), 3.95-3.88 (m, 1H), 3.78-3.75 (m, 1H), 3.69-3.67 (m, 4H), 3.08-3.04 (m, 1H), 2.43-2.37 (m, 1H), 2.25-2.15 (m, 2H), 1.91 (s, 1H), 1.74-1.72 (m, 1H), 1.52-1.50 (m, 1H), 1.35 (s, 12H), 1.24 (t, 2H, J=8.0 Hz), 1.12-1.10 (m, 1H), 0.93-0.88 (m, 1H).

Step 2) the Preparation of Compound 9-3

A suspension of compound 9-2 (0.66 g, 1.096 mmol), compound 7-1 (0.53 g, 1.096 mmol), $Pd(PPh_3)_4$ (60 mg, 0.05 mmol) and $K_2CO_3$ (0.38 g, 2.74 mmol) in mixed solvents of EtOH and $H_2O$ (10 mL, v/v=4/1) was stirred at 90° C. under $N_2$ for 3 hrs. After the reaction was completed, the mixture was poured into 40 mL of water and the resulting mixture was filtered. The filter cake was dissolved in EtOAc (30 mL), and the solution was washed with brine, dried over anhydrous $Na_2SO_4$ and concentrated in vacuo. The residue was purified by a silica gel column chromatography (DCM/MeOH (v/v)= 50/1) to give the title compound as a white solid (0.64 g, 73%). The compound was characterized by the following spectroscopic data:

MS (ESI, pos.ion) m/z: 813.01 $[M+H]^+$;

$^1H$ NMR (400 MHz, $CDCl_3$) δ (ppm): 10.64 (brs, 1H), 10.50 (brs, 1H), 7.84-7.61 (m, 4H), 7.52-7.47 (m, 3H), 7.42-7.30 (m, 5H), 7.26-7.24 (m, 3H), 5.70-5.50 (m, 2H), 5.47-5.44 (m, 1H), 5.30-5.27 (m, 1H), 4.38-4.33 (m, 2H), 3.88-3.84 (m, 2H), 3.73 (s, 3H), 3.71 (s, 3H), 2.48-2.33 (m, 2H), 2.32-2.18 (m, 2H), 2.15-1.94 (m, 8H), 1.58-1.36 (m, 4H), 1.13-1.02 (m, 1H), 0.97-0.71 (m, 6H).

Step 3) the Preparation of Compound 9-4

To a solution of compound 9-3 (0.64 g, 0.4 mmol) in EtOAc (8 mL) was added a solution of HCl in EtOAc (4 mL, 4 M) dropwise, and the mixture was stirred at rt for 8 hrs. The reaction process was monitored by LC-MS. After the reaction was completed, the mixture was filtered, and the filter cake was washed with EtOAc to give the title compound as a white solid (0.56 g, 86%). The compound was characterized by the following spectroscopic data:

MS (ESI, pos.ion) m/z: 712.89 $[M+H]^+$;

$^1H$ NMR (400 MHz, $CDCl_3$) δ (ppm): 8.10 (s, 1H), 7.97 (d, 2H, J=8.0 Hz), 7.88 (d, 2H, J=8.0 Hz), 7.82 (s, 1H), 7.75 (dd, 1H, J=8.0 Hz, 2 Hz), 7.68 (d, 2H, J=8.0 Hz), 5.48-5.44 (m, 1H), 5.26-5.22 (m, 1H), 4.29-4.27 (m, 1H), 4.11-4.20 (m, 1H), 4.06-3.95 (m, 1H), 3.66 (s, 3H), 3.64-3.60 (m, 4H), 3.52 (m, 1H), 2.74-2.61 (m, 4H), 2.48-2.20 (m, 5H), 2.10-2.01 (m, 2H), 2.01 (m, 2H), 1.85-1.72 (m, 2H), 1.57 (d, 1H, J=8.0 Hz), 1.50-1.46 (m, 3H), 1.17-1.15 (m, 1H), 0.91-0.85 (m, 6H).

Step 4) the Preparation of Compound 9-5

A suspension of compound 9-4 (279 mg, 0.34 mmol), compound 1-4-2 (75 mg, 0.41 mmol), EDCI (73 mg, 0.38 mmol) and HOAT (47 mg, 0.34 mmol) in DCM (8.0 mL) was stirred at 0° C. for 5 mins, then DIPEA (0.284 mL, 1.72 mmol) was added dropwise. At the end of addition, the mixture was stirred at rt for 12 hrs. After the reaction was completed, the mixture was diluted with DCM (20 mL), washed with saturated $NH_4Cl$ aqueous solution, dried over anhydrous $Na_2SO_4$ and concentrated in vacuo. The residue was purified by a silica gel column chromatography (DCM/MeOH (v/v)= 50/1) to give the title compound as a white solid (177.16 mg, 60%). The compound was characterized by the following spectroscopic data:

MS (ESI, pos.ion) m/z: 870.05 $[M+H]^+$;

$^1H$ NMR (400 MHz, $CDCl_3$) δ (ppm): 10.65 (brs, 1H), 7.84-7.61 (m, 4H), 7.52-7.47 (m, 3H), 7.42-7.30 (m, 5H), 7.26-7.24 (m, 3H), 5.70-5.50 (m, 2H), 5.47-5.44 (m, 1H), 5.30-5.27 (m, 1H), 4.38-4.33 (m, 2H), 3.88-3.84 (m, 2H), 3.73 (s, 3H), 3.71 (s, 3H), 2.48-2.33 (m, 2H), 2.32-2.18 (m, 2H), 2.15-1.94 (m, 8H), 1.58-1.36 (m, 4H), 1.13-1.02 (m, 1H), 0.97-0.71 (m, 6H).

Example 10
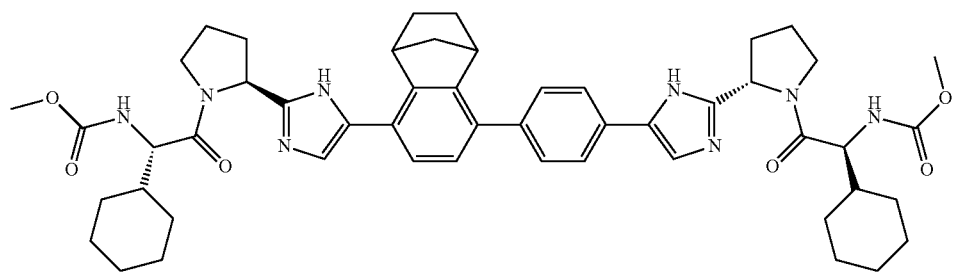 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C5CCCCC5)[nH]4)c4c3C3CCC4C3)cc2)[nH]1)C1CCCCC1]
Synthetic Route:
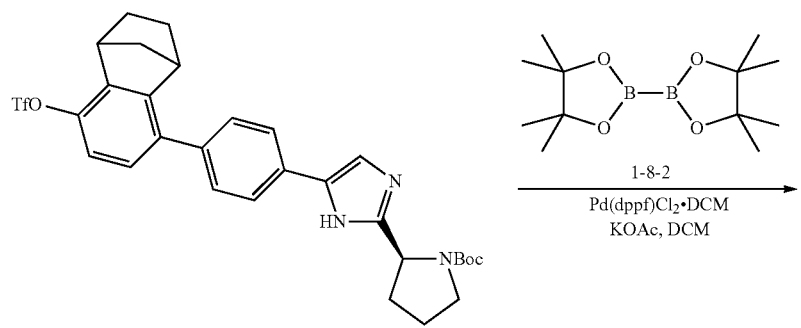
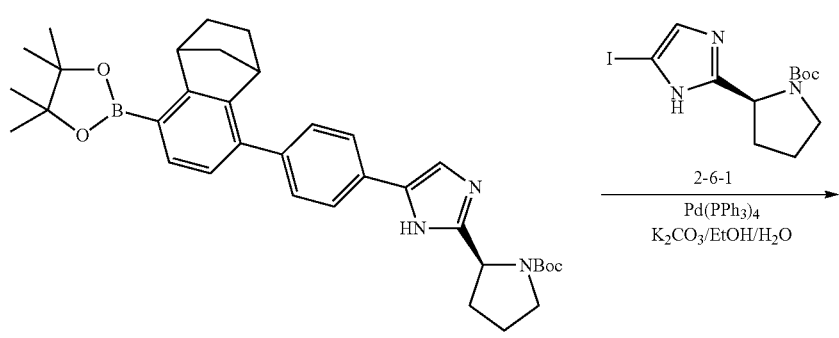
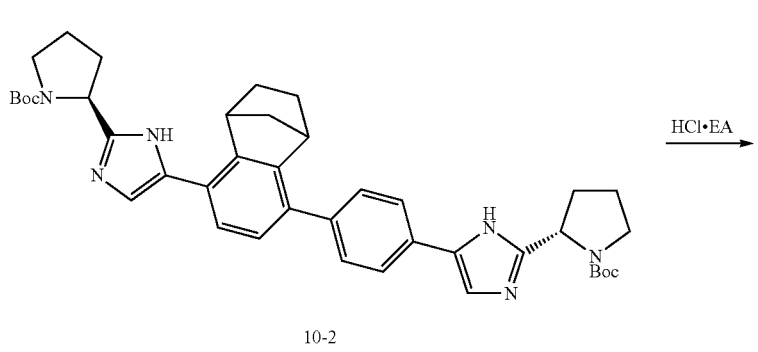

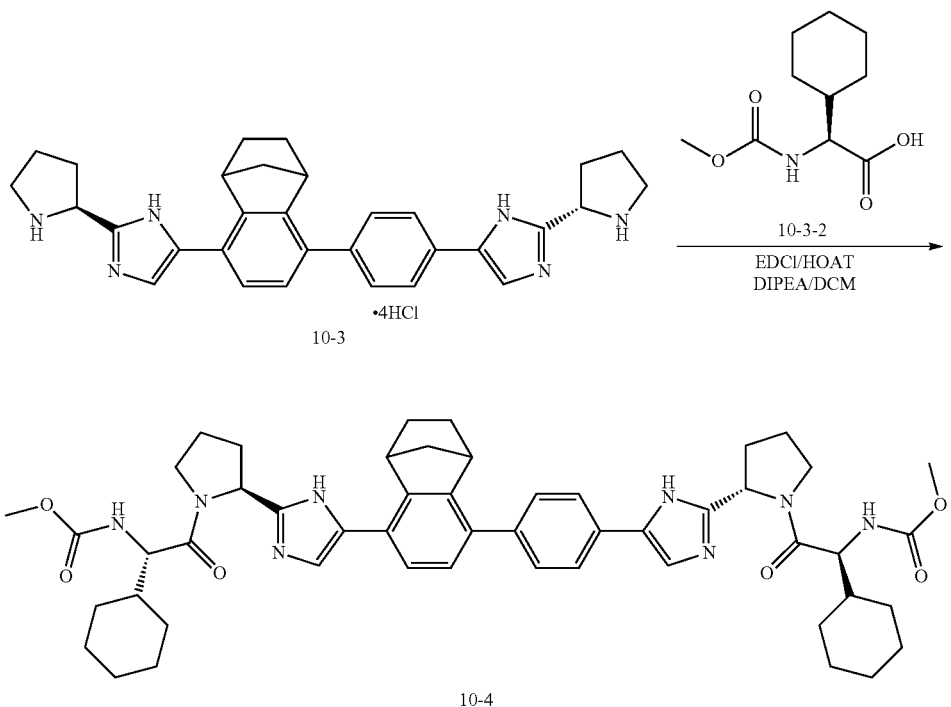

Step 1) the Preparation of Compound 10-1

A mixture of compound 7-1 (2 g, 3.32 mmol), compound 1-8-2 (1.68 g, 6.63 mmol), PdCl$_2$(dppf).CH$_2$Cl$_2$ (0.54 g, 0.66 mmol) and KOAc (0.98 g, 9.96 mmol) in DME (15 mL) was stirred at 90° C. under N$_2$ for 3 hrs. After the reaction was completed, EtOAc (20 mL) was added to the mixture. The resulting mixture was washed with brine, dried over anhydrous Na$_2$SO$_4$ and concentrated in vacuo. The residue was purified by recrystallization to give the title compound as a white solid (1.56 g, 81%). The compound was characterized by the following spectroscopic data:

MS (ESI, pos.ion) m/z: 582.4 [M+H]$^+$;

$^1$H NMR (400 MHz, CDCl$_3$) δ (ppm): 10.53 (br, 1H), 7.63-7.74 (m, 1H), 7.58 (d, 1H, J=7.8 Hz), 7.47 (d, 2H, J=8.2 Hz), 7.25 (s, 1H), 7.16 (d, 1H, J=7.8 Hz), 4.98-5.01 (m, 1H), 3.99 (s, 1H), 3.55 (s, 1H), 3.38-3.48 (m, 2H), 2.98 (s, 1H), 2.22-2.11 (m, 2H), 1.97-1.96 (m, 3H), 1.72-1.70 (m, 1H), 1.35-1.36 (d, 12H, J=3.08 Hz), 1.25-1.26 (m, 4H).

Step 2) the Preparation of Compound 10-2

A suspension of compound 10-1 (1.27 g, 2.18 mmol), compound 2-6-1 (0.95 g, 2.62 mmol), Pd(PPh$_3$)$_4$ (0.25 g, 0.22 mmol) and K$_2$CO$_3$ (0.9 g, 6.54 mmol) in mixed solvents of DME and H$_2$O (18 mL, v/v=5/1) was stirred at 90° C. under N$_2$ for 3 hrs. After the reaction was completed, to the mixture was added EtOAc (20 mL). The resulting mixture was washed with brine, dried over anhydrous Na$_2$SO$_4$ and concentrated in vacuo. The residue was purified by recrystallization to give the title compound as a white solid (1.12 g, 88.1%). The compound was characterized by the following spectroscopic data:

MS (ESI, pos.ion) m/z: 692.3 [M+H]$^+$;

$^1$H NMR (400 MHz, CDCl$_3$) δ (ppm): 10.98 (brs, 1H), 7.82-7.62 (m, 2H), 7.46-7.48 (m, 2H), 7.26 (s, 1H), 7.19-7.21 (m, 1H), 7.17 (s, 1H), 3.75-3.84 (m, 1H), 3.60 (s, 1H), 3.38-3.49 (m, 4H), 2.99 (s, 2H), 2.22-2.09 (m, 3H), 1.97-1.98 (m, 3H), 1.75-1.63 (m, 2H), 1.52 (s, 9H), 1.51 (s, 9H), 1.22-1.32 (m, 8H).

Step 3) the Preparation of Compound 10-3

To a solution of compound 10-2 (1.50 g, 2.17 mmol) in EtOAc (15 mL) was added a solution of HCl in EtOAc (10 mL, 4 M) dropwise. At the end of addition, the mixture was stirred at rt overnight. The mixture was filtered to give the title compound as a solid (1.19 g, 86%), which was used for the next step without further purification.

Step 4) the Preparation of Compound 10-4

A suspension of compound 10-3 (0.27 g, 0.426 mmol), compound 10-3-2 (0.20 g, 0.937 mmol), EDCI (0.18 g, 0.937 mmol) and HOAT (0.11 g, 0.85 mmol) in DCM (8.0 mL) was stirred at 0° C. for 5 mins, then DIPEA (0.694 mL, 4.2 mmol) was added dropwise. At the end of addition, the mixture was stirred at rt for 6 hrs. After the reaction was completed, the mixture was diluted with DCM (20 mL), washed with saturated NH$_4$Cl aqueous solution, dried over anhydrous Na$_2$SO$_4$ and concentrated in vacuo. The residue was purified by a silica gel column chromatography (DCM/MeOH (v/v)=50/1) to give the title compound as a white solid (0.2 g, 53%). The compound was characterized by the following spectroscopic data:

MS (ESI, pos.ion) m/z: 886.1 [M+H]$^+$;

$^1$H NMR (400 MHz, CDCl$_3$) δ (ppm): 10.48 (br, 1H), 7.85-7.70 (m, 2H), 7.43-7.41 (m, 2H), 7.26-7.22 (m, 2H), 7.15-7.14 (m, 2H), 5.55-5.50 (m, 2H), 5.29-5.28 (m, 2H), 4.37-4.32 (m, 2H), 3.87-3.85 (m, 2H), 3.67 (s, 6H), 2.98-2.95 (m, 2H), 2.36-2.34 (m, 2H), 2.21-1.95 (m, 6H), 1.75-1.59 (m, 10H), 1.50-1.49 (m, 4H), 1.18-1.10 (m, 8H).

Example 11
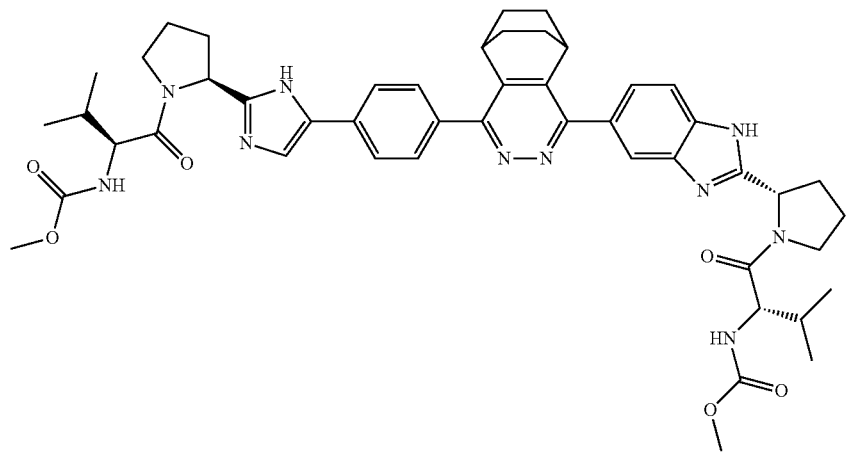 [SMILES: COC(=O)N[C@H](C(=O)N1CCC[C@H]1c1ncc(-c2ccc(-c3nnc(-c4ccc5[nH]c([C@@H]6CCCN6C(=O)[C@@H](NC(=O)OC)C(C)C)nc5c4)c4c3C3CCC4CC3)cc2)[nH]1)C(C)C]
Synthetic Route:
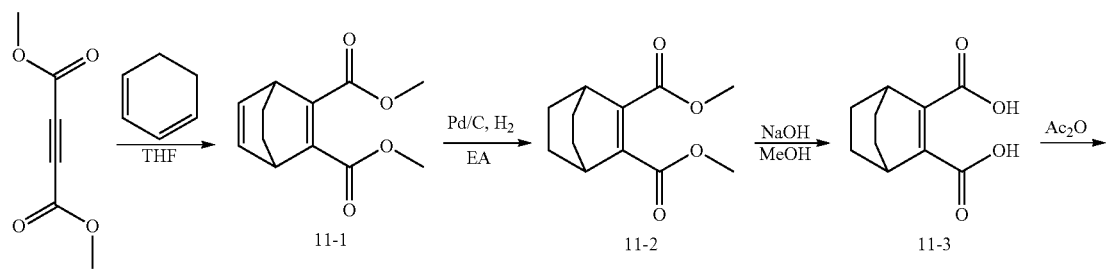
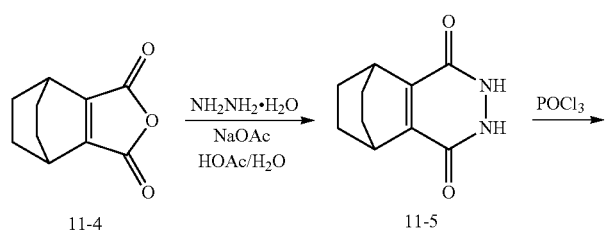
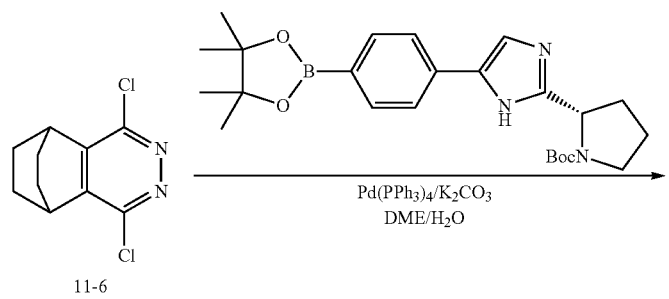

-continued
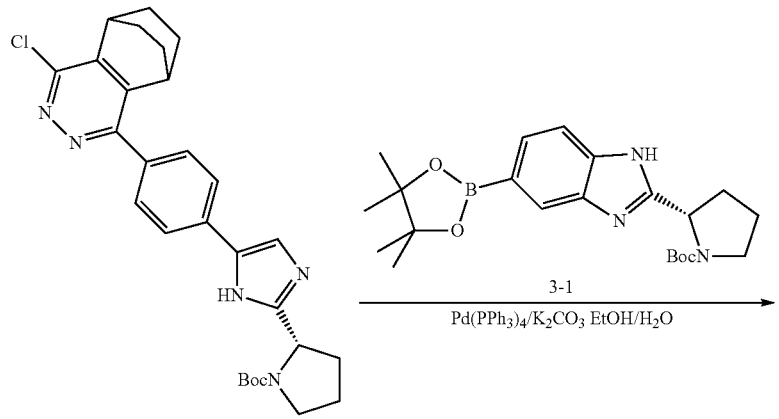
11-7
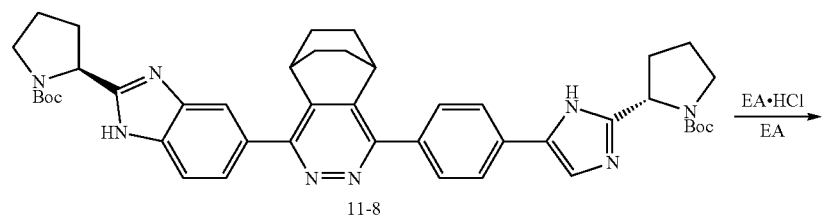
11-8
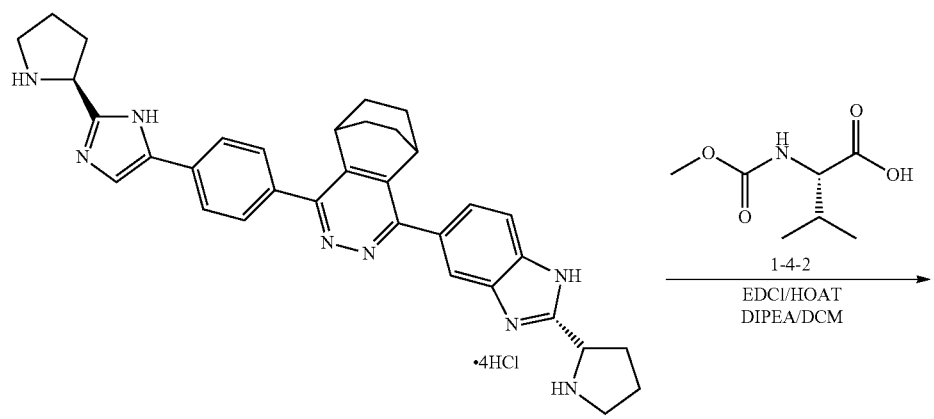
11-9

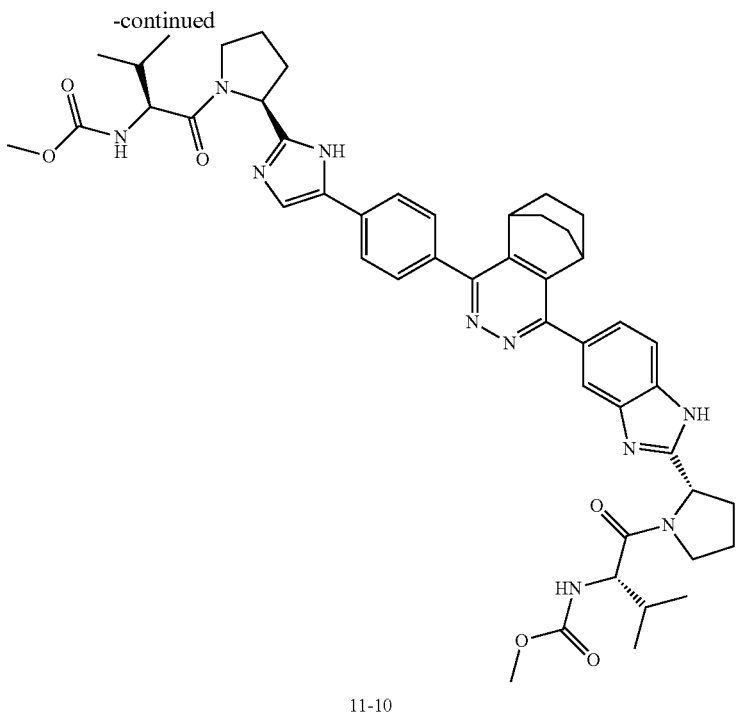

11-10

Step 1) the Preparation of Compound 11-1

A solution of dimethyl but-2-ynedioate (2.0 g, 14 mmol) and cyclohexa-1,3-diene (1.2 g, 15.48 mmol) in fresh THF (10.0 mL) was stirred at 60° C. for 18 hrs. After the reaction was completed, the mixture was concentrated in vacuo, and the residue was purified by a silica gel column chromatography (PE/EtOAc (v/v)=30/1) to give the title compound as colorless oil (2.4 g, 76.0%). The compound was characterized by the following spectroscopic data:

MS (ESI, pos.ion) m/z: 223.2 [M+H]$^+$;
$^1$H NMR (400 MHz, CDCl$_3$) δ (ppm): 6.35 (dd, 2H, J=3.2 Hz, 4.4 Hz), 4.00 (m, 2H), 3.74 (s, 6H), 1.45 (m, 2H), 1.38 (m, 2H).

Step 2) the Preparation of Compound 11-2

A mixture of compound 11-1 (0.8 g, 3.6 mmol) and a catalytic amount of Pd/C (0.04 g) in EtOAc (10 mL) was stirred under H$_2$ at rt for 2 hrs and filtered through a celite pad. The filtrate was concentrated in vacuo to give the title compound as colorless oil (0.78 g, 95%). The compound was characterized by the following spectroscopic data:

MS (ESI, pos.ion) m/z: 225.2 [M+H]$^+$;
$^1$H NMR (400 MHz, CDCl$_3$) δ (ppm): 3.78 (s, 6H), 3.02 (s, 2H), 1.62 (m, 2H), 1.40 (m, 2H).

Step 3) the Preparation of Compound 11-3

To a solution of compound 11-2 (0.78 g, 3.5 mmol) in MeOH (10 mL) was added NaOH aqueous solution (3.5 mL, 10%), and the mixture was stirred at 60° C. for 8 hrs. After the reaction was completed, the solvent MeOH was removed in vacuo, and the mixture was adjusted to pH 1 with hydrochloric acid (1 M), extracted with EtOAc (30 mL×3), dried over anhydrous Na$_2$SO$_4$ and concentrated in vacuo to give the title compound as a white solid (0.68 g, 98%). The compound was characterized by the following spectroscopic data:

MS (ESI, pos.ion) m/z: 197.2 [M+H]$^+$;
$^1$H NMR (400 MHz, DMSO-d$_6$) δ (ppm): 8.62 (brs, 2H), 3.37 (s, 2H), 1.66 (m, 4H), 1.38 (m, 4H).

Step 4) the Preparation of Compound 11-4

A mixture of compound 11-3 (3.7 g, 18.88 mmol) and acetic anhydride (20 mL) was stirred at 100° C. for 1.5 hrs, cooled to rt and concentrated in vacuo to give the title compound as a white solid (3.15 g, 92%). The compound was characterized by the following spectroscopic data:

MS (ESI, pos.ion) m/z: 179.1 [M+H]$^+$;
$^1$H NMR (400 MHz, CDCl$_3$) δ (ppm): 3.26 (m, 2H), 1.85 (d, 4H, J=8.0 Hz), 1.35 (d, 4H, J=8.0 Hz).

Step 5) the Preparation of Compound 11-5

A mixture of compound 11-4 (0.31 g, 1.74 mmol), sodium acetate (220 mg, 2.6 mmol) and hydrazine hydrate (0.13 mL, 2.6 mmol) in acetic acid aqueous solution (10 mL, 50%) was stirred at 100° C. for 16 hrs. After the reaction was completed, the mixture was cooled to rt and filtered. The filter cake was washed with water and MTBE, and dried to give the title compound as a white solid (0.28 g, 85%). The compound was characterized by the following spectroscopic data:

MS (ESI, pos.ion) m/z: 193.2 [M+H]$^+$;
$^1$H NMR (400 MHz, CDCl$_3$) δ (ppm): 3.17 (s, 2H), 1.69 (d, 4H, J=8.0 Hz), 1.15 (d, 4H, J=8.0 Hz).

Step 6) the Preparation of Compound 11-6

A mixture of compound 11-5 (70 mg, 0.36 mmol) and phosphorus oxychloride (3.0 mL) was stirred at 110° C. for 5 hrs. After the reaction was completed, the mixture was cooled to rt and concentrated in vacuo to give the title compound as a white solid (80 mg, 95%). The compound was characterized by the following spectroscopic data:

MS (ESI, pos.ion) m/z: 230.1 [M+H]$^+$;
$^1$H NMR (400 MHz, CDCl$_3$) δ (ppm): 3.46 (s, 2H), 1.90 (d, 4H, J=8.0 Hz), 1.37 (d, 4H, J=8.0 Hz).

Step 7) the Preparation of Compound 11-7

A suspension of compound 11-6 (0.3 g, 1.39 mmol), compound 5-3 (0.57 g, 1.39 mmol), Pd(PPh$_3$)$_4$ (75 mg, 0.94 mmol) and K$_2$CO$_3$ (0.45 g, 3.27 mmol) in mixed solvents of DME and H$_2$O (8 mL, v/v=3/1) was stirred at 90° C. under N$_2$ for 4 hrs. After the reaction was completed, to the mixture was added EtOAc (10 mL). The resulting mixture was washed with brine, dried over anhydrous Na$_2$SO$_4$ and concentrated in vacuo. The residue was purified by a silica gel column chromatography (DCM/MeOH (v/v)=50/1) to give the title compound (0.41 g, 67%). The compound was characterized by the following spectroscopic data:

MS (ESI, pos.ion) m/z: 507.04 [M+H]$^+$;

$^1$H NMR (400 MHz, CDCl$_3$) δ (ppm): 10.54 (brs, 1H), 8.01 (s, 1H), 7.90 (s, 1H), 7.61-7.60 (m, 1H), 7.30 (s, 1H), 4.99-4.98 (m, 1H), 3.53-3.52 (m, 1H), 3.42-3.41 (m, 2H), 2.95 (s, 1H), 2.88 (s, 1H), 2.21-2.16 (m, 2H), 2.04-1.83 (m, 6H), 1.48-1.40 (m, 4H), 1.28-1.27 (d, 9H, J=4.0 Hz).

Step 8) the Preparation of Compound 11-8

A suspension of compound 11-7 (0.397 g, 0.78 mmol), compound 3-1 (0.32 g, 0.78 mmol), Pd(PPh$_3$)$_4$ (45 mg, 0.04 mmol) and K$_2$CO$_3$ (0.27 g, 1.95 mmol) in mixed solvents of EtOH and H$_2$O (8 mL, v/v=3/1) was stirred at 90° C. under N$_2$ for 2 hrs. After the reaction was completed, the mixture was poured into water (20 mL) and filtered. The filter cake was dissolved in EtOAc (30 mL). The solution was washed with brine, dried over anhydrous Na$_2$SO$_4$ and concentrated in vacuo. The residue was purified by a silica gel column chromatography (DCM/MeOH (v/v)=40/1) to give the title compound as a white solid (0.24 g, 42%). The compound was characterized by the following spectroscopic data:

MS (ESI, pos.ion) m/z: 757.91 [M+H]$^+$;

$^1$H NMR (400 MHz, CDCl$_3$) δ (ppm): 10.9 (brs, 1H), 10.5 (brs, 1H), 7.95-7.85 (m, 3H), 7.72-7.70 (d, 3H, J=8.0 Hz), 7.62-7.40 (m, 1H), 7.26-7.30 (m, 1H), 5.18-5.17 (m, 1H), 5.01-4.99 (m, 1H), 3.53-3.44 (m, 6H), 3.07-3.05 (m, 2H), 2.23-2.17 (m, 4H), 2.03-1.98 (m, 2H), 1.87-1.85 (m, 8H), 1.48-1.46 (m, 4H), 1.28-1.27 (d, 18H, J=4.0 Hz).

Step 9) the Preparation of Compound 11-9

To a solution of compound 11-8 (0.24 g, 0.32 mmol) in EtOAc (4.0 mL) was added a solution of HCl in EtOAc (3.0 mL, 4 M) dropwise, and the mixture was stirred at rt for 8 hrs. The reaction process was monitored by LC-MS. The mixture was filtered. The filter cake was washed with EtOAc to give the title compound as a white solid (0.16 g, 73%). The compound was characterized by the following spectroscopic data:

MS (ESI, pos.ion) m/z: 557.9 [M+H]$^+$.

Step 10) the Preparation of Compound 11-10

A suspension of compound 11-9 (160 mg, 0.21 mmol), compound 1-4-2 (94 mg, 0.54 mmol), EDCI (90 mg, 0.47 mmol) and HOAT (58.5 mg, 0.43 mmol) in DCM (6.0 mL) was stirred at 0° C. for 5 mins, then DIPEA (0.355 mL, 2.15 mmol) was added dropwise. At the end of addition, the mixture was stirred at rt for 10 hrs. After the reaction was completed, the mixture was diluted with DCM (20 mL), washed with saturated NH$_4$Cl aqueous solution, dried over anhydrous Na$_2$SO$_4$ and concentrated in vacuo. The residue was purified by a silica gel column chromatography (DCM/MeOH (v/v)=30/1) to give the title compound as a white solid (180 mg, 96%). The compound was characterized by the following spectroscopic data:

MS (ESI, pos.ion) m/z: 872.04 [M+H]$^+$;

$^1$H NMR (400 MHz, CDCl$_3$) δ (ppm): 11.19 (brs, 1H), 10.91 (brs, 1H), 7.96-7.91 (m, 3H), 7.71-7.67 (m, 3H), 7.54-7.51 (m, 2H), 5.82-5.78 (m, 1H), 5.65-5.64 (m, 1H), 5.45 (m, 1H), 5.30 (m, 1H), 5.05-4.93 (m, 1H), 4.37-4.32 (m, 1H), 3.91-3.85 (m, 1H), 3.70 (s, 6H), 3.67-3.63 (m, 1H), 3.51-3.45 (m, 2H), 3.07-3.03 (m, 2H), 2.39-1.85 (m, 6H), 1.66-1.63 (m, 2H), 1.08-1.06 (m, 2H), 0.88 (s, 12H).

Example 12

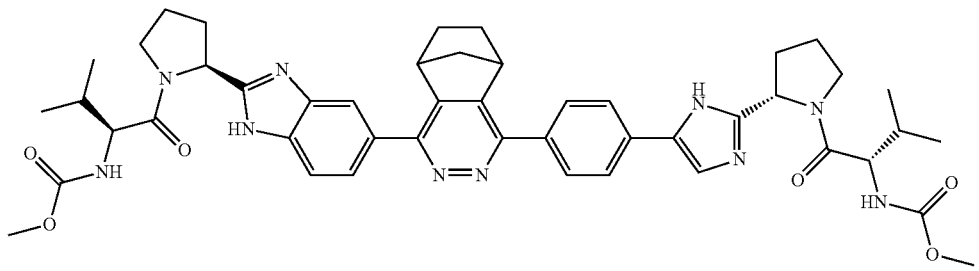

Synthetic Route:

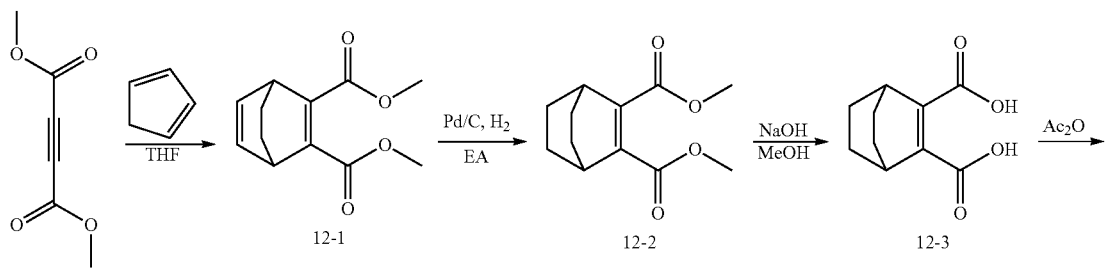

-continued
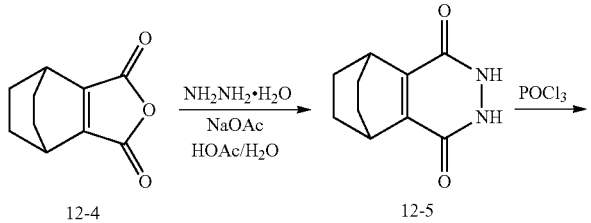
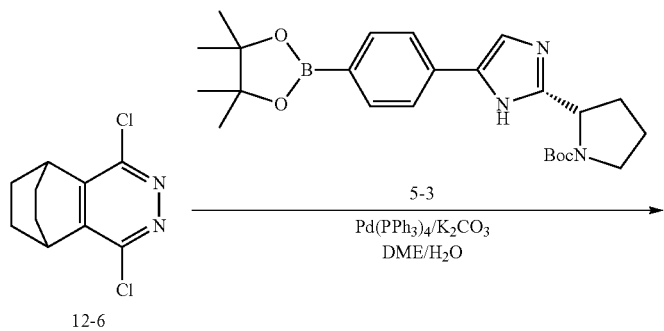
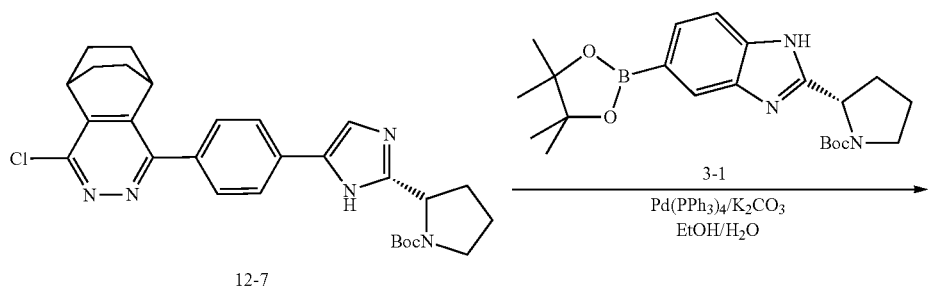
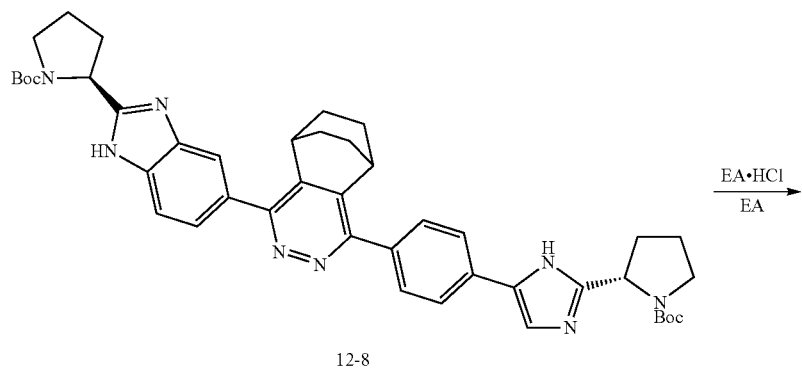
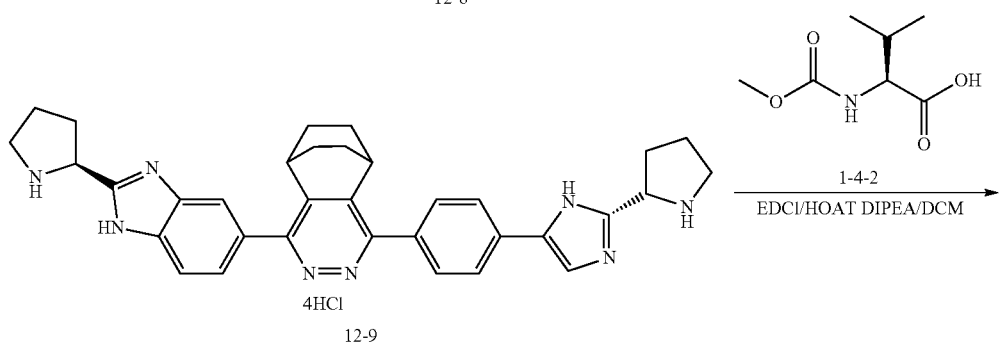

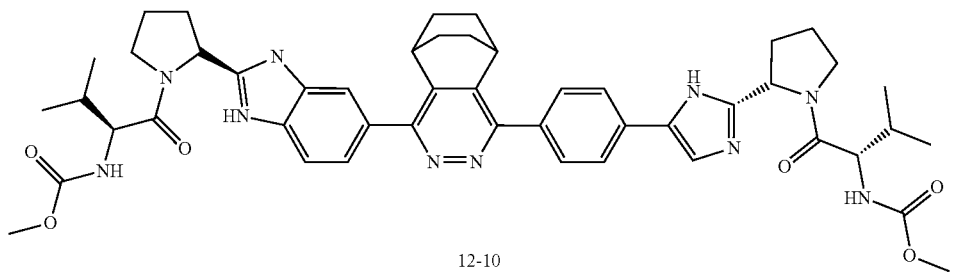

12-10

Step 1) the Preparation of Compound 12-1

A solution of dimethyl but-2-ynedioate (10 g, 70.4 mmol) and fresh cyclopenta-1,3-diene (5.12 g, 77.46 mmol) in fresh THF (20 mL) was stirred at 60° C. for 18 hrs. After the reaction was completed, the mixture was concentrated in vacuo, the residue was purified by a silica gel column chromatography (PE/EtOAc (v/v)=30/1) to give the title compound as colorless oil (9.6 g, 69%). The compound was characterized by the following spectroscopic data:

MS (ESI, pos.ion) m/z: 209.21 [M+H]$^+$;

$^1$H NMR (400 MHz, CDCl$_3$) δ (ppm): 6.91 (t, 2H, J=2.0 Hz), 3.93 (t, 2H, J=2.0 Hz), 3.78 (s, 6H), 2.29-2.26 (m, 1H), 2.11-2.09 (m, 1H).

Step 2) the Preparation of Compound 12-2

To a solution of compound 12-1 (0.5 g, 2.4 mmol) in acetone (8.0 mL) was added a catalytic amount of Pd/C (0.02 g). The mixture was exchanged with hydrogen for 3 times and stirred under H$_2$ at rt for 0.5 hr. The resulting mixture was filtered through a celite pad. The filtrate was concentrated in vacuo. The residue was purified by a silica gel column chromatography (PE/EtOAc (v/v)=25/1) to give the title compound as colorless liquid (0.36 g, 72%). The compound was characterized by the following spectroscopic data:

MS (ESI, pos.ion) m/z: 211.2 [M+H]$^+$;

$^1$H NMR (400 MHz, CDCl$_3$) δ (ppm): 3.64 (s, 6H), 2.97 (s, 2H), 2.55-2.54 (m, 2H), 1.85-1.78 (m, 2H), 1.46-1.41 (m, 2H).

Step 3) the Preparation of Compound 12-3

To a solution of compound 12-2 (7.3 g, 34.76 mmol) in MeOH (35 mL) was added NaOH aqueous solution (35 mL, 10%), and the mixture was stirred at 60° C. for 10 hrs. After the reaction was completed, the solvent MeOH was removed in vacuo. The mixture was adjusted to pH 1 with hydrochloric acid (2 M), extracted with EtOAc (30 mL×3), dried over anhydrous Na$_2$SO$_4$ and concentrated in vacuo to give the title compound as a white solid (3.7 g, 59%). The compound was characterized by the following spectroscopic data:

MS (ESI, pos.ion) m/z: 183.2 [M+H]$^+$;

$^1$H NMR (400 MHz, d$_6$-DMSO) δ (ppm): 8.62 (brs, 2H), 3.55 (s, 2H), 1.96-1.91 (m, 2H), 1.61-1.57 (m, 2H), 1.28-1.24 (m, 2H).

Step 4) the Preparation of Compound 12-4

A mixture of compound 12-3 (1.1 g, 6.04 mmol) and acetic anhydride (16 mL) was stirred at 100° C. for 1.5 hrs. After the reaction was completed, the mixture was cooled to rt and concentrated in vacuo to give the title compound as a white solid (0.8 g, 80%). The compound was characterized by the following spectroscopic data:

MS (ESI, pos.ion) m/z: 165.1 [M+H]$^+$;

$^1$H NMR (400 MHz, CDCl$_3$) δ (ppm): 3.46 (m, 2H), 1.75 (d, 4H, J=8.0 Hz), 1.32 (d, 2H, J=8.0 Hz).

Step 5) the Preparation of Compound 12-5

A mixture of compound 12-4 (0.18 g, 0.98 mmol), sodium acetate (123 mg, 1.5 mmol) and hydrazine hydrate (0.074 mL, 1.5 mmol) in acetic acid aqueous solution (6 mL, 50%) was stirred at 100° C. for 16 hrs. After the reaction was completed, the mixture was cooled to rt and concentrated in vacuo. The residue was washed with water and MTBE, and dried to give the title compound as a white solid (0.11 g, 59%). The compound was characterized by the following spectroscopic data:

MS (ESI, pos.ion) m/z: 179.2 [M+H]$^+$;

$^1$H NMR (400 MHz, CDCl$_3$) δ (ppm): 3.17 (s, 2H), 1.69 (d, 4H, J=8.0 Hz), 1.15 (d, 2H, J=8.0 Hz).

Step 6) the Preparation of Compound 12-6

A mixture of compound 12-5 (0.11 g, 0.62 mmol) and phosphorus oxychloride (3.0 mL) was stirred at 110° C. for 3 hrs. After the reaction was completed, the mixture was cooled to rt and concentrated in vacuo to give the title compound as a white solid (0.13 mg, 95%). The compound was characterized by the following spectroscopic data:

MS (ESI, pos.ion) m/z: 216.1 [M+H]$^+$;

$^1$H NMR (400 MHz, CDCl$_3$) δ (ppm): 3.67 (s, 2H), 2.15 (d, 2H, J=8.0 Hz), 1.95-1.91 (m, 1H), 1.69-1.66 (m, 1H), 1.29 (d, 2H, J=8.0 Hz).

Step 7) the Preparation of Compound 12-7

A suspension of compound 12-6 (0.29 g, 1.35 mmol), compound 5-3 (0.57 g, 1.35 mmol), Pd(PPh$_3$)$_4$ (78 mg, 0.94 mmol) and K$_2$CO$_3$ (0.45 g, 3.27 mmol) in mixed solvents of DME and H$_2$O (8.0 mL, v/v=3/1) was stirred at 90° C. under N$_2$ for 4 hrs. After the reaction was completed, to the mixture was added EtOAc (10 mL). The resulting mixture was washed with brine, dried over anhydrous Na$_2$SO$_4$ and concentrated in vacuo. The residue was purified by a silica gel column chromatography (DCM/MeOH (v/v)=50/1) to give the title compound (0.52 g, 80%). The compound was characterized by the following spectroscopic data:

MS (ESI, pos.ion) m/z: 493.01 [M+H]$^+$;

$^1$H NMR (400 MHz, CDCl$_3$) δ (ppm): 10.54 (brs, 1H), 7.65-7.60 (m, 2H), 7.50-7.48 (m, 1H), 7.43-7.47 (m, 1H), 7.30 (s, 1H), 4.99-4.98 (m, 1H), 3.74 (s, 1H), 3.65 (s, 1H), 3.43 (s, 2H), 2.98 (s, 1H), 2.18-2.10 (m, 4H), 2.03-1.97 (m, 2H), 1.64-1.62 (m, 2H), 1.28-1.27 (d, 9H, J=4.0 Hz).

Step 8) the Preparation of Compound 12-8

A suspension of compound 12-7 (0.52 g, 1.05 mmol), compound 3-1 (0.43 g, 1.05 mmol), Pd(PPh$_3$)$_4$ (60 mg, 0.05 mmol) and K$_2$CO$_3$ (0.36 g, 2.6 mmol) in mixed solvents of EtOH and H$_2$O (8.0 mL, v/v=3/1) was stirred at 90° C. under N$_2$ for 2 hrs. After the reaction was completed, the mixture was poured into water (20 mL) and filtered. The filter cake was dissolved in EtOAc (30 mL). The solution was washed with brine, dried over anhydrous Na$_2$SO$_4$ and concentrated in vacuo. The residue was purified by a silica gel column chromatography (DCM/MeOH (v/v)=40/1) to give the title compound as a white solid (0.7 g, 90%). The compound was characterized by the following spectroscopic data:

MS (ESI, pos.ion) m/z: 743.91 [M+H]$^+$;

$^1$H NMR (400 MHz, CDCl$_3$) δ (ppm): 10.90 (brs, 1H), 10.50 (brs, 1H), 7.95-7.85 (m, 3H), 7.72-7.70 (d, 3H, J=8.0 Hz), 7.62-7.40 (m, 1H), 7.26-7.30 (m, 1H), 5.18-5.17 (m, 1H), 5.01-4.99 (m, 1H), 3.83-3.74 (m, 4H), 3.07-3.05 (m, 2H), 2.23-2.17 (m, 4H), 2.03-1.98 (m, 2H), 1.87-1.85 (m, 8H), 1.48-1.46 (m, 4H), 1.28-1.27 (d, 18H, J=4.0 Hz).

Step 9) the Preparation of Compound 12-9

To a solution of compound 12-8 (0.7 g, 0.94 mmol) in EtOAc (4.0 mL) was added a solution of HCl in EtOAc (3.0 mL, 4 M) dropwise, and the mixture was stirred at rt for 8 hrs. The reaction process was monitored by LC-MS. After the reaction was completed, the mixture was filtered, and the filter cake was washed with EtOAc to give the title compound as a white solid (0.4 g, 62%). The compound was characterized by the following spectroscopic data:

MS (ESI, pos.ion) m/z: 543.9 [M+H]$^+$.

Step 10) the Preparation of Compound 12-10

A suspension of compound 12-9 (400 mg, 0.58 mmol), compound 1-4-2 (254 mg, 1.45 mmol), EDCI (244 mg, 1.27 mmol) and HOAT (158 mg, 1.16 mmo) in DCM (6.0 mL) was stirred at 0° C. for 5 mins, then DIPEA (0.96 mL, 5.8 mmol) was added dropwise. At the end of addition, the mixture was stirred at rt for 10 hrs. After the reaction was completed, the mixture was diluted with DCM (20 mL), washed with saturated NH$_4$Cl aqueous solution, dried over anhydrous Na$_2$SO$_4$ and concentrated in vacuo. The residue was purified by a silica gel column chromatography (DCM/MeOH (v/v)=30/1) to give the title compound as a white solid (460 mg, 92%). The compound was characterized by the following spectroscopic data:

MS (ESI, pos.ion) m/z: 858.01 [M+H]$^+$;

$^1$H NMR (400 MHz, CDCl$_3$) δ (ppm): 11.19 (brs, 1H), 10.91 (brs, 1H), 7.96-7.91 (m, 3H), 7.71-7.67 (m, 3H), 7.54-7.51 (m, 2H), 5.82-5.78 (m, 1H), 5.65-5.64 (m, 1H), 5.45 (m, 1H), 5.30 (m, 1H), 4.45-4.33 (m, 1H), 3.87-3.92 (m, 1H), 3.81-3.75 (m, 1H), 3.65 (s, 6H), 3.67-3.63 (m, 1H), 3.51-3.45 (m, 2H), 3.07-3.03 (m, 2H), 2.39-1.85 (m, 4H), 1.66-1.63 (m, 2H), 1.08-1.06 (m, 2H), 0.88 (s, 12H).

Example 13

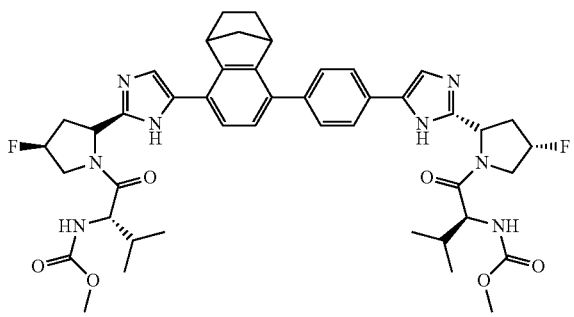

Synthetic Route:

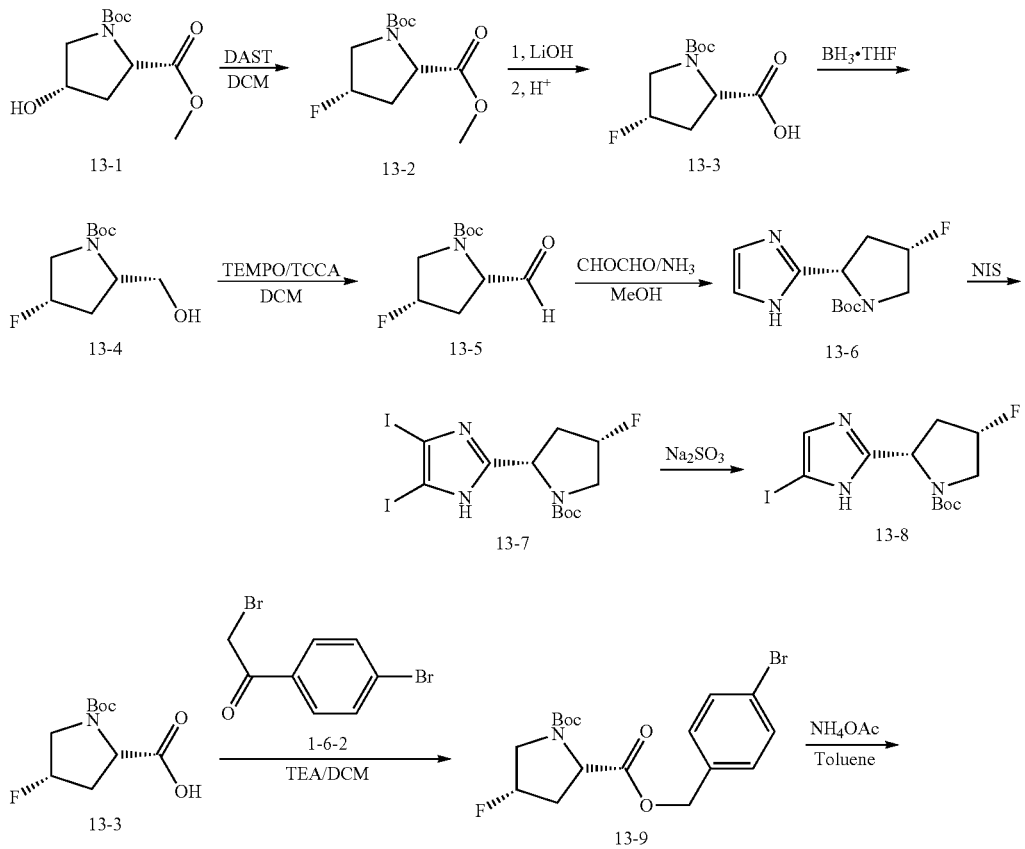

-continued
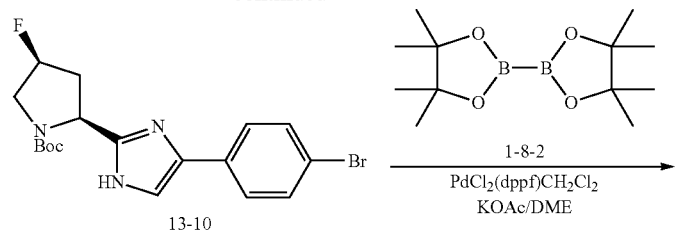
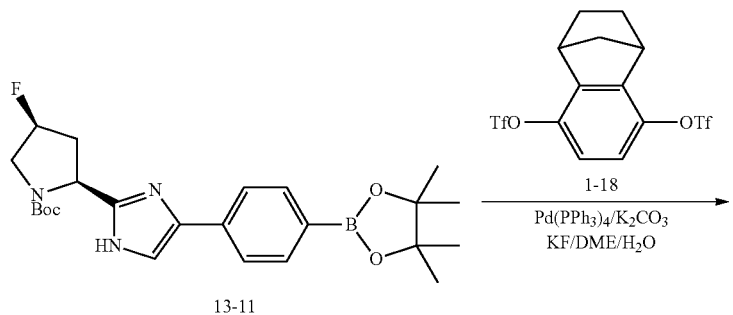
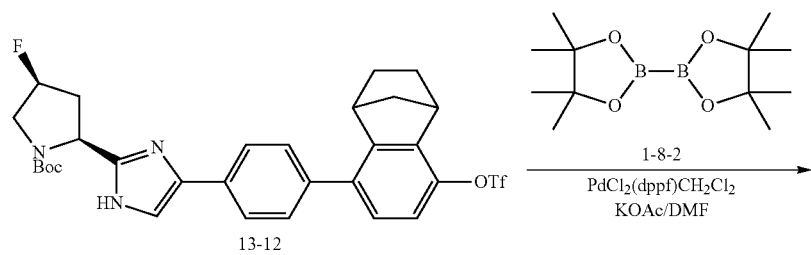
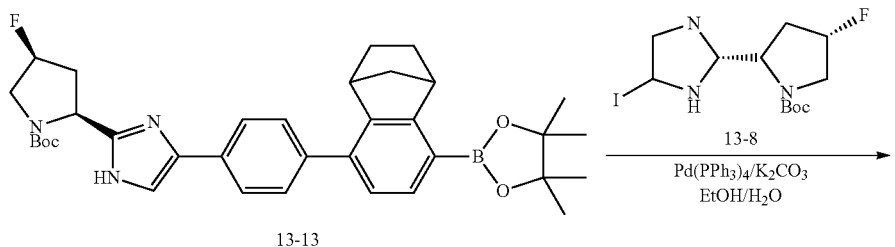
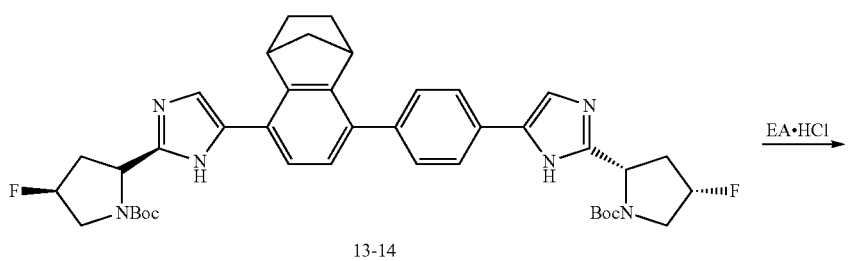
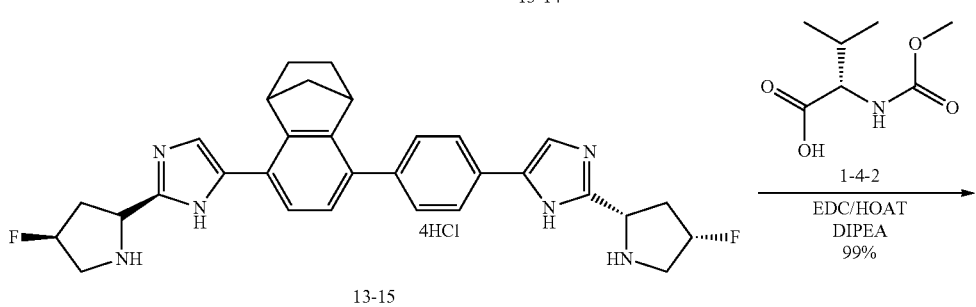

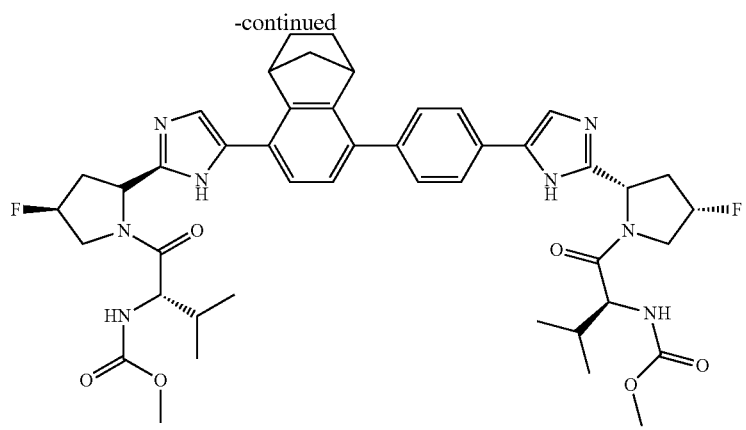

13-16

Step 1) the Preparation of Compound 13-2

To a solution of compound 13-1 (11 g, 44.84 mmol) in DCM (200 mL) at −78° C. was added Et$_2$NSF$_3$ (8.85 mL, 67.3 mmol) dropwise. At the end of addition, the mixture was stirred at −78° C. for 2 hrs and then at rt for another 19 hrs. After the reaction was completed, the reaction was quenched with NH$_4$Cl aqueous solution (100 mL). The resulting mixture was extracted with DCM (100 mL×3), and the combined organic layers were dried over anhydrous Na$_2$SO$_4$ and concentrated in vacuo. The residue was purified by a silica gel column chromatography (PE/EtOAc (v/v)=20/1) to give the title compound as a pale yellow solid (5.0 g, 70%). The compound was characterized by the following spectroscopic data:

MS (ESI, pos.ion) m/z: 248.26 [M+H]$^+$;

$^1$H NMR (400 MHz, CDCl$_3$) δ (ppm): 5.26 and 5.13 (ds, 1H), 4.55-4.41 (m, 1H), 3.88-3.74 (m, 1H), 3.73 (s, 3H), 3.64-3.58 (m, 1H), 2.52-2.44 (m, 1H), 2.40-2.32 (m, 1H), 1.42-1.47 (d, 9H, J=20 Hz).

Step 2) the Preparation of Compound 13-3

To a solution of compound 13-2 (5.83 g, 23.58 mmol) in THF (30 mL) at 0° C. was added LiOH aqueous solution (1.98 g, 30 mL), and the mixture was stirred at rt for 2 hrs and adjusted to pH 5 with diluted hydrochloric acid (1 M). The solvent THF was removed in vacuo, and the aqueous layer was adjusted to pH 2 with diluted hydrochloric acid (1 M) and extracted with EtOAc (80 mL×3). The combined organic layers were dried over Na$_2$SO$_4$ and concentrated in vacuo to give the title compound as a white solid (5.3 g, 96%). The compound was characterized by the following spectroscopic data:

MS (ESI, pos.ion) m/z: 234.24 [M+H]$^+$;

$^1$H NMR (400 MHz, CDCl$_3$) δ (ppm): 8.76 (brs, 1H), 5.28-5.12 (m, 1H), 4.56-4.44 (m, 1H), 3.86-3.58 (m, 2H), 2.77-2.01 (m, 2H), 1.48-1.44 (d, 9H, J=16 Hz).

Step 3) the Preparation of Compound 13-4

To a solution of compound 13-3 (1.3 g, 5.57 mmol) in THF (20 mL) at 0° C. was added borane (8.3 mL, 1 M in THF). The mixture was stirred at rt for 2 hrs, quenched with MeOH (4.0 mL) and concentrated in vacuo. The residue was dissolved in DCM (50 mL). The solution was washed with water (20 mL×3), dried over anhydrous Na$_2$SO$_4$ and concentrated in vacuo to give the title compound as colorless slurry (1.15 g, 88%). The compound was characterized by the following spectroscopic data:

MS (ESI, pos.ion) m/z: 220.24 [M+H]$^+$;

$^1$H NMR (400 MHz, CDCl$_3$) δ (ppm): 5.19-5.06 (m, 1H), 4.12-4.04 (m, 1H), 3.99-3.79 (m, 1H), 3.69-3.63 (m, 1H), 3.60-3.46 (m, 2H), 2.25-2.00 (m, 2H), 1.44 (s, 9H).

Step 4) the Preparation of Compound 13-6

To a solution of compound 13-4 (1.15 g, 5.24 mmol) in DCM (20 mL) at 0° C. was added TCCA (1.22 g, 5.24 mmol), followed by a solution of TEMPO in DCM (82 mg, 0.52 mmol, 3 mL) dropwise, and the mixture was stirred at 0° C. for 1 hr and then at rt for another 1 hr. After the reaction was completed, the reaction mixture was filtered, and the filtrate was washed with saturated Na$_2$SO$_3$ aqueous solution (20 mL×3). The organic layer was dried over anhydrous Na$_2$SO$_4$ and concentrated in vacuo, and the residue was dissolved in a solution of NH$_3$ in MeOH (7 mL, 7 M). The solution was stirred at 0° C. for 0.5 hr and then at rt for another 1 hr. To the mixture was added glyoxal (1.1 mL, 40%) dropwise at 0° C., and solid was precipitate out. At the end of addition, the mixture was stirred at rt for 24 hrs and concentrated in vacuo. The residue was dissolved in DCM. The solution was washed with water, and the aqueous layer was extracted with DCM (30 mL×3). The combined organic layers were dried over anhydrous Na$_2$SO$_4$ and concentrated in vacuo. The residue was purified by a silica gel column chromatography (DCM/MeOH (v/v)=50/1) to give the title compound as a pale yellow solid (0.63 g, 50%). The compound was characterized by the following spectroscopic data:

MS (ESI, pos.ion) m/z: 256.29 [M+H]$^+$;

$^1$H NMR (400 MHz, CDCl$_3$) δ (ppm): 6.98 (s, 2H), 5.36-5.13 (m, 2H), 3.72-3.31 (m, 2H), 2.58-2.32 (m, 2H), 1.48 (s, 9H).

Step 5) the Preparation of Compound 13-7

To a solution of compound 13-6 (0.63 g, 2.47 mmol) in DCM (8 mL) was added NIS (1.23 g, 5.43 mmol) at 0° C., and the mixture was stirred at 0° C. for 2 hrs and filtered. The filtrate was washed with saturated Na$_2$SO$_3$ aqueous solution (20 mL×3), dried over anhydrous Na$_2$SO$_4$ and concentrated in vacuo to give the title compound as a yellow solid (1.07 g), which was used for the next step. The compound was characterized by the following spectroscopic data:

MS (ESI, pos.ion) m/z: 508.08 [M+H]$^+$;

$^1$H NMR (400 MHz, CDCl$_3$) δ (ppm): 5.34-5.08 (m, 2H), 3.72-3.28 (m, 2H), 2.58-2.33 (m, 2H), 1.48 (s, 9H).

Step 6) the Preparation of Compound 13-8

To a solution of compound 13-7 (1.07 g, 2.12 mmol) in ethanol (6.0 mL) were added Na$_2$SO$_3$ (2.14 g, 17 mmol) and water (6 mL), and the mixture was stirred at 90° C. for 30 hrs. After the reaction was completed, the mixture was filtered, and the filtrate was concentrated in vacuo. The residue was dissolved in DCM (40 mL). The solution was washed with water, and the aqueous layer was extracted with DCM (30 mL×3). The combined organic layers were dried over anhydrous $Na_2SO_4$ and concentrated in vacuo. The residue was purified by a silica gel column chromatography (PE/EtOAc (v/v)=1/1) to give the title compound as a yellow solid (0.58 g, 73%). The compound was characterized by the following spectroscopic data:

MS (ESI, pos.ion) m/z: 382.19 $[M+H]^+$;

$^1$H NMR (400 MHz, $CDCl_3$) δ (ppm): 7.04 (s, 1H), 5.35-5.09 (m, 2H), 3.98-3.63 (m, 1H), 3.58-3.29 (m, 1H), 2.55-2.34 (m, 2H), 1.48 (s, 9H).

Step 7) the Preparation of Compound 13-9

To a solution of compound 13-3 (5.0 g, 21.45 mmol) and compound 1-6-2 (4.93 g, 17.87 mmol) in DCM (100 mL) at 0° C. was added TEA (4.34 g, 42.9 mmol) dropwise. At the end of addition, the mixture was stirred at rt for 3 hrs. After the reaction was completed, the reaction was quenched with water (50 mL), and the resulting mixture was extracted with DCM (60 mL×3). The combined organic layers were dried over anhydrous $Na_2SO_4$ and concentrated in vacuo. The residue was purified by a silica gel column chromatography (PE/EtOAc (v/v)=8/1) to give the title compound (4.8 g, 52.2%). The compound was characterized by the following spectroscopic data:

MS (ESI, pos.ion) m/z: 403.26 $[M+H]^+$.

Step 8) the Preparation of Compound 13-10

A mixture of compound 13-9 (4.8 g, 11.19 mmol) and ammonium acetate (12.5 g, 162 mmol) in toluene (50 mL) was refluxed at 110° C. for 5 hrs. After the reaction was completed, the mixture was cooled to rt, and 50 mL of water was added. The resulting mixture was extracted with EtOAc (80 mL×3), and the combined organic layers were dried over anhydrous $Na_2SO_4$ and concentrated in vacuo. The residue was purified by a silica gel column chromatography (PE/EtOAc (v/v)=3/1) to give the title compound (4.2 g, 92%). The compound was characterized by the following spectroscopic data:

MS (ESI, pos.ion) m/z: 411.20 $[M+H]^+$;

$^1$H NMR (400 MHz, $CDCl_3$) δ (ppm): 7.56-7.51 (m, 2H), 7.47-7.45 (m, 2H), 7.22 (s, 1H), 5.38-5.29 (m, 1H), 5.25-5.17 (m, 1H), 4.13-4.07, 3.62-3.39 (m, m, 1H), 3.68-3.58 (m, 1H), 2.68-2.38 (m, 2H), 1.38 (s, 9H).

Step 9) the Preparation of Compound 13-11

A mixture of compound 13-10 (2.0 g, 4.87 mmol), compound 1-8-2 (1.26 g, 4.97 mmol), $Pd(dppf)Cl_2 \cdot CH_2Cl_2$ (0.07 g, 0.097 mmol) and KOAc (1.19 g, 12.2 mmol) in DME (20 mL) was stirred at 90° C. under $N_2$ for 2 hrs. After the reaction was completed, the mixture was cooled to rt, diluted with EtOAc (100 mL) and filtered through a celite pad. Water (30 mL) was added to the filtrate, and the resulting mixture was extracted with EtOAc (40 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound (1.4 g, 64%). The compound was characterized by the following spectroscopic data:

MS (ESI, pos.ion) m/z: 458.35 $[M+H]^+$;

$^1$H NMR (400 MHz, $CDCl_3$) δ (ppm): 7.81-7.79 (m, 2H), 7.65-7.60 (m, 2H), 7.28 (s, 1H), 5.39-5.26 (m, 1H), 5.20-5.12 (m, 1H), 4.07-3.99, 3.59-3.41 (m, 1H), 3.69-3.62 (m, 1H), 2.62-2.51 (m, 2H), 1.34 (s, 12H), 1.28 (s, 9H).

Step 10) the Preparation of Compound 13-12

To a mixture of compound 12-11 (1.16 g, 2.62 mmol), compound 1-18 (1.2 g, 2.62 mmol), $Pd(PPh_3)_4$ (120 mg, 0.1 mmol) and KF (0.30 g, 5.24 mmol) were added DME (12 mL) and pure water (3 mL) via syringe. The mixture was stirred at 90° C. for 2 hrs. After the reaction was completed, the mixture was cooled to rt and diluted with EtOAc (20 mL), then 20 mL of water was added. The resulting mixture was extracted with EtOAc (30 mL×3). The combined organic layers were washed with brine, dried over anhydrous $Na_2SO_4$ and concentrated in vacuo. The residue was purified by a silica gel column chromatography (DCM/MeOH (v/v)=100/1) to give the title compound as a white solid (1.0 g, 62%). The compound was characterized by the following spectroscopic data:

MS (ESI, pos.ion) m/z: 622.3 $[M+H]^+$;

$^1$H NMR (400 MHz, $CDCl_3$) δ (ppm): 7.84-7.82 (m, 2H), 7.69-7.66 (m, 2H), 7.57-7.55 (m, 1H), 7.48-7.44 (m, 1H), 7.40-7.36 (m, 1H), 5.46-5.38 (m, 1H), 5.29-5.21 (m, 1H), 3.73-3.69 (m, 1H), 3.63-3.60 (m, 1H), 2.68-2.46 (m, 2H), 2.03-2.01 (m, 2H), 1.62-21.59 (m, 2H), 1.58-1.46 (m, 4H), 1.32 (s, 9H).

Step 11) the Preparation of Compound 13-13

To a mixture of compound 13-12 (1.0 g, 1.61 mmol), compound 1-8-2 (0.45 g, 10.7 mmol), $PdCl_2(dppf) \cdot CH_2Cl_2$ (80 mg, 0.096 mmol) and KOAc (0.4 g, 4.02 mmol) in DMF (10 mL) was stirred at 120° C. under $N_2$ for 4 hrs. After the reaction was completed, the mixture was cooled to rt, diluted with EtOAc and filtered through a celite pad. The filtrate was washed with water and brine, dried over anhydrous $Na_2SO_4$ and concentrated in vacuo. The residue was purified by a silica gel column chromatography (PE/EtOAc (v/v)=3/1) to give the title compound as a white solid (0.7 g, 73%). The compound was characterized by the following spectroscopic data:

MS (ESI, pos.ion) m/z: 600.4 $[M+H]^+$;

$^1$H NMR (400 MHz, $CDCl_3$) δ (ppm): 7.81-7.65 (m, 2H), 7.62-7.57 (m, 1H), 7.52-7.46 (m, 2H), 7.32-7.25 (m, 1H), 7.19-7.17 (m, 1H), 5.42-5.29 (m, 1H), 5.29-5.24 (m, 1H), 4.20-3.92 (m, 2H), 3.79-3.41 (m, 2H), 2.68-2.41 (m, 2H), 2.00-1.98 (m, 2H), 1.75-1.72 (m, 4H), 1.38 (s, 12H), 1.2 (s, 9H).

Step 12) the Preparation of Compound 13-14

A suspension of compound 13-8 (0.17 g, 0.446 mmol), compound 13-13 (0.25 g, 0.42 mmol), $Pd(PPh_3)_4$ (25 mg, 0.02 mmol) and $K_2CO_3$ (0.17 g, 1.27 mmol) in mixed solvents of EtOH and $H_2O$ (8 mL, v/v=3/1) was stirred at 90° C. under $N_2$ for 2 hrs. After the reaction was completed, the mixture was concentrated in vacuo. EtOAc (50 mL) was added to the residue. The resulting mixture was washed with brine, dried over anhydrous $Na_2SO_4$ and concentrated in vacuo. The residue was purified by a silica gel column chromatography (DCM/EtOH (v/v)=50/1) to give the title compound as a pale yellow solid (370 mg, 95%). The compound was characterized by the following spectroscopic data:

MS (ESI, pos.ion) m/z: 727.85 $[M+H]^+$;

$^1$H NMR (400 MHz, $CDCl_3$) δ (ppm): 7.84-7.82 (m, 1H), 7.70-7.69 (m, 1H), 7.45-7.43 (m, 2H), 7.34-7.33 (m, 1H), 7.27-7.26 (m, 1H), 7.20-7.18 (m, 2H), 5.49-5.43 (m, 4H), 4.24-4.22 (m, 2H), 3.96-3.90 (m, 2H), 3.69-3.67 (m, 2H), 3.58-3.54 (m, 2H), 3.11-3.06 (m, 2H), 2.56-2.31 (m, 4H), 1.52-1.50 (m, 2H), 1.40 (d, 18H, J=12 Hz).

Step 13) the Preparation of Compound 13-15

To a solution of compound 13-14 (0.37 g, 0.51 mmol) in EtOAc (4.0 mL) was added a solution of HCl in EtOAc (3.0 mL, 4 M) dropwise. At the end of addition, the mixture was stirred at rt for 8 hrs. After the reaction was completed, the reaction mixture was concentrated in vacuo, and EtOAc (4.0 mL) was added. The mixture was stirred and pulped, then filtered to give the title compound as a pale yellow solid (0.2 g, 60%), which was used for the next step without further purification. The compound was characterized by the following spectroscopic data:

MS (ESI, pos.ion) m/z: 527.85 [M+H]$^+$.

Step 14) the Preparation of Compound 13-16

A suspension of compound 13-15 (0.2 g, 0.29 mmol), compound 1-4-2 (0.11 g, 0.65 mmol), EDCI (0.12 g, 0.65 mmol) and HOAT (0.08 g, 0.59 mmol) in DCM (5.0 mL) was stirred at 0° C., then DIPEA (0.49 mL, 2.97 mmol) was added dropwise. At the end of addition, the mixture was stirred at rt for 3 hrs. After the reaction was completed, the mixture was diluted with DCM (20.0 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=40/1) to give the title compound as a white solid (0.2 g, 80%). The compound was characterized by the following spectroscopic data:

MS (ESI, pos.ion) m/z: 841.96 [M+H]$^+$;

$^1$H NMR (400 MHz, CDCl$_3$) δ (ppm): 7.84-7.82 (m, 1H), 7.70-7.69 (m, 1H), 7.45-7.43 (m, 2H), 7.34-7.33 (m, 1H), 7.27-7.26 (m, 1H), 7.20-7.18 (m, 2H), 5.49-5.43 (m, 4H), 5.37-5.34 (m, 2H), 4.24-4.22 (m, 2H), 3.96-3.90 (m, 2H), 3.70 (s, 6H), 3.69-3.67 (m, 2H), 3.58-3.54 (m, 2H), 3.11-3.06 (m, 2H), 2.56-2.31 (m, 4H), 1.74-1.72 (m, 2H), 1.52-1.50 (m, 2H), 1.25 (s, 12H).

Example 14

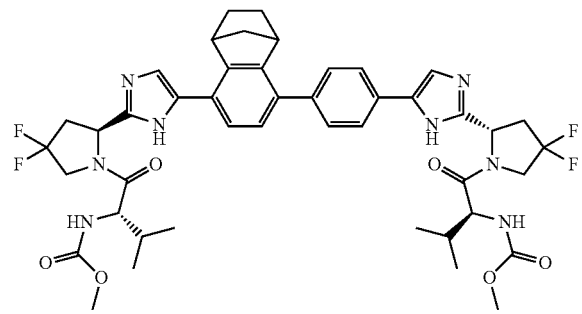 [SMILES: COC(=O)N[C@H](C(=O)N1CC(F)(F)C[C@H]1c1ncc(-c2ccc(-c3ccc(-c4cnc([C@@H]5CC(F)(F)CN5C(=O)[C@@H](NC(=O)OC)C(C)C)[nH]4)c4c3C3CCC4C3)cc2)[nH]1)C(C)C]

Synthetic Route:

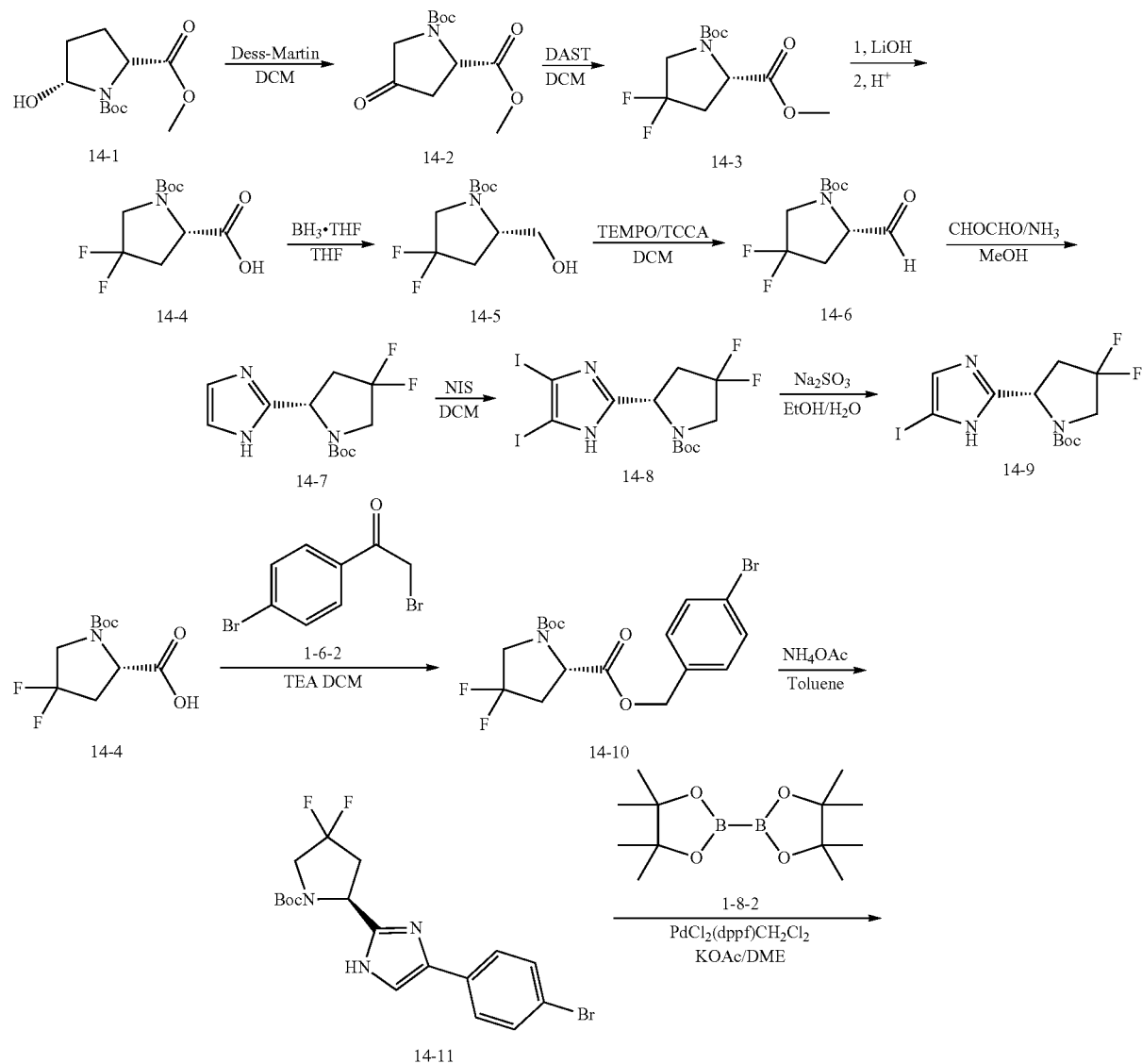

-continued
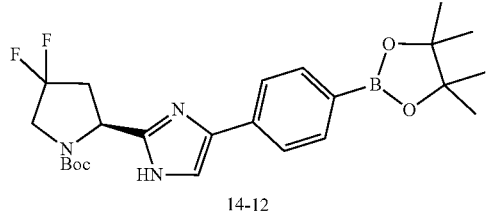 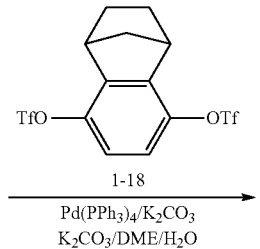
14-12
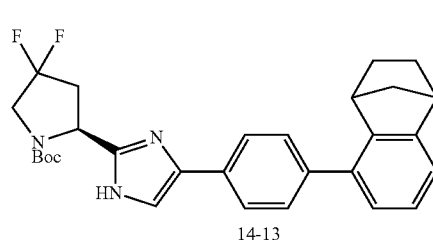 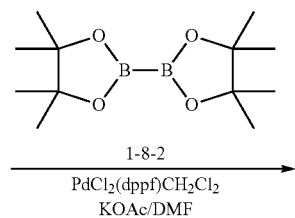
14-13
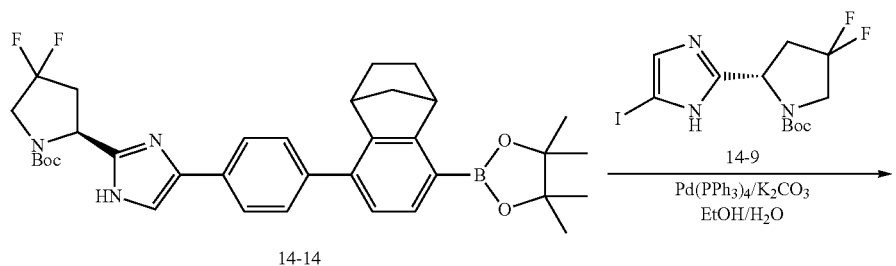
14-14
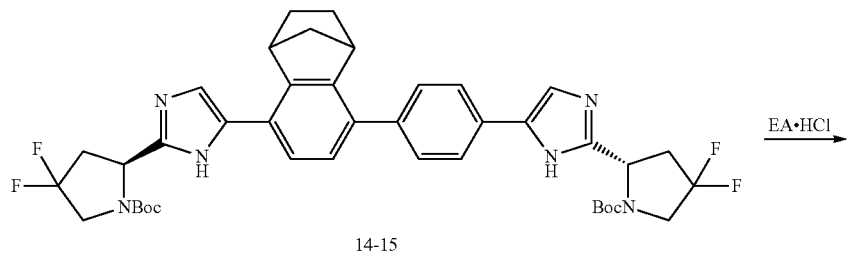
14-15
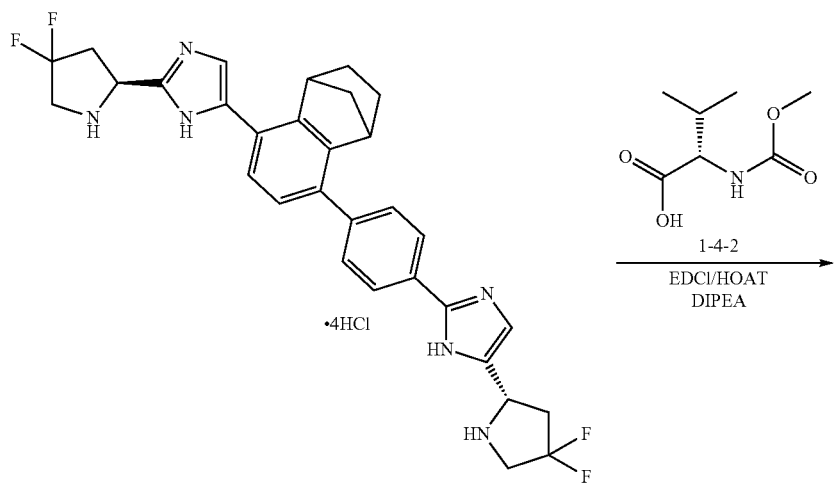
14-16

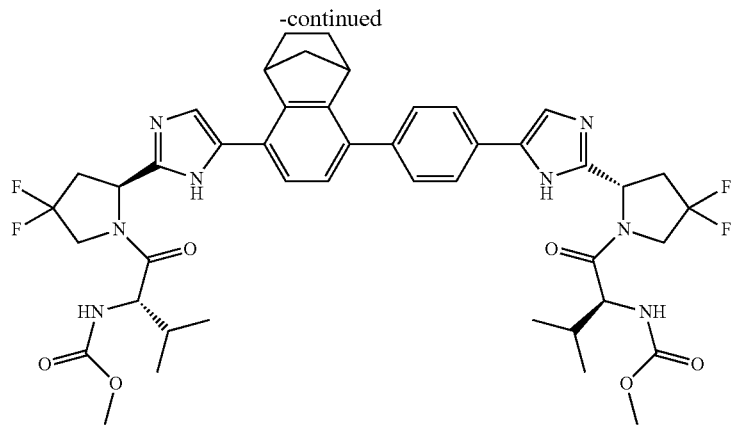

14-17

Step 1) the Preparation of Compound 14-2

To a solution of compound 14-1 (6.8 g, 27.97 mmol) in DCM (70 mL) at 0° C. was added Dess-Martin periodinane (23.7 g, 56 mmol) in portions. At the end of addition, the mixture was stirred at rt for 7 hrs. After the mixture was completed, the reaction was quenched with $Na_2S_2O_3$ aqueous solution, and the mixture was filtered through a celite pad. The filtrate was extracted with DCM (100 mL×3). The combined organic layers were dried over anhydrous $Na_2SO_4$ and concentrated in vacuo. The residue was purified by a silica gel column chromatography (PE/EtOAc (v/v)=6/1) to give the title compound as pale yellow liquid (5.86 g, 85%).

Step 2) the Preparation of Compound 14-3

To a solution of compound 14-2 (5.8 g, 23.9 mmol) in DCM (70 mL) at −78° C. was added $Et_2NF_3$ (4.85 mL, 35.9 mmol) dropwise. At the end of addition, the mixture was stirred at −78° C. for 2 hrs and then at rt for another 19 hrs. The reaction was quenched with $NH_4Cl$ aqueous solution (50 mL), and the resulting mixture was extracted with DCM (60 mL×3). The combined organic layers were dried over anhydrous $Na_2SO_4$ and concentrated in vacuo. The residue was purified by a silica gel column chromatography (PE/EtOAc (v/v)=20/1) to give the title compound as pale yellow liquid (5.0 g, 79%). The compound was characterized by the following spectroscopic data:

MS (ESI, pos.ion) m/z: 266.25 [M+H]$^+$;

$^1$H NMR (400 MHz, $CDCl_3$) δ (ppm): 4.68-4.63 (m, 1H), 4.01-3.87 (m, 1H), 3.78 (s, 3H), 3.75-3.63 (m, 1H), 2.84-2.66 (m, 1H), 2.51-2.31 (m, 1H), 1.43 (d, 9H, J=16 Hz).

Step 3) the Preparation of Compound 14-4

To a solution of compound 14-3 (5.0 g, 18.86 mmol) in THF (40 mL) at 0° C. was added LiOH aqueous solution (1.5 g, 20 mL), and the mixture was stirred at rt for 2 hrs. After the reaction was completed, the reaction was adjusted to pH 5 with diluted hydrochloric acid (1 M), and the solvent THF was removed in vacuo. The aqueous layer was adjusted to pH 2 with diluted hydrochloric acid (1 M). The resulting mixture was extracted with EtOAc (80 mL×3). The combined organic layers were dried over anhydrous $Na_2SO_4$ and concentrated in vacuo to give the title compound as a white solid (4.54 g, 94%). The compound was characterized by the following spectroscopic data:

MS (ESI, pos.ion) m/z: 252.23 [M+H]$^+$;

$^1$H NMR (400 MHz, $CDCl_3$) δ (ppm): 9.60 (brs, 1H), 4.94-4.72, 4.60-4.57 (m, m, 1H), 3.89-3.74 (m, 2H), 2.78-2.48 (m, 2H), 1.44 (d, 9H, J=16 Hz).

Step 4) the Preparation of Compound 14-5

To a solution of compound 14-4 (2.37 g, 9.43 mmol) in THF (30 mL) at 0° C. was added borane (14.2 mL, 1 M in THF), and the mixture was stirred at rt for 2 hrs. After the reaction was completed, the mixture was quenched with MeOH (4.0 mL), and the solvent THF was removed in vacuo. The residue was dissolved in DCM (100 mL). The solution was washed with water (40 mL×3), dried over anhydrous $Na_2SO_4$ and concentrated in vacuo to give the title compound as colorless slurry (1.8 g, 80%). The compound was characterized by the following spectroscopic data:

$^1$H NMR (400 MHz, $CDCl_3$) δ (ppm): 4.43-4.27 (m, 1H), 3.59-3.34 (m, 2H), 3.60-3.46 (m, 2H), 2.48-2.18 (m, 2H), 1.44 (d, 9H, J=16 Hz).

Step 5) the Preparation of Compound 14-7

To a solution of compound 14-5 (1.8 g, 7.59 mmol) in DCM (20 mL) at 0° C. was added TCCA (1.77 g, 7.59 mmol), followed by a solution of TEMPO in DCM (120 mg, 0.76 mmol, 5 mL) dropwise, and the mixture was stirred at 0° C. for 1 hr and then at rt for another 1 hr. The reaction mixture was filtered, and the filtrate was washed with saturated $Na_2SO_3$ aqueous solution (40 mL×3). The organic layers were dried over anhydrous $Na_2SO_4$ and concentrated in vacuo. The residue was dissolved in a solution of $NH_3$ in MeOH (20 mL, 7 M), and the solution was stirred at 0° C. for 0.5 hr and then at rt for another 1 hr. To the mixture was added a solution of glyoxal in water (2 mL, 40%) dropwise at 0° C., and solid precipitated out. At the end of addition, the mixture was stirred at rt for 24 hrs and concentrated in vacuo. The residue was dissolved in DCM (50 mL), and the solution was washed with water. The aqueous layer was extracted with DCM (50 mL×3). The combined organic layers were dried over anhydrous $Na_2SO_4$ and concentrated in vacuo. The residue was purified by a silica gel column chromatography (DCM/MeOH (v/v)=60/1) to give the title compound as a pale yellow solid (0.93 g, 50%). The compound was characterized by the following spectroscopic data:

MS (ESI, pos.ion) m/z: 274.28 [M+H]$^+$;

$^1$H NMR (400 MHz, $CDCl_3$) δ (ppm): 7.00 (s, 2H), 5.83-5.80 (m, 1H), 4.05-3.79 (m, 1H), 3.74-3.52 (m, 1H), 3.11-2.33 (m, 2H), 1.51 (s, 9H).

Step 6) the Preparation of Compound 14-8

To a solution of compound 14-7 (0.93 g, 3.4 mmol) in DCM (30 mL) was added NIS (1.7 g, 7.5 mmol) at 0° C., and the mixture was stirred at 0° C. for 2 hrs and filtered. The filtrate was washed with saturated $Na_2SO_3$ aqueous solution (50 mL×3), dried over anhydrous $Na_2SO_4$ and concentrated in vacuo to give the title compound as a yellow solid (1.03 g, 60%), which was used for the next step without further purification. The compound was characterized by the following spectroscopic data:

MS (ESI, pos.ion) m/z: 525.08 [M+H]$^+$;

$^1$H NMR (400 MHz, CDCl$_3$) δ (ppm): 5.13-5.08 (m, 1H), 3.91-3.87 (m, 1H), 3.58-3.46 (m, 2H), 2.74-2.72 (m, 1H), 1.51 (s, 9H).

Step 7) the Preparation of Compound 14-9

To a solution of compound 14-8 (1.03 g, 1.96 mmol) in ethanol (10 mL) were added Na$_2$SO$_3$ (2.47 g, 19.6 mmol) and water (10 mL), and the mixture was stirred at 90° C. for 30 hrs. The mixture was filtered, and the filtrate was concentrated in vacuo. The residue was dissolved in DCM (40 mL). The solution was washed with water, and the aqueous layer was extracted with DCM (40 mL×3). The combined organic layers were dried over anhydrous Na$_2$SO$_4$ and concentrated in vacuo. The residue was purified by a silica gel column chromatography (PE/EtOAc (v/v)=6/1) to give the title compound as a white solid (0.22 g, 33%). The compound was characterized by the following spectroscopic data:

MS (ESI, pos.ion) m/z: 400.18 [M+H]$^+$;

$^1$H NMR (400 MHz, CDCl$_3$) δ (ppm): 7.08 (s, 1H), 5.33-4.95 (m, 1H), 3.91-3.87 (m, 1H), 3.78-3.36 (m, 2H), 2.96-2.55 (m, 1H), 1.49 (s, 9H).

Step 8) the Preparation of Compound 14-10

To a solution of compound 1-6-2 (2.41 g, 8.66 mmol) and compound 14-4 (2.17 g, 8.66 mmol) in DCM (30 mL) at 0° C. was added TEA (2.5 mL, 17.32 mmol) dropwise. At the end of addition, the mixture was stirred at rt for 3 hrs. After the reaction was completed, the reaction was quenched with water (50 mL), and the resulting mixture was extracted with DCM (30 mL×3). The combined organic layers were dried over anhydrous Na$_2$SO$_4$ and concentrated in vacuo to give the title compound (3.6 g), which was used for the next step without further purification. The compound was characterized by the following spectroscopic data:

MS (ESI, pos.ion) m/z: 421.25 [M+H]$^+$.

Step 9) the Preparation of Compound 14-11

A mixture of compound 14-10 (3.6 g, 8.6 mmol) and ammonium acetate (7.0 g, 86 mmol) in toluene (30 mL) was refluxed at 110° C. for 5 hrs. After the reaction was completed, the mixture was cooled to rt, and 60 mL of water was added. The resulting mixture was extracted with EtOAc (80 mL×3), and the combined organic layers were dried over anhydrous Na$_2$SO$_4$ and concentrated in vacuo. The residue was purified by a silica gel column chromatography (PE/EtOAc (v/v)=6/1) to give the title compound (1.4 g, 40%). The compound was characterized by the following spectroscopic data:

MS (ESI, pos.ion) m/z: 429.27 [M+H]$^+$;

$^1$H NMR (400 MHz, CDCl$_3$) δ (ppm): 7.54-7.52 (m, 2H), 7.48-7.46 (m, 2H), 7.26-7.25 (m, 1H), 5.19-5.18 (m, 1H), 3.70-3.52 (m, 2H), 2.78-2.65 (m, 2H), 1.48 (s, 9H).

Step 10) the Preparation of Compound 14-12

A mixture of compound 14-11 (1.4 g, 3.27 mmol), compound 1-8-2 (0.92 g, 3.6 mmol), PdCl$_2$(dppf).CH$_2$Cl$_2$ (0.13 g, 1.16 mmol) and KOAc (0.81 g, 8.17 mmol) in DME (25 mL) was stirred at 90° C. under N$_2$ for 2 hrs. After the reaction was completed, the mixture was diluted with EtOAc (40 mL) and filtered through a celite pad. Water (30 mL) was added to the filtrate, and the resulting mixture was extracted with EtOAc (40 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound (1.5 g, 96%). The compound was characterized by the following spectroscopic data:

MS (ESI, pos.ion) m/z: 476.34 [M+H]$^+$;

$^1$H NMR (400 MHz, CDCl$_3$) δ (ppm): 7.54-7.52 (m, 2H), 7.48-7.46 (m, 2H), 7.26-7.25 (m, 1H), 5.19-5.18 (m, 1H), 3.70-3.52 (m, 2H), 2.78-2.65 (m, 2H), 1.48 (s, 9H), 1.35 (s, 12H).

Step 11) the Preparation of Compound 14-13

To a mixture of compound 14-12 (1.98 g, 4.5 mmol), compound 1-18 (2.14 g, 4.5 mmol), Pd(PPh$_3$)$_4$ (260 mg, 0.225 mmol) and K$_2$CO$_3$ (1.24 g, 9.0 mmol) were added DME (20 mL) and pure water (4.0 mL) via syringe. The mixture was stirred at 90° C. for 2 hrs. After the reaction was completed, the mixture was diluted with EtOAc (50 mL), and 30 mL of water was added. The resulting mixture was extracted with EtOAc (30 mL×3). The combined organic layers were washed with brine, dried over anhydrous Na$_2$SO$_4$ and concentrated in vacuo. The residue was purified by a silica gel column chromatography (PE/EtOAc (v/v)=7/1) to give the title compound as a white solid (1.45 g, 73%). The compound was characterized by the following spectroscopic data:

MS (ESI, pos.ion) m/z: 640.63 [M+H]$^+$;

$^1$H NMR (400 MHz, CDCl$_3$) δ (ppm): 7.77-7.74 (m, 2H), 7.49-7.46 (m, 2H), 7.37-7.32 (m, 1H), 7.28-7.20 (m, 1H), 7.08-7.03 (m, 1H), 5.30-5.23 (m, 1H), 4.00-3.92 (m, 1H), 3.70-3.60 (m, 3H), 2.75-2.80 (m, 2H), 2.03-1.99 (m, 2H), 1.81-1.76 (m, 2H), 1.58-1.46 (m, 2H), 1.51 (s, 9H).

Step 12) the Preparation of Compound 14-14

To a mixture of compound 14-13 (1.45 g, 2.3 mmol), compound 1-8-2 (0.64 g, 2.53 mmol), PdCl$_2$(dppf).CH$_2$Cl$_2$ (90 mg, 0.115 mmol) and KOAc (0.6 g, 5.75 mmol) in DMF (15 mL) was stirred at 120° C. under N$_2$ for 4 hrs. After the reaction was completed, the mixture was diluted with EtOAc (50 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=8/1) to give the title compound as a white solid (1.06 g, 76%). The compound was characterized by the following spectroscopic data:

MS (ESI, pos.ion) m/z: 618.53 [M+H]$^+$;

$^1$H NMR (400 MHz, CDCl$_3$) δ (ppm): 7.77-7.74 (m, 2H), 7.49-7.46 (m, 2H), 7.37-7.32 (m, 1H), 7.28-7.20 (m, 1H), 7.12-7.08 (m, 1H), 5.30-5.23 (m, 1H), 4.00-3.85 (m, 2H), 3.70-3.60 (m, 2H), 3.55-3.36 (m, 2H), 2.75-2.85 (m, 2H), 1.95-1.68 (m, 4H), 1.49 (s, 12H), 1.35 (s, 9H).

Step 13) the Preparation of Compound 14-15

A suspension of compound 14-9 (0.22 g, 0.55 mmol), compound 14-14 (0.34 g, 0.55 mmol), Pd(PPh$_3$)$_4$ (32 mg, 0.027 mmol) and K$_2$CO$_3$ (0.19 g, 1.37 mmol) in mixed solvents of EtOH and H$_2$O (7.5 mL, v/v=4/1) was stirred at 90° C. under N$_2$ for 2 hrs. After the reaction was completed, the mixture was concentrated in vacuo. EtOAc (50 mL) was added to the resulting mixture. The organic layers were washed with brine, dried over anhydrous Na$_2$SO$_4$ and concentrated in vacuo. The residue was purified by a silica gel column chromatography (DCM/MeOH (v/v)=100/1) to give the title compound as a white solid (0.24 g, 58%). The compound was characterized by the following spectroscopic data:

MS (ESI, pos.ion) m/z: 763.84 [M+H]$^+$;

$^1$H NMR (400 MHz, CDCl$_3$) δ (ppm): 10.53 (brs, 1H), 7.83 (brs, 1H), 7.42-7.49 (m, 2H), 7.36-7.32 (m, 2H), 7.20 (d, 1H, J=8.6 Hz), 7.02 (d, 1H, J=8.6 Hz), 5.28-5.21 (m, 2H), 3.98-3.93 (m, 2H), 3.83-3.62 (m, 6H), 2.83-2.79 (m, 2H), 2.06 (s, 2H), 1.77-1.80 (m, 2H), 1.51 (s, 18H), 1.43-1.39 (m, 2H).

Step 14) the Preparation of Compound 14-16

To a solution of compound 14-15 (0.24 g, 0.31 mmol) in EtOAc (4.0 mL) was added a solution of HCl in EtOAc (3 mL, 4 M) dropwise. At the end of addition, the mixture was stirred at rt for 8 hrs. The reaction process was monitored by LC-MS. After the reaction was completed, the reaction mixture was concentrated in vacuo, and EtOAc (4.0 mL) was added, the mixture was stirred and pulped, then filtered to give the title compound as a pale yellow solid (0.2 g, 60%), which was used for the next step without further purification.

Step 15) the Preparation of Compound 14-17

A suspension of compound 14-16 (0.18 g, 0.26 mmol), compound 1-4-2 (0.1 g, 0.57 mmol), EDCI (0.11 g, 0.57 mmol) and HOAT (0.07 g, 0.52 mmol) in DCM (6.0 mL) was stirred at 0° C., then DIPEA (0.43 mL, 2.6 mmol) was added dropwise. At the end of addition, the mixture was stirred at rt for 3 hrs. After the reaction was completed, the mixture was diluted with DCM (20 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=40/1) to give the title compound as a white solid (0.2 g, 80%). The compound was characterized by the following spectroscopic data:

MS (ESI, pos.ion) m/z: 877.94 [M+H]$^+$;

$^1$H NMR (400 MHz, CDCl$_3$) δ (ppm): 10.34 (brs, 2H), 7.94 (brs, 2H), 7.48-7.44 (m, 3H), 7.30-7.26 (m, 1H), 7.22-7.20 (m, 2H), 5.50-5.44 (m, 4H), 4.34-4.31 (m, 2H), 4.27-4.23 (m, 2H), 3.38-3.74 (m, 2H), 3.71 (s, 6H) 3.58-3.56 (m, 2H), 2.88-2.80 (m, 2H), 2.03-1.07 (m, 6H), 1.31 (s, 6H), 1.09 (m, 2H), 0.95-0.85 (m, 6H).

Example 15

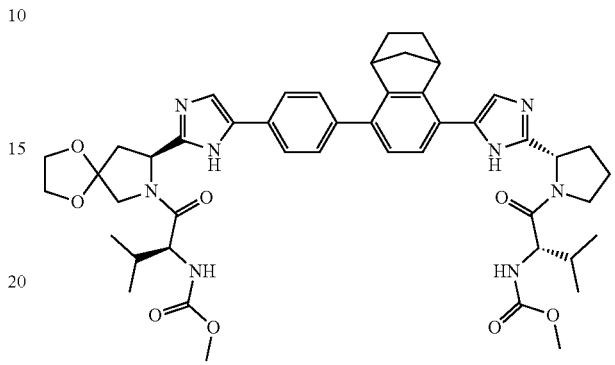

Synthetic Route:

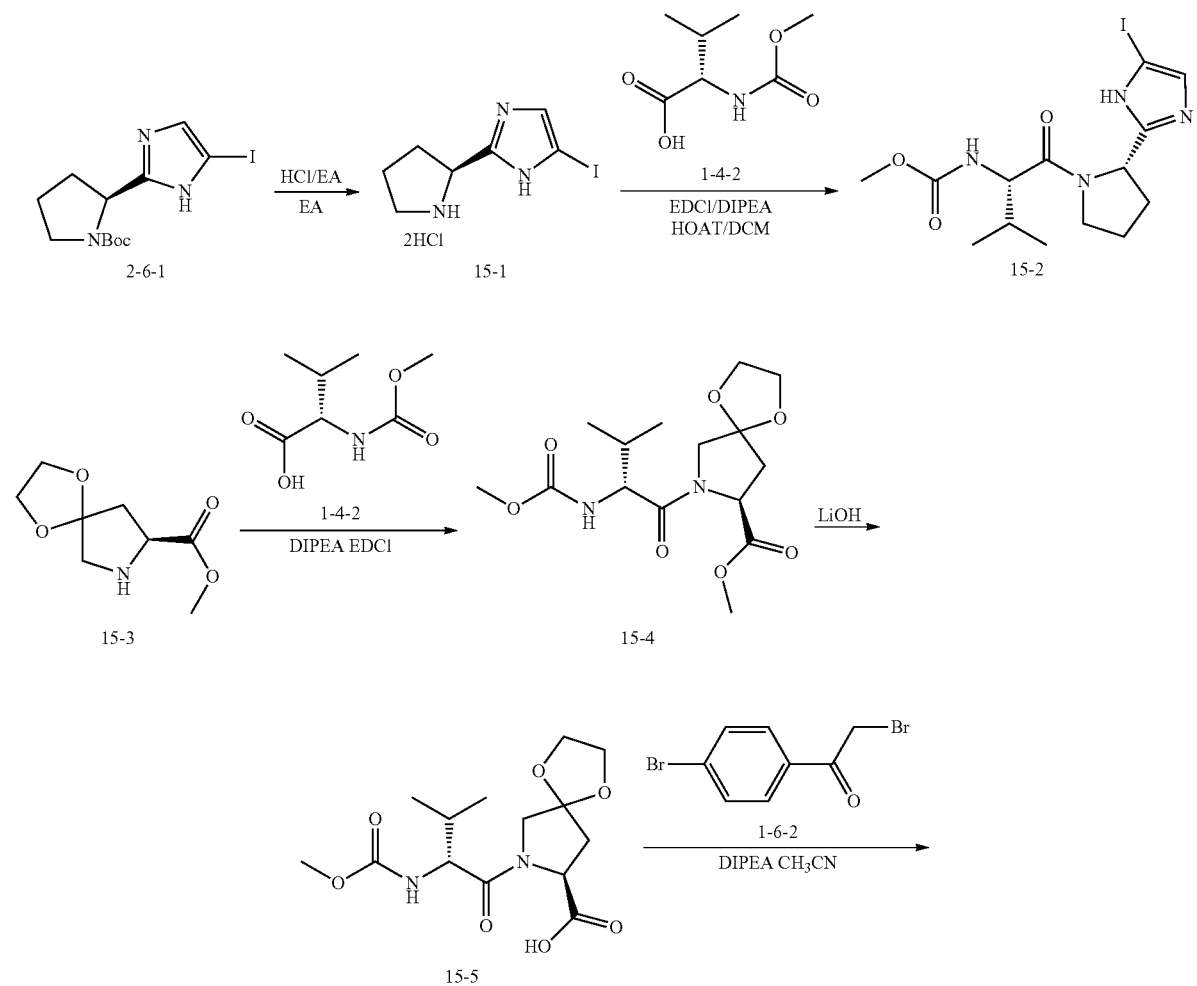

-continued
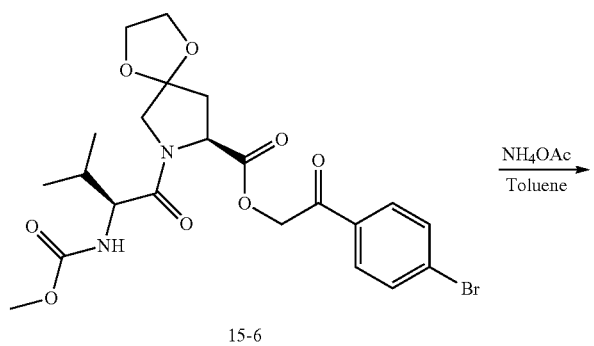
15-6
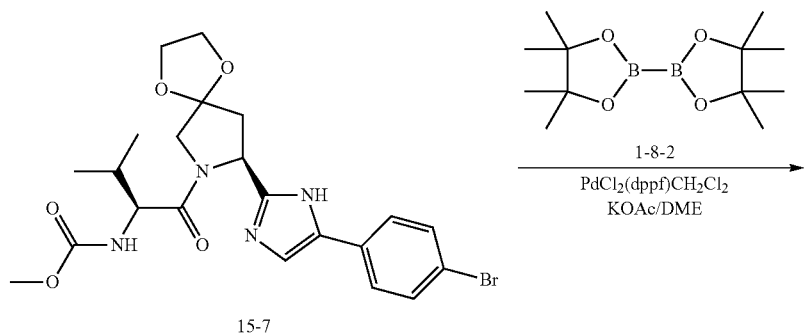
15-7
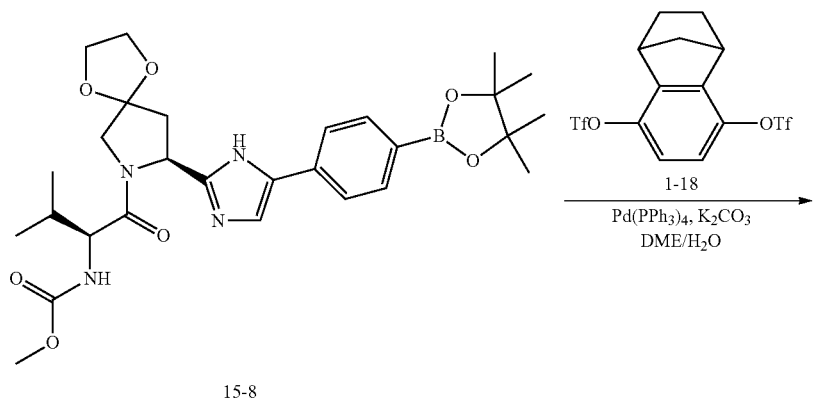
15-8
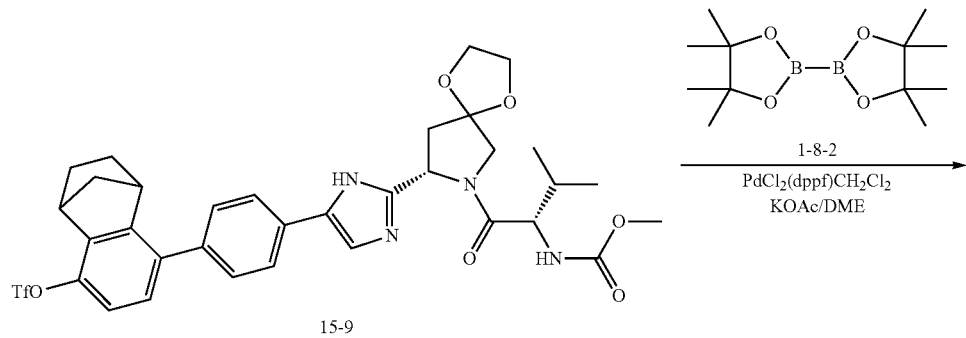
15-9

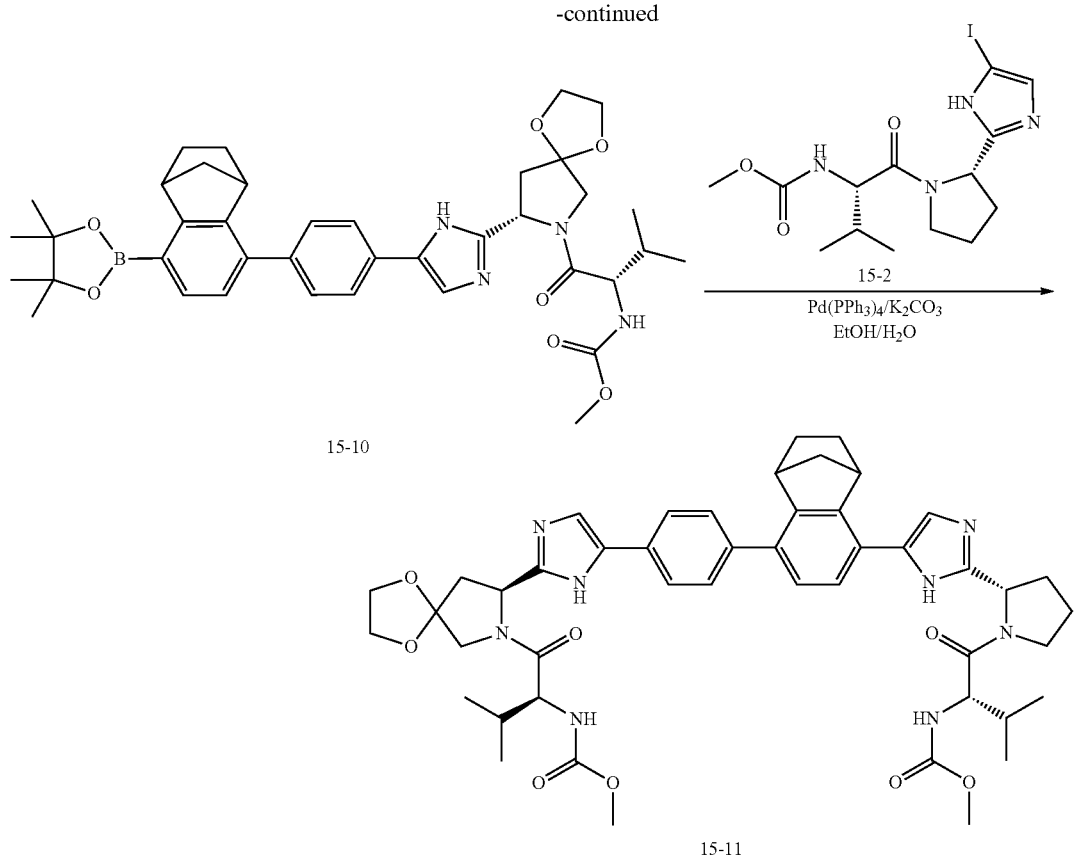

15-10

15-11

Step 1) the Preparation of Compound 15-1

To a solution of compound 2-6-1 (1.50 g, 4.1 mmol) in EtOAc (10 mL) was added a solution of HCl in EtOAc (5.0 mL, 4 M) dropwise. At the end of addition, the mixture was stirred at rt overnight. After the reaction was completed, the mixture was filtered, and the filter cake (1.2 g) was used for the next step without further purification. The compound was characterized by the following spectroscopic data:

MS (ESI, pos.ion) m/z: 264 [M+H]$^+$.

Step 2) the Preparation of Compound 15-2

A suspension of compound 15-1 (1.2 g, 3.6 mmol), compound 1-4-2 (0.69 g, 3.9 mmol) and EDCI (0.75 g, 3.9 mmol) in DCM (20 mL) was stirred at 0° C. for 5 mins, then DIPEA (2.38 mL, 14.4 mmol) was added. At the end of addition, the mixture was stirred at rt for 2 hrs. After the reaction was completed, the mixture was diluted with DCM (40 mL). The resulting mixture was washed with saturated NH$_4$Cl aqueous solution, dried over anhydrous Na$_2$SO$_4$ and concentrated in vacuo. The residue was purified by a silica gel column chromatography (DCM/EtOH (v/v)=50/1) to give the title compound as a pale yellow solid (1.31 g, 86.8%). The compound was characterized by the following spectroscopic data:

MS (ESI, pos. ion) m/z: 421.1[M+H]$^+$;

$^1$H NMR (400 MHz, CDCl$_3$) δ (ppm): 7.35 (s, 1H), 5.32, 5.29 (brs, brs, 1H), 5.20-5.15 (m, 1H), 4.41-4.37 (m, 1H), 3.85-3.78 (m, 1H), 3.69-3.65 (m, 1H), 3.63 (s, 3H), 2.28-2.17 (m, 3H), 2.11-1.96 (m, 2H), 0.97-0.95 (m, 3H), 0.91-0.89 (m, 3H).

Step 3) the Preparation of Compound 15-4

To a solution of compound 15-3 (3.48 g, 18.6 mmol), compound 1-4-2 (3.26 g, 18.6 mmol) and EDCI (7.1 g, 37 mmol) in DCM (50 mL) was added DIPEA (12.3 mL, 74.4 mmol) dropwise at 0° C., and the mixture was stirred at rt for 3 hrs. After the reaction was completed, 50 mL of water was added to the mixture, and the resulting mixture was extracted with CH$_2$Cl$_2$ (50 mL×3). The combined organic layers were dried over anhydrous Na$_2$SO$_4$ and concentrated in vacuo. The residue was purified by a silica gel column chromatography (PE/EtOAc (v/v)=3/1) to give the title compound 15-4 as yellow liquid (2.5 g, 39.1%). The compound was characterized by the following spectroscopic data:

$^1$H NMR (400 MHz, CD$_3$Cl) δ (ppm): 5.32, 5.29 (d, d, 1H), 4.95-4.91 (m, 1H), 4.33-4.29 (m, 1H), 4.01-4.00 (m, 4H), 3.80-3.78 (m, 1H), 3.72 (s, 3H), 3.63 (s, 3H), 3.55-3.50 (m, 1H), 2.76-2.70 (m, 1H), 2.35-2.29 (m, 1H), 2.18-2.06 (m, 1H), 0.97, 0.95 (m, m, 3H), 0.91, 0.89 (m, m, 3H).

Step 4) the Preparation of Compound 15-5

To a solution of compound 15-4 (0.9 g, 2.6 mmol) in THF (5.0 mL) was added lithium hydroxide monohydrate aqueous solution (0.12 g, 5.0 mmol, 5.0 mL) at 0° C., and the mixture was stirred at 40° C. for 12 hrs. The solvent THF was removed and 20 mL of water was added to the mixture, and the aqueous phase was adjusted to pH 2 with hydrochloric acid (1 M) and extracted with EtOAc (25 mL×3). The combined organic layers were washed by brine, dried over anhydrous Na$_2$SO$_4$ and concentrated in vacuo to give the title compound 15-5 as a white solid (0.85 g, 99%). The compound was characterized by the following spectroscopic data:

$^1$H NMR (400 MHz, CD$_3$Cl) δ (ppm): 9.80 (s, 1H), 4.54 (d, 1H, J=7.25 Hz), 4.28 (m, 1H), 4.06 (m, 4H), 3.76 (m, 2H), 3.50 (s, 3H), 2.71 (m, 2H), 2.65 (m, 1H), 0.87 (m, 3H), 0.81 (m, 3H).

Step 5) the Preparation of Compound 15-6

To a mixture of compound 1-6-2 (1.65 g, 5.9 mmol) and compound 15-5 (1.78 g, 5.4 mmol) in CH$_3$CN (30.0 mL) was added DIPEA (1.1 mL, 6.7 mmol) dropwise at 0° C., and the reaction mixture was stirred at rt for 3 hrs. After the reaction was completed, the mixture was concentrated in vacuo. The residue was purified by a silica gel column chromatography (PE/EtOAc (v/v)=3/1) to give the title compound 15-6 as a pale yellow solid (2.76 g, 97.3%). The compound was characterized by the following spectroscopic data:

$^1$H NMR (400 MHz, CDCl$_3$) δ (ppm): 9.30 (s, 1H), 7.95 (d, 2H, J=8.27 Hz), 7.71 (d, 2H, J=8.25 Hz), 5.72-5.34 (m, 2H), 4.52 (d, 1H), 4.29 (m, 1H), 4.19 (m, 4H), 3.77 (m, 2H), 3.69 (s, 3H), 2.71 (m, 1H), 2.65 (m, 2H), 0.91 (m, 3H), 0.89 (m, 3H).

Step 6) the Preparation of Compound 15-7

To a solution of compound 15-6 (3.0 g, 5.7 mmol) in toluene (20 mL) was added NH$_4$OAc (4.4 g, 57.1 mmol), and the mixture was stirred at 120° C. overnight. After the reaction was completed, the mixture was cooled to rt, 40 mL of EtOAc was added, and the resulting mixture was washed with brine, dried over anhydrous Na$_2$SO$_4$ and concentrated in vacuo. The residue was purified by a silica gel column chromatography (PE/EtOAc (v/v)=1/2) to give the title compound as a yellow solid (2.6 g, 89.9%). The compound was characterized by the following spectroscopic data:

$^1$H NMR (400 MHz, CDCl$_3$) δ (ppm): 9.30 (s, 1H), 7.95 (d, 2H, J=8.27 Hz,), 7.71 (d, 2H, J=8.25 Hz,), 4.52 (d, 1H), 4.29 (m, 1H), 4.19 (m, 4H), 3.77 (m, 2H), 3.69 (s, 3H), 2.71 (m, 1H), 2.65 (m, 2H), 0.91 (m, 3H), 0.89 (m, 3H).

Step 7) the Preparation of Compound 15-8

A suspension of compound 15-7 (1.68 g, 3.32 mmol), compound 1-8-2 (1.68 g, 6.63 mmol), PdCl$_2$(dppf).CH$_2$Cl$_2$ (0.54 g, 0.66 mmol) and KOAc (0.98 g, 9.96 mmol) in DME (20 mL) was stirred at 90° C. under N$_2$ for 4 hrs. After the reaction was completed, to the reaction mixture was added 20 mL of EtOAc. The resulting mixture was washed with brine, dried over anhydrous Na$_2$SO$_4$ and concentrated in vacuo. The residue was purified by recrystallization to give the title compound as a white solid (1.46 g, 79.2%). The compound was characterized by the following spectroscopic data:

MS (ESI, pos. ion) m/z: 555.3 [M+H]$^+$;

$^1$H NMR (400 MHz, CDCl$_3$) δ (ppm): 7.64-7.58 (m, 4H), 7.22 (s, 1H), 5.40-5.36 (m, 1H), 5.32, 5.29 (brs, brs, 1H), 4.42-4.38 (m, 1H), 3.98-3.96 (m, 2H), 3.94-3.92 (m, 2H), 3.71-3.69 (m, 1H), 3.67-3.66 (m, 1H), 3.63 (s, 3H), 2.83-2.78 (m, 1H), 2.45-2.39 (m, 1H), 2.23-2.11 (m, 1H), 1.35 (br, 6H), 1.32 (br, 6H), 0.97-0.95 (m, 3H), 0.91-0.89 (m, 3H).

Step 8) the Preparation of Compound 15-9

A suspension of compound 15-8 (1.3 g, 2.34 mmol), compound 1-18 (1.05 g, 2.4 mmol), Pd(PPh$_3$)$_4$ (0.14 g, 0.12 mmol) and K$_2$CO$_3$ (1.30 g, 9.4 mmol) in mixed solvents of DME and H$_2$O (16 mL, v/v=3/1) was stirred at 90° C. under N$_2$ for 3 hrs. After the reaction was completed, EtOAc (30 mL) was added to the mixture. The organic layer was washed with brine, dried over anhydrous Na$_2$SO$_4$ and concentrated in vacuo. The residue was purified by recrystallization to give the title compound as a white solid (1.45 g, 86.1%). The compound was characterized by the following spectroscopic data:

MS (ESI, pos. ion) m/z: 719.2 [M+H]$^+$;

$^1$H NMR (400 MHz, CDCl$_3$) δ (ppm): 7.62-7.58 (m, 2H), 7.52-7.48 (m, 2H), 7.35 (s, 1H), 7.25, 7.23 (s, s, 1H), 7.06, 7.04 (s, s, 1H), 5.56, 5.55 (brs, 1H), 5.40-5.36 (m, 1H), 4.35-4.31 (m, 1H), 3.98-3.96 (m, 2H), 3.94-3.92 (m, 2H), 3.71-3.69 (m, 1H), 3.68-3.67 (m, 1H), 3.66 (s, 3H), 3.60-3.57 (m, 1H), 3.52-3.49 (m, 1H), 2.83-2.77 (m, 1H), 2.45-2.39 (m, 1H), 2.28-2.16 (m, 1H), 2.07-2.01 (m, 1H), 1.98-1.92 (m, 1H), 1.86-1.82 (m, 1H), 1.63-1.59 (m, 1H), 1.34-1.28 (m, 1H), 1.25-1.19 (m, 1H), 1.02-1.00 (m, 3H), 0.93-0.91 (m, 3H).

Step 9) the Preparation of Compound 15-10

A suspension of compound 15-9 (1.3 g, 1.8 mmol), compound 1-8-2 (0.92 g, 3.6 mmol), PdCl$_2$(dppf).CH$_2$Cl$_2$ (0.29 g, 0.36 mmol) and KOAc (0.53 g, 5.4 mmol) in DME (15 mL) was stirred at 90° C. under N$_2$ for 3 hrs. After the reaction was completed, 20 mL of EtOAc was added to the mixture. The resulting mixture was washed with brine, dried over anhydrous Na$_2$SO$_4$ and concentrated in vacuo. The residue was purified by recrystallization to give the title compound as a white solid (1.10 g, 87.8%). The compound was characterized by the following spectroscopic data:

MS (ESI, pos. ion) m/z: 697.4 [M+H]$^+$;

$^1$H NMR (400 MHz, CDCl$_3$) δ (ppm): 7.79, 7.77 (s, s, 1H), 7.62-7.59 (m, 2H), 7.56-7.53 (m, 2H), 7.41, 7.39 (s, s, 1H), 7.35 (s, 1H), 5.40-5.36 (m, 1H), 5.32, 5.29 (brs, brs, 1H), 4.42-4.38 (m, 1H), 3.98-3.96 (m, 2H), 3.94-3.92 (m, 2H), 3.82-3.79 (m, 2H), 3.71-3.69 (m, 1H), 3.67-3.66 (m, 1H), 3.63 (s, 3H), 3.58-3.56 (m, 1H), 2.83-2.77 (m, 1H), 2.45-2.39 (m, 1H), 2.22-2.11 (m, 1H), 1.96-1.90 (m, 1H), 1.84-1.78 (m, 1H), 1.61-1.57 (m, 1H), 1.32 (br, 6H), 1.29 (br, 6H), 1.23-1.17 (m, 1H), 1.11-1.05 (m, 1H), 0.97-0.95 (m, 3H), 0.91-0.89 (m, 3H).

Step 10) the Preparation of Compound 15-11

A suspension of compound 15-10 (1.0 g, 1.4 mmol), compound 15-2 (0.72 g, 1.7 mmol), Pd(PPh$_3$)$_4$ (0.16 g, 0.14 mmol) and K$_2$CO$_3$ (0.58 g, 4.2 mmol) in mixed solvents of EtOH and H$_2$O (16 mL, v/v=3/1) was stirred at 90° C. under N$_2$ for 3 hrs. After the reaction was completed, EtOAc (20 mL) was added to the mixture. The resulting mixture was washed with brine, dried over anhydrous Na$_2$SO$_4$ and concentrated in vacuo. The residue was purified by recrystallization to give the title compound as a white solid (0.41 g, 34.2%). The compound was characterized by the following spectroscopic data:

MS (ESI, pos. ion) m/z: 863.4 [M+H]$^+$;

$^1$H NMR (400 MHz, CDCl$_3$) δ (ppm): 10.55 (,brs, 1H), 7.95-7.76 (m, 2H), 7.68-7.43 (m, 4H), 7.31-7.25 (m, 2H), 7.20-7.16 (m, 2H), 5.55-5.35 (m, 2H), 5.30-5.22 (m, 2H), 4.56-4.29 (m, 6H), 3.92-3.78 (m, 2H), 3.70 (s, 6H), 2.91-2.65 (m, 2H), 2.50-2.29 (m, 2H), 2.25-1.88 (m, 6H), 1.68-1.35 (m, 4H), 1.18-1.04 (m, 2H), 0.95-0.79 (m, 12H).

Example 16

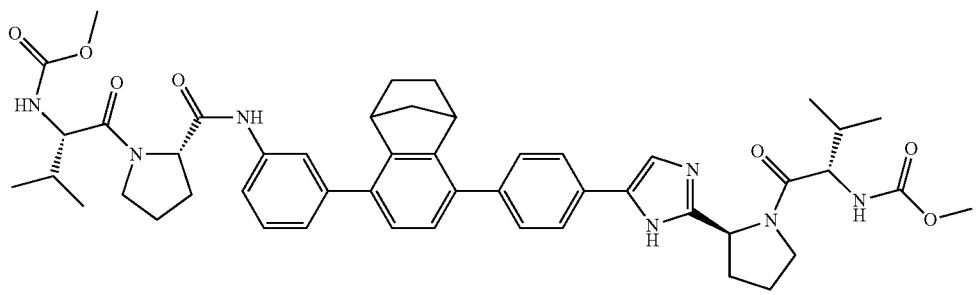 [SMILES: COC(=O)N[C@H](C(=O)N1CCC[C@H]1C(=O)Nc1cccc(-c2ccc(-c3ccc(-c4cnc([C@@H]5CCCN5C(=O)[C@@H](NC(=O)OC)C(C)C)[nH]4)cc3)c3c2C2CCC3C2)c1)C(C)C]

Synthetic Route:
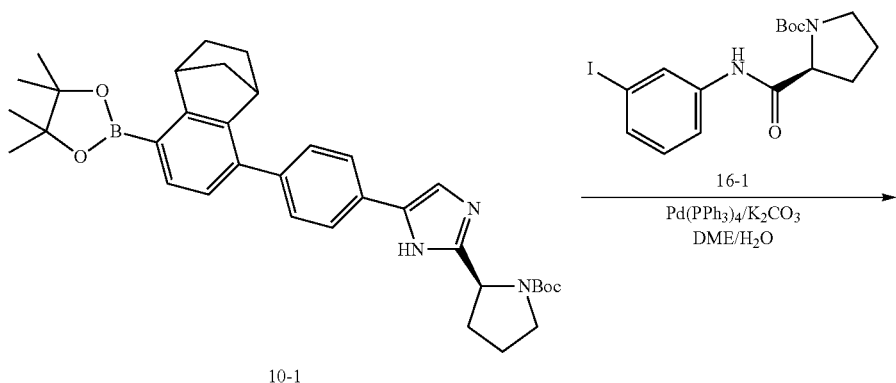
10-1
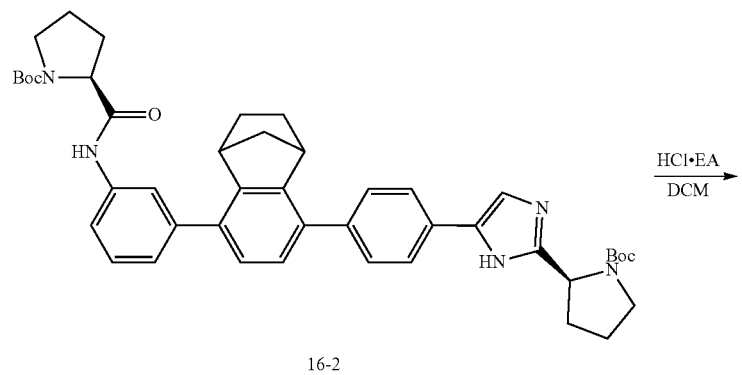
16-2
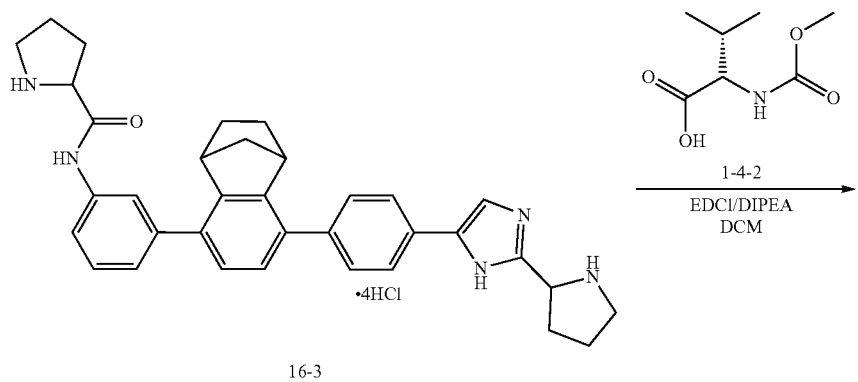
16-3
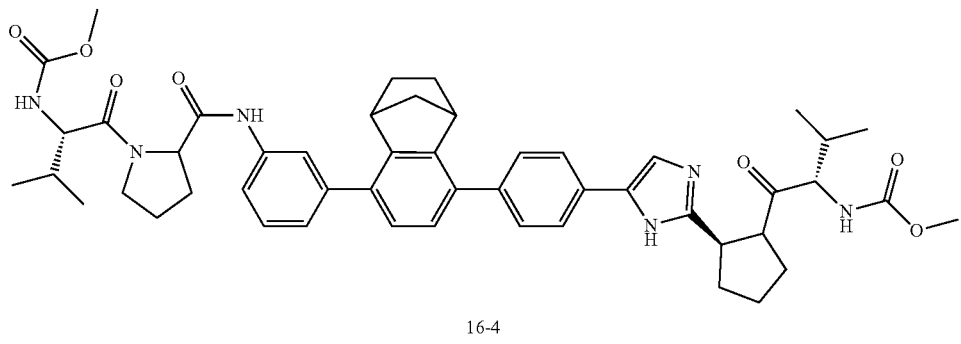
16-4

Step 1) the Preparation of Compound 16-2

To a mixture of compound 10-1 (2.0 g, 3.44 mmol), compound 16-1 (1.58 g, 3.78 mmol), Pd(PPh$_3$)$_4$ (397 mg, 0.34 mmol) and K$_2$CO$_3$ (1.19 g, 8.62 mmol) were added DME (12 mL) and distilled water (4.0 mL) via syringe under N$_2$, and the mixture was stirred at 90° C. for 4 hrs. After the reaction was completed, the solvent DME was removed in vacuo. To the mixture was added distilled water (15 mL). The resulting mixture was extracted with DCM (15 mL×3), and the combined organic layers were dried over anhydrous Na$_2$SO$_4$ and concentrated in vacuo. The residue was purified by a silica gel column chromatography (PE/EtOAc (v/v)=2/1) to give the title compound as a yellow solid (2.1 g, 82%). The compound was characterized by the following spectroscopic data:

MS (ESI, pos.ion) m/z: 744.3 [M+H]$^+$;
$^1$H NMR (400 MHz, CDCl$_3$) δ (ppm): 7.66-7.69 (m, 4H), 7.64-7.65 (m, 2H), 7.51-7.57 (m, 2H), 7.23 (s, 3H), 5.29 (s, 1H), 5.00-5.01 (br, 1H), 3.61 (br, 2H), 3.43 (br, 4H), 2.18 (br, 2H), 1.94-2.04 (m, 8H), 1.72 (br, 5H), 1.41-1.51 (m, 18H).

Step 2) the Preparation of Compound 16-3

To a solution of compound 16-2 (2.1 g, 2.82 mmol) in DCM (15 mL) was added a solution of HCl in EtOAc (20 mL, 4 M) dropwise. At the end of addition, the mixture was stirred at rt overnight. After the reaction was completed, the mixture was filtered, and the filter cake (2.0 g, 100%) was washed with EtOAc, which was used for the next step without further purification. The compound was characterized by the following spectroscopic data:

MS (ESI, pos.ion) m/z: 544.2 [M+H]$^+$;
$^1$H NMR (400 MHz, CD$_3$OD) δ (ppm): 7.69-7.76 (m, 4H), 7.56-7.60 (m, 2H), 7.29-7.42 (m, 2H), 7.21 (s, 3H), 5.15 (s, 1H), 3.42-3.55 (m, 6H), 2.43-2.63 (m, 4H), 1.99-2.06 (m, 6H), 1.49 (br, 2H), 1.28 (br, 2H).

Step 3) the Preparation of Compound 16-4

To a solution of compound 16-3 (689.3 mg, 1.0 mmol), compound 1-4-2 (525 mg, 3.0 mmol) and EDCI (958 mg, 5.0 mmol) in DCM (18 mL) at 0° C. was added DIPEA (1.65 mL, 10 mmol) dropwise, and the mixture was stirred at rt overnight. After the reaction was completed, 15 mL of water was added to the mixture, and the resulting mixture was extracted with DCM (25 mL×3). The combined organic layers were dried over anhydrous Na$_2$SO$_4$ and concentrated in vacuo. The residue was purified by a silica gel column chromatography (PE/EtOAc (v/v)=1/3) to give the title compound as a pale yellow solid (420 mg, 50%). The compound was characterized by the following spectroscopic data:

$^1$H NMR (400 MHz, CD$_3$OD) δ (ppm): 7.62-7.85 (m, 3H), 7.52-7.54 (m, 3H), 7.32-7.38 (m, 2H), 7.15-7.24 (m, 3H), 5.43 (d, 2H, J=9.0 Hz), 4.83-4.85 (m, 3H), 4.01 (d, 2H, J=6.5 Hz), 3.66-3.70 (m, 3H), 2.12-2.21 (m, 9H), 2.07-2.10 (m, 3H), 1.20-1.28 (m, 9H), 0.82-0.89 (m, 9H), 0.78-0.79 (m, 8H).

Example 17

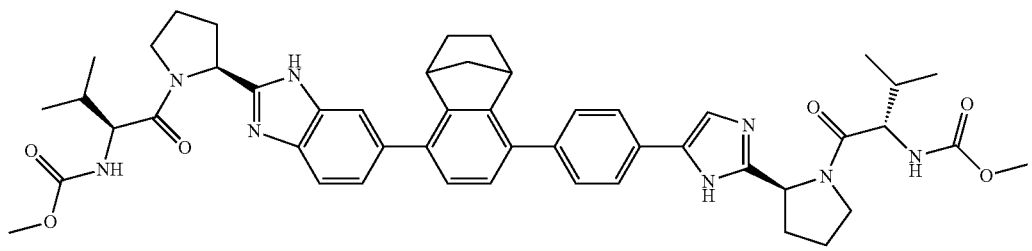

Synthetic Route:

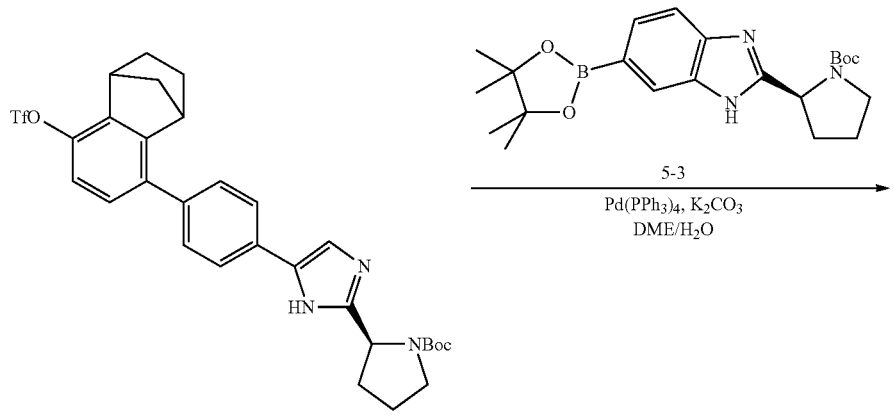

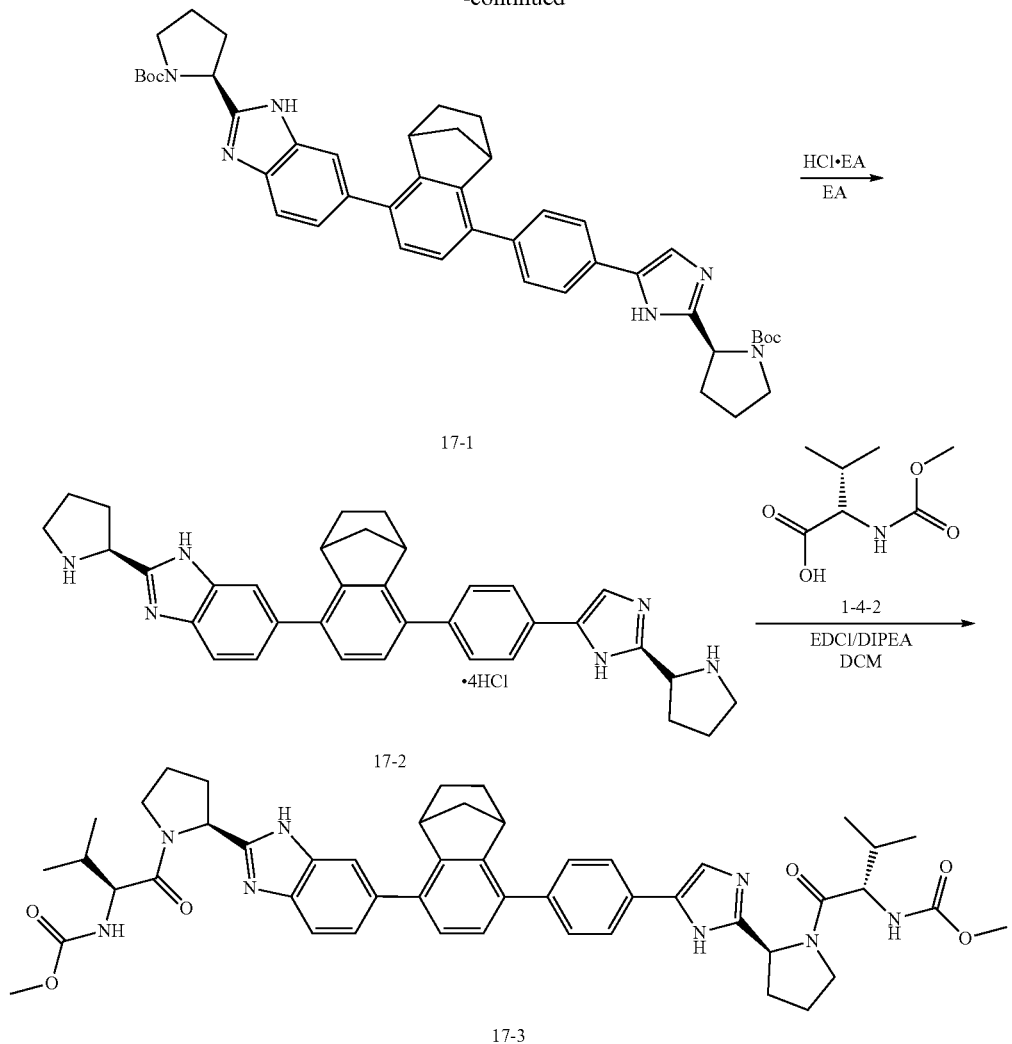

Step 1) the Preparation of Compound 17-1

A suspension of compound 7-1 (1.5 g, 2.5 mmol), compound 5-3 (1.13 g, 2.7 mmol), Pd(PPh$_3$)$_4$ (0.14 g, 0.12 mmol) and K$_2$CO$_3$ (1.38 g, 10.0 mmol) in mixed solvents of DME and H$_2$O (25 mL, v/v=3/1) was stirred at 90° C. under N$_2$ for 3 hrs. After the reaction was completed, EtOAc (20 mL) was added to the suspension. The resulting mixture was washed with brine, dried over anhydrous Na$_2$SO$_4$ and concentrated in vacuo. The residue was purified by recrystallization to give the title compound as a white solid (1.76 g, 95.1%). The compound was characterized by the following spectroscopic data:

MS (ESI, neg.ion) m/z: 739.2 [M−H]$^-$;

$^1$H NMR (400 MHz, CD$_3$OD) δ (ppm): 7.62-7.59 (m, 5H), 7.56-7.52 (m, 2H), 7.49, 7.47 (s, s, 1H), 7.42, 7.39 (s, s, 1H), 7.23, 7.21 (s, s, 1H), 5.04-4.99 (m, 1H), 4.97-4.93 (m, 1H), 3.92-3.86 (m, 1H), 3.82-3.76 (m, 1H), 3.67-3.66 (m, 1H), 3.64-3.56 (m, 2H), 3.31-3.24 (m, 1H), 2.62-2.54 (m, 2H), 2.47-2.36 (m, 2H), 2.28-2.16 (m, 2H), 2.10-1.93 (m, 6H), 1.87-1.84 (m, 1H), 1.65-1.61 (m, 1H), 1.53 (s, 18H).

Step 2) the Preparation of Compound 17-2

To a solution of compound 17-1 (2.20 g, 2.97 mmol) in EtOAc (20 mL) was added a solution of HCl in EtOAc (10 mL, 4 M) dropwise. At the end of addition, the mixture was stirred at rt overnight. After the reaction was completed, the mixture was filtered, and the filter cake was purified by recrystallization to give the title compound as a white solid (1.50 g, 73.5%). The compound was characterized by the following spectroscopic data:

MS (ESI, pos.ion) m/z: 541.2 [M+H]$^+$.

Step 3) the Preparation of Compound 17-3

A suspension of compound 17-2 (1.50 g, 2.2 mmol), compound 1-4-2 (0.8 g, 4.6 mmol), EDCI (0.88 g, 4.6 mmol) and HOAT (0.45 g, 3.3 mmol) in DCM (40 mL) at 0° C. was stirred for 5 mins, then DIPEA (2.91 mL, 17.6 mmol) was added dropwise, and the mixture was stirred at rt for 2 hrs. After the reaction was completed, the mixture was diluted with DCM (50 mL). The resulting mixture was washed with saturated NH$_4$Cl aqueous solution, dried over anhydrous Na$_2$SO$_4$ and concentrated in vacuo. The residue was purified by a silica gel column chromatography (DCM/EtOH (v/v)= 50/1) to give the title compound as a pale yellow solid (1.2 g, 63.8%). The compound was characterized by the following spectroscopic data:

MS (ESI, pos.ion) m/z: 856.4 [M+H]$^+$;

$^1$H NMR (400 MHz, CDCl$_3$) δ (ppm): 10.65 (brs, 1H), 8.03-7.61 (m, 2H), 7.56-7.42 (m, 3H), 7.41-7.30 (m, 2H), 7.25-7.14 (m, 3H), 5.70-5.50 (m, 2H), 5.47-5.44 (m, 1H), 5.30-5.27 (m, 1H), 4.38-4.33 (m, 2H), 3.88-3.84 (m, 2H), 3.73 (s, 3H), 3.71 (s, 3H), 2.48-2.33 (m, 2H), 2.32-2.18 (m, 2H), 2.15-1.94 (m, 8H), 1.58-1.36 (m, 4H), 1.13-1.02 (m, 2H), 0.97-0.71 (m, 12H).

Example 18
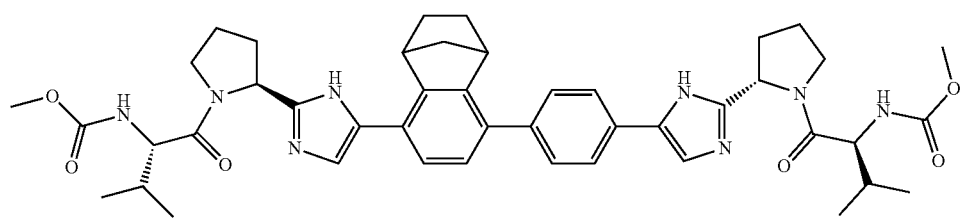 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3C3CCC4C3)cc2)[nH]1)C(C)C]
Synthetic Route:
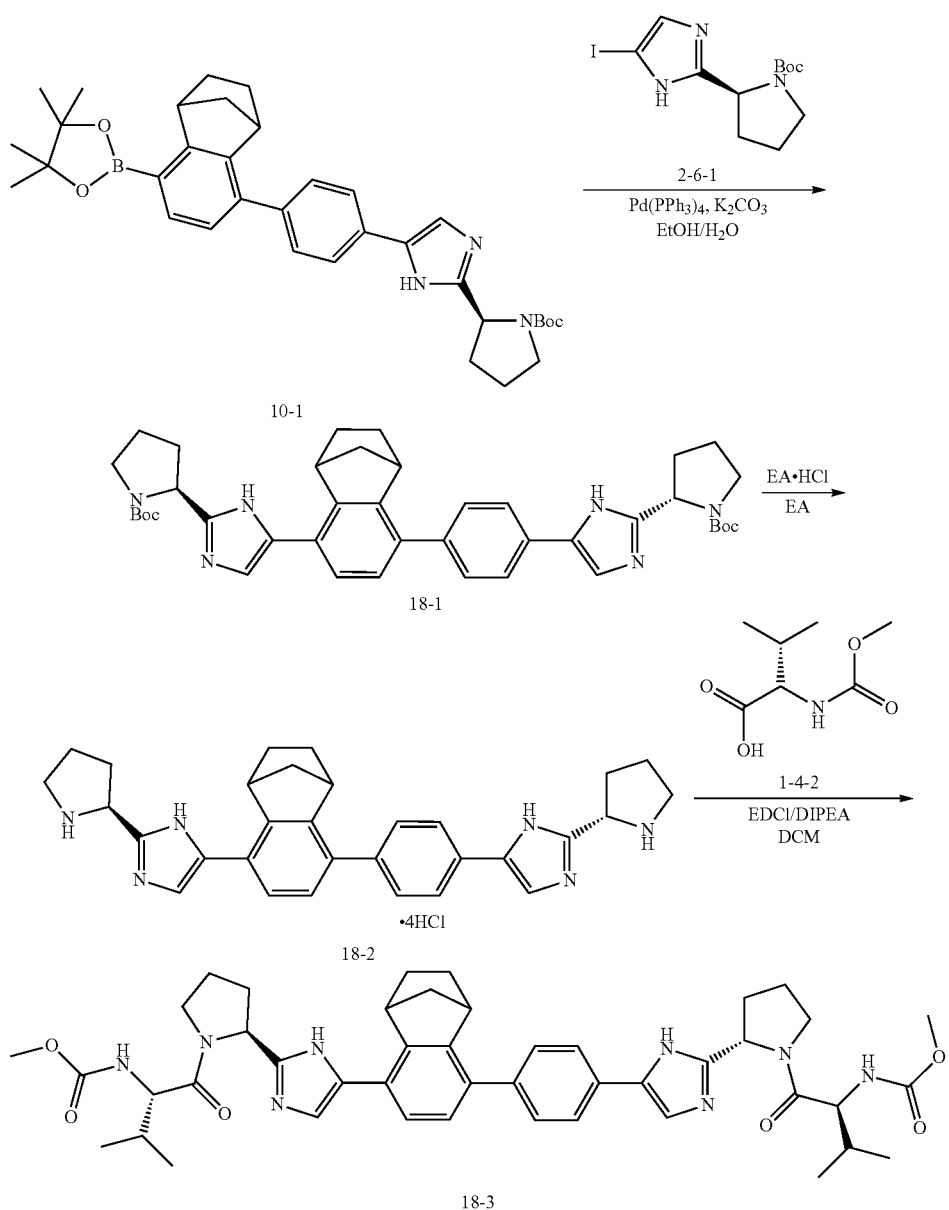
Step 1) the Preparation of Compound 18-1
A suspension of compound 10-1 (1.27 g, 2.18 mmol), compound 2-6-1 (0.95 g, 2.62 mmol), Pd(PPh$_3$)$_4$ (0.25 g, 0.22 mmol) and K$_2$CO$_3$ (0.9 g, 6.54 mmol) in mixed solvents of DME and H$_2$O (18 mL, v/v=5/1) was stirred at 90° C. under N$_2$ for 3 hrs. After the reaction was completed, to the mixture was added EtOAc (20 mL). The resulting mixture was washed with brine, dried over anhydrous Na₂SO₄ and concentrated in vacuo. The residue was purified by recrystallization to give the title compound as a white solid (1.12 g, 88.1%). The compound was characterized by the following spectroscopic data:

MS (ESI, pos.ion) m/z: 692.3 [M+H]⁺;

¹H NMR (400 MHz, CDCl₃) δ (ppm): 10.98 (brs, 1H), 7.82-7.62 (m, 2H), 7.46-7.48 (m, 2H), 7.26 (s, 1H), 7.19-7.21 (m, 1H), 7.17 (s, 1H), 3.75-3.84 (m, 1H), 3.60 (s, 1H), 3.38-3.49 (m, 4H), 2.99 (s, 2H), 2.22-2.09 (m, 3H), 1.97-1.98 (m, 3H), 1.75-1.63 (m, 2H), 1.52 (s, 9H), 1.51 (s, 9H), 1.22-1.32 (m, 8H).

Step 2) the Preparation of Compound 18-2

To a solution of compound 18-1 (1.50 g, 2.17 mmol) in EtOAc (10 mL) was added a solution of HCl in EtOAc (10 mL, 4 M) dropwise at rt. At the end of addition, the mixture was stirred at rt overnight. After the reaction was completed, the mixture was filtered, and the filter cake was used for the next step without further purification.

Step 3) the Preparation of Compound 18-3

A solution of compound 18-2 (0.43 g, 0.676 mmol), compound 1-4-2 (0.249 g, 1.419 mmol), EDCI (0.272 g, 1.419 mmol) and HOAT (0.138 g, 1.013 mmol) in DCM (20 mL) at 0° C. was stirred for 5 mins, then DIPEA (0.89 mL, 5.405 mmol) was added dropwise, and the mixture was stirred at rt for 2 hrs. After the reaction was completed, the mixture was diluted with DCM (40 mL), and the resulting mixture was washed with saturated NH₄Cl aqueous solution, dried over anhydrous Na₂SO₄ and concentrated in vacuo. The residue was purified by a silica gel column chromatography (DCM/EtOH (v/v)=50/1) to give the title compound as a pale yellow solid (0.06 g, 11%). The compound was characterized by the following spectroscopic data:

MS (ESI, pos.ion) m/z: 805.4 [M+H]⁺;

¹H NMR (400 MHz, CDCl₃) δ (ppm): 10.35 (brs, 1H), 7.85-7.70 (m, 2H), 7.68-7.40 (m, 4H), 7.26-7.23 (m, 2H), 7.18-7.15 (m, 2H), 5.55-5.35 (m, 2H), 5.30-5.22 (m, 2H), 4.42-4.28 (m, 2H), 3.92-3.78 (m, 2H), 3.70 (s, 6H), 2.90-2.15 (m, 2H), 2.48-2.29 (m, 2H), 2.25-1.85 (m, 8H), 1.60-1.35 (m, 4H), 1.15-1.00 (m, 2H), 0.95-0.75 (m, 12H).

Example 19

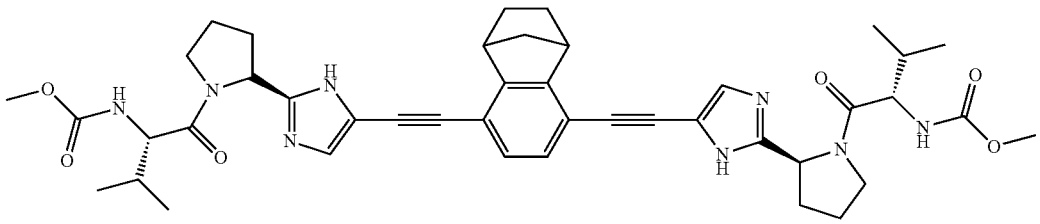

Synthetic Route:

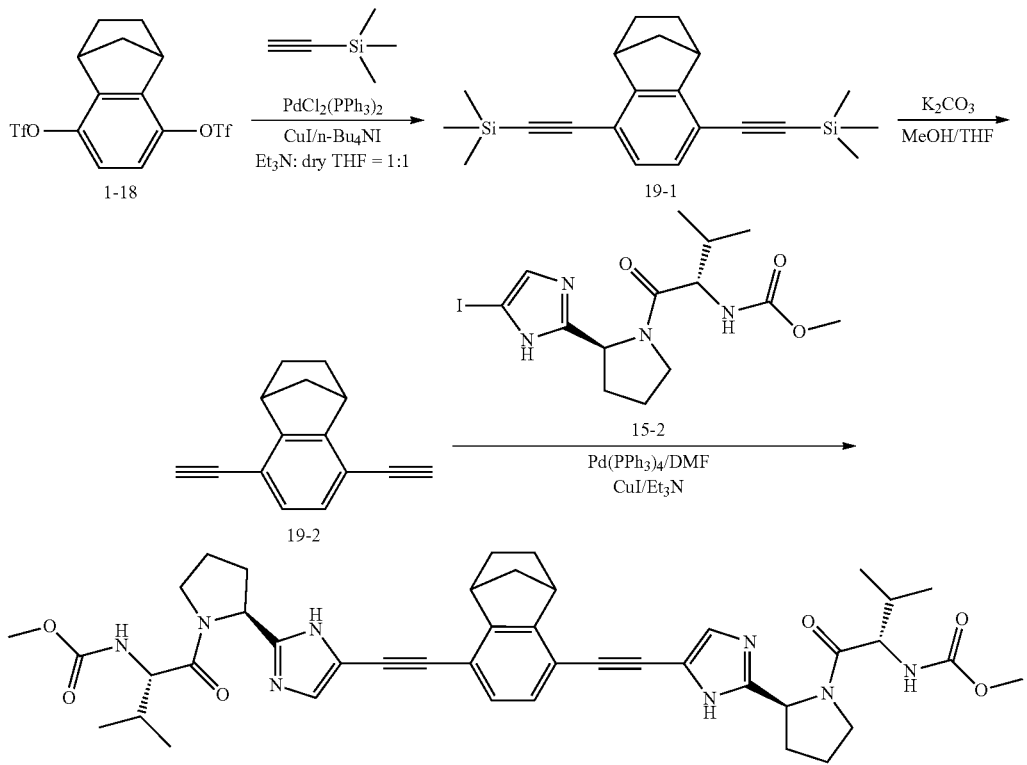

Step 1) the Preparation of Compound 19-1

To a mixture of compound 1-18 (1.5 g, 3.4 mmol), tetrabutylammonium iodide (3.77 g, 10.2 mmol), CuI (195 mg, 1.02 mmol) and PdCl$_2$(PPh$_3$)$_2$ (239 mg, 0.34 mmol) were added anhydrous THF (8.0 mL) and Et$_3$N (8.0 mL) in turn under N$_2$. The mixture was stirred at rt for 10 mins, then trimethylsilylacetylene (2.4 mL) was added. The resulting mixture was stirred at 50° C. for 2 hrs. After the reaction was completed, the mixture was concentrated in vacuo, and the residue was purified by a silica gel column chromatography (PE) to give the title compound as pale yellow liquid (600 mg, 53%). The compound was characterized by the following spectroscopic data:

MS (ESI, pos.ion) m/z: 337.3 [M+H]$^+$;
$^1$H NMR (400 MHz, CDCl$_3$) δ (ppm): 7.09 (s, 2H), 3.59 (s, 2H), 1.94 (d, 2H, J=7.2 Hz), 1.72-1.75 (m, 1H), 1.43-1.56 (m, 1H), 1.17-1.20 (m, 2H), 019-0.26 (m, 18H).

Step 2) the Preparation of Compound 19-2

To a solution of compound 19-1 (300 mg, 0.89 mmol) in mixed solvents of MeOH (4.0 mL) and THF (4.0 mL) was added K$_2$CO$_3$ (492 mg, 3.56 mmol), and the mixture was stirred at rt for 5 hrs. After the reaction was completed, the mixture was diluted with EtOAc (20 mL) and filtered. The filtrate was concentrated in vacuo, and the residue was purified by a silica gel column chromatography (PE) to give the title compound as a gray solid (140 mg, 82%). The compound was characterized by the following spectroscopic data:

MS (ESI, pos.ion) m/z: 193.5 [M+H]$^+$;
$^1$H NMR (400 MHz, CD$_3$OD) δ (ppm): 7.13 (s, 2H), 3.63 (s, 2H), 3.22 (s, 2H), 1.95 (d, 2H, J=7.2 Hz), 1.76 (d, 1H, J=7.2 Hz), 1.52-1.54 (m, 1H), 1.18-1.20 (m, 2H).

Step 3) the Preparation of Compound 19-3

To a mixture of compound 19-2 (140 mg, 0.73 mmol), compound 15-2 (673.3 mg, 1.6 mmol), CuI (28 mg, 0.147 mmol) and Pd(PPh$_3$)$_4$ (84 mg, 0.073 mmol) were added anhydrous DMF (6.0 mL) and Et$_3$N (0.2 mL) in turn under N$_2$, and the mixture was stirred at rt for 20 hrs. After the reaction was completed, the mixture was concentrated in vacuo, and the residue was purified by a silica gel column chromatography (EtOAc) to give the title compound as a yellow solid (200 mg, 45%). The compound was characterized by the following spectroscopic data:

MS (ESI, pos.ion) m/z: 778.3 [M+H]$^+$;
$^1$H NMR (400 MHz, CD$_3$OD) δ (ppm): 7.78 (s, 2H), 7.28 (s, 2H), 5.20 (d, 2H, J=4.9 Hz), 4.22-4.24 (m, 2H), 4.04-4.09 (m, 4H), 2.19-2.21 (m, 3H), 2.01-2.54 (br, 10H), 1.64-1.77 (br, 6H), 1.16-1.34 (m, 8H), 0.87-1.00 (m, 12H).

Example 20

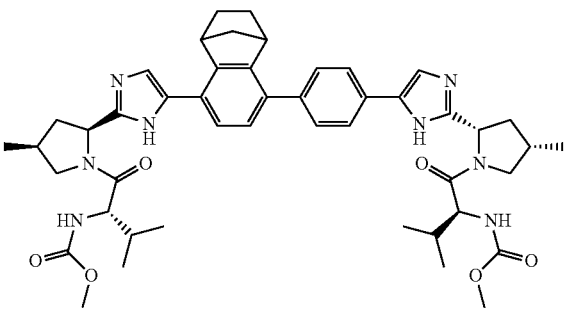

Synthetic Route:

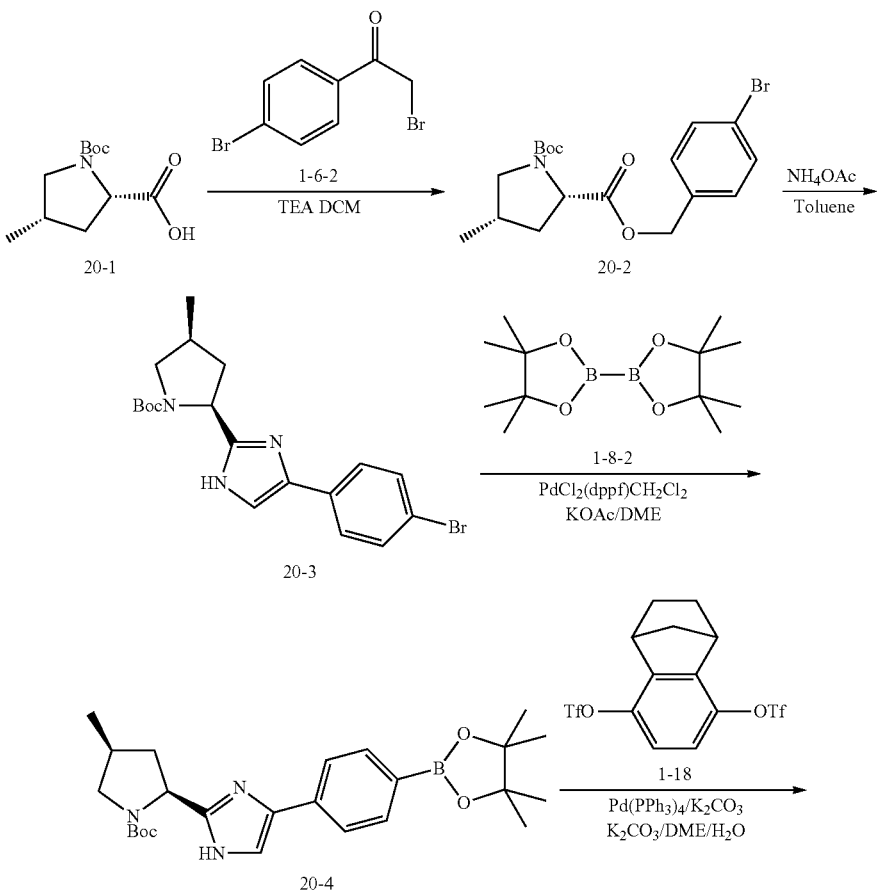

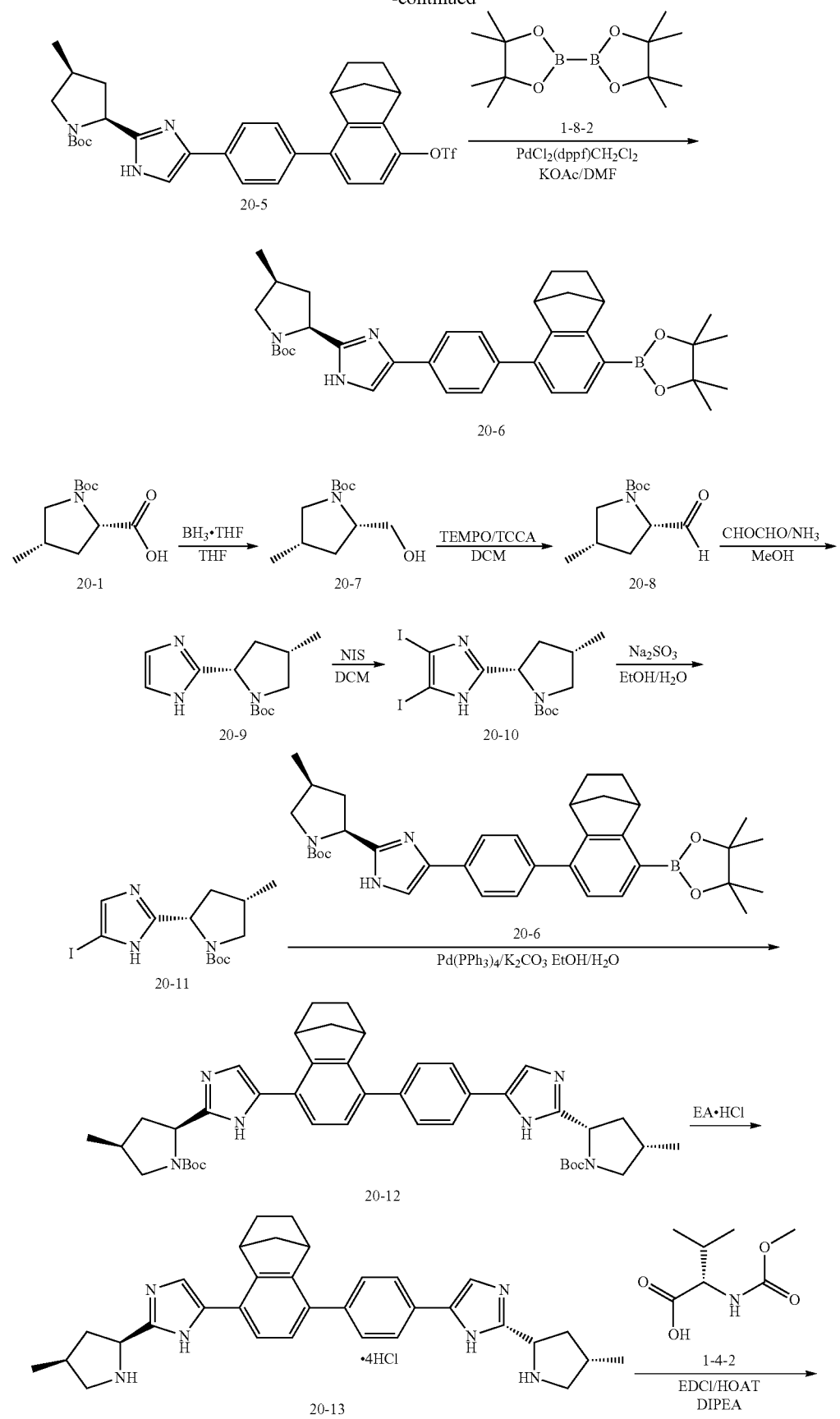

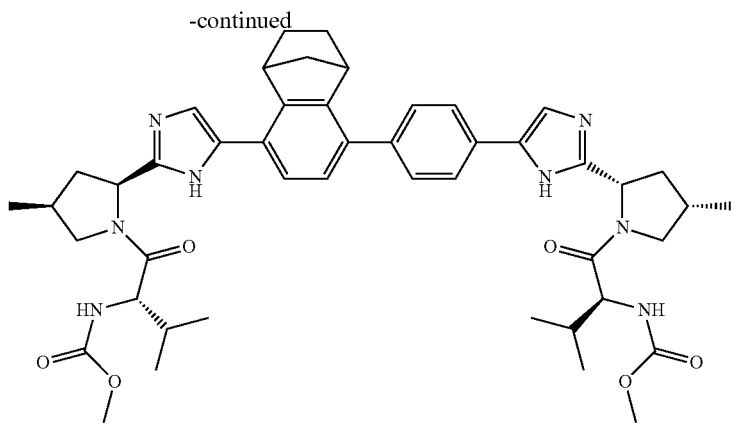

20-14

Step 1) the Preparation of Compound 20-2

To a solution of compound 20-1 (3.0 g, 13.1 mmol) and compound 1-6-2 (3.63 g, 13.1 mmol) in DCM (40 mL) at 0° C. was added Et$_3$N (2.73 mL, 19.65 mmol) dropwise, and the mixture was stirred at rt for 2 hrs. After the reaction was completed, the reaction was quenched with water (50 mL). The resulting mixture was extracted with DCM (50 mL×3), and the combined organic layers were dried over anhydrous Na$_2$SO$_4$ and concentrated in vacuo to give the title compound (3.27 g), which was used for the next step without further purification. The compound was characterized by the following spectroscopic data:

MS (ESI, pos.ion) m/z: 399.29 [M+H]$^+$.

Step 2) the Preparation of Compound 20-3

A mixture of compound 20-2 (3.27 g, 8.2 mmol) and ammonium acetate (5.1 g, 66 mmol) in toluene (34 mL) was stirred at 110° C. for 5 hrs. After the reaction was completed, the mixture was cooled to rt, and 50 mL of water was added. The resulting mixture was extracted with EtOAc (80 mL×3), and the combined organic layers were dried over anhydrous Na$_2$SO$_4$ and concentrated in vacuo. The residue was purified by a silica gel column chromatography (PE/EtOAc (v/v)=4/1) to give the title compound (2.8 g, 86%). The compound was characterized by the following spectroscopic data:

MS (ESI, pos.ion) m/z: 407.32 [M+H]$^+$;

$^1$H NMR (400 MHz, CDCl$_3$) δ (ppm): 7.45 (m, 4H), 7.20 (s, 1H), 4.93 (t, 1H, J=8.2 Hz), 3.88-3.66 (m, 1H), 2.90 (t, 1H, J=8 Hz), 2.50-2.47 (m, 2H), 2.27-2.25 (m, 1H), 1.48 (s, 7H), 1.26 (s, 2H), 1.12 (d, 3H, J=6.2 Hz).

Step 3) the Preparation of Compound 20-4

A suspension of compound 20-3 (2.8 g, 6.9 mmol), compound 1-8-2 (1.93 g, 7.6 mmol), PdCl$_2$(dppf).CH$_2$Cl$_2$ (0.28 g, 0.34 mmol) and KOAc (1.7 g, 17.25 mmol) in DME (30 mL) was stirred at 90° C. under N$_2$ for 2 hrs. After the reaction was completed, the mixture was diluted with 40 mL of EtOAc and filtered through a celite pad. To the filtrate was added 30 mL of water, and the resulting mixture was extracted with EtOAc (40 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound as a pale yellow solid (3.0 g, 88.2%). The compound was characterized by the following spectroscopic data:

MS (ESI, pos.ion) m/z: 454.38 [M+H]$^+$;

$^1$H NMR (400 MHz, CDCl$_3$) δ (ppm): 7.35 (m, 4H), 7.10 (s, 1H), 4.93 (t, 1H, J=8.2 Hz), 3.88-3.66 (m, 1H), 2.90 (t, 1H, J=8 Hz), 2.50-2.47 (m, 2H), 2.27-2.25 (m, 1H), 1.48 (s, 9H), 1.26 (s, 12H), 1.02 (d, 3H, J=6.2 Hz,).

Step 4) the Preparation of Compound 20-5

To a mixture of compound 20-4 (3.4 g, 7.7 mmol), compound 1-18 (3.4 g, 7.7 mmol), Pd(PPh$_3$)$_4$ (450 mg, 0.38 mmol) and K$_2$CO$_3$ (2.1 g, 15.4 mmol) were added DME (32 mL) and H$_2$O (8.0 mL) via syringe under N$_2$, and the mixture was stirred at 90° C. for 3 hrs. After the reaction was completed, the mixture was cooled to rt and diluted with EtOAc (40 mL), then 50 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a pale yellow solid (2.87 g, 70%). The compound was characterized by the following spectroscopic data:

MS (ESI, pos.ion) m/z: 618.68 [M+H]$^+$;

$^1$H NMR (400 MHz, CDCl$_3$) δ (ppm): 7.85-7.79 (m, 2H), 7.42-7.41 (m, 2H), 7.27 (s, 1H), 7.19 (d, 1H, J=8.6 Hz), 7.02 (d, 1H, J=8.6 Hz), 4.97 (t, 1H, J=8.0 Hz), 3.92-3.73 (m, 1H), 3.70 (s, 1H), 3.60 (s, 1H), 2.94-2.89 (m, 1H), 2.63 (s, 1H), 2.52 (s, 1H), 2.28 (s, 2H), 2.02 (d, 5H, J=7.1 Hz), 1.81 (d, 1H, J=9.1 Hz), 1.58 (s, 1H), 1.57 (d, 1H, J=9.0 Hz), 1.50 (s, 7H), 1.41 (d, 3H, J=10.7 Hz), 1.24 (s, 18H), 1.13 (d, 4H, J=6.1 Hz).

Step 5) the Preparation of Compound 20-6

To a mixture of compound 20-5 (1.0 g, 1.62 mmol), compound 1-8-2 (0.42 g, 1.7 mmol), PdCl$_2$(dppf).CH$_2$Cl$_2$ (67 mg, 0.08 mmol) and KOAc (0.4 g, 4.05 mmol) was added DMF (10 mL) via syringe under N$_2$, and the mixture was stirred at 90° C. for 3 hrs. After the reaction was completed, the mixture was cooled to rt and diluted with EtOAc (20 mL) and filtered through a celite pad. To the filtrate was added 30 mL of water, and the resulting mixture was extracted with EtOAc (30 mL×3). The combined organic layers were washed with brine, dried over anhydrous Na$_2$SO$_4$ and concentrated in vacuo. The residue was purified by a silica gel column chromatography (PE/EtOAc (v/v)=3/1) to give the title compound as a pale yellow solid (0.67 g, 70%). The compound was characterized by the following spectroscopic data:

MS (ESI, pos.ion) m/z: 596.58 [M+H]$^+$;

$^1$H NMR (400 MHz, CDCl$_3$) δ (ppm): 7.71 (s, 2H), 7.58 (d, 1H, J=8.0 Hz), 7.47 (d, 2H, J=8.0 Hz), 7.27 (d, 2H, J=3.8 Hz), 7.16 (d, 1H, J=7.8 Hz), 4.97 (t, 1H, J=8.1 Hz), 4.00 (s, 1H), 3.80-3.77 (m, 1H), 3.55 (s, 1H), 2.90 (t, 1H, J=10.0 Hz), 2.65-2.61 (m, 1H), 2.53-2.49 (m, 1H), 2.33-2.28 (m, 1H), 2.01-1.92 (m, 2H), 1.71 (d, 1H, J=8.8 Hz), 1.50 (s, 9H), 1.35 (t, 12H, J=8.0 Hz), 1.13 (d, 3H, J=6.3 Hz).

Step 6) the Preparation of Compound 20-7

To a solution of compound 20-1 (1.12 g, 4.88 mmol) in THF (10.0 mL) at 0° C. was added borane (7.3 mL, 1 M in THF), and the mixture was stirred at rt for 2 hrs. After the reaction was completed, the mixture was quenched with MeOH (4.0 mL). The solvent THF was removed in vacuo, and the residue was dissolved in DCM (50 mL). The solution was washed with water (20 mL×3), dried over anhydrous $Na_2SO_4$ and concentrated in vacuo, and the residue was purified by a silica gel column chromatography (PE/EtOAc (v/v)=3/1) to give the title compound as colorless slurry (1.03 g, 100%). The compound was characterized by the following spectroscopic data:

MS (ESI, pos.ion) m/z: 216.29 $[M+H]^+$;

$^1$H NMR (400 MHz, $CDCl_3$) δ (ppm): 4.02 (s, 1H), 3.99-3.87 (m, 1H), 3.75-3.68 (m, 1H), 3.66 (dd, 1H, J=11.6 Hz, 2.0 Hz), 3.57 (dd, 1H, J=11.6 Hz, 7.4 Hz), 2.76 (t, 1H, J=10.5 Hz), 2.19-2.06 (m, 2H), 1.46 (s, 9H), 1.01 (d, 3H, J=6.2 Hz).

Step 7) the Preparation of Compound 20-9

To a solution of compound 20-7 (1.0 g, 4.64 mmol) in DCM (12 mL) at 0° C. was added TCCA (1.08 g, 4.64 mmol), followed by a solution of TEMPO in DCM (64 mg, 0.46 mmol, 5.0 mL) dropwise. The mixture was stirred at 0° C. for 1 hr and then at rt for another 1 hr. After the reaction was completed, the mixture was filtered, and the filtrate was washed with saturated $Na_2SO_3$ aqueous solution (30 mL×3). The organic layer was dried over anhydrous $Na_2SO_4$ and concentrated in vacuo to give the compound 20-8 as colorless slurry, which was used for the next step directly.

Compound 20-8 was dissolved in a solution of $NH_3$ in MeOH (7.0 mL, 7 M). The solution was stirred at 0° C. for 0.5 hr and then at rt for another 1 hr. To the mixture was added a solution of glyoxal in water (1.2 mL, 40%) dropwise at 0° C., and solid precipitated out. At the end of addition, the mixture was stirred at rt for 24 hrs and concentrated in vacuo, and the residue was dissolved in DCM (20 mL). The solution was washed with water, and the aqueous layer was extracted with DCM (30 mL×3). The combined organic layers were dried over anhydrous $Na_2SO_4$ and concentrated in vacuo. The residue was purified by a silica gel column chromatography (DCM/MeOH (v/v)=50/1) to give the title compound as a pale yellow solid (0.51 g, two-step yield: 44%). The compound was characterized by the following spectroscopic data:

MS (ESI, pos.ion) m/z: 252.32 $[M+H]^+$;

$^1$H NMR (400 MHz, $CDCl_3$) δ (ppm): 6.97 (s, 2H), 4.90 (t, 1H, J=8.0 Hz), 3.76 (dd, 1H, J=10 Hz, 7.2 Hz), 2.83 (t, 1H, J=8.0 Hz), 2.64-2.33 (m, 2H), 2.32-2.12 (m, 1H), 1.47 (s, 9H), 1.09 (d, 3H, J=6.4 Hz).

Step 8) the Preparation of Compound 20-10

To a solution of compound 20-9 (0.51 g, 2.03 mmol) in DCM (10 mL) was added NIS (1.0 g, 4.46 mmol) at 0° C. The mixture was stirred at 0° C. for 2 hrs and filtered. The filtrate was washed with saturated $Na_2SO_3$ aqueous solution (30 mL×3), dried over anhydrous $Na_2SO_4$ and concentrated in vacuo to give the title compound as a yellow solid (0.9 g, 90%), which was used for the next step directly. The compound was characterized by the following spectroscopic data:

MS (ESI, pos.ion) m/z: 504.12 $[M+H]^+$;

$^1$H NMR (400 MHz, $CDCl_3$) δ (ppm): 4.85 (t, 1H, J=8.0 Hz), 3.75 (dd, 1H, J=10 Hz, 7.2 Hz), 2.84 (t, 1H, J=10 Hz), 2.52-2.29 (m, 2H), 2.21 (d, 1H, J=6.6 Hz), 1.48 (s, 9H), 1.08 (d, 3H, J=6.4 Hz).

Step 9) the Preparation of Compound 20-11

To a solution of compound 20-10 (0.9 g, 1.8 mmol) in ethanol (10 mL) were added $Na_2SO_3$ (2.0 g, 16 mmol) and water (10 mL). The mixture was stirred at 90° C. for 30 hrs and filtered. The filtrate was concentrated in vacuo, and the residue was dissolved in DCM (20 mL). The solution was washed with water, and the aqueous layer was extracted with DCM (40 mL×3). The combined organic layers were dried over anhydrous $Na_2SO_4$ and concentrated in vacuo. The residue was purified by a silica gel column chromatography (PE/EtOAc (v/v)=6/1) to give the title compound as a white solid (0.38 g, 60%). The compound was characterized by the following spectroscopic data:

MS (ESI, pos.ion) m/z: 378.22 $[M+H]^+$;

$^1$H NMR (400 MHz, $CDCl_3$) δ (ppm): 7.04 (s, 1H), 4.85 (t, 1H, J=8.4 Hz), 3.75 (dd, 1H, J=10.3 Hz, 7.3 Hz), 2.82 (t, 1H, J=10.4 Hz), 2.58-2.36 (m, 2H), 2.29-2.11 (m, 1H), 1.08 (d, 3H, J=6.4 Hz).

Step 10) the Preparation of Compound 20-12

To a mixture of compound 20-6 (0.34 g, 0.58 mmol), compound 20-11 (0.24 g, 0.63 mmol), $Pd(PPh_3)_4$ (35 mg, 0.03 mmol) and $K_2CO_3$ (0.08 g, 1.4 mmol) were added DME (8.0 mL) and pure water (2.0 mL). The mixture was stirred at 90° C. under $N_2$ for 4 hrs. After the reaction was completed, the mixture was cooled to rt, diluted with EtOAc (20 mL), and 10 mL of water was added. The resulting mixture was extracted with EtOAc (30 mL×3). The combined organic layers were washed with brine, dried over anhydrous $Na_2SO_4$ and concentrated in vacuo. The residue was purified by a silica gel column chromatography (DCM/MeOH (v/v)=60/1) to give the title compound as a pale yellow solid (0.27 g, 70%). The compound was characterized by the following spectroscopic data:

MS (ESI, pos.ion) m/z: 719.93 $[M+H]^+$;

$^1$H NMR (400 MHz, $CDCl_3$) δ (ppm): 7.85-7.60 (m, 2H), 7.53-7.40 (m, 2H), 7.30-7.23 (m, 2H), 7.22-7.10 (m, 2H), 5.02-4.95 (m, 2H), 4.05-3.72 (m, 3H), 3.60 (s, 1H), 2.90 (t, 2H, J=10.2 Hz), 2.73-2.44 (m, 4H), 2.36-2.22 (m, 3H), 2.10-1.90 (m, 3H), 1.72 (m, 2H), 1.50 (s, 18H), 1.13 (d, 6H, J=6.3 Hz).

Step 11) the Preparation of Compound 20-13

To a solution of compound 20-12 (0.27 g, 0.375 mmol) in EtOAc (4.0 mL) was added a solution of HCl in EtOAc (3.0 mL, 4 M) dropwise at rt. At the end of addition, the reaction mixture was stirred at rt for 8 hrs. The reaction process was monitored by LC-MS. After the reaction was completed, the mixture was concentrated in vacuo. Then EtOAc was added and the resulting mixture was stirred and pulped, then filtered to give the title compound as a pale yellow solid (0.2 g, 90%), which was used for the next step without further purification. The compound was characterized by the following spectroscopic data:

MS (ESI, pos.ion) m/z: 519.93 $[M+H]^+$.

Step 12) the Preparation of Compound 20-14

To a solution of compound 20-13 (0.2 g, 0.31 mmol), compound 1-4-2 (0.12 g, 0.68 mmol), EDCI (0.13 g, 0.68 mmol) and HOAT (85 mg, 0.62 mmol) in DCM (20 mL) at 0° C. was added DIPEA (0.51 mL, 3.1 mmol) dropwise. At the end of addition, the mixture was stirred at rt for 3 hrs. After the reaction was completed, the mixture was diluted with DCM. The resulting mixture was washed with $NH_4Cl$ aqueous solution and brine, dried over anhydrous $Na_2SO_4$ and concentrated in vacuo. The residue was purified by a silica gel column chromatography (DCM/MeOH (v/v)=50/1) to give the title compound as a white solid (0.2 g, 76%). The compound was characterized by the following spectroscopic data:

MS (ESI, pos.ion) m/z: 884.09 $[M+H]^+$;

$^1$H NMR (400 MHz, $CDCl_3$) δ (ppm): 11.02 (brs, 1H), 10.63 (brs, 1H), 7.84-7.81 (m, 2H), 7.53-7.43 (m, 4H), 7.25-7.18 (m, 2H), 5.50-5.47 (m, 2H), 5.23-5.17 (m, 2H), 4.39-4.31 (m, 2H), 4.08-4.04 (m, 2H), 3.71 (s, 6H), 3.59-3.57 (m, 2H), 3.18-3.15 (m, 2H), 2.81-2.62 (m, 2H), 2.52-2.47 (m, 2H), 2.41-2.36 (m, 2H), 2.05-1.95 (m, 6H), 1.68-1.54 (s, 6H), 1.45 (s, 6H), 1.24 (d, 6H, J=4.0 Hz).

Example 21
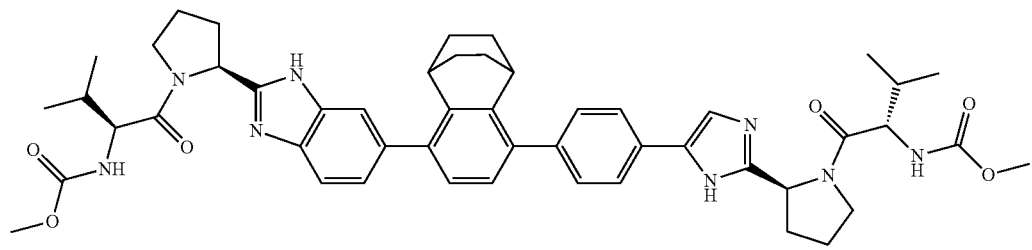
Synthetic Route:
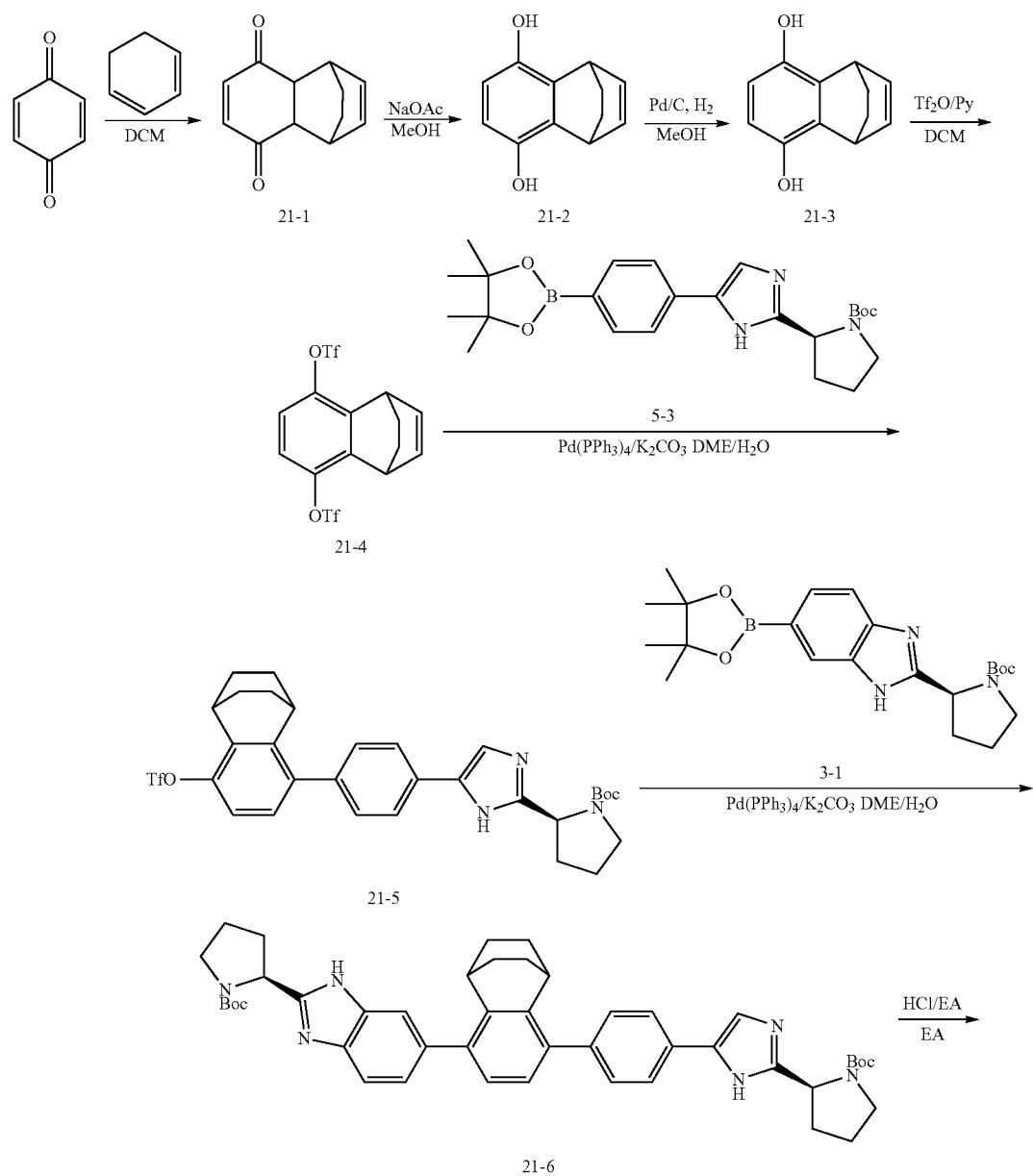

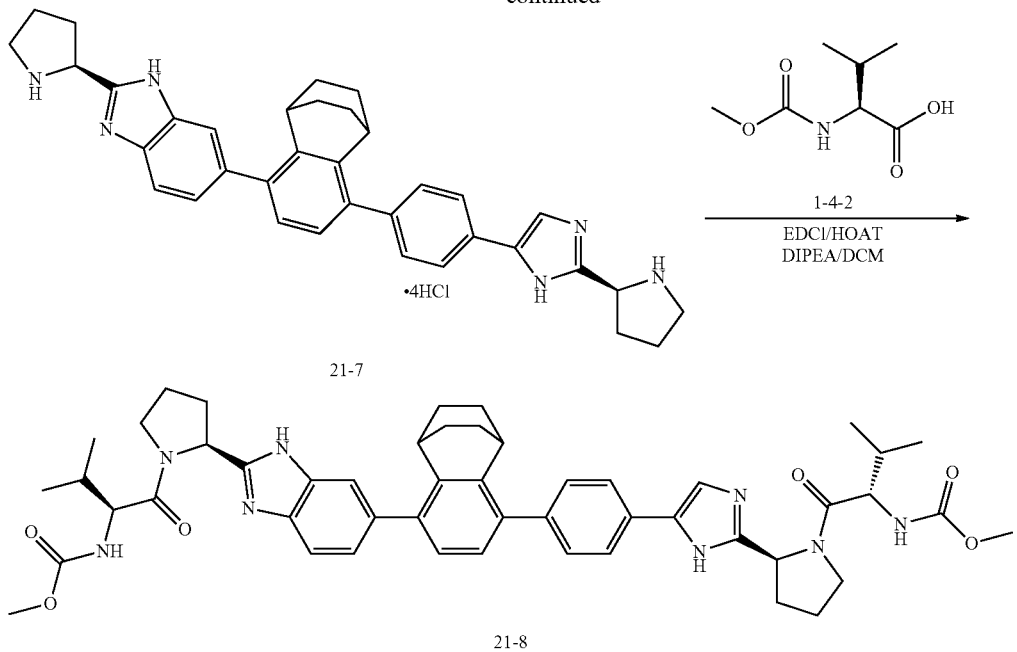

Step 1) the Preparation of Compound 21-1

To a solution of 1,4-benzoquinone (10.0 g, 92.5 mmol) in DCM (90 mL) was added 1,3-cyclohexadiene (11.12 g, 138.8 mmol) dropwise at −10° C. under dark conditions. The mixture was stirred at −10° C. for 1 hr and then at rt for another 48 hrs. After the reaction was completed, the mixture was concentrated in vacuo. Then 500 mL of hexane was added and the resulting mixture was stirred and filtered. The filtrate was concentrated in vacuo to give the title compound as a pale yellow solid (12.5 g, 71.8%), which was used for the next step without further purification. The compound was characterized by the following spectroscopic data:

MS (ESI, pos.ion) m/z: 189.09 [M+H]$^+$;

$^1$H NMR (400 MHz, CDCl$_3$) δ (ppm): 6.59 (s, 2H), 6.47 (s, 2H), 3.42 (s, 2H), 3.20-3.18 (m, 2H), 1.52-1.39 (m, 4H).

Step 2) the Preparation of Compound 21-2

A solution of compound 21-1 (5.0 g, 26.6 mmol) and sodium acetate (6.54 g, 79.7 mmol) in methanol (100 mL) was stirred at 50° C. under N$_2$ for 4 hrs. After the reaction was completed, the reaction mixture was concentrated in vacuo. The residue was purified by a silica gel column chromatography (DCM) to give the title compound as a white solid (4.56 g, 91.2%). The compound was characterized by the following spectroscopic data:

MS (ESI, pos.ion) m/z: 189.09 [M+H]$^+$;

$^1$H NMR (400 MHz, CDCl$_3$) δ (ppm): 6.43-6.39 (m, 2H), 6.28 (s, 2H), 3.65 (s, 2H), 3.45-3.41 (m, 2H), 2.48-2.44 (m, 2H), 2.09-2.01 (m, 2H).

Step 3) the Preparation of Compound 21-3

A suspension of compound 21-2 (4.0 g, 21.3 mmol) and a catalytic amount of Pd/C (0.4 g) in methanol (50 mL) was stirred at rt under H$_2$ for 1.5 hrs. After the reaction was completed, the mixture was filtered. The filtrate was concentrated in vacuo and the residue was purified by recrystallization to give the title compound as a white solid (3.06 g, 75.6%). The compound was characterized by the following spectroscopic data:

MS (ESI, pos.ion) m/z: 191.1[M+H]$^+$;

$^1$H NMR (400 MHz, d$_6$-DMSO) δ (ppm): 7.18 (s, 2H), 6.21 (s, 2H), 3.47-3.44 (m, 2H), 1.61-1.54 (m, 4H), 1.42-1.38 (m, 4H).

Step 4) the Preparation of Compound 21-4

To a solution of compound 21-3 (3.61 g, 19.0 mmol) in DCM (20 mL) was added pyridine (9.0 g, 114 mmol) dropwise at 0° C. After the mixture was stirred for 10 mins, trifluoromethanesulfonic anhydride (21.0 g, 76.0 mmol) was added, and then the mixture was stirred at rt for 1 hr. After the reaction was completed, the mixture was diluted with DCM (50 mL), washed with brine, dried over anhydrous Na$_2$SO$_4$ and concentrated in vacuo. The residue was purified by a silica gel column chromatography (PE/DCM (v/v)=10/1) to give the title compound as colorless oil (8.4 g, 97.3%). The compound was characterized by the following spectroscopic data:

$^1$H NMR (400 MHz, CDCl$_3$) δ (ppm): 7.15 (s, 2H), 3.69-3.67 (m, 2H), 1.75-1.71 (m, 4H), 1.36-1.32 (m, 4H).

Step 5) the Preparation of Compound 21-5

A suspension of compound 21-4 (8.0 g, 17.6 mmol), compound 5-3 (7.89 g, 18.0 mmol), Pd(PPh$_3$)$_4$ (1.02 g, 0.88 mmol) and K$_2$CO$_3$ (9.73 g, 70.4 mmol) in mixed solvents of DME and pure water (80 mL, v/v=3/1) was stirred at 90° C. under N$_2$ for 3 hrs. After the reaction was completed, EtOAc (50 mL) was added. The resulting mixture was washed with brine, dried over anhydrous Na$_2$SO$_4$ and concentrated in vacuo. The residue was purified by recrystallization to give the title compound as a white solid (6.1 g, 56.1%). The compound was characterized by the following spectroscopic data:

MS (ESI, pos.ion) m/z: 618.2[M+H]$^+$;

$^1$H NMR (400 MHz, CDCl$_3$) δ (ppm): 10.48 (brs, 1H), 7.72 (brs, 1H), 7.35 (d, 2H, J=8.1 Hz), 7.18 (m, 2H), 7.15 (d, 1H, J=8.6 Hz), 7.00 (d, 1H, J=8.6 Hz), 4.88 (d, 1H, J=5.2 Hz), 3.61 (s, 1H), 3.54 (s, 1H), 3.48-3.35 (m, 2H), 2.25-2.10 (m, 2H), 1.79-1.68 (m, 5H), 1.43-1.39 (m, 5H), 1.21 (s, 9H).

Step 6) the Preparation of Compound 21-6

A mixture of compound 21-5 (1.54 g, 2.5 mmol), compound 3-3 (1.13 g, 2.7 mmol), Pd(PPh$_3$)$_4$ (0.14 g, 0.12 mmol)

and K$_2$CO$_3$ (1.38 g, 10.0 mmol) in mixed solvents of DME and pure water (25 mL, v/v=3/1) was stirred at 90° C. under N$_2$ for 3 hrs. After the reaction was completed, EtOAc (20 mL) was added. The resulting mixture was washed with brine, dried over anhydrous Na$_2$SO$_4$ and concentrated in vacuo. The residue was purified by recrystallization to give the title compound as a white solid (1.56 g, 82.7%). The compound was characterized by the following spectroscopic data:

MS (ESI, neg.ion) m/z: 753.4[M−H]$^−$;

$^1$H NMR (400 MHz, CDCl$_3$) δ (ppm): 7.61-7.57 (m, 5H), 7.53-7.50 (m, 2H), 7.49, 7.47 (s, s, 1H), 7.39, 7.37 (s, s, 1H), 7.28-7.26 (m, 1H), 5.04-4.99 (m, 1H), 4.97-4.93 (m, 1H), 3.82-3.76 (m, 1H), 3.64-3.57 (m, 2H), 3.31-3.20 (m, 2H), 3.18-3.08 (m, 2H), 2.65-2.53 (m, 1H), 2.47-2.35 (m, 2H), 2.29-2.15 (m, 2H), 2.10-1.93 (m, 2H), 1.71-1.58 (m, 4H), 1.53 (s, 18H), 1.38-1.26 (m, 4H).

Step 7) the Preparation of Compound 21-7

To a solution of compound 21-6 (2.20 g, 2.91 mmol) in EtOAc (10 mL) was added a solution of HCl in EtOAc (10 mL, 4 M) dropwise at rt. At the end of addition, the reaction mixture was stirred at rt overnight. After the reaction was completed, the mixture was filtered. The filter cake was purified by recrystallization to give the title compound as a white solid (1.60 g, 78.4%). The compound was characterized by the following spectroscopic data:

MS (ESI, pos.ion) m/z: 555.3 [M+H]$^+$.

Step 8) the Preparation of Compound 21-8

A suspension of compound 21-7 (1.54 g, 2.2 mmol), compound 1-4-2 (0.80 g, 4.6 mmol), EDCI (0.88 g, 4.6 mmol) and HOAT (0.45 g, 3.3 mmol) in DCM (40 mL) at 0° C. was stirred for 5 mins, then DIPEA (2.91 mL, 17.6 mmol) was added dropwise. At the end of addition, the mixture was stirred at rt for 2 hrs. After the reaction was completed, the mixture was diluted with DCM (30 mL). The resulting mixture was washed with saturated NH$_4$Cl aqueous solution, dried over anhydrous Na$_2$SO$_4$ and concentrated in vacuo. The residue was purified by a silica gel column chromatography (DCM/EtOH (v/v)=50/1) to give the title compound as a pale yellow solid (1.1 g, 57.6%). The compound was characterized by the following spectroscopic data:

MS (ESI, pos.ion) m/z: 869.5[M+H]$^+$;

$^1$H NMR (400 MHz, CDCl$_3$) δ (ppm): 10.55 (brs, 1H), 8.01-7.60 (m, 2H), 7.53-7.40 (m, 3H), 7.39-7.30 (m, 2H), 7.22-7.14 (m, 3H), 5.74-5.52 (m, 2H), 5.46-5.41 (m, 1H), 5.30-5.27 (m, 1H), 4.39-4.35 (m, 2H), 3.88-3.84 (m, 2H), 3.73 (s, 3H), 3.69 (s, 3H), 2.48-2.33 (m, 2H), 2.32-2.18 (m, 2H), 2.15-1.94 (m, 8H), 1.68-1.36 (m, 6H), 1.13-1.02 (m, 2H), 0.97-0.71 (m, 12H).

Example 22

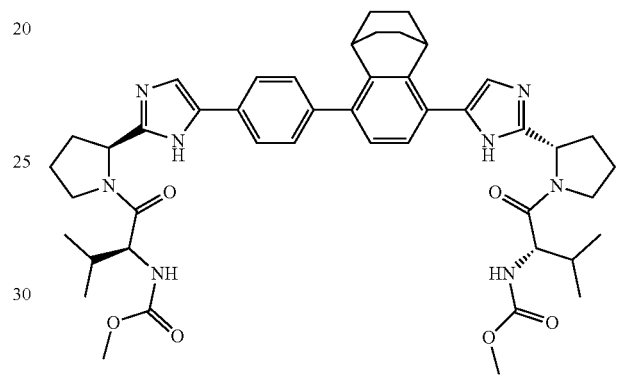

Synthetic Route:

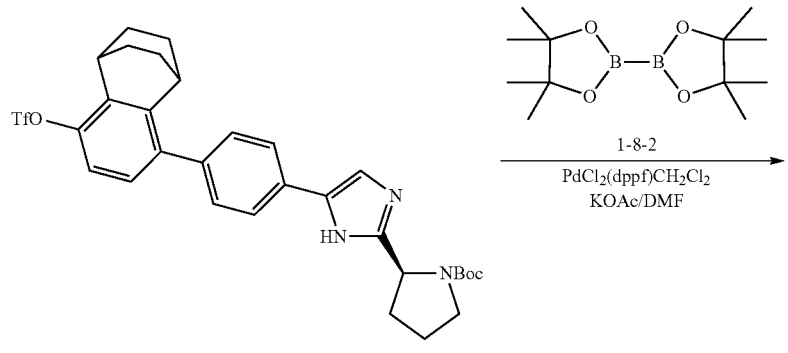

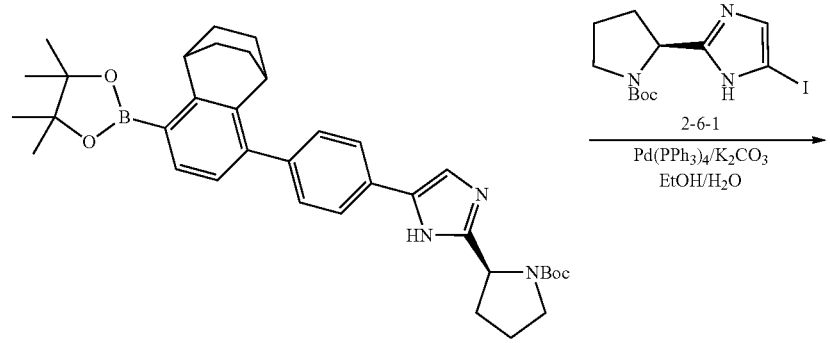

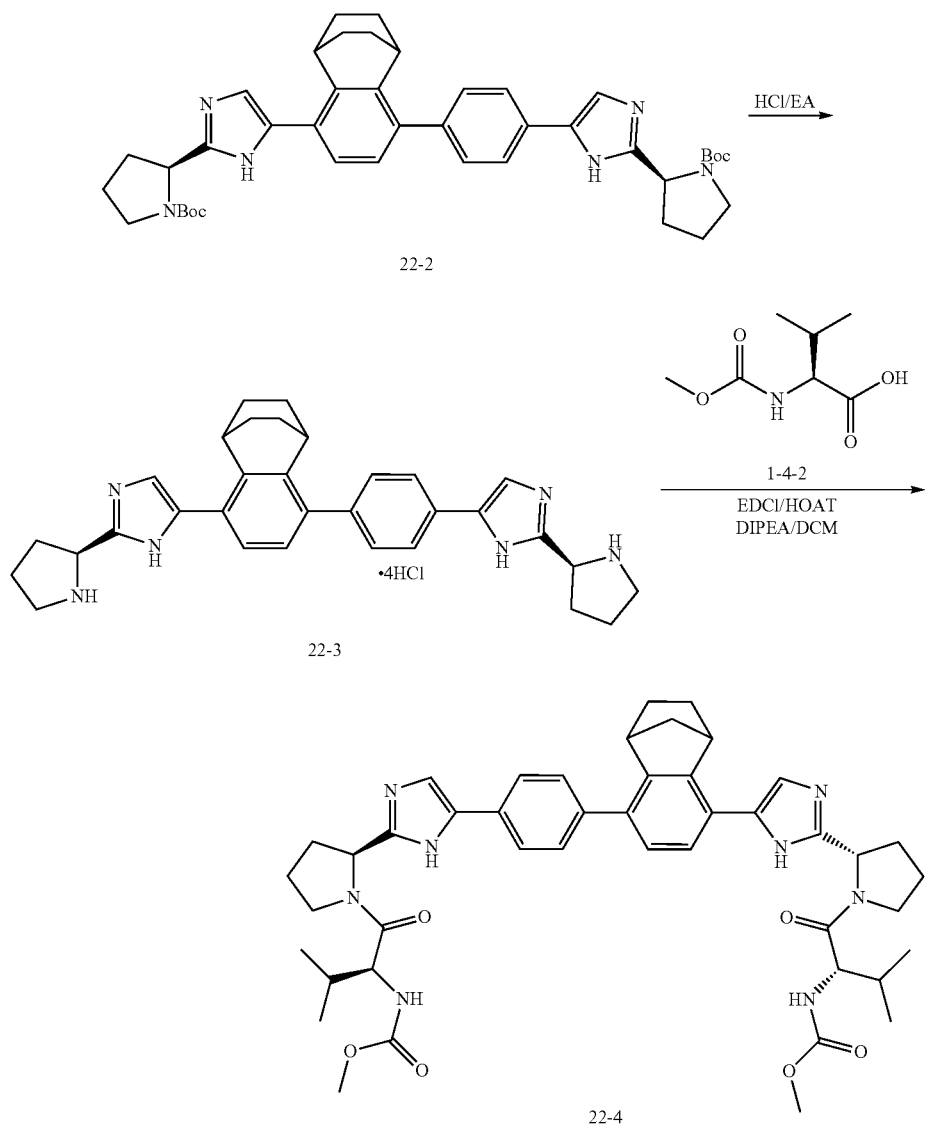

Step 1) the Preparation of Compound 22-1

A suspension of compound 21-5 (2.05 g, 3.32 mmol), compound 1-8-2 (1.68 g, 6.63 mmol), PdCl$_2$(dppf)·CH$_2$Cl$_2$ (0.54 g, 0.66 mmol) and KOAc (0.98 g, 9.96 mmol) in DME (15 mL) was stirred at 90° C. under N$_2$ for 3 hrs. After the reaction was completed, 20 mL of EtOAc was added. The resulting mixture was washed with brine, dried over anhydrous Na$_2$SO$_4$ and concentrated in vacuo. The residue was purified by recrystallization to give the title compound as a white solid (1.56 g, 78.9%). The compound was characterized by the following spectroscopic data:

MS (ESI, pos.ion) m/z: 596.4 [M+H]$^+$;

$^1$H NMR (400 MHz, CDCl$_3$) δ (ppm): 10.53 (brs, 1H), 7.74-7.69 (m, 1H), 7.58 (d, 1H, J=7.8 Hz), 7.47 (d, 2H, J=8.2 Hz), 7.25 (s, 1H), 7.16 (d, 1H, J=7.8 Hz), 4.98-5.01 (m, 1H), 3.99 (s, 1H), 3.55 (s, 1H), 3.38-3.48 (m, 2H), 2.22-2.11 (m, 2H), 1.97-1.88 (m, 5H), 1.72-1.65 (m, 5H), 1.35-1.36 (d, 12H, J=3.08 Hz), 1.25-1.26 (m, 9H).

Step 2) the Preparation of Compound 22-2

A mixture of compound 22-1 (1.30 g, 2.18 mmol), compound 2-6-1 (0.95 g, 2.62 mmol), Pd(PPh$_3$)$_4$ (0.25 g, 0.22 mmol) and K$_2$CO$_3$ (0.9 g, 6.54 mmol) in mixed solvents of EtOH and H$_2$O (18 mL, v/v=4/1) was stirred at 90° C. under N$_2$ for 5 hrs. After the reaction was completed, EtOAc (20 mL) was added. The resulting mixture was washed with brine, dried over anhydrous Na$_2$SO$_4$ and concentrated in vacuo. The residue was purified by recrystallization to give the title compound as a white solid (1.14 g, 74.3%). The compound was characterized by the following spectroscopic data:

MS (ESI, pos.ion) m/z: 705.4 [M+H]$^+$;

$^1$H NMR (400 MHz, CDCl$_3$) δ (ppm): 10.87 (brs, 1H), 7.80-7.62 (m, 2H), 7.46-7.44 (m, 2H), 7.29-7.25 (m, 2H), 7.21-7.19 (m, 2H), 3.38-3.49 (m, 4H), 2.22-2.09 (m, 4H), 1.97-1.84 (m, 6H), 1.75-1.61 (m, 6H), 1.52-1.46 (m, 4H), 1.23 (s, 9H), 1.11 (s, 9H).

Step 3) the Preparation of Compound 22-3

To a solution of compound 22-2 (1.53 g, 2.17 mmol) in EtOAc (10 mL) was added a solution of HCl in EtOAc (10 mL, 4 M) dropwise at rt. At the end of addition, the reaction mixture was stirred at rt overnight. After the reaction was completed, the mixture was filtered, and the filter cake was used for the next step without further purification.

Step 4) the Preparation of Compound 22-4

A suspension of compound 22-3 (0.44 g, 0.676 mmol), compound 1-4-2 (0.249 g, 1.419 mmol), EDCI (0.272 g, 1.419 mmol) and HOAT (0.138 g, 1.013 mmol) in DCM (40 mL) at 0° C. was stirred for 5 mins, then DIPEA (0.89 mL, 5.405 mmol) was added dropwise. At the end of addition, the mixture was stirred at rt for 2 hrs. After the reaction was completed, the mixture was diluted with DCM (20 mL). The resulting mixture was washed with saturated $NH_4Cl$ aqueous solution, dried over anhydrous $Na_2SO_4$ and concentrated in vacuo. The residue was purified by a silica gel column chromatography (DCM/EtOH (v/v)=50/1) to give the title compound as a pale yellow solid (0.44 g, 80.0%). The compound was characterized by the following spectroscopic data:

MS (ESI, pos.ion) m/z: 819.4[M+H]$^+$;

$^1$H NMR (400 MHz, CDCl$_3$) δ (ppm): 10.52 (brs, 1H), 7.82-7.69 (m, 2H), 7.65-7.40 (m, 4H), 7.26-7.23 (m, 2H), 7.18-7.15 (m, 2H), 5.55-5.35 (m, 2H), 5.30-5.22 (m, 2H), 4.42-4.28 (m, 2H), 3.88-3.78 (m, 2H), 3.70 (s, 6H), 2.90-2.15 (m, 2H), 2.48-2.29 (m, 2H), 2.25-1.81 (m, 8H), 1.68-1.35 (m, 6H), 1.12-1.08 (m, 2H), 0.98-0.75 (m, 12H).

Example 23

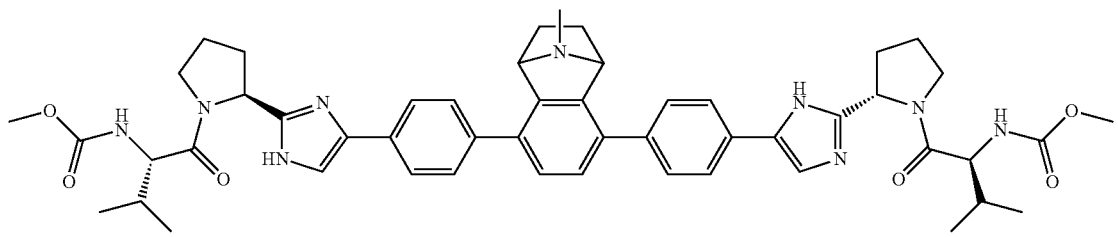

Synthetic Route:

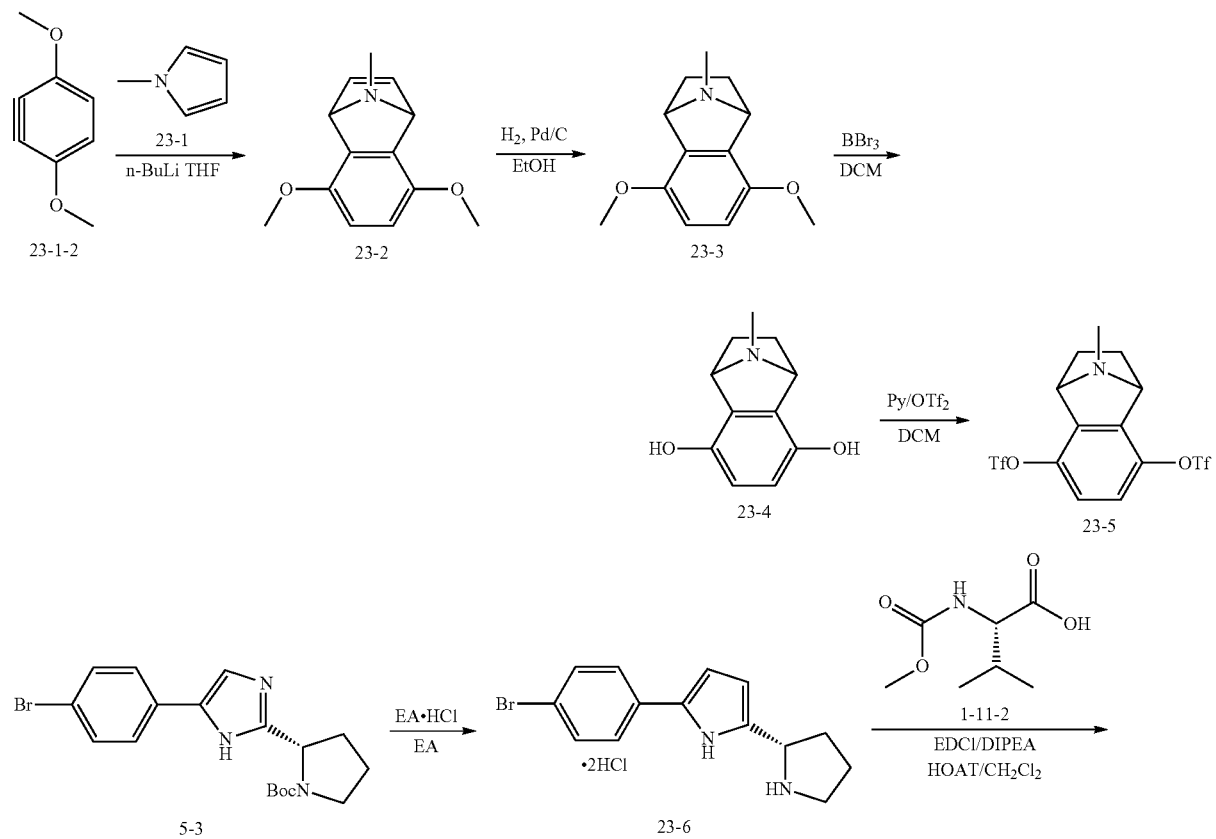

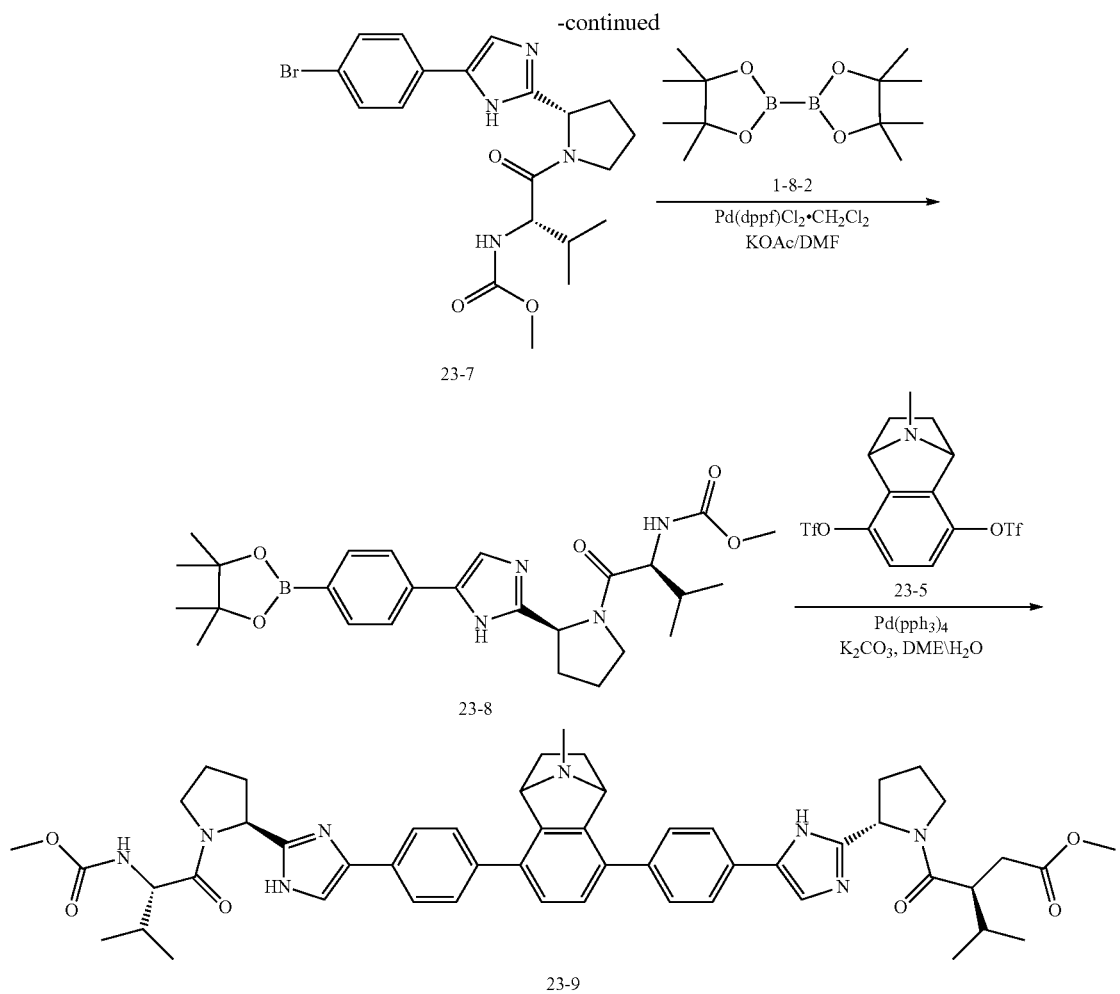

Step 1) the Preparation of Compound 23-2

A stirred mixture of compound 23-1 (1.54 g, 19 mmol) and compound 23-1-2 (1.36 g, 10 mmol) in dry THF (25 mL) was cooled to −78° C. under nitrogen. The addition of n-butyllithium (6.7 mL, 1.6 M in hexane) in portions from a syringe caused the solid to dissolve and the solution to turn cherry red. After stirring at −78° C. for 1 hr, the mixture was warmed to room temperature over 1-2 hrs and stirred overnight. After the reaction was completed, the mixture was poured into water (50 mL) and the organic phase separated. The aqueous layer was extracted further with diethyl ether (3×50 mL). The combined organic layers were dried over anhydrous $Na_2SO_4$ and concentrated in vacuo. The residue was purified by a silica gel column chromatography (PE/EtOAc (v/v)=5/1) to give the title compound 23-2 as yellow solid (1.09 g, 50.2%). The compound was characterized by the following spectroscopic data:

MS (ESI, pos.ion) m/z: 218.5 [M+H]$^+$;

$^1$H NMR (400 MHz, $CDCl_3$) δ (ppm): 6.93-6.91 (t, 1H, J=4.0 Hz), 6.83 (m, 2H), 4.71-4.69 (m, 2H), 3.71 (s, 6H), 2.11 (s, 3H).

Step 2) the Preparation of Compound 23-3

To a solution of compound 23-2 (1.74 g, 8.03 mmol) in ethanol (40 mL) was added Pd/C (0.35 g, 10%), and the mixture was stirred under 10 atm of $H_2$ gas at rt for 24 hrs. The reaction mixture was filtered, and the filtrate was concentrated in vacuo to give the title compound 23-3 as white solid (1.51 g, 86%). The compound was characterized by the following spectroscopic data:

MS (ESI, pos.ion) m/z: 220.3 [M+H]$^+$;

$^1$H NMR (400 MHz, $CDCl_3$) δ (ppm): 6.60-6.24 (s, 2H), 4.28-4.26 (m, 2H), 3.70 (s, 6H), 2.11 (s, 3H), 1.26-1.11 (m, 4H).

Step 3) the Preparation of Compound 23-4

To a solution of compound 23-3 (2.19 g, 10 mmol) in DCM (50 mL) was added boron tribromide (7.7 mL, 80 mmol) dropwise at −78° C. The mixture was stirred at −78° C. for 10 mins and at rt for another 1 hr. After the reaction was completed, the mixture was quenched with ice-water (50 mL) and the organic phase was separated. The aqueous layer was extracted with DCM (3×50 mL). The combined organic phases were washed with brine, dried over anhydrous $Na_2SO_4$ and concentrated in vacuo. The residue was purified by a silica gel column chromatography (PE/EtOAc (v/v)=10/1) to give the title compound 23-4 as colorless oil (1.72 g, 90.0%). The compound was characterized by the following spectroscopic data:

MS (ESI, pos.ion) m/z: 192.5 [M+H]$^+$;

$^1$H NMR (400 MHz, $CDCl_3$) δ (ppm): 6.42 (s, 2H), 5.77 (br, 2H), 4.24-4.22 (m, 2H), 2.15 (s, 3H), 1.31-1.18 (m, 4H).

Step 4) the Preparation of Compound 23-5

To a solution of compound 23-4 (1.91 g, 10 mmol) in DCM (20 mL) was added pyridine (4.8 mL, 60 mmol) dropwise at 0° C. After the mixture was stirred at 0° C. for 10 mins, trifluoromethanesulfonic anhydride (6.73 mL, 40 mmol) was added, and then the reaction mixture was stirred at rt for 1 hr. After the reaction was completed, the mixture was quenched with ice-water (25 mL). The aqueous layer was extracted with DCM (3×30 mL). The combined organic phase was washed with brine, dried over anhydrous $Na_2SO_4$ and concentrated in vacuo. The residue was purified by a silica gel column chromatography (PE/EtOAc (v/v)=40/1) to give the title compound 23-5 as colorless oil (4.32 g, 95.0%). The compound was characterized by the following spectroscopic data:

$^1$H NMR (400 MHz, CDCl$_3$) δ (ppm): 7.29 (s, 2H), 4.39-4.37 (m, 2H), 2.50 (s, 3H), 1.24-1.09 (m, 4H).

Step 5) the Preparation of Compound 23-6

To a solution of compound 5-3 (10.0 g, 25.5 mmol) in EtOAc (50.0 mL) was added a solution of HCl in EtOAc (60.0 mL, 4 M) dropwise, and the mixture was stirred at rt for 8 hrs. After the reaction was completed, the mixture was concentrated in vacuo and EtOAc (40 mL) was added. The resulting mixture was stirred and pulped, and then filtered to give the title compound as a pale yellow solid (8.0 g, 86.2%). The compound was characterized by the following spectroscopic data:

MS (ESI, pos.ion) m/z: 313.2 [M+H]$^+$;

$^1$H NMR (400 MHz, CDCl$_3$) δ (ppm): 7.76-7.73 (m, 2H), 7.66-7.63 (m, 2H), 7.21-7.20 (m, 1H), 5.50-5.22 (m, 2H), 4.49-4.39 (m, 1H), 3.61-3.56 (m, 1H), 3.49-3.39 (m, 1H), 2.31-2.21 (m, 2H), 2.12-2.01 (m, 1H), 1.98-1.85 (m, 1H).

Step 6) the Preparation of Compound 23-7

To a solution of compound 23-6 (7.03 g, 19.26 mmol), compound 1-11-2 (5.06 g, 28.88 mmol) and EDCI (5.56 g, 28.88 mmol) in DCM (100 mL) was added DIPEA (21 mL, 127 mmol) dropwise at 0° C., and the mixture was stirred at rt for 2 hrs. After the reaction was completed, 100 mL of water was added to the mixture, and the resulting mixture was extracted with CH$_2$Cl$_2$ (150 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound as a solid (7.6 g, 88%). The compound was characterized by the following spectroscopic data:

$^1$H NMR (400 MHz, CDCl$_3$) δ (ppm): 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.5-3.81 (m, 1H), 3.72 (s, 3H), 3.71-3.64 (m, 1H), 3.00 (s, 1H), 2.34-2.11 (m, 1H), 2.21-1.95 (m, 5H), 1.04-1.02 (m, 1H), 0.88-0.86 (d, 6H).

Step 7) the Preparation of Compound 23-8

To a mixture of compound 23-7 (5.0 g, 11.13 mmol), compound 1-8-2 (4.3 g, 16.7 mmol), Pd(dppf)Cl$_2$.CH$_2$Cl$_2$ (0.91 g, 1.11 mmol) and KOAc (3.3 g, 33.4 mmol) was added DMF (50 mL) via syringe under N$_2$, and the mixture was stirred at 90° C. for 3 hrs. After the reaction was completed, the mixture was cooled to rt, 80 mL of water was added, and the resulting mixture was extracted with EtOAc (40 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound as a beige solid (4.0 g, 72.4%). The compound was characterized by the following spectroscopic data:

$^1$H NMR (400 MHz, CDCl$_3$) δ (ppm): 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.5-3.81 (m, 1H), 3.72 (s, 3H), 3.71-3.64 (m, 1H), 3.00 (s, 1H), 2.34-2.11 (m, 1H), 2.21-1.95 (m, 5H), 1.32-1.45 (m, 12H), 1.04-1.02 (m, 1H), 0.88-0.86 (d, 6H).

Step 8) the Preparation of Compound 23-9

To a mixture of compound 23-5 (4.55 g, 10 mmol), compound 23-8 (10.42 g, 21 mmol), Pd(PPh$_3$)$_4$ (1.16 g, 1.0 mmol) and K$_2$CO$_3$ (3.45 g, 25 mmol) were added DME (60.0 mL) and H$_2$O (12 mL) via syringe. The mixture was stirred at 90° C. under N$_2$. After the reaction was completed, the mixture was cooled to rt, diluted with EtOAc (200 mL), and washed with water (50 mL×3). The combined organic layers were washed with brine, dried over anhydrous Na$_2$SO$_4$ and concentrated in vacuo. The residue was purified by a silica gel column chromatography (DCM/MeOH (v/v)=60/1) to give the title compound as a pale yellow solid (5.37 g, 60%). The compound was characterized by the following spectroscopic data:

MS (ESI, pos.ion) m/z: 897.5 [M+H]$^+$;

$^1$H NMR (400 MHz, CDCl$_3$) δ (ppm): 7.63-7.62 (m, 2H), 7.61-7.60 (m, 2H), 7.59-7.57 (m, 4H), 7.56-7.53 (m, 4H), 5.32-5.31 (d, 1H, J=4.0 Hz), 5.30-5.29 (d, 1H, J=4.0 Hz), 5.23-5.19 (m, 2H), 4.41-4.37 (m, 2H), 4.08-4.06 (m, 2H), 3.85-3.78 (m, 2H), 3.68-3.64 (m, 2H), 3.63 (s, 6H), 2.36 (s, 3H), 2.30-1.92 (m, 10H), 1.56-1.49 (m, 4H), 0.97-0.95 (m, 6H), 0.91-0.89 (m, 6H).

Example 24

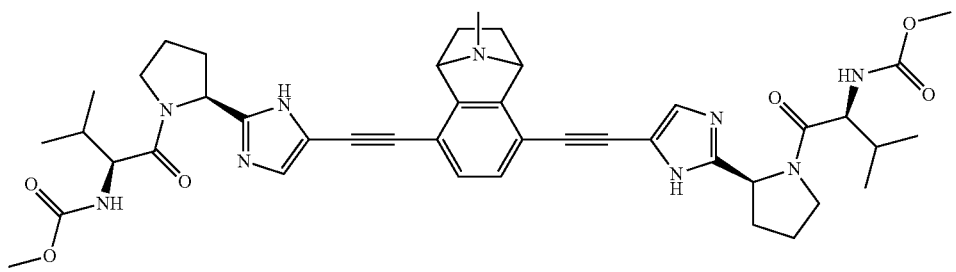

Synthetic Route:

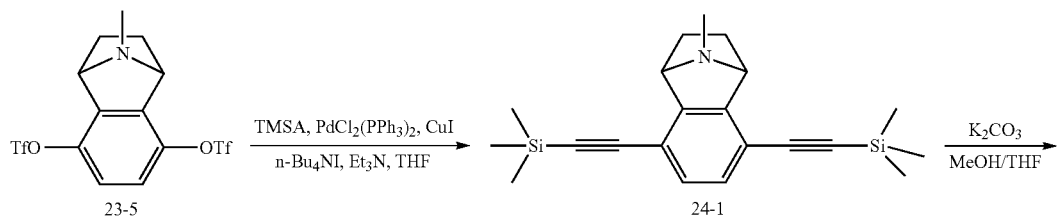

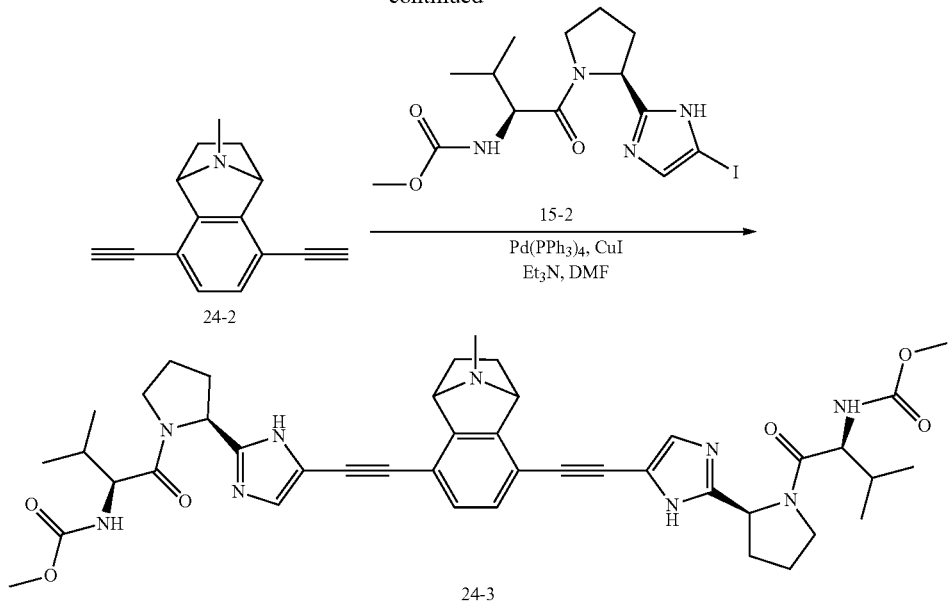

Step 1) the Preparation of Compound 24-1

To a mixture of compound 23-5 (910 mg, 2.0 mmol), tetrabutylammonium iodide (2.21 g, 6 mmol), CuI (114 mg, 0.6 mmol) and PdCl$_2$(PPh$_3$)$_2$ (140 mg, 0.2 mmol) were added anhydrous THF (8.0 mL) and Et$_3$N (8.0 mL) in turn under N$_2$. After the mixture was stirred at rt for 10 mins, trimethylsilylacetylene (1.4 mL, 10 mmol) was added, and the resulting mixture was stirred at 50° C. for 2 hrs. After the reaction was completed, the mixture was concentrated in vacuo. The residue was purified by a silica gel column chromatography (PE/EtOAc (v/v)=30/1) to give the title compound as pale yellow liquid (597 mg, 85%). The compound was characterized by the following spectroscopic data:

MS (ESI, pos.ion) m/z: 352.5 [M+H]$^+$;

$^1$H NMR (400 MHz, CDCl$_3$) δ (ppm): 7.32 (s, 2H), 4.45-4.43 (m, 2H), 2.03 (s, 3H), 1.60-1.51 (m, 2H), 0.96-0.90 (m, 2H), 0.29 (s, 18H).

Step 2) the Preparation of Compound 24-2

To a solution of compound 24-1 (702 mg, 2.0 mmol) in mixed solvents of MeOH (4.0 mL) and THF (4.0 mL) was added K$_2$CO$_3$ (1.1 g, 8.0 mmol). The mixture was stirred at rt for 5 hrs. After the reaction was completed, the mixture was concentrated in vacuo. The residue was dissolved in EtOAc (20 mL) and then washed with brine, dried over anhydrous Na$_2$SO$_4$ and concentrated in vacuo. The residue was purified by a silica gel column chromatography (PE/EtOAc (v/v)=40/1) to give the title compound as a brown solid (331 mg, 80%). The compound was characterized by the following spectroscopic data:

MS (ESI, pos.ion) m/z: 208.5 [M+H]$^+$;

$^1$H NMR (400 MHz, CDCl$_3$) δ (ppm): 7.23 (s, 2H), 4.45-4.43 (m, 2H), 3.16 (m, 2H), 2.05 (s, 3H), 1.70-1.63 (m, 2H), 1.07-1.01 (m, 2H).

Step 3) the Preparation of Compound 24-3

To a mixture of compound 24-2 (124 mg, 0.6 mmol), compound 15-2 (546 mg, 1.3 mmol), CuI (2.28 mg, 0.012 mmol) and Pd(PPh$_3$)$_4$ (69.24 mg, 0.06 mmol) were added anhydrous DMF (5.0 mL) and Et$_3$N (0.2 mL) in turn under N$_2$, and the mixture was stirred at rt for 20 hrs. After the reaction was completed, the mixture was concentrated in vacuo. The residue was purified by a silica gel column chromatography (EtOAc/MeOH (v/v)=60/1) to give the title compound as a yellow solid (332.4 mg, 70%). The compound was characterized by the following spectroscopic data:

MS (ESI, pos.ion) m/z: 792.5 [M+H]$^+$;

$^1$H NMR (400 MHz, CDCl$_3$) δ (ppm): 7.54 (s, 2H), 7.46 (s, 2H), 5.51-5.47 (m, 2H), 5.32-5.31 (d, 1H, J=4.0 Hz), 5.30-5.29 (d, 1H, J=4.0 Hz), 4.45-4.43 (m, 2H), 4.41-4.37 (m, 2H), 3.89-3.83 (m, 2H), 3.73-3.66 (m, 2H), 3.63 (s, 6H), 2.31-1.94 (m, 13H), 1.77-1.68 (m, 2H), 1.13-1.08 (m, 2H), 0.97-0.95 (m, 6H), 0.91-0.89 (m, 6H).

Example 25

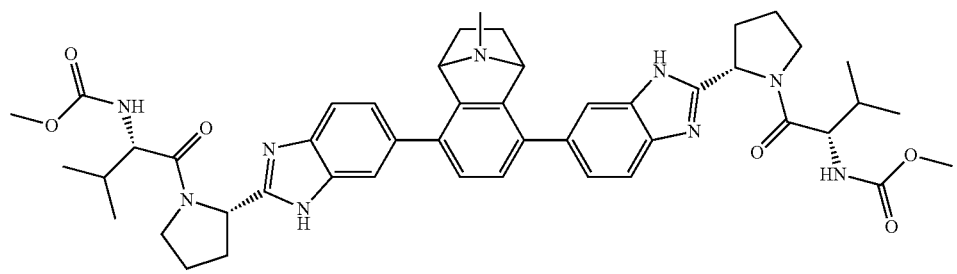

Synthetic Route:

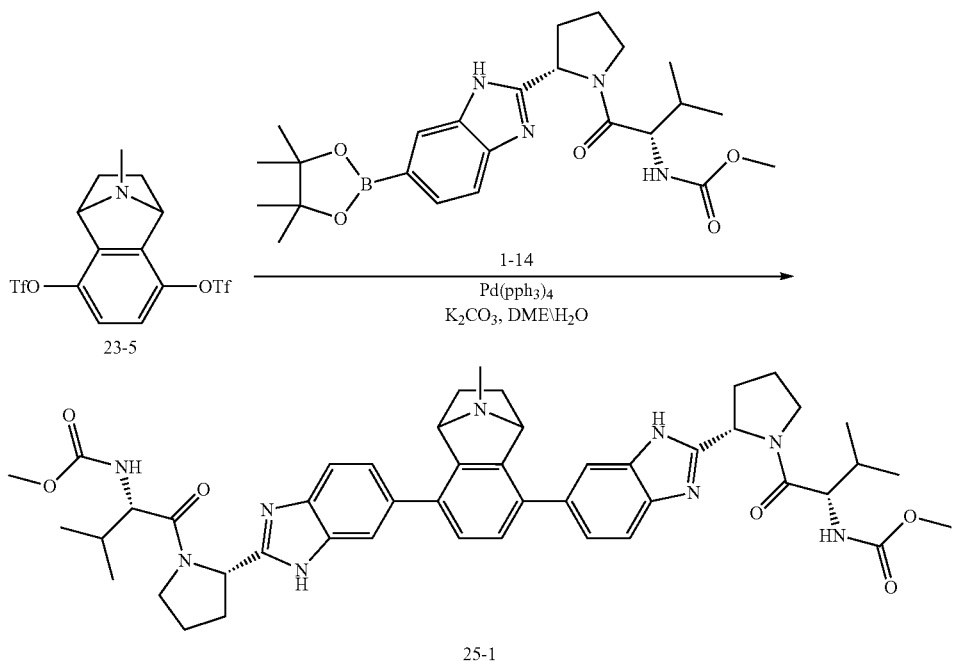

Step 1) the Preparation of Compound 25-1

To a mixture of compound 23-5 (4.55 g, 10 mmol), compound 1-14 (9.87 g, 21 mmol), Pd(PPh$_3$)$_4$ (1.16 g, 1.0 mmol) and K$_2$CO$_3$ (3.45 g, 25 mmol) were added DME (60 mL) and H$_2$O (12 mL) via syringe, and the mixture was stirred at 90° C. under N$_2$. After the reaction was completed, the mixture was cooled to rt, diluted with EtOAc (50 mL), and 50 mL of water was added. The resulting mixture was extracted with EtOAc (100 mL×3). The combined organic layers were washed with brine, dried over anhydrous Na$_2$SO$_4$ and concentrated in vacuo. The residue was purified by a silica gel column chromatography (DCM/MeOH (v/v)=60/1) to give the title compound as a pale yellow solid (4.89 g, 58%). The compound was characterized by the following spectroscopic data:

MS (ESI, pos.ion) m/z: 844.5 [M+H]$^+$;

$^1$H NMR (400 MHz, CDCl$_3$) δ (ppm): 7.65 (s, 2H), 7.62 (s, 1H), 7.60 (s, 1H), 7.52-7.50 (m, 4H), 5.56-5.55 (d, 2H, J=4.0 Hz), 5.54-5.53 (d, 1H, J=4.0 Hz), 5.24-5.20 (m, 2H), 4.36-4.32 (m, 2H), 4.29-4.26 (m, 2H), 3.84-3.77 (m, 2H), 3.66 (s, 6H), 3.65-3.61 (m, 2H), 2.36 (s, 3H), 2.35-2.11 (m, 6H), 1.97-1.91 (m, 4H), 1.59-1.56 (m, 2H), 1.02-1.01 (m, 6H), 0.97-0.95 (m, 2H), 0.91-0.89 (m, 6H).

Example 26

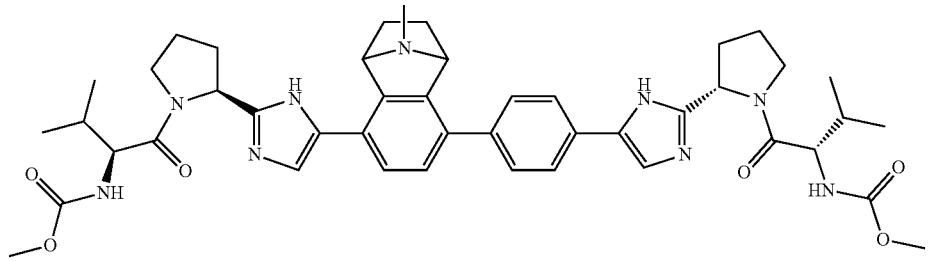

Synthetic Route:

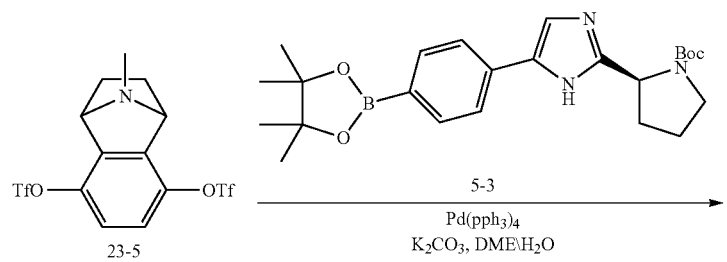

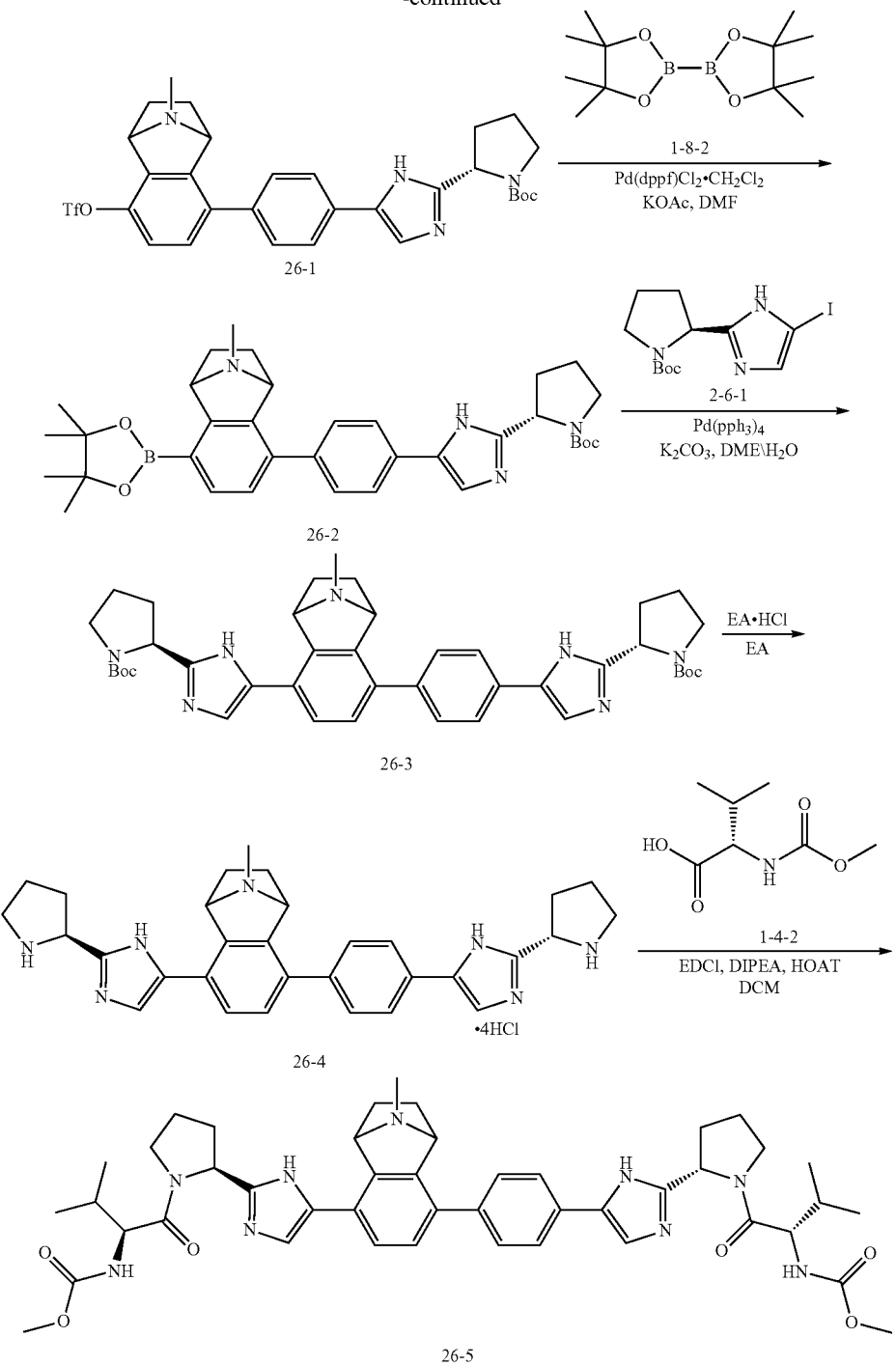

Step 1) the Preparation of Compound 26-1

To a mixture of compound 23-5 (518.7 mg, 1.14 mmol), compound 5-3 (500 mg, 1.14 mmol), Pd(PPh$_3$)$_4$ (131 mg, 0.114 mmol) and K$_2$CO$_3$ (391 mg, 2.84 mmol) were added DME (10 mL) and H$_2$O (2.4 mL) via syringe, and the mixture was stirred at 90° C. under N$_2$ for 3.0 hrs. After the reaction was completed, the mixture was cooled to rt, diluted with EtOAc (20 mL), and 20 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (DCM/MeOH (v/v)= 100/1) to give the title compound as a pale white solid (458 mg, 65%). The compound was characterized by the following spectroscopic data:

MS (ESI, pos.ion) m/z: 619.3 [M+H]$^+$;

$^1$H NMR (400 MHz, CDCl$_3$) δ (ppm): 7.63-7.59 (m, 3H), 7.52-7.49 (m, 2H), 7.20, 7.18 (s, s, 1H), 7.07, 7.05 (s, s, 1H), 4.98-4.92 (m, 1H), 4.44-4.41 (m, 1H), 3.95-3.92 (m, 1H), 3.64-3.58 (m, 1H), 3.31-3.23 (m, 1H), 2.47-2.38 (m, 1H), 2.25 (s, 3H), 2.24-2.19 (m, 1H), 2.10-1.98 (m, 2H), 1.59-1.54 (m, 1H), 1.53 (s, 9H), 1.28-1.13 (m, 2H), 0.97-0.89 (m, 1H).

Step 2) the Preparation of Compound 26-2

A mixture of compound 26-1 (251 mg, 0.406 mmol), compound 1-8-2 (123.8 mg, 0.487 mmol), PdCl$_2$(dppf).CH$_2$Cl$_2$ (33.18 mg, 0.0406 mmol) and KOAc (120 mg, 1.22 mmol) in DMF (4.0 mL) was stirred at 90° C. under N$_2$ for 3 hrs. After the reaction was completed, the mixture was cooled to rt, diluted with EtOAc (20 mL) and filtered through a celite pad. To the filtrate was added 30 mL of water, and the resulting mixture was extracted with EtOAc (30 mL×3). The combined organic layers were washed with brine, dried over anhydrous Na$_2$SO$_4$ and concentrated in vacuo. The residue was purified by a silica gel column chromatography (DCM/MeOH (v/v)=150/1) to give the title compound as a pale yellow solid (150 mg, 60%). The compound was characterized by the following spectroscopic data:

MS (ESI, pos.ion) m/z: 597.3 [M+H]$^+$;

$^1$H NMR (400 MHz, CDCl$_3$) δ (ppm): 7.81, 7.79 (s, s, 1H), 7.63-7.59 (m, 3H), 7.57-7.54 (m, 2H), 7.45, 7.43 (s, s, 1H), 4.98-4.92 (m, 1H), 4.57-4.54 (m, 1H), 4.02-3.99 (m, 1H), 3.64-3.58 (m, 2H), 3.31-3.24 (m, 1H), 2.47-2.38 (m, 1H), 2.27 (s, 3H), 2.25-2.18 (m, 1H), 2.10-1.98 (m, 3H), 1.80-1.73 (m, 1H), 1.71-1.65 (m, 1H), 1.53 (s, 9H), 1.32 (br, 6H), 1.29 (br, 6H), 1.27-1.21 (m, 2H).

Step 3) the Preparation of Compound 26-3

To a mixture of compound 26-2 (151 mg, 0.2533 mmol), compound 2-6-1 (91.95 mg, 0.2533 mmol), Pd(PPh$_3$)$_4$ (29.26 mg, 0.02533 mmol) and K$_2$CO$_3$ (123.23 mg, 0.8866 mmol) were added DME (4.0 mL) and H$_2$O (1.0 mL) via syringe, and the mixture was stirred at 90° C. under N$_2$. After the reaction was completed, the mixture was cooled to rt, and 10 mL of water was added. The resulting mixture was extracted with EtOAc (20 mL×3). The combined organic layers were washed with brine, dried over anhydrous Na$_2$SO$_4$ and concentrated in vacuo. The residue was purified by a silica gel column chromatography (DCM/MeOH (v/v)=80/1) to give the title compound as a pale yellow solid (107.2 mg, 60%). The compound was characterized by the following spectroscopic data:

MS (ESI, pos.ion) m/z: 706.5 [M+H]$^+$;

$^1$H NMR (400 MHz, CDCl$_3$) δ (ppm): 7.70 (s, 1H), 7.63-7.59 (m, 3H), 7.56-7.53 (m, 2H), 7.44, 7.41 (s, s, 1H), 7.31, 7.29 (s, s, 1H), 5.07-5.00 (m, 1H), 4.98-4.92 (m, 1H), 4.15-4.12 (m, 1H), 4.09-4.03 (m, 1H), 3.64-3.58 (m, 2H), 3.31-3.24 (m, 2H), 2.47-2.38 (m, 2H), 2.35 (s, 3H), 2.24-2.19 (m, 2H), 2.09-1.97 (m, 4H), 1.75-1.69 (m, 2H), 1.41 (s, 18H), 1.30-1.24 (m, 2H).

Step 4) the Preparation of Compound 26-4

To a solution of compound 26-3 (153.6 mg, 0.2178 mmol) in EtOAc (4.0 mL) was added a solution of HCl in EtOAc (3.0 mL, 4 M) dropwise, and the mixture was stirred at rt for 8 hrs. After the reaction was completed, the mixture was concentrated in vacuo, and the residue was washed with EtOAc (10 mL) to give the title compound as pale yellow powder (120.5 mg, 85%). The compound was characterized by the following spectroscopic data:

MS (ESI, pos.ion) m/z: 506.5 [M+H]$^+$.

Step 5) the Preparation of Compound 26-5

To a mixture of compound 26-4 (188.9 mg, 0.29 mmol), compound 1-4-2 (107 mg, 0.61 mmol), EDCI (117 mg, 0.61 mmol) and HOAT (79 mg, 0.58 mmol) in DCM (5.0 mL) at 0° C. was added DIPEA (0.42 mL, 2.53 mmol) dropwise. At the end of addition, the mixture was stirred at rt for 3 hrs. The mixture was diluted with DCM (20 mL), washed with saturated NH$_4$Cl aqueous solution and brine, dried over anhydrous Na$_2$SO$_4$ and concentrated in vacuo. The residue was purified by a silica gel column chromatography (DCM/EtOH (v/v)=60/1) to give the title compound as a pale yellow solid (118 mg, 50%). The compound was characterized by the following spectroscopic data:

MS (ESI, pos.ion) m/z: 820.5 [M+H]$^+$;

$^1$H NMR (400 MHz, CDCl$_3$) δ (ppm): 7.63-7.59 (m, 4H), 7.56-7.53 (m, 2H), 7.44, 7.41 (s, s, 1H), 7.31, 7.29 (s, s, 1H), 5.32, 5.30 (brs, brs, 2H), 5.29-5.25 (m, 1H), 5.23-5.19 (m, 1H), 4.41-4.37 (m, 2H), 4.14-4.12 (m, 1H), 4.06-4.05 (m, 1H), 3.84-3.78 (m, 2H), 3.68-3.64 (m, 2H), 3.63 (s, 6H), 2.35 (s, 3H), 2.30-1.92 (m, 10H), 1.76-1.67 (m, 2H), 1.30-1.24 (m, 2H), 0.97, 0.95 (m, m, 6H), 0.91, 0.89 (m, m, 6H).

Example 27

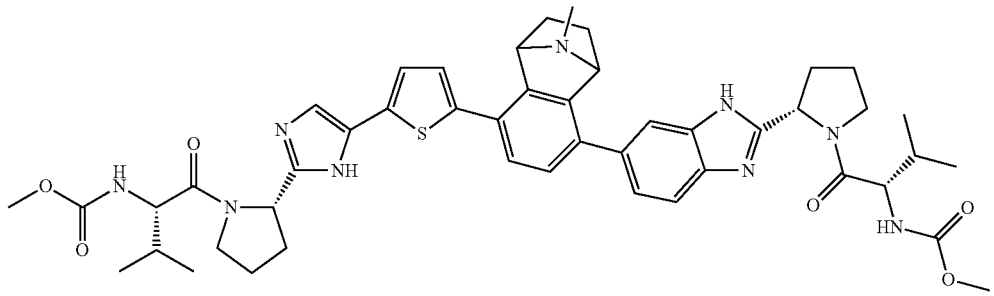

Synthetic Route:

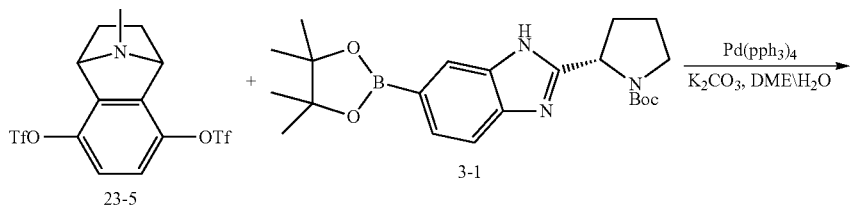

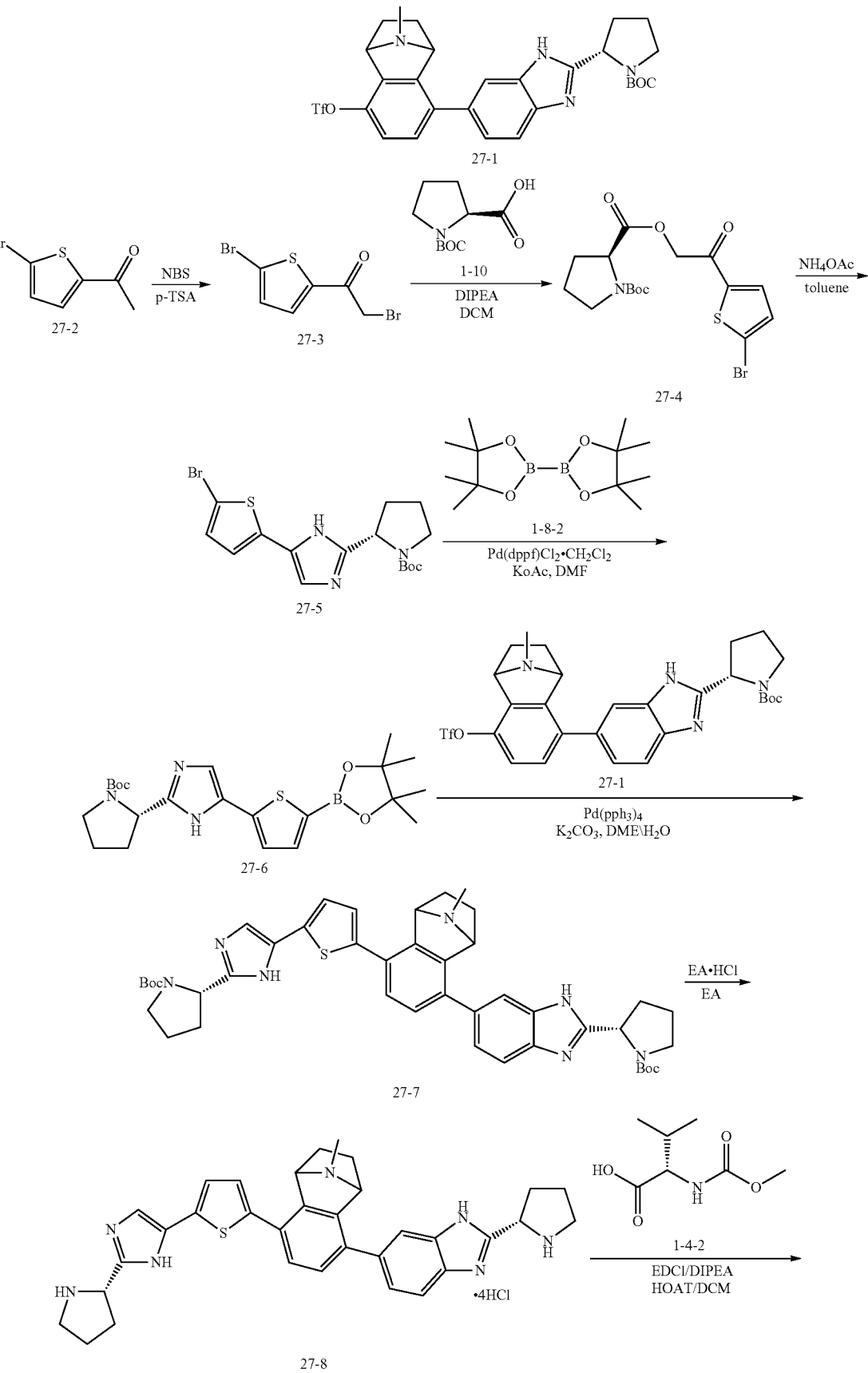

-continued

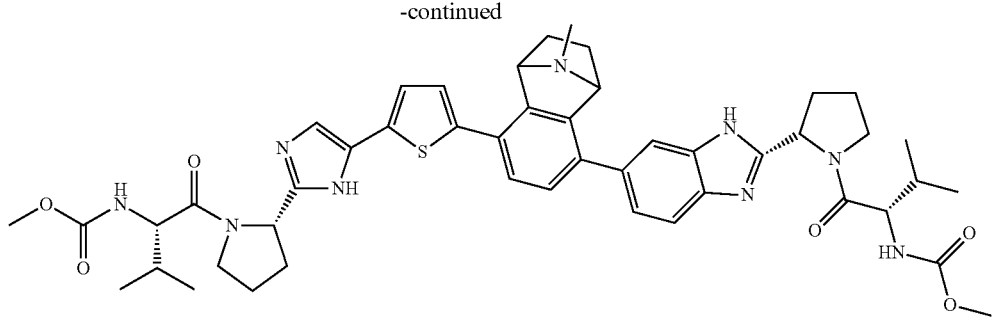

27-9

Step 1) the Preparation of Compound 27-1

To a mixture of compound 23-5 (4.55 g, 10 mmol), compound 3-1 (4.54 g, 11 mmol), Pd(PPh$_3$)$_4$ (1.16 g, 1.0 mmol) and K$_2$CO$_3$ (3.45 g, 25 mmol) were added DME (60 mL) and H$_2$O (12 mL) via syringe, and the mixture was stirred at 90° C. under N$_2$. After the reaction was completed, the mixture was cooled to rt, and 50 mL of water was added. The resulting mixture was extracted with EtOAc (100 mL×3). The combined organic layers were washed with brine, dried over anhydrous Na$_2$SO$_4$ and concentrated in vacuo. The residue was purified by a silica gel column chromatography (DCM/MeOH (v/v)=100/1) to give the title compound as a pale yellow solid (3.43 g, 58%). The compound was characterized by the following spectroscopic data:

MS (ESI, pos.ion) m/z: 593.5 [M+H]$^+$;

$^1$H NMR (400 MHz, CDCl$_3$) δ (ppm): 7.62, 7.60 (s, s, 1H), 7.59-7.50 (m, 3H), 7.26, 7.24 (s, s, 1H), 5.04-4.99 (m, 1H), 4.46-4.44 (m, 1H), 4.15-4.12 (m, 1H), 3.82-3.76 (m, 1H), 3.64-3.56 (m, 1H), 2.62-2.55 (m, 1H), 2.46-2.37 (m, 1H), 2.25 (s, 3H), 2.24-2.16 (m, 1H), 2.04-1.95 (m, 1H), 1.64-1.57 (m, 1H), 1.53 (s, 9H), 1.28-1.15 (m, 2H), 1.03-0.94 (m, 1H).

Step 2) the Preparation of Compound 27-3

The mixture of compound 27-2 (6.0 g, 29 mmol), NBS (5.76 g, 32 mmol) and p-TSA (1.0 g, 5.2 mmol) was stirred at 100° C. for 0.5 hr. After the reaction was completed, the mixture was cooled to rt, and 100 mL of DCM and 50 mL of water were added. The resulting mixture was extracted with DCM (50 mL×3). The combined organic layers were washed with brine, dried over anhydrous Na$_2$SO$_4$ and concentrated in vacuo. The residue was purified by a silica gel column chromatography (DCM/PE (v/v)=1/5) to give the title compound as a yellow slurry (5.64 g, 70%). The compound was characterized by the following spectroscopic data:

MS (ESI, pos.ion) m/z: 284.97 [M+H]$^+$;

$^1$H NMR (400 MHz, CDCl$_3$) δ (ppm): 7.55 (d, 1H, J=4.0 Hz), 7.14 (d, 1H, J=4.0 Hz), 4.29 (s, 2H).

Step 3) the Preparation of Compound 27-4

To a mixture of compound 27-3 (5.64 g, 19.8 mmol) and compound 1-10 (4.7 g, 21.8 mmol) in CH$_3$CN (100 mL) was added DIPEA (3.62 mL, 21.9 mmol) via syringe, and the mixture was stirred at rt for 3.0 hrs. After the reaction was completed, 50 mL of water was added, and the resulting mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a yellow solid (5.8 g, 70%). The compound was characterized by the following spectroscopic data:

MS (ESI, pos.ion) m/z: 418.3 [M+H]$^+$;

$^1$H NMR (400 MHz, CDCl$_3$) δ (ppm): 7.49 (d, 1H, J=4.0 Hz), 7.13 (t, 1H, J=4.0 Hz), 5.02-5.23 (m, 2H), 4.37-4.48 (m, 1H), 3.38-3.60 (m, 2H), 2.26-2.29 (m, 2H), 1.92-2.11 (m, 2H), 1.44 (s, 9H).

Step 4) the Preparation of Compound 27-5

The mixture of compound 27-4 (8.0 g, 19 mmol) and NH$_4$OAc (22.2 g, 288 mmol) in xylene (100 mL) was stirred at 140° C. for 5.0 hrs. After the reaction was completed, the mixture was cooled to rt, and 100 mL of water was added. The resulting mixture was extracted with EtOAc (100 mL×3). The combined organic layers were washed with brine, dried over anhydrous Na$_2$SO$_4$ and concentrated in vacuo. The residue was purified by a silica gel column chromatography (PE/EtOAc (v/v)=4/1) to give the title compound 27-5 as a yellow solid (7.0 g, 92%). The compound was characterized by the following spectroscopic data:

MS (ESI, pos.ion) m/z: 398.32 [M+H]$^+$;

$^1$H NMR (400 MHz, CDCl$_3$) δ (ppm): 10.51 (br, 1H), 7.07 (s, 1H), 6.94 (s, 2H), 4.90-4.91 (m, 1H), 3.39 (s, 2H), 2.98 (s, 1H), 2.12 (s, 2H), 1.95 (s, 1H), 1.48 (s, 9H).

Step 5) the Preparation of Compound 27-6

A mixture of compound 27-5 (1.0 g, 2.5 mmol), compound 1-8-2 (0.96 g, 3.8 mmol), PdCl$_2$(dppf).CH$_2$Cl$_2$ (0.11 g, 0.13 mmo) and KOAc (0.74 g, 7.5 mmol) in DMF (12 mL) was stirred at 90° C. under N$_2$ for 4 hrs. After the reaction was completed, the mixture was cooled to rt, diluted with EtOAc (60 mL) and filtered through a celite pad. The filtrate was washed with water (30 mL×3) and brine. The combined organic layers were dried over anhydrous Na$_2$SO$_4$ and concentrated in vacuo. The residue was purified by a silica gel column chromatography (PE/EtOAc (v/v)=3/1) to give the title compound as a white solid (0.89 g, 80%). The compound was characterized by the following spectroscopic data:

$^1$H NMR (400 MHz, CDCl$_3$) δ (ppm): 10.51 (br, 1H), 7.53 (s, 1H), 7.27 (s, 1H), 7.15 (s, 1H), 4.93-4.94 (m, 1H), 3.39 (s, 2H), 2.99 (s, 1H), 1.94-2.12 (m, 4H), 1.49 (s, 9H), 1.34 (s, 12H), 1.24 (m, 8H).

Step 6) the Preparation of Compound 27-7

To a mixture of compound 27-6 (470 mg, 1.0 mmol), compound 27-1 (414 mg, 0.7 mmol), Pd(PPh$_3$)$_4$ (80 mg, 0.07 mmol) and K$_2$CO$_3$ (250 mg, 1.8 mmol) were added DME (6.0 mL) and H$_2$O (1.5 mL) via syringe, and the mixture was stirred at 90° C. under N$_2$ for 3 hrs. After the reaction was completed, the mixture was cooled to rt, and 10 mL of water was added. The resulting mixture was extracted with EtOAc (20 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a pale yellow solid (320 mg, 60%). The compound was characterized by the following spectroscopic data:

MS (ESI, pos.ion) m/z: 762.3 [M+H]⁺;

¹H NMR (400 MHz, CDCl₃) δ (ppm): 7.69, 7.67 (s, s, 1H), 7.62-7.60 (m, 1H), 7.52-7.50 (m, 2H), 7.49, 7.47 (s, s, 1H), 7.48 (s, 1H), 7.21, 7.20 (s, s, 1H), 7.01, 7.00 (s, s, 1H), 5.16-5.10 (m, 1H), 5.04-4.99 (m, 1H), 4.14-4.11 (m, 1H), 4.00-3.97 (m, 1H), 3.82-3.76 (m, 1H), 3.63-3.56 (m, 2H), 3.31-3.24 (m, 1H), 2.62-2.55 (m, 1H), 2.46-2.37 (m, 2H), 2.23 (s, 3H), 2.27-2.19 (m, 2H), 2.10-1.97 (m, 3H), 1.74-1.67 (m, 1H), 1.53 (s, 18H), 1.64-1.57 (m, 1H), 1.13-0.97 (m, 2H).

Step 7) the Preparation of Compound 27-8

To a solution of compound 27-7 (304 mg, 0.4 mmol) in EtOAc (2.0 mL) was added a solution of HCl in EtOAc (5 mL, 4 M) dropwise, and the mixture was stirred at rt for 8 hrs. After the reaction was completed, the mixture was concentrated in vacuo. The residue was washed with EtOAc (10 mL) and filtered to give the title compound as pale yellow powder (282.9 mg, 100%). The compound was characterized by the following spectroscopic data:

MS (ESI, pos.ion) m/z: 562.3 [M+H]⁺.

Step 8) the Preparation of Compound 27-9

To a mixture of compound 27-8 (275.8 mg, 0.39 mmol), compound 1-4-2 (200 mg, 1.1 mmol) and EDCI (300 mg, 1.6 mmol) in DCM (8.0 mL) at 0° C. was added DIPEA (0.6 mL, 3.6 mmol) dropwise. At the end of addition, the mixture was stirred at rt for 3 hrs. The mixture was diluted with DCM (50 mL), washed with saturated NH₄Cl aqueous solution and brine, dried over anhydrous Na₂SO₄ and concentrated in vacuo. The residue was purified by a silica gel column chromatography (DCM/EtOH (v/v)=50/1) to give the title compound as pale yellow powder (204.8 mg, 60%). The compound was characterized by the following spectroscopic data:

MS (ESI, pos.ion) m/z: 876.5 [M+H]⁺;

¹H NMR (400 MHz, CDCl₃) δ (ppm): 7.69, 7.67 (s, s, 1H), 7.62-7.60 (m, 1H), 7.52-7.50 (m, 2H), 7.69, 7.67 (s, s, 1H), 7.41 (s, 1H), 7.21, 7.20 (s, s, 1H), 7.01, 7.00 (s, s, 1H), 5.42, 5.37 (m, m, 1H), 5.32, 5.29 (brs, brs, 2H), 5.24-5.20 (m, 1H), 4.41-4.36 (m, 2H), 4.14-4.11 (m, 1H), 4.00-3.97 (m, 1H), 3.84-3.78 (m, 2H), 3.69-3.64 (m, 2H), 3.63 (s, 6H), 2.33 (s, 3H), 2.32-1.87 (m, 10H), 1.74-1.67 (m, 1H), 1.65-1.57 (m, 1H), 1.13-0.99 (m, 2H), 0.97-0.95 (m, 6H), 0.91-0.89 (m, 6H).

Example 28

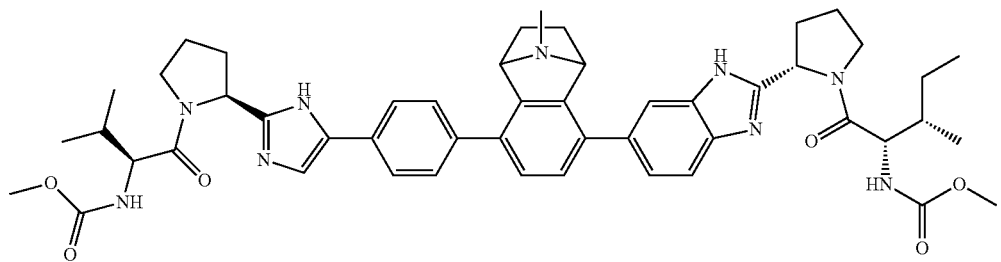

Synthetic Route:

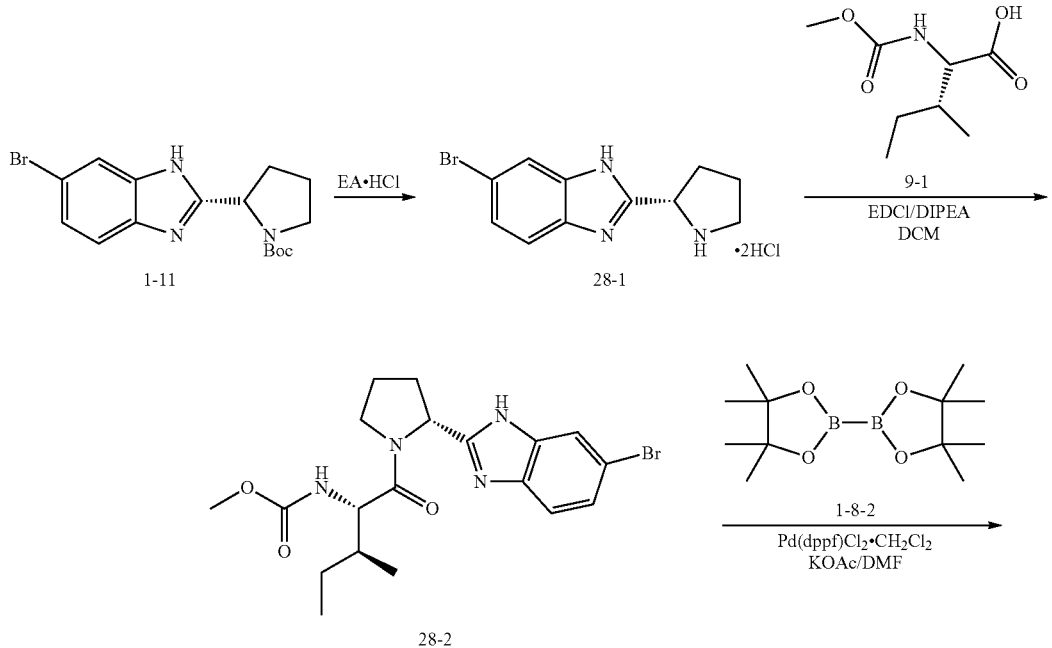

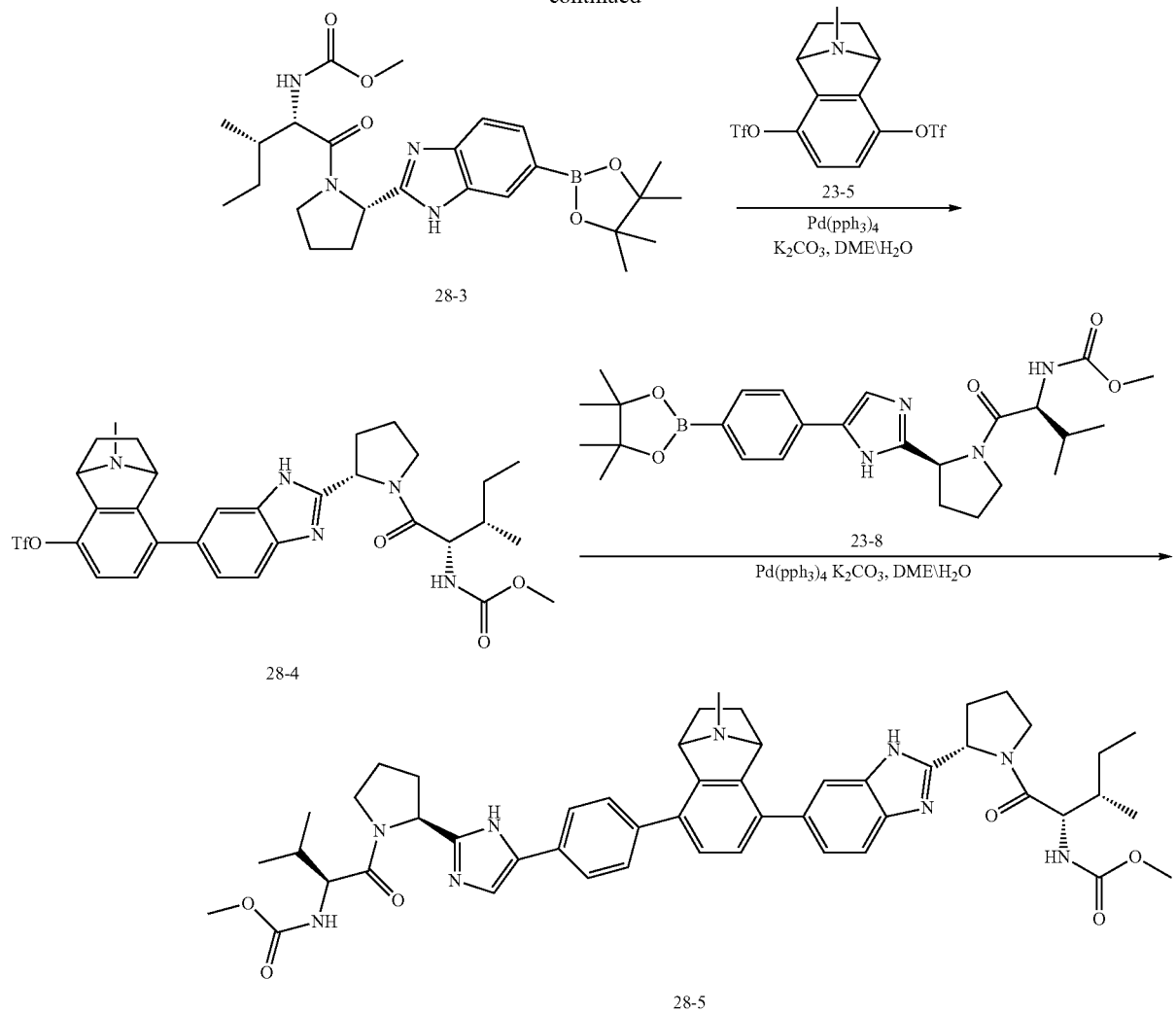

Step 1) the Preparation of Compound 28-1

To a solution of compound 1-11 (366 mg, 1.0 mmol) in EtOAc (3.0 mL) was added a solution of HCl in EtOAc (5.0 mL, 4 M) dropwise, and the mixture was stirred at rt for 8 hrs. After the reaction was completed, the mixture was concentrated in vacuo. The residue was washed with EtOAc (10 mL) and filtered to give the title compound as a pale beige solid (260 mg, 97.8%). The compound was characterized by the following spectroscopic data:

MS (ESI, pos.ion) m/z: 313.2 [M+H]$^+$;

$^1$H NMR (400 MHz, CDCl$_3$) δ (ppm): 8.01 (s, 1H), 7.70-7.76 (m, 2H), 5.25-5.27 (m, 1H), 3.30-3.31 (m, 2H), 2.74-2.77 (m, 1H), 2.54-2.52 (m, 1H), 2.40-2.37 (m, 1H), 2.30-2.10 (m, 1H).

Step 2) the Preparation of Compound 28-2

To a mixture of compound 28-1 (771 mg, 2.274 mmol), compound 9-1 (644.8 mg, 3.41 mmol) and EDCI (654 mg, 3.412 mmol) in DCM (15.0 mL) at 0° C. was added DIPEA (0.65 mL, 3.94 mmol) dropwise. At the end of addition, the mixture was stirred at rt for 3 hrs. After the reaction was completed, 20 mL of water was added, and the resulting mixture was extracted with DCM (20 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a pale yellow solid (694 mg, 70%). The compound was characterized by the following spectroscopic data:

MS (ESI, pos.ion) m/z: 437.3 [M+H]$^+$;

$^1$H NMR (400 MHz, CDCl$_3$) δ (ppm): 7.73-7.72 (d, 1H, J=4.0 Hz), 7.33, 7.30 (s, s, 1H), 7.20-7.19 (d, 1H, J=4.0 Hz), 5.39, 5.36 (brs, brs, 1H), 5.10-5.06 (m, 1H), 4.42-4.40 (t, 1H, J=8.0 Hz), 3.84-3.78 (m, 1H), 3.67-3.64 (m, 1H), 3.63 (s, 3H), 2.43-2.33 (m, 1H), 2.27-2.11 (m, 2H), 2.04-1.86 (m, 2H), 1.60-1.49 (m, 1H), 1.23-1.11 (m, 1H), 0.98-0.96 (m, 3H), 0.92-0.89 (m, 3H).

Step 3) the Preparation of Compound 28-3

A mixture of compound 28-2 (420 mg, 0.961 mmol), compound 1-8-2 (366 mg, 1.44 mmol), Pd(dppf)Cl$_2$.CH$_2$Cl$_2$ (79 mg, 0.0961 mmol) and KOAc (283 mg, 2.88 mmol) in DMF (6.0 mL) was stirred at 90° C. under N$_2$ for 3 hrs. After the reaction was completed, the mixture was cooled to rt, diluted with EtOAc (60 mL) and filtered through a celite pad. The filtrate was washed with water (30 mL×3) and brine. The combined organic layers were dried over anhydrous Na$_2$SO$_4$ and concentrated in vacuo. The residue was purified by a silica gel column chromatography (PE/EtOAc (v/v)=1/2) to give the title compound as a beige solid (0.28 g, 60.2%). The compound was characterized by the following spectroscopic data:

MS (ESI, pos.ion) m/z: 485.3 [M+H]$^+$;

$^1$H NMR (400 MHz, CDCl$_3$) δ (ppm): 7.88 (s, 1H), 7.71-7.73 (m, 1H), 7.66-7.67 (m, 1H), 5.33-5.40 (br, 2H), 4.30-4.34 (t, 1H, J=8.72 Hz), 3.89-3.91 (m, 1H), 3.70 (s, 3H), 3.64-3.62 (m, 1H), 3.07-3.09 (m, 1H), 2.21-2.22 (m, 1H), 2.2-2.13 (m, 2H), 1.50-1.53 (m, 1H), 1.35 (s, 12H), 1.27-1.30 (m, 2H), 0.88-0.84 (m, 6H).

Step 4) the Preparation of Compound 28-4

To a mixture of compound 23-5 (4.55 g, 10 mmol), compound 28-3 (4.84 g, 10 mmol), Pd(PPh$_3$)$_4$ (0.578 g, 0.5 mmol) and K$_2$CO$_3$ (3.45 g, 25 mmol) were added DME (50.0 mL) and H$_2$O (10.0 mL) via syringe, and the mixture was stirred at 90° C. under N$_2$ for 3 hrs. After the reaction was completed, the mixture was cooled to rt, and 50 mL of water was added. The resulting mixture was extracted with EtOAc (30 mL×3). The combined organic layers were washed with brine, dried over anhydrous Na$_2$SO$_4$ and concentrated in vacuo. The residue was purified by a silica gel column chromatography (PE/EtOAc (v/v)=1/2) to give the title compound as a beige solid (3.84 g, 58%). The compound was characterized by the following spectroscopic data:

MS (ESI, pos.ion) m/z: 664.5 [M+H]$^+$;

$^1$H NMR (400 MHz, CDCl$_3$) δ (ppm): 7.62, 7.60 (s, s, 1H), 7.59-7.50 (m, 3H), 7.26, 7.24 (s, s, 1H), 5.57, 5.54 (brs, brs, 1H), 5.13-5.09 (brs, 1H), 4.46-4.41 (m, 2H), 4.15-4.12 (m, 1H), 3.84-3.77 (m, 1H), 3.68-3.65 (m, 1H), 3.64 (s, 3H), 2.42-2.34 (m, 1H), 2.25 (s, 3H), 2.24-2.08 (m, 3H), 1.95-1.86 (m, 1H), 1.64-1.57 (m, 1H), 1.41-1.31 (m, 1H), 1.28-1.13 (m, 2H), 1.10-0.94 (m, 2H), 0.88-0.81 (m, 6H).

Step 5) the Preparation of Compound 28-5

To a mixture of compound 23-8 (4.96 g, 10 mmol), compound 28-4 (6.63 g, 10 mmol), Pd(PPh$_3$)$_4$ (0.578 g, 0.5 mmol) and K$_2$CO$_3$ (3.45 g, 25 mmol) were added DME (50.0 mL) and H$_2$O (10.0 mL) via syringe, and the mixture was stirred at 90° C. under N$_2$ for 3 hrs. After the reaction was completed, the mixture was cooled to rt, and 50 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (DCM/MeOH (v/v)=50/1) to give the title compound as a beige solid (3.84 g, 58%). The compound was characterized by the following spectroscopic data:

MS (ESI, pos.ion) m/z: 442.5 [M+2H]$^{2+}$;

$^1$H NMR (400 MHz, CDCl$_3$) δ (ppm): 7.63-7.59 (m, 4H), 7.58-7.50 (m, 5H), 7.46, 7.44 (s, s, 1H), 5.57, 5.54 (brs, brs, 2H), 5.23, 5.19 (m, m, 1H), 5.13-5.09 (m, 1H), 4.45-4.41 (m, 1H), 4.34-4.30 (m, 1H), 4.29-4.26 (m, 1H), 4.09-4.06 (m, 1H), 3.85-3.77 (m, 2H), 3.66 (s, 3H), 3.64 (s, 3H), 3.63-3.61 (m, 2H), 2.42-2.38 (m, 1H), 2.37-2.36 (m, 3H), 2.30-1.88 (m, 9H), 1.63-1.49 (m, 4H), 1.42-1.31 (m, 1H), 1.12-1.03 (m, 1H), 1.02-1.00 (br, 3H), 0.93-0.92 (br, 3H), 0.88-0.81 (m, 6H).

Example 29

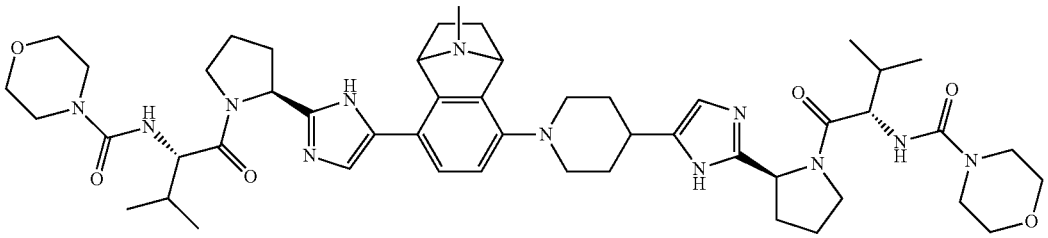 [SMILES: CC(C)[C@H](NC(=O)N1CCOCC1)C(=O)N1CCC[C@H]1c1ncc(-c2ccc(N3CCC(c4cnc([C@@H]5CCCN5C(=O)[C@@H](NC(=O)N5CCOCC5)C(C)C)[nH]4)CC3)c3c2C2CCC3N2C)[nH]1]

Synthetic Route:

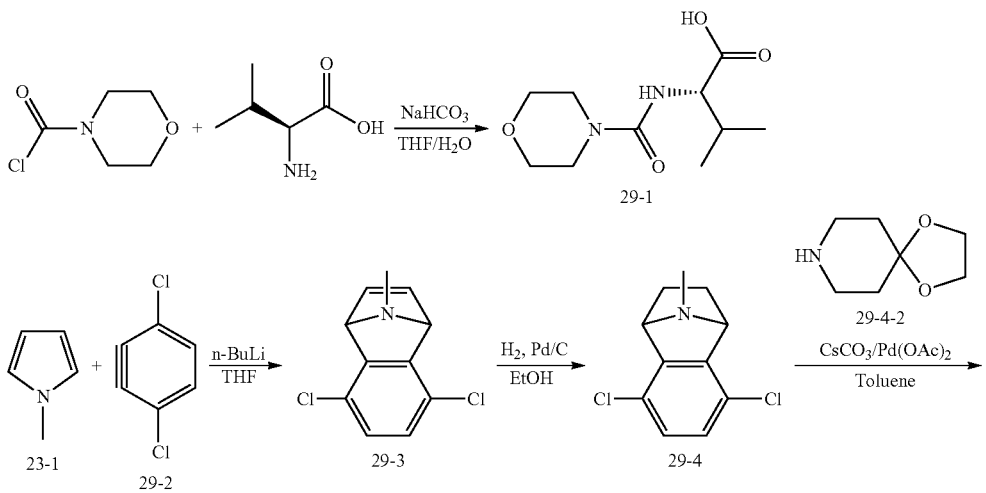

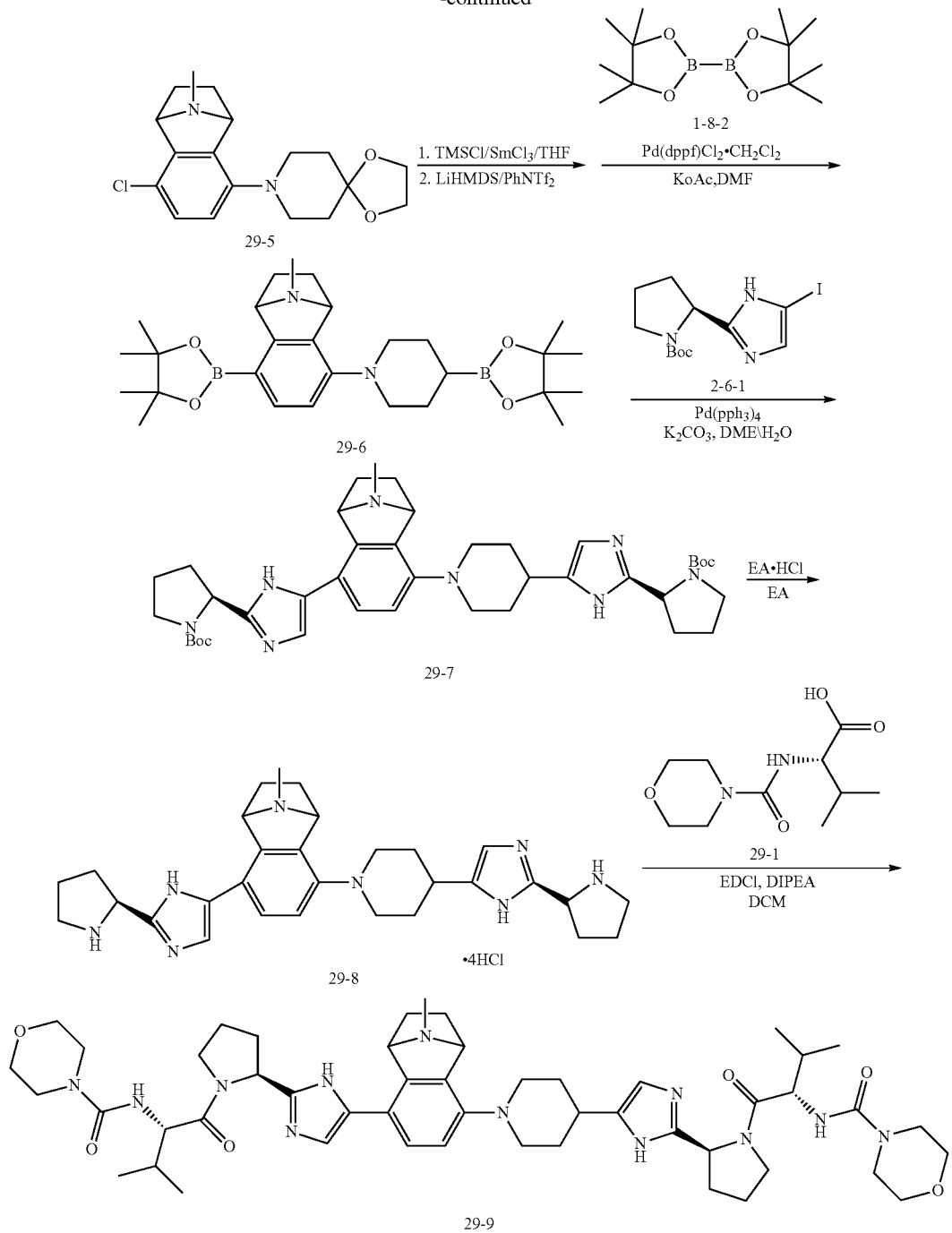

Step 1) the Preparation of Compound 29-1

To a solution of L-Valine (2.49 g, 21.3 mmol) in THF (64.5 mL) was added NaHCO$_3$ aqueous solution (5.37 g, 64 mmol, 64.5 mL), after the solution was stirred at rt for 10 mins later, morpholine-4-carbonyl chloride (2.8 mL, 23.5 mmol) was added. At the end of addition, the mixture was stirred at rt overnight. After the reaction was completed, the resulting mixture was adjusted to pH 3 with hydrochloric acid (1 M) and extracted with EtOAc (50 mL×3). The combined organic layers were dried over anhydrous Na$_2$SO$_4$ and concentrated in vacuo to give the title compound 29-1 as a white solid (2.9g, 60%). The compound was characterized by the following spectroscopic data:

MS (ESI, pos.ion) m/z: 231.3 [M+H]$^+$;

$^1$H NMR (400 MHz, CDCl$_3$) δ (ppm): 9.31 (br, 1H), 5.75, 5.73 (br, br, 1H), 4.27-4.22 (m, 1H), 3.73-3.65 (m, 4H), 3.34-3.28 (m, 4H), 2.35-2.24 (m, 1H), 0.97-0.95 (m, 3H), 0.88-0.85 (m, 3H).

Step 2) the Preparation of Compound 29-3

To a stirred mixture of compound 23-1 (1.54 g, 19 mmol) and compound 29-2 (1.44 g, 10 mmol) in dry THF (25 mL) was added n-butyllithium (6.7 mL, 1.6 M in hexane) dropwise at −78° C. under nitrogen. The mixture was stirred at −78° C. for 1 hr and stirred at rt overnight. After the reaction was completed, the mixture was poured into water (50 mL) and the organic phase was separated. The aqueous layer was extracted further with diethyl ether (3×50 mL). The combined organic layers were dried over anhydrous $Na_2SO_4$ and concentrated in vacuo. The residue was purified by a silica gel column chromatography (PE/EtOAc (v/v)=5/1) to give the title compound 29-3 as a yellow solid (1.13 g, 50.2%). The compound was characterized by the following spectroscopic data:

MS (ESI, pos.ion) m/z: 226.3 [M+H]$^+$;

$^1$H NMR (400 MHz, $CDCl_3$) δ (ppm): 7.94 (s, 2H), 6.91-6.90 (d, 2H, J=4 Hz), 4.88-4.86 (m, 2H), 2.41 (s, 3H).

Step 3) the Preparation of Compound 29-4

To a solution of compound 29-3 (1.8 g, 8.03 mmol) in ethanol (40 mL) was added a catalytic amount of Pd/C (0.0.18 g), and the mixture was stirred under 10 atm of $H_2$ gas at rt for 24 hrs. After the reaction was completed, the mixture was filtered, and the filtrate was concentrated in vacuo to give the title compound 29-4 as a white solid (1.57 g, 86%). The compound was characterized by the following spectroscopic data:

MS (ESI, pos.ion) m/z: 228.3 [M+H]$^+$;

$^1$H NMR (400 MHz, $CDCl_3$) δ (ppm): 6.96 (s, 2H), 4.22-4.20 (m, 2H), 2.25 (s, 3H), 1.53-1.40 (m, 4H).

Step 4) the Preparation of Compound 29-5

To a mixture of compound 29-4 (601 mg, 2.65 mmol), compound 29-4-2 (417.8 mg, 2.92 mmol), $Cs_2CO_3$ (1.54 g, 7.95 mmol) and Pd(OAc)$_2$ (60 mg, 0.265 mmol) was added toluene (10.0 mL) via syringe, and the mixture was stirred at 100° C. under $N_2$ for 10 hrs. After the reaction was completed, the mixture was cooled to rt, diluted with EtOAc (50 mL) and water (20 mL), then filtered through a celite pad. The combined organic layers were washed with brine, dried over anhydrous $Na_2SO_4$ and concentrated in vacuo. The residue was purified by a silica gel column chromatography (PE/EtOAc (v/v)=1/1) to give the title compound as yellow liquid (708 mg, 80%). The compound was characterized by the following spectroscopic data:

MS (ESI, pos.ion) m/z: 335.5 [M+H]$^+$;

$^1$H NMR (400 MHz, $CDCl_3$) δ (ppm): 7.07, 7.05 (s, s, 1H), 6.21, 6.19 (s, s, 1H), 4.24-4.22 (m, 1H), 4.15-4.13 (m, 1H), 4.01-3.87 (m, 4H), 3.21-3.17 (m, 4H), 2.24 (s, 3H), 1.79-1.75 (m, 4H), 1.74-1.67 (m, 1H), 1.27-1.15 (m, 3H).

Step 5) the Preparation of Compound 29-6

To a mixture of compound 29-5 (1.7 g, 5.1 mmol) and $SmCl_3$ (131 mg, 0.51 mmol) was added THF (20 mL) under $N_2$. The mixture was stirred at rt for 15 mins, and TMSCl (610 mg, 5.61 mmol) was added dropwise. The mixture was stirred at rt for 10 hrs. After the reaction was completed, the mixture was filtered through a celite pad. The filtrate was concentrated in vacuo to give the compound (a) (1.5 g), which was used for the next step without further purification.

To a solution of compound (a) in THF (20 mL) was added LiHMDS (6.5 mL, 6.46 mmol, 1 M in THF) dropwise at −78° C. The mixture was stirred at −78° C. for 30 mins, and PhNTf$_2$ (2.77 g, 7.76 mmol) was added. The mixture was stirred at −78° C. for 30 mins and at rt for another 10 hrs. After the reaction was completed, the mixture was quenched with water (50 mL), and extracted with EtOAc (3×50 mL). The combined organic layers were washed by brine, dried over anhydrous $Na_2SO_4$ and concentrated in vacuo to give the compound (b) (1.0 g), which was used for the next step without further purification.

A mixture of compound (b) (1.0 g, 2.0 mmol), compound 1-8-2 (1.27 g, 5.0 mmol), Pd(dppf)Cl$_2$.CH$_2$Cl$_2$ (0.16 g, 0.2 mmol) and KOAc (0.78 g, 8.0 mmol) in DMF (20 mL) was stirred at 90° C. overnight under $N_2$. After the reaction was completed, the mixture was cooled to rt, diluted with EtOAc (200 mL) and water (40 mL), and filtered through a celite pad. The filtrate was washed with water (40 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound as a beige solid (960 mg, 38%). The compound was characterized by the following spectroscopic data:

MS (ESI, pos.ion) m/z: 495.5 [M+H]$^+$;

$^1$H NMR (400 MHz, $CDCl_3$) δ (ppm): 7.57, 7.55 (s, s, 1H), 6.91, 6.89 (s, s, 1H), 4.43-4.40 (m, 1H), 4.20-4.17 (m, 1H), 3.13-3.08 (m, 4H), 2.18 (s, 3H), 2.00-1.92 (m, 2H), 1.88-1.65 (m, 6H), 1.32 (m, 6H), 1.29 (m, 6H), 1.25 (m, 6H), 1.22 (m, 6H), 0.81-0.78 (m, 1H).

Step 6) the Preparation of Compound 29-7

To a mixture of compound 29-6 (2.92 g, 5.91 mmol), compound 2-6-1 (4.94 g, 13.6 mmol), Pd(PPh$_3$)$_4$ (342 mg, 0.296 mmol) and $K_2CO_3$ (2.47 g, 17.73 mmol) were added DME (60.0 mL) and $H_2O$ (12 mL) via syringe, and the mixture was stirred at 90° C. for 3 hrs under $N_2$. After the reaction was completed, the mixture was cooled to rt, and DME was removed in vacuo. To the residue was added 100 mL of water, and the resulting mixture was extracted with EtOAc (100 mL×3). The combined organic layers were washed with brine, dried over anhydrous $Na_2SO_4$ and concentrated in vacuo. The residue was purified by a silica gel column chromatography (DCM/MeOH (v/v)=200/1) to give the title compound 29-7 as a beige solid (2.53 g, 60%). The compound was characterized by the following spectroscopic data:

MS (ESI, pos.ion) m/z: 713.5 [M+H]$^+$;

$^1$H NMR (400 MHz, $CDCl_3$) δ (ppm): 7.55 (s, 1H), 6.95, 6.93 (s, s, 1H), 6.81 (s, 1H), 6.16, 6.14 (s, s, 1H), 5.05-5.01 (m, 1H), 4.86-4.81 (m, 1H), 4.30-4.27 (m, 1H), 3.87-3.85 (m, 1H), 3.73-3.67 (m, 1H), 3.64-3.58 (m, 1H), 3.31-3.24 (m, 4H), 2.65-2.56 (m, 1H), 2.48-2.37 (m, 9H), 2.36 (m, 3H), 2.27-2.17 (m, 2H), 2.15-1.97 (m, 2H), 1.77-1.67 (m, 4H), 1.53 (s, 18H).

Step 7) the Preparation of Compound 29-8

To a solution of compound 29-7 (1.0 g, 1.4 mmol) in EtOAc (10 mL) was added a solution of HCl in EtOAc (10.0 mL, 4 M) dropwise, and the mixture was stirred at rt for 8 hrs. After the reaction was completed, the mixture was concentrated in vacuo, and residue was washed with EtOAc (20 mL) to give the title compound 29-8 as a pale yellow solid (829 mg, 90%). The compound was characterized by the following spectroscopic data:

MS (ESI, pos.ion) m/z: 513.5 [M+H]$^+$.

Step 8) the Preparation of Compound 29-9

To a mixture of compound 29-8 (438 mg, 0.6654 mmol), EDCI (192 mg, 0.998 mmol) and compound 29-1 (246 mg, 0.998 mmol) in DCM (10 mL) at 0° C. was added DIPEA (0.74 mL, 4.5 mmol) dropwise. The mixture was stirred at rt for 10 hrs, diluted with DCM (50 mL), washed with saturated NH$_4$Cl aqueous solution and brine, dried over anhydrous $Na_2SO_4$ and concentrated in vacuo. The residue was purified by a silica gel column chromatography (DCM/EtOH (v/v)=50/1) to give the title compound as pale yellow powder (249 mg, 40%). The compound was characterized by the following spectroscopic data:

MS (ESI, pos.ion) m/z: 469.5 [M+2H]$^{2+}$;

$^1$H NMR (400 MHz, $CDCl_3$) δ (ppm): 7.49 (s, 1H), 6.95 and 6.93 (s, s, 1H), 6.82 (s, 1H), 6.16 and 6.14 (s, s, 1H), 5.67 and 5.65 (br, 2H), 5.36-5.31 (m, 1H), 5.12-5.08 (m, 1H), 4.51-4.47 (m, 2H), 4.29-4.27 (m, 1H), 3.87-3.79 (m, 3H), 3.74-3.62 (m, 10H), 3.35-3.25 (m, 12H), 2.65-2.56 (m, 1H), 2.48-2.37 (m, 2H), 2.36 (s, 3H), 2.31-2.16 (m, 10H), 2.15-2.07 (m, 2H), 1.77-1.67 (m, 2H), 1.29-1.23 (m, 2H), 1.02-1.01 (m, 6H), 0.92-0.91 (m, 6H).

Example 30
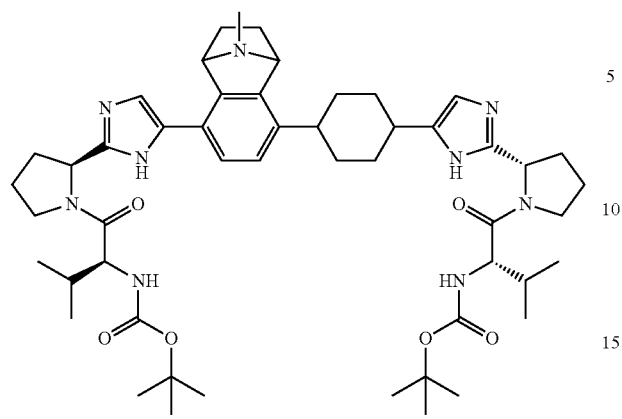
Synthetic Route:
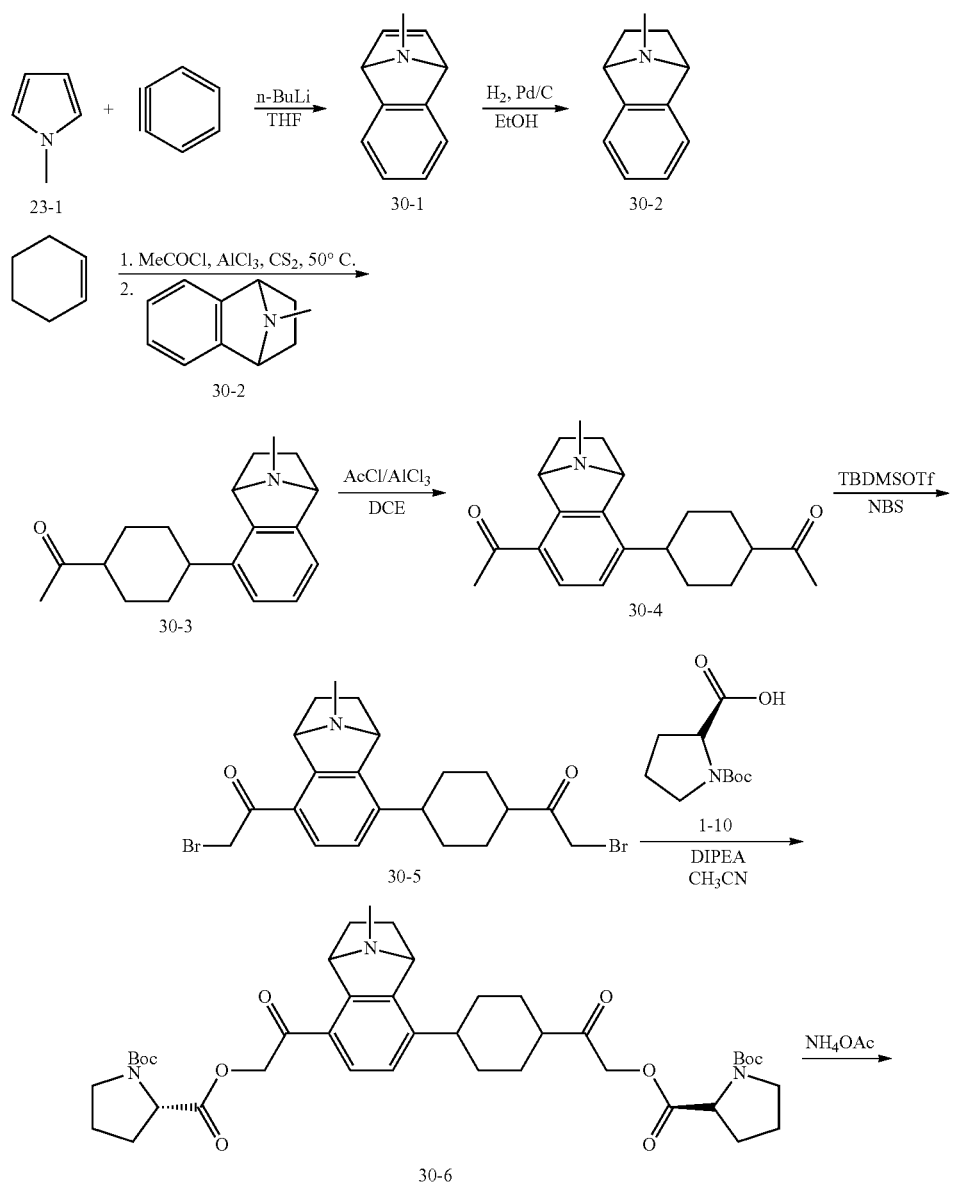

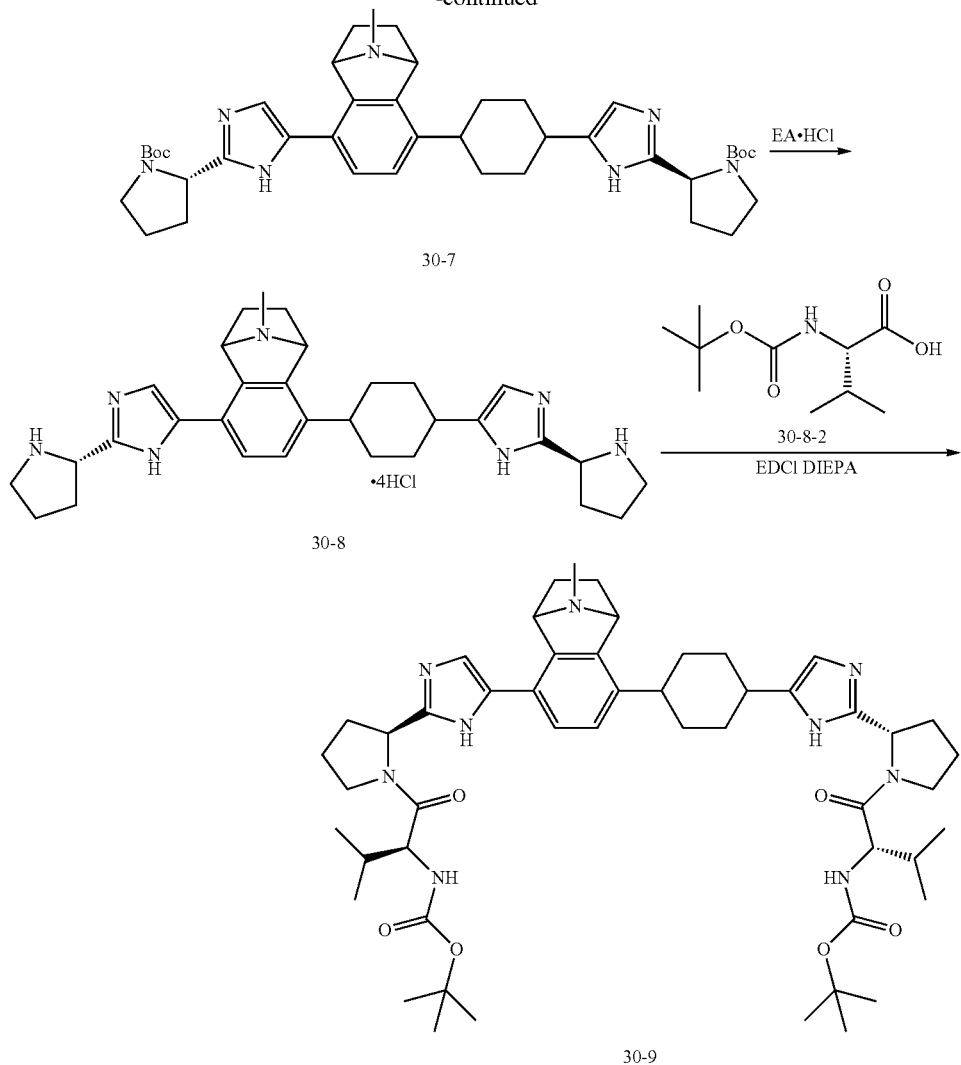

Step 1) the Preparation of Compound 30-1

To a mixture of compound 23-1 (1.54 g, 19 mmol) and benzyne (760 mg, 10 mmol) in dry THF (25 mL) was added n-butyllithium (6.7 mL, 1.6 M in hexane) dropwise at −78° C. under $N_2$. The mixture was stirred at −78° C. for 1 hr and at rt overnight. After the reaction was completed, the mixture was poured into water (50 mL). The aqueous layer was extracted further with diethyl ether (3×50 mL). The combined organic layers were dried over anhydrous $Na_2SO_4$ and concentrated in vacuo. The residue was purified by a silica gel column chromatography (PE/EtOAc (v/v)=5/1) to give the title compound 30-1 as a yellow solid (628 mg, 40%). The compound was characterized by the following spectroscopic data:

MS (ESI, pos.ion) m/z: 158.3 [M+H]$^+$;

$^1$H NMR (400 MHz, CDCl$_3$) δ (ppm): 7.37-7.42 (m, 2H), 7.00-6.95 (m, 2H), 6.78-6.76 (t, 2H, J=4.0 Hz), 4.45-4.42 (m, 2H), 2.01 (s, 3H).

Step 2) the Preparation of Compound 30-2

To a solution of compound 30-1 (1.26 g, 8.03 mmol) in ethanol (40 mL) was added a catalytic amount of Pd/C (0.126 g), and the mixture was stirred under 10 atm of $H_2$ gas at rt for 24 hrs. The reaction mixture was filtered, and the filtrate was concentrated in vacuo to give the title compound 30-2 as a white solid (1.1 g, 86%). The compound was characterized by the following spectroscopic data:

MS (ESI, pos.ion) m/z: 160.3 [M+H]$^+$;

$^1$H NMR (400 MHz, CDCl$_3$) δ (ppm): 7.21-7.13 (m, 4H), 4.09-4.03 (m, 2H), 2.14-2.08 (m, 4H), 2.03 (s, 3H).

Step 3) the Preparation of Compound 30-3

To a suspension of aluminium chloride (2.15 g, 16.2 mmol) in Carbon disulphide (40 mL) was added acetyl chloride (1.4 mL, 19.7 mmol) dropwise, then a solution of cyclohexene (1 mL, 10 mmol) in $CS_2$ (20 mL) was added. At the end of addition, the mixture was stirred at rt for 2 hrs. The mixture was concentrated in vacuo to give the compound as slurry. Compound 30-2 (2.38 g, 15 mmol) was added to the above slurry, and the mixture was stirred at 50° C. for 5 hrs. After the reaction was completed, the mixture was quenched with ice-water (40 mL). The aqueous layer was extracted with EtOAc (3×100 mL). The combined organic lays were washed with brine, dried over anhydrous $Na_2SO_4$ and concentrated in vacuo. The residue was purified by a silica gel column chromatography (PE/DCM (v/v)=10/1) to give the title compound 30-3 as colorless oil (1.42 g, 30%). The compound was characterized by the following spectroscopic data:

MS (ESI, pos.ion) m/z: 284.3 [M+H]$^+$;

$^1$H NMR (400 MHz, CDCl$_3$) δ (ppm): 7.30-7.27 (m, 1H), 7.24-7.22 (m, 1H), 6.98-6.96 (m, 1H), 4.20-4.17 (m, 1H), 3.96-3.92 (m, 1H), 2.96-2.87 (m, 1H), 2.25-2.18 (m, 1H), 2.14 (s, 3H), 2.11 (s, 3H), 1.78-1.85 (m, 4H), 1.65-1.46 (m, 4H), 1.62-1.76 (m, 2H), 1.24-1.16 (m, 2H).

Step 4) the Preparation of Compound 30-4

To a suspension of aluminium chloride (2.12 g, 15.9 mmol) in 1,2-dichloroethane (40 mL) was added acetyl chloride (1.2 mL, 16.8 mmol) dropwise, then a solution of compound 30-3 (3.68 g, 13 mmol) in 1,2-dichloroethane (20 mL) was added dropwise. At the end of addition, the mixture was stirred at rt for 2 hrs. After the reaction was completed, the mixture was quenched with ice-water (40 mL). The aqueous layer was extracted with EtOAc (3×100 mL). The combined organic layers were washed with brine, dried over anhydrous Na$_2$SO$_4$ and concentrated in vacuo. The residue was purified by a silica gel column chromatography (PE/EtOAc (v/v)=10/1) to give the title compound 30-4 as a white solid (1.63 g, 38.5%). The compound was characterized by the following spectroscopic data:

MS (ESI, pos.ion) m/z: 326.3 [M+H]$^+$;

$^1$H NMR (400 MHz, CDCl$_3$) δ (ppm): 7.64, 7.61 (s, s, 1H), 6.97, 6.95 (s, s, 1H), 4.24-4.19 (m, 2H), 3.23-3.14 (m, 1H), 2.55 (s, 3H), 2.31 (s, 3H), 2.26-2.18 (m, 1H), 2.11 (s, 3H), 1.85-1.46 (m, 10H), 1.26-1.18 (m, 2H).

Step 5) the Preparation of Compound 30-5

To a solution of compound 30-4 (1.54 g, 4.73 mmol) in DCM (30 mL) at 0° C. were added DIPEA (2.33 mL, 14.1 mmol) and TBDMSOTf (3.5 mL, 11.5 mmol) dropwise in turn. At the end of addition, the mixture was stirred at rt for 2.0 hrs. After the reaction was completed, the mixture was quenched with water (20 mL). The aqueous layer was extracted with DCM (3×40 mL). The combined organic layers were washed with brine, dried over anhydrous Na$_2$SO$_4$ and concentrated in vacuo to give the compound as yellow gel-like substance. To the solution of yellow gel-like substance in THF (20 mL) was added NBS (1.56 g, 8.76 mmol) at 0° C. The mixture was stirred at 0° C. for 4 hrs. After the reaction was completed, THF was removed, and 20 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=10/1) to give the title compound 30-5 as white slurry (1.6 g, 57.76%). The compound was characterized by the following spectroscopic data:

MS (ESI, pos.ion) m/z: 484.3 [M+H]$^+$;

$^1$H NMR (400 MHz, CDCl$_3$) δ (ppm): 7.72, 7.70 (s, s, 1H), 7.27, 7.24 (s, s, 1H), 4.40 (s, 2H), 4.27-4.22 (m, 2H), 3.93 (s, 2H), 3.27-3.19 (m, 1H), 2.76-2.68 (m, 1H), 2.32 (s, 3H), 1.80-1.52 (m, 10H), 1.28-1.19 (m, 2H).

Step 6) the Preparation of Compound 30-6

To a solution of compound 30-5 (1.05 g, 2.18 mmol) in CH$_3$CN (22 mL) were added DIPEA (1.02 mL, 6.2 mmol) and compound 1-10 (1.08 g, 5.014 mmol) at 0° C. in turn. At the end of addition, the mixture was stirred at rt for 1.0 hr. After the reaction was completed, the mixture was concentrated in vacuo, and the residue was purified by a silica gel column chromatography (PE/EtOAc (v/v)=2/3) to give the title compound 30-6 as pale yellow slurry (1.4 g, 85%). The compound was characterized by the following spectroscopic data:

MS (ESI, pos.ion) m/z: 752.3 [M+H]$^+$.

Step 7) the Preparation of Compound 30-7

A suspension of compound 30-6 (1.38 g, 1.83 mmol) and NH$_4$OAc (2.82 g, 36.6 mmol) in xylene (20 mL) was stirred at 140° C. for 5.0 hrs. After the reaction was completed, the mixture was cooled to rt, and 40 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (DCM/MeOH (v/v)=50/1) to give the title compound 30-7 as a pale yellow solid (0.95 g, 73%). The compound was characterized by the following spectroscopic data:

MS (ESI, pos.ion) m/z: 712.3 [M+H]$^+$;

$^1$H NMR (400 MHz, CDCl$_3$) δ (ppm): 7.60 (s, 1H), 7.16, 7.14 (s, s, 1H), 6.81 (s, 1H), 6.70, 6.68 (s, s, 1H), 5.01-4.97 (m, 1H), 4.86-4.81 (m, 1H), 4.21-4.17 (m, 1H), 3.88-3.84 (m, 1H), 3.83-3.75 (m, 2H), 3.70-3.62 (m, 2H), 3.08-2.99 (m, 1H), 2.77-2.68 (m, 1H), 2.55-2.47 (m, 1H), 2.37 (s, 3H), 2.33-2.16 (m, 4H), 2.14-2.01 (m, 3H), 2.00-1.94 (m, 4H), 1.88-1.68 (m, 6H), 1.51 (s, 9H), 1.42 (s, 9H).

Step 8) the Preparation of Compound 30-8

To a solution of compound 30-7 (950 mg, 1.33 mmol) in EtOAc (10 mL) was added a solution of HCl in EtOAc (10 mL, 4 M) dropwise, and the mixture was stirred at rt for 8 hrs. After the reaction was completed, the mixture was concentrated in vacuo. The residue was washed with EtOAc (20 mL) and filtered to give the title compound 30-8 as a pale yellow solid (730 mg, 83.5%). The compound was characterized by the following spectroscopic data:

MS (ESI, pos.ion) m/z: 512.7 [M+H]$^+$.

Step 9) the Preparation of Compound 30-9

To a suspension of compound 30-8 (394 mg, 0.6 mmol), EDCI (300.56 mg, 1.56 mmol) and compound 30-8-2 (341 mg, 1.56 mmol) in DCM (10.0 mL) at 0° C. was added DIPEA (1.02 mL, 6.14 mmol) dropwise. At the end of addition, the mixture was stirred at rt for 10 hrs. After the reaction was completed, the mixture was diluted with DCM (20 mL), washed with saturated NH$_4$Cl aqueous solution and brine, dried over anhydrous Na$_2$SO$_4$ and concentrated in vacuo. The residue was purified by a silica gel column chromatography (DCM/EtOH (v/v)=50/1) to give the title compound 30-9 as pale yellow powder (350 mg, 64.13%). The compound was characterized by the following spectroscopic data:

MS (ESI, pos.ion) m/z: 456.3 [M+H]$^{2+}$;

$^1$H NMR (400 MHz, CDCl$_3$) δ (ppm): 7.54 (s, 1H), 7.16, 7.14 (s, s, 1H), 6.82 (s, 1H), 6.70, 6.68 (s, s, 1H), 5.29-5.25 (m, 1H), 5.20, 5.18 (br, br, 2H), 5.12-5.07 (m, 1H), 4.40-4.36 (m, 2H), 4.22-4.17 (m, 1H), 3.86-3.79 (m, 3H), 3.70-3.61 (m, 2H), 3.08-3.00 (m, 1H), 2.77-2.68 (m, 1H), 2.37 (s, 3H), 2.30-1.65 (m, 20H), 1.43 (s, 18H), 1.30-1.21 (m, 2H), 0.97-0.95 (m, 6H), 0.91-0.89 (m, 6H).

Example 31

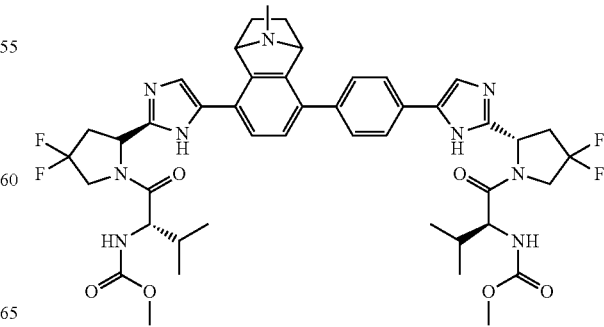

Synthetic Route:
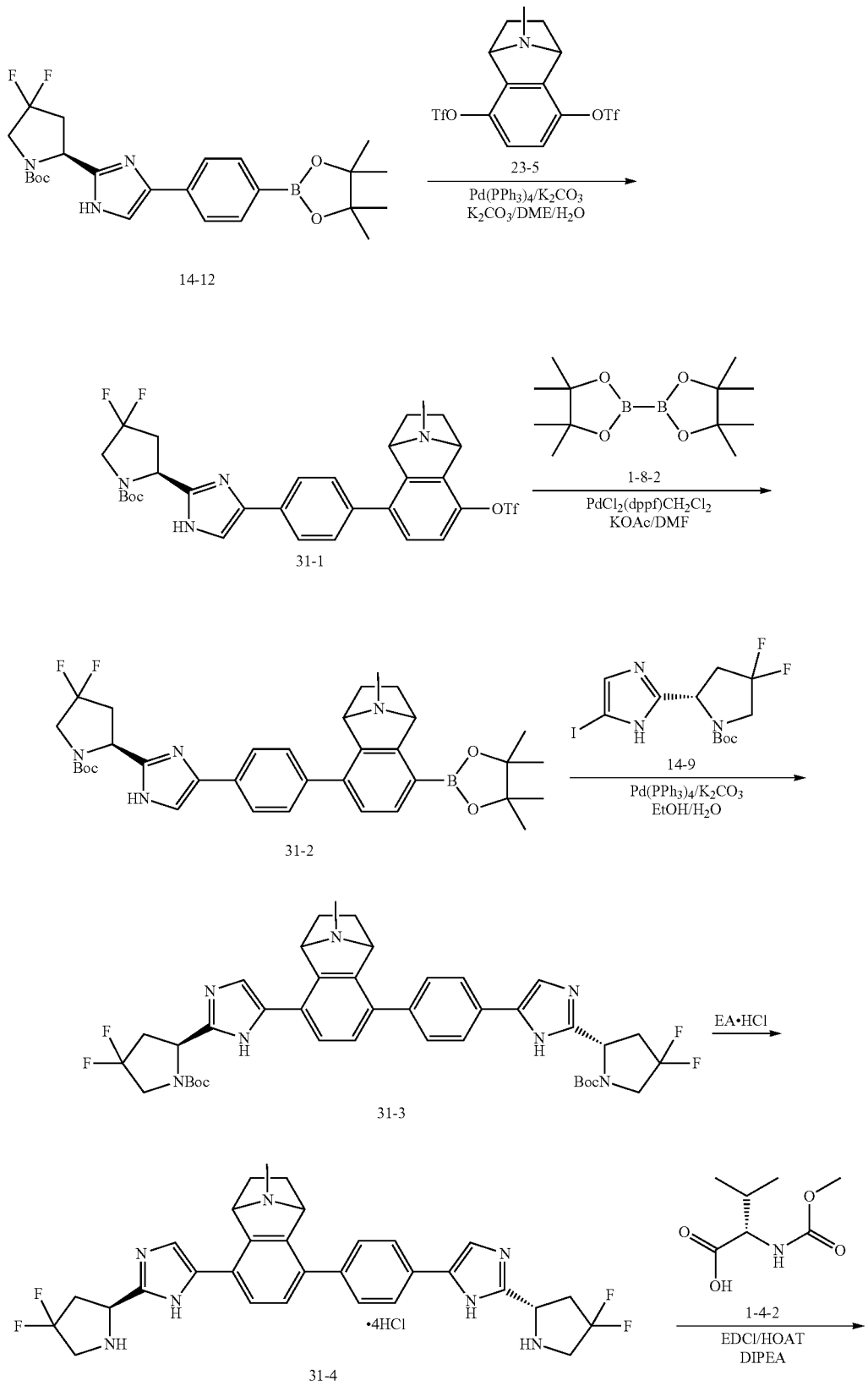

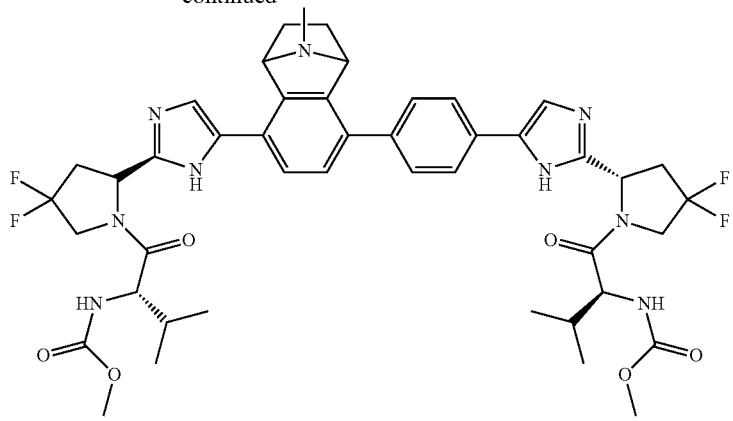

31-5

Step 1) the Preparation of Compound 31-1

To a mixture of compound 14-12 (1.98 g, 4.5 mmol), compound 23-5 (2.05 g, 4.5 mmol), Pd(PPh$_3$)$_4$ (260 mg, 0.225 mmol) and K$_2$CO$_3$ (1.24 g, 9.0 mmol) were added DME (20.0 mL) and H$_2$O (4.0 mL) via syringe, and the mixture was stirred at 90° C. under N$_2$ for 3.0 hrs. After the reaction was completed, the mixture was cooled to rt, and 20 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=5/1) to give the title compound 31-1 as a white solid (1.45 g, 49.3%). The compound was characterized by the following spectroscopic data:

MS (ESI, pos.ion) m/z: 654.63 [M+H]$^+$;

$^1$H NMR (400 MHz, CDCl$_3$) δ (ppm): 7.72 (m, 4H), 7.46 (s, 1H), 7.20, 7.18 (s, s, 1H), 7.07, 7.05 (s, s, 1H), 4.93-4.88 (m, 1H), 4.44-4.41 (m, 1H), 4.18-4.06 (m, 1H), 3.95-3.93 (m, 1H), 3.92-3.80 (m, 1H), 2.86-2.70 (m, 1H), 2.47-2.26 (m, 1H), 2.25 (m, 3H), 1.59-1.57 (m, 1H), 1.53 (s, 9H), 1.28-1.16 (m, 2H), 0.97-0.89 (m, 1H).

Step 2) the Preparation of Compound 31-2

A mixture of compound 31-1 (1.50 g, 2.3 mmol), compound of 1-8-2 (0.64 g, 2.53 mmol), PdCl$_2$(dppf).CH$_2$Cl$_2$ (90 mg, 0.115 mmol) and KOAc (0.6 g, 5.75 mmol) in DMF (15 mL) was stirred at 120° C. under N$_2$ for 4.0 hrs. After the reaction was completed, the mixture was cooled to rt, diluted with EtOAc (100 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=8/1) to give the title compound 31-2 as a white solid (1.06 g, 73%). The compound was characterized by the following spectroscopic data:

MS (ESI, pos.ion) m/z: 632.5 [M+H]$^+$;

$^1$H NMR (400 MHz, CDCl$_3$) δ (ppm): 7.81, 7.79 (s, s, 1H), 7.78-7.70 (m, 4H), 7.46 (s, 1H), 7.45, 7.43 (s, s, 1H), 4.93-4.88 (m, 1H), 4.57-4.54 (m, 1H), 4.18-4.05 (m, 1H), 4.02-3.99 (m, 1H), 3.92-3.79 (m, 1H), 2.86-2.68 (m, 1H), 2.47-2.29 (m, 1H), 2.28-2.27 (m, 3H), 1.80-1.64 (m, 2H), 1.41 (s, 9H), 1.33-1.32 (m, 6H), 1.29 (m, 6H), 1.28-1.19 (m, 2H).

Step 3) the Preparation of Compound 31-3

A suspension of compound 14-9 (220 mg, 0.55 mmol), compound 31-2 (347 mg, 0.55 mmol), Pd(PPh$_3$)$_4$ (32 mg, 0.027 mmol) and K$_2$CO$_3$ (190 mg, 1.37 mmol) in mixed solvents of EtOH and H$_2$O (7.5 mL, v/v=4/1) was stirred at 90° C. under N$_2$ for 2 hrs. After the reaction was completed, the mixture was concentrated in vacuo, and the residue was dissolved in EtOAc (50 mL). The resulting mixture was washed with brine, dried over anhydrous Na$_2$SO$_4$ and concentrated in vacuo. The residue was purified by a silica gel column chromatography (DCM/EtOH (v/v)=100/1) to give the title compound as a white solid (240 mg, 56.2%). The compound was characterized by the following spectroscopic data:

MS (ESI, pos.ion) m/z: 778.5 [M+H]$^+$;

$^1$H NMR (400 MHz, CDCl$_3$) δ (ppm): 7.87 (s, 1H), 7.63-7.59 (m, 2H), 7.56-7.53 (m, 2H), 7.44 (m, 1H), 7.43, 7.41 (s, s, 1H), 7.31, 7.29 (s, s, 1H), 5.06-5.01 (m, 1H), 5.00-4.95 (m, 1H), 4.18-4.05 (m, 4H), 3.92-3.79 (m, 2H), 2.88-2.68 (m, 2H), 2.49-2.36 (m, 2H), 2.35 (m, 3H), 1.75-1.67 (m, 2H), 1.53 (s, 9H), 1.41 (s, 9H), 1.32-1.24 (m, 2H).

Step 4) the Preparation of Compound 31-4

To a solution of compound 31-3 (240 mg, 0.31 mmol) in EtOAc (4.0 mL) was added a solution of HCl in EtOAc (3.0 mL, 4 M) dropwise. At the end of addition, the mixture was stirred at rt for 8.0 hrs. After the reaction was completed, the mixture was concentrated in vacuo. The residue was washed with EtOAc and filtered to give the title compound as a pale yellow solid (200 mg, 60%). The compound was characterized by the following spectroscopic data:

MS (ESI, pos.ion) m/z: 577.3 [M+H]$^+$.

Step 5) the Preparation of Compound 31-5

A suspension of compound 31-4 (188 mg, 0.26 mmol), compound 1-4-2 (100 mg, 0.57 mmol), EDCI (110 mg, 0.57 mmol) and HOAT (70 mg, 0.52 mmol) in DCM (6.0 mL) was stirred at 0° C., then DIPEA (0.46 mL, 2.81 mmol) was added dropwise. At the end of addition, the mixture was stirred at rt for 3 hrs. After the reaction was completed, the mixture was diluted with DCM (50 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=40/1) to give the title compound as a white solid (200 mg, 86%). The compound was characterized by the following spectroscopic data:

MS (ESI, pos.ion) m/z: 892.3 [M+H]$^+$;

$^1$H NMR (400 MHz, CDCl$_3$) δ (ppm): 7.76 (s, 1H), 7.63-7.59 (m, 2H), 7.56-7.53 (m, 2H), 7.44, 7.41 (s, s, 1H), 7.40 (s, 1H), 7.31, 7.29 (s, s, 1H), 5.56 (br, 1H), 5.55 (br, 1H), 5.19-5.11 (m, 2H), 4.32-4.28 (m, 2H), 4.21-4.05 (m, 4H), 3.91-3.81 (m, 2H), 3.66 (s, 6H), 2.92-2.74 (m, 2H), 2.51-2.36 (m, 2H), 2.28-2.16 (m, 2H), 2.35 (m, 3H), 1.75-1.67 (m, 2H), 1.32-1.23 (m, 2H), 1.02-1.00 (m, 6H), 0.93-0.91 (m, 6H).

Example 32

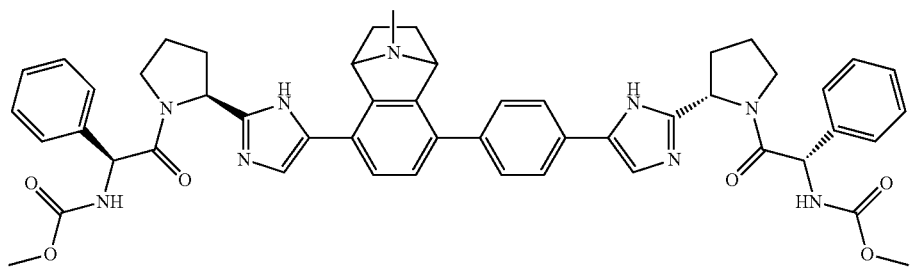

Synthetic Route:

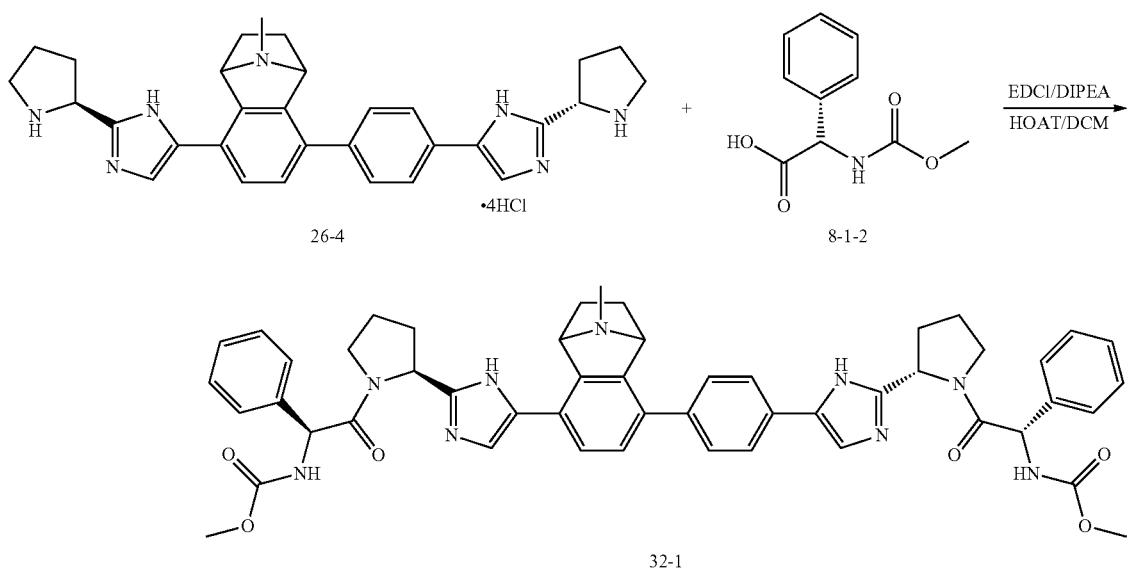

Step 1) the Preparation of Compound 32-1

A suspension of compound 26-4 (221 mg, 0.34 mmol), compound 8-1-2 (150 mg, 71.4 mmol), EDCI (73 mg, 0.38 mmol) and HOAT (47 mg, 0.34 mmol) in DCM (8.0 mL) was stirred at 0° C., then DIPEA (0.4 mL, 2.42 mmol) was added dropwise. At the end of addition, the mixture was stirred at rt for 3 hrs. After the reaction was completed, the mixture was diluted with DCM (20 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=50/1) to give the title compound as a white solid (220 mg, 73%). The compound was characterized by the following spectroscopic data:

MS (ESI, pos.ion) m/z: 888.3 [M+H]$^+$;

$^1$H NMR (400 MHz, CDCl$_3$) δ (ppm): 7.63-7.60 (m, 3H), 7.59 (s, 1H), 7.56-7.53 (m, 2H), 7.44, 7.41 (s, s, 1H), 7.35-7.27 (m, 7H), 7.19-7.15 (m, 4H), 5.91 (br, 1H), 5.89 (br, 1H), 5.35-5.34 (m, 2H), 5.33-5.32 (m, 1H), 5.19-5.13 (m, 2H), 4.14-4.12 (m, 1H), 4.06-4.05 (m, 1H), 3.91-3.85 (m, 2H), 3.75-3.69 (m, 2H), 3.64 (s, 6H), 2.35 (s, 3H), 2.34-2.07 (m, 4H), 2.03-1.92 (m, 4H), 1.76-1.67 (m, 2H), 1.30-1.24 (m, 2H).

Example 33

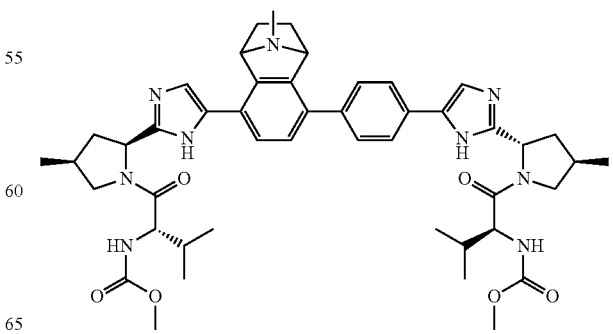

Synthetic Route:
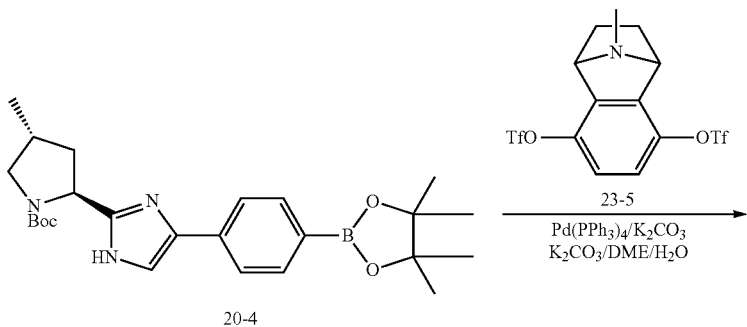
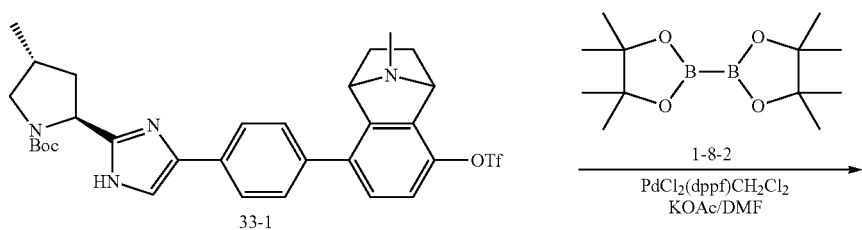
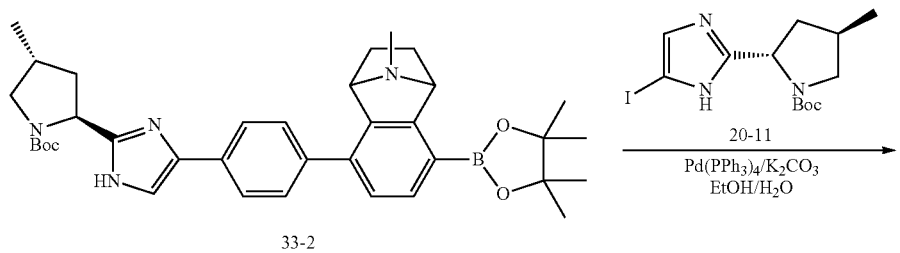
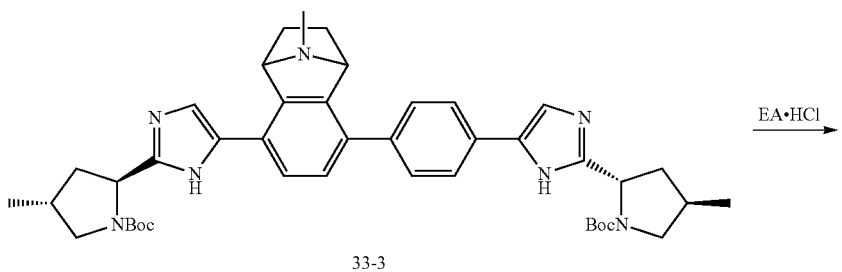
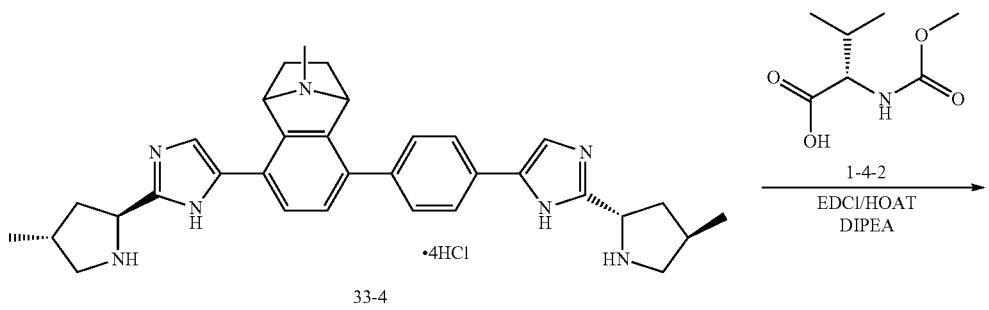

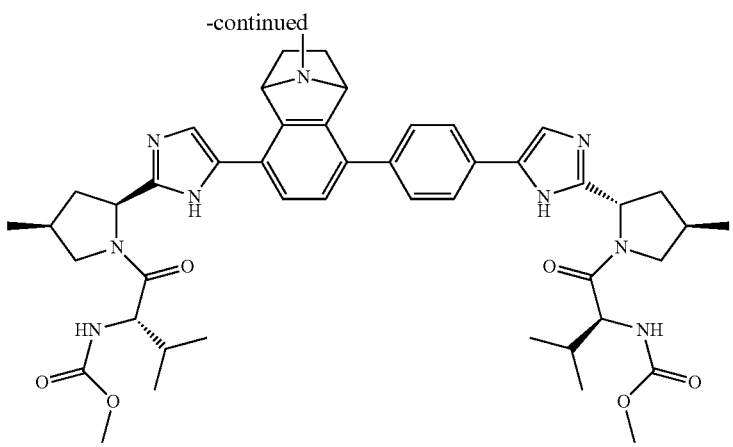

33-5

Step 1) the Preparation of Compound 33-1

To a mixture of compound 20-4 (3.4 g, 7.7 mmol), compound 23-5 (3.5 g, 7.7 mmol), Pd(PPh$_3$)$_4$ (450 mg, 0.38 mmol) and K$_2$CO$_3$ (2.1 g, 15.4 mmol) were added DME (32.0 mL) and H$_2$O (8.0 mL) via syringe, and the mixture was stirred at 90° C. under N$_2$ for 3 hrs. After the reaction was completed, the mixture was cooled to rt, and 40 mL of water was added. The resulting mixture was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a pale yellow solid (2.87 g, 58.9%). The compound was characterized by the following spectroscopic data:

MS (ESI, pos.ion) m/z: 633.4 [M+H]$^+$;

$^1$H NMR (400 MHz, CDCl$_3$) δ (ppm): 7.72 (s, 4H), 7.36 (s, 1H), 7.20, 7.18 (s, s, 1H), 7.07, 7.05 (s, s, 1H), 4.81-4.76 (m, 1H), 4.44-4.41 (m, 1H), 3.95-3.92 (m, 1H), 3.80-3.73 (m, 1H), 3.09-3.02 (m, 1H), 2.32-2.19 (m, 5H), 1.41 (s, 9H), 1.73-1.67 (m, 1H), 1.59-1.51 (m, 1H), 1.28-1.13 (m, 2H), 0.97-0.89 (m, 4H).

Step 2) the Preparation of Compound 33-2

To a mixture of compound 33-1 (1.02 g, 1.62 mmol), compound of 1-8-2 (0.42 g, 1.7 mmol), PdCl$_2$(dppf).CH$_2$Cl$_2$ (67 mg, 0.08 mmol) and KOAc (0.4 g, 4.05 mmol) in DMF (10 mL) was stirred at 90° C. for 3.0 hrs under N$_2$. After the reaction was completed, the mixture was cooled to rt, diluted with EtOAc (80 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=3/1) to give the title compound as a pale yellow solid (0.67 g, 67.8%). The compound was characterized by the following spectroscopic data:

MS (ESI, pos.ion) m/z: 612.5 [M+H]$^+$;

$^1$H NMR (400 MHz, CDCl$_3$) δ (ppm): 7.81, 7.79 (s, s, 1H), 7.78-7.70 (m, 4H), 7.45, 7.43 (s, s, 1H), 7.36 (s, 1H), 4.80-4.77 (m, 1H), 4.57-4.54 (m, 1H), 4.02-3.99 (m, 1H), 3.80-3.73 (m, 1H), 3.09-3.02 (m, 1H), 2.32-2.19 (m, 5H), 1.80-1.64 (m, 3H), 1.14 (s, 9H), 1.32 (m, 6H), 1.29 (m, 6H), 1.28-1.19 (m, 2H), 0.96-0.93 (m, 4H).

Step 3) the Preparation of Compound 33-3

A suspension of compound 33-2 (354 mg, 0.58 mmol), compound 20-11 (240 mg, 0.63 mmol), Pd(PPh$_3$)$_4$ (35 mg, 0.03 mmol) and K$_2$CO$_3$ (80 mg, 1.4 mmol) in mixed solvents of EtOH and H$_2$O (10 mL, v/v=4/1) was stirred at 90° C. under N$_2$ for 4 hrs. After the reaction was completed, the mixture was concentrated in vacuo, and the residue was dissolved in EtOAc (50 mL). The resulting mixture was washed with brine, dried over anhydrous Na$_2$SO$_4$ and concentrated in vacuo. The residue was purified by a silica gel column chromatography (DCM/EtOH (v/v)=60/1) to give the title compound as a white solid (270 mg, 63.5%). The compound was characterized by the following spectroscopic data:

MS (ESI, pos.ion) m/z: 734.5 [M+H]$^+$;

$^1$H NMR (400 MHz, CDCl$_3$) δ (ppm): 7.72 (s, 1H), 7.63-7.60 (m, 2H), 7.59 (s, 1H), 7.56-7.53 (m, 2H), 7.44, 7.41 (s, s, 1H), 7.31, 7.29 (s, s, 1H), 4.97-4.92 (m, 1H), 4.88-4.84 (m, 1H), 4.16-4.12 (m, 1H), 4.07-4.03 (m, 1H), 3.81-3.73 (m, 2H), 3.09-3.02 (m, 2H), 2.35 (s, 3H), 2.34-2.19 (m, 4H), 1.76-1.66 (m, 4H), 1.42 (s, 9H), 1.41 (s, 9H), 1.30-1.24 (m, 2H), 0.96-0.93 (m, 6H).

Step 4) the Preparation of Compound 33-4

To a solution of compound 33-3 (275 mg, 0.375 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (10 mL) and filtered to give the title compound as pale yellow powder (200 mg, 78.7%). The compound was characterized by the following spectroscopic data:

MS (ESI, pos.ion) m/z: 534.5 [M+H]$^+$.

Step 5) the Preparation of Compound 33-5

A suspension of compound 33-4 (210 mg, 0.31 mmol), compound 1-4-2 (1121 mg, 0.68 mmol), EDCI (130 mg, 0.68 mmol) and HOAT (85 mg, 0.62 mmol) in DCM (10.0 mL) was stirred at 0° C., then DIPEA (0.56 mL, 3.39 mmol) was added dropwise. At the end of addition, the mixture was stirred at rt for 3 hrs. After the reaction was completed, the mixture was diluted with DCM (50 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=50/1) to give the title compound as a white solid (200 mg, 76.1%). The compound was characterized by the following spectroscopic data:

MS (ESI, pos.ion) m/z: 849.3 [M+H]$^+$;

$^1$H NMR (400 MHz, CDCl$_3$) δ (ppm): 7.63-7.60 (m, 3H), 7.59 (s, 1H), 7.56-7.53 (m, 2H), 7.44, 7.41 (s, s, 1H), 7.31, 7.29 (s, s, 1H), 5.56 (br, 1H), 5.55 (br, 1H), 5.35-5.30 (m, 1H), 5.07-5.02 (m, 1H), 4.31-4.27 (m, 2H), 4.14-4.12 (m, 1H), 4.06-3.85 (m, 4H), 3.66 (s, 6H), 3.61-3.55 (m, 1H), 2.35 (s, 3H), 2.34-2.14 (m, 6H), 1.84-1.63 (m, 4H), 1.30-1.22 (m, 2H), 1.02-1.00 (m, 6H), 0.94-0.90 (m, 12H).

Example 34
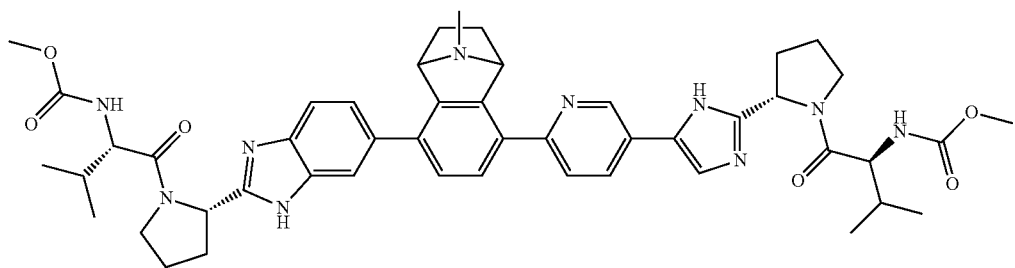
Synthetic Route:
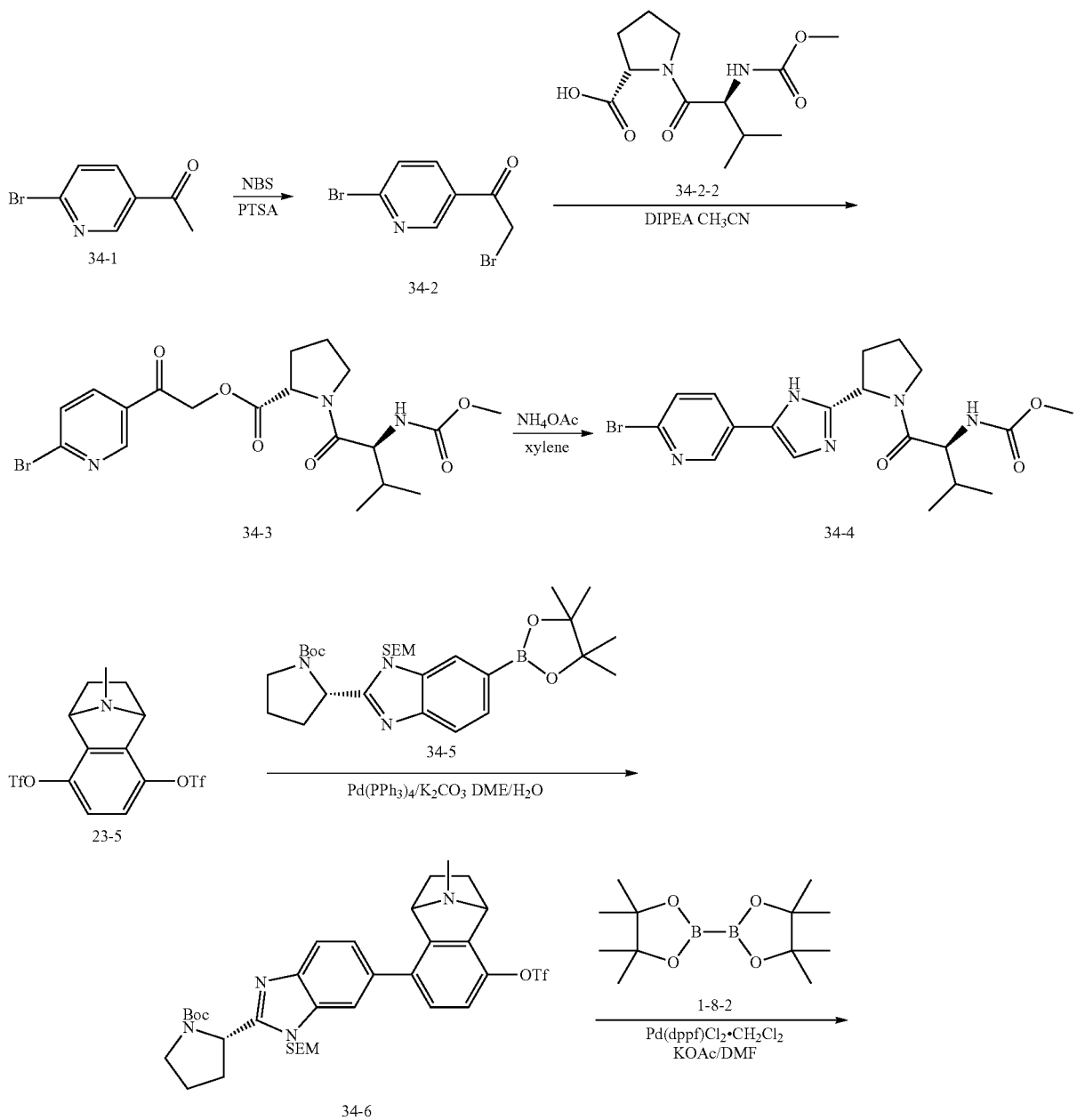

-continued
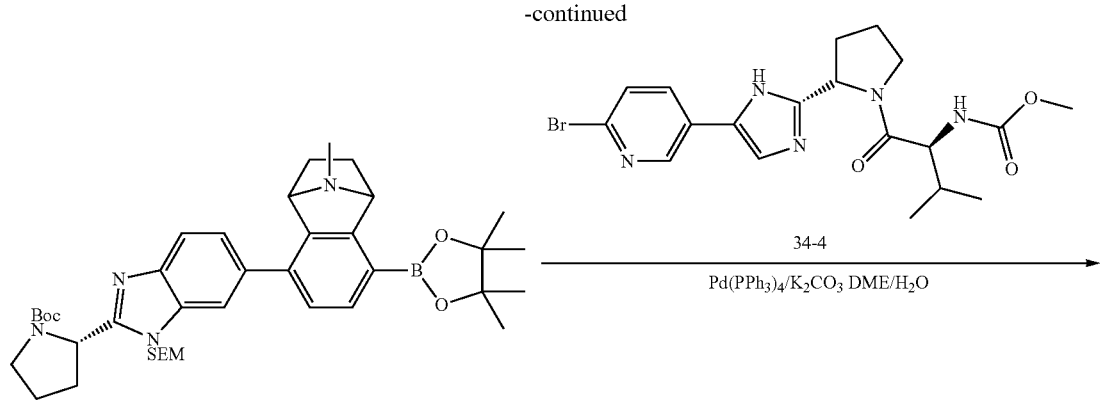
34-7
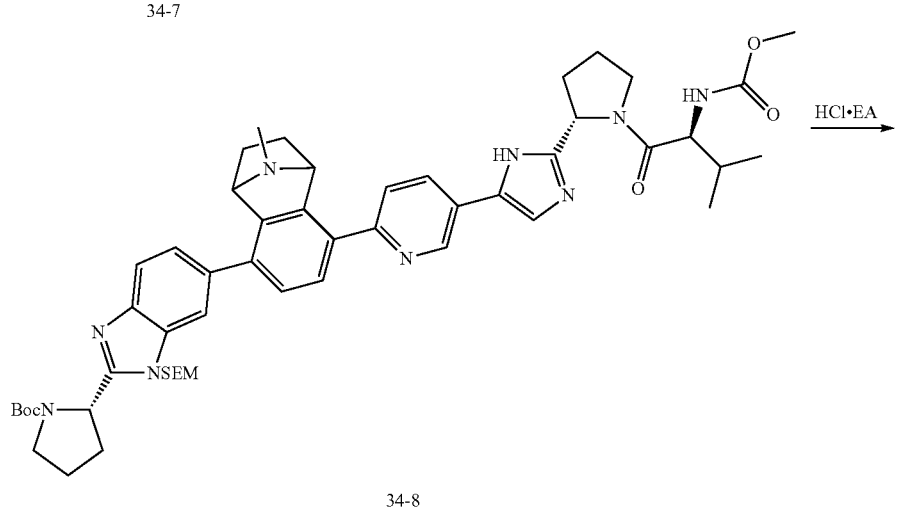
34-8
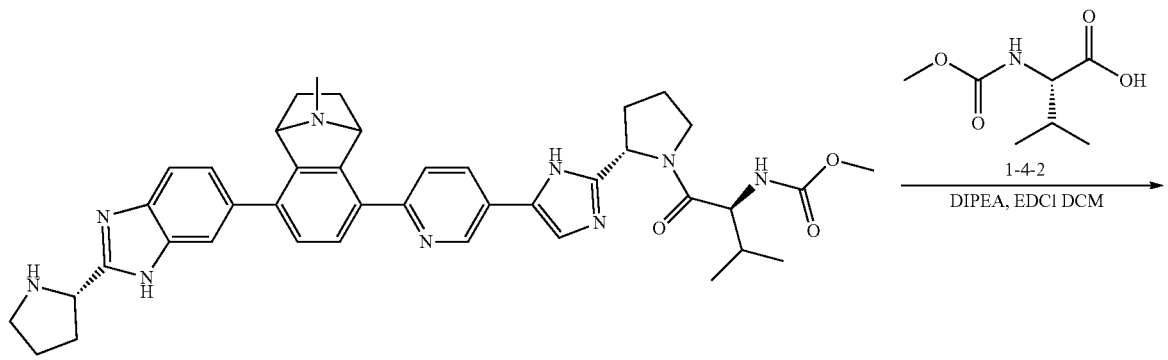
34-9
34-10
Step 1) the Preparation of Compound 34-2
The mixture of compound 34-1 (25 g, 125.6 mmol), NBS (24.5 g, 138.2 mmol) and p-TSA (3.4 g, 20.9 mmol) was stirred at 100° C. for 2 hrs under $N_2$. After the reaction was completed, the mixture was cooled to rt, and 200 mL of DCM was added. The organic layer were washed with water (50 mL×3) and brine, dried over anhydrous Na$_2$SO$_4$ and concentrated in vacuo. The residue was purified by a silica gel column chromatography (PE/EtOAc (v/v)=5/1) to give the title compound as yellow slurry (25 g, 71%). The compound was characterized by the following spectroscopic data:

MS (ESI, pos.ion) m/z: 279.9 [M+H]$^+$;

$^1$H NMR (400 MHz, CDCl$_3$) δ (ppm): 8.95 (d, 1H, J=1.12 Hz), 8.11-8.14 (m, 1H), 7.66-7.68 (m, 1H), 4.41 (s, 2H).

Step 2) the Preparation of Compound 34-3

To a solution of compound 34-2 (5.0 g, 17.9 mmol) and compound 34-2-2 (5.4 g, 19.7 mmol) in MeCN (100 mL) at 0° C. was added DIPEA (3.3 mL, 19.7 mmol) dropwise. At the end of addition, the mixture was stirred at rt for 3 hrs. After the reaction was completed, the mixture was quenched with ice-water (50 mL), and the resulting mixture was extracted with EtOAc (60 mL×3). The combined organic layers were dried over anhydrous Na$_2$SO$_4$ and concentrated in vacuo. The residue was purified by a silica gel column chromatography (PE/EtOAc (v/v)=3/1) to give the title compound (8.0 g, 96%). The compound was characterized by the following spectroscopic data:

MS (ESI, pos.ion) m/z: 470.1 [M+H]$^+$;

$^1$H NMR (400 MHz, CDCl$_3$) δ (ppm): 8.88 (s, 1H), 8.04 (d, 1H, J=3.88 Hz), 7.65 (d, 1H, J=4.16 Hz), 5.59-5.61 (m, 1H), 5.48 (d, 1H, J=8.32 Hz), 5.23 (d, 1H, J=8.3 Hz), 4.67 (t, 1H, J=5.72 Hz), 4.31 (t, 1H, J=7.52 Hz), 3.84-3.86 (m, 1H), 3.71-3.73 (m, 1H), 3.66 (s, 3H), 2.34-2.15 (m, 4H), 1.01 (t, 3H), 0.93-0.94 (m, 3H), 0.85-0.88 (m, 1H).

Step 3) the Preparation of Compound 34-4

A mixture of compound 34-3 (2.0 g, 4.25 mmol) and ammonium acetate (4.9 g, 83 mmol) in xylene (50 mL) was refluxed at 130° C. for 5 hrs. After the reaction was completed, the mixture was cooled to rt, and quenched with 50 mL of water. The resulting mixture was extracted with EtOAc (50 mL×3), and the combined organic layers were dried over anhydrous Na$_2$SO$_4$ and concentrated in vacuo. The residue was purified by a silica gel column chromatography (PE/EtOAc (v/v)=2/1) to give the title compound (1.39 g, 73%). The compound was characterized by the following spectroscopic data:

MS (ESI, pos.ion) m/z: 450.1 [M+H]$^+$;

$^1$H NMR (400 MHz, CDCl$_3$) δ (ppm): 8.70 (s, 1H), 7.93 (d, 1H, J=6.92 Hz), 7.45 (d, 1H, J=8.28 Hz), 5.41 (d, 1H, J=4.6 Hz), 5.22-5.24 (m, 1H), 4.32 (m, 1H), 3.83-3.85 (m, 1H), 3.67 (s, 3H), 3.62-3.63 (m, 3H), 3.03-3.05 (m, 1H), 2.31-1.93 (m, 4H), 1.03-1.04 (m, 1H), 0.88 (s, 3H), 0.86 (s, 3H).

Step 4) the Preparation of Compound 34-6

To a mixture of compound 23-5 (327 mg, 0.72 mmol), compound 34-5 (390 mg, 0.72 mmol), Pd(PPh$_3$)$_4$ (83 mg, 0.07 mmol) and K$_2$CO$_3$ (300 mg, 2.12 mmol) were added DME (4.0 mL) and water (1.0 mL) via syringe. The mixture was stirred at 90° C. for 4 hrs under N$_2$. After the reaction was completed, the mixture was cooled to rt, and quenched with 10 mL of water. The resulting mixture was extracted with EtOAc (20 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound as a white solid (424 mg, 80%). The compound was characterized by the following spectroscopic data:

MS (ESI, pos.ion) m/z: 723.3 [M+H]$^+$;

$^1$H NMR (400 MHz, CDCl$_3$) δ (ppm): 8.03-8.02, 8.01-8.00 (d, d, 1H, J=4.0 Hz), 7.39, 7.37 (d, d, 1H), 7.33, 7.31 (s, s, 1H), 7.28 (m, 1H), 7.27, 7.24 (s, s, 1H), 4.99-4.94 (m, 1H), 4.54-4.51 (m, 1H), 4.46-4.44 (m, 1H), 4.06-4.03 (m, 2H), 3.73-3.71 (m, 1H), 3.59-3.51 (m, 1H), 2.52-2.42 (m, 1H), 2.27-2.17 (m, 4H), 2.15-1.95 (m, 2H), 1.85-1.77 (m, 2H), 1.64-1.57 (m, 2H), 1.53 (s, 9H), 1.28-1.13 (m, 1H), 1.03-0.94 (m, 1H), 0.57-0.52 (m, 2H), 0.01-0.00 (m, 9H).

Step 5) the Preparation of Compound 34-7

A mixture of compound 34-6 (657 mg, 0.91 mmol), compound 1-8-2 (463 mg, 1.82 mmol), PdCl$_2$(dppf).CH$_2$Cl$_2$ (71 mg, 0.09 mmol) and KOAc (268 mg, 2.73 mmol) in DMF (10.0 mL) was stirred at 90° C. for 3.0 hrs under N$_2$. After the reaction was completed, the mixture was cooled to rt, diluted with EtOAc (60 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=2/1) to give the title compound as a white solid (559 mg, 87.7%). The compound was characterized by the following spectroscopic data:

MS (ESI, pos.ion) m/z: 701.5 [M+H]$^+$;

$^1$H NMR (400 MHz, CDCl$_3$) δ (ppm): 8.25-8.22 (m, 1H), 7.99, 7.97 (s, s, 1H), 7.78, 7.76 (s, s, 1H), 7.39-7.37 (m, 2H), 4.99-4.94 (m, 1H), 4.59-4.57 (m, 1H), 4.22-4.19 (m, 1H), 4.06-4.03 (m, 2H), 3.77-3.71 (m, 1H), 3.59-3.51 (m, 1H), 2.52-2.42 (m, 1H), 2.27 (m, 3H), 2.24-1.96 (m, 3H), 1.84-1.80 (m, 2H), 1.79-1.64 (m, 2H), 1.53 (s, 9H), 1.33-1.32 (m, 6H), 1.30-1.29 (m, 6H), 1.28-1.21 (m, 2H), 0.58-0.52 (m, 2H), 0.01-0.00 (m, 9H).

Step 6) the Preparation of Compound 34-8

A suspension of compound 34-7 (427 mg, 0.61 mmol), compound 34-4 (274 mg, 0.60 mmol), Pd(PPh$_3$)$_4$ (70 mg, 0.05 mmol) and K$_2$CO$_3$ (254 mg, 1.83 mmol) in mixed solvents of DME and H$_2$O (6 mL, v/v=5/1) was stirred at 90° C. under N$_2$ for 4.0 hrs. After the reaction was completed, the mixture was concentrated in vacuo, and the residue was dissolved in EtOAc (50 mL). The resulting mixture was washed with brine, dried over anhydrous Na$_2$SO$_4$ and concentrated in vacuo. The residue was purified by a silica gel column chromatography (PE/EtOAc (v/v)=1/1) to give the title compound as a pale yellow solid (528 mg, 93.3%). The compound was characterized by the following spectroscopic data:

MS (ESI, pos.ion) m/z: 472.75 [M+2H]$^{2+}$;

$^1$H NMR (400 MHz, CDCl$_3$) δ (ppm): 8.77-8.76 (m, 1H), 8.10-8.09, 8.08-8.07 (d, d, 1H, J=4.0 Hz), 7.90, 7.88 (s, s, 1H), 7.68, 7.66 (s, s, 1H), 7.67 (s, 1H), 7.63-7.59 (m, 2H), 7.39-7.37 (m, 1H), 7.28-7.27 (m, 1H), 5.38-5.33 (m, 1H), 5.32-5.31, 5.30-5.29 (d, d, 1H, J=4.0 Hz), 4.99-4.94 (m, 1H), 4.41-4.37 (m, 1H), 4.20-4.15 (m, 2H), 4.06-4.03 (m, 2H), 3.85-3.78 (m, 1H), 3.75-3.71 (m, 1H), 3.69-3.64 (m, 1H), 3.63 (s, 3H), 3.59-3.51 (m, 1H), 2.52-2.42 (m, 1H), 2.39 (m, 3H), 2.30-1.94 (m, 8H), 1.84-1.77 (m, 2H), 1.73-1.58 (m, 2H), 1.53 (s, 9H), 1.30-1.23 (m, 1H), 1.04-0.98 (m, 1H), 0.97-0.95 (m, 3H), 0.91-0.89 (m, 3H), 0.57-0.52 (m, 2H), 0.01-0.00 (m, 9H).

Step 7) the Preparation of Compound 34-9

To a solution of compound 34-8 (75 mg, 0.08 mmol) in EtOAc (5.0 mL) was added a solution of HCl in EtOAc (5.0 mL, 4 M) dropwise. At the end of addition, the mixture was stirred at rt for 8 hrs. After the reaction was completed, the mixture was concentrated in vacuo. The residue was washed with EtOAc (20 mL) and filtered to give the title compound as a pale yellow solid (60 mg, 95.38%). The compound was characterized by the following spectroscopic data:

MS (ESI, pos.ion) m/z: 714.5 [M+H]$^+$.

Step 8) the Preparation of Compound 34-10

A suspension of compound 34-9 (52.68 mg, 0.067 mmol), compound 1-4-2 (21 mg, 0.116 mmol) and EDCI (30 mg, 0.154 mmol) in DCM (1.0 mL) was stirred at 0° C., then DIPEA (0.09 mL, 0.539 mmol) was added dropwise. At the end of addition, the mixture was stirred at rt for 3.0 hrs. After the reaction was completed, the mixture was diluted with DCM (20 mL), washed with NH₄Cl aqueous solution and brine, dried over anhydrous Na₂SO₄ and concentrated in vacuo. The residue was purified by a silica gel column chromatography (EtOAc) to give the title compound as a white solid (30 mg, 51.44%). The compound was characterized by the following spectroscopic data:

MS (ESI, pos.ion) m/z: 871.5 [M+H]$^+$;

$^1$H NMR (400 MHz, CDCl$_3$) δ (ppm): 8.77-8.76 (m, 1H), 7.94, 7.92 (s, s, 1H), 7.68-7.66 (m, 2H), 7.63-7.60 (m, 3H), 7.52-7.50 (m, 2H), 5.38-5.33 (m, 1H), 5.32, 5.30 (br, br, 2H), 5.24-5.20 (m, 1H), 4.41-4.35 (m, 2H), 4.20-4.15 (m, 2H), 3.84-3.78 (m, 2H), 3.69-3.64 (m, 2H), 3.63 (s, 6H), 2.39 (s, 3H), 2.38-1.89 (m, 10H), 1.74-1.58 (m, 2H), 1.30-1.22 (m, 1H), 1.04-0.98 (m, 1H), 0.97-0.96 (m, 6H), 0.91-0.89 (m, 6H).

Example 35

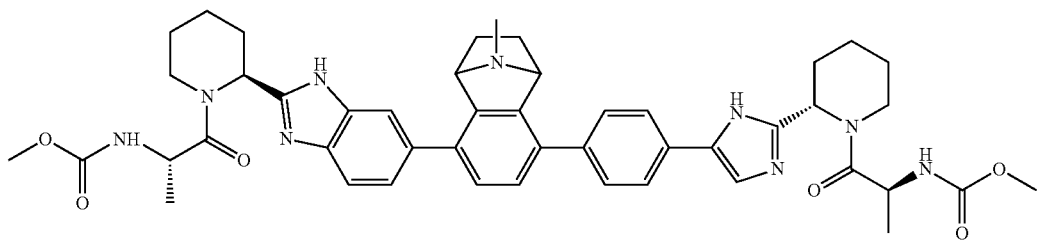

Synthetic Route:

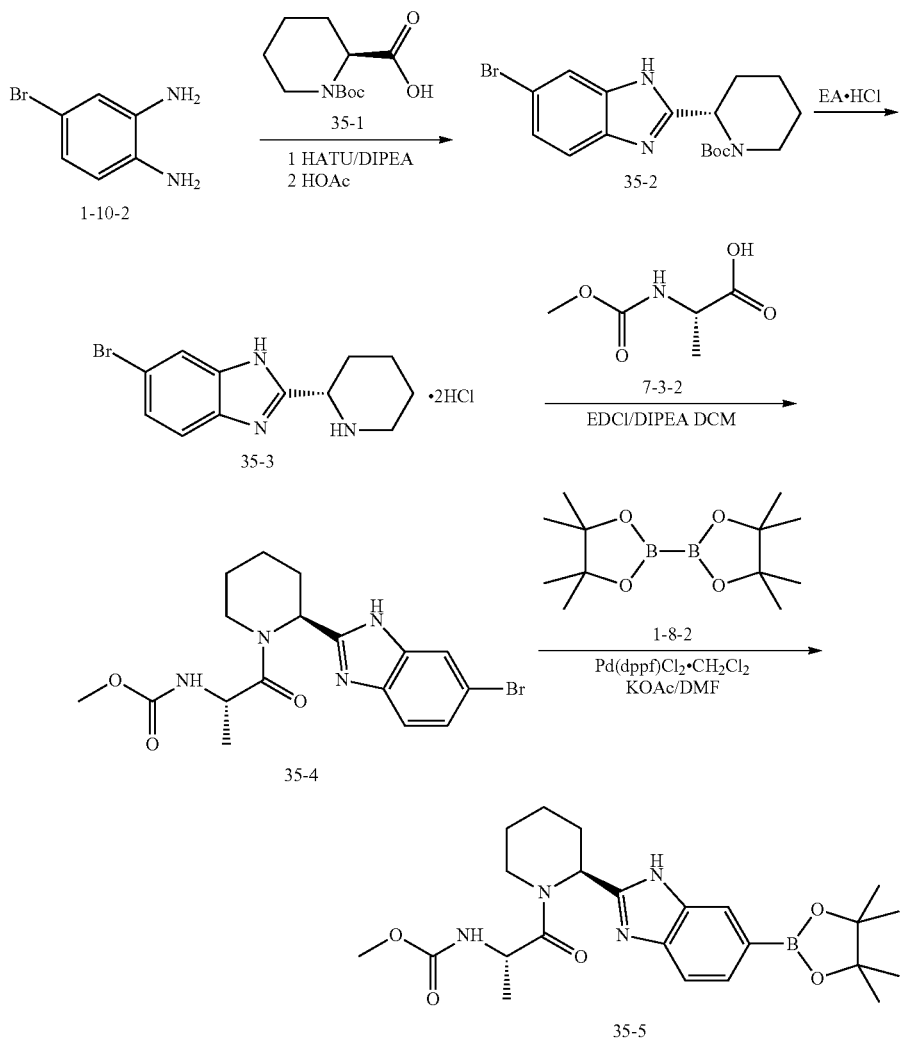

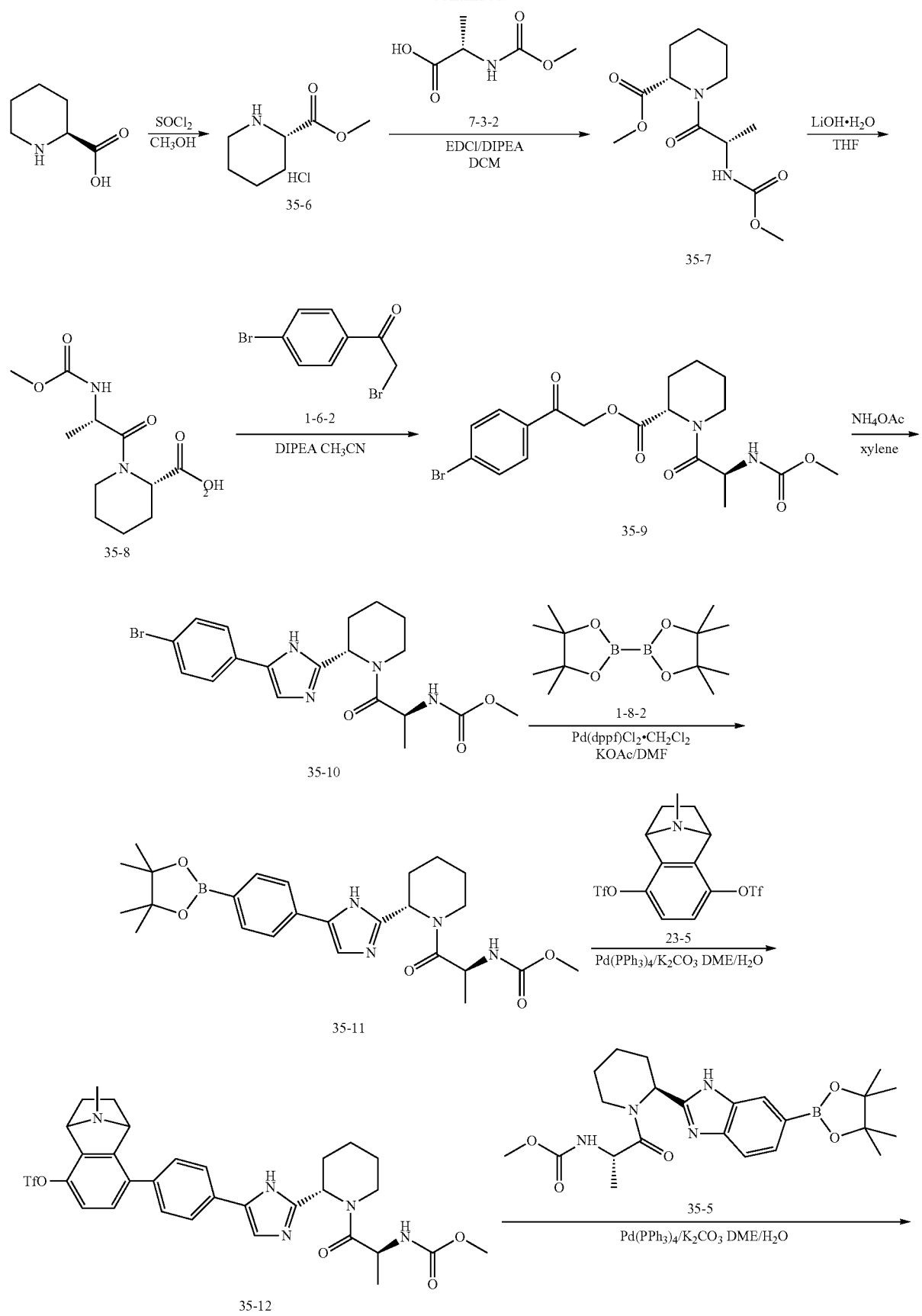

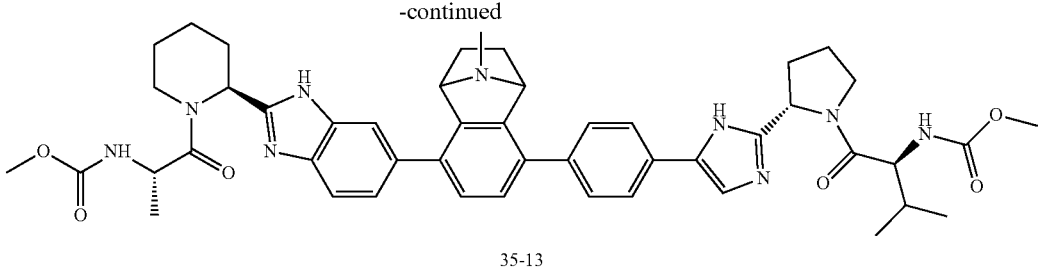

35-13

Step 1) the Preparation of Compound 35-2

To a solution of compound 35-1 (30.86 g, 134.7 mmol) and HATU (53.99 g, 141.46 mmol) in THF (300 mL) was added DIPEA (26.7 mL, 161.6 mmol) at 0° C., the mixture was stirred at rt for 0.5 hr and then added a solution of compound 1-10-2 (27.71 g, 148.2 mmol) in THF (140 mL) at 0° C. At the end of addition, the mixture was stirred at rt for 2 hrs. After the reaction was completed, the mixture was quenched with water (200 mL), and the solvent THF was removed. The resulting mixture was extracted with EtOAc (250 mL×3). The combined organic layers were dried over anhydrous $Na_2SO_4$ and concentrated in vacuo. The residue was dissolved in acetic acid glacial (140 mL), and the mixture was stirred at 40° C. overnight. After the reaction was completed, the solvent acetic acid glacial was removed, and water (200 mL) was added. The resulting mixture was extracted with EtOAc (250 mL×3). The combined organic layers were washed with brine, dried over anhydrous $Na_2SO_4$ and concentrated in vacuo. The residue was purified by a silica gel column chromatography (PE/EtOAc (v/v)=1/1) to give the title compound as a brown solid (40 g, 74.6%). The compound was characterized by the following spectroscopic data:

MS (ESI, pos. ion) m/z: 380.5 $[M+H]^+$;
$^1$H NMR (400 MHz, $CDCl_3$) δ (ppm): 7.75-7.74 (m, 1H), 7.36, 7.33 (d, d, 1H), 7.20, 7.19, 7.17 (s, s, s, 1H), 5.12-5.06 (m, 1H), 4.30-4.22 (m, 1H), 2.96-2.87 (m, 1H), 2.21-2.13 (m, 1H), 1.93-1.80 (m, 1H), 1.70-1.63 (m, 1H), 1.54-1.51 (m, 1H), 1.50 (s, 9H), 1.24-1.06 (m, 2H).

Step 2) the Preparation of Compound 35-3

To a solution of compound 35-2 (379 mg, 1.0 mmol) in EtOAc (3.0 mL) was added a solution of HCl in EtOAc (5.0 mL, 4 M) dropwise, and the mixture was stirred at rt overnight. After the reaction was completed, the mixture was filtered, and the filter cake was washed with EtOAc to give the title compound as a pale yellow solid (280 mg, 79%). The compound was characterized by the following spectroscopic data:

MS (ESI, pos.ion) m/z: 280.5 $[M+H]^+$.

Step 3) the Preparation of Compound 35-4

To a solution of compound 35-3 (800 mg, 2.274 mmol), compound 7-3-2 (501.73 mg, 3.412 mmol) and EDCI (654 mg, 3.412 mmol) in DCM (15.0 mL) was added DIPEA (0.7 mL, 4.23 mmol) dropwise at 0° C. At the end of addition, the mixture was stirred at rt for 3 hrs. After the reaction was completed, 20 mL of water was added, and the resulting mixture was extracted with $CH_2Cl_2$ (50 mL×3). The combined organic layers were dried over $Na_2SO_4$ and concentrated in vacuo. The residue was purified by a silica gel column chromatography (PE/EtOAc (v/v)=1/2) to give the title compound as a pale yellow solid (421 mg, 45.36%). The compound was characterized by the following spectroscopic data:

MS (ESI, pos.ion) m/z: 409.3 $[M+H]^+$;
$^1$H NMR (400 MHz, $CDCl_3$) δ (ppm): 7.75-7.74 (m, 1H), 7.36, 7.33 (d, d, 1H), 7.20, 7.19, 7.17 (s, s, s, 1H), 5.44, 5.42 (br, br, 1H), 4.78-4.73 (m, 1H), 4.72-4.65 (m, 1H), 3.71-3.65 (m, 1H), 3.64 (s, 3H), 2.88-2.79 (m, 1H), 2.07-1.98 (m, 1H), 1.89-1.76 (m, 1H), 1.64-1.46 (m, 2H), 1.35, 1.33 (s, s, 3H), 1.23-1.04 (m, 2H).

Step 4) the Preparation of Compound 35-5

To a mixture of compound 35-4 (392 mg, 0.961 mmol), compound 1-8-2 (366 mg, 1.44 mmol), $Pd(dppf)Cl_2.CH_2Cl_2$ (79 mg, 0.0961 mmol) and KOAc (283 mg, 2.88 mmol) was added DMF (6.0 mL) via syringe under $N_2$, and the mixture was stirred at 90° C. for 3 hrs. After the reaction was completed, the mixture was cooled to rt, and 50 mL of water was added. The resulting mixture was extracted with EtOAc (30 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound as a beige solid (280 mg, 63.86%). The compound was characterized by the following spectroscopic data:

MS (ESI, pos. ion) m/z: 457.3 $[M+H]^+$;
$^1$H NMR (400 MHz, $CDCl_3$) δ (ppm): 7.88 (m, 1H), 7.65, 7.63 (d, d, 1H), 7.37, 7.35 (s, s, 1H), 5.44, 5.42 (br, br, 1H), 4.84-4.78 (m, 1H), 4.72-4.65 (m, 1H), 3.71-3.65 (m, 1H), 3.64 (s, 3H), 2.88-2.79 (m, 1H), 2.06-1.99 (m, 1H), 1.89-1.78 (m, 1H), 1.64-1.46 (m, 2H), 1.35, 1.33 (s, s, 3H), 1.32 (m, 6H), 1.29 (m, 6H), 1.23-1.04 (m, 2H).

Step 5) the Preparation of Compound 35-6

To a solution of (s)-piperidine-2-carboxylic acid (10.0 g, 77.4 mmol) in MeOH (50 mL) was added thionyl chloride (8.5 mL, 117.2 mmol) dropwise at 0° C. The mixture was stirred at 0° C. for 1 hr and at 70° C. for another 3 hrs. After the reaction was completed, the mixture was concentrated in vacuo to give the title compound as a white solid (11.0 g, 79.1%). The compound was characterized by the following spectroscopic data:

MS (ESI, pos.ion) m/z: 144.1 $[M+H]^+$;
$^1$H NMR (400 MHz, $CDCl_3$) δ (ppm): 5.02 (br, 1H), 4.00 (br, 1H), 3.85 (s, 3H), 3.63 (br, 1H), 3.15 (br, 1H), 2.28 (m, 1H), 2.08 (m, 2H), 1.86 (m, 2H), 1.63 (br, 1H).

Step 6) the Preparation of Compound 35-7

To a solution of compound 35-6 (1.0 g, 5.57 mmol), compound 7-3-2 (1.23 g, 8.38 mmol) and EDCI (2.142 g, 11.17 mmol) in DCM (40.0 mL) was added DIPEA (5.0 mL, 30.25 mmol) dropwise at 0° C. At the end of addition, the mixture was stirred at rt for 3 hrs. After the reaction was completed, 40 mL of water was added, and the resulting mixture was extracted with $CH_2Cl_2$ (50 mL×3). The combined organic layers were dried over $Na_2SO_4$ and concentrated in vacuo. The residue was purified by a silica gel column chromatography (PE/EtOAc (v/v)=2/1) to give the title compound as colorless liquid (1.36 g, 90%). The compound was characterized by the following spectroscopic data:

MS (ESI, pos. ion) m/z: 301.2 $[M+H]^+$;

¹H NMR (400 MHz, CDCl₃) δ (ppm): 5.44, 5.42 (br, br, 1H), 5.04-5.02, 5.02-5.01 (m, m, 1H), 4.56-4.49 (m, 1H), 3.74-3.71 (m, 1H), 3.70 (s, 3H), 3.64 (s, 3H), 3.14-3.07 (m, 2H), 2.14-2.06 (m, 2H), 1.35, 1.33 (s, s, 3H), 1.18-1.02 (m, 3H).

Step 7) the Preparation of Compound 35-8

To a solution of compound 35-7 (1.28 g, 4.7 mmol) in THF (40 mL) was added lithium hydroxide monohydrate aqueous solution (0.987 g, 23.5 mmol, 20 mL) at 0° C., and the mixture was stirred at 40° C. for 12 hrs. After the reaction was completed, the solvent THF was removed and 20 mL of water was added to mixture. The resulting mixture was washed with EtOAc (20 mL×3), and the aqueous phase was adjusted to pH 1 with hydrochloric acid (10%) and extracted with EtOAc (35 mL×3). The combined organic layers were dried over anhydrous Na₂SO₄ and concentrated in vacuo to give the title compound 35-8 as a white solid (1.1 g, 90.9%). The compound was characterized by the following spectroscopic data:

MS (ESI, pos.ion) m/z: 259.3 [M+H]⁺;

¹H NMR (400 MHz, CDCl₃) δ (ppm): 5.34-5.32 (m, 1H), 4.55-4.48 (m, 1H), 4.46-4.44, 4.44-4.42 (m, m, 1H), 3.85-3.79 (m, 1H), 3.64 (s, 3H), 3.17-3.09 (m, 1H), 2.19-2.11 (m, 2H), 1.45, 1.43 (s, s, 3H), 1.21-1.05 (m, 4H).

Step 8) the Preparation of Compound 35-9

To a mixture of compound 1-6-2 (30 g, 107.9 mmol) and compound 35-8 (30.64 g, 118.7 mmol) in CH₃CN (250 mL) was added DIPEA (21.4 mL, 129.5 mmol) dropwise at 0° C., and the mixture was stirred at rt for 3.0 hrs. After the reaction was completed, the mixture was was quenched with ice-water (100 mL), and the solvent CH₃CN was removed. The resulting mixture was extracted with EtOAc (100 mL×3). The combined organic layers were washed with brine, dried over anhydrous Na₂SO₄ and concentrated in vacuo. The residue was purified by a silica gel column chromatography (PE/EtOAc (v/v)=10/1) to give the title compound as a white solid (44.58 g, 91%). The compound was characterized by the following spectroscopic data:

MS (ESI, pos.ion) m/z: 455.1 [M+H]⁺;

¹H NMR (400 MHz, CDCl₃) δ (ppm): 7.82-7.78 (m, 2H), 7.67-7.64 (m, 2H), 5.44-5.42 (br, br, 1H), 5.28 (s, 2H), 5.18-5.12 (m, 1H), 4.56-4.99 (m, 1H), 3.79-3.72 (m, 1H), 3.64 (s, 3H), 3.16-3.07 (m, 1H), 2.14-2.04 (m, 2H), 1.35, 1.33 (s, s, 3H), 1.19-0.99 (m, 4H).

Step 9) the Preparation of Compound 35-10

A suspension of compound 35-9 (16.53 g, 36.4 mmol) and NH₄OAc (42 g, 54.6 mmol) in toluene (150 mL) was stirred at 120° C. for 5 hrs. After the reaction was completed, the mixture was cooled to rt, and quenched with 100 mL of water. The resulting mixture was extracted with EtOAc (100 mL×3). The combined organic layers were washed with brine, dried over anhydrous Na₂SO₄ and concentrated in vacuo. The residue was purified by a silica gel column chromatography (PE/EtOAc (v/v)=4/1) to give the title compound as a yellow solid (13.43 g, 85%). The compound was characterized by the following spectroscopic data:

MS (ESI, pos.ion) m/z: 435.3 [M+H]⁺;

¹H NMR (400 MHz, CDCl₃) δ (ppm): 7.58 (s, 1H), 7.45-7.41 (m, 2H), 7.29-7.26 (m, 2H), 5.44, 5.42 (br, br, 1H), 4.99-4.88 (m, 1H), 4.72-4.65 (m, 1H), 3.87-3.81 (m, 1H), 3.64 (s, 3H), 2.89-2.80 (m, 1H), 2.02-1.94 (m, 1H), 1.87-1.70 (m, 1H), 1.66-1.52 (m, 2H), 1.35, 1.33 (s, s, 3H), 1.23-1.16 (m, 1H), 1.11-0.99 (m, 1H).

Step 10) the Preparation of Compound 35-11

To a mixture of compound 35-10 (4.44 g, 10.23 mmol), compound 1-8-2 (2.86 g, 11.25 mmol), Pd(dppf)Cl₂·CH₂Cl₂ (418 mg, 0.51 mmol) and KOAc (2.51 g, 25.57 mmol) was added DMF (40.0 mL) via syringe under N₂, and the mixture was stirred at 90° C. for 3 hrs. After the reaction was completed, the mixture was cooled to rt, diluted with EtOAc (200 mL) and filtered through a celite pad. The filtrate was washed with water (30 mL×3) and brine, dried over anhydrous Na₂SO₄ and concentrated in vacuo. The residue was purified by a silica gel column chromatography (PE/EtOAc (v/v)=2/1) to give the title compound as a pale yellow solid (3.94 g, 80%). The compound was characterized by the following spectroscopic data:

MS (ESI, pos.ion) m/z: 483.5 [M+H]⁺;

¹H NMR (400 MHz, CDCl₃) δ (ppm): 7.64-7.57 (m, 4H), 7.19 (s, 1H), 5.44, 5.42 (br, br, 1H), 4.94-4.88 (m, 1H), 4.72-4.65 (m, 1H), 3.87-3.81 (m, 1H), 3.64 (s, 3H), 2.88-2.80 (m, 1H), 2.01-1.94 (m, 1H), 1.84-1.70 (m, 1H), 1.66-1.51 (m, 2H), 1.35 (m, 6H), 1.33 (s, 3H), 1.32 (m, 6H), 1.22-1.00 (m, 2H).

Step 11) the Preparation of Compound 35-12

To a mixture of compound 23-5 (8.55 g, 18.8 mmol), compound 35-11 (9.26 g, 19.2 mmol), Pd(PPh₃)₄ (1.10 g, 0.94 mmol) and K₂CO₃ (10.4 g, 75.4 mmol) were added DME (60.0 mL) and pure water (20.0 mL) via syringe, and the mixture was stirred at 90° C. under N₂ for 3 hrs. After the reaction was completed, the mixture was cooled to rt and diluted with EtOAc (150 mL). The organic layers were washed with brine, dried over anhydrous Na₂SO₄ and concentrated in vacuo. The residue was purified by a silica gel column chromatography (PE/EtOAc (v/v)=2/1) to give the title compound as a pale yellow solid (6.21 g, 50%). The compound was characterized by the following spectroscopic data:

MS (ESI, pos.ion) m/z: 604.3 [M+H]⁺;

¹H NMR (400 MHz, CDCl₃) δ (ppm): 7.63-7.59 (m, 2H), 7.57 (s, 1H), 7.52-7.49 (m, 2H), 7.20, 7.18 (s, s, 1H), 7.07-7.05 (s, s, 1H), 5.44, 5.42 (br, br, 1H), 4.94-4.88 (m, 1H), 4.72-4.65 (m, 1H), 4.44-4.41 (m, 1H), 3.95-3.92 (m, 1H), 3.87-3.80 (m, 1H), 3.64 (s, 3H), 2.89-2.80 (m, 1H), 2.25 (s, 3H), 2.01-1.93 (m, 1H), 1.84-1.70 (m, 1H), 1.66-1.51 (m, 2H), 1.35, 1.33 (s, s, 3H), 1.28-0.89 (m, 6H).

Step 12) the Preparation of Compound 35-13

To a mixture of compound 35-5 (378 mg, 0.83 mmol), compound 35-13 (548.8 mg, 0.83 mmol), Pd(PPh₃)₄ (48 mg, 0.04 mmol) and K₂CO₃ (0.28 g, 2.07 mmol) were added DME (6.0 mL) and water (2.0 mL) via syringe, and the mixture was stirred at 90° C. under N₂ for 3 hrs. After the reaction was completed, the mixture was cooled to rt and diluted with EtOAc (50 mL). The separated organic layers were washed with brine, dried over anhydrous Na₂SO₄ and concentrated in vacuo. The residue was purified by a silica gel column chromatography (DCM/MeOH (v/v)=50/1) to give the title compound as a pale yellow solid (614.58 mg, 88%). The compound was characterized by the following spectroscopic data:

MS (ESI, pos.ion) m/z: 841.3 [M+H]⁺;

¹H NMR (400 MHz, CDCl₃) δ (ppm): 7.63-7.59 (m, 3H), 7.58-7.53 (m, 5H), 7.46, 7.44 (s, s, 1H), 7.23-7.20 (m, 1H), 5.44, 5.42 (br, br, 2H), 5.34-5.29 (m, 1H), 4.93-4.89 (m, 1H), 4.72-4.65 (m, 2H), 4.29-4.26 (m, 1H), 4.08-4.06 (m, 1H), 3.87-3.81 (m, 1H), 3.71-3.65 (m, 1H), 3.64 (s, 6H), 2.88-2.79 (m, 2H), 2.36 (s, 3H), 2.07-1.94 (m, 2H), 1.89-1.71 (m, 2H), 1.66-1.46 (m, 4H), 1.35, 1.33 (s, s, 6H), 1.28-0.86 (m, 8H).

Example 36
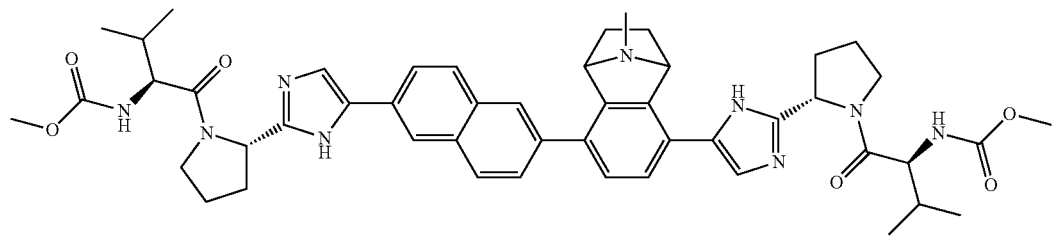
Synthetic Route:
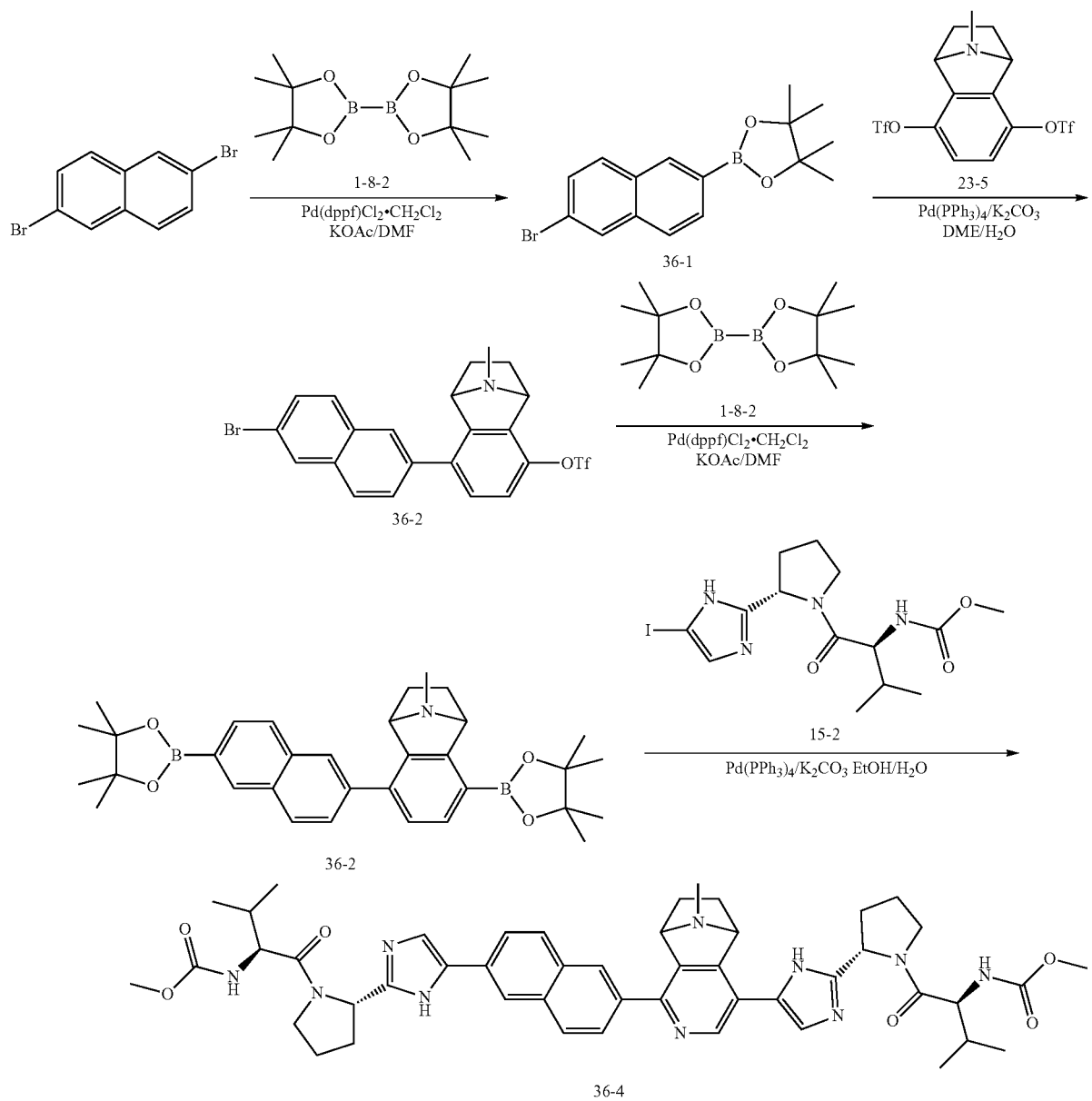

Step 1) the Preparation of Compound 36-1

To a mixture of 2,6-dibromonaphthalene (2.93 g, 10.23 mmol), compound 1-8-2 (2.6 g, 10.23 mmol), Pd(dppf)Cl$_2$.CH$_2$Cl$_2$ (418 mg, 0.51 mmol) and KOAc (2.51 g, 25.57 mmol) was added DMF (40.0 mL) via syringe under N$_2$, and the mixture was stirred at 90° C. for 3 hrs. After the reaction was completed, the mixture was cooled to rt, diluted with EtOAc (200 mL) and filtered through a celite pad. The filtrate was washed with water (100 mL×3) and brine, dried over anhydrous Na$_2$SO$_4$ and concentrated in vacuo. The residue was purified by a silica gel column chromatography (PE/EtOAc (v/v)=8/1) to give the title compound as a pale yellow solid (2.72 g, 80%). The compound was characterized by the following spectroscopic data:

$^1$H NMR (400 MHz, CDCl$_3$) δ (ppm): 8.19 (m, 1H), 8.09, 8.07 (m, m, 1H), 7.97, 7.94 (m, m, 1H), 7.87-7.86 (m, 1H), 7.84-7.82 (m, 1H), 7.29, 7.26 (m, m, 1H), 1.33-1.32 (m, 6H), 1.30-1.29 (m, 6H).

Step 2) the Preparation of Compound 36-2

To a mixture of compound 23-5 (8.55 g, 18.8 mmol), compound 36-1 (6.24 g, 18.8 mmol), Pd(PPh$_3$)$_4$ (1.10 g, 0.94 mmol) and K$_2$CO$_3$ (10.4 g, 75.4 mmol) were added DME (60.0 mL) and pure water (20.0 mL) via syringe, and the mixture was stirred at 90° C. under N$_2$ for 3.0 hrs. After the reaction was completed, the mixture was cooled to rt and diluted with EtOAc (200 mL). The separated organic layers were washed with brine, dried over anhydrous Na$_2$SO$_4$ and concentrated in vacuo. The residue was purified by a silica gel column chromatography (PE/EtOAc (v/v)=4/1) to give the title compound as a pale yellow solid (4.8 g, 50%). The compound was characterized by the following spectroscopic data:

$^1$H NMR (400 MHz, CDCl$_3$) δ (ppm): 8.11-8.10 (m, 1H), 8.00-7.99 (m, 1H), 7.79-7.75 (m, 2H), 7.72-7.71, 7.70-7.69 (m, m, 1H), 7.57-7.56, 7.55-7.54 (m, m, 1H), 7.21, 7.19 (s, s, 1H), 7.10, 7.08 (s, s, 1H), 4.46-4.43 (m, 1H), 3.98-3.95 (m, 1H), 2.25 (s, 3H), 1.64-1.57 (m, 1H), 1.28-1.13 (m, 2H), 1.03-0.94 (m, 1H).

Step 3) the Preparation of Compound 36-3

To a mixture of compound 36-2 (5.22 g, 10.23 mmol), compound 1-8-2 (5.46 g, 21.48 mmol), Pd(dppf)Cl$_2$.CH$_2$Cl$_2$ (418 mg, 0.51 mmol) and KOAc (2.51 g, 25.57 mmol) was added DMF (60.0 mL) via syringe under N$_2$, and the mixture was stirred at 90° C. for 3.0 hrs. After the reaction was completed, the mixture was cooled to rt, diluted with EtOAc (200 mL) and filtered through a celite pad. The filtrate was washed with water (120 mL×3) and brine, dried over anhydrous Na$_2$SO$_4$ and concentrated in vacuo. The residue was purified by a silica gel column chromatography (PE/EtOAc (v/v)=6/1) to give the title compound as a pale yellow solid (2.75 g, 50%). The compound was characterized by the following spectroscopic data:

$^1$H NMR (400 MHz, CDCl$_3$) δ (ppm): 8.24-8.23 (m, 1H), 8.20-8.19, 8.18-8.17 (m, m, 1H), 8.02, 8.00 (m, m, 1H), 7.92, 7.91 (s, s, 1H), 7.90-7.87 (m, 2H), 7.80-7.79, 7.78-7.77 (m, m, 1H), 7.54, 7.52 (s, s, 1H), 4.59-4.56 (m, 1H), 4.05-4.02 (m, 1H), 2.28 (s, 3H), 1.80-1.64 (m, 2H), 1.32-1.29 (m, m, 24H), 1.28-1.19 (m, 2H).

Step 4) the Preparation of Compound 36-4

A suspension of compound 36-3 (5.37 g, 10 mmol), compound 15-2 (8.82 g, 21 mmol), Pd(PPh$_3$)$_4$ (1.156 g, 1.0 mmol) and K$_2$CO$_3$ (3.45 g, 25 mmol) in mixed solvents of EtOH and H$_2$O (80 mL, v/v=3/1) was stirred at 90° C. under N$_2$ for 3.0 hrs. After the reaction was completed, the mixture was concentrated in vacuo, and the residue was dissolved in EtOAc (50 mL). The resulting mixture was washed with brine, dried over anhydrous Na$_2$SO$_4$ and concentrated in vacuo. The residue was purified by a silica gel column chromatography (DCM/EtOH (v/v)=40/1) to give the title compound as a pale yellow solid (3.47 g, 40%). The compound was characterized by the following spectroscopic data:

MS (ESI, pos.ion) m/z: 870.5 [M+H]$^+$;

$^1$H NMR (400 MHz, CDCl$_3$) δ (ppm): 8.25-8.24 (m, 1H), 8.15-8.14 (m, 1H), 7.89-7.88, 7.87-7.85 (m, m, 2H), 7.84-7.83 (m, 1H), 7.82-7.81, 7.80-7.79 (m, m, 1H), 7.62 (s, 1H), 7.60 (s, 1H), 7.50, 7.48 (s, s, 1H), 7.31, 7.28 (s, s, 1H), 5.40-5.36 (m, 1H), 5.32, 5.29 (br, br, 2H), 5.28-5.25 (m, 1H), 4.41-4.37 (m, 2H), 4.18-4.15 (m, 1H), 4.06-4.05 (m, 1H), 3.85-3.78 (m, 2H), 3.69-3.64 (m, 2H), 3.63 (s, 6H), 2.35 (s, 3H), 2.30-1.92 (m, 10H), 1.75-1.67 (m, 2H), 1.31-1.23 (m, 1H), 1.13-1.05 (m, 1H), 0.97, 0.95 (m, m, 6H), 0.91, 0.89 (m, m, 6H).

Example 37

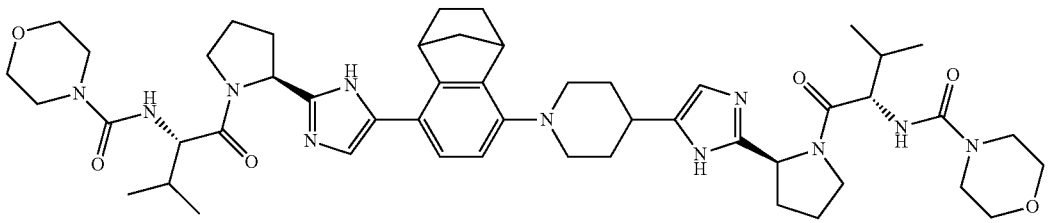 [SMILES: CC(C)[C@H](NC(=O)N1CCOCC1)C(=O)N1CCC[C@H]1c1ncc(-c2ccc(N3CCC(c4cnc([C@@H]5CCCN5C(=O)[C@@H](NC(=O)N5CCOCC5)C(C)C)[nH]4)CC3)c3c2C2CCC3C2)[nH]1]

Synthetic Route:

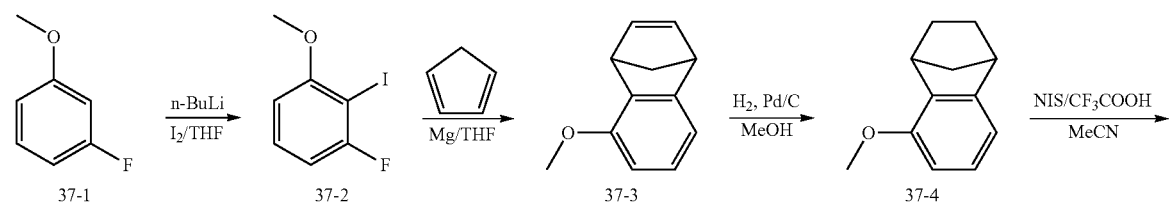

-continued
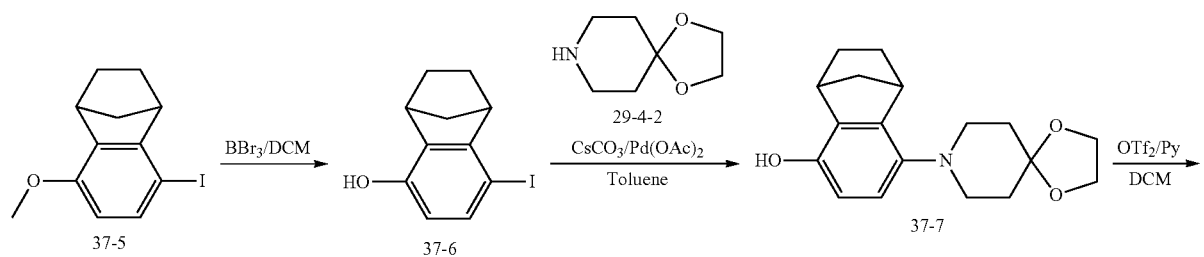
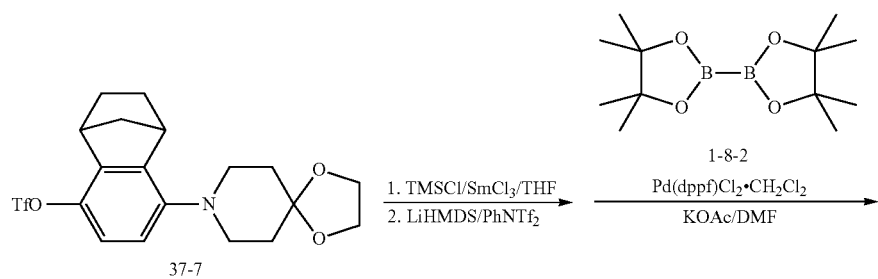
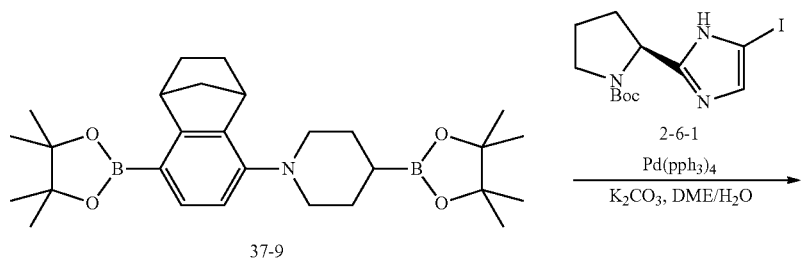
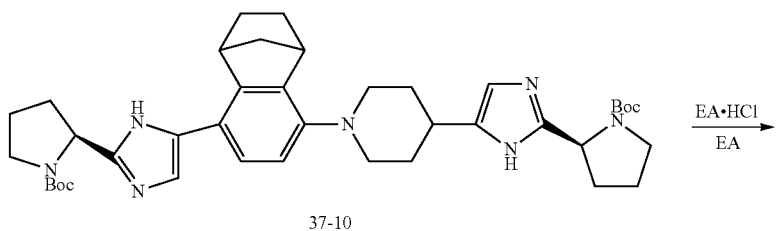
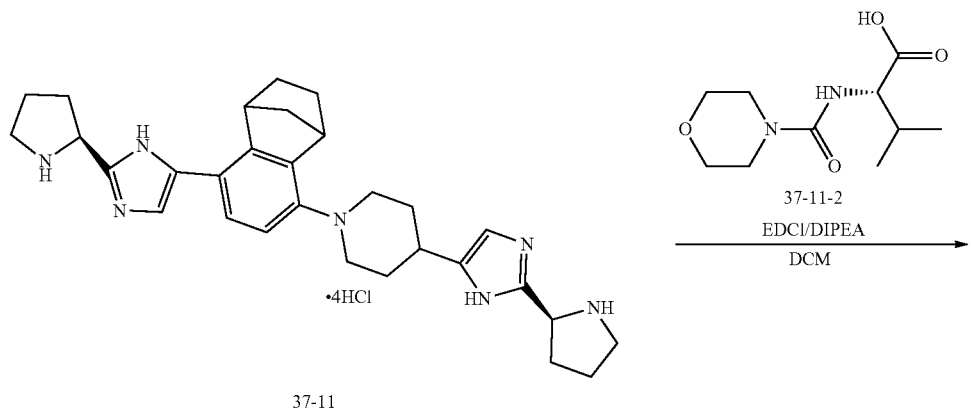

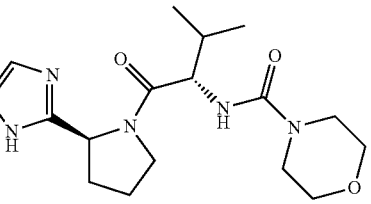

37-12

Step 1) the Preparation of Compound 37-2

A mixture of n-butyllithium (7.93 mmol, 1.6 M in hexane) and dry THF (20 mL) was cooled to −70° C. under nitrogen. To the mixture were added a solution of compound 37-1 (1.0 g, 7.93 mmol) in THF (10 mL) and a solution of $I_2$ (2.32 g, 9.12 mmol) in THF (15 mL) in turn. The mixture was stirred at −70° C. for 10 mins, and warmed to −60° C. slowly. Sodium thiosulfate aqueous solution (3.0 mL, 10%) was added to the mixture at −60° C. After the reaction was completed, the mixture was poured into water (10.0 mL) and the organic phase was separated. The aqueous layer was extracted further with hexane (3×50 mL). The combined organic layers were washed with 10% sodium thiosulfate aqueous solution, dried over anhydrous $Na_2SO_4$ and concentrated in vacuo. The residue was purified by a silica gel column chromatography (PE/EtOAc (v/v)=1/10) to give the title compound 37-2 as oil (1.6 g, 80%). The compound was characterized by the following spectroscopic data:

$^1$H NMR (400 MHz, $CDCl_3$) δ (ppm): 7.43-7.07 (m, 1H), 6.78-6.53 (m, 2H), 3.90 (s, 3H).

Step 2) the Preparation of Compound 37-3

To a suspension of Mg (152 mg, 6.35 mmol) in THF (10.0 mL) were added a solution of compound 37-2 (1.6 g, 6.35 mmol) in THF (20 mL) and fresh 1,3-cyclopentadiene (713 mg, 10.8 mmol) via syringe, and the mixture was stirred at 70° C. under $N_2$. After the reaction was completed, the mixture was quenched with $NH_4Cl$ aqueous solution (50 mL). The aqueous layer was extracted with diethyl ether (3×50 mL). The combined organic layers were washed with 10% sodium thiosulfate aqueous solution, water and saturated $NH_4Cl$ aqueous solution, then dried over anhydrous $Na_2SO_4$ and concentrated in vacuo. The residue was purified by a silica gel column chromatography (PE/EtOAc (v/v)=15/1) to give the title compound as oil (754 mg, 69%). The compound was characterized by the following spectroscopic data:

$^1$H NMR (400 MHz, $CDCl_3$) δ (ppm): 7.15-7.13 (m, 1H), 6.81-6.75 (m, 2H), 5.80 (m, 2H), 3.90 (s, 3H), 3.39 (m, 2H), 2.03-1.82 (m, 2H).

Step 3) the Preparation of Compound 37-4

A suspension of compound 37-3 (750 mg, 4.36 mmol) and a catalytic amount of Pd/C (75 mg) in methanol (10.0 mL) was stirred at 50° C. under $H_2$ for 4.0 hrs. After the reaction was completed, the mixture was filtered. The filtrate was concentrated in vacuo and the residue was purified by recrystallization to give the title compound as a white solid (645 mg, 85%). The compound was characterized by the following spectroscopic data:

$^1$H NMR (400 MHz, $CDCl_3$) δ (ppm): 6.81-6.69 (m, 1H), 6.48-6.32 (m, 2H), 3.82 (s, 3H), 2.85 (m, 2H), 1.72-1.45 (m, 6H).

Step 4) the Preparation of Compound 37-5

A solution of compound 37-4 (645 mg, 3.7 mmol) and NIS (916 mg, 4.07 mmol) in MeCN (10.0 mL) was stirred at 50° C. overnight. After the reaction was completed, MeCN was removed, and 20 mL of water was added. The aqueous layer was extracted with $CH_2Cl_2$ (25 mL×3). The combined organic layers were washed with brine, dried over anhydrous $Na_2SO_4$ and concentrated in vacuo. The residue was purified by a silica gel column chromatography (PE) to give the title compound as colorless liquid (832 mg, 75%). The compound was characterized by the following spectroscopic data:

MS (ESI, pos.ion) m/z: 301.5 $[M+H]^+$;

$^1$H NMR (400 MHz, $CDCl_3$) δ (ppm): 7.29 (d, 1H, J=8.0 Hz), 6.78 (d, 1H, J=8.0 Hz), 3.85 (s, 3H), 2.85 (m, 2H), 1.62-1.72 (m, 4H), 1.41-1.51 (m, 2H).

Step 5) the Preparation of Compound 37-6

To a solution of compound 37-5 (832 mg, 2.77 mmol) in DCM (20 mL) was added boron tribromide (0.36 mL, 3.88 mmol) dropwise at −78° C. The mixture was stirred at −78° C. for 10 mins and at rt for another 1.0 hr. After the reaction was completed, the mixture was quenched with ice-water (20 mL) and the organic phase separated. The aqueous layer was extracted with DCM (50 mL×3). The combined organic phases were washed with brine, dried over anhydrous $Na_2SO_4$ and concentrated in vacuo. The residue was purified by a silica gel column chromatography (PE/EtOAc (v/v)=12/1) to give the title compound (792 mg, 100%) as colorless oil. The compound was characterized by the following spectroscopic data:

MS (ESI, pos.ion) m/z: 287.3 $[M+H]^+$;

$^1$H NMR (400 MHz, $CDCl_3$) δ (ppm): 7.09 (d, 1H, J=8.0 Hz), 6.05 (d, 1H, J=8.0 Hz), 5.15 (br, 1H), 2.83 (m, 2H), 1.62-1.72 (m, 4H), 1.41-1.51 (m, 2H).

Step 6) the Preparation of Compound 37-7

To a mixture of compound 37-6 (758 mg, 2.65 mmol), compound 29-4-2 (417.8 mg, 2.92 mmol), $Cs_2CO_3$ (1.54 g, 7.95 mmol) and $Pd(OAc)_2$ (60 mg, 0.265 mmol) was added toluene (8.0 mL) via syringe, and the mixture was stirred at 100° C. under $N_2$ for 10 hrs. After the reaction was completed, the mixture was cooled to rt, diluted with EtOAc (50 mL) and water (50 mL), then filtered through a celite pad. The combined organic layers were washed with brine, dried over anhydrous $Na_2SO_4$ and concentrated in vacuo. The residue was purified by a silica gel column chromatography (PE/EtOAc (v/v)=1/1) to give the title compound (708 mg, 88.7%) as yellow liquid. The compound was characterized by the following spectroscopic data:

MS (ESI, pos.ion) m/z: 302.5 $[M+H]^+$;

$^1$H NMR (400 MHz, $CDCl_3$) δ (ppm): 6.50, 6.48 (s, s, 1H), 6.41, 6.39 (s, s, 1H), 5.77 (br, 1H), 4.01-3.87 (m, 4H), 3.55-3.52 (m, 1H), 3.38-3.34 (m, 1H), 3.22-3.17 (m, 4H), 1.92-1.86 (m, 2H), 1.75-1.71 (m, 5H), 1.52-1.48 (m, 1H), 1.19-1.13 (m, 2H).

Step 7) the Preparation of Compound 37-8

To a solution of compound 37-7 (2.32 g, 7.7 mmol) in DCM (50 mL) was added pyridine (3.1 mL, 38.6 mmol) dropwise at 0° C. After stirring at 0° C. for 10 mins, trifluoromethanesulfonic anhydride (3.9 mL, 23.1 mmol) was added, then the reaction mixture was further stirred at rt for 1.0 hr. After the reaction was completed, the mixture was quenched with ice-water (50 mL), the aqueous layer was extracted with DCM (60 mL×3). The combined organic layers were washed with brine, dried over anhydrous Na$_2$SO$_4$ and concentrated in vacuo. The residue was purified by a silica gel column chromatography (PE/EtOAc (v/v)=1/8) to give the title compound (2.768 g, 83%) as pale yellow oil. The compound was characterized by the following spectroscopic data:

MS (ESI, pos.ion) m/z: 434.5 [M+H]$^+$;
$^1$H NMR (400 MHz, CDCl$_3$) δ (ppm): 6.95, 6.93 (s, s, 1H), 6.40, 6.37 (s, s, 1H), 4.01-3.87 (m, 4H), 3.51-3.48 (m, 2H), 3.19-3.16 (m, 4H), 1.96-1.87 (m, 2H), 1.74-1.71 (m, 5H), 1.52-1.48 (m, 1H), 1.23-1.13 (m, 2H).

Step 8) the Preparation of Compound 37-9

A suspension of compound 37-8 (2.2 g, 5.1 mmol) and SmCl$_3$ (131 mg, 0.51 mmol) in THF (20.0 mL) was stirred at rt for 15 mins, and then TMSCl (610 mg, 5.61 mmol) was added dropwise. At the end of addition, the mixture was stirred at rt for 10 hrs. After the reaction was completed, the mixture was filtered through a celite pad, and the filtrate was concentrated in vacuo to give the compound (d) (1.5 g), which was used for the next step without further purification.

To a solution of compound (d) in THF (20.0 mL) was added LiHMDS (6.5 mL, 6.46 mmol, 1 M in THF) dropwise at −78° C. At the end of addition, the mixture was stirred at −78° C. for 30 mins, and then PhNTf$_2$ (2.77 g, 7.76 mmol) was added. The mixture was stirred at −78° C. for 30 mins and stirred at rt for another 10 hrs. After the reaction was completed, the mixture was quenched with water (50 mL), and extracted with EtOAc (50 mL×3). The combined organic layers were washed with brine, dried over anhydrous Na$_2$SO$_4$ and concentrated in vacuo to give the compound (e) (1.0 g), which was used for the next step without further purification.

A mixture of compound (e) (1.0 g, 2.0 mmol), compound 1-8-2 (1.27 g, 5.0 mmol), Pd(dppf)Cl$_2$·CH$_2$Cl$_2$ (0.16 g, 0.2 mmol) and KOAc (0.78 g, 8.0 mmol) in DMF (10.0 mL) was stirred at 90° C. overnight under N$_2$. After the reaction was completed, the mixture was cooled to rt, diluted with EtOAc (100 mL) and water (30.0 mL), and then filtered through a celite pad. The filtrate was washed with water (30 mL×3) and brine, the combined organic layers were dried over anhydrous Na$_2$SO$_4$ and concentrated in vacuo. The residue was purified by a silica gel column chromatography (PE/EtOAc (v/v)=1/2) to give the title compound (929 mg, 38%) as a beige solid. The compound was characterized by the following spectroscopic data:

MS (ESI, pos.ion) m/z: 480.5 [M+H]$^+$;
$^1$H NMR (400 MHz, CDCl$_3$) δ (ppm): 7.55, 7.53 (s, s, 1H), 6.43, 6.41 (s, s, 1H), 3.72-3.69 (m, 1H), 3.31-3.29 (m, 1H), 3.10-3.05 (m, 4H), 1.99-1.75 (m, 5H), 1.73-1.67 (m, 2H), 1.50-1.46 (m, 1H), 1.32 (m, 6H), 1.29 (m, 6H), 1.25 (m, 6H), 1.22 (m, 6H), 1.17-1.13 (m, 1H), 1.00-0.87 (m, 2H).

Step 9) the Preparation of Compound 37-10

To a mixture of compound 37-9 (2.83 g, 5.91 mmol), compound 2-6-1 (4.5 g, 12.4 mmol), Pd(PPh$_3$)$_4$ (342 mg, 0.296 mmol) and K$_2$CO$_3$ (2.47 g, 17.73 mmol) were added DME (60.0 mL) and pure water (12.0 mL) via syringe, the mixture was stirred at 90° C. under N$_2$ for 3.0 hrs. After the reaction was completed, the mixture was cooled to rt and concentrated in vacuo. The residue was dissolved in EtOAc (100 mL). The resulting mixture was washed with water (50 mL×3) and brine, dried over anhydrous Na$_2$SO$_4$ and concentrated in vacuo. The residue was purified by a silica gel column chromatography (DCM/EtOH (v/v)=200/1) to give the title compound (2.47 g, 60%) as a pale yellow solid. The compound was characterized by the following spectroscopic data:

MS (ESI, pos.ion) m/z: 698.5 [M+H]$^+$;
$^1$H NMR (400 MHz, CDCl$_3$) δ (ppm): 7.66 (s, 1H), 6.94, 6.92 (s, s, 1H), 6.81 (s, 1H), 6.44, 6.42 (s, s, 1H), 5.06-5.00 (m, 1H), 4.87-4.80 (m, 1H), 3.79-3.77 (m, 1H), 3.74-3.66 (m, 1H), 3.64-3.58 (m, 2H), 3.44-3.37 (m, 1H), 3.31-3.24 (m, 5H), 2.65-2.56 (m, 1H), 2.47-2.33 (m, 4H), 2.28-2.17 (m, 2H), 2.14-1.91 (m, 8H), 1.78-1.72 (m, 2H), 1.70-1.66 (m, 1H), 1.47-1.44 (m, 1H), 1.41 (s, 18H).

Step 10) the Preparation of Compound 37-11

To a solution of compound 37-10 (976 mg, 1.4 mmol) in EtOAc (10.0 mL) was added a solution of HCl in EtOAc (12.0 mL, 4 M) dropwise. At the end of addition, the mixture was stirred at rt for 8.0 hrs. After the reaction was completed, the mixture was concentrated in vacuo. The residue was washed with EtOAc (20.0 mL), and filtered to give the title compound (810 mg, 90%) as a pale yellow solid, which was used for the next step without further purification. The compound was characterized by the following spectroscopic data:

MS (ESI, pos.ion) m/z: 498.5 [M+H]$^+$.

Step 11) the Preparation of Compound 37-12

To a suspension of compound 37-11 (428 mg, 0.6654 mmol), EDCI (192 mg, 0.998 mmol) and compound 37-11-2 (230 mg, 0.998 mmol) in DCM (10.0 mL) was added DIPEA (0.8 mL, 4.84 mmol) dropwise at 0° C. At the end of addition, the mixture was stirred at rt for 3.0 hrs. After the reaction was completed, the mixture was diluted with DCM (20.0 mL), and then washed with NH$_4$Cl aqueous solution and brine, dried over Na$_2$SO$_4$ and concentrated in vacuo. The residue was purified by a silica gel column chromatography (DCM/MeOH (v/v)=50/1) to give the title compound (245 mg, 40%) as pale yellow powder. The compound was characterized by the following spectroscopic data:

MS (ESI, pos.ion) m/z: 461.5 [M+2H]$^{2+}$;
$^1$H NMR (400 MHz, CDCl$_3$) δ (ppm): 7.59 (s, 1H), 6.94, 6.92 (s, s, 1H), 6.82 (s, 1H), 6.44, 6.42 (s, s, 1H), 5.67, 5.65 (br, br, 2H), 5.36-5.31 (m, 1H), 5.12-5.08 (m, 1H), 4.51-4.47 (m, 2H), 3.87-3.77 (m, 3H), 3.73-3.62 (m, 10H), 3.60-3.57 (m, 1H), 3.35-3.26 (m, 12H), 2.65-2.56 (m, 1H), 2.47-2.36 (m, 2H), 2.31-1.90 (m, 14H), 1.78-1.72 (m, 1H), 1.70-1.66 (m, 1H), 1.47-1.43 (m, 1H), 1.24-1.18 (m, 1H), 1.02-1.01, 1.00-0.99 (m, m, 6H), 0.93-0.92, 0.91-0.90 (m, m, 6H).

Example 38

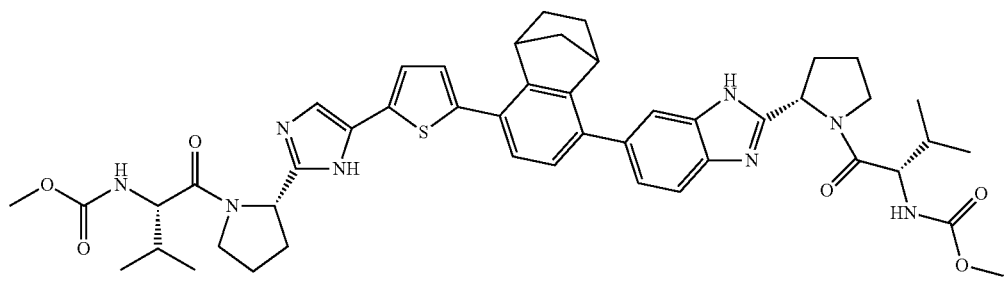

Synthetic Route:
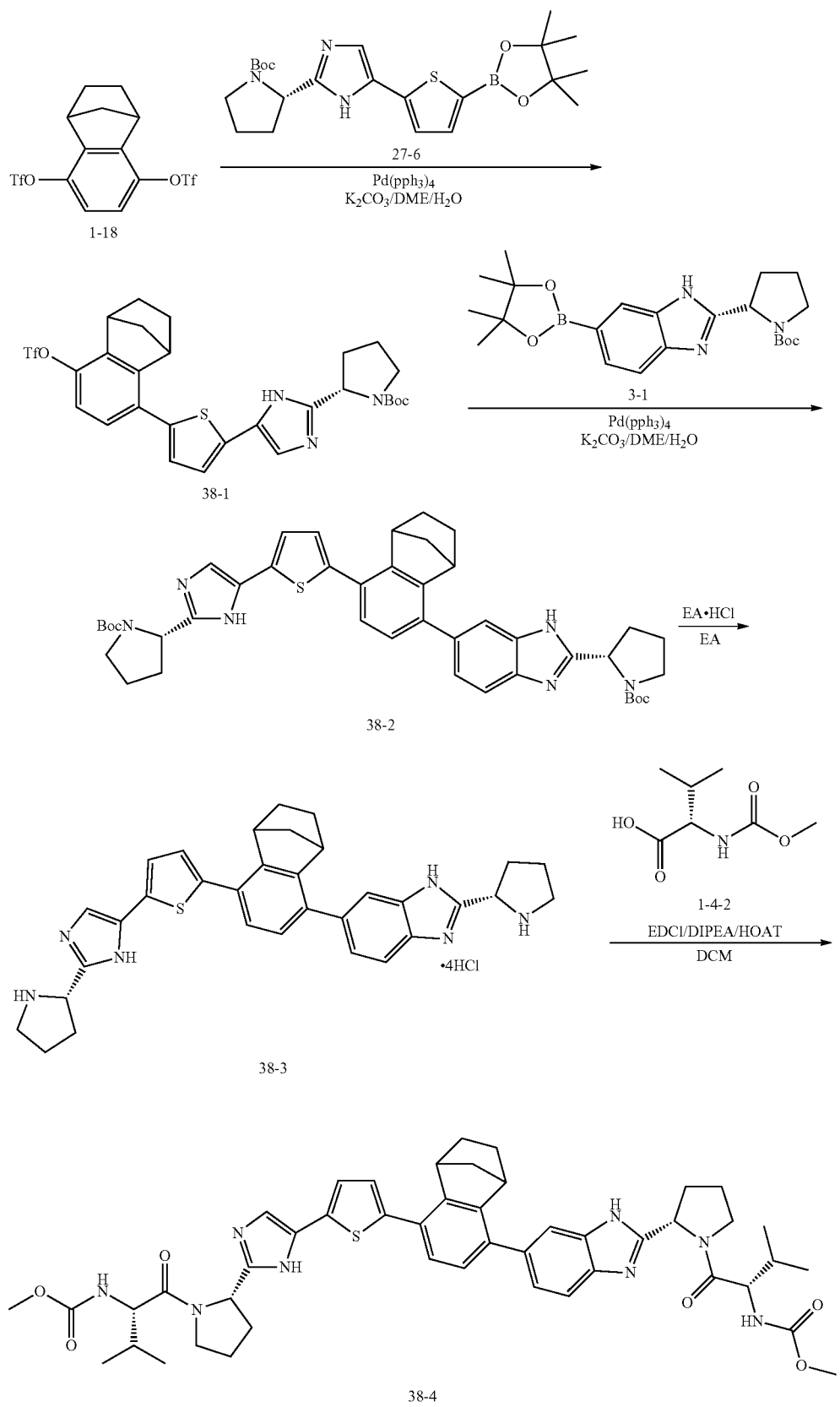

Step 1) the Preparation of Compound 38-1

To a mixture of compound 1-18 (4.4 g, 10.0 mmol), compound 27-6 (4.45 g, 10.0 mmol), Pd(PPh$_3$)$_4$ (1.16 g, 1.0 mmol) and K$_2$CO$_3$ (3.45 g, 25.0 mmol) were added DME (60.0 mL) and pure water (12.0 mL) via syringe. The mixture was stirred at 90° C. under N$_2$ for 3.0 hrs. After the reaction was completed, the mixture was cooled to rt, 50 mL of water was added, and the resulting mixture was extracted with EtOAc (50 mL×3). The combined organic layers were washed with brine, dried over anhydrous Na$_2$SO$_4$ and concentrated in vacuo. The residue was purified by a silica gel column chromatography (DCM/EtOH (v/v)=60/1) to give the title compound (3.53 g, 58%) as a pale yellow solid. The compound was characterized by the following spectroscopic data:

MS (ESI, pos.ion) m/z: 610.5 [M+H]$^+$;

$^1$H NMR (400 MHz, CDCl$_3$) δ (ppm): 7.54-7.52 (s, s, 1H), 7.48 (s, 1H), 7.31, 7.28 (s, s, 1H), 7.14, 7.13 (s, s, 1H), 6.97, 6.96 (s, s, 1H), 5.16-5.10 (m, 1H), 3.64-3.58 (m, 1H), 3.54-3.51 (m, 1H), 3.31-3.24 (m, 2H), 2.24-2.39 (m, 1H), 2.27-2.18 (m, 1H), 2.11-2.01 (m, 4H), 1.89-1.85 (m, 1H), 1.66-1.62 (m, 1H), 1.53 (s, 9H), 1.37-1.31 (m, 1H), 1.27-1.21 (m, 1H).

Step 2) the Preparation of Compound 38-2

To a mixture of compound 3-1 (413 mg, 1.0 mmol), compound 38-1 (426 mg, 0.70 mmol), Pd(PPh$_3$)$_4$ (80 mg, 0.07 mmol) and K$_2$CO$_3$ (250 mg, 1.8 mmol) were added DME (6.0 mL) and water (1.5 mL) via syringe, the mixture was stirred at 90° C. under N$_2$ for 3.0 hrs. After the reaction was completed, the mixture was cooled to rt and 20 mL of water was added. The resulting mixture was extracted with EtOAc (20 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound (313.4 mg, 60%) as a pale yellow solid. The compound was characterized by the following spectroscopic data:

MS (ESI, pos.ion) m/z: 747.3 [M+H]$^+$;

$^1$H NMR (400 MHz, CDCl$_3$) δ (ppm): 7.67, 7.64 (s, s, 1H), 7.62-7.59 (m, 2H), 7.48 (s, 1H), 7.41, 7.39 (s, s, 1H), 7.23, 7.21 (d, d, 1H), 7.14, 7.13 (s, s, 1H), 7.01, 7.00 (s, s, 1H), 5.04-4.99 (m, 1H), 3.95-3.90 (m, 2H), 3.82-3.76 (m, 1H), 3.64-3.56 (m, 2H), 3.31-3.24 (m, 1H), 2.62-2.54 (m, 1H), 2.47-2.36 (m, 2H), 2.27-2.16 (m, 2H), 2.11-1.93 (m, 5H), 1.91-1.87, 1.68-1.64 (m, m, 2H), 1.53 (s, 18H), 1.31-1.22 (m, 2H).

Step 3) the Preparation of Compound 38-3

To a solution of compound 38-2 (298 mg, 0.40 mmol) in EtOAc (2.0 mL) was added a solution of HCl in EtOAc (5.0 mL, 4 M) dropwise. At the end of addition, the mixture was stirred at rt for 8.0 hrs. After the reaction was completed, the mixture was concentrated in vacuo. The residue was washed with EtOAc (10.0 mL) and filtered, to give the title compound (276.9 mg, 100%) as a pale yellow solid, which was used for the next step without further purification. The compound was characterized by the following spectroscopic data:

MS (ESI, pos.ion) m/z: 547.3 [M+H]$^+$.

Step 4) the Preparation of Compound 38-4

To a suspension of compound 38-3 (270 mg, 0.39 mmol), EDCI (300 mg, 1.6 mmol) and compound 1-4-2 (200 mg, 1.1 mmol) in DCM (8.0 mL) was added DIPEA (0.64 mL, 3.87 mmol) dropwise at 0° C. At the end of addition, the mixture was stirred at rt for 3.0 hrs. After the reaction was completed, the mixture was diluted with DCM (20.0 mL), and then the resulting mixture was washed with NH$_4$Cl aqueous solution and brine, dried over Na$_2$SO$_4$ and concentrated in vacuo. The residue was purified by a silica gel column chromatography (DCM/MeOH (v/v)=50/1) to give the title compound (201.3 mg, 60%) as pale yellow powder. The compound was characterized by the following spectroscopic data:

MS (ESI, pos.ion) m/z: 864.5 [M+H]$^+$;

$^1$H NMR (400 MHz, CDCl$_3$) δ (ppm): 7.67, 7.64 (s, s, 1H), 7.62-7.59 (m, 2H), 7.41-7.39 (s, s, 1H), 7.23, 7.21 (d, d, 1H), 7.14, 7.13 (s, s, 1H), 7.01, 7.00 (s, s, 1H), 5.42-5.37 (m, 1H), 5.32, 5.29 (br, br, 2H), 5.24-5.20 (m, 1H), 4.41-4.35 (m, 2H), 3.94-3.91 (m, 2H), 3.85-3.77 (m, 2H), 3.68-3.64 (m, 2H), 3.63 (s, 6H), 2.37-2.05 (m, 9H), 2.03-1.87 (m, 6H), 1.68-1.64 (m, 1H), 1.31-1.23 (m, 1H), 0.97, 0.95 (m, m, 6H), 0.91, 0.89 (m, m, 6H).

Example 39

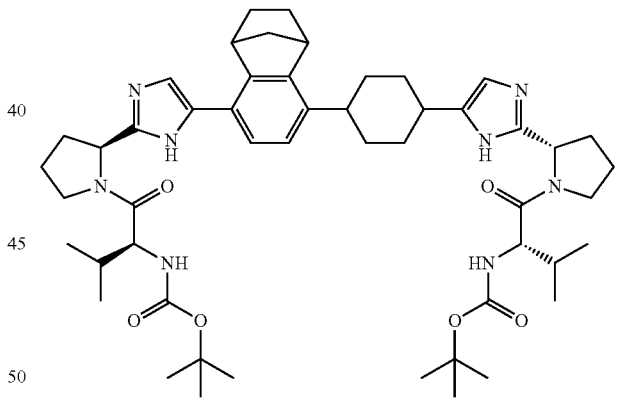

Synthetic Route:

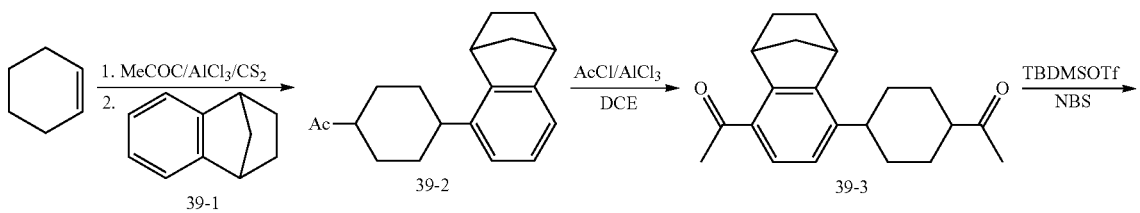

-continued
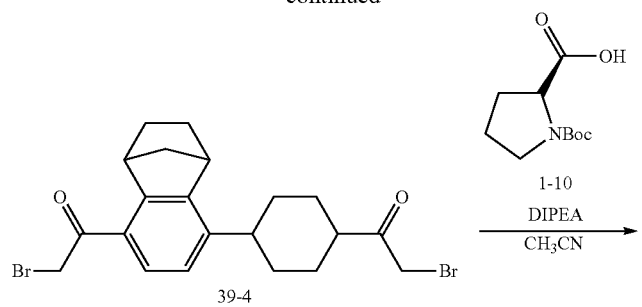
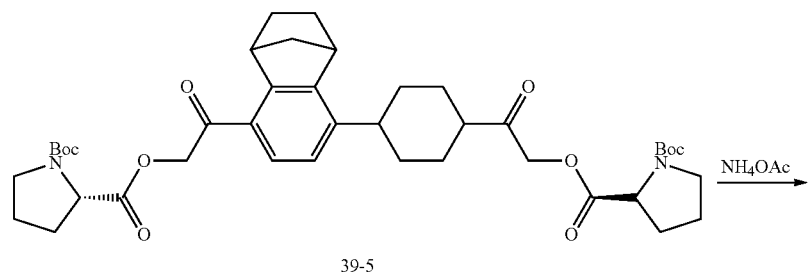
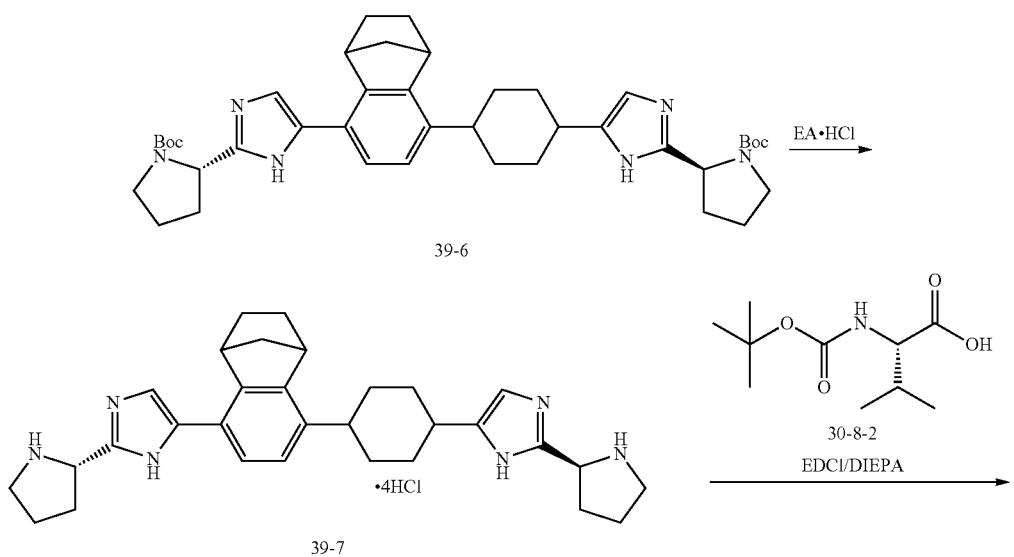
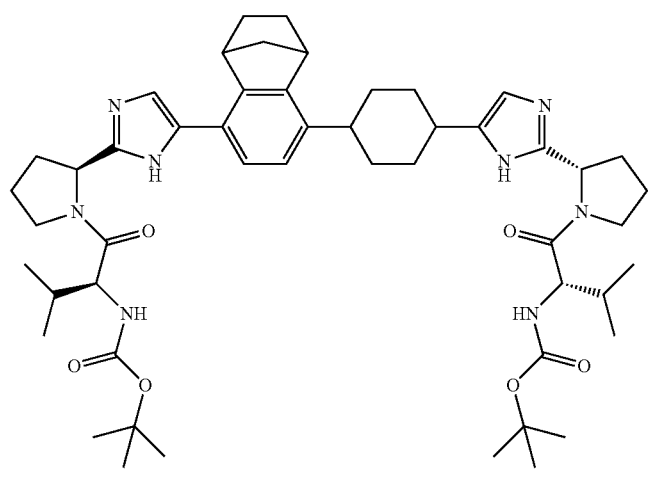

Step 1) the Preparation of Compound 39-2

To a suspension of aluminium chloride (2.15 g, 16.2 mmol) in carbon disulphide (40.0 mL) was added acetyl chloride (1.4 mL, 19.7 mmol) dropwise. When the solution turned to pale yellow, cyclohexene (1.0 mL, 10 mmol) was added. At the end of addition, the mixture was stirred at rt for 2.0 hrs. After the reaction was completed, the mixture was concentrated in vacuo to give the compound as slurry. Compound 39-1 (2.16 g, 15.0 mmol) was added to the above slurry, the mixture was stirred at 50° C. for 4.0 hrs. After the reaction was completed, the mixture was quenched with ice-water (40 mL). The aqueous layer was extracted with EtOAc (3×100 mL). The combined organic lays were washed with brine, dried over anhydrous $Na_2SO_4$ and concentrated in vacuo. The residue was purified by a silica gel column chromatography (PE/DCM (v/v)=10/1) to give the title compound 39-2 (1.2 g, 30%) as a colorless oil. The compound was characterized by the following spectroscopic data:

MS (ESI, pos.ion) m/z: 269.5 [M+H]$^+$;

$^1$H NMR (400 MHz, CDCl$_3$) δ (ppm): 7.12-7.09 (m, 1H), 7.02-7.01, 7.00-6.99 (m, m, 1H), 6.90-6.89, 6.88-6.87 (m, m, 1H), 3.44-3.41 (m, 1H), 3.21-3.18 (m, 1H), 3.07-2.98 (m, 1H), 2.26-2.18 (m, 1H), 2.11 (s, 3H), 1.93-1.82 (m, 6H), 1.72-1.68 (m, 1H), 1.65-1.51 (m, 4H), 1.49-1.45 (m, 1H), 1.20-1.10 (m, 2H).

Step 2) the Preparation of Compound 39-3

To a suspension of aluminium chloride (2.12 g, 15.9 mmol) in 1,2-dichloroethane (40.0 mL) was added acetyl chloride (1.2 mL, 16.8 mmol) dropwise. When the solution turned to pale yellow, compound 39-2 (3.48 g, 13.0 mmol) in 1,2-dichloroethane (20.0 mL) was added dropwise. At the end of addition, the mixture was stirred at rt for 2 hrs. After the reaction was completed, the mixture was quenched with ice-water (40.0 mL). The aqueous layer was extracted with EtOAc (3×50 mL). The combined organic lays were washed with brine, dried over anhydrous $Na_2SO_4$ and concentrated in vacuo. The residue was purified by a silica gel column chromatography (PE/EtOAc (v/v)=10/1) to give the title compound 39-3 (1.55 g, 38.5%) as a white solid. The compound was characterized by the following spectroscopic data:

MS (ESI, pos.ion) m/z: 311.3 [M+H]$^+$;

$^1$H NMR (400 MHz, CDCl$_3$) δ (ppm): 7.61, 7.59 (s, s, 1H), 6.95-6.92 (m, m, 1H), 3.50-3.45 (m, 2H), 3.07-2.98 (m, 1H), 2.58 (s, 3H), 2.26-2.18 (m, 1H), 2.11 (s, 3H), 1.93-1.81 (m, 6H), 1.72-1.68 (m, 1H), 1.65-1.51 (m, 4H), 1.49-1.45 (m, 1H), 1.20-1.14 (m, 2H).

Step 3) the Preparation of Compound 39-4

To a solution of compound 39-3 (1.47 g, 4.73 mmol) in DCM (30.0 mL) at 0° C. was added DIPEA (2.5 mL, 15.12 mmol) and TBDMSOTf (3.5 mL, 11.5 mmol) dropwise. At the end of addition, the mixture was stirred at rt for 2 hrs. After the reaction was completed, the mixture was quenched with water (20.0 mL). The aqueous layer was extracted with DCM (3×40 mL). The combined organic lays were washed with brine, dried over anhydrous $Na_2SO_4$ and concentrated in vacuo to give compound as a yellow gel-like substance. To the solution of yellow gel-like substance in THF (20.0 mL) was added NBS (1.56 g, 8.76 mmol) at 0° C. The mixture was stirred at 0° C. for 4.0 hrs. After the reaction was completed, THF was removed, and the residue was dissolved in EtOAc (40.0 mL). The resulting mixture was washed with H$_2$O (50 mL×3) and brine. The combined organic layers were dried over anhydrous $Na_2SO_4$ and concentrated in vacuo. The residue was purified by a silica gel column chromatography (PE/EtOAc (v/v)=10/1) to give the title compound 39-4 (1.27 g, 57.6%) as white slurry. The compound was characterized by the following spectroscopic data:

MS (ESI, pos.ion) m/z: 467.3 [M+H]$^+$;

$^1$H NMR (400 MHz, CDCl$_3$) δ (ppm): 7.70, 7.68 (s, s, 1H), 6.94, 6.91 (s, s, 1H), 4.40 (s, 2H), 3.93 (s, 2H), 3.52-3.49 (m, 1H), 3.40-3.37 (m, 1H), 3.09-3.00 (m, 1H), 2.76-2.68 (m, 1H), 1.96-1.87 (m, 2H), 1.76-1.57 (m, 9H), 1.52-1.48 (m, 1H), 1.23-1.14 (m, 2H).

Step 4) the Preparation of Compound 39-5

To a solution of compound 39-4 (1.01 g, 2.18 mmol) in CH$_3$CN (22.0 mL) was added DIPEA (1.1 mL, 6.6 mmol) and compound 1-10 (1.08 g, 5.014 mmol) at 0° C. in turn. At the end of addition, the mixture was stirred at rt for 1.0 hr. After the reaction was completed, the mixture was concentrated in vacuo, and the residue was purified by a silica gel column chromatography (PE/EtOAc (v/v)=2/3) to give the title compound 39-5 (1.36 g, 85%) as pale yellow slurry. The compound was characterized by the following spectroscopic data:

MS (ESI, pos.ion) m/z: 737.5 [M+H]$^+$.

Step 5) the Preparation of Compound 39-6

The suspension of compound 39-5 (1.345 g, 1.83 mmol) and NH$_4$OAc (2.82 g, 36.6 mmol in xylene (20.0 mL) was stirred at 140° C. for 5 hrs. After the reaction was completed, the mixture was cooled to rt, and 40 mL of water was added. The resulting mixture was extracted with EtOAc (50 mL×3). The combined organic layers were washed with brine, dried over anhydrous $Na_2SO_4$ and concentrated in vacuo. The residue was purified by a silica gel column chromatography (DCM/MeOH(v/v)=50/1) to give the title compound 39-9 (0.93 g, 73%) as a pale yellow solid. The compound was characterized by the following spectroscopic data:

MS (ESI, pos.ion) m/z: 697.5 [M+H]$^+$;

$^1$H NMR (400 MHz, CDCl$_3$) δ (ppm): 7.71 (s, 1H), 7.14, 7.12 (s, s, 1H), 6.81 (d, 1H), 6.77, 6.75 (d, d, 1H), 5.06-5.00 (m, 1H), 4.87-4.80 (m, 1H), 3.73-3.67 (m, 2H), 3.64-3.58 (m, 1H), 3.44-3.36 (m, 1H), 3.34-3.15 (m, 1H), 2.78-2.68 (m, 1H), 2.47-2.33 (m, 2H), 2.28-2.16 (m, 2H), 2.10-1.95 (m, 6H), 1.92-1.76 (m, 6H), 1.57-1.53 (m, 2H), 1.53 (s, 9H), 1.41 (s, 9H), 1.28-1.22 (m, 2H), 1.15-1.09 (m, 2H).

Step 6) the Preparation of Compound 39-7

To a solution of compound 39-6 (926 mg, 1.33 mmol) in EtOAc (10.0 mL) was added a solution of HCl in EtOAc (10.0 mL, 4 M) dropwise. At the end of addition, the mixture was stirred at rt for 8.0 hrs. After the reaction was completed, the mixture was concentrated in vacuo, and the residue was washed with EtOAc (20.0 mL) to give the title compound 39-7 (536 mg, 83.5%) as a pale yellow solid. The compound was characterized by the following spectroscopic data:

MS (ESI, pos.ion) m/z: 497.5 [M+H]$^+$.

Step 7) the Preparation of Compound 39-8

To a mixture of compound 39-7 (385.4 mg, 0.6 mmol), EDCI (300.56 mg, 1.56 mmol) and compound 30-8-2 (341 mg, 1.56 mmol) in DCM (10.0 mL) at 0° C. was added DIPEA (1.09 mL, 6.60 mmol) dropwise. At the end of addition, the mixture was stirred at rt for 10 hrs. The mixture was diluted with DCM (20.0 mL), washed with saturated NH$_4$Cl aqueous solution and brine, dried over anhydrous $Na_2SO_4$ and concentrated in vacuo. The residue was purified by a silica gel column chromatography (DCM/EtOH (v/v)=50/1) to give the title compound 39-8 (343.5 mg, 64%) as pale yellow powder. The compound was characterized by the following spectroscopic data:

MS (ESI, pos.ion) m/z: 895.5 [M+H]$^+$;

$^1$H NMR (400 MHz, CDCl$_3$) δ (ppm): 7.66 (s, 1H), 7.14, 7.12 (s, s, 1H), 6.82 (s, 1H), 6.77, 6.75 (s, s, 1H), 5.29-5.25 (m, 1H), 5.20, 5.18 (br, br, 2H), 5.12-5.07 (m, 1H), 4.40-4.35 (m, 2H), 3.86-3.78 (m, 2H), 3.72-3.61 (m, 3H), 3.34-3.31 (m, 1H), 3.24-3.15 (m, 1H), 2.78-2.68 (m, 1H), 2.30-1.76 (m, 18H), 1.57-1.53 (m, 2H), 1.43 (s, 18H), 1.28-1.22 (m, 2H), 1.15-1.09 (m, 2H), 0.97, 0.96 (m, m, 6H), 0.90, 0.89 (m, m, 6H).

Example 40
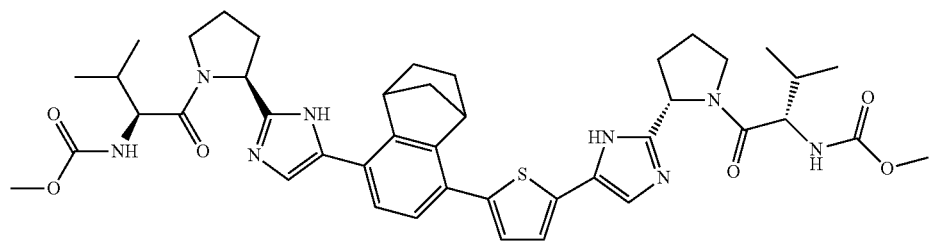
Synthetic Route:
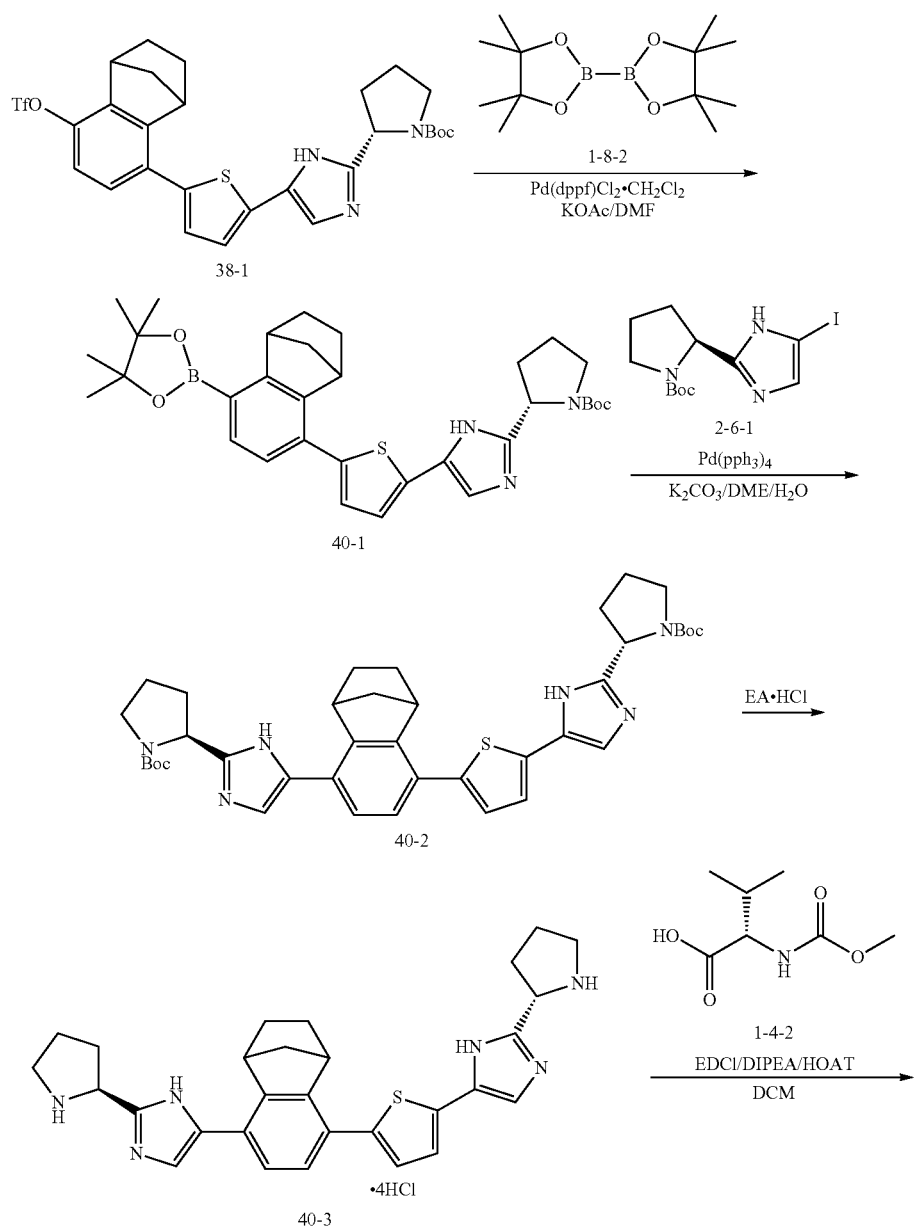

-continued

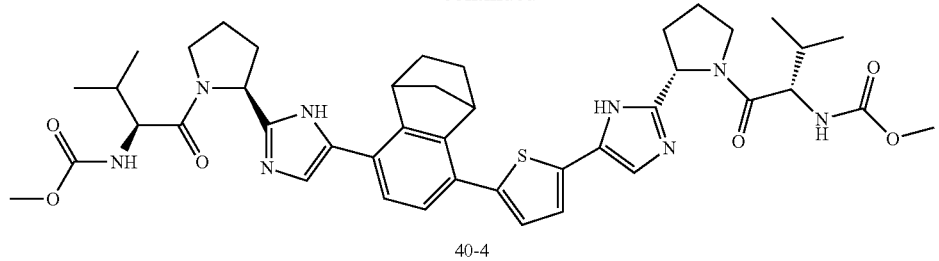

40-4

Step 1) the Preparation of Compound 40-1

A mixture of compound 38-1 (247.31 mg, 0.406 mmol), compound of 1-8-2 (123.8 mg, 0.487 mmol), PdCl$_2$(dppf).CH$_2$Cl$_2$ (33.18 mg, 0.0406 mmol) and KOAc (120 mg, 1.22 mmol) dissolved in DMF (4.0 mL) was stirred at 90° C. for 4 hrs under N$_2$. After the reaction was completed, the mixture was cooled to rt, diluted with EtOAc (20.0 mL) and filtered through a celite pad. The filtrate was washed with water (30 mL×3) and brine, dried over anhydrous Na$_2$SO$_4$ and concentrated in vacuo. The residue was purified by a silica gel column chromatography (DCM/MeOH (v/v)=150/1) to give the title compound (143 mg, 60%) as a pale yellow solid. The compound was characterized by the following spectroscopic data:

MS (ESI, pos.ion) m/z: 588.3 [M+H]$^+$;

$^1$H NMR (400 MHz, CDCl$_3$) δ (ppm): 7.87, 7.85 (s, s, 1H), 7.75, 7.73 (s, s, 1H), 7.48 (s, 1H), 7.14, 7.13 (s, s, 1H), 7.01, 7.00 (s, s, 1H), 5.16-5.10 (m, 1H), 3.90-3.87 (m, 1H), 3.86-3.83 (m, 1H), 3.64-3.58 (m, 1H), 3.31-3.24 (m, 1H), 2.47-2.39 (m, 1H), 2.27-2.17 (m, 1H), 2.11-1.92 (m, 3H), 1.87-1.81 (m, 2H), 1.64-1.60 (m, 1H), 1.53 (s, 9H), 1.32 (m, 6H), 1.29 (m, 6H), 1.25-1.19 (m, 1H), 1.14-1.09 (m, 1H).

Step 2) the Preparation of Compound 40-2

A suspension of compound 40-1 (148.76 mg, 0.2533 mmol), compound 2-6-1 (92 mg, 0.2533 mmol), Pd(PPh$_3$)$_4$ (29.26 mg, 0.02533 mmol) and K$_2$CO$_3$ (123.23 mg, 0.8866 mmol) in mixed solvents of EtOH and H$_2$O (5.0 mL, v/v=4/1) was stirred at 90° C. under N$_2$ for 4 hrs. After the reaction was completed, the mixture was concentrated in vacuo. The residue was dissolved in EtOAc (20.0 mL). The resulting mixture was washed with water (10 mL×3) and brine, dried over anhydrous Na$_2$SO$_4$ and concentrated in vacuo. The residue was purified by a silica gel column chromatography (DCM/MeOH (v/v)=80/1) to give the title compound (102 mg, 57.9%) as a pale yellow solid. The compound was characterized by the following spectroscopic data:

MS (ESI, pos.ion) m/z: 697.5 [M+H]$^+$;

$^1$H NMR (400 MHz, CDCl$_3$) δ (ppm): 7.90 (s, 1H), 7.48 (s, 1H), 7.37 (s, 2H), 7.14, 7.13 (s, s, 1H), 7.01, 7.00 (s, s, 1H), 5.16-5.10 (m, 1H), 5.05-5.01 (m, 1H), 3.94-3.92 (m, 1H), 3.85-3.82 (m, 1H), 3.64-3.58 (m, 2H), 3.31-3.24 (m, 2H), 2.47-2.38 (m, 2H), 2.29-2.16 (m, 2H), 2.11-1.96 (m, 6H), 1.94-1.90 (m, 1H), 1.71-1.67 (m, 1H), 1.53 (s, 9H), 1.41 (s, 9H), 1.32-1.23 (m, 2H).

Step 3) the Preparation of Compound 40-3

To a solution of compound 40-2 (151.66 mg, 0.2178 mmol) in EtOAc (4.0 mL) was added a solution of HCl in EtOAc (3.0 mL, 4 M) dropwise. At the end of addition, the mixture was stirred at rt for 8.0 hrs. After the reaction was completed, the reaction mixture was concentrated in vacuo. The residue was washed with EtOAc (10.0 mL), and then filtered to give the title compound (139.88 mg, 73%) as pale yellow powder. The compound was characterized by the following spectroscopic data:

MS (ESI, pos.ion) m/z: 497.3 [M+H]$^+$.

Step 4) the Preparation of Compound 40-4

A suspension of compound 40-3 (102.11 mg, 0.159 mmol), compound 1-4-2 (58.42 mg, 0.333 mmol), EDCI (63.84 mg, 0.333 mmol) and HOAT (32.42 mg, 0.238 mmol) in DCM (5.0 mL) was stirred at 0° C., then DIPEA (0.22 mL, 1.33 mmol) was added dropwise. At the end of addition, the mixture was stirred at rt for 3 hrs. After the reaction was completed, the mixture was diluted with DCM (20.0 mL), washed with NH$_4$Cl aqueous solution and brine, dried over anhydrous Na$_2$SO$_4$ and concentrated in vacuo. The residue was purified by a silica gel column chromatography (DCM/MeOH (v/v)= 60/1) to give the title compound (43.8 mg, 34%) as a pale yellow solid. The compound was characterized by the following spectroscopic data:

MS (ESI, pos.ion) m/z: 406.3 [M+2H]$^{2+}$;

$^1$H NMR (400 MHz, CDCl$_3$) δ (ppm): 7.81 (s, 1H), 7.41 (s, 1H), 7.37 (s, 2H), 7.14, 7.13 (s, s, 1H), 7.01, 7.00 (s, s, 1H), 5.42-5.37 (m, 1H), 5.32, 5.29 (br, br, 2H), 5.28-5.25 (m, 1H), 4.41-4.36 (m, 2H), 3.94-3.92 (m, 1H), 3.85-3.78 (m, 3H), 3.69-3.64 (m, 2H), 3.63 (s, 6H), 2.31-2.16 (m, 6H), 2.15-1.90 (m, 6H), 1.71-1.67 (m, 2H), 1.32-1.23 (m, 2H), 0.97, 0.96 (m, m, 6H), 0.91-0.89 (m, m, 6H).

Example 41

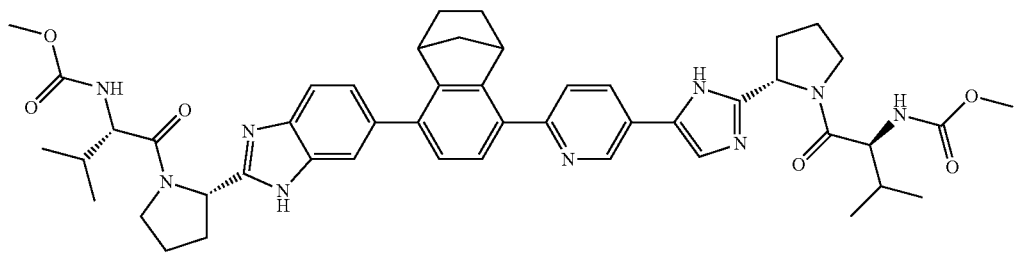

Synthetic Route:
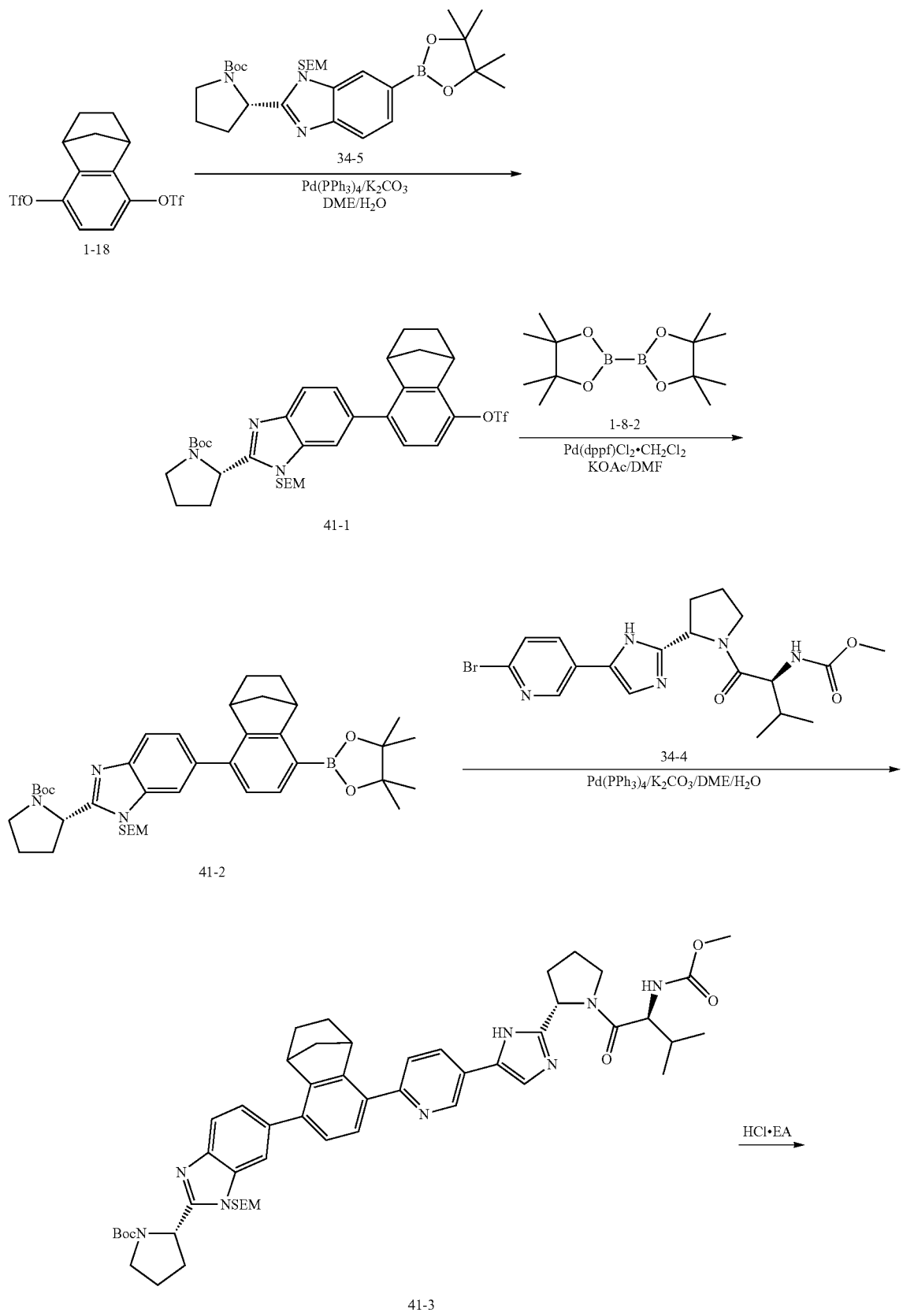

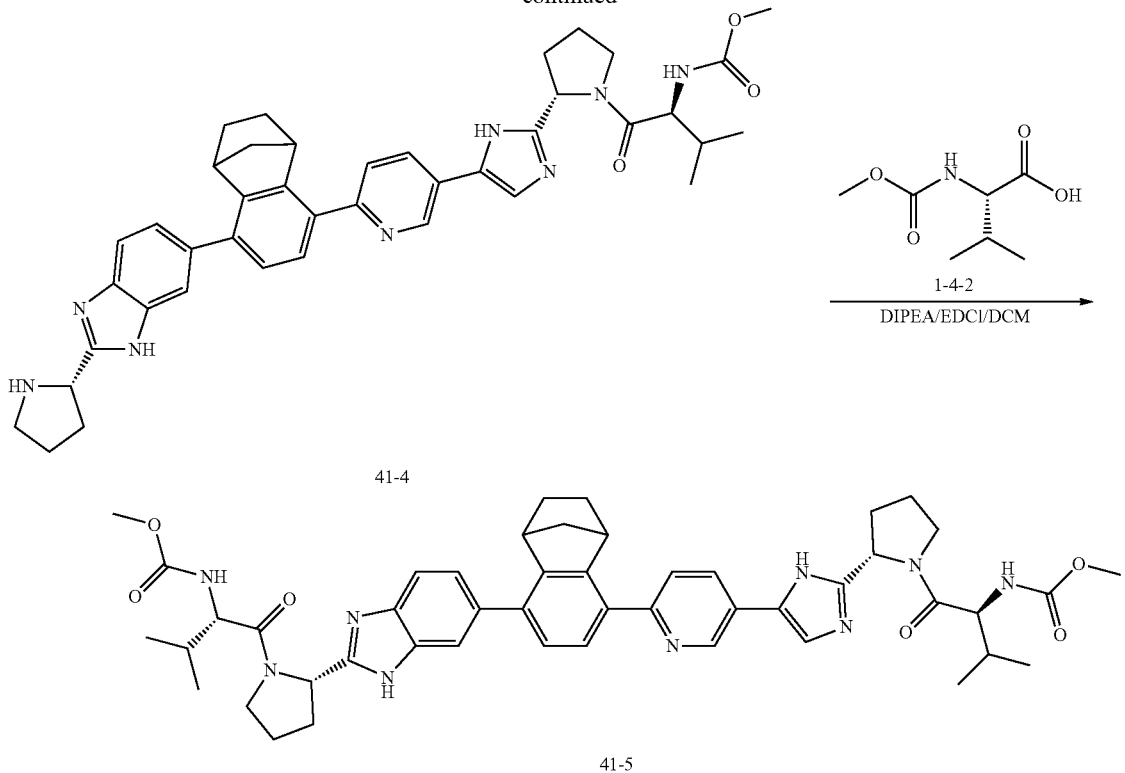

Step 1) the Preparation of Compound 41-1

To a mixture of compound 1-18 (316.8 mg, 0.72 mmol), compound 34-5 (390 mg, 0.72 mmol), Pd(PPh$_3$)$_4$ (83 mg, 0.07 mmol) and K$_2$CO$_3$ (300 mg, 2.12 mmol) were added DME (4.0 mL) and water (1.0 mL) via syringe. The mixture was stirred at 90° C. for 4 hrs under N$_2$. After the reaction was completed, the mixture was cooled to rt and quenched with 10.0 mL of water. The resulting mixture was extracted with EtOAc (20 mL×3). The combined organic layers were washed with brine, dried over anhydrous Na$_2$SO$_4$ and concentrated in vacuo. The residue was purified by a silica gel column chromatography (PE/EtOAc (v/v)=2/1) to give the title compound (407.38 mg, 80%) as a white solid. The compound was characterized by the following spectroscopic data:

$^1$H NMR (400 MHz, CDCl$_3$) δ (ppm): 8.05-8.04, 8.03-8.02 (d, d, 1H, J=4.0 Hz), 7.54-7.53 (m, 1H), 7.41, 7.39 (s, s, 1H), 7.41-7.40, 7.39-7.38 (d, d, 1H, J=4.0 Hz), 7.29, 7.27 (s, s, 1H), 4.99-4.94 (m, 1H), 3.77-3.71 (m, 1H), 3.61-3.51 (m, 3H), 2.52-2.42 (m, 1H), 2.27-2.17 (m, 1H), 2.15-1.92 (m, 4H), 1.86-1.78 (m, 3H), 1.63-1.59 (m, 1H), 1.53 (s, 9H), 1.34-1.28 (m, 2H), 1.25-1.19 (m, 2H), 0.58-0.51 (m, 2H), 0.01-0.00 (m, 9H).

Step 2) the Preparation of Compound 41-2

A mixture of compound 41-1 (643.6 mg, 0.91 mmol), compound 1-8-2 (463 mg, 1.82 mmol), PdCl$_2$(dppf).CH$_2$Cl$_2$ (71 mg, 0.09 mmol) and KOAc (268 mg, 2.73 mmol) in DMF (6.0 mL) was stirred at 90° C. for 3.0 hrs under N$_2$. After the reaction was completed, the mixture was diluted with EtOAc (40.0 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=2/1) to give the title compound (547 mg, 87.7%) as a white solid. The compound was characterized by the following spectroscopic data:

MS (ESI, pos.ion) m/z: 686.5 [M+H]$^+$;

$^1$H NMR (400 MHz, CDCl$_3$) δ (ppm): 8.27, 8.25 (d, d, 1H, J=4.0 Hz), 8.01, 7.98 (s, s, 1H), 7.49-7.47 (m, 1H), 7.41, 7.39 (s, s, 1H), 7.41-7.40, 7.39-7.38 (d, d, 1H, J=4.0 Hz), 7.29, 7.27 (s, s, 1H), 4.99-4.94 (m, 1H), 3.77-3.71 (m, 1H), 3.61-3.51 (m, 3H), 2.52-2.42 (m, 1H), 2.27-2.17 (m, 1H), 2.15-1.92 (m, 4H), 1.86-1.78 (m, 3H), 1.63-1.59 (m, 1H), 1.53 (s, 9H), 1.34-1.28 (m, 2H), 1.25-1.19 (m, 2H), 0.58-0.51 (m, 2H), 0.01-0.00 (m, 9H).

Step 3) the Preparation of Compound 41-3

A suspension of compound 41-2 (418 mg, 0.61 mmol), compound 34-4 (274 mg, 0.60 mmol), Pd(PPh$_3$)$_4$ (70 mg, 0.05 mmol) and K$_2$CO$_3$ (254 mg, 1.83 mmol) in mixed solvents of DME and H$_2$O (6.0 mL, v/v=5/1) was stirred at 90° C. under N$_2$ for 4 hrs. After the reaction was completed, the mixture was concentrated in vacuo. The residue was dissolved in EtOAc (20.0 mL). The resulting mixture was washed with brine, dried over anhydrous Na$_2$SO$_4$ and concentrated in vacuo. The residue was purified by a silica gel column chromatography (PE/EtOAc (v/v)=1/1) to give the title compound (528 mg, 93.3%) as a pale yellow solid. The compound was characterized by the following spectroscopic data:

MS (ESI, pos.ion) m/z: 944.5 [M+H]$^+$;

$^1$H NMR (400 MHz, CDCl$_3$): δ (ppm): 8.84, 8.83 (d, d, 1H, J=4.0 Hz), 8.13, 8.11 (m, m, 1H), 7.88, 7.86 (s, s, 1H), 7.67, 7.65 (d, d, 2H), 7.60, 7.58 (s, s, 1H), 7.49, 7.48 (s, s, 1H), 7.41-7.40, 7.39-7.38 (m, m, 2H), 5.38-5.33 (m, 1H), 5.32, 5.30 (br, br, 1H), 4.99-4.94 (m, 1H), 4.41-4.36 (m, 1H), 4.06-4.03 (m, 2H), 3.91-3.87 (m, 2H), 3.85-3.79 (m, 1H), 3.77-3.71 (m, 1H), 3.69-3.64 (m, 1H), 3.63 (s, 3H), 3.59-3.51 (m, 1H), 2.52-2.42 (m, 1H), 2.30-1.93 (m, 11H), 1.92-1.88 (m, 1H), 1.85-1.77 (m, 2H), 1.69-1.65 (m, 1H), 1.53 (s, 9H), 1.31-1.22 (m, 2H), 0.97, 0.95 (m, m, 3H), 0.91, 0.89 (m, m, 3H), 0.58-0.51 (m, 2H), 0.01-0.00 (m, 9H).

Step 4) the Preparation of Compound 41-4

To a solution of compound 41-3 (528 mg, 0.568 mmol) in EtOAc (5.0 mL) was added a solution of HCl in EtOAc (5.0 mL, 4 M) dropwise. At the end of addition, the mixture was stirred at rt for 8.0 hrs. After the reaction was completed, the mixture was concentrated in vacuo. The residue was washed with EtOAc (10.0 mL), and then filtered to give the title compound (416 mg, 95%) as a pale yellow solid. The compound was characterized by the following spectroscopic data:

MS (ESI, pos.ion) m/z: 699.5 [M+H]$^+$.

Step 5) the Preparation of Compound 41-5

A suspension of compound 41-4 (51.68 mg, 0.067 mmol), compound 1-4-2 (21.0 mg, 0.116 mmol) and EDCI (30.0 mg, 0.154 mmol) in DCM (1.0 mL) was stirred at 0° C., then DIPEA (0.09 mL, 0.544 mmol) was added dropwise. At the end of addition, the mixture was stirred at rt for 3.0 hrs. After the reaction was completed, the mixture was diluted with DCM (20.0 mL), washed with NH$_4$Cl aqueous solution and brine, dried over anhydrous Na$_2$SO$_4$ and concentrated in vacuo. The residue was purified by a silica gel column chromatography (EtOAc) to give the title compound (29.8 mg, 52%) as a white solid. The compound was characterized by the following spectroscopic data:

MS (ESI, pos.ion) m/z: 856.5 [M+H]$^+$;

$^1$H NMR (400 MHz, CDCl$_3$) δ (ppm): 8.84, 8.83 (d, d, 1H), 8.10, 8.08 (s, s, 1H), 7.67, 7.65 (d, d, 2H), 7.62-7.59 (m, 3H), 7.49-7.46 (m, 1H), 7.24-7.21 (m, 1H), 5.38-5.33 (m, 1H), 5.32, 5.29 (br, br, 2H), 5.24-5.20 (m, 1H), 4.41-4.35 (m, 2H), 3.91-3.88 (m, 1H), 3.85-3.77 (m, 3H), 3.69-3.64 (m, 2H), 3.63 (s, 6H), 2.38-1.87 (m, 13H), 1.69-1.65 (m, 1H), 1.31-1.20 (m, 2H), 0.97, 0.95 (m, m, 6H), 0.91, 0.89 (m, m, 6H), 0.01-0.00 (m, 9H).

Example 42

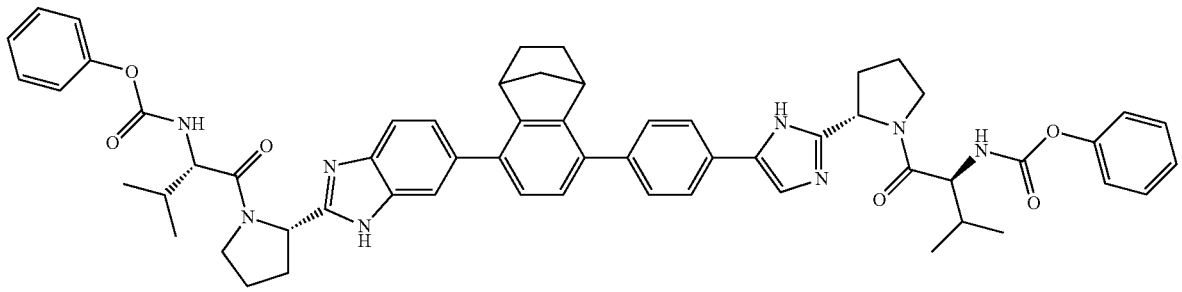 [SMILES: CC(C)[C@H](NC(=O)Oc1ccccc1)C(=O)N1CCC[C@H]1c1ncc(-c2ccc(-c3ccc(-c4ccc5nc([C@@H]6CCCN6C(=O)[C@@H](NC(=O)Oc6ccccc6)C(C)C)[nH]c5c4)c4c3C3CCC4C3)cc2)[nH]1]

Synthetic Route:

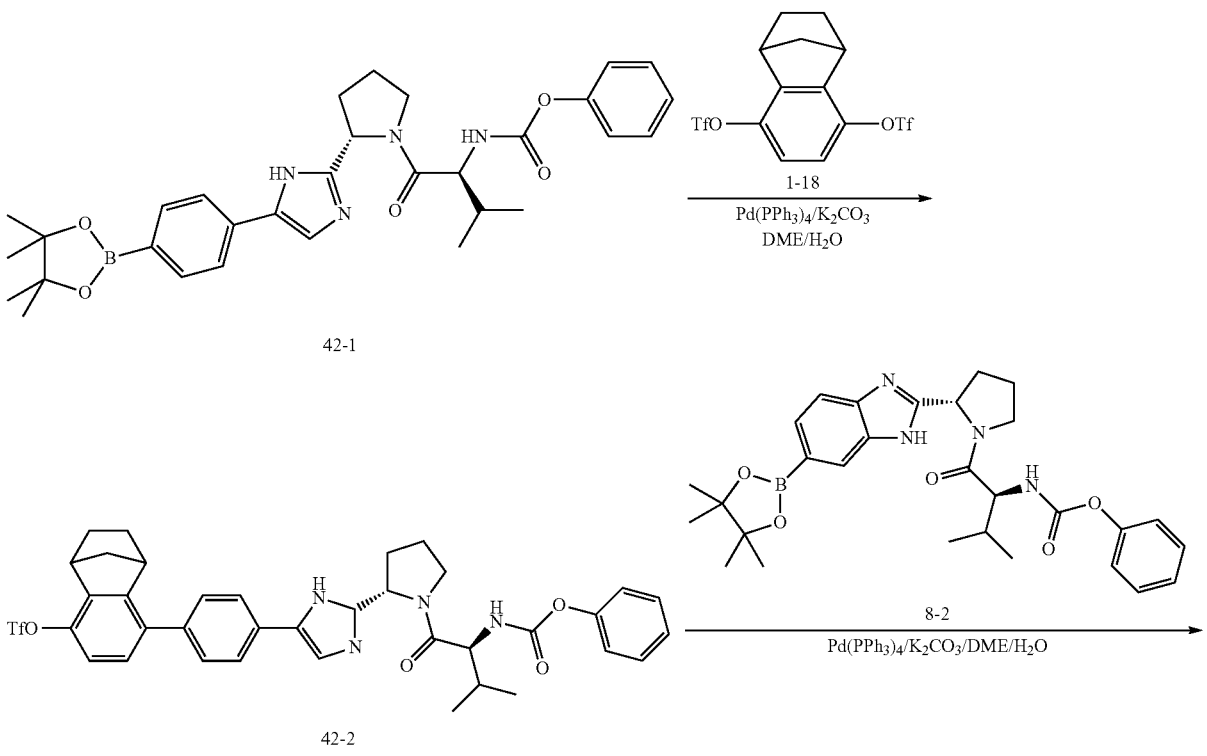

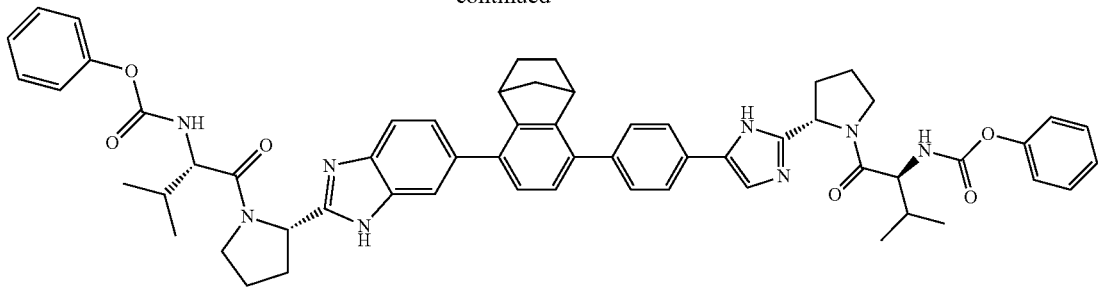

42-3

Step 1) the Preparation of Compound 42-2

To a mixture of compound 1-18 (2.92 g, 6.65 mmol), compound 42-1 (3.71 g, 6.65 mmol), Pd(PPh₃)₄ (768 mg, 0.66 mmol) and K₂CO₃ (2.77 g, 20.1 mmol) were added DME (50.0 mL) and pure water (10.0 mL) via syringe, the mixture was stirred at 90° C. under N₂ for 3 hrs. After the reaction was completed, the mixture was cooled to rt and concentrated in vacuo. The residue was dissolved in EtOAc (60.0 mL). The resulting mixture was washed with water (20 mL×3) and brine, dried over anhydrous Na₂SO₄ and concentrated in vacuo. The residue was purified by a silica gel column chromatography (DCM/MeOH (v/v)=50/1) to give the title compound (3.95 g, 82.3%) as a beige solid. The compound was characterized by the following spectroscopic data:

$^1$H NMR (400 MHz, CDCl₃) δ (ppm): 7.62-7.58 (m, 3H), 7.52-7.48 (m, 2H), 7.36-7.30 (m, 2H), 7.25-7.19 (m, 2H), 7.13-7.10 (m, 2H), 7.06, 7.04 (s, s, 1H), 5.49, 5.46 (br, br, 1H), 5.23-5.19 (m, 1H), 4.48-4.44 (m, 1H), 3.85-3.78 (m, 1H), 3.69-3.61 (m, 1H), 3.60-3.57 (m, 1H), 3.52-3.49 (m, 1H), 2.30-2.16 (m, 3H), 2.13-1.92 (m, 4H), 1.86-1.82 (m, 1H), 1.63-1.59 (m, 1H), 1.34-1.28 (m, 1H), 1.25-1.19 (m, 1H), 0.97, 0.95 (m, m, 3H), 0.91, 0.89 (m, m, 3H).

Step 2) the Preparation of Compound 42-3

To a mixture of compound 42-2 (2.63 g, 3.65 mmol), compound 8-2 (1.94 g, 3.65 mmol), Pd(PPh₃)₄ (404 mg, 0.35 mmol) and K₂CO₃ (1.23 g, 0.89 mmol) were added DME (20.0 mL) and water (4.0 mL) via syringe, the mixture was stirred at 90° C. under N₂ for 3.0 hrs. After the reaction was completed, the mixture was cooled to rt and concentrated in vacuo. The residue was dissolved in EtOAc (60.0 mL). The resulting mixture was washed with water (20 mL×3) and brine, dried over anhydrous Na₂SO₄ and concentrated in vacuo. The residue was purified by a silica gel column chromatography (DCM/MeOH (v/v)=50/1) to give the title compound (1.21 g, 33.89%) as a pale yellow solid. The compound was characterized by the following spectroscopic data:

MS (ESI, pos.ion) m/z: 490.3 [M+2H]$^{2+}$;

$^1$H NMR (400 MHz, CDCl₃) δ (ppm): 7.62-7.61 (m, 3H), 7.60-7.59 (m, 3H), 7.56-7.52 (m, 2H), 7.49, 7.47 (s, s, 1H), 7.42, 7.39 (s, s, 1H), 7.36-7.30 (m, 4H), 7.24-7.19 (m, 2H), 7.13-7.10 (m, 4H), 5.49, 5.46 (br, br, 2H), 5.24-5.19 (m, 2H), 4.48-4.42 (m, 2H), 3.92-3.87 (m, 1H), 3.85-3.78 (m, 2H), 3.69-3.60 (m, 3H), 2.38-1.84 (m, 13H), 1.65-1.61 (m, 1H), 1.27-1.21 (m, 2H), 0.97, 0.95 (m, m, 6H), 0.91, 0.89 (m, m, 6H).

Example 43

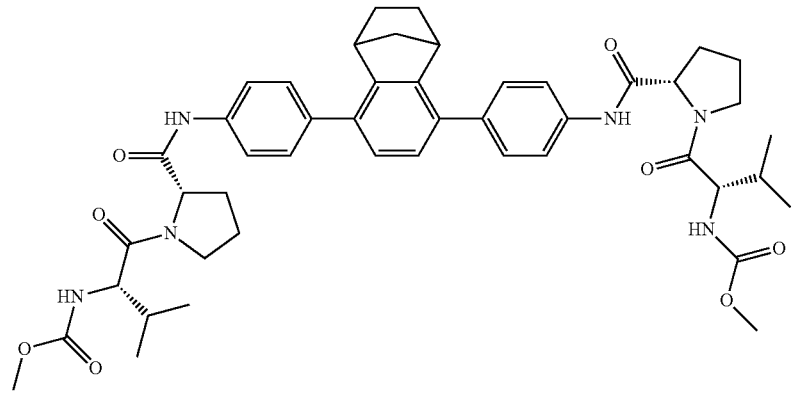 [SMILES: COC(=O)N[C@H](C(=O)N1CCC[C@H]1C(=O)Nc1ccc(-c2ccc(-c3ccc(NC(=O)[C@@H]4CCCN4C(=O)[C@@H](NC(=O)OC)C(C)C)cc3)c3c2C2CCC3C2)cc1)C(C)C]

Synthetic Route:

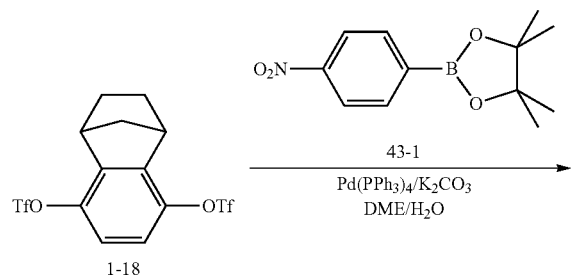

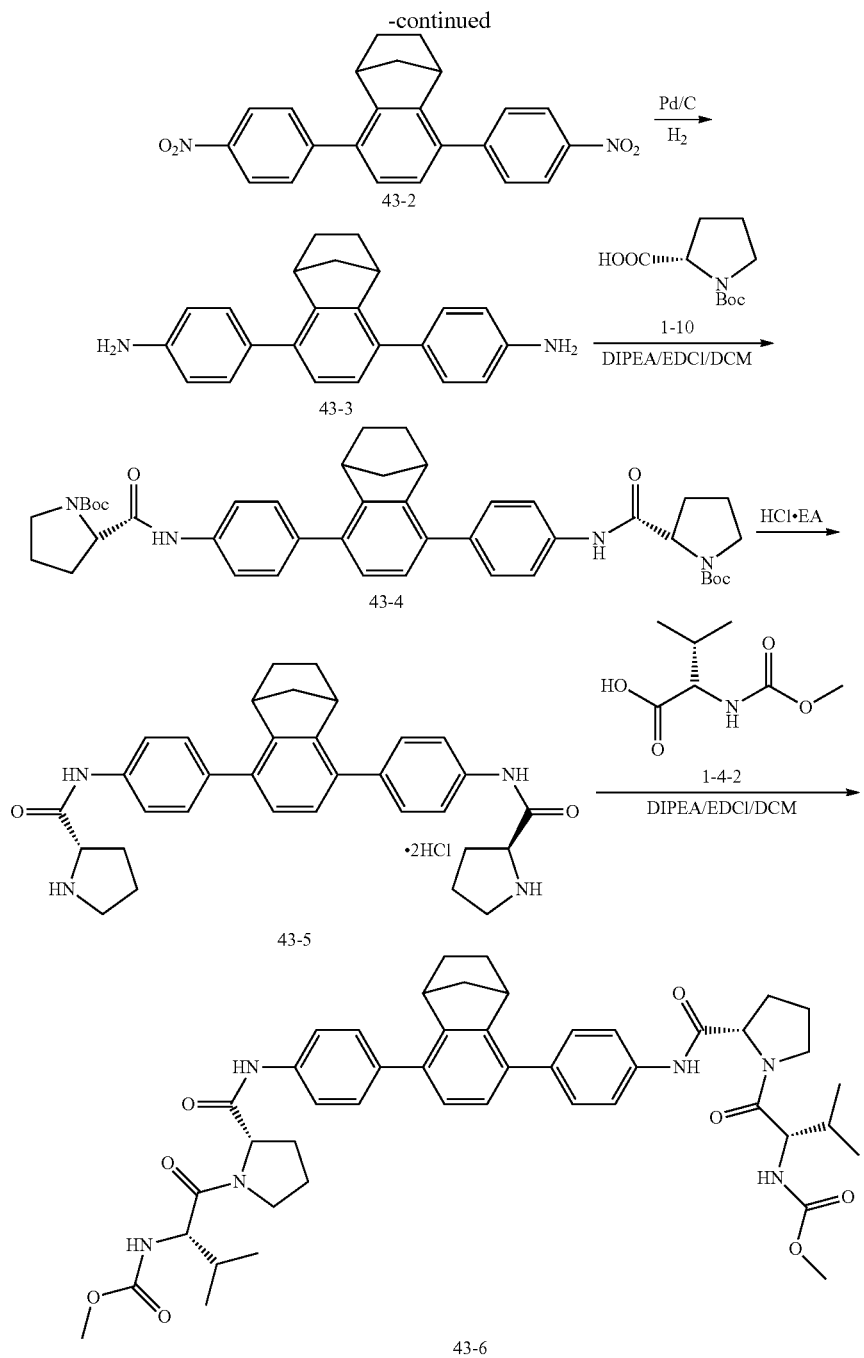

Step 1) the Preparation of Compound 43-2

To a mixture of compound 43-1 (380 mg, 1.526 mmol), compound 1-18 (324.6 mg, 0.693 mmol), Pd(PPh$_3$)$_4$ (80.1 mg, 0.0693 mmol) and K$_2$CO$_3$ (478.6 mg, 3.463 mmol) were added DME (8.0 mL) and water (2.0 mL) via syringe, the mixture was stirred at 90° C. under N$_2$ for 3.0 hrs. After the reaction was completed, the mixture was cooled to rt, 15 mL of water was added, and the resulting mixture was extracted with DCM (25.0 mL×3). The combined organic layers were washed with brine, dried over anhydrous Na$_2$SO$_4$ and concentrated in vacuo. The residue was purified by a silica gel column chromatography (PE/EtOAc (v/v)=5/1) to give the title compound (254.2 mg, 95%) as a yellow solid. The compound was characterized by the following spectroscopic data:

MS (ESI, pos.ion) m/z: 387.3 [M+H]$^+$;

$^1$H NMR (400 MHz, CDCl$_3$) δ (ppm): 8.36-8.33 (m, 4H), 7.59-7.56 (m, 4H), 7.49 (s, 2H), 3.89-3.84 (m, 2H), 2.00-1.94 (m, 2H), 1.88-1.84 (m, 1H), 1.65-1.61 (m, 1H), 1.27-1.21 (m, 2H).

Step 2) the Preparation of Compound 43-3

A suspension of compound 43-2 (270 mg, 0.651 mmol) and a catalytic amount of Pd/C (10%) in DCM (15.0 mL) was stirred at rt under H$_2$ for 4 hrs. After the reaction was completed, the mixture was filtered, and then the filtrated was concentrated in vacuo to give the title compound (201.7 mg, 95%) as a white solid. The compound was characterized by the following spectroscopic data:

MS (ESI, pos.ion) m/z: 327.3 [M+H]$^+$;

$^1$H NMR (400 MHz, CDCl$_3$) δ (ppm): 7.48 (s, 2H), 7.39-7.35 (m, 4H), 6.62-6.59 (m, 4H), 3.89-3.84 (m, 2H), 3.47 (br, 4H), 2.00-1.94 (m, 2H), 1.88-1.84 (m, 1H), 1.65-1.61 (m, 1H), 1.27-1.21 (m, 2H).

Step 3) the Preparation of Compound 43-4

A suspension of compound 43-3 (110.6 mg, 0.339 mmol), compound 1-10 (218.6 mg, 1.016 mmol) and EDCI (259.9 mg, 1.356 mmol) in DCM (10.0 mL) was stirred at 0° C., then DIPEA (0.336 mL, 2.033 mmol) was added dropwise. At the end of addition, the mixture was stirred at rt for 3 hrs. After the reaction was completed, 20 mL of water was added. The aqueous layers was extracted with DCM (25.0 mL×3), the combined organic layers were washed with NH$_4$Cl aqueous solution and brine, dried over anhydrous Na$_2$SO$_4$ and concentrated in vacuo. The residue was purified by a silica gel column chromatography (PE/EtOAc (v/v)=1/1) to give the title compound (195.3 mg, 80%) as a white solid. The compound was characterized by the following spectroscopic data:

MS (ESI, pos.ion) m/z: 721.5 [M+H]$^+$;

$^1$H NMR (400 MHz, CDCl$_3$) δ (ppm): 8.96 (br, 2H), 7.64-7.60 (m, 4H), 7.51-7.47 (m, 4H), 7.45 (s, 2H), 4.40-4.36 (m, 2H), 3.89-3.84 (m, 2H), 3.56-3.49 (m, 2H), 3.44-3.36 (m, 2H), 2.39-2.32 (m, 2H), 2.17-2.07 (m, 2H), 2.01-1.75 (m, 5H), 1.65-1.61 (m, 1H), 1.40 (s, 18H), 1.27-1.21 (m, 2H).

Step 4) the Preparation of Compound 43-5

To a solution of compound 43-4 (91.3 mg, 0.1268 mmol) in EtOAc (5.0 mL) was added a solution of HCl in EtOAc (5.0 mL, 4 M) dropwise. At the end of addition, the mixture was stirred at rt for 8.0 hrs. After the reaction was completed, the mixture was concentrated in vacuo, and the residue was washed with EtOAc (10.0 mL) and then filtered to give the title compound (71.46 mg, 95%) as a pale yellow solid. The compound was characterized by the following spectroscopic data:

MS (ESI, pos.ion) m/z: 261.3 [M+2H]$^{2+}$.

Step 5) the Preparation of Compound 43-6

A suspension of compound 43-5 (107.4 mg, 0.181 mmol), compound 1-4-2 (95.2 mg, 0.543 mmol) and EDCI (139 mg, 0.725 mmol) in DCM (5.0 mL) was stirred at 0° C., then DIPEA (0.3 mL, 1.815 mmol) was added dropwise. At the end of addition, the mixture was stirred at rt for 3.0 hrs. After the reaction was completed, the mixture was diluted with DCM (20.0 mL). The resulting mixture was washed with NH$_4$Cl aqueous solution and brine, dried over anhydrous Na$_2$SO$_4$ and concentrated in vacuo. The residue was purified by a silica gel column chromatography (EtOAc) to give the title compound (143.5 mg, 95%) as a white solid. The compound was characterized by the following spectroscopic data:

MS (ESI, pos.ion) m/z: 835.5 [M+H]$^+$;

$^1$H NMR (400 MHz, CDCl$_3$) δ (ppm): 8.96 (br, 1H), 8.90 (br, 1H), 7.77-7.73 (m, 2H), 7.66-7.62 (m, 2H), 7.45 (s, 2H), 7.42-7.38 (m, 4H), 5.32-5.29 (br, br, 2H), 4.31-4.30 (m, 1H), 4.29-4.28 (m, 1H), 4.27-4.23 (m, 2H), 3.89-3.84 (m, 2H), 3.63 (s, 6H), 3.61-3.55 (m, 2H), 3.44-3.16 (m, 2H), 2.20-2.02 (m, 6H), 2.00-1.94 (m, 2H), 1.88-1.84 (m, 1H), 1.75-1.61 (m, 5H), 1.27-1.21 (m, 2H), 0.97, 0.95 (m, m, 6H), 0.91, 0.89 (m, m, 6H).

Example 44

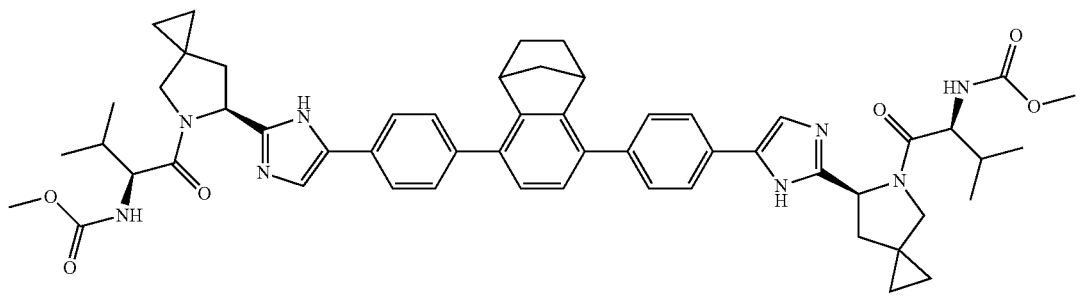

Synthetic Route:

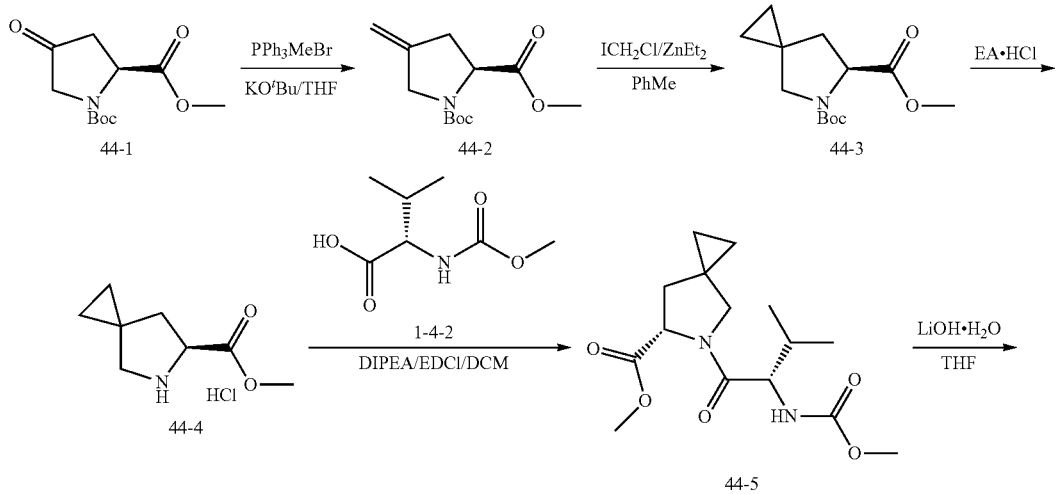

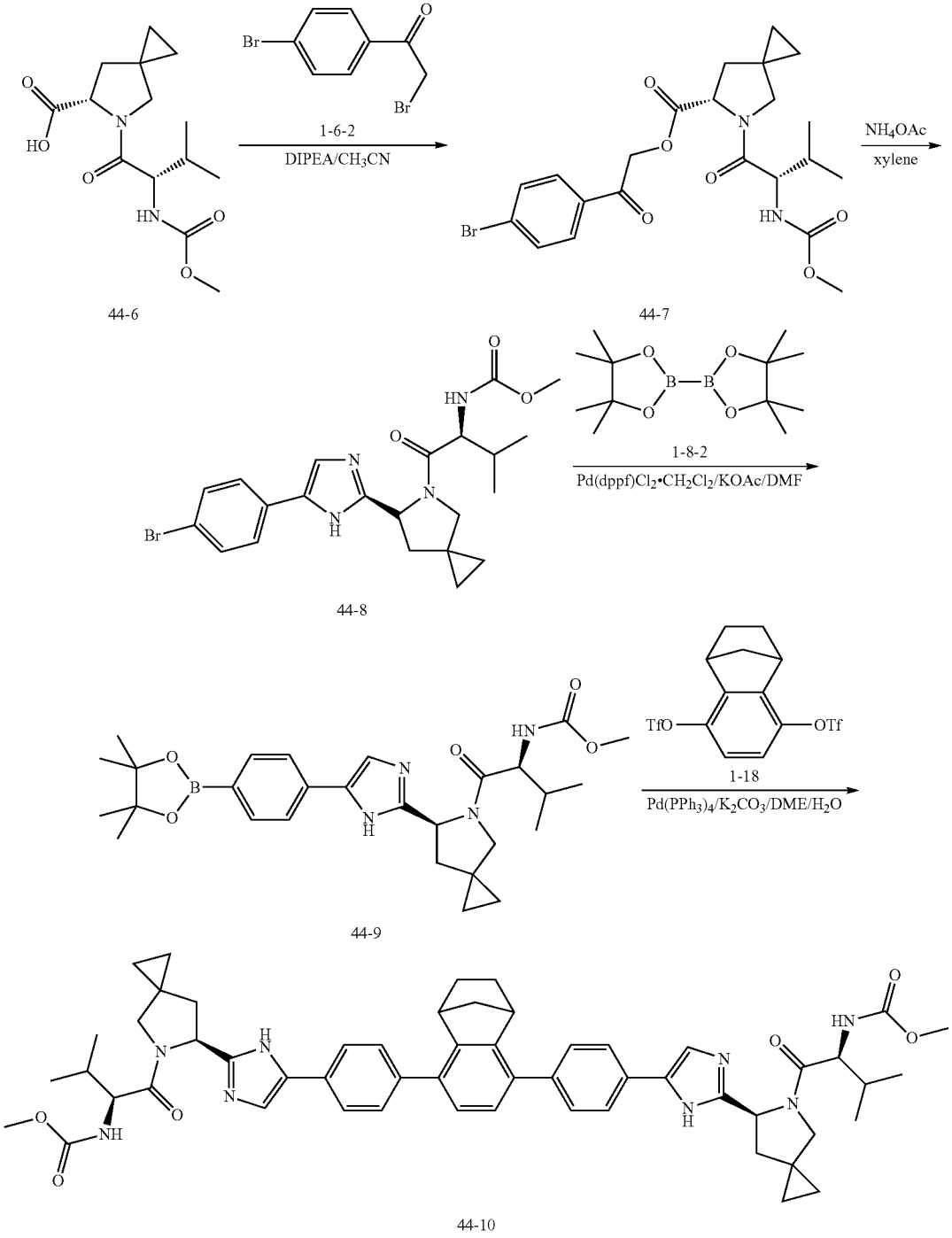

Step 1) the Preparation of Compound 44-2

To a suspension of PPh₃MeBr (5.05 g, 14.2 mmol) in THF (50.0 mL) was added potassium tert-butanolate (14.9 mL, 14.9 mmol, 1.0 M in THF) dropwise at −20° C. At the end of addition, the mixture was warmed to −5° C. and stirred for 30 mins, and then compound 44-1 (1.72 g, 7.07 mmol) was added. The mixture was stirred at rt for 3 hrs. After the reaction was completed, the mixture was quenched with ice-water (20.0 mL), and THF was removed. The aqueous layer was extracted with EtOAc (3×50 mL). The combined organic layers were washed with brine, dried over anhydrous $Na_2SO_4$ and concentrated in vacuo. The residue was purified by a silica gel column chromatography (PE/EtOAc (v/v)=5/1) to give the title compound 44-2 (1.07 g, 62.9%) as pale yellow oil. The compound was characterized by the following spectroscopic data:

MS (ESI, pos.ion) m/z: 242.12 [M+H]⁺;

$^1$H NMR (400 MHz, DMSO-$d_6$) δ (ppm): 5.01 (d, 2H, J=10.8 Hz), 4.36 (t, 1H, J=11.2 Hz), 3.95 (s, 2H), 3.64 (s, 3H), 3.01 (q, 1H, J=14.6 Hz), 2.57-2.50 (m, 1H), 1.38 (s, 9H).

Step 2) the Preparation of Compound 44-3

To a solution of diethylzinc (2.297 g, 18.60 mmol) in toluene (30.0 mL) was added chloroiodomethane (6.569 g, 37.24 mmol) dropwise at 0° C., the mixture was stirred at 0° C. for 45 mins, and then a solution of compound 44-2 (1.5 g, 6.22 mmol) in toluene (15.0 mL) was added. At the end of addition, the mixture was stirred at 0° C. for 18.0 hrs. After the reaction was completed, the reaction was quenched with saturated $NH_4Cl$ aqueous solution (20.0 mL), the aqueous layer was extracted with EtOAc (25 mL×3). The combined organic layers were dried over anhydrous $Na_2SO_4$ and concentrated in vacuo. The residue was purified by a silica gel column chromatography (PE/EtOAc (v/v)=10/1) to give the title compound 44-3 (0.58 g, 36.5%) as white oil. The compound was characterized by the following spectroscopic data:

MS (ESI, pos.ion) m/z: 156.2 [M-Boc]$^+$;
$^1$H NMR (400 MHz, CDCl$_3$) δ (ppm): 4.33-4.47 (m, 1H), 3.71 (s, 3H), 3.29-3.37 (m, 2H), 2.17-2.25 (m, 1H), 1.75-1.86 (m, 1H), 1.44, 1.40 (s, s, 9H), 0.50-0.62 (m, 4H).

Step 3) the Preparation of Compound 44-4

To a solution of compound 44-3 (0.69 g, 2.7 mmol) in EtOAc (6.0 mL) was added a solution of HCl in EtOAc (5.0 mL, 4 M) dropwise. At the end of addition, the mixture was stirred at rt for 8 hrs. After the reaction was completed, the mixture was concentrated in vacuo to give the title compound (0.5 g, 96.5%) as colorless oil. The compound was characterized by the following spectroscopic data:

MS (ESI, pos.ion) m/z: 156.2 [M+H]$^+$;
$^1$H NMR (400 MHz, CD$_3$OD) δ (ppm): 4.62-4.66 (m, 1H), 4.44-4.45 (m, 1H), 3.86 (s, 3H), 3.60-3.61 (m, 1H), 2.34-2.39 (m, 1H), 2.14-2.19 (m, 1H), 1.46-1.49 (m, 1H), 1.16-1.19 (m, 1H), 0.87-0.88 (m, 1H), 0.79-0.81 (m, 1H).

Step 4) the Preparation of Compound 44-5

A suspension of compound 44-4 (0.53 g, 2.77 mmol), compound 1-4-2 (0.729 g, 4.16 mmol) and EDCI (1.063 g, 5.55 mmol) in DCM (10.0 mL) was stirred at 0° C., and then DIPEA (2.4 mL, 14.52 mmol) was added dropwise. At the end of addition, the mixture was stirred at rt for 3.0 hrs. After the reaction was completed, the mixture was diluted with DCM (20.0 mL), washed with $NH_4Cl$ aqueous solution and brine, dried over anhydrous $Na_2SO_4$ and concentrated in vacuo. The residue was purified by a silica gel column chromatography (PE/EtOAc (v/v)=1/1) to give the title compound (0.6067 g, 70.2%) as white liquid. The compound was characterized by the following spectroscopic data:

MS (ESI, pos.ion) m/z: 313.2 [M+H]$^+$;
$^1$H NMR (400 MHz, CDCl$_3$) δ (ppm): 5.42-5.44 (br, 1H), 4.68-4.71 (m, 1H), 4.20-4.29 (m, 1H), 3.73 (s, 3H), 3.69-3.72 (m, 1H), 3.67 (s, 3H), 3.54-3.59 (m, 1H), 2.15-2.20 (m, 1H), 2.01-2.06 (m, 1H), 1.90-1.95 (m, 1H), 0.93-1.05 (m, 6H), 0.61-0.66 (m, 4H).

Step 5) the Preparation of Compound 44-6

To a solution of compound 44-5 (0.20 g, 0.64 mmol) in THF (5.0 mL) was added lithium hydroxide aqueous solution (0.1346 g, 3.20 mmol, 5.0 mL) at 0° C. At the end of addition, the mixture was stirred at 40° C. for 12 hrs. After the reaction was completed, the solvent THF was removed and 10 mL of water was added. The resulting mixture was extracted with EtOAc (25 mL×3), and the aqueous layer was adjusted to pH 1 with hydrochloric acid (10%), and then extracted with EtOAc (25 mL×3). The combined organic layers were dried over anhydrous $Na_2SO_4$ and concentrated in vacuo to give the title compound (0.1581 g, 82.8%) as a white solid. The compound was characterized by the following spectroscopic data:

MS (ESI, pos.ion) m/z: 299.2 [M+H]$^+$;
$^1$H NMR (400 MHz, CDCl$_3$) δ (ppm): 7.06 (br, 1H), 5.76 (br, 1H), 4.69-4.73 (m, 1H), 4.18-4.23 (m, 1H), 3.79 (d, 1H, J=9.7 Hz), 3.66 (s, 3H), 3.49 (d, 1H, J=9.7 Hz), 2.18-2.26 (m, 1H), 1.93-2.07 (m, 2H), 0.94-1.00 (m, 6H), 0.64-0.68 (m, 4H).

Step 6) the Preparation of Compound 44-7

A solution of compound 1-6-2 (308 mg, 1.1074 mmol), compound 44-6 (300 mg, 1.0067 mmol) in MeCN (30.0 mL) was stirred at 0° C. under $N_2$, and then DIPEA (0.21 mL, 1.27 mmol) was added dropwise. At the end of addition, the mixture was stirred at rt for 2 hrs. After the reaction was completed, 20 mL of water was added and MeCN was removed. The resulting mixture was dissolved in EtOAc (30.0 mL), washed with $NH_4Cl$ aqueous solution and brine, dried over anhydrous $Na_2SO_4$ and concentrated in vacuo. The residue was purified by a silica gel column chromatography (PE/EtOAc (v/v)=1/1) to give the title compound (331.7 mg, 66.7%) as a pale yellow solid. The compound was characterized by the following spectroscopic data:

MS (ESI, pos.ion) m/z: 495.3 [M+H]$^+$;
$^1$H NMR (400 MHz, CDCl$_3$) δ (ppm): 7.82-7.78 (m, 2H), 7.67-7.64 (m, 2H), 5.32, 5.29 (br, br, 1H), 5.31 (s, 2H), 4.72-4.70 (m, 1H), 4.35-4.30 (m, 1H), 3.67 (s, 3H), 3.61-3.59 (m, 1H), 3.55-3.49 (m, 1H), 2.20-2.07 (m, 2H), 1.83-1.76 (m, 1H), 0.97, 0.96 (m, m, 3H), 0.91, 0.89 (m, m, 3H), 0.52-0.39 (m, 4H).

Step 7) the Preparation of Compound 44-8

To a solution of compound 44-7 (331.7 mg, 0.6714 mmol) in xylene (10.0 mL) was added $NH_4OAc$ (1.035 g, 13.43 mmol), the mixture was stirred at 120° C. for 3 hrs. After the reaction was completed, the mixture was cooled to rt and 20 mL of water was added. The resulting mixture was extracted with EtOAc (20.0 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound (187.6 mg, 58.94%) as a yellow solid. The compound was characterized by the following spectroscopic data:

MS (ESI, pos.ion) m/z: 475.3 [M+H]$^+$;
$^1$H NMR (400 MHz, CDCl$_3$) δ (ppm): 7.58 (s, 1H), 7.45-7.41 (m, 2H), 7.29-7.26 (m, 2H), 5.46, 5.44 (br, br, 1H), 4.93-4.89 (m, 1H), 4.41-4.37 (m, 1H), 3.71-3.67 (m, 1H), 3.67 (s, 3H), 3.50-3.44 (m, 1H), 2.39-2.32 (m, 1H), 2.23-2.11 (m, 1H), 2.05-1.97 (m, 1H), 0.97, 0.95 (m, m, 3H), 0.91, 0.89 (m, m, 3H), 0.52-0.39 (m, 4H).

Step 8) the Preparation of Compound 44-9

To a mixture of compound 44-8 (187.6 mg, 0.3957 mmol), compound 1-8-2 (150.75 mg, 0.5935 mmol), Pd(dppf)Cl$_2$.CH$_2$Cl$_2$ (33 mg, 0.03956 mmol) and KOAc (116.45 mg, 1.187 mmol) was added DMF (10.0 mL) via syringe under $N_2$, the mixture was stirred at 90° C. for 3 hrs. After the reaction was completed, the mixture was cooled to rt and 50 mL of water was added. The resulting mixture was extracted with EtOAc (40.0 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound (165.34 mg, 80%) as a beige solid. The compound was characterized by the following spectroscopic data:

MS (ESI, pos.ion) m/z: 523.3 [M+H]$^+$;
$^1$H NMR (400 MHz, CDCl$_3$) δ (ppm): 7.64-7.57 (m, 4H), 7.21 (s, 1H), 5.46, 5.44 (br, br, 1H), 4.93-4.89 (m, 1H), 4.42-4.37 (m, 1H), 3.71-3.67 (m, 1H), 3.66 (s, 3H), 3.50-3.44 (m, 1H), 2.39-2.32 (m, 1H), 2.23-2.11 (m, 1H), 2.05-1.97 (m, 1H), 1.35 (m, 6H), 1.32 (m, 6H), 0.97, 0.95 (m, m, 3H), 0.91, 0.89 (m, m, 3H), 0.55-0.42 (m, 4H).

Step 9) the Preparation of Compound 44-10

To a mixture of compound 1-18 (230 mg, 0.522 mmol), compound 44-9 (572.5 mg, 1.096 mmol), Pd(PPh$_3$)$_4$ (60.29 mg, 0.0522 mmol) and K$_2$CO$_3$ (216 mg, 1.566 mmol) were added DME (6.0 mL) and water (1.5 mL) via syringe, the mixture was stirred at 90° C. under $N_2$ for 3 hrs. After the reaction was completed, the mixture was cooled to rt and diluted with EtOAc (30.0 mL). The combined organic layers were washed with water (10 mL×3) and brine, dried over anhydrous Na$_2$SO$_4$ and concentrated in vacuo. The residue was purified by a silica gel column chromatography (DCM/EtOH (v/v)=50/1) to give the title compound (243.4 mg, 50%) as a pale yellow solid. The compound was characterized by the following spectroscopic data:

MS (ESI, pos.ion) m/z: 467.5 [M+2H]$^{2+}$;

$^1$H NMR (400 MHz, CDCl$_3$) δ (ppm): 7.62-7.59 (m, 4H), 7.57 (s, 2H), 7.56-7.52 (m, 6H), 5.46, 5.44 (br, br, 2H), 4.93-4.89 (m, 2H), 4.42-4.37 (m, 2H), 3.89-3.84 (m, 2H), 3.71-3.67 (m, 2H), 3.66 (s, 6H), 3.50-3.44 (m, 2H), 2.39-2.32 (m, 2H), 2.23-2.11 (m, 2H), 2.05-1.97 (m, 4H), 1.88-1.84 (m, 1H), 1.65-1.61 (m, 1H), 1.28-1.21 (m, 2H), 0.97, 0.95 (m, m, 6H), 0.90, 0.89 (m, m, 6H), 0.55-0.42 (m, 8H).

Example 45

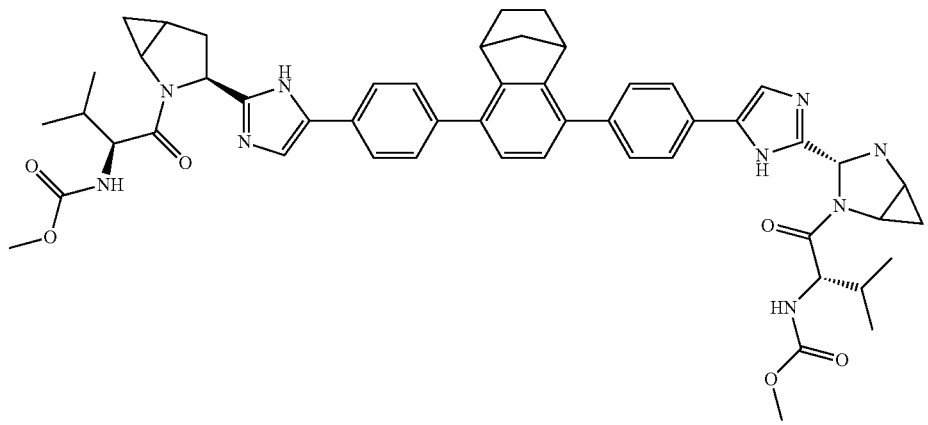 [SMILES: COC(=O)N[C@H](C(=O)N1C2CC2C[C@H]1c1ncc(-c2ccc(-c3ccc(-c4ccc(-c5cnc([C@@H]6NC7CC7N6C(=O)[C@@H](NC(=O)OC)C(C)C)[nH]5)cc4)c4c3C3CCC4C3)cc2)[nH]1)C(C)C]

Synthetic Route:

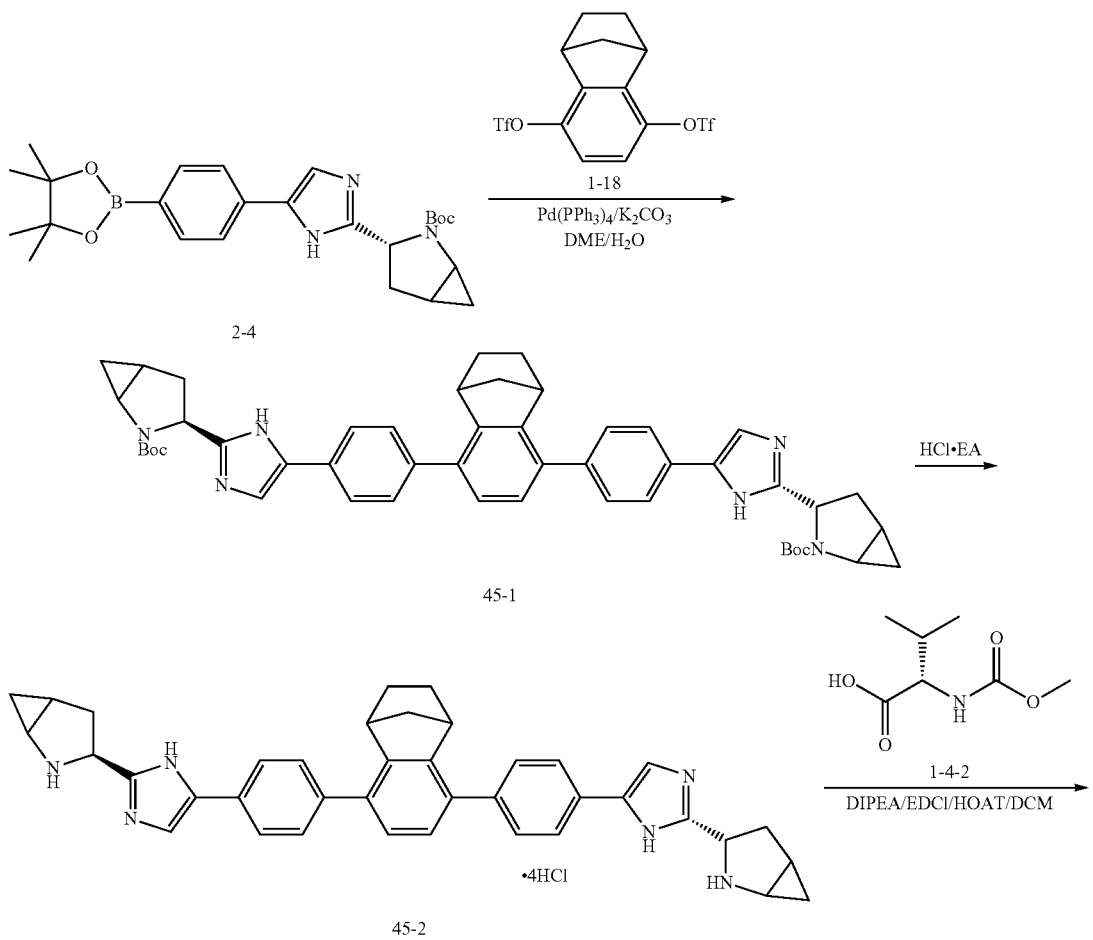

-continued

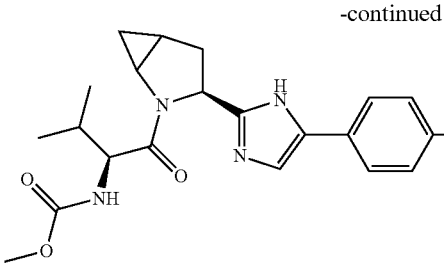
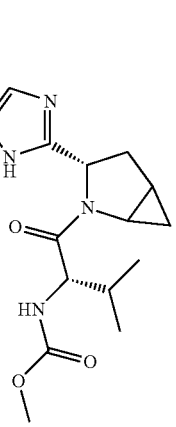

45-3

Step 1) the Preparation of Compound 45-1

A suspension of compound 1-18 (1.5 g, 3.4 mmol), compound 2-4 (3.33 g, 7.38 mmol), Pd(PPh$_3$)$_4$ (196.7 mg, 0.17 mmol) and K$_2$CO$_3$ (1.412 g, 10.22 mmol) in mixed solvents of DME and H$_2$O (15.0 mL, v/v=4/1) was stirred at 90° C. under N$_2$ for 3 hrs. After the reaction was completed, the mixture was cooled to rt and diluted with EtOAc (100 mL). The combined organic layers were washed with water (50.0 mL×3) and brine, dried over anhydrous Na$_2$SO$_4$ and concentrated in vacuo. The residue was purified by a silica gel column chromatography (DCM/EtOH (v/v)=60/1) to give the title compound (4.61 g, 60%) as a pale yellow solid. The compound was characterized by the following spectroscopic data:

MS (ESI, pos.ion) m/z: 791.5 [M+H]$^+$;
$^1$H NMR (400 MHz, CDCl$_3$) δ (ppm): 7.62-7.59 (m, 4H), 7.56-7.52 (m, 6H), 7.47 (s, 2H), 4.75-4.72 (m, 2H), 3.89-3.84 (m, 2H), 3.29-3.23 (m, 2H), 2.42-2.35 (m, 2H), 2.01-1.95 (m, 2H), 1.94-1.92 (m, 2H), 1.88-1.84 (m, 1H), 1.65-1.61 (m, 1H), 1.46 (s, 9H), 1.43 (s, 9H), 1.42-1.34 (m, 4H), 1.28-1.21 (m, 2H), 1.02-0.95 (m, 2H).

Step 2) the Preparation of Compound 45-2

To a solution of compound 45-1 (773 mg, 0.978 mmol) in EtOAc (5.0 mL) was added a solution of HCl in EtOAc (5.0 mL, 4 M) dropwise. At the end of addition, the mixture was stirred at rt for 8 hrs. After the reaction was completed, the mixture was concentrated in vacuo. The residue was washed with EtOAc (20.0 mL) and filtered to give the title compound (720 mg, 100%) as pale yellow powder. The compound was characterized by the following spectroscopic data:

MS (ESI, pos.ion) m/z: 591.5 [M+H]$^+$.

Step 3) the Preparation of Compound 45-3

A suspension of compound 45-2 (496.3 mg, 0.674 mmol), compound 1-4-2 (235.8 mg, 1.35 mmol), EDCI (271.3 mg, 1.415 mmol) and HOAT (137.58 mg, 1.01 mmol) in DCM (20.0 mL) was stirred at 0° C., then DIPEA (0.93 mL, 5.63 mmol) was added dropwise. At the end of addition, the mixture was stirred at rt for 3 hrs. After the reaction was completed, the mixture was diluted with DCM (30.0 mL), washed with NH$_4$Cl aqueous solution and brine, dried over anhydrous Na$_2$SO$_4$ and concentrated in vacuo. The residue was purified by a silica gel column chromatography (DCM/MeOH (v/v)= 60/1) to give the title compound (365.7 mg, 60%) as a white solid. The compound was characterized by the following spectroscopic data:

MS (ESI, pos.ion) m/z: 453.5 [M+2H]$^{2+}$;
$^1$H NMR (400 MHz, CDCl$_3$) δ (ppm): 7.62-7.59 (m, 6H), 7.56-7.52 (m, 6H), 5.32, 5.29 (br, br, 2H), 4.89-4.85 (m, 2H), 4.09-4.04 (m, 2H), 3.89-3.84 (m, 2H), 3.63 (s, 6H), 3.45-3.38 (m, 2H), 2.46-2.39 (m, 2H), 2.22-2.09 (m, 2H), 2.00-1.94 (m, 4H), 1.88-1.84 (m, 1H), 1.65-1.61 (m, 1H), 1.43-1.36 (m, 2H), 1.28-1.21 (m, 2H), 0.97, 0.95 (m, m, 6H), 0.94-0.92 (m, 4H), 0.91, 0.89 (m, m, 6H).

Example 46

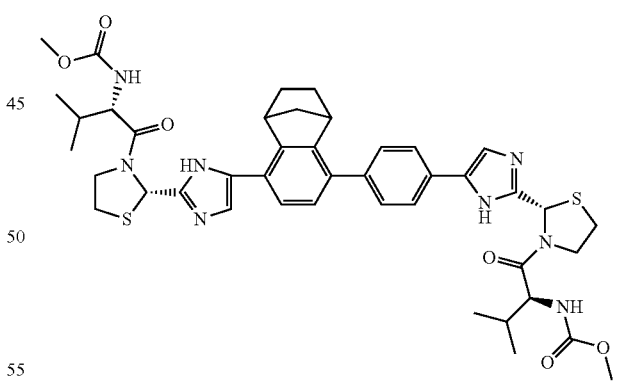

Synthetic Route:

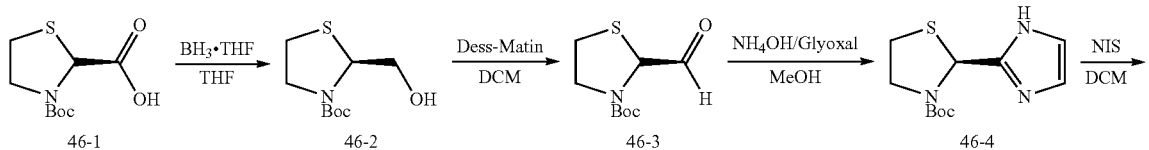

493 494
-continued
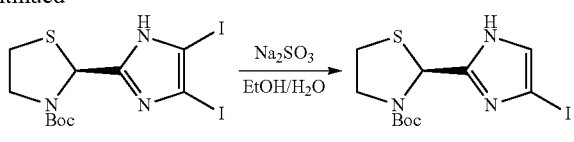
46-5 46-6
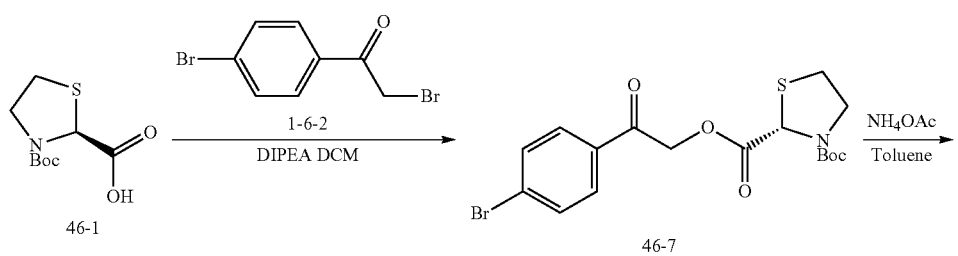
46-1 46-7
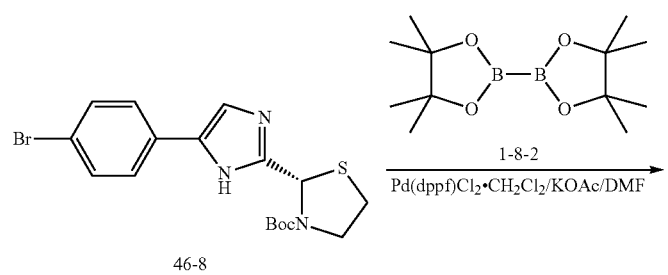
46-8
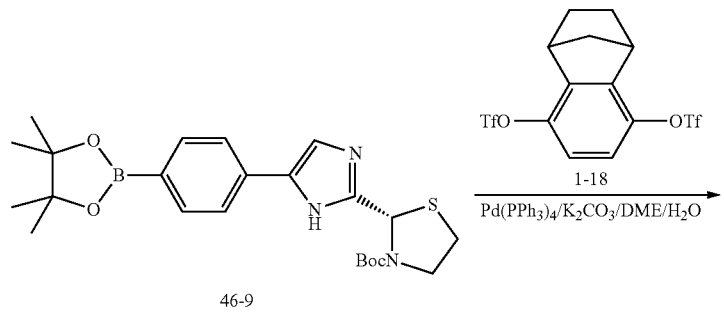
46-9
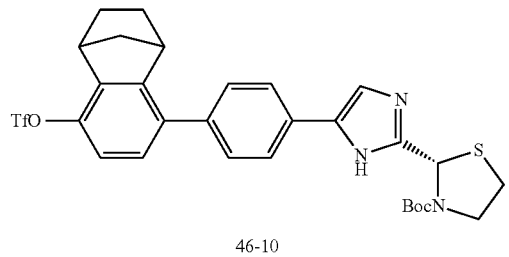
46-10
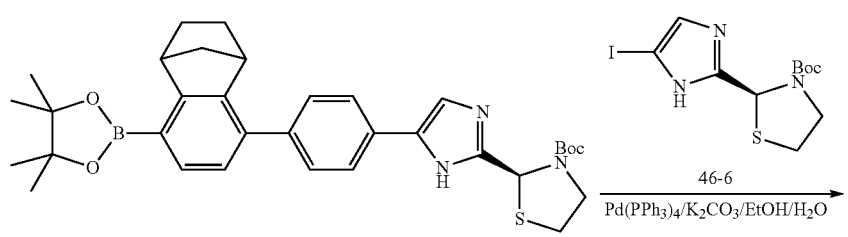
46-11
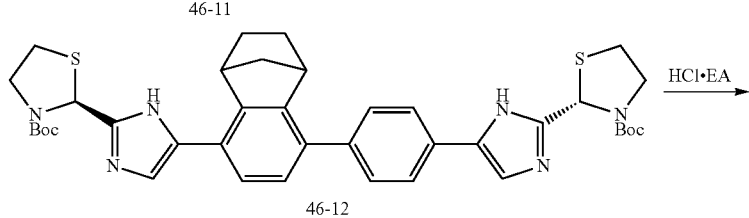
46-12

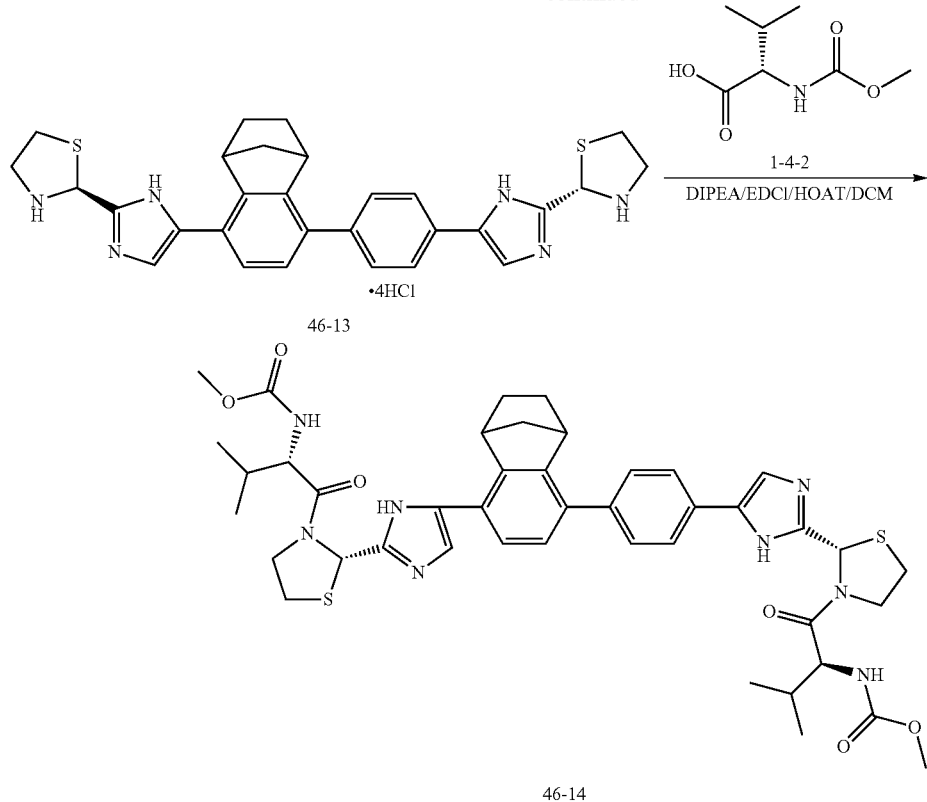

Step 1) the Preparation of Compound 46-2

To a solution of compound 46-1 (10.86 g, 46.6 mmol) in THF (100.0 mL) was added diborane (100.0 mL, 1M in THF) dropwise at 0° C. At the end of addition, the mixture was stirred at 0° C. under $N_2$ for 3 hrs. After the reaction was completed, the mixture was quenched with MeOH (80.0 mL) and concentrated in vacuo. The residue was purified by a silica gel column chromatography (PE/EtOAc (v/v)=3/2) to give the title compound 46-2 (7.65 g, 75%) as colorless oil. The compound was characterized by the following spectroscopic data:

$^1$H NMR (400 MHz, CDCl$_3$) δ (ppm): 5.16-5.12 (m, 1H), 3.91-3.84 (m, 1H), 3.76-3.72 (m, 1H), 3.63-3.58 (m, 1H), 3.56-3.48 (m, 1H), 3.17-3.10 (m, 1H), 3.00 (br, 1H), 2.90-2.83 (m, 1H), 1.43 (s, 9H).

Step 2) the Preparation of Compound 46-3

To a solution of compound 46-2 (7.62 g, 34.8 mmol) in DCM (250 mL) was added Dess-Martin periodinane (20.7 g, 48.8 mmol) in a portionwise manner at 0° C. At the end of addition, the mixture was stirred at rt for 2 hrs. After the reaction was completed, 250 mL of water was added to the mixture, and then the resulting mixture was filtered. After the layers were partitioned, the organic layers were washed with brine, dried over anhydrous Na$_2$SO$_4$ and concentrated in vacuo. The residue was purified by a silica gel column chromatography (PE/EtOAc (v/v)=3/2) to give the title compound (3.83 g, 50.7%) as colorless oil. The compound was characterized by the following spectroscopic data:

$^1$H NMR (400 MHz, CDCl$_3$) δ (ppm): 8.67-8.65 (m, 1H), 5.01-4.97 (m, 1H), 4.01-3.94 (m, 1H), 3.49-3.41 (m, 1H), 3.11-3.03 (m, 1H), 2.77-2.69 (m, 1H), 1.42 (s, 9H).

Step 3) the Preparation of Compound 46-4

To a solution of compound 46-3 (3.82 g, 17.6 mmol) and ammonia (13.0 mL) in MeOH (30.0 mL) was added glyoxal (8.0 mL, 40% in water) dropwsie at 0° C. At the end of addition, the mixture was stirred at rt overnight. After the reaction was completed, the mixture was concentrated in vacuo. The residue was purified by a silica gel column chromatography (PE/EtOAc (v/v)=3/2) to give the title compound (2.14 g, 47.6%) as a white solid. The compound was characterized by the following spectroscopic data:

MS (ESI, pos.ion) m/z: 256.5 [M+H]$^+$;

$^1$H NMR (400 MHz, CDCl$_3$) δ (ppm): 7.16 (s, 2H), 6.46-6.43 (m, 1H), 4.05-3.99 (m, 1H), 3.47-3.40 (m, 1H), 3.31-3.23 (m, 1H), 2.92-2.85 (m, 1H), 1.41 (s, 9H).

Step 4) the Preparation of Compound 46-5

To a solution of compound 46-4 (2.14 g, 8.4 mmol) in DCM (60.0 mL) was added N-iodosuccinimide (3.8 g, 16.8 mmol) at 0° C. in a portionwise manner. At the end of addition, the mixture was stirred at 0° C. for 1.5 hrs. After the reaction was completed, the mixture was washed with brine, dried over anhydrous Na$_2$SO$_4$ and concentrated in vacuo. The residue was purified by a silica gel column chromatography (PE/EtOAc (v/v)=3/2) to give the title compound (2.68 g, 63.1%) as a white solid. The compound was characterized by the following spectroscopic data:

MS (ESI, pos.ion) m/z: 507.5 [M+H]$^+$;

$^1$H NMR (400 MHz, CDCl$_3$) δ (ppm): 5.97-5.95 (m, 1H), 4.15-4.08 (m, 1H), 3.46-3.39 (m, 1H), 3.38-3.31 (m, 1H), 3.00-2.92 (m, 1H), 1.41 (s, 9H).

Step 5) the Preparation of Compound 46-6

To a suspension of compound 46-5 (1.66 g, 3.27 mmol) in mixed solvents of ethanol and water (50 mL, v/v=3/7) was added Na$_2$SO$_3$ (3.7 g, 29.0 mmol). At the end of addition, the mixture was refluxed for 17 hrs. After the reaction was completed, the solvent ethanol was removed, and 20 mL of water was added to the mixture. The resulting mixture was extracted with EtOAc (30 mL×3), and then the combined organic layers were dried over anhydrous $Na_2SO_4$ and concentrated in vacuo. The residue was purified by a silica gel column chromatography (PE/EtOAc (v/v)=3/2) to give the title compound (1.04 g, 84%) as a white solid. The compound was characterized by the following spectroscopic data:

MS (ESI, pos.ion) m/z: 382.5 $[M+H]^+$;

$^1$H NMR (400 MHz, $CDCl_3$) δ (ppm): 7.19 (s, 1H), 6.71-6.68 (m, 1H), 4.12-4.05 (m, 1H), 3.49-3.42 (m, 1H), 3.34-3.27 (m, 1H), 2.96-2.88 (m, 1H), 1.41 (s, 9H).

Step 6) the Preparation of Compound 46-7

To a solution of compound 1-6-2 (30 g, 107.9 mmol) and compound 46-1 (27.66 g, 118.7 mmol) in MeCN (250 mL) was added DIPEA (21.4 mL, 129.48 mmol) dropwise at 0° C. At the end of addition, the mixture was stirred at rt for 3 hrs. After the reaction was completed, the reaction was quenched with water (100 mL). The resulting mixture was extracted with EtOAc (100 mL×3), and then the combined organic layers were dried over $Na_2SO_4$ and concentrated in vacuo. The residue was purified by a silica gel column chromatography (PE/EtOAc (v/v)=10/1) to give the title compound (42.12 g, 91%) as a white solid. The compound was characterized by the following spectroscopic data:

MS (ESI, pos.ion) m/z: 430.5 $[M+H]^+$;

$^1$H NMR (400 MHz, $CDCl_3$) δ (ppm): 7.82-7.78 (m, 2H), 7.67-7.64 (m, 2H), 5.55-5.52 (m, 1H), 5.29 (s, 2H), 4.11-4.04 (m, 1H), 3.73-3.66 (m, 1H), 3.19-3.12 (m, 1H), 2.93-2.86 (m, 1H), 1.43 (s, 9H).

Step 7) the Preparation of Compound 46-8

A mixture of compound 46-7 (15.62 g, 36.4 mmol) and ammonium acetate (42.0 g, 54.6 mmol) in toluene (150.0 mL) was stirred at 120° C. for 5 hrs. After the reaction was completed, the mixture was cooled to rt and quenched with water (100 mL). The resulting mixture was extracted with EtOAc (100 mL×3), and then the combined organic layers were dried over anhydrous $Na_2SO_4$ and concentrated in vacuo. The residue was purified by a silica gel column chromatography (PE/EtOAc (v/v)=6/1) to give the title compound (12.65 g, 85%). The compound was characterized by the following spectroscopic data:

MS (ESI, pos.ion) m/z: 410.5 $[M+H]^+$;

$^1$H NMR (400 MHz, $CDCl_3$) δ (ppm): 7.64 (s, 1H), 7.45-7.41 (m, 2H), 7.29-7.26 (m, 2H), 6.54-6.51 (m, 1H), 4.08-4.01 (m, 1H), 3.44-3.37 (m, 1H), 3.30-3.22 (m, 1H), 2.91-2.84 (m, 1H), 1.42 (s, 9H).

Step 8) the Preparation of Compound 46-9

A mixture of compound 46-8 (4.18 g, 10.23 mmol), compound 1-8-2 (2.86 g, 11.25 mmol), $Pd(dppf)Cl_2.CH_2Cl_2$ (418 mg, 0.51 mmol) and KOAc (2.51 g, 25.57 mmol) in DMF (40.0 mL) was stirred at 90° C. under $N_2$. After the reaction was completed, the mixture was cooled to rt, diluted with EtOAc (250 mL) and filtered through a celite pad. The filtrate was washed with water (100 mL×3) and brine, dried over anhydrous $Na_2SO_4$ and concentrated in vacuo. The residue was purified by a silica gel column chromatography (PE/EtOAc (v/v)=2/1) to give the title compound (3.74 g, 80%). The compound was characterized by the following spectroscopic data:

$^1$H NMR (400 MHz, $CDCl_3$) δ (ppm): 7.63-7.57 (m, 4H), 7.32 (s, 1H), 6.54-6.51 (m, 1H), 4.08-4.01 (m, 1H), 3.44-3.37 (m, 1H), 3.30-3.22 (m, 1H), 2.91-2.84 (m, 1H), 1.42 (s, 9H), 1.35 (m, 6H), 1.32 (m, 6H).

Step 9) the Preparation of Compound 46-10

To a mixture of compound 46-9 (1.19 g, 2.62 mmol), compound 1-18 (1.2 g, 2.62 mmol), $Pd(PPh_3)_4$ (120 mg, 0.1 mmol) and KF (0.30 g, 5.24 mmol) were added DME (12.0 mL) and pure water (3.0 mL) via syringe, and then the mixture was stirred at 90° C. under $N_2$ for 2 hrs. After the reaction was completed, the mixture was cooled to rt and diluted with EtOAc (60.0 mL). The resulting mixture was washed with water (20 mL×3) and brine, dried over anhydrous $Na_2SO_4$ and concentrated in vacuo. The residue was purified by a silica gel column chromatography (DCM/EtOH (v/v)=100/1) to give the title compound (1.0 g, 62%) as a white solid. The compound was characterized by the following spectroscopic data:

MS (ESI, pos.ion) m/z: 622.3 $[M+H]^+$;

$^1$H NMR (400 MHz, $CDCl_3$) δ (ppm): 7.64-7.60 (m, 3H), 7.52-7.48 (m, 2H), 7.25, 7.23 (s, s, 1H), 7.06, 7.04 (s, s, 1H), 6.54-6.51 (m, 1H), 4.08-4.01 (m, 1H), 3.60-3.57 (m, 1H), 3.52-3.49 (m, 1H), 3.44-3.37 (m, 1H), 3.30-3.22 (m, 1H), 2.91-2.84 (m, 1H), 2.07-2.01 (m, 1H), 1.98-1.92 (m, 1H), 1.86-1.82 (m, 1H), 1.63-1.59 (m, 1H), 1.42 (s, 9H), 1.34-1.28 (m, 1H), 1.25-1.19 (m, 1H).

Step 10) the Preparation of Compound 46-11

A mixture of compound 46-10 (1.0 g, 1.61 mmol), compound 1-8-2 (0.45 g, 10.7 mmol), $Pd(dppf)Cl_2.CH_2Cl_2$ (80 mg, 0.096 mmol) and KOAc (0.4 g, 4.02 mmol) in DMF (10.0 mL) was stirred at 120° C. under $N_2$ for 4 hrs. After the reaction was completed, the mixture was cooled to rt, diluted with EtOAc (40.0 mL) and filtered through a celite pad. The filtrate was washed with water (20 mL×3) and brine, dried over anhydrous $Na_2SO_4$ and concentrated in vacuo. The residue was purified by a silica gel column chromatography (PE/EtOAc (v/v)=3/1) to give the title compound (0.7 g, 73%) as a pale yellow solid. The compound was characterized by the following spectroscopic data:

MS (ESI, pos.ion) m/z: 600.4 $[M+H]^+$;

$^1$H NMR (400 MHz, $CDCl_3$) δ (ppm): 7.77 (s, s, 1H), 7.64-7.60 (m, 3H), 7.56-7.53 (m, 2H), 7.41, 7.39 (s, s, 1H), 6.54-6.51 (m, 1H), 4.08-4.01 (m, 1H), 3.82-3.79 (m, 1H), 3.58-3.55 (m, 1H), 3.44-3.37 (m, 1H), 3.30-3.22 (m, 1H), 2.91-2.84 (m, 1H), 1.96-1.90 (m, 1H), 1.84-1.78 (m, 2H), 1.61-1.57 (m, 1H), 1.42 (s, 9H), 1.32 (m, 6H), 1.29 (m, 6H), 1.23-1.17 (m, 1H), 1.11-1.05 (m, 1H).

Step 11) the Preparation of Compound 46-12

To a mixture of compound 46-6 (0.17 g, 0.446 mmol), compound 46-11 (0.25 g, 0.42 mmol), $Pd(PPh_3)_4$ (25 mg, 0.02 mmol) and $K_2CO_3$ (0.17 g, 1.27 mmol) were added EtOH (6.0 mL) and pure water (1.0 mL) via syringe, the mixture was stirred at 90° C. under $N_2$ for 2 hrs. After the reaction was completed, the mixture was concentrated in vacuo. The residue was dissolved in EtOAc (20.0 mL). The organic layers were washed with brine, dried over anhydrous $Na_2SO_4$ and concentrated in vacuo. The residue was purified by a silica gel column chromatography (DCM/EtOH (v/v)=50/1) to give the title compound (370 mg, 95%) as a pale yellow solid. The compound was characterized by the following spectroscopic data:

MS (ESI, pos.ion) m/z: 727.85 $[M+H]^+$;

$^1$H NMR (400 MHz, $CDCl_3$) δ (ppm): 7.74 (s, 1H), 7.64-7.60 (m, 3H), 7.56-7.52 (m, 2H), 7.48, 7.46 (s, s, 1H), 7.34, 7.32 (s, s, 1H), 6.54-6.51 (m, 1H), 6.08-6.06 (m, 1H), 4.08-4.01 (m, 2H), 3.87-3.81 (m, 2H), 3.44-3.37 (m, 2H), 3.30-3.22 (m, 2H), 2.91-2.84 (m, 2H), 2.03-1.93 (m, 2H), 1.91-1.87 (m, 1H), 1.68-1.64 (m, 1H), 1.42 (s, 9H), 1.41 (s, 9H), 1.30-1.20 (m, 2H).

Step 12) the Preparation of Compound 46-13

To a solution of compound 46-12 (0.37 g, 0.51 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (20 mL), and then filtered to give the title compound (0.2 g, 60%) as pale yellow powder. The compound was characterized by the following spectroscopic data:

MS (ESI, pos.ion) m/z: 527.85 [M+H]$^+$.

Step 13) the Preparation of Compound 46-14

To a suspension of compound 46-13 (195 mg, 0.29 mmol), compound 1-4-2 (110 mg, 0.65 mmol), EDCI (120 mg, 0.65 mmol) and HOAT (80 mg, 0.59 mmol) in DCM (5.0 mL) was added DIPEA (0.6 mL, 3.63 mmol) dropwise at 0° C. At the end of addition, the mixture was stirred at rt for 3 hrs. After the reaction was completed, the mixture was diluted with DCM (20.0 mL), and then the resulting mixture was washed with NH$_4$Cl aqueous solution and brine, dried over Na$_2$SO$_4$ and concentrated in vacuo. The residue was purified by a silica gel column chromatography (DCM/MeOH (v/v)=40/1) to give the title compound (195 mg, 80%) as a white solid. The compound was characterized by the following spectroscopic data:

MS (ESI, pos.ion) m/z: 841.96 [M+H]$^+$;

$^1$H NMR (400 MHz, CDCl$_3$) δ (ppm): 7.65 (s, 1H), 7.64 (s, 1H), 7.63-7.60 (m, 2H), 7.56-7.52 (m, 2H), 7.48, 7.46 (s, s, 1H), 7.34, 7.32 (s, s, 1H), 6.29-6.26 (m, 1H), 6.25-6.23 (m, 1H), 5.56, 5.55 (br, br, 1H), 5.32, 5.29 (br, br, 1H), 4.43-4.30 (m, 4H), 3.87-3.79 (m, 4H), 3.65 (s, 3H), 3.63 (s, 3H), 3.59-3.53 (m, 2H), 3.25-3.17 (m, 2H), 2.31-2.14 (m, 2H), 2.03-1.93 (m, 2H), 1.91-1.87 (m, 1H), 1.68-1.64 (m, 1H), 1.30-1.20 (m, 2H), 1.02-0.89 (m, 12H).

Example 47

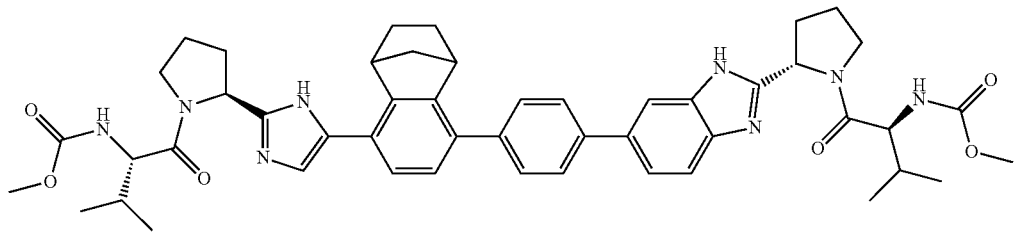

Synthetic Route:

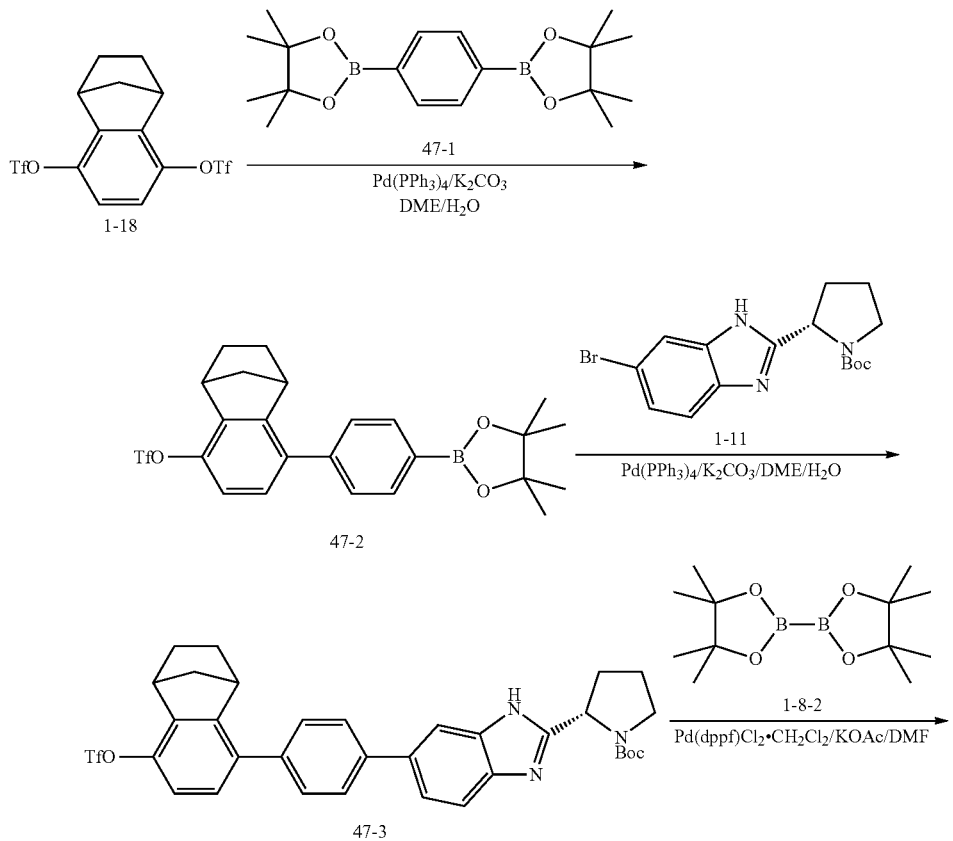

-continued

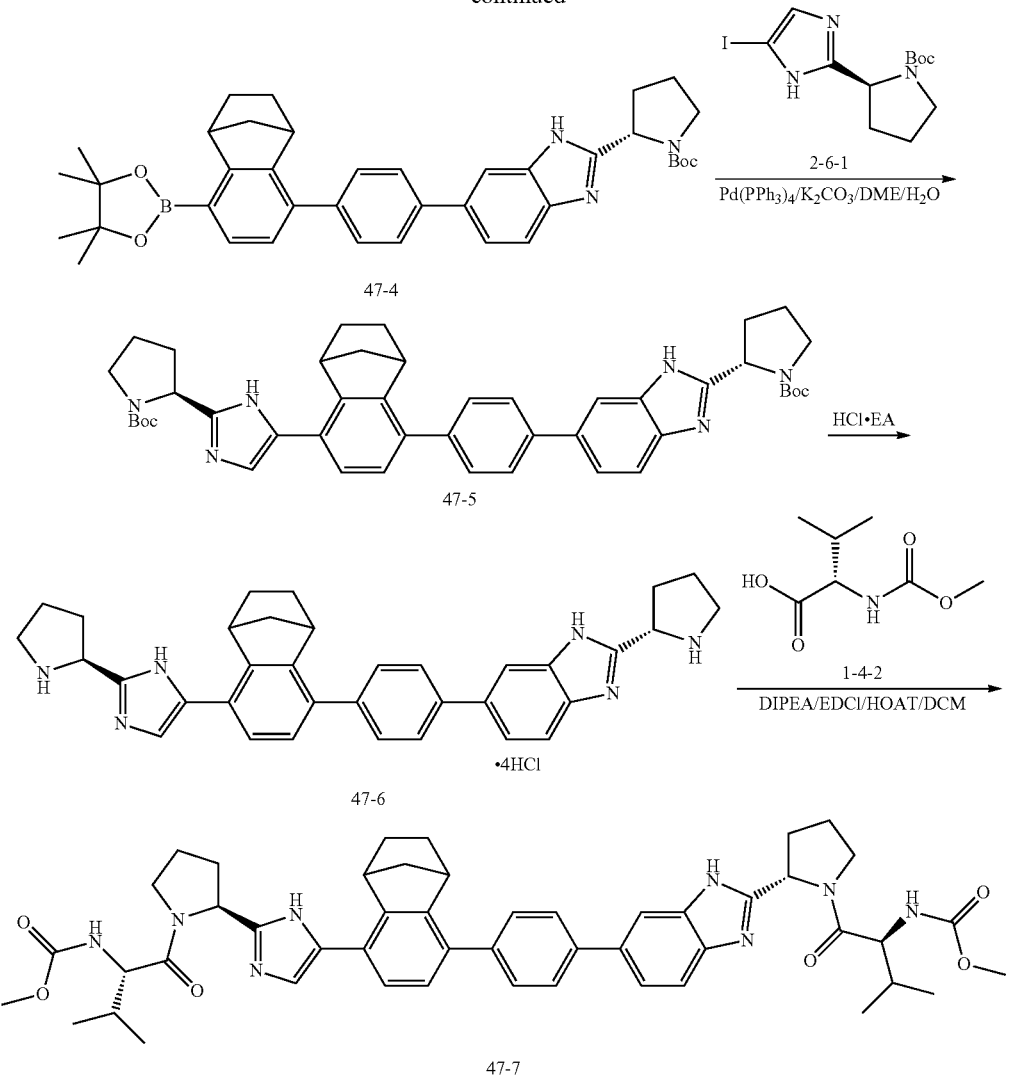

Step 1) the Preparation of Compound 47-2

A suspension of compound 1-18 (1.5 g, 3.4 mmol), compound 47-1 (1.12 g, 3.4 mmol), Pd(PPh$_3$)$_4$ (196.7 mg, 0.17 mmol) and K$_2$CO$_3$ (1.412 g, 10.22 mmol) in mixed solvents of DME and H$_2$O (15 mL, v/v=4/1) was stirred at 90° C. under N$_2$ for 3 hrs. After the reaction was completed, the mixture was cooled to rt, and diluted with EtOAc (60.0 mL). The combined organic layers were washed with water (20 mL×3) and brine, dried over anhydrous Na$_2$SO$_4$ and concentrated in vacuo. The residue was purified by a silica gel column chromatography (PE/EtOAc (v/v)=4/1) to give the title compound (500 mg, 30%) as a pale yellow solid. The compound was characterized by the following spectroscopic data:

MS (ESI, pos.ion) m/z: 495.3[M+H]$^+$;

$^1$H NMR (400 MHz, CDCl$_3$) δ (ppm): 7.79-7.76 (m, 2H), 7.56-7.53 (m, 2H), 7.25, 7.23 (s, s, 1H), 7.08, 7.06 (s, s, 1H), 3.60-3.57 (m, 1H), 3.52-3.49 (m, 1H), 2.07-2.01 (m, 1H), 1.98-1.92 (m, 1H), 1.86-1.82 (m, 1H), 1.63-1.59 (m, 1H), 1.35 (m, 6H), 1.32 (m, 6H), 1.25-1.19 (m, 2H).

Step 2) the Preparation of Compound 47-3

A suspension of compound 47-2 (102.28 mg, 0.207 mmol), compound 1-11 (89.53 mg, 0.207 mmol), Pd(PPh$_3$)$_4$ (23.97 mg, 0.0207 mmol) and K$_2$CO$_3$ (85.93 mg, 0.6227 mmol) in mixed solvents of DME and H$_2$O (5.0 mL, v/v=4/1) was stirred at 90° C. under N$_2$ for 3 hrs. After the reaction was completed, the mixture was cooled to rt, and diluted with EtOAc (20.0 mL). The combined organic layers were washed with water (10 mL×3) and brine, dried over anhydrous Na$_2$SO$_4$ and concentrated in vacuo. The residue was purified by a silica gel column chromatography (DCM/EtOH (v/v)= 100/1) to give the title compound (128 mg, 95%) as a pale yellow solid. The compound was characterized by the following spectroscopic data:

MS (ESI, pos.ion) m/z: 654.3 [M+H]$^+$;

$^1$H NMR (400 MHz, CDCl$_3$) δ (ppm): 7.69-7.68 (m, 1H), 7.62-7.59 (m, 1H), 7.55 (s, 4H), 7.45, 7.43 (d, d, 1H), 7.25, 7.23 (s, s, 1H), 7.06, 7.04 (s, s, 1H), 5.04-4.99 (m, 1H), 3.82-3.76 (m, 1H), 3.64-3.56 (m, 2H), 3.52-3.49 (m, 1H), 2.62-2.54 (m, 1H), 2.46-2.36 (m, 1H), 2.24-2.16 (m, 1H), 2.07-2.01 (m, 1H), 2.00-1.92 (m, 2H), 1.86-1.82 (m, 1H), 1.63-1.59 (m, 1H), 1.53 (s, 9H), 1.34-1.28 (m, 1H), 1.25-1.19 (m, 1H).

Step 3) the Preparation of Compound 47-4

A mixture of compound 47-3 (7.36 g, 11.27 mmol), compound 1-8-2 (4.29 g, 16.9 mmol), Pd(dppf)Cl$_2$·CH$_2$Cl$_2$ (653 mg, 0.80 mmol) and KOAc (2.09 g, 21.3 mmol) in DMF (30.0 mL) was stirred at 90° C. under $N_2$ for 3 hrs. After the reaction was completed, the mixture was cooled to rt, diluted with EtOAc (200 mL) and filtered through a celite pad. The filtrate was washed with water (60 mL×3) and brine, dried over anhydrous $Na_2SO_4$ and concentrated in vacuo. The residue was purified by a silica gel column chromatography (PE/EtOAc (v/v)=1/1) to give the title compound (3.55 g, 50%). The compound was characterized by the following spectroscopic data:

MS (ESI, pos.ion) m/z: 632.3 [M+H]$^+$;

$^1$H NMR (400 MHz, CDCl$_3$) δ (ppm): 7.79, 7.77 (s, s, 1H), 7.75-7.71 (m, 2H), 7.69-7.68 (m, 1H), 7.62-7.59 (m, 1H), 7.56-7.53 (m, 2H), 7.45, 7.43 (d, d, 1H), 7.41, 7.39 (s, s, 1H), 5.04-4.99 (m, 1H), 3.82-3.76 (m, 2H), 3.64-3.56 (m, 2H), 2.62-2.54 (m, 2H), 2.46-2.36 (m, 1H), 2.24-2.16 (m, 1H), 2.04-1.97 (m, 1H), 1.96-1.90 (m, 1H), 1.84-1.78 (m, 1H), 1.61-1.57 (m, 1H), 1.53 (s, 9H), 1.32 (m, 6H), 1.29 (m, 6H), 1.23-1.17 (m, 1H), 1.11-1.05 (m, 1H).

Step 4) the Preparation of Compound 47-5

A suspension of compound 47-4 (2.15 g, 3.4 mmol), compound 2-6-1 (1.23 g, 3.4 mmol), Pd(PPh$_3$)$_4$ (196.7 mg, 0.17 mmol) and $K_2CO_3$ (1.412 g, 10.22 mmol) in mixed solvents of DME and $H_2O$ (15 mL, v/v=4/1) was stirred at 90° C. under $N_2$ for 3 hrs. After the reaction was completed, the mixture was cooled to rt, and diluted with EtOAc (100 mL). The combined organic layers were washed with water (30 mL×3) and brine, dried over anhydrous $Na_2SO_4$ and concentrated in vacuo. The residue was purified by a silica gel column chromatography (PE/EtOAc (v/v)=4/1) to give the title compound (1.26 g, 60%) as a pale yellow solid. The compound was characterized by the following spectroscopic data:

MS (ESI, pos.ion) m/z: 741.4 [M+H]$^+$;

$^1$H NMR (400 MHz, CDCl$_3$) δ (ppm): 7.90 (s, 1H), 7.69-7.65 (m, 3H), 7.62-7.59 (m, 1H), 7.56-7.53 (m, 2H), 7.48, 7.46 (s, s, 1H), 7.45, 7.43 (d, d, 1H), 7.34, 7.32 (s, s, 1H), 5.05-4.99 (m, 2H), 3.87-3.76 (m, 2H), 3.64-3.56 (m, 1H), 3.31-3.24 (m, 1H), 2.62-2.54 (m, 2H), 2.47-2.36 (m, 2H), 2.27-2.16 (m, 2H), 2.10-1.93 (m, 6H), 1.91-1.87 (m, 1H), 1.68-1.64 (m, 1H), 1.53 (s, 9H), 1.41 (s, 9H), 1.30-1.20 (m, 2H).

Step 5) the Preparation of Compound 47-6

To a solution of compound 47-5 (146.6 mg, 0.198 mmol) in EtOAc (4.0 mL) was added a solution of HCl in EtOAc (3.0 mL, 4 M) dropwise. At the end of addition, the mixture was stirred at rt for 8.0 hrs. After the reaction was completed, the mixture was concentrated in vacuo. The residue was washed with EtOAc (10.0 mL) and then filtered to give the title compound (122.3 mg, 90%) as pale yellow powder. The compound was characterized by the following spectroscopic data:

MS (ESI, pos.ion) m/z: 541.3[M+H]$^+$.

Step 6) the Preparation of Compound 47-7

A suspension of compound 47-6 (462.5 mg, 0.674 mmol), compound 1-4-2 (235.8 mg, 1.35 mmol), EDCI (271.3 mg, 1.415 mmol) and HOAT (137.58 mg, 1.01 mmol) in DCM (20.0 mL) was stirred at 0° C., and DIPEA (0.93 mL, 5.63 mmol) was added dropwise. At the end of addition, the mixture was stirred at rt for 3.0 hrs. After the reaction was completed, the mixture was diluted with DCM (30.0 mL), washed with NH$_4$Cl aqueous solution and brine, dried over anhydrous $Na_2SO_4$ and concentrated in vacuo. The residue was purified by a silica gel column chromatography (DCM/MeOH (v/v)=60/1) to give the title compound (345.5 mg, 60%) as a white solid. The compound was characterized by the following spectroscopic data:

MS (ESI, pos.ion) m/z: 428.5 [M+2H]$^{2+}$;

$^1$H NMR (400 MHz, CDCl$_3$) δ (ppm): 7.81 (s, 1H), 7.69-7.65 (m, 3H), 7.62-7.59 (m, 1H), 7.56-7.53 (m, 2H), 7.48, 7.46 (s, s, 1H), 7.45, 7.43 (d, d, 1H), 7.34, 7.32 (s, s, 1H), 5.56, 5.55 (br, br, 1H), 5.46, 5.44 (br, br, 1H), 5.29-5.25 (m, 1H), 5.24-5.20 (m, 1H), 4.40-4.30 (m, 2H), 3.87-3.77 (m, 4H), 3.68-3.67 (m, 2H), 3.66 (s, 6H), 2.37-1.87 (m, 2H), 1.68-1.64 (m, 1H), 1.30-1.20 (m, 2H), 1.20-0.89 (m, 12H).

Example 48

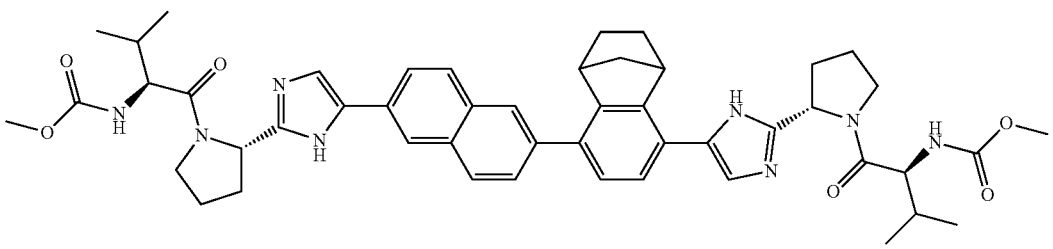

Synthetic Route:

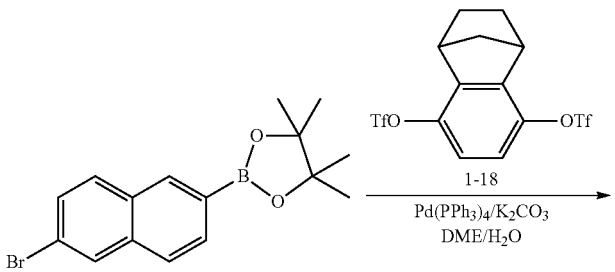

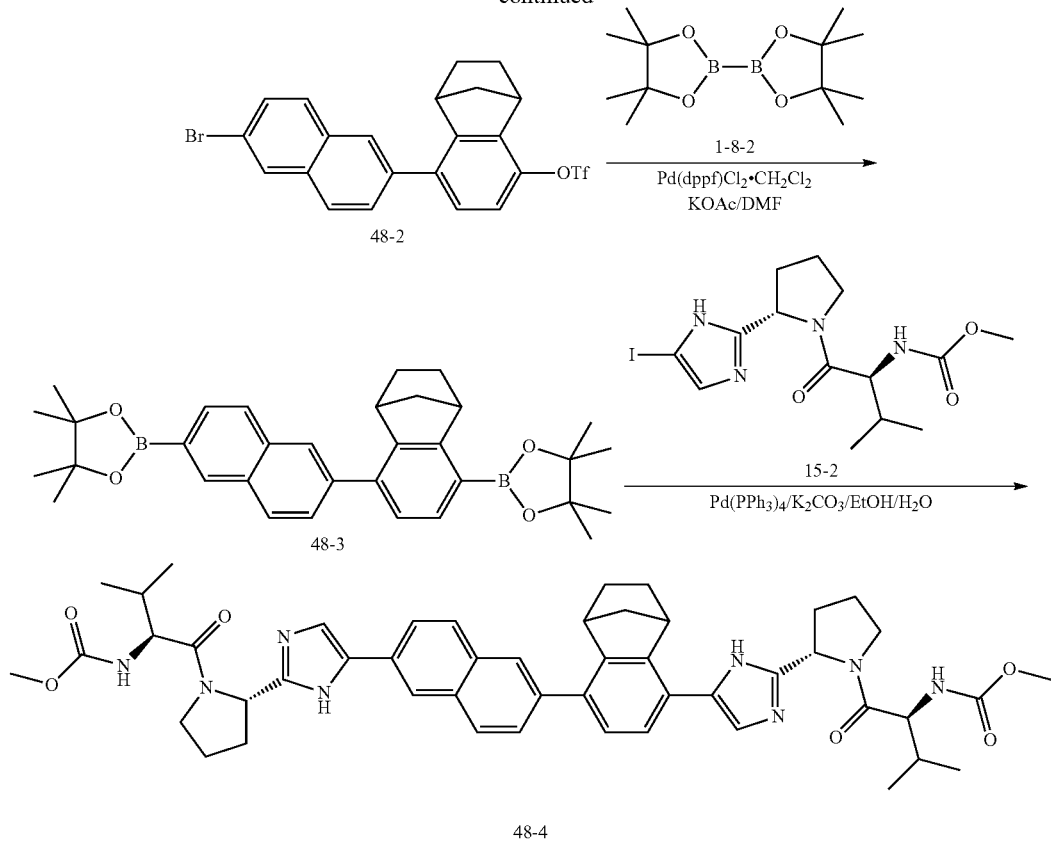

Step 1) the Preparation of Compound 48-2

A suspension of compound 1-18 (8.27 g, 18.8 mmol), compound 48-1 (6.24 g, 18.8 mmol), Pd(PPh$_3$)$_4$ (1.10 g, 0.94 mmol) and K$_2$CO$_3$ (10.4 g, 75.4 mmol) in mixed solvents of DME and H$_2$O (80 mL, v/v=3/1) was stirred at 90° C. under N$_2$ for 3 hrs. After the reaction was completed, the mixture was cooled to rt, and diluted with EtOAc (200 mL). The combined organic layers were washed with water (50.0 mL×3) and brine, dried over anhydrous Na$_2$SO$_4$ and concentrated in vacuo. The residue was purified by a silica gel column chromatography (PE/EtOAc (v/v)=1/2) to give the title compound (4.66 g, 50%) as a pale yellow solid. The compound was characterized by the following spectroscopic data:

$^1$H NMR (400 MHz, CDCl$_3$) δ (ppm) 8.11-8.10 (br, 1H), 8.00-7.99 (br, 1H), 7.81, 7.79 (br, br, 1H), 7.78, 7.76 (br, br, 1H), 7.71, 7.69 (br, br, 1H), 7.56, 7.54 (br, br, 1H), 7.28, 7.25 (s, s, 1H), 7.14, 7.12 (s, s, 1H), 3.60-3.57 (m, 1H), 3.56-3.53 (m, 1H), 2.07-2.10 (m, 1H), 1.98-1.92 (m, 1H), 1.86-1.82 (m, 1H), 1.63-1.59 (m, 1H), 1.34-1.28 (m, 1H), 1.25-1.19 (m, 1H).

Step 2) the Preparation of Compound 48-3

A mixture of compound 48-2 (5.074 g, 10.23 mmol), compound 1-8-2 (5.46 g, 21.48 mmol), Pd(dppf)Cl$_2$.CH$_2$Cl$_2$ (418 mg, 0.51 mmol) and KOAc (2.51 g, 25.57 mmol) in DMF (60.0 mL) was stirred at 90° C. under N$_2$ for 3 hrs. After the reaction was completed, the mixture was cooled to rt, diluted with EtOAc (300 mL) and filtered through a celite pad. The filtrate was washed with water (100 mL×3) and brine, dried over anhydrous Na$_2$SO$_4$ and concentrated in vacuo. The residue was purified by a silica gel column chromatography (PE/EtOAc (v/v)=6/1) to give the title compound (2.67 g, 50%). The compound was characterized by the following spectroscopic data:

MS (ESI, pos.ion) m/z: 523.5 [M+H]$^+$;

$^1$H NMR (400 MHz, CDCl$_3$) δ (ppm): 8.24 (br, 1H), 8.03, 8.00 (br, br, 1H), 7.96-7.90 (m, 3H), 7.87 (br, 1H), 7.71, 7.68 (br, br, 1H), 7.54, 7.52 (s, s, 1H), 3.88-3.85 (m, 2H), 1.96-1.90 (m, 1H), 1.84-1.78 (m, 2H), 1.61-1.57 (m, 1H), 1.33-1.32 (m, 12H), 1.30-1.29 (m, 12H), 1.23-1.17 (m, 1H), 1.11-1.05 (m, 1H).

Step 3) the Preparation of Compound 48-4

A suspension of compound 48-3 (5.22 g, 10.0 mmol), compound 15-2 (8.82 g, 21.0 mmol), Pd(PPh$_3$)$_4$ (1.156 g, 1.0 mmol) and K$_2$CO$_3$ (3.45 g, 25.0 mmol) in mixed solvents of DME and H$_2$O (80 mL, v/v=3/1) was stirred at 90° C. under N$_2$ for 3 hrs. After the reaction was completed, the mixture was cooled to rt, and diluted with EtOAc (200 mL). The combined organic layers were washed with brine, dried over anhydrous Na$_2$SO$_4$ and concentrated in vacuo. The residue was purified by a silica gel column chromatography (DCM/EtOH (v/v)=50/1) to give the title compound (3.41 g, 40%) as a pale yellow solid. The compound was characterized by the following spectroscopic data:

MS (ESI, pos.ion) m/z: 855.5 [M+H]$^+$;

$^1$H NMR (400 MHz, CDCl$_3$) δ (ppm): 8.24 (br, 1H), 8.15 (br, 1H), 7.88, 7.86 (m, m, 2H), 7.85, 7.83 (m, m, 1H), 7.81 (s, 1H), 7.60 (s, 1H), 7.55, 7.53 (s, s, 1H), 7.51, 7.49 (br, br, 1H), 7.34, 7.32 (s, s, 1H), 5.40-5.36 (m, 1H), 5.32, 5.30 (br, br, 2H), 5.29-5.25 (m, 1H), 4.41-4.36 (m, 2H), 3.91-3.88 (m, 1H), 3.87-3.78 (m, 3H), 3.69-3.64 (m, 2H), 3.63 (s, 6H), 2.30-1.87 (m, 13H), 1.68-1.64 (m, 1H), 1.30-1.20 (m, 2H), 0.97, 0.95 (m, 6H), 0.91, 0.89 (m, 6H).

Example 49
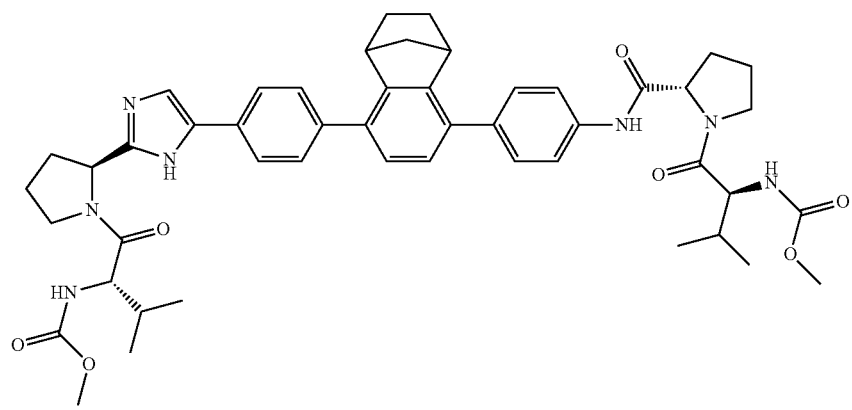 [SMILES: COC(=O)N[C@H](C(=O)N1CCC[C@H]1C(=O)Nc1ccc(-c2ccc(-c3ccc(-c4cnc([C@@H]5CCCN5C(=O)[C@@H](NC(=O)OC)C(C)C)[nH]4)cc3)c3c2C2CCC3C2)cc1)C(C)C]
Synthetic Route:
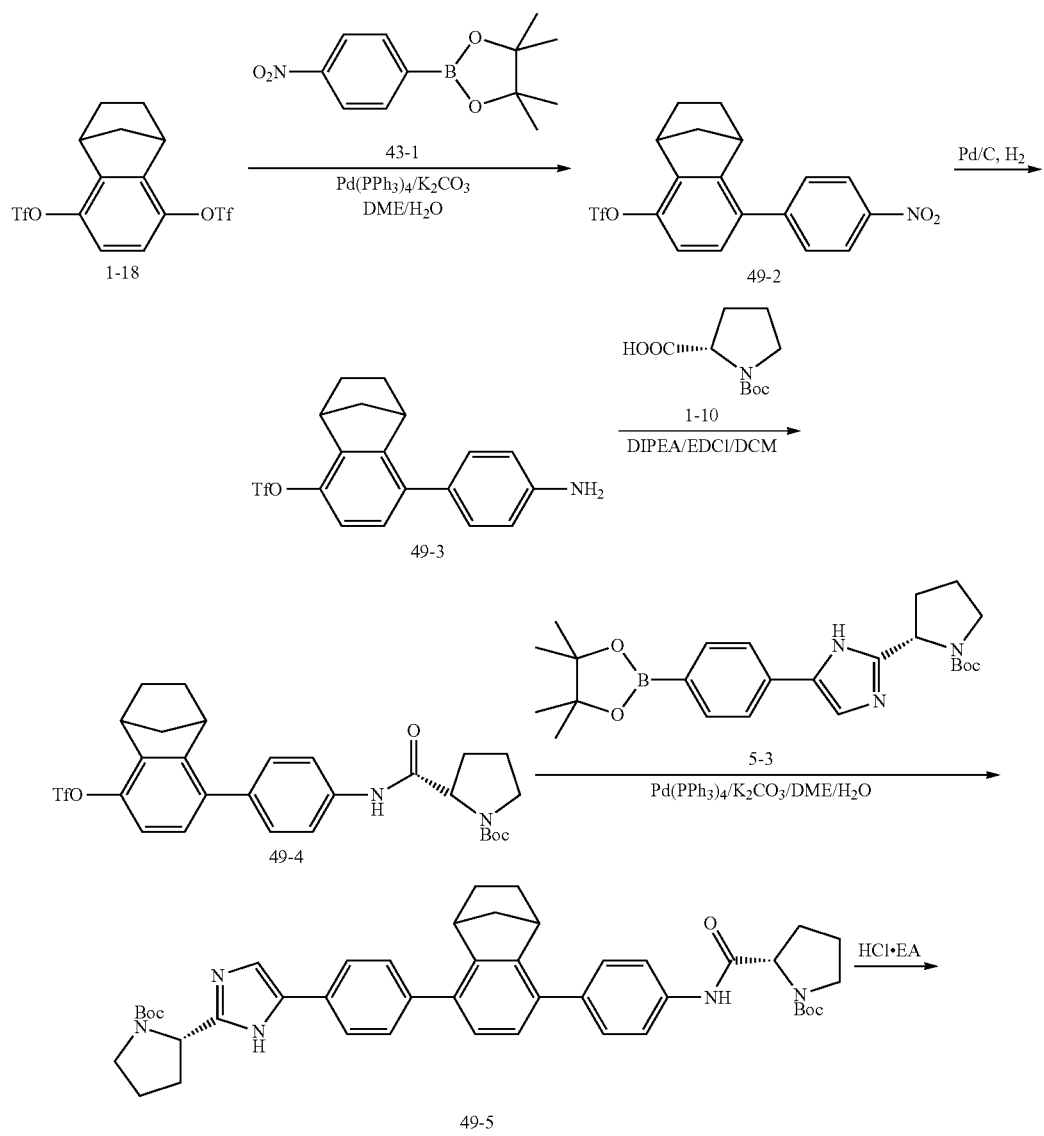

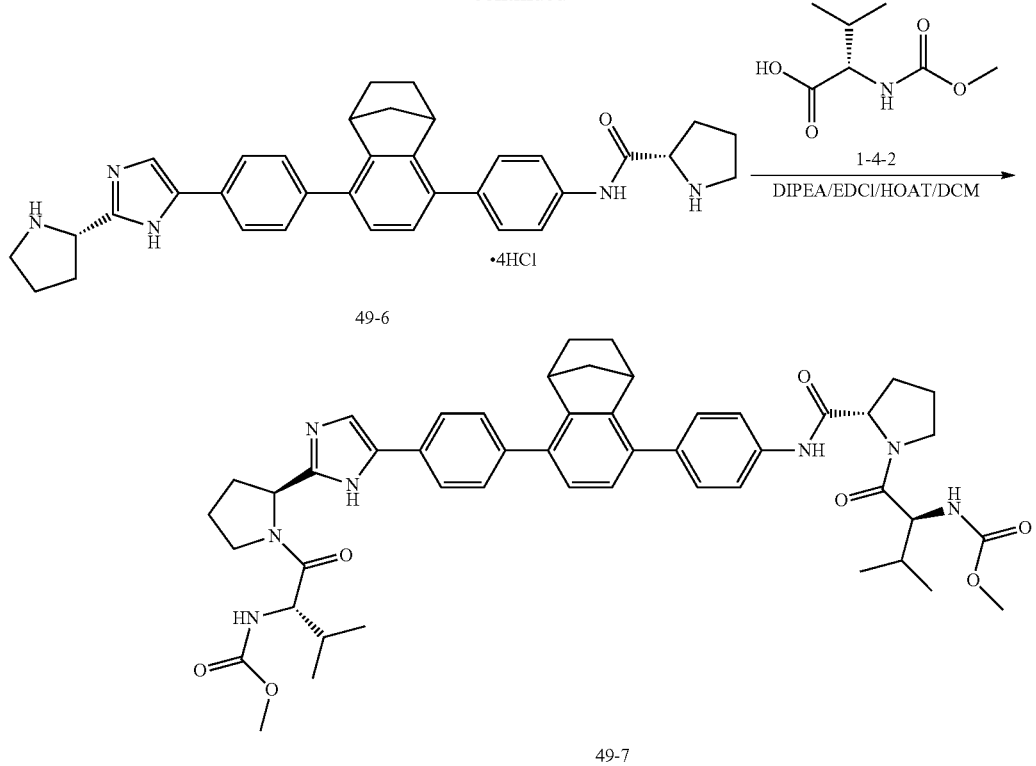

49-6

49-7

Step 1) the Preparation of Compound 49-2

To a mixture of compound 43-1 (172.64 mg, 0.693 mmol), compound 1-18 (324.6 mg, 0.693 mmol), Pd(PPh$_3$)$_4$ (80.1 mg, 0.0693 mmol) and K$_2$CO$_3$ (478.6 mg, 3.463 mmol) were added DME (8.0 mL) and water (2.0 mL) via syringe, the mixture was stirred at 90° C. under N$_2$ for 2 hrs. After the reaction was completed, the mixture was cooled to rt, and 15 mL of water was added. The resulting mixture was extracted with DCM (25 mL×3). The combined organic layers were washed with brine, dried over anhydrous Na$_2$SO$_4$ and concentrated in vacuo. The residue was purified by a silica gel column chromatography (PE/EtOAc (v/v)=5/1) to give the title compound (257.6 mg, 90%) as a yellow solid. The compound was characterized by the following spectroscopic data:

MS (ESI, pos.ion) m/z: 414.3 [M+H]$^+$;

$^1$H NMR (400 MHz, CDCl$_3$) δ (ppm): 8.37-8.33 (m, 2H), 7.46-7.42 (m, 2H), 7.25, 7.23 (s, s, 1H), 7.14, 7.12 (s, s, 1H), 3.60-3.57 (m, 1H), 3.52-3.49 (m, 1H), 2.07-2.01 (m, 1H), 1.98-1.92 (m, 1H), 1.86-1.82 (m, 1H), 1.63-1.59 (m, 1H), 1.34-1.28 (m, 1H), 1.25-1.19 (m, 1H).

Step 2) the Preparation of Compound 49-3

A suspension of compound 49-2 (268.89 mg, 0.651 mmol) and a catalytic amount of Pd/C (20.0 mg) in DCM (10.0 mL) was stirred at rt under H$_2$ for 4 hrs. After the reaction was completed, the mixture was filtered. The filtrated was concentrated in vacuo to give the title compound (237 mg, 95%) as a white solid. The compound was characterized by the following spectroscopic data:

MS (ESI, pos.ion) m/z: 384.3 [M+H]$^+$;

$^1$H NMR (400 MHz, CDCl$_3$) δ (ppm): 7.35-7.31 (m, 2H), 7.25, 7.23 (s, s, 1H), 7.07, 7.05 (s, s, 1H), 6.62-6.59 (m, 2H), 3.60-3.57 (m, 1H), 3.52-3.49 (m, 1H), 3.47 (br, 2H), 2.07-2.01 (m, 1H), 1.98-1.92 (m, 1H), 1.86-1.82 (m, 1H), 1.63-1.59 (m, 1H), 1.34-1.28 (m, 1H), 1.25-1.19 (m, 1H).

Step 3) the Preparation of Compound 49-4

A suspension of compound 49-3 (129.9 mg, 0.339 mmol), compound 1-10 (72.9 mg, 0.339 mmol) and EDCI (259.9 mg, 1.356 mmol) in DCM (10.0 mL) was stirred at 0° C., and then DIPEA (0.336 mL, 2.033 mmol) was added dropwise. At the end of addition, the mixture was stirred at rt for 3 hrs. After the reaction was completed, 20 mL of water was added. The aqueous layer was extracted with DCM (25 mL×3), and then the combined organic layers were washed with NH$_4$Cl aqueous solution and brine, dried over anhydrous Na$_2$SO$_4$ and concentrated in vacuo. The residue was purified by a silica gel column chromatography (PE/EtOAc (v/v)=1/1) to give the title compound (157.3 mg, 80%) as a white solid. The compound was characterized by the following spectroscopic data:

MS (ESI, pos.ion) m/z: 581.5 [M+H]$^+$;

$^1$H NMR (400 MHz, CDCl$_3$) δ (ppm): 8.96 (br, 1H), 7.64-7.60 (m, 2H), 7.58, 7.56 (s, s, 1H), 7.39-7.35 (m, 2H), 7.25, 7.23 (s, s, 1H), 4.40-4.36 (m, 1H), 3.60-3.57 (m, 1H), 3.56-3.49 (m, 2H), 3.44-3.36 (m, 1H), 2.39-2.32 (m, 1H), 2.17-2.07 (m, 1H), 2.07-2.01 (m, 1H), 1.98-1.87 (m, 2H), 1.86-1.75 (m, 2H), 1.63-1.59 (m, 1H), 1.40 (s, 9H), 1.34-1.28 (m, 1H), 1.25-1.19 (m, 1H).

Step 4) the Preparation of Compound 49-5

To a mixture of compound 49-4 (402 mg, 0.693 mmol), compound 5-3 (304 mg, 0.693 mmol), Pd(PPh$_3$)$_4$ (80.1 mg, 0.0693 mmol) and K$_2$CO$_3$ (478.6 mg, 3.463 mmol) were added DME (8.0 mL) and water (2.0 mL) via syringe, the mixture was stirred at 90° C. under N$_2$ for 2 hrs. After the reaction was completed, the mixture was cooled to rt, 15.0 mL of water was added, and the resulting mixture was extracted with DCM (25 mL×3). The combined organic layers were washed with brine, dried over anhydrous Na$_2$SO$_4$ and concentrated in vacuo. The residue was purified by a silica gel column chromatography (PE/EtOAc (v/v)=3/1) to give the title compound (463.6 mg, 90%) as a yellow solid. The compound was characterized by the following spectroscopic data:

MS (ESI, pos.ion) m/z: 744.5 [M+H]⁺;
¹H NMR (400 MHz, CDCl₃) δ (ppm): 8.96 (br, 1H), 7.64-7.59 (m, 5H), 7.56-7.52 (m, 3H), 7.51-7.47 (m, 2H), 7.46, 7.44 (s, s, 1H), 4.97-4.93 (m, 1H), 4.40-4.36 (m, 1H), 3.89-3.84 (m, 2H), 3.65-3.58 (m, 1H), 3.56-3.49 (m, 1H), 3.44-3.36 (m, 1H), 3.31-3.24 (m, 1H), 2.47-2.32 (m, 2H), 2.28-1.75 (m, 9H), 1.65-1.61 (m, 1H), 1.53 (s, 9H), 1.40 (s, 9H), 1.27-1.21 (m, 2H).

Step 5) the Preparation of Compound 49-6

To a solution of compound 49-5 (278.7 mg, 0.375 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (10.0 mL) and filtered to give the title compound (232.6 mg, 90%) as a pale yellow solid. The compound was characterized by the following spectroscopic data:

MS (ESI, pos.ion) m/z: 544.5 [M+H]⁺.

Step 6) the Preparation of Compound 49-7

A suspension of compound 49-6 (213.6 mg, 0.31 mmol), compound 1-4-2 (120 mg, 0.68 mmol), EDCI (130 mg, 0.68 mmol) and HOAT (85 mg, 0.62 mmol) in DCM (10.0 mL) was stirred at 0° C., then DIPEA (0.56 mL, 3.4 mmol) was added dropwise. At the end of addition, the mixture was stirred at rt for 3 hrs. After the reaction was completed, the mixture was diluted with DCM (20.0 mL), washed with NH₄Cl aqueous solution and brine, dried over anhydrous Na₂SO₄ and concentrated in vacuo. The residue was purified by a silica gel column chromatography (DCM/MeOH (v/v)= 50/1) to give the title compound (202 mg, 76%) as a white solid. The compound was characterized by the following spectroscopic data:

MS (ESI, pos.ion) m/z: 858.5 [M+H]⁺;
¹H NMR (400 MHz, CDCl₃) δ (ppm): 8.96 (br, 1H), 7.66-7.59 (m, 5H), 7.56-7.52 (m, 3H), 7.46, 7.44 (s, s, 1H), 7.42-7.38 (m, 2H), 5.56, 5.55 (br, br, 1H), 5.46, 5.44 (br, br, 1H), 5.23-5.19 (m, 1H), 4.34-4.23 (m, 3H), 3.89-3.86 (m, 2H), 3.85-3.78 (m, 1H), 3.66 (s, 6H), 3.65-3.62 (m, 1H), 3.61-3.56 (m, 1H), 3.44-3.36 (m, 1H), 2.30-1.92 (m, 10H), 1.88-1.84 (m, 1H), 1.75-1.61 (m, 3H), 1.28-1.20 (m, 2H), 1.02-0.89 (m, 2H).

Example 50

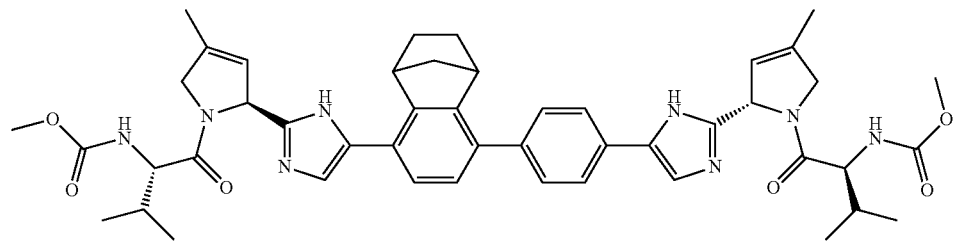 [SMILES: COC(=O)N[C@H](C(=O)N1CC(C)=C[C@H]1c1ncc(-c2ccc(-c3ccc(-c4cnc([C@@H]5C=C(C)CN5C(=O)[C@@H](NC(=O)OC)C(C)C)[nH]4)c4c3C3CCC4C3)cc2)[nH]1)C(C)C]

Synthetic Route:

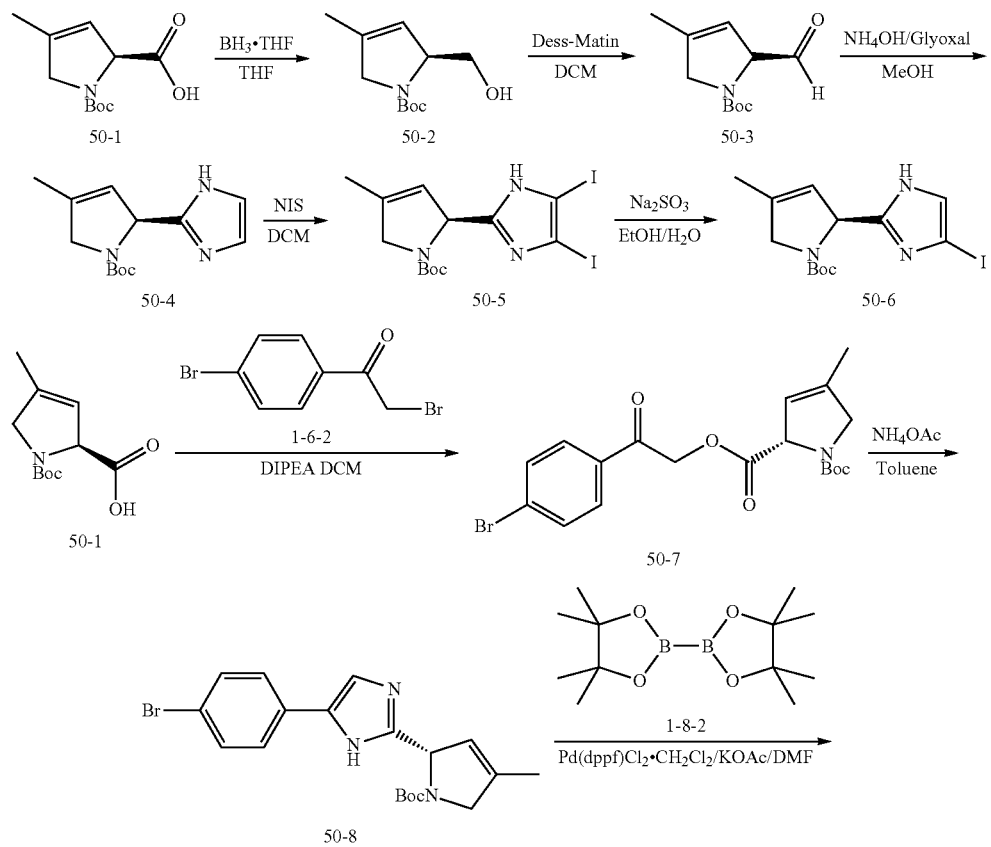

-continued
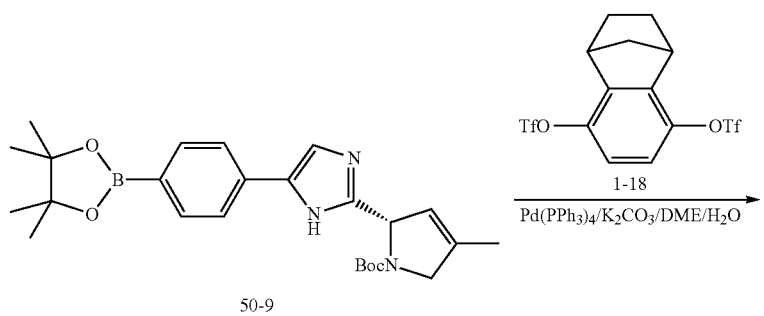
50-9
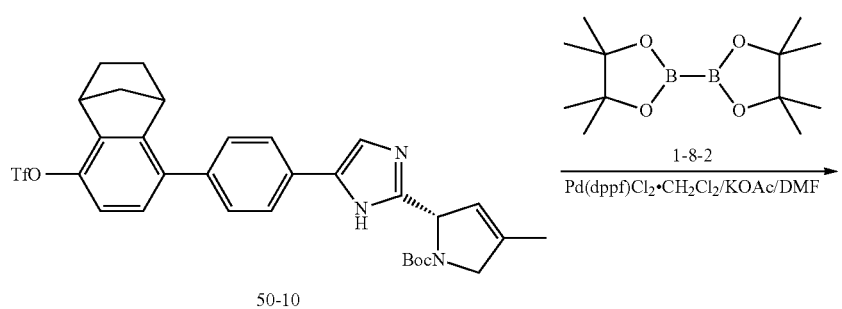
50-10
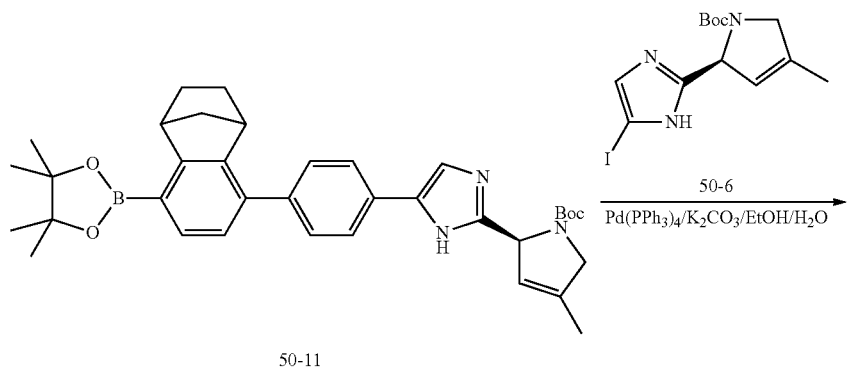
50-11
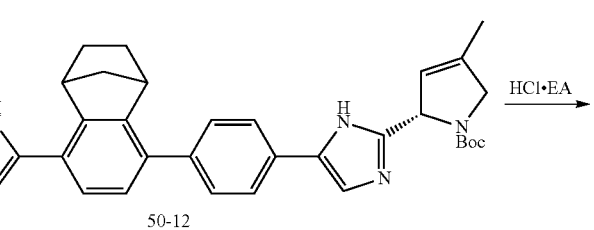
50-12
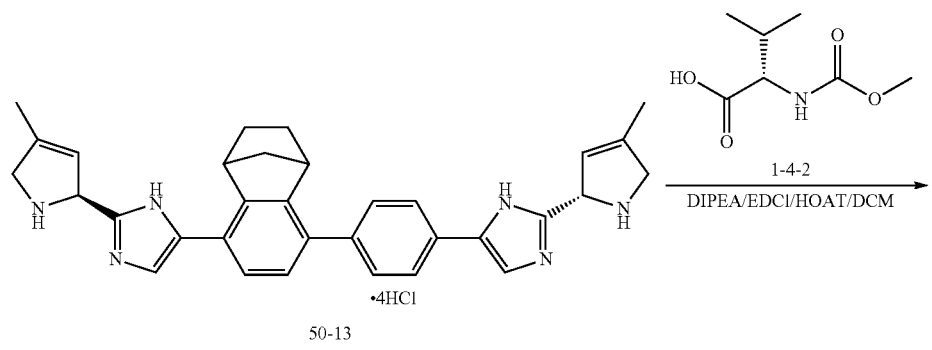
50-13

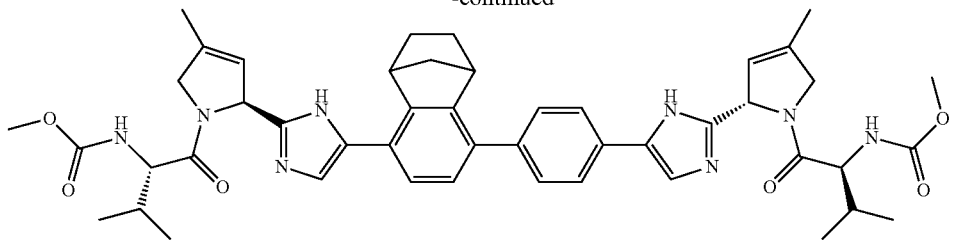

50-14

Step 1) the Preparation of Compound 50-2

To a solution of compound 50-1 (10.58 g, 46.6 mmol) in THF (100 mL) was added diborane (100 mL, 1M in THF) dropwise at 0° C. At the end of addition, the mixture was stirred at 0° C. for 3 hrs. After the reaction was completed, the reaction was quenched with MeOH (80 mL), and then concentrated in vacuo. The residue was purified by a silica gel column chromatography (PE/EtOAc (v/v)=3/2) to give the title compound 50-2 (7.65 g, 75%) as colorless oil. The compound was characterized by the following spectroscopic data:

$^1$H NMR (400 MHz, CDCl$_3$) δ (ppm): 5.32-5.29 (m, 1H), 4.63-4.54 (m, 1H), 4.16-4.09 (m, 1H), 3.97-3.92 (m, 1H), 3.88-3.82 (m, 1H), 3.80-3.79 (m, 1H), 3.22 (br, 1H), 1.62-1.61 (m, 3H), 1.43 (s, 9H).

Step 2) the Preparation of Compound 50-3

To a solution of compound 50-2 (7.42 g, 34.8 mmol) in DCM (250 mL) was added Dess-Martin periodinane (20.7 g, 48.8 mmol) in a portionwise manner at 0° C. At the end of addition, the mixture was stirred at rt for 2 hrs. After the reaction was completed, 150 mL of water was added. The resulting mixture was filtered, and the filtrate was washed with brine, dried over anhydrous Na$_2$SO$_4$ and concentrated in vacuo. The residue was purified by a silica gel column chromatography (PE/EtOAc (v/v)=3/1) to give the title compound (3.72 g, 50.7%) as colorless oil. The compound was characterized by the following spectroscopic data:

$^1$H NMR (400 MHz, CDCl$_3$) δ (ppm): 9.77-9.75 (m, 1H), 5.41-5.38 (m, 1H), 4.64-4.59 (m, 1H), 4.24-4.17 (m, 1H), 3.96-3.89 (m, 1H), 1.65-1.64 (m, 3H), 1.44 (s, 9H).

Step 3) the Preparation of Compound 50-4

To a solution of compound 50-3 (3.71 g, 17.6 mmol) and ammonia (13.0 mL) in MeOH (30.0 mL) was added glyoxal (8.0 mL, 40% in water) dropwsie at 0° C. At the end of addition, the mixture was stirred at rt overnight. After the reaction was completed, the mixture was concentrated in vacuo. The residue was purified by a silica gel column chromatography (PE/EtOAc (v/v)=4/1) to give the title compound (2.08 g, 47.6%) as a white solid. The compound was characterized by the following spectroscopic data:

MS (ESI, pos.ion) m/z: 250.5 [M+H]$^+$;

$^1$H NMR (400 MHz, CDCl$_3$) δ (ppm): 7.05 (s, 2H), 6.32-6.28 (m, 1H), 5.38-5.35 (m, 1H), 4.23-4.17 (m, 1H), 3.86-3.80 (m, 1H), 1.68-1.67 (m, 3H), 1.40 (s, 9H).

Step 4) the Preparation of Compound 50-5

To a solution of compound 50-4 (2.09 g, 8.4 mmol) in DCM (60.0 mL) was added N-iodosuccinimide (3.8 g, 16.8 mmol) at 0° C. in a portionwise manner. At the end of addition, the mixture was stirred at 0° C. for 1.5 hrs. After the reaction was completed, the mixture was washed with brine, dried over anhydrous Na$_2$SO$_4$ and concentrated in vacuo. The residue was purified by a silica gel column chromatography (PE/EtOAc (v/v)=3/2) to give the title compound (2.65 g, 63%) as a white solid. The compound was characterized by the following spectroscopic data:

MS (ESI, pos.ion) m/z: 501.5 [M+H]$^+$;

$^1$H NMR (400 MHz, CDCl$_3$) δ (ppm): 5.52-5.45 (m, 2H), 4.35-4.29 (m, 1H), 3.94-3.88 (m, 1H), 1.67-1.66 (m, 3H), 1.40 (s, 9H).

Step 5) the Preparation of Compound 50-6

To a suspension of compound 50-5 (1.638 g, 3.27 mmol) in mixed solvents of ethanol and water (50.0 mL, v/v=3/7) was added Na$_2$SO$_3$ (3.7 g, 29 mmol), the mixture was refluxed for 17 hrs. After the reaction was completed, the ethanol was removed, and 20.0 mL of water was added to the mixture. The resulting mixture was extracted with EtOAc (30.0 mL×3), and then the combined organic layers were dried over anhydrous Na$_2$SO$_4$ and concentrated in vacuo. The residue was purified by a silica gel column chromatography (PE/EtOAc (v/v)=3/2) to give the title compound (1.03 g, 84%) as a white solid. The compound was characterized by the following spectroscopic data:

MS (ESI, pos.ion) m/z: 376.5 [M+H]$^+$;

$^1$H NMR (400 MHz, CDCl$_3$) δ (ppm): 7.18 (s, 1H), 5.35-5.32 (m, 1H), 5.28-5.24 (m, 1H), 4.29-4.23 (m, 1H), 3.91-3.85 (m, 1H), 1.67-1.66 (m, 3H), 1.40 (s, 9H).

Step 6) the Preparation of Compound 50-7

To a solution of compound 1-6-2 (3.0 g, 10.79 mmol) and compound 50-1 (2.69 g, 11.87 mmol) in MeCN (250 mL) was added DIPEA (2.14 mL, 12.95 mmol) dropwise at 0° C. At the end of addition, the mixture was stirred at rt for 3 hrs. After the reaction was completed, the mixture was quenched with ice-water (100 mL). The resulting mixture was extracted with EtOAc (100 mL×3), and then the combined organic layers were dried over Na$_2$SO$_4$ and concentrated in vacuo. The residue was purified by a silica gel column chromatography (PE/EtOAc (v/v)=10/1) to give the title compound (4.1 g, 90%) as a white solid. The compound was characterized by the following spectroscopic data:

MS (ESI, pos.ion) m/z: 424.5 [M+H]$^+$;

$^1$H NMR (400 MHz, CDCl$_3$) δ (ppm): 7.82-7.78 (m, 2H), 7.67-7.64 (m, 2H), 5.61-5.59 (m, 1H), 5.33 (s, 2H), 4.73-4.69 (m, 1H), 4.35-4.28 (m, 1H), 3.99-3.92 (m, 1H), 1.76-1.74 (m, 3H), 1.42 (s, 9H).

Step 7) the Preparation of Compound 50-8

A mixture of compound 50-7 (1.54 g, 3.64 mmol) and acetamide (4.2 g, 5.46 mmol) in toluene (30.0 mL) was stirred at 120° C. for 5 hrs. After the reaction was completed, the mixture was cooled to rt and quenched with water (20.0 mL). The resulting mixture was extracted with EtOAc (20.0 mL×3), and then the combined organic layers were dried over anhydrous Na$_2$SO$_4$ and concentrated in vacuo. The residue was purified by a silica gel column chromatography (PE/EtOAc (v/v)=6/1) to give the title compound (1.25 g, 85%). The compound was characterized by the following spectroscopic data:

MS (ESI, pos.ion) m/z: 404.5 [M+H]$^+$;

$^1$H NMR (400 MHz, CDCl$_3$) δ (ppm): 7.64 (s, 1H), 7.45-7.41 (m, 2H), 7.35-7.32 (m, 2H), 5.78-5.75 (m, 1H), 5.55-5.52 (m, 1H), 4.24-4.17 (m, 1H), 3.77-3.69 (m, 1H), 1.78-1.77 (m, 3H), 1.39 (s, 9H).

Step 8) the Preparation of Compound 50-9

A mixture of compound 50-8 (4.12 g, 10.23 mmol), compound 1-8-2 (2.86 g, 11.25 mmol), Pd(dppf)Cl$_2$.CH$_2$Cl$_2$ (418 mg, 0.51 mmol) and KOAc (2.51 g, 25.57 mmol) in DMF (40.0 mL) was stirred at 90° C. under N$_2$ for 3 hrs. After the reaction was completed, the mixture was cooled to rt, diluted with EtOAc (100 mL) and filtered through a celite pad. The filtrate was washed with water (80 mL×3) and brine, dried over anhydrous Na$_2$SO$_4$ and concentrated in vacuo. The residue was purified by a silica gel column chromatography (PE/EtOAc (v/v)=2/1) to give the title compound (3.69 g, 80%). The compound was characterized by the following spectroscopic data:

$^1$H NMR (400 MHz, CDCl$_3$) δ (ppm): 7.75-7.72 (m, 2H), 7.61-7.58 (m, 2H), 7.28 (s, 1H), 5.78-5.75 (m, 1H), 5.55-5.52 (m, 1H), 4.24-4.17 (m, 1H), 3.77-3.69 (m, 1H), 1.78-1.77 (m, 3H), 1.39 (s, 9H).

Step 9) the Preparation of Compound 50-10

To a mixture of compound 50-9 (1.18 g, 2.62 mmol), compound 1-18 (1.2 g, 2.62 mmol), Pd(PPh$_3$)$_4$ (120 mg, 0.10 mmol) and KF (0.30 g, 5.24 mmol) were added DME (12.0 mL) and pure water (3.0 mL) via syringe, the mixture was stirred at 90° C. under N$_2$ for 2 hrs. After the reaction was completed, the mixture was cooled to rt and diluted with EtOAc (80.0 mL), and the resulting mixture was washed with water (20.0 mL×3) and brine, dried over anhydrous Na$_2$SO$_4$ and concentrated in vacuo. The residue was purified by a silica gel column chromatography (DCM/EtOH (v/v)=100/1) to give the title compound (999 mg, 62%) as a white solid. The compound was characterized by the following spectroscopic data:

MS (ESI, pos.ion) m/z: 616.3 [M+H]$^+$;

$^1$H NMR (400 MHz, CDCl$_3$) δ (ppm): 7.64-7.60 (m, 3H), 7.52-7.48 (m, 2H), 7.25, 7.23 (s, s, 1H), 7.06, 7.04 (s, s, 1H), 5.78-5.75 (m, 1H), 5.55-5.52 (m, 1H), 4.24-4.17 (m, 1H), 3.76-3.69 (m, 1H), 3.60-3.57 (m, 1H), 3.52-3.49 (m, 1H), 2.07-2.01 (m, 1H), 1.98-1.92 (m, 1H), 1.86-1.82 (m, 1H), 1.78-1.77 (m, 3H), 1.63-1.59 (m, 1H), 1.39 (s, 9H), 1.34-1.28 (m, 1H), 1.25-1.19 (m, 1H).

Step 10) the Preparation of Compound 50-11

A mixture of compound 50-10 (990 mg, 1.61 mmol), compound 1-8-2 (450 mg, 10.7 mmol), Pd(dppf)Cl$_2$.CH$_2$Cl$_2$ (80 mg, 0.096 mmol) and KOAc (400 mg, 4.02 mmol) in DMF (10.0 mL) was stirred at 120° C. under N$_2$ for 4 hrs. After the reaction was completed, the mixture was cooled to rt, diluted with EtOAc (80.0 mL) and filtered through a celite pad. The filtrate was washed with water (20.0 mL×3) and brine, dried over anhydrous Na$_2$SO$_4$ and concentrated in vacuo. The residue was purified by a silica gel column chromatography (PE/EtOAc (v/v)=3/1) to give the title compound (697 mg, 73%) as a white solid. The compound was characterized by the following spectroscopic data:

MS (ESI, pos.ion) m/z: 594.5 [M+H]$^+$;

$^1$H NMR (400 MHz, CDCl$_3$) δ (ppm): 7.79, 7.77 (s, s, 1H), 7.64-7.60 (m, 3H), 7.56-7.53 (m, 2H), 7.41, 7.39 (s, s, 1H), 5.78-5.75 (m, 1H), 5.55-5.52 (m, 1H), 4.24-4.17 (m, 1H), 3.82-3.79 (m, 1H), 3.77-3.69 (m, 1H), 3.58-3.55 (m, 1H), 1.96-1.90 (m, 2H), 1.84-1.79 (m, 1H), 1.78-1.77 (m, 3H), 1.61-1.57 (m, 1H), 1.39 (s, 9H), 1.32 (m, 6H), 1.29 (m, 6H), 1.23-1.17 (m, 1H), 1.11-1.05 (m, 1H).

Step 11) the Preparation of Compound 50-12

A suspension of compound 50-6 (167 mg, 0.446 mmol), compound 50-11 (249 mg, 0.42 mmol), Pd(PPh$_3$)$_4$ (25 mg, 0.02 mmol) and K$_2$CO$_3$ (170 mg, 1.27 mmol) in mixed solvents of ethanol and water (8.0 mL, v/v=3/1) was stirred at 90° C. under N$_2$ for 3 hrs. After the reaction was completed, the mixture was concentrated in vacuo. The residue was dissolved in EtOAc (50.0 mL) and then the organic layers were washed with brine, dried over anhydrous Na$_2$SO$_4$ and concentrated in vacuo. The residue was purified by a silica gel column chromatography (DCM/EtOH (v/v)=50/1) to give the title compound (285 mg, 95%) as a pale yellow solid. The compound was characterized by the following spectroscopic data:

MS (ESI, pos.ion) m/z: 715.5 [M+H]$^+$;

$^1$H NMR (400 MHz, CDCl$_3$) δ (ppm) 7.95 (s, 1H), 7.64-7.60 (m, 3H), 7.56-7.52 (m, 2H), 7.48, 7.46 (s, s, 1H), 7.41, 7.39 (s, s, 1H), 5.78-5.75 (m, 2H), 5.59-5.52 (m, 2H), 4.24-4.16 (m, 2H), 3.87-3.79 (m, 2H), 3.77-3.69 (m, 2H), 2.03-1.93 (m, 2H), 1.91-1.87 (m, 1H), 1.78-1.77 (m, 6H), 1.68-1.64 (m, 1H), 1.40 (s, 9H), 1.39 (s, 9H), 1.30-1.20 (m, 2H).

Step 12) the Preparation of Compound 50-13

To a solution of compound 50-12 (364.33 mg, 0.51 mmol) in EtOAc (4.0 mL) was added a solution of HCl in EtOAc (3.0 mL, 4 M) dropwise, the mixture was stirred at rt for 8 hrs. After the reaction was completed, the mixture was concentrated in vacuo. The residue was washed with EtOAc (20.0 mL) and filtered to give the title compound (202 mg, 60%) as pale yellow powder. The compound was characterized by the following spectroscopic data:

MS (ESI, pos.ion) m/z: 515.5 [M+H]$^+$.

Step 13) the Preparation of Compound 50-14

To a suspension of compound 50-13 (149 mg, 0.29 mmol), compound 1-4-2 (110 mg, 0.65 mmol), EDCI (120 mg, 0.65 mmol) and HOAT (80 mg g, 0.59 mmol) in DCM (5.0 mL) was added DIPEA (0.6 mL, 3.63 mmol) dropwise at 0° C. At the end of addition, the mixture was stirred at rt for 3 hrs and diluted with DCM (20.0 mL). The resulting mixture was washed with NH$_4$Cl aqueous solution and brine, dried over Na$_2$SO$_4$ and concentrated in vacuo. The residue was purified by a silica gel column chromatography (DCM/MeOH (v/v)=40/1) to give the title compound (192.2 mg, 80%) as a white solid. The compound was characterized by the following spectroscopic data:

MS (ESI, pos.ion) m/z: 829.3 [M+H]$^+$;

$^1$H NMR (400 MHz, CDCl$_3$) δ (ppm): 7.85 (s, 1H), 7.64-7.60 (m, 3H), 7.56-7.52 (m, 2H), 7.48, 7.46 (s, s, 1H), 7.41, 7.39 (s, s, 1H), 5.80-5.55 (m, 2H), 5.69-5.66 (m, 2H), 5.32, 5.30 (br, br, 2H), 4.45-4.39 (m, 2H), 4.38-4.31 (m, 2H), 4.20-4.13 (m, 2H), 3.87-3.81 (m, 2H), 3.63 (s, 6H), 2.29-2.17 (m, 2H), 2.03-1.93 (m, 2H), 1.91-1.87 (m, 1H), 1.81-1.80 (m, 6H), 1.68-1.64 (m, 1H), 1.30-1.20 (m, 2H), 0.97-0.89 (m, 12H).

Example 51

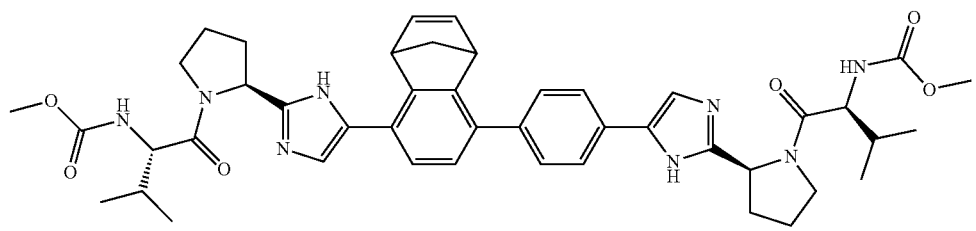

Synthetic Route:

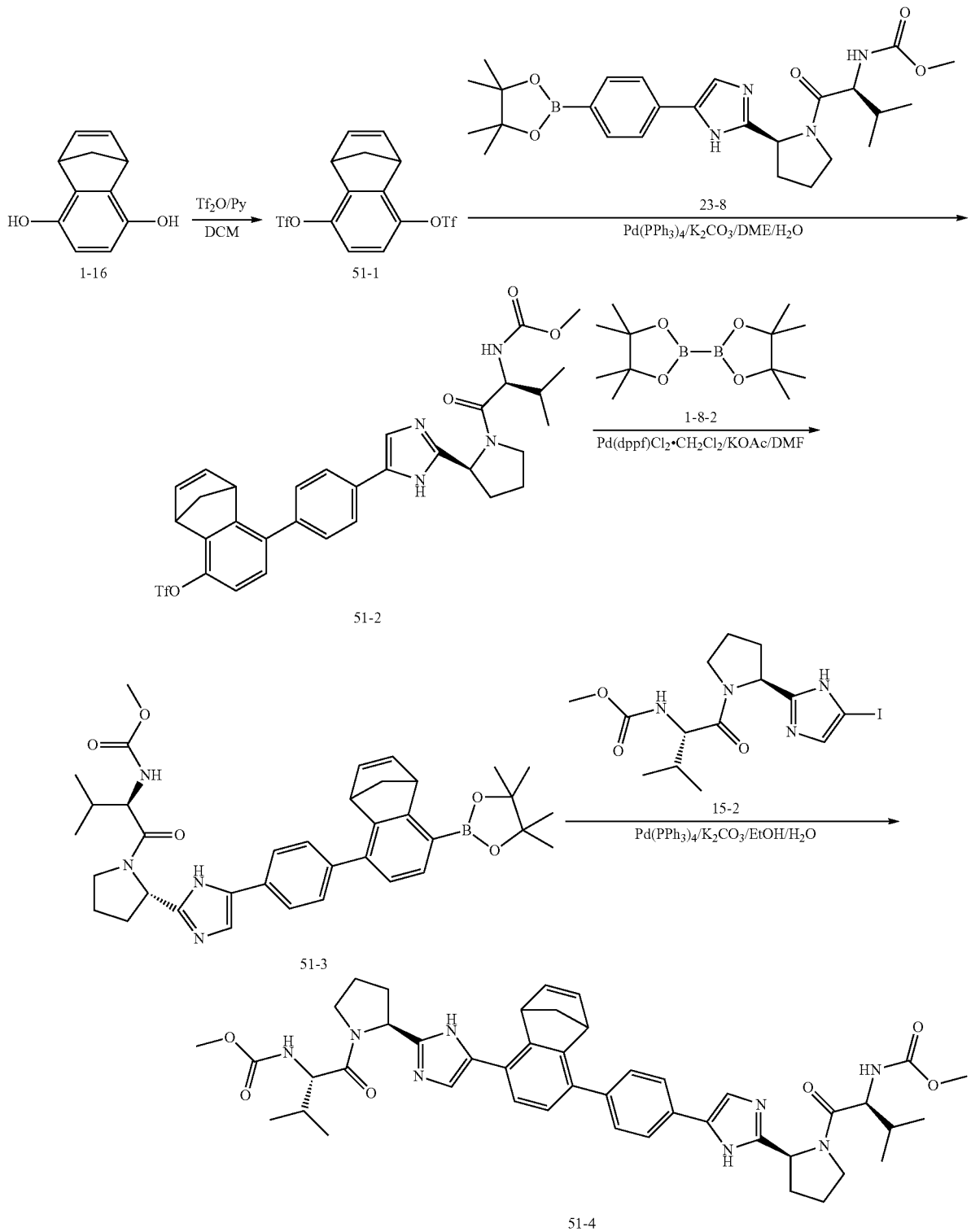

Step 1) the Preparation of Compound 51-1

To a solution of compound 1-16 (3.307 g, 19.0 mmol) in DCM (100 mL) was added pyridine (9.0 g, 114 mmol) dropwise at 0° C. After stirring for 10 mins, trifluoromethanesulfonic anhydride (21.0 g, 76.0 mmol) was added. At the end of addition, the mixture was further stirred at rt for 1.0 hr. After the reaction was completed, the mixture was quenched with water (50.0 mL) and diluted with DCM (100 mL). The organic layers were washed with brine, dried over anhydrous $Na_2SO_4$ and concentrated in vacuo. The residue was purified by a silica gel column chromatography (PE/DCM (v/v)=20/1) to give the title compound (7.9 g, 95.0%) as colorless oil. The compound was characterized by the following spectroscopic data:

$^1$H NMR (400 MHz, CDCl$_3$) δ (ppm): 7.34 (s, 2H), 6.64-6.61 (m, 2H), 4.12-4.08 (m, 2H), 1.89-1.85 (m, 1H), 1.82-1.78 (m, 1H).

Step 2) the Preparation of Compound 51-2

To a mixture of compound 51-1 (315 mg, 0.72 mmol), compound 23-8 (357.3 mg, 0.72 mmol), Pd(PPh$_3$)$_4$ (83 mg, 0.07 mmol) and K$_2$CO$_3$ (300 mg, 2.12 mmol) were added DME (4.0 mL) and pure water (1.0 mL) via syringe and the mixture was stirred at 90° C. under N$_2$ for 4 hrs. After the reaction was completed, the mixture was cooled to rt and diluted with EtOAc (40.0 mL). The resulting mixture was washed with water (20.0 mL×3) and brine, dried over anhydrous Na$_2$SO$_4$ and concentrated in vacuo. The residue was purified by a silica gel column chromatography (PE/EtOAc (v/v)=1/2) to give the title compound (379 mg, 80%) as a white solid. The compound was characterized by the following spectroscopic data:

$^1$H NMR (400 MHz, CDCl$_3$) δ (ppm): 7.63-7.59 (m, 3H), 7.53-7.50 (m, 2H), 7.33, 7.31 (s, s, 1H), 7.10, 7.08 (s, s, 1H), 6.93-6.90 (m, 1H), 6.62-6.59 (m, 1H), 5.56, 5.55 (br, br, 1H), 5.23-5.19 (m, 1H), 4.34-4.30 (m, 1H), 4.18-4.15 (m, 1H), 4.06-4.03 (m, 1H), 3.85-3.78 (m, 1H), 3.66 (s, 3H), 3.65-3.61 (m, 1H), 2.35-2.16 (m, 5H), 2.13-1.92 (m, 2H), 1.02-0.91 (m, 6H).

Step 3) the Preparation of Compound 51-3

A mixture of compound 51-2 (599 mg, 0.91 mmol), compound 1-8-2 (463 mg, 1.82 mmol), Pd(dppf)Cl$_2$·CH$_2$Cl$_2$ (71 mg, 0.09 mmol) and KOAc (268 mg, 2.73 mmol) in DMF (10.0 mL) was stirred at 90° C. under N$_2$ for 3 hrs. After the reaction was completed, the mixture was cooled to rt, diluted with EtOAc (80.0 mL) and filtered through a celite pad. The filtrate was washed with water (30 mL×3) and brine, dried over anhydrous Na$_2$SO$_4$ and concentrated in vacuo. The residue was purified by a silica gel column chromatography (PE/EtOAc (v/v)=2/1) to give the title compound (492 mg, 85%) as a pale yellow solid. The compound was characterized by the following spectroscopic data:

MS (ESI, pos.ion) m/z: 637.5 [M+H]$^+$;

$^1$H NMR (400 MHz, CDCl$_3$) δ (ppm): 7.80, 7.78 (s, s, 1H), 7.70, 7.68 (s, s, 1H), 7.63-7.59 (m, 3H), 7.58-7.55 (m, 2H), 7.15-7.12 (m, 1H), 6.84-6.81 (m, 1H), 5.56, 5.55 (br, br, 1H), 5.23-5.19 (m, 1H), 4.52-4.49 (m, 1H), 4.38-4.35 (m, 1H), 4.34-4.30 (m, 1H), 3.85-3.78 (m, 1H), 3.66 (s, 3H), 3.65-3.61 (m, 1H), 2.33-2.16 (m, 5H), 2.13-1.92 (m, 2H), 1.32 (m, 6H), 1.29 (m, 6H), 1.02-0.91 (m, 6H).

Step 4) the Preparation of Compound 51-4

To a mixture of compound 51-3 (388 mg, 0.61 mmol), compound 15-2 (256 mg, 0.61 mmol), Pd(PPh$_3$)$_4$ (70 mg, 0.05 mmol) and K$_2$CO$_3$ (254 mg, 1.83 mmol) were added DME (5.0 mL) and pure water (1.0 mL) via syringe and the mixture was stirred at 90° C. under N$_2$ for 4 hrs. After the reaction was completed, the mixture was cooled to rt and diluted with EtOAc (40.0 mL). The resulting mixture was washed with water (20.0 mL×3) and brine, dried over anhydrous Na$_2$SO$_4$ and concentrated in vacuo. The residue was purified by a silica gel column chromatography (PE/EtOAc (v/v)=1/2) to give the title compound (440 mg, 90%). The compound was characterized by the following spectroscopic data:

MS (ESI, pos.ion) m/z: 803.5 [M+H]$^+$;

$^1$H NMR (400 MHz, CDCl$_3$) δ (ppm): 7.86 (s, 1H), 7.63-7.59 (m, 3H), 7.57-7.54 (m, 2H), 7.51, 7.49 (s, s, 1H), 7.39, 7.37 (s, s, 1H), 6.99-6.96 (m, 1H), 6.92-6.89 (m, 1H), 5.56, 5.55 (br, br, 1H), 5.32, 5.30 (br, br, 1H), 5.29-5.25 (m, 1H), 5.23-5.19 (m, 1H), 4.48-4.43 (m, 2H), 4.41-4.30 (m, 2H), 3.85-3.78 (m, 2H), 3.66 (s, 3H), 3.65-3.64 (m, 2H), 3.63 (s, 3H), 2.40-2.36 (m, 1H), 2.32-1.92 (m, 11H), 1.02-0.89 (m, 12H).

Example 52

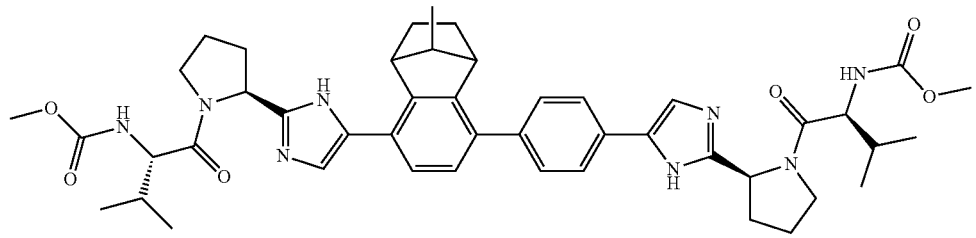

Synthetic Route:

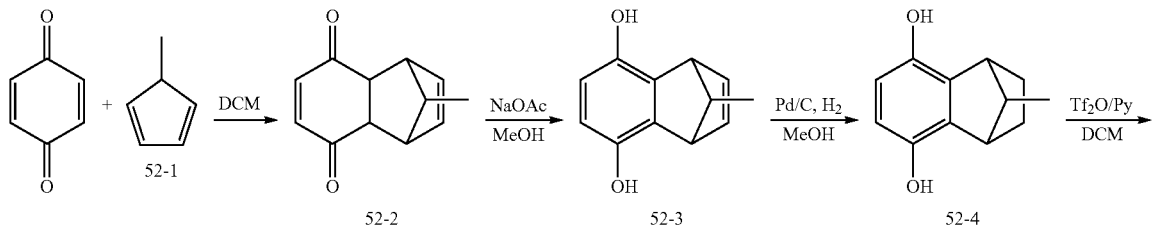

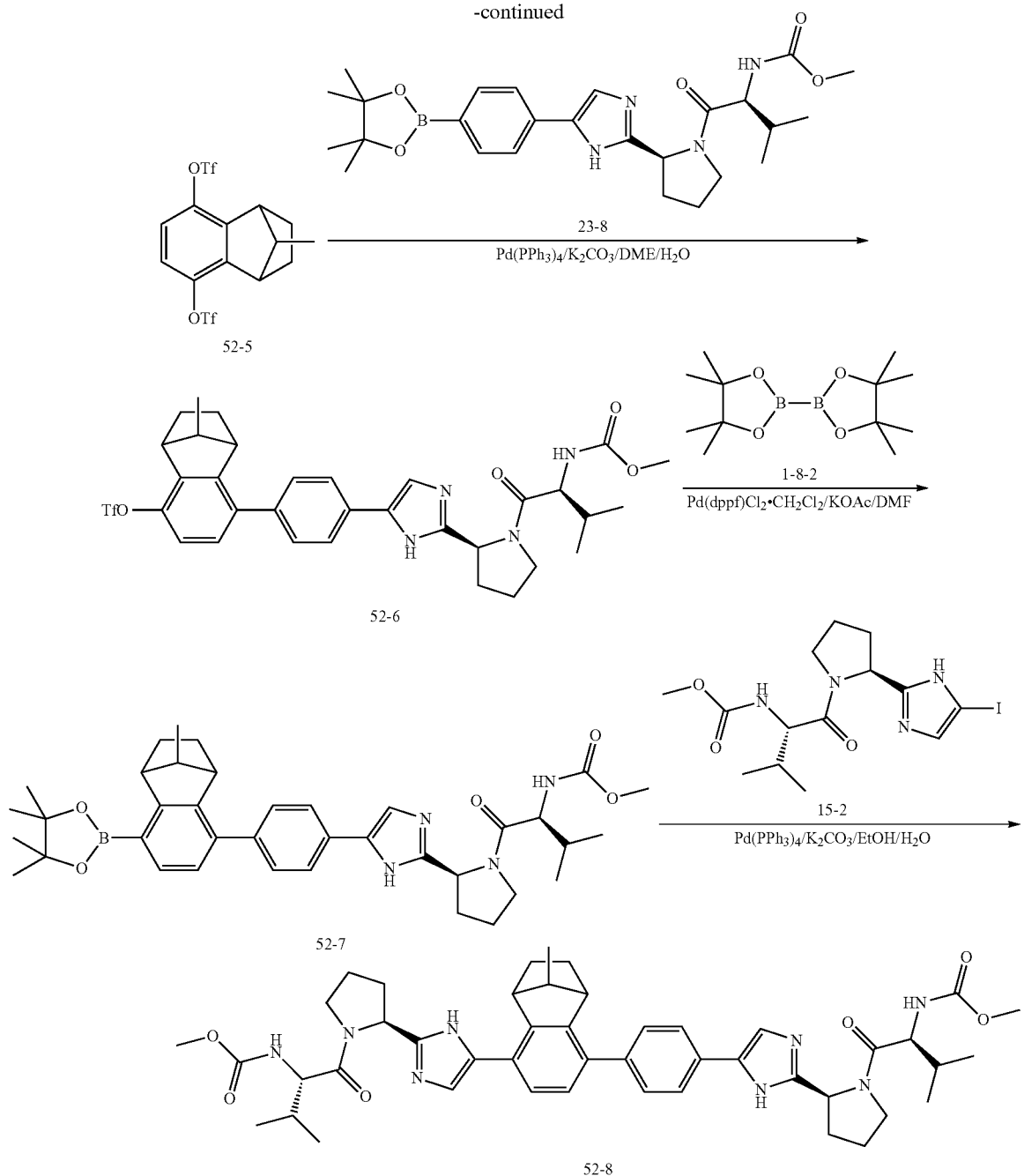

Step 1) the Preparation of Compound 52-2

To a solution of 1,4-benzoquinone (10.0 g, 92.5 mmol) in DCM (50.0 mL) was added compound 52-1 (11.12 g, 138.8 mmol) dropwsie at −10° C. At the end of addition, the mixture was stirred at −10° C. for 1 hr and at rt for another 0.5 hr. After the reaction was completed, the mixture was concentrated in vacuo. The residue was added 500 mL of hexane, and then stirred and filtered. The filtrate was concentrated in vacuo to give the title compound (11.3 g, 65%) as a pale yellow solid. The compound was characterized by the following spectroscopic data:

MS (ESI, pos.ion) m/z: 189.3 [M+H]$^+$;

$^1$H NMR (400 MHz, CDCl$_3$) δ (ppm): 6.71 (d, 2H), 6.20-6.19 (m, 2H), 3.08-3.05 (m, 2H), 2.46-2.44 (m, 2H), 2.30-2.23 (m, 1H), 0.96-0.93 (m, 3H).

Step 2) the Preparation of Compound 52-3

A suspension of compound 52-2 (5.94 g, 31.6 mmol) and sodium acetate (7.77 g, 94.7 mmol) in methanol (100 mL) was stirred at 50° C. under N$_2$ for 3 hrs. After the reaction was completed, the mixture was concentrated in vacuo to give the title compound (5.5 g, 92.7%) as a white solid. The compound was characterized by the following spectroscopic data:

MS (ESI, pos.ion) m/z: 189.5 [M+H]$^+$;

$^1$H NMR (400 MHz, CDCl$_3$) δ (ppm): 6.65-6.64 (m, 2H), 6.47 (s, 2H), 5.41 (br, 2H), 3.76-3.72 (m, 2H), 2.64-2.57 (m, 1H), 1.15-1.12 (m, 3H).

Step 3) the Preparation of Compound 52-4

A suspension of compound 52-3 (5.07 g, 27.0 mmol) and a catalytic amount of Pd/C (500 mg) in methanol (50.0 mL) was stirred at rt under $H_2$ for 1.5 hrs. After the reaction was completed, the mixture was filtered, and then the filtrated was concentrated in vacuo and the residue was purified by recrystallization to give the title compound (3.59 g, 70%) as a white solid. The compound was characterized by the following spectroscopic data:

$^1$H NMR (400 MHz, CDCl$_3$) δ (ppm): 6.40 (s, 2H), 5.77 (br, 2H), 3.10-3.08 (m, 2H), 2.42-2.34 (m, 1H), 2.08-2.04 (m, 2H), 1.34-1.30 (m, 2H), 0.90-0.87 (m, 3H).

Step 4) the Preparation of Compound 52-5

To a solution of compound 52-4 (3.61 g, 19.0 mmol) in DCM (90.0 mL) was added pyridine (9.0 g, 114 mmol) dropwise at 0° C. After stirring for 10 mins, trifluoromethanesulfonic anhydride (21.0 g, 76.0 mmol) was added. At the end of addition, the mixture was stirred at rt for 1 hr. After the reaction was completed, the mixture was quenched with water (50.0 mL) and diluted with DCM (50.0 mL). The organic layers were washed with brine, dried over anhydrous Na$_2$SO$_4$ and concentrated in vacuo. The residue was purified by a silica gel column chromatography (PE/DCM (v/v)=20/1) to give the title compound (8.45 g, 98.0%) as colorless oil. The compound was characterized by the following spectroscopic data:

$^1$H NMR (400 MHz, CDCl$_3$) δ (ppm): 7.27 (s, 2H), 3.22-3.19 (m, 2H), 2.17-2.10 (m, 1H), 2.03-1.99 (m, 2H), 1.29-1.25 (m, 2H), 1.03-1.01 (m, 3H).

Step 5) the Preparation of Compound 52-6

To a mixture of compound 52-5 (461 mg, 1.016 mmol), compound 23-8 (504 mg, 1.016 mmol), Pd(PPh$_3$)$_4$ (117 mg, 0.1016 mmol) and K$_2$CO$_3$ (420.7 mg, 3.048 mmol) were added DME (10.0 mL) and pure water (2.5 mL) via syringe. The mixture was stirred at 90° C. under N$_2$ for 4 hrs. After the reaction was completed, the mixture was cooled to rt and diluted with EtOAc (40.0 mL). The resulting mixture was washed with water (20 mL×3) and brine, dried over anhydrous Na$_2$SO$_4$ and concentrated in vacuo. The residue was purified by a silica gel column chromatography (PE/EtOAc (v/v)=1/2) to give the title compound (440 mg, 90%). The compound was characterized by the following spectroscopic data:

MS (ESI, pos.ion) m/z: 675.5 [M+H]$^+$;

$^1$H NMR (400 MHz, CDCl$_3$) δ (ppm) 7.62-7.59 (m, 3H), 7.52-7.48 (m, 2H), 7.23, 7.21 (s, s, 1H), 7.06, 7.04 (s, s, 1H), 5.56, 5.55 (br, br, 1H), 5.23-5.19 (m, 1H), 4.34-4.30 (m, 1H), 3.85-3.78 (m, 1H), 3.66 (s, 3H), 3.65-3.61 (m, 1H), 3.48-3.45 (m, 1H), 3.15-3.12 (m, 2H), 2.36-2.16 (m, 4H), 2.13-1.92 (m, 2H), 1.31-1.24 (m, 4H), 1.02-0.91 (m, 6H), 0.85-0.83 (m, 3H).

Step 6) the Preparation of Compound 52-7

A mixture of compound 52-6 (3.5 g, 5.2 mmol), compound 1-8-2 (1.59 g, 6.25 mmol), Pd(dppf)Cl$_2$·CH$_2$Cl$_2$ (425 mg, 0.52 mmol) and KOAc (1.54 g, 15.63 mmol) in DMF (30.0 mL) was stirred at 90° C. under N$_2$ for 3 hrs. After the reaction was completed, the mixture was cooled to rt, diluted with EtOAc (200 mL) and filtered through a celite pad. The filtrate was washed with water (100 mL×3) and brine, dried over anhydrous Na$_2$SO$_4$ and concentrated in vacuo. The residue was purified by a silica gel column chromatography (PE/EtOAc (v/v)=2/1) to give the title compound (3.05 g, 90%) as a pale yellow solid. The compound was characterized by the following spectroscopic data:

MS (ESI, pos.ion) m/z: 652.3 [M+H]$^+$;

$^1$H NMR (400 MHz, CDCl$_3$) δ (ppm) 7.85, 7.83 (s, s, 1H), 7.65, 7.63 (s, s, 1H), 7.62-7.59 (m, 3H), 7.56-7.53 (m, 2H), 5.56, 5.55 (br, br, 1H), 5.23-5.19 (m, 1H), 4.34-4.30 (m, 1H), 3.85-3.78 (m, 1H), 3.66 (s, 3H), 3.65-3.61 (m, 1H), 3.17-3.12 (m, 1H), 3.13-3.09 (m, 1H), 2.72-2.65 (m, 1H), 2.30-2.16 (m, 3H), 2.13-1.92 (m, 4H), 1.34-1.24 (m, 14H), 1.02-0.91 (m, 6H), 0.82-0.80 (m, 3H).

Step 7) the Preparation of Compound 52-8

To a mixture of compound 52-7 (340.5 mg, 0.522 mmol), compound 15-2 (241.1 mg, 0.574 mmol), Pd(PPh$_3$)$_4$ (60.29 mg, 0.0522 mmol) and K$_2$CO$_3$ (216 mg, 1.566 mmol) were added DME (6.0 mL) and pure water (1.5 mL) via syringe and the mixture was stirred at 90° C. under N$_2$ for 4 hrs. After the reaction was completed, the mixture was cooled to rt and diluted with EtOAc (50.0 mL). The resulting mixture was washed with water (20 mL×3) and brine, dried over anhydrous Na$_2$SO$_4$ and concentrated in vacuo. The residue was purified by a silica gel column chromatography (DCM/EtOH (v/v)=100/1) to give the title compound (213.6 mg, 50%). The compound was characterized by the following spectroscopic data:

MS (ESI, pos.ion) m/z: 410.5 [M+2H]$^{2+}$;

$^1$H NMR (400 MHz, CDCl$_3$) δ (ppm): 7.80 (s, 1H), 7.63-7.59 (m, 3H), 7.56-7.52 (m, 2H), 7.45, 7.42 (s, s, 1H), 7.33, 7.31 (s, s, 1H), 5.56, 5.55 (br, br, 1H), 5.32, 5.30 (br, br, 1H), 5.29-5.25 (m, 1H), 5.23-5.19 (m, 1H), 4.41-4.30 (m, 2H), 3.85-3.78 (m, 2H), 3.66 (s, 3H), 3.65-3.64 (m, 1H), 3.63 (s, 3H), 3.52-3.48 (m, 1H), 3.41-3.37 (m, 1H), 2.40-2.33 (m, 1H), 2.30-2.15 (m, 6H), 2.13-1.92 (m, 6H), 1.34-1.27 (m, 2H), 1.02-0.89 (m, 12H), 0.88-0.86 (m, 3H).

Example 53

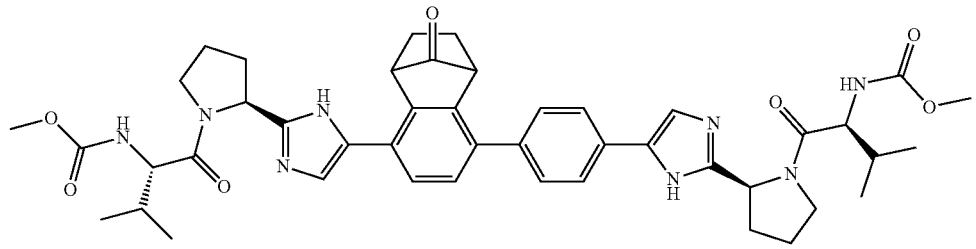

Synthetic Route:
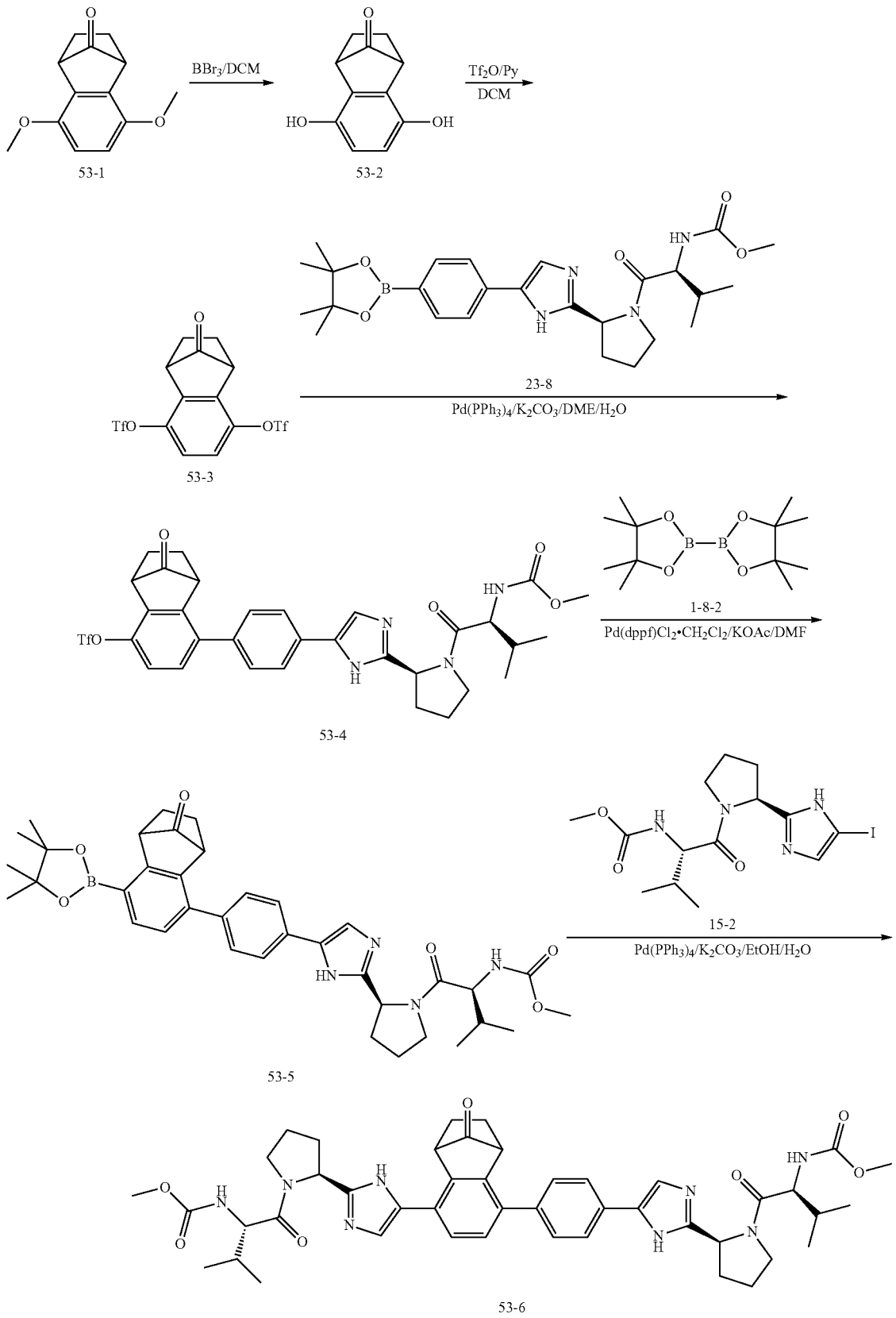

Step 1) the Preparation of Compound 53-2

To a solution of compound 53-1 (1.48 g, 6.8 mmol) in DCM (20.0 mL) was added boron tribromide (9.0 mL, 22.5 mmol, 2.5 M in DCM) dropwise at −78° C. At the end of addition, the mixture was stirred at rt for 1 hr. After the reaction was completed, the mixture was quenched with ice-water (50 mL). The aqueous layer was extracted with DCM (50 mL×3). The combined organic layers were washed with brine, dried over anhydrous $Na_2SO_4$ and concentrated in vacuo. The residue was purified by a silica gel column chromatography (PE/EtOAc (v/v)=10/1) to give the title compound (1.19 g, 92%) as colorless oil. The compound was characterized by the following spectroscopic data:

MS (ESI, pos.ion) m/z: 191.5 $[M+H]^+$;
$^1$H NMR (400 MHz, $CDCl_3$) δ (ppm): 6.59 (s, 2H), 5.49 (br, 2H), 3.64-3.58 (m, 2H), 2.50-2.41 (m, 2H), 2.15-2.05 (m, 2H).

Step 2) the Preparation of Compound 53-3

To a solution of compound 53-2 (3.61 g, 19.0 mmol) in DCM (50.0 mL) was added pyridine (9.00 g, 114 mmol) dropwise at 0° C. After stirring for 10 mins, trifluoromethanesulfonic anhydride (21.0 g, 76.0 mmol) was added. At the end of addition, the mixture was stirred at rt for 1 hr. After the reaction was completed, the mixture was quenched with ice-water (50.0 mL). The aqueous layer was extracted with DCM (50 mL×3). The combined organic layers were washed with brine, dried over anhydrous $Na_2SO_4$ and concentrated in vacuo. The residue was purified by a silica gel column chromatography (PE/DCM (v/v)=20/1) to give the title compound (7.76 g, 90%) as colorless oil. The compound was characterized by the following spectroscopic data:

$^1$H NMR (400 MHz, $CDCl_3$) δ (ppm): 7.36 (s, 2H), 3.61-3.55 (m, 2H), 2.56-2.47 (m, 2H), 2.20-2.12 (m, 2H).

Step 3) the Preparation of Compound 53-4

To a mixture of compound 53-3 (461 mg, 1.016 mmol), compound 23-8 (504 mg, 1.016 mmol), $Pd(PPh_3)_4$ (117 mg, 0.1016 mmol) and $K_2CO_3$ (420.7 mg, 3.048 mmol) were added DME (10.0 mL) and pure water (2.5 mL) via syringe and the mixture was stirred at 90° C. under $N_2$ for 4 hrs. After the reaction was completed, the mixture was cooled to rt and diluted with EtOAc (20.0 mL). The resulting mixture was washed with water (10 mL×3) and brine, dried over anhydrous $Na_2SO_4$ and concentrated in vacuo. The residue was purified by a silica gel column chromatography (DCM/EtOH (v/v)=100/1) to give the title compound (363 mg, 53%). The compound was characterized by the following spectroscopic data:

MS (ESI, pos.ion) m/z: 675.5 $[M+H]^+$;
$^1$H NMR (400 MHz, $CDCl_3$) δ (ppm): 7.64-7.59 (m, 3H), 7.56-7.53 (m, 2H), 7.26, 7.24 (s, s, 1H), 7.11, 7.09 (s, s, 1H), 5.56, 5.55 (br, br, 1H), 5.23-5.19 (m, 1H), 4.34-4.30 (m, 1H), 3.85-3.78 (m, 2H), 3.76-3.74 (m, 1H), 3.68-3.67 (m, 1H), 3.66 (s, 3H), 2.57-2.45 (m, 2H), 2.30-1.92 (m, 7H), 1.02-0.91 (m, 6H).

Step 4) the Preparation of Compound 53-5

A mixture of compound 53-4 (1.75 g, 2.60 mmol), compound 1-8-2 (795 mg, 3.125 mmol), $Pd(dppf)Cl_2 \cdot CH_2Cl_2$ (212.5 mg, 0.26 mmol) and KOAc (770 mg, 7.82 mmol) in DMF (15.0 mL) was stirred at 90° C. under $N_2$ for 3 hrs. After the reaction was completed, the mixture was cooled to rt, diluted with EtOAc (100 mL) and filtered through a celite pad. The filtrate was washed with water (50 mL×3) and brine, dried over anhydrous $Na_2SO_4$ and concentrated in vacuo. The residue was purified by a silica gel column chromatography (PE/EtOAc (v/v)=2/1) to give the title compound (1.53 g, 90%) as a pale yellow solid. The compound was characterized by the following spectroscopic data:

MS (ESI, pos.ion) m/z: 652.3 $[M+H]^+$;
$^1$H NMR (400 MHz, $CDCl_3$) δ (ppm): 7.80, 7.78 (s, s, 1H), 7.64-7.57 (m, 5H), 7.55, 7.52 (s, s, 1H), 5.56, 5.55 (br, br, 1H), 5.23-5.19 (m, 1H), 4.34-4.30 (m, 1H), 3.85-3.79 (m, 2H), 3.66 (s, 3H), 3.65-3.61 (m, 1H), 3.04-3.02 (m, 1H), 2.46-2.35 (m, 2H), 2.30-2.16 (m, 3H), 2.13-1.92 (m, 4H), 1.32 (m, 6H), 1.29 (m, 6H), 1.02-0.91 (m, 6H).

Step 5) the Preparation of Compound 53-6

To a mixture of compound 53-5 (340.5 mg, 0.522 mmol), compound 15-2 (241.1 mg, 0.574 mmol), $Pd(PPh_3)_4$ (60.29 mg, 0.0522 mmol) and $K_2CO_3$ (216 mg, 1.566 mmol) were added DME (6.0 mL) and pure water (1.5 mL) via syringe and the mixture was stirred at 90° C. under $N_2$ for 4 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by a silica gel column chromatography (DCM/EtOH (v/v)=100/1) to give the title compound (213.6 mg, 50%). The compound was characterized by the following spectroscopic data:

MS (ESI, pos.ion) m/z: 410.5 $[M+2H]^{2+}$;
$^1$H NMR (400 MHz, $CDCl_3$) δ (ppm): 7.83 (s, 1H), 7.64-7.57 (m, 5H), 7.51, 7.49 (s, s, 1H), 7.46, 7.44 (s, s, 1H), 5.56, 5.55 (br, br, 1H), 5.32, 5.29 (br, br, 1H), 5.29-5.25 (m, 1H), 5.23-5.19 (m, 1H), 4.41-4.30 (m, 2H), 3.99-3.97 (m, 1H), 3.85-3.78 (m, 2H), 3.68-3.67 (m, 1H), 3.66 (s, 3H), 3.65-3.64 (m, 1H), 3.63 (m, 3H), 3.28-3.26 (m, 1H), 2.59-2.51 (m, 1H), 2.47-2.39 (m, 1H), 2.30-2.15 (m, 7H), 2.13-1.92 (m, 5H), 1.02-0.89 (m, 12H).

Example 54

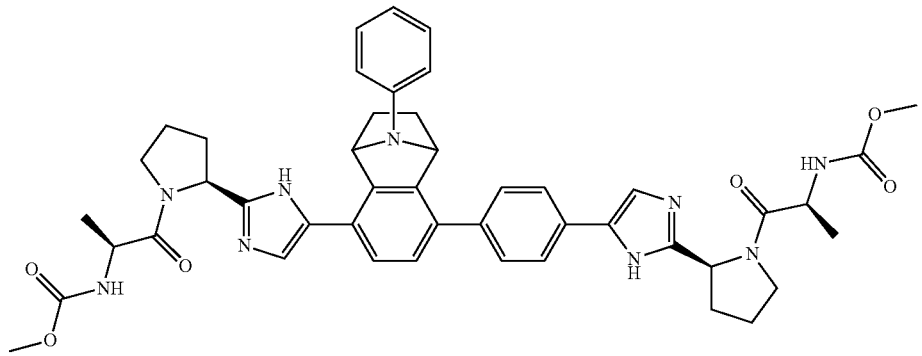

Synthetic Route:
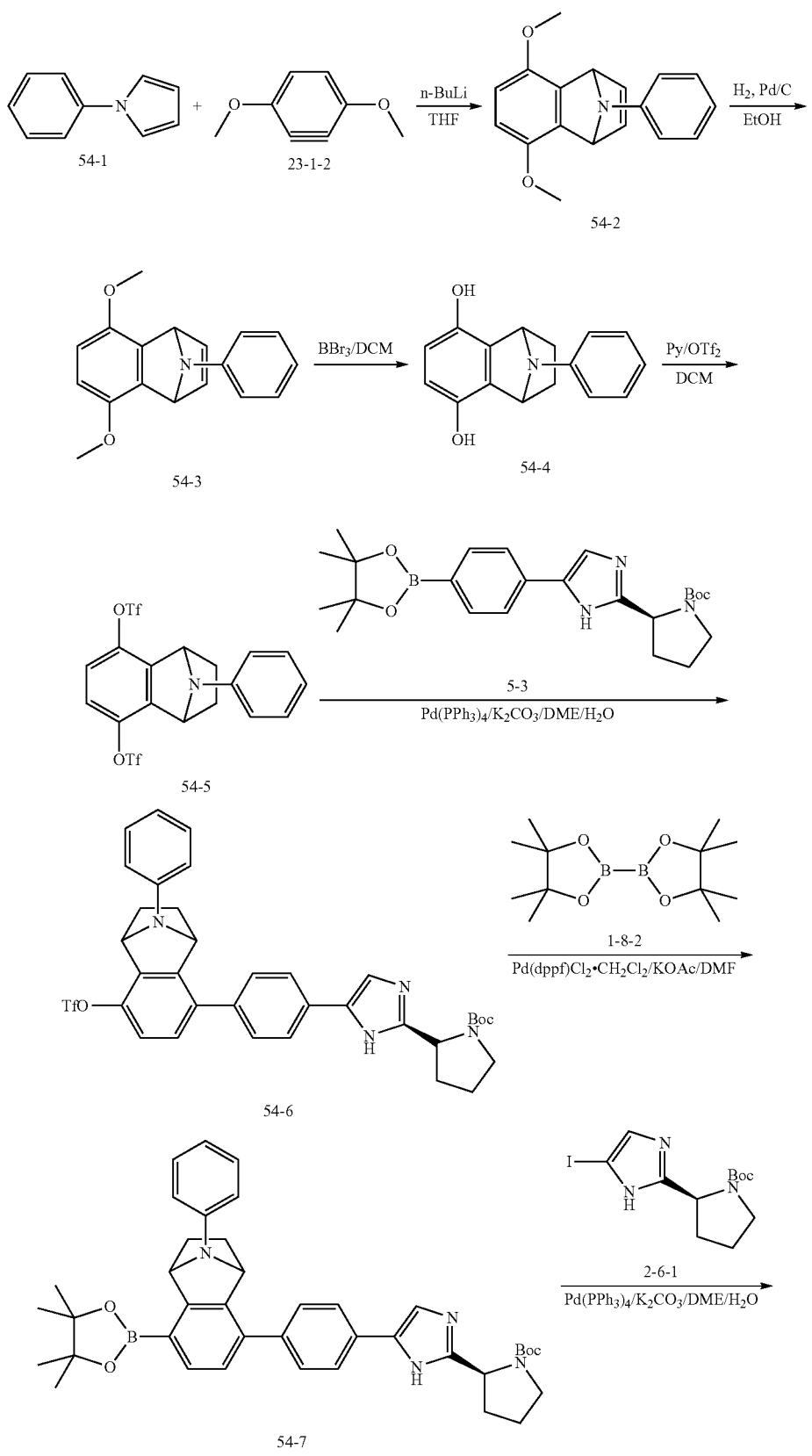

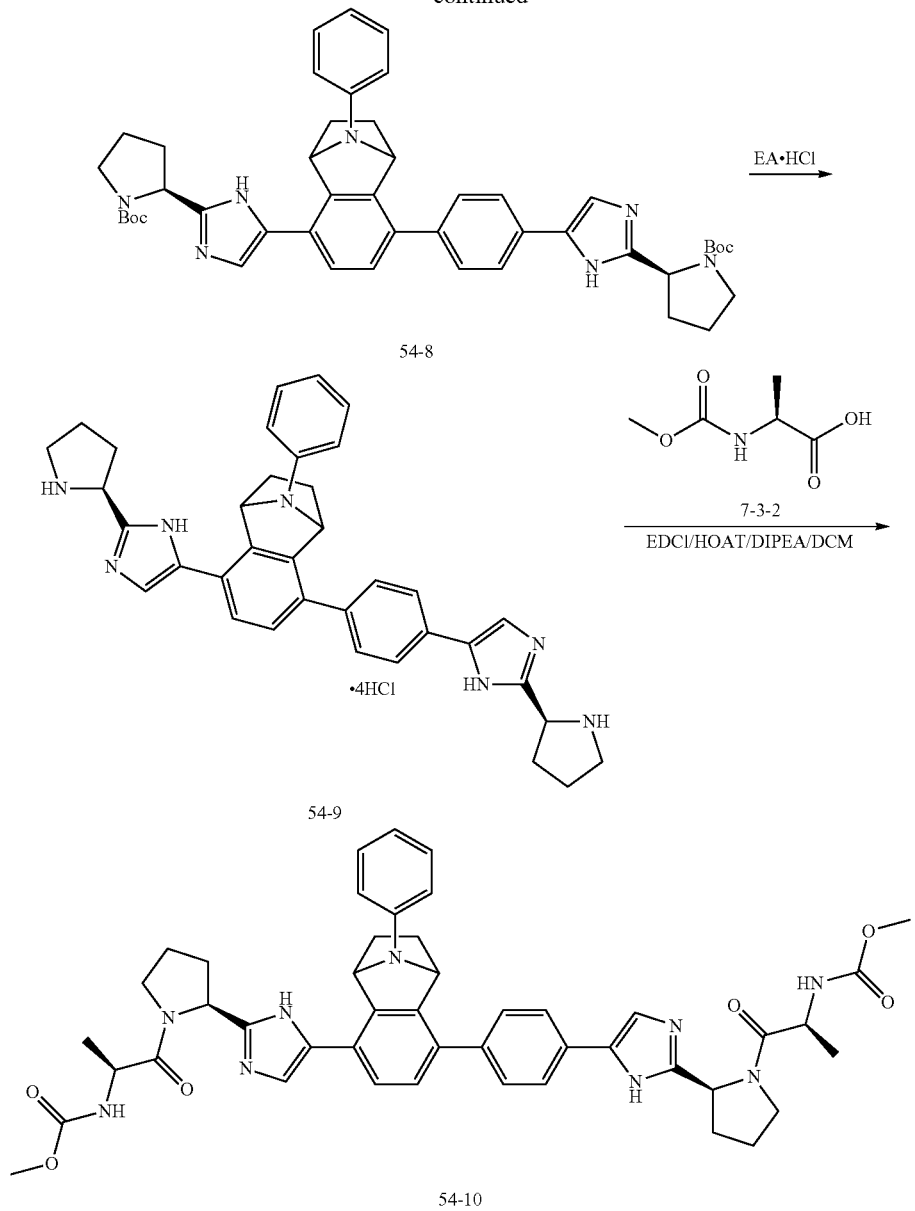

54-8

54-9

54-10

Step 1) the Preparation of Compound 54-2

To a mixture of compound 54-1 (2.72 g, 19.0 mmol) and compound 23-1-2 (1.36 g, 10.0 mmol) in dry THF (50.0 mL) was added n-butyllithium (1.6 M solution in hexane, 6.7 mL) at −78° C. under nitrogen. After stirring at −78° C. for 1 hr, the mixture was warmed to room temperature over 1-2 hrs and stirred overnight. After the reaction was completed, the mixture was poured into water (50.0 mL) and the organic phase separated. The aqueous layer was extracted further with diethyl ether (50 mL×3). The combined organic layers were dried over anhydrous $Na_2SO_4$ and concentrated in vacuo. The residue was purified by a silica gel column chromatography (PE/EtOAc (v/v)=5/1) to give the title compound (1.395 g, 50%) as a pale yellow solid. The compound was characterized by the following spectroscopic data:

MS (ESI, pos.ion) m/z: 280.5 $[M+H]^+$;

$^1H$ NMR (400 MHz, $CDCl_3$) δ (ppm): 7.36-7.31 (m, 2H), 7.01-7.00 (t, 2H), 6.82-6.78 (m, 1H), 6.70-6.69 (m, 2H), 6.53-6.50 (m, 2H), 5.52-5.51 (t, 2H), 3.69 (br, 6H).

Step 2) the Preparation of Compound 54-3

To a solution of compound 54-2 (2.24 g, 8.03 mmol) in ethanol (40.0 mL) was added a catalytic amount of Pd/C (0.35 g), the mixture was stirred under 10 atm of $H_2$ gas at rt for 24 hrs. After the reaction was completed, the mixture was filtered. The filtrate was concentrated in vacuo to give the title compound 54-3 (1.8 g, 80%) as a white solid. The compound was characterized by the following spectroscopic data:

MS (ESI, pos.ion) m/z: 282.5 $[M+H]^+$;

$^1H$ NMR (400 MHz, $CDCl_3$) δ (ppm): 7.30-7.25 (m, 2H), 6.78-6.74 (m, 1H), 6.73-6.69 (m, 2H), 6.59 (br, 2H), 5.01-4.96 (m, 2H), 3.73 (s, 6H), 2.20-2.11 (m, 2H), 1.77-1.71 (m, 2H).

Step 3) the Preparation of Compound 54-4

To a solution of compound 54-3 (2.81 g, 10.0 mmol) in DCM (50.0 mL) was added boron tribromide (7.7 mL, 80 mmol) dropwise at −78° C. After stirring for 10 mins, the mixture was stirred at rt for 1 hr. After the reaction was completed, the mixture was quenched with ice-water (50.0 mL) and the organic phase separated. The aqueous layer was extracted with DCM (50 mL×3). The combined organic layers were washed with brine, dried over anhydrous $Na_2SO_4$ and concentrated in vacuo. The residue was purified by a silica gel column chromatography (PE/EtOAc (v/v)=15/1) to give the title compound 23-4 (2.15 g, 85%) as colorless oil. The compound was characterized by the following spectroscopic data:

MS (ESI, pos.ion) m/z: 254.5 $[M+H]^+$;
$^1$H NMR (400 MHz, CDCl$_3$) δ (ppm): 7.30-7.25 (m, 2H), 6.81-6.77 (m, 2H), 6.76-6.74 (m, 1H), 6.48 (s, 2H), 5.77 (br, 2H), 4.89-4.84 (m, 2H), 2.34-2.25 (m, 2H), 1.94-1.83 (m, 2H).

Step 4) the Preparation of Compound 54-5

To a solution of compound 54-4 (2.53 g, 10.0 mmol) in DCM (20.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous $Na_2SO_4$ and concentrated in vacuo. The residue was purified by a silica gel column chromatography (PE/EtOAc (v/v)=40/1) to give the title compound (4.65 g, 90.0%) as colorless oil. The compound was characterized by the following spectroscopic data:

$^1$H NMR (400 MHz, CDCl$_3$) δ (ppm): 7.30-7.25 (m, 4H), 6.81-6.77 (m, 2H), 6.76-6.74 (m, 1H), 5.21-5.15 (m, 2H), 2.09-2.01 (m, 2H), 1.68-1.59 (m, 2H).

Step 5) the Preparation of Compound 54-6

To a mixture of compound 5-3 (1.15 g, 2.62 mmol), compound 54-5 (1.35 g, 2.62 mmol), Pd(PPh$_3$)$_4$ (120 mg, 0.10 mmol) and KF (0.30 g, 5.24 mmol) were added DME (12.0 mL) and H$_2$O (3.0 mL) via syringe, the mixture was stirred at 90° C. under N$_2$ for 2 hrs. After the reaction was completed, the mixture was cooled to rt, diluted with EtOAc (50.0 mL) and washed with water (20 mL×3). The combined organic layers were dried over anhydrous $Na_2SO_4$ and concentrated in vacuo. The residue was purified by a silica gel column chromatography (DCM/MeOH (v/v)=100/1) to give the title compound (1.1 g, 62%) as a white solid. The compound was characterized by the following spectroscopic data:

MS (ESI, pos.ion) m/z: 681.3 $[M+H]^+$;
$^1$H NMR (400 MHz, CDCl$_3$) δ (ppm): 7.63-7.60 (m, 2H), 7.59 (s, 1H), 7.52-7.49 (m, 2H), 7.30-7.25 (m, 2H), 7.19, 7.17 (s, s, 1H), 7.05, 7.03 (s, s, 1H), 6.78-6.74 (m, 3H), 4.98-4.92 (m, 1H), 4.91-4.89 (m, 1H), 4.85-4.83 (m, 1H), 3.65-3.58 (m, 1H), 3.31-3.23 (m, 1H), 2.47-2.38 (m, 1H), 2.28-2.13 (m, 2H), 2.10-1.97 (m, 3H), 1.80-1.72 (m, 1H), 1.65-1.57 (m, 1H), 1.53 (s, 9H).

Step 6) the Preparation of Compound 54-7

A mixture of compound 54-6 (1.1 g, 1.61 mmol), compound 1-8-2 (450 mg, 10.7 mmol), Pd(dppf)Cl$_2$.CH$_2$Cl$_2$ (80 mg, 0.096 mmol) and KOAc (400 mg, 4.02 mmol) in DMF (10.0 mL) was stirred at 120° C. under N$_2$ for 4 hrs. After the reaction was completed, the mixture was cooled to rt, diluted with EtOAc (100 mL) and filtered through a celite pad. The filtrate was washed with water (30 mL×3) and brine, dried over anhydrous $Na_2SO_4$ and concentrated in vacuo. The residue was purified by a silica gel column chromatography (PE/EtOAc (v/v)=3/1) to give the title compound (1.53 g, 90%) as a white solid. The compound was characterized by the following spectroscopic data:

MS (ESI, pos.ion) m/z: 659.5 $[M+H]^+$;
$^1$H NMR (400 MHz, CDCl$_3$) δ (ppm): 7.83-7.80 (s, s, 1H), 7.63-7.60 (m, 2H), 7.59 (s, 1H), 7.57-7.53 (m, 2H), 7.47, 7.45 (s, s, 1H), 7.30-7.25 (m, 2H), 6.79-6.74 (m, 3H), 5.21-5.19 (m, 1H), 4.97-4.93 (m, 1H), 4.62-4.60 (m, 1H), 3.65-3.58 (m, 1H), 3.31-3.23 (m, 1H), 2.47-2.38 (m, 1H), 2.28-2.16 (m, 1H), 2.10-1.97 (m, 2H), 1.93-1.81 (m, 2H), 1.53 (s, 9H), 1.48-1.34 (m, 2H), 1.32 (m, 6H), 1.29 (m, 6H).

Step 7) the Preparation of Compound 54-8

A mixture of compound 2-6-1 (167 mg, 0.446 mmol), compound 54-7 (276.5 mg, 0.42 mmol), Pd(PPh$_3$)$_4$ (25.0 mg, 0.02 mmol) and K$_2$CO$_3$ (170 mg, 1.27 mmol) in the mixed solvent of EtOH/H$_2$O (8.0 mL, v/v=3/1) was stirred at 90° C. under N$_2$ for 2 hrs. After the reaction was completed, the mixture was cooled to rt, diluted with EtOAc (50.0 mL) and washed with water (20.0 mL×3) and brine. The combined organic layers were dried over anhydrous $Na_2SO_4$ and concentrated in vacuo. The residue was purified by a silica gel column chromatography (DCM/MeOH (v/v)=50/1) to give the title compound (274 mg, 85%) as a pale yellow solid. The compound was characterized by the following spectroscopic data:

MS (ESI, pos.ion) m/z: 768.5 $[M+H]^+$;
$^1$H NMR (400 MHz, CDCl$_3$) δ (ppm): 7.73 (s, 1H), 7.63-7.60 (m, 2H), 7.59 (s, 1H), 7.56-7.53 (m, 2H), 7.49, 7.47 (s, s, 1H), 7.36, 7.34 (s, s, 1H), 7.30-7.25 (m, 2H), 6.78-6.71 (m, 3H), 5.05-5.01 (m, 2H), 4.97-4.93 (m, 1H), 4.60-4.58 (m, 1H), 3.65-3.58 (m, 2H), 3.31-3.24 (m, 2H), 2.47-2.38 (m, 2H), 2.29-2.16 (m, 3H), 2.13-1.97 (m, 5H), 1.88-1.80 (m, 1H), 1.72-1.64 (m, 1H), 1.53 (s, 18H).

Step 8) the Preparation of Compound 54-9

To a solution of compound 54-8 (391.38 mg, 0.51 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (20.0 mL), and then filtered to give the title compound (309 mg, 85%) as pale yellow powder. The compound was characterized by the following spectroscopic data:

MS (ESI, pos.ion) m/z: 568.5 $[M+H]^+$.

Step 9) the Preparation of Compound 50-10

To a suspension of compound 54-9 (207 mg, 0.29 mmol), compound 1-4-2 (95.58 mg, 0.65 mmol), EDCI (120 mg, 0.65 mmol) and HOAT (80 mg, 0.59 mmol) in DCM (5.0 mL) was added DIPEA (0.6 mL, 3.63 mmol) dropwise at 0° C. At the end of addition, the mixture was stirred at rt for 3 hrs. After the reaction was completed, the mixture was diluted with DCM (20.0 mL). The resulting mixture was washed with NH$_4$Cl aqueous solution and brine, dried over Na$_2$SO$_4$ and concentrated in vacuo. The residue was purified by a silica gel column chromatography (DCM/MeOH (v/v)=40/1) to give the title compound (107.7 mg, 45%) as a yellow solid. The compound was characterized by the following spectroscopic data:

MS (ESI, pos.ion) m/z: 826.3 $[M+H]^+$;
$^1$H NMR (400 MHz, CDCl$_3$) δ (ppm): 7.65 (s, 1H), 7.63-7.59 (m, 3H), 7.56-7.53 (m, 2H), 7.49, 7.47 (s, s, 1H), 7.36, 7.34 (s, s, 1H), 7.30-7.25 (m, 2H), 6.78-6.71 (m, 3H), 5.44 (m, 1H), 5.42 (m, 1H), 5.15-5.11 (m, 1H), 5.10-5.05 (m, 1H), 5.04-5.02 (m, 1H), 4.64-4.57 (m, 3H), 3.88-3.81 (m, 2H), 3.71-3.65 (m, 2H), 3.64 (s, 6H), 2.33-2.06 (m, 8H), 2.04-1.94 (m, 2H), 1.88-1.80 (m, 1H), 1.72-1.64 (m, 1H), 1.36 (d, 3H), 1.34 (d, 3H).

Example 55
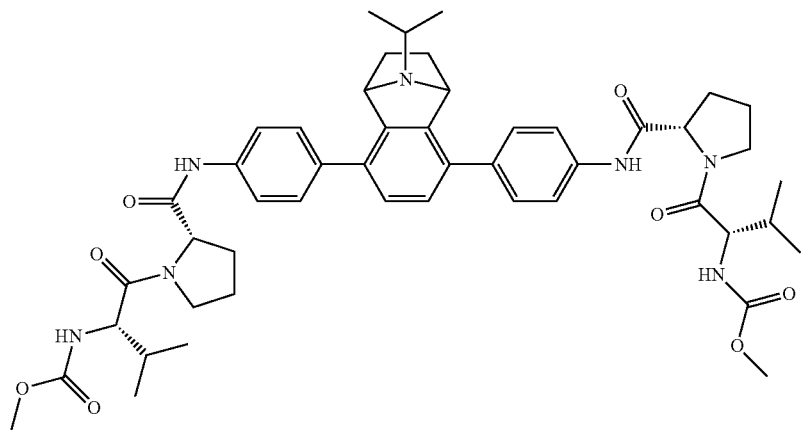 [SMILES: COC(=O)N[C@H](C(=O)N1CCC[C@H]1C(=O)Nc1ccc(-c2ccc(-c3ccc(NC(=O)[C@@H]4CCCN4C(=O)[C@@H](NC(=O)OC)C(C)C)cc3)c3c2C2CCC3N2C(C)C)cc1)C(C)C]
Synthetic Route:
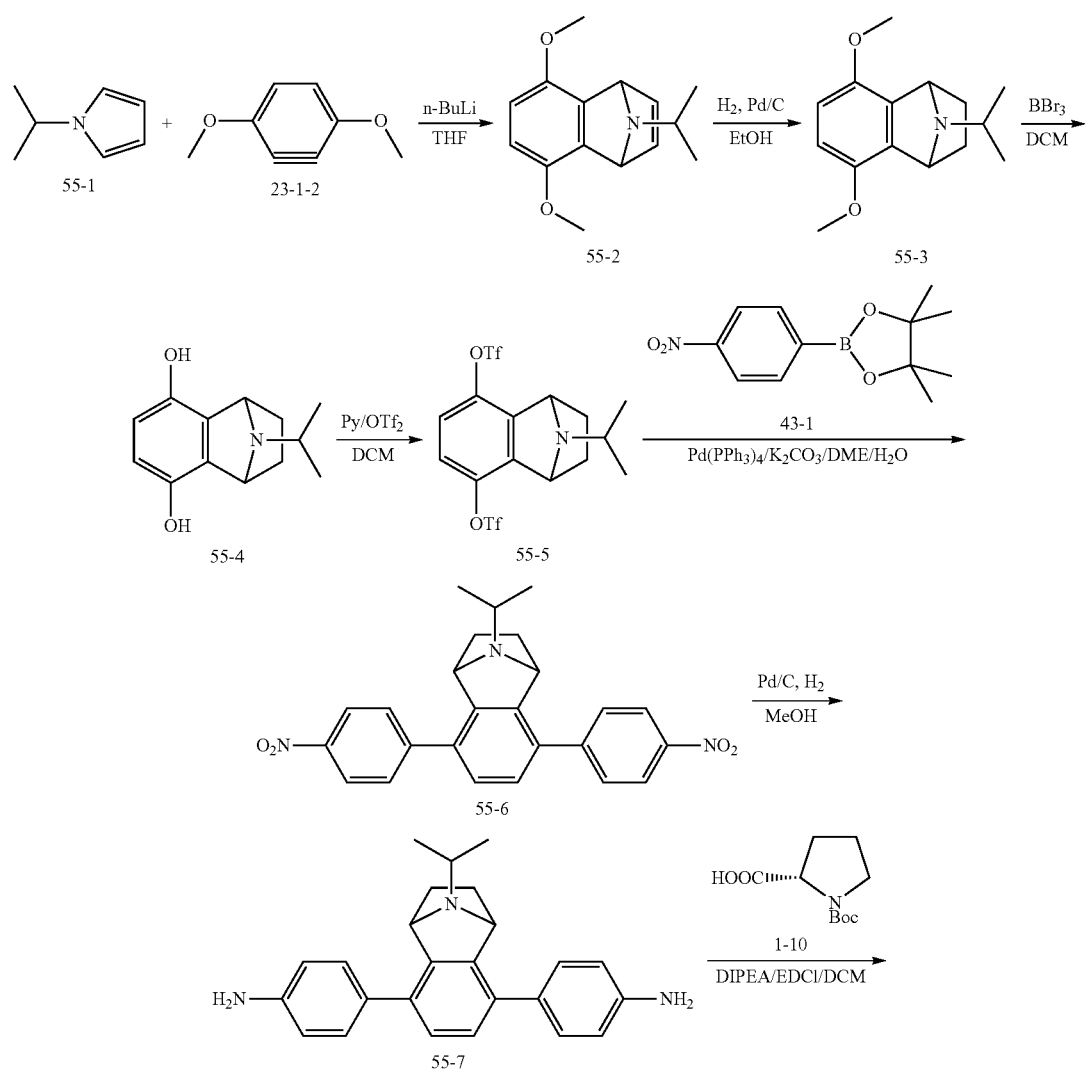

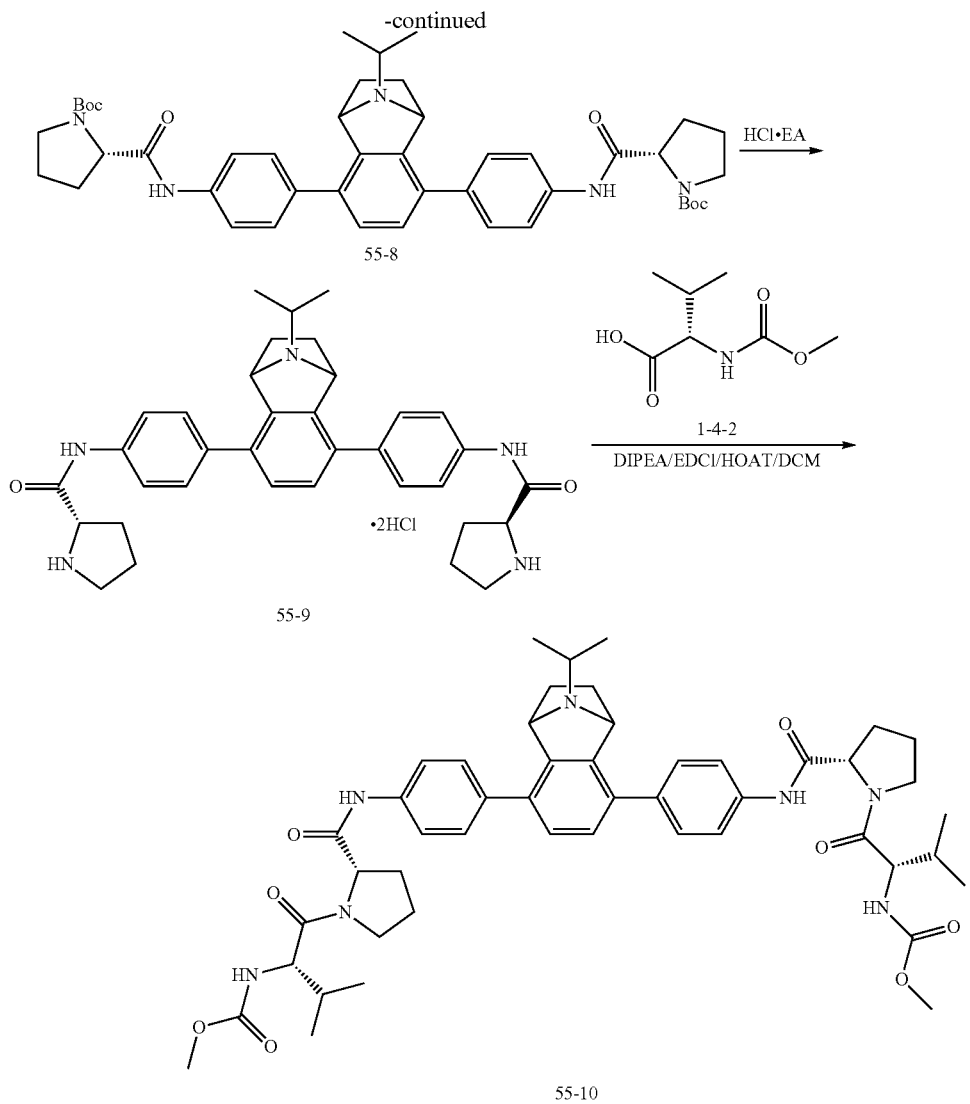

Step 1) the Preparation of Compound 55-2

To a mixture of compound 55-1 (2.07 g, 19.0 mmol) and compound 23-1-2 (1.36 g, 10.0 mmol) in dry THF (50.0 mL) was added n-butyllithium (1.6 M solution in hexane, 6.7 mL) at −78° C. under nitrogen. After stirring at −78° C. for 1 hr, the mixture was warmed to room temperature over 1-2 hrs and stirred overnight. After the reaction was completed, the mixture was poured into water (50.0 mL) and the organic phase separated. The aqueous layer was extracted further with diethyl ether (50 mL×3). The combined organic layers were dried and concentrated in vacuo. The residue was purified by a silica gel column chromatography (PE/EtOAc (v/v)=5/1) to give the title compound (1.225 g, 50%) as a yellow solid. The compound was characterized by the following spectroscopic data:

MS (ESI, pos.ion) m/z: 246.5 $[M+H]^+$;

$^1$H NMR (400 MHz, CDCl$_3$) δ (ppm): 6.86-6.85 (t, 2H), 6.82 (br, 2H), 5.09-5.07 (m, 2H), 3.71 (s, 6H), 2.92-2.86 (m, 1H), 1.13, 1.12 (s, s, 6H).

Step 2) the Preparation of Compound 55-3

To a solution of compound 55-2 (1.97 g, 8.03 mmol) in ethanol (40.0 mL) was added a catalytic amount of Pd/C (200 mg) and the mixture was stirred under 10 atm of H$_2$ gas at rt for 24 hrs. After the reaction was completed, the mixture was filtered. The filtrate was concentrated in vacuo to give the title compound 55-3 (1.39 g, 70%) as a white solid. The compound was characterized by the following spectroscopic data:

MS (ESI, pos.ion) m/z: 248.3 $[M+H]^+$;

$^1$H NMR (400 MHz, CDCl$_3$) δ (ppm): 6.60 (br, 2H), 4.28-4.25 (m, 2H), 3.70 (s, 6H), 3.21-3.12 (m, 1H), 1.51-1.42 (m, 2H), 1.18-1.12 (m, 2H), 0.89, 0.87 (s, s, 6H).

Step 3) the Preparation of Compound 55-4

To a solution of compound 55-3 (2.47 g, 10.0 mmol) in DCM (50.0 mL) was added boron tribromide (7.7 mL, 80 mmol) dropwise at −78° C. After stirring for 10 mins, the reaction mixture was stirred at rt for 1 hr. After the reaction was completed, the mixture was quenched with ice-water (50.0 mL) and the organic phase separated. The aqueous layer was extracted with DCM (50 mL×3). The combined organic layers were washed with brine, dried over anhydrous Na$_2$SO$_4$ and concentrated in vacuo. The residue was purified by a silica gel column chromatography (PE/EtOAc (v/v)=10/1) to give the title compound (1.86 g, 85%) as colorless oil. The compound was characterized by the following spectroscopic data:

MS (ESI, pos.ion) m/z: 220.5 $[M+H]^+$;

¹H NMR (400 MHz, CDCl₃) δ (ppm): 6.45 (s, 2H), 5.77 (br, 2H), 4.25-4.20 (m, 2H), 3.31-3.22 (m, 1H), 1.58-1.49 (m, 2H), 1.25-1.19 (m, 2H), 0.91, 0.89 (s, s, 6H).

Step 4) the Preparation of Compound 55-5

To a solution of compound 55-4 (2.19 g, 10.0 mmol) in DCM (20.0 mL) was added pyridine (4.8 mL, 60 mmol) dropwise at 0° C. After stirring for 10 mins, trifluoromethane-sulfonic anhydride (6.73 mL, 40.0 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous Na₂SO₄ and concentrated in vacuo. The residue was purified by a silica gel column chromatography (PE/EtOAc (v/v)=40/1) to give the title compound (4.35 g, 90.0%) as colorless oil. The compound was characterized by the following spectroscopic data:

¹H NMR (400 MHz, CDCl₃) δ (ppm): 7.32 (s, 2H), 4.41-4.35 (m, 2H), 3.05-2.96 (m, 1H), 1.48-1.40 (m, 2H), 0.96-0.92 (m, 2H), 0.91, 0.89 (s, s, 6H).

Step 5) the Preparation of Compound 55-6

To a mixture of compound 43-1 (380 mg, 1.526 mmol), compound 55-5 (335 mg, 0.693 mmol), Pd(PPh₃)₄ (80.1 mg, 0.0693 mmol) and K₂CO₃ (478.6 mg, 3.463 mmol) were added DME (8.0 mL) and H₂O (2.0 mL) via syringe and the mixture was stirred at 90° C. under N₂ for 2 hrs. After the reaction was completed, the mixture was cooled to rt and 15 mL of water was added. The aqueous layer was extracted with DCM (25 mL×3). The combined organic layers were dried over anhydrous Na₂SO₄ and concentrated in vacuo. The residue was purified by a silica gel column chromatography (PE/EtOAc (v/v)=2/1) to give the title compound (268 mg, 90%) as a white solid. The compound was characterized by the following spectroscopic data:

MS (ESI, pos.ion) m/z: 430.3 [M+H]⁺;

¹H NMR (400 MHz, CDCl₃) δ (ppm): 8.38-8.34 (m, 4H), 7.58-7.54 (m, 4H), 7.46 (s, 2H), 4.49-4.44 (m, 2H), 3.21-3.12 (m, 1H), 1.57-1.48 (m, 2H), 0.94-0.88 (m, 2H), 0.83, 0.81 (s, s, 6H).

Step 6) the Preparation of Compound 55-7

To a solution of compound 55-6 (279 mg, 0.651 mmol) in DCM (10.0 mL) was added a catalytic amount of Pd/C (20.0 mg) and the mixture was stirred under 10 atm of H₂ gas at rt for 4 hrs. After the reaction was completed, the mixture was filtered. The filtrate was concentrated in vacuo to give the title compound 55-7 (216 mg, 90%) as a white solid. The compound was characterized by the following spectroscopic data:

MS (ESI, pos.ion) m/z: 370.3 [M+H]⁺;

¹H NMR (400 MHz, CDCl₃) δ (ppm): 7.49 (s, 2H), 7.40-7.36 (m, 4H), 6.61-6.58 (m, 4H), 4.49-4.44 (m, 2H), 3.47 (br, 4H), 3.21-3.12 (m, 1H), 1.57-1.48 (m, 2H), 0.94-0.88 (m, 2H), 0.83, 0.81 (s, s, 6H).

Step 7) the Preparation of Compound 55-8

To a suspension of compound 55-7 (125.16 mg, 0.339 mmol), compound 1-10 (218.6 mg, 1.016 mmol) and EDCI (259.9 mg, 1.356 mmol) in DCM (10.0 mL) was added DIPEA (0.336 mL, 2.033 mmol) dropwise at 0° C. At the end of addition, the mixture was stirred at rt for 3 hrs. After the reaction was completed, 20 mL of water was added. The angeous layer was extracted with DCM (25.0 mL×3). The combined organic layers were dried over anhydrous Na₂SO₄ and concentrated in vacuo. The residue was purified by a silica gel column chromatography (PE/EtOAc (v/v)=1/1) to give the title compound (207 mg, 80%) as a yellow solid. The compound was characterized by the following spectroscopic data:

MS (ESI, pos.ion) m/z: 764.5 [M+H]⁺;

¹H NMR (400 MHz, CDCl₃) δ (ppm): 8.96 (br, 2H), 7.63-7.55 (m, 8H), 7.43 (s, 2H), 4.50-4.44 (m, 4H), 3.56-3.50 (m, 2H), 3.34-3.27 (m, 2H), 3.21-3.12 (m, 1H), 2.31-2.16 (m, 4H), 2.14-2.04 (m, 2H), 1.98-1.88 (m, 2H), 1.57-1.48 (m, 2H), 1.43 (s, 18H), 0.94-0.88 (m, 2H), 0.83, 0.81 (s, s, 6H).

Step 8) the Preparation of Compound 55-9

To a solution of compound 55-8 (96.8 mg, 0.1268 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (10.0 mL) and filtered to give the title compound (76.65 mg, 95%) as pale yellow powder, which was used for next step without further purification. The compound was characterized by the following spectroscopic data:

MS (ESI, pos.ion) m/z: 564.3 [M+H]⁺.

Step 9) the Preparation of Compound 55-10

To a suspension of compound 55-9 (115.2 mg, 0.181 mmol), compound 1-4-2 (95.2 mg, 0.543 mmol) and EDCI (139 mg, 0.725 mmol) in DCM (5.0 mL) was added DIPEA (0.3 mL, 1.815 mmol) dropwise at 0° C. At the end of addition, the mixture was stirred at rt for 3 hrs. After the reaction was completed, the mixture was diluted with DCM (20.0 mL). The resulting mixture was washed with NH₄Cl aqueous solution and brine, dried over Na₂SO₄ and concentrated in vacuo, the residue was purified by a silica gel column chromatography (DCM/MeOH (v/v)=40/1) to give the title compound (107.7 mg, 45%) as a white solid. The compound was characterized by the following spectroscopic data:

MS (ESI, pos.ion) m/z: 878.5 [M+H]⁺;

¹H NMR (400 MHz, CDCl₃) δ (ppm): 8.96 (br, 1H), 8.90 (br, 1H), 7.76-7.72 (m, 2H), 7.65-7.61 (m, 2H), 7.50-7.46 (m, 4H), 7.43 (s, 2H), 5.32, 5.29 (d, d, 2H), 4.49-4.44 (m, 2H), 4.31-4.22 (m, 4H), 3.63 (s, 6H), 3.61-3.55 (m, 2H), 3.44-3.36 (m, 2H), 3.21-3.12 (m, 2H), 2.20-2.02 (m, 6H), 1.75-1.60 (m, 4H), 1.57-1.48 (m, 2H), 0.97, 0.96 (m, m, 6H), 0.94-0.93 (m, 1H), 0.91, 0.89 (m, m, 6H), 0.88 (m, 1H), 0.83, 0.81 (s, s, 6H).

Example 56

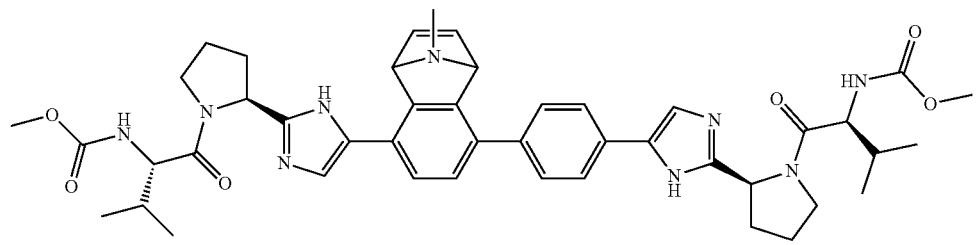

Synthetic Route:
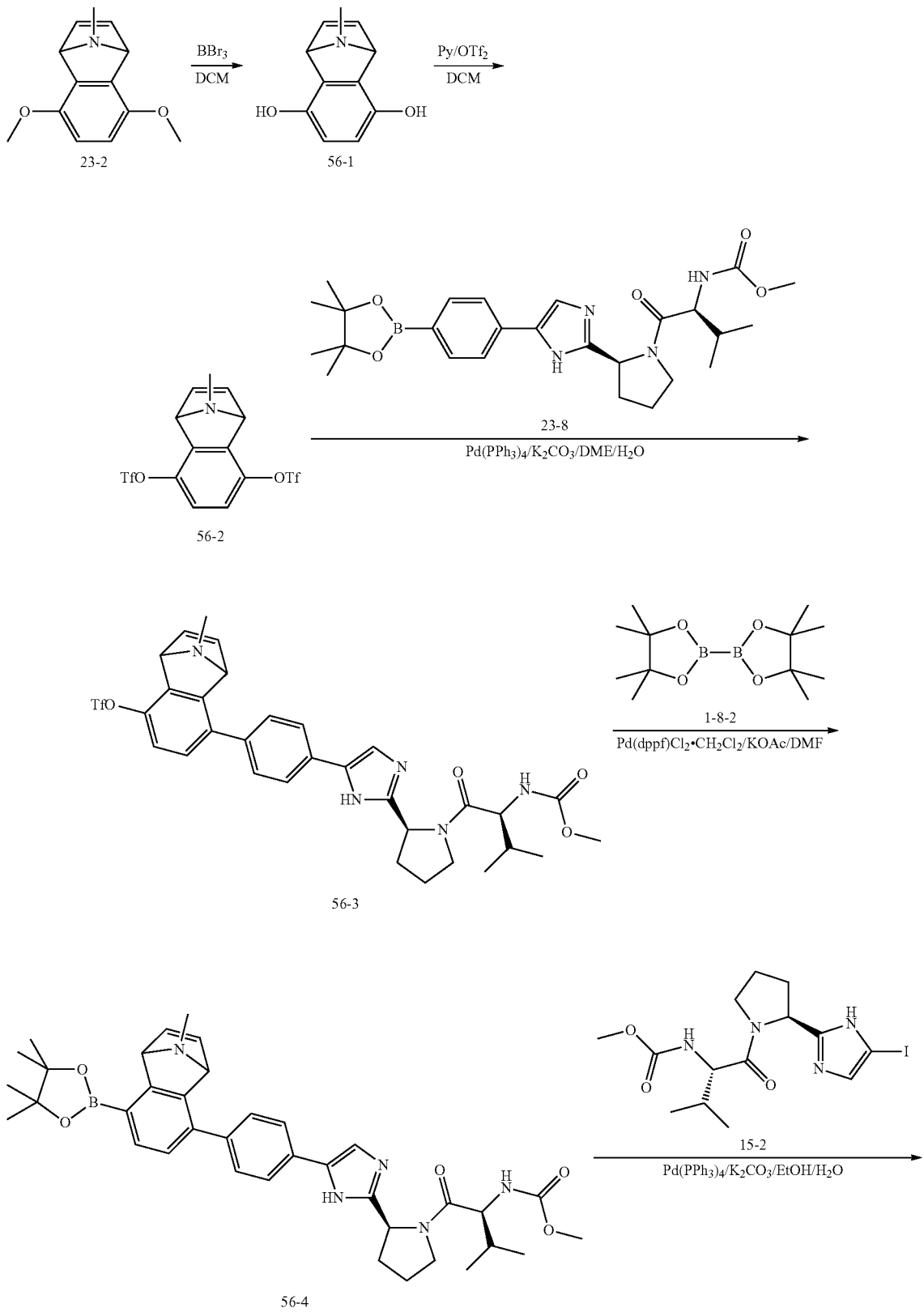

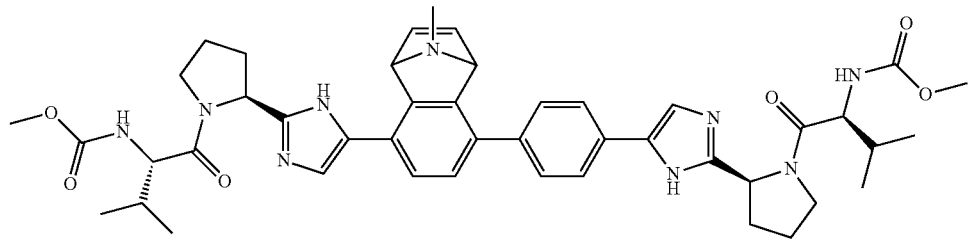

56-5

Step 1) the Preparation of Compound 56-1

To a solution of compound 23-2 (2.17 g, 10.0 mmol) in DCM (50.0 mL) was added boron tribromide (7.7 mL, 80 mmol) dropwise at −78° C. After stirring for 10 mins, the mixture was stirred at rt for 1 hr. After the reaction was completed, the mixture was quenched with ice-water (50.0 mL) and the organic phase separated. The aqueous layer was extracted with DCM (50 mL×3). The combined organic layers were washed with brine, dried over anhydrous $Na_2SO_4$ and concentrated in vacuo. The residue was purified by a silica gel column chromatography (PE/EtOAc (v/v)=10/1) to give the title compound (1.7 g, 90%) as colorless oil. The compound was characterized by the following spectroscopic data:

MS (ESI, pos.ion) m/z: 190.5 $[M+H]^+$;

$^1$H NMR (400 MHz, $CDCl_3$) δ (ppm): 7.04-7.03 (t, 2H), 6.49 (s, 2H), 5.66 (s, 2H), 4.67-4.65 (m, 2H), 2.15 (t, 3H).

Step 2) the Preparation of Compound 56-2

To a solution of compound 56-1 (1.89 g, 10.0 mmol) in DCM (20.0 mL) was added pyridine (4.8 mL, 60.0 mmol) dropwise at 0° C. After stirring for 10 mins, trifluoromethanesulfonic anhydride (6.73 mL, 40 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous $Na_2SO_4$ and concentrated in vacuo. The residue was purified by a silica gel column chromatography (PE/EtOAc (v/v)=40/1) to give the title compound (4.07 g, 90.0%) as colorless oil. The compound was characterized by the following spectroscopic data:

$^1$H NMR (400 MHz, $CDCl_3$) δ (ppm): 7.38 (s, 2H), 6.69-6.68 (m, 2H), 4.82-4.80 (m, 2H), 2.19 (t, 3H).

Step 3) the Preparation of Compound 56-3

To a mixture of compound 56-2 (460 mg, 1.016 mmol), compound 23-8 (504 mg, 1.016 mmol), $Pd(PPh_3)_4$ (117 mg, 0.1016 mmol) and $K_2CO_3$ (420.7 mg, 3.048 mmol) were added DME (10.0 mL) and $H_2O$ (2.5 mL) via syringe and the mixture was stirred at 90° C. under $N_2$ for 3 hrs. After the reaction was completed, the mixture was cooled to rt and diluted with EtOAc (50.0 mL). The combined organic layers were washed with water (20 mL×3) and brine, dried over anhydrous $Na_2SO_4$ and concentrated in vacuo. The residue was purified by a silica gel column chromatography (DCM/EtOH (v/v)=100/1) to give the title compound (362.5 mg, 53%) as a pale yellow solid. The compound was characterized by the following spectroscopic data:

MS (ESI, pos.ion) m/z: 674.5 $[M+H]^+$;

$^1$H NMR (400 MHz, $CDCl_3$) δ (ppm): 7.64-7.59 (m, 3H), 7.54-7.51 (m, 2H), 7.28, 7.26 (s, s, 1H), 7.12, 7.10 (s, s, 1H), 6.96-6.91 (m, 2H), 5.56, 5.55 (br, br, 1H), 5.23-5.19 (m, 1H), 4.87-4.84 (m, 1H), 4.74-4.72 (m, 1H), 4.34-4.30 (m, 1H), 3.85-3.78 (m, 1H), 3.66-3.62 (m, 1H), 3.66 (s, 3H), 2.30-1.92 (m, 8H), 1.02-1.00 (m, 3H), 0.93, 0.91 (m, 3H).

Step 4) the Preparation of Compound 56-4

A mixture of compound 56-3 (3.5 g, 5.2 mmol), compound 1-8-2 (1.59 g, 6.25 mmol), $Pd(dppf)Cl_2 \cdot CH_2Cl_2$ (425 mg, 0.52 mmol) and KOAc (1.54 g, 15.63 mmol) in DMF (30.0 mL) was stirred at 90° C. under $N_2$ for 4 hrs. After the reaction was completed, the mixture was cooled to rt, diluted with EtOAc (250 mL) and filtered through a celite pad. The filtrate was washed with water (100 mL×3) and brine, dried over anhydrous $Na_2SO_4$ and concentrated in vacuo. The residue was purified by a silica gel column chromatography (PE/EtOAc (v/v)=2/1) to give the title compound (2.91 g, 86%) as a white solid. The compound was characterized by the following spectroscopic data:

MS (ESI, pos.ion) m/z: 652.3 $[M+H]^+$;

$^1$H NMR (400 MHz, $CDCl_3$) δ (ppm): 7.83, 7.81 (s, s, 1H), 7.76-7.73 (m, 2H), 7.72, 7.70 (s, s, 1H), 7.64-7.60 (m, 2H), 7.59 (s, 1H), 6.81-6.78 (m, 1H), 6.73-6.70 (m, 1H), 5.56, 5.55 (br, br, 1H), 5.23-5.19 (m, 1H), 4.98-4.96 (m, 1H), 4.65-4.63 (m, 1H), 4.34-4.30 (m, 1H), 3.85-3.78 (m, 1H), 3.66 (s, 3H), 3.65-3.61 (m, 1H), 2.42-2.41 (t, 3H), 2.30-2.16 (m, 3H), 2.13-1.92 (m, 2H), 1.32 (m, 6H), 1.29 (m, 6H), 1.02-1.00 (m, 3H), 0.94, 0.91 (m, 3H).

Step 5) the Preparation of Compound 56-5

To a mixture of compound 56-4 (340 mg, 0.522 mmol), compound 15-2 (241.1 mg, 0.574 mmol), $Pd(PPh_3)_4$ (60.29 mg, 0.0522 mmol) and $K_2CO_3$ (216 mg, 1.566 mmol) were added DME (6.0 mL) and $H_2O$ (1.5 mL) via syringe and the mixture was stirred at 90° C. under $N_2$ for 3 hrs. After the reaction was completed, the mixture was cooled to rt and diluted with EtOAc (30.0 mL). The combined organic layers were washed with water (10.0 mL×3) and brine, dried over anhydrous $Na_2SO_4$ and concentrated in vacuo. The residue was purified by a silica gel column chromatography (DCM/EtOH (v/v)=100/1) to give the title compound (213.4 mg, 50%) as a pale yellow solid. The compound was characterized by the following spectroscopic data:

MS (ESI, pos.ion) m/z: 409.5 $[M+2H]^{2+}$;

$^1$H NMR (400 MHz, $CDCl_3$) δ (ppm): 7.64-7.61 (m, 2H), 7.59 (s, 1H), 7.58-7.55 (m, 2H), 7.47, 7.45 (s, s, 1H), 7.34, 7.32 (s, s, 1H), 6.97, 6.93 (m, 2H), 5.56, 5.55 (br, br, 1H), 5.32, 5.29 (br, br, 1H), 5.29-5.25 (m, 1H), 5.23-5.19 (m, 1H), 4.95, 4.93 (m, 1H), 4.59-4.56 (m, 1H), 4.41-4.30 (m, 2H), 3.85-3.78 (m, 2H), 3.68-3.67 (m, 2H), 3.66 (s, 3H), 3.65-3.64 (m, 1H), 3.63 (s, 3H), 2.45-2.44 (t, 3H), 2.30-2.16 (m, 6H), 2.13-1.92 (m, 4H), 1.02-0.89 (m, 12H).

547
Example 57
548
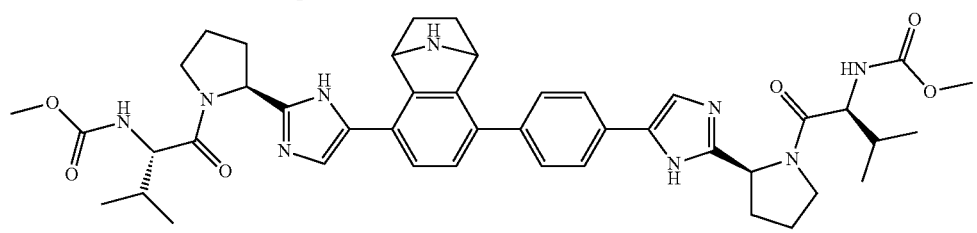
Synthetic Route:
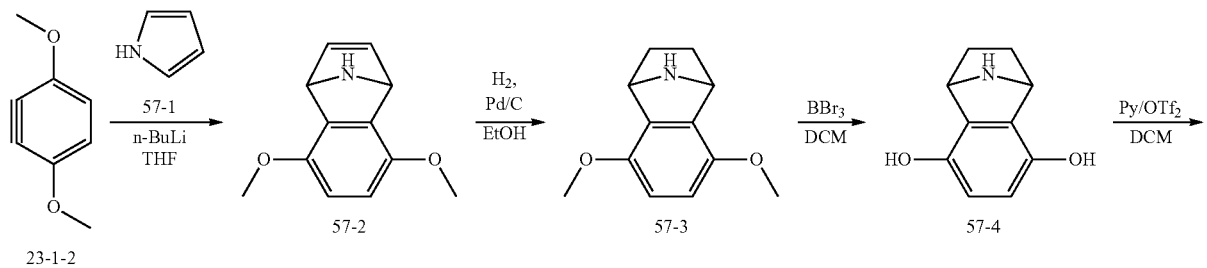
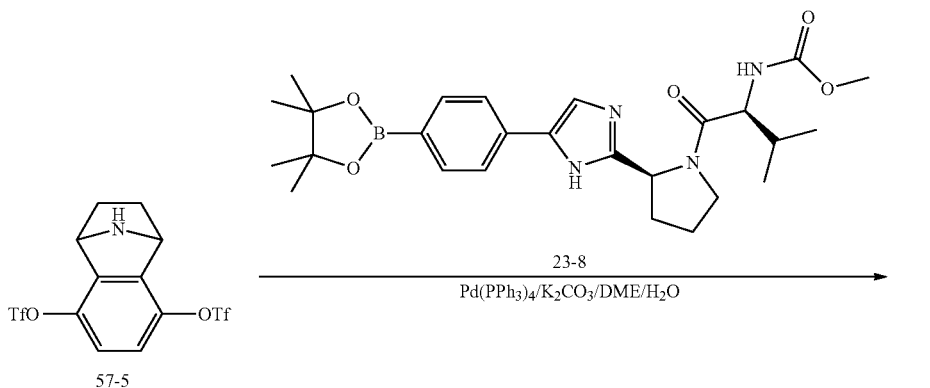
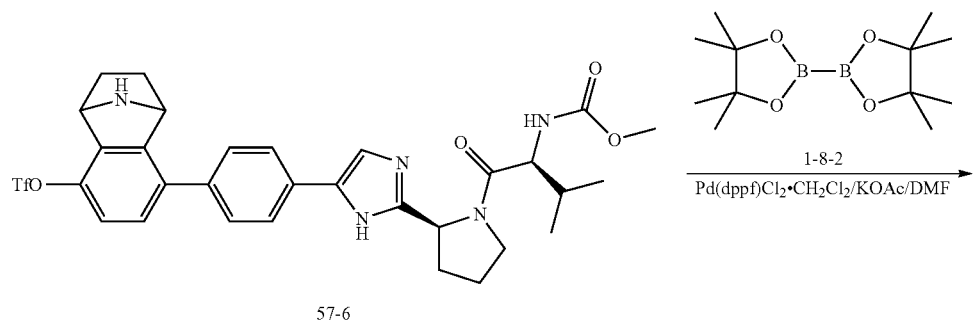
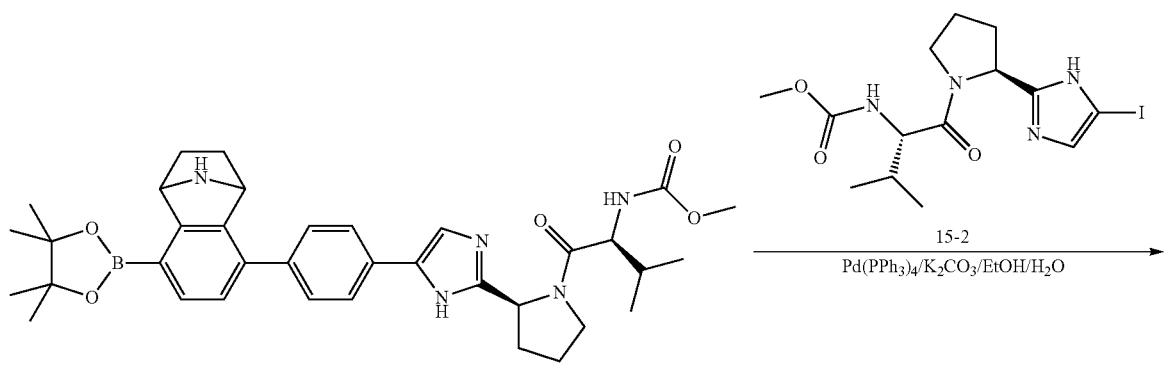

-continued

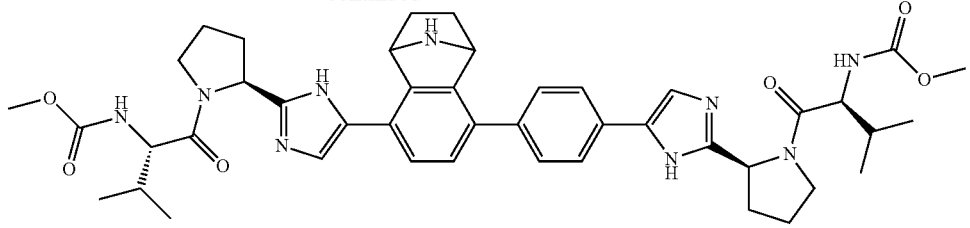

57-8

Step 1) the Preparation of Compound 57-2

To a mixture of compound 57-1 (1.27 g, 19.0 mmol) and compound 23-1-2 (1.36 g, 10.0 mmol) in dry THF (25.0 mL) was added n-butyllithium (1.6 M solution in hexane, 6.7 mL) at −78° C. under nitrogen. After stirring at −78° C. for 1 hr, the mixture was warmed to room temperature over 1-2 hrs and stirred overnight. After the reaction was completed, the mixture was poured into water (50.0 mL) and the organic phase separated. The aqueous layer was extracted further with diethyl ether (50 mL×3). The combined organic layers were dried and concentrated in vacuo. The residue was purified by a silica gel column chromatography (PE/EtOAc (v/v)=5/1) to give the title compound (1.93 g, 50%) as a yellow solid. The compound was characterized by the following spectroscopic data:

MS (ESI, pos.ion) m/z: 204.5 [M+H]$^+$;
$^1$H NMR (400 MHz, CDCl$_3$) δ (ppm): 6.97-6.95 (m, 2H), 6.45 (s, 2H), 5.21-5.19 (t, 2H, J=4.0 Hz), 3.73 (s, 6H), 2.77 (br, 1H).

Step 2) the Preparation of Compound 57-3

To a solution of compound 57-2 (1.63 g, 8.03 mmol) in ethanol (40.0 mL) was added Pd/C (170 mg) and the mixture was stirred under 10 atm of H$_2$ gas at rt for 24 hrs. After the reaction was completed, the mixture was filtered. The filtrate was concentrated in vacuo to give the title compound 57-3 (1.4 g, 85%) as a white solid. The compound was characterized by the following spectroscopic data:

MS (ESI, pos.ion) m/z: 206.3 [M+H]$^+$;
$^1$H NMR (400 MHz, CDCl$_3$) δ (ppm): 6.50 (br, 2H), 4.71-4.65 (m, 2H), 3.70 (s, 6H), 2.43 (brs, 1H), 2.20-2.10 (m, 2H), 1.27-1.21 (m, 2H).

Step 3) the Preparation of Compound 57-4

To a solution of compound 57-3 (2.05 g, 10.0 mmol) in DCM (50.0 mL) was added boron tribromide (7.7 mL, 80.0 mmol) dropwise at −78° C. After stirring at −78° C. for 10 mins, the mixture was stirred at rt for 1 hr. After the reaction was completed, the mixture was quenched with ice-water (50.0 mL) and the organic phase separated. The aqueous layer was extracted with DCM (50 mL×3). The combined organic layers were washed with brine, dried over anhydrous Na$_2$SO$_4$ and concentrated in vacuo. The residue was purified by a silica gel column chromatography (PE/EtOAc (v/v)=10/1) to give the title compound 57-4 (1.593 g, 90%) as colorless oil. The compound was characterized by the following spectroscopic data:

MS (ESI, pos.ion) m/z: 178.5 [M+H]$^+$;
$^1$H NMR (400 MHz, CDCl$_3$) δ (ppm): 6.42 (s, 2H), 4.68-4.61 (m, 2H), 2.17-2.08 (m, 2H), 1.33-1.28 (m, 2H).

Step 4) the Preparation of Compound 57-5

To a solution of compound 57-4 (1.77 g, 10.0 mmol) in DCM (20.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous Na$_2$SO$_4$ and concentrated in vacuo. The residue was purified by a silica gel column chromatography (PE/EtOAc (v/v)=40/1) to give the title compound (4.19 g, 95%) as colorless oil. The compound was characterized by the following spectroscopic data:

$^1$H NMR (400 MHz, CDCl$_3$) δ (ppm): 7.32 (s, 2H), 4.80-4.78 (m, 2H), 2.43 (brs, 1H), 2.12-2.04 (m, 2H), 1.30-1.21 (m, 2H).

Step 5) the Preparation of Compound 57-6

To a mixture of compound 57-5 (448 mg, 1.016 mmol), compound 23-8 (504 mg, 1.016 mmol), Pd(PPh$_3$)$_4$ (117 mg, 0.1016 mmol) and K$_2$CO$_3$ (420.7 mg, 3.048 mmol) were added DME (10.0 mL) and H$_2$O (2.5 mL) via syringe and the mixture was stirred at 90° C. under N$_2$ for 2 hrs. After the reaction was completed, the mixture was cooled to rt, diluted with EtOAc (30.0 mL), and washed with water (10.0 mL×3). The combined organic layers were dried over anhydrous Na$_2$SO$_4$ and concentrated in vacuo. The residue was purified by a silica gel column chromatography (DCM/EtOH (v/v)= 100/1) to give the title compound (302.3 mg, 45%) as a pale yellow solid. The compound was characterized by the following spectroscopic data:

MS (ESI, pos.ion) m/z: 662.5 [M+H]$^+$;
$^1$H NMR (400 MHz, CDCl$_3$) δ (ppm): 7.62-7.58 (m, 3H), 7.52-7.48 (m, 2H), 7.26, 7.24 (s, s, 1H), 7.09, 7.07 (s, s, 1H), 6.47 (brs, 2H), 5.56, 5.55 (d, d, 1H), 5.23-5.19 (m, 1H), 4.84-4.83 (m, 1H), 4.40-4.39 (m, 1H), 4.34-4.30 (m, 1H), 3.85-3.78 (m, 1H), 3.66 (s, 3H), 3.65-3.61 (m, 1H), 2.30-2.16 (m, 3H), 2.13-1.92 (m, 4H), 1.31-1.20 (m, 2H), 1.02-0.91 (m, 6H).

Step 6) the Preparation of Compound 57-7

A mixture of compound 57-6 (3.44 g, 5.2 mmol), compound 1-8-2 (1.59 g, 6.25 mmol), Pd(dppf)Cl$_2$.CH$_2$Cl$_2$ (425 mg, 0.52 mmol) and KOAc (1.54 g, 15.63 mmol) in DMF (30.0 mL) was stirred at 90° C. under N$_2$ for 4 hrs. After the reaction was completed, the mixture was cooled to rt, diluted with EtOAc (250 mL) and filtered through a celite pad. The filtrate was washed with water (100 mL×3) and brine, dried over anhydrous Na$_2$SO$_4$ and concentrated in vacuo. The residue was purified by a silica gel column chromatography (PE/EtOAc (v/v)=2/1) to give the title compound (2.66 g, 80%) as a white solid. The compound was characterized by the following spectroscopic data:

MS (ESI, pos.ion) m/z: 640.5 [M+H]$^+$;
$^1$H NMR (400 MHz, CDCl$_3$) δ (ppm): 7.75, 7.72 (s, s, 1H), 7.62-7.58 (m, 3H), 7.56-7.53 (m, 2H), 7.42, 7.40 (s, s, 1H), 6.47 (br, 2H), 5.56, 5.55 (d, d, 2H), 5.23-5.19 (m, 1H), 5.00-4.98 (m, 1H), 4.67-4.64 (m, 1H), 4.34-4.30 (m, 1H), 3.85-3.78 (m, 1H), 3.66 (s, 3H), 3.65-3.61 (m, 1H), 2.30-1.92 (m, 6H), 1.32 (m, 6H), 1.29 (m, 6H), 1.27-1.21 (m, 2H), 1.02, 1.00 (m, 3H), 0.94, 0.91 (m, 3H).

Step 7) the Preparation of Compound 57-8

A mixture of compound 57-7 (333.7 mg, 0.522 mmol), compound 15-2 (241.1 mg, 0.574 mmol), Pd(PPh$_3$)$_4$ (60.29 mg, 0.0522 mmol) and K$_2$CO$_3$ (216 mg, 1.566 mmol) in the mixed solvents of DME/H₂O (7.5 mL, v/v=4/1) was stirred at 90° C. under N₂ for 2 hrs. After the reaction was completed, the mixture was cooled to rt, diluted with EtOAc (30.0 mL), and washed with water (10 mL×3) and brine. The combined organic layers were dried over anhydrous Na₂SO₄ and concentrated in vacuo. The residue was purified by a silica gel column chromatography (DCM/MeOH (v/v)=50/1) to give the title compound (274 mg, 85%) as a pale yellow solid. The compound was characterized by the following spectroscopic data:

MS (ESI, pos.ion) m/z: 806.5 [M+H]⁺;
¹H NMR (400 MHz, CDCl₃) δ (ppm): 7.77 (s, 1H), 7.72 (brs, 3H), 7.62-7.58 (m, 3H), 7.56-7.52 (m, 2H), 7.46, 7.44 (s, s, 1H), 7.31, 7.29 (s, s, 1H), 5.56, 5.55 (d, d, 1H), 5.32, 5.29 (d, d, 1H), 5.29-5.25 (m, 1H), 5.23-5.19 (m, 1H), 4.99-4.93 (m, 1H), 4.41-4.36 (m, 1H), 4.35-4.30 (m, 2H), 3.85-3.78 (m, 2H), 3.66 (s, 3H), 3.65-3.64 (m, 2H), 3.63 (s, 3H), 2.30-1.92 (m, 12H), 1.34-1.24 (m, 2H), 1.02-0.89 (m, 12H).

Example 58

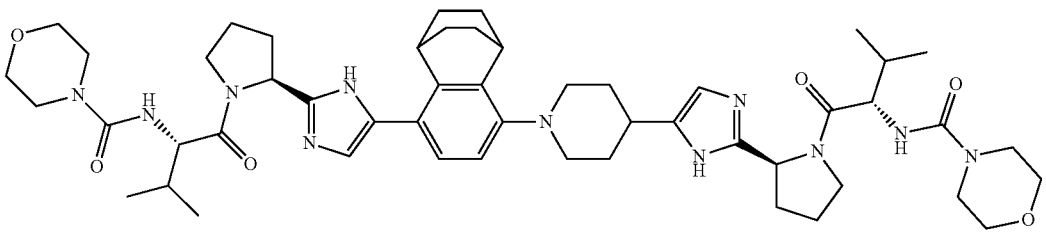 [SMILES: CC(C)[C@H](NC(=O)N1CCOCC1)C(=O)N1CCC[C@H]1c1ncc(-c2ccc(N3CCC(c4cnc([C@@H]5CCCN5C(=O)[C@@H](NC(=O)N5CCOCC5)C(C)C)[nH]4)CC3)c3c2C2CCC3CC2)[nH]1]

Synthetic Route:

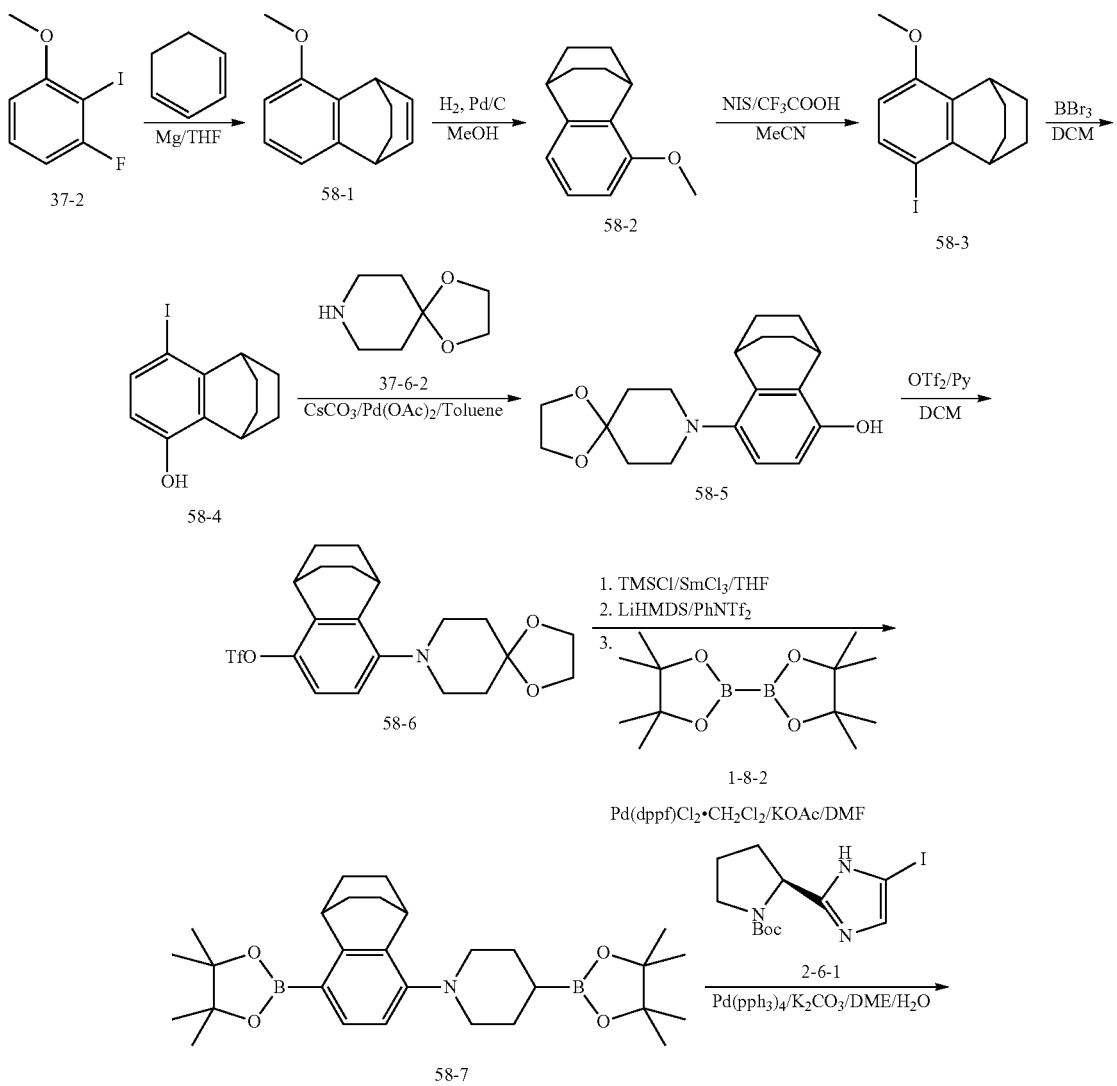

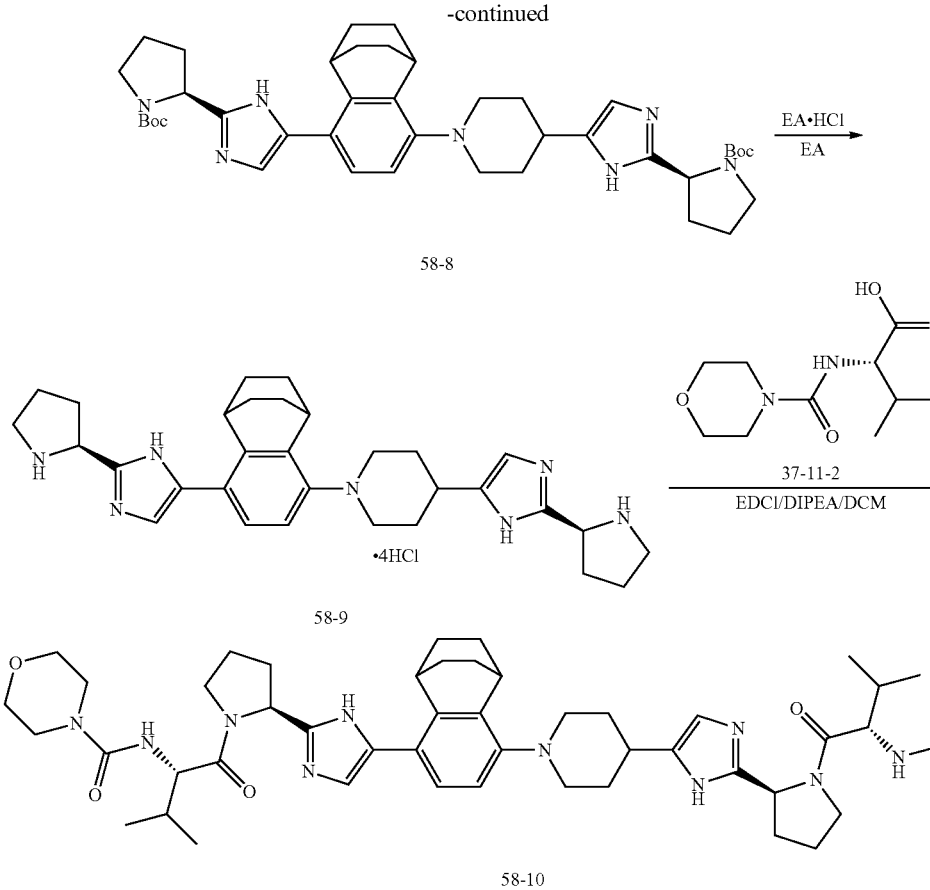

Compounds disclosed herein can be synthesized through the procedure as depicted in Example 29.

Compound 58-1 was characterized by the following spectroscopic data:

MS (ESI, pos.ion) m/z: 187.5 [M+H]$^+$;

$^1$H NMR (400 MHz, CDCl$_3$) δ (ppm) 7.05-7.00 (m, 2H), 6.77-6.73 (m, 1H), 6.36-6.27 (m, 2H), 4.19-4.14 (m, 1H), 3.94-3.89 (m, 1H), 3.79 (s, 3H), 1.55-1.38 (m, 4H).

Compound 58-2 was characterized by the following spectroscopic data:

MS (ESI, pos.ion) m/z: 189.5 [M+H]$^+$;

$^1$H NMR (400 MHz, CD$_3$Cl) δ (ppm): 7.17-7.13 (m, 1H), 6.73-6.71 (m, 1H), 6.58-6.57, 6.56-6.55 (m, m, 1H), 3.84 (s, 3H), 2.99-2.80 (m, 2H), 1.69-1.54 (m, 4H), 1.37-1.22 (m, 4H).

Compound 58-3 was characterized by the following spectroscopic data:

MS (ESI, pos.ion) m/z: 315.5 [M+H]$^+$;

$^1$H NMR (400 MHz, CD$_3$Cl) δ (ppm): 7.46, 7.44 (s, s, 1H), 6.47, 6.45 (br, br, 1H), 3.83 (s, 3H), 3.09-2.89 (m, 2H), 1.75-1.65 (m, 2H), 1.60-1.50 (m, 2H), 1.43-1.33 (m, 2H), 1.28-1.17 (m, 2H).

Compound 58-4 was characterized by the following spectroscopic data:

MS (ESI, pos.ion) m/z: 301.5 [M+H]$^+$;

$^1$H NMR (400 MHz, CD$_3$Cl) δ (ppm): 7.36, 7.34 (s, s, 1H), 6.39, 6.37 (s, s, 1H), 5.77 (brs, 1H), 3.10-2.94 (m, 2H), 1.75-1.65 (m, 2H), 1.59-1.49 (m, 2H), 1.43-1.33 (m, 2H), 1.27-1.17 (m, 2H).

Compound 58-5 was characterized by the following spectroscopic data:

MS (ESI, pos.ion) m/z: 316.5 [M+H]$^+$;

$^1$H NMR (400 MHz, CD$_3$Cl) δ (ppm): 6.58, 6.56 (s, s, 1H), 6.54, 6.52 (s, s, 1H), 5.77 (brs, 1H), 4.01-3.87 (m, 4H), 3.20-3.15 (m, 4H), 3.05-2.84 (m, 2H), 1.76-1.71 (m, 4H), 1.56-1.36 (m, 4H), 1.24-1.04 (m, 4H).

Compound 58-6 was characterized by the following spectroscopic data:

MS (ESI, pos.ion) m/z: 448.5 [M+H]$^+$;

$^1$H NMR (400 MHz, CD$_3$Cl) δ (ppm): 7.01, 6.99 (s, s, 1H), 6.43, 6.40 (s, s, 1H), 4.01-3.87 (m, 4H), 3.17-3.13 (m, 4H), 3.04-2.94 (m, 1H), 2.90-2.81 (m, 1H), 1.76-1.62 (m, 4H), 1.51-1.30 (m, 4H), 1.19-1.09 (m, 4H).

Compound 58-7 was characterized by the following spectroscopic data:

MS (ESI, pos.ion) m/z: 494.5 [M+H]$^+$;

$^1$H NMR (400 MHz, CD$_3$Cl) δ (ppm): 7.56, 7.54 (s, s, 1H), 6.75, 6.73 (s, s, 1H), 3.07-3.01 (m, 4H), 3.00-2.82 (m, 2H), 1.97-1.90 (m, 2H), 1.85-1.73 (m, 2H), 1.68-1.58 (m, 4H), 1.53-1.43 (m, 4H), 1.32, 1.29 (m, m, 12H), 1.25, 1.22 (m, m, 12H), 0.95-1.87 (m, 1H).

Compound 58-8 was characterized by the following spectroscopic data:

MS (ESI, pos.ion) m/z: 712.5 [M+H]$^+$;

$^1$H NMR (400 MHz, CD$_3$Cl) δ (ppm): 7.63 (s, 1H), 6.98, 6.96 (s, s, 1H), 6.81, 6.80 (s, s, 2H), 6.47, 6.45 (s, s, 1H), 5.06-5.00 (m, 1H), 4.87-4.80 (m, 1H), 3.73-3.67 (m, 1H), 3.64-3.58 (m, 1H), 3.44-3.36 (m, 1H), 3.31-3.17 (m, 6H), 2.65-2.56 (m, 1H), 2.47-2.33 (m, 5H), 2.28-2.17 (m, 2H), 2.12-1.96 (m, 5H), 1.74-1.63 (m, 2H), 1.61-1.54 (m, 2H), 1.42-1.31 (m, 2H), 1.53 (s, 18H), 1.29-1.19 (m, 2H).
Compound 58-10 was characterized by the following spectroscopic data:
MS (ESI, pos.ion) m/z: 468.5 [M+H]$^{2+}$;
$^1$H NMR (400 MHz, CD$_3$Cl) δ (ppm): 7.57 (s, 1H), 6.98, 6.96 (s, s, 1H), 6.82 (d, 1H), 6.47, 6.45 (s, s, 1H), 5.67, 5.65 (d, d, 2H), 5.36-5.31 (m, 1H), 5.12-5.08 (m, 1H), 4.51-4.47 (m, 2H), 3.87-3.79 (m, 2H), 3.74-3.62 (m, 8H), 3.35-3.18 (m, 13H), 2.65-2.56 (m, 1H), 2.45-2.34 (m, 4H), 2.30-2.16 (m, 6H), 2.13-1.91 (m, 7H), 1.74-1.63 (m, 2H), 1.61-1.51 (m, 2H), 1.42-1.31 (m, 2H), 1.29-1.19 (m, 2H), 1.02-0.99 (m, m, 6H), 0.93, 0.90 (m, m, 6H).
Example 59
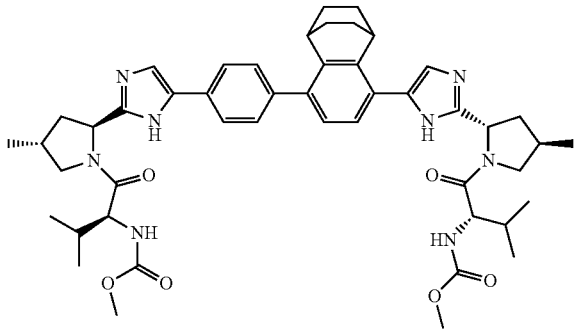
Synthetic Route:
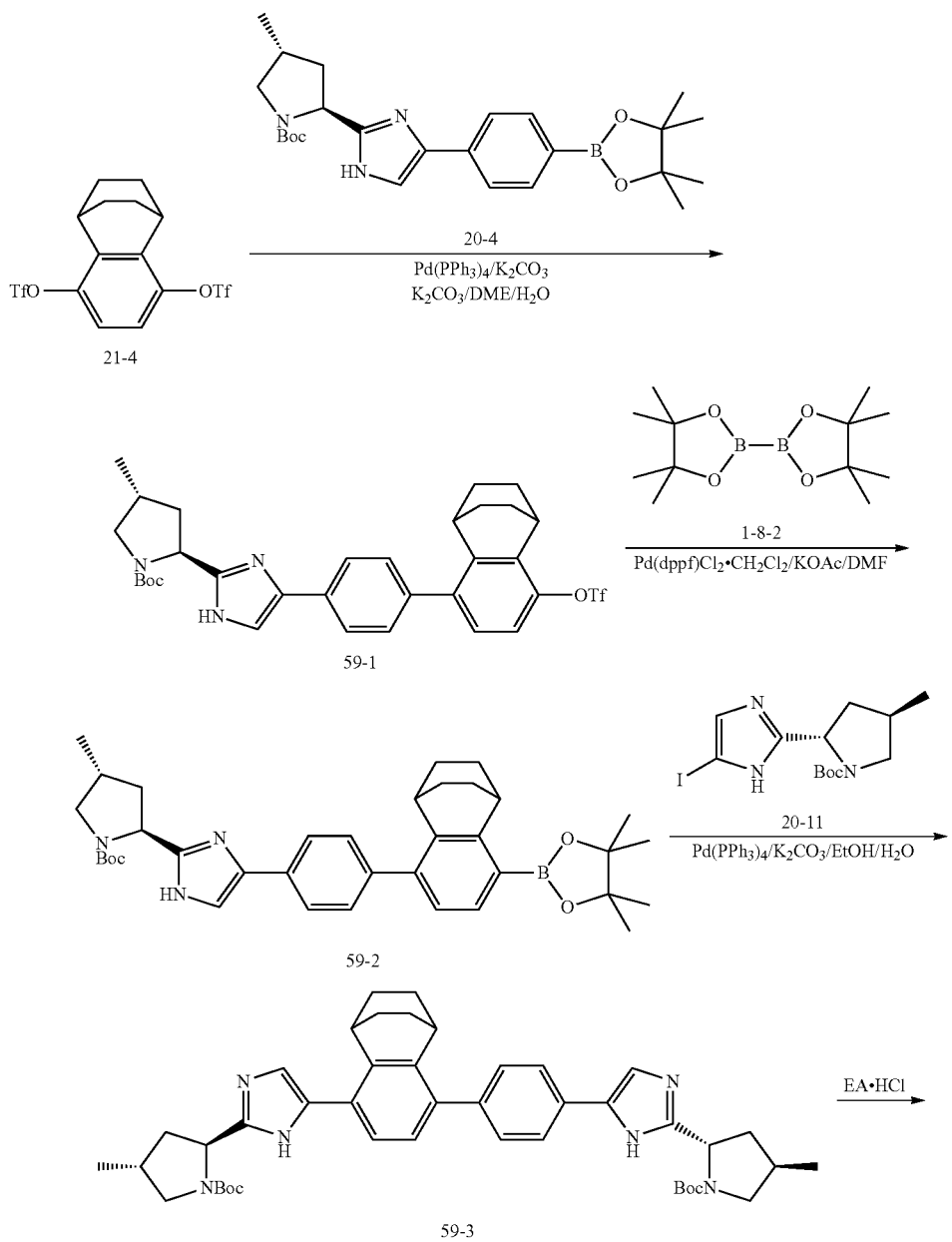

-continued

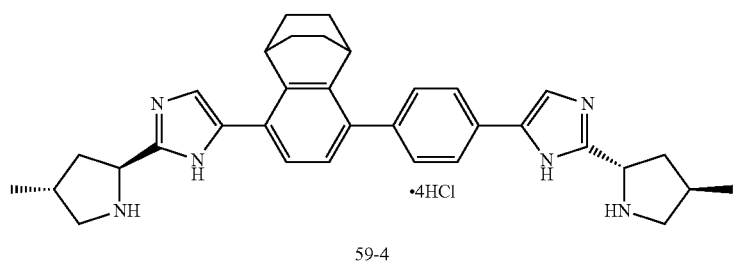
59-4

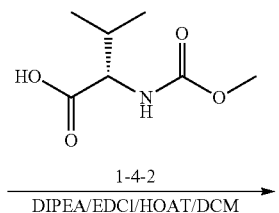

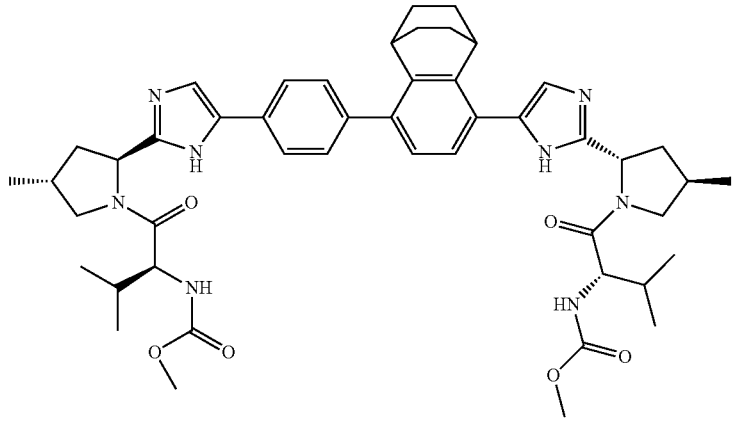
59-5

Step 1) the Preparation of Compound 59-1

To a mixture of compound 20-4 (3.4 g, 7.7 mmol), compound 21-4 (3.5 g, 7.7 mmol), Pd(PPh$_3$)$_4$ (450 mg, 0.38 mmol) and K$_2$CO$_3$ (2.1 g, 15.4 mmol) were added DME (32.0 mL) and H$_2$O (8.0 mL) via syringe and the mixture was stirred at 90° C. under N$_2$ for 3 hrs. After the reaction was completed, the mixture was cooled to rt, diluted with EtOAc (200 mL), and washed with water (30.0 mL×3). The combined organic layers were dried over anhydrous Na$_2$SO$_4$ and concentrated in vacuo. The residue was purified by a silica gel column chromatography (PE/EtOAc (v/v)=2/1) to give the title compound (5.37 g, 60%) as a pale yellow solid. The compound was characterized by the following spectroscopic data:

MS (ESI, pos.ion) m/z: 632.5 [M+H]$^+$;

$^1$H NMR (400 MHz, CDCl$_3$) δ (ppm): 7.73-7.67 (m, 4H), 7.36 (s, 1H), 7.31, 7.28 (s, s, 1H), 7.05, 7.02 (s, s, 1H), 4.81-4.76 (m, 1H), 3.80-3.73 (m, 1H), 3.12-3.02 (m, 3H), 2.33-2.16 (m, 2H), 1.88-1.77 (m, 2H), 1.74-1.66 (m, 1H), 1.65-1.46 (m, 4H), 1.42 (s, 9H), 1.35-1.25 (m, 2H), 0.96-0.93 (m, 3H).

Step 2) the Preparation of Compound 59-2

A mixture of compound 59-1 (988 mg, 1.62 mmol), compound 1-8-2 (0.42 g, 1.7 mmol), Pd(dppf)Cl$_2$.CH$_2$Cl$_2$ (67 mg, 0.08 mmol) and KOAc (0.4 g, 4.05 mmol) in DMF (10.0 mL) was stirred at 90° C. under N$_2$ for 3 hrs. After the reaction was completed, the mixture was cooled to rt, diluted with EtOAc (50.0 mL) and filtered through a celite pad. The filtrate was washed with water (20.0 mL×3) and brine, dried over anhydrous Na$_2$SO$_4$ and concentrated in vacuo. The residue was purified by a silica gel column chromatography (PE/EtOAc (v/v)=3/1) to give the title compound (691 mg, 70%) as a pale yellow solid. The compound was characterized by the following spectroscopic data:

MS (ESI, pos.ion) m/z: 610.5 [M+H]$^+$;

$^1$H NMR (400 MHz, CDCl$_3$) δ (ppm): 7.84, 7.82 (s, s, 1H), 7.75-7.68 (m, 4H), 7.65, 7.63 (s, s, 1H), 7.36 (s, 1H), 4.81-4.76 (m, 1H), 3.80-3.73 (m, 1H), 3.13-2.99 (m, 3H), 2.33-2.16 (m, 2H), 1.74-1.57 (m, 5H), 1.50-1.46 (m, 2H), 1.42 (s, 9H), 1.32, 1.29 (m, m, 12H), 1.18-1.08 (m, 2H), 0.96-0.93 (m, 3H).

Step 3) the Preparation of Compound 59-3

A mixture of compound 59-2 (353.4 mg, 0.58 mmol), compound 20-11 (240 mg, 0.63 mmol), Pd(PPh$_3$)$_4$ (35 mg, 0.03 mmol) and K$_2$CO$_3$ (80 mg, 1.4 mmol) in the mixed solvent of DME/H$_2$O (10 mL, v/v=4/1) was stirred at 90° C. under N$_2$ for 4 hrs. After the reaction was completed, the mixture was cooled to rt, diluted with EtOAc (50.0 mL), and washed with water (20.0 mL×3) and brine. The combined organic layers were dried over anhydrous Na$_2$SO$_4$ and concentrated in vacuo. The residue was purified by a silica gel column chromatography (DCM/MeOH (v/v)=60/1) to give the title compound (255 mg, 60%) as a pale yellow solid. The compound was characterized by the following spectroscopic data:

MS (ESI, pos.ion) m/z: 733.5[M+H]$^+$;

$^1$H NMR (400 MHz, CDCl$_3$) δ (ppm): 7.91 (s, 1H), 7.75-7.68 (m, 4H), 7.48-7.46 (s, s, 1H), 7.38 (s, 1H), 7.36 (s, 1H), 4.97-4.92 (m, 1H), 4.81-4.76 (m, 1H), 3.80-3.73 (m, 2H), 3.48-3.38 (m, 1H), 3.37-3.27 (m, 1H), 3.09-3.02 (m, 2H), 2.35-2.16 (m, 4H), 1.76-1.65 (m, 4H), 1.60-1.50 (m, 2H), 1.42 (s, 18H), 1.41-1.33 (m, 2H), 1.28-1.18 (m, 2H), 0.96-0.93 (m, 6H).

Step 4) the Preparation of Compound 59-4

To a solution of compound 59-3 (275 mg, 0.375 mmol) in EtOAc (4.0 mL) was added a solution of HCl in EtOAc (3.0 mL, 4 M) dropwise. At the end of addition, the mixture was stirred at rt for 8 hrs. After the reaction was completed, the mixture was concentrated in vacuo. The residue was washed with EtOAc (10.0 mL) and filtered to give the title compound (229 mg, 90%) as pale yellow powder, which was used for the next step without further purification. The compound was characterized by the following spectroscopic data:

MS (ESI, pos.ion) m/z: 533.5 [M+H]$^+$.

Step 5) the Preparation of Compound 59-5

To a suspension of compound 59-4 (210.3 mg, 0.31 mmol), compound 1-4-2 (120 mg, 0.68 mmol), EDCI (130 mg, 0.68 mmol) and HOAT (85 mg, 0.62 mmol) in DCM (20.0 mL) was added DIPEA (0.56 mL, 3.39 mmol) dropwise at 0° C. At the end of addition, the mixture was stirred at rt for 3 hrs. After the reaction was completed, the mixture was diluted with DCM (20.0 mL). The resulting mixture was washed with NH$_4$Cl aqueous solution and brine, dried over Na$_2$SO$_4$ and concentrated in vacuo. The residue was purified by a silica gel column chromatography (DCM/MeOH (v/v)=50/1) to give the title compound (118 mg, 45%) as a yellow solid. The compound was characterized by the following spectroscopic data:

MS (ESI, pos.ion) m/z: 847.5 [M+H]$^+$;

$^1$H NMR (400 MHz, CDCl$_3$) δ (ppm): 7.80 (s, 1H), 7.61-7.58 (m, 3H), 7.53-7.50 (m, 2H), 7.48, 7.46 (s, s, 1H), 7.38, 7.36 (s, s, 1H), 6.08, 6.06 (d, d, 1H), 5.56, 5.55 (d, d, 1H), 5.35-5.29 (m, 1H), 5.07-5.02 (m, 1H), 4.32-4.27 (m, 2H), 4.05-3.85 (m, 3H), 3.66 (s, 6H), 3.61-3.55 (m, 1H), 3.48-3.27 (m, 2H), 2.36-2.14 (m, 6H), 1.84-1.76 (m, 1H), 1.75-1.63 (m, 3H), 1.60-1.50 (m, 2H), 1.43-1.33 (m, 2H), 1.28-1.18 (m, 2H), 1.02, 1.00 (m, 6H), 0.94-0.89 (m, 12H).

Example 60

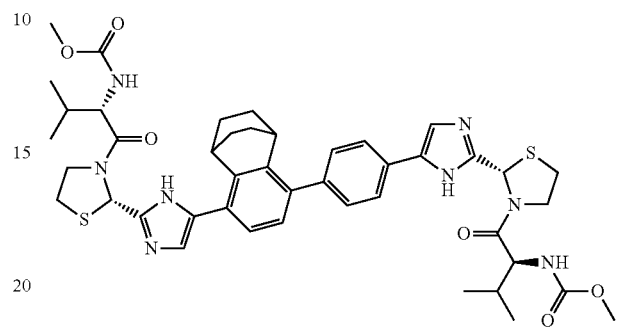

Synthetic Route:

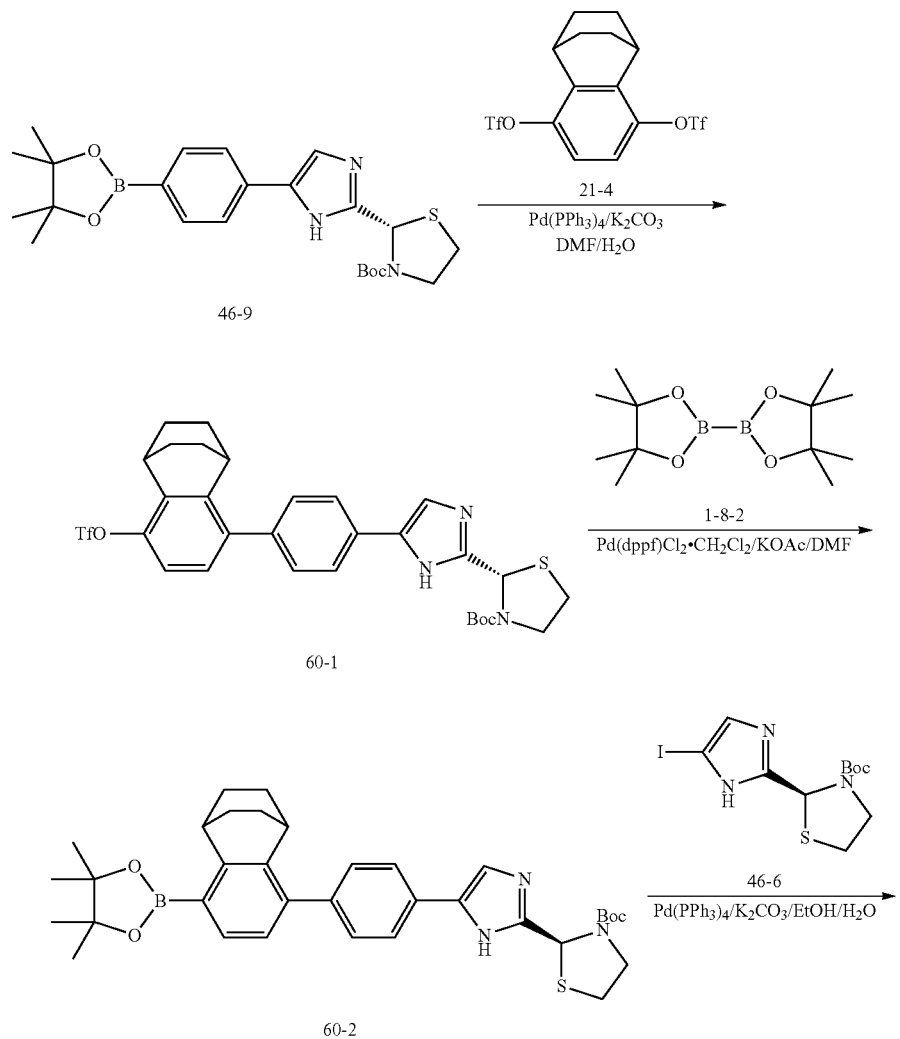

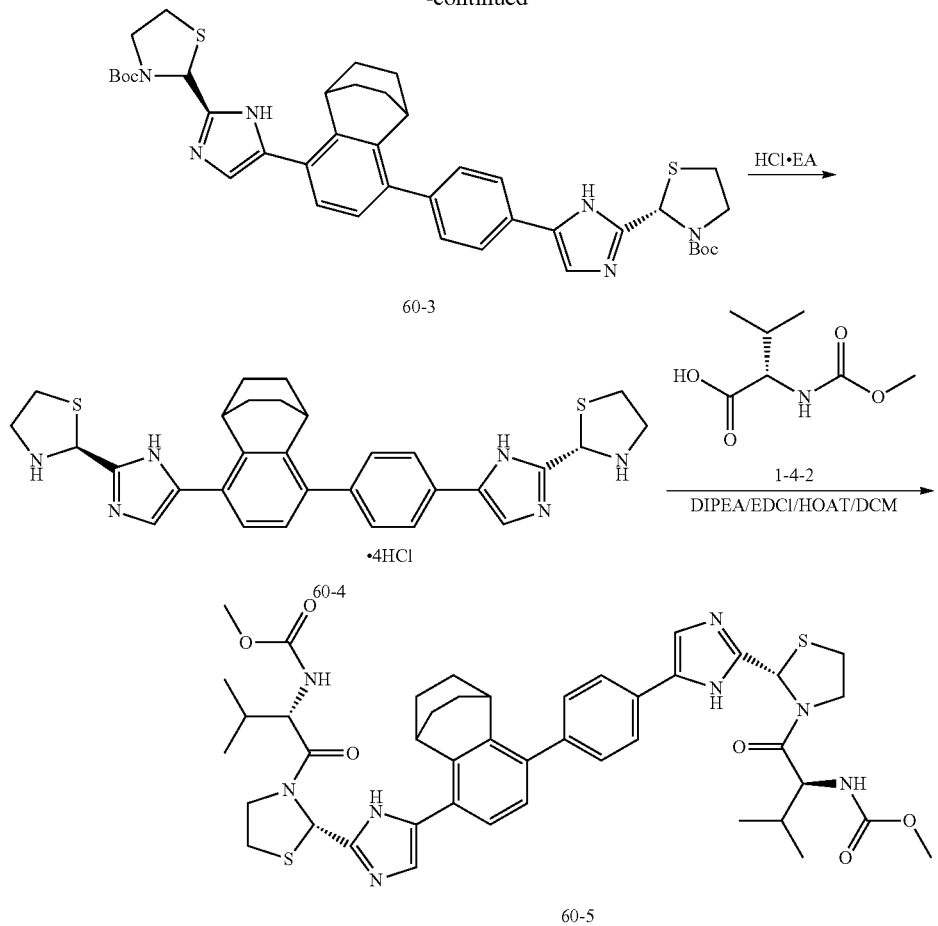

Compounds disclosed herein can be synthesized through the procedure as depicted in Example 46.

Compound 60-1 was characterized by the following spectroscopic data:

MS (ESI, pos.ion) m/z: 636.5 [M+H]$^+$;

$^1$H NMR (400 MHz, CDCl$_3$) δ (ppm): 7.63-7.60 (m, 3H), 7.49-7.46 (m, 2H), 7.31, 7.28 (s, s, 1H), 7.05, 7.02 (s, s, 1H), 6.54-6.51 (m, 1H), 4.08-4.01 (m, 1H), 3.44-3.37 (m, 1H), 3.30-3.22 (m, 1H), 3.12-3.02 (m, 2H), 2.91-2.84 (m, 1H), 1.88-1.77 (m, 2H), 1.67-1.45 (m, 4H), 1.41 (s, 9H), 1.35-1.25 (m, 2H).

Compound 60-2 was characterized by the following spectroscopic data:

MS (ESI, pos.ion) m/z: 614.5 [M+H]$^+$;

$^1$H NMR (400 MHz, CDCl$_3$) δ (ppm): 7.84, 7.82 (s, s, 1H), 7.65 (s, 1H), 7.63-7.60 (m, 3H), 7.54-7.51 (m, 2H), 6.54-6.51 (m, 1H), 4.08-4.01 (m, 1H), 3.44-3.37 (m, 1H), 3.30-3.22 (m, 1H), 3.13-2.99 (m, 2H), 2.91-2.84 (m, 1H), 1.68-1.57 (m, 2H), 1.50-1.41 (m, 2H), 1.41 (s, 9H), 1.36-1.33 (m, 2H), 1.32 (m, 6H), 1.29 (m, 6H), 1.18-1.08 (m, 2H).

Compound 60-3 was characterized by the following spectroscopic data:

MS (ESI, pos.ion) m/z: 741.5 [M+H]$^+$;

$^1$H NMR (400 MHz, CD$_3$Cl) δ (ppm): 7.17 (s, 1H), 7.63 (s, 1H), 7.62-7.60 (m, 2H), 7.53-7.50 (m, 2H), 7.48, 7.46 (s, s, 1H), 7.38, 7.36 (s, s, 1H), 6.54-6.51 (m, 1H), 6.08-6.06 (m, 1H), 4.08-4.01 (m, 2H), 3.48-3.38 (m, 3H), 3.37-3.22 (m, 3H), 2.91-2.84 (m, 2H), 1.74-1.65 (m, 2H), 1.60-1.50 (m, 2H), 1.42 (s, 9H), 1.41 (s, 9H), 1.40-1.33 (m, 2H).

Compound 60-5 was characterized by the following spectroscopic data:

MS (ESI, pos.ion) m/z: 855.5 [M+H]$^+$;

$^1$H NMR (400 MHz, CD$_3$Cl) δ (ppm): 7.64-7.60 (m, 4H), 7.53-7.50 (m, 2H), 7.48, 7.46 (s, s, 1H), 7.38, 7.36 (s, s, 1H), 6.29-6.26 (m, 1H), 6.25-6.23 (m, 1H), 5.56, 5.55 (d, d, 1H), 5.32, 5.30 (d, d, 1H), 4.43-4.30 (m, 4H), 3.66 (s, 3H), 3.63 (s, 3H), 3.59-3.53 (m, 2H), 3.48-3.29 (m, 2H), 3.25-3.17 (m, 2H), 2.86-2.79 (m, 2H), 2.31-2.14 (m, 2H), 1.75-1.65 (m, 2H), 1.60-1.50 (m, 2H), 1.43-1.33 (m, 2H), 1.28-1.18 (m, 2H), 1.02-0.89 (m, 12H).

Example 61

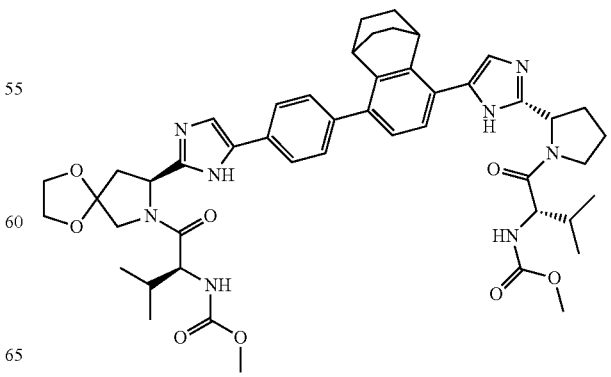

Synthetic Route:
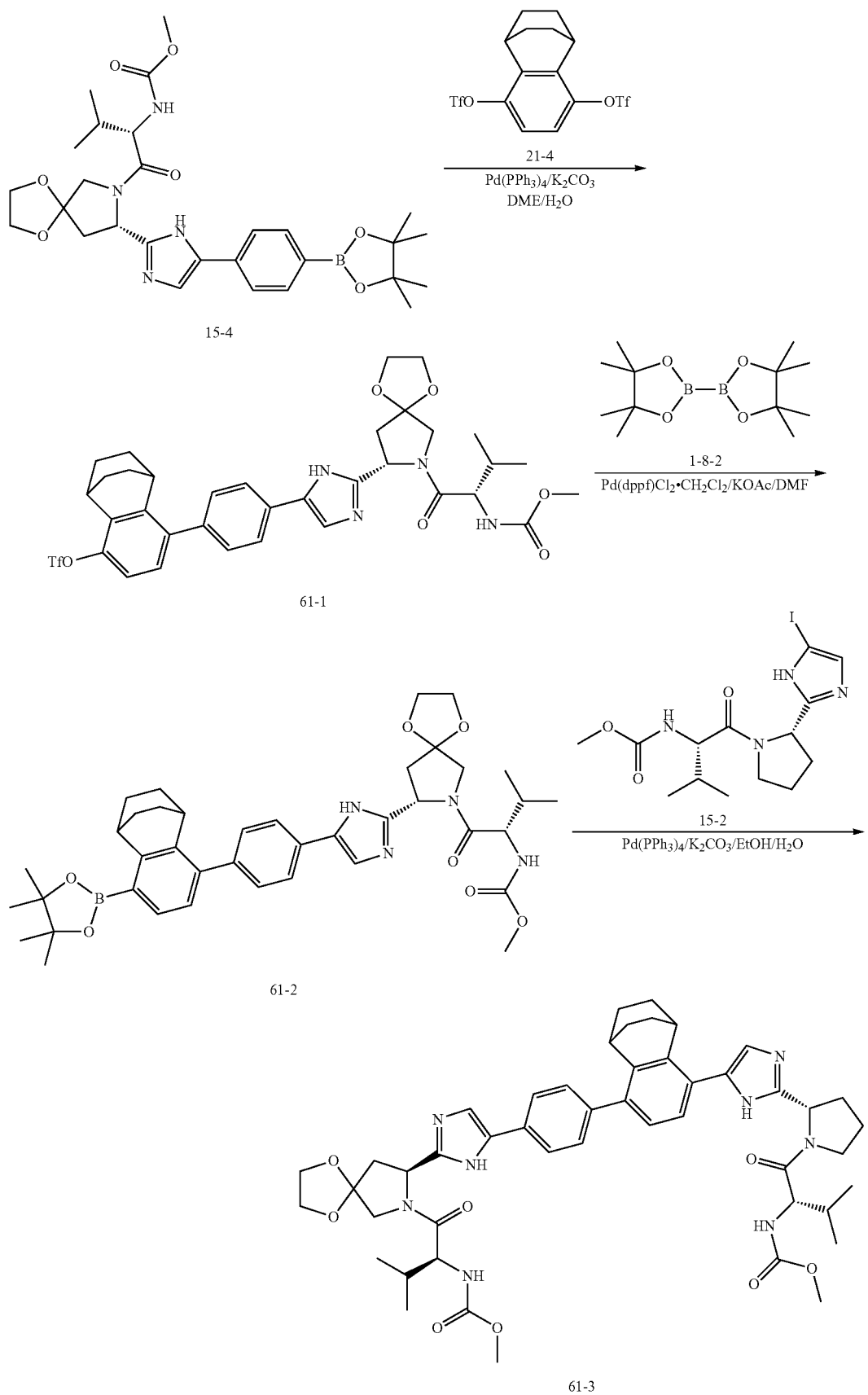

Compounds disclosed herein can be synthesized through the procedure as depicted in Example 15.

Compound 61-1 was characterized by the following spectroscopic data:

MS (ESI, pos.ion) m/z: 733.5 [M+H]$^+$;

$^1$H NMR (400 MHz, CDCl$_3$) δ (ppm): 7.61-7.58 (m, 2H), 7.49-7.46 (m, 2H), 7.35 (s, 1H), 7.31, 7.28 (s, s, 1H), 7.05, 7.02 (s, s, 1H), 5.56, 5.55 (d, d, 1H), 5.40-5.36 (m, 1H), 4.35-4.31 (m, 1H), 3.98-3.92 (m, 5H), 3.71-3.67 (m, 1H), 3.66 (s, 3H), 3.12-3.02 (m, 2H), 2.83-2.77 (m, 1H), 2.45-2.39 (m, 1H), 2.28-2.16 (m, 1H), 1.88-1.77 (m, 2H), 1.67-1.45 (m, 4H), 1.35-1.25 (m, 2H), 1.02, 1.00 (m, m, 3H), 0.93, 0.91 (m, m, 3H).

Compound 61-2 was characterized by the following spectroscopic data:

MS (ESI, pos.ion) m/z: 711.5 [M+H]$^+$;

$^1$H NMR (400 MHz, CDCl$_3$) δ (ppm): 7.84, 7.82 (s, s, 1H), 7.65, 7.63 (s, s, 1H), 7.61-7.58 (m, 2H), 7.54-7.50 (m, 2H), 7.35 (s, 1H), 5.40-5.36 (m, 1H), 5.32, 5.29 (d, d, 1H), 4.43-4.38 (m, 1H), 3.98-3.92 (m, 5H), 3.71-3.69 (m, 1H), 3.63 (s, 3H), 3.13-2.99 (m, 2H), 2.83-2.77 (m, 1H), 2.45-2.39 (m, 1H), 2.24-2.11 (m, 1H), 1.68-1.57 (m, 2H), 1.50-1.40 (m, 2H), 1.36-1.34 (m, 2H), 1.33, 1.29 (m, m, 12H), 1.18-1.08 (m, 2H), 0.97, 0.96 (m, m, 3H), 0.91, 0.89 (m, m, 3H).

Compound 61-3 was characterized by the following spectroscopic data:

MS (ESI, pos.ion) m/z: 877.5 [M+H]$^+$;

$^1$H NMR (400 MHz, CD$_3$Cl) δ (ppm) 7.80 (s, 1H), 7.61-7.58 (m, 3H), 7.53-7.50 (m, 2H), 7.48, 7.46 (s, s, 1H), 7.38, 7.36 (s, s, 1H), 7.35 (s, 1H), 5.56, 5.55 (d, d, 1H), 5.40-5.36 (m, 1H), 5.32, 5.29 (d, d, 1H), 5.29, 5.25 (m, 1H), 4.43-4.38 (m, 1H), 4.34-4.30 (m, 1H), 3.99-3.92 (m, 5H), 3.85-3.78 (m, 2H), 3.71-3.69 (m, 1H), 3.66 (s, 3H), 3.63 (s, 3H), 3.48-3.38 (m, 1H), 3.37-3.27 (m, 1H), 2.83-2.77 (m, 1H), 2.45-2.39 (m, 1H), 2.30-1.92 (m, 6H), 1.75-1.65 (m, 2H), 1.60-1.50 (m, 2H), 1.43-1.33 (m, 2H), 1.28-1.18 (m, 2H), 1.02-0.89 (m, 12H).

Example 62

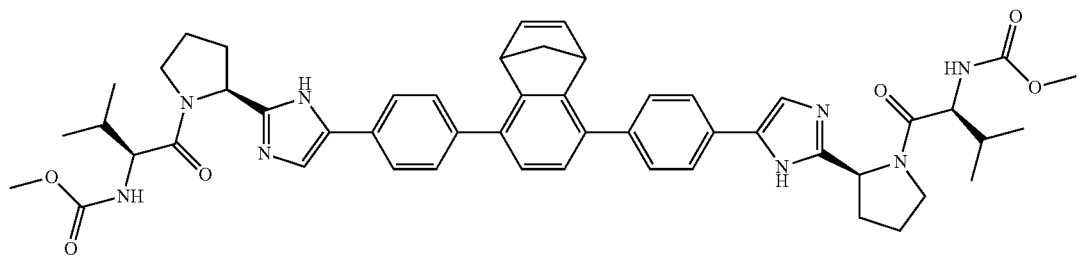

Synthetic Route:

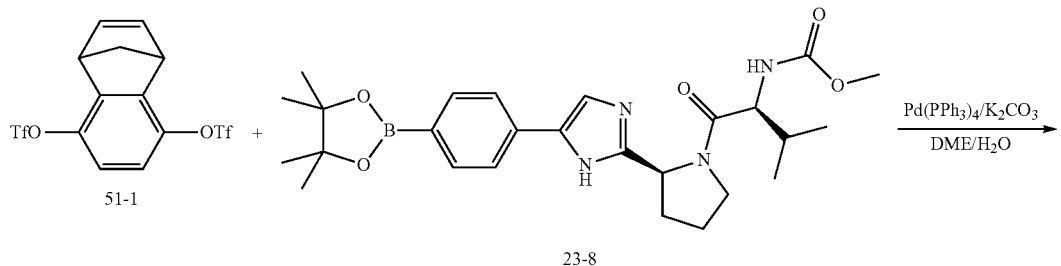

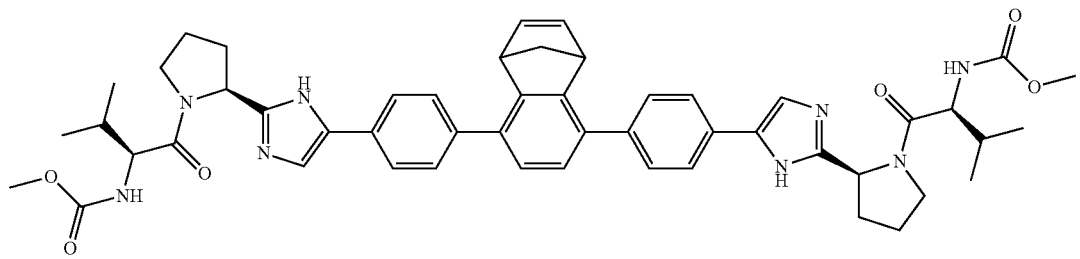

62-1

Step 1) the Preparation of Compound 62-1

A mixture of compound 51-1 (1.49 g, 3.4 mmol), compound 23-8 (3.66 g, 7.38 mmol), Pd(PPh$_3$)$_4$ (196.7 mg, 0.17 mmol) and K$_2$CO$_3$ (1.412 g, 10.22 mmol) in the mixed solvents of DME/H$_2$O (15.0 mL, v/v=4/1) was stirred at 90° C. under N$_2$ for 4 hrs. After the reaction was completed, the mixture was cooled to rt, diluted with EtOAc (100 mL), and washed with water (20.0 mL×3) and brine. The combined organic layers were dried over anhydrous Na$_2$SO$_4$ and concentrated in vacuo. The residue was purified by a silica gel column chromatography (DCM/MeOH (v/v)=50/1) to give the title compound (1.344 g, 45%) as a pale yellow solid. The compound was characterized by the following spectroscopic data:

MS (ESI, pos.ion) m/z: 440.3 [M+2H]$^{2+}$;

$^1$H NMR (400 MHz, CDCl$_3$) δ (ppm): 7.63-7.59 (m, 6H), 7.57-7.54 (m, 6H), 6.97-6.95 (m, 2H), 5.56, 5.55 (d, d, 2H), 5.23-5.19 (m, 2H), 4.47-4.43 (m, 2H), 4.34-4.30 (m, 2H), 3.85-3.78 (m, 2H), 3.66 (s, 6H), 3.65-3.61 (m, 2H), 2.37-2.33 (m, 1H), 2.30-2.16 (m, 7H), 2.13-1.92 (m, 4H), 1.02, 1.00 (m, 6H), 0.94-0.91 (m, 6H).

Example 63

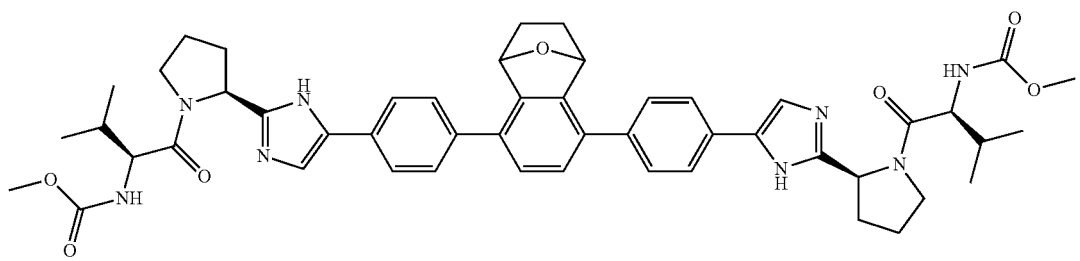

Synthetic Route:

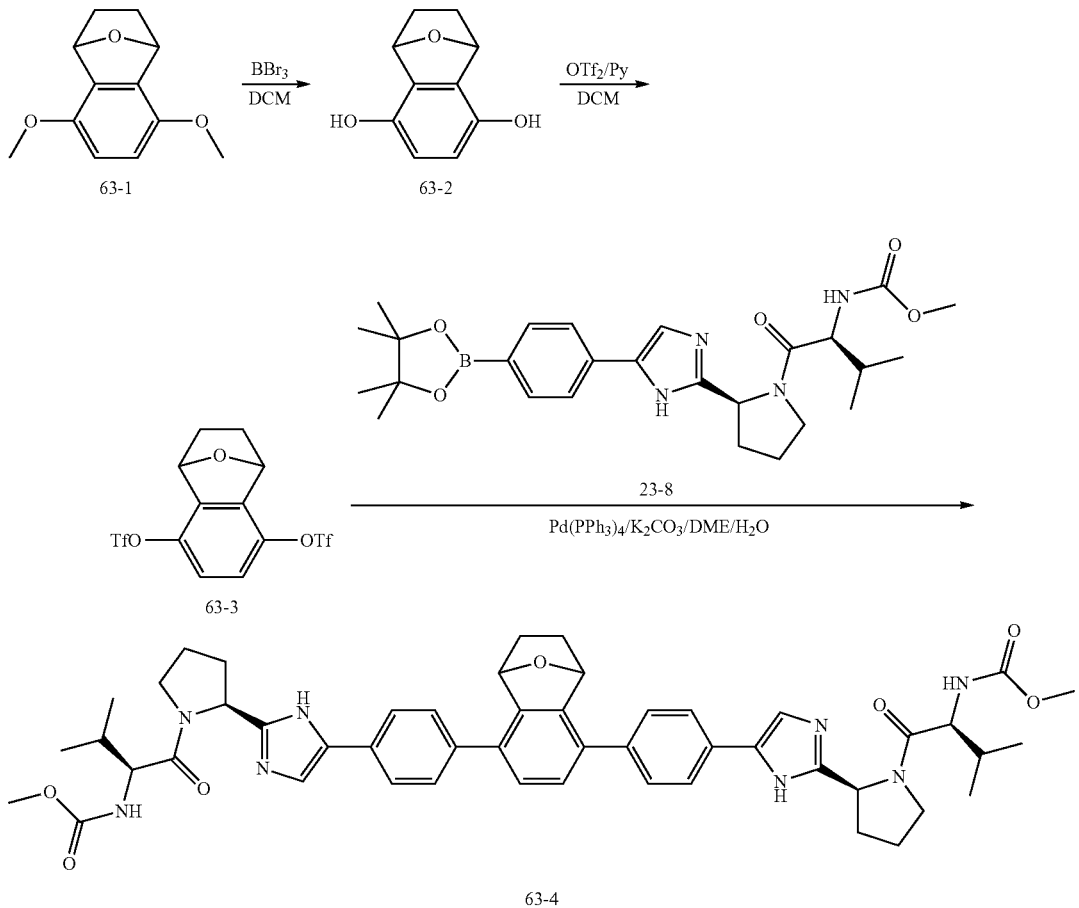

Step 1) the Preparation of Compound 63-2

To a solution of compound 63-1 (2.06 g, 10.0 mmol) in DCM (50.0 mL) was added boron tribromide (7.7 mL, 80.0 mmol) dropwise at −78° C. After stirring at −78° C. for 10 mins, the mixture was stirred at rt for 1 hr. After the reaction was completed, the mixture was quenched with ice-water (50.0 mL) and the organic phase separated. The aqueous layer was extracted with DCM (50 mL×3). The combined organic layers were washed with brine, dried over anhydrous $Na_2SO_4$ and concentrated in vacuo. The residue was purified by a silica gel column chromatography (PE/EtOAc (v/v)=10/1) to give the title compound (1.6 g, 90%) as colorless oil. The compound was characterized by the following spectroscopic data:

MS (ESI, pos.ion) m/z: 179.5 $[M+H]^+$;
$^1$H NMR (400 MHz, $CDCl_3$) δ (ppm): 6.55 (s, 2H), 6.51 (br, 2H), 5.51-5.45 (m, 2H), 1.78-1.65 (m, 2H), 1.00-0.87 (m, 2H)

Step 2) the Preparation of Compound 63-3

To a solution of compound 63-2 (1.78 g, 10.0 mmol) in DCM (20.0 mL) was added pyridine (4.8 mL, 60.0 mmol) dropwise at 0° C. After the mixture was stirred for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous $Na_2SO_4$ and concentrated in vacuo. The residue was purified by a silica gel column chromatography (PE/EtOAc (v/v)=40/1) to give the title compound (3.98 g, 90%) as colorless oil. The compound was characterized by the following spectroscopic data:

$^1$H NMR (400 MHz, $CDCl_3$) δ (ppm): 7.36 (s, 2H), 5.53-5.47 (m, 2H), 1.69-1.56 (m, 2H), 0.91-0.78 (m, 2H).

Step 3) the Preparation of Compound 63-4

To a mixture of compound 63-3 (1.5 g, 3.4 mmol), compound 23-8 (3.66 g, 7.38 mmol), Pd(PPh$_3$)$_4$ (196.7 mg, 0.17 mmol) and $K_2CO_3$ (1.412 g, 10.22 mmol) were added DME (12.0 mL) and $H_2O$ (3.0 mL) via syringe and the mixture was stirred at 90° C. under $N_2$ for 3 hrs. After the reaction was completed, the mixture was cooled to rt, diluted with EtOAc (100.0 mL), and washed with water (50 mL×3). The combined organic layers were dried over anhydrous $Na_2SO_4$ and concentrated in vacuo. The residue was purified by a silica gel column chromatography (DCM/EtOH (v/v)=50/1) to give the title compound (1.35 g, 45%) as a pale yellow solid. The compound was characterized by the following spectroscopic data:

MS (ESI, pos.ion) m/z: 442.3 $[M+2H]^{2+}$;
$^1$H NMR (400 MHz, $CDCl_3$) δ (ppm): 7.66 (s, 1H), 7.62-7.55 (m, 10H), 5.56, 5.55 (d, d, 2H), 5.37-5.30 (m, 2H), 5.23-5.19 (m, 2H), 4.34-4.30 (m, 2H), 3.85-3.78 (m, 2H), 3.66 (s, 6H), 3.65-3.61 (m, 2H), 2.30-1.92 (m, 12H), 1.77-1.65 (m, 2H), 1.02, 1.01 (m, m, 6H), 0.97-0.94 (m, 2H), 0.93, 0.91 (m, m, 6H).

Example 64

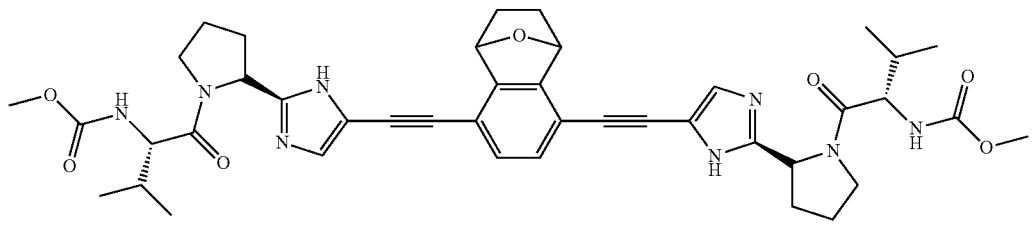

Synthetic Route:

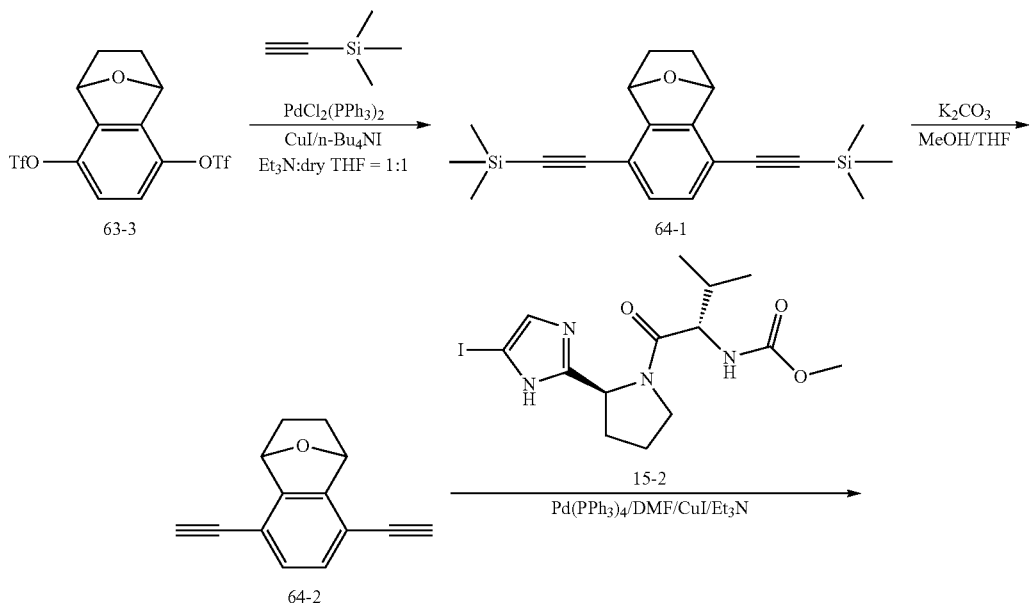

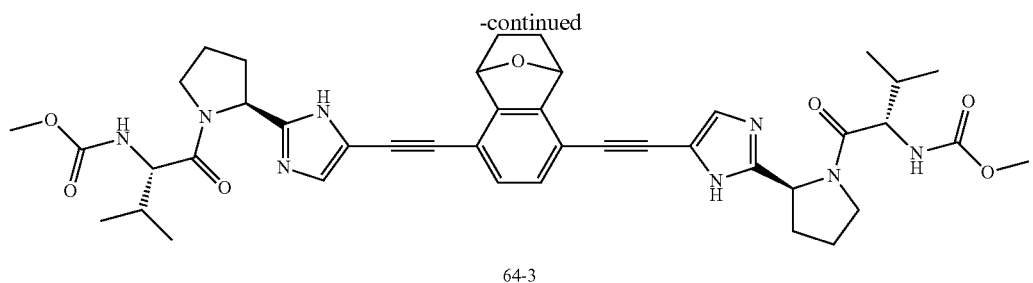

64-3

Compounds disclosed herein can be synthesized through the procedure as depicted in Example 19.

Compound 64-1 was characterized by the following spectroscopic data:

MS (ESI, pos.ion) m/z: 339.5 [M+H]$^+$;

$^1$H NMR (400 MHz, CDCl$_3$) δ (ppm): 7.15 (s, 2H), 5.92-5.86 (m, 2H), 1.82-1.69 (m, 2H), 1.04-0.91 (m, 2H), 0.30 (s, 18H).

Compound 64-2 was characterized by the following spectroscopic data:

MS (ESI, pos.ion) m/z: 195.5 [M+H]$^+$;

$^1$H NMR (400 MHz, CDCl$_3$) δ (ppm): 6.91 (s, 2H), 5.72-5.65 (m, 2H), 3.27 (s, 2H), 1.96-1.83 (m, 2H), 1.18-1.05 (m, 2H).

Compound 64-3 was characterized by the following spectroscopic data:

MS (ESI, pos.ion) m/z: 779.5 [M+H]$^+$;

$^1$H NMR (400 MHz, CD$_3$Cl) δ (ppm): 7.46 (s, 2H), 7.63 (s, 1H), 7.62-7.60 (m, 2H), 7.53-7.50 (m, 2H), 7.48, 7.46 (s, s, 1H), 7.38, 7.36 (s, s, 1H), 6.54-6.51 (m, 1H), 6.08-6.06 (m, 1H), 4.08-4.01 (m, 2H), 3.48-3.38 (m, 3H), 3.37-3.22 (m, 3H), 2.91-2.84 (m, 2H), 1.74-1.65 (m, 2H), 1.60-1.50 (m, 2H), 1.42 (s, 9H), 1.41 (s, 9H), 1.40-1.33 (m, 2H).

Example 65

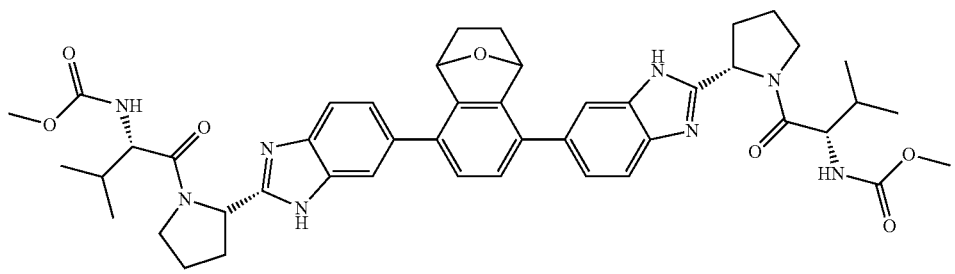

Synthetic Route:

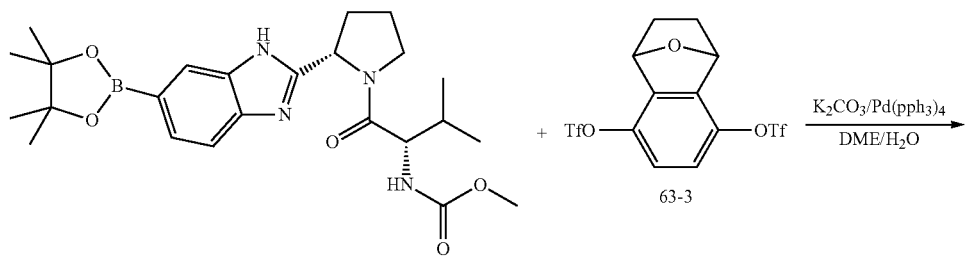

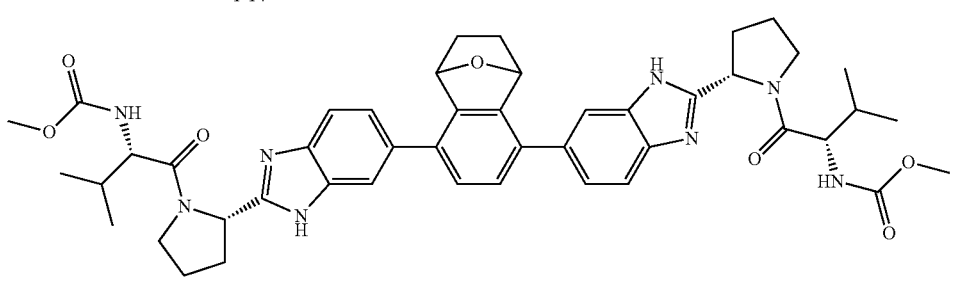

65-1

Step 1) the Preparation of Compound 65-1

A mixture of compound 63-3 (1.5 g, 3.4 mmol), compound 1-14 (3.47 g, 7.38 mmol), Pd(PPh$_3$)$_4$ (196.7 mg, 0.17 mmol) and K$_2$CO$_3$ (1.412 g, 10.22 mmol) in the mixed solvent of DME/H$_2$O (15.0 mL, v/v=4/1) was stirred at 90° C. under N$_2$ for 3 hrs. After the reaction was completed, the mixture was cooled to rt, diluted with EtOAc (100 mL), and washed with water (50 mL×3) and brine. The combined organic layers were dried over anhydrous Na$_2$SO$_4$ and concentrated in vacuo. The residue was purified by a silica gel column chromatography (DCM/MeOH (v/v)=50/1) to give the title compound (1.27 g, 45%) as a pale yellow solid. The compound was characterized by the following spectroscopic data:

MS (ESI, pos.ion) m/z: 416.3 [M+2H]$^{2+}$;

$^1$H NMR (400 MHz, CDCl$_3$) δ (ppm): 7.65-7.62 (m, 4H), 7.40 (s, 2H), 7.26, 7.24 (d, d, 2H), 5.65-5.59 (m, 2H), 5.56, 5.55 (d, d, 2H), 5.25-5.20 (m, 2H), 4.36-4.30 (m, 2H), 3.84-3.77 (m, 2H), 3.66 (s, 6H), 3.65-3.60 (m, 2H), 2.37-2.11 (m, 8H), 1.98-1.87 (m, 2H), 1.82-1.69 (m, 2H), 1.02, 1.00 (m, 6H), 0.99-0.94 (m, 2H), 0.93, 0.92 (m, 6H).

Example 66

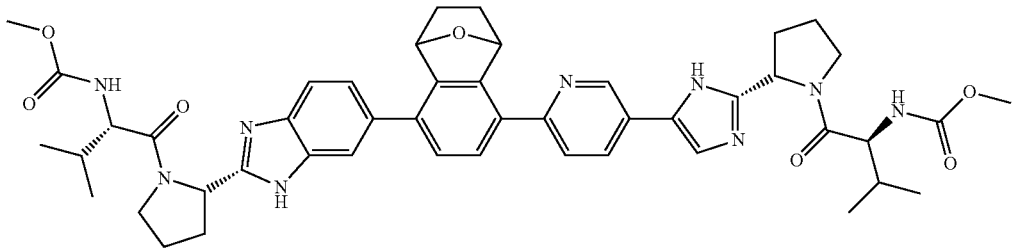

Synthetic Route:

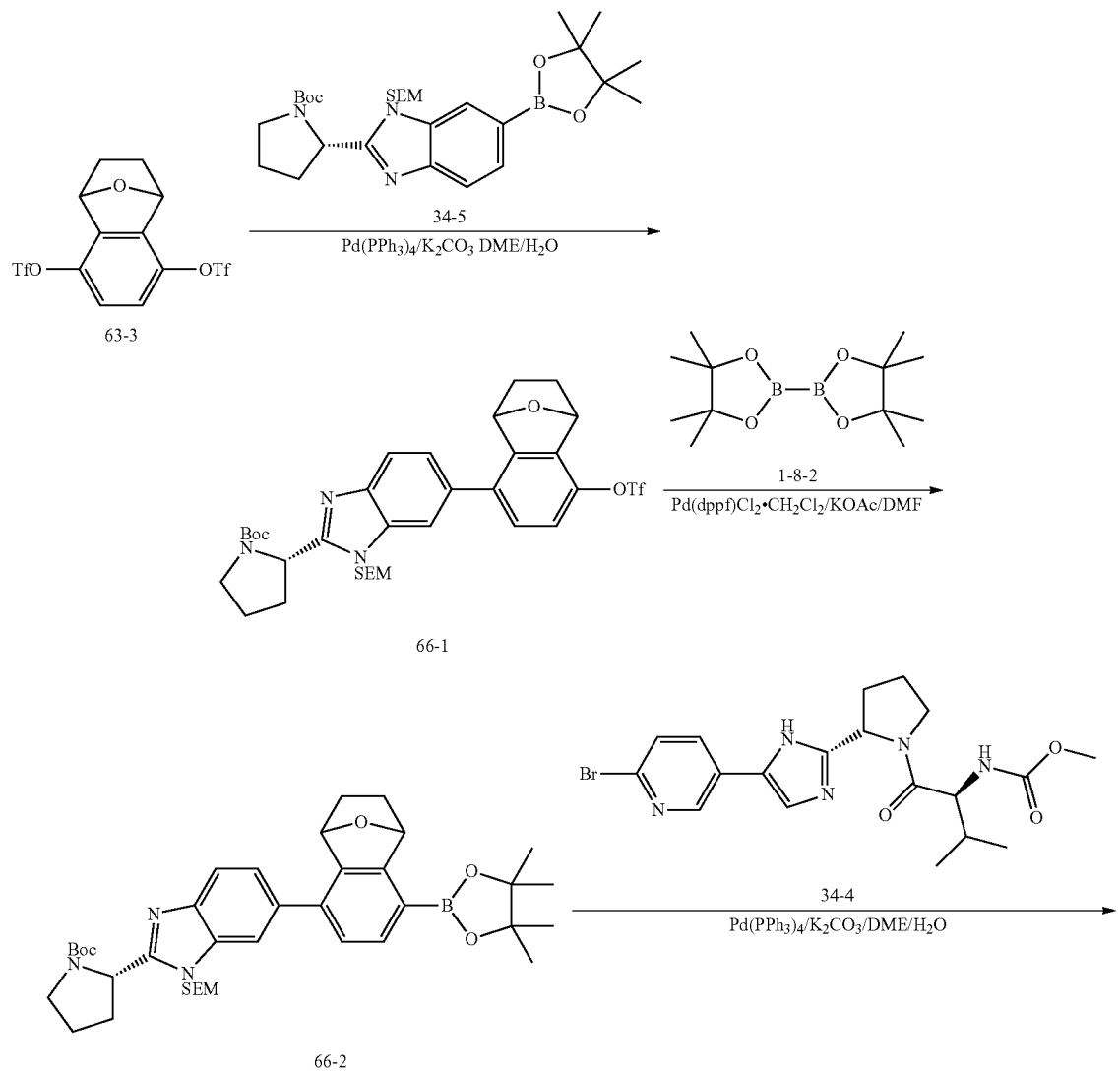

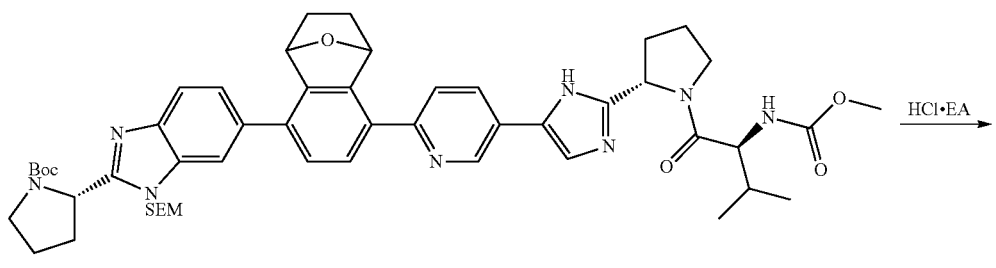

66-3

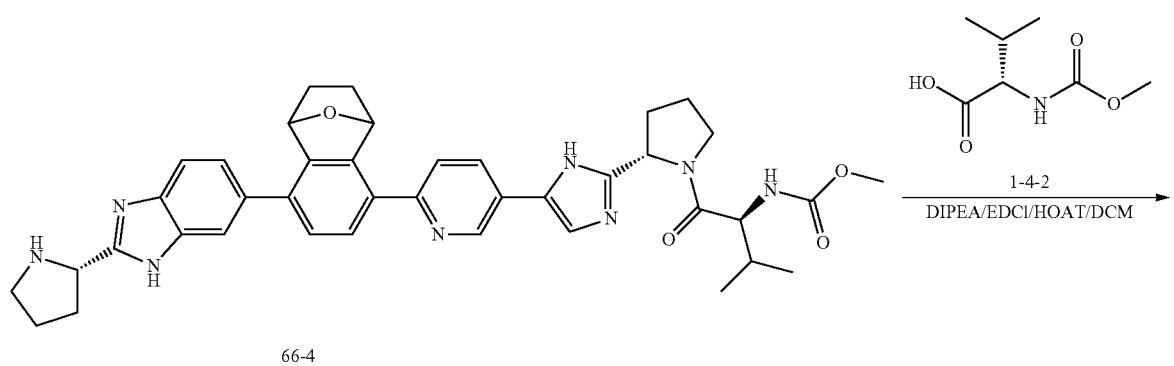

66-4

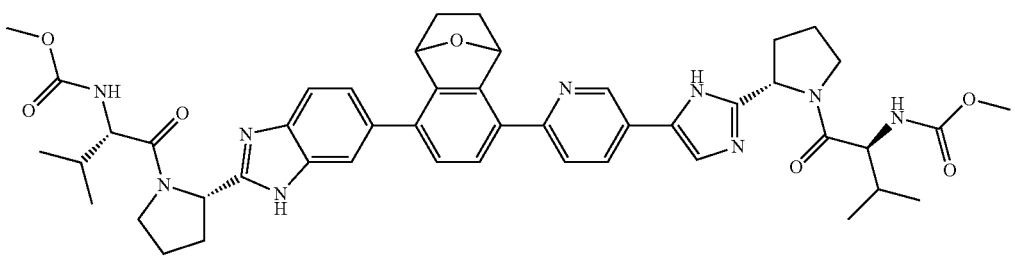

66-5

Compounds disclosed herein can be synthesized through the procedure depicted in Example 41.

Compound 66-1 was characterized by the following spectroscopic data:

MS (ESI, pos.ion) m/z: 710.5 [M+H]$^+$;

$^1$H NMR (400 MHz, CDCl$_3$) δ (ppm): 8.13-8.12, 8.11-8.10 (d, d, 1H, J=4.0 Hz), 7.56-7.55 (q, 1H), 7.46, 7.44 (d, d, 1H), 7.42, 7.40 (s, s, 1H), 7.37, 7.35 (s, s, 1H), 5.60-5.57 (m, 3H), 5.48-5.45 (m, 1H), 5.03-4.99 (m, 1H), 3.75-3.69 (m, 1H), 3.57-3.48 (m, 3H), 2.59-2.50 (m, 1H), 2.27-1.94 (m, 3H), 1.79-1.61 (m, 2H), 1.53 (s, 9H), 1.01-0.83 (m, 4H), 0.01-0.00 (m, 9H).

Compound 66-2 was characterized by the following spectroscopic data:

MS (ESI, pos.ion) m/z: 688.5 [M+H]$^+$;

$^1$H NMR (400 MHz, CDCl$_3$) δ (ppm): 8.36-8.35, 8.34-8.33 (d, d, 1H, J=4.0 Hz), 7.96, 7.94 (s, s, 1H), 7.82, 7.80 (s, s, 1H), 7.61-7.60 (m, 1H), 7.46, 7.44 (d, d, 1H), 5.75-5.72 (m, 1H), 5.59 (t, 2H), 5.53-5.50 (m, 1H), 5.03-4.99 (m, 1H), 3.75-3.69 (m, 1H), 3.57-3.48 (m, 3H), 2.59-2.50 (m, 1H), 2.27-1.94 (m, 3H), 1.83-1.69 (m, 2H), 1.53 (s, 9H), 1.32, 1.29 (m, m, 12H), 1.05-0.86 (m, 4H), 0.01-0.00 (m, 9H).

Compound 66-3 was characterized by the following spectroscopic data:

MS (ESI, pos.ion) m/z: 931.5 [M+H]$^+$;

$^1$H NMR (400 MHz, CD$_3$Cl) δ (ppm): 8.84, 8.83 (d, d, 1H), 8.23-8.21 (m, 1H), 7.71-7.70, 7.69-7.68 (d, d, 1H, J=4.0 Hz), 7.67 (s, 1H), 7.60 (t, 1H), 7.59, 7.57 (s, s, 1H), 7.56 (s, 1H), 7.54 (s, 1H), 7.46, 7.44 (d, d, 1H), 5.67-5.64 (m, 1H), 5.59 (t, 2H), 5.52-5.49 (m, 1H), 5.38-5.33 (m, 1H), 5.32-5.29 (d, d, 1H), 5.03-4.99 (m, 1H), 4.41-4.36 (m, 1H), 3.85-3.78 (m, 1H), 3.75-3.64 (m, 2H), 3.63 (s, 3H), 3.57-3.49 (m, 3H), 2.59-2.50 (m, 1H), 2.30-1.92 (m, 8H), 1.82-1.64 (m, 2H), 1.53 (s, 9H), 1.03-0.86 (m, 10H), 0.01-0.00 (m, 9H).

Compound 66-5 was characterized by the following spectroscopic data:

MS (ESI, pos.ion) m/z: 858.5 [M+H]$^+$;

$^1$H NMR (400 MHz, CD$_3$Cl) δ (ppm): 8.84, 8.83 (d, d, 1H), 8.18, 8.16 (s, s, 1H), 7.71, 7.68 (d, d, 1H), 7.68, 7.66 (s, s, 1H), 7.67 (s, 1H), 7.65 (s, 1H), 7.63-7.62 (m, 2H), 7.56, 7.54 (d, d, 1H), 5.66-5.63 (m, 1H), 5.52-5.49 (m, 1H), 5.38-5.33 (m, 1H), 5.32, 5.30 (d, d, 2H), 5.24-5.20 (m, 1H), 4.41-4.35 (m, 2H), 3.85-3.78 (m, 2H), 3.68-3.64 (m, 2H), 3.63 (s, 6H), 2.38-1.87 (m, 10H), 1.81-1.65 (m, 2H), 1.03-0.87 (m, 14H).

Example 67
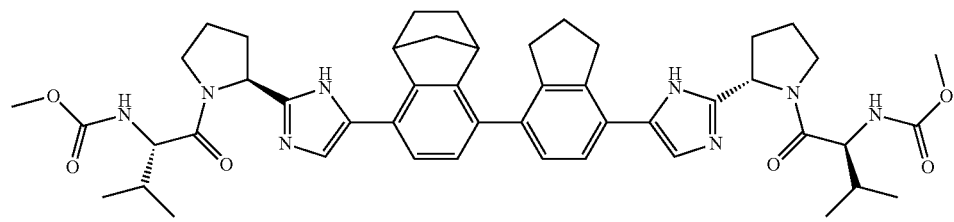 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3C3CCC4C3)c3c2CCC3)[nH]1)C(C)C]
Synthetic Route:
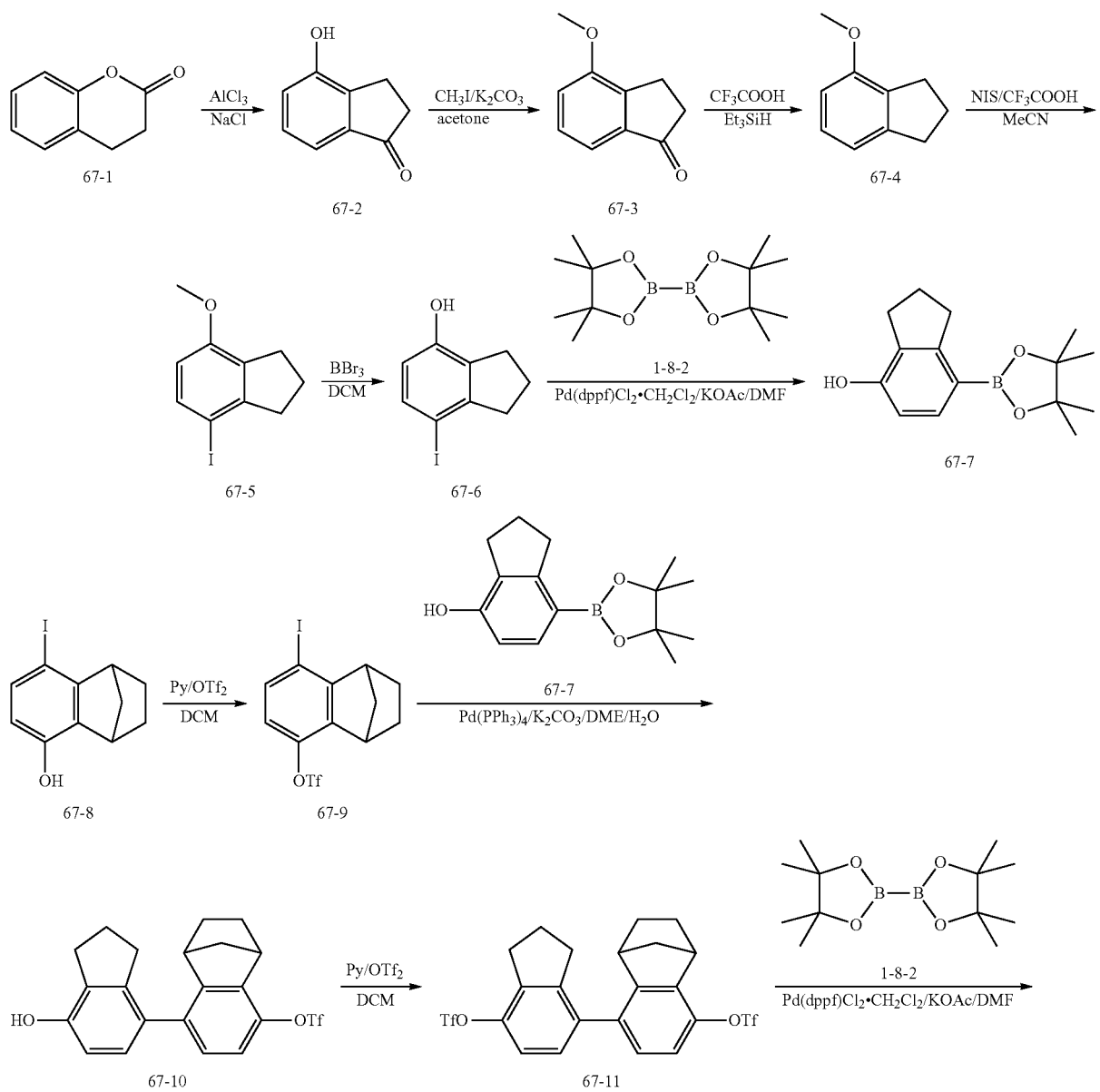

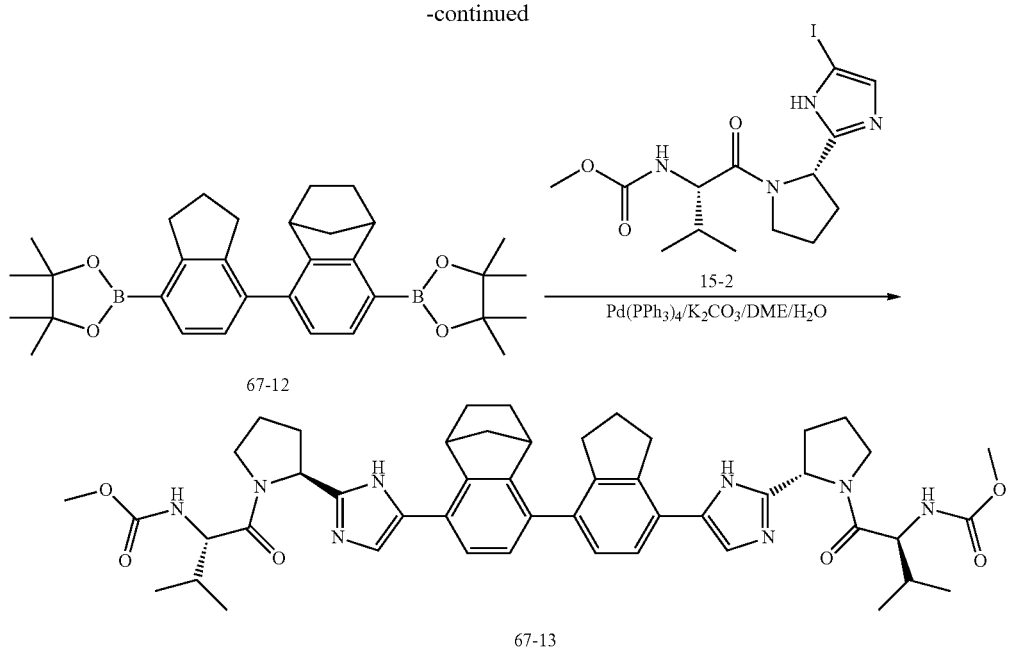

Step 1) the Preparation of Compound 67-2

A mixture of aluminium chloride (90.0 g, 676 mmol) and sodium chloride was stirred at 150° C. until the solid dissolved, and then compound 67-1 (20.0 g, 135 mmol) was added dropwise. At the end of addition, the mixture was stirred at 200° C. for 1 hr. After the reaction was completed, the mixture was cooled to rt and poured slowly into ice-water (500 mL), then filtered to get the crude product. The crude product was purified by beating to give the title compound 67-2 (19 g, 95%) as a gray solid. The compound was characterized by the following spectroscopic data:

MS (ESI, pos.ion) m/z: 149.5 [M+H]$^+$;

$^1$HNMR (400 MHz, CDCl$_3$) δ (ppm): 7.41-7.38 (m, 1H), 7.24-7.19 (m, 1H), 6.80-6.79, 6.78-6.77 (d, d, 1H, J=4.0 Hz), 5.46 (br, 1H), 3.06-3.03 (m, 2H), 2.69-2.66 (m, 2H).

Step 2) the Preparation of Compound 67-3

To a solution of compound 67-2 (5.0 g, 33.7 mmol) and K$_2$CO$_3$ (23.4 g, 168.5 mmol) in acetone (50.0 mL) was added iodomethane (3.15 mL, 50.55 mmol) dropwise. At the end of addition, the mixture was stirred at 60° C. for 5 hrs. After the reaction was completed, the mixture was concentrated in vacuo. The residue was dissolved in EtOAc (150 mL) and water (150 mL), and then filtered through a celite pad. The aqueous layer was extracted with EtOAc (150 mL×2). The combine organic layers were washed with brine, dried over anhydrous Na$_2$SO$_4$ and concentrated in vacuo. The residue was purified by a silica gel column chromatography (PE/EtOAc (v/v)=10/1) to give the title compound (2.5 g, 45%) as colorless oil. The compound was characterized by the following spectroscopic data:

MS (ESI, pos.ion) m/z: 163.5 [M+H]$^+$;

$^1$HNMR (400 MHz, CDCl$_3$) δ (ppm): 7.51-7.48 (m, 1H), 7.30-7.26 (m, 1H), 6.91-6.87 (m, 1H), 3.90 (s, 3H), 3.08-3.05 (m, 2H), 2.70-2.67 (m, 2H).

Step 3) the Preparation of Compound 67-4

To a suspension of compound 67-3 (7.29 g, 45.0 mmol) and triethylsilane (20.98 g, 180 mmol) was added TFA (30.0 mL) dropwise at 0° C. At the end of addition, the mixture was stirred at 40° C. overnight. After the reaction was completed, the mixture was concentrated in vacuo. The residue was dissolved in EtOAc (150 mL). The resulting mixture was washed with brine (50 mL×2), dried over anhydrous Na$_2$SO$_4$ and concentrated in vacuo. The residue was purified by a silica gel column chromatography (PE) to give the title compound (5.2 g, 78%). The compound was characterized by the following spectroscopic data:

MS (ESI, pos.ion) m/z: 149.5 [M+H]$^+$;

$^1$HNMR (400 MHz, CDCl$_3$) δ (ppm): 7.03-6.96 (m, 2H), 6.68-6.66 (m, 1H), 3.86 (s, 3H), 2.99-2.81 (m, 4H), 2.24-2.05 (m, 2H).

Step 4) the Preparation of Compound 67-5

To a solution of compound 67-4 (10.34 g, 69.8 mmol) and NIS (17.2 g, 76.8 mmol) in MeCN (200 mL) was added TFA (0.52 mL, 6.98 mmol) dropwise at 0° C. At the end of addition, the mixture was stirred at rt overnight. After the reaction was completed, the mixture was quenched with saturated NaHCO$_3$ aqueous solution (50 mL). The aqueous layer was extracted with EtOAc (100 mL×3). The combined organic layers were washed with brine, dried over anhydrous Na$_2$SO$_4$ and concentrated in vacuo. The residue was purified by a silica gel column chromatography (PE) to give the title compound (16.44 g, 86%). The compound was characterized by the following spectroscopic data:

MS (ESI, pos.ion) m/z: 275.5 [M+H]$^+$;

$^1$HNMR (400 MHz, CDCl$_3$) δ (ppm): 7.42, 7.40 (t, t, 1H), 6.41-6.40, 6.39-6.38 (m, m, 1H), 3.87 (s, 3H), 2.96-2.76 (m, 4H), 2.37-2.18 (m, 2H).

Step 5) the Preparation of Compound 67-6

To a solution of compound 67-5 (16.35 g, 59.7 mmol) in DCM (150.0 mL) was added boron tribromide (74.7 g, 298.8 mmol) dropwise at −78° C. At the end of addition, the reaction mixture was stirred at rt for 1 hr. After the reaction was completed, the mixture was quenched with ice-water (200 mL) and the organic phase separated. The aqueous layer was extracted with EtOAc (100 mL×3). The combined organic layers were washed with brine, dried over anhydrous Na$_2$SO$_4$ and concentrated in vacuo. The residue was purified by a silica gel column chromatography (PE/EtOAc (v/v)=40/1) to give the title compound (14.28 g, 92%). The compound was characterized by the following spectroscopic data:

MS (ESI, pos.ion) m/z: 261.3 [M+H]$^+$;

$^1$H NMR (400 MHz, CDCl$_3$) δ (ppm): 7.32, 7.30 (t, t, 1H), 6.32, 6.30 (t, t, 1H), 4.81 (br, 1H), 2.90-2.74 (m, 4H), 2.36-2.18 (m, 2H).

Step 6) the Preparation of Compound 67-7

A mixture of compound 67-6 (421 mg, 1.62 mmol), compound 1-8-2 (420 mg, 1.7 mmol), Pd(dppf)Cl$_2$.CH$_2$Cl$_2$ (67 mg, 0.08 mmol) and KOAc (400 mg, 4.05 mmol) in DMF (5.0 mL) was stirred at 90° C. under N$_2$ for 3 hrs. After the reaction was completed, the mixture was cooled to rt, diluted with EtOAc (50.0 mL) and filtered through a celite pad. The filtrate was washed with water (20.0 mL×3) and brine, dried over anhydrous Na$_2$SO$_4$ and concentrated in vacuo. The residue was purified by a silica gel column chromatography (PE/EtOAc (v/v)=10/1) to give the title compound (295 mg, 70%) as a pale yellow solid. The compound was characterized by the following spectroscopic data:

MS (ESI, pos.ion) m/z: 261.5 [M+H]$^+$;

$^1$H NMR (400 MHz, CDCl$_3$) δ (ppm): 7.94, 7.92 (t, t, 1H), 6.71, 6.69 (t, t, 1H), 4.81 (br, 1H), 2.97-2.92 (m, 2H), 2.87-2.70 (m, 2H), 2.29-2.10 (m, 2H), 1.32, 1.29 (m, m, 12H).

Step 7) the Preparation of Compound 67-9

To a solution of compound 67-8 (2.86 g, 10.0 mmol) in DCM (20.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (25.0 mL). The aqueous layer was extracted with DCM (30 mL×3). The combined organic layers were washed with brine, dried over anhydrous Na$_2$SO$_4$ and concentrated in vacuo. The residue was purified by a silica gel column chromatography (PE) to give the title compound (3.76 g, 90%) as colorless oil. The compound was characterized by the following spectroscopic data:

$^1$H NMR (400 MHz, CDCl$_3$) δ (ppm) 7.60, 7.59 (s, s, 1H), 6.80, 6.77 (s, s, 1H), 3.89-3.86 (m, 1H), 3.41-3.38 (m, 1H), 2.09-2.03 (m, 1H), 1.96-1.90 (m, 1H), 1.88-1.84 (m, 1H), 1.65-1.61 (m, 1H), 1.36-1.30 (m, 1H), 1.23-1.17 (m, 1H).

Step 8) the Preparation of Compound 67-10

A mixture of compound 67-7 (884.5 mg, 3.40 mmol), compound 67-9 (1.42 g, 3.40 mmol), Pd(PPh$_3$)$_4$ (196.7 mg, 0.17 mmol) and K$_2$CO$_3$ (1.412 g, 10.22 mmol) in the mixed solvents of DME/H$_2$O (15 mL, v/v=4/1) was stirred at 90° C. under N$_2$ for 4 hrs. After the reaction was completed, the mixture was cooled to rt, diluted with EtOAc (80 mL), and washed with water (20 mL×3) and brine. The combined organic layers were dried over anhydrous Na$_2$SO$_4$ and concentrated in vacuo. The residue was purified by a silica gel column chromatography (PE/EtOAc (v/v)=20/1) to give the title compound (648.8 mg, 45%) as a pale yellow solid. The compound was characterized by the following spectroscopic data:

MS (ESI, pos.ion) m/z: 425.5 [M+H]$^+$;

$^1$H NMR (400 MHz, CDCl$_3$) δ (ppm): 7.40, 7.38 (s, s, 1H), 7.13, 7.11 (s, s, 1H), 6.92, 6.90 (t, t, 1H), 6.50, 6.48 (t, t, 1H), 4.81 (brs, 1H), 3.79-3.76 (m, 1H), 3.44-3.41 (m, 1H), 3.01-2.84 (m, 2H), 2.73-2.68 (m, 2H), 2.34-2.15 (m, 2H), 2.06-2.00 (m, 1H), 1.98-1.92 (m, 1H), 1.85-1.81 (m, 1H), 1.62-1.58 (m, 1H), 1.33-1.27 (m, 1H), 1.25-1.19 (m, 1H).

Step 9) the Preparation of Compound 67-11

To a solution of compound 67-10 (4.24 g, 10.0 mmol) in DCM (20.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (50.0 mL). The aqueous layer was extracted with DCM (30 mL×3). The combined organic layers were washed with brine, dried over anhydrous Na$_2$SO$_4$ and concentrated in vacuo. The residue was purified by a silica gel column chromatography (PE/EtOAc (v/v)=40/1) to give the title compound (5.0 g, 90%) as colorless oil. The compound was characterized by the following spectroscopic data:

$^1$H NMR (400 MHz, CDCl$_3$) δ (ppm): 7.40, 7.38 (s, s, 1H), 7.10, 7.08 (s, s, 1H), 7.01-6.99 (t, t, 1H), 6.96, 6.94 (t, t, 1H), 3.79-3.76 (m, 1H), 3.44-3.41 (m, 1H), 3.03-2.86 (m, 2H), 2.68-2.63 (m, 2H), 2.39-2.20 (m, 2H), 2.06-2.00 (m, 1H), 1.98-1.92 (m, 1H), 1.85-1.81 (m, 1H), 1.62-1.58 (m, 1H), 1.33-1.27 (m, 1H), 1.25-1.19 (m, 1H).

Step 10) the Preparation of Compound 67-12

A mixture of compound 67-11 (900.7 mg, 1.62 mmol), compound 1-8-2 (420 mg, 1.7 mmol), Pd(dppf)Cl$_2$.CH$_2$Cl$_2$ (67 mg, 0.08 mmol) and KOAc (400 mg, 4.05 mmol) in DMF (8.0 mL) was stirred at 90° C. under N$_2$ for 3 hrs. After the reaction was completed, the mixture was cooled to rt, diluted with EtOAc (80 mL) and filtered through a celite pad. The filtrate was washed with water (20 mL×3) and brine, dried over anhydrous Na$_2$SO$_4$ and concentrated in vacuo. The residue was purified by a silica gel column chromatography (PE/EtOAc (v/v)=8/1) to give the title compound (581 mg, 70%) as a pale yellow solid. The compound was characterized by the following spectroscopic data:

MS (ESI, pos.ion) m/z: 513.5 [M+H]$^+$;

$^1$H NMR (400 MHz, CDCl$_3$) δ (ppm): 7.76-7.72 (m, 2H), 7.57, 7.55 (s, s, 1H), 7.44, 7.42 (t, t, 1H), 3.78-3.74 (m, 2H), 3.02-2.97 (m, 2H), 2.74-2.69 (m, 2H), 2.19-2.01 (m, 2H), 1.96-1.90 (m, 1H), 1.83-1.77 (m, 1H), 1.60-1.56 (m, 1H), 1.32 (m, 12H), 1.29 (m, 12H), 1.23-1.17 (m, 1H), 1.10-1.04 (m, 1H).

Step 11) the Preparation of Compound 67-13

A mixture of compound 67-12 (1.74 g, 3.40 mmol), compound 15-2 (3.10 g, 7.38 mmol), Pd(PPh$_3$)$_4$ (196.7 mg, 0.17 mmol) and K$_2$CO$_3$ (1.412 g, 10.22 mmol) in the mixed solvents of DME/H$_2$O (15.0 mL, v/v=4/1) was stirred at 90° C. under N$_2$ for 4 hrs. After the reaction was completed, the mixture was cooled to rt, diluted with EtOAc (100 mL), and washed with water (50 mL×3) and brine. The combined organic layers were dried over anhydrous Na$_2$SO$_4$ and concentrated in vacuo. The residue was purified by a silica gel column chromatography (DCM/MeOH (v/v)=50/1) to give the title compound (1.29 g, 45%) as a pale yellow solid. The compound was characterized by the following spectroscopic data:

MS (ESI, pos.ion) m/z: 423.5 [M+2H]$^{2+}$;

$^1$H NMR (400 MHz, CDCl$_3$) δ (ppm): 7.85 (s, 1H), 7.81 (s, 1H), 7.49, 7.47 (s, s, 1H), 7.40, 7.37 (t, t, 1H), 7.34, 7.32 (s, 1H), 6.99-6.97 (t, t, 1H), 5.32-5.25 (m, 4H), 4.41-4.36 (m, 2H), 3.85-3.76 (m, 3H), 3.75-3.72 (m, 1H), 3.63 (s, 6H), 3.16-3.11 (m, 4H), 2.81-2.76 (m, 2H), 2.30-1.92 (m, 14H), 1.90-1.86 (m, 1H), 1.67-1.63 (m, 1H), 1.30-1.19 (m, 2H), 0.97, 0.96 (m, m, 6H), 0.91, 0.89 (m, m, 6H).

Example 68
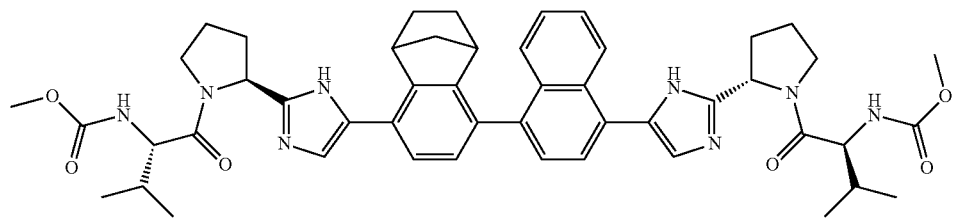 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4ccccc34)c3c2C2CCC3C2)[nH]1)C(C)C]
Synthetic Route:
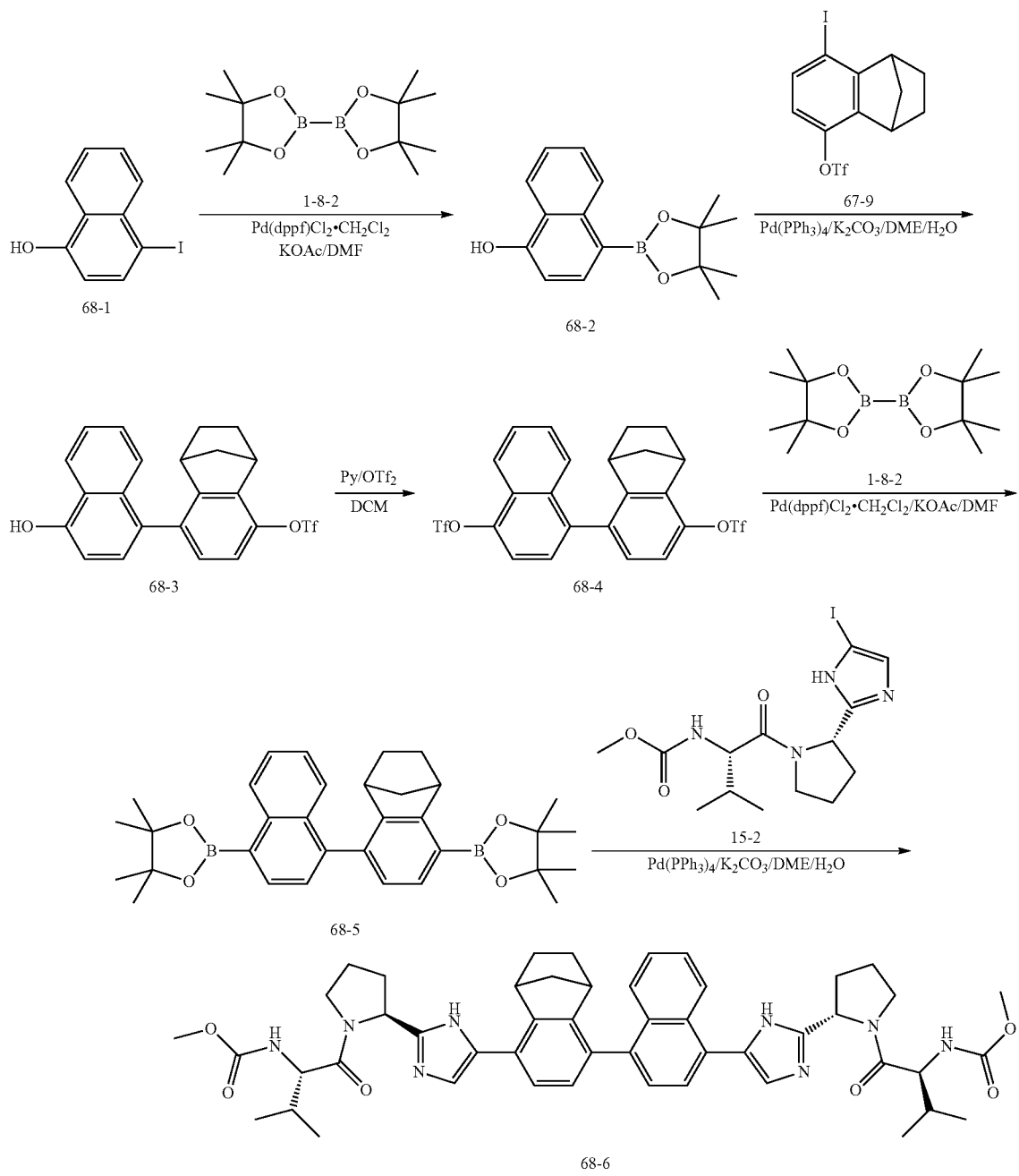

Step 1) the Preparation of Compound 68-2

A mixture of compound 68-1 (437 mg, 1.62 mmol), compound 1-8-2 (420 mg, 1.7 mmol), Pd(dppf)Cl$_2$.CH$_2$Cl$_2$ (67 mg, 0.08 mmol) and KOAc (400 mg, 4.05 mmol) in DMF (5.0 mL) was stirred at 90° C. under N$_2$ for 3 hrs. After the reaction was completed, the mixture was cooled to rt, diluted with EtOAc (50.0 mL) and filtered through a celite pad. The filtrate was washed with water (20.0 mL×3) and brine, dried over anhydrous Na$_2$SO$_4$ and concentrated in vacuo. The residue was purified by a silica gel column chromatography (PE/EtOAc (v/v)=15/1) to give the title compound (306 mg, 70%) as a pale yellow solid. The compound was characterized by the following spectroscopic data:

MS (ESI, pos.ion) m/z: 271.5 [M+H]$^+$;

$^1$H NMR (400 MHz, CDCl$_3$) δ (ppm): 8.53-8.50 (m, 1H), 8.45-8.43 (m, 1H), 7.83, 7.81 (m, m, 1H), 7.62-7.58 (m, 1H), 7.52-7.48 (m, 1H), 7.06, 7.04 (br, br, 1H), 6.17 (br, 1H), 1.57 (m, 6H), 1.54 (m, 6H).

Step 2) the Preparation of Compound 68-3

A mixture of compound 68-2 (918 mg, 3.4 mmol), compound 67-9 (1.42 g, 3.4 mmol), Pd(PPh$_3$)$_4$ (196.7 mg, 0.17 mmol) and K$_2$CO$_3$ (1.412 g, 10.22 mmol) in the mixed solvents of DME/H$_2$O (15.0 mL, v/v=4/1) was stirred at 90° C. under N$_2$ for 4 hrs. After the reaction was completed, the mixture was cooled to rt, diluted with EtOAc (60 mL), and then washed with water (20.0 mL×3) and brine. The combined organic layers were dried over anhydrous Na$_2$SO$_4$ and concentrated in vacuo. The residue was purified by a silica gel column chromatography (PE/EtOAc (v/v)=20/1) to give the title compound (664 mg, 45%) as a pale yellow solid. The compound was characterized by the following spectroscopic data:

MS (ESI, pos.ion) m/z: 449.5 [M+H]$^+$;

$^1$H NMR (400 MHz, CDCl$_3$) δ (ppm): 8.28, 8.25 (m, m, 1H), 7.48-7.44 (m, 1H), 7.36-7.34 (m, 1H), 7.33, 7.30 (br, br, 1H), 7.26, 7.24 (s, s, 1H), 7.23-7.20 (m, 1H), 7.20, 7.17 (m, m, 1H), 7.06, 7.04 (br, br, 1H), 6.17 (br, 1H), 3.66-3.60 (m, 2H), 2.10-2.04 (m, 1H), 1.98-1.92 (m, 1H), 1.89-1.85 (m, 1H), 1.66-1.62 (m, 1H), 1.37-1.31 (m, 1H), 1.25-1.19 (m, 1H).

Step 3) the Preparation of Compound 68-4

To a solution of compound 68-3 (4.34 g, 10.0 mmol) in DCM (40.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched with ice-water (50.0 mL). The aqueous layer was extracted with DCM (30 mL×3). The combined organic layers were washed with brine, dried over anhydrous Na$_2$SO$_4$ and concentrated in vacuo. The residue was purified by a silica gel column chromatography (PE/EtOAc (v/v)=40/1) to give the title compound (5.09 g, 90%) as colorless oil. The compound was characterized by the following spectroscopic data:

$^1$H NMR (400 MHz, CDCl$_3$): δ (ppm): 8.41, 8.39 (m, m, 1H), 7.73, 7.71 (m, 1H), 7.63-7.59 (m, 1H), 7.41-7.38 (m, 1H), 7.31-7.26 (m, 1H), 7.21-7.17 (m, 3H), 3.66-3.60 (m, 2H), 2.10-2.04 (m, 1H), 1.98-1.92 (m, 1H), 1.89-1.85 (m, 1H), 1.66-1.62 (m, 1H), 1.37-1.31 (m, 1H), 1.25-1.19 (m, 1H).

Step 4) the Preparation of Compound 68-5

A mixture of compound 68-4 (917 mg, 1.62 mmol), compound 1-8-2 (420 mg, 1.7 mmol), Pd(dppf)Cl$_2$.CH$_2$Cl$_2$ (67 mg, 0.08 mmol) and KOAc (400 mg, 4.05 mmol) in DMF (5.0 mL) was stirred at 90° C. under N$_2$ for 3 hrs. After the reaction was completed, the mixture was cooled to rt, diluted with EtOAc (60.0 mL) and filtered through a celite pad. The filtrate was washed with water (20.0 mL×3) and brine, dried over anhydrous Na$_2$SO$_4$ and concentrated in vacuo. The residue was purified by a silica gel column chromatography (PE/EtOAc (v/v)=8/1) to give the title compound (592 mg, 70%) as a pale yellow solid. The compound was characterized by the following spectroscopic data:

MS (ESI, pos.ion) m/z: 537.5 [M+H]$^+$;

$^1$H NMR (400 MHz, CDCl$_3$) δ (ppm): 8.80, 8.78 (m, 1H), 7.93, 7.91 (br, br, 1H), 7.89, 7.87 (s, s, 1H), 7.85, 7.83 (m, m, 1H), 7.76-7.75, 7.74-7.73 (m, m, 1H), 7.69, 7.67 (s, s, 1H), 7.60-7.56 (m, 1H), 7.23-7.19 (m, 1H), 3.58-3.54 (m, 2H), 1.96-1.90 (m, 2H), 1.87-1.81 (m, 1H), 1.64-1.60 (m, 1H), 1.56, 1.54 (m, m, 12H), 1.32, 1.29 (m, m, 12H), 1.23-1.17 (m, 1H), 1.14-1.08 (m, 1H).

Step 5) the Preparation of Compound 68-6

A mixture of compound 68-5 (1.82 g, 3.4 mmol), compound 15-2 (3.1 g, 7.38 mmol), Pd(PPh$_3$)$_4$ (196.7 mg, 0.17 mmol) and K$_2$CO$_3$ (1.412 g, 10.22 mmol) in the mixed solvents of DME/H$_2$O (15.0 mL, v/v=4/1) was stirred at 90° C. under N$_2$ for 3 hrs. After the reaction was completed, the mixture was cooled to rt, diluted with EtOAc (100 mL), and washed with water (20 mL×3) and brine. The combined organic layers were dried over anhydrous Na$_2$SO$_4$ and concentrated in vacuo. The residue was purified by a silica gel column chromatography (DCM/MeOH (v/v)=50/1) to give the title compound (1.16 g, 40%) as a pale yellow solid. The compound was characterized by the following spectroscopic data:

MS (ESI, pos.ion) m/z: 428.5 [M+2H]$^{2+}$;

$^1$H NMR (400 MHz, CDCl$_3$) δ (ppm): 7.88, 7.86 (m, m, 1H), 7.81 (s, 1H), 7.74 (s, 1H), 7.73, 7.70 (br, br, 1H), 7.54, 7.52 (s, s, 1H), 7.43-7.39 (m, 1H), 7.36-7.33 (m, 2H), 7.29-7.26 (m, 1H), 7.12-7.08 (m, 1H), 5.36-5.25 (m, 4H), 4.41-4.36 (m, 2H), 3.98-3.94 (m, 1H), 3.90-3.86 (m, 1H), 3.85-3.78 (m, 2H), 3.69-3.64 (m, 2H), 3.63 (s, 6H), 2.30-1.90 (m, 13H), 1.71-1.67 (m, 1H), 1.30-1.23 (m, 2H), 0.97-0.89 (m, 12H).

Example 69

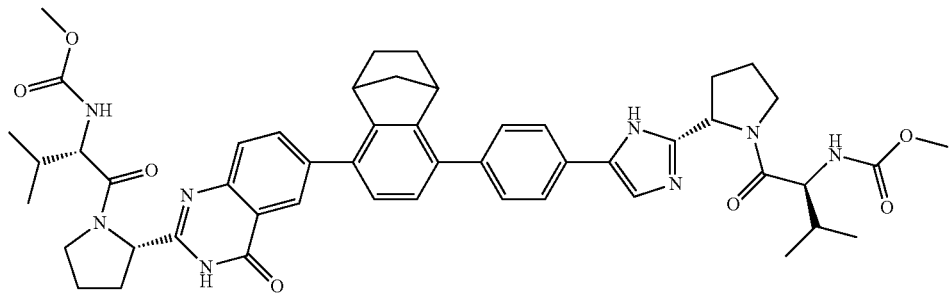

Synthetic Route:
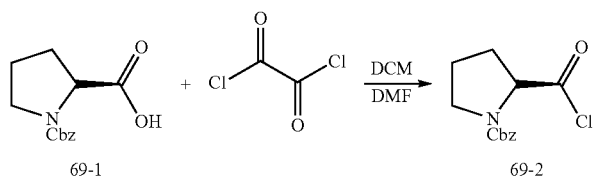
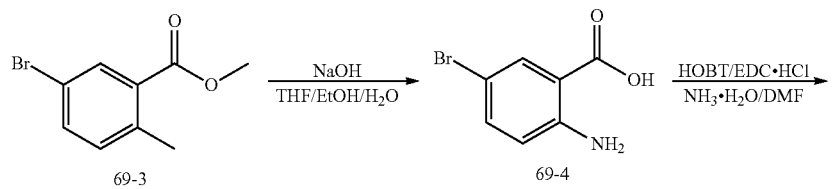
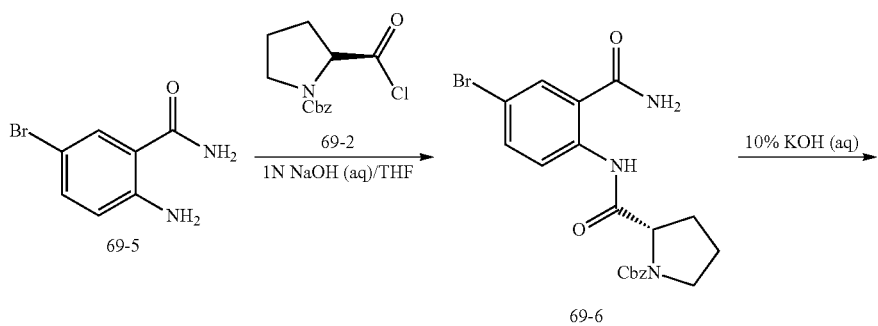
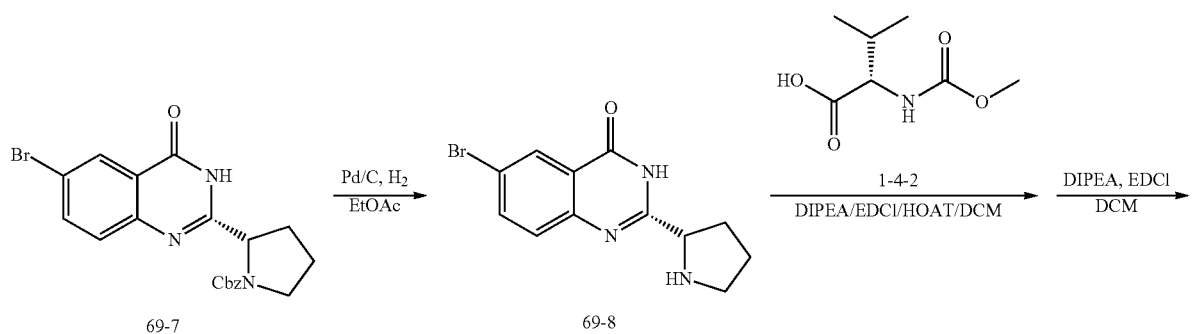
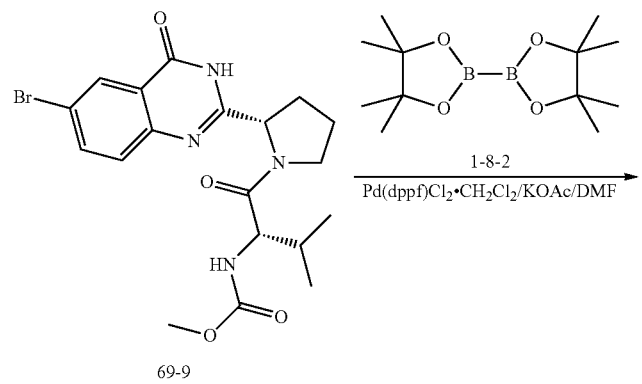

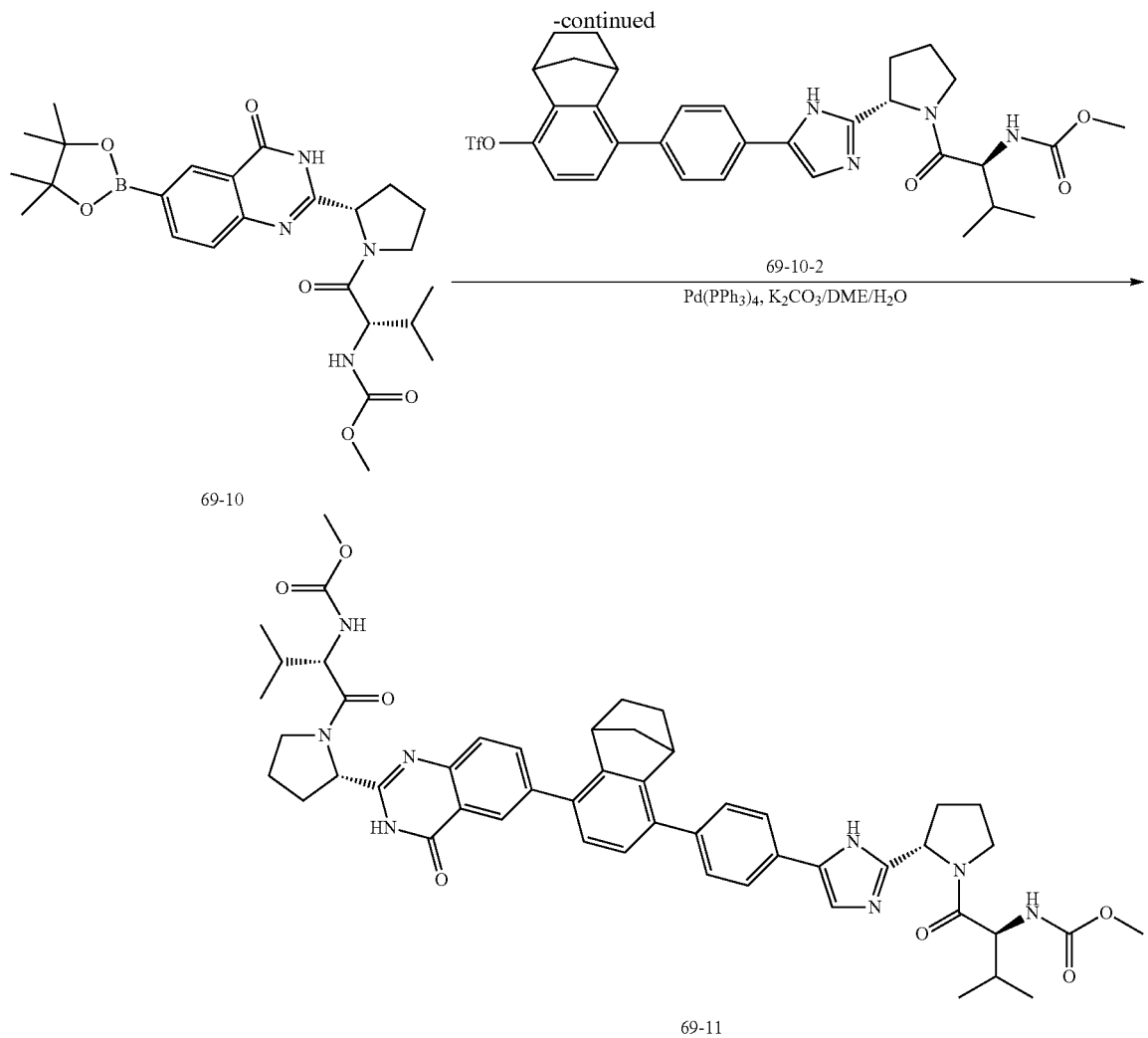

Step 1) the Preparation of Compound 69-2

To a solution of compound 69-1 (1.57 g, 6.31 mmol) in dry DCM (20.0 mL) and DMF (1.5 mL) was added Oxalyl chloride (1.35 mL, 15.75 mmol) dropwise at rt. At the end of addition, the mixture was stirred at rt for 0.5 hr. After the reaction was completed, the mixture was concentrated in vacuo and the residue (2.2 g) was used for the next step without further purification. The compound was characterized by the following spectroscopic data:

MS (ESI, pos.ion) m/z: 268.5 [M+H]$^+$;
$^1$H NMR (400 MHz, CDCl$_3$) δ (ppm): 7.28-7.22 (m, 5H), 5.14-5.13 (m, 2H), 4.47-4.42 (m, 1H), 3.66-3.60 (m, 1H), 3.46-3.38 (m, 1H), 2.23-2.09 (m, 2H), 2.03-1.96 (m, 1H), 1.83-1.73 (m, 1H).

Step 2) the Preparation of Compound 69-4

A solution of compound 69-3 (10.0 g, 43.5 mmol) and NaOH (5.20 g, 130.4 mmol) in H$_2$O (60.0 mL), EtOH (60.0 mL) and THF (180 mL) was stirred at rt for 12 hrs. After the reaction was completed, the solvent was removed. The residue was extracted with EtOAc (100 mL×2). The aqueous phase was adjusted to pH 4 with hydrochloric acid (1 M) and extracted with EtOAc (25 mL×3). The combined organic layers were washed with brine, dried over anhydrous Na$_2$SO$_4$ and concentrated in vacuo to give the title compound 69-4 (9.1 g, 97%). The compound was characterized by the following spectroscopic data:

MS (ESI, pos.ion) m/z: 216.5 [M+H]$^+$;
$^1$H NMR (400 MHz, CDCl$_3$) δ (ppm): 8.03 (d, 1H), 7.34, 7.31 (d, d, 1H), 6.97 (brs, 3H), 6.86, 6.84 (d, d, 1H).

Step 3) the Preparation of Compound 69-5

To a suspension of compound 69-4 (9.1 g, 42.1 mmol), HOBT (13.6 g, 101.1 mmol) and EDC.HCl (19.4 g, 101.1 mmol) in DMF (60.0 mL) was added NH$_3$.H$_2$O (30.0 mL) dropwise. At the end of addition, the mixture was stirred at rt for 15 hrs. After the reaction was completed, the solvent was removed. The residue was dissolved in EtOAc (100 mL). The resulting mixture was washed with NaOH aqueous solution (20 mL, 1 M) and brine, dried over anhydrous Na$_2$SO$_4$ and concentrated in vacuo to give the title compound 69-5 (7.6 g, 84%). The compound was characterized by the following spectroscopic data:

MS (ESI, pos.ion) m/z: 216.5 [M+H]$^+$;
$^1$H NMR (400 MHz, CDCl$_3$) δ (ppm): 7.57 (d, 1H), 7.22, 7.19 (d, d, 1H), 6.58, 6.56 (d, d, 1H), 6.40 (s, 2H), 5.98 (brs, 2H).

Step 4) the Preparation of Compound 69-6

To a solution of compound 69-2 (22.0 g, crude product) in dry THF (250 mL), compound 69-5 (7.6 g, 35.5 mmol) and 1M NaOH (aq. 85 mL, 85 mmol) were added in turn. At the end of addition, the mixture was stirred at rt for 1 hr. After the reaction was completed, the mixture was extracted with EtOAc (100 mL×3). The combined organic layers were washed with 1M NaOH aqueous solution (15.0 mL) and brine, dried over Na₂SO₄ and concentrated in vacuo to give the title compound 69-6. The compound was characterized by the following spectroscopic data:

MS (ESI, pos.ion) m/z: 446.5 [M+H]⁺;
¹H NMR (400 MHz, CDCl₃) δ (ppm): 9.06 (br, 1H), 7.75 (d, 1H), 7.35, 7.33 (d, d, 1H), 7.28-7.22 (m, 5H), 6.69, 6.67 (d, d, 1H), 5.68 (brs, 2H), 5.14-5.13 (m, 2H), 4.29-4.25 (m, 1H), 3.66-3.60 (m, 1H), 3.45-3.37 (m, 1H), 2.39-2.32 (m, 1H), 2.09-2.00 (m, 1H), 1.96-1.77 (m, 2H).

Step 5) the Preparation of Compound 69-7

A solution of compound 69-6 (17.0 g, 38.1 mmol) and KOH (34.0 mL, 10% aq) in EtOH (200 mL) was stirred at 80° C. for 3 hrs. After the reaction was completed, the mixture was cooled to 0° C. and neutralized to pH 7 by carefully adding concentrated HCl. The resulting precipitate was collected by filtration and washed with EtOAc/hexane (v/v=5/1) to give the title compound 69-7 (12.6 g, 77.0%). The compound was characterized by the following spectroscopic data:

MS (ESI, pos.ion) m/z: 428.5 [M+H]⁺;
¹H NMR (400 MHz, CDCl₃) δ (ppm): 8.02, 8.01 (d, d, 1H), 7.65, 7.62 (d, d, 1H), 7.28-7.22 (m, 5H), 7.20, 7.18 (d, d, 1H), 5.14-5.13 (m, 2H), 5.00-4.95 (m, 1H), 3.64-3.57 (m, 1H), 3.44-3.37 (m, 1H), 2.49-2.41 (m, 1H), 2.36-2.26 (m, 1H), 2.02-1.93 (m, 1H), 1.91-1.81 (m, 1H).

Step 6) the Preparation of Compound 69-8

To a solution of compound 69-7 (3.43 g, 8.03 mmol) in EtOAc (40.0 mL) was added a catalytic amount of Pd/C (350 mg), the mixture was stirred at 40° C. under 10 atm of H₂ gas for 5 hrs. After the reaction was completed, the mixture was filtered. The filtrate was concentrated in vacuo to give the title compound 69-8 (2.02 g, 86%). The compound was characterized by the following spectroscopic data:

MS (ESI, pos.ion) m/z: 294.5 [M+H]⁺.

Step 7) the Preparation of Compound 69-9

To a suspension of compound 69-8 (2.93 g, 10.0 mmol), compound 1-4-2 (1.93 g, 11.0 mmol) and EDCI (2.10 g, 11.0 mmol) in DCM (30.0 mL) was added DIPEA (6.6 mL, 39.9 mmol) dropwise at 0° C. At the end of addition, the mixture was stirred at rt for 3 hrs. After the reaction was completed, the mixture was diluted with DCM (50.0 mL), and the resulting mixture was washed with NH₄Cl aqueous solution and brine, dried over Na₂SO₄ and concentrated in vacuo. The residue was purified by a silica gel column chromatography (PE/EtOAc (v/v)=4/1) to give the title compound 69-9 (2.25 g, 50%). The compound was characterized by the following spectroscopic data:

MS (ESI, pos.ion) m/z: 451.5 [M+H]⁺;
¹H NMR (400 MHz, CDCl₃) δ (ppm): 8.02, 8.01 (m, 1H), 7.65, 7.63 (d, d, 1H), 7.22, 7.20 (d, d, 1H), 5.32, 5.29 (br, br, 1H), 5.21-5.16 (m, 1H), 4.30-4.25 (m, 1H), 3.63 (s, 3H), 3.60-3.54 (m, 1H), 3.24-3.16 (m, 1H), 2.44-2.37 (m, 1H), 2.11-1.98 (m, 2H), 1.93-1.85 (m, 1H), 1.83-1.73 (m, 1H), 0.97-0.89 (m, 6H).

Step 8) the Preparation of Compound 69-10

A suspension of compound 69-9 (409 mg, 0.91 mmol), compound 1-8-2 (463 mg, 1.82 mmol), Pd(dppf)Cl₂·CH₂Cl₂ (71.0 mg, 0.09 mmol) and KOAc (268 mg, 2.73 mmol) in DMF (10.0 mL) was stirred at 90° C. under N₂ for 3 hrs. After the reaction was completed, the mixture was cooled to rt, diluted with EtOAc (60.0 mL) and filtered through a celite pad. The filtrate was washed with water (20 mL×3) and brine, dried over anhydrous Na₂SO₄ and concentrated in vacuo. The residue was purified by a silica gel column chromatography (PE/EtOAc (v/v)=2/1) to give the title compound 69-10 (399 mg, 88%). The compound was characterized by the following spectroscopic data:

MS (ESI, pos.ion) m/z: 499.5 [M+H]⁺;
¹H NMR (400 MHz, CDCl₃) δ (ppm): 8.50 (d, 1H), 7.78, 7.76 (d, d, 1H), 7.63, 7.61 (d, d, 1H), 5.32, 5.30 (d, d, 1H), 5.21-5.16 (m, 1H), 4.30-4.25 (m, 1H), 3.63 (s, 3H), 3.60-3.54 (m, 1H), 3.24-3.16 (m, 1H), 2.44-2.37 (m, 1H), 2.11-1.98 (m, 2H), 1.93-1.85 (m, 1H), 1.83-1.73 (m, 1H), 1.24, 1.20 (m, 12H), 0.97, 0.95 (m, m, 3H), 0.90, 0.89 (m, m, 3H).

Step 9) the Preparation of Compound 69-11

A mixture of compound 69-10 (304 mg, 0.61 mmol), compound 69-10⁻² (402.8 mg, 0.61 mmol), Pd(PPh₃)₄ (35.26 mg, 0.03 mmol) and K₂CO₃ (254 mg, 1.83 mmol) in the mixed solvents of DME/H₂O (v/v=5/1, 6.0 mL) was stirred at 90° C. under N₂ for 4 hrs. After the reaction was completed, the mixture was cooled to rt, diluted with EtOAc (50 mL), and washed with water (20.0 mL×3) and brine. The combined organic layers were dried over anhydrous Na₂SO₄ and concentrated in vacuo. The residue was purified by a silica gel column chromatography (EtOAc) to give the title compound 69-11 (350 mg, 65%). The compound was characterized by the following spectroscopic data:

MS (ESI, pos.ion) m/z: 443.5 [M+2H]²⁺;
¹H NMR (400 MHz, CDCl₃) δ (ppm): 7.97-7.96 (m, 1H), 7.65-7.59 (m, 5H), 7.56-7.52 (m, 2H), 7.47-7.42 (m, 2H), 5.32, 5.30 (d, d, 2H), 5.23-5.16 (m, 2H), 4.41-4.37 (m, 1H), 4.30-4.25 (m, 1H), 4.05-4.00 (m, 1H), 3.92-3.87 (m, 1H), 3.85-3.78 (m, 1H), 3.69-3.64 (m, 2H), 3.63 (s, 6H), 3.24-3.16 (m, 1H), 2.44-2.37 (m, 1H), 2.30-2.15 (m, 2H), 2.13-1.73 (m, 10H), 1.65-1.61 (m, 1H), 1.27-1.21 (m, 2H), 0.97, 0.95 (m, m, 6H), 0.91, 0.89 (m, m, 6H).

Example 70

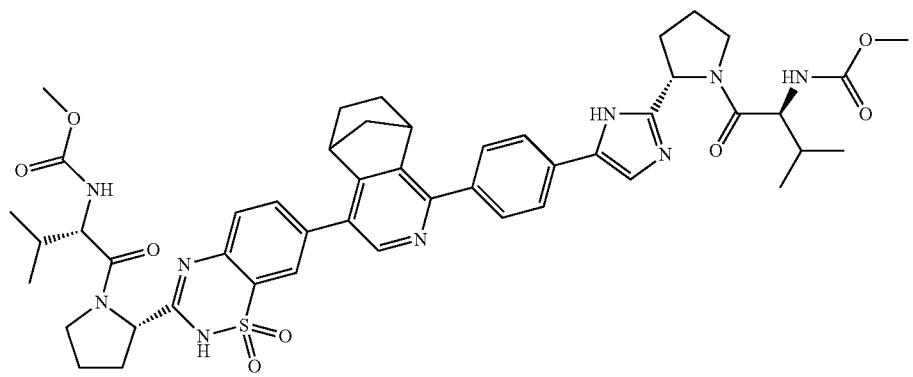 [SMILES: COC(=O)N[C@H](C(=O)N1CCC[C@H]1C1=Nc2ccc(-c3cnc(-c4ccc(-c5cnc([C@@H]6CCCN6C(=O)[C@@H](NC(=O)OC)C(C)C)[nH]5)cc4)c4c3C3CCC4C3)cc2S(=O)(=O)N1)C(C)C]

Synthetic Route:
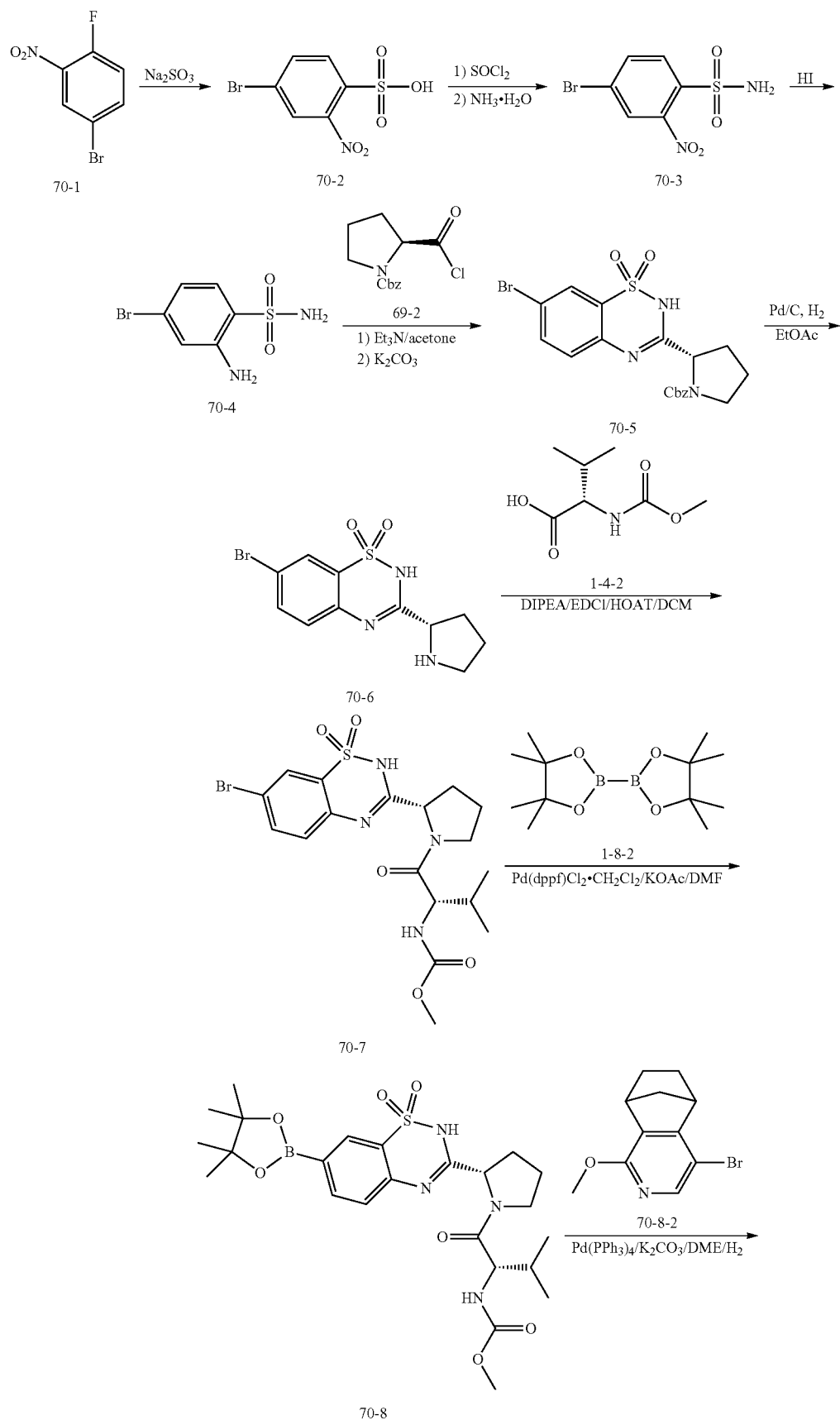

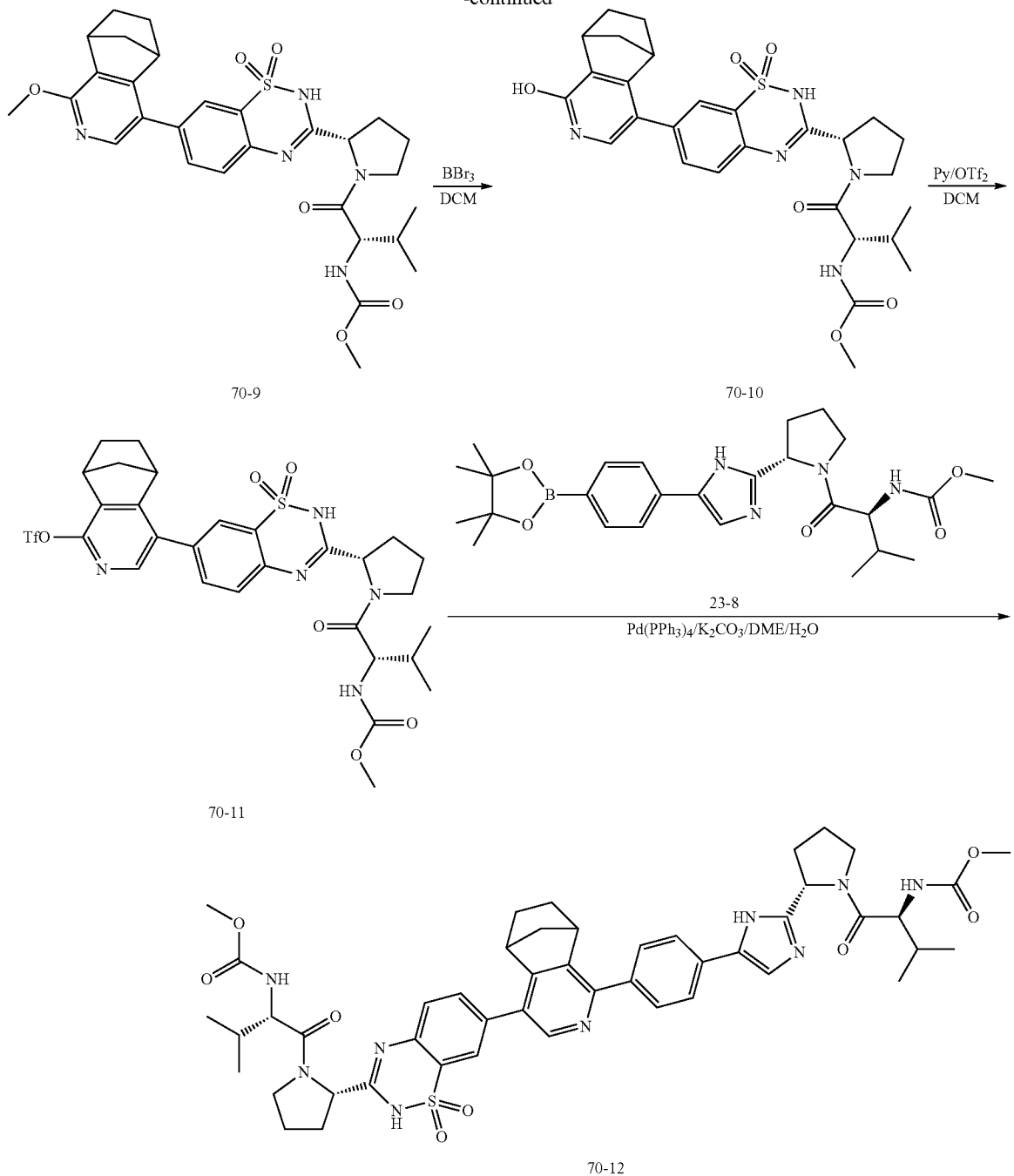

Step 1) the Preparation of Compound 70-2

To a solution of compound 70-1 (5.0 g, 22.7 mmol) in EtOH (60.0 mL) was added a suspension of $Na_2SO_3$ (7.16 g, 56.8 mmol) in EtOH (60 mL) and water (125 mL). At the end of addition, the suspension was stirred at 70° C. for 15 hrs. After the reaction was completed, the mixture was cooled to rt, and the reaction was acidified with HCl (2 M) to pH 2, and then concentrated in vacuo. The residue was dissolved under reflux in brine (100 mL). Subsequently, water (10.0 mL) was added and the solution was cooled in an ice bath. The precipitate was collected by filtration, resulting in compound 70-2 (5.73 g, 89%). The compound was characterized by the following spectroscopic data:

MS (ESI, pos.ion) m/z: 268.5 [M+H]$^+$;

$^1$H NMR (400 MHz, $CDCl_3$) δ (ppm): 8.75 (br, 1H), 8.31 (m, 1H), 8.07 (m, 2H).

Step 2) the Preparation of Compound 70-3

To a solution of compound 70-2 (3.0 g, 10.6 mmol) in toluene (50.0 mL) and DMF (1 drop) was added thionyl chloride (5.0 mL). At the end of addition, the reaction was refluxed for 4 hrs. After the reaction was completed, the mixture was cooled and concentrated in vacuo. The residue was dissolved in toluene (4.0 mL), and then to the resulting mixture was added a mixture of concentrated aqueous ammonium hydroxide solution (1.0 mL) and THF (10.0 mL) at −10° C. After stirring for 2 hrs, the reaction was quenched by adding a solution of hydrochloric acid until pH 4. The organic layers were separated and then dried over anhydrous Na$_2$SO$_4$ and concentrated in vacuo. PE (15.0 mL) was added to the resulting slurry and the product was collected by vacuum filtration to afford compound 70-3. The compound was characterized by the following spectroscopic data:

MS (ESI, pos.ion) m/z: 280.5 [M+H]$^+$;
$^1$H NMR (400 MHz, CDCl$_3$) δ (ppm): 8.18, 8.17 (d, d, 1H), 8.03, 8.00 (d, d, 1H), 7.84, 7.81 (d, d, 1H), 5.47 (br, 2H).

Step 3) the Preparation of Compound 70-4

A suspension of compound 70-3 (2.12 g, 7.5 mmol) in HI (25.0 mL, 57% aq.) was stirred at 90° C. for 4 hrs. After cooling to room temperature, the dark purple mixture was diluted with EtOAc (50.0 mL) and washed successively with saturated aq. Na$_2$S$_2$O$_3$, saturated aq. NaHCO$_3$ and brine. The colorless organic layers were dried over anhydrous Na$_2$SO$_4$ and concentrated in vacuo. The crude product was purified by high-performance liquid chromatography (eluent: CH$_3$CN/H$_2$O from 22/78 to 52/48 with 0.01% NH$_3$.H$_2$O as buffer). Resulting in compound 70-4 (1.86 g). The compound was characterized by the following spectroscopic data:

MS (ESI, pos.ion) m/z: 251.5 [M+H]$^+$;
$^1$H NMR (400 MHz, CDCl$_3$) δ (ppm): 7.62-7.60 (m, 1H), 7.18-7.15 (m, 2H), 4.85 (brs, 4H).

Step 4) the Preparation of Compound 70-5

To a solution of compound 70-4 (1.86 g, 7.4 mmol) in acetone (20.0 mL) was added triethylamine (4.05 mL, 29.6 mmol). Compound 69-2 (1.28 g, 4.8 mmol) was added to the reaction at 0° C. After stirring for 5 hrs, the mixture was diluted with water (10.0 mL) and acidified to pH 4 with HCl (2 M). The resulting precipitate was collected by filtration and then transferred to another flask. A solution of K$_2$CO$_3$ (1.5 g) in water (10.0 mL) was added and then the mixture was refluxed for 2 hrs until the reaction became homogeneous. The reaction was acidified to pH 4 with HCl (2 M). The precipitate was filtered off and washed with water. The crude product was purified by high-performance liquid chromatography (eluent: CH$_3$CN/H$_2$O from 35/65 to 65/35 with 0.75% CF$_3$COOH as buffer). Resulting in compound 70-5 (0.83 g, 45%). The compound was characterized by the following spectroscopic data:

MS (ESI, pos.ion) m/z: 464.5 [M+H]$^+$;
$^1$H NMR (400 MHz, CDCl$_3$) δ (ppm): 7.93, 7.90 (d, d, 1H), 7.77-7.76 (m, 1H), 7.43, 7.41 (d, d, 1H), 7.28-7.22 (m, 5H), 6.30 (brs, 1H), 5.14-5.13 (m, 2H), 4.86-4.80 (m, 1H), 3.68-3.62 (m, 1H), 3.50-3.43 (m, 1H), 2.22-1.98 (m, 4H).

Step 5) the Preparation of Compound 70-6

To a solution of compound 70-5 (3.72 g, 8.03 mmol) in EtOAc (40.0 mL) was added a catalytic amount of Pd/C (350 mg) and the mixture was stirred at 40° C. under 10 atm of H$_2$ gas for 5 hrs. After the reaction was completed, the mixture was filtered and the filtrate was concentrated in vacuo to give the title compound 70-6 (2.27 g, 86%). The compound was characterized by the following spectroscopic data:

MS (ESI, pos.ion) m/z: 330.5 [M+H]$^+$.

Step 6) the Preparation of Compound 70-7

To a suspension of compound 70-6 (3.29 g, 10.0 mmol), compound 1-4-2 (1.93 g, 11.0 mmol) and EDCI (2.10 g, 11.0 mmol) in DCM (30.0 mL) was added DIPEA (6.6 mL, 39.9 mmol) dropwise at 0° C. At the end of addition, the mixture was stirred at rt for 3 hrs. After the reaction was completed, the mixture was diluted with DCM (50.0 mL). The resulting mixture was washed successively with water (30 mL×3), saturated aq. NH$_4$Cl and brine, dried over Na$_2$SO$_4$ and concentrated in vacuo. The residue was purified by a silica gel column chromatography (PE/EtOAc (v/v)=2/1) to give the title compound (2.43 g, 50%). The compound was characterized by the following spectroscopic data:

MS (ESI, pos.ion) m/z: 487.5 [M+H]$^+$;
$^1$H NMR (400 MHz, CDCl$_3$) δ (ppm): 7.93, 7.90 (d, d, 1H), 7.77-7.76 (m, 1H), 7.43, 7.41 (d, d, 1H), 6.30 (brs, 1H), 5.32, 5.29 (d, d, 1H), 5.08-5.04 (m, 1H), 4.31-4.26 (m, 1H), 3.63 (s, 3H), 3.62-3.57 (m, 1H), 3.26-3.18 (m, 1H), 2.38-2.31 (m, 1H), 2.10-1.97 (m, 2H), 1.91-1.71 (m, 2H), 0.97, 0.95 (m, m, 3H), 0.91, 0.89 (m, m, 3H).

Step 7) the Preparation of Compound 70-8

A mixture of compound 70-7 (442.3 mg, 0.91 mmol), compound 1-8-2 (463 mg, 1.82 mmol), Pd(dppf)Cl$_2$.CH$_2$Cl$_2$ (71.0 mg, 0.09 mmol) and KOAc (268 mg, 2.73 mmol) in DMF (5.0 mL) was stirred at 90° C. under N$_2$ for 3 hrs. After cooling to room temperature, the mixture was diluted with EtOAc (50.0 mL) and filtered through a celite pad. The filtration was washed with water (20.0 mL×3) and brine, dried over anhydrous Na$_2$SO$_4$ and concentrated in vacuo. The residue was purified by a silica gel column chromatography (PE/EtOAc (v/v)=2/1) to give the title compound (427.8 mg, 88%). The compound was characterized by the following spectroscopic data:

MS (ESI, pos.ion) m/z: 535.3 [M+H]$^+$;
$^1$H NMR (400 MHz, CDCl$_3$) δ (ppm): 8.02 (t, 1H), 7.80, 7.78 (d, d, 1H), 7.46, 7.44 (d, d, 1H), 6.30 (brs, 1H), 5.32, 5.29 (d, d, 1H), 5.08-5.04 (m, 1H), 4.31-4.26 (m, 1H), 3.63 (s, 3H), 3.62-3.57 (m, 1H), 3.26-3.18 (m, 1H), 2.38-2.31 (m, 1H), 2.10-1.97 (m, 2H), 1.91-1.71 (m, 2H), 1.32, 1.29 (m, 12H), 0.97, 0.95 (m, m, 3H), 0.91, 0.89 (m, m, 3H).

Step 8) the Preparation of Compound 70-9

A mixture of compound 70-8 (325.88 mg, 0.61 mmol), compound 70-8-2 (154 mg, 0.61 mmol), Pd(PPh$_3$)$_4$ (70.0 mg, 0.05 mmol) and K$_2$CO$_3$ (254 mg, 1.83 mmol) in the mixed solvents of DME/H$_2$O (6.0 mL, v/v=5/1) was stirred at 90° C. under N$_2$ for 4 hrs. After cooling to room temperature, 20.0 mL of water was added to quench the reaction. The aqueous phase was extracted with EtOAc (20 mL×3). The combined organic layers were washed with brine, dried over anhydrous Na$_2$SO$_4$ and concentrated in vacuo. The residue was purified by a silica gel column chromatography (PE/EtOAc (v/v)=1/1) to give the title compound (230.46 mg, 65%). The compound was characterized by the following spectroscopic data:

MS (ESI, pos.ion) m/z: 582.5 [M+H]$^+$;
$^1$H NMR (400 MHz, CDCl$_3$) δ (ppm): 8.11-8.09 (m, 3H), 7.39, 7.37 (d, d, 1H), 6.30 (brs, 1H), 5.32, 5.30 (brs, 1H), 5.08-5.04 (m, 1H), 4.31-4.26 (m, 1H), 3.95 (s, 3H), 3.63 (s, 3H), 3.62-3.54 (m, 2H), 3.43-3.40 (m, 1H), 3.26-3.18 (m, 1H), 2.38-2.31 (m, 1H), 2.08-1.95 (m, 4H), 1.91-1.71 (m, 2H), 1.68-1.64 (m, 1H), 1.49-1.45 (m, 1H), 1.28-1.22 (m, 1H), 1.14-1.08 (m, 1H), 0.97, 0.95 (m, m, 3H), 0.91, 0.89 (m, m, 3H).

Step 9) the Preparation of Compound 70-10

To a solution of compound 70-9 (3.47 g, 5.97 mmol) in DCM (15.0 mL) was added boron tribromide (7.47 g, 29.88 mmol) dropwise at −78° C. At the end of addition, the mixture was stirred at rt for 1 hr. After the reaction was completed, the mixture was quenched with ice-water (50.0 mL) and the organic phase separated. The aqueous layer was extracted with EtOAc (50 mL×3). The combined organic layers were washed with brine, dried over anhydrous Na$_2$SO$_4$ and concentrated in vacuo. The residue was purified by a silica gel column chromatography (PE/EtOAc (v/v)=20/1) to give the title compound 70-10 (3.05 g, 90%). The compound was characterized by the following spectroscopic data:

MS (ESI, pos.ion) m/z: 568.3 [M+H]$^+$;
$^1$H NMR (400 MHz, CDCl$_3$) δ (ppm): 8.03-8.01 (m, 2H), 7.98-7.97 (m, 1H), 7.39, 7.37 (d, d, 1H), 5.32, 5.30 (d, d, 1H), 5.08-5.04 (m, 1H), 4.31-4.26 (m, 1H), 3.63 (s, 3H), 3.62-3.57 (m, 2H), 3.50-3.48 (m, 1H), 3.26-3.19 (m, 1H), 2.38-2.31 (m, 1H), 2.10-1.97 (m, 4H), 1.91-1.83 (m, 1H), 1.82-1.71 (m, 1H), 1.68-1.64 (m, 1H), 1.49-1.45 (m, 1H), 1.34-1.28 (m, 1H), 1.15-1.09 (m, 1H), 0.97, 0.95 (m, m, 3H), 0.91, 0.89 (m, m, 3H).

Step 10) the Preparation of Compound 70-11

To a solution of compound 70-10 (5.67 g, 10.0 mmol) in DCM (40.0 mL) was added pyridine (4.8 mL, 60.0 mmol) dropwise at 0° C. After stirring for 10 mins, trifluoromethanesulfonic anhydride (6.73 mL, 40.0 mmol) was added. At the end of addition, the mixture was stirred at rt for 1 hr. After the reaction was completed, the mixture was quenched by ice-water (50.0 mL). The aqueous layer was extracted with DCM (30 mL×3). The combined organic layers were washed with brine, dried over anhydrous $Na_2SO_4$ and concentrated in vacuo. The residue was purified by a silica gel column chromatography (PE/EtOAc (v/v)=10/1) to give the title compound (6.29 g, 90%) as colorless oil. The compound was characterized by the following spectroscopic data:

$^1$H NMR (400 MHz, CDCl$_3$) δ (ppm): 8.31 (s, 1H), 8.11-8.10 (m, 1H), 8.03, 8.01 (d, d, 1H), 7.39, 7.37 (d, d, 1H), 6.30 (brs, 1H), 5.32, 5.30 (d, d, 1H), 5.08-5.04 (m, 1H), 4.31-4.26 (m, 1H), 3.63 (s, 3H), 3.60-3.57 (m, 2H), 3.49-3.46 (m, 1H), 3.26-3.18 (m, 1H), 2.38-2.31 (m, 1H), 2.11-1.97 (m, 4H), 1.91-1.83 (m, 1H), 1.82-1.71 (m, 1H), 1.67-1.63 (m, 1H), 1.48-1.44 (m, 1H), 1.38-1.32 (m, 1H), 1.15-1.09 (m, 1H), 0.97, 0.95 (m, m, 3H), 0.91, 0.89 (m, m, 3H).

Step 11) the Preparation of Compound 70-12

A mixture of compound 70-11 (426.5 mg, 0.61 mmol), compound 23-8 (302.74 mg, 0.61 mmol), Pd(PPh$_3$)$_4$ (35.25 mg, 0.03 mmol) and K$_2$CO$_3$ (254 mg, 1.83 mmol) in the mixed solvent of DME/H$_2$O (6.0 mL, v/v=5/1) was stirred at 90° C. under N$_2$ for 4 hrs. After the reaction was completed, 20 mL of water was added. The aqueous layer was extracted with EtOAc (20 mL×3). The combined organic layers were washed with brine, dried over anhydrous Na$_2$SO$_4$ and concentrated in vacuo. The residue was purified by a silica gel column chromatography (EtOH/EtOAc (v/v)=1/60) to give the title compound (364.5 mg, 65%). The compound was characterized by the following spectroscopic data:

MS (ESI, pos.ion) m/z: 460.5 [M+2H]$^{2+}$;

$^1$H NMR (400 MHz, CDCl$_3$) δ (ppm): 8.67 (s, 1H), 8.27-8.26 (m, 3H), 8.15, 8.13 (d, d, 1H), 7.94-7.91 (m, 2H), 7.77-7.74 (m, 2H), 7.59 (s, 1H), 7.39, 7.37 (d, d, 1H), 5.32, 5.30 (d, d, 12H), 5.23-5.19 (m, 1H), 5.08-5.04 (m, 1H), 4.41-4.36 (m, 1H), 4.31-4.26 (m, 1H), 3.85-3.78 (m, 3H), 3.69-3.64 (m, 1H), 3.63 (s, 6H), 3.61-3.57 (m, 1H), 3.26-3.18 (m, 1H), 2.38-1.66 (m, 14H), 1.31-1.25 (m, 1H), 1.17-1.11 (m, 1H), 0.97, 0.95 (m, m, 6H), 0.91, 0.89 (m, m, 3H).

Example 71

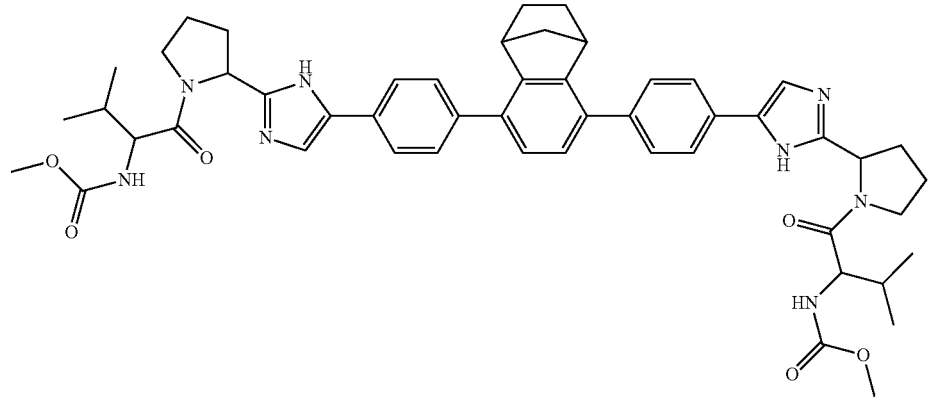 [SMILES: COC(=O)NC(C(=O)N1CCCC1c1ncc(-c2ccc(-c3ccc(-c4ccc(-c5cnc(C6CCCN6C(=O)C(NC(=O)OC)C(C)C)[nH]5)cc4)c4c3C3CCC4C3)cc2)[nH]1)C(C)C]

Synthetic Route:

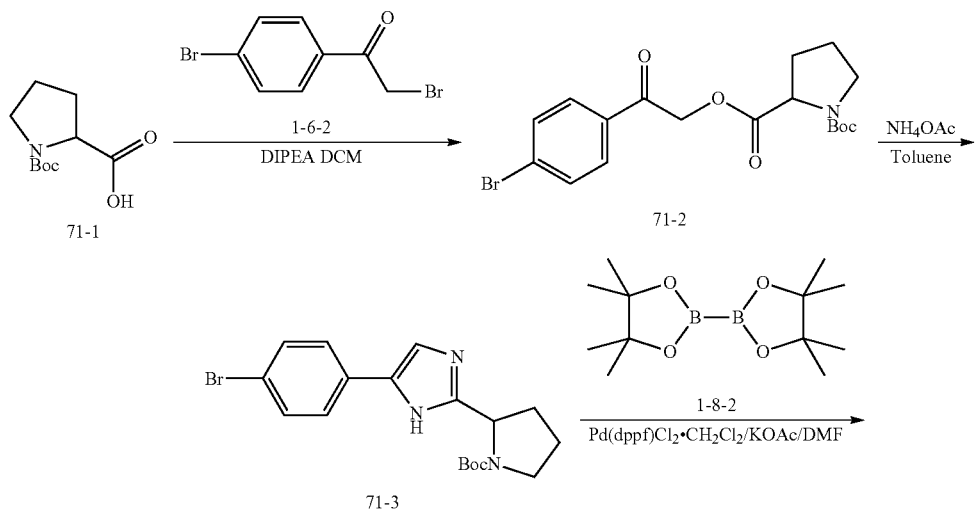

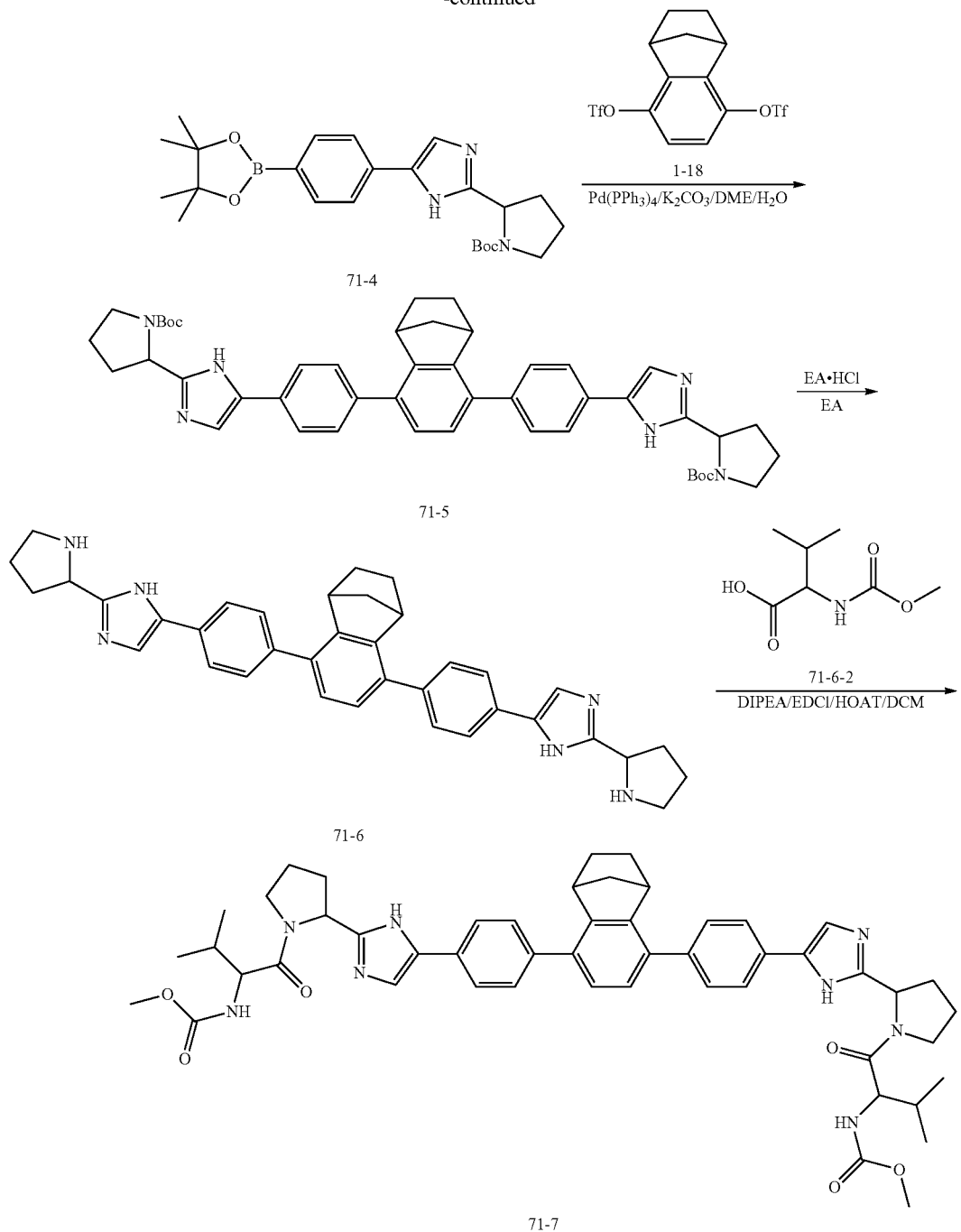

Compounds disclosed herein can be synthesized through the procedure as depicted in Example 5.

Compound 71-2 was characterized by the following spectroscopic data:

MS (ESI, pos.ion) m/z: 412.7 [M+H]+;

$^1$H NMR (400 MHz, CDCl$_3$) δ (ppm): 7.78-7.75 (m, 2H), 7.65-7.63 (m, 2H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Compound 71-3 was characterized by the following spectroscopic data:

MS (ESI, pos.ion) m/z: 392.2 [M+H]+;

$^1$H NMR (400 MHz, CDCl$_3$) δ (ppm): 7.78-7.75 (m, 2H), 7.65-7.63 (m, 2H), 7.21-7.20 (m, 1H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Compound 71-4 was characterized by the following spectroscopic data:

$^1$H NMR (400 MHz, CDCl$_3$) δ (ppm): 7.35 (m, 4H), 7.10 (s, 1H), 4.93 (t, 1H, J=8.2 Hz), 3.88-3.66 (m, 2H), 2.90 (t, 1H, J=8.0 Hz), 2.50-2.47 (m, 2H), 2.27-2.25 (m, 1H), 1.48 (s, 9H), 1.26 (s, 12H).

Compound 71-5 was characterized by the following spectroscopic data:

MS (ESI, pos.ion) m/z: 767.3 [M+H]$^+$;

$^1$H NMR (400 MHz, CDCl$_3$) δ (ppm): 7.72 (m, 4H), 7.50-7.52 (d, 6H, J=8.0 Hz), 7.24 (s, 2H), 5.00-5.01 (d, 2H, J=4.0 Hz), 3.59-3.63 (br, 2H), 3.37-3.47 (br, 2H), 2.94-3.06 (br, 2H), 2.11-2.24 (m, 4H), 1.98-2.06 (m, 8H), 1.73-1.75 (m, 2H), 1.51 (s, 18H).

Compound 71-6 was characterized by the following spectroscopic data:

MS (ESI, pos.ion) m/z: 567.3[M+H]$^+$.

Compound 71-7 was characterized by the following spectroscopic data:

MS (ESI, pos.ion) m/z: 441.3 [M+2H]$^{2+}$;

$^1$H NMR (400 MHz, CDCl$_3$) δ (ppm): 7.79-7.87 (m, 2H), 7.62-7.69 (m, 2H), 7.45-7.52 (m, 6H), 7.24 (m, 2H), 5.26-5.34 (m, 2H), 4.30-4.41 (m, 2H), 3.75-3.78 (m, 2H), 3.72 (s, 6H), 3.64-3.68 (br, 2H), 3.60-3.63 (br, 2H), 2.20-2.32 (m, 6H), 2.05-2.07 (m, 2H), 1.81-1.93 (m, 6H), 0.94-0.97 (m, 12H).

Example 72

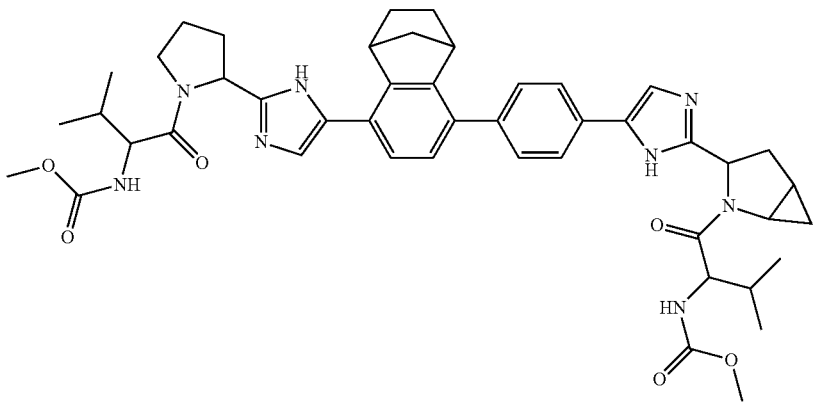 [SMILES: COC(=O)NC(C(=O)N1CCCC1c1ncc(-c2ccc(-c3ccc(-c4cnc(C5CC6CC6N5C(=O)C(NC(=O)OC)C(C)C)[nH]4)cc3)c3c2C2CCC3C2)[nH]1)C(C)C]

Synthetic Route:

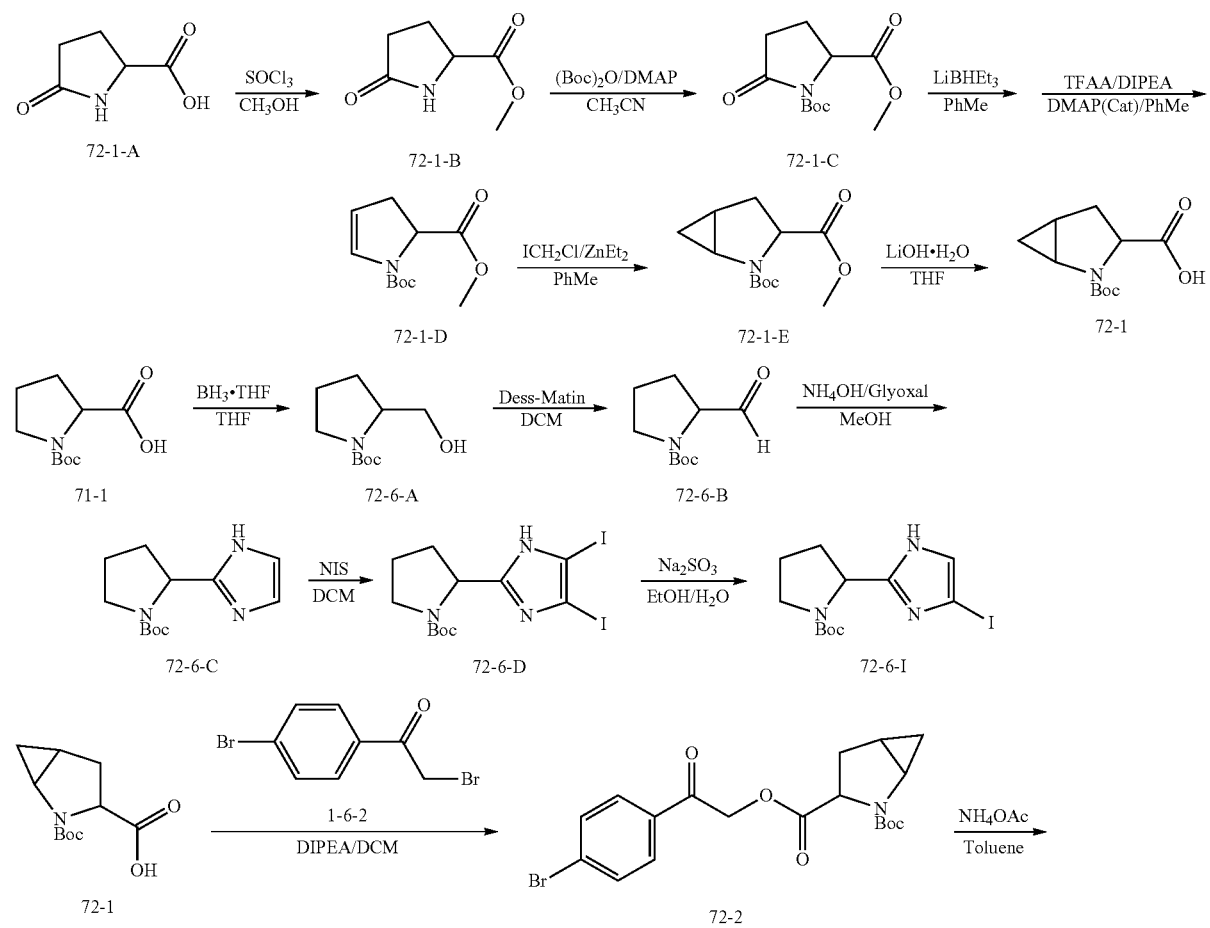

-continued

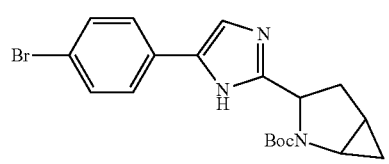 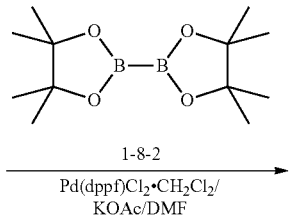

72-3

$\xrightarrow{\underset{\text{KOAc/DMF}}{\text{1-8-2}\\ \text{Pd(dppf)Cl}_2\cdot\text{CH}_2\text{Cl}_2/}}$

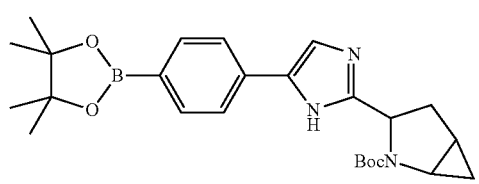 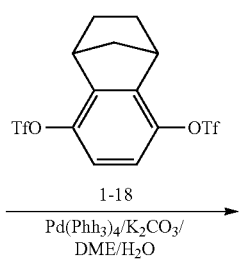

72-4

$\xrightarrow{\underset{\text{DME/H}_2\text{O}}{\text{1-18}\\ \text{Pd(Phh}_3)_4/\text{K}_2\text{CO}_3/}}$

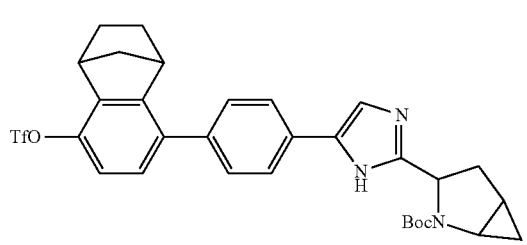 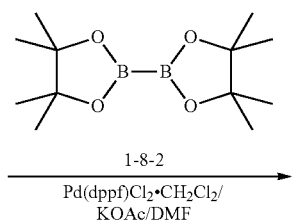

72-5

$\xrightarrow{\underset{\text{KOAc/DMF}}{\text{1-8-2}\\ \text{Pd(dppf)Cl}_2\cdot\text{CH}_2\text{Cl}_2/}}$

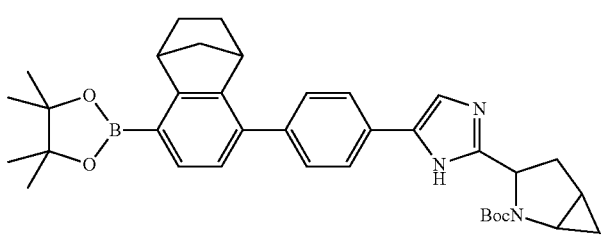 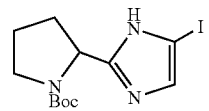

72-6

$\xrightarrow{\underset{\text{DME/H}_2\text{O}}{\text{72-6-1}\\ \text{Pd(PPh}_3)_4/\text{K}_2\text{CO}_3/}}$

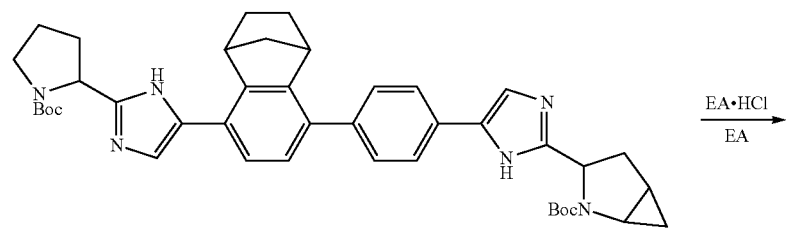

72-7

$\xrightarrow{\underset{\text{EA}}{\text{EA}\cdot\text{HCl}}}$

-continued

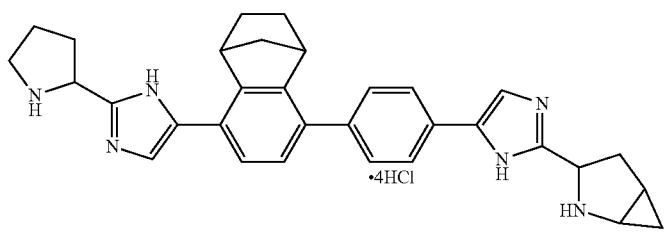

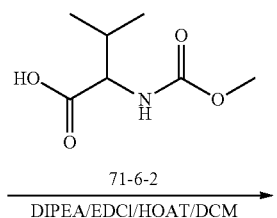

72-8

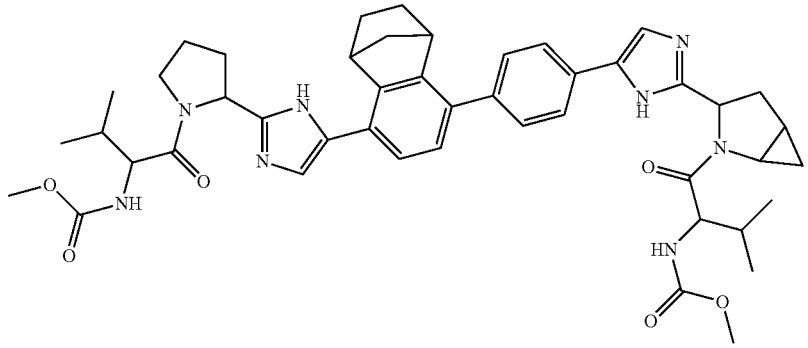

72-9

Compounds disclosed herein can be synthesized through the procedure as depicted in Example 2.

Compound 72-1-B was characterized by the following spectroscopic data:
MS (ESI, pos.ion) m/z: 144.2 [M-Boc]$^+$;
$^1$H NMR (400 MHz, CDCl$_3$) δ (ppm): 7.38 (br, 1H), 4.16-4.20 (m, 1H), 3.67 (s, 3H), 2.23-2.39 (m, 3H), 2.07-2.14 (m, 1H).

Compound 72-1-C was characterized by the following spectroscopic data:
MS (ESI, pos.ion) m/z: 144.2 [M-Boc]$^+$;
$^1$H NMR (400 MHz, CDCl$_3$) δ (ppm): 4.57-4.60 (m, 1H), 3.75 (s, 3H), 2.55-2.65 (m, 1H), 2.42-2.50 (m, 1H), 2.24-2.36 (m, 1H), 1.96-2.04 (m, 1H), 1.45 (s, 9H).

Compound 72-1-D was characterized by the following spectroscopic data:
MS (ESI, pos.ion) m/z: 128.2 [M-Boc]$^+$;
$^1$H NMR (400 MHz, CDCl$_3$) δ (ppm): 6.52-6.65 (br, 1H), 4.91-4.96 (br, 1H), 4.57-4.68 (m, 1H), 3.76 (s, 3H), 3.00-3.12 (m, 1H), 2.61-2.71 (m, 1H), 1.44-1.49 (br, 9H).

Compound 72-1-E was characterized by the following spectroscopic data:
MS (ESI, pos.ion) m/z: 142.2 [M-Boc]$^+$;
$^1$H NMR (400 MHz, CDCl$_3$) δ (ppm): 4.51-4.64 (m, 1H), 3.70 (s, 3H), 3.45-3.56 (m, 1H), 2.54-2.64 (m, 1H), 2.01-2.05 (m, 1H), 1.50, 1.41 (s, s, 9H), 0.65-0.75 (m, 3H).

Compound 72-2 was characterized by the following spectroscopic data:
MS (ESI, neg.ion) m/z: 226.2 [M–H]$^-$;
$^1$H NMR (400 MHz, CD$_3$OD) δ (ppm): 4.46-4.53 (m, 1H), 3.42-3.48 (m, 1H), 2.57-2.70 (m, 1H), 2.01-2.05 (m, 1H), 1.54-1.60 (m, 1H), 1.48, 1.41 (s, s, 9H), 0.80-0.89 (m, 1H), 0.66-0.73 (m, 1H).

Compound 72-6-A was characterized by the following spectroscopic data:
$^1$H NMR (400 MHz, CDCl$_3$) δ (ppm): 3.87-3.99 (br, 1H), 3.51-3.68 (m, 2H), 3.39-3.48 (m, 1H), 3.25-3.34 (m, 1H), 1.92-2.05 (m, 2H), 1.71-1.88 (m, 2H), 1.45 (s, 9H).

Compound 72-6-B was characterized by the following spectroscopic data:
$^1$H NMR (400 MHz, CDCl$_3$) δ (ppm): 9.46 (d, 1H, J=2.8 Hz), 4.03-4.08 (m, 1H), 3.42-3.51 (m, 2H), 1.84-1.91 (m, 2H), 1.93-2.01 (m, 2H), 1.43 (s, 9H).

Compound 72-6-C was characterized by the following spectroscopic data:
MS (ESI, pos.ion) m/z: 238.2 [M+H]$^+$;
$^1$H NMR (400 MHz, CDCl$_3$) δ (ppm): 6.96 (s, 1H), 4.94 (dd, 1H, J=7.68, 2.40 Hz), 3.38 (t, 2H, J=6.24 Hz), 2.03-2.17 (m, 2H), 1.91-1.99 (m, 2H), 1.48 (s, 9H).

Compound 72-6-D was characterized by the following spectroscopic data:
MS (ESI, pos.ion) m/z: 490.0 [M+H]$^+$;
$^1$H NMR (400 MHz, CDCl$_3$) δ (ppm): 4.89 (dd, 1H, J=7.64, 2.52 Hz), 3.36 (t, 2H), 2.02-2.14 (m, 2H), 1.85-1.97 (m, 2H), 1.49 (s, 9H).

Compound 72-6-1 was characterized by the following spectroscopic data:
MS (ESI, pos.ion) m/z: 364.1 [M+H]$^+$; MS (ESI, neg.ion) m/z: 362.1 [M–H]$^-$;
$^1$H NMR (400 MHz, CDCl$_3$) δ (ppm): 7.04 (d, 1H, J=1.84 Hz), 4.89 (dd, 1H, J=7.72, 2.56 Hz), 3.36 (t, 2H), 2.03-2.18 (m, 2H), 1.82-1.97 (m, 2H), 1.47 (s, 9H).

Compound 72-2 was characterized by the following spectroscopic data:
MS (ESI, pos.ion) m/z: 424.3 [M+H]$^+$;
$^1$H NMR (400 MHz, CDCl$_3$) δ (ppm): 7.73-7.77 (m, 2H), 7.62-7.64 (m, 2H), 5.09-5.53 (m, 2H), 4.67-4.78 (m, 1H), 3.46-3.59 (m, 1H), 2.62-2.69 (m, 1H), 2.40-2.43 (m, 1H), 1.42 (s, 9H), 0.96-1.00 (m, 1H), 0.69-0.76 (m, 2H).

Compound 72-3 was characterized by the following spectroscopic data:
MS (ESI, pos.ion) m/z: 404.3 [M+H]$^+$;
$^1$H NMR (400 MHz, CDCl$_3$) δ (ppm): 7.52-7.62 (br, 2H), 7.46-7.49 (d, 2H, J=12 Hz), 7.21 (s, 1H), 5.24-5.27 (d, 1H, J=10.0 Hz), 3.27-3.31 (m, 1H), 1.67-1.71 (m, 2H), 1.52 (s, 9H), 0.86-0.89 (m, 1H), 0.64-0.69 (m, 2H).

Compound 72-4 was characterized by the following spectroscopic data:

MS (ESI, pos.ion) m/z: 452.3 [M+H]$^+$;

$^1$H NMR (400 MHz, CDCl$_3$) δ (ppm): 7.79-7.81 (d, 2H, J=8.04 Hz), 7.60 (br, 2H), 7.26 (s, 1H), 5.26-5.28 (d, 1H, J=8.0 Hz), 3.53 (br, 1H), 3.27-3.30 (br, 1H), 1.66-1.67 (m, 2H), 1.52 (s, 9H), 1.34 (s, 12H), 0.86-0.89 (m, 1H), 0.64-0.69 (m, 2H).

Compound 72-5 was characterized by the following spectroscopic data:

MS (ESI, pos.ion) m/z: 616.3 [M+H]$^+$;

$^1$H NMR (400 MHz, CDCl$_3$) δ (ppm): 7.73 (br, 1H), 7.42-7.45 (d, 2H, J=8.12 Hz), 7.29 (s, 2H), 7.18-7.20 (d, 1H, J=8.8 Hz), 7.02-7.04 (d, 1H, J=8.56 Hz), 5.29-5.32 (m, 1H), 3.59 (br, 1H), 3.33-3.36 (m, 1H), 2.02-2.03 (m, 2H), 1.56-1.58 (m, 8H), 1.54 (s, 9H), 0.86-0.89 (br, 1H), 0.64-0.70 (m, 2H).

Compound 72-6 was characterized by the following spectroscopic data:

MS (ESI, pos.ion) m/z: 594.3 [M+H]$^+$;

$^1$H NMR (400 MHz, CDCl$_3$) δ (ppm): 7.64-7.73 (m, 2H), 7.57-7.59 (d, 1H, J=8.0 Hz), 7.49-7.51 (m, 2H), 7.31 (m, 1H), 7.14-7.16 (d, 1H, J=8.0 Hz), 5.33-5.34 (br, 1H), 3.98 (br, 1H), 2.11-2.26 (m, 2H), 1.94 (br, 1H), 1.80-1.82 (d, 2H, J=8.0 Hz), 1.56-1.59 (m, 3H), 1.39-1.42 (m, 11H), 1.24 (s, 12H), 0.86-0.89 (br, 1H), 0.64-0.70 (m, 2H).

Compound 72-7 was characterized by the following spectroscopic data:

MS (ESI, pos.ion) m/z: 703.3 [M+H]$^+$;

$^1$H NMR (400 MHz, CDCl$_3$) δ (ppm): 7.64-7.69 (m, 2H), 7.52-7.55 (m, 1H), 7.46-7.48 (m, 2H), 7.35 (br, 1H), 7.24 (s, 1H), 7.18-7.21 (br, 1H), 5.27-5.29 (br, 1H), 4.96-4.97 (br, 1H), 3.77-3.97 (br, 2H), 3.66 (br, 1H), 3.54-3.60 (m, 2H), 2.02-2.04 (m, 4H), 1.49-1.54 (m, 8H), 1.45 (s, 18H), 0.86-0.89 (br, 1H), 0.64-0.70 (m, 2H).

Compound 72-8 was characterized by the following spectroscopic data:

MS (ESI, pos.ion) m/z: 503.3 [M+H]$^+$.

Compound 72-9 was characterized by the following spectroscopic data:

MS (ESI, pos.ion) m/z: 409.3 [M+2H]$^{2+}$;

$^1$H NMR (400 MHz, CDCl$_3$) δ (ppm): 7.85-7.87 (d, 2H, J=8.0 Hz), 7.47 (m, 3H), 7.38 (s, 1H), 7.18 (br, 2H), 5.16-5.22 (br, 2H), 4.64 (br, 2H), 4.19-4.24 (m, 2H), 3.69 (s, 6H), 3.59-3.57 (m, 2H), 3.24 (br, 2H), 2.33-2.40 (m, 4H), 2.24-2.26 (m, 3H), 1.73-1.75 (m, 4H), 1.51 (m, 2H), 0.97-1.05 (m, 12H), 0.86-0.89 (br, 1H), 0.64-0.70 (m, 2H).

Example 73

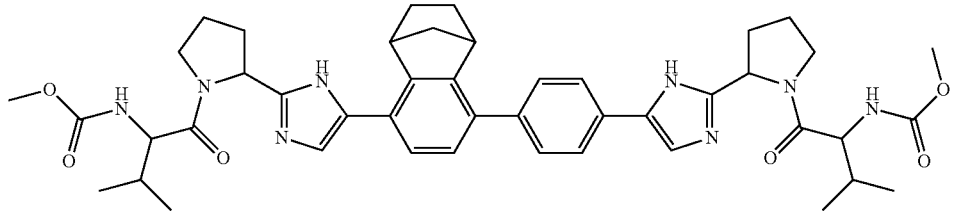 [SMILES: COC(=O)NC(C(=O)N1CCCC1c1ncc(-c2ccc(-c3ccc(-c4cnc(C5CCCN5C(=O)C(NC(=O)OC)C(C)C)[nH]4)c4c3C3CCC4C3)cc2)[nH]1)C(C)C]

Synthetic Route:

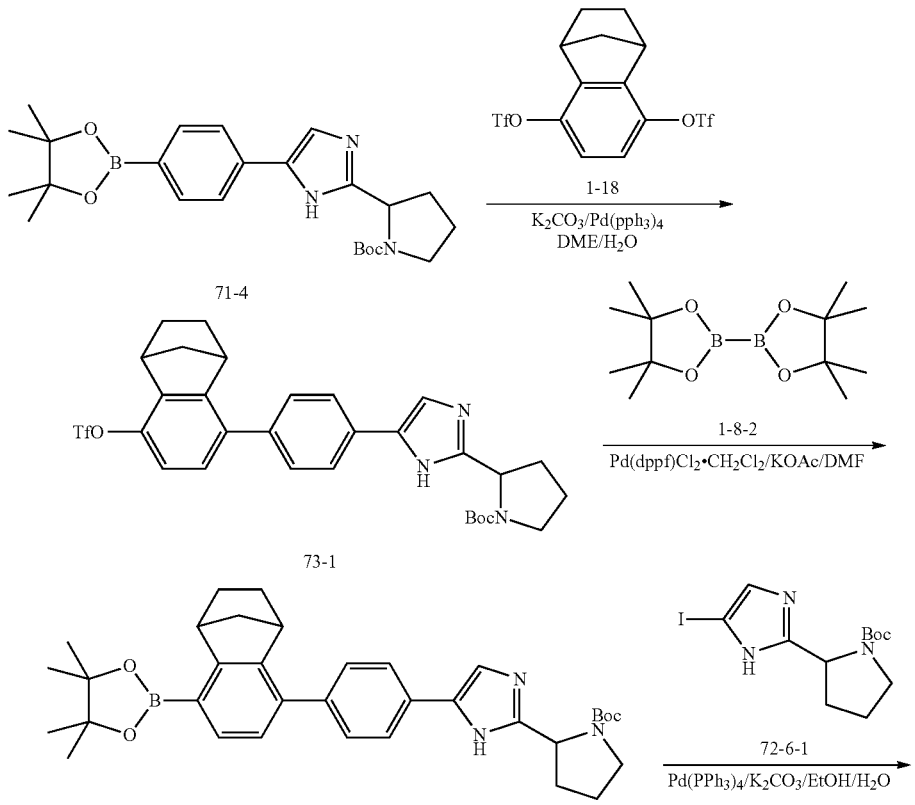

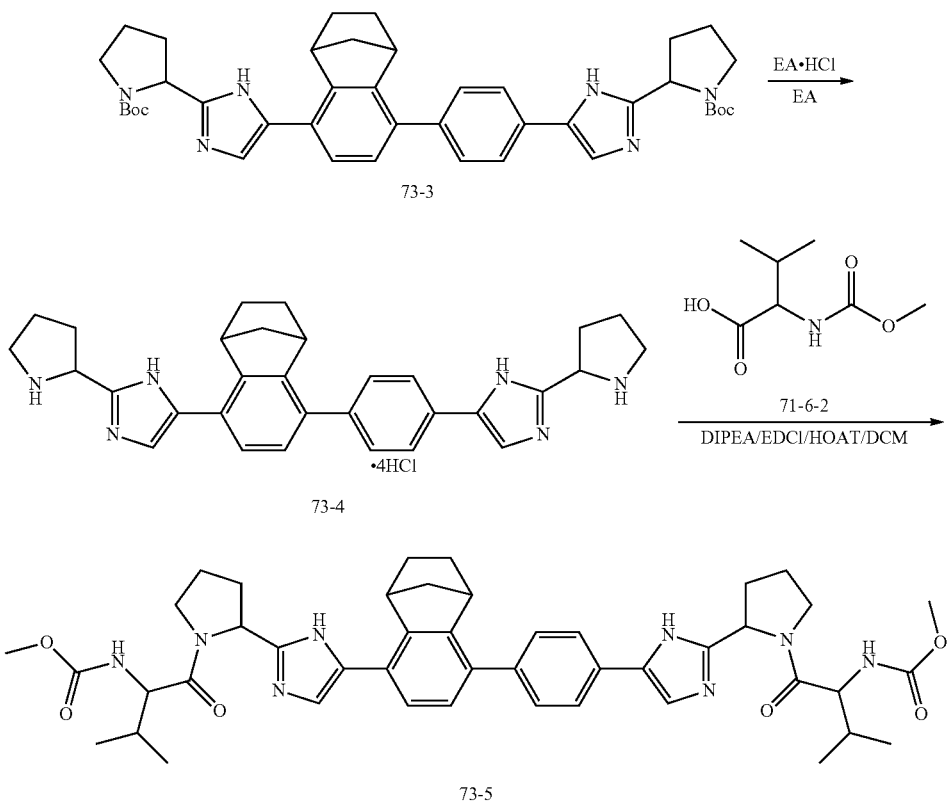

Compounds disclosed herein can be synthesized through the procedure as depicted in Example 18.

Compound 73-1 was characterized by the following spectroscopic data:

MS (ESI, pos.ion) m/z: 604.3 [M+H]$^+$;

$^1$H NMR (400 MHz, CDCl$_3$) δ (ppm): 10.53 (brs, 1H), 7.83 (brs, 1H), 7.42 (d, 2H, J=8.1 Hz), 7.26 (m, 2H), 7.20 (d, 1H, J=8.6 Hz), 7.02 (d, 1H, J=8.6 Hz), 4.98 (d, 1H, J=5.2 Hz), 3.70 (s, 1H), 3.60 (s, 1H), 3.48-3.35 (m, 2H), 2.25-2.10 (m, 2H), 2.04-1.96 (m, 3H), 1.82-1.80 (m, 1H), 1.59-1.56 (m, 1H), 1.51 (s, 9H), 1.43-1.39 (m, 3H).

Compound 73-2 was characterized by the following spectroscopic data:

MS (ESI, pos.ion) m/z: 582.4 [M+H]$^+$;

$^1$H NMR (400 MHz, CDCl$_3$) δ (ppm): 10.53 (br, 1H), 7.63-7.74 (m, 1H), 7.58 (d, 1H, J=7.8 Hz), 7.47 (d, 2H, J=8.2 Hz), 7.25 (s, 1H), 7.16 (d, 1H, J=7.8 Hz), 4.98-5.01 (m, 1H), 3.99 (s, 1H), 3.55 (s, 1H), 3.38-3.48 (m, 2H), 2.98 (s, 1H), 2.22-2.11 (m, 2H), 1.97-1.96 (m, 3H), 1.72-1.70 (m, 1H), 1.35-1.36 (d, 12H, J=3.08 Hz), 1.25-1.26 (m, 4H).

Compound 73-3 was characterized by the following spectroscopic data:

MS (ESI, pos.ion) m/z: 692.3 [M+H]$^+$;

$^1$H NMR (400 MHz, CDCl$_3$) δ (ppm): 10.98 (brs, 1H), 7.82-7.62 (m, 2H), 7.46-7.48 (m, 2H), 7.26 (s, 1H), 7.19-7.21 (m, 1H), 7.17 (s, 1H), 3.75-3.84 (m, 1H), 3.60 (s, 1H), 3.38-3.49 (m, 4H), 2.99 (s, 2H), 2.22-2.09 (m, 3H), 1.97-1.98 (m, 3H), 1.75-1.63 (m, 2H), 1.52 (s, 9H), 1.51 (s, 9H), 1.22-1.32 (m, 8H).

Compound 73-5 was characterized by the following spectroscopic data:

MS (ESI, pos.ion) m/z: 805.4 [M+H]$^+$;

$^1$H NMR (400 MHz, CDCl$_3$) δ (ppm): 10.35 (brs, 1H), 7.85-7.70 (m, 2H), 7.68-7.40 (m, 4H), 7.26-7.23 (m, 2H), 7.18-7.15 (m, 2H), 5.55-5.35 (m, 2H), 5.30-5.22 (m, 2H), 4.42-4.28 (m, 2H), 3.92-3.78 (m, 2H), 3.70 (s, 6H), 2.90-2.15 (m, 2H), 2.48-2.29 (m, 2H), 2.25-1.85 (m, 8H), 1.60-1.35 (m, 4H), 1.15-1.00 (m, 2H), 0.95-0.75 (m, 12H).

Example 74

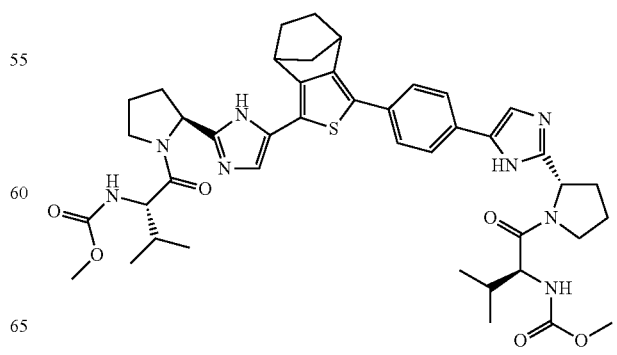

Synthetic Route:
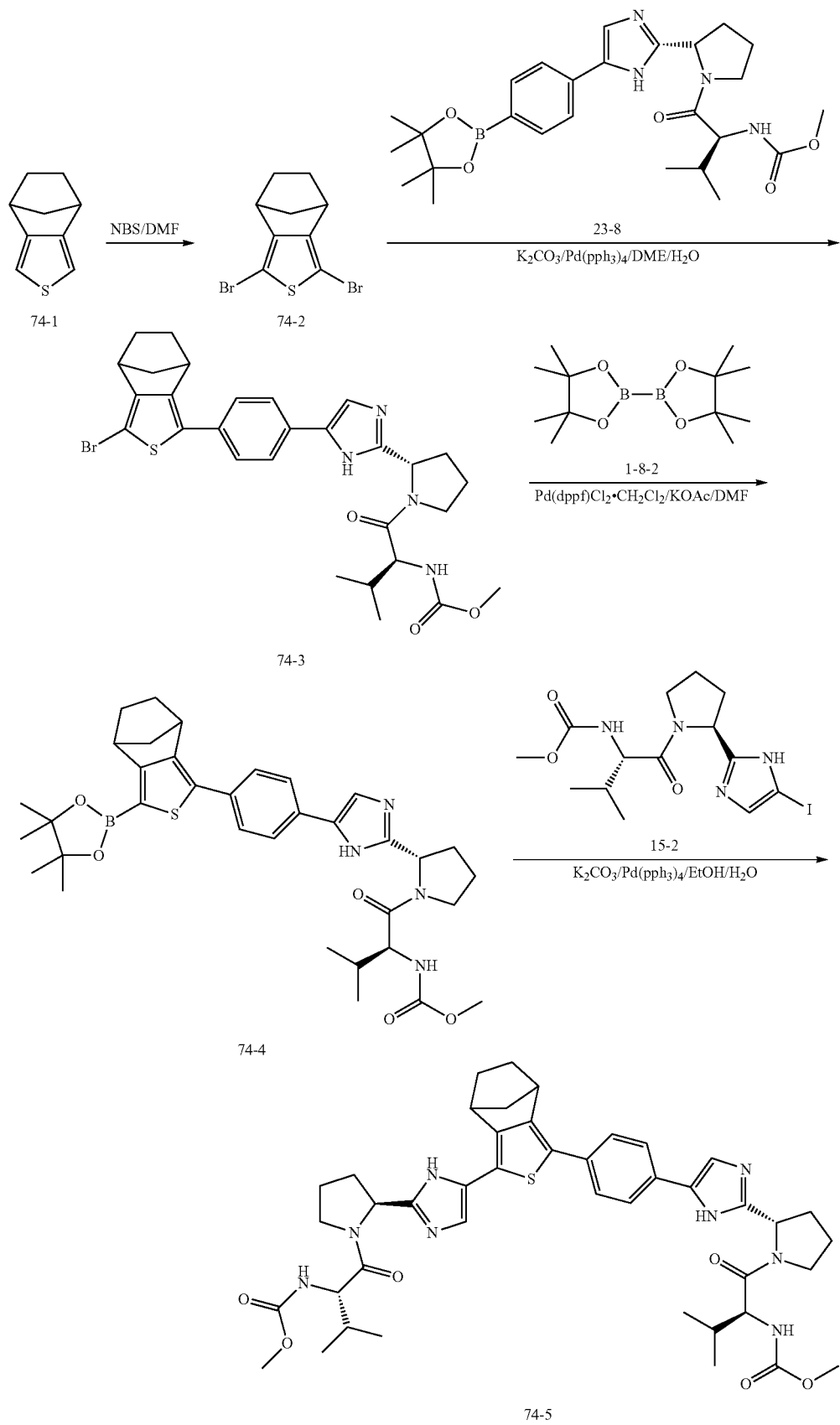

Step 1) the Preparation of Compound 74-2

A solution of n-bromosuccinimide (NBS) (2.16 g, 12 mmol) in anhydrous DMF (6.0 mL) was slowly added dropwise in the dark to a solution of thiophene (0.9 g, 6.0 mmol) in anhydrous DMF (6.0 mL) at −15° C. At the end of addition, the mixture was initially stirred at room temperature for 0.5 hr and then at 60° C. for another 5 hrs. After the reaction was completed, the mixture was poured into 50.0 mL of ice water and 60.0 mL of ethyl ether. The organic layers were separated, washed several times with water to neutral pH, and dried with anhydrous $Na_2SO_4$. The solvent was evaporated to give the title compound as oily liquid (1.165 g, 80%). The compound was characterized by the following spectroscopic data:

MS (ESI, pos.ion) m/z: 307.3 $[M+H]^+$;

$^1$H NMR (400 MHz, CDCl$_3$) δ (ppm): 3.67-3.62 (m, 2H), 2.00-1.97 (m, 1H), 1.96-1.90 (m, 2H), 1.73-1.69 (m, 2H), 1.20-1.13 (m, 1H).

Step 2) the Preparation of Compound 74-3

To a mixture of compound 74-2 (559.7 mg, 1.83 mmol), compound 23-8 (908.21 mg, 1.83 mmol), Pd(PPh$_3$)$_4$ (105.8 mg, 0.0915 mmol) and $K_2CO_3$ (632.31 mg, 4.575 mmol) were added DME (10.0 mL) and water (2.0 mL) via syringe. The mixture was stirred at 90° C. under $N_2$ for 4 hrs. After the reaction was completed, the mixture was cooled to rt, 20.0 mL of water was added, and the resulting mixture was extracted with EtOAc (20.0 mL×3). The combined organic layers were washed with brine, dried over anhydrous $Na_2SO_4$ and concentrated in vacuo. The residue was purified by a silica gel column chromatography (PE/EtOAc (v/v)=1/2) to give the title compound (763.67 mg, 70%). The compound was characterized by the following spectroscopic data:

MS (ESI, pos.ion) m/z: 597.5 $[M+H]^+$;

$^1$H NMR (400 MHz, CDCl$_3$) δ (ppm): 7.69-7.65 (m, 2H), 7.59 (s, 1H), 7.55-7.51 (m, 2H), 5.32, 5.30 (d, d, 1H), 5.23-5.19 (m, 1H), 4.41-4.36 (m, 1H), 3.85-3.78 (m, 1H), 3.72-3.66 (m, 2H), 3.63 (s, 3H), 3.47-3.44 (m, 1H), 2.30-1.88 (m, 8H), 1.76-1.72 (m, 1H), 1.22-1.10 (m, 2H), 0.97, 0.96 (m, m, 3H), 0.91, 0.89 (m, m, 3H).

Step 3) the Preparation of Compound 74-4

A mixture of compound 74-3 (757.1 mg, 1.27 mmol), compound 1-8-2 (354 mg, 1.39 mmol), Pd(dppf)Cl$_2$.CH$_2$Cl$_2$ (103 mg, 0.13 mmol) and KOAc (311 mg, 3.17 mmol) in DMF (5.0 mL) was stirred at 90° C. under $N_2$ for 3 hrs. After cooling to room temperature, the mixture was diluted with EtOAc (50.0 mL) and filtered through a celite pad. The filtration was washed with water (20 mL×3) and brine, dried over anhydrous $Na_2SO_4$ and concentrated in vacuo. The residue was purified by a silica gel column chromatography (PE/EtOAc (v/v)=2/1) to give the title compound (572.8 mg, 70%). The compound was characterized by the following spectroscopic data:

MS (ESI, pos.ion) m/z: 645.5 $[M+H]^+$;

$^1$H NMR (400 MHz, CDCl$_3$) δ (ppm): 7.68-7.65 (m, 2H), 7.59 (s, 1H), 7.27-7.23 (m, 2H), 5.32, 5.30 (d, d, 1H), 5.23-5.19 (m, 1H), 4.41-4.36 (m, 1H), 3.93-3.90 (m, 1H), 3.85-3.78 (m, 1H), 3.68-3.66 (m, 2H), 3.63 (s, 3H), 3.32-3.29 (m, 1H), 2.30-1.87 (m, 6H), 1.81-1.71 (m, 2H), 1.33 (m, 6H), 1.30 (m, 6H), 1.15-1.09 (m, 1H), 1.03-0.98 (m, 1H), 0.97, 0.96 (m, m, 3H), 0.91, 0.89 (m, m, 3H).

Step 4) the Preparation of Compound 74-5

To a mixture of compound 74-4 (644.32 mg, 1.0 mmol), compound 15-2 (428.47 mg, 1.02 mmol), Pd(PPh$_3$)$_4$ (116 mg, 0.10 mmol) and $K_2CO_3$ (346 mg, 2.5 mmol) were added EtOH (10.0 mL) and water (2.0 mL) via syringe and the mixture was stirred at 90° C. under $N_2$ for 5 hrs. After the reaction was completed, the mixture was cooled to rt, 20.0 mL of water was added, and the resulting mixture was extracted with EtOAc (20.0 mL×3). The combined organic layers were washed with brine, dried over anhydrous $Na_2SO_4$ and concentrated in vacuo. The residue was purified by a silica gel column chromatography (DCM/MeOH (v/v)=50/1) to give the title compound (486.2 mg, 60%). The compound was characterized by the following spectroscopic data:

MS (ESI, pos.ion) m/z: 811.5 $[M+H]^+$;

$^1$H NMR (400 MHz, CDCl$_3$) δ (ppm): 7.68-7.65 (m, 2H), 7.64-7.61 (m, 2H), 7.59 (s, 1H), 7.52 (s, 1H), 5.56, 5.55 (d, d, 1H), 5.45-5.40 (m, 1H), 5.32, 5.30 (d, d, 1H), 5.23-5.19 (m, 1H), 4.41-4.36 (m, 1H), 4.34-4.30 (m, 1H), 3.85-3.78 (m, 2H), 3.68-3.67 (m, 1H), 3.63 (s, 3H), 3.65-3.64 (m, 1H), 3.63 (s, 3H), 3.62-3.61 (m, 1H), 3.62-3.61 (m, 1H), 3.56-3.53 (m, 1H), 2.31-1.90 (m, 13H), 1.82-1.78 (m, 1H), 1.22-1.12 (m, 2H), 1.02-0.89 (m, 12H).

Example 75

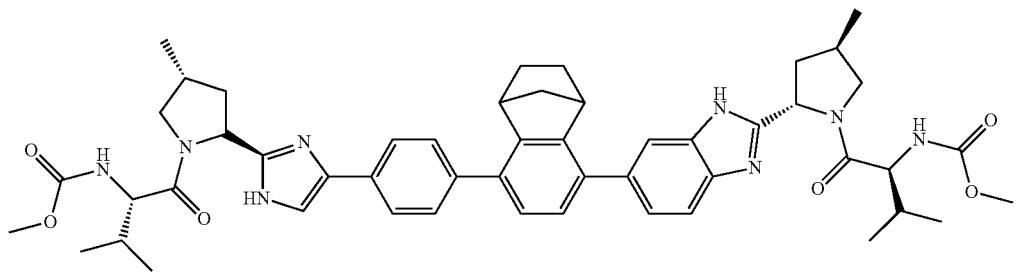

Synthetic Route:

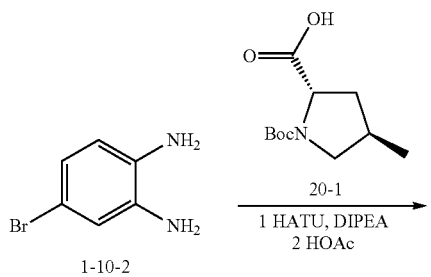

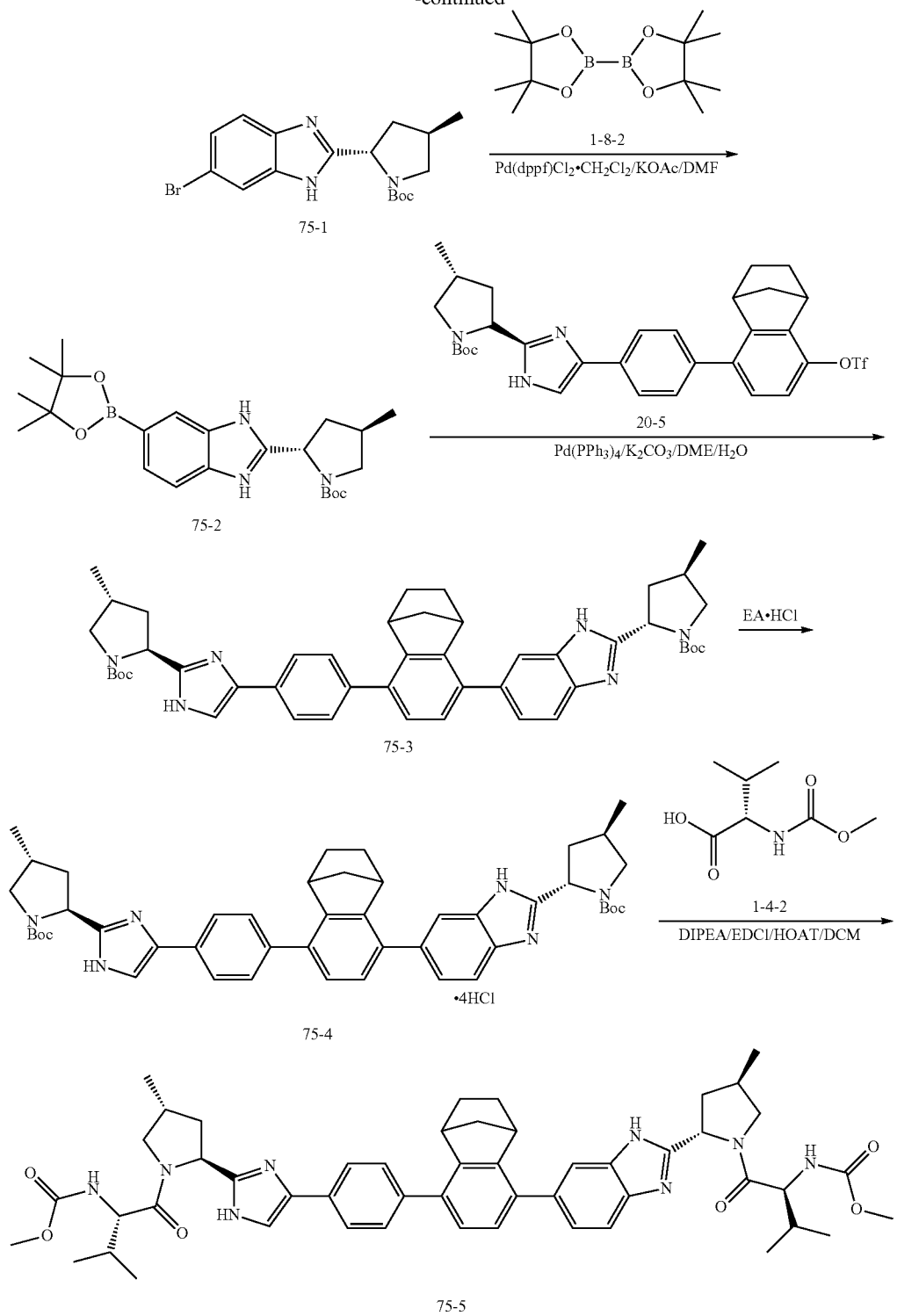

Step 1) the Preparation of Compound 75-1

To a solution of compound 20-1 (2.0 g, 8.7 mmol) and compound HATU (3.5 g, 9.2 mmol) in THF (30.0 mL) was added DIPEA (6.0 mL, 36.3 mmol) at 0° C. After stirring at rt for 0.5 hr, compound 1-10-2 (1.8 g, 9.6 mmol) was added in a portionwise manner and the mixture was stirred at rt for 2.0 hrs. After the reaction was completed, the reaction was quenched with water (10 mL). The solvent THF was removed, and the resulting mixture was extracted with EtOAc (50 mL×3). The organic layers were dried over anhydrous $Na_2SO_4$ and concentrated in vacuo. The residue was dissolved in HOAc (35.0 mL), and the mixture was stirred at 40° C. overnight. After the reaction was completed, HOAc was removed. The resulting mixture was dissolved in EtOAc (100 mL), washed with Na₂CO₃ aq (20.0 mL×3), dried over anhydrous Na₂SO₄ and concentrated in vacuo. The residue was purified by a silica gel column chromatography (PE/EtOAc (v/v)=1/4) to give the title compound (2.4 g, 72%) as a reddish brown solid. The compound was characterized by the following spectroscopic data:

¹H NMR (400 MHz, CDCl₃) δ (ppm): 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.49 (s, 9H), 1.23 (d, 3H).

Step 2) the Preparation of Compound 75-2

A mixture of compound 75-1 (2.4 g, 6.3 mmol), compound 1-8-2 (1.8 g, 7.0 mmol), Pd(dppf)Cl₂·CH₂Cl₂ (0.1 g, 0.12 mmol) and KOAc (1.6 g, 16.0 mmol) in DME (30.0 mL) was stirred at 90° C. under N₂ for 3 hrs. After the reaction was completed, DME was removed. Water (25 ml) was then added. The mixture was extracted with EtOAc (50.0 mL×3). The combined organic layers were washed with brine, dried over anhydrous Na₂SO₄ and concentrated in vacuo. The residue was purified by a silica gel column chromatography (PE/EtOAc (v/v)=3/1) to give the title compound (2.1 g, 78%) as a beige solid. The compound was characterized by the following spectroscopic data:

¹H NMR (400 MHz, CDCl₃) δ (ppm): 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.49 (s, 9H), 1.23 (d, 3H).

Step 3) the Preparation of Compound 75-3

A mixture of compound 20-5 (0.8 g, 1.3 mmol), compound 75-2 (0.56 g, 1.3 mmol), Pd(PPh₃)₄ (75 mg, 0.065 mmol) and K₂CO₃ (0.38 g, 2.6 mmol) in the mixed solvents of DME/H₂O (15.0 mL, v/v=4/1) was stirred at 90° C. under N₂ for 4 hrs. After cooling to room temperature, 10.0 mL of EtOAc and 20.0 mL of water were added to the reaction mixture. The aqueous phase was extracted with EtOAc (50.0 mL×3). The combined organic layers were washed with brine, dried over anhydrous Na₂SO₄ and concentrated in vacuo. The residue was purified by a silica gel column chromatography (DCM/MeOH (v/v)=100/1) to give the title compound (570 mg, 75%). The compound was characterized by the following spectroscopic data:

MS (ESI, pos.ion) m/z: 769.99 [M+H]⁺;

¹H NMR (400 MHz, CDCl₃) δ (ppm): 10.92 (brs, 2H), 7.70 (s, 3H), 7.49 (s, 3H), 7.37 (s, 1H), 7.32-7.03 (m, 4H), 5.12 (t, 1H, J=8.2 Hz), 4.98 (t, 1H, J=8.1 Hz), 3.81 (dd, 2H, J=19.7, 11.0 Hz), 3.62 (s, 2H), 2.95 (s, 2H), 2.76-2.41 (m, 4H), 2.43-2.16 (m, 2H), 2.04 (d, 2H, J=7.9 Hz), 1.73 (d, 1H, J=7.7 Hz), 1.51 (s, 18H), 1.26 (t, 5H, J=8.0 Hz), 1.14 (d, 6H, J=5.2 Hz).

Step 4) the Preparation of Compound 75-4

To a solution of compound 75-3 (0.58 g, 0.75 mmol) in EtOAc (4.0 mL) was added a solution of HCl in EtOAc (5.0 mL, 4 M) dropwise. At the end of addition, the mixture was stirred at rt for 8 hrs. After the reaction was completed, the mixture was concentrated in vacuo. EtOAc (10.0 mL) was added and the mixture was stirred and pulped, then filtered to give the title compound (0.48 g, 90%) as pale yellow powder, which was used for next step without further purification. The compound was characterized by the following spectroscopic data:

MS (ESI, pos.ion) m/z: 569.99 [M+H]⁺.

Step 5) the Preparation of Compound 75-5

A suspension of compound 75-4 (0.47 g, 0.67 mmol), compound 1-4-2 (0.29 g, 1.67 mmol), EDCI (0.28 g, 1.47 mmol) and HOAT (0.18 g, 1.34 mmol) in DCM (20.0 mL) was stirred at 0° C. and DIPEA (0.18 g, 1.34 mmol) was then added dropwise. At the end of addition, the mixture was stirred at rt for 3 hrs. After the reaction was completed, the mixture was diluted with DCM (20.0 mL). The resulting mixture was washed with NH₄Cl aqueous solution and brine, dried over anhydrous Na₂SO₄ and concentrated in vacuo. The residue was purified by a silica gel column chromatography (DCM/MeOH (v/v)=60/1) to give the title compound (0.36 g, 62%) as a white solid. The compound was characterized by the following spectroscopic data:

MS (ESI, pos.ion) m/z: 884.09 [M+H]

¹H NMR (400 MHz, CDCl₃) δ (ppm): 10.89 (brs, 1H), 10.67 (brs, 1H), 7.84-7.81 (m, 2H), 7.45-7.36 (m, 4H), 7.25-7.18 (m, 4H), 5.54 (s, 1H), 5.35 (t, 1H, J=8.5 Hz), 5.21 (t, 1H, J=8.4 Hz), 4.54-4.35 (m, 1H), 4.14-4.06 (m, 2H), 3.71 (s, 6H), 3.59-3.57 (m, 2H), 3.22-3.19 (m, 2H), 2.71-2.69 (m, 2H), 2.60-2.58 (m, 1H), 2.52-2.48 (m, 1H), 2.45-2.20 (m, 2H), 2.01 (s, 4H), 1.45 (m, 4H), 0.88 (s, 6H), 0.85 (s, 6H).

Example 76

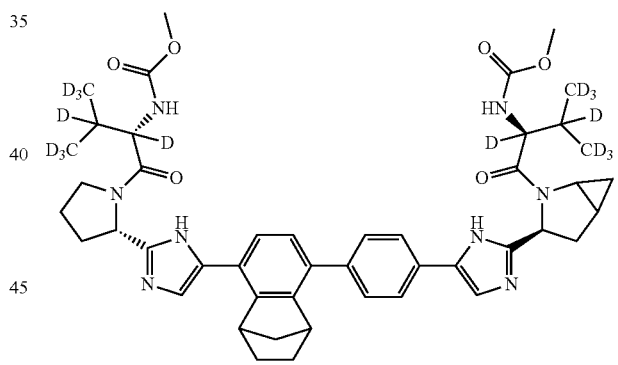

Synthetic Route:

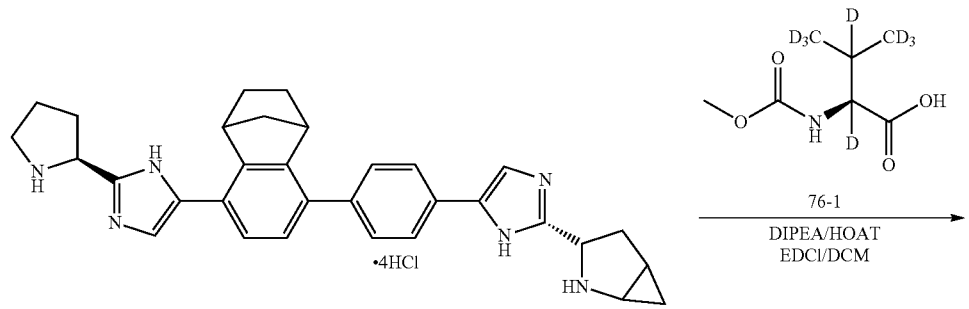

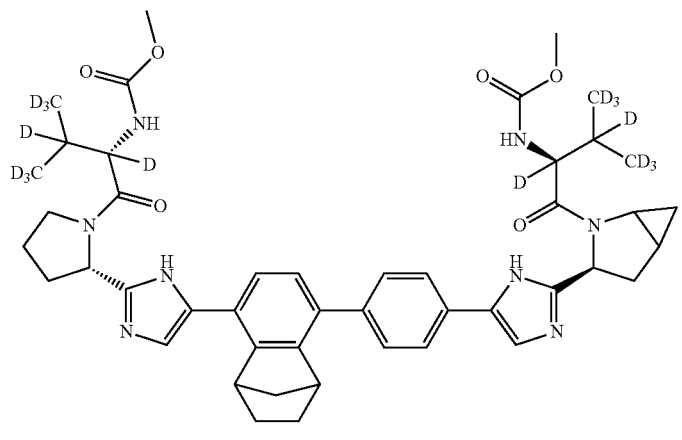

76-2

Step 1) the Preparation of Compound 76-2

To a suspension of compound 2-8 (103 mg, 0.159 mmol), compound 76-1 (61.2 mg, 0.334 mmol), EDCI (63.84 mg, 0.333 mmol) and HOAT (32.42 mg, 0.238 mmol) in DCM (5.0 mL) was added DIPEA (0.21 mL, 1.27 mmol) dropwise at 0° C., and the mixture was stirred at rt for 3 hrs. After the reaction was completed, the mixture was diluted with DCM (20 mL). The organic phase was washed with NH$_4$Cl aqueous solution and brine, dried over anhydrous Na$_2$SO$_4$ and concentrated in vacuo. The residue was purified by a silica gel column chromatography (DCM/MeOH (v/v)=60/1) to give the title compound as a pale yellow solid (50 mg, 37.77%). The compound was characterized by the following spectroscopic data:

MS (ESI, pos.ion) m/z: 417.3 [M+2H]$^{2+}$;

$^1$H NMR (400 MHz, CDCl$_3$) δ (ppm): 7.81 (s, 1H), 7.62 (s, 1H), 7.61-7.59 (m, 2H), 7.56-7.52 (m, 2H), 7.48, 7.46 (s, s, 1H), 7.34, 7.32 (s, s, 1H), 6.06 (brs, 2H), 5.29-5.25 (m, 1H), 4.89-4.85 (m, 1H), 3.87-3.78 (m, 3H), 3.68-3.67 (m, 1H), 3.66 (s, 3H), 3.63 (s, 3H), 3.45-3.38 (m, 1H), 2.46-2.39 (m, 1H), 2.30-2.16 (m, 2H), 2.13-1.93 (m, 5H), 1.91-1.87 (m, 1H), 1.68-1.64 (m, 1H), 1.43-1.36 (m, 1H), 1.30-1.20 (m, 2H), 0.94-0.90 (m, 2H).

Example 77

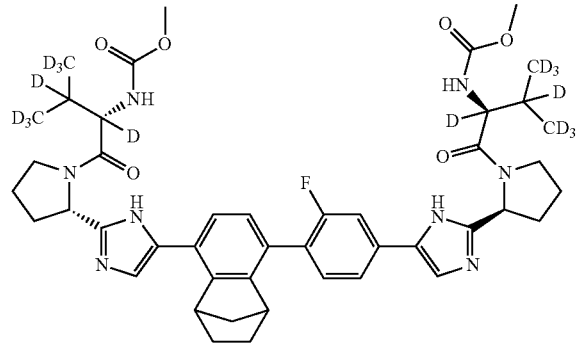 [SMILES: [2H]C([2H])([2H])C([2H])(C([2H])([2H])[2H])[C@]([2H])(NC(=O)OC)C(=O)N1CCC[C@H]1c1ncc(-c2ccc(-c3ccc(-c4cnc([C@@H]5CCCN5C(=O)[C@@]([2H])(NC(=O)OC)C([2H])(C([2H])([2H])[2H])C([2H])([2H])[2H])[nH]4)c4c3C3CCC4C3)c(F)c2)[nH]1]

Synthetic Route:

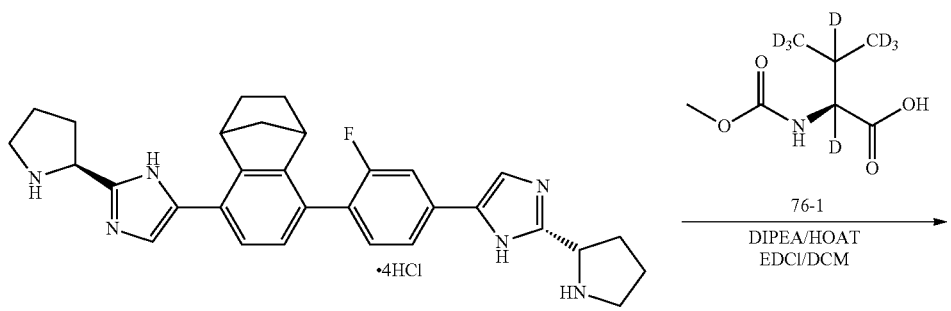

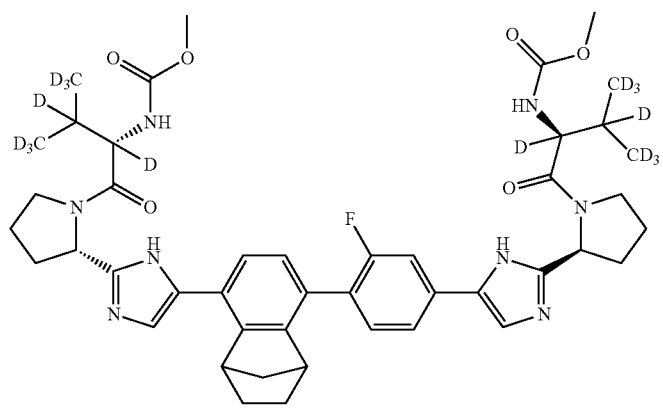

77-1

Step 1) the Preparation of Compound 77-1

To a mixture of compound 4-9 (0.45 g, 0.687 mmol), compound 76-1 (0.265 g, 1.44 mmol), EDCI (0.28 g, 1.51 mmol) and HOAT (0.187 g, 0.137 mmol) in DCM (5.0 mL) was added DIPEA (0.144 mL, 0.87 mmol) dropwise at −10° C. At the end of addition, the mixture was stirred at rt for 3 hrs. After the reaction was completed, the mixture was quenched with saturated NH$_4$Cl aqueous solution. The resulting mixture was extracted with DCM (50 mL×3), and the combined organic layers were dried over anhydrous Na$_2$SO$_4$ and concentrated in vacuo. The residue was purified by a silica gel column chromatography (DCM/MeOH (v/v)=40/1) to give the title compound as a white solid (380 mg, 65.97%). The compound was characterized by the following spectroscopic data:

MS (ESI, pos.ion) m/z: 420.26 [M+2H]$^{2+}$;

$^1$H NMR (400 MHz, CDCl$_3$) δ (ppm): 7.81 (s, 1H), 7.63 (s, 1H), 7.61-7.57 (m, 2H), 7.42, 7.40 (d, d, 1H), 7.34, 7.32 (s, s, 1H), 6.98, 6.96 (dd, dd, 1H), 6.06 (brs, 2H), 5.40-5.36 (m, 1H), 5.29-5.25 (m, 1H), 3.95-3.92 (m, 1H), 3.85-3.78 (m, 3H), 3.69-3.67 (m, 1H), 3.66 (s, 3H), 3.63 (s, 3H), 3.62-3.61 (m, 1H), 2.30-2.16 (m, 4H), 2.13-1.88 (m, 7H), 1.69-1.65 (m, 1H), 1.30-1.21 (m, 2H).

Example 78

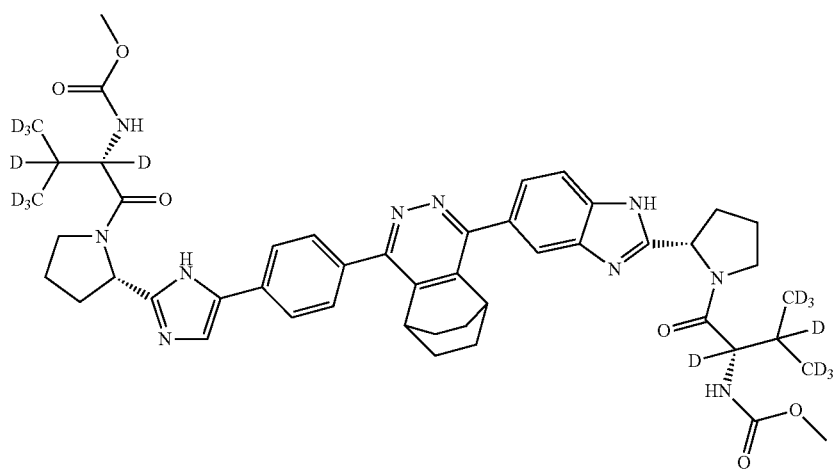 [SMILES: [2H]C([2H])([2H])C([2H])(C([2H])([2H])[2H])[C@]([2H])(NC(=O)OC)C(=O)N1CCC[C@H]1c1ncc(-c2ccc(-c3nnc(-c4ccc5[nH]c([C@@H]6CCCN6C(=O)[C@@]([2H])(NC(=O)OC)C([2H])(C([2H])([2H])[2H])C([2H])([2H])[2H])nc5c4)c4c3C3CCC4CC3)cc2)[nH]1]

Synthetic Route:

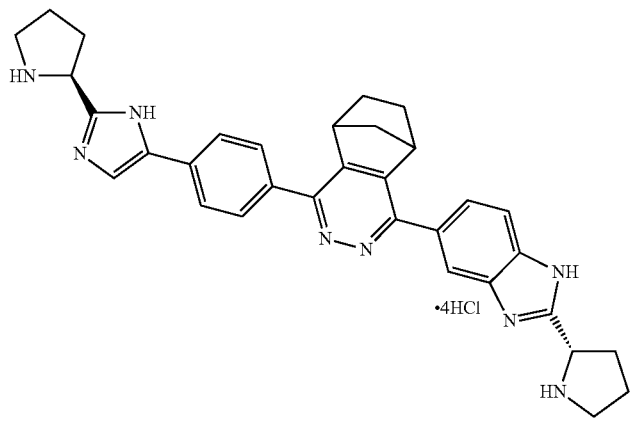

11-9

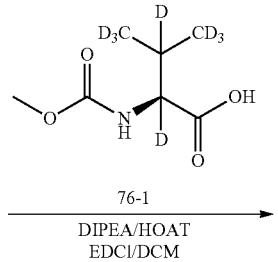

76-1
DIPEA/HOAT
EDCI/DCM

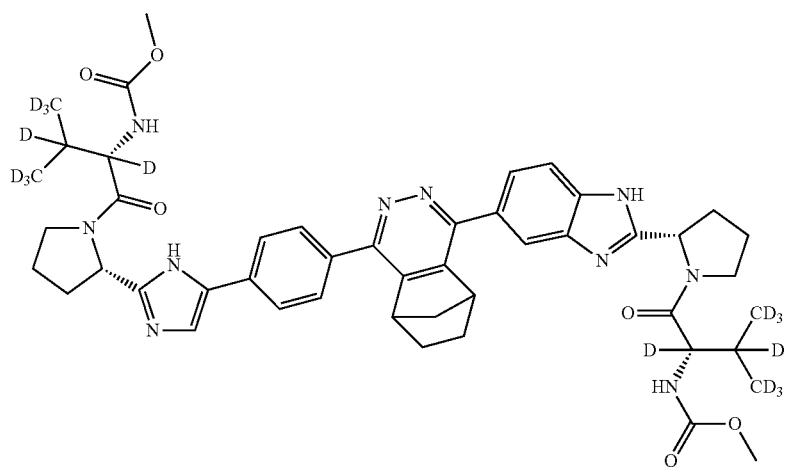

78-1

Step 1) the Preparation of Compound 78-1

A suspension of compound 11-9 (160 mg, 0.21 mmol), compound 76-1 (80.8 mg, 0.441 mmol), EDCI (90 mg, 0.47 mmol) and HOAT (58.5 mg, 0.43 mmol) in DCM (6.0 mL) was stirred at 0° C. for 5 mins, then DIPEA (0.355 mL, 2.15 mmol) was added dropwise. At the end of addition, the mixture was stirred at rt for 10 hrs. After the reaction was completed, the mixture was diluted with DCM (20 mL), washed with saturated NH$_4$Cl aqueous solution, dried over anhydrous Na$_2$SO$_4$ and concentrated in vacuo. The residue was purified by a silica gel column chromatography (DCM/MeOH (v/v) =30/1) to give the title compound as a white solid (150 mg, 80.55%). The compound was characterized by the following spectroscopic data:

MS (ESI, pos.ion) m/z: 444.28 [M+2H]$^{2+}$;

$^1$H NMR (400 MHz, CDCl$_3$) δ (ppm): 8.07-8.04 (m, 2H), 7.88-7.85 (m, 2H), 7.78, 7.76 (d, d, 1H), 7.70-7.69 (m, 1H), 7.59 (s, 1H), 7.31, 7.29 (d, d, 1H), 6.06 (brs, 2H), 5.25-5.18 (m, 2H), 3.85-3.78 (m, 2H), 3.68-3.67 (m, 1H), 3.66 (s, 3H), 3.63 (s, 3H), 3.62-3.60 (m, 1H), 3.39-3.27 (m, 2H), 2.39-1.87 (m, 8H), 1.75-1.63 (m, 4H), 1.41-1.31 (m, 4H).

Example 79

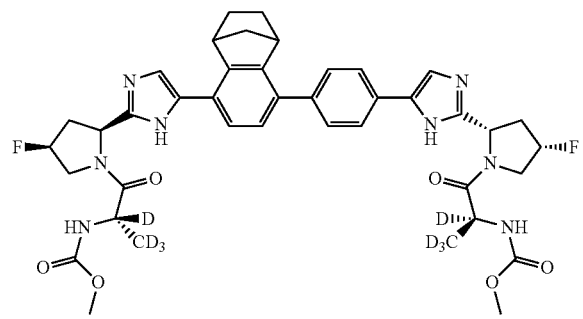 [SMILES: [2H]C([2H])([2H])[C@]([2H])(NC(=O)OC)C(=O)N1C[C@@H](F)C[C@H]1c1ncc(-c2ccc(-c3ccc(-c4cnc([C@@H]5C[C@H](F)CN5C(=O)[C@@]([2H])(NC(=O)OC)C([2H])([2H])[2H])[nH]4)c4c3C3CCC4C3)cc2)[nH]1]

Synthetic Route:

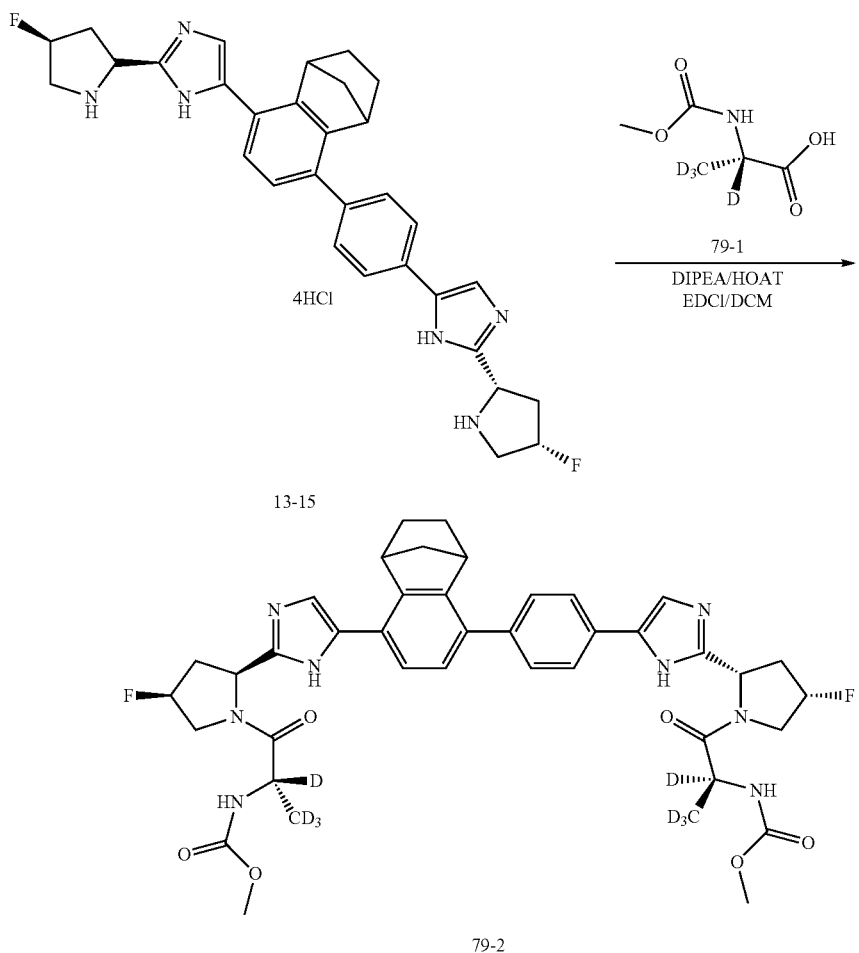

Step 1) the Preparation of Compound 79-2

A suspension of compound 13-15 (200 mg, 0.29 mmol), compound 79-1 (922 mg, 0.61 mmol), EDCI (120 mg, 0.65 mmol) and HOAT (80 mg, 0.59 mmol) in DCM (5.0 mL) was added DIPEA (0.49 mL, 2.97 mmol) dropwise at 0° C. At the end of addition, the mixture was stirred at rt for 3 hrs. After the reaction was completed, the mixture was diluted with DCM (20.0 mL), washed with NH$_4$Cl aqueous solution and brine, dried over anhydrous Na$_2$SO$_4$ and concentrated in vacuo. The residue was purified by a silica gel column chromatography (DCM/MeOH (v/v)=40/1) to give the title compound as a white solid (150 mg, 65.28%). The compound was characterized by the following spectroscopic data:

MS (ESI, pos.ion) m/z: 793.4 [M+H]$^+$;

$^1$H NMR (400 MHz, CDCl$_3$) δ (ppm): 8.00 (s, 1H), 7.62-7.59 (m, 2H), 7.56-7.52 (m, 2H), 7.48, 7.46 (s, s, 1H), 7.38 (s, 1H), 7.34, 7.32 (s, s, 1H), 6.06 (m, 2H), 5.36-5.28 (m, 1H), 5.23-5.15 (m, 1H), 4.97-4.92 (m, 1H), 4.90-4.86 (m, 1H), 4.16-4.04 (m, 2H), 3.87-3.81 (m, 2H), 3.78-3.66 (m, 2H), 3.64 (s, 6H), 2.98-2.77 (m, 2H), 2.30-2.14 (m, 2H), 2.03-1.93 (m, 2H), 1.91-1.87 (m, 1H), 1.68-1.64 (m, 1H), 1.30-1.20 (m, 2H).

Example 80

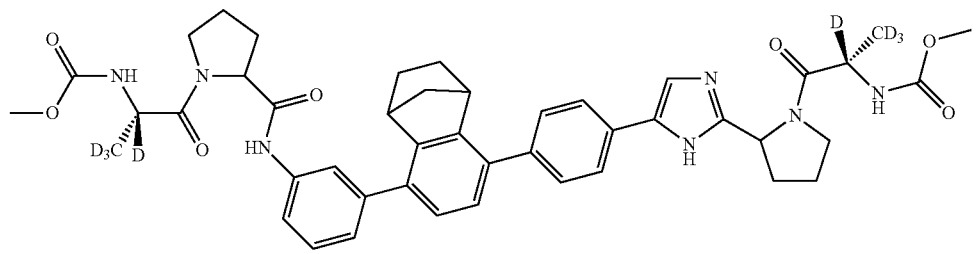

Synthetic Route:

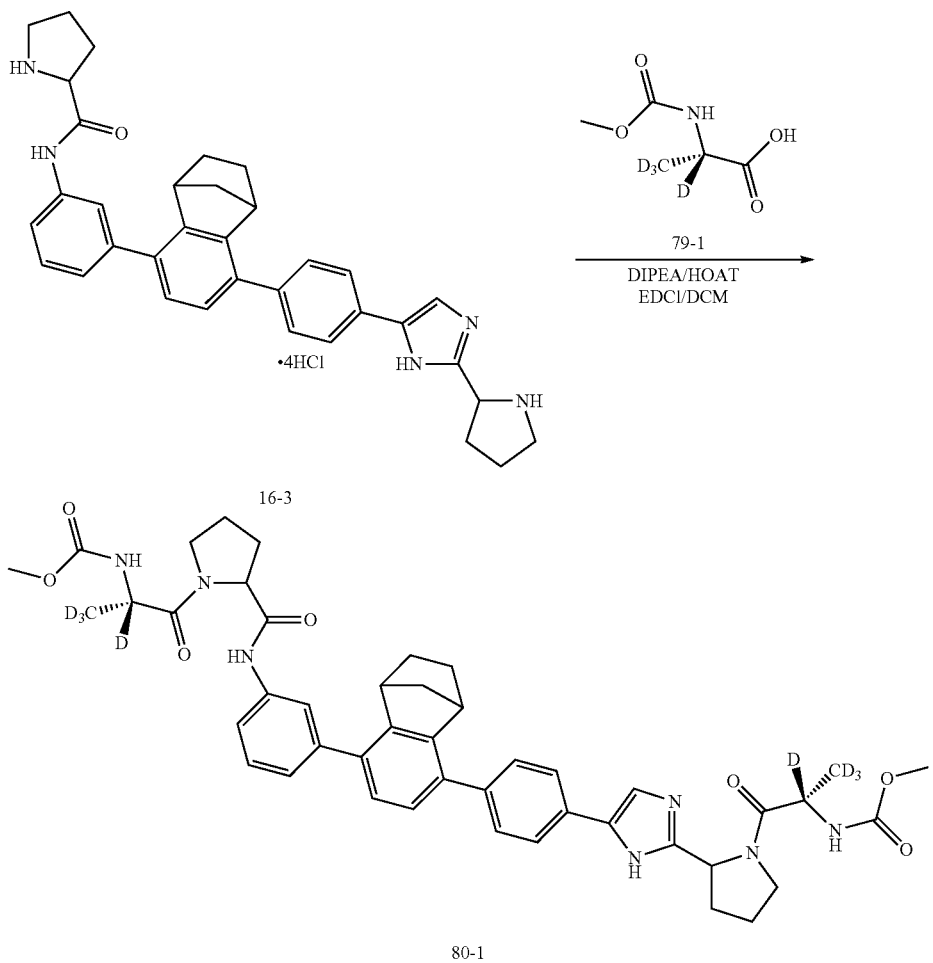

Step 1) the Preparation of Compound 80-1

To a solution of compound 16-3 (689.3 mg, 1.0 mmol), compound 79-1 (302.24 mg, 2.0 mmol) and EDCI (958 mg, 5.0 mmol) in DCM (18 mL) was added DIPEA (1.65 mL, 10 mmol) dropwise at 0° C. At the end of addition, the mixture was stirred at rt for 3 hrs. After the reaction was completed, water (15 mL) was added to the mixture, and the resulting mixture was extracted with DCM (25 mL×3). The combined organic layers were dried over anhydrous $Na_2SO_4$ and concentrated in vacuo. The residue was purified by a silica gel column chromatography (DCM/MeOH (v/v)=50/1) to give the title compound as a pale yellow solid (400 mg, 49.44%). The compound was characterized by the following spectroscopic data:

$^1$H NMR (400 MHz, $CD_3OD$) δ (ppm): 8.93 (m, 1H), 8.00-7.99 (m, 1H), 7.62 (s, 1H), 7.61-7.59 (m, 2H), 7.56-7.53 (m, 3H), 7.52-7.49 (m, 1H), 7.47, 7.45 (s, s, 1H), 7.44-7.42 (m, 1H), 7.22-7.18 (m, 1H), 6.06 (m, 2H), 5.07-5.00 (m, 1H), 4.28-4.23 (m, 1H), 4.07-4.03 (m, 1H), 3.92-3.82 (m, 2H), 3.78-3.71 (m, 1H), 3.64 (s, 6H), 3.60-3.52 (m, 1H), 3.47-3.39 (m, 1H), 2.34-2.03 (m, 6H), 1.99-1.94 (m, 2H), 1.88-1.61 (m, 4H), 1.25-1.22 (m, 2H).

BIOLOGICAL ACTIVITY

An HCV Replicon assay was utilized in the present disclosure, and was prepared, developed and validated as described in Science, 1999, 285 (5424), 110-3 and J. Virol., 2003, 77 (5), 3007-19.

HCV GT1a, GT1b and GT2a replicon cells were used to test the currently described compound series as well as wild-type cells HCV 1b and resistant cells $Y^{93}H$, L31F, P32L and I302V. GT1a and CT1b are HCV Replicon System which is transfected HCV 1a, 1b genotype respectively. The system containing G418 resistance gene NEO and Luciferase Reporter Gene can be used to determine the level of HCV replication, and evaluate the effects of the compounds inhibit HCV replication, by using a real-time quantitative polymerase chain reaction (qPCR) method to detect NEO, and chemiluminescence method to test Luciferase Reporter Gene.

Operating Procedure:

1. Testing $EC_{50}$ of the Compounds by Luciferase Assay

The GT1b cells and GT1a cells were seeded into 96-well plates (8,000 cells in 125 μl/well) respectively; each compound was diluted to desired concentration using 5-fold serial dilutions protocol, 10 dose in duplicate, and added to wells with POD™ 810 Plate Assembler. The final concentration of DMSO was 0.5%; the plates were incubated in a $CO_2$ incubator for 72 hours; after that, 40 μl of Luciferase assay substrate (Promega Bright-Glo) was added to each well, and detected by a chemiluminescence detection system (Topcount Microplate Scintillation and Luminescence Counter) 5 minutes later; data analysis.

2. Testing $EC_{50}$ of the Compounds by Detecting Antibiotic G418 Resistance Gene NEO Gene The GT1b cells and GT1a cells were seeded into 96-well plates (8,000 cells in 125 μl/well) respectively; each compound was diluted to desired concentration using 5-fold serial dilutions protocol, 10 dose in duplicate, and added to wells with POD™ 810 Plate Assembler., the final concentration of DMSO was 0.5%; the cells were incubated in a $CO_2$ incubator for 72 hours; quantitative PCR.

Sample preparation: the supernatant was removed, 100 μl of FCW buffer solution was added to each well, washed carefully and discarded the solution; 50 μl of lysate FCP was added to each well, the cells was lysed as PCR template and diluted with DEPC water.

Quantitative PCR: preparation of reaction mixture according to PCR system; the reaction mixture was dispensed into a 384-well PCR reaction plate (specially for quantitative); and a standard template which was diluted in proportion was distributed into the plate; and the sample template was distributed into the plate; then the 384-well plate was sealed with closure plate membrane; the qualitative PCR machine was operated by procedures; data analysis.

3. Data Processing: The $EC_{50}$ Values of Compounds were Analyzed by GraphPad Prism Software.

The compounds of the present disclosure can be effective against the HCV 1b genotype according to the experiment data, and $EC_{50}$ ranges of compounds which have different groups against HCV 1b are 1-999 pM, 1-99 nM; the compounds of the present disclosure can inhibit multiple genotypes of HCV (such as HCV 1a or HCV 2a). Table 2 shows the $EC_{50}$ values of representative compounds of the present disclosure against the HCV 1a and HCV 1b genotypes. In one embodiment compounds of the present disclosure are active against the 1a, 1b, 2a, 2b, 3a, 3b, 4a, and 5a genotypes.

The experiment results of wild-type and resistance cells and the simulation results of molecular modeling and docking show that the present disclosure plays an excellent anti-HCV role, which suggest a novel anti-HCV mechanism by interfering with HCV NS5A protein

TABLE 2

| Example | 1a (nM) | 1b (nM) |
|---|---|---|
| 1 | 0.029 | 0.008 |
| 3 | 0.053 | 0.013 |
| 4 | 0.497 | 0.007 |
| 5 | 1.053 | 0.098 |
| 6 | 0.047 | 0.006 |
| 7 | 0.094 | 0.076 |
| 8 | 0.033 | 0.019 |
| 9 | 0.104 | 0.009 |
| 10 | 0.374 | 0.013 |
| 11 | 0.049 | 0.023 |
| 12 | 0.658 | 0.373 |
| 13 | 0.530 | 0.034 |
| 14 | 0.487 | 0.006 |
| 16 | 3.496 | 0.009 |
| 17 | 0.767 | 0.007 |
| 18 | 0.138 | 0.014 |
| 19 | 0.087 | 0.026 |
| 20 | <0.001 | 0.045 |
| 21 | 0.093 | 0.013 |
| 22 | 11.400 | 0.004 |
| 24 | 0.453 | 0.096 |
| 25 | 0.083 | 0.032 |
| 26 | 0.653 | 0.077 |
| 28 | 0.063 | 0.015 |
| 31 | 0.077 | 0.038 |
| 33 | 0.038 | 0.009 |
| 34 | 0.054 | 0.006 |
| 35 | 0.103 | 0.017 |
| 38 | 0.064 | 0.017 |
| 40 | 0.083 | 0.012 |
| 41 | 0.067 | 0.010 |

TABLE 2-continued

| Example | 1a (nM) | 1b (nM) |
|---|---|---|
| 43 | 1.132 | 0.073 |
| 45 | 3.073 | 0.113 |
| 46 | 0.439 | 0.035 |
| 47 | 0.053 | 0.013 |
| 48 | 0.043 | 0.029 |
| 49 | 0.855 | 0.083 |
| 59 | 0.037 | 0.008 |
| 61 | 0.088 | 0.011 |
| 63 | 2.254 | 0.815 |
| 65 | 0.064 | 0.013 |
| 67 | 0.953 | 0.053 |
| 76 | 0.127 | 0.013 |
| 77 | 0.206 | 0.009 |
| 78 | 0.045 | 0.007 |
| 79 | 0.314 | 0.043 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. The compounds of the present disclosure may inhibit multiple genotypes of HCV.

The invention claimed is:

1. A compound of Formula (I):

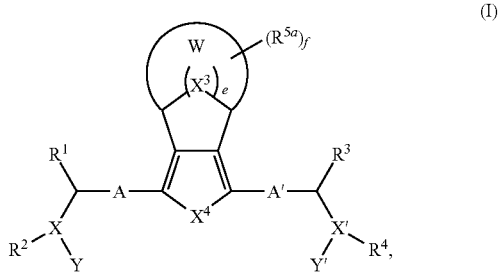

or a stereoisomer, a geometric isomer, a tautomer, an N-oxide, a hydrate, a solvate, a pharmaceutically acceptable salt or a prodrug thereof, wherein each of A and A' is independently a bond, alkyl, alkenyl, cycloalkyl, heterocycloalkyl, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, or —$(CR^8R^{8a})_n$—N($R^5$)—C(=O)—O—$(CR^8R^{8a})_p$—, or each of A and A' is independently

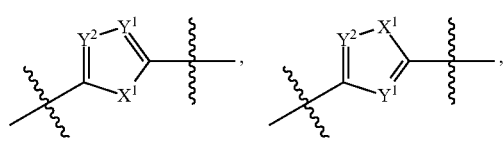
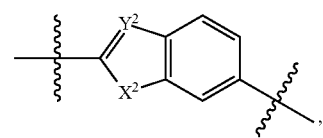
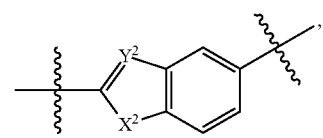
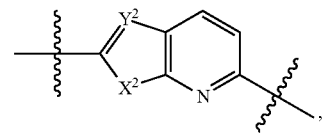
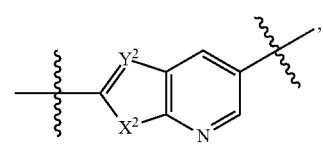
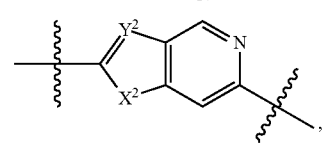
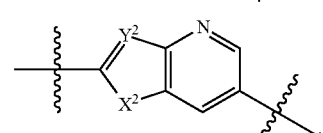
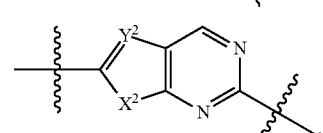
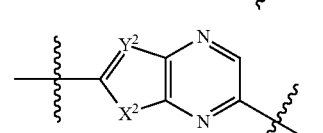
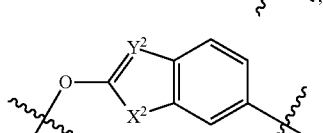
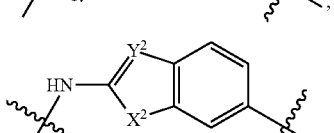
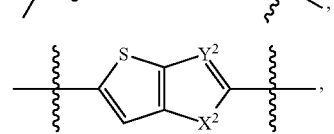
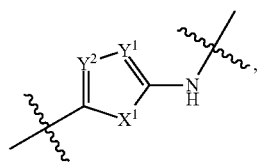
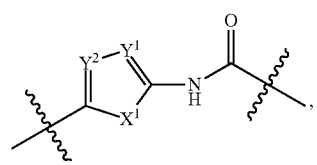
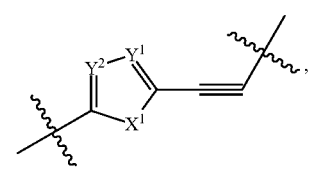
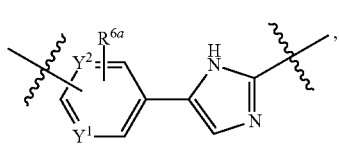
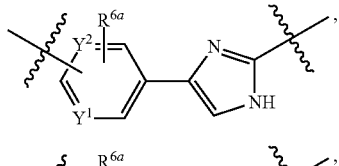
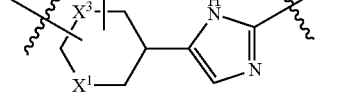
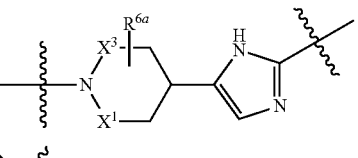
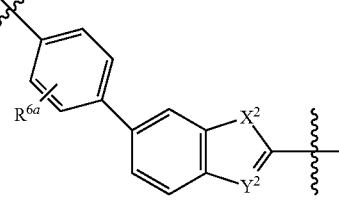
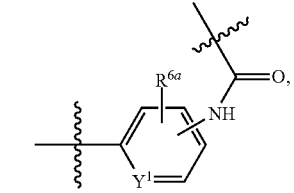
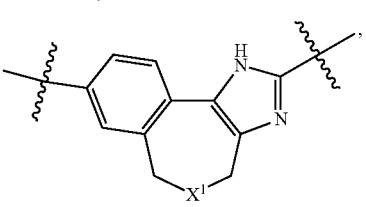

635
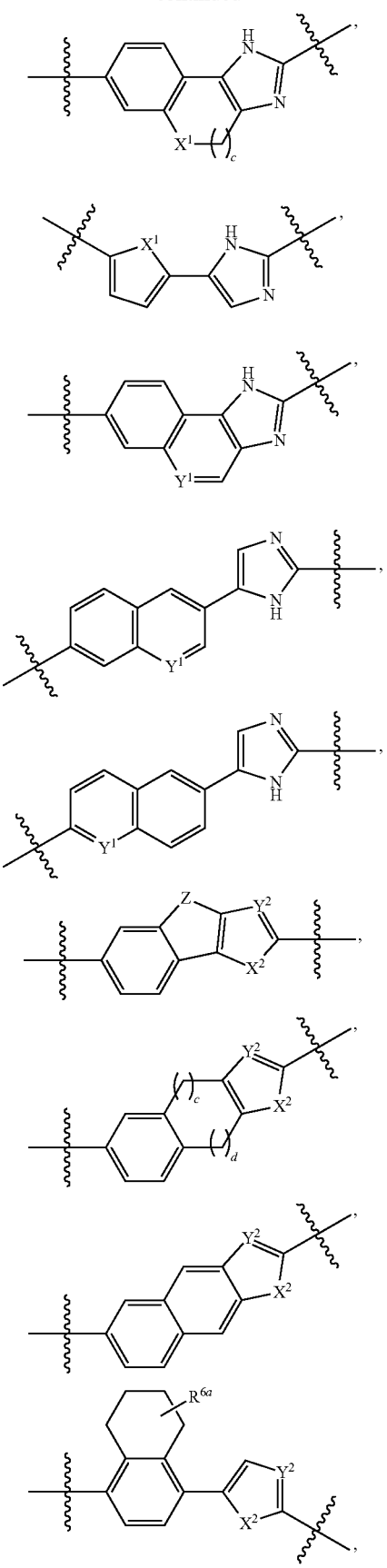
636
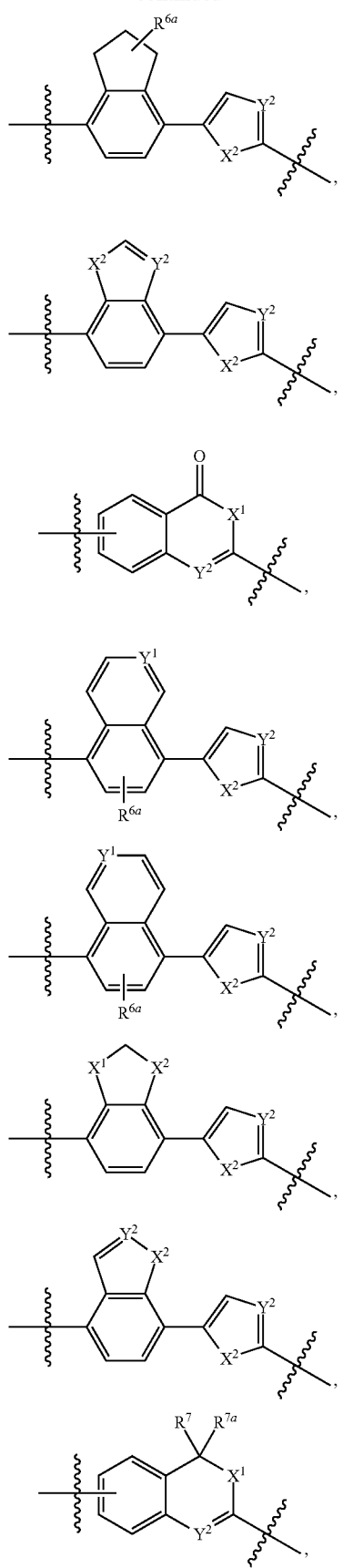

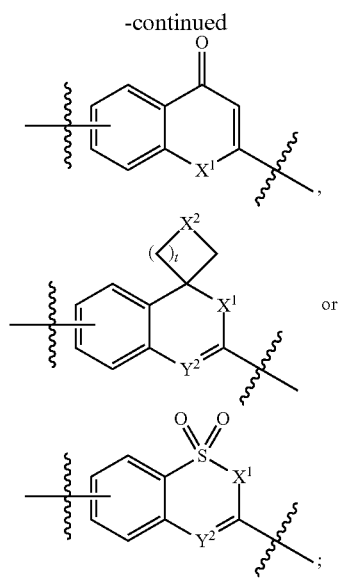

wherein each $X^1$ is independently O, S, $NR^6$, or $CR^7R^{7a}$;
each $X^2$ is independently $NR^6$, O or S;

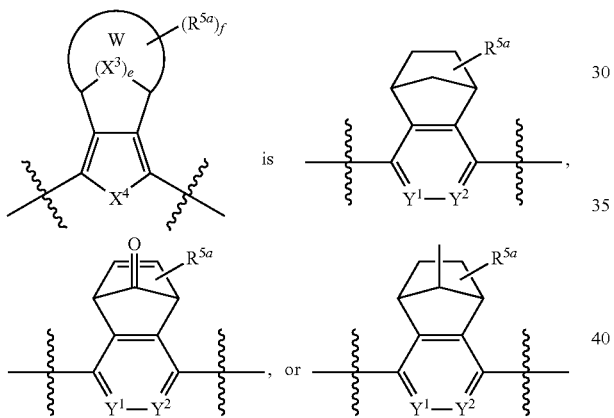

each $Y^1$ and $Y^2$ is independently $CR^7$;
Z is —$(CH_2)_a$—, —CH=CH—, —N=CH—, —$(CH_2)_a$—$N(R^5)$—$(CH_2)_b$—, or —$(CH_2)_a$—O—$(CH_2)_b$—, wherein
each a and b is independently 0, 1, 2 or 3;
each c is independently 1 or 2;
each d is independently 1 or 2;
each n is independently 0, 1, 2 or 3;
each p is independently 0, 1, 2 or 3;
each r is independently 0, 1 or 2;
f is 0, 1, 2, 3 or 4;
each of X and X' is independently N;
each of Y and Y' is independently —C(=O)—$(CR^9R^{9a})_n$—$N(R^{11})$—C(=O)—O—$R^{13}$ where n is selected from 1, 2, or 3;
$R^1$ and $R^2$, together with X—CH they are attached to, form a 3-8 membered heterocycle, $C_{5-12}$ fused heterobicycle or $C_{5-12}$ spiro heterobicycle and $R^3$ and $R^4$, together with X'—CH they are attached to, form a 3-8 membered heterocycle, $C_{5-12}$ fused heterobicycle or $C_{5-12}$ spiro heterobicycle;
each $R^5$ is independently H, deuterium, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;
each $R^{5a}$ is independently H, deuterium, oxo (=O), hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —$N(R^7)C(=O)NR^7R^{7a}$, —$N(R^7)C(=O)OR^{7a}$, —$N(R^7)C(=O)$—$R^{7a}$, $R^7R^{7a}N$—S(=O)$_2$—, $R^7S(=O)_2$—, $R^7S(=O)_2N(R^{7a})$—, $R^{7a}R^7N$-alkyl, $R^7S(=O)$-alkyl, $R^7R^{7a}N$—C(=O)-alkyl, $R^{7a}R^7N$-alkoxy, $R^7S(=O)$-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;
each $R^6$ is independently H, deuterium, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;
each $R^{6a}$ is independently H, deuterium, hydroxy, amino, F, Cl, Br, I, cyano, oxo (=O), $R^{7a}R^7N$—, —C(=O)$NR^7R^{7a}$, —OC(=O)$NR^7R^{7a}$, —OC(=O)$OR^7$, —$N(R^7)C(=O)NR^7R^{7a}$, —$N(R^7)C(=O)OR^{7a}$, —$N(R^7)C(=O)$—$R^{7a}$, $R^7R^{7a}N$—S(=O)$_2$—, $R^7S(=O)_2$—, $R^7S(=O)_2N(R^{7a})$—, $R^{7a}R^7N$-alkyl, $R^7S(=O)$-alkyl, $R^7R^{7a}N$—C(=O)-alkyl, $R^{7a}R^7N$-alkoxy, $R^7S(=O)$-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino, or aryloxy;
each $R^7$ and $R^{7a}$ is independently H, deuterium, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl, with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring;
each $R^8$ and $R^{8a}$ is independently H, deuterium, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_c$—, alkyl-S(=O)$_c$O—, alkyl-S(=O)$_c$—, or aminosulfonyl;
each $R^9$, $R^{9a}$, and $R^{11}$ is independently H, deuterium, alkyl, cycloalkyl, aryl, or cycloalkylalkyl;

each $R^{13}$ and $R^{13a}$ is independently H, deuterium, alkyl, heteroalkyl, cycloalkyl, heterocyclyl, aryl, heteroaryl, or aralkyl;

wherein each of $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_t-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, $NR^6$, $CR^7R^{7a}$, $CR^7$, $-(CH_2)_q-$, $-CH=CH-$, $-N=CH-$, $-(CH_2)_a-N(R^5)-(CH_2)_b-$, $-(CH_2)_a-O-(CH_2)_b-$, $R^{13a}R^{13}N-$, $-C(=O)R^{13}$, $-C(=S)R^{13}$, $-C(=O)-O-R^{13}$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $R^{13}OS(=O)_2-$, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, alkyl-OC(=O)—, alkyl-C(=O)—, alkyl-OS(=O)$_c$—, alkyl-S(=O)$_c$O—, alkyl-S(=O)$_c$—, $R^7R^{7a}NC(=O)-$, $R^7OC(=O)-$, $R^7C(=O)-$, $R^7R^{7a}NS(=O)-$, $R^7OS(=O)-$, $R^7S(=O)-$, $R^7R^{7a}NS(=O)_2-$, $R^7OS(=O)_2-$, $R^{7a}R^7N$-alkyl, $R^7S(=O)$-alkyl, $R^{7a}R^7N-C(=O)$-alkyl, $R^{7a}R^7N$-alkoxy, $R^7S(=O)$-alkoxy, $R^7R^{7a}N-C(=O)$-alkylamino, alkyl, heteroalkyl, carbocyclyl, cycloalkyl, heterocyclyl, heterocycloalkyl, aryl, heteroaryl, aralkyl, $C_{5-12}$ fused bicycle, $C_{5-12}$ fused heterobicycle, $C_{5-12}$ spiro bicycle, $C_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted with one or more substituents, wherein the substituent is deuterium, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, or carboxy-substituted alkoxy.

2. The compound according to claim 1, wherein each $R^{5a}$ is independently H, deuterium, oxo (=O), hydroxy, amino, F, Cl, Br, I, cyano, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $S(=O)_2-$, $R^7S(=O)_2N(R^{7a})-$, $R^{7a}R^7N-C_{1-6}$ alkyl, $R^7S(=O)-C_{1-6}$ alkyl, $R^7R^{7a}N-C(=O)-C_{1-6}$ alkyl, $R^{7a}R^7N-C_{1-6}$ alkoxy, $R^7S(=O)-C_{1-6}$ alkoxy, $R^7R^{7a}N-C(=O)-C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aralkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino or $C_{6-10}$ aryloxy;

each $R^6$ is independently H, deuterium, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-6}$ heteroaryl, $C_{6-10}$ aryl, $C_{3-6}$ heterocyclyl or $C_{3-8}$ carbocyclyl; and each $R^7$ and $R^{7a}$ is independently H, deuterium, F, Cl, $C_{1-6}$ alkyl, $C_{1-6}$ heteroalkyl, $C_{1-6}$ haloalkyl, hydroxy, amino, $C_{1-6}$ alkoxy, $C_{6-10}$ aryl, $C_{2-9}$ heterocyclyl, $C_{3-9}$ cycloalkyl, $C_{6-10}$ aryloxy, $C_{2-9}$ heterocyclyloxy, $C_{6-10}$ arylamino, $C_{2-9}$ heterocyclylamino, $C_{3-9}$ cycloalkylamino, $C_{1-9}$ heteroaryl or $C_{3-9}$ carbocyclyl, with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted spiro or fused bicyclic ring.

3. The compound according to claim 1, wherein each $R^{5a}$ is independently H, deuterium, oxo (=O), hydroxy, amino, F, Cl, Br, I, cyano, $C_{1-4}$ alkyl, $-CF_3$, $-OCF_3$, mercapto, nitro, or $C_{1-4}$ alkylamino.

4. The compound according to claim 1, wherein each of A and A' is independently a bond, $C_{1-6}$ alkyl, $C_{2-6}$ alkenyl, $C_{3-8}$ cycloalkyl, $C_{2-10}$ heterocycloalkyl, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently

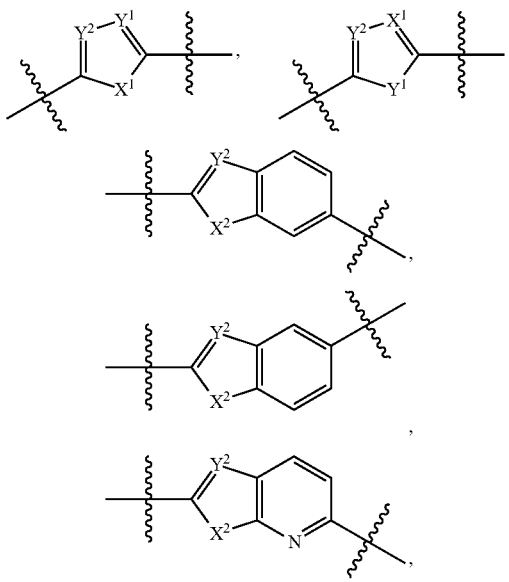

641
-continued
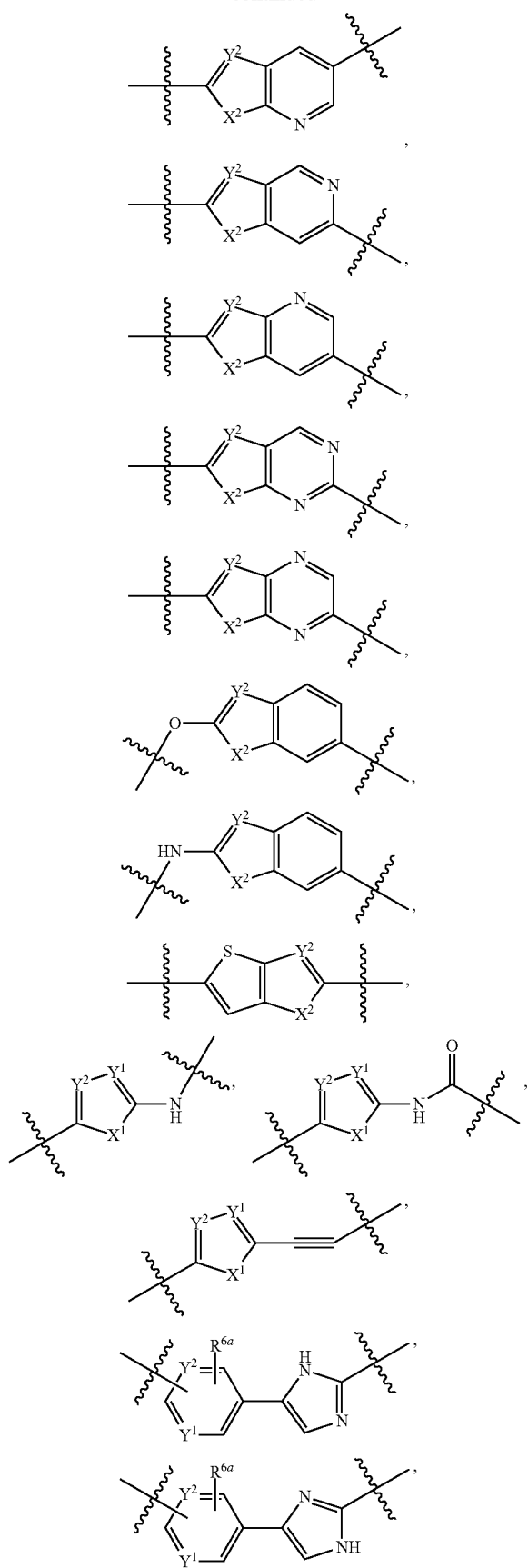
642
-continued
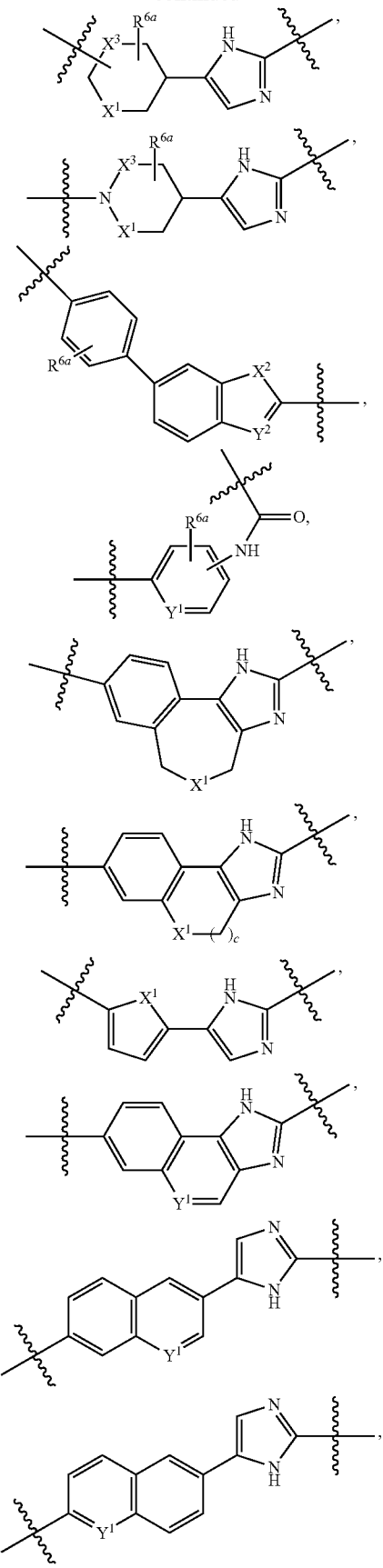

-continued

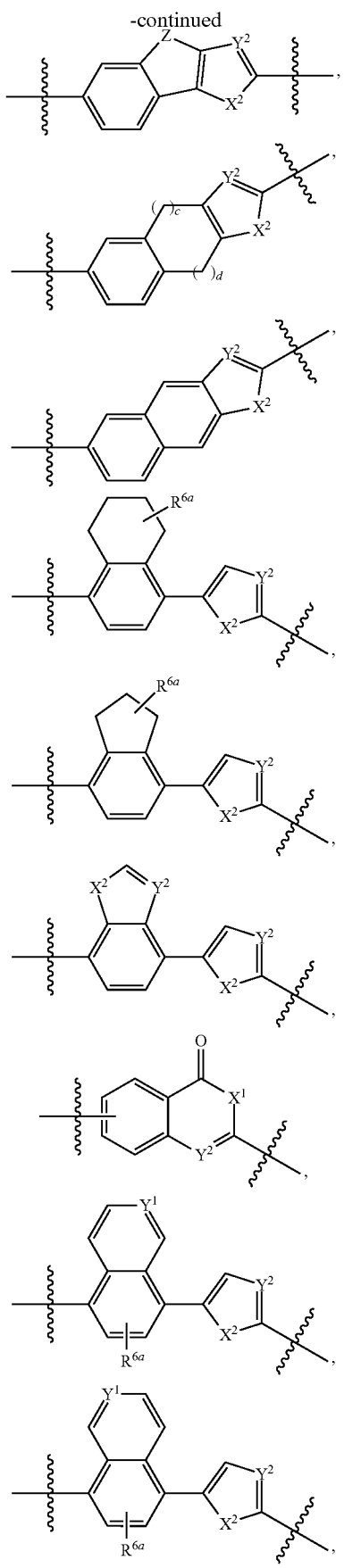

-continued

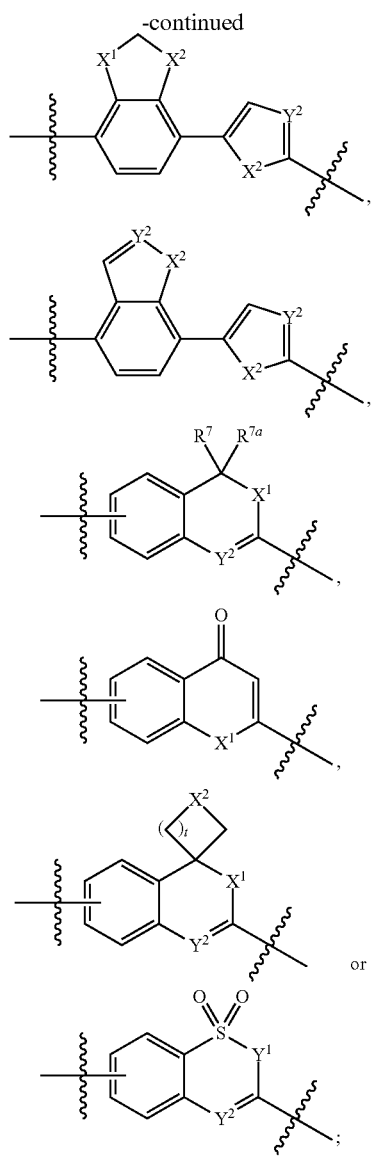

wherein each $R^5$ is independently H, deuterium, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_n$—, $C_{1-6}$ alkyl-S(=O)$_n$O—, $C_{1-6}$ alkyl-S(=O)$_n$—, or aminosulfonyl;

each $R^{6a}$ is independently H, deuterium, oxo (=O), hydroxy, amino, F, Cl, Br, I, cyano, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, R$^7$S(=O)$_2$—, R$^7$S(=O)$_2$N(R$^{7a}$)—, R$^{7a}R^7N$—C$_{1-6}$ alkyl, R$^7$S(=O)—C$_{1-6}$ alkyl, R$^7R^{7a}N$—C(=O)—C$_{1-6}$ alkyl, R$^{7a}R^7N$—C$_{1-6}$ alkoxy, R$^7$S(=O)—C$_{1-6}$ alkoxy, R$^7R^{7a}N$—C(=O)—C$_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-6}$ heteroarylamino, or $C_{6-10}$ aryloxy;

each $R^7$ and $R^{7a}$ is independently H, deuterium, F, Cl, $C_{1-6}$ alkyl, $C_{1-6}$ heteroalkyl, $C_{1-6}$ haloaliphatic, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-6}$ heterocyclyl-$C_{1-6}$-alkyl, $C_{3-8}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-8}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-8}$ cycloalkylamino-$C_{1-6}$-alkyl, $C_{6-10}$ aryl, $C_{1-9}$ heteroaryl, $C_{2-10}$ heterocyclyl, or $C_{3-8}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted $C_{5-12}$ spiro or fused bicyclic ring; and each $R^8$ and $R^{8a}$ is independently H, deuterium, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_n$—, $C_{1-6}$ alkyl-S(=O)$_n$O—, $C_{1-6}$ alkyl-S(=O)$_n$—, or aminosulfonyl.

5. The compound according to claim 1, wherein each of A and A' is independently a bond, —CH$_2$—, —(CH$_2$)$_2$—, —CH=CH—, —CH=CH—CH$_2$—, —C(=O)—O—, —C(=O)—N(R$^5$)—, —N(R$^5$)—C(=O)O—, —N(R$^5$)C(=O)N(R$^5$)—, —(R$^5$)N—S(=O)$_2$—, —(R$^5$)N—S(=O)—, or each of A and A' is independently

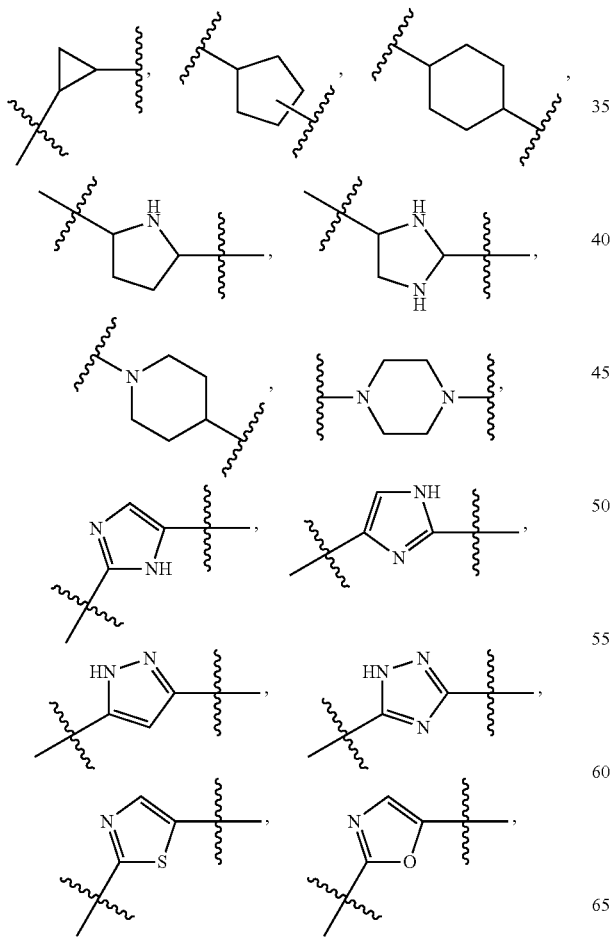

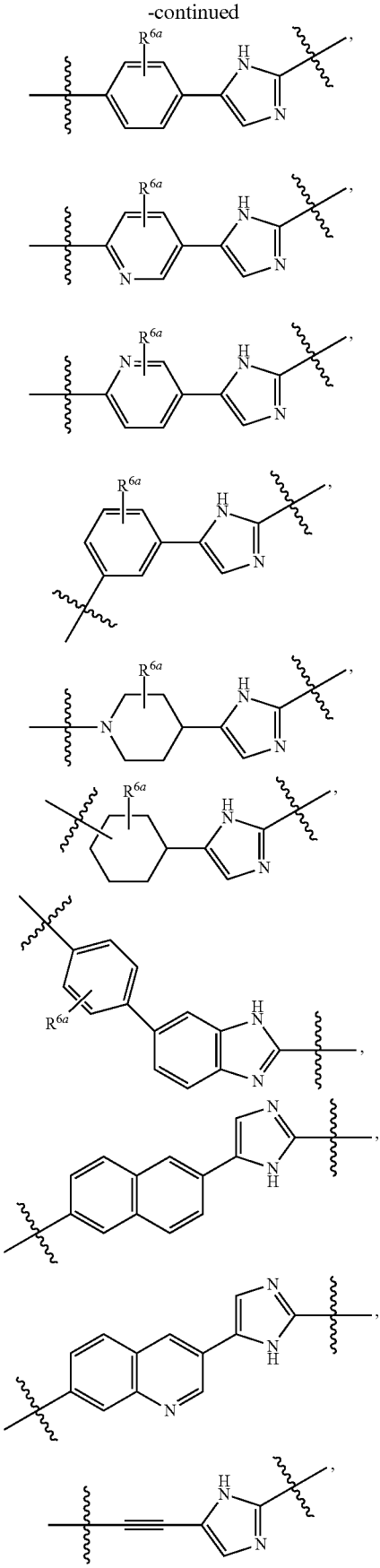

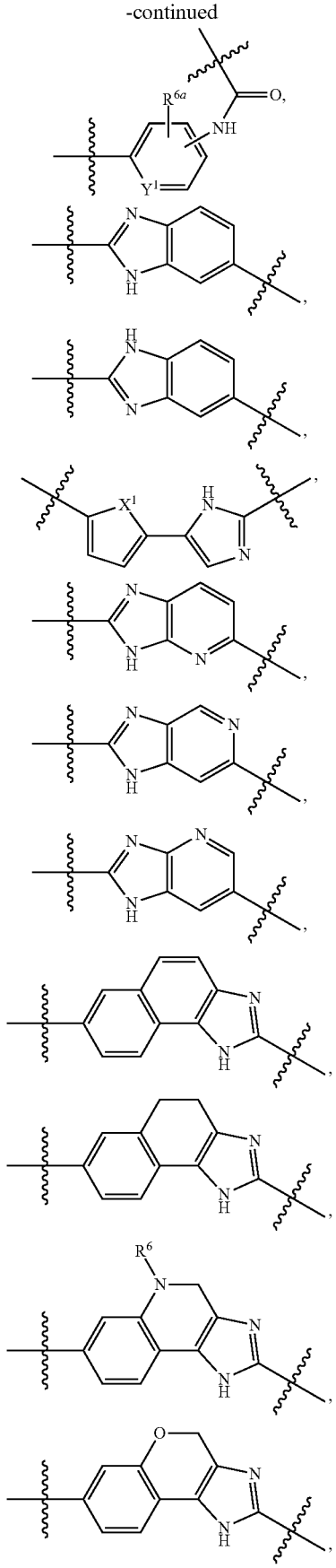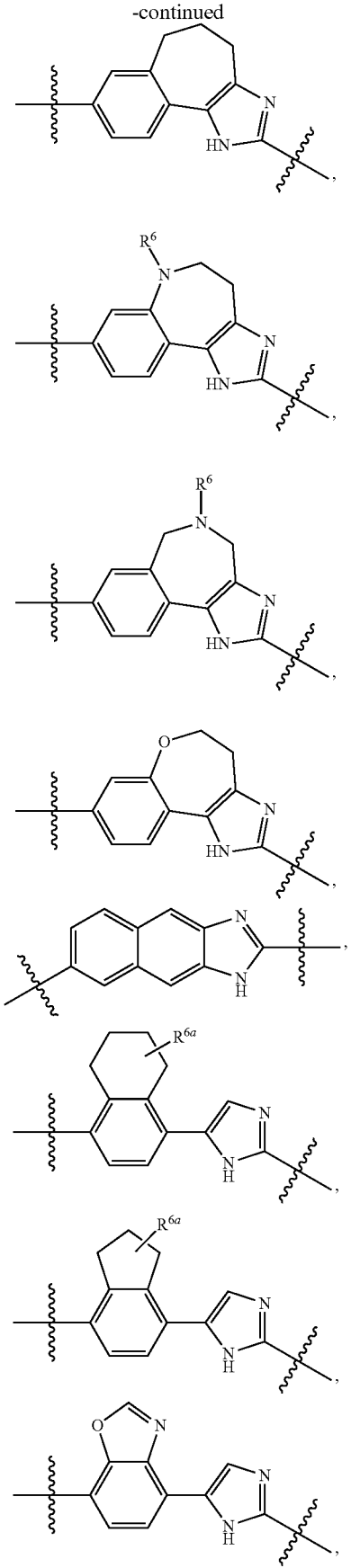

wherein $X^1$ is O or S;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl;

each $R^{6a}$ is independently H, deuterium, oxo (=O), hydroxy, amino, F, Cl, Br, I, cyano, $R^{7a}R^7N-$, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro; and each $R^7$ and $R^{7a}$ is independently H, deuterium, F, Cl, $C_{1-6}$ alkyl, $C_{1-6}$ heteroalkyl, $C_{1-6}$ haloalkyl, hydroxy $C_{1-6}$ alkyl, amino $C_{1-6}$ alkyl, $C_{1-6}$ alkoxy-$C_{1-6}$-alkyl, $C_{1-6}$ alkylamino-$C_{1-6}$-alkyl, or $C_{1-6}$ alkylthio-$C_{1-6}$-alkyl.

6. The compound according to claim 1, wherein the $R^1$, $R^2$ and X—CH together form one of the following monovalent groups:

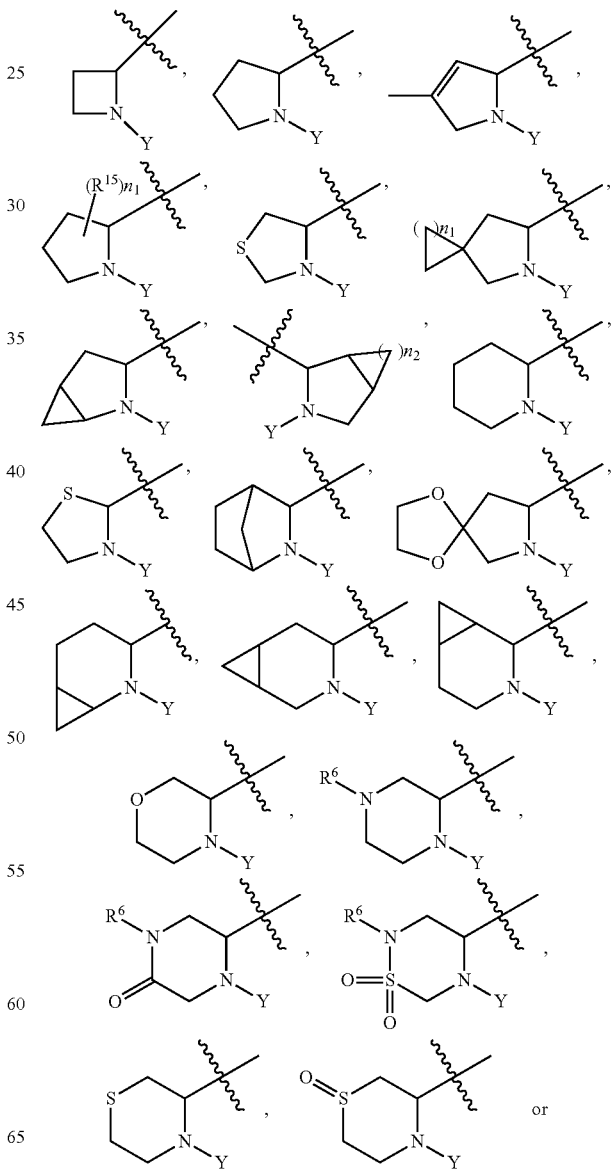

-continued

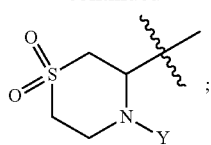

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{3-9}$ heterocyclyl or $C_{3-8}$ carbocyclyl; and each $n_1$ and $n_2$ is independently 1, 2, 3 or 4.

7. The compound according to claim 1, wherein the $R^3$, $R^4$ and X'—CH together form one of the following monovalent groups:

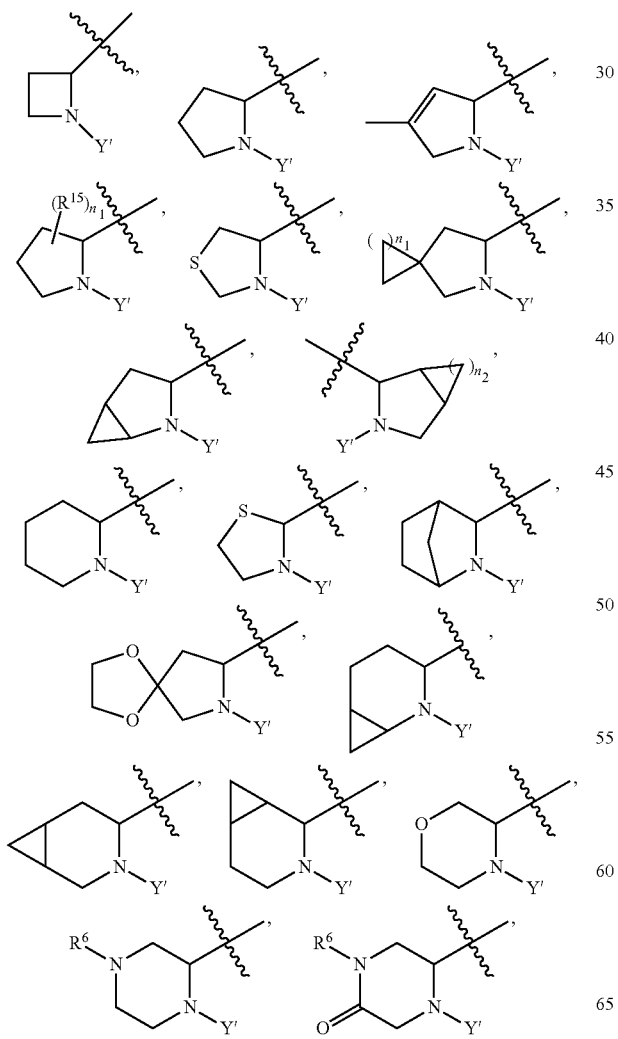

-continued

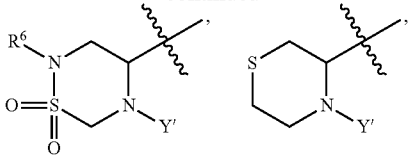

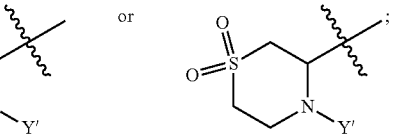

wherein each $R^{15}$ is independently H, deuterium, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

8. The compound according to claim 1 having Formula (IV):

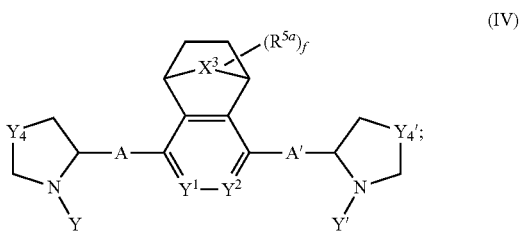

(IV)

wherein $X^3$ is C(=O) or $CH_2$;

each of $Y_4$ and $Y_4'$ is independently a bond, O, S, —CH=CH—, —S(=O)$_n$—, —$CH_2$O—, —$CH_2$S—, —$CH_2$S(=O)$_n$—, —$CHR^{5a}$— or —$CH_2$N($R^6$)—;

each $R^{5a}$ is independently H, deuterium, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

f is 0, 1, 2, or 3; and each $R^7$ and $R^{7a}$ is independently H, deuterium, $C_{1-4}$ alkyl, $C_{1-4}$ heteroalkyl, $C_{1-6}$ alkoxyalkyl, $C_{1-6}$ alkylaminoalkyl, $C_{6-10}$ aryl, $C_{2-10}$ heterocyclyl, $C_{3-8}$ cycloalkyl, $C_{1-6}$ heteroaryl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, a substituted or unsubstituted spiro or fused bicyclic ring.

9. The compound according to claim 1, wherein each of $R^9$, $R^{9a}$, and $R^H$ is independently H, deuterium, $C_{1-6}$ alkyl, $C_{3-10}$ cycloalkyl, $C_{6-10}$ aryl, or $C_{3-8}$ cycloalkyl-$C_{1-6}$-alkyl; and $R^{13}$ is H, deuterium, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl.

10. The compound according to claim 9, wherein each of $R^9$, $R^{9a}$, and $R^{11}$ is independently H, deuterium, methyl, ethyl, isopropyl, cyclohexyl, isobutyl or phenyl; and $R^{13}$ is H, deuterium, methyl, ethyl, propyl, phenyl, or cyclohexyl.

11. The compound according to claim 1 having Formula (VIII):

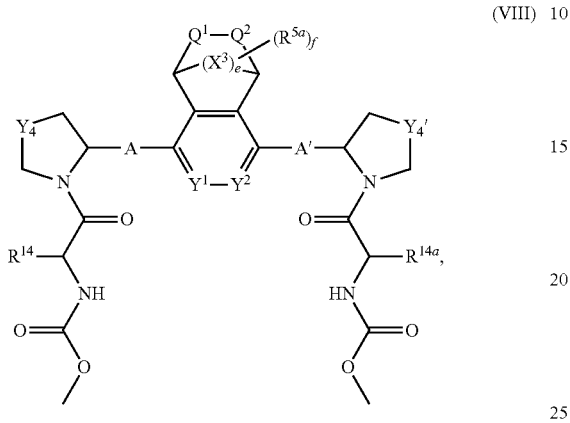

(VIII)

wherein each of $R^{14}$ and $R^{14a}$ is independently H, deuterium, methyl, ethyl, isopropyl, isobutyl, tert-butyl, phenyl, cyclopentyl, cyclopropyl, or cyclohexyl; wherein each of methyl, ethyl, isopropyl, isobutyl, tert-butyl, phenyl, cyclopentyl, cyclopropyl and cyclohexyl is optionally substituted with one or more substituents, wherein the substituent is deuterium, F, Cl, Br, hydroxy or cyano;

each $Q^1$ and $Q^2$ is independently $CH_2$;

each $Y^1$ and $Y^2$ is independently $CR^7$;

each of $Y_4$ and $Y_4'$ is independently a bond, O, S, —$(CH_2)_n$—, —CH=CH—, —S(=O)$_r$—, —$CH_2O$—, —$CH_2S$—, —$CH_2S(=O)_r$—, —$CF_2$—, —$CHR^{5a}$— or —$CH_2N(R^6)$—;

each $X^3$ is independently C(=O) or $CH_2$; e is 1;

f is 0, 1, 2, 3 or 4; and each of A and A' is independently a bond, $C_{1-6}$ alkyl, $C_{2-6}$ alkenyl, $C_{3-8}$ cycloalkyl, $C_{2-10}$ heterocycloalkyl, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—N($R^5$)—C(=O)—O—$(CR^8R^{8a})_p$—, or each of A and A' is independently

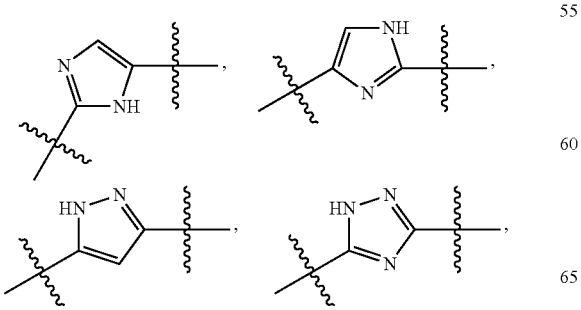

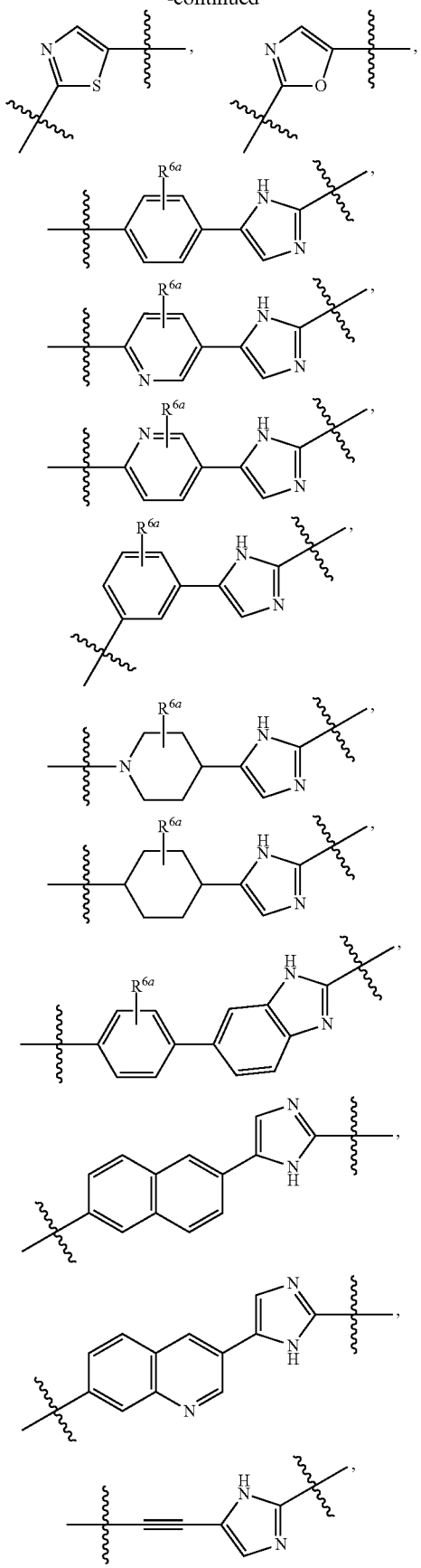

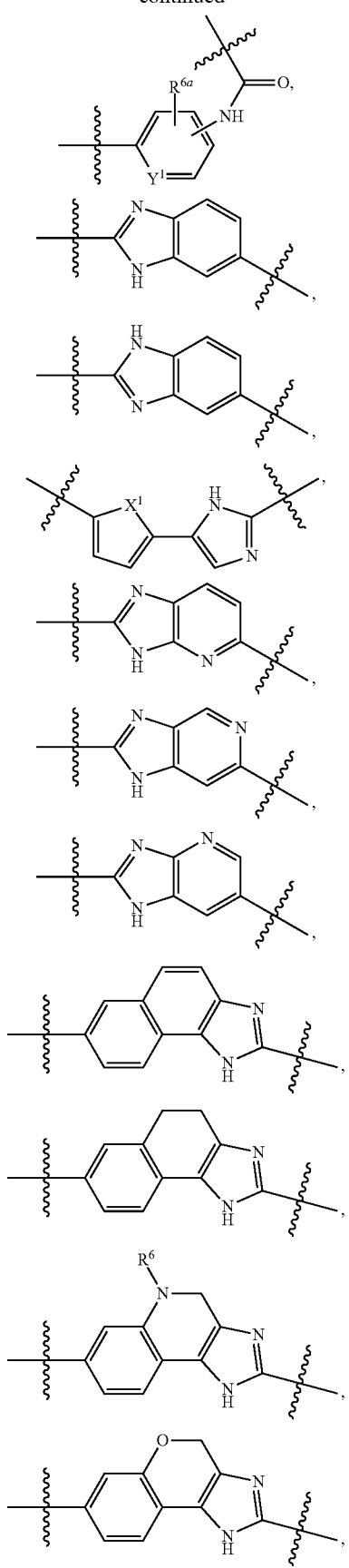
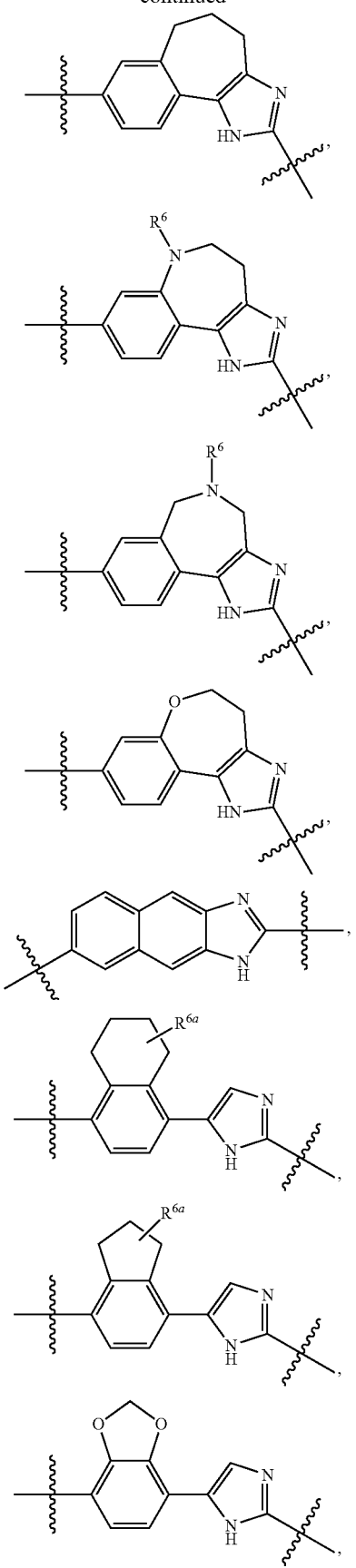

-continued

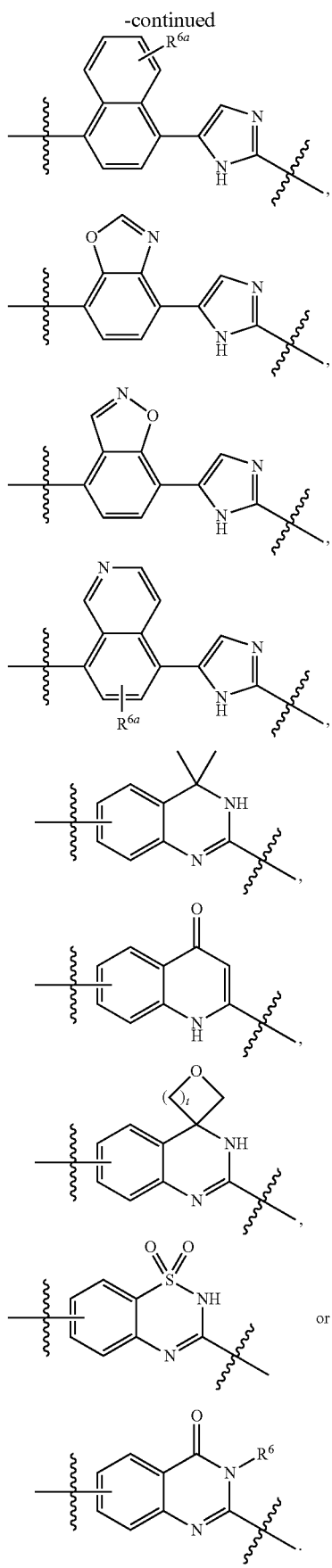

12. A compound having Formula (XI):

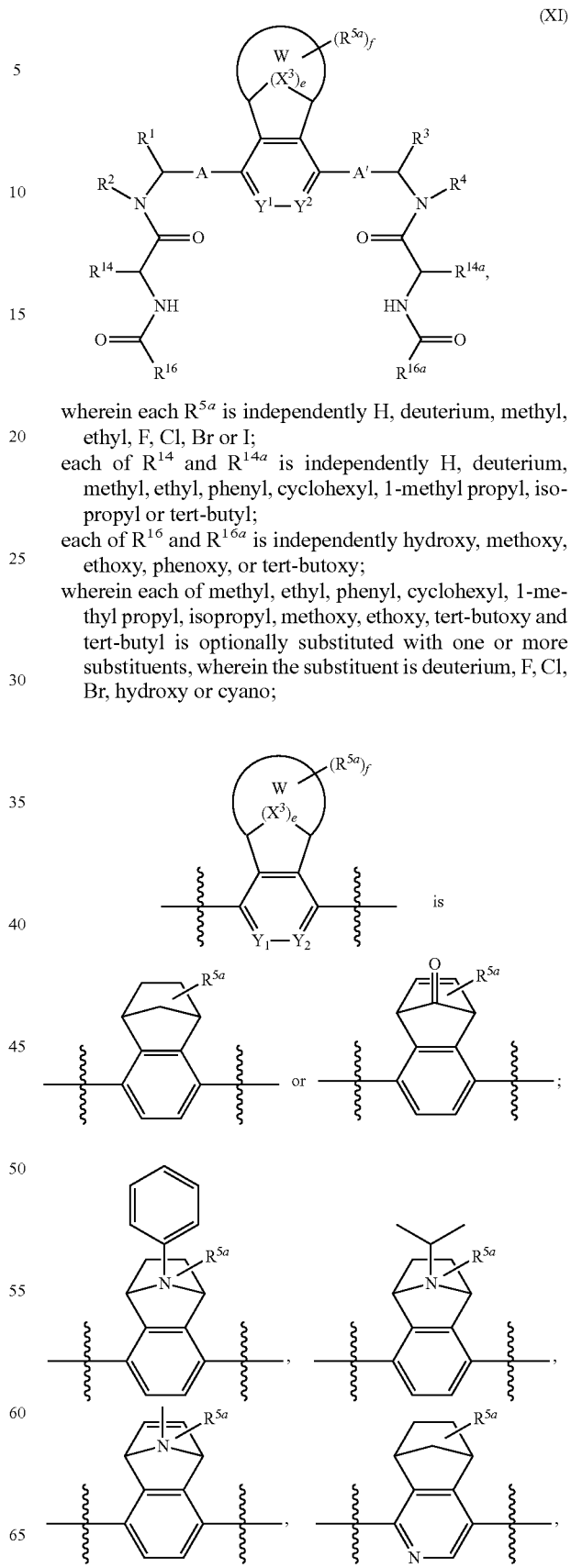

wherein each $R^{5a}$ is independently H, deuterium, methyl, ethyl, F, Cl, Br or I;

each of $R^{14}$ and $R^{14a}$ is independently H, deuterium, methyl, ethyl, phenyl, cyclohexyl, 1-methyl propyl, isopropyl or tert-butyl;

each of $R^{16}$ and $R^{16a}$ is independently hydroxy, methoxy, ethoxy, phenoxy, or tert-butoxy;

wherein each of methyl, ethyl, phenyl, cyclohexyl, 1-methyl propyl, isopropyl, methoxy, ethoxy, tert-butoxy and tert-butyl is optionally substituted with one or more substituents, wherein the substituent is deuterium, F, Cl, Br, hydroxy or cyano;

-continued
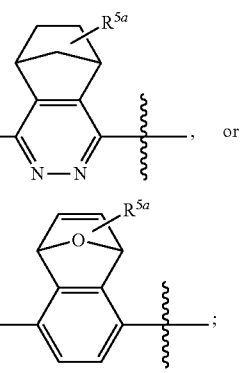
, or
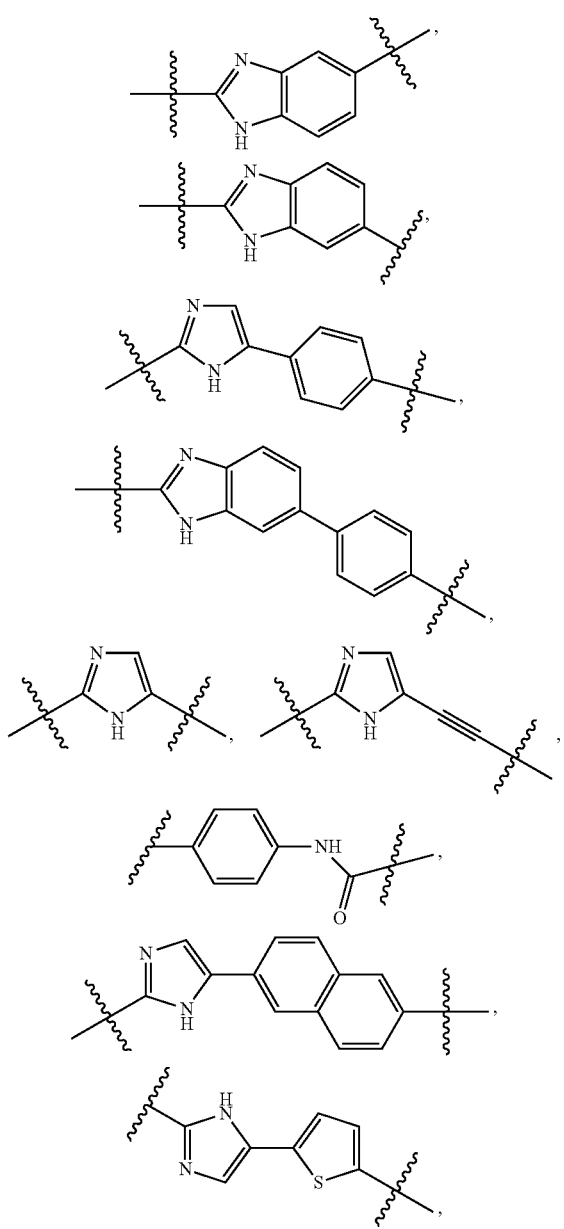
each of A and A' is independently
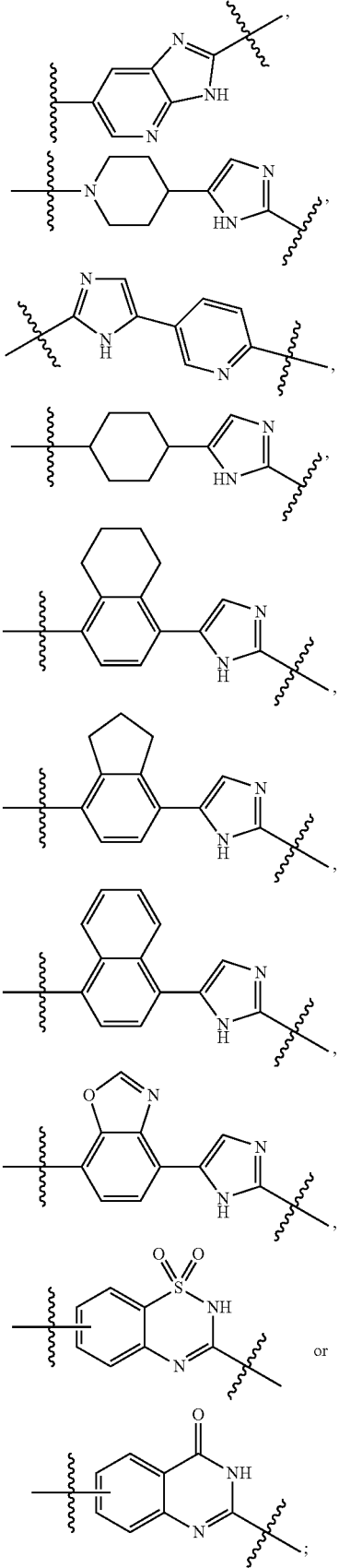
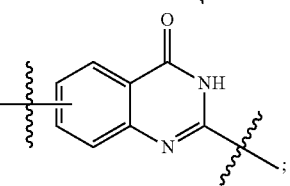

wherein $R^1$, $R^2$ and N—CH together form one of the following divalent groups:

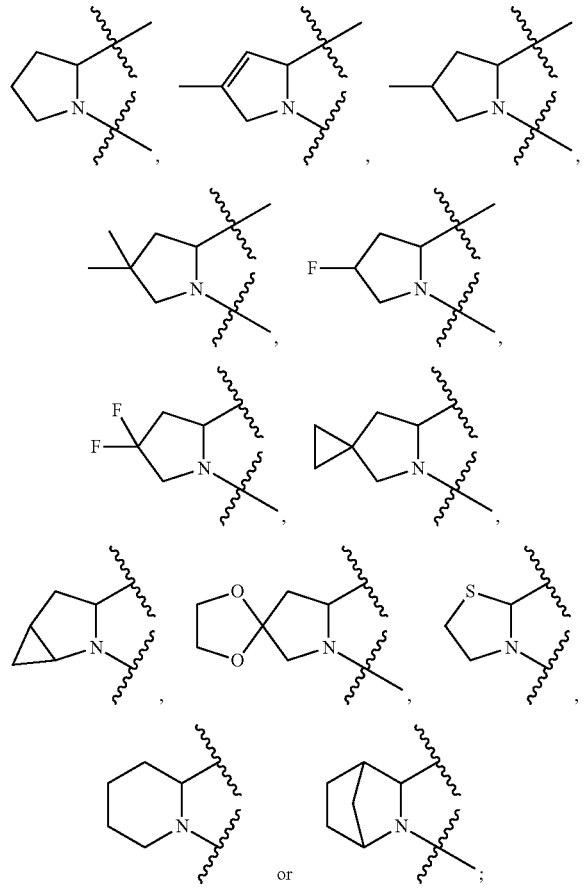

and wherein $R^3$, $R^4$ and N—CH together form one of the following divalent groups:

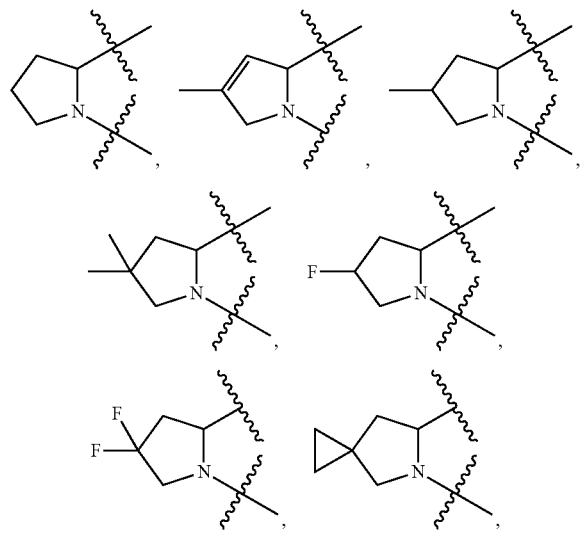

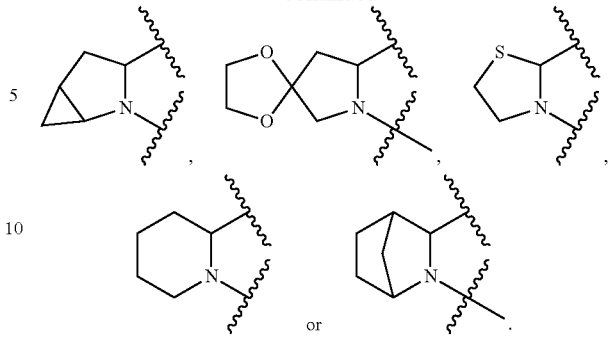

13. The compound according to claim 12 having Formula (XII):

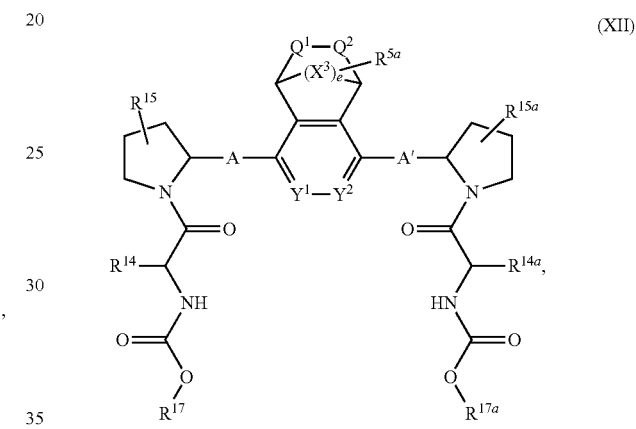

(XII)

wherein $R^{5a}$ is H or methyl;
each of $Q^1$ and $Q^2$ is independently $CH_2$;
each of $Y^1$ and $Y^2$ is independently $CH_2$;
each of $R^{14}$ and $R^{14a}$ is independently H, deuterium, methyl, ethyl, isobutyl, cyclohexyl, phenyl or isopropyl;
each of $R^{15}$ and $R^{15a}$ is independently H, deuterium, F, Cl, Br, methyl, ethyl, isopropyl or tert-butyl;
each of $R^{17}$ and $R^{17a}$ is independently methyl, phenyl or ethyl;
each $X^3$ is independently C(=O) or $CH_2$;
e is 1 or 2 with the proviso that where $X^3$ is C(=O), e is 1;
wherein each of methyl, ethyl, phenyl, cyclohexyl, isopropyl and tert-butyl is optionally substituted with one or more substituents, wherein the substituent is deuterium, F, Cl, Br, hydroxy or cyano; and
each of A and A' is independently

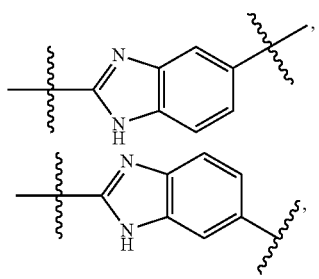

663
-continued
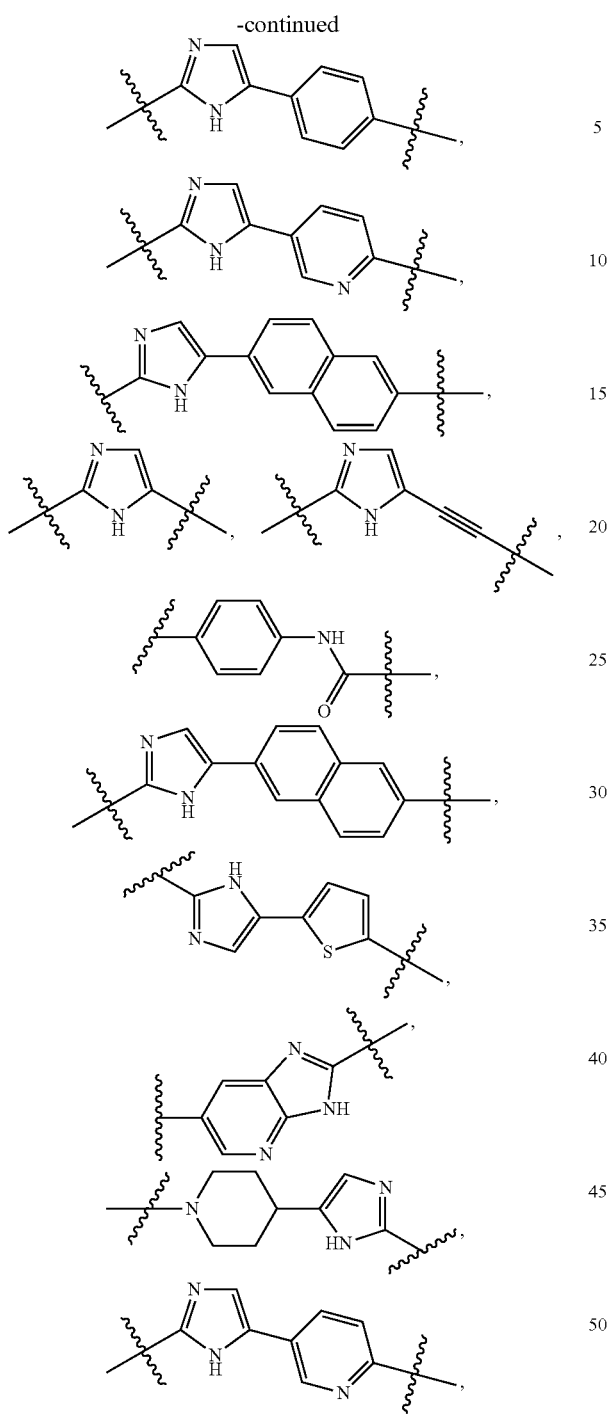
664
-continued
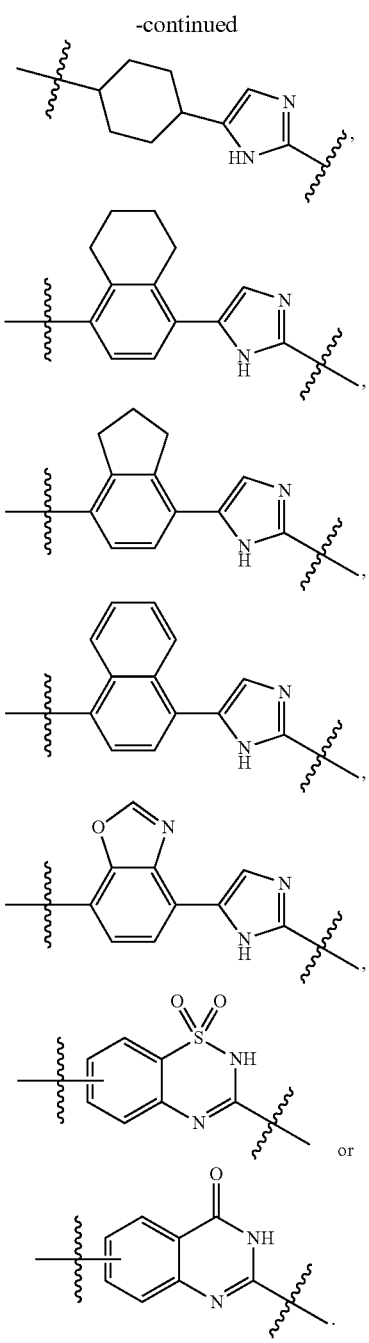
14. A compound of claim 1 having one of the following structures:
(1)
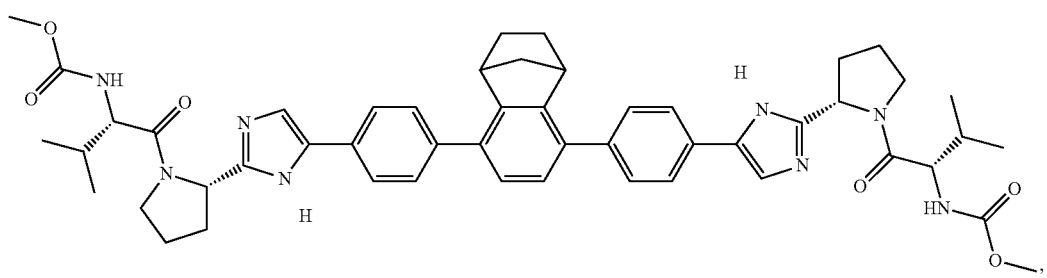

(2)
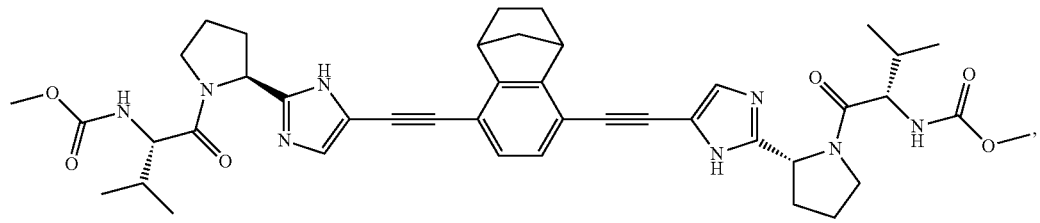
(3)
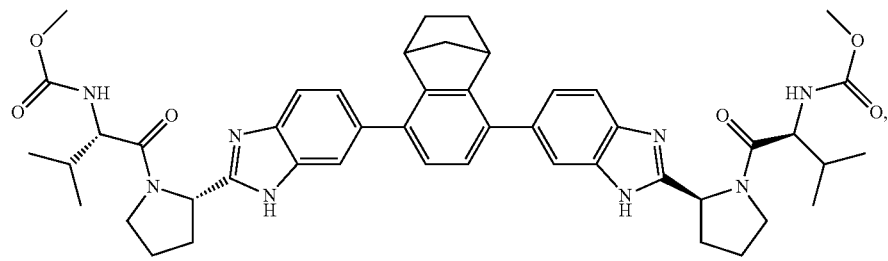
(4)
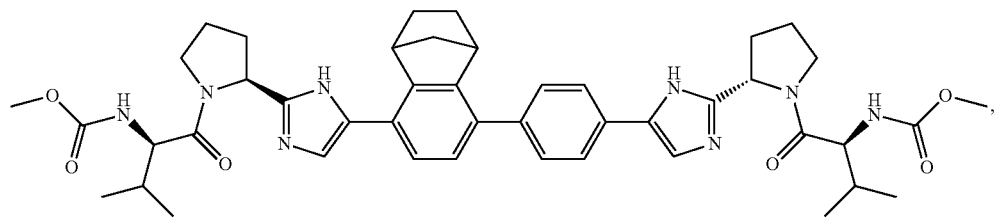
(6)
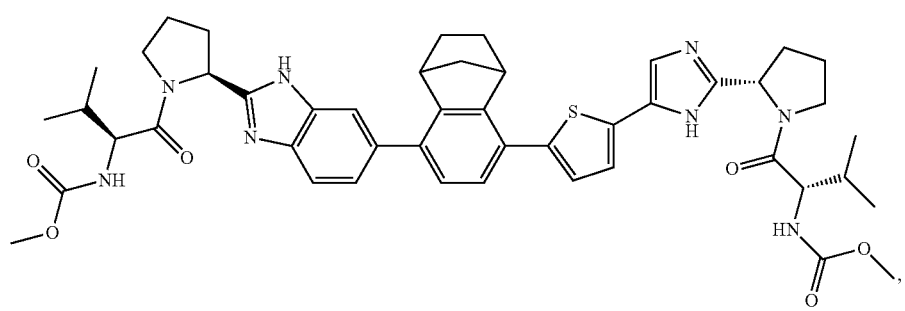
(9)
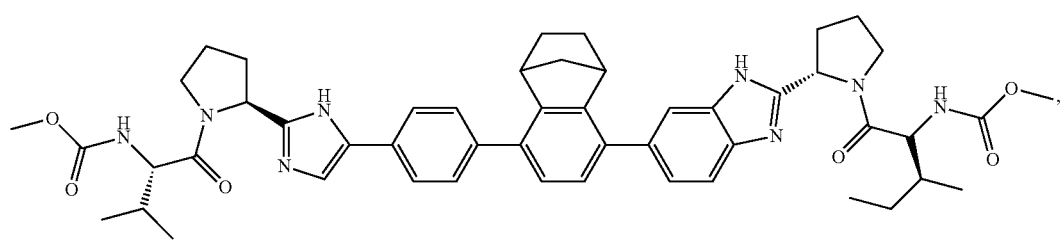

(10)
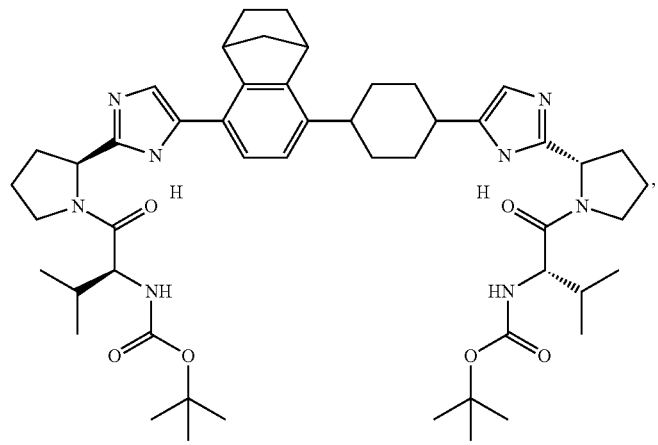
(11)
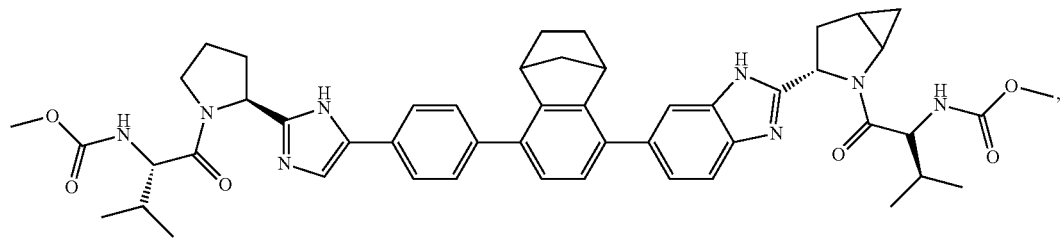
(12)
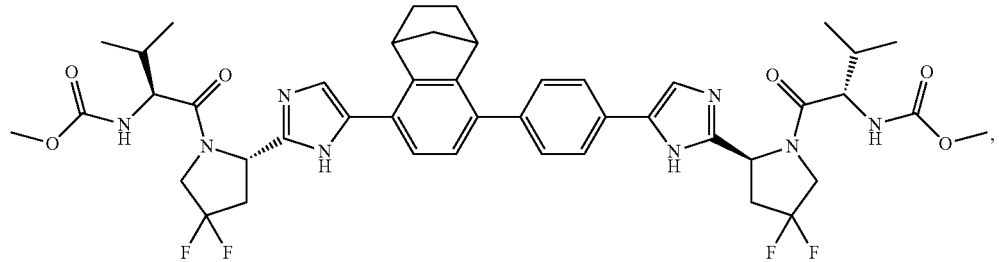
(13)
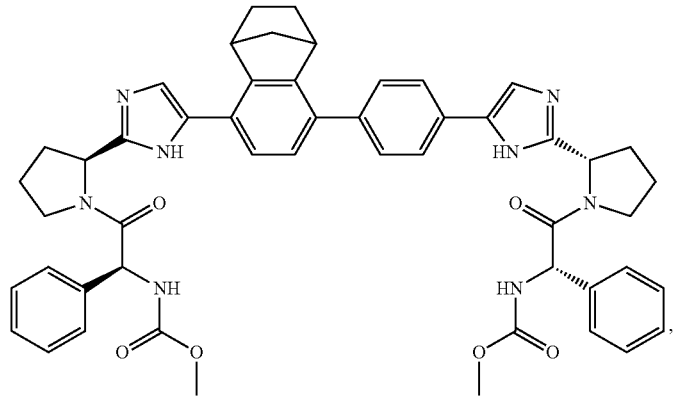
(14)
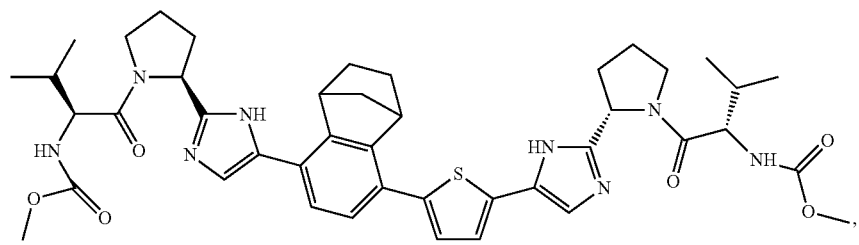

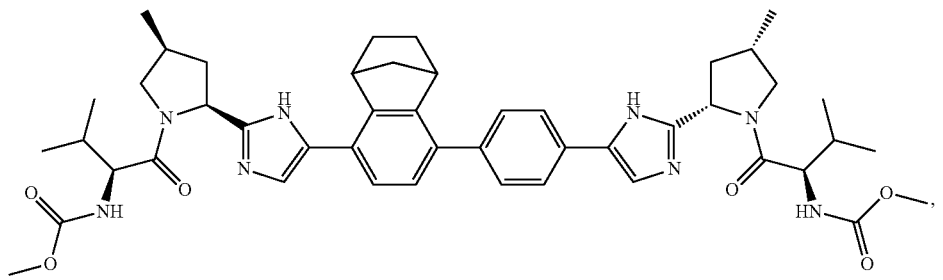
(15)
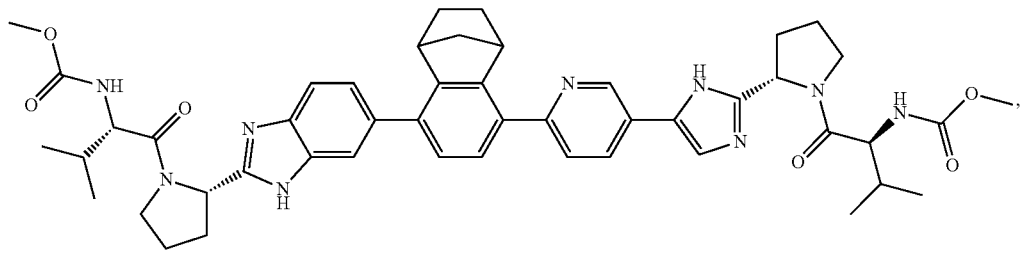
(16)
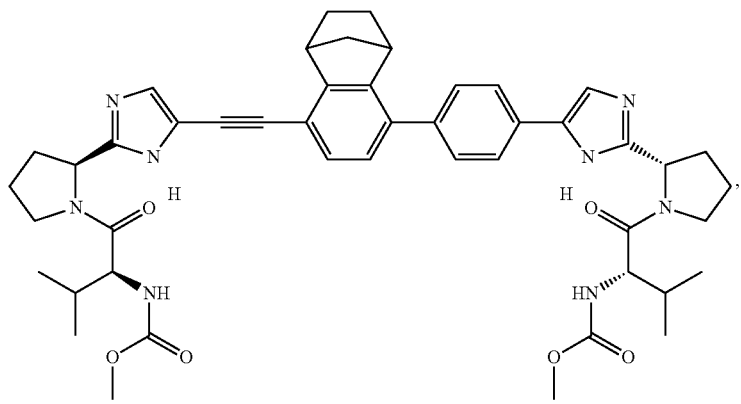
(17)
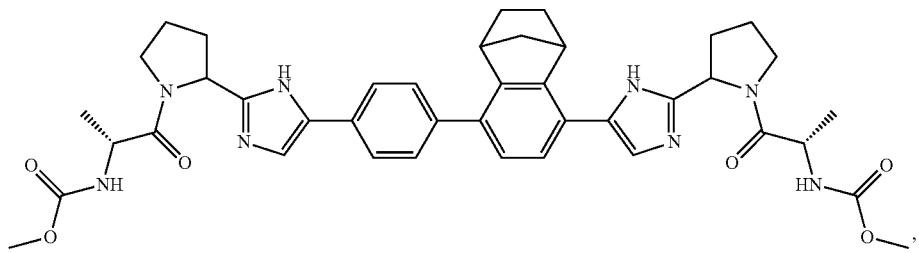
(18)
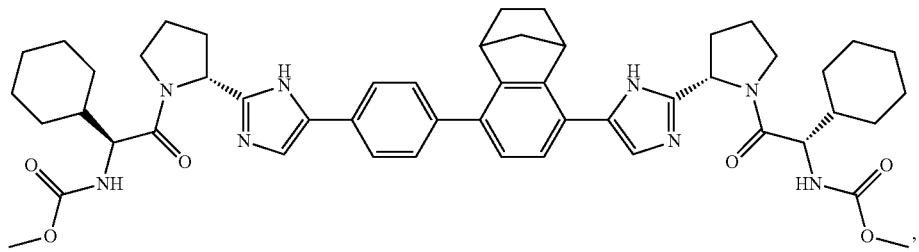
(19)

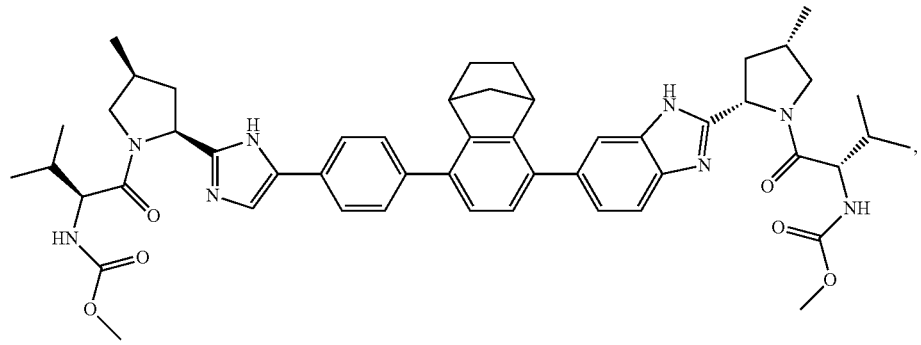
(20)
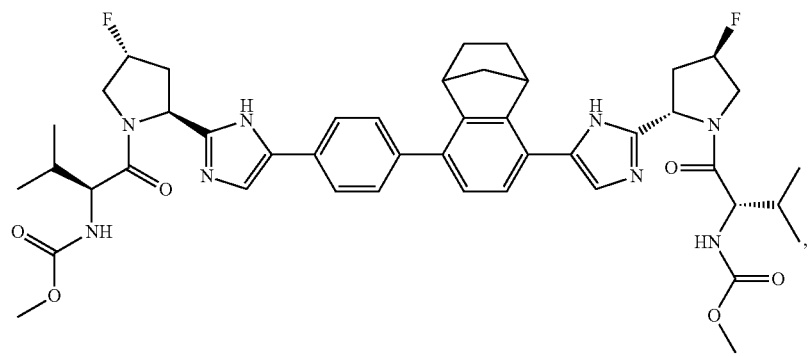
(21)
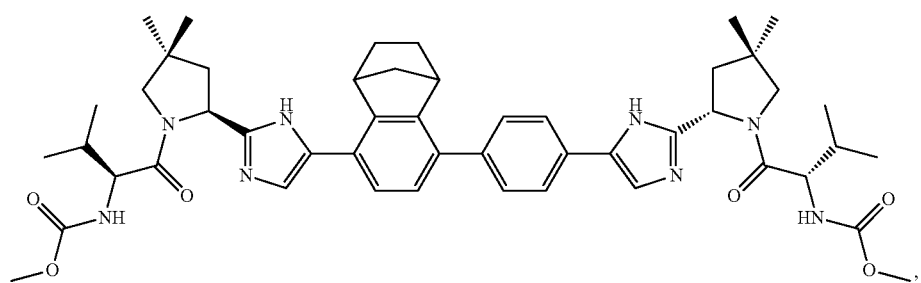
(22)
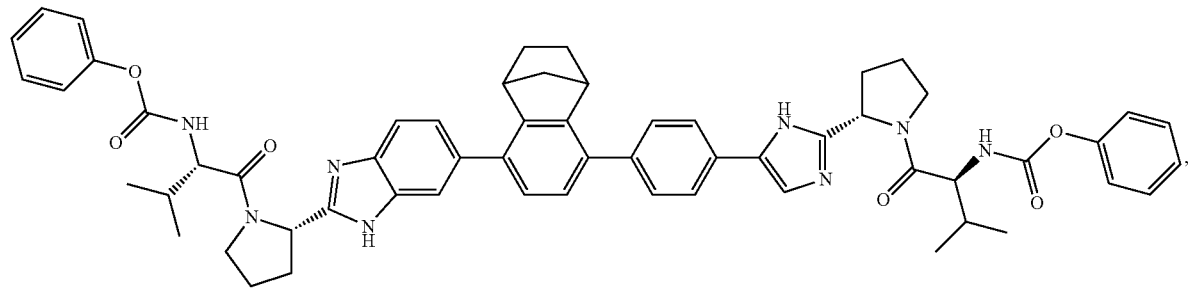
(23)

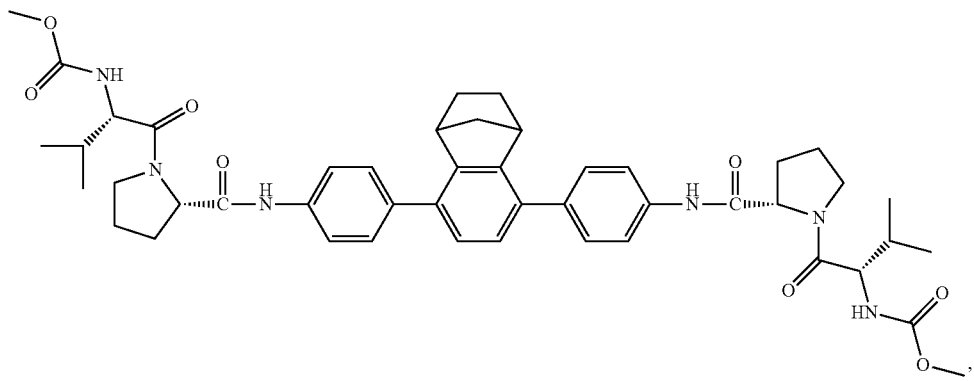
(24)
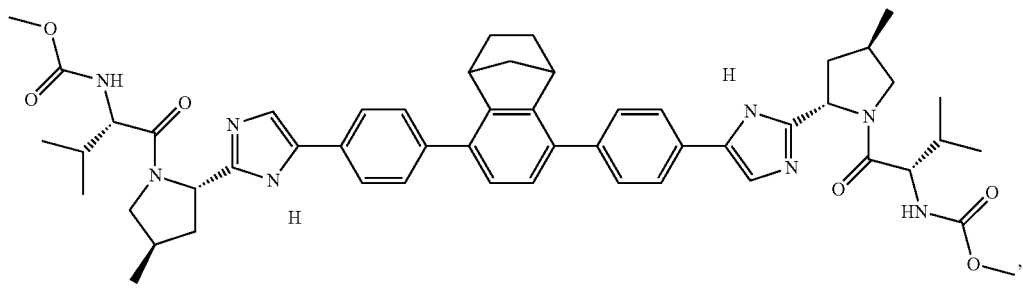
(25)
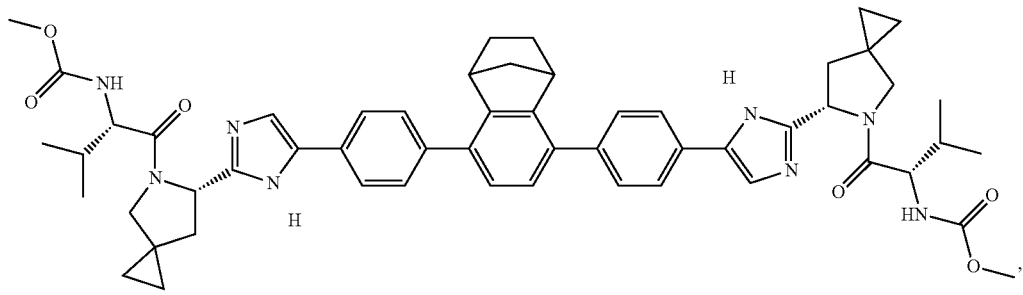
(26)
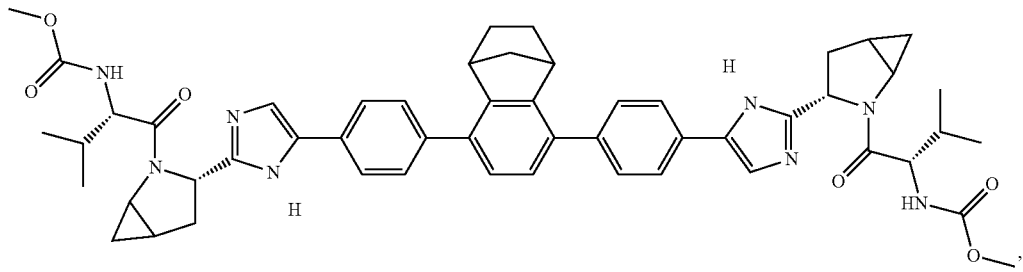
(27)
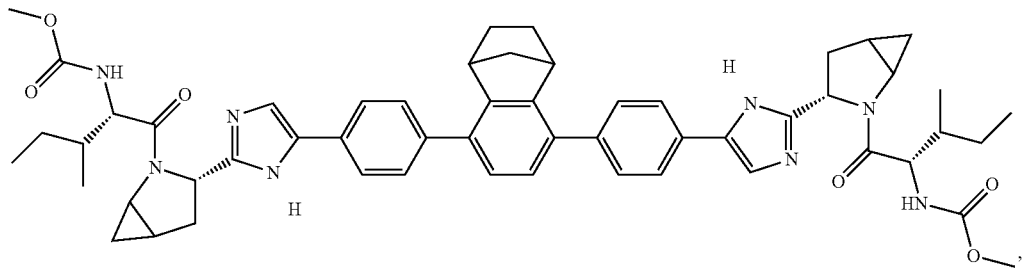
(28)

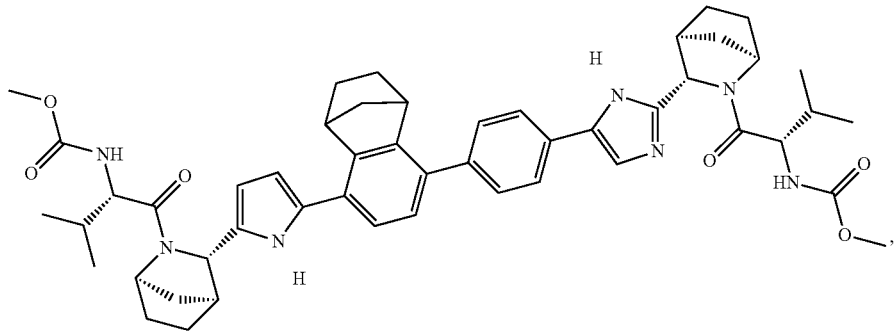
(29)
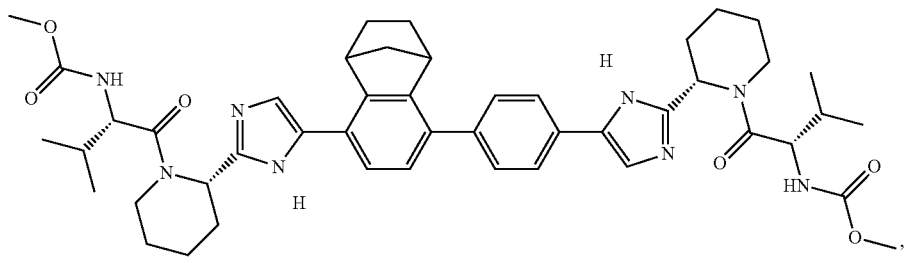
(30)
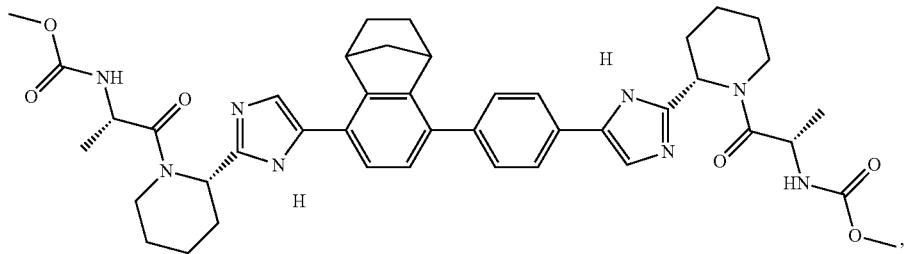
(31)
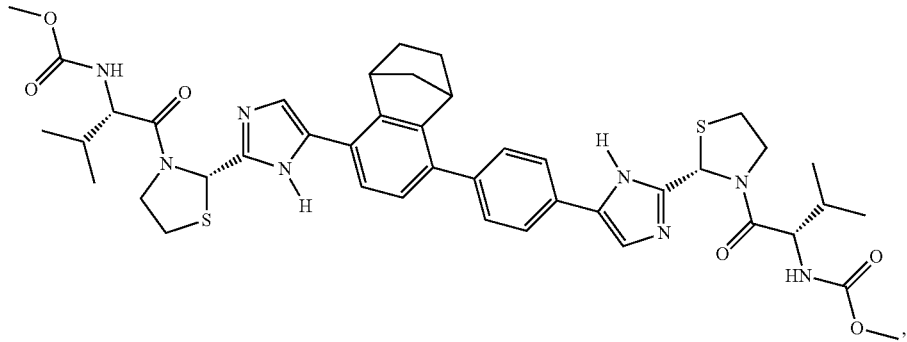
(32)
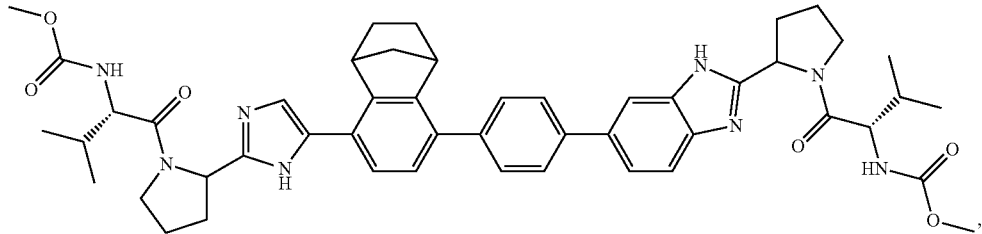
(33)

(34)
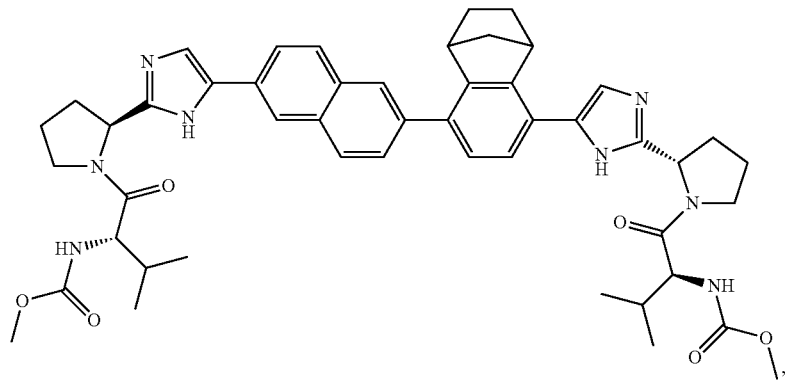
(35)
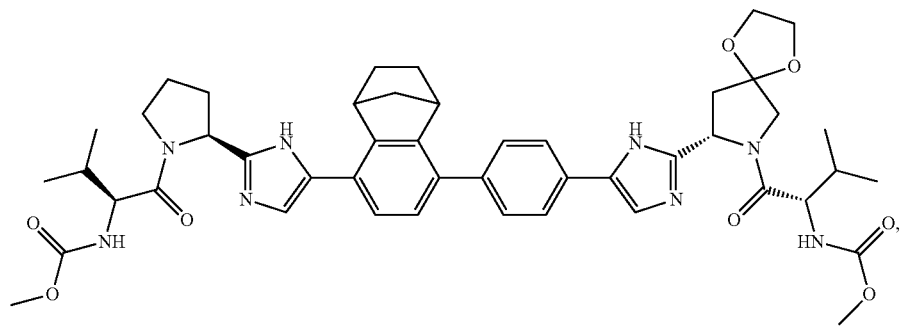
(36)
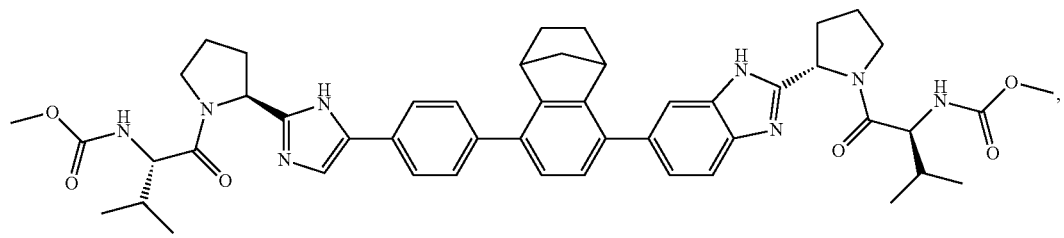
(37)
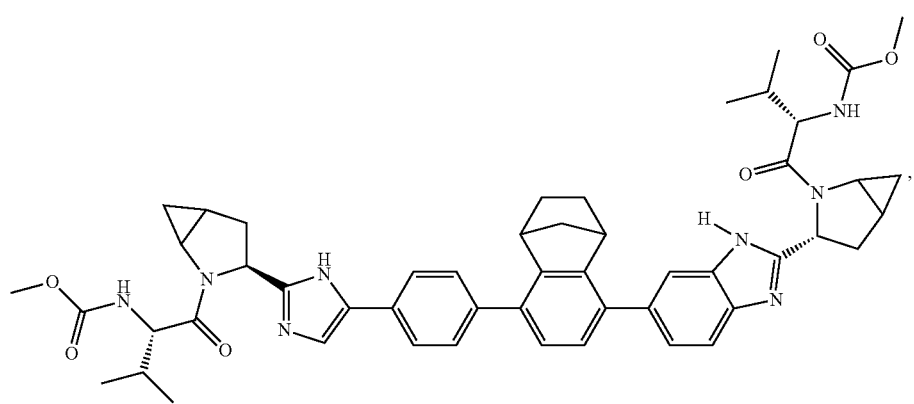

-continued
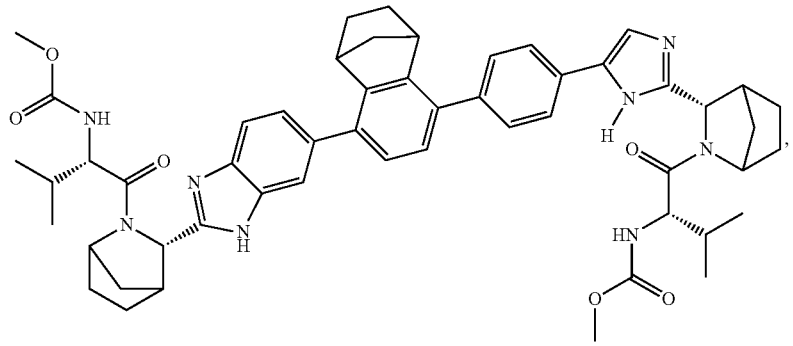
(38)
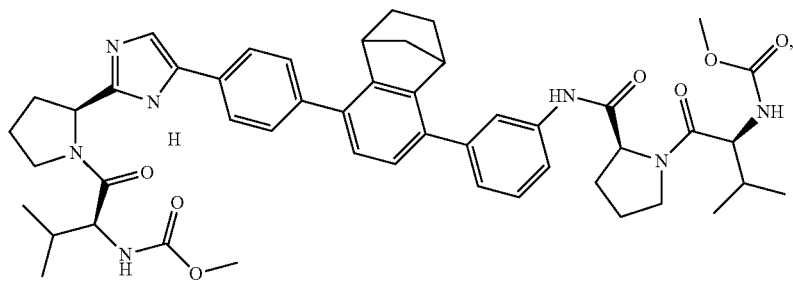
(39)
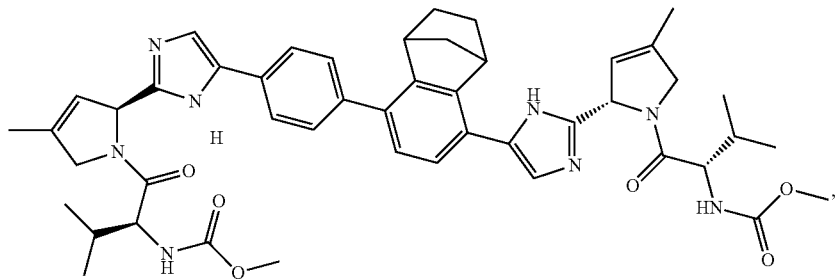
(40)
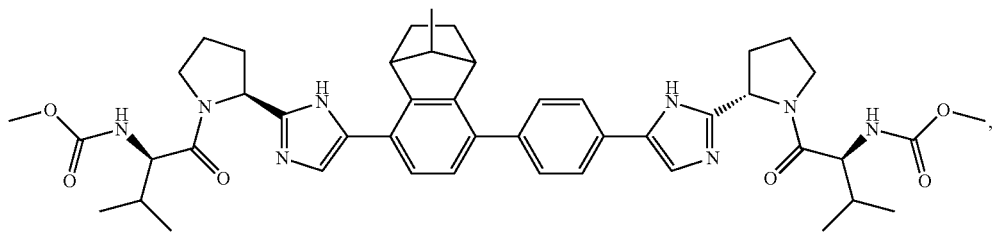
(43)
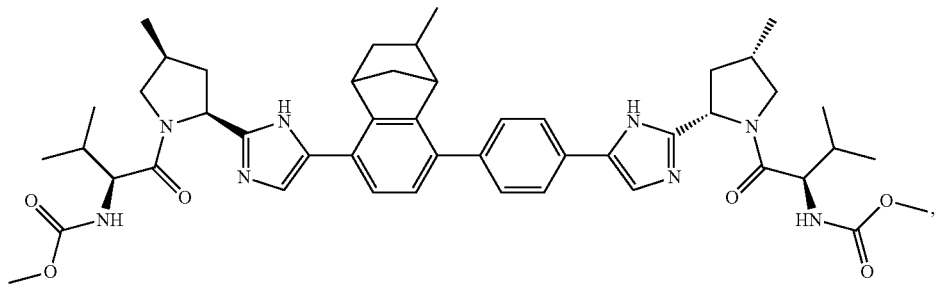
(44)

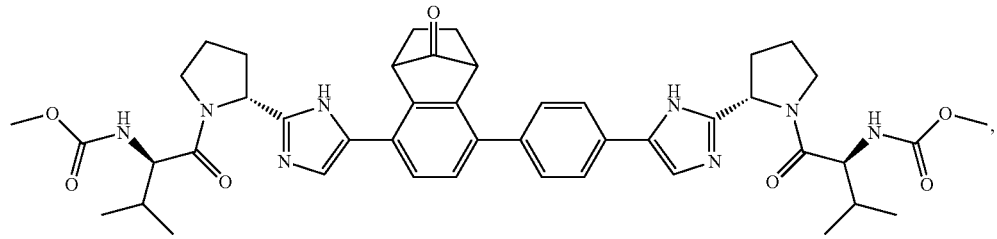
(46)
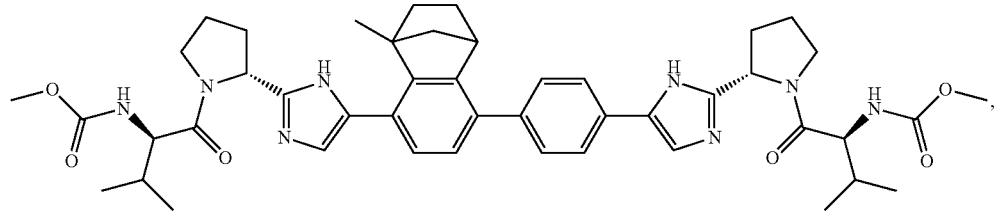
(47)
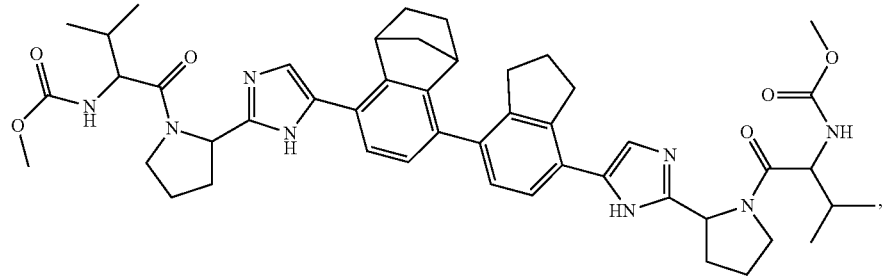
(173)
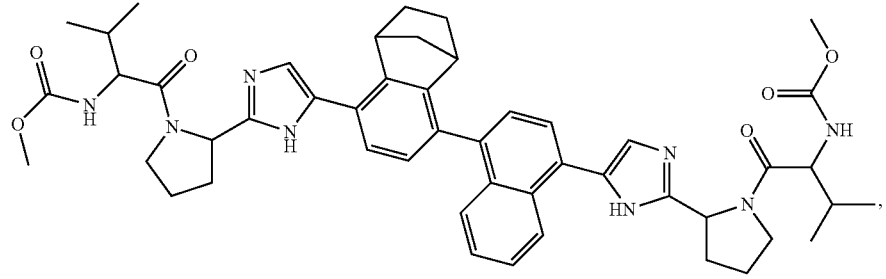
(174)
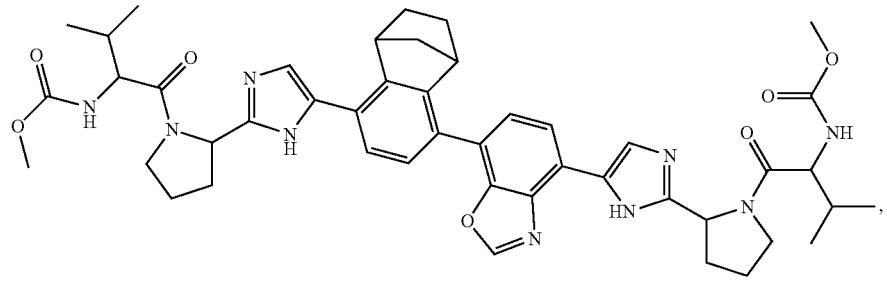
(175)
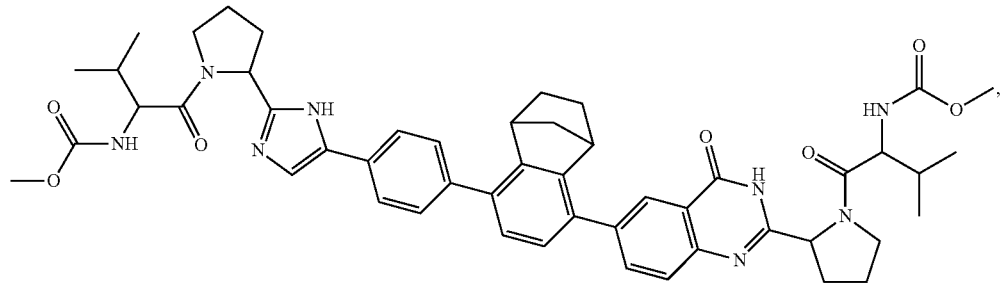
(176)

-continued
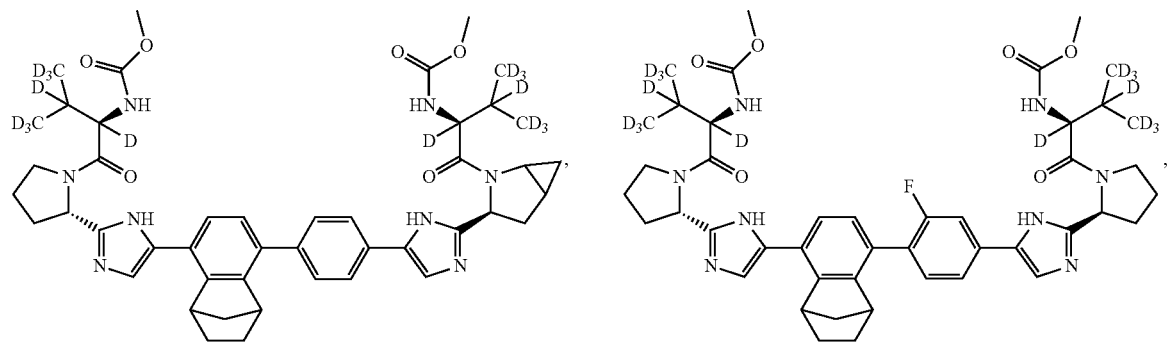
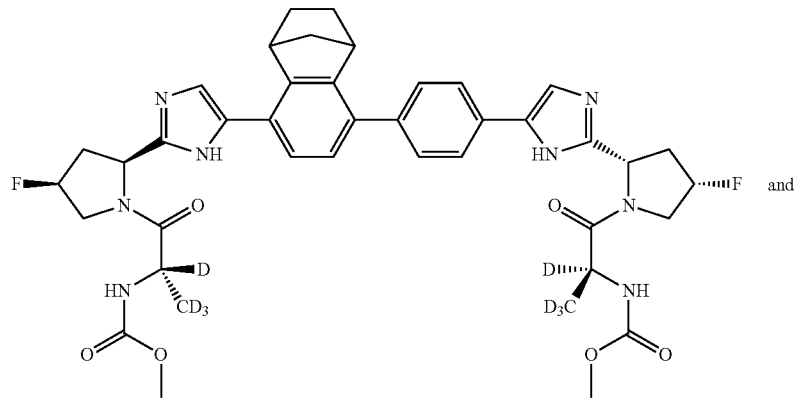
and
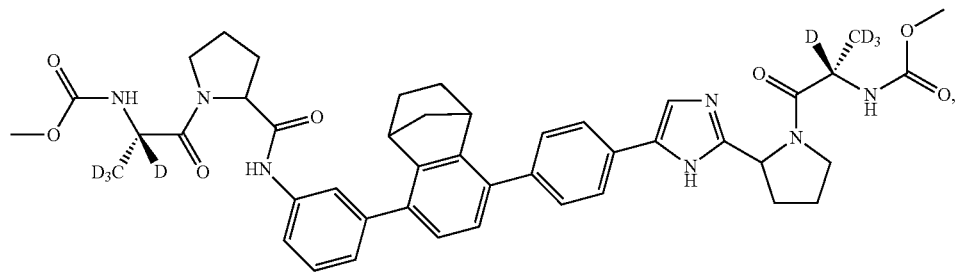
or a stereoisomer, a geometric isomer, a tautomer, an N-oxide, a hydrate, a solvate, pharmaceutically acceptable salt thereof.
15. A pharmaceutical composition comprising the compound according to claim 1; and a pharmaceutically acceptable carrier, excipient, diluent, adjuvant, vehicle or a combination thereof.
* * * * *